US012331039B2

(12) United States Patent
Kaldor et al.

(10) Patent No.: US 12,331,039 B2
(45) Date of Patent: Jun. 17, 2025

(54) INHIBITORS OF FIBROBLAST GROWTH FACTOR RECEPTOR KINASES

(71) Applicant: Khora SPV 1, LLC, Boston, MA (US)

(72) Inventors: Stephen W. Kaldor, San Diego, CA (US); John Tyhonas, San Diego, CA (US); Eric A. Murphy, San Marcos, CA (US); Toufike Kanouni, Rancho Santa Fe, CA (US); Lee D. Arnold, Rancho Santa Fe, CA (US); Robert Kania, Del Mar, CA (US); Jason M. Cox, Rancho Santa Fe, CA (US)

(73) Assignee: Khora SPV 1, LLC, Boston, MA (US)

( * ) Notice: Subject to any disclaimer, the term of this patent is extended or adjusted under 35 U.S.C. 154(b) by 620 days.

(21) Appl. No.: 17/702,444

(22) Filed: Mar. 23, 2022

(65) Prior Publication Data
US 2023/0078839 A1 Mar. 16, 2023

Related U.S. Application Data

(63) Continuation of application No. 17/339,123, filed on Jun. 4, 2021, now Pat. No. 11,345,681.

(60) Provisional application No. 63/106,812, filed on Oct. 28, 2020, provisional application No. 63/035,155, filed on Jun. 5, 2020.

(51) Int. Cl.
C07D 403/14 (2006.01)
A61K 45/06 (2006.01)
C07D 401/14 (2006.01)
C07D 405/14 (2006.01)
C07D 413/04 (2006.01)
C07D 417/14 (2006.01)
C07D 471/04 (2006.01)
C07D 487/04 (2006.01)

(52) U.S. Cl.
CPC ............ C07D 403/14 (2013.01); A61K 45/06 (2013.01); C07D 401/14 (2013.01); C07D 405/14 (2013.01); C07D 413/04 (2013.01); C07D 417/14 (2013.01); C07D 471/04 (2013.01); C07D 487/04 (2013.01)

(58) Field of Classification Search
CPC .............................. C07D 403/14; A61K 45/06
USPC ........................................................ 514/213
See application file for complete search history.

(56) References Cited

U.S. PATENT DOCUMENTS

| | | |
|---|---|---|
| 5,846,514 A | 12/1998 | Foster et al. |
| 5,886,022 A | 3/1999 | Kluender et al. |
| 6,334,997 B1 | 1/2002 | Foster et al. |
| 9,840,517 B2 | 12/2017 | Liu et al. |
| 10,077,271 B2 | 9/2018 | Grembecka et al. |
| 10,174,041 B2 | 1/2019 | Grembecka et al. |
| 10,206,931 B2 | 2/2019 | Romero et al. |
| 10,239,861 B2 | 3/2019 | Albrecht et al. |
| 10,377,743 B2 | 8/2019 | Li et al. |
| 10,450,303 B2 | 10/2019 | Smolinski et al. |
| 10,588,907 B2 | 3/2020 | Grembecka et al. |
| 10,927,111 B2 | 2/2021 | Kaldaor et al. |
| 11,345,681 B1 | 5/2022 | Kaldor et al. |
| 2007/0135461 A1 | 6/2007 | Rodgers et al. |
| 2008/0015191 A1 | 1/2008 | Springer et al. |
| 2008/0045536 A1 | 2/2008 | Vaccaro et al. |
| 2008/0161280 A1 | 7/2008 | Gandhi et al. |
| 2008/0269234 A1 | 10/2008 | Gandhi et al. |
| 2012/0196847 A1 | 8/2012 | Arnold et al. |
| 2012/0208811 A1 | 8/2012 | Taka et al. |
| 2013/0190496 A1 | 7/2013 | Mulvihill et al. |
| 2014/0343035 A1 | 11/2014 | Sagara et al. |
| 2016/0136168 A1 | 5/2016 | Sootome |
| 2016/0193210 A1 | 7/2016 | Ochiiwa et al. |
| 2017/0222160 A1 | 8/2017 | Lee et al. |
| 2017/0298055 A1 | 10/2017 | Rennie et al. |
| 2019/0092767 A1 | 3/2019 | Li et al. |
| 2019/0183897 A1 | 6/2019 | Ochiiwa et al. |
| 2019/0210997 A1* | 7/2019 | Chen .................. A61K 31/4155 |
| 2019/0345158 A1 | 11/2019 | Li et al. |
| 2019/0367489 A1 | 12/2019 | Li et al. |
| 2019/0382377 A1 | 12/2019 | Li et al. |
| 2020/0024273 A1 | 1/2020 | Wang et al. |
| 2020/0030312 A1 | 1/2020 | Shao et al. |
| 2020/0165224 A1 | 5/2020 | Li et al. |
| 2020/0339541 A1 | 10/2020 | Chen et al. |
| 2021/0130357 A1 | 5/2021 | Zhang et al. |
| 2023/0174535 A1 | 6/2023 | Kaldor et al. |
| 2023/0374015 A1 | 11/2023 | Kaldor et al. |

FOREIGN PATENT DOCUMENTS

| | | |
|---|---|---|
| AU | 2014291161 A1 | 2/2016 |
| CN | 103958512 A | 7/2014 |
| CN | 104341425 A | 2/2015 |
| CN | 107406455 A | 11/2017 |
| CN | 107698593 A | 2/2018 |
| CN | 108623562 A | 10/2018 |

(Continued)

OTHER PUBLICATIONS

Chemical Structure Search dated Jun. 3, 2020.
Jiang et al. GZD824 overcomes FGFR1-V561F/M mutant resistance in vitro and in vivo. Cancer Med 10(14):4874-4884 (2021).
PCT/US2022/080874 International Search Report and Written Opinion dated Mar. 8, 2023.
PubChem-SID-442878695, Modify Date: Sep. 2, 2021.
Zhao, Bin et al. Discovery of Substituted 1H-Pyrazolo[3,4-b]pyridine Derivatives as Potent and Selective FGFR Kinase Inhibitors. ACS Med Chem Lett 7(6):629-634 (2016).
Babina et al. Advances and challenges in targeting FGFR signaling in cancer. Nat Rev Cancer 17(5):318-332 (2017).

(Continued)

Primary Examiner — Jeffrey H Murray
Assistant Examiner — Rilla Marie Samsell
(74) Attorney, Agent, or Firm — Goodwin Procter LLP

(57) ABSTRACT

Provided herein are heteroaryl inhibitors of fibroblast growth factor receptor kinases, pharmaceutical compositions comprising said compounds, and methods for using said compounds for the treatment of diseases.

14 Claims, No Drawings

(56) References Cited

FOREIGN PATENT DOCUMENTS

| | | |
|---|---|---|
| CN | 108690016 A | 10/2018 |
| CN | 110117285 A | 8/2019 |
| CN | 110139865 A | 8/2019 |
| EP | 2112150 B1 | 10/2013 |
| EP | 2657233 A1 | 10/2013 |
| EP | 3023101 A1 | 5/2016 |
| EP | 3279202 A1 | 2/2018 |
| EP | 3498706 A1 | 6/2019 |
| FR | 2860431 A1 | 4/2005 |
| WO | WO-9827094 A1 | 6/1998 |
| WO | WO-0018733 A1 | 4/2000 |
| WO | WO-0018735 A1 | 4/2000 |
| WO | WO-03037894 A1 | 5/2003 |
| WO | WO-03037895 A1 | 5/2003 |
| WO | WO-2004005293 A2 | 1/2004 |
| WO | WO-2005009479 A1 | 2/2005 |
| WO | WO-2005051304 A2 | 6/2005 |
| WO | WO-2005087765 A1 | 9/2005 |
| WO | WO-2005097140 A2 | 10/2005 |
| WO | WO-2005097800 A1 | 10/2005 |
| WO | WO-2006023630 A2 | 3/2006 |
| WO | WO-2006071958 A1 | 7/2006 |
| WO | WO-2007024814 A1 | 3/2007 |
| WO | WO-2007038314 A2 | 4/2007 |
| WO | WO-2007064931 A2 | 6/2007 |
| WO | WO-2007087283 A2 | 8/2007 |
| WO | WO-2007120760 A2 | 10/2007 |
| WO | WO-2007128460 A1 | 11/2007 |
| WO | WO-2007139795 A1 | 12/2007 |
| WO | WO-2007139816 A2 | 12/2007 |
| WO | WO-2008006583 A1 | 1/2008 |
| WO | WO-2008012010 A1 | 1/2008 |
| WO | WO-2009030725 A2 | 3/2009 |
| WO | WO-2009087225 A2 | 7/2009 |
| WO | WO-2009092764 A1 | 7/2009 |
| WO | WO-2009158719 A2 | 12/2009 |
| WO | WO-2010135014 A1 | 11/2010 |
| WO | WO-2011029043 A1 | 3/2011 |
| WO | WO-2011094890 A1 | 8/2011 |
| WO | WO-2011097300 A1 | 8/2011 |
| WO | WO-2011117381 A1 | 9/2011 |
| WO | WO-2011117382 A1 | 9/2011 |
| WO | WO-2011119858 A1 | 9/2011 |
| WO | WO-2011119860 A1 | 9/2011 |
| WO | WO-2011119870 A1 | 9/2011 |
| WO | WO-2011146401 A1 | 11/2011 |
| WO | WO-2011162515 A2 | 12/2011 |
| WO | WO-2012010704 A1 | 1/2012 |
| WO | WO-2012068440 A1 | 5/2012 |
| WO | WO-2012068450 A1 | 5/2012 |
| WO | WO-2012085127 A1 | 6/2012 |
| WO | WO-2012116135 A2 | 8/2012 |
| WO | WO-2012135581 A1 | 10/2012 |
| WO | WO-2012154608 A1 | 11/2012 |
| WO | WO-2013025484 A1 | 2/2013 |
| WO | WO-2013025498 A1 | 2/2013 |
| WO | WO-2013056915 A1 | 4/2013 |
| WO | WO-2013072502 A1 | 5/2013 |
| WO | WO-2013078440 A2 | 5/2013 |
| WO | WO-2013104605 A2 | 7/2013 |
| WO | WO-2013108809 A1 | 7/2013 |
| WO | WO-2013154712 A1 | 10/2013 |
| WO | WO-2013154878 A1 | 10/2013 |
| WO | WO-2013170113 A1 | 11/2013 |
| WO | WO-2013170115 A1 | 11/2013 |
| WO | WO-2013170118 A1 | 11/2013 |
| WO | WO-2014045305 A1 | 3/2014 |
| WO | WO-2014143241 A1 | 9/2014 |
| WO | WO-2014145493 A1 | 9/2014 |
| WO | WO-2014151147 A1 | 9/2014 |
| WO | WO-2014158943 A1 | 10/2014 |
| WO | WO-2014190096 A1 | 11/2014 |
| WO | WO-2014190097 A1 | 11/2014 |
| WO | WO-2014202638 A1 | 12/2014 |
| WO | WO-2014206343 A1 | 12/2014 |
| WO | WO-2014210456 A1 | 12/2014 |
| WO | WO-2015008839 A1 | 1/2015 |
| WO | WO-2015008844 A1 | 1/2015 |
| WO | WO-2015011284 A2 | 1/2015 |
| WO | WO-2015017812 A1 | 2/2015 |
| WO | WO-2015031608 A1 | 3/2015 |
| WO | WO-2015039613 A1 | 3/2015 |
| WO | WO-2015073833 A1 | 5/2015 |
| WO | WO-2015083008 A1 | 6/2015 |
| WO | WO-2015134357 A1 | 9/2015 |
| WO | WO-2016010926 A1 | 1/2016 |
| WO | WO-2016040449 A1 | 3/2016 |
| WO | WO-2016044445 A2 | 3/2016 |
| WO | WO-2016055028 A1 | 4/2016 |
| WO | WO-2016112298 A1 | 7/2016 |
| WO | WO-2016159327 A1 | 10/2016 |
| WO | WO-2016195776 A1 | 12/2016 |
| WO | WO-2016197027 A1 | 12/2016 |
| WO | WO-2017058915 A1 | 4/2017 |
| WO | WO-2018028438 A1 | 2/2018 |
| WO | WO-2018054365 A1 | 3/2018 |
| WO | WO-2018068017 A1 | 4/2018 |
| WO | WO-2018121650 A1 | 7/2018 |
| WO | WO-2018140512 A1 | 8/2018 |
| WO | WO-2018140513 A1 | 8/2018 |
| WO | WO-2018140598 A1 | 8/2018 |
| WO | WO-2018140600 A1 | 8/2018 |
| WO | WO-2018170225 A1 | 9/2018 |
| WO | WO-2018177296 A1 | 10/2018 |
| WO | WO-2018177297 A1 | 10/2018 |
| WO | WO-2018226976 A1 | 12/2018 |
| WO | WO-2019023448 A1 | 1/2019 |
| WO | WO-2019034076 A1 | 2/2019 |
| WO | WO-2019034686 A1 | 2/2019 |
| WO | WO-2019195278 A1 | 10/2019 |
| WO | WO-2019226991 A1 | 11/2019 |
| WO | WO-2019231270 A1 | 12/2019 |
| WO | WO-2019238067 A1 | 12/2019 |
| WO | WO-2020028706 A1 | 2/2020 |
| WO | WO-2020035465 A1 | 2/2020 |
| WO | WO-2020236524 A1 | 11/2020 |
| WO | WO-2021072319 A1 | 4/2021 |
| WO | WO-2021076602 A1 | 4/2021 |
| WO | WO-2021247969 A1 | 12/2021 |
| WO | WO-2021247971 A1 | 12/2021 |
| WO | WO-2023107870 A1 | 6/2023 |
| WO | WO-2023107979 A1 | 6/2023 |
| WO | WO-2023107980 A1 | 6/2023 |

OTHER PUBLICATIONS

Berge et al. Pharmaceutical Salts. Journal of Pharmaceutical Sciences 66(1):1-19 (Jan. 1977).
Chemical Abstract search dated Jun. 4, 2020.
Evans. Synthesis of radiolabeled compounds. J Radioanal Chem 64(1-2):9-32 (1981).
Garcia-Closas et al. Heterogeneity of breast cancer associations with five susceptibility loci by clinical and pathological characteristics. PLoS Genet. 4(4):e1000054 (2008).
Haugsten et al. Roles of fibroblast growth factor receptors in carcinogenesis. Mol Cancer Res. 8(11):1439-1452 (2010).
Kabalka et al. The Synthesis of Radiolabeled Compounds via Organometallic Intermediates. Tetrahedron 45(21):6601-6621 (1989).
Katoh et al. FGFR inhibitors: Effects on cancer cells, tumor microenvironment and whole-body homeostasis (Review). Int J Mol Med. 38(1):3-15 (2016).
PCT/US2020/032939 International Invitation to Pay Additional Fees dated Jul. 7, 2020.
PCT/US2020/032939 International Search Report and Written Opinion dated Aug. 31, 2020.
PCT/US2021/035854 International Search Report and Written Opinion dated Sep. 8, 2021.
PCT/US2021/035865 International Search Report and Written Opinion dated Sep. 8, 2021.
Porta et al. FGFR a promising druggable target in cancer: Molecular biology and new drugs. Crit Rev Oncol Hematol 113:256-67 (2017).

(56) References Cited

OTHER PUBLICATIONS

Thisse et al. Functions and regulations of fibroblast growth factor signaling during embryonic development. Dev Biol. 287(2):390-402 (2005).
Tiong et al. Functional roles of fibroblast growth factor receptors (FGFRs) signaling in human cancers. Apoptosis 18(12):1447-68 (2013).
Trueb. Biology of FGFRL1, the fifth fibroblast growth factor receptor. Cell Mol Life Sci. 68(6):951-964 (2011).
U.S. Appl. No. 17/339,123 Office Action dated Sep. 9, 2021.
Wesche et al. Fibroblast growth factors and their receptors in cancer. Biochem J. 437(2):199-213 (2011).
Co-Pending U.S. Appl. No. 17/605,127, inventor Kaldor; Stephen W., filed Oct. 20, 2021.
Co-Pending U.S. Appl. No. 18/000,616, inventor Kaldor; Stephen W., filed Jul. 28, 2023.
Co-pending U.S. Appl. No. 18/717,345, inventors Franovic; Aleksandra et al., filed on Jun. 6, 2024.
Co-pending U.S. Appl. No. 18/717,390, inventors Kaldor; Stephen W. et al., filed on Jun. 6, 2024.
PCT/US2022/081059 International Search Report and Written Opinion dated Mar. 6, 2023.
PCT/US2022/081060 International Search Report and Written Opinion dated Mar. 30, 2023.
Pubchem CID 162381323. Create date: Jan. 3, 2022.
U.S. Appl. No. 17/605,127 Office Action dated Aug. 1, 2024.

\* cited by examiner

INHIBITORS OF FIBROBLAST GROWTH FACTOR RECEPTOR KINASES

CROSS-REFERENCE TO RELATED APPLICATION

This is a continuation application of U.S. patent application Ser. No. 17/339,123, filed on Jun. 4, 2021, and claims benefit of U.S. Patent Application No. 63/106,812, filed on Oct. 28, 2020, and U.S. Patent Application No. 63/035,155, filed on Jun. 5, 2020, all of which are hereby incorporated by reference in their entireties.

BACKGROUND

Fibroblast growth factor receptors (FGFRs) are a subfamily of receptor tyrosine kinases (RTKs) that bind to members of the fibroblast growth factor family of proteins. Deregulation of the fibroblast growth factor/FGF receptor network occurs frequently in tumors. Accordingly, therapies that target aberrant FGFR kinase activity are desired for use in the treatment of cancer and other disorders.

BRIEF SUMMARY OF THE INVENTION

Provided herein are inhibitors of fibroblast growth factor receptor (FGFR) kinases, pharmaceutical compositions comprising said compounds, and methods for using said compounds for the treatment of diseases.

One embodiment provides a compound, or pharmaceutically acceptable salt or solvate thereof, having the structure of Formula (I):

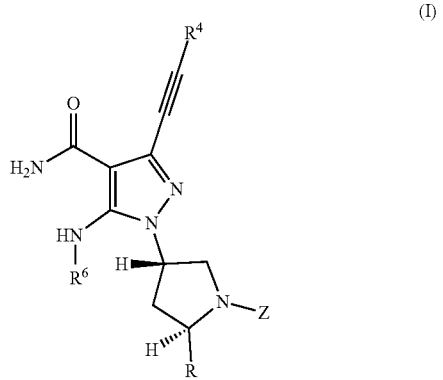

(I)

wherein,

Z is selected from a group having the structure:

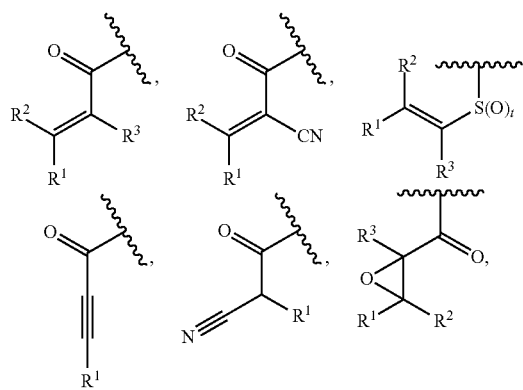

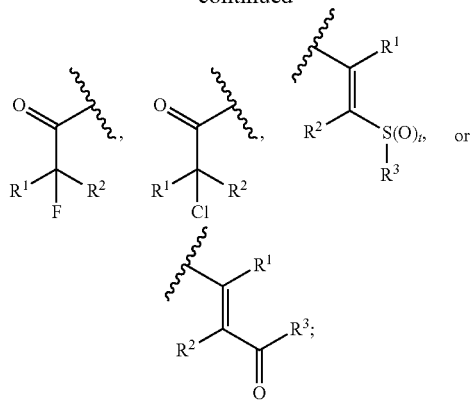

t is 1 or 2;

$R^1$, $R^2$, and $R^3$ are each independently selected from hydrogen, fluoro, optionally substituted C1-C4 alkyl, or optional substituted heterocyclylalkyl;

$R^4$ is an optionally substituted nitrogen-containing 9 or 10-atom heteroaryl;

R is selected from hydrogen, optionally substituted C1-C6 alkyl, optionally substituted C3-C7 carbocyclyl, optionally substituted C3-C7 carbocyclylalkyl, optionally substituted C3-C7 heterocyclyl, optionally substituted C3-C7 heterocyclylalkyl, optionally substituted C2-C7 alkenyl, —$CO_2R^5$, —$CONHR^5$, or —$CON(R^5)_2$;

each $R^5$ is independently selected from optionally substituted C1-C6 alkyl, optionally substituted C3-C7 carbocyclyl, optionally substituted C3-C7 carbocyclylalkyl, optionally substituted C3-C7 heterocyclyl, or optionally substituted C3-C7 heterocyclylalkyl; and $R^6$ is an optionally substituted alkyl, optionally substituted carbocyclylalkyl, or optionally substituted heterocyclylalkyl.

One embodiment provides a pharmaceutical composition comprising a compound of Formula (I), or pharmaceutically acceptable salt or solvate thereof, and at least one pharmaceutically acceptable excipient.

One embodiment provides a method of treating a disease or disorder in a patient in need thereof comprising administering to the patient a compound of Formula (I), or pharmaceutically acceptable salt or solvate thereof. Another embodiment provides the method wherein the disease or disorder is cancer.

INCORPORATION BY REFERENCE

All publications, patents, and patent applications mentioned in this specification are herein incorporated by reference for the specific purposes identified herein.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

Definitions

As used in the specification and appended claims, unless specified to the contrary, the following terms have the meaning indicated below.

"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—NH$_2$ radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkenylene" or "alkenylene chain" refers to a straight or branched divalent hydrocarbon chain linking the rest of the molecule to a radical group, consisting solely of carbon and hydrogen, containing at least one carbon-carbon double bond, and having from two to twelve carbon atoms. The alkenylene chain is attached to the rest of the molecule through a single bond and to the radical group through a single bond. In certain embodiments, an alkenylene comprises two to eight carbon atoms (e.g., $C_2$-$C_8$ alkenylene). In other embodiments, an alkenylene comprises two to five carbon atoms (e.g., $C_2$-$C_5$ alkenylene). In other embodiments, an alkenylene comprises two to four carbon atoms (e.g., $C_2$-$C_4$ alkenylene). In other embodiments, an alkenylene comprises two to three carbon atoms (e.g., $C_2$-$C_3$ alkenylene). In other embodiments, an alkenylene comprises two carbon atoms (e.g., $C_2$ alkenylene). In other embodiments, an alkenylene comprises five to eight carbon atoms (e.g., $C_5$-$C_8$ alkenylene). In other embodiments, an alkenylene comprises three to five carbon atoms (e.g., $C_3$-$C_5$ alkenylene). Unless stated otherwise specifically in the specification, an alkenylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atoms (e.g., $C_2$ alkynylene). In other embodiments, an alkynylene comprises five to eight carbon atoms (e.g., $C_5$-$C_8$ alkynylene). In other embodiments, an alkynylene comprises three to five carbon atoms (e.g., $C_3$-$C_5$ alkynylene). Unless stated otherwise specifically in the specification, an alkynylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—$C(O)R^a$, —$R^b$—C(O)$OR^a$, —$R^b$—C(O)$N(R^a)_2$, —$R^b$—O—$R^c$—C(O)$N(R^a)_2$, —$R^b$—$N(R^a)C(O)OR^a$, —$R^b$—$N(R^a)C(O)R^a$, —$R^b$—N($R^a$)S(O)$_tR^a$ (where t is 1 or 2), —$R^b$—S(O)$R^a$ (where t is 1 or 2), —$R^b$—S(O)$OR^a$ (where t is 1 or 2) and —$R^b$—S(O)$_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—$C(O)R^a$, —$R^b$—$C(O)OR^a$, —$R^b$—C(O)$N(R^a)_2$, —$R^b$—O—$R^c$—C(O)$N(R^a)_2$, —$R^b$—$N(R^a)C$(O)$OR^a$, —$R^b$—$N(R^a)C(O)R^a$, —$R^b$—N($R^a$)S(O)$_tR^a$ (where t is 1 or 2), —$R^b$—S(O)$R^a$ (where t is 1 or 2), —$R^b$—S(O)$OR^a$ (where t is 1 or 2) and —$R^b$—S(O)$_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Carbocyclylalkynyl" refers to a radical of the formula —$R^c$-carbocyclyl where $R^c$ is an alkynylene chain as defined above. The alkynylene chain and the carbocyclyl radical is optionally substituted as defined above.

"Carbocyclylalkoxy" refers to a radical bonded through an oxygen atom of the formula —O—$R^c$-carbocyclyl where $R^c$ is an alkylene chain as defined above. The alkylene chain and the carbocyclyl radical is optionally substituted as defined above.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

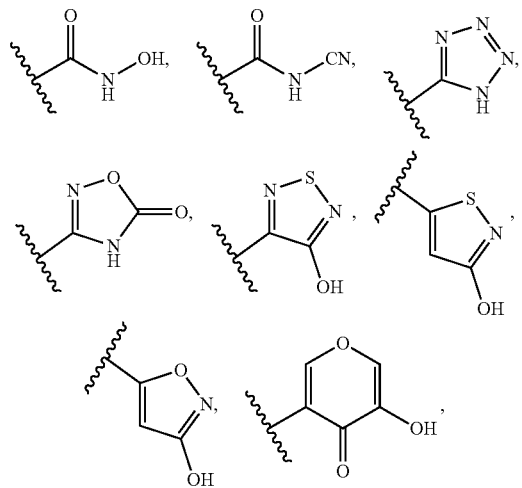

and the like.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$R^a$ (where t is 1 or 2), —$R^b$—S(O)$OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N(R^a)_2$, —$R^b$—N(R^a)_2$, —$R^b$—C(O)R^a$, —$R^b$—C(O)OR^a$, —$R^b$—C(O)N(R^a)_2$, —$R^b$—O—$R^c$—C(O)N(R^a)_2$, —$R^b$—N(R^a)C(O)OR^a$, —$R^b$—N(R^a)C(O)R^a$, —$R^b$—N(R^a)S(O)_tR^a$ (where t is 1 or 2), —$R^b$—S(O)R^a$ (where t is 1 or 2), —$R^b$—S(O)OR^a$ (where t is 1 or 2) and —$R^b$—S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

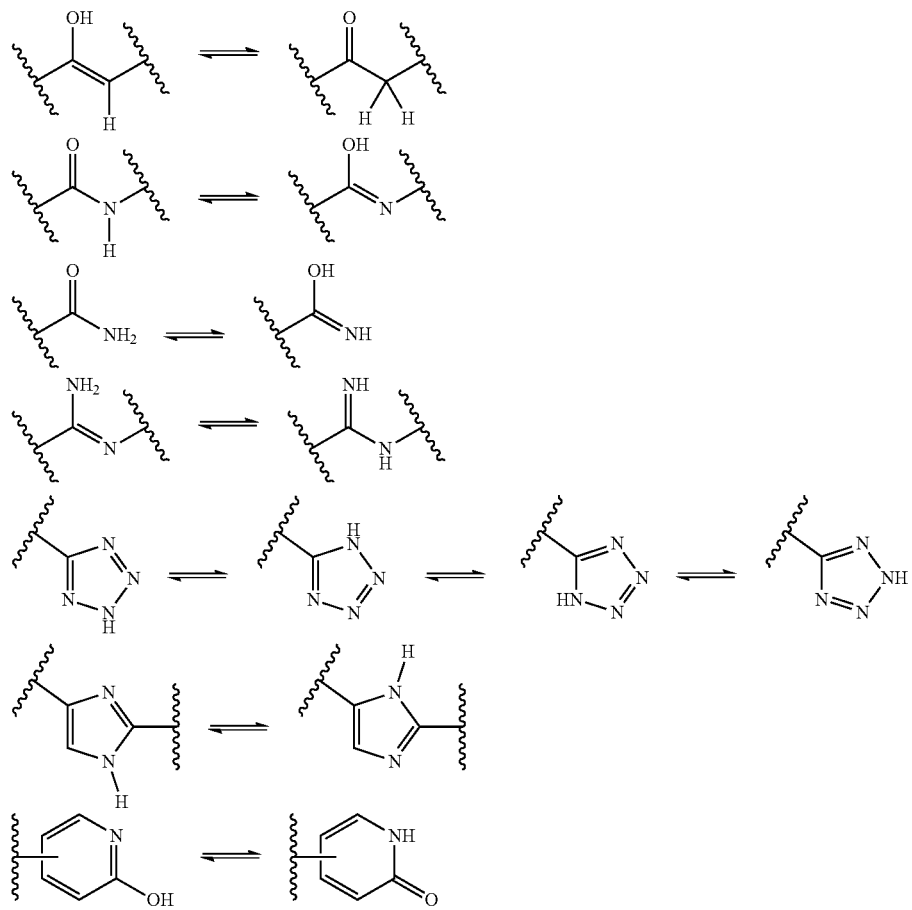

The compounds disclosed herein, in some embodiments, are used in different enriched isotopic forms, e.g., enriched in the content of $^2H$, $^3H$, $^{11}C$, $^{13}C$ and/or $^{14}C$. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2H$), tritium ($^3H$), iodine-125 ($^{125}I$) or carbon-14 ($^{14}C$). Isotopic substitution with $^2H$, $^{11}C$, $^{13}C$, $^{14}C$, $^{15}C$, $^{12}N$, $^{13}N$, $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, $^{125}I$ are all contemplated. In some embodiments, isotopic substitution with $^{18}$F is contemplated. All isotopic variations of the compounds of the present invention, whether radioactive or not, are encompassed within the scope of the present invention.

In certain embodiments, the compounds disclosed herein have some or all of the $^{1}$H atoms replaced with $^{2}$H atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Deuterium-transfer reagents suitable for use in nucleophilic substitution reactions, such as iodomethane-d$_3$ (CD$_3$I), are readily available and may be employed to transfer a deuterium-substituted carbon atom under nucleophilic substitution reaction conditions to the reaction substrate. The use of CD$_3$I is illustrated, by way of example only, in the reaction schemes below.

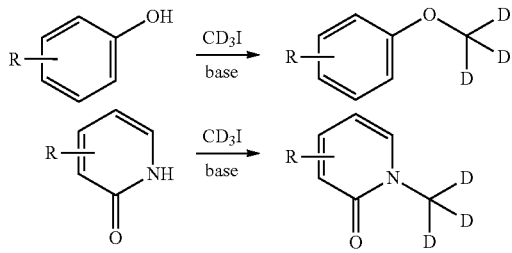

Deuterium-transfer reagents, such as lithium aluminum deuteride (LiAlD$_4$), are employed to transfer deuterium under reducing conditions to the reaction substrate. The use of LiAlD$_4$ is illustrated, by way of example only, in the reaction schemes below.

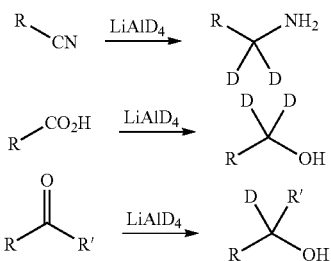

Deuterium gas and palladium catalyst are employed to reduce unsaturated carbon-carbon linkages and to perform a reductive substitution of aryl carbon-halogen bonds as illustrated, by way of example only, in the reaction schemes below.

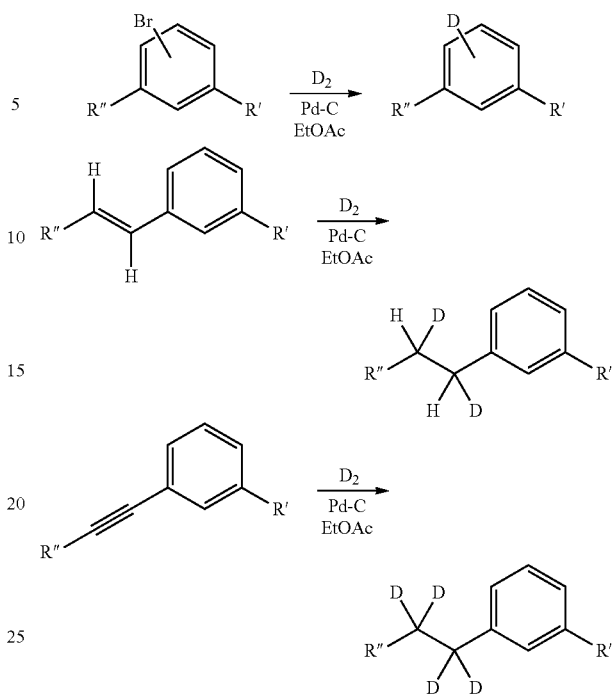

In one embodiment, the compounds disclosed herein contain one deuterium atom. In another embodiment, the compounds disclosed herein contain two deuterium atoms. In another embodiment, the compounds disclosed herein contain three deuterium atoms. In another embodiment, the compounds disclosed herein contain four deuterium atoms. In another embodiment, the compounds disclosed herein contain five deuterium atoms. In another embodiment, the compounds disclosed herein contain six deuterium atoms. In another embodiment, the compounds disclosed herein contain more than six deuterium atoms. In another embodiment, the compound disclosed herein is fully substituted with deuterium atoms and contains no non-exchangeable $^{1}$H hydrogen atoms. In one embodiment, the level of deuterium incorporation is determined by synthetic methods in which a deuterated synthetic building block is used as a starting material.

"Pharmaceutically acceptable salt" includes both acid and base addition salts. A pharmaceutically acceptable salt of any one of the inhibitor of fibroblast growth factor receptors (FGFRs) compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Pharmaceutically acceptable solvate" refers to a composition of matter that is the solvent addition form. In some embodiments, solvates contain either stoichiometric or non-stoichiometric amounts of a solvent, and are formed during the process of making with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. The compounds provided herein optionally exist in either unsolvated as well as solvated forms. The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

Fibroblast Growth Factor Receptor (FGFR)

Fibroblast growth factor receptors (FGFRs) are a subfamily of receptor tyrosine kinases (RTKs) that bind to members of the fibroblast growth factor family of proteins. FGFR genes generally contain 18 exons, possess similar exon-intron organization, and are randomly dispersed throughout the genome with no apparent linkages to FGF gene locations. FGFRs are differentially expressed in a tissue-specific manner throughout development and into adulthood and comprise an extracellular ligand-binding domain, a single-transmembrane domain, and a split intracellular kinase domain. The extracellular region contains two to three immunoglobulin (Ig)-like domains that are involved in FGF binding. These Ig-like domains regulate both ligand affinity and ligand specificity. The intracellular region has the functional domain responsible for FGFR tyrosine kinase activity, as well as additional sites that play a role in protein binding and phosphorylation or autophosphorylation of the receptor molecule. Fibroblast grouth factor receptor pharmacology has been reviewed in the scientific literature by Porta et al. (Critical Reviews in Oncology/Hematology 113 (2017) 256-67) and Babina and Turner (Nature Review-Cancer 2017 doi: 10.1038/nrc.2017.8).

The FGFR family comprises of four family members—FGFR1, FGFR2, FGFR3, and FGFR4, but the four members are capable of producing multiple receptor isoforms through alternative splicing of primary transcripts. A closely-related receptor which lacks the FGF signaling tyrosine kinase domain, FGFR5, (also known as FGFRL1) was recently discovered on the basis of interaction with FGFR-binding ligands, known as fibroblast growth factors (FGFs) (Trueb B. Biology of FGFRL1, the fifth fibroblast growth factor receptor. Cell Mol Life Sci. 2011; 68(6):951-964). Collectively, FGFR signaling is associated with the activation of multiple cellular cascades and responses such as cell growth, proliferation, differentiation, and survival (Thisse B et al. Functions and regulations of fibroblast growth factor signaling during embryonic development. Dev Biol. 2005; 287(2):390-402; Wesche J et al. Fibroblast growth factors and their receptors in cancer. Biochem J. 2011; 437(2):199-213; Haugsten E M et al. Roles of fibroblast growth factor receptors in carcinogenesis. Mol Cancer Res. 2010; 8(11): 1439-1452).

Numerous human pathological conditions are associated with the deregulation of FGFR signaling. Aberrant FGFR signaling is largely attributed to several underlying mechanisms involving gene amplification, gain-of-function coding mutation, gene fusions, single nucleotide polymorphism (SNP), ligand availability and impaired termination program in FGF-mediated signaling (Tiong K H et al. Functional roles of fibroblast growth factor receptors (FGFRs) signaling in human cancers. Apoptosis. 2013; 18(12):1447-68). In addition, a further layer of complexity is added by the fact that FGFRs are subjected to alternative splicing, giving rise to multiple isoforms which may promote or repress tumorigenesis, under different circumstances.

FGFR Fusions

FGFR fusions in human cancers are classified into type 1 fusions caused by chromosomal translocations in hematological malignancies, and type 2 fusions caused by chromosomal rearrangements in solid tumors (FGFR inhibitors: Effects on cancer cells, tumor microenvironment and whole-body homeostasis (Review). Int J Mol Med. 2016; 38(1):3-15). Both types of FGFR fusion proteins are endowed with oncogenic potential through the acquisition of protein-protein-interaction modules from fusion partners for ligand-independent dimerization and/or recruitment of aberrant substrates. Human FGFR fusion proteins generally consist of two main segments—the anterior being a dimerized domain from a partnering gene and tyrosine kinase domain at the posterior (Garcia-Closas M et al. Heterogeneity of breast cancer associations with five susceptibility loci by clinical and pathological characteristics. PLoS Genet. 2008; 4(4):e1000054). Unlike wild type receptors, mutant FGFRs are expressed intracellularly and retained in the cytosol, thus they escape the typical receptor degradation processes, further prolonging the activation signal.

Deregulation of the fibroblast growth factor (FGF)/FGF receptor (FGFR) network occurs frequently in tumors, resulting in the development of FGF/FGFR-targeting therapies as the focus of several basic, preclinical, and clinical studies.

Heteroaromatic FGFR Inhibitory Compounds

In one aspect, provided herein is a heteroaromatic FGFR inhibitory compound.

One embodiment provides a compound, or pharmaceutically acceptable salt or solvate thereof, having the structure of Formula (I):

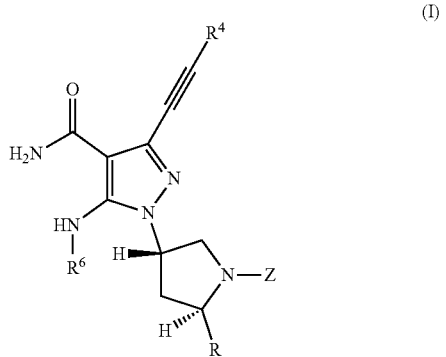

(I)

wherein,
Z is selected from a group having the structure:

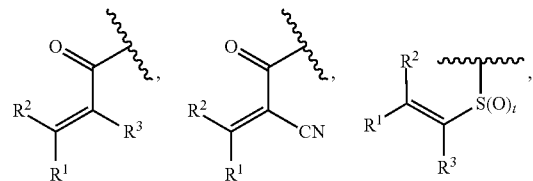

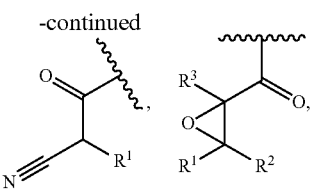

-continued

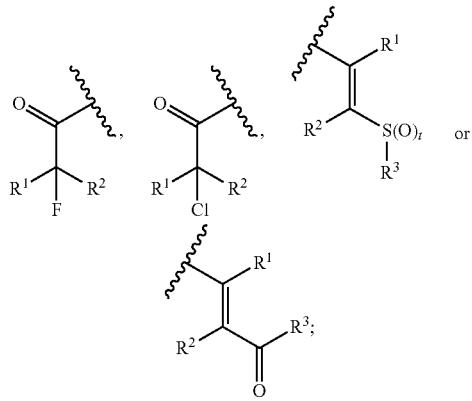

$t$ is 1 or 2;

$R^1$, $R^2$, and $R^3$ are each independently selected from hydrogen, fluoro, optionally substituted $C_1$-$C_4$ alkyl, or optional substituted heterocyclylalkyl;

$R^4$ is an optionally substituted nitrogen-containing 9 or 10-atom heteroaryl;

R is selected from hydrogen, optionally substituted $C_1$-$C_6$ alkyl, optionally substituted $C_3$-$C_7$ carbocyclyl, optionally substituted $C_3$-$C_7$ carbocyclylalkyl, optionally substituted $C_3$-$C_7$ heterocyclyl, optionally substituted $C_3$-$C_7$ heterocyclylalkyl, optionally substituted $C_2$-$C_7$ alkenyl, —$CO_2R^5$, —$CONHR^5$, or —$CON(R^5)_2$;

each $R^5$ is independently selected from optionally substituted $C_1$-$C_6$ alkyl, optionally substituted $C_3$-$C_7$ carbocyclyl, optionally substituted $C_3$-$C_7$ carbocyclylalkyl, optionally substituted $C_3$-$C_7$ heterocyclyl, or optionally substituted $C_3$-$C_7$ heterocyclylalkyl; and $R^6$ is an optionally substituted alkyl, optionally substituted carbocyclylalkyl, or optionally substituted heterocyclylalkyl.

Another embodiment provides the compound of Formula (I), or a pharmaceutically acceptable salt or solvate thereof, wherein Z is

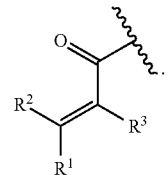

Another embodiment provides the compound, or pharmaceutically acceptable salt or solvate thereof, wherein $R^2$ is hydrogen. Another embodiment provides the compound, or pharmaceutically acceptable salt or solvate thereof, wherein $R^3$ is hydrogen or fluoro. Another embodiment provides the compound, or pharmaceutically acceptable salt or solvate thereof, wherein $R^2$ and $R^3$ are hydrogen. Another embodiment provides the compound, or pharmaceutically acceptable salt or solvate thereof, wherein $R^1$ is hydrogen. Another embodiment provides the compound, or pharmaceutically acceptable salt or solvate thereof, wherein $R^1$ is optionally substituted $C_1$-$C_4$ alkyl. Another embodiment provides the compound, or pharmaceutically acceptable salt or solvate thereof, wherein $R^1$ is optionally substituted C1-C2 alkyl. Another embodiment provides the compound, or pharmaceutically acceptable salt or solvate thereof, wherein $R^1$ is optionally substituted C1 alkyl. Another embodiment provides the compound, or pharmaceutically acceptable salt or solvate thereof, wherein the optionally substituted alkyl is substituted with an optionally substituted amino group. Another embodiment provides the compound, or pharmaceutically acceptable salt or solvate thereof, wherein the optionally substituted amino group is a dimethylamino.

Another embodiment provides the compound of Formula (I), or a pharmaceutically acceptable salt or solvate thereof, wherein $R^4$ is selected from an optionally substituted nitrogen-containing 9 or 10-atom heteroaryl is selected from optionally substituted benzimidazole, optionally substituted 1H-indazole, optionally substituted 2H-indazole, optionally substituted benzotriazole, optionally substituted benzoxazole, optionally substituted imidazo[4,5-c]pyridine, or optionally substituted imidazo[4,5-b]pyridine. Another embodiment provides the compound of Formula (I), or a pharmaceutically acceptable salt or solvate thereof, wherein $R^4$ is selected from an optionally substituted nitrogen-containing 9 or 10-atom heteroaryl is selected from quinoline, quinoxaline, pyrazolo[1,5-a]pyrimidine, imidazo[1,2-a]pyridine, pyrazolo[1,5-a]pyridine, imidazo[1,2-a]pyrimidine, imidazo[1,2-b]pyridazine, or pyrazolo[1,5-a]pyridine. Another embodiment provides the compound, or a pharmaceutically acceptable salt or solvate thereof, wherein $R^4$ is an optionally substituted benzimidazole. Another embodiment provides the compound, or a pharmaceutically acceptable salt or solvate thereof, wherein $R^4$ is an optionally substituted 1H-indazole. Another embodiment provides the compound, or a pharmaceutically acceptable salt or solvate thereof, wherein $R^4$ is an optionally substituted 2H-indazole. Another embodiment provides the compound, or a pharmaceutically acceptable salt or solvate thereof, wherein $R^4$ is an optionally substituted benzoxazole, optionally substituted imidazo[4,5-c]pyridine, or optionally substituted imidazo[4,5-b]pyridine. Another embodiment provides the compound, or a pharmaceutically acceptable salt or solvate thereof, wherein optionally substituted nitrogen-containing 9 or 10-atom heteroaryl is optionally substituted with alkyl, cycloalkyl, or halogen. Another embodiment provides the compound, or a pharmaceutically acceptable salt or solvate thereof, wherein the optionally substituted benzimidazole is optionally substituted with alkyl, cycloalkyl, or halogen. Another embodiment provides the compound, or a pharmaceutically acceptable salt or solvate thereof, wherein the optionally substituted 1H-indazole is optionally substituted with alkyl, cycloalkyl, or halogen. Another embodiment provides the compound, or a pharmaceutically acceptable salt or solvate thereof, wherein the optionally substituted 2H-indazole is optionally substituted with alkyl, cycloalkyl, or halogen.

Another embodiment provides the compound of Formula (I), or a pharmaceutically acceptable salt or solvate thereof, wherein R is hydrogen. Another embodiment provides the compound, or a pharmaceutically acceptable salt or solvate thereof, wherein R is optionally substituted C1-C6 alkyl. Another embodiment provides the compound, or a pharmaceutically acceptable salt or solvate thereof, wherein R is optionally substituted C3-C7 carbocyclyl. Another embodiment provides the compound, or a pharmaceutically acceptable salt or solvate thereof, wherein R is optionally substituted C3-C7 carbocyclylalkyl. Another embodiment provides the compound, or a pharmaceutically acceptable salt or solvate thereof, wherein R is optionally substituted C3-C7 heterocyclyl. Another embodiment provides the compound, or a pharmaceutically acceptable salt or solvate thereof, wherein R is optionally substituted C3-C7 heterocyclylalkyl. Another embodiment provides the compound, or a pharmaceutically acceptable salt or solvate thereof, wherein R is —$CO_2R^5$. Another embodiment provides the compound, or a pharmaceutically acceptable salt or solvate thereof, wherein R is —$CONHR^5$ or —$CON(R^5)_2$. Another embodiment provides the compound, or a pharmaceutically acceptable salt or solvate thereof, wherein the optionally substituted C1-C6 alkyl is a C1-C3 alkyl substituted with a C1-C3 alkoxy.

Another embodiment provides the compound of Formula (I), or a pharmaceutically acceptable salt or solvate thereof, wherein $R^6$ is an optionally substituted alkyl. Another embodiment provides the compound, or a pharmaceutically acceptable salt or solvate thereof, wherein $R^6$ is an optionally substituted C1-C4 alkyl. Another embodiment provides the compound, or a pharmaceutically acceptable salt or solvate thereof, wherein $R^6$ is an optionally substituted C1-C3 alkyl. Another embodiment provides the compound, or a pharmaceutically acceptable salt or solvate thereof, wherein $R^6$ is an optionally substituted C1-C2 alkyl. Another embodiment provides the compound, or a pharmaceutically acceptable salt or solvate thereof, wherein $R^6$ is an optionally substituted C1 alkyl. Another embodiment provides the compound, or a pharmaceutically acceptable salt or solvate thereof, wherein $R^6$ is $CH_3$.

Another embodiment provides the compound of Formula (I), or a pharmaceutically acceptable salt or solvate thereof, wherein $R^6$ is an optionally substituted carbocyclylalkyl. Another embodiment provides the compound, or a pharmaceutically acceptable salt or solvate thereof, wherein $R^6$ is optionally substituted carbocyclylmethyl. Another embodiment provides the compound, or a pharmaceutically acceptable salt or solvate thereof, wherein $R^6$ is optionally substituted ($C_3$-$C_6$carbocyclyl)methyl. Another embodiment provides the compound, or a pharmaceutically acceptable salt or solvate thereof, wherein $R^6$ is optionally substituted cyclopropylmethyl. Another embodiment provides the compound of Formula (I), or a pharmaceutically acceptable salt or solvate thereof, wherein $R^6$ is an optionally substituted heterocyclylalkyl. Another embodiment provides the compound, or a pharmaceutically acceptable salt or solvate thereof, wherein $R^6$ is optionally substituted heterocyclylethyl. Another embodiment provides the compound, or a pharmaceutically acceptable salt or solvate thereof, wherein $R^6$ is optionally substituted heterocyclylethyl and the heterocyclyl is a piperidinyl, pyrrolidinyl, morpholinyl, or piperazinyl.

Another embodiment provides the compound of Formula (I), or a pharmaceutically acceptable salt or solvate thereof, wherein $R^4$ is an optionally substituted benzimidazole further substituted with a cycloalkyl group, and at least one halogen.

Another embodiment provides the compound of Formula (I), or a pharmaceutically acceptable salt or solvate thereof, wherein $R^4$ is an optionally substituted benzimidazole further substituted with a cycloalkyl group, and at least one halogen; R is a —$CH_2OCH_3$ group; and $R^6$ is methyl.

Another embodiment provides the compound of Formula (I), or a pharmaceutically acceptable salt or solvate thereof, wherein R⁴ is an optionally substituted benzimidazole further substituted with a cycloalkyl group, and at least one halogen; R is a hydrogen; and R⁶ is methyl.

One embodiment provides a compound, or pharmaceutically acceptable salt or solvate thereof, having the structure of Formula (II):

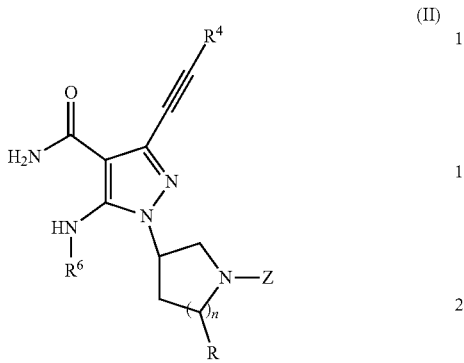

(II)

wherein,
n is 0 or 1;
Z is selected from a group having the structure:

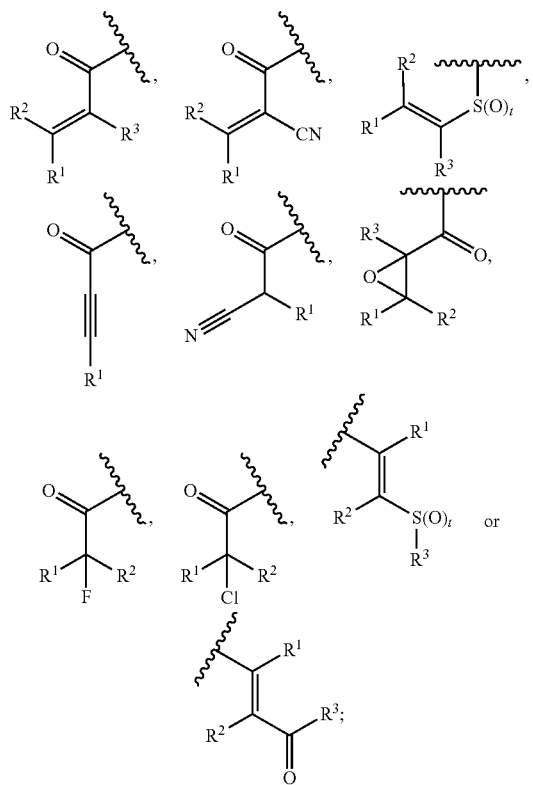

t is 1 or 2;
R¹, R², and R³ are each independently selected from hydrogen, fluoro, optionally substituted C1-C4 alkyl, or optional substituted heterocyclylalkyl;
R⁴ is an optionally substituted nitrogen-containing 9 or 10-atom heteroaryl;
R is selected from hydrogen, optionally substituted C1-C6 alkyl, optionally substituted C3-C7 carbocyclyl, optionally substituted C3-C7 carbocyclylalkyl, optionally substituted C3-C7 heterocyclyl, optionally substituted C3-C7 heterocyclylalkyl, optionally substituted C2-C7 alkenyl, —CO₂R⁵, —CONHR⁵, or —CON(R⁵)₂;
each R⁵ is independently selected from optionally substituted C1-C6 alkyl, optionally substituted C3-C7 carbocyclyl, optionally substituted C3-C7 carbocyclylalkyl, optionally substituted C3-C7 heterocyclyl, or optionally substituted C3-C7 heterocyclylalkyl; and
R⁶ is hydrogen, optionally substituted alkyl, optionally substituted carbocyclyl, optionally substituted carbocyclylalkyl, or optionally substituted heterocyclylalkyl.

Another embodiment provides the compound of Formula (II), or a pharmaceutically acceptable salt or solvate thereof, wherein n is 0.

Another embodiment provides the compound of Formula (II), or a pharmaceutically acceptable salt or solvate thereof, wherein n is 1. Another embodiment provides the compound of Formula (II), or a pharmaceutically acceptable salt or solvate thereof, wherein n is 1 and the stereochemistry across the pyrrolidine ring is cis. Another embodiment provides the compound of Formula (II), or a pharmaceutically acceptable salt or solvate thereof, wherein n is 1 and the stereochemistry across the pyrrolidine ring is trans.

Another embodiment provides the compound of Formula (II), or a pharmaceutically acceptable salt or solvate thereof, wherein Z is

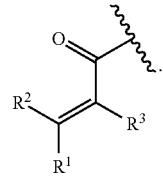

Another embodiment provides the compound, or pharmaceutically acceptable salt or solvate thereof, wherein R² is hydrogen. Another embodiment provides the compound, or pharmaceutically acceptable salt or solvate thereof, wherein R³ is hydrogen or fluoro. Another embodiment provides the compound, or pharmaceutically acceptable salt or solvate thereof, wherein R² and R³ are hydrogen. Another embodiment provides the compound, or pharmaceutically acceptable salt or solvate thereof, wherein R¹ is hydrogen. Another embodiment provides the compound, or pharmaceutically acceptable salt or solvate thereof, wherein R¹ is optionally substituted C1-C4 alkyl. Another embodiment provides the compound, or pharmaceutically acceptable salt or solvate thereof, wherein R¹ is optionally substituted C1-C2 alkyl. Another embodiment provides the compound, or pharmaceutically acceptable salt or solvate thereof, wherein R¹ is optionally substituted C1 alkyl. Another embodiment provides the compound, or pharmaceutically acceptable salt or solvate thereof, wherein the optionally substituted alkyl is substituted with an optionally substituted amino group. Another embodiment provides the compound, or pharmaceutically acceptable salt or solvate thereof, wherein the optionally substituted amino group is a dimethylamino.

Another embodiment provides the compound of Formula (II), or a pharmaceutically acceptable salt or solvate thereof, wherein R⁴ is selected from an optionally substituted nitrogen-containing 9 or 10-atom heteroaryl is selected from optionally substituted benzimidazole, optionally substituted 1H-indazole, optionally substituted 2H-indazole, optionally substituted benzotriazole, optionally substituted benzoxazole, optionally substituted imidazo[4,5-c]pyridine, or optionally substituted imidazo[4,5-b]pyridine. Another embodiment provides the compound of Formula (II), or a pharmaceutically acceptable salt or solvate thereof, wherein $R^4$ is selected from an optionally substituted nitrogen-containing 9 or 10-atom heteroaryl is selected from quinoline, quinoxaline, pyrazolo[1,5-a]pyrimidine, imidazo[1,2-a]pyridine, pyrazolo[1,5-a]pyridine, imidazo[1,2-a]pyrimidine, imidazo[1,2-b]pyridazine, or pyrazolo[1,5-a]pyridine. Another embodiment provides the compound, or a pharmaceutically acceptable salt or solvate thereof, wherein $R^4$ is an optionally substituted benzimidazole. Another embodiment provides the compound, or a pharmaceutically acceptable salt or solvate thereof, wherein $R^4$ is an optionally substituted 1H-indazole. Another embodiment provides the compound, or a pharmaceutically acceptable salt or solvate thereof, wherein $R^4$ is an optionally substituted 2H-indazole. Another embodiment provides the compound, or a pharmaceutically acceptable salt or solvate thereof, wherein $R^4$ is an optionally substituted benzoxazole, optionally substituted imidazo[4,5-c]pyridine, or optionally substituted imidazo[4,5-b]pyridine. Another embodiment provides the compound, or a pharmaceutically acceptable salt or solvate thereof, wherein optionally substituted nitrogen-containing 9 or 10-atom heteroaryl is optionally substituted with alkyl, cycloalkyl, or halogen. Another embodiment provides the compound, or a pharmaceutically acceptable salt or solvate thereof, wherein the optionally substituted benzimidazole is optionally substituted with alkyl, cycloalkyl, or halogen. Another embodiment provides the compound, or a pharmaceutically acceptable salt or solvate thereof, wherein the optionally substituted 1H-indazole is optionally substituted with alkyl, cycloalkyl, or halogen. Another embodiment provides the compound, or a pharmaceutically acceptable salt or solvate thereof, wherein the optionally substituted 2H-indazole is optionally substituted with alkyl, cycloalkyl, or halogen.

Another embodiment provides the compound of Formula (II), or a pharmaceutically acceptable salt or solvate thereof, wherein R is hydrogen. Another embodiment provides the compound, or a pharmaceutically acceptable salt or solvate thereof, wherein R is optionally substituted C1-C6 alkyl. Another embodiment provides the compound, or a pharmaceutically acceptable salt or solvate thereof, wherein R is optionally substituted C3-C7 carbocyclyl. Another embodiment provides the compound, or a pharmaceutically acceptable salt or solvate thereof, wherein R is optionally substituted C3-C7 carbocyclylalkyl. Another embodiment provides the compound, or a pharmaceutically acceptable salt or solvate thereof, wherein R is optionally substituted C3-C7 heterocyclyl. Another embodiment provides the compound, or a pharmaceutically acceptable salt or solvate thereof, wherein R is optionally substituted C3-C7 heterocyclylalkyl. Another embodiment provides the compound, or a pharmaceutically acceptable salt or solvate thereof, wherein R is —$CO_2R^5$. Another embodiment provides the compound, or a pharmaceutically acceptable salt or solvate thereof, wherein R is —$CONHR^5$ or —$CON(R^5)_2$. Another embodiment provides the compound, or a pharmaceutically acceptable salt or solvate thereof, wherein the optionally substituted C1-C6 alkyl is a C1-C3 alkyl substituted with a C1-C3 alkoxy.

Another embodiment provides the compound of Formula (II), or a pharmaceutically acceptable salt or solvate thereof, wherein $R^6$ is hydrogen.

Another embodiment provides the compound of Formula (II), or a pharmaceutically acceptable salt or solvate thereof, wherein $R^6$ is an optionally substituted alkyl. Another embodiment provides the compound, or a pharmaceutically acceptable salt or solvate thereof, wherein $R^6$ is an optionally substituted C1-C4 alkyl. Another embodiment provides the compound, or a pharmaceutically acceptable salt or solvate thereof, wherein $R^6$ is an optionally substituted C1-C3 alkyl. Another embodiment provides the compound, or a pharmaceutically acceptable salt or solvate thereof, wherein $R^6$ is an optionally substituted C1-C2 alkyl. Another embodiment provides the compound, or a pharmaceutically acceptable salt or solvate thereof, wherein $R^6$ is an optionally substituted C1 alkyl. Another embodiment provides the compound, or a pharmaceutically acceptable salt or solvate thereof, wherein $R^6$ is $CH_3$.

Another embodiment provides the compound of Formula (II), or a pharmaceutically acceptable salt or solvate thereof, wherein $R^6$ is an optionally substituted carbocyclylalkyl. Another embodiment provides the compound, or a pharmaceutically acceptable salt or solvate thereof, wherein $R^6$ is optionally substituted carbocyclylmethyl. Another embodiment provides the compound, or a pharmaceutically acceptable salt or solvate thereof, wherein $R^6$ is optionally substituted (C3-C6carbocyclyl)methyl. Another embodiment provides the compound, or a pharmaceutically acceptable salt or solvate thereof, wherein $R^6$ is optionally substituted cyclopropylmethyl. Another embodiment provides the compound of Formula (II), or a pharmaceutically acceptable salt or solvate thereof, wherein $R^6$ is an optionally substituted heterocyclylalkyl. Another embodiment provides the compound, or a pharmaceutically acceptable salt or solvate thereof, wherein $R^6$ is optionally substituted heterocyclylethyl. Another embodiment provides the compound, or a pharmaceutically acceptable salt or solvate thereof, wherein $R^6$ is optionally substituted heterocyclylethyl and the heterocyclyl is a piperidinyl, pyrrolidinyl, morpholinyl, or piperazinyl.

Another embodiment provides the compound of Formula (II), or a pharmaceutically acceptable salt or solvate thereof, wherein $R^4$ is an optionally substituted benzimidazole further substituted with a cycloalkyl group, and at least one halogen.

Another embodiment provides the compound of Formula (II), or a pharmaceutically acceptable salt or solvate thereof, wherein $R^4$ is an optionally substituted benzimidazole further substituted with a cycloalkyl group, and at least one halogen; R is a —$CH_2OCH_3$ group; and $R^6$ is methyl.

Another embodiment provides the compound of Formula (II), or a pharmaceutically acceptable salt or solvate thereof, wherein $R^4$ is an optionally substituted benzimidazole further substituted with a cycloalkyl group, and at least one halogen; R is a hydrogen; and $R^6$ is methyl.

In some embodiments, the heteroaromatic FGFR kinase inhibitory compound disclosed herein has a structure provided in Table 1.

TABLE 1
| Synthetic Chemistry Example | Compound Structure | Compound Name |
|---|---|---|
| 1 | 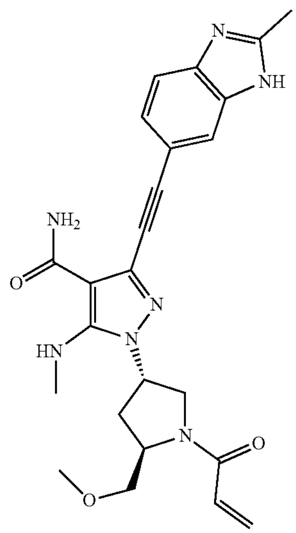 [SMILES: C=CC(=O)N1C[C@@H](n2nc(C#Cc3ccc4nc(C)[nH]c4c3)c(C(N)=O)c2NC)C[C@@H]1COC] | 1-[(3S,5R)-5-(methoxymethyl)-1-(prop-2-enoyl)pyrrolidin-3-yl]-3-[2-(2-methyl-3H-1,3-benzodiazol-5-yl)ethynyl]-5-(methylamino)pyrazole-4-carboxamide |
| 2 | 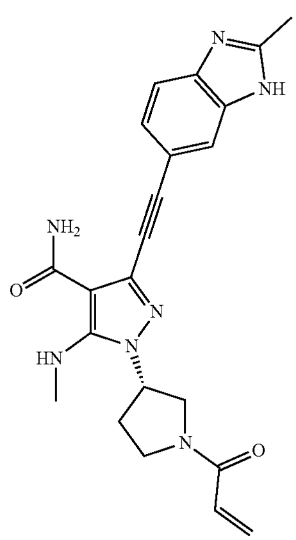 [SMILES: C=CC(=O)N1CC[C@H](n2nc(C#Cc3ccc4nc(C)[nH]c4c3)c(C(N)=O)c2NC)C1] | (S)-1-(1-acryloylpyrrolidin-3-yl)-3-((2-methyl-1H-benzo[d]imidazol-6-yl)ethynyl)-5-(methylamino)-1H-pyrazole-4-carboxamide |

TABLE 1-continued
| Synthetic Chemistry Example | Compound Structure | Compound Name |
|---|---|---|
| 3 | 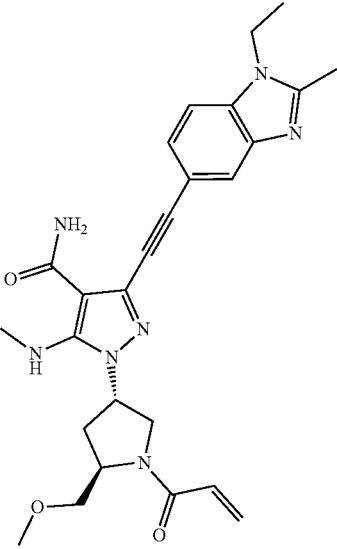 | 3-[2-(1-ethyl-2-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |
| 4 | 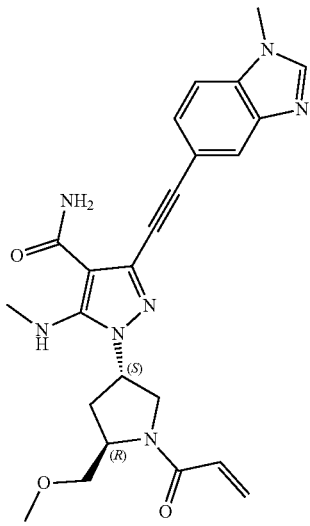 | 1-[(3S,5R)-5-(methoxymethyl)-1-(prop-2-enoyl)pyrrolidin-3-yl]-3-[2-(1-methyl-1,3-benzodiazol-5-yl)ethynyl]-5-(methylamino)pyrazole-4-carboxamide |

TABLE 1-continued

| Synthetic Chemistry Example | Compound Structure | Compound Name |
|---|---|---|
| 5 | 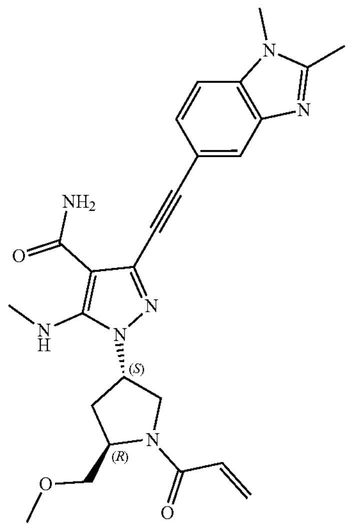 | 1-((3S,5R)-1-acryloyl-5-(methoxymethyl)pyrrolidin-3-yl)-3-((1,2-dimethyl-1H-benzo[d]imidazol-5-yl)ethynyl)-5-(methylamino)-1H-pyrazole-4-carboxamide |
| 6 | 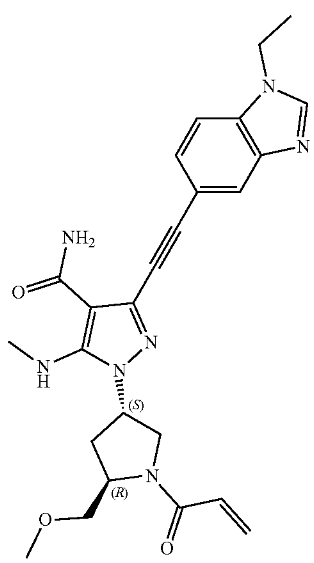 | 1-((3S,5R)-1-acryloyl-5-(methoxymethyl)pyrrolidin-3-yl)-3-((1-ethyl-1H-benzo[d]imidazol-5-yl)ethynyl)-5-(methylamino)-1H-pyrazole-4-carboxamide |

TABLE 1-continued

| Synthetic Chemistry Example | Compound Structure | Compound Name |
|---|---|---|
| 7 | 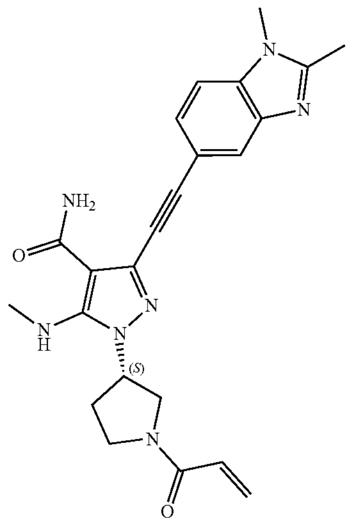 | (S)-1-(1-acryloylpyrrolidin-3-yl)-3-((1,2-dimethyl-1H-benzo[d]imidazol-5-yl)ethynyl)-5-(methylamino)-1H-pyrazole-4-carboxamide |
| 8 | 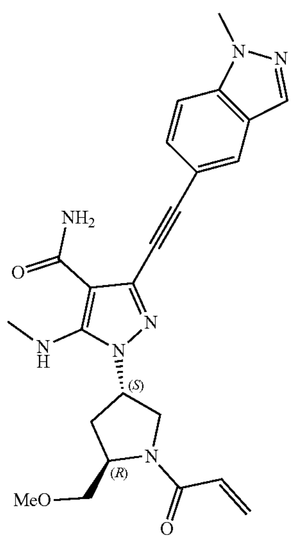 | 1-((3S,5R)-1-acryloyl-5-(methoxymethyl)pyrrolidin-3-yl)-3-((1-methyl-1H-indazol-5-yl)ethynyl)-5-(methylamino)-1H-pyrazole-4-carboxamide |
| 9 | 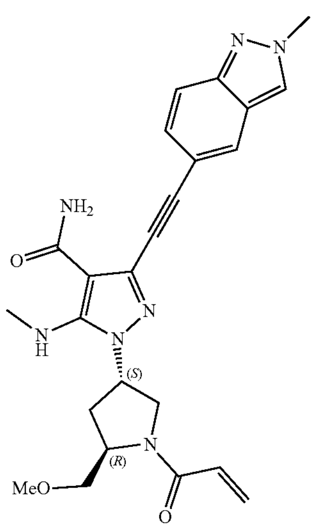 | 1-((3S,5R)-1-acryloyl-5-(methoxymethyl)pyrrolidin-3-yl)-3-((2-methyl-2H-indazol-5-yl)ethynyl)-5-(methylamino)-1H-pyrazole-4-carboxamide |

TABLE 1-continued
| Synthetic Chemistry Example | Compound Structure | Compound Name |
|---|---|---|
| 10 | 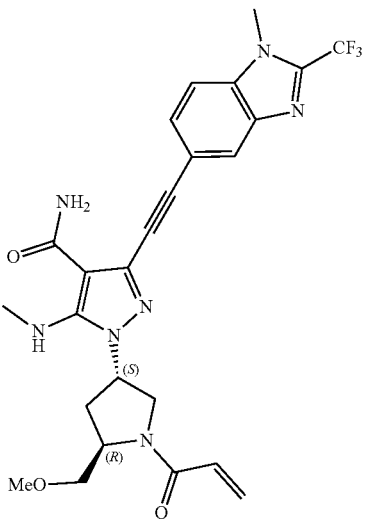 | 1-((3S,5R)-1-acryloyl-5-(methoxymethyl)pyrrolidin-3-yl)-3-((1-methyl-2-(trifluoromethyl)-1H-benzo[d]imidazol-5-yl)ethynyl)-5-(methylamino)-1H-pyrazole-4-carboxamide |
| 11 | 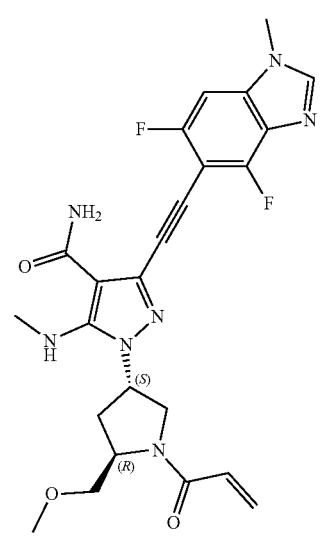 | 1-((3S,5R)-1-acryloyl-5-(methoxymethyl)pyrrolidin-3-yl)-3-((4,6-difluoro-1-methyl-1H-benzo[d]imidazol-5-yl)ethynyl)-5-(methylamino)-1H-pyrazole-4-carboxamide |

TABLE 1-continued

| Synthetic Chemistry Example | Compound Structure | Compound Name |
|---|---|---|
| 12 | 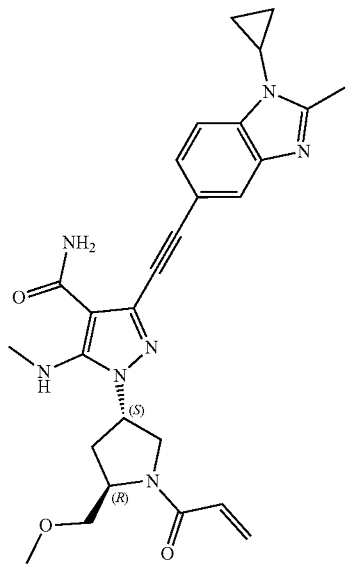 | 1-((3S,5R)-1-acryloyl-5-(methoxymethyl)pyrrolidin-3-yl)-3-((1-cyclopropyl-2-methyl-1H-benzo[d]imidazol-5-yl)ethynyl)-5-(methylamino)-1H-pyrazole-4-carboxamide |
| 13 | 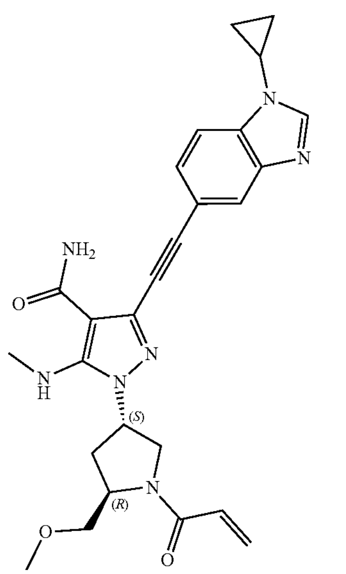 | 1-((3S,5R)-1-acryloyl-5-(methoxymethyl)pyrrolidin-3-yl)-3-((1-cyclopropyl-1H-benzo[d]imidazol-5-yl)ethynyl)-5-(methylamino)-1H-pyrazole-4-carboxamide |

TABLE 1-continued

| Synthetic Chemistry Example | Compound Structure | Compound Name |
|---|---|---|
| 14 | 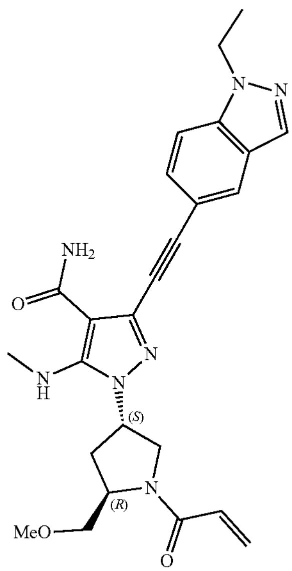 | 1-((3S,5R)-1-acryloyl-5-(methoxymethyl)pyrrolidin-3-yl)-3-((1-ethyl-1H-indazol-5-yl)ethynyl)-5-(methylamino)-1H-pyrazole-4-carboxamide |
| 15 | 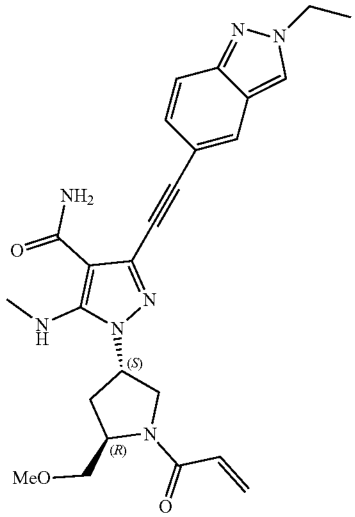 | 1-((3S,5R)-1-acryloyl-5-(methoxymethyl)pyrrolidin-3-yl)-3-((2-ethyl-2H-indazol-5-yl)ethynyl)-5-(methylamino)-1H-pyrazole-4-carboxamide |

TABLE 1-continued

| Synthetic Chemistry Example | Compound Structure | Compound Name |
|---|---|---|
| 16 | 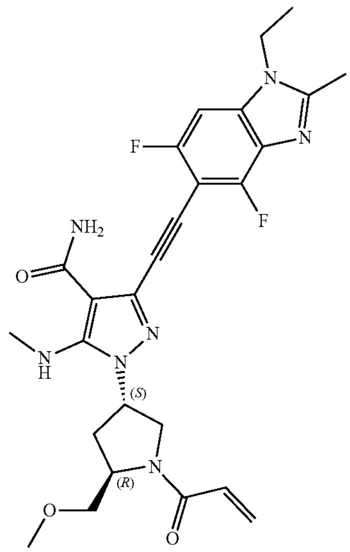 | 1-((3S,5R)-1-acryloyl-5-(methoxymethyl)pyrrolidin-3-yl)-3-((1-ethyl-4,6-difluoro-2-methyl-1H-benzo[d]imidazol-4-yl)ethynyl)-5-(methylamino)-1H-pyrazole-4-carboxamide |
| 17 | 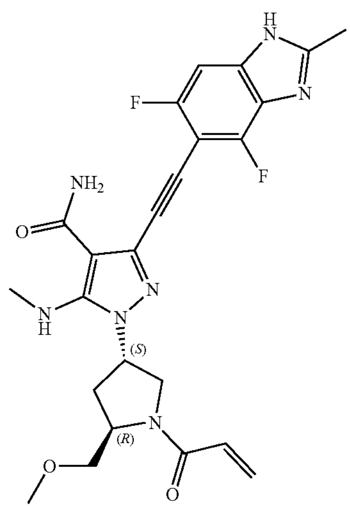 | 1-((3S,5R)-1-acryloyl-5-(methoxymethyl)pyrrolidin-3-yl)-3-((4,6-difluoro-2-methyl-1H-benzo[d]imidazol-5-yl)ethynyl)-5-(methylamino)-1H-pyrazole-4-carboxamide |
| 18 | 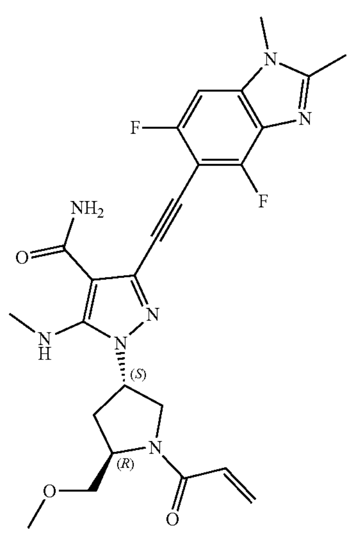 | 1-((3S,5R)-1-acryloyl-5-(methoxymethyl)pyrrolidin-3-yl)-3-((4,6-difluoro-1,2-dimethyl-1H-benzo[d]imidazol-5-yl)ethynyl)-5-(methylamino)-1H-pyrazole-4-carboxamide |

TABLE 1-continued
| Synthetic Chemistry Example | Compound Structure | Compound Name |
|---|---|---|
| 19 | 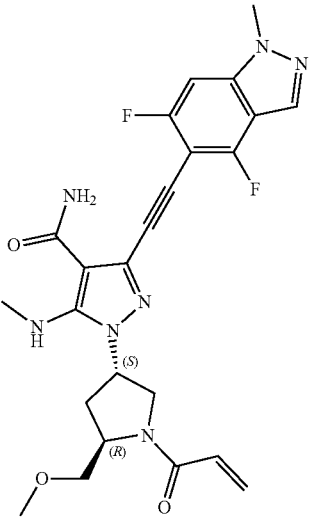 | 1-((3S,5R)-1-acryloyl-5-(methoxymethyl)pyrrolidin-3-yl)-3-((4,6-difluoro-1-methyl-1H-indazol-5-yl)ethynyl)-5-(methylamino)-1H-pyrazole-4-carboxamide |
| 20 | 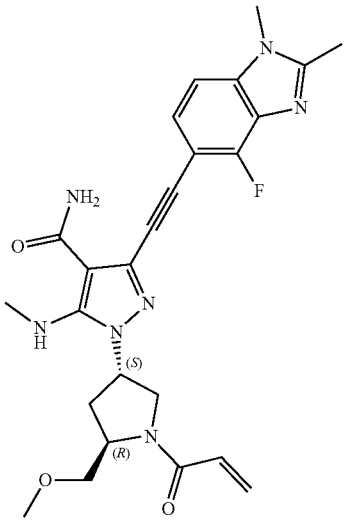 | 1-((3S,5R)-1-acryloyl-5-(methoxymethyl)pyrrolidin-3-yl)-3-((4-fluoro-1,2-dimethyl-1H-benzo[d]imidazol-5-yl)ethynyl)-5-(methylamino)-1H-pyrazole-4-carboxamide |

TABLE 1-continued

| Synthetic Chemistry Example | Compound Structure | Compound Name |
|---|---|---|
| 21 | 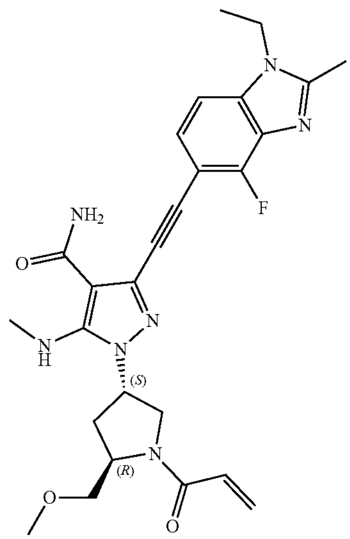 | 1-((3S,5R)-1-acryloyl-5-(methoxymethyl)pyrrolidin-3-yl)-3-((1-ethyl-4-fluoro-2-methyl-1H-benzo[d]imidazol-5-yl)ethynyl)-5-(methylamino)-1H-pyrazole-4-carboxamide |
| 22 | 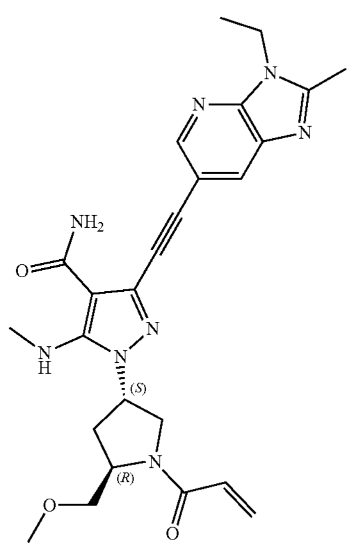 | 1-((3S,5R)-1-acryloyl-5-(methoxymethyl)pyrrolidin-3-yl)-3-((3-ethyl-2-methyl-3H-imidazo[4,5-b]pyridin-6-yl)ethynyl)-5-(methylamino)-1H-pyrazole-4-carboxamide |

TABLE 1-continued

| Synthetic Chemistry Example | Compound Structure | Compound Name |
|---|---|---|
| 23 | 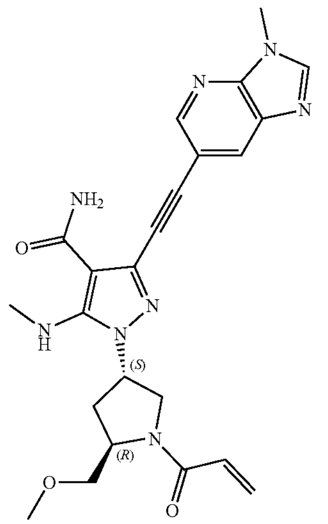 | 1-((3S,5R)-1-acryloyl-5-(methoxymethyl)pyrrolidin-3-yl)-3-((3-methyl-3H-imidazo[4,5-b]pyridin-6-yl)ethynyl)-5-(methylamino)-1H-pyrazole-4-carboxamide |
| 24 | 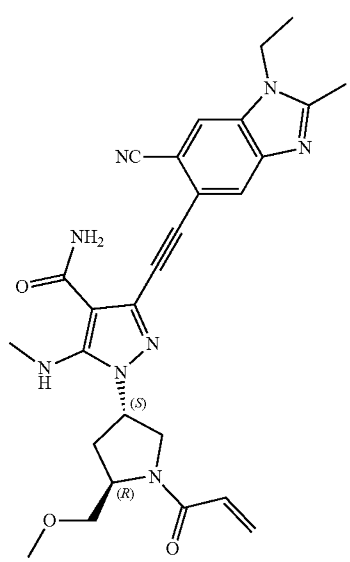 | 1-((3S,5R)-1-acryloyl-5-(methoxymethyl)pyrrolidin-3-yl)-3-((6-cyano-1-ethyl-2-methyl-1H-benzo[d]imidazol-5-yl)ethynyl)-5-(methylamino)-1H-pyrazole-4-carboxamide |

TABLE 1-continued

| Synthetic Chemistry Example | Compound Structure | Compound Name |
|---|---|---|
| 25 | 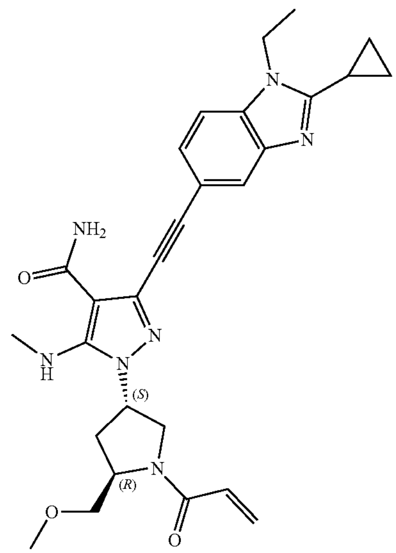 | 1-((3S,5R)-1-acryloyl-5-(methoxymethyl)pyrrolidin-3-yl)-3-((2-cyclopropyl-1-ethyl-1H-benzo[d]imidazol-5-yl)ethynyl)-5-(methylamino)-1H-pyrazole-4-carboxamide |
| 26 | 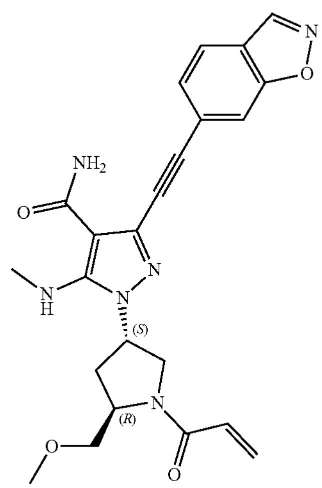 | 1-((3S,5R)-1-acryloyl-5-(methoxymethyl)pyrrolidin-3-yl)-3-(benzo[d]isoxazol-6-ylethynyl)-5-(methylamino)-1H-pyrazole-4-carboxamide |
| 27 | 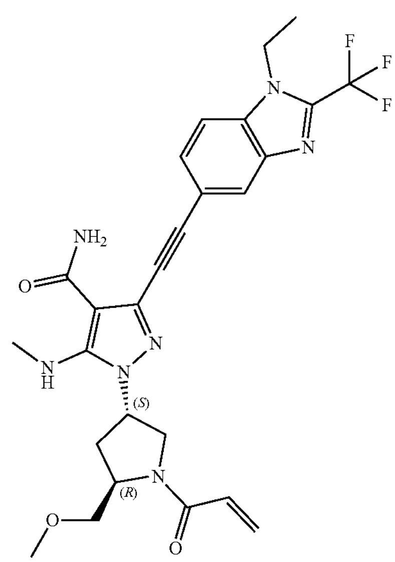 | 1-((3S,5R)-1-acryloyl-5-(methoxymethyl)pyrrolidin-3-yl)-3-((1-ethyl-2-(trifluoromethyl)-1H-benzo[d]imidazol-5-yl)ethynyl)-5-(methylamino)-1H-pyrazole-4-carboxamide |

TABLE 1-continued
| Synthetic Chemistry Example | Compound Structure | Compound Name |
|---|---|---|
| 28 | 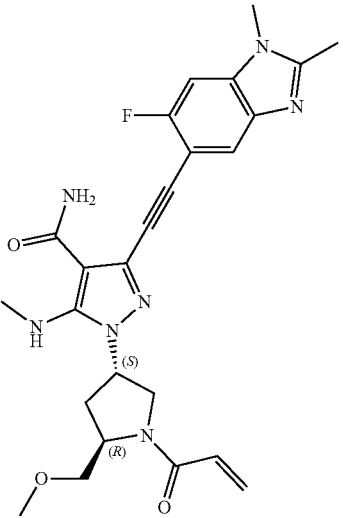 | 1-((3S,5R)-1-acryloyl-5-(methoxymethyl)pyrrolidin-3-yl)-3-((6-fluoro-1,2-dimethyl-1H-benzo[d]imidazol-5-yl)ethynyl)-5-(methylamino)-1H-pyrazole-4-carboxamide |
| 29 | 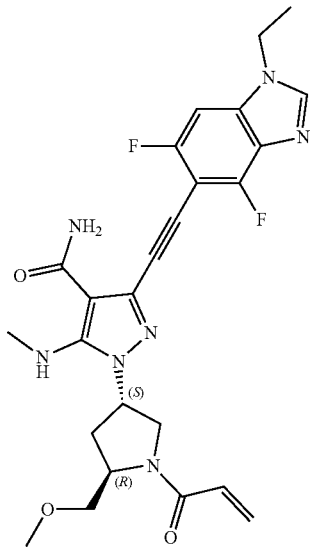 | 1-((3S,5R)-1-acryloyl-5-(methoxymethyl)pyrrolidin-3-yl)-3-((1-ethyl-4,6-difluoro-1H-benzo[d]imidazol-5-yl)ethynyl)-5-(methylamino)-1H-pyrazole-4-carboxamide |

TABLE 1-continued

| Synthetic Chemistry Example | Compound Structure | Compound Name |
|---|---|---|
| 30 | 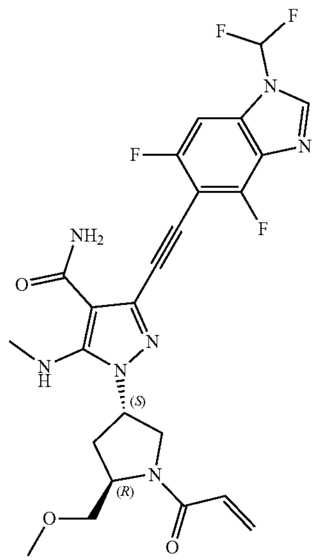 | 1-((3S,5R)-1-acryloyl-5-(methoxymethyl)pyrrolidin-3-yl)-3-((1-(difluoromethyl)-4,6-difluoro-1H-benzo[d]imidazol-5-yl)ethynyl)-5-(methylamino)-1H-pyrazole-4-carboxamide |
| 31 | 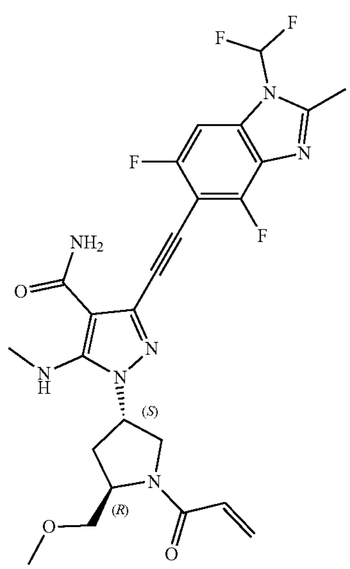 | 1-((3S,5R)-1-acryloyl-5-(methoxymethyl)pyrrolidin-3-yl)-3-((1-(difluoromethyl)-4,6-difluoro-2-methyl-1H-benzo[d]imidazol-5-yl)ethynyl)-5-(methylamino)-1H-pyrazole-4-carboxamide |

TABLE 1-continued

| Synthetic Chemistry Example | Compound Structure | Compound Name |
|---|---|---|
| 32 | 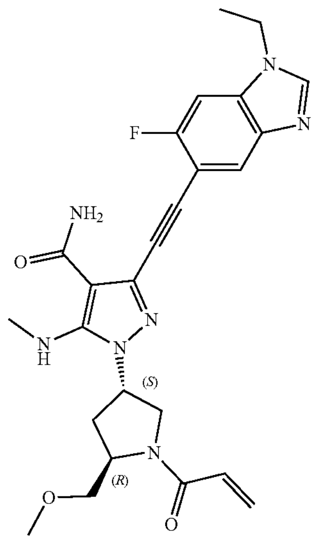 | 1-((3S,5R)-1-acryloyl-5-(methoxymethyl)pyrrolidin-3-yl)-3-((1-ethyl-6-fluoro-1H-benzo[d]imidazol-5-yl)ethynyl)-5-(methylamino)-1H-pyrazole-4-carboxamide |
| 33 | 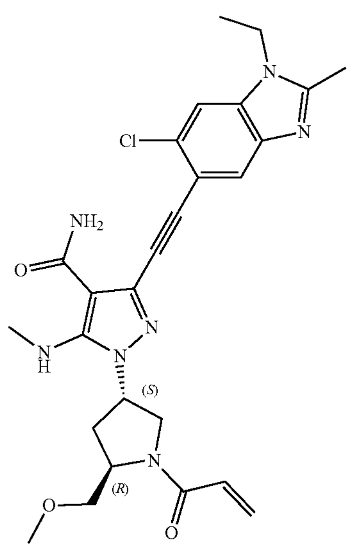 | 1-((3S,5R)-1-acryloyl-5-(methoxymethyl)pyrrolidin-3-yl)-3-((6-chloro-1-ethyl-2-methyl-1H-benzo[d]imidazol-5-yl)ethynyl)-5-(methylamino)-1H-pyrazole-4-carboxamide |

TABLE 1-continued

| Synthetic Chemistry Example | Compound Structure | Compound Name |
|---|---|---|
| 34 | 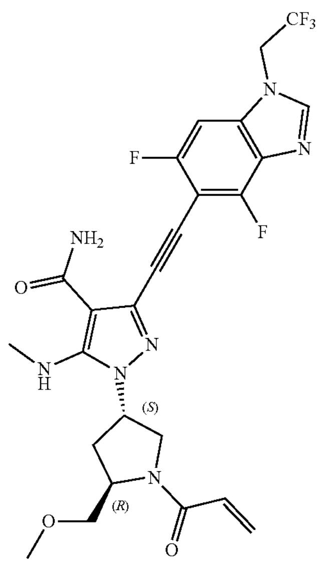 | 1-((3S,5R)-1-acryloyl-5-(methoxymethyl)pyrrolidin-3-yl)-3-((4,6-difluoro-1-(2,2,2-trifluoroethyl)-1H-benzo[d]imidazol-5-yl)ethynyl)-5-(methylamino)-1H-pyrazole-4-carboxamide |
| 35 | 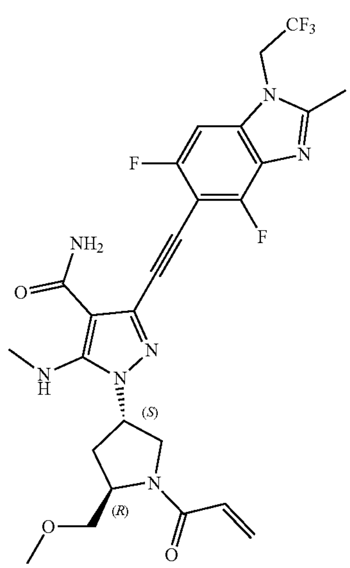 | 1-((3S,5R)-1-acryloyl-5-(methoxymethyl)pyrrolidin-3-yl)-3-((4,6-difluoro-2-methyl-1-(2,2,2-trifluoroethyl)-1H-benzo[d]imidazol-5-yl)ethynyl)-5-(methylamino)-1H-pyrazole-4-carboxamide |

TABLE 1-continued

| Synthetic Chemistry Example | Compound Structure | Compound Name |
|---|---|---|
| 36 | 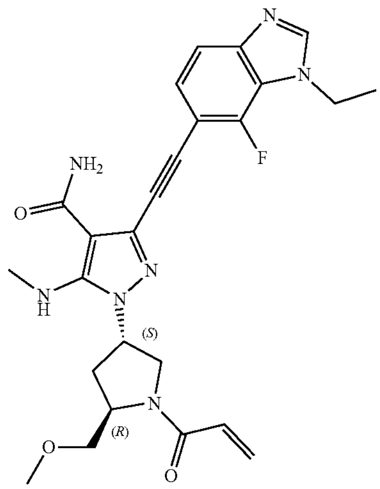 | 3-[2-(3-ethyl-4-fluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |
| 37 | 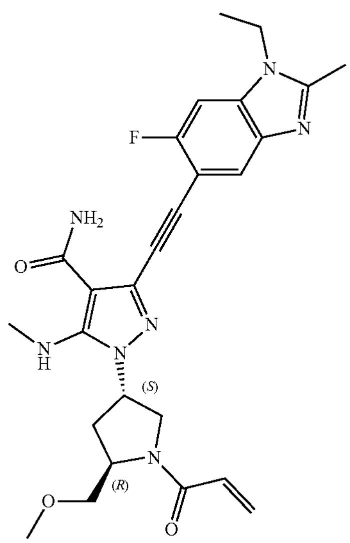 | 3-[2-(1-ethyl-6-fluoro-2-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |
| 38 | 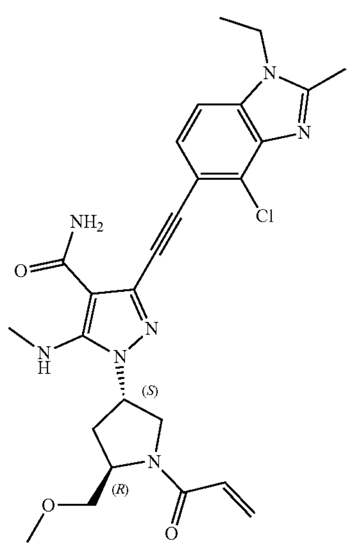 | 3-[2-(4-chloro-1-ethyl-2-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |

TABLE 1-continued

| Synthetic Chemistry Example | Compound Structure | Compound Name |
|---|---|---|
| 39 | 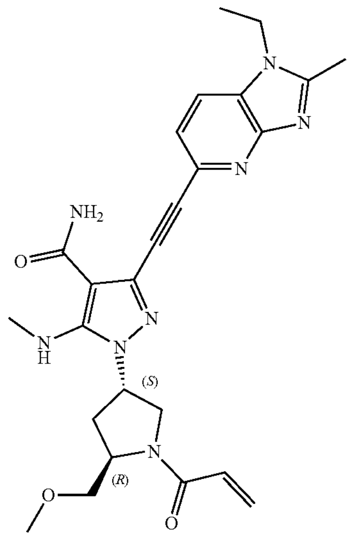 | 3-(2-[1-ethyl-2-methylimidazo[4,5-b]pyridin-5-yl]ethynyl)-1-[(3S,5R)-5-(methoxymethyl)-1-(prop-2-enoyl)pyrrolidin-3-yl]-5-(methylamino)pyrazole-4-carboxamide |
| 40 | 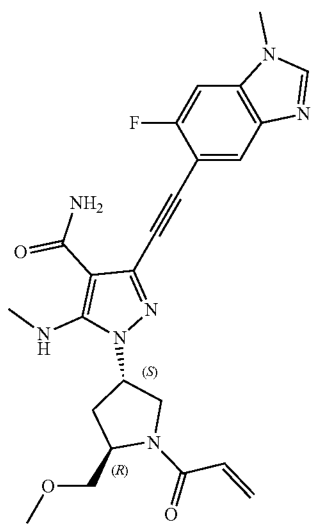 | 3-[2-(6-fluoro-2-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |
| 41 | 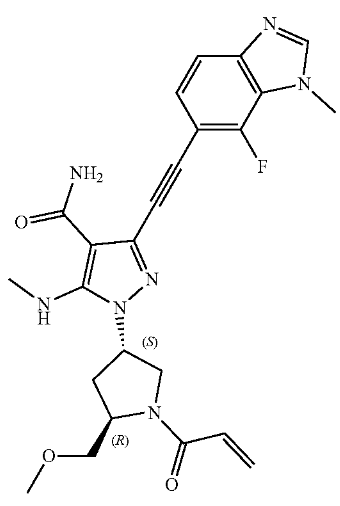 | 3-[2-(4-fluoro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |

TABLE 1-continued

| Synthetic Chemistry Example | Compound Structure | Compound Name |
|---|---|---|
| 42 | 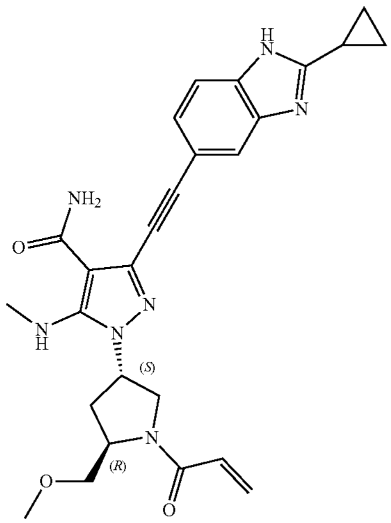 | 3-[2-(2-cyclopropyl-1H-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |
| 43 | 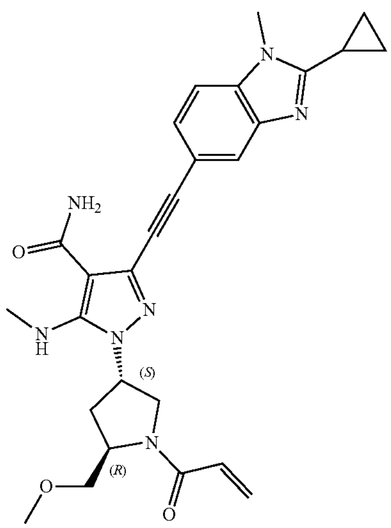 | 3-[2-(2-cyclopropyl-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |
| 44 | 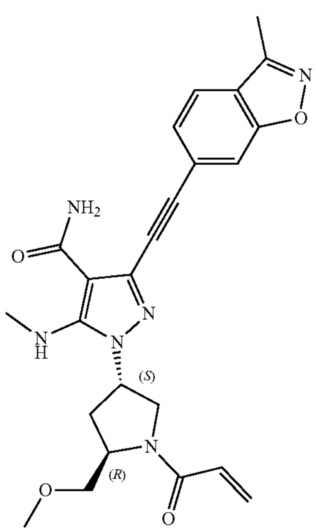 | 1-[(3S,5R)-5-(methoxymethyl)-1-(prop-2-enoyl)pyrrolidin-3-yl]-3-[2-(3-methyl-1,2-benzoxazol-6-yl)ethynyl]-5-(methylamino)pyrazole-4-carboxamide |

TABLE 1-continued

| Synthetic Chemistry Example | Compound Structure | Compound Name |
|---|---|---|
| 45 | 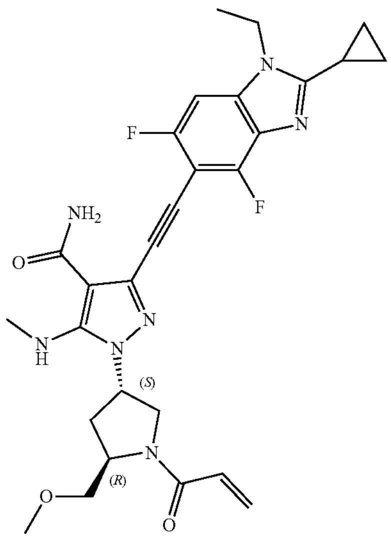 | 3-[2-(2-cyclopropyl-1-ethyl-4,6-difluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |
| 46 | 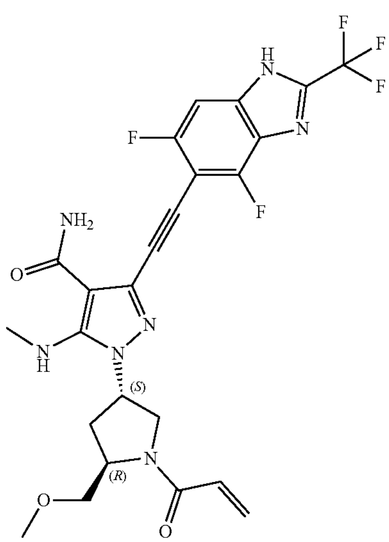 | 3-[2-[4,6-difluoro-2-(trifluoromethyl)-1H-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide |

TABLE 1-continued
| Synthetic Chemistry Example | Compound Structure | Compound Name |
|---|---|---|
| 47 | 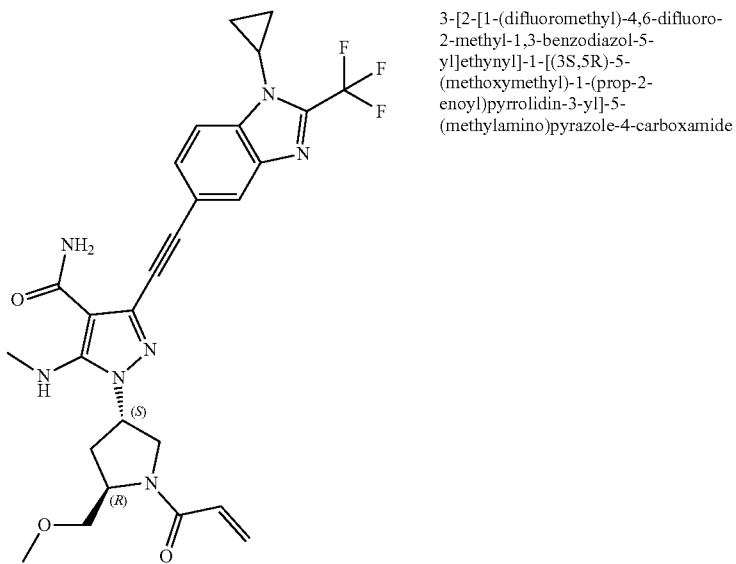 | 3-[2-[1-(difluoromethyl)-4,6-difluoro-2-methyl-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide |
| 48 | 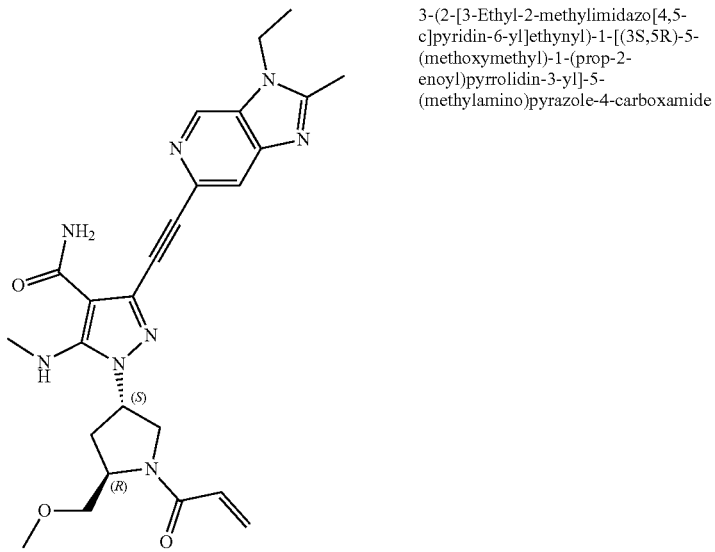 | 3-(2-[3-Ethyl-2-methylimidazo[4,5-c]pyridin-6-yl]ethynyl)-1-[(3S,5R)-5-(methoxymethyl)-1-(prop-2-enoyl)pyrrolidin-3-yl]-5-(methylamino)pyrazole-4-carboxamide |

TABLE 1-continued

| Synthetic Chemistry Example | Compound Structure | Compound Name |
|---|---|---|
| 49 | 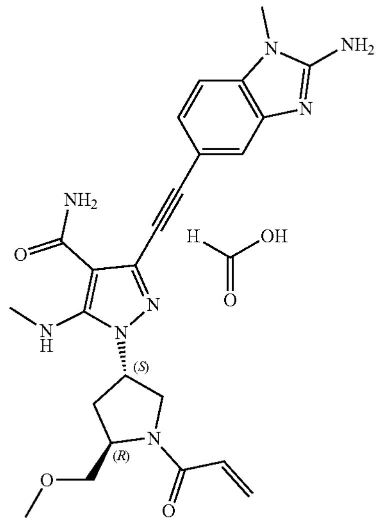 | 3-[2-(2-Amino-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide; formic acid |
| 50 | 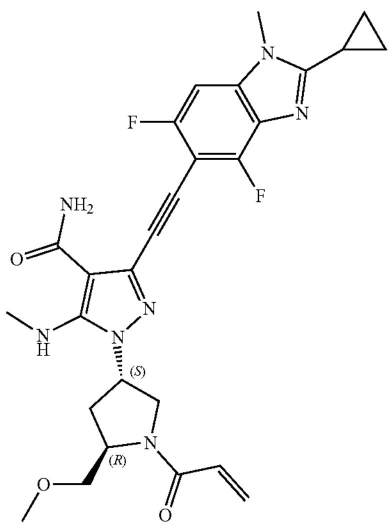 | 3-[2-(2-Cyclopropyl-4,6-difluoro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |
| 51 | 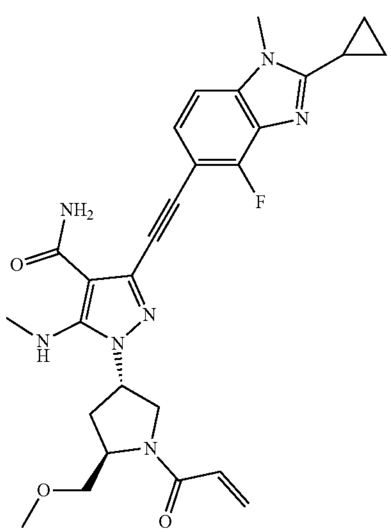 [SMILES: C=CC(=O)N1C[C@@H](n2nc(C#Cc3ccc4c(nc(C5CC5)n4C)c3F)c(C(N)=O)c2NC)C[C@@H]1COC] | 1-((3S,5R)-1-Acryloyl-5-(methoxymethyl)pyrrolidin-3-yl)-3-((2-cyclopropyl-4-fluoro-1-methyl-1H-benzo[d]imidazol-5-yl)ethynyl)-5-(methylamino)-1H-pyrazole-4-carboxamide |

TABLE 1-continued

| Synthetic Chemistry Example | Compound Structure | Compound Name |
|---|---|---|
| 52 | 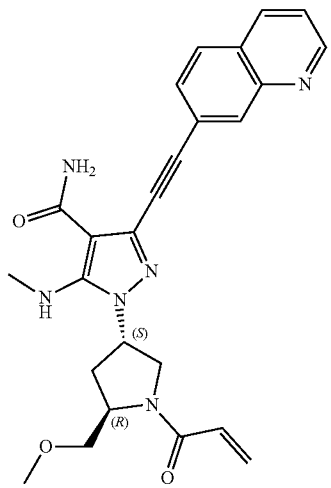 | 1-[(3S,5R)-5-(Methoxymethyl)-1-(prop-2-enoyl)pyrrolidin-3-yl]-5-(methylamino)-3-[2-(quinolin-7-yl)ethynyl]pyrazole-4-carboxamide |
| 53 | 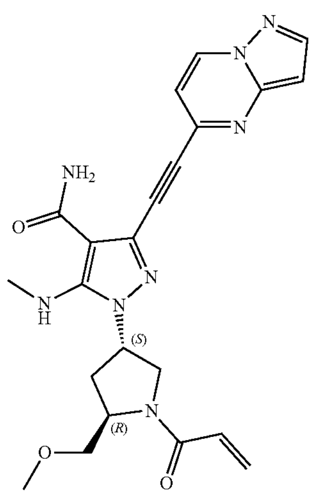 | 1-[(3S,5R)-5-(Methoxymethyl)-1-(prop-2-enoyl)pyrrolidin-3-yl]-5-(methylamino)-3-(2-[pyrazolo-[1,5-a]pyrimidin-5-yl]ethynyl)pyrazole-4-carboxamide |
| 54 | 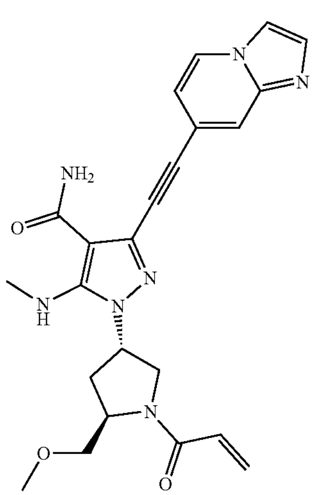 [SMILES: C=CC(=O)N1C[C@@H](n2nc(C#Cc3ccn4ccnc4c3)c(C(N)=O)c2NC)C[C@@H]1COC] | 1-((3S,5R)-1-Acryloyl-5-(methoxymethyl)pyrrolidin-3-yl)-3-(imidazo[1,2-a]pyridin-7-ylethynyl)-5-(methylamino)-1H-pyrazole-4-carboxamide |

TABLE 1-continued

| Synthetic Chemistry Example | Compound Structure | Compound Name |
|---|---|---|
| 55 | 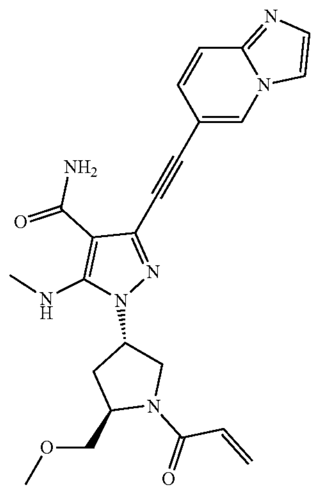 [SMILES: C=CC(=O)N1C[C@@H](n2nc(C#Cc3ccc4nccn4c3)c(C(N)=O)c2NC)C[C@@H]1COC] | 1-((3S,5R)-1-Acryloyl-5-(methoxymethyl)pyrrolidin-3-yl)-3-(imidazo[1,2-a]pyridin-6-ylethynyl)-5-(methylamino)-1H-pyrazole-4-carboxamide |
| 56 | 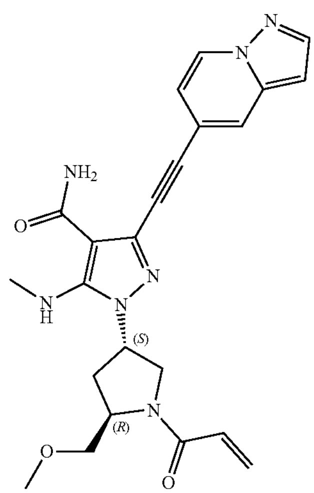 | 1-[(3S,5R)-5-(Methoxymethyl)-1-(prop-2-enoyl)pyrrolidin-3-yl]-5-(methylamino)-3-(2-[pyrazolo[1,5-a]pyridin-5-yl]ethynyl)pyrazole-4-carboxamide |
| 57 | 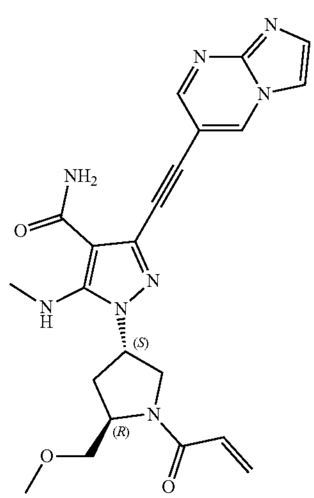 | 3-(2-[Imidazo[1,2-a]pyrimidin-6-yl]ethynyl)-1-[(3S,5R)-5-(methoxymethyl)-1-(prop-2-enoyl)pyrrolidin-3-yl]-5-(methylamino)pyrazole-4-carboxamide |

TABLE 1-continued

| Synthetic Chemistry Example | Compound Structure | Compound Name |
|---|---|---|
| 58 | 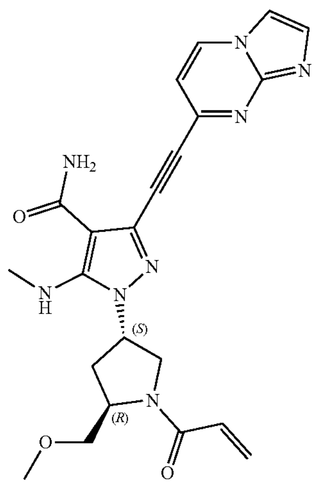 | 3-(2-[Imidazo[1,2-a]pyrimidin-7-yl]ethynyl)-1-[(3S,5R)-5-(methoxymethyl)-1-(prop-2-enoyl)pyrrolidin-3-yl]-5-(methylamino)pyrazole-4-carboxamide |
| 59 | 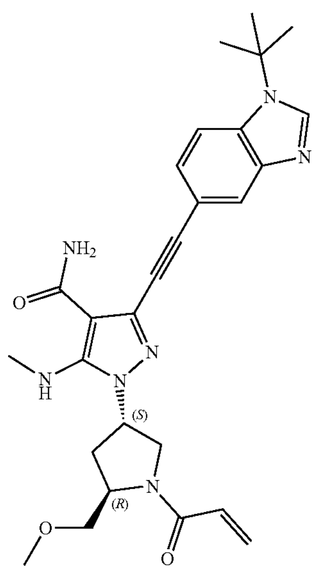 | 3-[2-(1-Tert-butyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |
| 60 | 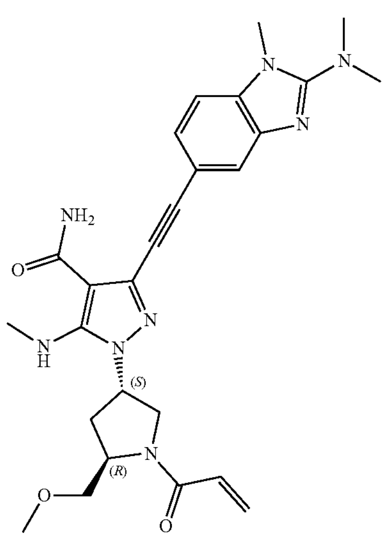 | 3-[2-[2-(Dimethylamino)-1-methyl-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide |

TABLE 1-continued

| Synthetic Chemistry Example | Compound Structure | Compound Name |
|---|---|---|
| 61 | 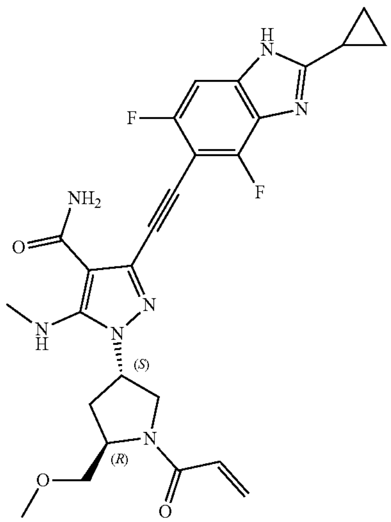 | 3-[2-(2-Cyclopropyl-4,6-difluoro-1H-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |
| 62 | 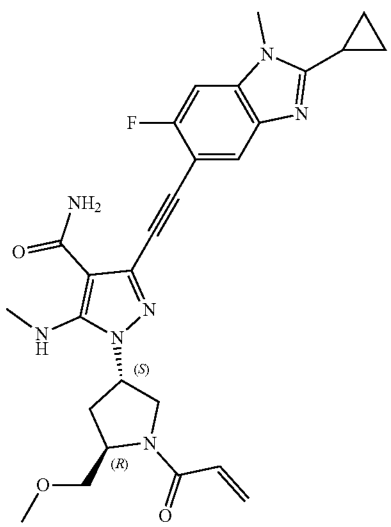 | 3-[2-(2-Cyclopropyl-6-fluoro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |
| 63 | 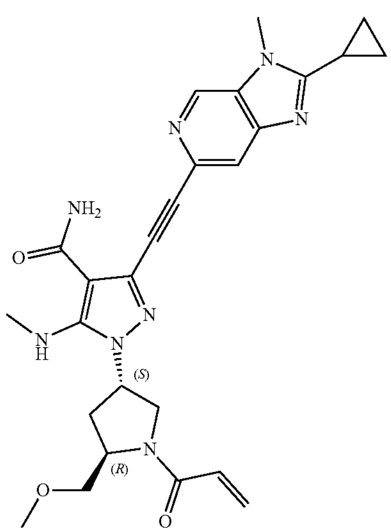 | 3-(2-[2-Cyclopropyl-3-methylimidazo[4,5-c]pyridin-6-yl]ethynyl)-1-[(3S,5R)-5-(methoxymethyl)-1-(prop-2-enoyl)pyrrolidin-3-yl]-5-(methylamino)pyrazole-4-carboxamide |

TABLE 1-continued

| Synthetic Chemistry Example | Compound Structure | Compound Name |
|---|---|---|
| 64 | 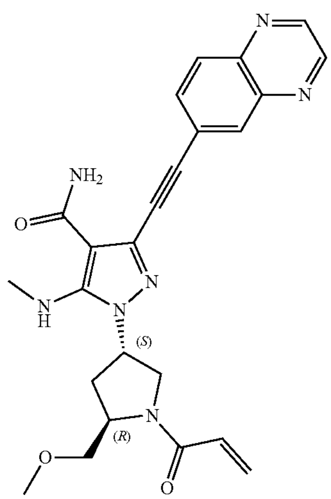 | 1-[(3S,5R)-5-(Methoxymethyl)-1-(prop-2-enoyl)pyrrolidin-3-yl]-5-(methylamino)-3-[2-(quinoxalin-6-yl)ethynyl]pyrazole-4-carboxamide |
| 65 | 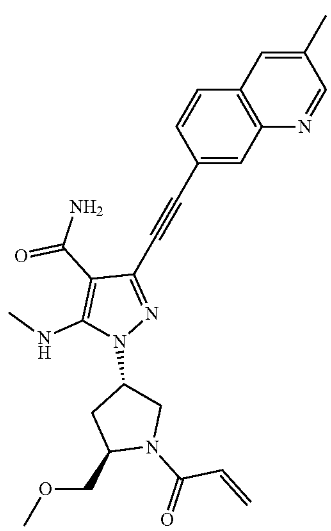 | 1-((3S,5R)-1-Acryloyl-5-(methoxymethyl)pyrrolidin-3-yl)-5-(methylamino)-3-((3-methylquinolin-7-yl)ethynyl)-1H-pyrazole-4-carboxamide |
| 66 | 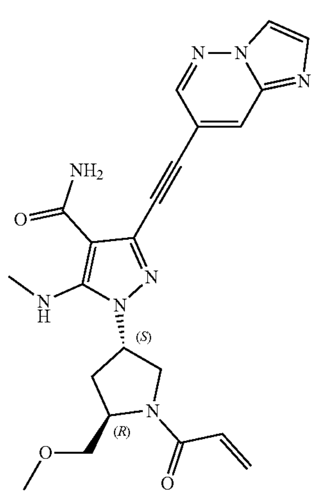 | 3-(2-[Imidazo[1,2-b]pyridazin-7-yl]ethynyl)-1-[(3S,5R)-5-(methoxymethyl)-1-(prop-2-enoyl)pyrrolidin-3-yl]-5-(methylamino)pyrazole-4-carboxamide |

TABLE 1-continued

| Synthetic Chemistry Example | Compound Structure | Compound Name |
|---|---|---|
| 67 | 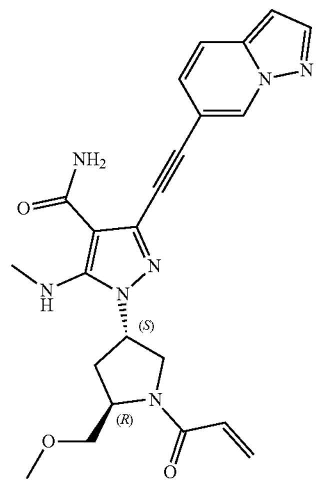 | 1-[(3S,5R)-5-(Methoxymethyl)-1-(prop-2-enoyl)pyrrolidin-3-yl]-5-(methylamino)-3-(2-[pyrazolo[1,5-a]pyridin-6-yl]ethynyl)pyrazole-4-carboxamide |
| 68 | 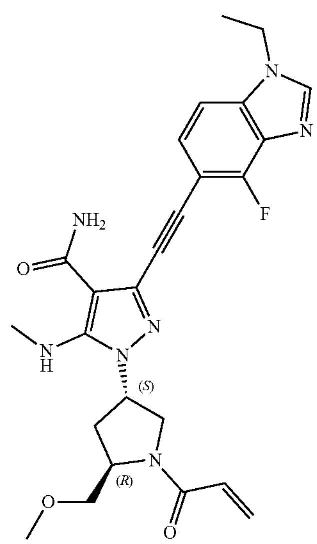 | 1-((3S,5R)-1-Acryloyl-5-(methoxymethyl)pyrrolidin-3-yl)-3-((1-ethyl-4-fluoro-1H-benzo[d]imidazol-5-yl)ethynyl)-5-(methylamino)-1H-pyrazole-4-carboxamide |
| 69 | 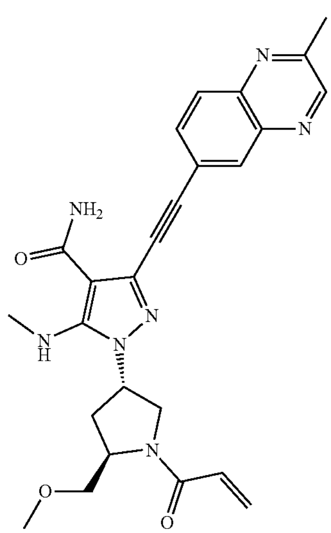 | 1-((3S,5R)-1-Acryloyl-5-(methoxymethyl)pyrrolidin-3-yl)-5-(methylamino)-3-((2-methylquinoxalin-6-yl)ethynyl)-1H-pyrazole-4-carboxamide |

TABLE 1-continued

| Synthetic Chemistry Example | Compound Structure | Compound Name |
|---|---|---|
| 70 | 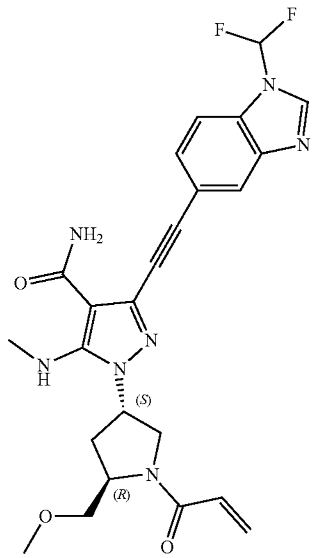 | 3-[2-[1-(Difluoromethyl)-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide |
| 71 | 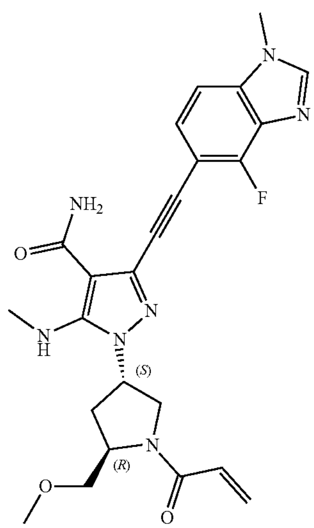 | 1-((3S,5R)-1-Acryloyl-5-(methoxymethyl)pyrrolidin-3-yl)-3-((4-fluoro-1-methyl-1H-benzo[d]imidazol-5-yl)ethynyl)-5-(methylamino)-1H-pyrazole-4-carboxamide |
| 72 | 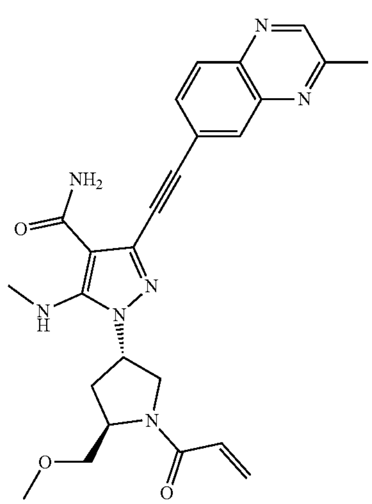 | 1-((3S,5R)-1-Acryloyl-5-(methoxymethyl)pyrrolidin-3-yl)-5-(methylamino)-3-((3-methylquinoxalin-6-yl)ethynyl)-1H-pyrazole-4-carboxamide |

TABLE 1-continued

| Synthetic Chemistry Example | Compound Structure | Compound Name |
|---|---|---|
| 73 | 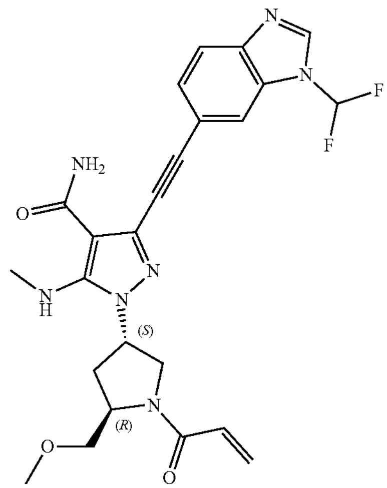 | 3-[2-[3-(Difluoromethyl)-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide |
| 74 | 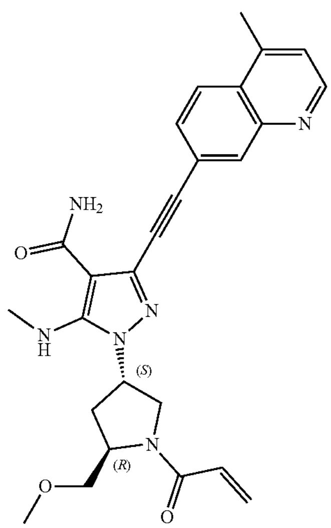 | 1-[(3S,5R)-5-(Methoxymethyl)-1-(prop-2-enoyl)pyrrolidin-3-yl]-5-(methylamino)-3-[2-(4-methylquinolin-7-yl)ethynyl]pyrazole-4-carboxamide |
| 75 | 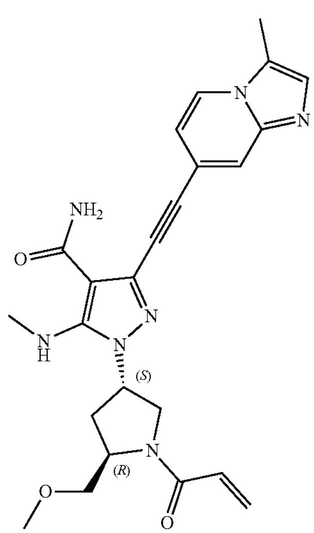 | 1-[(3S,5R)-5-(Methoxymethyl)-1-(prop-2-enoyl)pyrrolidin-3-yl]-5-(methylamino)-3-(2-[3-methylimidazo[1,2-a]pyridin-7-yl]ethynyl)pyrazole-4-carboxamide |

TABLE 1-continued

| Synthetic Chemistry Example | Compound Structure | Compound Name |
|---|---|---|
| 76 | 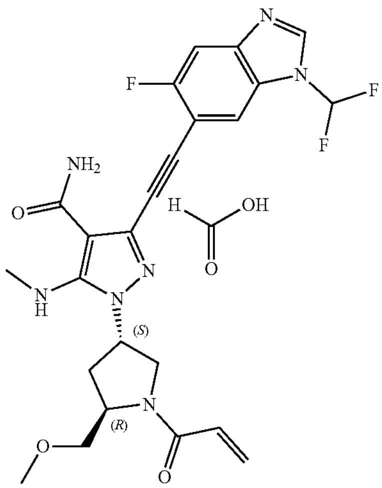 | 3-[2-[3-(Difluoromethyl)-6-fluoro-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide; formic acid |
| 77 | 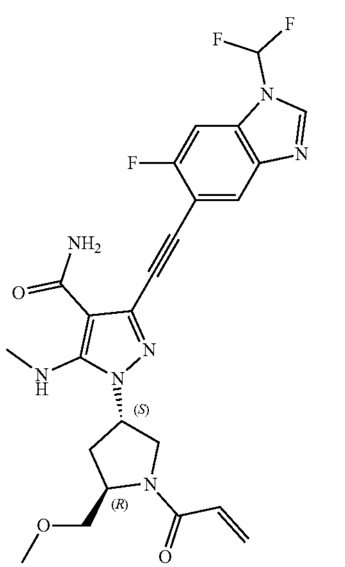 | 3-[2-[1-(Difluoromethyl)-6-fluoro-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide |

TABLE 1-continued

| Synthetic Chemistry Example | Compound Structure | Compound Name |
|---|---|---|
| 78 | 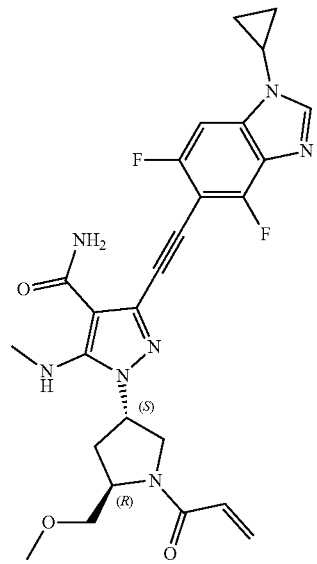 | 3-[2-(1-Cyclopropyl-4,6-difluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |
| 79 | 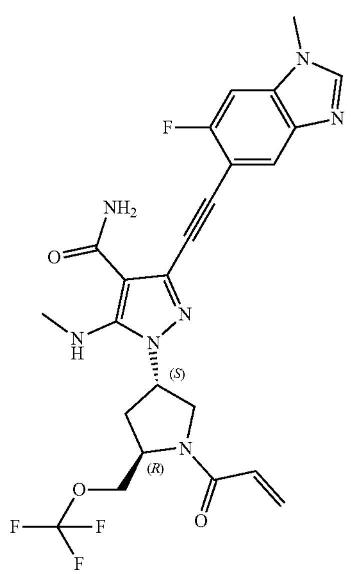 | 3-[2-(6-Fluoro-1-methyl-1,3-benzodiazol-5-yl)ethynyl]-5-(methylamino)-1-[(3S,5R)-1-(prop-2-enoyl)-5-[(trifluoromethoxy)methyl]pyrrolidin-3-yl]pyrazole-4-carboxamide |

TABLE 1-continued
| Synthetic Chemistry Example | Compound Structure | Compound Name |
|---|---|---|
| 80 | 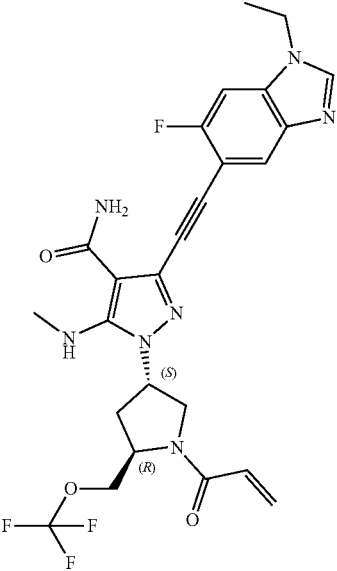 | 3-[2-(1-Ethyl-6-fluoro-1,3-benzodiazol-5-yl)ethynyl]-5-(methylamino)-1-[(3S,5R)-1-(prop-2-enoyl)-5-[(trifluoromethoxy)methyl]pyrrolidin-3-yl]pyrazole-4-carboxamide |
| 81 | 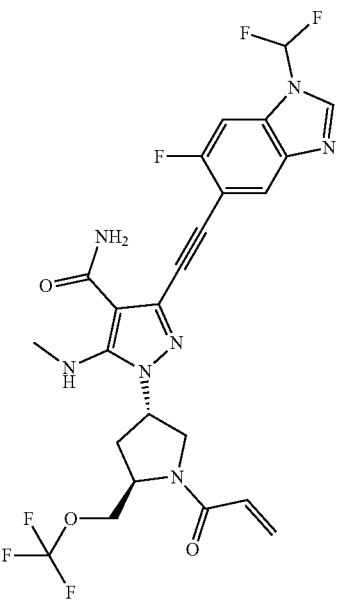 [SMILES: C=CC(=O)N1C[C@@H](n2nc(C#Cc3cc4ncn(C(F)F)c4cc3F)c(C(N)=O)c2NC)C[C@@H]1COC(F)(F)F] | 3-[2-[1-(Difluoromethyl)-6-fluoro-1,3-benzodiazol-5-yl]ethynyl]-5-(methylamino)-1-[(3S,5R)-1-(prop-2-enoyl)-5-[(trifluoromethoxy)methyl]pyrrolidin-3-yl]pyrazole-4-carboxamide |

TABLE 1-continued
| Synthetic Chemistry Example | Compound Structure | Compound Name |
|---|---|---|
| 82 | 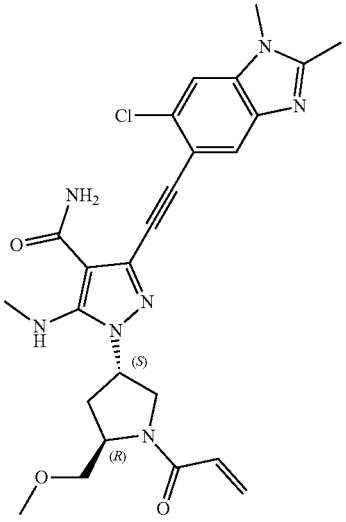 | 3-[2-(6-Chloro-1,2-dimethyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |
| 83 | 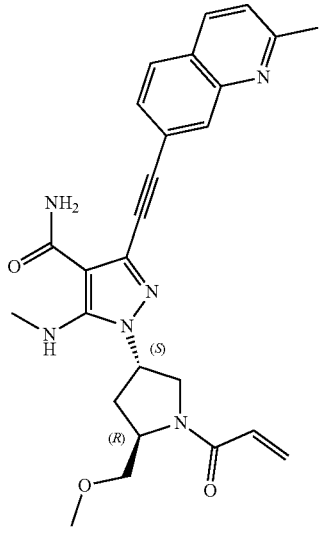 | 1-[(3S,5R)-5-(Methoxymethyl)-1-(prop-2-enoyl)pyrrolidin-3-yl]-5-(methylamino)-3-[2-(2-methylquinolin-7-yl)ethynyl]pyrazole-4-carboxamide |

TABLE 1-continued
| Synthetic Chemistry Example | Compound Structure | Compound Name |
|---|---|---|
| 84 | 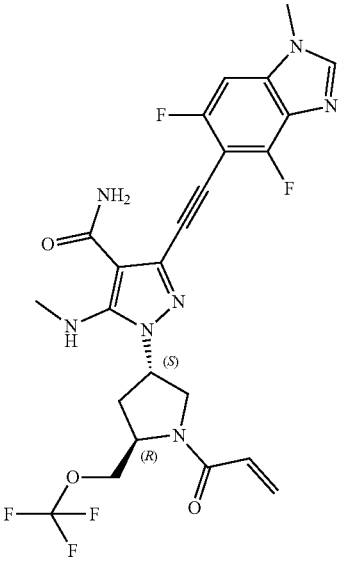 | 3-[2-(4,6-Difluoro-1-methyl-1,3-benzodiazol-5-yl)ethynyl]-5-(methylamino)-1-[(3S,5R)-1-(prop-2-enoyl)-5-[(trifluoromethoxy)methyl]pyrrolidin-3-yl]pyrazole-4-carboxamide |
| 85 | 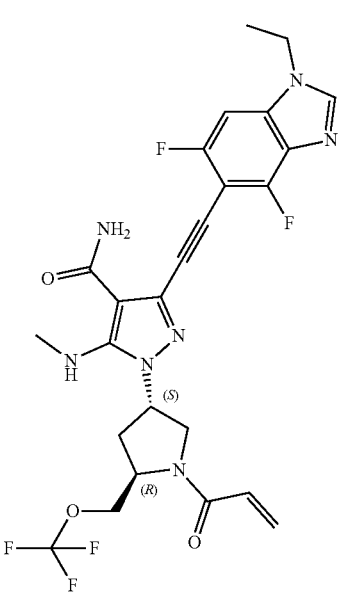 | 3-[2-(1-Ethyl-4,6-difluoro-1,3-benzodiazol-5-yl)ethynyl]-5-(methylamino)-1-[(3S,5R)-1-(prop-2-enoyl)-5-[(trifluoromethoxy)methyl]pyrrolidin-3-yl]pyrazole-4-carboxamide |

TABLE 1-continued

| Synthetic Chemistry Example | Compound Structure | Compound Name |
|---|---|---|
| 86 | 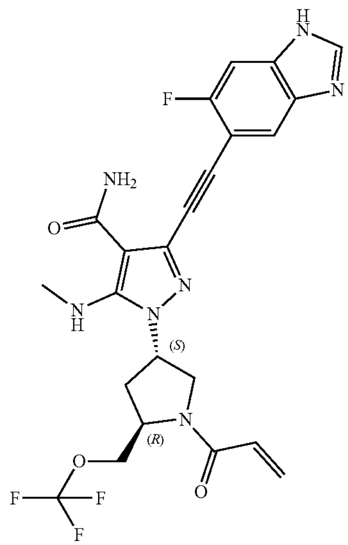 | 3-[2-(6-Fluoro-1H-1,3-benzodiazol-5-yl)ethynyl]-5-(methylamino)-1-[(3S,5R)-1-(prop-2-enoyl)-5-[(trifluoromethoxy)methyl]pyrrolidin-3-yl]pyrazole-4-carboxamide |
| 87 | 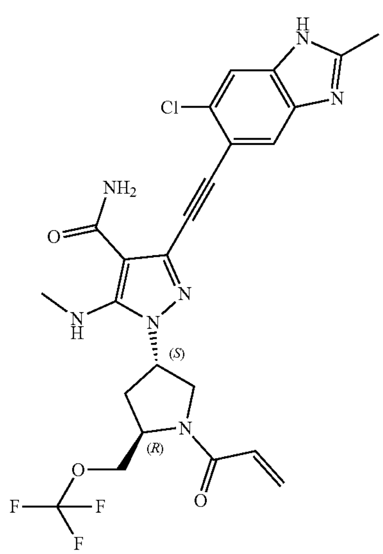 | 3-[2-(6-Chloro-2-methyl-1H-1,3-benzodiazol-5-yl)ethynyl]-5-(methylamino)-1-[(3S,5R)-1-(prop-2-enoyl)-5-[(trifluoromethoxy)methyl]pyrrolidin-3-yl]pyrazole-4-carboxamide |

TABLE 1-continued

| Synthetic Chemistry Example | Compound Structure | Compound Name |
|---|---|---|
| 88 | 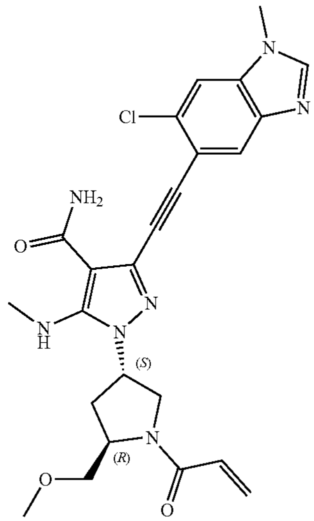 | 3-[2-(6-Chloro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |
| 89 | 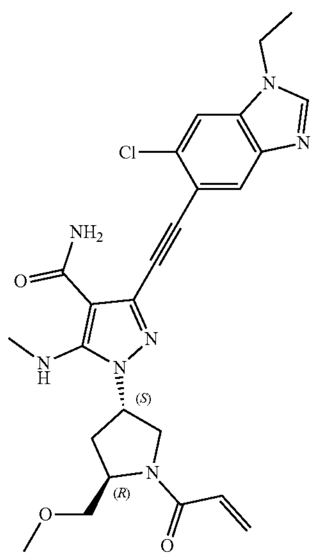 | 3-[2-(6-Chloro-1-ethyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |
| 90 | 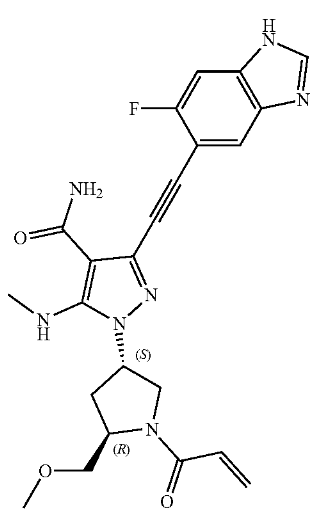 | 3-[2-(6-Fluoro-1H-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |

TABLE 1-continued

| Synthetic Chemistry Example | Compound Structure | Compound Name |
|---|---|---|
| 91 | 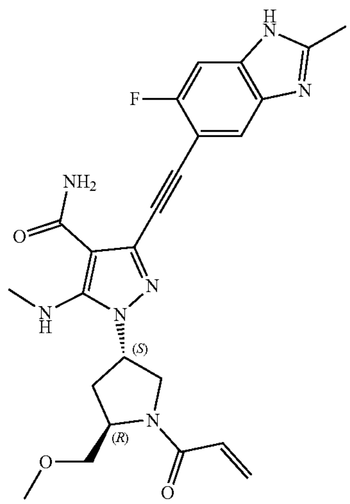 | 3-[2-(6-Fluoro-2-methyl-1H-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |
| 92 | 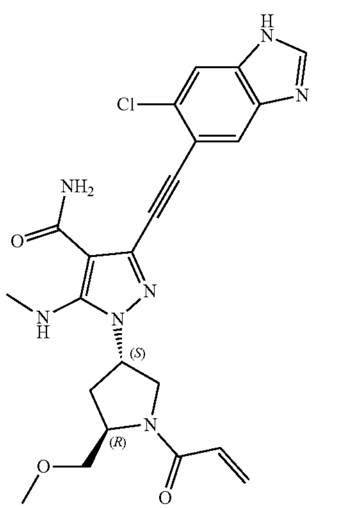 | 3-[2-(6-Chloro-1H-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |
| 93 | 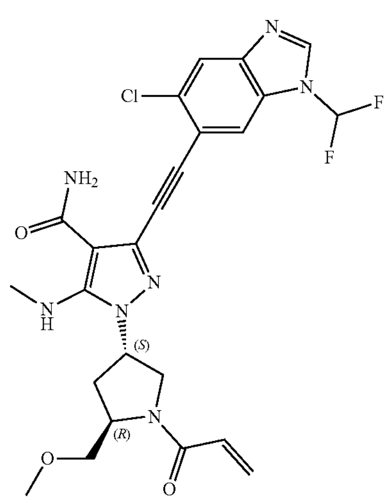 | 3-[2-[6-Chloro-3-(difluoromethyl)-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide |

TABLE 1-continued
| Synthetic Chemistry Example | Compound Structure | Compound Name |
|---|---|---|
| 94 | 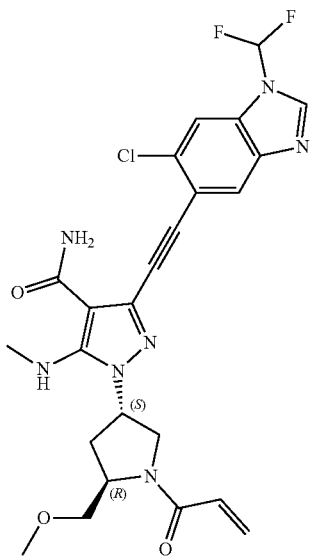 | 3-[2-[6-Chloro-1-(difluoromethyl)-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide |
| 95 | 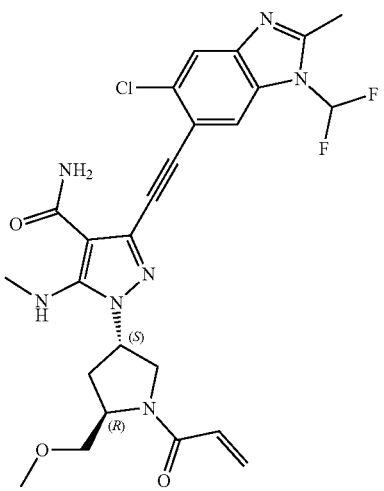 | 3-[2-[6-Chloro-3-(difluoromethyl)-2-methyl-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide |

TABLE 1-continued

| Synthetic Chemistry Example | Compound Structure | Compound Name |
|---|---|---|
| 96 | 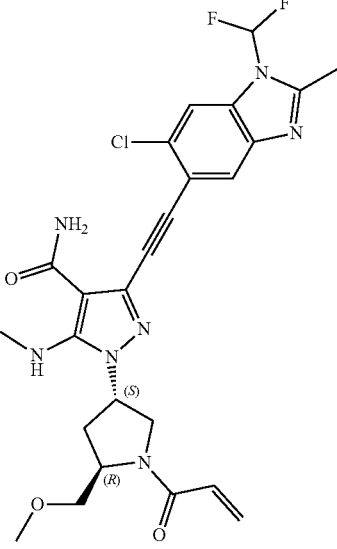 | 3-[2-[6-Chloro-1-(difluoromethyl)-2-methyl-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide |
| 97 | 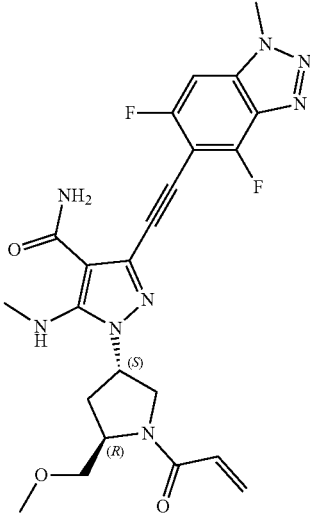 | 3-[2-(4,6-Difluoro-1-methyl-1,2,3-benzotriazol-5-yl)ethynyl]-1-[(3S,5R)-5-(methoxymethyl)-1-(prop-2-enoyl)pyrrolidin-3-yl]-5-(methylamino)pyrazole-4-carboxamide |
| 98 | 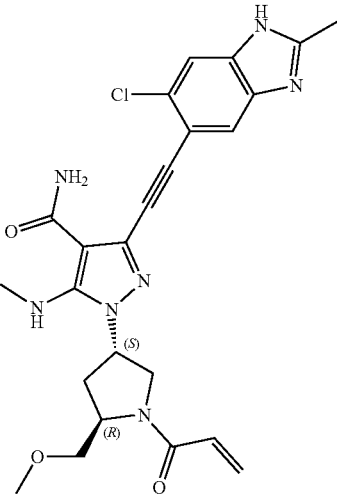 | 3-[2-(6-Chloro-2-methyl-1H-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamid |

TABLE 1-continued
| Synthetic Chemistry Example | Compound Structure | Compound Name |
|---|---|---|
| 99 | 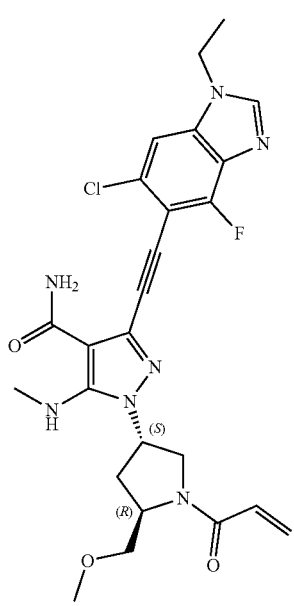 | 3-[2-(6-Chloro-1-ethyl-4-fluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |
| 100 | 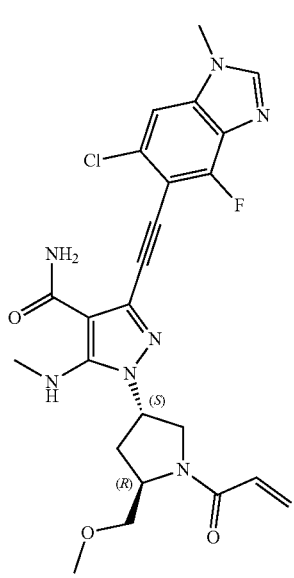 | 3-[2-(6-Chloro-4-fluoro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |

TABLE 1-continued
| Synthetic Chemistry Example | Compound Structure | Compound Name |
|---|---|---|
| 101 | 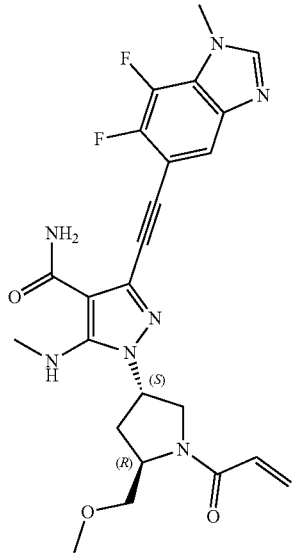 | 3-[2-(6,7-Difluoro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |
| 102 | 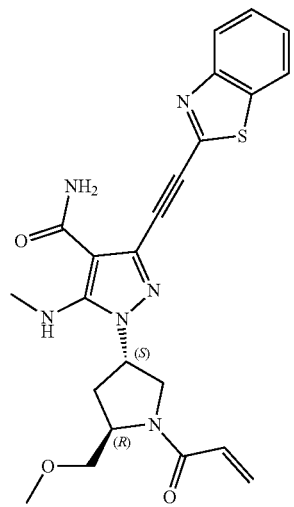 | 3-[2-(1,3-Benzothiazol-2-yl)ethynyl]-1-[(3S,5R)-5-(methoxymethyl)-1-(prop-2-enoyl)pyrrolidin-3-yl]-5-(methylamino)pyrazole-4-carboxamide |

TABLE 1-continued

| Synthetic Chemistry Example | Compound Structure | Compound Name |
|---|---|---|
| 103 | 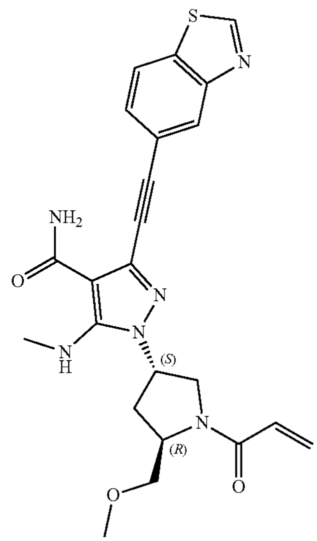 | 3-[2-(1,3-Benzothiazol-2-yl)ethynyl]-1-[(3S,5R)-5-(methoxymethyl)-1-(prop-2-enoyl)pyrrolidin-3-yl]-5-(methylamino)pyrazole-4-carboxamide |
| 104 | 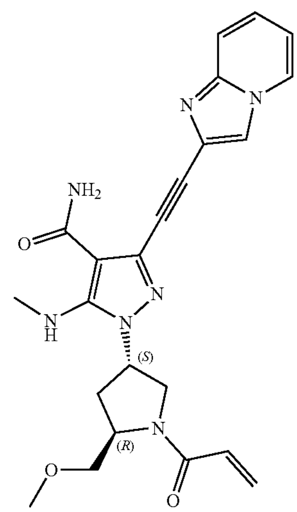 | 3-(2-[Imidazol[1,2-a]pyridin-2-yl]ethynyl)-1-[(3S,5R)-5-(methoxymethyl)-1-(prop-2-enoyl)pyrrolidin-3-yl]-5-(methylamino)pyrazole-4-carboxamide |
| 105 | 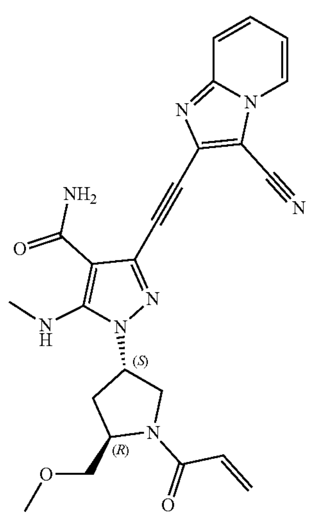 | 1-((3S,5R)-1-Acryloyl-5-(methoxymethyl)pyrrolidin-3-yl)-3-((3-cyanoimidazo[1,2-a]pyridin-2-yl)ethynyl)-5-(methylamino)-1H-pyrazole-4-carboxamide |

TABLE 1-continued

| Synthetic Chemistry Example | Compound Structure | Compound Name |
|---|---|---|
| 106 | 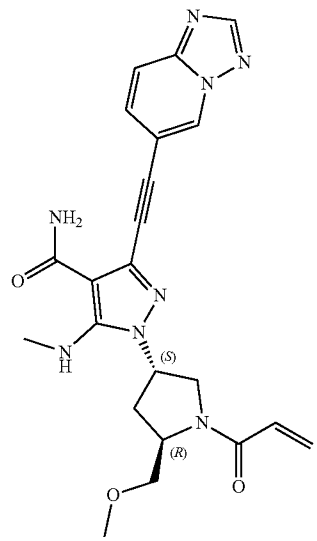 | 1-[(3S,5R)-5-(Methoxymethyl)-1-(prop-2-enoyl)pyrrolidin-3-yl]-5-(methylamino)-3-(2-[[1,2,4]triazolo[1,5-a]pyridin-6-yl]ethynyl)pyrazole-4-carboxamide |
| 107 | 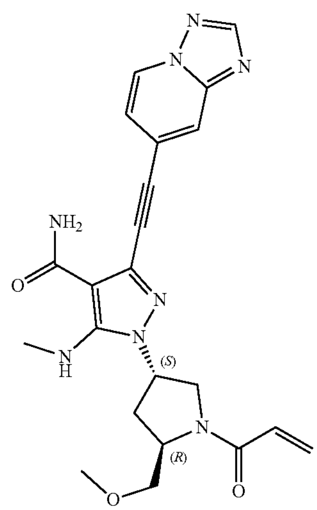 | 1-[(3S,5R)-5-(Methoxymethyl)-1-(prop-2-enoyl)pyrroldin-3-yl]-5-(methylamino)-3-(2-[[1,2,4]triazolo[1,5-a]pyridin-7-yl]ethynyl)pyrazole-4-carboxamide |
| 108 | 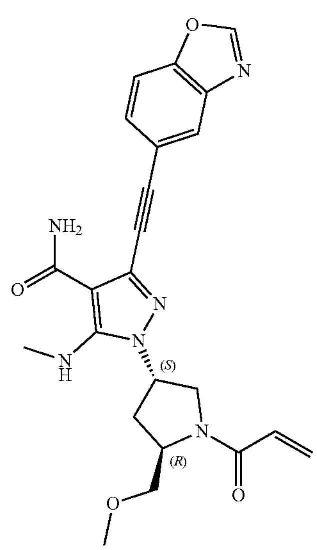 | 3-[2-(1,3-Benzoxazol-5-yl)ethynyl]-1-[(3S,5R)-5-(methoxymethyl)-1-(prop-2-enoyl)pyrrolidin-3-yl]-5-(methylamino)pyrazole-4-carboxamide |

TABLE 1-continued
| Synthetic Chemistry Example | Compound Structure | Compound Name |
|---|---|---|
| 109 | 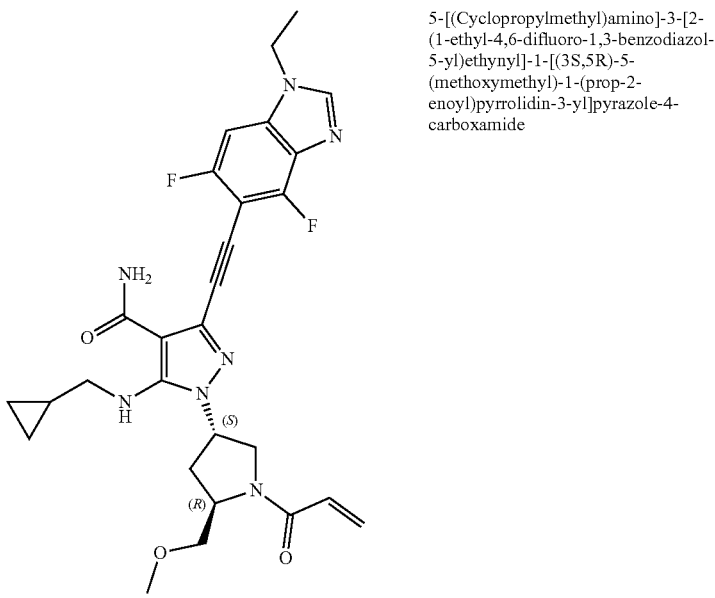 | 5-[(Cyclopropylmethyl)amino]-3-[2-(1-ethyl-4,6-difluoro-1,3-benzodiazol-5-yl)ethynyl]-1-[(3S,5R)-5-(methoxymethyl)-1-(prop-2-enoyl)pyrrolidin-3-yl]pyrazole-4-carboxamide |
| 110 | 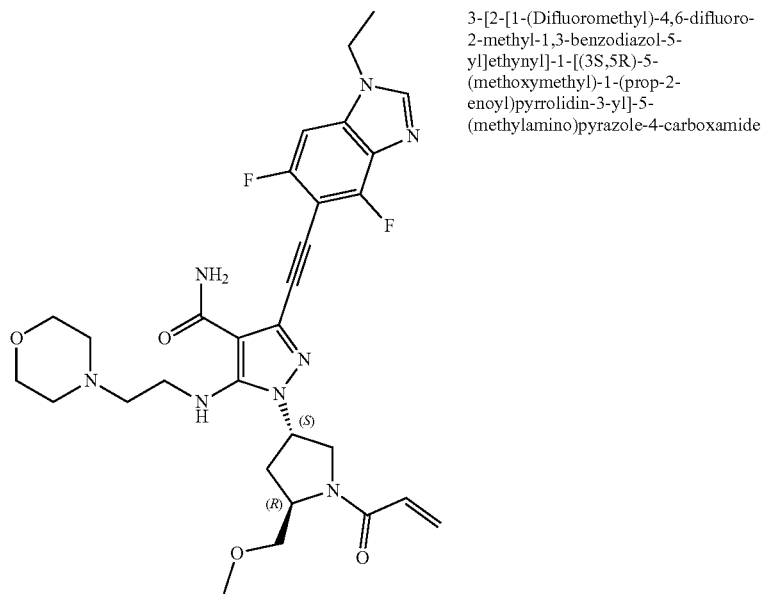 | 3-[2-[1-(Difluoromethyl)-4,6-difluoro-2-methyl-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide |

TABLE 1-continued
| Synthetic Chemistry Example | Compound Structure | Compound Name |
|---|---|---|
| 111 | 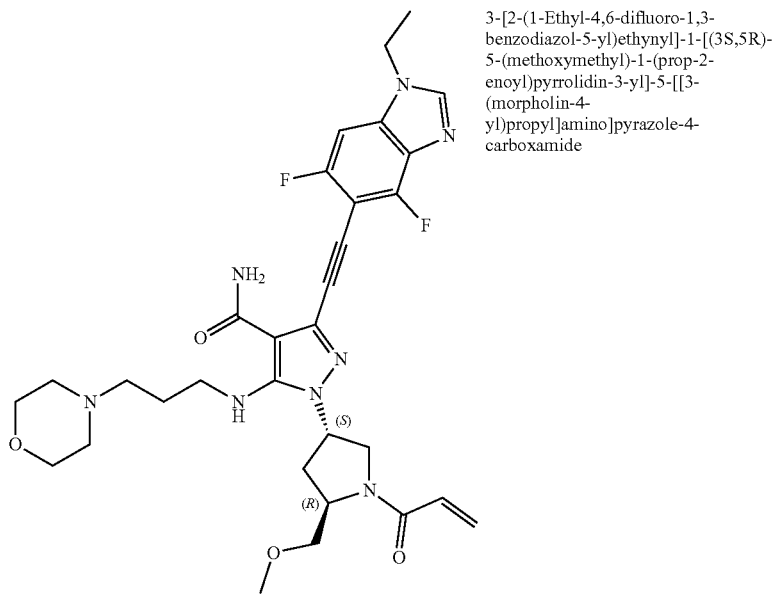 | 3-[2-(1-Ethyl-4,6-difluoro-1,3-benzodiazol-5-yl)ethynyl]-1-[(3S,5R)-5-(methoxymethyl)-1-(prop-2-enoyl)pyrrolidin-3-yl]-5-[[3-(morpholin-4-yl)propyl]amino]pyrazole-4-carboxamide |
| 112 | 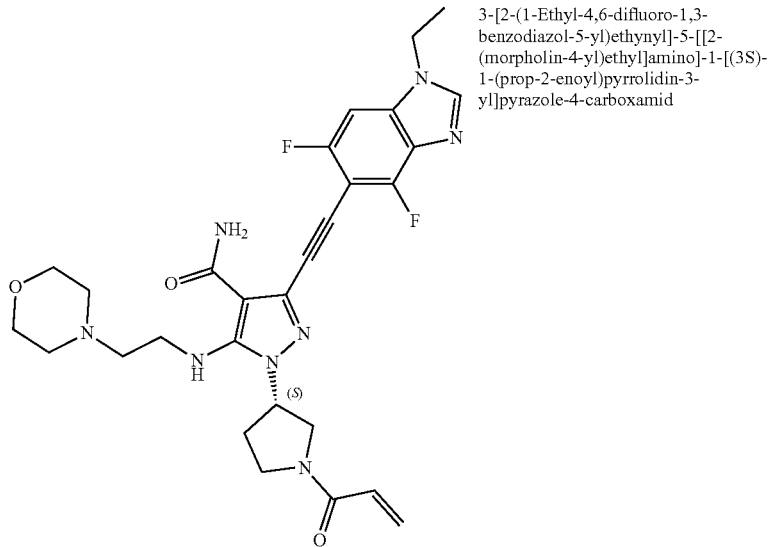 | 3-[2-(1-Ethyl-4,6-difluoro-1,3-benzodiazol-5-yl)ethynyl]-5-[[2-(morpholin-4-yl)ethyl]amino]-1-[(3S)-1-(prop-2-enoyl)pyrrolidin-3-yl]pyrazole-4-carboxamid |

TABLE 1-continued
| Synthetic Chemistry Example | Compound Structure | Compound Name |
|---|---|---|
| 113 | 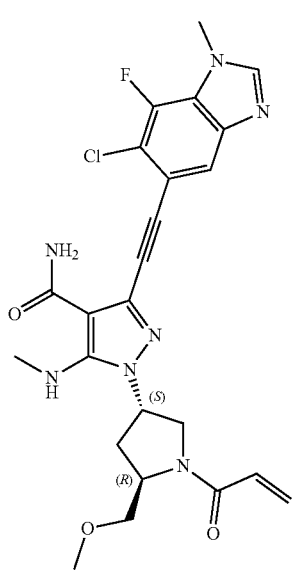 | 3-[2-(6-Chloro-7-fluoro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |
| 114 | 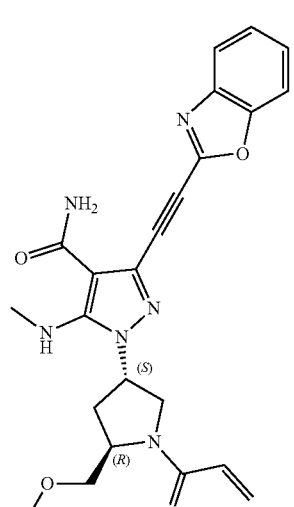 | 3-[2-(1,3-Benzoxazol-2-yl)ethynyl]-1-[(3S,5R)-5-(methoxymethyl)-1-(prop-2-enoyl)pyrrolidin-3-yl]-5-(methylamino)pyrazole-4-carboxamide |

TABLE 1-continued
| Synthetic Chemistry Example | Compound Structure | Compound Name |
|---|---|---|
| 115 | 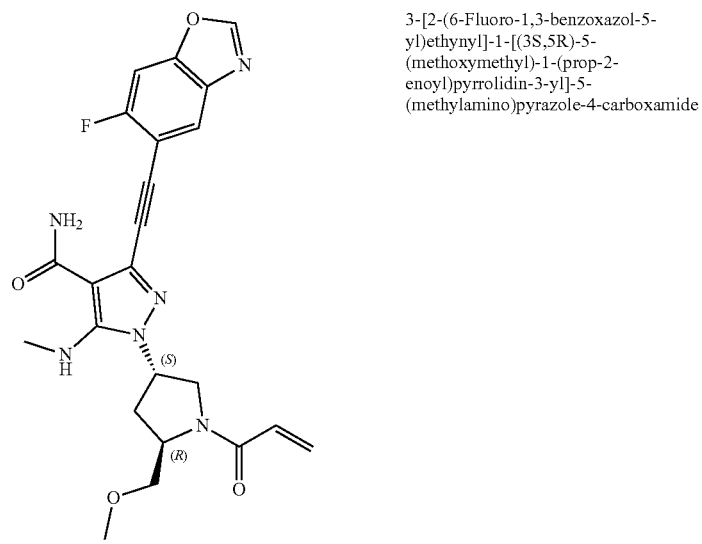 | 3-[2-(6-Fluoro-1,3-benzoxazol-5-yl)ethynyl]-1-[(3S,5R)-5-(methoxymethyl)-1-(prop-2-enoyl)pyrrolidin-3-yl]-5-(methylamino)pyrazole-4-carboxamide |
| 116 | 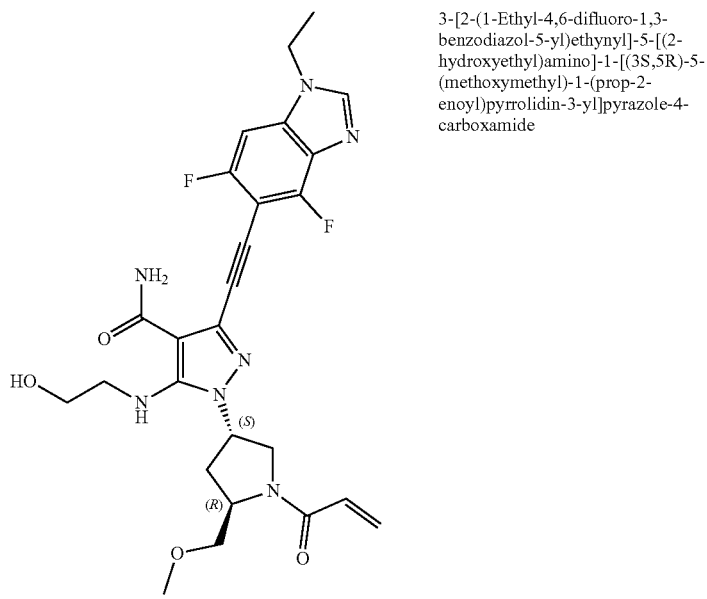 | 3-[2-(1-Ethyl-4,6-difluoro-1,3-benzodiazol-5-yl)ethynyl]-5-[(2-hydroxyethyl)amino]-1-[(3S,5R)-5-(methoxymethyl)-1-(prop-2-enoyl)pyrrolidin-3-yl]pyrazole-4-carboxamide |

TABLE 1-continued
| Synthetic Chemistry Example | Compound Structure | Compound Name |
|---|---|---|
| 117 | 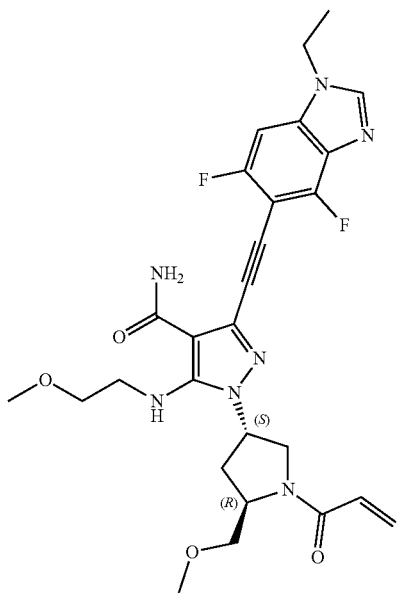 | 3-[2-(1-Ethyl-4,6-difluoro-1,3-benzodiazol-5-yl)ethynyl]-5-[(2-methoxyethyl)amino]-1-[(3S,5R)-5-(methoxymethyl)-1-(prop-2-enoyl)pyrrolidin-3-yl]pyrazole-4-carboxamide |
| 118 | 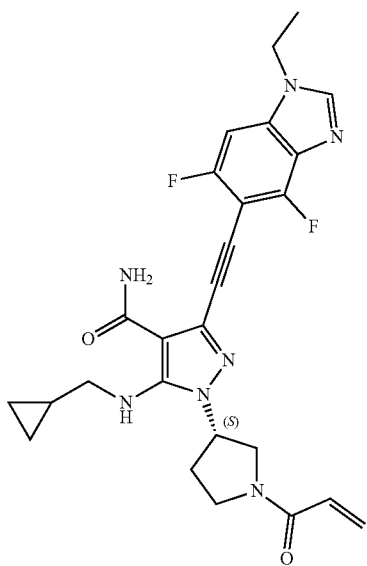 | 5-[(Cyclopropylmethyl)amino]-3-[2-(1-ethyl-4,6-difluoro-1,3-benzodiazol-5-yl)ethynyl]-1-[(3S)-1-(prop-2-enoyl)pyrrolidin-3-yl]pyrazole-4-carboxamide |

TABLE 1-continued
| Synthetic Chemistry Example | Compound Structure | Compound Name |
|---|---|---|
| 119 | 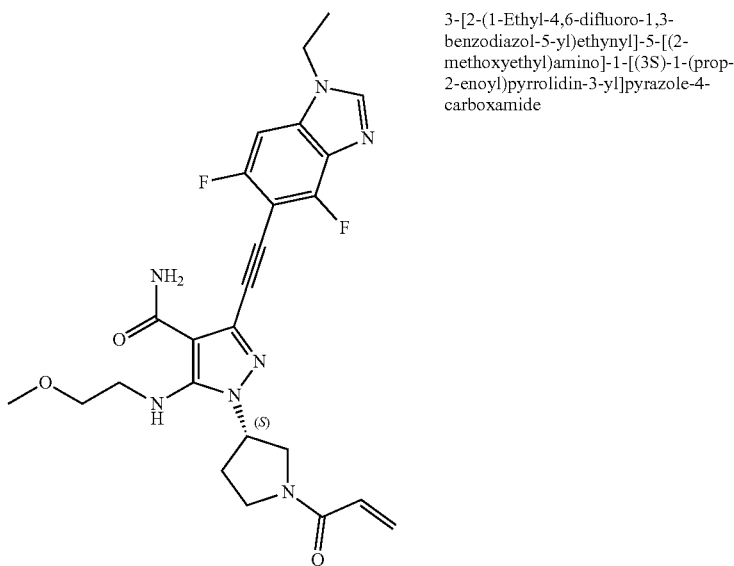 | 3-[2-(1-Ethyl-4,6-difluoro-1,3-benzodiazol-5-yl)ethynyl]-5-[(2-methoxyethyl)amino]-1-[(3S)-1-(prop-2-enoyl)pyrrolidin-3-yl]pyrazole-4-carboxamide |
| 120 | 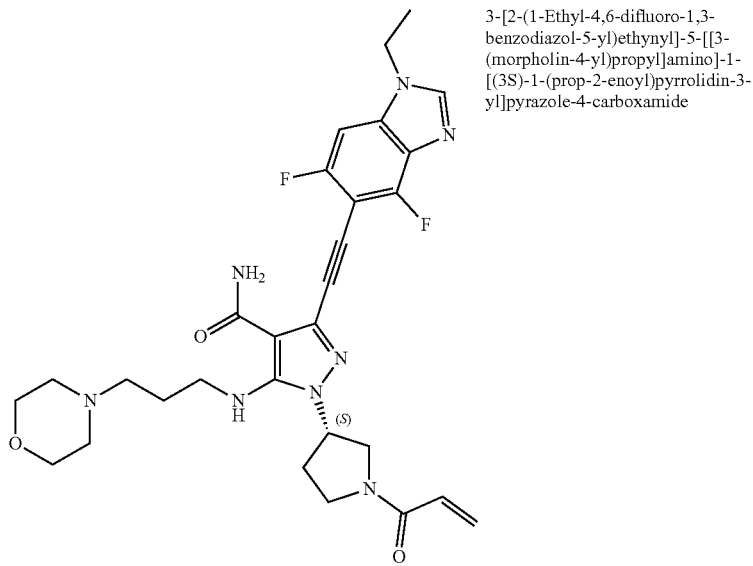 | 3-[2-(1-Ethyl-4,6-difluoro-1,3-benzodiazol-5-yl)ethynyl]-5-[[3-(morpholin-4-yl)propyl]amino]-1-[(3S)-1-(prop-2-enoyl)pyrrolidin-3-yl]pyrazole-4-carboxamide |

TABLE 1-continued
| Synthetic Chemistry Example | Compound Structure | Compound Name |
|---|---|---|
| 121 | 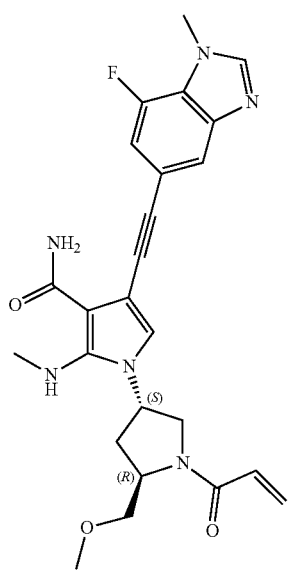 | 1-((3S,5R)-1-Acryloyl-5-(methoxymethyl)pyrrolidin-3-yl)-3-((4-fluoro-1-methyl-1H-benzo[d]imidazol-5-yl)ethynyl)-5-(methylamino)-1H-pyrazole-4-carboxamide |
| 122 | 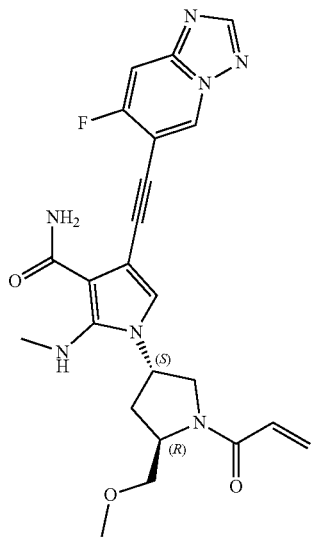 | 3-(2-[7-Fluoro-[1,2,4]triazolo[1,5-a]pyridin-6-yl]ethynyl)-1-[(3S,5R)-5-(methoxymethyl)-1-(prop-2-enoyl)pyrrolidin-3-yl]-5-(methylamino)pyrazole-4-carboxamide |

TABLE 1-continued

| Synthetic Chemistry Example | Compound Structure | Compound Name |
|---|---|---|
| 123 | 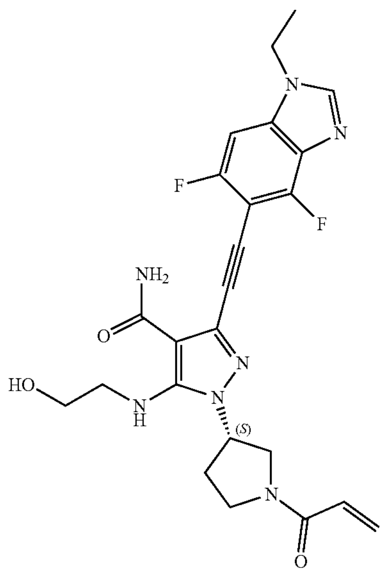 | 3-[2-(1-Ethyl-4,6-difluoro-1,3-benzodiazol-5-yl)ethynyl]-5-[(2-hydroxyethyl)amino]-1-[(3S)-1-(prop-2-enoyl)pyrroldiin-3-yl]pyrazole-4-carboxamide |
| 124 | 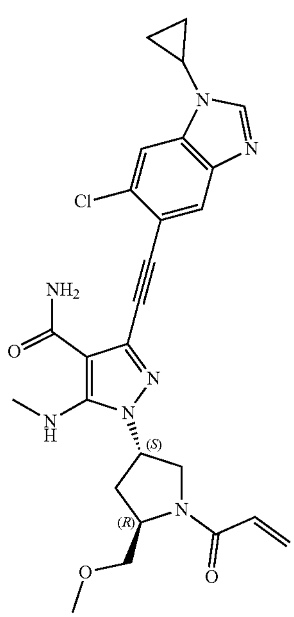 | 3-[2-(6-Chloro-1-cyclopropyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |

TABLE 1-continued
| Synthetic Chemistry Example | Compound Structure | Compound Name |
|---|---|---|
| 125 | 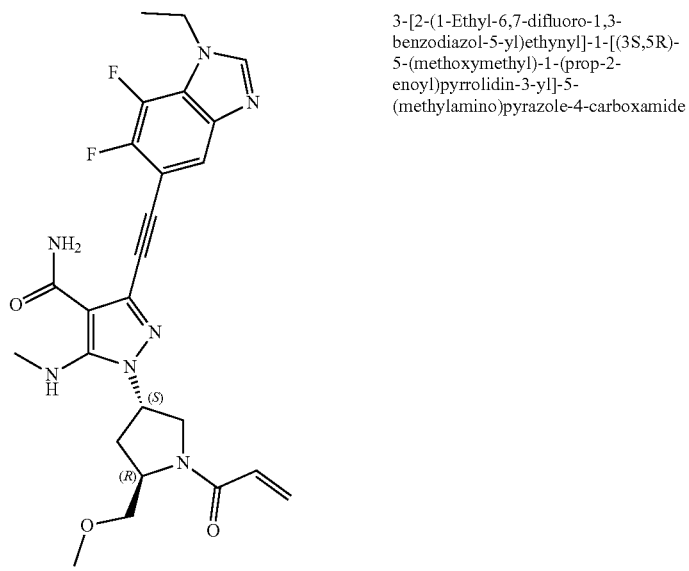 | 3-[2-(1-Ethyl-6,7-difluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |
| 126 | 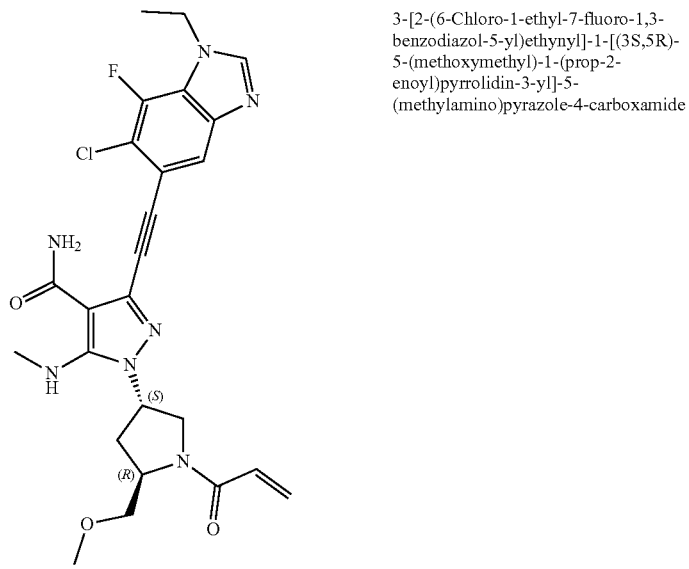 | 3-[2-(6-Chloro-1-ethyl-7-fluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |

TABLE 1-continued

| Synthetic Chemistry Example | Compound Structure | Compound Name |
|---|---|---|
| 127 | 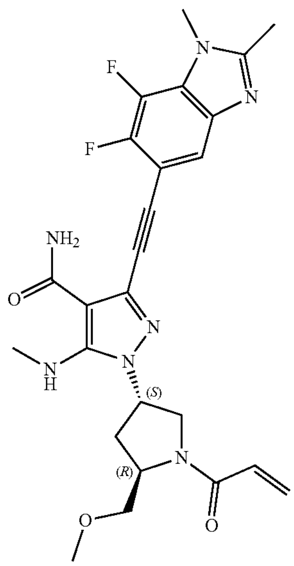 | 3-[2-(6,7-Difluoro-1,2-dimethyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |
| 128 | 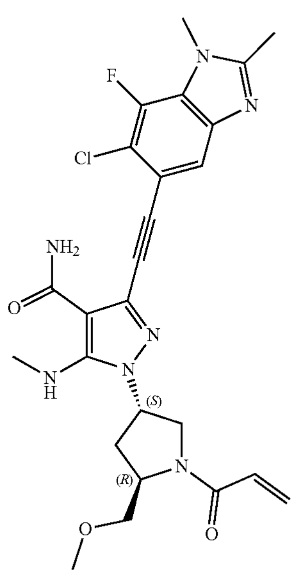 | 3-[2-(6-Chloro-7-fluoro-1,2-dimethyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |

TABLE 1-continued
| Synthetic Chemistry Example | Compound Structure | Compound Name |
|---|---|---|
| 129 | 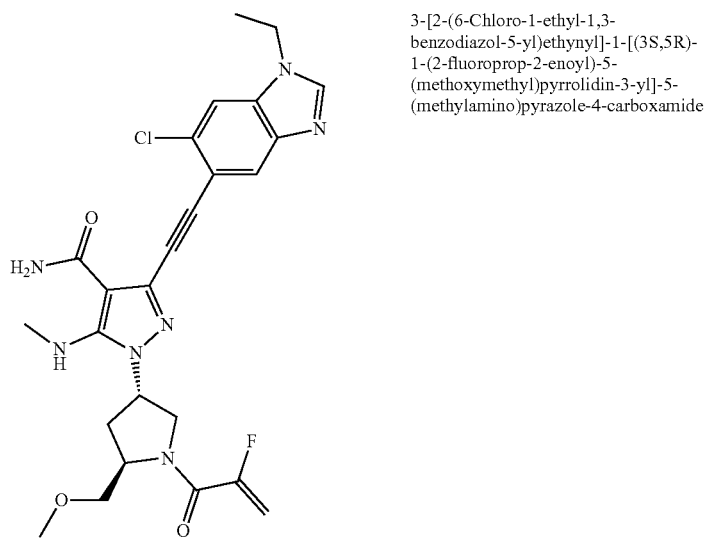 | 3-[2-(6-Chloro-1-ethyl-1,3-benzodiazol-5-yl)ethynyl]-1-[(3S,5R)-1-(2-fluoroprop-2-enoyl)-5-(methoxymethyl)pyrrolidin-3-yl]-5-(methylamino)pyrazole-4-carboxamide |
| 130 | 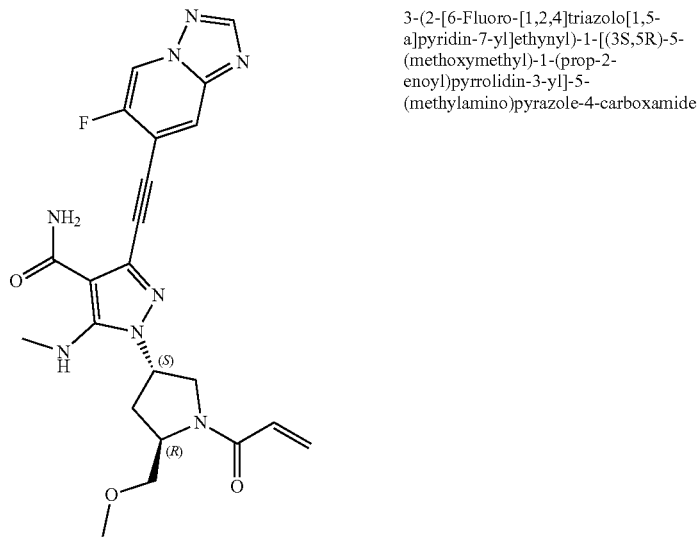 | 3-(2-[6-Fluoro-[1,2,4]triazolo[1,5-a]pyridin-7-yl]ethynyl)-1-[(3S,5R)-5-(methoxymethyl)-1-(prop-2-enoyl)pyrrolidin-3-yl]-5-(methylamino)pyrazole-4-carboxamide |

TABLE 1-continued

| Synthetic Chemistry Example | Compound Structure | Compound Name |
|---|---|---|
| 131 | 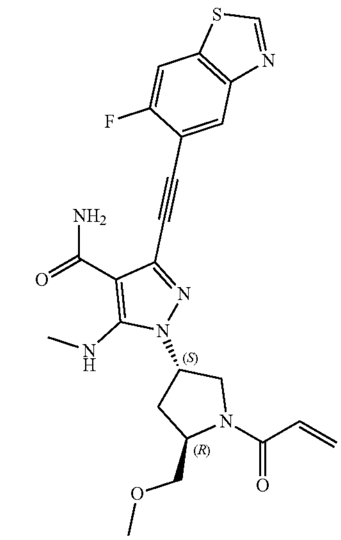 | 3-[2-(6-Fluoro-1,3-benzothiazol-5-yl)ethynyl]-1-[(3S,5R)-5-(methoxymethyl)-1-(prop-2-enoyl)pyrrolidin-3-yl]-5-(methylamino)pyrazole-4-carboxamide |
| 132 | 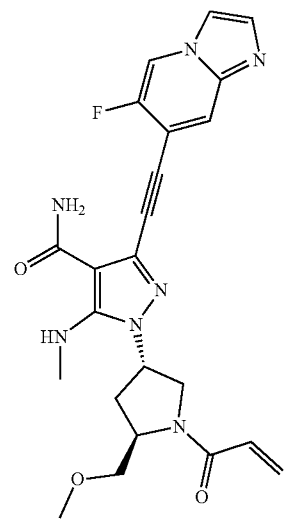 [SMILES: C=CC(=O)N1C[C@@H](n2nc(C#Cc3cc4nccn4cc3F)c(C(N)=O)c2NC)C[C@@H]1COC] | 1-((3S,5R)-1-Acryloyl-5-(methoxymethyl)pyrrolidin-3-yl)-3-((6-fluoroimidazo[1,2-a]pyridin-7-yl)ethynyl)-5-(methylamino)-1H-pyrazole-4-carboxamide |
| 133 | 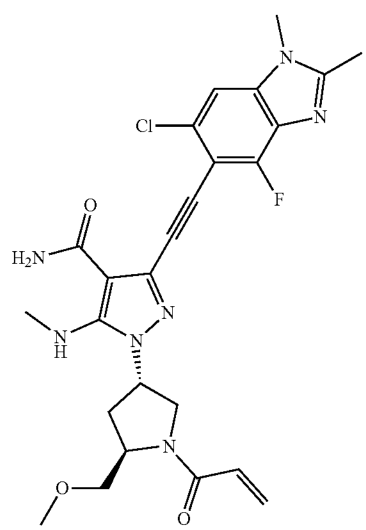 | 3-[2-(6-Chloro-4-fluoro-1,2-dimethyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |

TABLE 1-continued

| Synthetic Chemistry Example | Compound Structure | Compound Name |
|---|---|---|
| 134 | 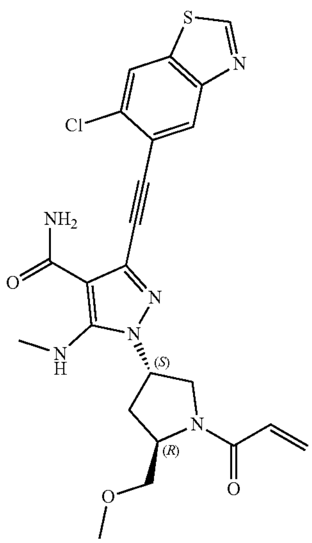 | 3-[2-(6-Chloro-1,3-benzothiazol-5-yl)ethynyl]-1-[(3S,5R)-5-(methoxymethyl)-1-(prop-2-enoyl)pyrrolidin-3-yl]-5-(methylamino)pyrazole-4-carboxamide |
| 135 | 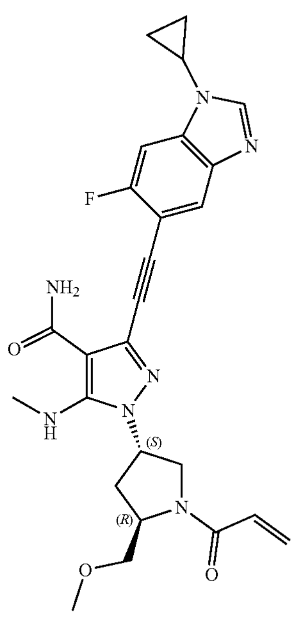 | 3-[2-(1-Cyclopropyl-6-fluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |

| Synthetic Chemistry Example | Compound Structure | Compound Name |
|---|---|---|
| 136 | 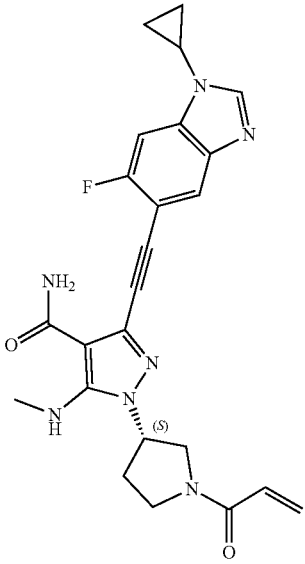 | 3-[2-(1-Cyclopropyl-6-fluoro-1,3-benzodiazol-5-yl)ethynyl]-5-(methylamino)-1-[(3S)-1-(prop-2-enoyl)pyrrolidin-3-yl]pyrazole-4-carboxamide |
| 137 | 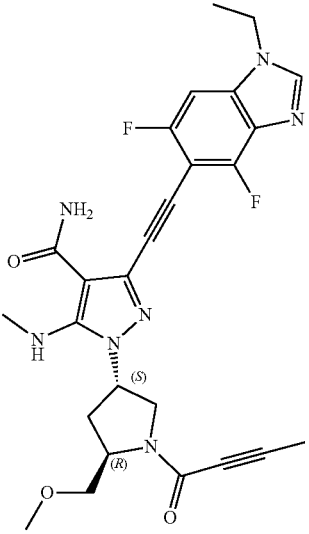 | 1-((3S,5R)-1-(but-2-ynoyl)-5-(methoxymethyl)pyrrolidin-3-yl)-3-((1-ethyl-4,6-difluoro-1H-benzo[d]imidazol-5-yl)ethynyl)-5-(methylamino)-1H-pyrazole-4-carboxamide |

TABLE 1-continued

| Synthetic Chemistry Example | Compound Structure | Compound Name |
|---|---|---|
| 138 | 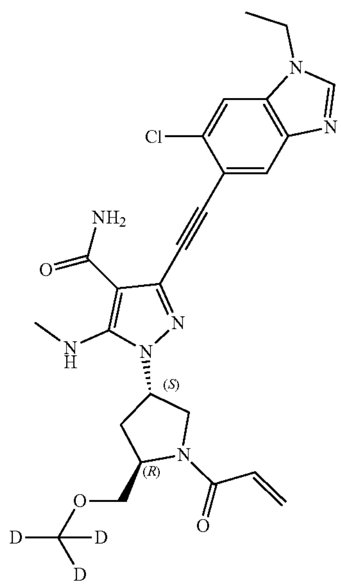 | 1-((3S,5R)-1-acryloyl-5-((methoxy-d3)methyl)pyrrolidin-3-yl)-3-((6-chloro-1-ethyl-1H-benzo[d]imidazol-5-yl)ethynyl)-5-(methylamino)-1H-pyrazole-4-carboxamide |
| 139 | 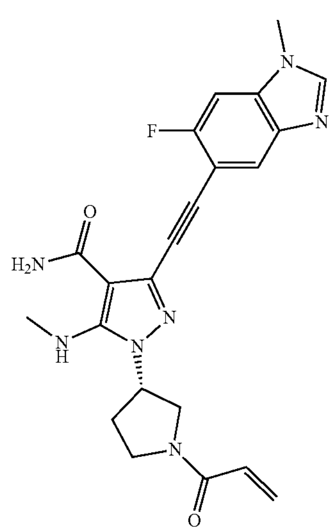 [SMILES: C=CC(=O)N1CC[C@H](n2nc(C#Cc3cc4ncn(C)c4cc3F)c(C(N)=O)c2NC)C1] | 3-[2-(6-fluoro-1-methyl-1,3-benzodiazol-5-yl)ethynyl]-5-(methylamino)-1-[(3S)-1-(prop-2-enoyl)pyrrolidin-3-yl]pyrazole-4-carboxamide |

TABLE 1-continued
| Synthetic Chemistry Example | Compound Structure | Compound Name |
|---|---|---|
| 140 | 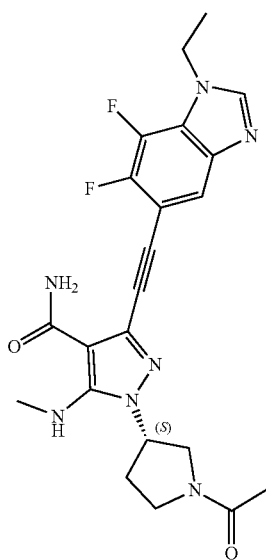 | 3-[2-(1-ethyl-6,7-difluoro-1,3-benzodiazol-5-yl)ethynyl]-5-(methylamino)-1-[(3S)-1-(prop-2-enoyl)pyrrolidin-3-yl]pyrazole-4-carboxamide |
| 141 | 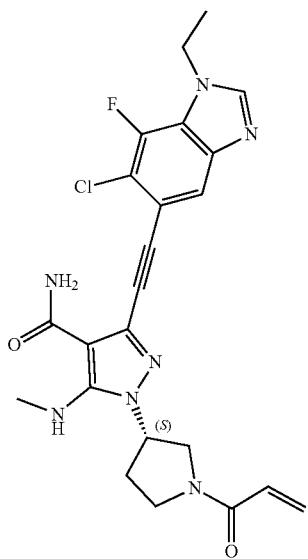 | 3-[2-(6-chloro-1-ethyl-7-fluoro-1,3-benzodiazol-5-yl)ethynyl]-5-(methylamino)-1-[(3S)-1-(prop-2-enoyl)pyrrolidin-3-yl]pyrazole-4-carboxamide |

TABLE 1-continued
| Synthetic Chemistry Example | Compound Structure | Compound Name |
|---|---|---|
| 142 | 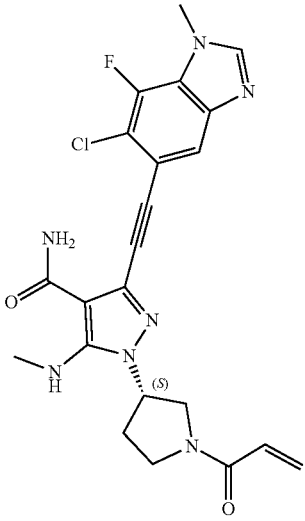 | 3-[2-(6-chloro-7-fluoro-1-methyl-1,3-benzodiazol-5-yl)ethynyl]-5-(methylamino)-1-[(3S)-1-(prop-2-enoyl)pyrrolidin-3-yl]pyrazole-4-carboxamide |
| 143 | 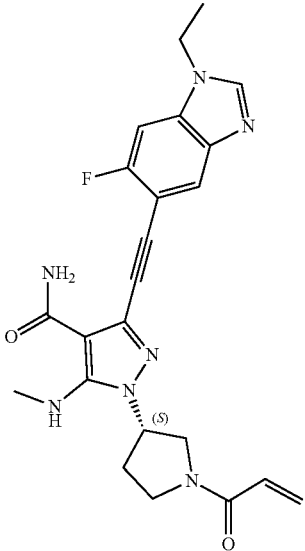 | 3-[2-(1-ethyl-6-fluoro-1,3-benzodiazol-5-yl)ethynyl]-5-(methylamino)-1-[(3S)-1-(prop-2-enoyl)pyrrolidin-3-yl]pyrazole-4-carboxamide |

TABLE 1-continued
| Synthetic Chemistry Example | Compound Structure | Compound Name |
|---|---|---|
| 144 | 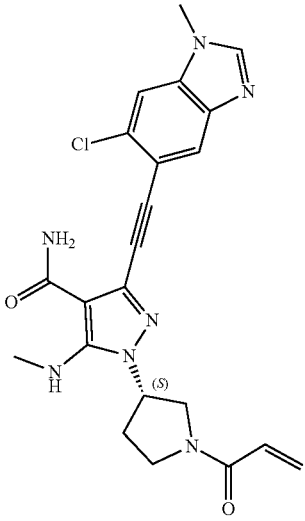 | 3-[2-(6-chloro-1-methyl-1,3-benzodiazol-5-yl)ethynyl]-5-(methylamino)-1-[(3S)-1-(prop-2-enoyl)pyrrolidin-3-yl]pyrazole-4-carboxamide |
| 145 | 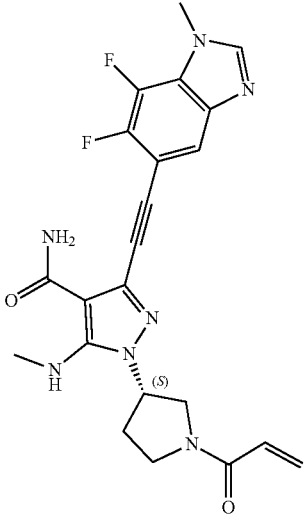 | 3-[2-(6,7-difluoro-1-methyl-1,3-benzodiazol-5-yl)ethynyl]-5-(methylamino)-1-[(3S)-1-(prop-2-enoyl)pyrrolidin-3-yl]pyrazole-4-carboxamide |

TABLE 1-continued

| Synthetic Chemistry Example | Compound Structure | Compound Name |
|---|---|---|
| 147 | 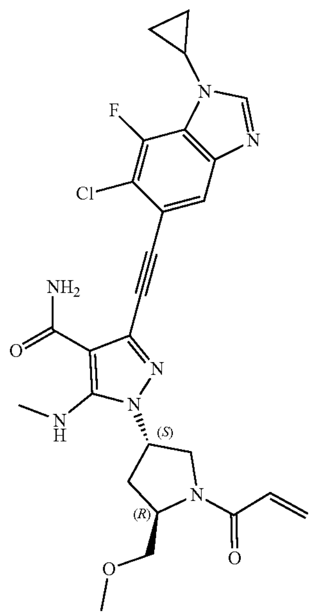 | 3-[2-(6-chloro-1-cyclopropyl-7-fluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |
| 148 | 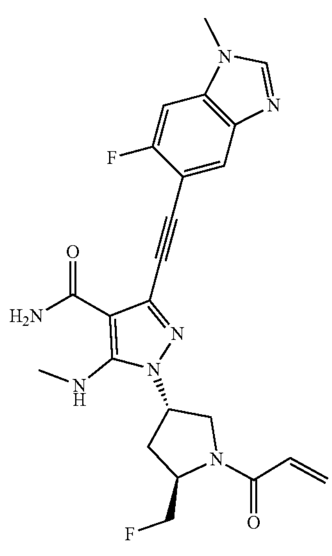 [SMILES: C=CC(=O)N1C[C@@H](n2nc(C#Cc3cc4ncn(C)c4cc3F)c(C(N)=O)c2NC)C[C@@H]1CF] | 3-[2-(6-fluoro-1-methyl-1,3-benzodiazol-5-yl)ethynyl]-1-[(3S,5R)-5-(fluoromethyl)-1-(prop-2-enoyl)pyrrolidin-3-yl]-5-(methylamino)pyrazole-4-carboxamide |

TABLE 1-continued
| Synthetic Chemistry Example | Compound Structure | Compound Name |
|---|---|---|
| 149 | 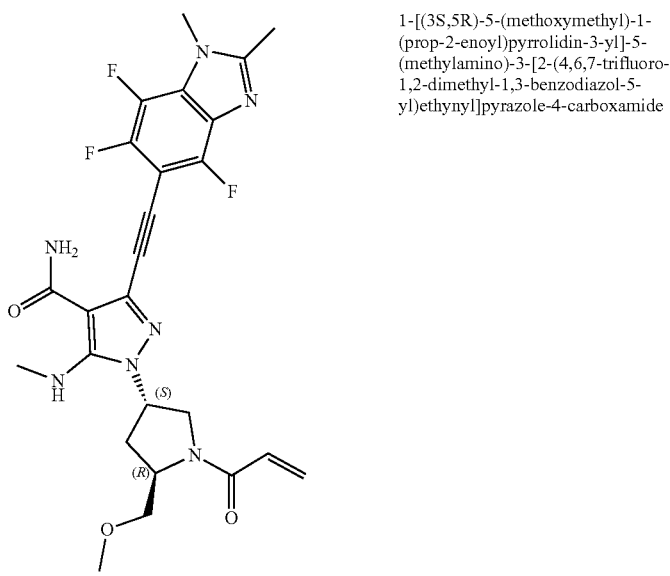 | 1-[(3S,5R)-5-(methoxymethyl)-1-(prop-2-enoyl)pyrrolidin-3-yl]-5-(methylamino)-3-[2-(4,6,7-trifluoro-1,2-dimethyl-1,3-benzodiazol-5-yl)ethynyl]pyrazole-4-carboxamide |
| 150 | 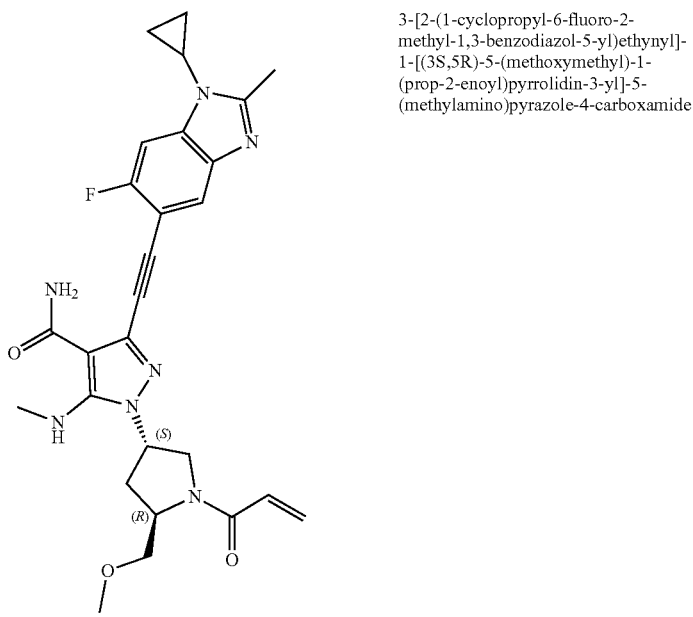 | 3-[2-(1-cyclopropyl-6-fluoro-2-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |

TABLE 1-continued

| Synthetic Chemistry Example | Compound Structure | Compound Name |
|---|---|---|
| 151 | 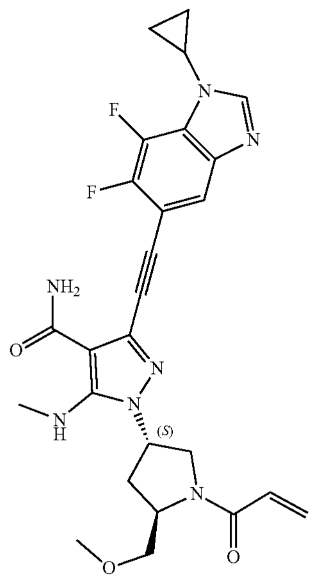 | 3-[2-(1-cyclopropyl-6,7-difluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |
| 152 | 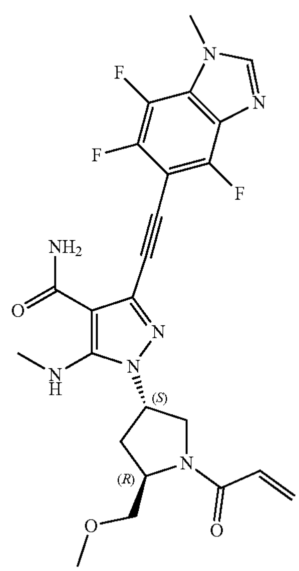 | 1-[(3S,5R)-5-(methoxymethyl)-1-(prop-2-enoyl)pyrrolidin-3-yl]-5-(methylamino)-3-[2-(4,6,7-trifluoro-1-methyl-1,3-benzodiazol-5-yl)ethynyl]pyrazole-4-carboxamide |

TABLE 1-continued
| Synthetic Chemistry Example | Compound Structure | Compound Name |
|---|---|---|
| 153 | 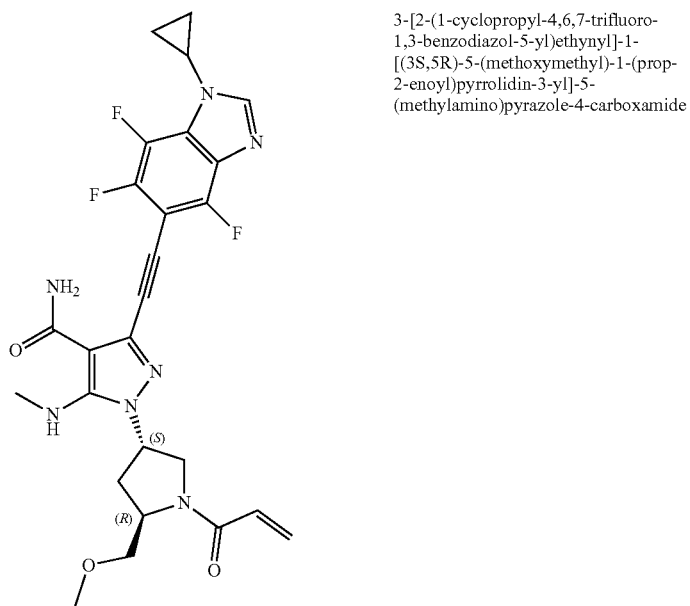 | 3-[2-(1-cyclopropyl-4,6,7-trifluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |
| 154 | 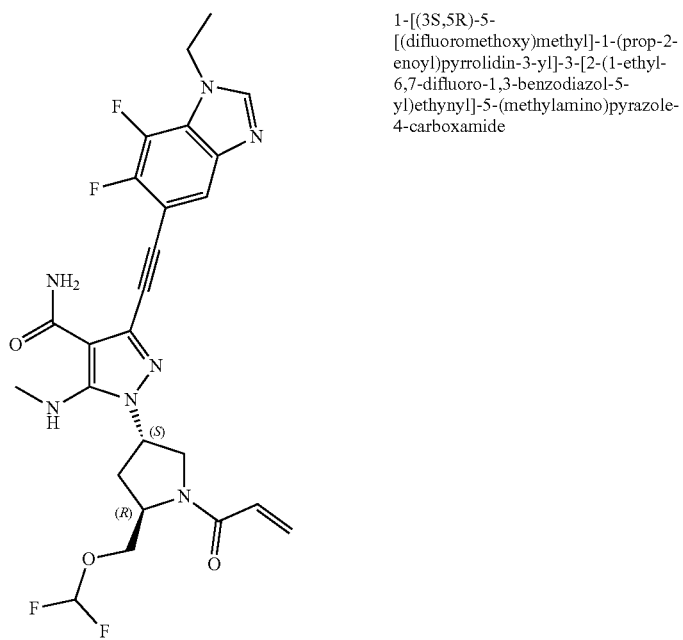 | 1-[(3S,5R)-5-[(difluoromethoxy)methyl]-1-(prop-2-enoyl)pyrrolidin-3-yl]-3-[2-(1-ethyl-6,7-difluoro-1,3-benzodiazol-5-yl)ethynyl]-5-(methylamino)pyrazole-4-carboxamide |

TABLE 1-continued
| Synthetic Chemistry Example | Compound Structure | Compound Name |
|---|---|---|
| 155 | 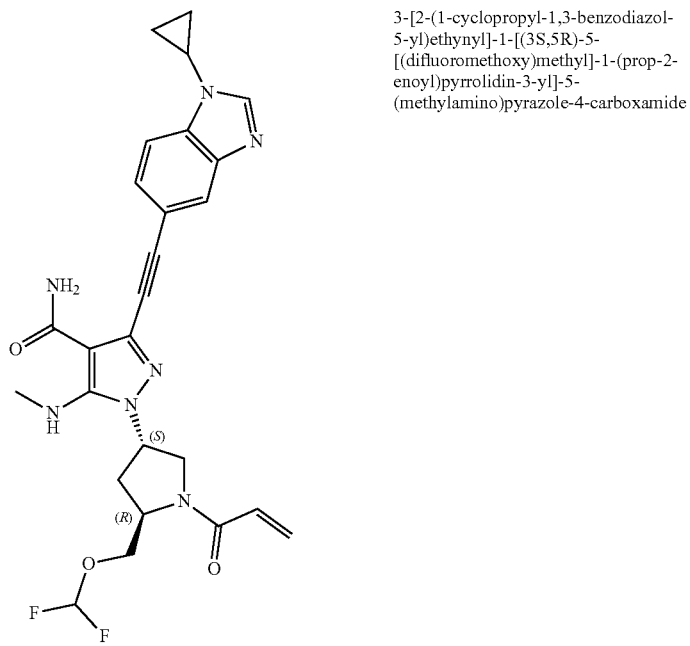 | 3-[2-(1-cyclopropyl-1,3-benzodiazol-5-yl)ethynyl]-1-[(3S,5R)-5-[(difluoromethoxy)methyl]-1-(prop-2-enoyl)pyrrolidin-3-yl]-5-(methylamino)pyrazole-4-carboxamide |
| 156 | 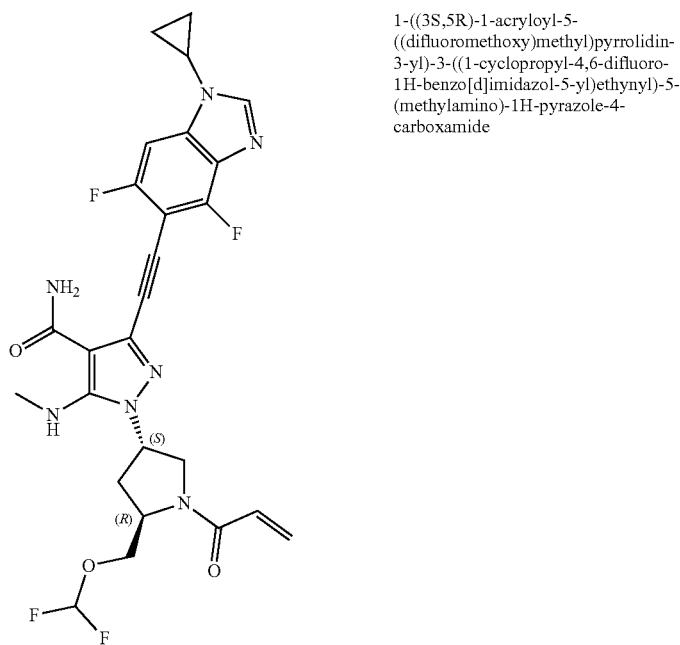 | 1-((3S,5R)-1-acryloyl-5-((difluoromethoxy)methyl)pyrrolidin-3-yl)-3-((1-cyclopropyl-4,6-difluoro-1H-benzo[d]imidazol-5-yl)ethynyl)-5-(methylamino)-1H-pyrazole-4-carboxamide |

TABLE 1-continued

| Synthetic Chemistry Example | Compound Structure | Compound Name |
|---|---|---|
| 157 | 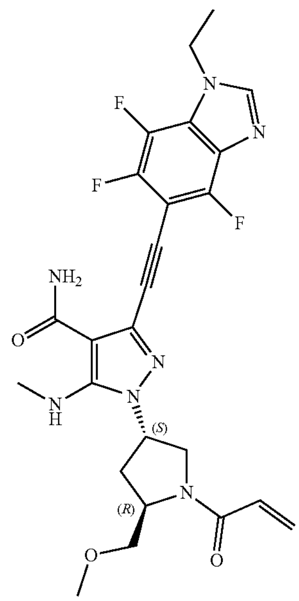 | 3-[2-(1-ethyl-4,6,7-trifluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |
| 158 | 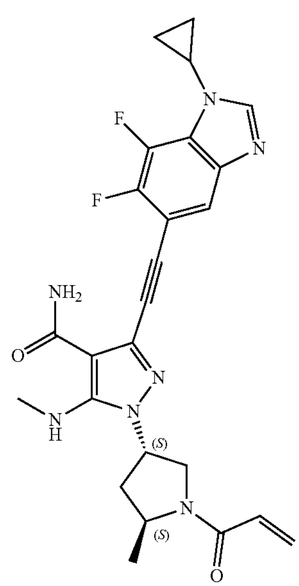 | 3-[2-(1-cyclopropyl-6,7-difluoro-1,3-benzodiazol-5-yl)ethynyl]-1-[(3S,5S)-5-methyl-1-(prop-2-enoyl)pyrrolidin-3-yl]-5-(methylamino)pyrazole-4-carboxamide |

TABLE 1-continued

| Synthetic Chemistry Example | Compound Structure | Compound Name |
|---|---|---|
| 159 | 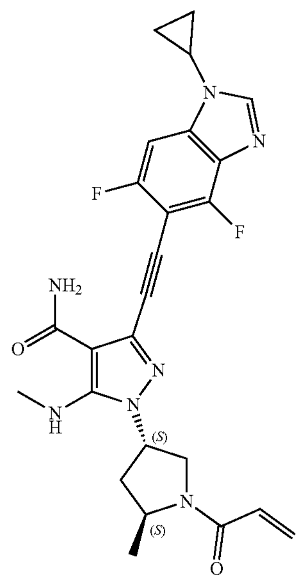 | 3-[2-(1-cyclopropyl-4,6-difluoro-1,3-benzodiazol-5-yl)ethynyl]-1-[(3S,5S)-5-methyl-1-(prop-2-enoyl)pyrrolidin-3-yl]-5-(methylamino)pyrazole-4-carboxamide |
| 161 | 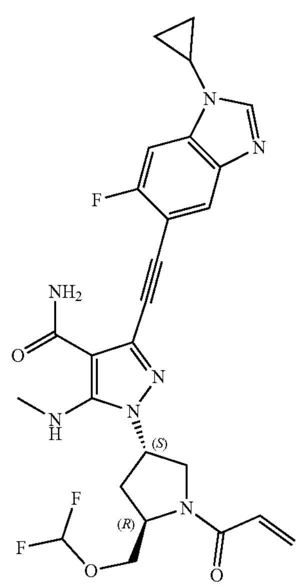 | 1-((3S,5R)-1-acryloyl-5-((difluoromethoxy)methyl)pyrrolidin-3-yl)-3-((1-cyclopropyl-6-fluoro-1H-benzo[d]imidazol-5-yl)ethynyl)-5-(methylamino)-1H-pyrazole-4-carboxamide |

TABLE 1-continued
| Synthetic Chemistry Example | Compound Structure | Compound Name |
|---|---|---|
| 162 | 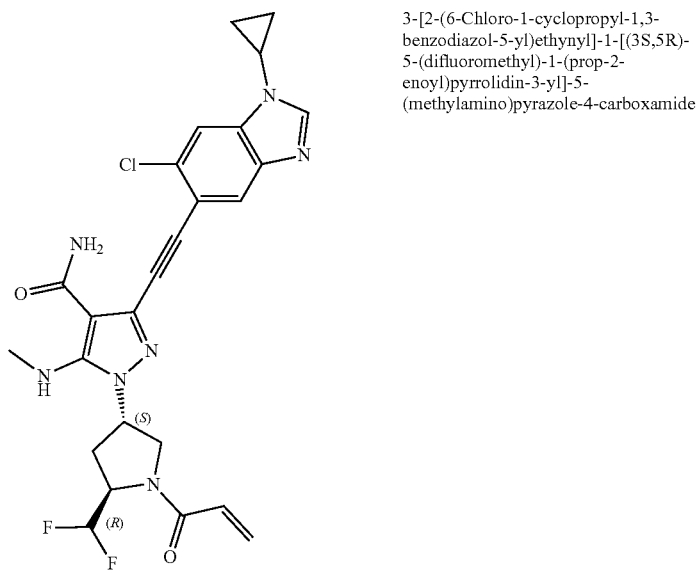 | 3-[2-(6-Chloro-1-cyclopropyl-1,3-benzodiazol-5-yl)ethynyl]-1-[(3S,5R)-5-(difluoromethyl)-1-(prop-2-enoyl)pyrrolidin-3-yl]-5-(methylamino)pyrazole-4-carboxamide |
| 163 | 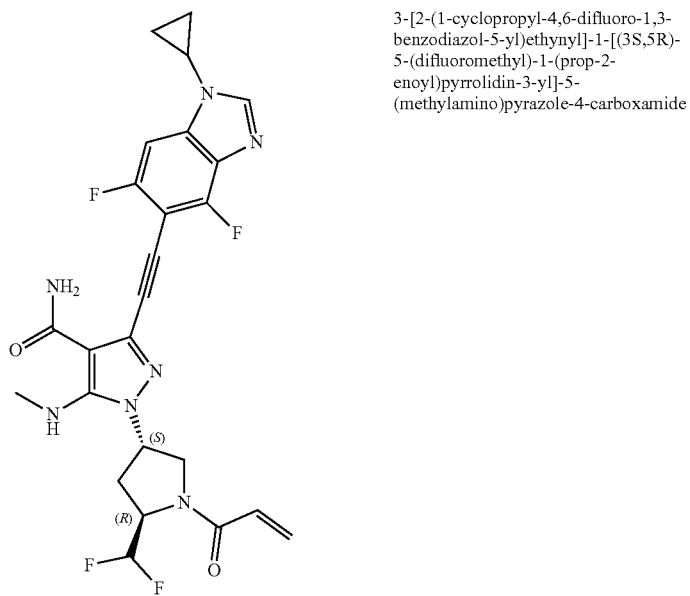 | 3-[2-(1-cyclopropyl-4,6-difluoro-1,3-benzodiazol-5-yl)ethynyl]-1-[(3S,5R)-5-(difluoromethyl)-1-(prop-2-enoyl)pyrrolidin-3-yl]-5-(methylamino)pyrazole-4-carboxamide |

TABLE 1-continued
| Synthetic Chemistry Example | Compound Structure | Compound Name |
|---|---|---|
| 164 | 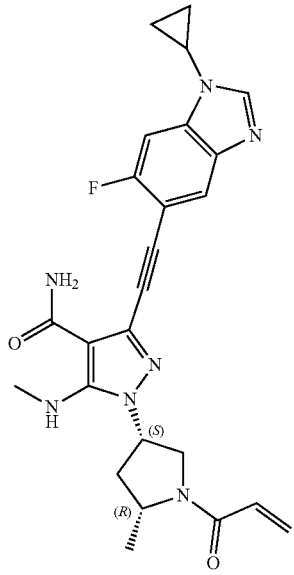 | 1-((3S,5R)-1-acryloyl-5-methylpyrrolidin-3-yl)-3-((1-cyclopropyl-6-fluoro-1H-benzo[d]imidazol-5-yl)ethynyl)-5-(methylamino)-1H-pyrazole-4-carboxamide |
| 165 | 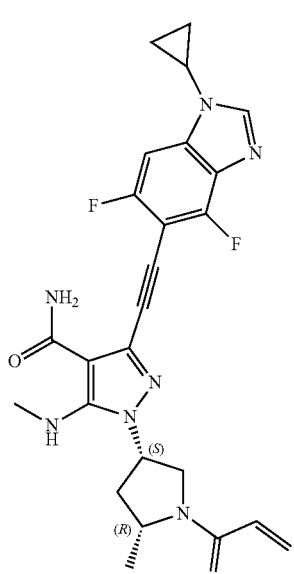 | 3-[2-(1-cyclopropyl-4,6-difluoro-1,3-benzodiazol-5-yl)ethynyl]-1-[(3S,5R)-5-methyl-1-(prop-2-enoyl)pyrrolidin-3-yl]-5-(methylamino)pyrazole-4-carboxamide |

TABLE 1-continued
| Synthetic Chemistry Example | Compound Structure | Compound Name |
|---|---|---|
| 166 | 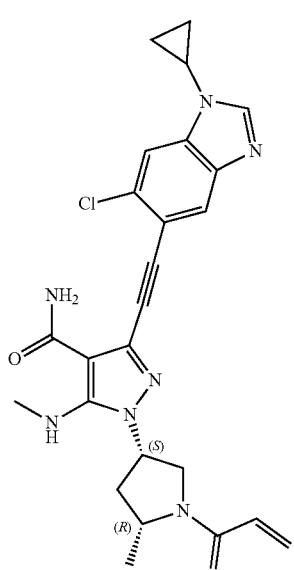 | 1-((3S,5R)-1-acryloyl-5-methylpyrrolidin-3-yl)-3-((6-chloro-1-cyclopropyl-1H-benzo[d]imidazol-5-yl)ethynyl)-5-(methylamino)-1H-pyrazole-4-carboxamide |
| 167 | 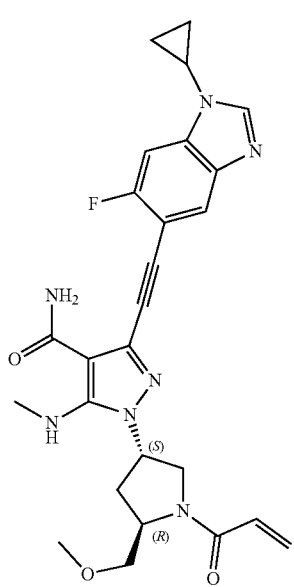 | 5-amino-3-[2-(1-cyclopropyl-6-fluoro-1,3-benzodiazol-5-yl)ethynyl]-1-[(3S,5R)-5-(methoxymethyl)-1-(prop-2-enoyl)pyrrolidin-3-yl]pyrazole-4-carboxamide |

TABLE 1-continued
| Synthetic Chemistry Example | Compound Structure | Compound Name |
|---|---|---|
| 168 | 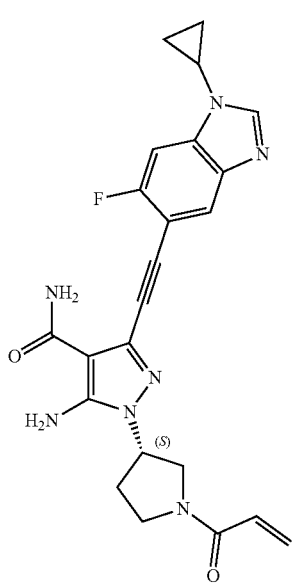 | 5-amino-3-[2-(1-cyclopropyl-6-fluoro-1,3-benzodiazol-5-yl)ethynyl]-1-[(3S)-1-(prop-2-enoyl)pyrrolidin-3-yl]pyrazole-4-carboxamide |
| 169 | 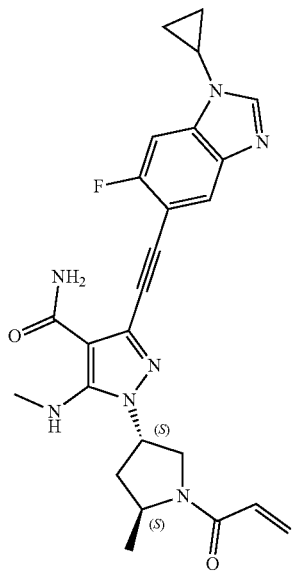 | 1-((3S,5S)-1-acryloyl-5-methylpyrrolidin-3-yl)-3-((1-cyclopropyl-6-fluoro-1H-benzo[d]imidazol-5-yl)ethynyl)-5-(methylamino)-1H-pyrazole-4-carboxamide |

TABLE 1-continued
| Synthetic Chemistry Example | Compound Structure | Compound Name |
|---|---|---|
| 170 | 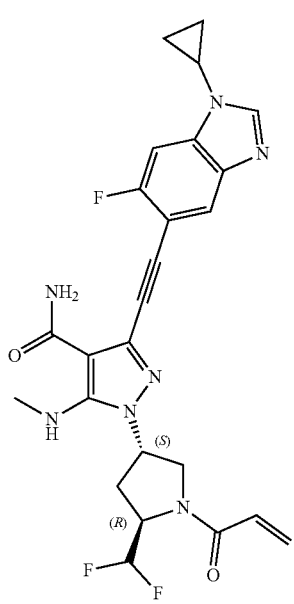 | 3-[2-(1-cyclopropyl-6-fluoro-1,3-benzodiazol-5-yl)ethynyl]-1-[(3S,5R)-5-(difluoromethyl)-1-(prop-2-enoyl)pyrrolidin-3-yl]-5-(methylamino)pyrazole-4-carboxamide |
| 171 | 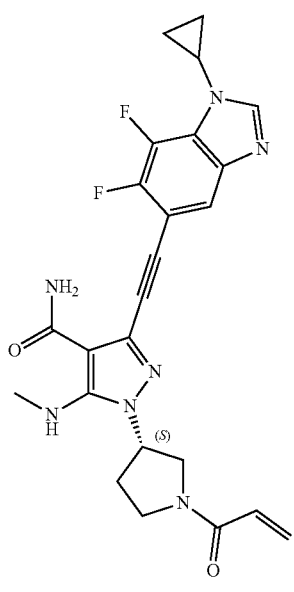 | 3-[2-(1-cyclopropyl-6,7-difluoro-1,3-benzodiazol-5-yl)ethynyl]-5-(methylamino)-1-[(3S)-1-(prop-2-enoyl)pyrrolidin-3-yl]pyrazole-4-carboxamide |

TABLE 1-continued
| Synthetic Chemistry Example | Compound Structure | Compound Name |
|---|---|---|
| 172 | 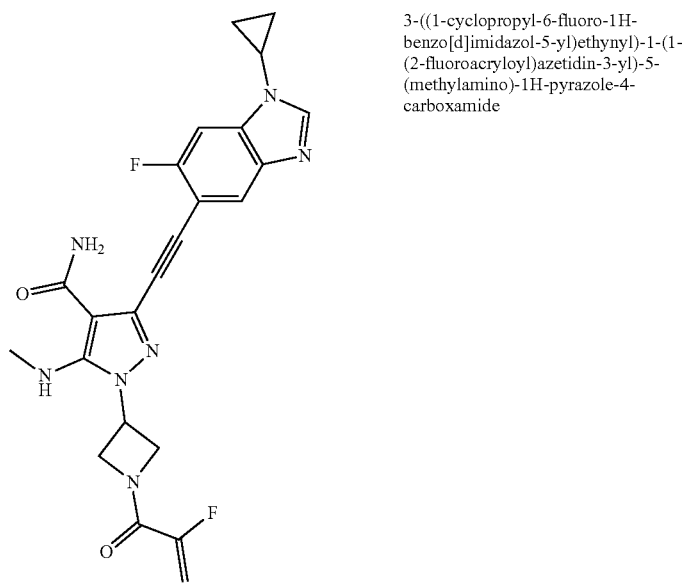 | 3-((1-cyclopropyl-6-fluoro-1H-benzo[d]imidazol-5-yl)ethynyl)-1-(1-(2-fluoroacryloyl)azetidin-3-yl)-5-(methylamino)-1H-pyrazole-4-carboxamide |
| 173 | 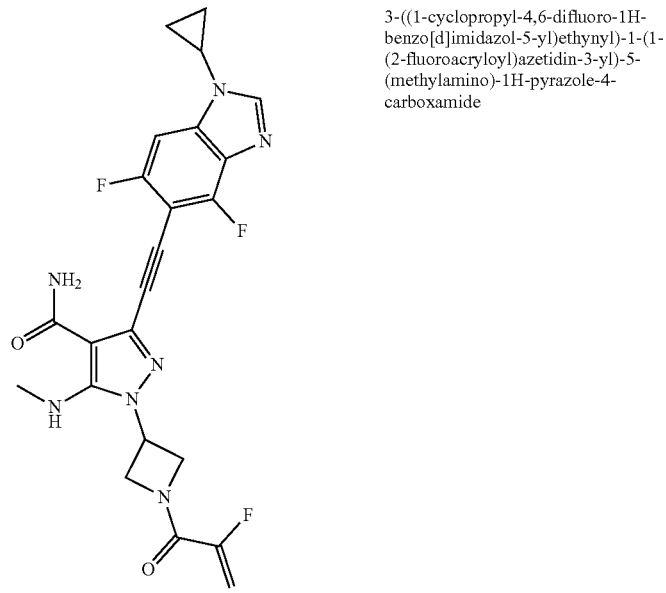 | 3-((1-cyclopropyl-4,6-difluoro-1H-benzo[d]imidazol-5-yl)ethynyl)-1-(1-(2-fluoroacryloyl)azetidin-3-yl)-5-(methylamino)-1H-pyrazole-4-carboxamide |

TABLE 1-continued

| Synthetic Chemistry Example | Compound Structure | Compound Name |
|---|---|---|
| 174 | 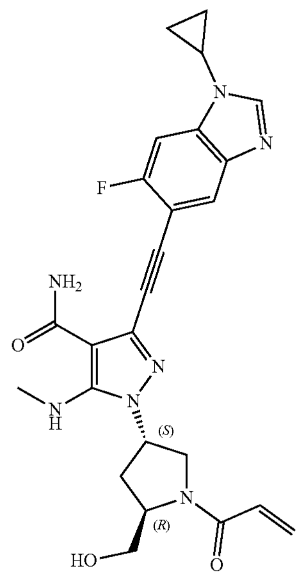 | 1-((3S,5R)-1-acryloyl-5-(hydroxymethyl)pyrrolidin-3-yl)-3-((1-cyclopropyl-6-fluoro-1H-benzo[d]imidazol-5-yl)ethynyl)-5-(methylamino)-1H-pyrazole-4-carboxamide |
| 175 | 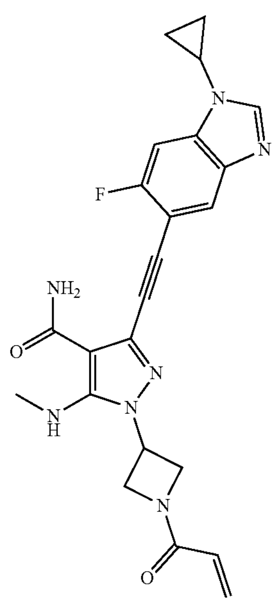 [SMILES: C=CC(=O)N1CC(n2nc(C#Cc3cc4ncn(C5CC5)c4cc3F)c(C(N)=O)c2NC)C1] | tert-butyl 3-[2-(1-cyclopropyl-6-fluoro-1,3-benzodiazol-5-yl)ethynyl]-5-(methylamino)-1-[1-(prop-2-enoyl)azetidin-3-yl]pyrazole-4-carboxamide |

TABLE 1-continued
| Synthetic Chemistry Example | Compound Structure | Compound Name |
|---|---|---|
| 176 | 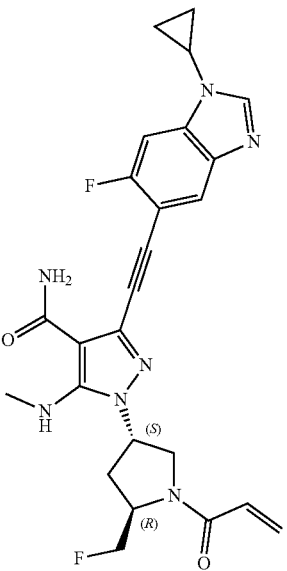 | 1-((3S,5R)-1-acryloyl-5-(fluoromethyl)pyrrolidin-3-yl)-3-((1-cyclopropyl-6-fluoro-1H-benzo[d]imidazol-5-yl)ethynyl)-5-(methylamino)-1H-pyrazole-4-carboxamide |
| 177 | 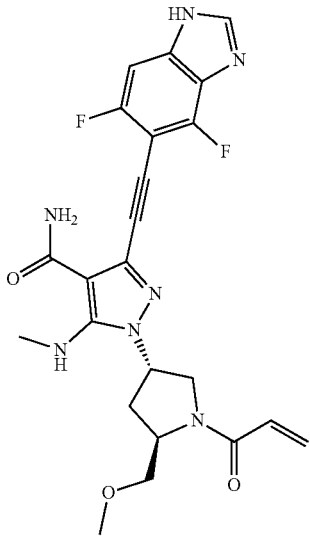 [SMILES: C=CC(=O)N1C[C@@H](n2nc(C#Cc3c(F)cc4[nH]cnc4c3F)c(C(N)=O)c2NC)C[C@@H]1COC] | 1-((3S,5R)-1-acryloyl-5-(methoxymethyl)pyrrolidin-3-yl)-3-((4,6-difluoro-1H-benzo[d]imidazol-5-yl)ethynyl)-5-(methylamino)-1H-pyrazole-4-carboxamide |

TABLE 1-continued
| Synthetic Chemistry Example | Compound Structure | Compound Name |
|---|---|---|
| 178 | 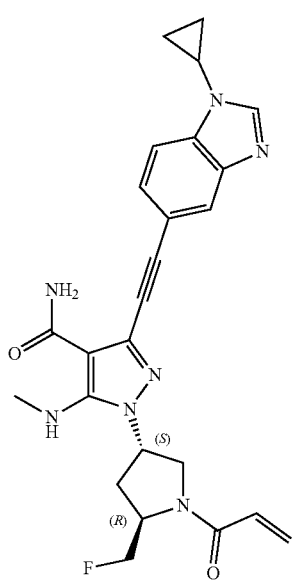 | 1-((3S,5R)-1-acryloyl-5-(fluoromethyl)pyrrolidin-3-yl)-3-((1-cyclopropyl-1H-benzo[d]imidazol-5-yl)ethynyl)-5-(methylamino)-1H-pyrazole-4-carboxamide |
| 179 | 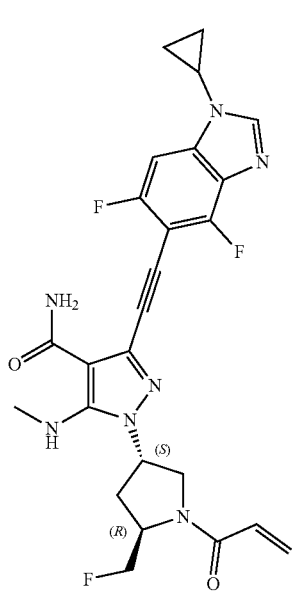 | 1-((3S,5R)-1-acryloyl-5-(fluoromethyl)pyrrolidin-3-yl)-3-((1-cyclopropyl-4,6-difluoro-1H-benzo[d]imidazol-5-yl)ethynyl)-5-(methylamino)-1H-pyrazole-4-carboxamide |

TABLE 1-continued

| Synthetic Chemistry Example | Compound Structure | Compound Name |
|---|---|---|
| 180 | 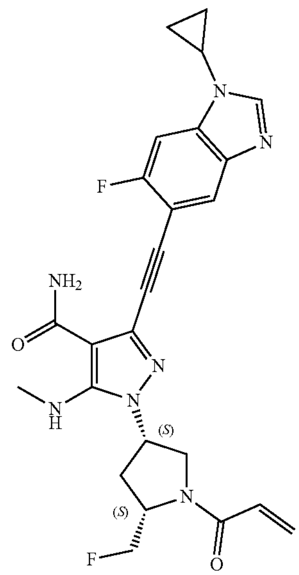 | 3-[2-(1-cyclopropyl-6-fluoro-1,3-benzodiazol-5-yl)ethynyl]-1-[(3S,5S)-5-(fluoromethyl)-1-(prop-2-enoyl)pyrrolidin-3-yl]-5-(methylamino)pyrazole-4-carboxamide |
| 181 | 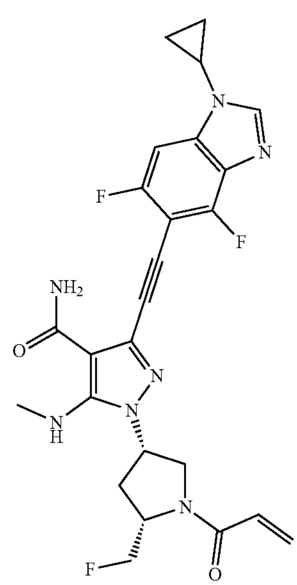 [SMILES: C=CC(=O)N1C[C@@H](n2nc(C#Cc3c(F)cc4c(ncn4C4CC4)c3F)c(C(N)=O)c2NC)C[C@H]1CF] | 3-[2-(1-cyclopropyl-4,6-difluoro-1,3-benzodiazol-5-yl)ethynyl]-1-[(3S,5S)-5-(fluoromethyl)-1-(prop-2-enoyl)pyrrolidin-3-yl]-5-(methylamino)pyrazole-4-carboxamide |

TABLE 1-continued
| Synthetic Chemistry Example | Compound Structure | Compound Name |
|---|---|---|
| 182 | 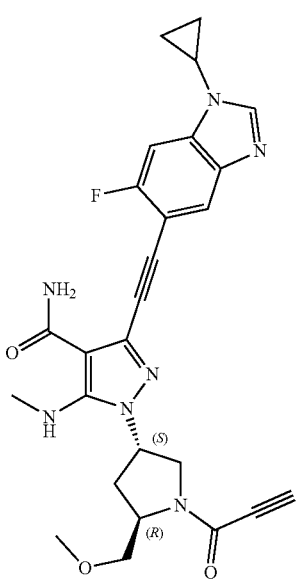 | 3-((1-cyclopropyl-6-fluoro-1H-benzo[d]imidazol-5-yl)ethynyl)-1-((3S,5R)-5-(methoxymethyl)-1-propioloylpyrrolidin-3-yl)-5-(methylamino)-1H-pyrazole-4-carboxamide |
| 183 | 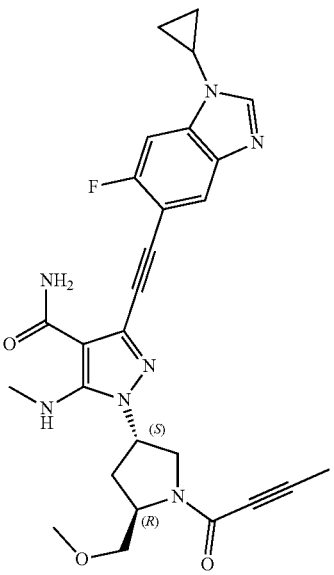 | 1-((3S,5R)-1-(but-2-ynoyl)-5-(methoxymethyl)pyrrolidin-3-yl)-3-((1-cyclopropyl-6-fluoro-1H-benzo[d]imidazol-5-yl)ethynyl)-5-(methylamino)-1H-pyrazole-4-carboxamide |

| Synthetic Chemistry Example | Compound Structure | Compound Name |
|---|---|---|
| 184 | 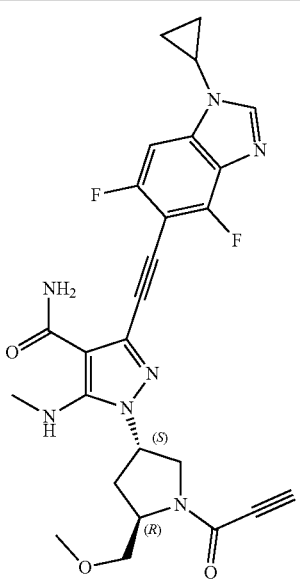 | 3-[2-(1-cyclopropyl-4,6-difluoro-1,3-benzodiazol-5-yl)ethynyl]-1-[(3S,5R)-5-(methoxymethyl)-1-(prop-2-ynoyl)pyrrolidin-3-yl]-5-(methylamino)pyrazole-4-carboxamide |
| 185 | 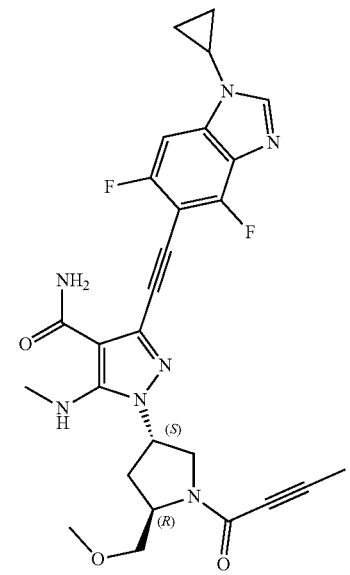 | 1-[(3S,5R)-1-(but-2-ynoyl)-5-(methoxymethyl)pyrrolidin-3-yl]-3-[2-(1-cyclopropyl-4,6-difluoro-1,3-benzodiazol-5-yl)ethynyl]-5-(methylamino)pyrazole-4-carboxamide |

TABLE 1-continued
| Synthetic Chemistry Example | Compound Structure | Compound Name |
|---|---|---|
| 186 | 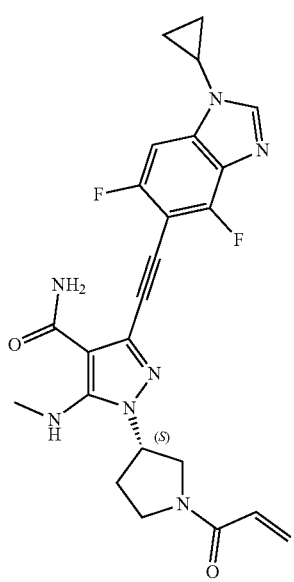 | 3-[2-(1-cyclopropyl-4,6-difluoro-1,3-benzodiazol-5-yl)ethynyl]-5-(methylamino)-1-[(3S)-1-(prop-2-enoyl)pyrrolidin-3-yl]pyrazole-4-carboxamide |
| 187 | 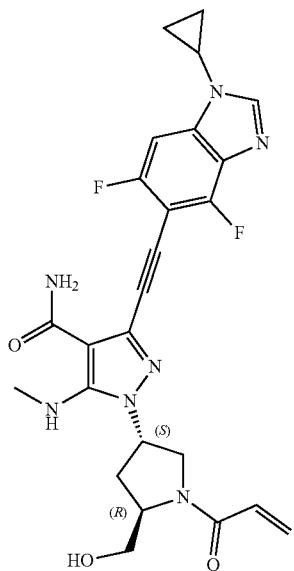 | 3-[2-(1-cyclopropyl-4,6-difluoro-1,3-benzodiazol-5-yl)ethynyl]-1-[(3S,5R)-5-(hydroxymethyl)-1-(prop-2-enoyl)pyrrolidin-3-yl]-5-(methylamino)pyrazole-4-carboxamide |

TABLE 1-continued
| Synthetic Chemistry Example | Compound Structure | Compound Name |
|---|---|---|
| 188 | 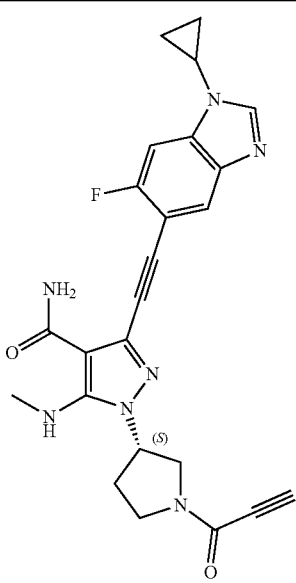 | 3-[2-(1-cyclopropyl-6-fluoro-1,3-benzodiazol-5-yl)ethynyl]-5-(methylamino)-1-[1-(prop-2-ynoyl)pyrrolidin-3-yl]pyrazole-4-carboxamide |
| 189 | 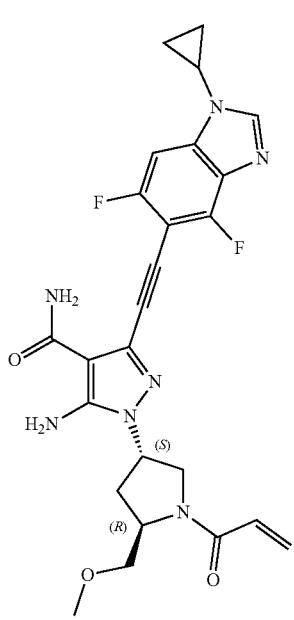 | 5-amino-3-[2-(1-cyclopropyl-4,6-difluoro-1,3-benzodiazol-5-yl)ethynyl]-1-[(3S,5R)-5-(methoxymethyl)-1-(prop-2-enoyl)pyrrolidin-3-yl]pyrazole-4-carboxamide |

TABLE 1-continued
| Synthetic Chemistry Example | Compound Structure | Compound Name |
|---|---|---|
| 190 | 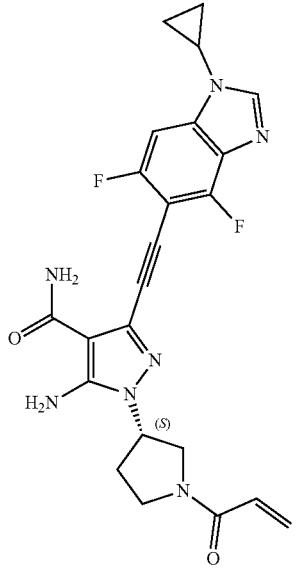 | 5-amino-3-[2-(1-cyclopropyl-4,6-difluoro-1,3-benzodiazol-5-yl)ethynyl]-1-[(3S)-1-(prop-2-enoyl)pyrrolidin-3-yl]pyrazole-4-carboxamide |
| 191 | 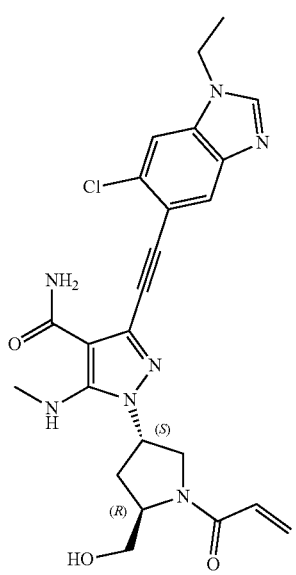 | 3-[2-(6-chloro-1-ethyl-1,3-benzodiazol-5-yl)ethynyl]-1-[(3S,5R)-5-(hydroxymethyl)-1-(prop-2-enoyl)pyrrolidin-3-yl]-5-(methylamino)pyrazole-4-carboxamide |

TABLE 1-continued

| Synthetic Chemistry Example | Compound Structure | Compound Name |
|---|---|---|
| 192 | 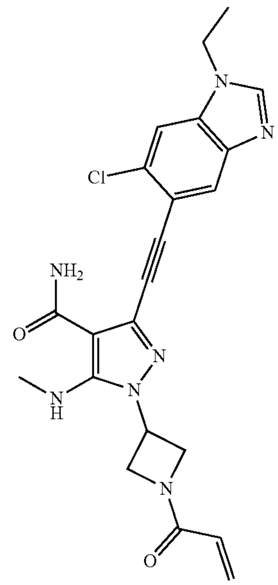 [SMILES: C=CC(=O)N1CC(n2nc(C#Cc3cc4ncn(CC)c4cc3Cl)c(C(N)=O)c2NC)C1] | 3-[2-(6-chloro-1-ethyl-1,3-benzodiazol-5-yl)ethynyl]-5-(methylamino)-1-[1-(prop-2-enoyl)azetidin-3-yl]pyrazole-4-carboxamide |
| 193 | 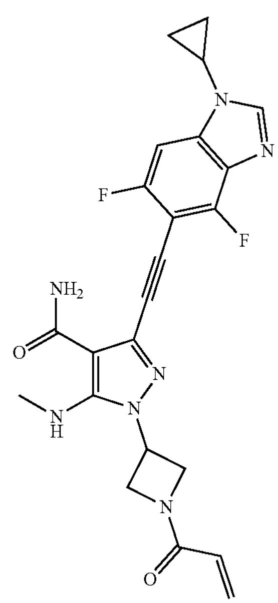 [SMILES: C=CC(=O)N1CC(n2nc(C#Cc3c(F)cc4c(ncn4C4CC4)c3F)c(C(N)=O)c2NC)C1] | 3-[2-(1-cyclopropyl-4,6-difluoro-1,3-benzodiazol-5-yl)ethynyl]-5-(methylamino)-1-[1-(prop-2-enoyl)azetidin-3-yl]pyrazole-4-carboxamide |

TABLE 1-continued
| Synthetic Chemistry Example | Compound Structure | Compound Name |
|---|---|---|
| 194 | 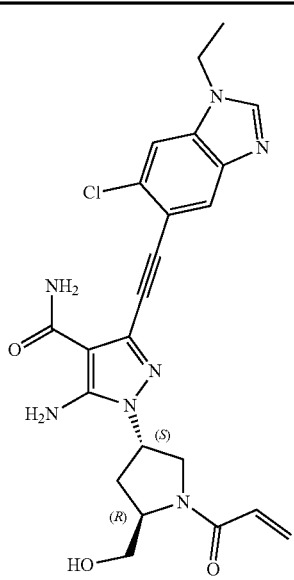 | 5-amino-3-[2-(6-chloro-1-ethyl-1,3-benzodiazol-5-yl)ethynyl]-1-[(3S,5R)-5-(hydroxymethyl)-1-(prop-2-enoyl)pyrrolidin-3-yl]pyrazole-4-carboxamide |
| 195 | 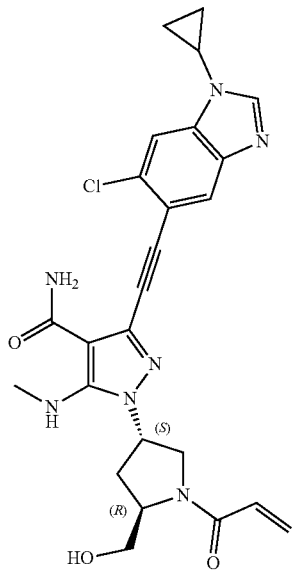 | 3-[2-(6-chloro-1-cyclopropyl-1,3-benzodiazol-5-yl)ethynyl]-1-[(3S,5R)-5-(hydroxymethyl)-1-(prop-2-enoyl)pyrrolidin-3-yl]-5-(methylamino)pyrazole-4-carboxamide |

TABLE 1-continued

| Synthetic Chemistry Example | Compound Structure | Compound Name |
|---|---|---|
| 196 | 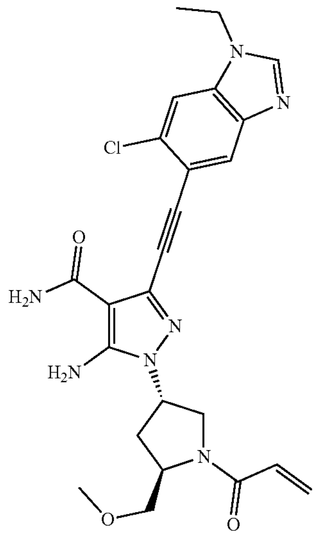 [SMILES: C=CC(=O)N1C[C@@H](n2nc(C#Cc3cc4ncn(CC)c4cc3Cl)c(C(N)=O)c2N)C[C@@H]1COC] | 5-amino-3-[2-(6-chloro-1-ethyl-1,3-benzodiazol-5-yl)ethynyl]-1-[(3S,5R)-5-(methoxymethyl)-1-(prop-2-enoyl)pyrrolidin-3-yl]pyrazole-4-carboxamide |
| 197 | 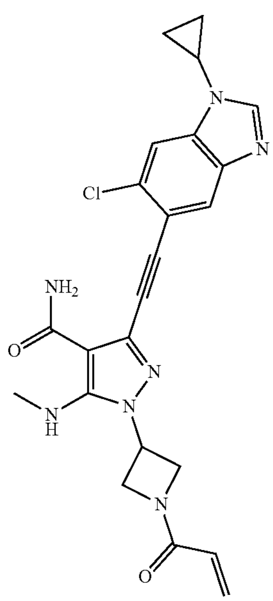 [SMILES: C=CC(=O)N1CC(n2nc(C#Cc3cc4ncn(C5CC5)c4cc3Cl)c(C(N)=O)c2NC)C1] | 3-[2-(6-chloro-1-cyclopropyl-1,3-benzodiazol-5-yl)ethynyl]-5-(methylamino)-1-[1-(prop-2-enoyl)azetidin-3-yl]pyrazole-4-carboxamide |

TABLE 1-continued
| Synthetic Chemistry Example | Compound Structure | Compound Name |
|---|---|---|
| 198 | 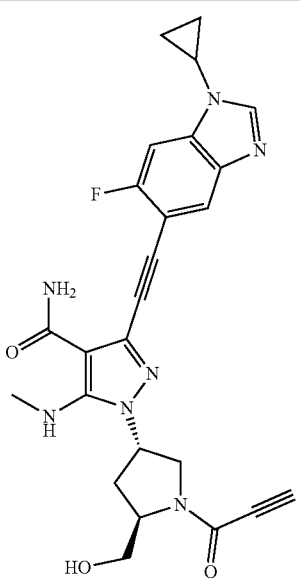 [SMILES: C#CC(=O)N1C[C@@H](n2nc(C#Cc3cc4ncn(C5CC5)c4cc3F)c(C(N)=O)c2NC)C[C@@H]1CO] | 3-[2-(1-cyclopropyl-6-fluoro-1,3-benzodiazol-5-yl)ethynyl]-1-[(3S,5R)-5-(hydroxymethyl)-1-(prop-2-ynoyl)pyrrolidin-3-yl]-5-(methylamino)pyrazole-4-carboxamide |
| 199 | 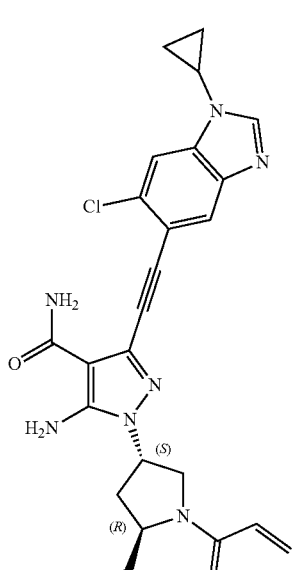 | 5-amino-3-[2-(6-chloro-1-cyclopropyl-1,3-benzodiazol-5-yl)ethynyl]-1-[(3S,5R)-5-(hydroxymethyl)-1-(prop-2-enoyl)pyrrolidin-3-yl]pyrazole-4-carboxamide |

TABLE 1-continued

| Synthetic Chemistry Example | Compound Structure | Compound Name |
|---|---|---|
| 200 | 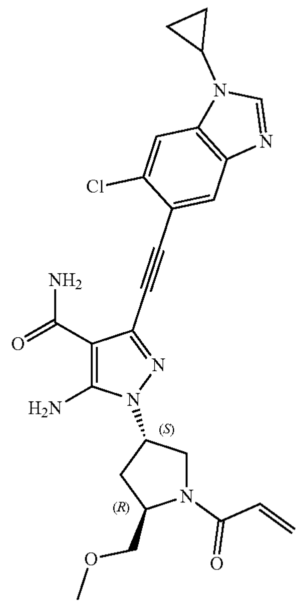 | 5-amino-3-[2-(6-chloro-1-cyclopropyl-1,3-benzodiazol-5-yl)ethynyl]-1-[(3S,5R)-5-(methoxymethyl)-1-(prop-2-enoyl)pyrrolidin-3-yl]pyrazole-4-carboxamide |
| 201 | 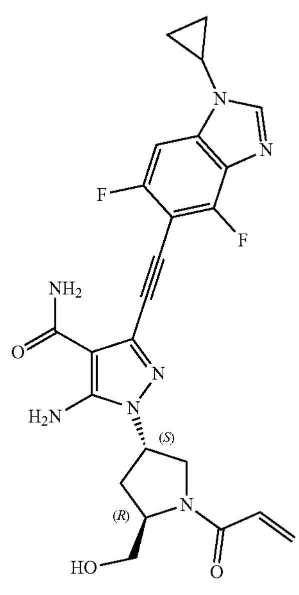 | 5-amino-3-[2-(1-cyclopropyl-4,6-difluoro-1,3-benzodiazol-5-yl)ethynyl]-1-[(3S,5R)-5-(hydroxymethyl)-1-(prop-2-enoyl)pyrrolidin-3-yl]pyrazole-4-carboxamide |

TABLE 1-continued
| Synthetic Chemistry Example | Compound Structure | Compound Name |
|---|---|---|
| 202 | 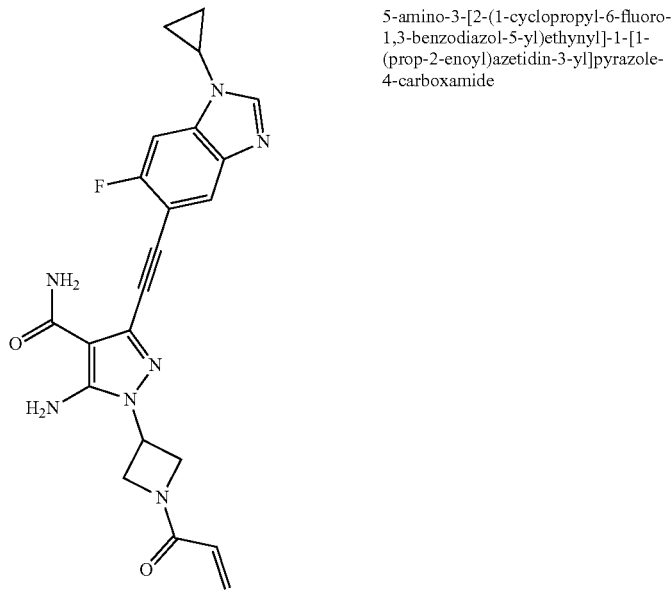 | 5-amino-3-[2-(1-cyclopropyl-6-fluoro-1,3-benzodiazol-5-yl)ethynyl]-1-[1-(prop-2-enoyl)azetidin-3-yl]pyrazole-4-carboxamide |
| 203 | 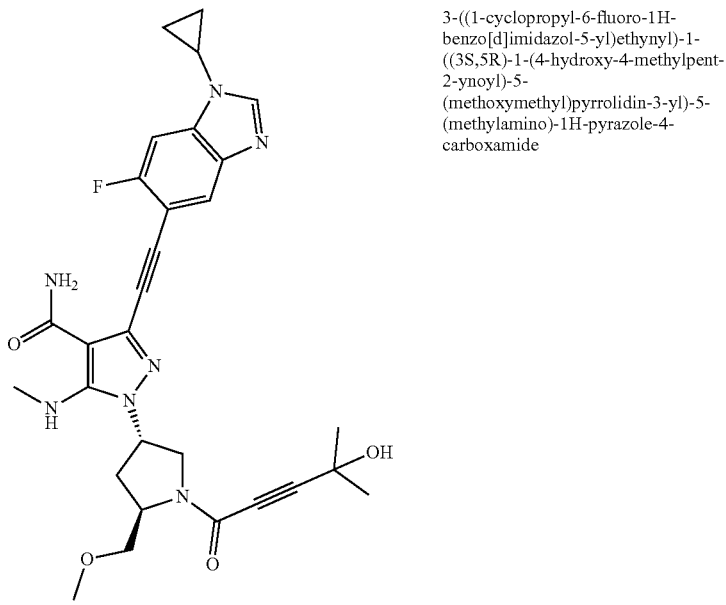 | 3-((1-cyclopropyl-6-fluoro-1H-benzo[d]imidazol-5-yl)ethynyl)-1-((3S,5R)-1-(4-hydroxy-4-methylpent-2-ynoyl)-5-(methoxymethyl)pyrrolidin-3-yl)-5-(methylamino)-1H-pyrazole-4-carboxamide |

TABLE 1-continued

| Synthetic Chemistry Example | Compound Structure | Compound Name |
|---|---|---|
| 204 | 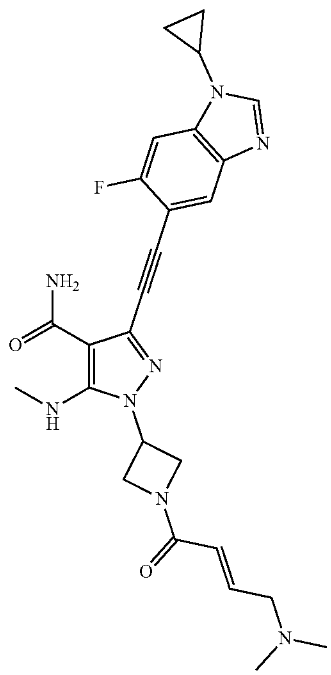 [SMILES: CNc1c(C(N)=O)c(C#Cc2cc3ncn(C4CC4)c3cc2F)nn1C1CN(C(=O)/C=C/CN(C)C)C1] | 3-[2-(1-cyclopropyl-6-fluoro-1,3-benzodiazol-5-yl)ethynyl]-1-{1-[(2E)-4-dimethylamino)but-2-enoyl]azetidin-3-yl}-5-(methylamino)pyrazole-4-carboxamide |
| 205 | 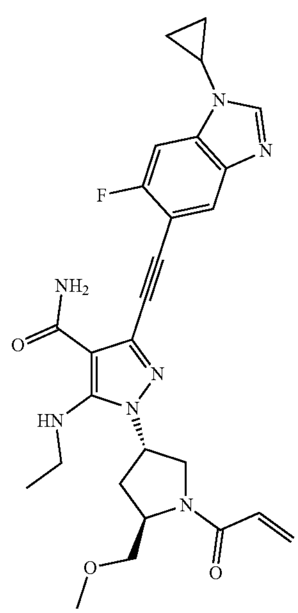 [SMILES: C=CC(=O)N1C[C@@H](n2nc(C#Cc3cc4ncn(C5CC5)c4cc3F)c(C(N)=O)c2NCC)C[C@@H]1COC] | 1-((3S,5R)-1-acryloyl-5-(methoxymethyl)pyrrolidin-3-yl)-3-((1-cyclopropyl-6-fluoro-1H-benzo[d]imidazol-5-yl)ethynyl)-5-(ethylamino)-1H-pyrazole-4-carboxamide |

TABLE 1-continued

| Synthetic Chemistry Example | Compound Structure | Compound Name |
|---|---|---|
| 206 | 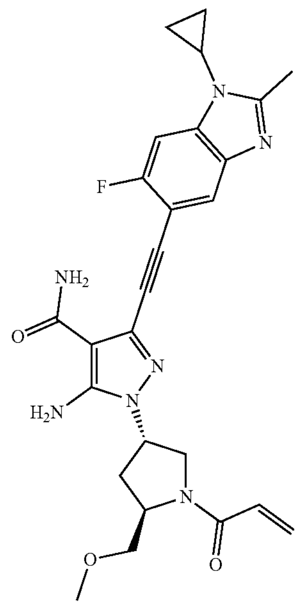 [SMILES: C=CC(=O)N1C[C@@H](n2nc(C#Cc3cc4nc(C)n(C5CC5)c4cc3F)c(C(N)=O)c2N)C[C@@H]1COC] | 5-amino-3-[2-(1-cyclopropyl-6-fluoro-2-methyl-1,3-benzodiazol-5-yl)ethynyl]-1-[(3S,5R)-5-(methoxymethyl)-1-(prop-2-enoyl)pyrrolidin-3-yl]pyrazole-4-carboxamide |
| 207 | 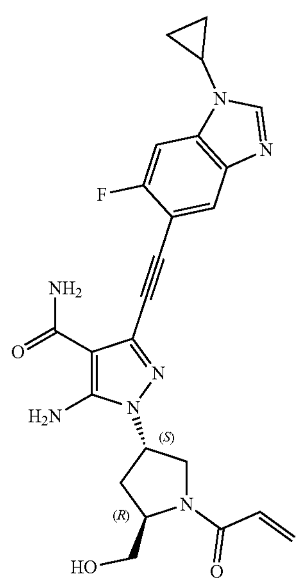 | 5-amino-3-[2-(1-cyclopropyl-6-fluoro-1,3-benzodiazol-5-yl)ethynyl]-1-[(3S,5R)-5-(hydroxymethyl)-1-(prop-2-enoyl)pyrrolidin-3-yl]pyrazole-4-carboxamide |

TABLE 1-continued
| Synthetic Chemistry Example | Compound Structure | Compound Name |
|---|---|---|
| 208 | 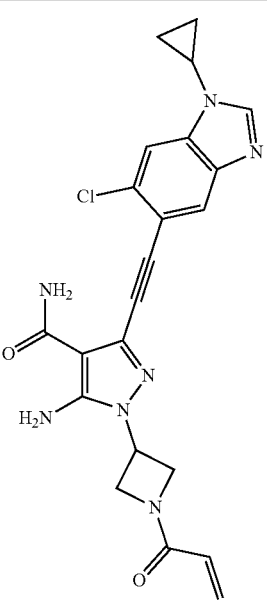 [SMILES: C=CC(=O)N1CC(n2nc(C#Cc3cc4ncn(C5CC5)c4cc3Cl)c(C(N)=O)c2N)C1] | 5-amino-3-[2-(6-chloro-1-cyclopropyl-1,3-benzodiazol-5-yl)ethynyl]-1-[1-(prop-2-enoyl)azetidin-3-yl]pyrazole-4-carboxamide |
| 209 | 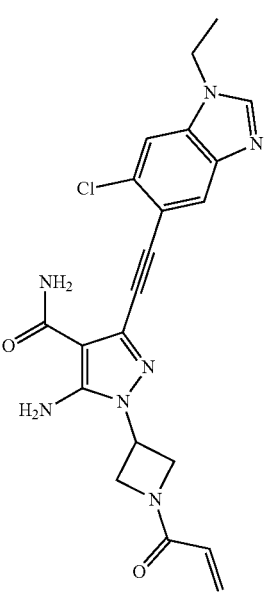 [SMILES: C=CC(=O)N1CC(n2nc(C#Cc3cc4ncn(CC)c4cc3Cl)c(C(N)=O)c2N)C1] | 5-amino-3-[2-(6-chloro-1-ethyl-1,3-benzodiazol-5-yl)ethynyl]-1-[1-(prop-2-enoyl)azetidin-3-yl]pyrazole-4-carboxamide |

TABLE 1-continued

| Synthetic Chemistry Example | Compound Structure | Compound Name |
|---|---|---|
| 210 | 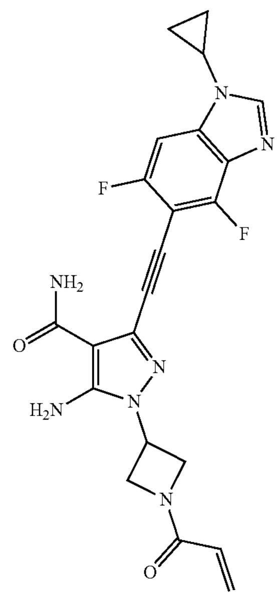 [SMILES: C=CC(=O)N1CC(n2nc(C#Cc3c(F)cc4c(ncn4C4CC4)c3F)c(C(N)=O)c2N)C1] | 5-amino-3-[2-(1-cyclopropyl-4,6-difluoro-1,3-benzodiazol-5-yl)ethynyl]-1-[1-(prop-2-enoyl)azetidin-3-yl]pyrazole-4-carboxamide |
| 211 | 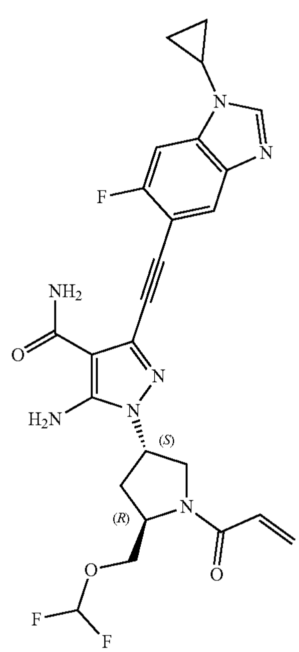 | 5-amino-3-[2-(1-cyclopropyl-6-fluoro-1,3-benzodiazol-5-yl)ethynyl]-1-[(3S,5R)-5-[(difluoromethoxy)methyl]-1-(prop-2-enoyl)pyrrolidin-3-yl]pyrazole-4-carboxamide |

TABLE 1-continued
| Synthetic Chemistry Example | Compound Structure | Compound Name |
|---|---|---|
| 212 | 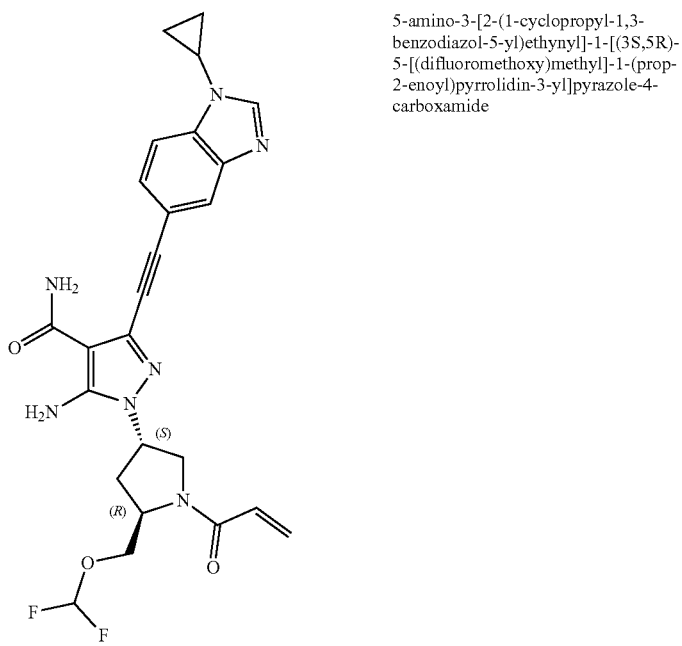 | 5-amino-3-[2-(1-cyclopropyl-1,3-benzodiazol-5-yl)ethynyl]-1-[(3S,5R)-5-[(difluoromethoxy)methyl]-1-(prop-2-enoyl)pyrrolidin-3-yl]pyrazole-4-carboxamide |
| 213 | 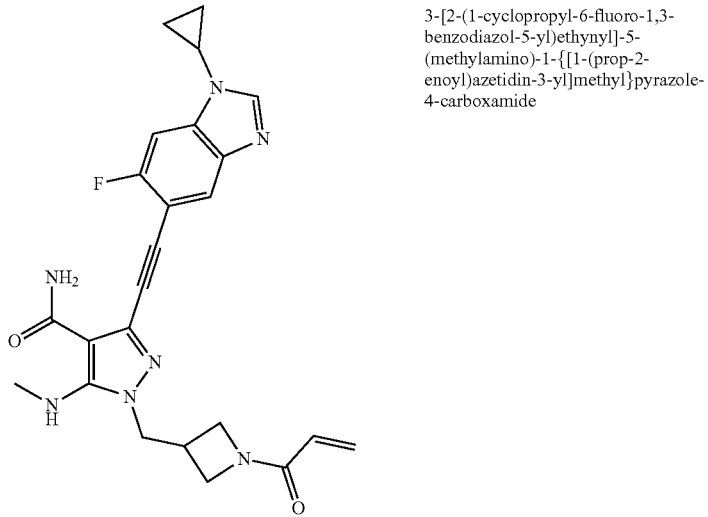 | 3-[2-(1-cyclopropyl-6-fluoro-1,3-benzodiazol-5-yl)ethynyl]-5-(methylamino)-1-{[1-(prop-2-enoyl)azetidin-3-yl]methyl}pyrazole-4-carboxamide |

TABLE 1-continued

| Synthetic Chemistry Example | Compound Structure | Compound Name |
|---|---|---|
| 214 | 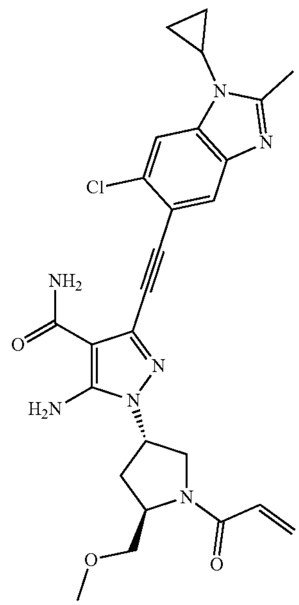 [SMILES: C=CC(=O)N1C[C@@H](n2nc(C#Cc3cc4nc(C)n(C5CC5)c4cc3Cl)c(C(N)=O)c2N)C[C@@H]1COC] | 5-amino-3-[2-(6-chloro-1-cyclopropyl-2-methyl-1,3-benzodiazol-5-yl)ethynyl]-1-[(3S,5R)-5-(methoxymethyl)-1-(prop-2-enoyl)pyrrolidin-3-yl]pyrazole-4-carboxamide |
| 215 | 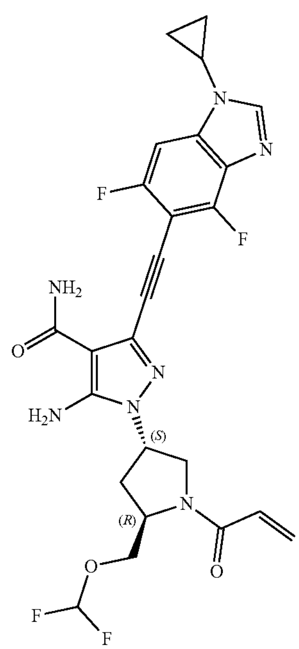 | 5-amino-3-[2-(1-cyclopropyl-4,6-difluoro-1,3-benzodiazol-5-yl)ethynyl]-1-[(3S,5R)-5-[(difluoromethoxy)methyl]-1-(prop-2-enoyl)pyrrolidin-3-yl]pyrazole-4-carboxamide |

TABLE 1-continued

| Synthetic Chemistry Example | Compound Structure | Compound Name |
|---|---|---|
| 216 | 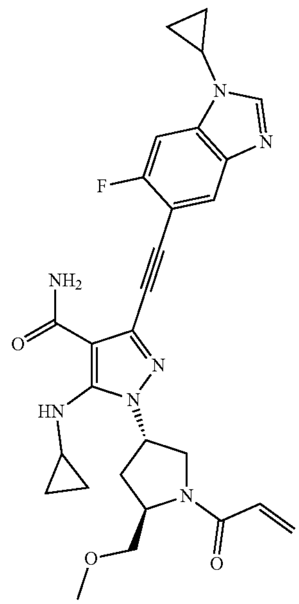 [SMILES: C=CC(=O)N1C[C@@H](n2nc(C#Cc3cc4ncn(C5CC5)c4cc3F)c(C(N)=O)c2NC2CC2)C[C@@H]1COC] | 3-[2-(1-cyclopropyl-6-fluoro-1,3-benzodiazol-5-yl)ethynyl]-5-(cyclopropylamino)-1-[(3S,5R)-5-(methoxymethyl)-1-(prop-2-enoyl)pyrrolidin-3-yl]pyrazole-4-carboxamide |
| 217 | 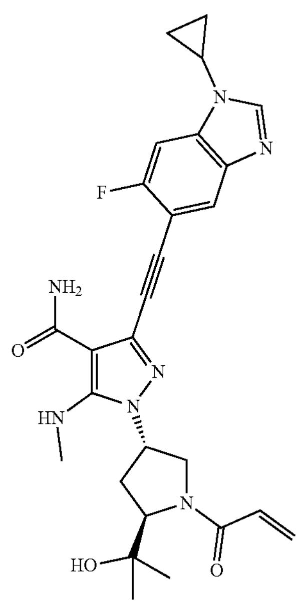 [SMILES: C=CC(=O)N1C[C@@H](n2nc(C#Cc3cc4ncn(C5CC5)c4cc3F)c(C(N)=O)c2NC)C[C@@H]1C(C)(C)O] | 3-[2-(1-cyclopropyl-6-fluoro-1,3-benzodiazol-5-yl)ethynyl]-1-[(3S,5R)-5-(2-hydroxypropan-2-yl)-1-(prop-2-enoyl)pyrrolidin-3-yl]-5-(methylamino)pyrazole-4-carboxamide |

TABLE 1-continued
| Synthetic Chemistry Example | Compound Structure | Compound Name |
|---|---|---|
| 218 | 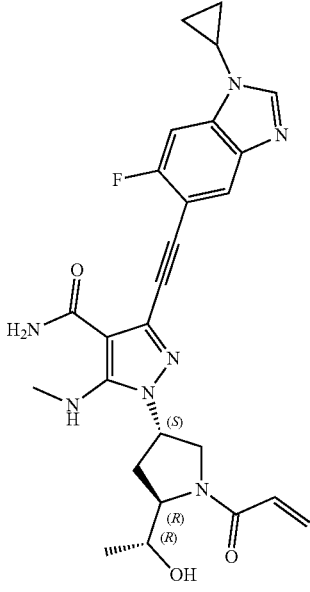 | 3-[2-(1-cyclopropyl-6-fluoro-1,3-benzodiazol-5-yl)ethynyl]-1-[(3S,5R)-5-[(1R)-1-hydroxyethyl]-1-(prop-2-enoyl)pyrrolidin-3-yl]-5-(methylamino)pyrazole-4-carboxamide |
| 219 | 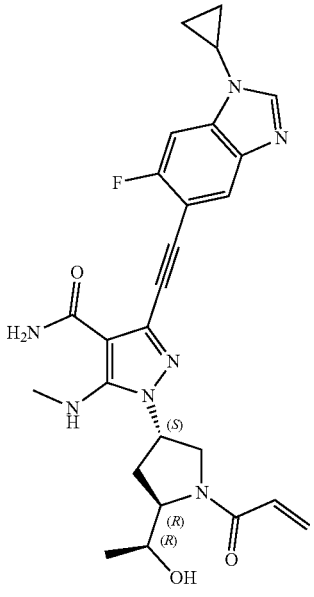 | 3-[2-(1-cyclopropyl-6-fluoro-1,3-benzodiazol-5-yl)ethynyl]-1-[(3S,5R)-5-[(1S)-1-hydroxyethyl]-1-(prop-2-enoyl)pyrrolidin-3-yl]-5-(methylamino)pyrazole-4-carboxamide |

TABLE 1-continued
| Synthetic Chemistry Example | Compound Structure | Compound Name |
|---|---|---|
| 220 | 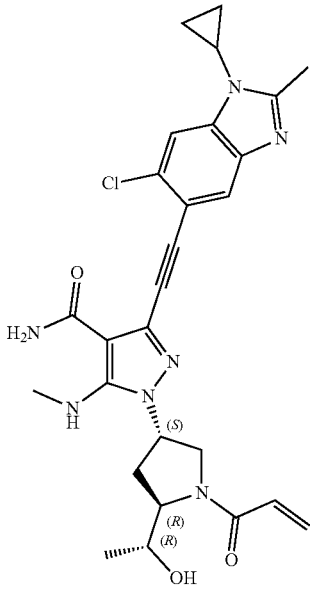 | 1-((3S,5R)-1-acryloyl-5-((R)-1-hydroxyethyl)pyrrolidin-3-yl)-3-((6-chloro-1-cyclopropyl-2-methyl-1H-benzo[d]imidazol-5-yl)ethynyl)-5-(methylamino)-1H-pyrazole-4-carboxamide |
| 221 | 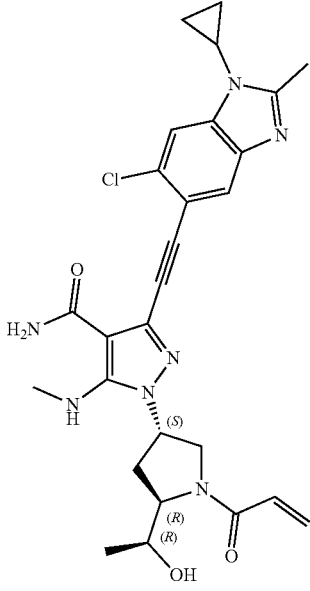 | 1-((3S,5R)-1-acryloyl-5-((S)-1-hydroxyethyl)pyrrolidin-3-yl)-3-((6-chloro-1-cyclopropyl-2-methyl-1H-benzo[d]imidazol-5-yl)ethynyl)-5-(methylamino)-1H-pyrazole-4-carboxamide |

TABLE 1-continued
| Synthetic Chemistry Example | Compound Structure | Compound Name |
|---|---|---|
| 222 | 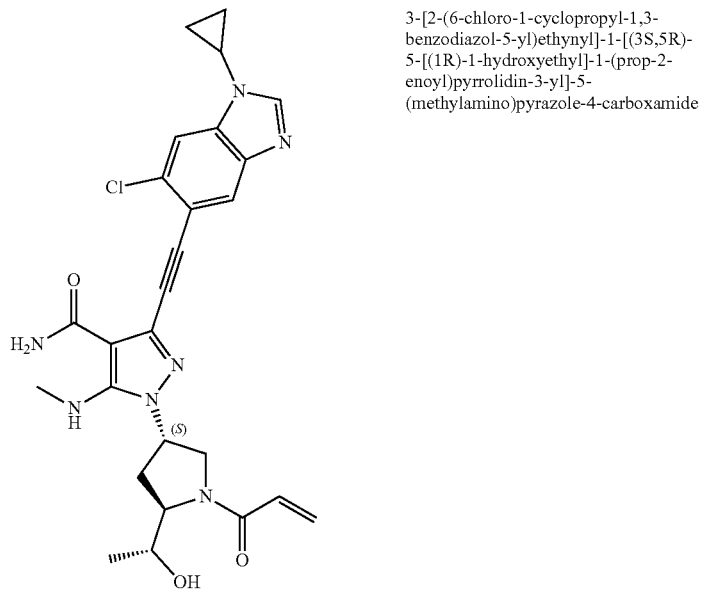 | 3-[2-(6-chloro-1-cyclopropyl-1,3-benzodiazol-5-yl)ethynyl]-1-[(3S,5R)-5-[(1R)-1-hydroxyethyl]-1-(prop-2-enoyl)pyrrolidin-3-yl]-5-(methylamino)pyrazole-4-carboxamide |
| 223 | 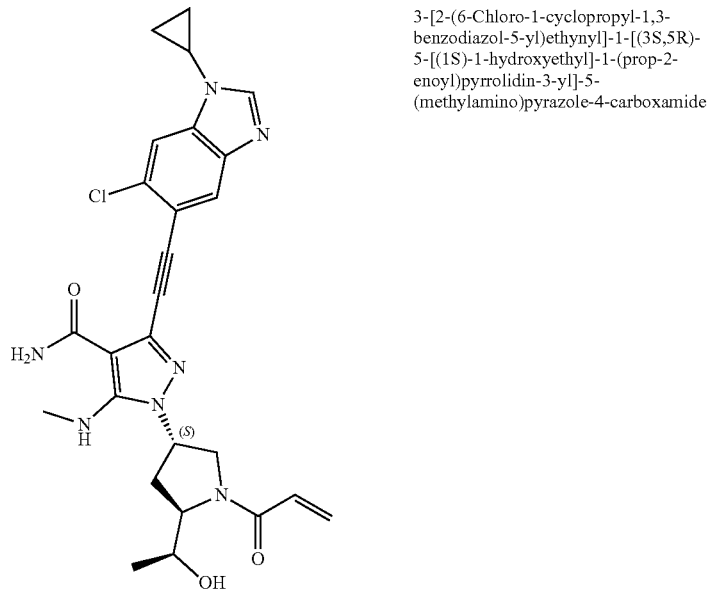 | 3-[2-(6-Chloro-1-cyclopropyl-1,3-benzodiazol-5-yl)ethynyl]-1-[(3S,5R)-5-[(1S)-1-hydroxyethyl]-1-(prop-2-enoyl)pyrrolidin-3-yl]-5-(methylamino)pyrazole-4-carboxamide |

| Synthetic Chemistry Example | Compound Structure | Compound Name |
|---|---|---|
| 224 | 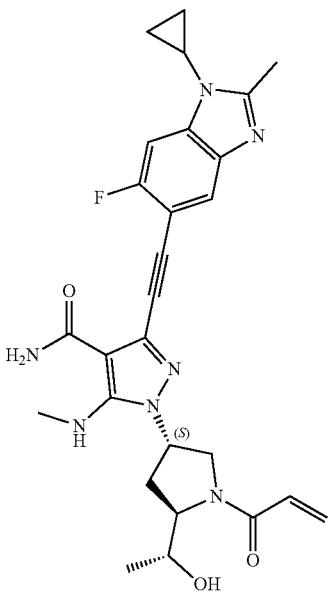 | 3-[2-(1-cyclopropyl-6-fluoro-2-methyl-1,3-benzodiazol-5-yl)ethynyl]-1-[(3S,5R)-5-[(1R)-1-hydroxyethyl]-1-(prop-2-enoyl)pyrrolidin-3-yl]-5-(methylamino)pyrazole-4-carboxamide |
| 225 | 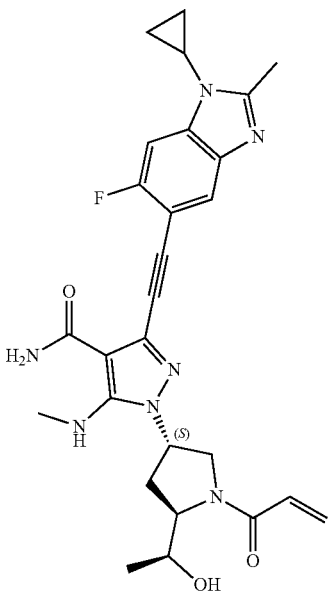 | 3-[2-(1-cyclopropyl-6-fluoro-2-methyl-1,3-benzodiazol-5-yl)ethynyl]-1-[(3S,5R)-5-[(1S)-1-hydroxyethyl]-1-(prop-2-enoyl)pyrrolidin-3-yl]-5-(methylamino)pyrazole-4-carboxamide |

TABLE 1-continued

| Synthetic Chemistry Example | Compound Structure | Compound Name |
|---|---|---|
| 226 | 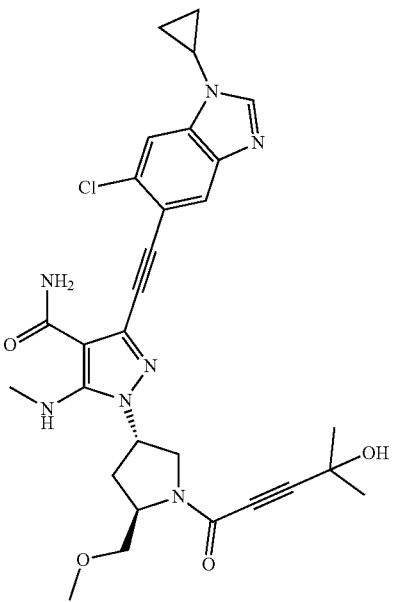 | 3-[2-(6-chloro-1-cyclopropyl-1,3-benzodiazol-5-yl)ethynyl]-1-[(3S,5R)-1-(4-hydroxy-4-methylpent-2-ynoyl)-5-(methoxymethyl)pyrrolidin-3-yl]-5-(methylamino)pyrazole-4-carboxamide |
| 227 | 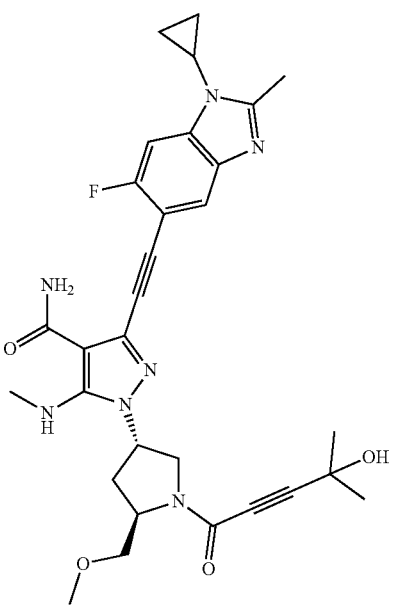 [SMILES: CNc1c(C(N)=O)c(C#Cc2cc3nc(C)n(C4CC4)c3cc2F)nn1[C@H]1C[C@H](COC)N(C(=O)C#CC(C)(C)O)C1] | 3-[2-(1-cyclopropyl-6-fluoro-2-methyl-1,3-benzodiazol-5-yl)ethynyl]-1-[(3S,5R)-1-(4-hydroxy-4-methylpent-2-ynoyl)-5-(methoxymethyl)pyrrolidin-3-yl]-5-(methylamino)pyrazole-4-carboxamide |

| Synthetic Chemistry Example | Compound Structure | Compound Name |
|---|---|---|
| 228 | 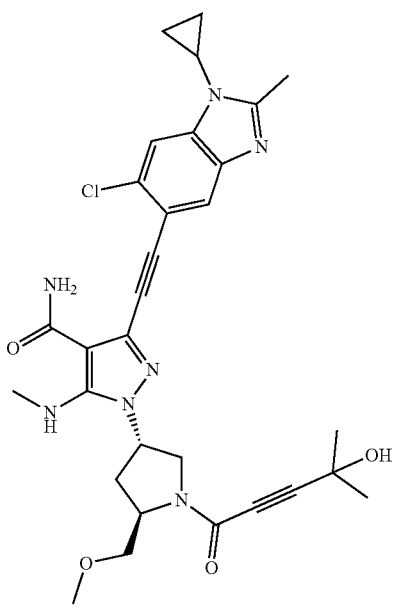 [SMILES: CNc1c(C(N)=O)c(C#Cc2cc3nc(C)n(C4CC4)c3cc2Cl)nn1[C@H]1C[C@H](COC)N(C(=O)C#CC(C)(C)O)C1] | 3-[2-(6-chloro-1-cyclopropyl-2-methyl-1,3-benzodiazol-5-yl)ethynyl]-1-[(3S,5R)-1-(4-hydroxy-4-methylpent-2-ynoyl)-5-(methoxymethyl)pyrrolidin-3-yl]-5-(methylamino)pyrazole-4-carboxamide |
| 230 | 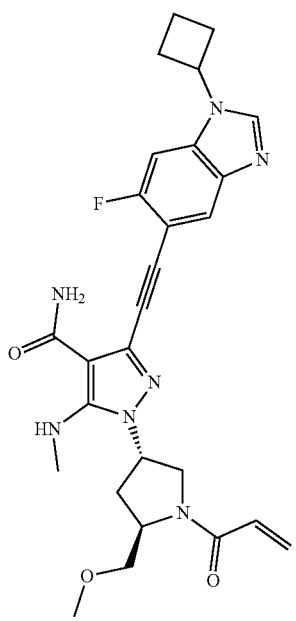 [SMILES: C=CC(=O)N1C[C@@H](n2nc(C#Cc3cc4ncn(C5CCC5)c4cc3F)c(C(N)=O)c2NC)C[C@@H]1COC] | 1-((3S,5R)-1-acryloyl-5-(methoxymethyl)pyrrolidin-3-yl)-3-((1-cyclobutyl-6-fluoro-1H-benzo[d]imidazol-5-yl)ethynyl)-5-(methylamino)-1H-pyrazole-4-carboxamide |

TABLE 1-continued

| Synthetic Chemistry Example | Compound Structure | Compound Name |
|---|---|---|
| 231 | 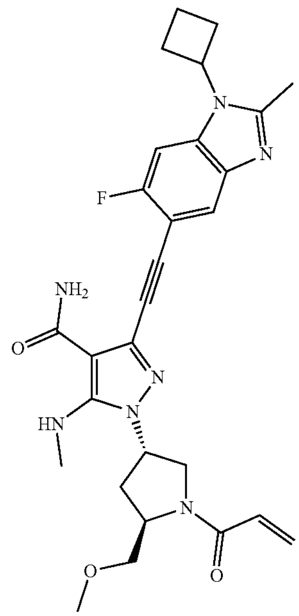 [SMILES: C=CC(=O)N1C[C@@H](n2nc(C#Cc3cc4nc(C)n(C5CCC5)c4cc3F)c(C(N)=O)c2NC)C[C@@H]1COC] | 1-((3S,5R)-1-acryloyl-5-(methoxymethyl)pyrrolidin-3-yl)-3-((1-cyclobutyl-6-fluoro-2-methyl-1H-benzo[d]imidazol-5-yl)ethynyl)-5-(methylamino)-1H-pyrazole-4-carboxamide |
| 232 | 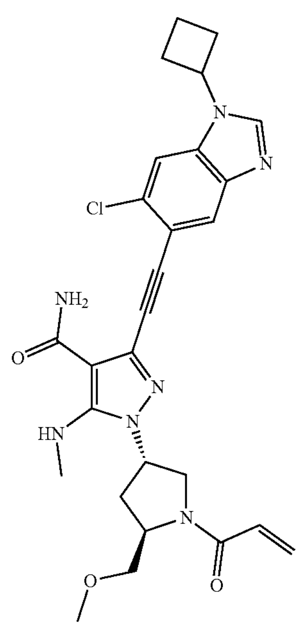 [SMILES: C=CC(=O)N1C[C@@H](n2nc(C#Cc3cc4ncn(C5CCC5)c4cc3Cl)c(C(N)=O)c2NC)C[C@@H]1COC] | 3-[2-(6-chloro-1-cyclobutyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |

TABLE 1-continued
| Synthetic Chemistry Example | Compound Structure | Compound Name |
|---|---|---|
| 233 | 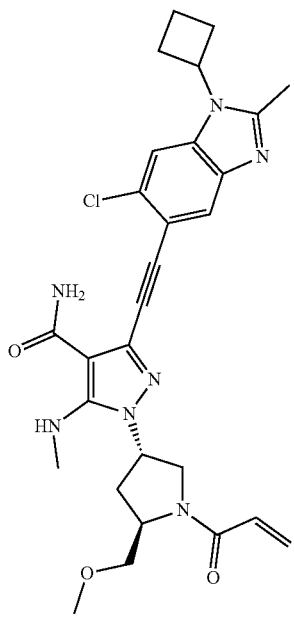 [SMILES: C=CC(=O)N1C[C@@H](n2nc(C#Cc3cc4nc(C)n(C5CCC5)c4cc3Cl)c(C(N)=O)c2NC)C[C@@H]1COC] | 1-((3S,5R)-1-acryloyl-5-(methoxymethyl)pyrrolidin-3-yl)-3-((6-chloro-1-cyclobutyl-2-methyl-1H-benzo[d]imidazol-5-yl)ethynyl)-5-(methylamino)-1H-pyrazole-4-carboxamide |
| 234 | 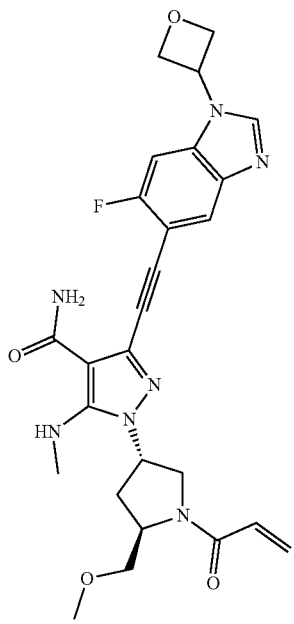 [SMILES: C=CC(=O)N1C[C@@H](n2nc(C#Cc3cc4ncn(C5COC5)c4cc3F)c(C(N)=O)c2NC)C[C@@H]1COC] | 3-{2-[6-fluoro-1-(oxetan-3-yl)-1,3-benzodiazol-5-yl]ethynyl}-1-[(3S,5R)-5-(methoxymethyl)-1-(prop-2-enoyl)pyrrolidin-3-yl]-5-(methylamino)pyrazole-4-carboxamide |

TABLE 1-continued
| Synthetic Chemistry Example | Compound Structure | Compound Name |
|---|---|---|
| 235 | 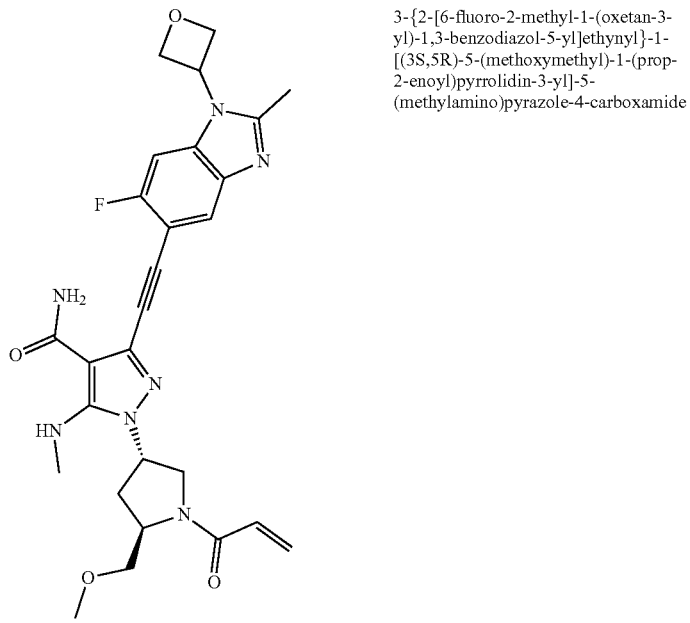 | 3-{2-[6-fluoro-2-methyl-1-(oxetan-3-yl)-1,3-benzodiazol-5-yl]ethynyl}-1-[(3S,5R)-5-(methoxymethyl)-1-(prop-2-enoyl)pyrrolidin-3-yl]-5-(methylamino)pyrazole-4-carboxamide |
| 236 | 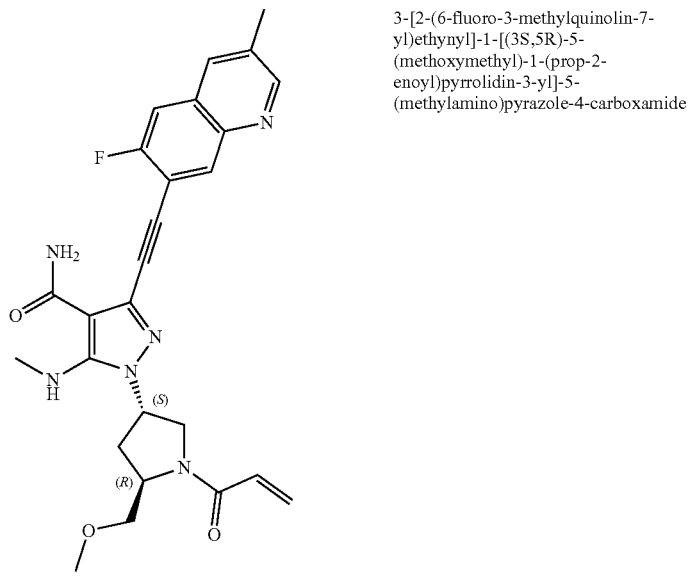 | 3-[2-(6-fluoro-3-methylquinolin-7-yl)ethynyl]-1-[(3S,5R)-5-(methoxymethyl)-1-(prop-2-enoyl)pyrrolidin-3-yl]-5-(methylamino)pyrazole-4-carboxamide |

TABLE 1-continued
| Synthetic Chemistry Example | Compound Structure | Compound Name |
|---|---|---|
| 237 | 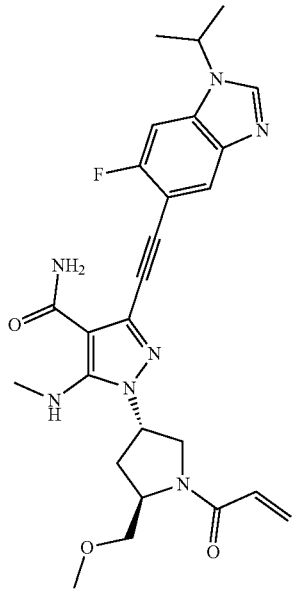 [SMILES: C=CC(=O)N1C[C@@H](n2nc(C#Cc3cc4ncn(C(C)C)c4cc3F)c(C(N)=O)c2NC)C[C@@H]1COC] | 1-((3S,5R)-1-acryloyl-5-(methoxymethyl)pyrrolidin-3-yl)-3-((6-fluoro-1-isopropyl-1H-benzo[d]imidazol-5-yl)ethynyl)-5-(methylamino)-1H-pyrazole-4-carboxamide |
| 238 | 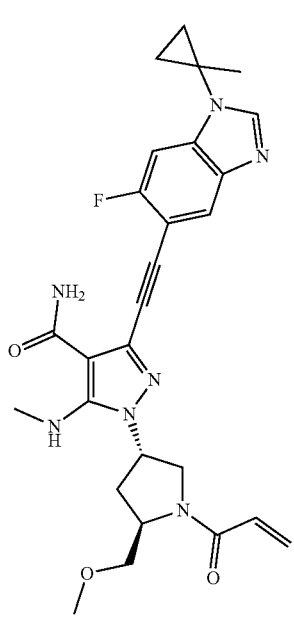 [SMILES: C=CC(=O)N1C[C@@H](n2nc(C#Cc3cc4ncn(C5(C)CC5)c4cc3F)c(C(N)=O)c2NC)C[C@@H]1COC] | 3-{2-[6-fluoro-1-(1-methylcyclopropyl)-1,3-benzodiazol-5-yl]ethynyl}-1-[(3S,5R)-5-(methoxymethyl)-1-(prop-2-enoyl)pyrrolidin-3-yl]-5-(methylamino)pyrazole-4-carboxamide |

TABLE 1-continued
| Synthetic Chemistry Example | Compound Structure | Compound Name |
|---|---|---|
| 239 | 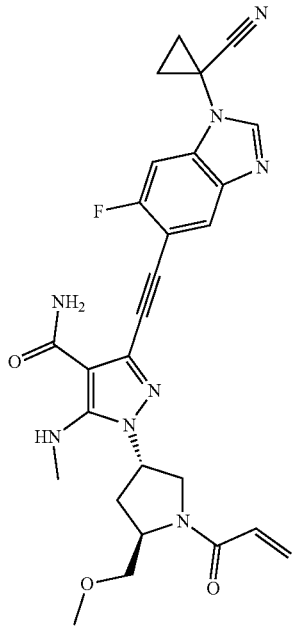 [SMILES: C=CC(=O)N1C[C@@H](n2nc(C#Cc3cc4ncn(C5(C#N)CC5)c4cc3F)c(C(N)=O)c2NC)C[C@@H]1COC] | 1-((3S,5R)-1-acryloyl-5-(methoxymethyl)pyrrolidin-3-yl)-3-((1-(1-cyanocyclopropyl)-6-fluoro-1H-benzo[d]imidazol-5-yl)ethynyl)-5-(methylamino)-1H-pyrazole-4-carboxamide |
| 240 | 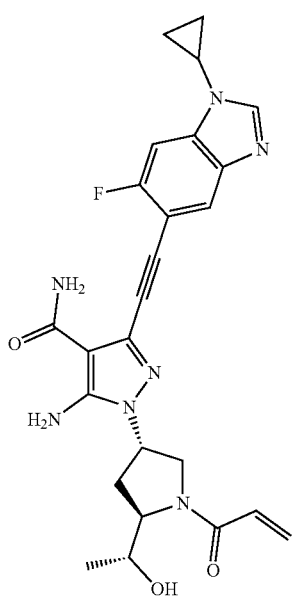 [SMILES: C=CC(=O)N1C[C@@H](n2nc(C#Cc3cc4ncn(C5CC5)c4cc3F)c(C(N)=O)c2N)C[C@@H]1[C@@H](C)O] | 5-amino-3-[2-(1-cyclopropyl-6-fluoro-1,3-benzodiazol-5-yl)ethynyl]-1-[(3S,5R)-5-[(1R)-1-hydroxyethyl]-1-(prop-2-enoyl)pyrrolidin-3-yl]pyrazole-4-carboxamide |

TABLE 1-continued
| Synthetic Chemistry Example | Compound Structure | Compound Name |
|---|---|---|
| 241 | 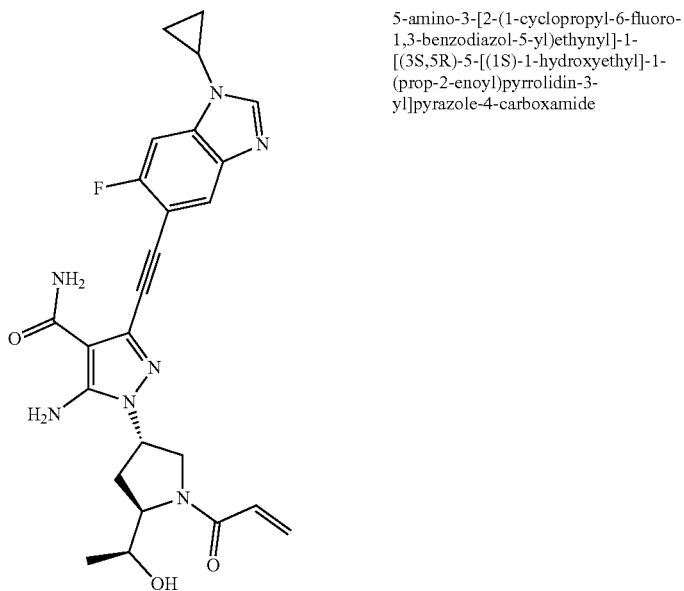 | 5-amino-3-[2-(1-cyclopropyl-6-fluoro-1,3-benzodiazol-5-yl)ethynyl]-1-[(3S,5R)-5-[(1S)-1-hydroxyethyl]-1-(prop-2-enoyl)pyrrolidin-3-yl]pyrazole-4-carboxamide |
| 242 | 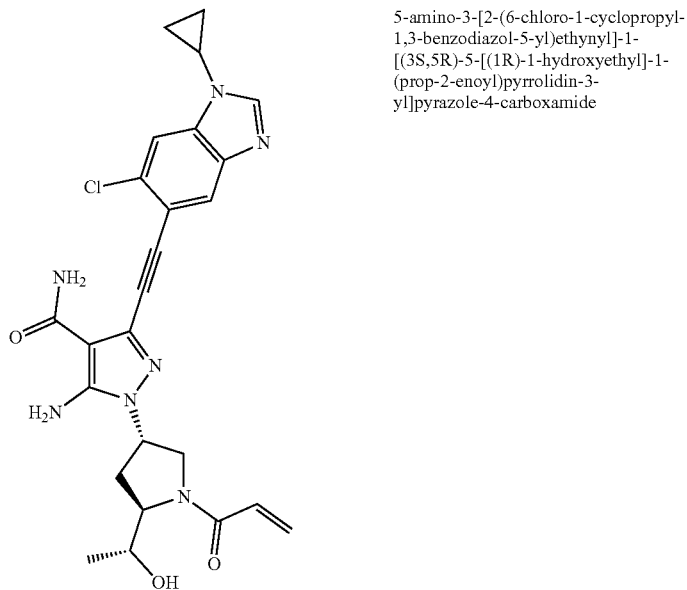 | 5-amino-3-[2-(6-chloro-1-cyclopropyl-1,3-benzodiazol-5-yl)ethynyl]-1-[(3S,5R)-5-[(1R)-1-hydroxyethyl]-1-(prop-2-enoyl)pyrrolidin-3-yl]pyrazole-4-carboxamide |

TABLE 1-continued
| Synthetic Chemistry Example | Compound Structure | Compound Name |
|---|---|---|
| 243 | 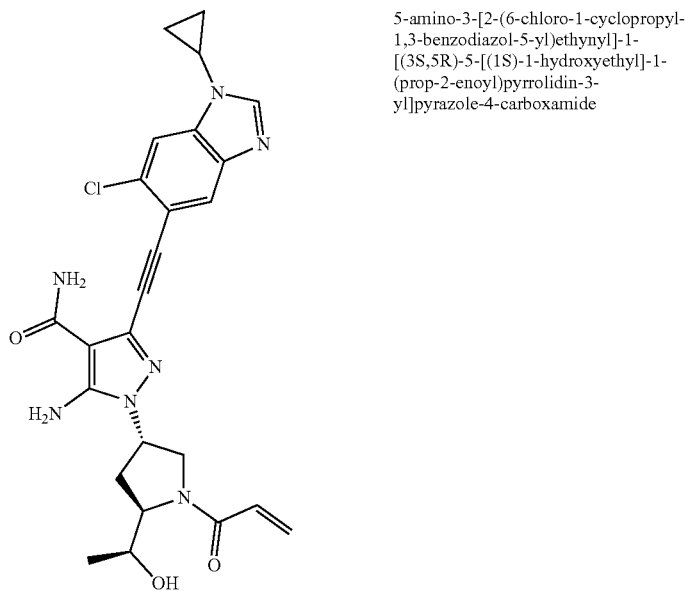 | 5-amino-3-[2-(6-chloro-1-cyclopropyl-1,3-benzodiazol-5-yl)ethynyl]-1-[(3S,5R)-5-[(1S)-1-hydroxyethyl]-1-(prop-2-enoyl)pyrrolidin-3-yl]pyrazole-4-carboxamide |
| 244 | 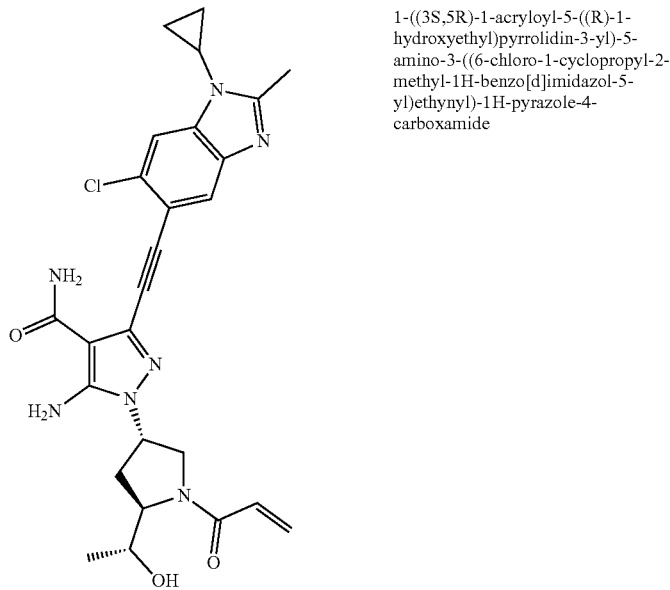 | 1-((3S,5R)-1-acryloyl-5-((R)-1-hydroxyethyl)pyrrolidin-3-yl)-5-amino-3-((6-chloro-1-cyclopropyl-2-methyl-1H-benzo[d]imidazol-5-yl)ethynyl)-1H-pyrazole-4-carboxamide |

TABLE 1-continued
| Synthetic Chemistry Example | Compound Structure | Compound Name |
|---|---|---|
| 245 | 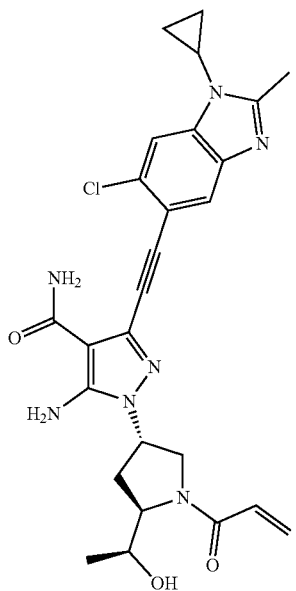 [SMILES: C=CC(=O)N1C[C@@H](n2nc(C#Cc3cc4nc(C)n(C5CC5)c4cc3Cl)c(C(N)=O)c2N)C[C@@H]1[C@H](C)O] | 1-((3S,5R)-1-Acryloyl-5-((S)-1-hydroxyethyl)pyrrolidin-3-yl)-5-amino-3-((6-chloro-1-cyclopropyl-2-methyl-1H-benzo[d]imidazol-5-yl)ethynyl)-1H-pyrazole-4-carboxamide |
| 246 | 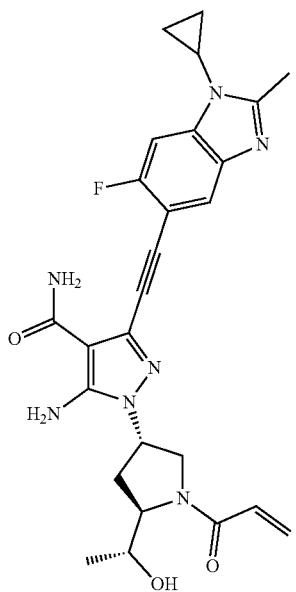 [SMILES: C=CC(=O)N1C[C@@H](n2nc(C#Cc3cc4nc(C)n(C5CC5)c4cc3F)c(C(N)=O)c2N)C[C@@H]1[C@@H](C)O] | 5-amino-3-[2-(1-cyclopropyl-6-fluoro-2-methyl-1,3-benzodiazol-5-yl)ethynyl]-1-[(3S,5R)-5-[(1R)-1-hydroxyethyl]-1-(prop-2-enoyl)pyrrolidin-3-yl]pyrazole-4-carboxamide |

TABLE 1-continued

| Synthetic Chemistry Example | Compound Structure | Compound Name |
|---|---|---|
| 247 | 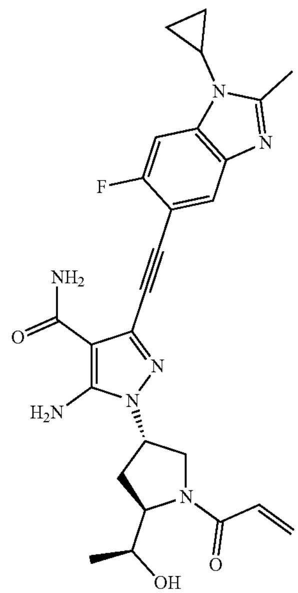 [SMILES: C=CC(=O)N1C[C@@H](n2nc(C#Cc3cc4nc(C)n(C5CC5)c4cc3F)c(C(N)=O)c2N)C[C@@H]1[C@H](C)O] | 5-amino-3-[2-(1-cyclopropyl-6-fluoro-2-methyl-1,3-benzodiazol-5-yl)ethynyl]-1-[(3S,5R)-5-[(1S)-1-hydroxyethyl]-1-(prop-2-enoyl)pyrrolidin-3-yl]pyrazole-4-carboxamide |
| 248 | 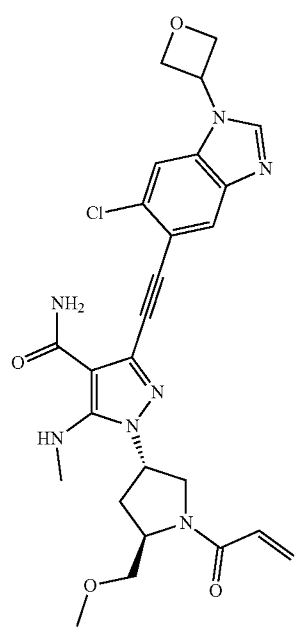 [SMILES: C=CC(=O)N1C[C@@H](n2nc(C#Cc3cc4ncn(C5COC5)c4cc3Cl)c(C(N)=O)c2NC)C[C@@H]1COC] | 3-{2-[6-chloro-1-(oxetan-3-yl)-1,3-benzodiazol-5-yl]ethynyl}-1-[3S,5R)-5-(methoxymethyl)-1-(prop-2-enoyl)pyrrolidin-3-yl]-5-(methylamino)pyrazole-4-carboxamide |

TABLE 1-continued

| Synthetic Chemistry Example | Compound Structure | Compound Name |
|---|---|---|
| 249 | 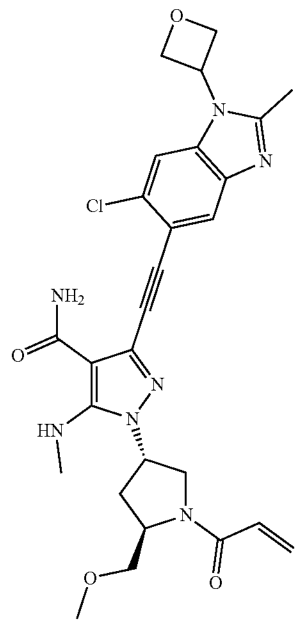 [SMILES: C=CC(=O)N1C[C@@H](n2nc(C#Cc3cc4nc(C)n(C5COC5)c4cc3Cl)c(C(N)=O)c2NC)C[C@@H]1COC] | 3-{2-[6-chloro-2-methyl-1-(oxetan-3-yl)-1,3-benzodiazol-5-yl]ethynyl}-1-[(3S,5R)-5-(methoxymethyl)-1-(prop-2-enoyl)pyrrolidin-3-yl]-5-(methylamino)pyrazole-4-carboxamide |
| 250 | 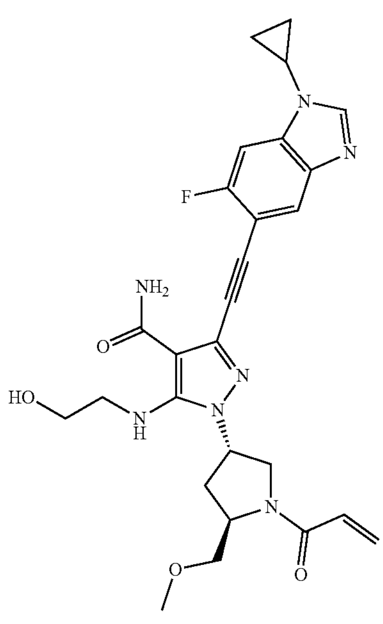 [SMILES: C=CC(=O)N1C[C@@H](n2nc(C#Cc3cc4ncn(C5CC5)c4cc3F)c(C(N)=O)c2NCCO)C[C@@H]1COC] | 3-[2-(1-cyclopropyl-6-fluoro-1,3-benzodiazol-5-yl)ethynyl]-5-[(2-hydroxyethyl)amino]-1-[(3S,5R)-5-(methoxymethyl)-1-(prop-2-enoyl)pyrrolidin-3-yl]pyrazole-4-carboxamide |

TABLE 1-continued
| Synthetic Chemistry Example | Compound Structure | Compound Name |
|---|---|---|
| 251 | 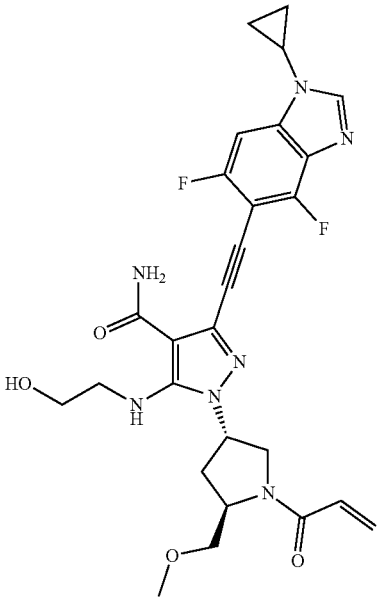 [SMILES: C=CC(=O)N1C[C@@H](n2nc(C#Cc3c(F)cc4c(ncn4C4CC4)c3F)c(C(N)=O)c2NCCO)C[C@@H]1COC] | 3-[2-(1-cyclopropyl-4,6-difluoro-1,3-benzodiazol-5-yl)ethynyl]-5-[(2-hydroxyethyl)amino]-1-[(3S,5R)-5-(methoxymethyl)-1-(prop-2-enoyl)pyrrolidin-3-yl]pyrazole-4-carboxamide |
| 252 | 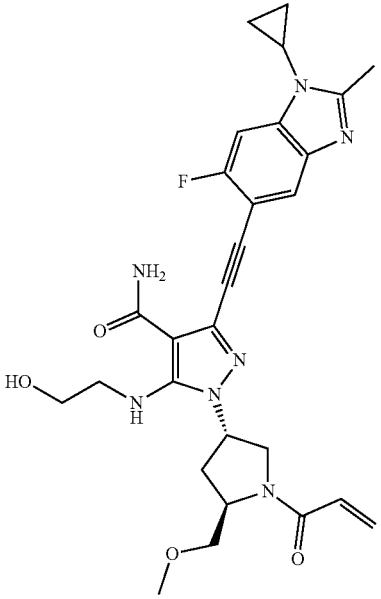 [SMILES: C=CC(=O)N1C[C@@H](n2nc(C#Cc3cc4nc(C)n(C5CC5)c4cc3F)c(C(N)=O)c2NCCO)C[C@@H]1COC] | 3-[2-(1-cyclopropyl-6-fluoro-2-methyl-1,3-benzodiazol-5-yl)ethynyl]-5-[(2-hydroxyethyl)amino]-1-[(3S,5R)-5-(methoxymethyl)-1-(prop-2-enoyl)pyrrolidin-3-yl]pyrazole-4-carboxamide |

TABLE 1-continued
| Synthetic Chemistry Example | Compound Structure | Compound Name |
|---|---|---|
| 253 | 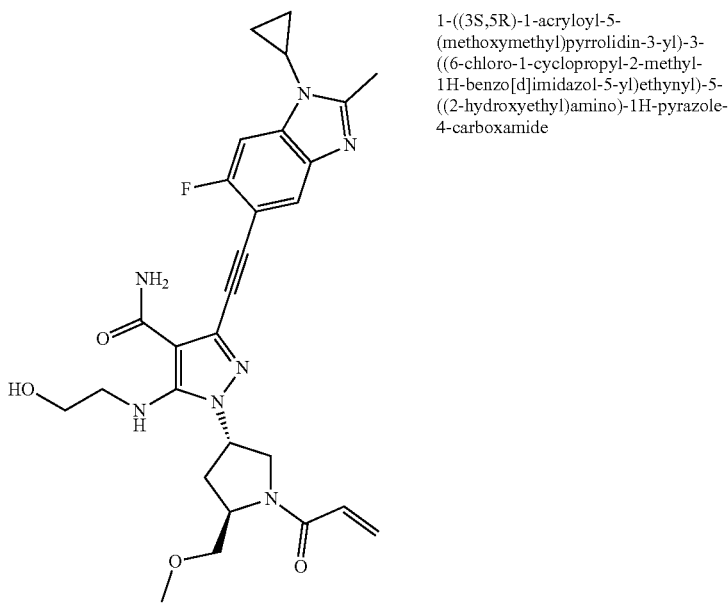 | 1-((3S,5R)-1-acryloyl-5-(methoxymethyl)pyrrolidin-3-yl)-3-((6-chloro-1-cyclopropyl-2-methyl-1H-benzo[d]imidazol-5-yl)ethynyl)-5-((2-hydroxyethyl)amino)-1H-pyrazole-4-carboxamide |
| 254 | 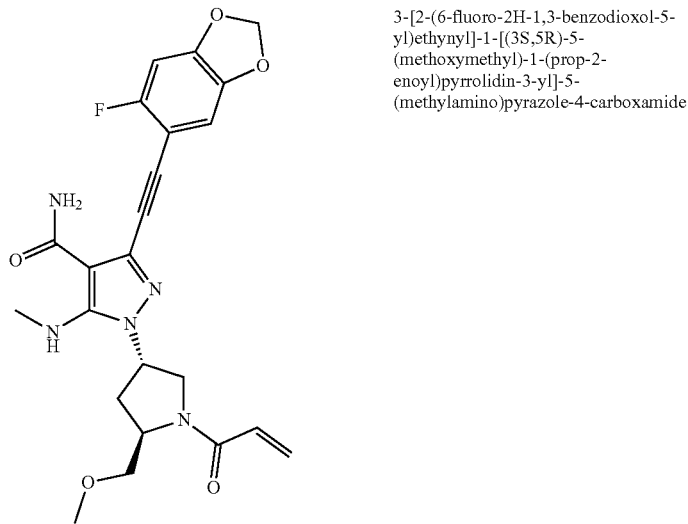 | 3-[2-(6-fluoro-2H-1,3-benzodioxol-5-yl)ethynyl]-1-[(3S,5R)-5-(methoxymethyl)-1-(prop-2-enoyl)pyrrolidin-3-yl]-5-(methylamino)pyrazole-4-carboxamide |

TABLE 1-continued
| Synthetic Chemistry Example | Compound Structure | Compound Name |
|---|---|---|
| 256 | 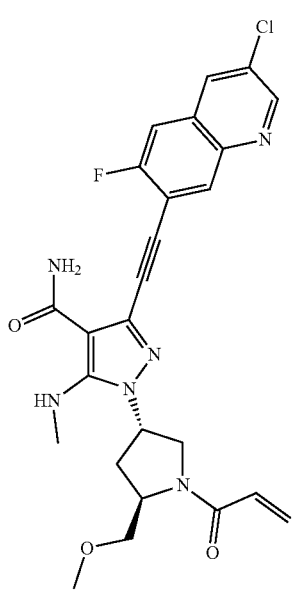 [SMILES: C=CC(=O)N1C[C@@H](n2nc(C#Cc3cc4ncc(Cl)cc4cc3F)c(C(N)=O)c2NC)C[C@@H]1COC] | 3-[2-(3-chloro-6-fluoroquinolin-7-yl)ethynyl]-1-[(3S,5R)-5-(methoxymethyl)-1-(prop-2-enoyl)pyrrolidin-3-yl]-5-(methylamino)pyrazole-4-carboxamide |
| 257 | 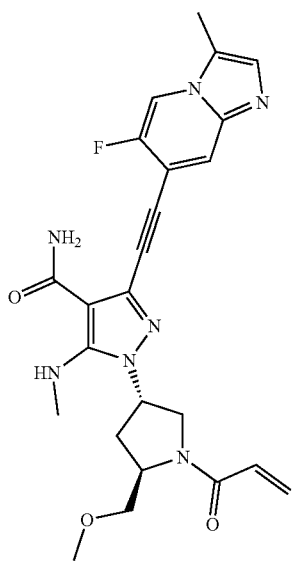 [SMILES: C=CC(=O)N1C[C@@H](n2nc(C#Cc3cc4ncc(C)n4cc3F)c(C(N)=O)c2NC)C[C@@H]1COC] | 1-((3S,5R)-1-acryloyl-5-(methoxymethyl)pyrrolidin-3-yl)-3-((6-fluoro-3-methylimidazo[1,2-a]pyridin-7-yl)ethynyl)-5-(methylamino)-1H-pyrazole-4-carboxamide |

TABLE 1-continued

| Synthetic Chemistry Example | Compound Structure | Compound Name |
|---|---|---|
| 258 | 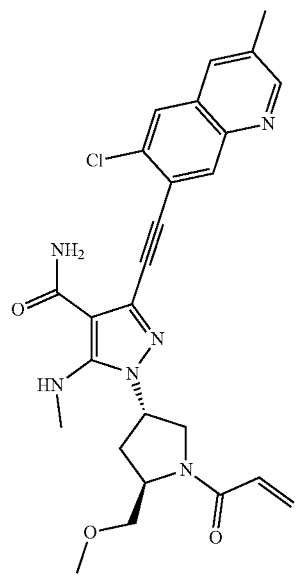 [SMILES: C=CC(=O)N1C[C@@H](n2nc(C#Cc3cc4ncc(C)cc4cc3Cl)c(C(N)=O)c2NC)C[C@@H]1COC] | 1-((3S,5R)-1-acryloyl-5-(methoxymethyl)pyrrolidin-3-yl)-3-((6-chloro-3-methylquinolin-7-yl)ethynyl)-5-(methylamino)-1H-pyrazole-4-carboxamide |
| 259 | 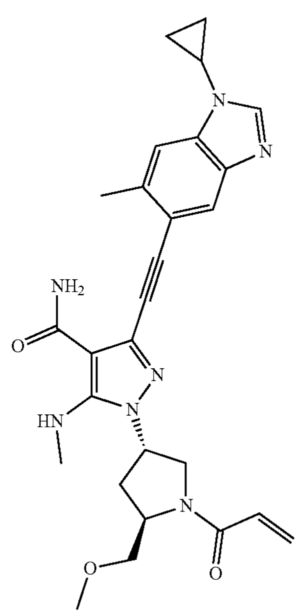 [SMILES: C=CC(=O)N1C[C@@H](n2nc(C#Cc3cc4ncn(C5CC5)c4cc3C)c(C(N)=O)c2NC)C[C@@H]1COC] | 3-[2-(1-cyclopropyl-6-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide |

TABLE 1-continued
| Synthetic Chemistry Example | Compound Structure | Compound Name |
|---|---|---|
| 260 | 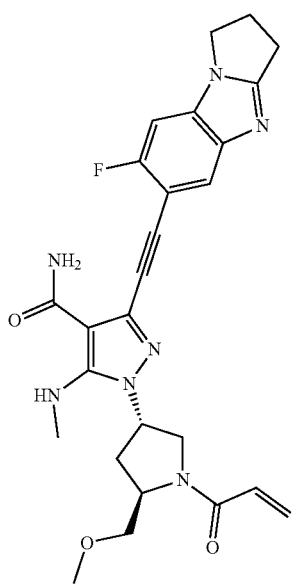 [SMILES: C=CC(=O)N1C[C@@H](n2nc(C#Cc3cc4nc5n(c4cc3F)CCC5)c(C(N)=O)c2NC)C[C@@H]1COC] | 1-((3S,5R)-1-acryloyl-5-(methoxymethyl)pyrrolidin-3-yl)-3-((7-fluoro-2,3-dihydro-1H-benzo[d]pyrrolo[1,2-a]imidazol-6-yl)ethynyl)-5-(methylamino)-1H-pyrazole-4-carboxamide |
| 261 | 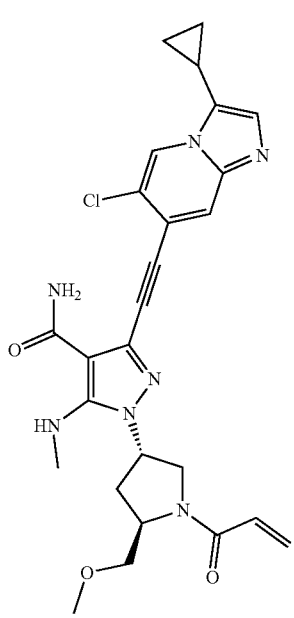 [SMILES: C=CC(=O)N1C[C@@H](n2nc(C#Cc3cc4ncc(C5CC5)n4cc3Cl)c(C(N)=O)c2NC)C[C@@H]1COC] | 3-(2-{6-chloro-3-cyclopropylimidazo[1,2-a]pyridin-7-yl}ethynyl)-1-[(3S,5R)-5-(methoxymethyl)-1-(prop-2-enoyl)pyrrolidin-3-yl]-5-(methylamino)pyrazole-4-carboxamide |

TABLE 1-continued

| Synthetic Chemistry Example | Compound Structure | Compound Name |
|---|---|---|
| 262 | 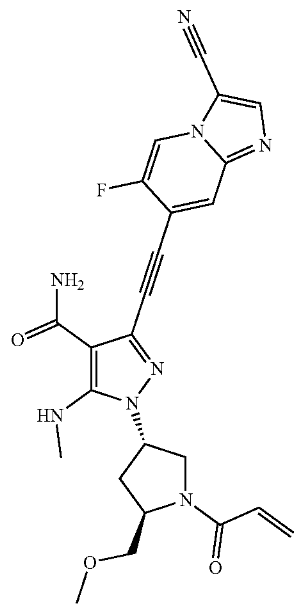 [SMILES: C=CC(=O)N1C[C@@H](n2nc(C#Cc3cc4ncc(C#N)n4cc3F)c(C(N)=O)c2NC)C[C@@H]1COC] | 3-(2-{3-cyano-6-fluoroimidazo[1,2-a]pyridin-7-yl}ethynyl)-1-[(3S,5R)-5-(methoxymethyl)-1-(prop-2-enoyl)pyrrolidin-3-yl]-5-(methylamino)pyrazole-4-carboxamide |
| 263 | 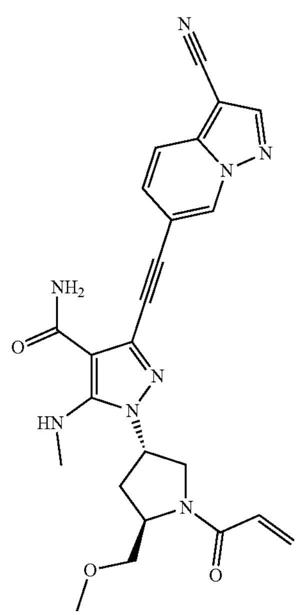 [SMILES: C=CC(=O)N1C[C@@H](n2nc(C#Cc3ccc4c(C#N)cnn4c3)c(C(N)=O)c2NC)C[C@@H]1COC] | 3-(2-{3-cyanopyrazolo[1,5-a]pyridin-6-yl}ethynyl)-1-[(3S,5R)-5-(methoxymethyl)-1-(prop-2-enoyl)pyrrolidin-3-yl]-5-(methylamino)pyrazole-4-carboxamide |

TABLE 1-continued
| Synthetic Chemistry Example | Compound Structure | Compound Name |
|---|---|---|
| 264 | 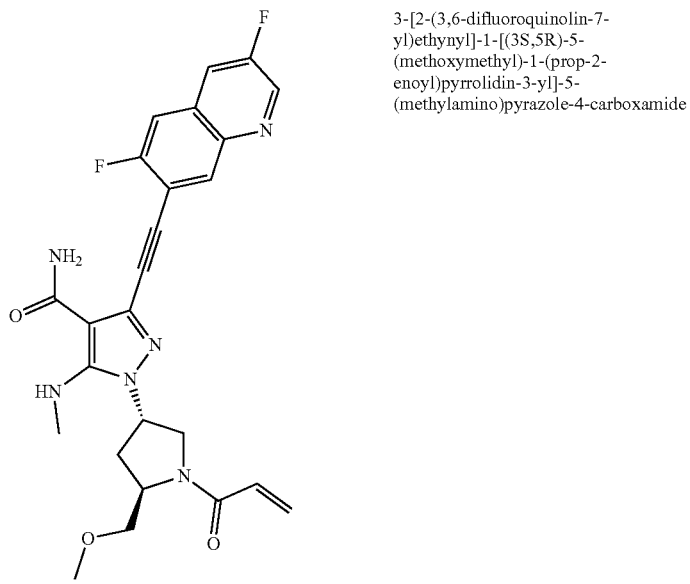 | 3-[2-(3,6-difluoroquinolin-7-yl)ethynyl]-1-[(3S,5R)-5-(methoxymethyl)-1-(prop-2-enoyl)pyrrolidin-3-yl]-5-(methylamino)pyrazole-4-carboxamide |
| 265 | 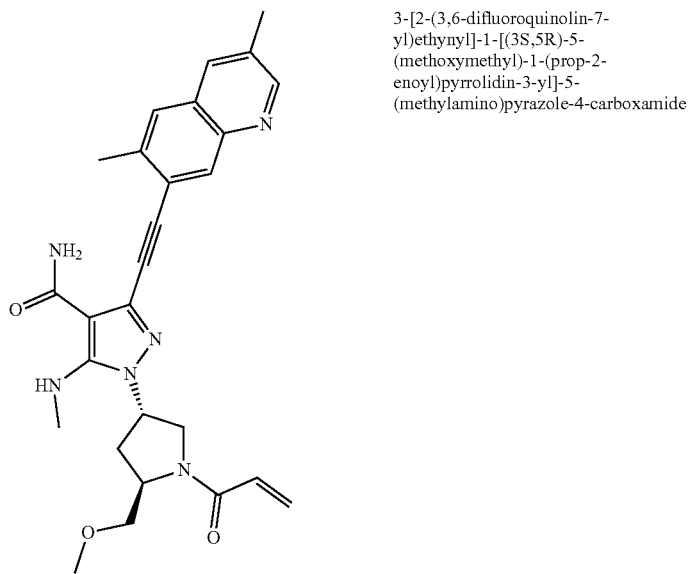 | 3-[2-(3,6-difluoroquinolin-7-yl)ethynyl]-1-[(3S,5R)-5-(methoxymethyl)-1-(prop-2-enoyl)pyrrolidin-3-yl]-5-(methylamino)pyrazole-4-carboxamide |

TABLE 1-continued

| Synthetic Chemistry Example | Compound Structure | Compound Name |
|---|---|---|
| 266 | 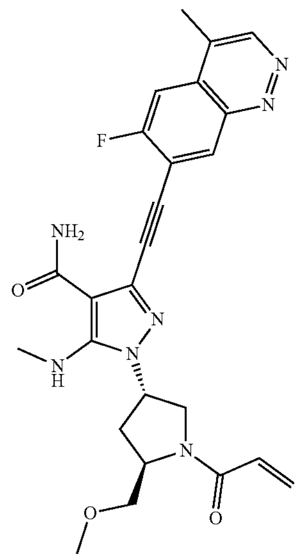 [SMILES: C=CC(=O)N1C[C@@H](n2nc(C#Cc3cc4nncc(C)c4cc3F)c(C(N)=O)c2NC)C[C@@H]1COC] | 1-((3S,5R)-1-acryloyl-5-(methoxymethyl)pyrrolidin-3-yl)-3-((6-fluoro-4-methylcinnolin-7-yl)ethynyl)-5-(methylamino)-1H-pyrazole-4-carboxamide |
| 267 | 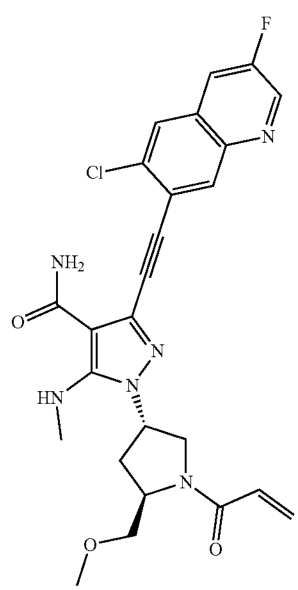 [SMILES: C=CC(=O)N1C[C@@H](n2nc(C#Cc3cc4ncc(F)cc4cc3Cl)c(C(N)=O)c2NC)C[C@@H]1COC] | 3-[2-(6-chloro-3-fluoroquinolin-7-yl)ethynyl]-1-[(3S,5R)-5-(methoxymethyl)-1-(prop-2-enoyl)pyrrolidin-3-yl]-5-(methylamino)pyrazole-4-carboxamide |

TABLE 1-continued

| Synthetic Chemistry Example | Compound Structure | Compound Name |
|---|---|---|
| 268 | 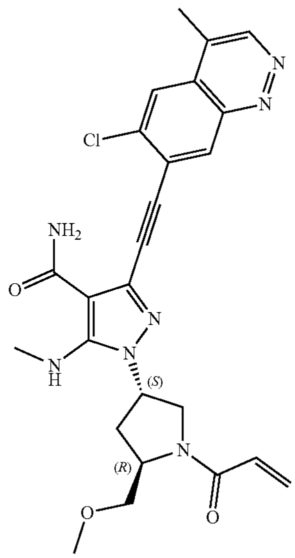 | 1-((3S,5R)-1-acryloyl-5-(methoxymethyl)pyrrolidin-3-yl)-3-((6-chloro-4-methylcinnolin-7-yl)ethynyl)-5-(methylamino)-1H-pyrazole-4-carboxamide |
| 269 | 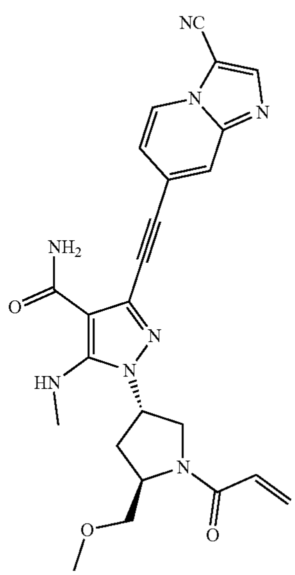 [SMILES: C=CC(=O)N1C[C@@H](n2nc(C#Cc3ccn4c(C#N)cnc4c3)c(C(N)=O)c2NC)C[C@@H]1COC] | 3-(2-{3-cyanoimidazo[1,2-a]pyridin-7-yl}ethynyl)-1-[(3S,5R)-5-(methoxymethyl)-1-(prop-2-enoyl)pyrrolidin-3-yl]-5-(methylamino)pyrazole-4-carboxamide |

TABLE 1-continued
| Synthetic Chemistry Example | Compound Structure | Compound Name |
|---|---|---|
| 270 | 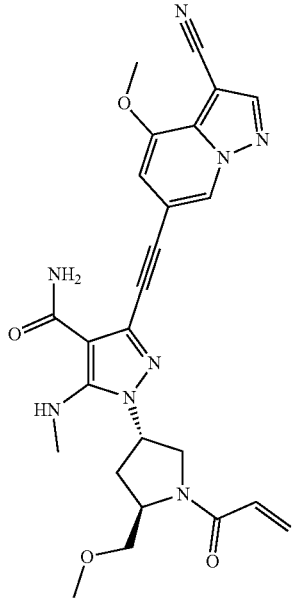 [SMILES: C=CC(=O)N1C[C@@H](n2nc(C#Cc3cc(OC)c4c(C#N)cnn4c3)c(C(N)=O)c2NC)C[C@@H]1COC] | 1-((3S,5R)-1-acryloyl-5-(methoxymethyl)pyrrolidin-3-yl)-3-((3-cyano-4-methoxypyrazolo[1,5-a]pyridin-6-yl)ethynyl)-5-(methylamino)-1H-pyrazole-4-carboxamide |
| 271 | 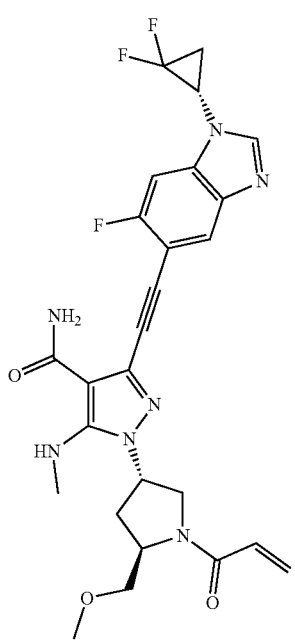 [SMILES: C=CC(=O)N1C[C@@H](n2nc(C#Cc3cc4ncn([C@H]5CC5(F)F)c4cc3F)c(C(N)=O)c2NC)C[C@@H]1COC] | 3-(2-{1-[(1S)-2,2-Difluorocyclopropyl]-6-fluoro-1,3-benzodiazol-5-yl}ethynyl)-1-[(3S,5R)-5-(methoxymethyl)-1-(prop-2-enoyl)pyrrolidin-3-yl]-5-(methylamino)pyrazole-4-carboxamide |

TABLE 1-continued

| Synthetic Chemistry Example | Compound Structure | Compound Name |
|---|---|---|
| 272 | 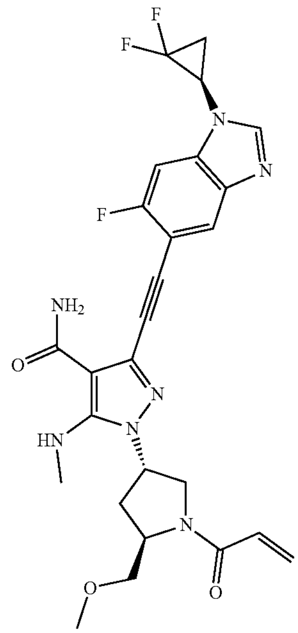 [SMILES: C=CC(=O)N1C[C@@H](n2nc(C#Cc3cc4ncn([C@@H]5CC5(F)F)c4cc3F)c(C(N)=O)c2NC)C[C@@H]1COC] | 3-(2-{1-[((R)-2,2-difluorocyclopropyl)-6-fluoro-1,3-benzodiazol-5-yl]ethynyl}-1-[(3S,5R)-5-(methoxymethyl)-1-(prop-2-enoyl)pyrrolidin-3-yl]-5-(methylamino)pyrazole-4-carboxamide |
| 273 | 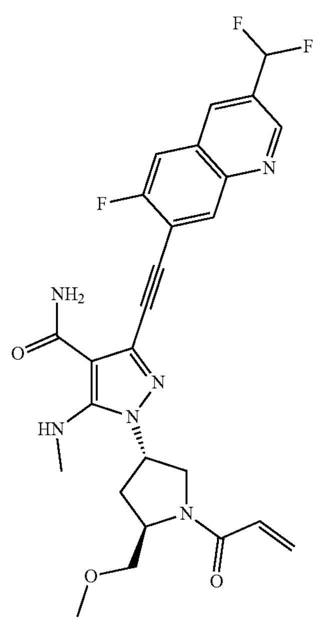 [SMILES: C=CC(=O)N1C[C@@H](n2nc(C#Cc3cc4ncc(C(F)F)cc4cc3F)c(C(N)=O)c2NC)C[C@@H]1COC] | 3-{2-[3-(difluoromethyl)-6-fluoroquinolin-7-yl]ethynyl}-1-[(3S,5R)-5-(methoxymethyl)-1-(prop-2-enoyl)pyrrolidin-3-yl]-5-(methylamino)pyrazole-4-carboxamide |

TABLE 1-continued

| Synthetic Chemistry Example | Compound Structure | Compound Name |
|---|---|---|
| 274 | 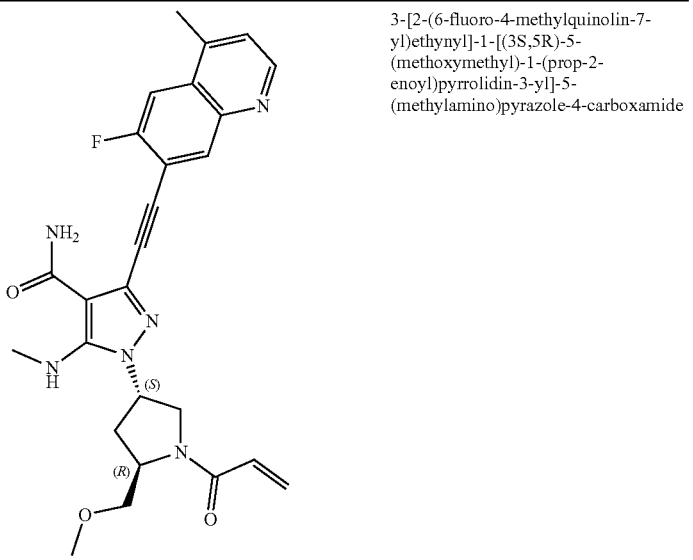 | 3-[2-(6-fluoro-4-methylquinolin-7-yl)ethynyl]-1-[(3S,5R)-5-(methoxymethyl)-1-(prop-2-enoyl)pyrrolidin-3-yl]-5-(methylamino)pyrazole-4-carboxamide |
| 275 | 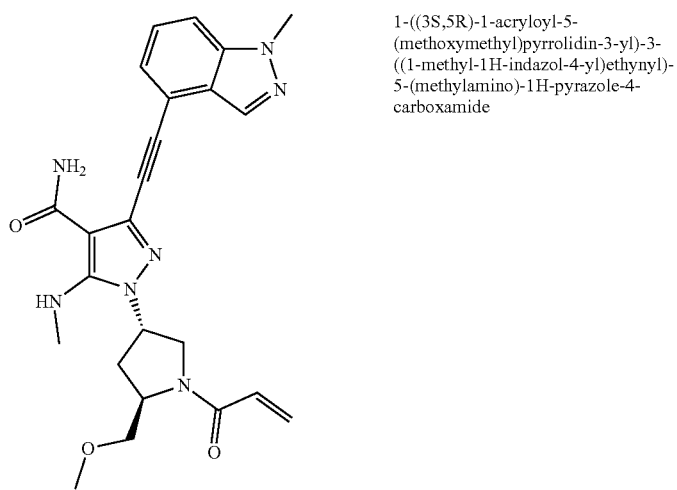 | 1-((3S,5R)-1-acryloyl-5-(methoxymethyl)pyrrolidin-3-yl)-3-((1-methyl-1H-indazol-4-yl)ethynyl)-5-(methylamino)-1H-pyrazole-4-carboxamide |
| 276 | 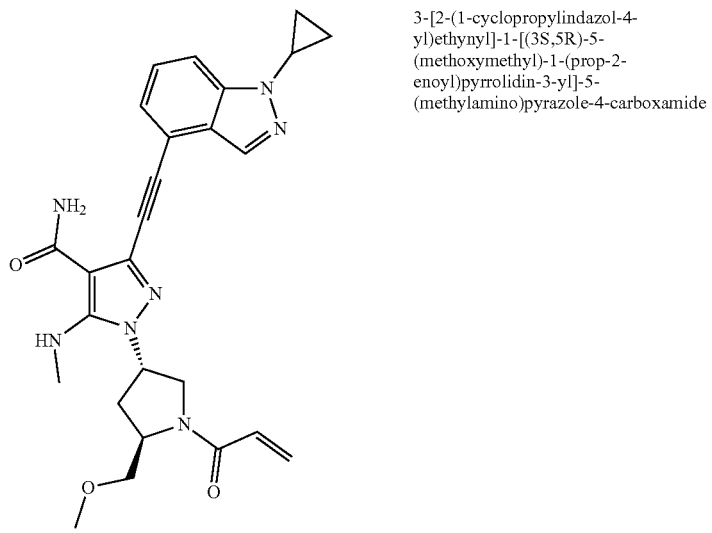 | 3-[2-(1-cyclopropylindazol-4-yl)ethynyl]-1-[(3S,5R)-5-(methoxymethyl)-1-(prop-2-enoyl)pyrrolidin-3-yl]-5-(methylamino)pyrazole-4-carboxamide |

TABLE 1-continued
| Synthetic Chemistry Example | Compound Structure | Compound Name |
|---|---|---|
| 277 | 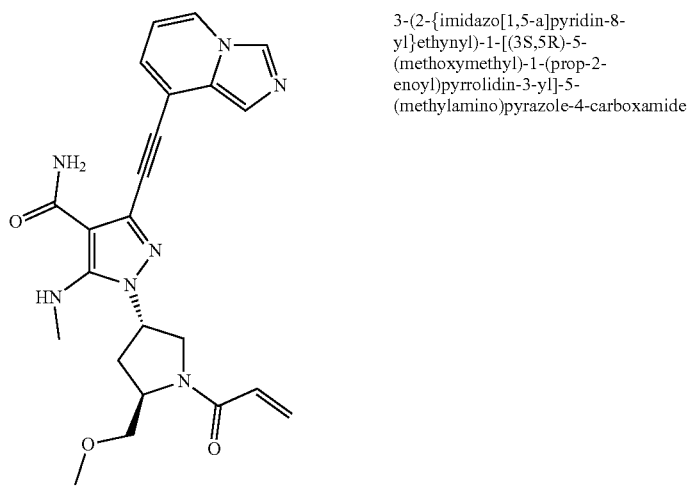 | 3-(2-{imidazo[1,5-a]pyridin-8-yl}ethynyl)-1-[(3S,5R)-5-(methoxymethyl)-1-(prop-2-enoyl)pyrrolidin-3-yl]-5-(methylamino)pyrazole-4-carboxamide |
| 278 | 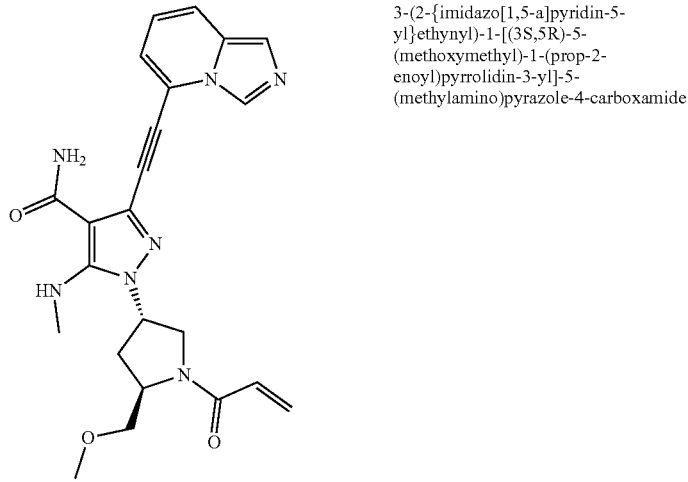 | 3-(2-{imidazo[1,5-a]pyridin-5-yl}ethynyl)-1-[(3S,5R)-5-(methoxymethyl)-1-(prop-2-enoyl)pyrrolidin-3-yl]-5-(methylamino)pyrazole-4-carboxamide |

TABLE 1-continued
| Synthetic Chemistry Example | Compound Structure | Compound Name |
|---|---|---|
| 279 | 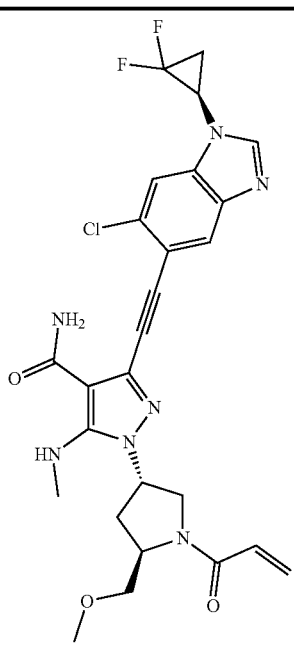 | 3-(2-{6-chloro-1-[(1R)-2,2-difluorocyclopropyl]-1,3-benzodiazol-5-yl}ethynyl)-1-[(3S,5R)-5-(methoxymethyl)-1-(prop-2-enoyl)pyrrolidin-3-yl]-5-(methylamino)pyrazole-4-carboxamide |
| 280 | 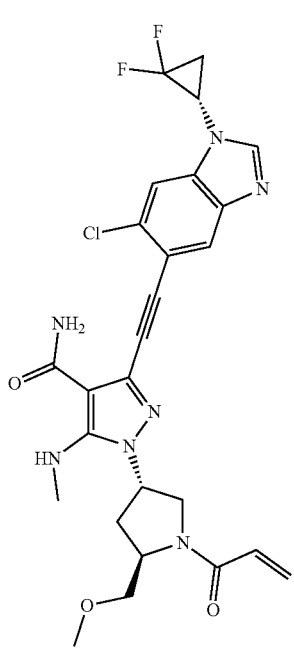 [SMILES: C=CC(=O)N1C[C@@H](n2nc(C#Cc3cc4ncn([C@H]5CC5(F)F)c4cc3Cl)c(C(N)=O)c2NC)C[C@@H]1COC] | 3-(2-{6-Chloro-1-[(1S)-2,2-difluorocyclopropyl]-1,3-benzodiazol-5-yl}ethynyl)-1-[(3S,5R)-5-(methoxymethyl)-1-(prop-2-enoyl)pyrrolidin-3-yl]-5-(methylamino)pyrazole-4-carboxamide |

TABLE 1-continued
| Synthetic Chemistry Example | Compound Structure | Compound Name |
|---|---|---|
| 281 | 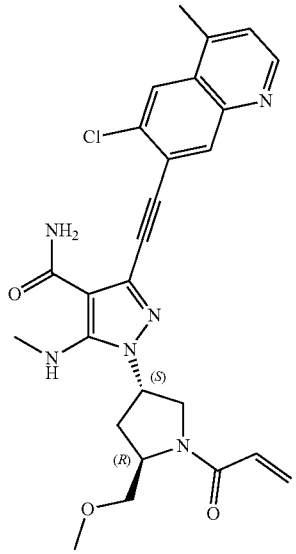 | 3-[2-(6-chloro-4-methylquinolin-7-yl)ethynyl]-1-[(3S,5R)-5-(methoxymethyl)-1-(prop-2-enoyl)pyrrolidin-3-yl]-5-(methylamino)pyrazole-4-carboxamide |
| 282 | 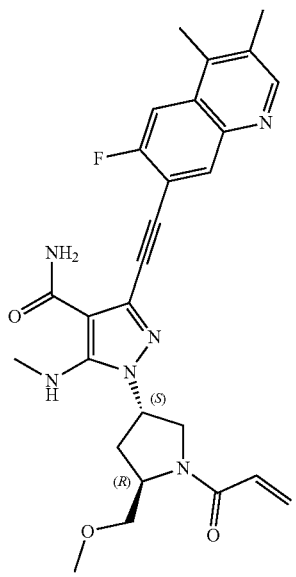 | 1-((3S,5R)-1-acryloyl-5-(methoxymethyl)pyrrolidin-3-yl)-3-((6-fluoro-3,4-dimethylquinolin-7-yl)ethynyl)-5-(methylamino)-1H-pyrazole-4-carboxamide |

TABLE 1-continued
| Synthetic Chemistry Example | Compound Structure | Compound Name |
|---|---|---|
| 283 | 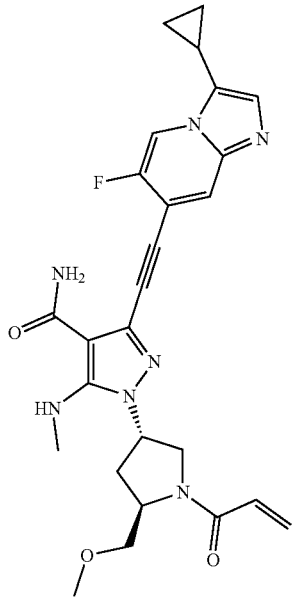 [SMILES: C=CC(=O)N1C[C@@H](n2nc(C#Cc3cc4ncc(C5CC5)n4cc3F)c(C(N)=O)c2NC)C[C@@H]1COC] | 3-(2-{3-cyclopropyl-6-fluoroimidazo[1,2-a]pyridin-7-yl}ethynyl)-1-[(3S,5R)-5-(methoxymethyl)-1-(prop-2-enoyl)pyrrolidin-3-yl]-5-(methylamino)pyrazole-4-carboxamide |
| 284 | 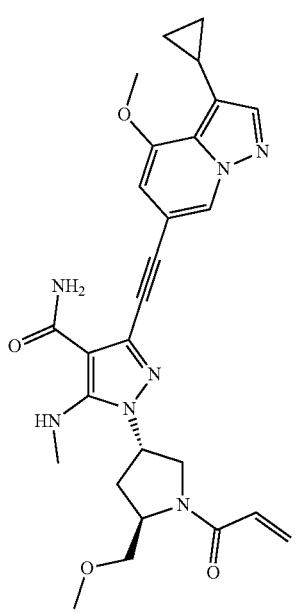 [SMILES: C=CC(=O)N1C[C@@H](n2nc(C#Cc3cc(OC)c4c(C5CC5)cnn4c3)c(C(N)=O)c2NC)C[C@@H]1COC] | 3-(2-{3-cyclopropyl-4-methoxypyrazolo[1,5-a]pyridin-6-yl}ethynyl)-1-[(3S,5R)-5-(methoxymethyl)-1-(prop-2-enoyl)pyrrolidin-3-yl]-5-(methylamino)pyrazole-4-carboxamide |

| Synthetic Chemistry Example | Compound Structure | Compound Name |
|---|---|---|
| 285 | 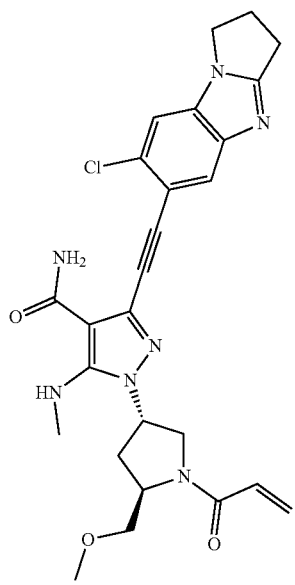 [SMILES: C=CC(=O)N1C[C@@H](n2nc(C#Cc3cc4nc5n(c4cc3Cl)CCC5)c(C(N)=O)c2NC)C[C@@H]1COC] | 1-((3S,5R)-1-acryloyl-5-(methoxymethyl)pyrrolidin-3-yl)-3-((7-chloro-2,3-dihydro-1H-benzo[d]pyrrolo[1,2-a]imidazol-6-yl)ethynyl)-5-(methylamino)-1H-pyrazole-4-carboxamide |
| 287 | 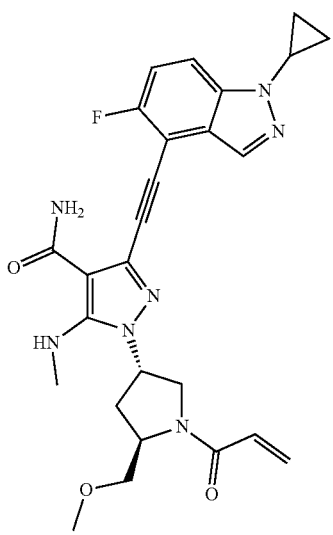 [SMILES: C=CC(=O)N1C[C@@H](n2nc(C#Cc3c(F)ccc4c3cnn4C3CC3)c(C(N)=O)c2NC)C[C@@H]1COC] | 1-((3S,5R)-1-acryloyl-5-(methoxymethyl)pyrrolidin-3-yl)-3-((1-cyclopropyl-6-fluoro-1H-indazol-4-yl)ethynyl)-5-(methylamino)-1H-pyrazole-4-carboxamide |

TABLE 1-continued

| Synthetic Chemistry Example | Compound Structure | Compound Name |
|---|---|---|
| 288 | 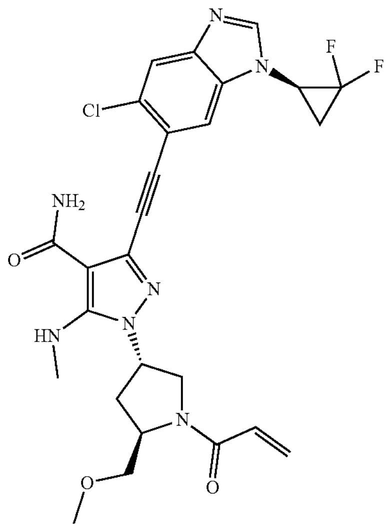 [SMILES: C=CC(=O)N1C[C@@H](n2nc(C#Cc3cc4c(cc3Cl)ncn4[C@@H]3CC3(F)F)c(C(N)=O)c2NC)C[C@@H]1COC] | 3-(2-{6-chloro-3-[(1R)-2,2-difluorocyclopropyl]-1,3-benzodiazol-5-yl}ethynyl)-1-[(3S,5R)-5-(methoxymethyl)-1-(prop-2-enoyl)pyrrolidin-3-yl]-5-(methylamino)pyrazole-4-carboxamide |
| 289 | 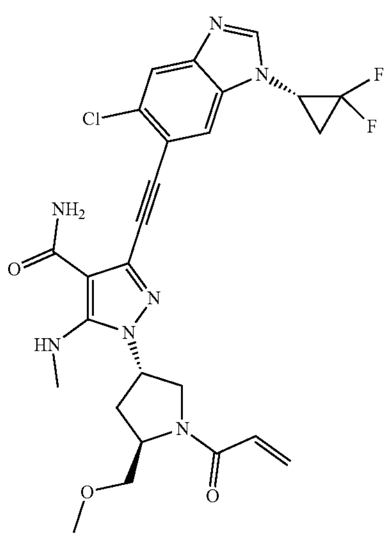 [SMILES: C=CC(=O)N1C[C@@H](n2nc(C#Cc3cc4c(cc3Cl)ncn4[C@H]3CC3(F)F)c(C(N)=O)c2NC)C[C@@H]1COC] | 3-(2-{6-chloro-3-[(1S)-2,2-difluorocyclopropyl]-1,3-benzodiazol-5-yl}ethynyl)-1-[(3S,5R)-5-(methoxymethyl)-1-(prop-2-enoyl)pyrrolidin-3-yl]-5-(methylamino)pyrazole-4-carboxamide |

TABLE 1-continued

| Synthetic Chemistry Example | Compound Structure | Compound Name |
|---|---|---|
| 290 | 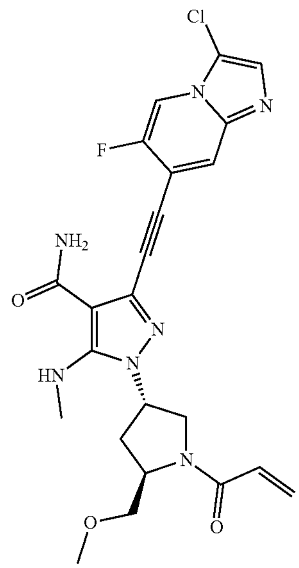 [SMILES: C=CC(=O)N1C[C@@H](n2nc(C#Cc3cc4ncc(Cl)n4cc3F)c(C(N)=O)c2NC)C[C@@H]1COC] | 3-(2-{3-chloro-6-fluoroimidazo[1,2-a]pyridin-7-yl}ethynyl)-1-[(3S,5R)-5-(methoxymethyl)-1-(prop-2-enoyl)pyrrolidin-3-yl]-5-(methylamino)pyrazole-4-carboxamide |

In some embodiments, the heteroaromatic FGFR kinase inhibitory compound disclosed herein has a structure provided in Table 2.

TABLE 2

| | |
|---|---|
| | 1-((3S,5R)-1-acryloyl-5-((methoxy-d3)methyl)pyrrolidin-3-yl)-3-((6-chloro-1-ethyl-1H-benzo[d]imidazol-5-yl)ethynyl)-5-(methylamino)-1H-pyrazole-4-carboxamide |

TABLE 2-continued

| | |
|---|---|
| | (S)-1-(1-acryloylpyrrolidin-3-yl)-3-((6-fluoro-1-methyl-1H-benzo[d]imidazol-5-yl)ethynyl)-5-(methylamino)-1H-pyrazole-4-carboxamide |

TABLE 2-continued

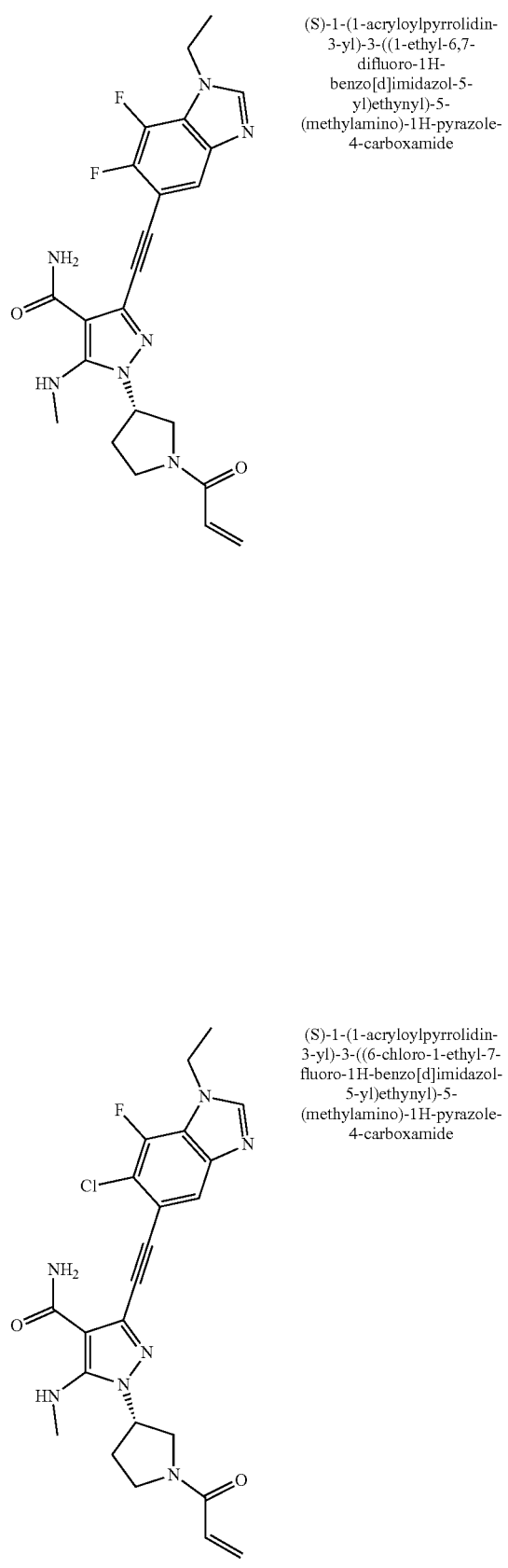

(S)-1-(1-acryloylpyrrolidin-3-yl)-3-((1-ethyl-6,7-difluoro-1H-benzo[d]imidazol-5-yl)ethynyl)-5-(methylamino)-1H-pyrazole-4-carboxamide (S)-1-(1-acryloylpyrrolidin-3-yl)-3-((6-chloro-1-ethyl-7-fluoro-1H-benzo[d]imidazol-5-yl)ethynyl)-5-(methylamino)-1H-pyrazole-4-carboxamide

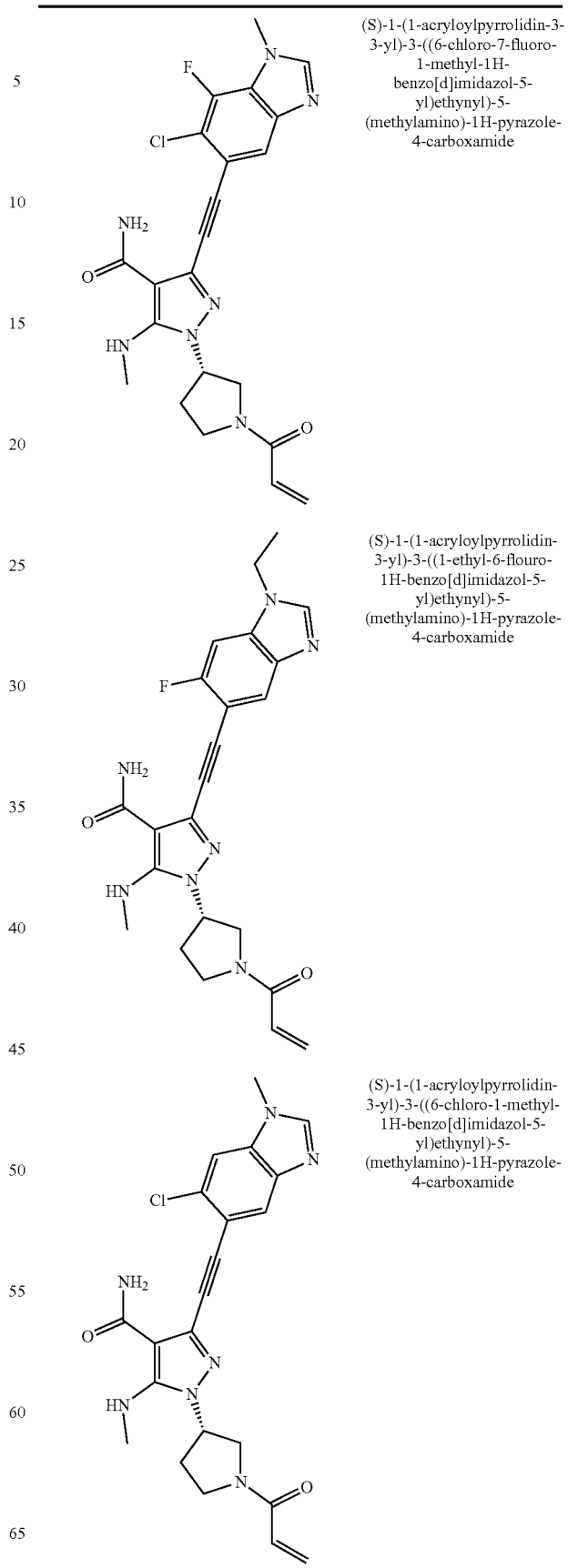

(S)-1-(1-acryloylpyrrolidin-3-yl)-3-((6-chloro-7-fluoro-1-methyl-1H-benzo[d]imidazol-5-yl)ethynyl)-5-(methylamino)-1H-pyrazole-4-carboxamide (S)-1-(1-acryloylpyrrolidin-3-yl)-3-((1-ethyl-6-flouro-1H-benzo[d]imidazol-5-yl)ethynyl)-5-(methylamino)-1H-pyrazole-4-carboxamide (S)-1-(1-acryloylpyrrolidin-3-yl)-3-((6-chloro-1-methyl-1H-benzo[d]imidazol-5-yl)ethynyl)-5-(methylamino)-1H-pyrazole-4-carboxamide

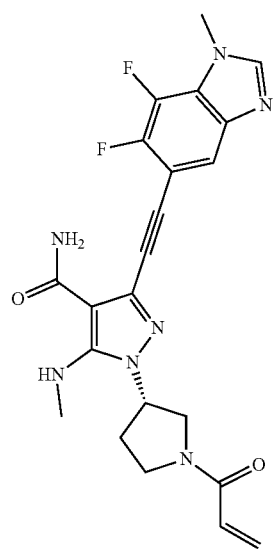 [SMILES: C=CC(=O)N1CC[C@H](n2nc(C#Cc3cc4ncn(C)c4c(F)c3F)c(C(N)=O)c2NC)C1]

(S)-1-(1-acryloylpyrrollidin-3-yl)-3-((6,7-difluoro-1-methyl-1H-benzo[d]imidazol-5-yl)ethynyl)-5-(methylamino)-1H-pyrazole-4-carboxamide

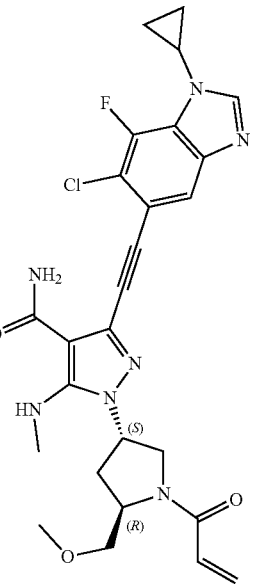

1-((3S,5R)-1-acryloyl-5-(methoxymethyl)pyrrolidin-3-yl)-3-((6-chloro-1-cyclopropyl-7-fluoro-1H-benzo[d]imidazol-5-yl)ethynyl)-5-(methylamino)-1H-pyrazole-4-carboxamide

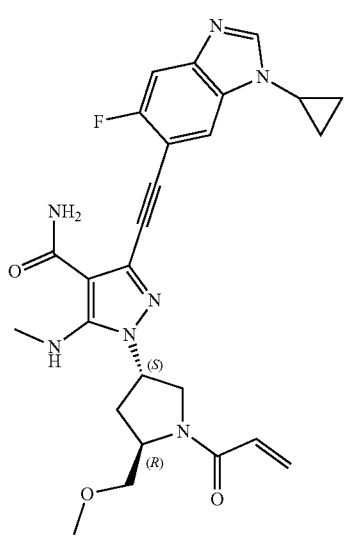

1-((3S,5R)-1-acryloyl-5-(methoxymethyl)pyrrolidin-3-yl)-3-((1-cyclopropyl-5-fluoro-1H-benzo[d]imidazol-6-yl)ethynyl)-5-(methylamino)-1H-pyrazole-4-carboxamide

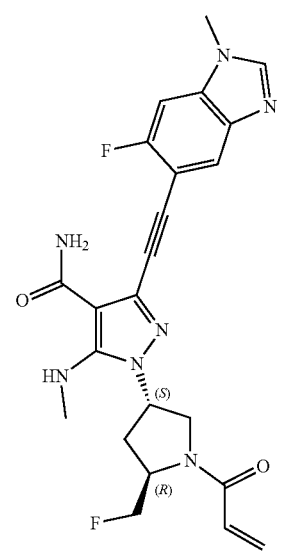

1-((3S,5R)-1-acryloyl-5-(fluoromethyl)pyrrolidin-3-yl)-3-((6-fluoro-1-methyl-1H-benzo[d]imidazol-5-yl)ethynyl)-5-(methylamino)-1H-pyrazole-4-carboxamide

| | |
|---|---|
| 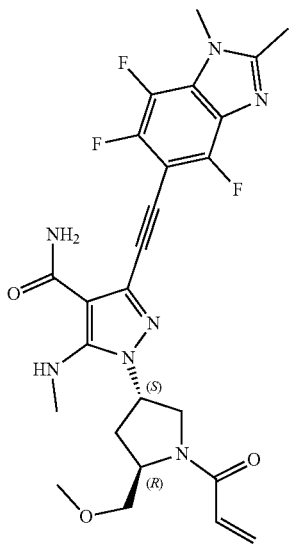 | 1-((3S,5R)-1-acryloyl-5-(methoxymethyl)pyrrolidin-3-yl)-5-(methylamino)-3-((4,6,7-trifluoro-1,2-dimethyl-1H-benzo[d]imidazol-5-yl)ethynyl)-1H-pyrazole-4-carboxamide |
| 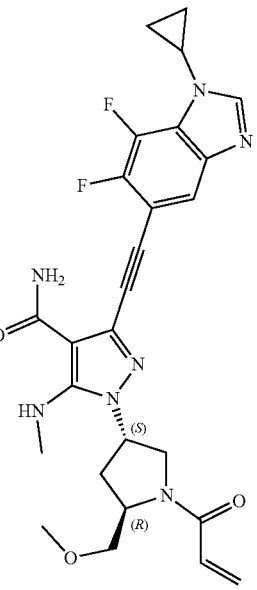 | 1-((3S,5R)-1-acryloyl-5-(methoxymethyl)pyrrolidin-3-yl)-3-((1-cyclopropyl-6,7-difluoro-1H-benzo[d]imidazol-5-yl)ethynyl)-5-(methylamino)-1H-pyrazole-4-carboxamide |
| 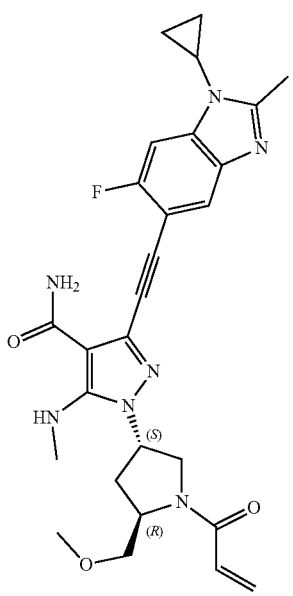 | 1-((3S,5R)-1-acryloyl-5-(methoxymethyl)pyrrolidin-3-yl)-3-((1-cyclopropyl-6-fluoro-2-methyl-1H-benzo[d]imidazol-5-yl)ethynyl)-5-(methylamino)-1H-pyrazole-4-carboxamide |
| 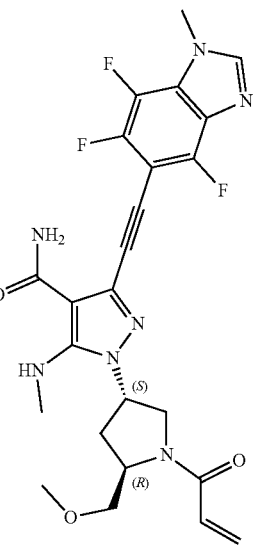 | 1-((3S,5R)-1-acryloyl-5-(methoxymethyl)pyrrolidin-3-yl)-5-(methylamino)-3-((4,6,7-trifluoro-1-methyl-1H-benzo[d]imidazol-5-yl)ethynyl)-1H-pyrazole-4-carboxamide |

TABLE 2-continued

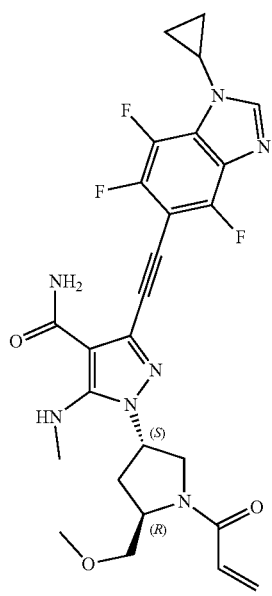

1-((3S,5R)-1-acryloyl-5-(methoxymethyl)pyrrolidin-3-yl-3-((1-cyclopropyl-4,6,7-trifluoro-1H-benzo[d]imidazol-5-yl)ethynyl)-5-(methylamino)-1H-pyrazole-4-carboxamide

1-((3S,5R)-1-acryloyl-5-((difluoromethoxy)methyl)pyrrolidin-3-yl)-3-((1-cyclopropyl-1H-benzo[d]imidazol-5-yl)ethynyl)-5-(methylamino)-1H-pyrazole-4-carboxamide

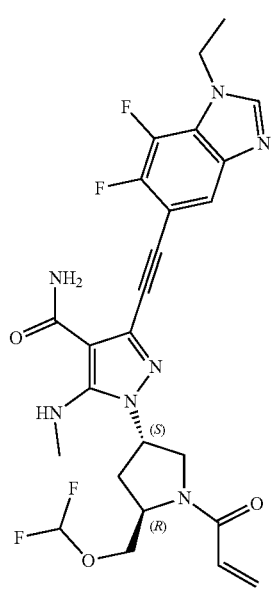

1-((3S,5R)-1-acryloyl-5-((difluoromethoxy)methyl)pyrrolidin-3-yl)-3-((1-ethyl-6,7-difluoro-1H-benzo[d]imidazol-5-yl)ethynyl)-5-(methylamino)-1H-pyrazole-4-carboxamide 1-((3S,5R)-1-acryloyl-5-((difluoromethoxy)methyl)pyrrolidin-3-yl)-3-((1-cyclopropyl-4,6-difluoro-1H-benzo[d]imidazol-5-yl)ethynyl)-5-(methylamino)-1H-pyrazole-4-carboxamide TABLE 2-continued

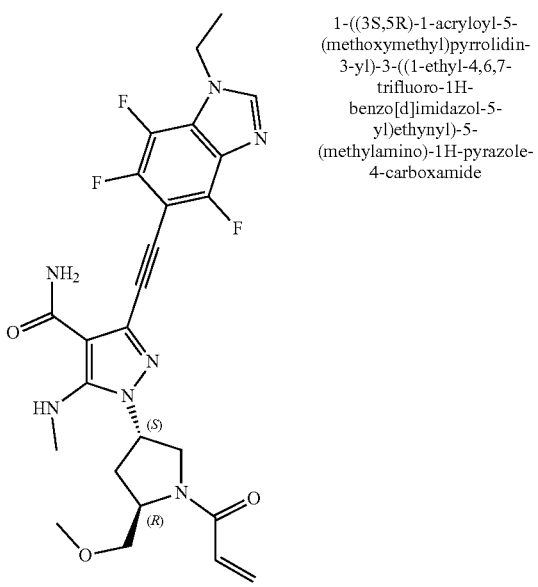

1-((3S,5R)-1-acryloyl-5-(methoxymethyl)pyrrolidin-3-yl)-3-((1-ethyl-4,6,7-trifluoro-1H-benzo[d]imidazol-5-yl)ethynyl)-5-(methylamino)-1H-pyrazole-4-carboxamide

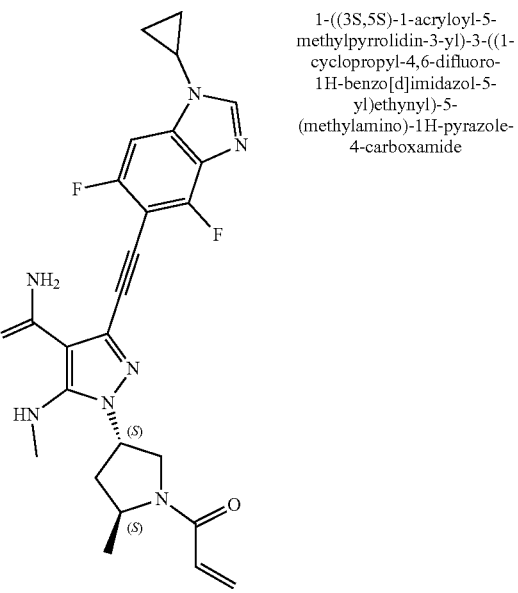

1-((3S,5S)-1-acryloyl-5-methylpyrrolidin-3-yl)-3-((1-cyclopropyl-4,6-difluoro-1H-benzo[d]imidazol-5-yl)ethynyl)-5-(methylamino)-1H-pyrazole-4-carboxamide

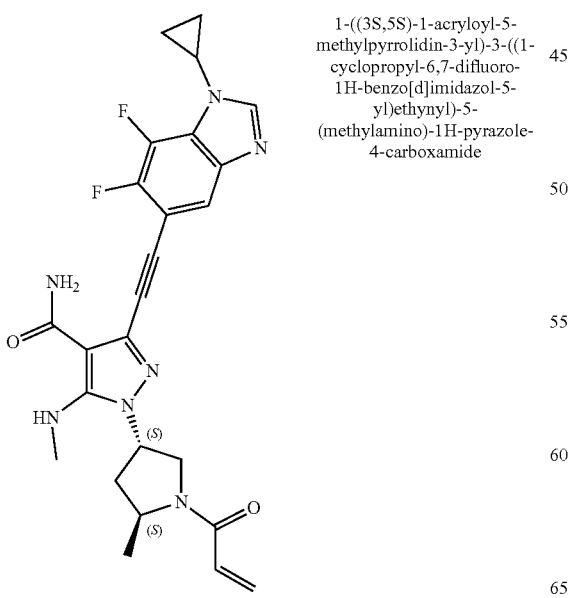

1-((3S,5S)-1-acryloyl-5-methylpyrrolidin-3-yl)-3-((1-cyclopropyl-6,7-difluoro-1H-benzo[d]imidazol-5-yl)ethynyl)-5-(methylamino)-1H-pyrazole-4-carboxamide

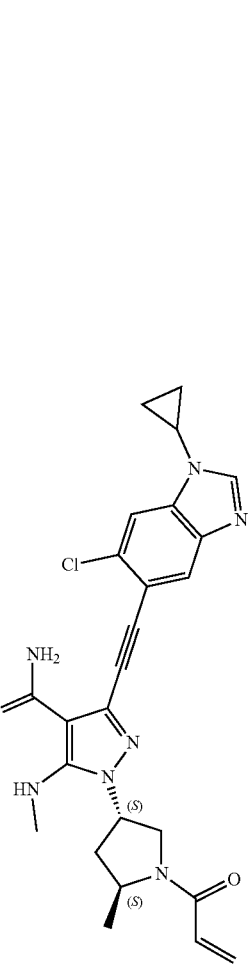
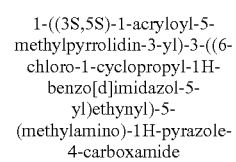

1-((3S,5S)-1-acryloyl-5-methylpyrrolidin-3-yl)-3-((6-chloro-1-cyclopropyl-1H-benzo[d]imidazol-5-yl)ethynyl)-5-(methylamino)-1H-pyrazole-4-carboxamide

| | |
|---|---|
| 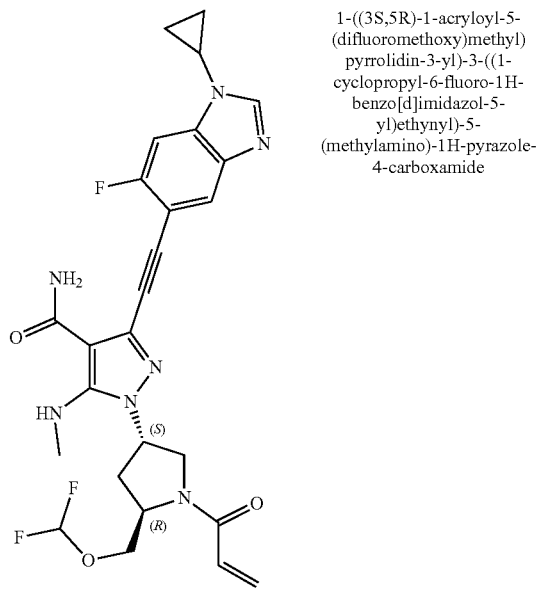 | 1-((3S,5R)-1-acryloyl-5-(difluoromethoxy)methyl)pyrrolidin-3-yl)-3-((1-cyclopropyl-6-fluoro-1H-benzo[d]imidazol-5-yl)ethynyl)-5-(methylamino)-1H-pyrazole-4-carboxamide |
| 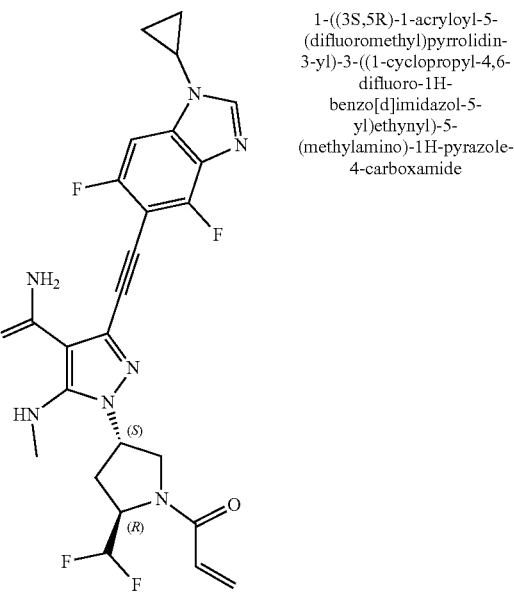 | 1-((3S,5R)-1-acryloyl-5-(difluoromethyl)pyrrolidin-3-yl)-3-((1-cyclopropyl-4,6-difluoro-1H-benzo[d]imidazol-5-yl)ethynyl)-5-(methylamino)-1H-pyrazole-4-carboxamide |
| 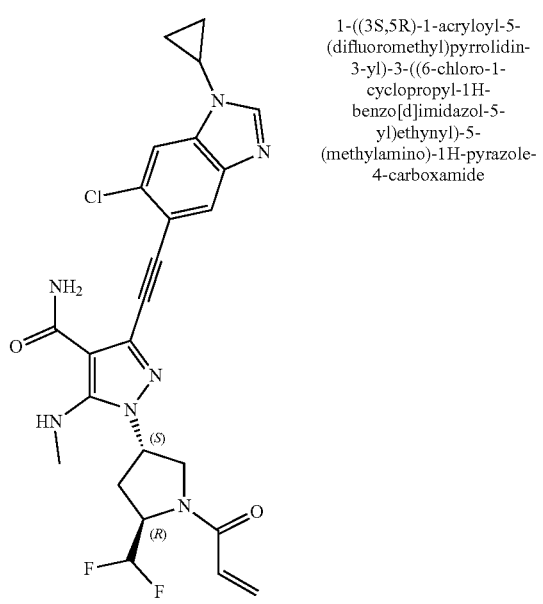 | 1-((3S,5R)-1-acryloyl-5-(difluoromethyl)pyrrolidin-3-yl)-3-((6-chloro-1-cyclopropyl-1H-benzo[d]imidazol-5-yl)ethynyl)-5-(methylamino)-1H-pyrazole-4-carboxamide |
| 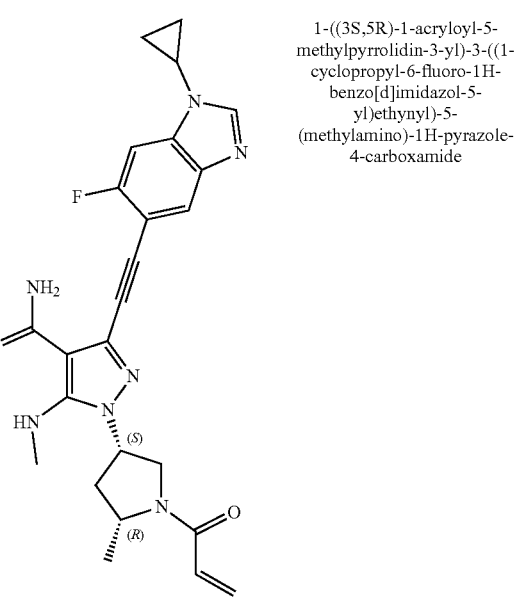 | 1-((3S,5R)-1-acryloyl-5-methylpyrrolidin-3-yl)-3-((1-cyclopropyl-6-fluoro-1H-benzo[d]imidazol-5-yl)ethynyl)-5-(methylamino)-1H-pyrazole-4-carboxamide |

TABLE 2-continued

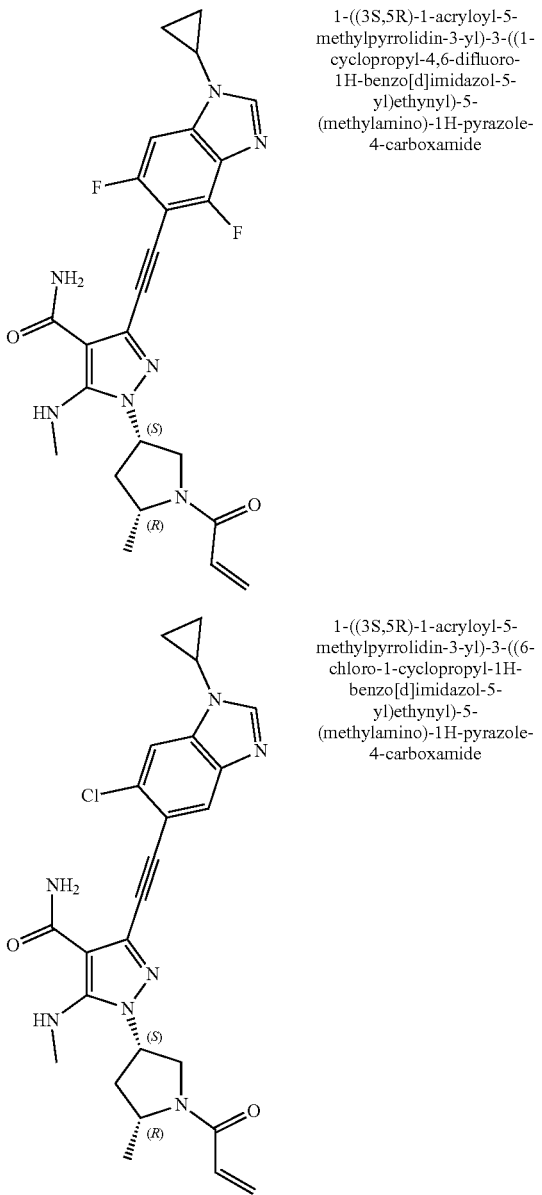

| | |
|---|---|
| | 1-((3S,5R)-1-acryloyl-5-methylpyrrolidin-3-yl)-3-((1-cyclopropyl-4,6-difluoro-1H-benzo[d]imidazol-5-yl)ethynyl)-5-(methylamino)-1H-pyrazole-4-carboxamide |
| | 1-((3S,5R)-1-acryloyl-5-methylpyrrolidin-3-yl)-3-((6-chloro-1-cyclopropyl-1H-benzo[d]imidazol-5-yl)ethynyl)-5-(methylamino)-1H-pyrazole-4-carboxamide |

Preparation of Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, PA), Aldrich Chemical (Milwaukee, WI, including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, PA), Crescent Chemical Co. (Hauppauge, NY), Eastman Organic Chemicals, Eastman Kodak Company (Rochester, NY), Fisher Scientific Co. (Pittsburgh, PA), Fisons Chemicals (Leicestershire, UK), Frontier Scientific (Logan, UT), ICN Biomedicals, Inc. (Costa Mesa, CA), Key Organics (Cornwall, U.K.), Lancaster Synthesis (Windham, NH), Maybridge Chemical Co. Ltd. (Cornwall, U.K.), Parish Chemical Co. (Orem, UT), Pfaltz & Bauer, Inc. (Waterbury, CN), Polyorganix (Houston, TX), Pierce Chemical Co. (Rockford, IL), Riedel de Haen AG (Hanover, Germany), Spectrum Quality Product, Inc. (New Brunswick, NJ), TCI America (Portland, OR), Trans World Chemicals, Inc. (Rockville, MD), and Wako Chemicals USA, Inc. (Richmond, VA).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference useful for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

Pharmaceutical Compositions

In certain embodiments, the heteroaromatic FGFR kinase inhibitory compound described herein is administered as a pure chemical. In other embodiments, the heteroaromatic FGFR kinase inhibitory compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, PA (2005)).

Provided herein is a pharmaceutical composition comprising at least one heteroaromatic FGFR kinase inhibitory compound as described herein, or a stereoisomer, pharmaceutically acceptable salt, hydrate, or solvate thereof, together with one or more pharmaceutically acceptable carriers. The carrier(s) (or excipient(s)) is acceptable or suitable if the carrier is compatible with the other ingredients of the composition and not deleterious to the recipient (i.e., the subject or the patient) of the composition.

One embodiment provides a pharmaceutical composition comprising a pharmaceutically acceptable excipient and a compound of Formula (I), or a pharmaceutically acceptable salt or solvate thereof.

One embodiment provides a method of preparing a pharmaceutical composition comprising mixing a compound of Formula (I), or a pharmaceutically acceptable salt or solvate thereof, and a pharmaceutically acceptable carrier.

In certain embodiments, the heteroaromatic FGFR kinase inhibitory compound as described by Formula (I), or a pharmaceutically acceptable salt or solvate thereof, is substantially pure, in that it contains less than about 5%, or less than about 1%, or less than about 0.1%, of other organic small molecules, such as unreacted intermediates or synthesis by-products that are created, for example, in one or more of the steps of a synthesis method.

One embodiment provides a pharmaceutical composition comprising a pharmaceutically acceptable excipient and a compound of Formula (II), or a pharmaceutically acceptable salt or solvate thereof.

One embodiment provides a method of preparing a pharmaceutical composition comprising mixing a compound of Formula (II), or a pharmaceutically acceptable salt or solvate thereof, and a pharmaceutically acceptable carrier.

In certain embodiments, the heteroaromatic FGFR kinase inhibitory compound as described by Formula (II), or a pharmaceutically acceptable salt or solvate thereof, is substantially pure, in that it contains less than about 5%, or less than about 1%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, PA (2005)).

In some embodiments, the heteroaromatic FGFR kinase inhibitory compound as described by Formula (I) or (II), or pharmaceutically acceptable salt or solvate thereof, is formulated for administration by injection. In some instances, the injection formulation is an aqueous formulation. In some instances, the injection formulation is a non-aqueous formulation. In some instances, the injection formulation is an oil-based formulation, such as sesame oil, or the like.

The dose of the composition comprising at least one heteroaromatic FGFR kinase inhibitory compound as described herein differs depending upon the subject or patient's (e.g., human) condition. In some embodiments, such factors include general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

Oral doses typically range from about 1.0 mg to about 1000 mg, one to four times, or more, per day.

Methods of Treatment

One embodiment provides a compound of Formula (I), or a pharmaceutically acceptable salt or solvate thereof, for use in a method of treatment of the human or animal body.

One embodiment provides a compound of Formula (I), or a pharmaceutically acceptable salt or solvate thereof, for use in a method of treatment of cancer or neoplastic disease.

One embodiment provides a use of a compound of Formula (I), or a pharmaceutically acceptable salt or solvate thereof, in the manufacture of a medicament for the treatment of cancer or neoplastic disease.

In some embodiments, described herein is a method of treating cancer in a patient in need thereof comprising administering to the patient a compound of Formula (I), or a pharmaceutically acceptable salt or solvate thereof. In some embodiments, described herein is a method of treating cancer in a patient in need thereof comprising administering to the patient a pharmaceutical composition comprising a compound of Formula (I), or a pharmaceutically acceptable salt or solvate thereof, and a pharmaceutically acceptable excipient.

One embodiment provides a compound of Formula (II), or a pharmaceutically acceptable salt or solvate thereof, for use in a method of treatment of the human or animal body.

One embodiment provides a compound of Formula (II), or a pharmaceutically acceptable salt or solvate thereof, for use in a method of treatment of cancer or neoplastic disease.

One embodiment provides a use of a compound of Formula (II), or a pharmaceutically acceptable salt or solvate thereof, in the manufacture of a medicament for the treatment of cancer or neoplastic disease.

In some embodiments, described herein is a method of treating cancer in a patient in need thereof comprising administering to the patient a compound of Formula (I), or a pharmaceutically acceptable salt or solvate thereof. In some embodiments, described herein is a method of treating cancer in a patient in need thereof comprising administering to the patient a pharmaceutical composition comprising a compound of Formula (I), or a pharmaceutically acceptable salt or solvate thereof, and a pharmaceutically acceptable excipient.

Provided herein is the method wherein the pharmaceutical composition is administered orally.

Provided herein is the method wherein the pharmaceutical composition is administered by injection.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

In some embodiments, the heteroaromatic FGFR kinase inhibitory compounds disclosed herein are synthesized according to the following examples. As used below, and throughout the description of the invention, the following abbreviations, unless otherwise indicated, shall be understood to have the following meanings:

° C. degrees Celsius $\delta_H$ chemical shift in parts per million downfield from tetramethylsilane DCM dichloromethane ($CH_2Cl_2$)

DMF dimethylformamide

DMSO dimethylsulfoxide

EA ethyl acetate

ESI electrospray ionization

Et ethyl g gram(s)

h hour(s)

HPLC high performance liquid chromatography

Hz hertz

J coupling constant (in NMR spectrometry)

LCMS liquid chromatography mass spectrometry

μ micro m multiplet (spectral); meter(s); milli

M molar $M^+$ parent molecular ion

Me methyl

MHz megahertz min minute(s)

mol mole(s); molecular (as in mol wt)

mL milliliter

MS mass spectrometry nm nanometer(s)

NMR nuclear magnetic resonance pH potential of hydrogen; a measure of the acidity or basicity of an aqueous solution PE petroleum ether RT room temperature s singlet (spectral)

t triplet (spectral)

T temperature

TFA trifluoroacetic acid

THF tetrahydrofuran

Intermediate 1: 1-((3S,5R)-1-acryloyl-5-(methoxymethyl)pyrrolidin-3-yl)-3-bromo-5-(methylamino)-1H-pyrazole-4-carboxamide

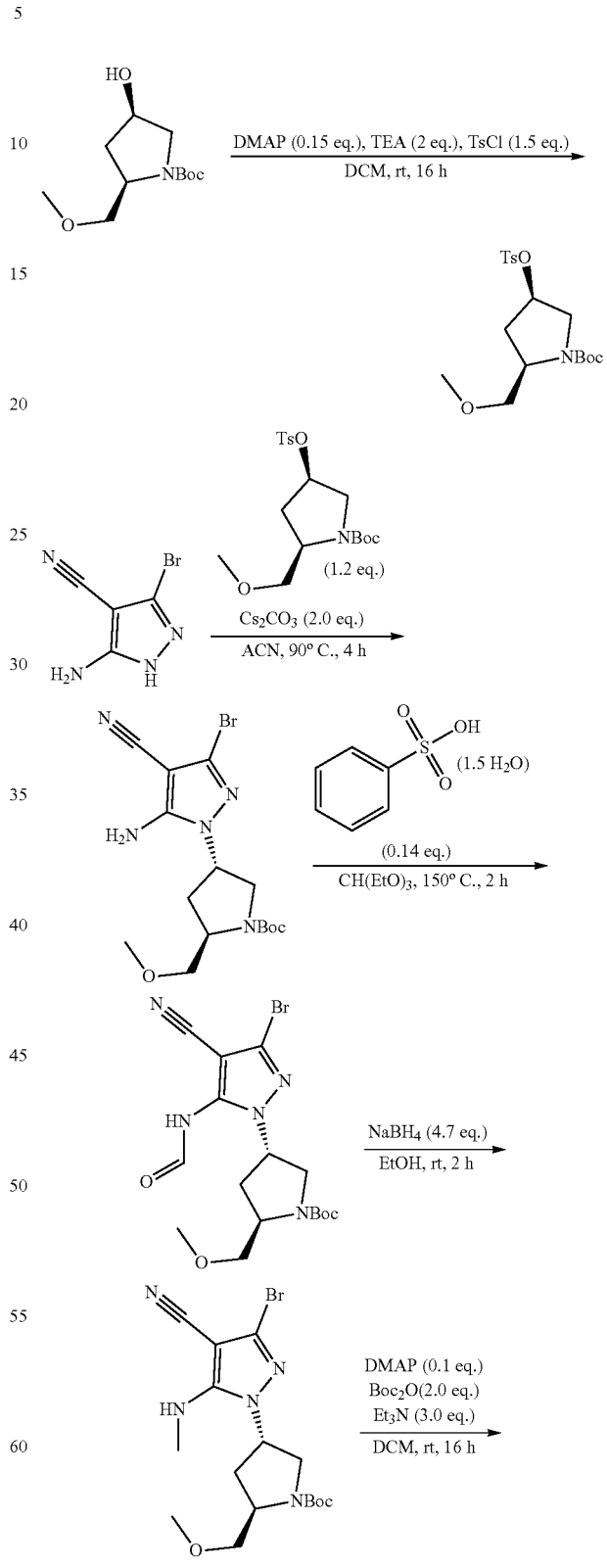

-continued

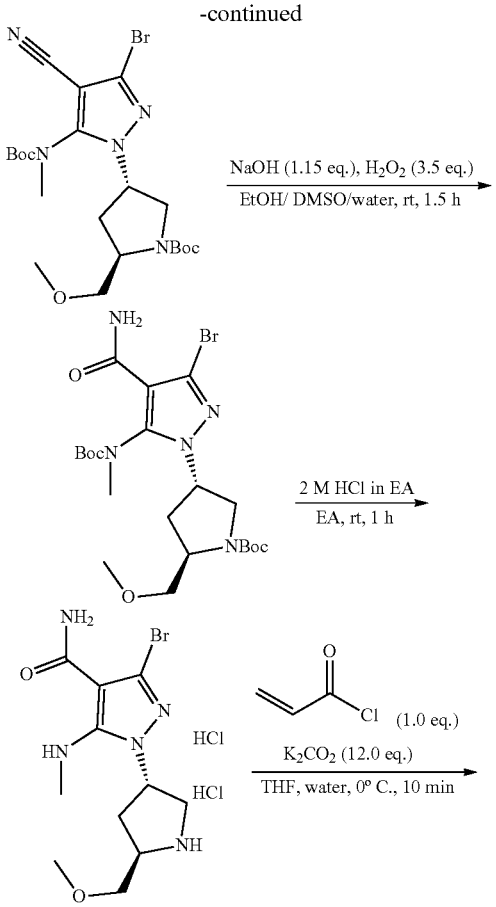

tert-butyl (2R,4R)-2-(methoxymethyl)-4-(tosyloxy)pyrrolidine-1-carboxylate

To a stirred solution of tert-butyl (2R,4R)-4-hydroxy-2-(methoxymethyl)pyrrolidine-1-carboxylate (15.20 g, 65.72 mmol), TEA (18.27 mL, 131.44 mmol) and DMAP (1.21 g, 9.86 mmol) in DCM (150.00 mL) was added TsCl (18.79 g, 98.58 mmol) at 0° C. The reaction mixture was stirred for 16 h at room temperature under nitrogen atmosphere. The resulting mixture was diluted with water (80 mL) and extracted with DCM (3×150 mL). The combined organic layers were washed with brine (2×80 mL), dried over anhydrous Na2SO4 and filtered. The filtrate was concentrated under reduced pressure. The residue was purified by silica gel column chromatography, eluted with 33% EA in PE. The fractions that contained desired product were combined and concentrated to afford tert-butyl (2R,4R)-2-(methoxymethyl)-4-(tosyloxy)pyrrolidine-1-carboxylate (18.5 g, 73%) as a yellow oil. MS ESI calculated for C18H27NO6S [M+H]+, 386.16, found 386.10.

tert-butyl (2R,4S)-4-(5-amino-3-bromo-4-cyano-1H-pyrazol-1-yl)-2-(methoxymethyl)pyrrolidine-1-carboxylate To a mixture of 3-amino-5-bromo-2H-pyrazole-4-carbonitrile (7.20 g, 38.50 mmol) and Cs2CO3 (25.09 g, 77.01 mmol) in ACN (190.00 mL) was added tert-butyl (2R,4R)-2-(methoxymethyl)-4-(tosyloxy)pyrrolidine-1-carboxylate (17.81 g, 46.20 mmol). The reaction mixture was stirred for 4 h at 90° C. The reaction mixture was allowed to cool down to room temperature and filtered. The filter cake was washed with DCM (3×70 mL). The filtrate was concentrated under reduced pressure. The residue was purified by silica gel column chromatography, eluted with 46% EA in PE to get about 6.2 g product which was further purified by reverse phase-flash chromatography with the following conditions: column, C18 silica gel; mobile phase, ACN in water, 5% to 46% gradient in 30 min; detector, UV 254 nm. The fractions that contained desired product were combined and concentrated to afford tert-butyl (2R,4S)-4-(5-amino-3-bromo-4-cyano-1H-pyrazol-1-yl)-2-(methoxymethyl)pyrrolidine-1-carboxylate (5 g, 32%) as an off-white solid. MS ESI calculated for C15H22BrN5O3 [M+H]+, 400.09, 402.09; found 400.15, 402.15.

tert-butyl (2R,4S)-4-(3-bromo-4-cyano-5-formamido-1H-pyrazol-1-yl)-2-(methoxymethyl)pyrrolidine-1-carboxylate To a mixture of tert-butyl (2R,4S)-4-(5-amino-3-bromo-4-cyano-1H-pyrazol-1-yl)-2-(methoxymethyl)pyrrolidine-1-carboxylate (3.50 g, 8.74 mmol) in (diethoxymethoxy)ethane (70.00 mL) was added benzenesulfonic acid (0.23 g, 1.22 mmol). The reaction mixture was stirred for 2 h at 150° C. under nitrogen atmosphere. The resulting mixture was concentrated under reduced pressure. The residue was dispersed in water (50 mL). The resulting mixture was extracted with EA (3×150 mL). The combined organic layers were washed with brine (80 mL), dried over anhydrous Na2SO4 and filtered. The filtrate was concentrated to afford tert-butyl (2R,4S)-4-(3-bromo-4-cyano-5-formamido-1H-pyrazol-1-yl)-2-(methoxymethyl)pyrrolidine-1-carboxylate (3.75 g, crude) as a yellow oil which was directly used to next step without further purification. MS ESI calculated for C16H22BrN5O4 [M–H]–, 426.09, 428.09; found 426.15, 428.15.

tert-butyl (2R,4S)-4-(3-bromo-4-cyano-5-(methylamino)-1H-pyrazol-1-yl)-2-(methoxymethyl)pyrrolidine-1-carboxylate To a stirred solution of tert-butyl (2R,4S)-4-(3-bromo-4-cyano-5-formamido-1H-pyrazol-1-yl)-2-(methoxymethyl)pyrrolidine-1-carboxylate (3.75 g, 8.76 mmol) in EtOH (200.00 mL) was added NaBH4 (1.56 g, 41.23 mmol) at 0° C. under nitrogen atmosphere. The reaction mixture was stirred for 2 h at room temperature. The resulting mixture was quenched with brine at 0° C. The resulting mixture was extracted with EA (3×150 mL). The combined organic layers were washed with brine (70 mL), dried over anhydrous Na2SO4 and filtered. The filtrate was concentrated under reduced pressure. The residue was purified by silica gel column chromatography, eluted with 62% EA in PE. The fractions that contained desired product were combined and concentrated to afford tert-butyl (2R,4S)-4-(3-bromo-4-cyano-5-(methylamino)-1H-pyrazol-1-yl)-2-(methoxymethyl)pyrrolidine-1-carboxylate (3.3 g, 91%) as an off-white solid. MS ESI calculated for C16H24BrN5O3 [M−H]−, 412.11, 414.11; found 412.20, 414.20.

tert-butyl (2R,4S)-4-(3-bromo-5-((tert-butoxycarbonyl)(methyl)amino)-4-cyano-1H-pyrazol-1-yl)-2-(methoxymethyl)pyrrolidine-1-carboxylate To a stirred solution of tert-butyl (2R,4S)-4-[3-bromo-4-cyano-5-(methylamino)pyrazol-1-yl]-2-(methoxymethyl)pyrrolidine-1-carboxylate (1.74 g, 4.20 mmol) in DCM (40.00 mL) were added Et3N (1.75 mL, 12.61 mmol), Boc2O (2.22 g, 8.40 mmol) in DCM (2.00 mL) and DMAP (51.31 mg, 0.42 mmol) at room temperature under nitrogen atmosphere. The reaction mixture was stirred for 16 h at room temperature. The resulting mixture was concentrated under reduced pressure.

The residue was purified by silica gel column chromatography, eluted with 39% EA in PE. The fractions that contained desired product were combined and concentrated to afford tert-butyl (2R,4S)-4-(3-bromo-5-((tert-butoxycarbonyl)(methyl)amino)-4-cyano-1H-pyrazol-1-yl)-2-(methoxymethyl)pyrrolidine-1-carboxylate (2.12 g, 98%) as an off-white solid. MS ESI calculated for C21H32BrN5O5 [M+H−56]+, 458.16, found 458.10.

tert-butyl (2R,4S)-4-(3-bromo-5-((tert-butoxycarbonyl)(methyl)amino)-4-carbamoyl-1H-pyrazol-1-yl)-2-(methoxymethyl)pyrrolidine-1-carboxylate To a stirred solution of tert-butyl (2R,4S)-4-(3-bromo-5-((tert-butoxycarbonyl)(methyl)amino)-4-cyano-1H-pyrazol-1-yl)-2-(methoxymethyl)pyrrolidine-1-carboxylate (3.17 g, 6.16 mmol) in EtOH (23.50 mL) and DMSO (4.70 mL) were added 0.5 M NaOH (8.14 mL, 7.08 mmol) and H2O2 (30%) (1.69 mL, 14.77 mmol) at 0° C. The reaction mixture was stirred for 30 min at 0° C. and stirred for 1.5 h at room temperature. The resulting mixture was extracted with EA (3×90 mL). The combined organic layers were washed with brine (2×60 mL), dried over anhydrous Na2SO4 and filtered. The filtrate was concentrated under reduced pressure. The residue was purified by silica gel column chromatography, eluted with 60% EA in PE. The fractions that contained desired product were combined and concentrated to afford tert-butyl (2R,4S)-4-(3-bromo-5-((tert-butoxycarbonyl)(methyl)amino)-4-carbamoyl-1H-pyrazol-1-yl)-2-(methoxymethyl)pyrrolidine-1-carboxylate (3.09 g, 94%) as an off-white solid. MS ESI calculated for C21H34BrN5O6 [M+H−156]+, 376.17, found 376.00.

3-bromo-1-((3S,5R)-5-(methoxymethyl)pyrrolidin-3-yl)-5-(methylamino)-1H-pyrazole-4-carboxamide dihydrochloride To a stirred solution of tert-butyl (2R,4S)-4-(3-bromo-5-((tert-butoxycarbonyl)(methyl)amino)-4-carbamoyl-1H-pyrazol-1-yl)-2-(methoxymethyl)pyrrolidine-1-carboxylate (1.68 g, 3.16 mmol) in EA (8.5 mL) was added 2 M hydrogen chloride solution in EA (17 mL) dropwise at 0° C. under nitrogen atmosphere. The reaction mixture was stirred for 1 h at room temperature. The precipitated solids were collected by filtration and washed with EA (3×30 mL). The filter cake was dried to afford 3-bromo-1-((3S,5R)-5-(methoxymethyl)pyrrolidin-3-yl)-5-(methylamino)-1H-pyrazole-4-carboxamide dihydrochloride (1.3 g, crude) as an off-white solid. MS ESI calculated for C11H18BrN5O2 [M+H]+, 332.06, found 332.15

1-((3S,5R)-1-acryloyl-5-(methoxymethyl)pyrrolidin-3-yl)-3-bromo-5-(methylamino)-1H-pyrazole-4-carboxamide To a stirred mixture of 3-bromo-1-((3S,5R)-5-(methoxymethyl)pyrrolidin-3-yl)-5-(methylamino)-1H-pyrazole-4-carboxamide dihydrochloride (1.20 g, 2.96 mmol) in THF (24.00 mL) were added 2.5 M aqueous K2CO3 (14.40 mL, 36 mmol) and acryloyl chloride (0.23 g, 2.96 mmol) in THF (6.00 mL) at 0° C. The reaction mixture was stirred for 10 min at 0° C. The resulting mixture was extracted with EA (3×100 mL). The combined organic layers were washed with brine (2×60 mL), dried over anhydrous Na2SO4 and filtered. The filtrate was concentrated under reduced pressure. The residue was purified by silica gel column chromatography, eluted with CH2Cl2/MeOH (10:1). The fractions that contained desired product were combined and concentrated to afford 1-((3S,5R)-1-acryloyl-5-(methoxymethyl)pyrrolidin-3-yl)-3-bromo-5-(methylamino)-1H-pyrazole-4-carboxamide (0.89 g, 78%) as an off-white solid. MS ESI calculated for C14H20BrN5O3 [M+H]+, 386.07, found 386.05.

Example 1: 1-[(3S,5R)-5-(methoxymethyl)-1-(prop-2-enoyl)pyrrolidin-3-yl]-3-[2-(2-methyl-3H-1,3-benzodiazol-5-yl)ethynyl]-5-(methylamino)pyrazole-4-carboxamide

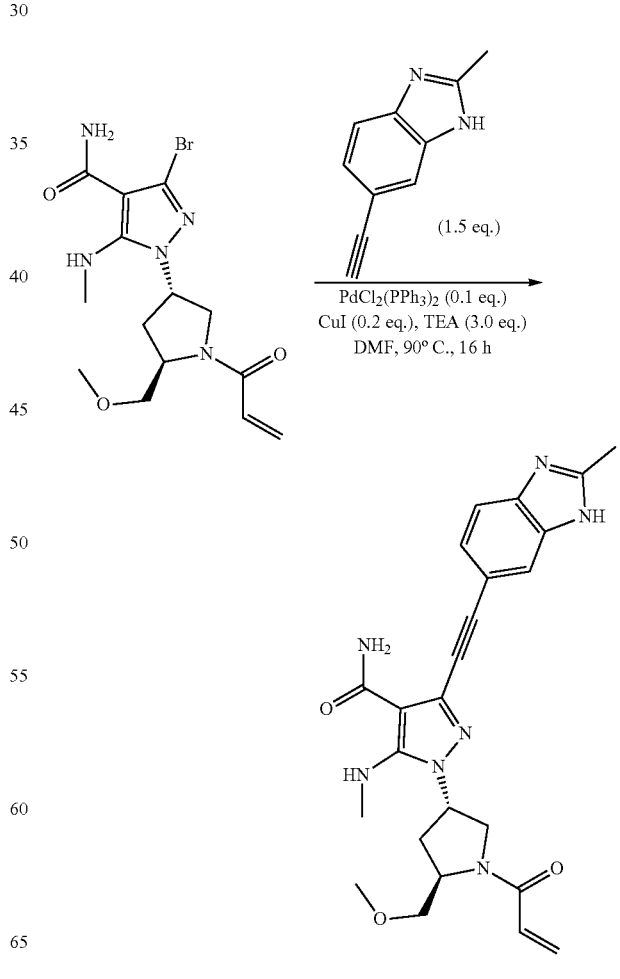

313

To a mixture of 3-bromo-1-[(3S,5R)-5-(methoxymethyl)-1-(prop-2-enoyl)pyrrolidin-3-yl]-5-(methylamino)pyrazole-4-carboxamide (0.10 g, 0.26 mmol), 5-ethynyl-2-methyl-3H-1,3-benzodiazole (60.66 mg, 0.39 mmol), CuI (9.86 mg, 0.05 mmol) in DMF (2.50 mL) were added Pd(PPh3)2Cl2 (18.17 mg, 0.03 mmol) and TEA (0.11 mL, 1.07 mmol). The reaction mixture was degassed with nitrogen for three times and stirred for 16 h at 90° C. The resulting mixture was diluted with water (20 mL) and extracted with EtOAc (3×20 mL). The combined organic layers were washed with brine (50 mL), dried over anhydrous Na2SO4 and filtered. The filtrate was concentrated under reduced pressure. The residue was purified by Prep-HPLC with the following conditions Column: SunFire Prep C18 OBD Column, 19×150 mm 5um 10 nm; Mobile Phase A: Water (0.1% FA), Mobile Phase B: ACN; Flow rate: 20 ml/min; Gradient: 20 B to 50 B in 4.3 min. The fractions that contained desired product were combined and concentrated to afford 1-[(3S,5R)-5-(methoxymethyl)-1-(prop-2-enoyl)pyrrolidin-3-yl]-3-[2-(2-methyl-3H-1,3-benzodiazol-5-yl)ethynyl]-5-(methylamino)pyrazole-4-carboxamide (35.8 mg, 29%) as an off-white solid. MS ESI calculated for C24H27N7O3 [M+H]+, 462.22, found 462.15. H-NMR (400 MHz, DMSO-d6+D2O): δ 7.70 (s, 1H), 7.52 (d, J=8.0 Hz, 1H), 7.34-7.32 (m, 1H), 6.73-6.55 (m, 1H), 6.19-6.14 (m, 1H), 5.71-5.67 (m, 1H), 5.23-5.10 (m, 1H), 4.59-4.35 (m, 1H), 3.90-3.85 (m, 1H), 3.76-3.61 (m, 1H), 3.59-3.31 (m, 2H), 3.30 (d, J=5.2 Hz, 3H), 2.93 (d, J=4.4 Hz, 3H), 2.56 (s, 3H), 2.51-2.33 (m, 1H), 2.31-2.27 (m, 1H).

Example 2: (S)-1-(1-acryloylpyrrolidin-3-yl)-3-((2-methyl-1H-benzo[d]imidazol-6-yl)ethynyl)-5-(methylamino)-1H-pyrazole-4-carboxamide

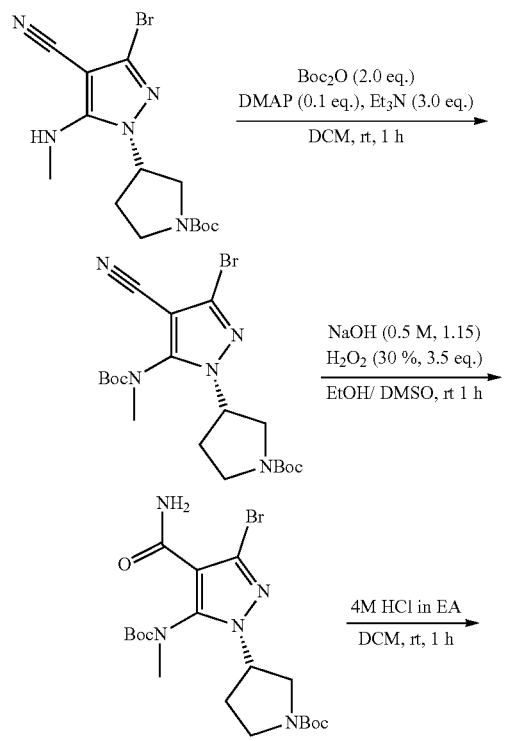

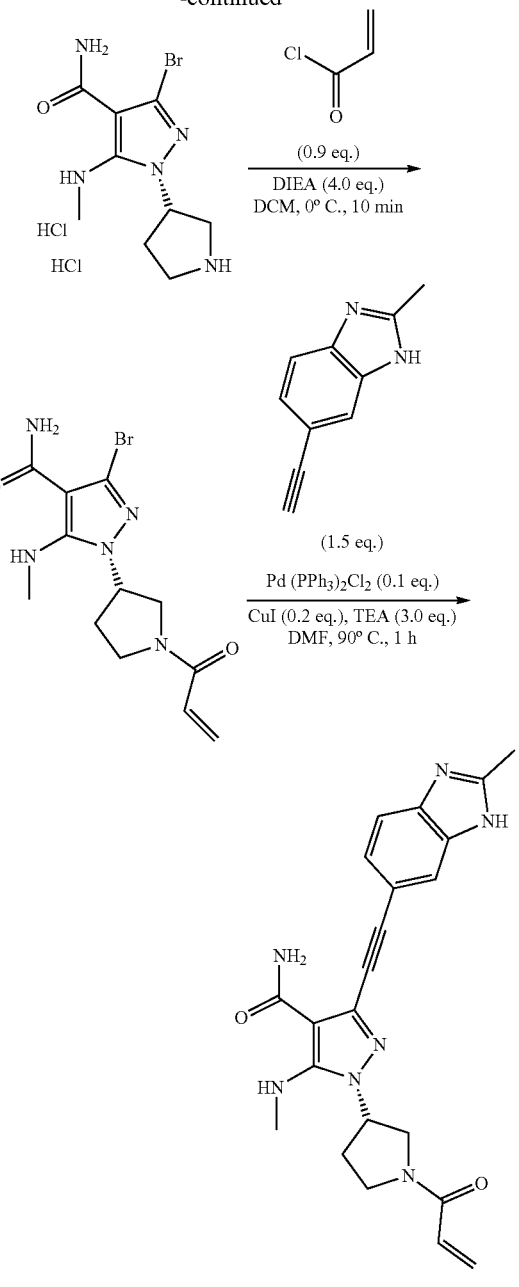

Step 1: tert-butyl (S)-3-(3-bromo-5-((tert-butoxycarbonyl)(methyl)amino)-4-cyano-1H-pyrazol-1-yl)pyrrolidine-1-carboxylate To a stirred solution of tert-butyl (3S)-3-[3-bromo-4-cyano-5-(methylamino)pyrazol-1-yl]pyrrolidine-1-carboxylate (0.5 g, 1.35 mmol) in DCM (10.00 mL) were added TEA (0.56 mL, 4.03 mmol), Boc2O (0.56 g, 2.70 mmol) in DCM (3.00 mL) and DMAP (16.50 mg, 0.14 mmol) at room temperature under nitrogen atmosphere. The reaction mixture was stirred for 1 h. The resulting mixture was concentrated under reduced pressure. The residue was purified by silica gel column chromatography, eluted with 31% EA in PE, The fractions that contained desired product were concentrated to afford tert-butyl (S)-3-(3-bromo-5-((tert-butoxycarbonyl)(methyl)amino)-4-cyano-1H-pyrazol-1-yl)

pyrrolidine-1-carboxylate (0.6 g, 94%) as an off-white solid. MS ESI calculated for C19H28BrN5O4 [M+H−112]+, 470.13, found 358.10.

Step 2: tert-butyl (S)-3-(3-bromo-5-((tert-butoxycarbonyl)(methyl)amino)-4-carbamoyl-1H-pyrazol-1-yl)pyrrolidine-1-carboxylate To a stirred solution of tert-butyl (S)-3-(3-bromo-5-((tert-butoxycarbonyl)(methyl)amino)-4-cyano-1H-pyrazol-1-yl)pyrrolidine-1-carboxylate (0.5 g, 1.06 mmol) in EtOH (4.00 mL) and DMSO (0.80 mL) were added 0.5 M NaOH (2.44 mL, 1.22 mmol) and H2O2 (30%) (0.29 mL, 3.73 mmol) at 0° C. The reaction mixture was stirred for 1 h at ambient temperature. The resulting mixture was diluted with water (5 mL), extracted with EtOAc (3×20 mL). The combined organic layers were washed with brine (3×15 mL), dried over anhydrous Na2SO4 and filtered. The filtrate was concentrated under reduced pressure. The residue was purified by silica gel column chromatography, eluted with 60% EA in PE, The fractions that contained desired product were combined and concentrated to afford tert-butyl (S)-3-(3-bromo-5-((tert-butoxycarbonyl)(methyl)amino)-4-carbamoyl-1H-pyrazol-1-yl)pyrrolidine-1-carboxylate (0.56 g, 97%) as an off-white solid. MS ESI calculated for C19H30BrN5O5 [M+H−156]+, 488.13, found 332.05.

Step 3: (S)-3-bromo-5-(methylamino)-1-(pyrrolidin-3-yl)-1H-pyrazole-4-carboxamide dihydrochloride To a stirred solution of tert-butyl (S)-3-(3-bromo-5-((tert-butoxycarbonyl)(methyl)amino)-4-carbamoyl-1H-pyrazol-1-yl)pyrrolidine-1-carboxylate (0.25 g, 0.51 mmol) in DCM (1.50 mL) was added hydrogen chloride solution 4 M in EA (3 mL) dropwise at 0° C. under nitrogen atmosphere. The reaction mixture was stirred for 1 h at room temperature under nitrogen atmosphere. The precipitated solids were collected by filtration and washed with DCM (3×10 mL). The solid was dried under reduced pressure to afford (S)-3-bromo-5-(methylamino)-1-(pyrrolidin-3-yl)-1H-pyrazole-4-carboxamide dihydrochloride (0.20 g, crude) as an off-white solid. MS ESI calculated for C9H14BrN5O [M+H]+, 288.04, found 288.10.

Step 4: (S)-1-(1-acryloylpyrrolidin-3-yl)-3-bromo-5-(methylamino)-1H-pyrazole-4-carboxamide To a stirred solution of (S)-3-bromo-5-(methylamino)-1-(pyrrolidin-3-yl)-1H-pyrazole-4-carboxamide dihydrochloride (0.16 g, 0.44 mmol) in DCM (5.00 mL) were added acryloyl chloride (36.10 mg, 0.40 mmol) and DIEA (0.32 mL, 1.84 mmol) dropwise at 0° C. The reaction mixture was stirred for 10 min at 0° C. The resulting mixture was concentrated under reduced pressure. The residue was diluted with water (5 mL), extracted with EtOAc (3×10 mL). The combined organic layers were washed with brine (2×10 mL), dried over anhydrous Na2SO4 and filtered. The filtrate was concentrated under reduced pressure. The residue was purified by silica gel column chromatography, eluted with CH2Cl2/MeOH (10:1). The fractions that contained desired product were combined and concentrated to afford (S)-1-(1-acryloylpyrrolidin-3-yl)-3-bromo-5-(methylamino)-1H-pyrazole-4-carboxamide (0.12 g, 75%) as an off-white solid. MS ESI calculated for C12H18BrN5O2 [M+H]+, 342.05, found 342.00.

Step 5: (S)-1-(1-acryloylpyrrolidin-3-yl)-3-((2-methyl-1H-benzo[d]imidazol-6-yl)ethynyl)-5-(methylamino)-1H-pyrazole-4-carboxamide To a stirred mixture of (S)-1-(1-acryloylpyrrolidin-3-yl)-3-bromo-5-(methylamino)-1H-pyrazole-4-carboxamide (90.00 mg, 0.26 mmol), 5-ethynyl-2-methyl-3H-1,3-benzodiazole (61.62 mg, 0.40 mmol), CuI (10.02 mg, 0.05 mmol) and Pd(PPh3)2Cl2 (18.46 mg, 0.03 mmol) in DMF (2.00 mL) was added TEA (0.09 mL, 0.89 mmol). The reaction mixture was degassed with argon for three times and stirred for 1 h at 90° C. The resulting mixture was concentrated under reduced pressure. The residue was purified by Prep-HPLC with the following conditions Column: XBridge Shield RP18 OBD Column, 30*150 mm, 5 um; Mobile Phase A: Water (10 mmol/L NH4HCO3), Mobile Phase B: ACN; Flow rate: 20 mL/min; Gradient: 35 B to 70 B in 10 min; 210/254 nm; RT1: 9.75. The fractions that contained desired product were combined and concentrated to afford (S)-1-(1-acryloylpyrrolidin-3-yl)-3-((2-methyl-1H-benzo[d]imidazol-6-yl)ethynyl)-5-(methylamino)-1H-pyrazole-4-carboxamide (22 mg, 20%) as an off-white solid. MS ESI calculated for C22H23N7O2 [M+H]+, 418.19, found 418.10. H-NMR (300 MHz, CDCl3) δ 7.70 (s, 1H), 7.51-7.48 (m, 1H), 7.38-7.26 (d, J=8.3 Hz, 1H), 6.97 (s, 1H), 6.66-6.31 (m, 3H), 5.77-5.66 (m, 1H), 5.48 (s, 1H), 5.04-4.99 (m, 1H), 4.16-3.94 (m, 3H), 3.82-3.62 (m, 1H), 2.99 (t, J=6.1 Hz, 3H), 2.65 (s, 4H), 2.40 (m, 2H).

Example 3: 3-[2-(1-ethyl-2-methyl-1,3-benzodiazol-5-yl)ethynyl]-1-[(3S,5R)-5-(methoxymethyl)-1-(prop-2-enoyl)pyrrolidin-3-yl]-5-(methylamino) pyrazole-4-carboxamide

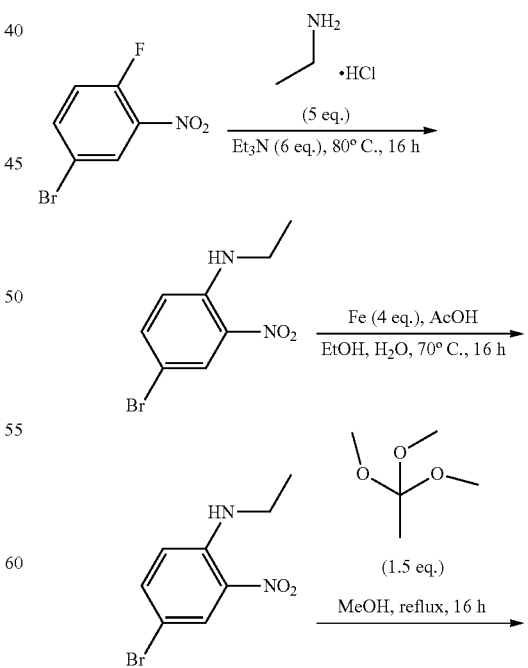

-continued

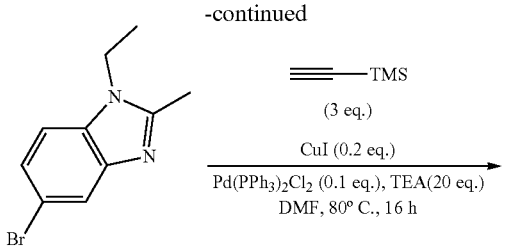

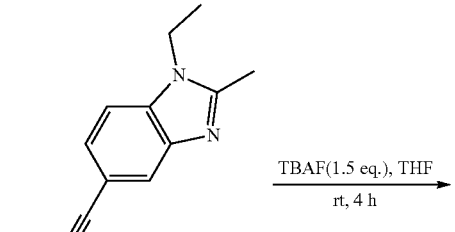

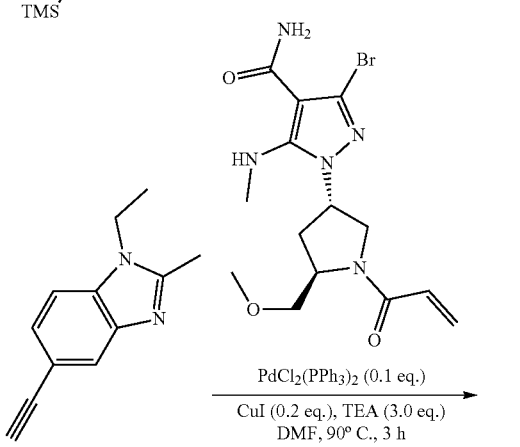

Step 1: 4-bromo-N-ethyl-2-nitroaniline

A solution of 4-bromo-1-fluoro-2-nitrobenzene (5.00 g, 22.73 mmol) and ethylamine hydrochloride (9.27 g, 113.64 mmol) in Et3N (13.80 g, 136.38 mmol) was stirred for 16 h at 80° C. The resulting mixture was concentrated under reduced pressure. The residue was quenched with sat. NH4HCO3 (aq.) at room temperature. The resulting mixture was extracted with EtOAc (3×50 mL). The combined organic layers were dried over anhydrous Na2SO4 and filtered. The filtrate was concentrated under reduced pressure to afford 4-bromo-N-ethyl-2-nitroaniline (5 g, 89%) as a red solid which was used in the next step without further purification. MS ESI calculated for C8H9BrN2O2 [M+H]+, 244.98, 246.98, found 245.05, 247.05.

Step 2: 4-bromo-N1-ethylbenzene-1,2-diamine

To a mixture of Fe (2.73 g, 48.96 mmol) in EtOH (66.00 mL) was added AcOH (3.30 mL, 54.90 mmol). The resulting mixture was stirred for 30 min at 70° C. under nitrogen atmosphere. To the above mixture was added 4-bromo-N-ethyl-2-nitroaniline (3.00 g, 12.24 mmol). The reaction mixture was stirred for 16 h at 70° C. The resulting mixture was filtered, the filter cake was washed with THF. The filtrate was concentrated under reduced pressure. The residue was quenched by the addition of sat. NH4HCO3 (aq.) (50 mL) at room temperature. The resulting mixture was extracted with EtOAc (3×50 mL), dried over anhydrous Na2SO4 and filtered. The filtrate was concentrated under reduced pressure to afford 4-bromo-N1-ethylbenzene-1,2-diamine (2 g, 75%) as a brown solid which was used in next step without further purification. MS ESI calculated for C8H11BrN2 [M+H]+, 215.01, 217.01, found 215.10, 217.10.

Step 3: 5-bromo-1-ethyl-2-methyl-1,3-benzodiazole

To a stirred solution of 4-bromo-N1-ethylbenzene-1,2-diamine (1.30 g, 6.04 mmol) in MeOH (13.00 mL) was added 1,1,1-trimethoxyethane (1.09 g, 0.01 mmol). The reaction mixture was stirred for 16 h at 70° C. The resulting mixture was concentrated under reduced pressure. The residue was purified by silica gel column chromatography, eluted with CH2Cl2/MeOH (12:1). The fractions that contained desired product were combined and concentrated to afford 5-bromo-1-ethyl-2-methyl-1,3-benzodiazole (1.00 g, 69%) as a light-yellow solid. MS ESI calculated for C10H11BrN2 [M+H]+, 239.01, 241.01, found 238.90, 240.90.

Step 4: 1-ethyl-2-methyl-5-[2-(trimethylsilyl) ethynyl]-1,3-benzodiazole

To a stirred mixture of 5-bromo-1-ethyl-2-methyl-1,3-benzodiazole (1.50 g, 6.27 mmol), trimethylsilylacetylene (1.85 g, 0.02 mmol), CuI (0.24 g, 1.26 mmol) and Pd(PPh3)2Cl2 (0.88 g, 1.25 mmol) in DMF (15.00 mL) was added TEA (12.70 g, 0.13 mmol). The reaction mixture was degassed with argon for three times and stirred for 16 h at 80° C. The resulting mixture was extracted with EtOAc (3×30 mL). The combined organic layers were washed with brine (30 mL), dried over anhydrous Na2SO4 and filtered. The filtrate was concentrated under reduced pressure. The residue was purified by silica gel column chromatography, eluted with CH2Cl2/MeOH (12:1). The fractions that contained desired product were combined and concentrated to afford 1-ethyl-2-methyl-5-[2-(trimethylsilyl) ethynyl]-1,3-benzodiazole (0.5 g, 31%) as a light-yellow solid. MS ESI calculated for C15H20N2Si [M+H]+, 257.14, found 257.15.

Step 5: 1-ethyl-5-ethynyl-2-methyl-1,3-benzodiazole

To a solution of 1-ethyl-2-methyl-5-[2-(trimethylsilyl) ethynyl]-1,3-benzodiazole (0.5 g, 1.95 mmol) in THF (5.00 mL) was added TBAF (0.76 g, 2.92 mmol) at 0° C. under nitrogen atmosphere. The reaction mixture was stirred for 4 h at room temperature. The resulting mixture was concentrated under reduced pressure. The residue was purified by silica gel column chromatography, eluted with CH2Cl2/MeOH (12:1). The fractions that contained desired product were combined and concentrated to afford 1-ethyl-5-ethynyl-2-methyl-1,3-benzodiazole (0.30 g, 83%) as a light-yellow solid. MS ESI calculated for C12H12N2 [M+H]+, 185.10, found 185.10.

Step 6: 3-[2-(1-ethyl-2-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide To a stirred mixture of 3-bromo-1-[(3S,5R)-5-(methoxymethyl)-1-(prop-2-enoyl)pyrrolidin-3-yl]-5-(methylamino)pyrazole-4-carboxamide (0.20 g, 0.52 mmol), 1-ethyl-5-ethynyl-2-methyl-1,3-benzodiazole (0.14 g, 0.78 mmol), CuI (19.72 mg, 0.10 mmol) and Pd(PPh3)2Cl2 (36.34 mg, 0.05 mmol) in DMF (3 mL) was added TEA (0.16 g, 1.55 mmol). The reaction mixture was degassed with argon for three times and stirred for 3 h at 90° C. The resulting mixture was concentrated under reduced pressure. The residue was purified by Prep-HPLC with the following conditions Column: XBridge Prep C18 OBD Column, 19×150 mm 5 um; Mobile Phase A: Water (10 mmol/L NH4HCO3), Mobile Phase B: ACN; Flow rate: 20 mL/min; Gradient: 50 B to 80 B in 4.3 min; 210/254 nm; RT1:4.02. The fractions that contained desired product were concentrated to afford 3-[2-(1-ethyl-2-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (50 mg, 19%) as a white solid. MS ESI calculated for C26H31N7O3 [M+H]+, 490.25, found 490.25. H-NMR (300 MHz, CDCl3) δ 7.90 (s, 1H), 7.43 (d, J=8.2 Hz, 1H), 6.98 (s, 1H), 6.98-6.77 (m, 2H), 6.54-6.37 (m, 2H), 5.70 (dd, J=8.2, 4.2 Hz, 1H), 5.58-5.26 (m, 2H), 4.56 (d, J=9.0 Hz, 1H), 4.26-3.85 (m, 5H), 3.54-3.34 (m, 4H), 3.05-3.01 (m, 3H), 2.79-2.53 (m, 4H), 2.33-2.29 (m, 1H), 1.43 (t, J=7.2 Hz, 3H).

Example 4: 1-[(3S,5R)-5-(methoxymethyl)-1-(prop-2-enoyl)pyrrolidin-3-yl]-3-[2-(1-methyl-1,3-benzodiazol-5-yl)ethynyl]-5-(methylamino)pyrazole-4-carboxamide

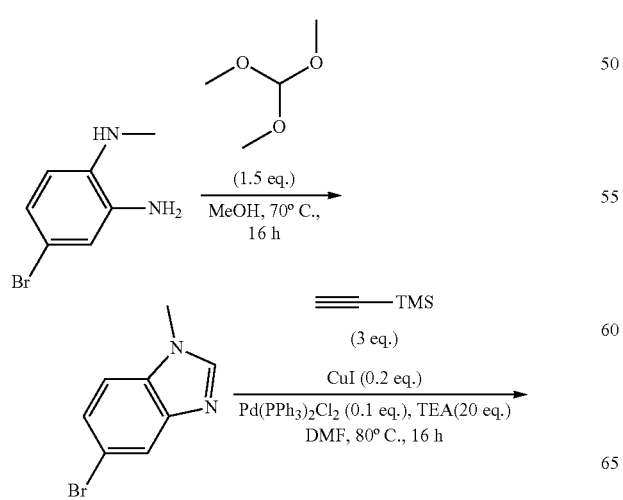

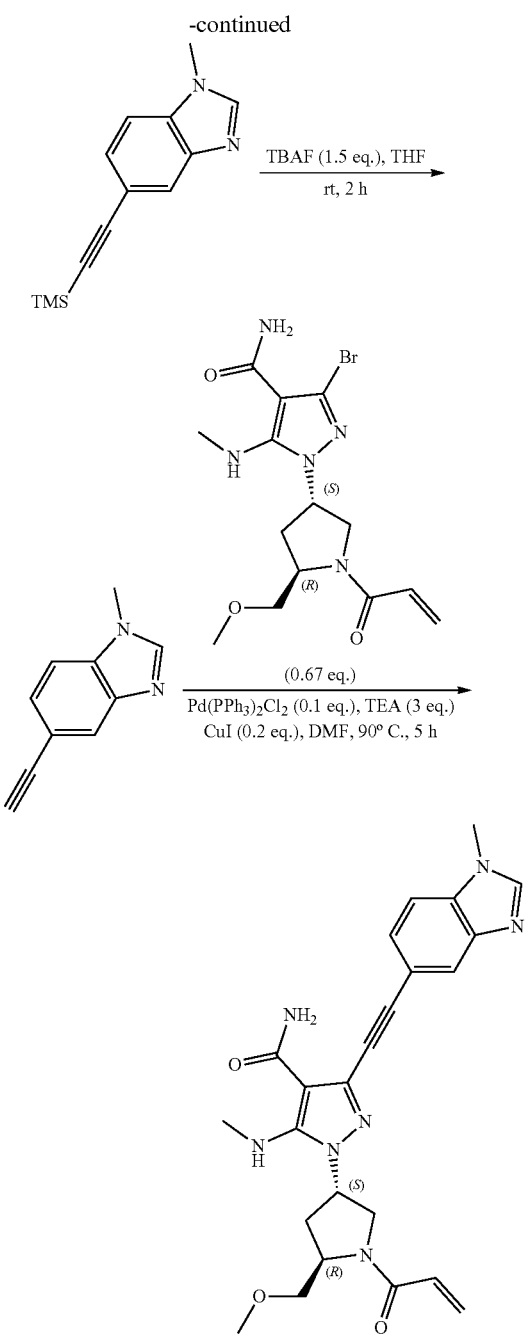

Step 1: 5-bromo-1-methyl-1,3-benzodiazole

To a stirred solution of 4-bromo-N1-methylbenzene-1,2-diamine (1.10 g, 5.47 mmol) in MeOH (11.00 mL) was added trimethyl orthoformate (0.87 g, 8.21 mmol). The reaction mixture was stirred for 16 h at 70° C. under nitrogen atmosphere. The resulting mixture was concentrated under reduced pressure. The residue was purified by silica gel column chromatography, eluted with 4% MeOH in DCM. The fractions that contained desired product were combined and concentrated to afford 5-bromo-1-methyl-1,3-benzodiazole (1.02 g, 79%) as a brown solid. MS ESI calculated for C8H7BrN2 [M+H]+, 210.98, found 210.95.

Step 2: 1-methyl-5-[2-(trimethylsilyl)ethynyl]-1,3-benzodiazole

To a mixture of 5-bromo-1-methyl-1,3-benzodiazole (1.00 g, 4.74 mmol), trimethylsilylacetylene (2.01 mL, 20.45 mmol), CuI (0.18 g, 0.95 mmol and Pd(PPh3)2Cl2 (0.33 g, 0.47 mmol) in DMF (20.00 mL) was added TEA (13.17 mL, 130.16 mmol). The reaction mixture was degassed with argon for three times and stirred for 16 h at 80° C. The resulting mixture was diluted with water (60 mL) and extracted with EA (3×70 mL). The combined organic layers were washed with brine (2×100 mL), dried over anhydrous Na2SO4, filtered and concentrated under reduced pressure. The residue was purified by silica gel column chromatography, eluted with 8% MeOH in DCM. The crude product was purified by reverse flash chromatography with the following conditions: column, C18 silica gel; mobile phase, NH4HCO3 in water, 30% to 70% gradient in 30 min; detector, UV 254 nm. The fractions that contained desired product were combined and concentrated to afford 1-methyl-5-[2-(trimethylsilyl)ethynyl]-1,3-benzodiazole (0.51 g, 42%) as a light brown solid. MS ESI calculated for C13H16N2Si [M+H]+, 229.11, found 229.20.

Step 3: 5-ethynyl-1-methylindazole

To a stirred solution of 1-methyl-5-[2-(trimethylsilyl)ethynyl]indazole (0.51 g, 2.25 mmol) in THF (5.00 mL) was added TBAF (1 M in THF) (3.38 mL, 3.37 mmol) dropwise at 0° C. under nitrogen atmosphere. The resulting mixture was stirred for 2 h at room temperature. The resulting mixture was diluted with water (20 mL), extracted with EtOAc (3×20 mL). The combined organic layers were washed with brine (50 mL), dried over anhydrous Na2SO4 and filtered. The filtrate was concentrated under reduced pressure. The residue was purified by silica gel column chromatography, eluted with CH2Cl2/MeOH (20:1). The fractions that contained desired product were combined and concentrated to afford 5-ethynyl-1-methylindazole (0.32 g, 81%) as an off-white solid. MS ESI calculated for C10H8N2 [M+H]+, 157.07, found 157.10.

Step 4: 1-[(3S,5R)-5-(methoxymethyl)-1-(prop-2-enoyl)pyrrolidin-3-yl]-3-[2-(1-methyl-1,3-benzodiazol-5-yl)ethynyl]-5-(methylamino)pyrazole-4-carboxamide To a stirred mixture of 3-bromo-1-[(3S,5R)-5-(methoxymethyl)-1-(prop-2-enoyl)pyrrolidin-3-yl]-5-(methylamino)pyrazole-4-carboxamide (0.23 g, 0.59 mmol), 5-ethynyl-1-methyl-1,3-benzodiazole (0.14 g, 0.89 mmol), CuI (22.68 mg, 0.12 mmol) and Pd(PPh3)2Cl2 (41.80 mg, 0.06 mmol) in DMF (4.00 mL) was added TEA (0.25 mL, 2.45 mmol) dropwise at room temperature. The reaction mixture was degassed with argon for three times and stirred for 5 h at 90° C. The resulting mixture was concentrated under reduced pressure. The residue was purified by reverse flash chromatography with the following conditions: column, C18 silica gel; mobile phase, NH4HCO3 in water, 20% to 55% gradient in 30 min; detector, UV 254 nm. The crude product was purified by Prep-HPLC with the following conditions Column: SunFire Prep C18 OBD Column, 19×150 mm 5 um 10 nm; Mobile Phase A: Water (0.1% FA), Mobile Phase B: ACN; Flow rate: 20 mL/min; Gradient: 35 B to 70 B in 4.3 min; 210/254 nm; RT1: 4.12 min. The fractions that contained desired product were combined and concentrated to afford 1-[(3S,5R)-5-(methoxymethyl)-1-(prop-2-enoyl)pyrrolidin-3-yl]-3-[2-(1-methyl-1,3-benzodiazol-5-yl)ethynyl]-5-(methylamino)pyrazole-4-carboxamide (0.11 g, 37%) as an off-white solid. MS ESI calculated for C24H27N7O3 [M+H]+, 462.22, found 462.10. H-NMR (400 MHz, DMSO-d6): δ 12.75 (brs, 1H), 8.33-8.30 (m, 1H), 8.15-8.13 (m, 1H), 7.92-7.86 (m, 1H), 7.66 (d, J=8.4 Hz, 1H), 7.47 (d, J=8.4 Hz, 1H), 7.38-7.34 (m, 1H), 6.83-6.76 (m, 1H), 6.73-6.54 (m, 1H), 6.19-6.14 (m, 1H), 5.71-5.67 (m, 1H), 5.27-5.25 (m, 1H), 4.59-4.35 (m, 1H), 4.03-4.02 (m, 1H), 3.93-3.91 (m, 4H), 3.86-3.71 (m, 1H), 3.45-3.30 (m, 3H), 2.95 (t, J=5.1 Hz, 3H), 2.61-2.51 (m, 1H), 2.33-2.24 (m, 1H).

Example 5: 1-((3S,5R)-1-acryloyl-5-(methoxymethyl)pyrrolidin-3-yl)-3-((1,2-dimethyl-1H-benzo[d]imidazol-5-yl)ethynyl)-5-(methylamino)-1H-pyrazole-4-carboxamide

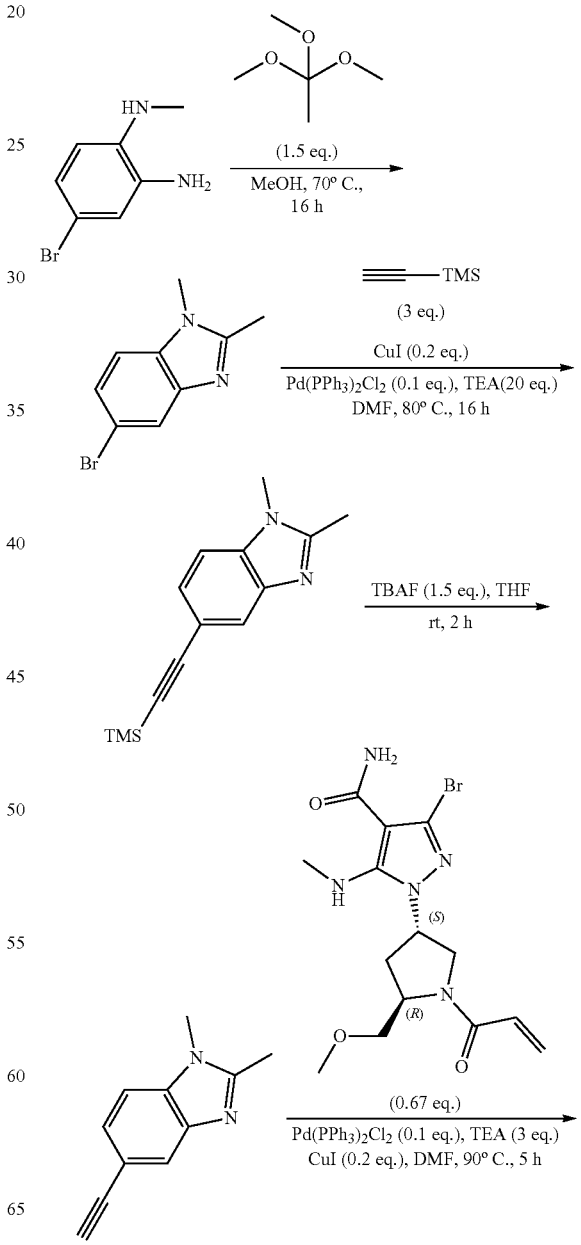

-continued

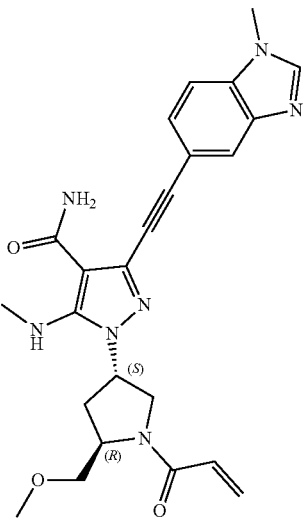

Step 1: 5-bromo-1,2-dimethyl-1,3-benzodiazole

To a stirred solution of 4-bromo-N1-methylbenzene-1,2-diamine (4.00 g, 19.89 mmol) in MeOH (40.00 mL) was added 1,1,1-trimethoxyethane (3.59 g, 29.84 mmol). The reaction mixture was stirred for 16 h at 70° C. under nitrogen atmosphere. The resulting mixture was concentrated under reduced pressure. The residue was purified by silica gel column chromatography, eluted with 6% MeOH in DCM. The fractions contained desired product were combined and concentrated to afford 5-bromo-1,2-dimethyl-1,3-benzodiazole (3.91 g, 78%) as a light yellow solid. MS ESI calculated for C9H9BrN2 [M+H]+, 224.99, 226.99; found 225.00, 227.00.

Step 2: 1,2-dimethyl-5-[2-(trimethylsilyl)ethynyl]-1,3-benzodiazole

To a stirred mixture of 5-bromo-1,2-dimethyl-1,3-benzodiazole (2.53 g, 11.24 mmol), trimethylsilylacetylene (4.77 mL, 48.52 mmol), CuI (428.13 mg, 2.25 mmol) and Pd(PPh$_3$)$_2$Cl$_2$ (788.94 mg, 1.12 mmol) in DMF (50.00 mL) was added TEA (31.25 mL, 308.79 mmol). The reaction mixture was degassed with nitrogen for three times and stirred for 16 h at 80° C. The resulting mixture was diluted with water (200 mL) and extracted with EA (3×200 mL). The combined organic layers were washed with brine (2×200 mL), dried over anhydrous Na$_2$SO$_4$, filtered and concentrated under reduced pressure. The residue was purified by silica gel column chromatography, eluted with 8% MeOH in DCM. The fractions contained desired product were combined and concentrated. The residue was purified by reverse flash chromatography with the following conditions: column, C18 silica gel; mobile phase, NH$_4$HCO$_3$ in water, 30% to 70% gradient in 35 min; detector, UV 254 nm. The fractions contained desired product were combined and concentrated to afford 1,2-dimethyl-5-[2-(trimethylsilyl)ethynyl]-1,3-benzodiazole (0.52 g, 17%) as a brown solid. MS ESI calculated for C$_{14}$H$_{18}$N$_2$Si [M+H]$^+$, 243.12, found 243.00.

Step 3: 5-ethynyl-1,2-dimethyl-1,3-benzodiazole

To a stirred solution of 1,2-dimethyl-5-[2-(trimethylsilyl)ethynyl]-1,3-benzodiazole (1.06 g, 4.37 mmol) in THF (20.00 mL) was added TBAF (6.56 mL, 6.56 mmol) dropwise at 0° C. under nitrogen atmosphere. The reaction mixture was stirred for 2 h at room temperature. The resulting mixture was concentrated under reduced pressure. The residue was diluted with water (100 mL), extracted with EtOAc (3×100 mL). The combined organic layers were washed with brine (200 mL), dried over anhydrous Na$_2$SO$_4$ and filtered. The filtrate was concentrated under reduced pressure. The residue was purified by silica gel column chromatography, eluted with CH$_2$Cl$_2$/MeOH (20:1). The fractions contained desired product were combined and concentrated to afford 5-ethynyl-1,2-dimethyl-1,3-benzodiazole (0.68 g, 81%) as an off-white solid. MS ESI calculated for C$_{11}$H$_{10}$N$_2$ [M+H]$^+$, 171.08, found 171.15.

Step 4: 3-[2-(1,2-dimethyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide To a stirred mixture of 3-bromo-1-[(3S,5R)-5-(methoxymethyl)-1-(prop-2-enoyl)pyrrolidin-3-yl]-5-(methylamino)pyrazole-4-carboxamide (0.27 g, 0.70 mmol), 5-ethynyl-1,2-dimethyl-1,3-benzodiazole (0.18 g, 1.05 mmol), CuI (26.63 mg, 0.14 mmol) and Pd(PPh$_3$)$_2$Cl$_2$ (49.06 mg, 0.07 mmol) in DMF (4.50 mL) was added TEA (0.29 mL, 2.88 mmol). The reaction mixture was degassed with argon for three times and stirred for 5 h at 90° C. The resulting mixture was diluted with water (30 mL) and extracted with EA (3×50 mL). The combined organic layers were washed with brine (2×100 mL), dried over anhydrous Na$_2$SO$_4$, filtered and concentrated under reduced pressure. The residue was purified by reverse flash chromatography with the following conditions: column, C18 silica gel; mobile phase, NH$_4$HCO$_3$ in water, 25% to 40% gradient in 25 min; detector, UV 254 nm. The fractions contained desired product were combined and concentrated. The residue was purified by Prep-HPLC with the following conditions Column: XBridge Prep C18 OBD Column, 19×150 mm 5 um; Mobile Phase A: Water (10 mmol/L NH$_4$HCO$_3$), Mobile Phase B: ACN; Flow rate: 20 mL/min; Gradient: 35 B to 70 B in 4.3 min; 210/254 nm; RT1: 4.02. The fractions contained desired product were combined and concentrated to afford 3-[2-(1,2-dimethyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (0.16 g, 46%) as an off-white solid. MS ESI calculated for C$_{25}$H$_{29}$N$_7$O$_3$ [M+H]$^+$, 476.23, found 476.25. H-NMR (400 MHz, DMSO-d$_6$): δ 7.76 (s, 1H), 7.58 (d, J=8.3 Hz, 1H), 7.43-7.38 (m, 2H), 6.76-6.59 (m, 3H), 6.19 (d, J=16.5 Hz, 1H), 5.71 (d, J=10.2 Hz, 1H), 5.27-5.21 (m, 1H), 4.48-4.35 (m, 1H), 4.11-3.82 (m, 1H), 3.77-3.71 (m, 4H), 3.67-3.38 (m, 2H), 3.34 (d, J=1.1 Hz, 3H), 2.96 (t, J=4.5 Hz, 3H), 2.66-2.50 (m, 4H), 2.29-2.21 (m, 1H).

22Example 6: 1-((3S,5R)-1-acryloyl-5-(methoxymethyl)pyrrolidin-3-yl)-3-((1-ethyl-1H-benzo[d]imidazol-5-yl)ethynyl)-5-(methylamino)-1H-pyrazole-4-carboxamide

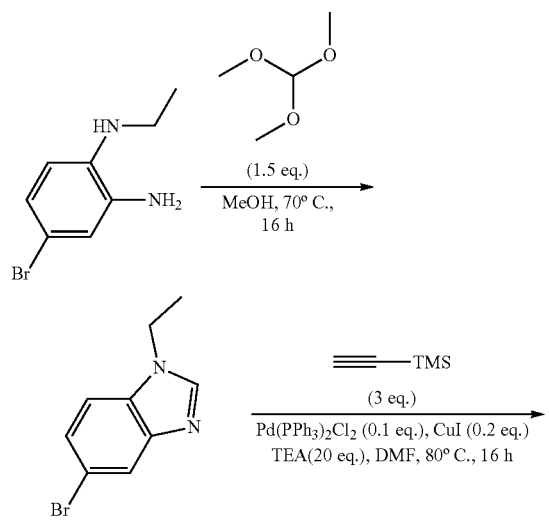

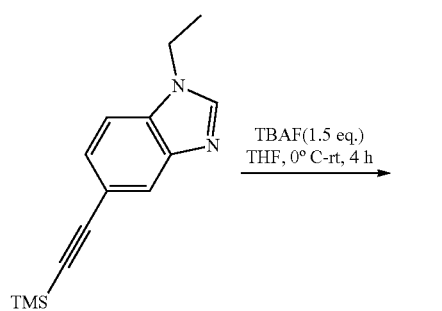

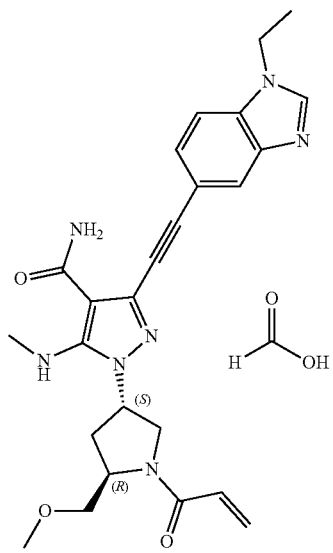

Step 1: 5-bromo-1-methyl-1,3-benzodiazole

To a stirred solution of 4-bromo-N1-ethylbenzene-1,2-diamine (1.08 g, 5.02 mmol) in MeOH (10.00 mL) was added trimethyl orthoformate (0.80 g, 7.53 mmol). The reaction mixture was stirred for 16 h at 70° C. The resulting mixture was concentrated under reduced pressure. The residue was purified by silica gel column chromatography, eluted with CH$_2$Cl$_2$/MeOH (12:1). The fractions contained desired product were combined and concentrated to afford 5-bromo-1-ethyl-1,3-benzodiazole (1 g, 88%) as a light yellow solid. MS ESI calculated for C$_9$H$_9$BrN$_2$ [M+H]$^+$, 224.99, 226.99; found 225.00, 227.00.

Step 2: 1-ethyl-5-[2-(trimethylsilyl)ethynyl]-1,3-benzodiazole

To a stirred mixture of 5-bromo-1-ethyl-1,3-benzodiazole (1.00 g, 4.44 mmol), trimethylsilylacetylene (1.31 g, 13.33 mmol), CuI (0.17 g, 0.89 mmol) and Pd(PPh$_3$)$_2$Cl$_2$ (0.62 g, 0.89 mmol) in DMF (10.00 mL) was added TEA (8.99 g, 88.85 mmol). The reaction mixture was degassed with argon for three times and stirred for 16 h at 80° C. The resulting mixture was diluted with water (60 mL) and extracted with EtOAc (3×80 mL). The combined organic layers were washed with brine (150 mL), dried over anhydrous Na$_2$SO$_4$ and filtered. The filtrate was concentrated under reduced pressure. The residue was purified by silica gel column chromatography, eluted with CH$_2$Cl$_2$/MeOH (15:1). The fractions contained desired product were combined and concentrated to afford 1-ethyl-5-[2-(trimethylsilyl)ethynyl]-1,3-benzodiazole (0.80 g, 74%) as a light yellow solid. MS ESI calculated for C$_{14}$H$_{18}$N$_2$Si [M+H]$^+$, 243.12; found 243.20.

Step 3: 1-ethyl-5-ethynyl-1,3-benzodiazole

To a solution of 1-ethyl-5-[2-(trimethylsilyl)ethynyl]-1,3-benzodiazole (0.80 g, 3.30 mmol) in THF (8.00 mL) was added TBAF (1 M in THF, 4.95 mL, 4.95 mmol) at 0° C. under nitrogen atmosphere. The reaction mixture was stirred for 4 h at room temperature. The resulting mixture was concentrated under reduced pressure. The residue was purified by silica gel column chromatography, eluted with $CH_2Cl_2$/PE (15:1). The fractions contained desired product were combined and concentrated to afford 1-ethyl-5-ethynyl-1,3-benzodiazole (0.40 g, 71%) as a yellow solid. MS ESI calculated for $C_{11}H_{10}N_2$ [M+H]$^+$, 171.08; found 171.15.

Step 4: 3-[2-(1-ethyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide formic acid To a stirred mixture of 3-bromo-1-[(3S,5R)-5-(methoxymethyl)-1-(prop-2-enoyl)pyrrolidin-3-yl]-5-(methylamino) pyrazole-4-carboxamide (0.20 g, 0.52 mmol), 1-ethyl-5-ethynyl-1,3-benzodiazole (0.13 g, 0.78 mmol), CuI (19.72 mg, 0.10 mmol) and Pd(PPh$_3$)$_2$Cl$_2$ (36.34 mg, 0.05 mmol) in DMF (3 mL) was added TEA (0.16 g, 1.55 mmol). The reaction mixture was degassed with argon for three times and stirred for 3 h at 90° C. The resulting mixture was concentrated under reduced pressure. The residue was purified by Prep-HPLC with the following conditions Column: Atlantis Prep T3 OBD Column, 19*250 mm 10 um; Mobile Phase A: Water (0.1% FA), Mobile Phase B: ACN; Flow rate: 20 mL/min; Gradient: 25 B to 60 B in 6 min; 210/254 nm; RT1: 5.88. The fractions contained desired product were combined and concentrated to afford 3-[2-(1-ethyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide formic acid (50.6 mg, 18%) as a light yellow solid. MS ESI calculated for $C_{26}H_{31}N_7O_5$ [M+H−FA]$^+$, 476.23, found 476.15. $^1$H-NMR (400 MHz, d$_6$-DMSO) δ 8.38 (s, 1H), 7.90 (s, 1H), 7.71 (d, J=8.4 Hz, 1H), 7.49-7.31 (m, 2H), 6.85-6.54 (m, 3H), 6.19-6.15 (m, 1H), 5.71-5.67 (m, 1H), 5.24 (dd, J=16.9, 7.5 Hz, 1H), 4.57-4.37 (m, 1H), 4.31 (q, J=7.3 Hz, 2H), 4.07-3.70 (m, 2H), 3.64-3.43 (m, 2H), 3.30 (s, 3H), 2.95 (t, J=5.2 Hz, 3H), 2.67-2.53 (m, 1H), 2.36-2.25 (m, 1H), 1.42 (t, J=7.2 Hz, 3H).

Example 7: (S)-1-(1-acryloylpyrrolidin-3-yl)-3-((1,2-dimethyl-1H-benzo[d]imidazol-5-yl)ethynyl)-5-(methylamino)-1H-pyrazole-4-carboxamide

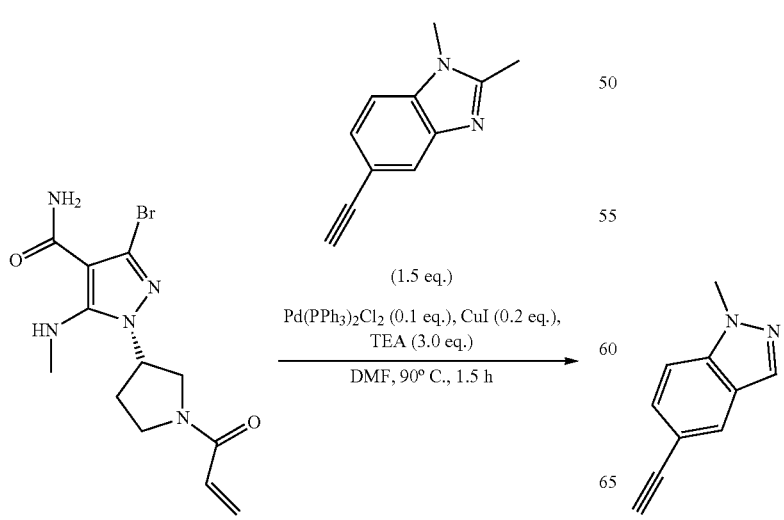

(1.5 eq.)

Pd(PPh$_3$)$_2$Cl$_2$ (0.1 eq.), CuI (0.2 eq.),
TEA (3.0 eq.)
───────────────→
DMF, 90° C., 1.5 h

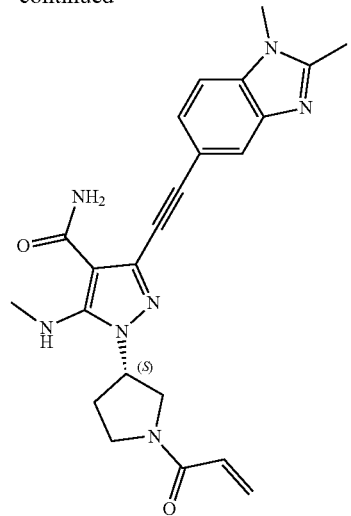

To a stirred mixture of 3-bromo-5-(methylamino)-1-[1-(prop-2-enoyl)pyrrolidin-3-yl]pyrazole-4-carboxamide (0.2 g, 0.58 mmol), 5-ethynyl-1,2-dimethyl-1,3-benzodiazole (0.15 g, 0.88 mmol), CuI (22.26 mg, 0.12 mmol) and Pd(PPh$_3$)$_2$Cl$_2$ (41.02 mg, 0.06 mmol) in DMF (2.00 mL) was added and TEA (0.24 mL, 2.41 mmol). The reaction mixture was degassed with argon for three times and stirred for 1.5 h at 90° C. The residue was purified by Prep-HPLC with the following conditions: Column: XBridge Prep C18 OBD Column, 19×150 mm 5 um; Mobile Phase A: Water (10 mmol/L NH$_4$HCO$_3$), Mobile Phase B: ACN; Flow rate: 20 mL/min; Gradient: 20 B to 50 B in 4.3 min; 210/254 nm; RT1: 4.02. The fractions contained desired product were combined and concentrated to afford 3-[2-(1,2-dimethyl-1,3-benzodiazol-5-yl)ethynyl]-5-(methylamino)-1-[(3S)-1-(prop-2-enoyl)pyrrolidin-3-yl]pyrazole-4-carboxamide (89 mg, 35%) as an off-white solid. MS ESI calculated for $C_{23}H_{25}N_7O_2$ [M+H]$^+$, 431.21, found 431.20. H NMR (400 MHz, DMSO-d$_6$) δ 7.60 (s, 2H), 7.39-7.37 (d, J=8.3 Hz, 2H), 6.81 (s, 1H), 6.68-6.56 (m, 2H), 6.19-6.13 (m, 1H), 5.72-5.66 (m, 1H), 5.18-5.09 (m, 1H), 3.89-3.79 (m, 2H), 3.78-3.70 (m, 4H), 3.73 (m, 1H), 3.32 (s, 3H), 2.97-2.90 (m, 2H), 2.51-2.49 (m, 1H), 2.41-2.36 (m, 1H), 2.32-2.26 (m, 1H).

Example 8: 1-((3S,5R)-1-acryloyl-5-(methoxymethyl)pyrrolidin-3-yl)-3-((1-methyl-1H-indazol-5-yl)ethynyl)-5-(methylamino)-1H-pyrazole-4-carboxamide

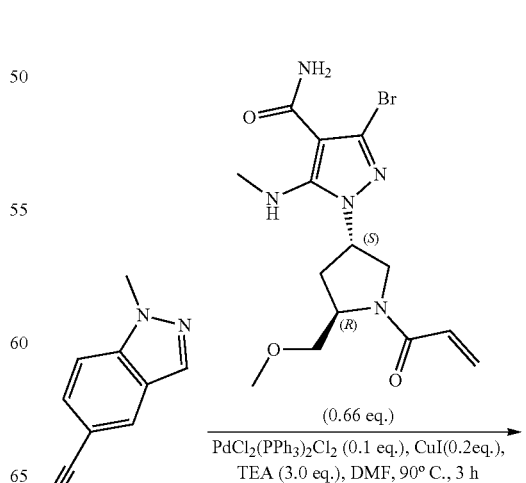

(0.66 eq.)

PdCl$_2$(PPh$_3$)$_2$Cl$_2$ (0.1 eq.), CuI(0.2eq.),
TEA (3.0 eq.), DMF, 90° C., 3 h
───────────────→

-continued

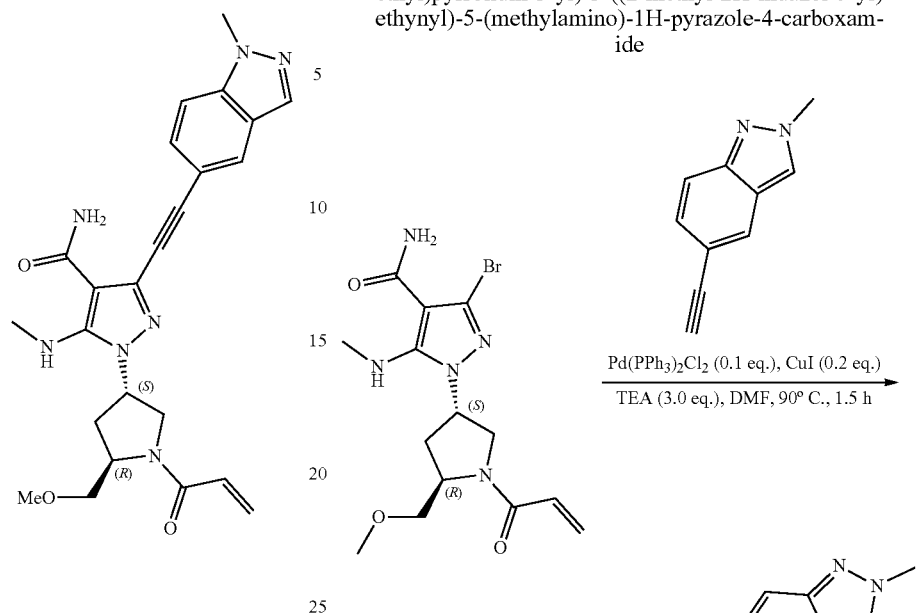

To a stirred mixture of 3-bromo-1-[(3S,5R)-5-(methoxymethyl)-1-(prop-2-enoyl)pyrrolidin-3-yl]-5-(methylamino) pyrazole-4-carboxamide (0.20 g, 0.52 mmol), 5-ethynyl-1-methylindazole (0.12 g, 0.78 mmol), CuI (19.72 mg, 0.10 mmol) and Pd(PPh$_3$)$_2$Cl$_2$ (36.34 mg, 0.05 mmol) in DMF (2.50 mL) was added TEA (0.16 g, 1.55 mmol). The reaction mixture was degassed with argon for three times and stirred for 3 h at 90° C. The reaction mixture was concentrated under reduced pressure. The residue was purified by Prep-HPLC with the following conditions Column: XBridge Prep C18 OBD Column, 19×150 mm 5 um; Mobile Phase A: Water (10 mmol/L NH$_4$HCO$_3$), Mobile Phase B: ACN; Flow rate: 20 mL/min; Gradient: 30 B to 60 B in 4.3 min; 254/210 nm; RT1:4.350. The fractions contained desired product were combined and concentrated to afford 1-[(3S,5R)-5-(methoxymethyl)-1-(prop-2-enoyl)pyrrolidin-3-yl]-5-(methylamino)-3-[2-(1-methylindazol-5-yl) ethynyl]pyrazole-4-carboxamide (80.0 mg, 33%) as a white solid. MS ESI calculated for C$_{24}$H$_{27}$N$_7$O$_3$ [M+H]$^+$, 462.22, found 462.05. $^1$H-NMR (300 MHz, d$_6$-DMSO) δ 8.10 (d, J=21.4 Hz, 2H), 7.74 (d, J=8.8 Hz, 1H), 7.55 (dd, J=8.7, 1.7 Hz, 1H), 7.36 (s, 1H), 6.89-6.52 (m, 3H), 6.18 (d, J=16.6 Hz, 1H), 5.71 (d, J=10.3 Hz, 1H), 5.27 (dd, J=13.6, 6.9 Hz, 1H), 4.48 (d, J=39.4 Hz, 1H), 4.14-4.00 (m, 4H), 3.96-3.84 (m, 1H), 3.81-3.57 (m, 1H), 3.50-3.48 (m, 1H), 3.37-3.29 (m, 4H), 2.96 (t, J=4.5 Hz, 3H), 2.33-2.30 (m, 1H).

Example 9: 1-((3S,5R)-1-acryloyl-5-(methoxymethyl)pyrrolidin-3-yl)-3-((2-methyl-2H-indazol-5-yl)ethynyl)-5-(methylamino)-1H-pyrazole-4-carboxamide

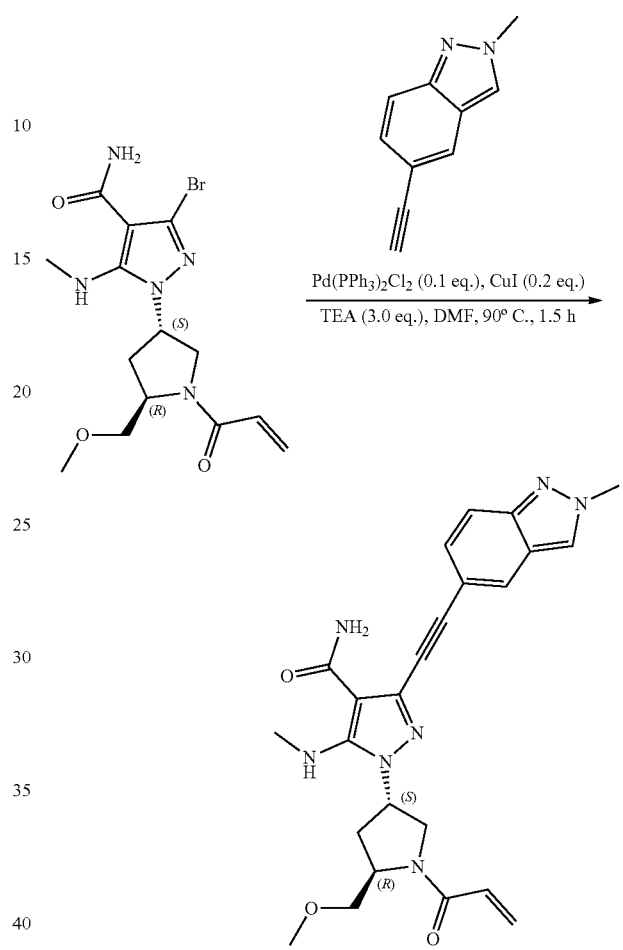

To a stirred solution 3-bromo-1-[(3S,5R)-5-(methoxymethyl)-1-(prop-2-enoyl)pyrrolidin-3-yl]-5-(methylamino) pyrazole-4-carboxamide (0.30 g, 0.78 mmol) in DMF (5.00 mL) were added 5-ethynyl-2-methylindazole (0.18 g, 1.17 mmol), palladium chloride; bis(triphenylphosphine) (54.52 mg, 0.08 mmol), copper (I) iodide (29.58 mg, 0.16 mmol) and TEA (0.24 g, 2.33 mmol). The reaction mixture was degassed with argon for three times and stirred for 1.5 h at 90° C. The resulting mixture was directly purified by reverse phase chromatography with the following conditions: Column: Spherical C18, 20-40 um, 80 g; Mobile Phase A: Water (10 mM NH$_4$HCO$_3$), Mobile Phase B: ACN; Flow rate: 40 mL/min; Gradient (B %): 0% hold 5 min, 0%-23% within 20 min, 23% hold 5 min, 23%-31% within 15 min, 31% hold 6 min, 31%-95% within 5 min, 95% hold 3 min; Detector: UV 254 & 220 nm; RT: 45 min. The fractions contained desired product were combined and concentrated under reduced pressure. The residue was further purified by Prep-HPLC with the following conditions: Column: XBridge Prep C18 OBD Column, 19×150 mm, 5 um; Mobile Phase A: Water (10 mM NH$_4$HCO$_3$), Mobile Phase B: ACN; Flow rate: 20 mL/min; Gradient: 20% B to 50% B in 4.3 min; Detector: UV 210 & 254 nm; RT: 4.02 min. The fractions contained desired product were combined and concentrated under reduced pressure to afford 1-[(3S,5R)-5-(methoxymethyl)-1-(prop-2-enoyl)pyrrolidin-3-yl]-5-(methylamino)-3-[2-(2-methylindazol-5-yl)ethynyl]pyrazole-4-carboxamide (74.0 mg, 20%) as a white solid. MS ESI calculated for $C_{24}H_{27}N_7O_3$ $[M+H]^+$, 462.22, found 462.10. H-NMR (300 MHz, $d_6$-DMSO) δ 8.44 (s, 1H), 8.02 (s, 1H), 7.64 (d, J=8.9 Hz, 1H), 7.33 (brs, 1H), 7.31 (dd, J=8.9, 1.6 Hz, 1H), 6.80 (brs, 1H), 6.76-6.54 (m, 2H), 6.20-6.13 (m, 1H), 5.71-5.66 (m, 1H), 5.31-5.17 (m, 1H), 4.56-4.38 (m, 1H), 4.19 (s, 3H), 4.05-3.70 (m, 2H), 3.63-3.43 (m, 2H), 3.29 (s, 3H), 2.94-2.92 (m, 3H), 2.66-2.56 (m, 0.5H), 2.47-2.42 (m, 0.5H), 2.33-2.25 (m, 1H).

Example 10: 1-((3S,5R)-1-acryloyl-5-(methoxymethyl)pyrrolidin-3-yl)-3-((1-methyl-2-(trifluoromethyl)-1H-benzo[d]imidazol-5-yl)ethynyl)-5-(methylamino)-1H-pyrazole-4-carboxamide

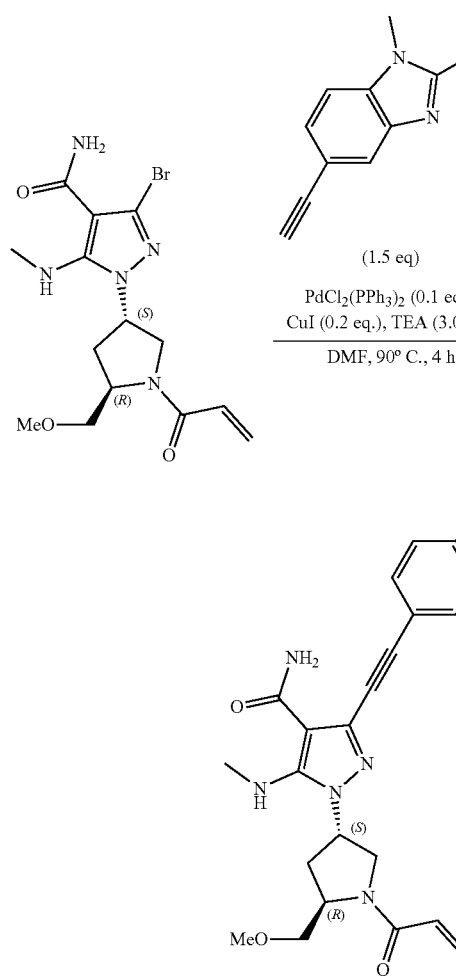

To a mixture of 3-bromo-1-[(3S,5R)-5-(methoxymethyl)-1-(prop-2-enoyl)pyrrolidin-3-yl]-5-(methylamino)pyrazole-4-carboxamide (0.86 g, 2.23 mmol), 5-ethynyl-1-methyl-2-(trifluoromethyl)-1,3-benzodiazole (1.00 g, 4.45 mmol), $Pd(PPh_3)_2Cl_2$ (0.16 g, 0.22 mmol) and CuI (84.81 mg, 0.45 mmol) in DMF (9.00 mL) was added TEA (0.93 mL, 9.17 mmol). The reaction mixture was degassed with nitrogen three times and stirred for 4 h at 90° C. The resulting mixture was purified by reverse flash chromatography with the following conditions: column, C18 silica gel; mobile phase, $NH_4HCO_3$ in water, 10% to 50% gradient in 25 min; detector, UV 254 nm. The fractions contained desired product were combined and concentrated. The residue was purified by Prep-HPLC with the following conditions Column: XBridge Prep OBD C18 Column, 19*250 mm, 5 um; Mobile Phase A: Water (10 mmol/L $NH_4HCO_3$), Mobile Phase B: ACN; Flow rate: 20 mL/min; Gradient: 30 B to 50 B in 5.8 min; 210/254 nm; RT1: 5.58. The fractions contained desired product were combined and concentrated to afford 1-[(3S,5R)-5-(methoxymethyl)-1-(prop-2-enoyl)pyrrolidin-3-yl]-3-[2-[1-methyl-2-(trifluoromethyl)-1,3-benzodiazol-5-yl]ethynyl]-5-(methylamino)pyrazole-4-carboxamide (0.37 g, 30%) as an off-white solid. MS ESI calculated for $C_{25}H_{26}F_3N_7O_3$ $[M+H]^+$, 530.20, found 530.15. H-NMR (400 MHz, DMSO-$d_6$): δ 8.09 (d, J=1.6 Hz, 1H), 7.89 (d, J=8.6 Hz, 1H), 7.67 (dd, J=8.5, 1.5 Hz, 1H), 7.35 (s, 1H), 6.88-6.47 (m, 3H), 6.23-6.18 (m, 1H), 5.71-5.68 (m, 1H), 5.27-5.24 (m, 1H), 4.52-4.41 (m, 1H), 4.02-4.00 (m, 4H), 3.93-3.82 (m, 1H), 3.63-3.42 (m, 2H), 3.31 (d, J=5.4 Hz, 3H), 2.94 (t, J=5.1 Hz, 3H), 2.63-260 (m, 1H), 2.34-2.24 (m, 1H).

Example 11: 1-((3S,5R)-1-acryloyl-5-(methoxymethyl)pyrrolidin-3-yl)-3-((4,6-difluoro-1-methyl-1H-benzo[d]imidazol-5-yl)ethynyl)-5-(methylamino)-1H-pyrazole-4-carboxamide

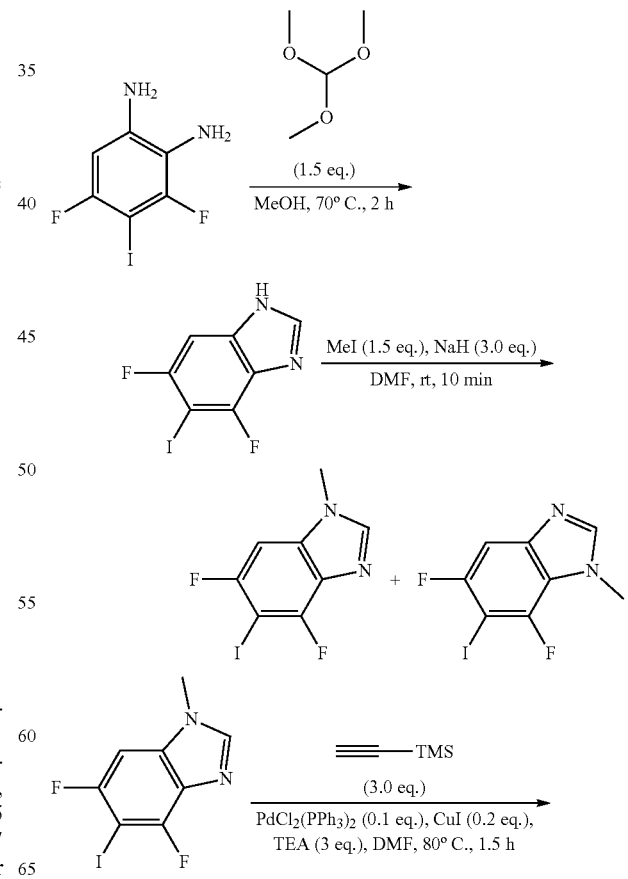

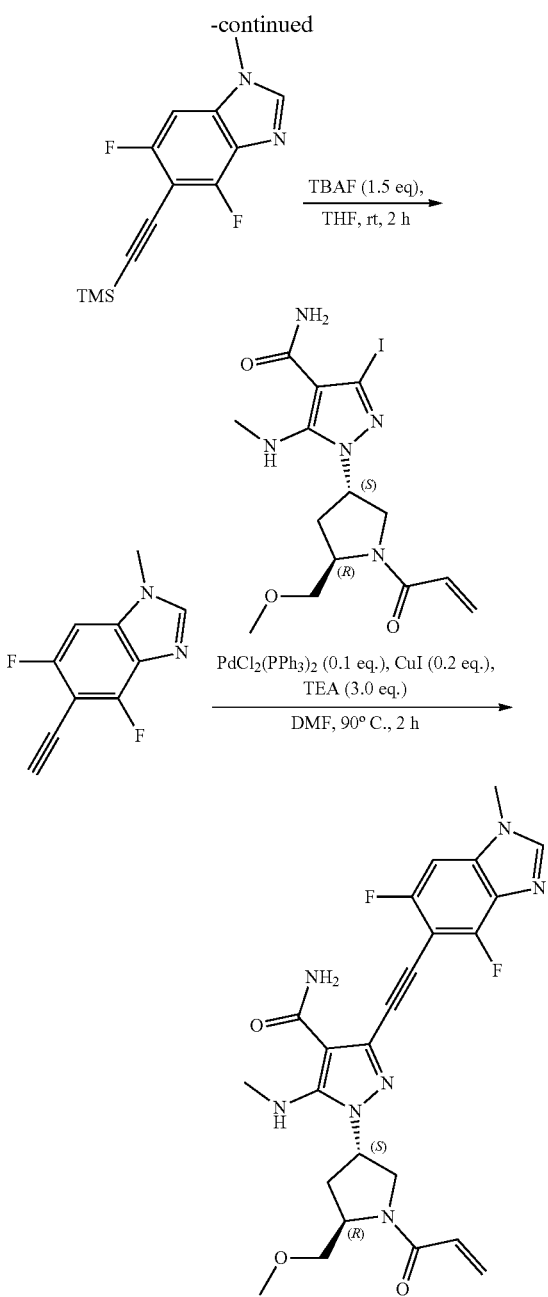

Step 1: 4,6-difluoro-5-iodo-1H-1,3-benzodiazole

To a solution of 3,5-difluoro-4-iodobenzene-1,2-diamine (5.00 g, 18.51 mmol) in MeOH (50.00 mL) was added trimethyl orthoformate (2.94 g, 27.70 mmol) at room temperature. The reaction mixture was stirred for 2 h at 70° C. The resulting mixture was concentrated under reduced pressure. The resulting mixture was diluted with EtOAc (50.00 mL). The residue was washed with water (3×40.00 mL). The combined organic layers was dried over anhydrous Na$_2$SO$_4$ and filtered. The filtrate was concentrated under reduced pressure. The residue was purified by silica gel column chromatography, eluted with EA in PE (0-60%). The fractions contained desired product were combined and concentrated to afford 4,6-difluoro-5-iodo-1H-1,3-benzodiazole (4.9 g, 94%) as a brown solid. MS ESI calculated for C$_7$H$_3$F$_2$IN$_2$ [M+H]$^+$, 280.93, found 280.95.

Step 2: 4,6-difluoro-5-iodo-1-methyl-1,3-benzodiazole

To a solution of 4,6-difluoro-5-iodo-1H-1,3-benzodiazole (0.30 g, 1.07 mmol) in DMF (12.00 mL) was added NaH (0.13 g, 3.21 mmol, 60%) at 0° C. under nitrogen atmosphere. The reaction mixture was stirred at ambient temperature for 30 min. methyl iodide (0.23 g, 1.60 mmol) was added dropwise at 0° C. under nitrogen atmosphere. The resulting mixture was stirred for 10 min at room temperature. The resulting mixture was quenched with Water (1.00 mL) at 0° C. The resulting mixture was diluted with EtOAc (20.00 mL). The residue was washed with water (3×10.00 mL). The combined organic layers were washed with brine (20 mL), dried over anhydrous Na$_2$SO$_4$. After filtration, the filtrate was concentrated under reduced pressure. The residue was purified by reverse phase chromatography with the following conditions: Column: Spherical C18, 20-40 um, 40 g; Mobile Phase A: Water (10 mM NH$_4$HCO$_3$), Mobile Phase B: ACN; Flow rate: 50 mL/min; Gradient (B %): 5% hold 5 min, 5%-29% within 25 min; 29% hold 8 min, 29%~95% within 5 min, 95% hold 5 min; Detector: UV 254 & 220 nm; RT: 48 min. The fractions contained desired product were combined and concentrated under reduced pressure to afford 4,6-difluoro-5-iodo-1-methyl-1,3-benzodiazole (0.18 g, 57%) as a light yellow solid and 5,7-difluoro-6-iodo-1-methyl-1,3-benzodiazole (0.15 g, 47%) as a yellow solid. MS ESI calculated for C$_8$H$_5$F$_2$IN$_2$ [M+H]$^+$, 294.95, found 295.00.

Step 3: 4,6-difluoro-1-methyl-5-[2-(trimethylsilyl)ethynyl]-1,3-benzodiazole

Into a 50 mL vial were added 4,6-difluoro-5-iodo-1-methyl-1,3-benzodiazole (1.60 g, 5.44 mmol), trimethylsilylacetylene (1.60 g, 16.32 mmol), Pd(PPh$_3$)$_2$Cl$_2$ (0.38 g, 0.54 mmol), CuI (0.21 g, 1.09 mmol) and TEA (1.65 g, 16.32 mmol) in DMF (20.00 mL) at room temperature. The reaction mixture was degassed with argon for three times and stirred for 2 h at 80° C. The mixture was allowed to cool down to room temperature. The resulting mixture was concentrated under reduced pressure. The resulting mixture was extracted with EtOAc (3×100 mL). The combined organic layers were washed with brine (3×100 mL), dried over anhydrous Na$_2$SO$_4$ and filtered. The filtrate was concentrated under reduced pressure. The residue was purified by silica gel column chromatography, eluted with PE/EtOAc (1:9). The fractions contained desired product were combined and concentrated to afford 4,6-difluoro-1-methyl-5-[2-(trimethylsilyl)ethynyl]-1,3-benzodiazole4,6-difluoro-1-methyl-5-[2-(trimethylsilyl)ethynyl]-1,3-benzodiazole (1.2 g, 83%) as a yellow solid. MS ESI calculated for C$_{13}$H$_{14}$F$_2$N$_2$Si [M+H]$^+$, 264.08, found 265.35.

Step 4: 5-ethynyl-4,6-difluoro-1-methyl-1,3-benzodiazole

To a stirred solution of 4,6-difluoro-1-methyl-5-[2-(trimethylsilyl)ethynyl]-1,3-benzodiazole (1.30 g, 4.92 mmol) in THF (10.00 mL) was added TBAF (1.93 g, 7.38 mmol) dropwise at room temperature. The resulting mixture was stirred for 2 h at room temperature. The resulting mixture was extracted with EtOAc (3×200 mL). The combined organic layers were washed with brine (3×50 mL), dried over anhydrous Na₂SO₄ and filtered. The filtrate was concentrated under reduced pressure. The residue was purified by silica gel column chromatography, eluted with PE/EtOAc (1:9). The fractions contained desired product were combined and concentrated to afford 5-ethynyl-4,6-difluoro-1-methyl-1,3-benzodiazole (0.90 g, 95%) as a yellow solid. MS ESI calculated for C₁₀H₆F₂N₂ [M+H]⁺, 192.04, found 193.16.

Step 5: 3-[2-(4,6-difluoro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide Into a 50 mL vial were added 3-iodo-1-[(3S,5R)-5-(methoxymethyl)-1-(prop-2-enoyl)pyrrolidin-3-yl]-5-(methylamino)pyrazole-4-carboxamide (0.70 g, 1.62 mmol), 5-ethynyl-4,6-difluoro-1-methyl-1,3-benzodiazole (0.37 g, 1.94 mmol), Pd(PPh₃)₂Cl₂ (0.11 g, 0.16 mmol), CuI (61.54 mg, 0.32 mmol) and TEA (0.49 g, 4.85 mmol) in DMF (10.00 mL) at room temperature. The reaction mixture was degassed with argon for three times and stirred for 2 h at 90° C. The mixture was allowed to cool down to room temperature. The resulting mixture was concentrated under rescued pressure. The residue was purified by silica gel column chromatography, eluted with CH₂Cl₂/MeOH (0-6%). The fractions contained desired product were combined and concentrated. The residue was purified by reverse phase flash chromatography with the following conditions: Column: Spherical C18, 20-40 um, 330 g; Mobile Phase A: Water (plus 3.2 g NH₄HCO₃); Mobile Phase B: ACN; Flow rate: 90 mL/min; Gradient: 5%-5% B, 10 min, 25% B-50% B gradient in 20 min; Detector: 254 nm. The fractions contained the desired product were collected at 44% B and concentrated under reduced pressure to afford 3-[2-(4,6-difluoro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (0.51 g, 62%) as a white solid. MS ESI calculated for C₂₄H₂₅F₂N₇O₃ [M+H]⁺, 497.19, found 498.50. 1H-NMR (400 MHz, DMSO-d₆) δ 8.37 (s, 1H), 7.70-7.48 (m, 2H), 6.87-6.53 (m, 3H), 6.13-6.19 (m, 1H), 5.71-5.68 (m, 1H), 5.28-5.25 (m, 1H), 4.46 (dd, J=56.9, 4.3 Hz, 1H), 4.07-3.71 (m, 5H), 3.65-3.42 (m, 2H), 3.31 (d, J=5.5 Hz, 3H), 2.97 (t, J=5.4 Hz, 3H), 2.65-2.62 (m, 1H), 2.32-2.29 (m, 1H).

Example 12: 1-((3S,5R)-1-acryloyl-5-(methoxymethyl)pyrrolidin-3-yl)-3-((1-cyclopropyl-2-methyl-1H-benzo[d]imidazol-5-yl)ethynyl)-5-(methylamino)-1H-pyrazole-4-carboxamide

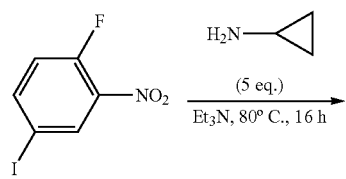

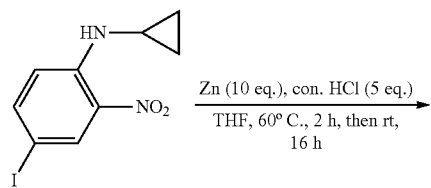

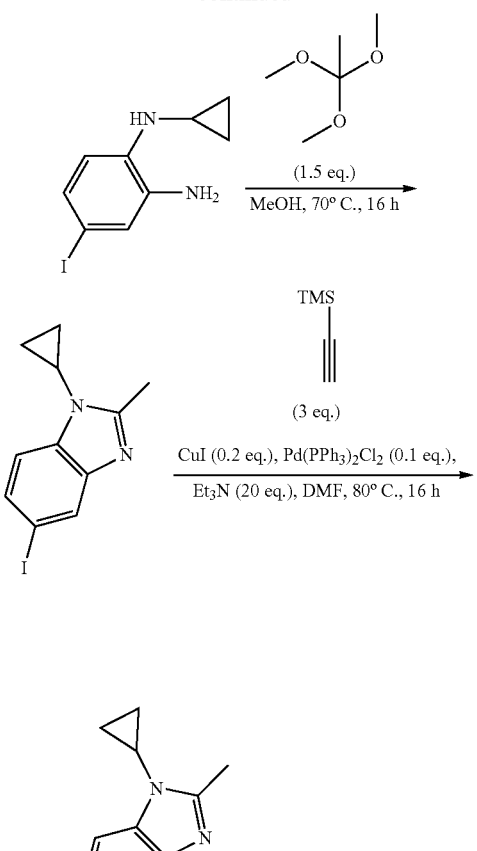

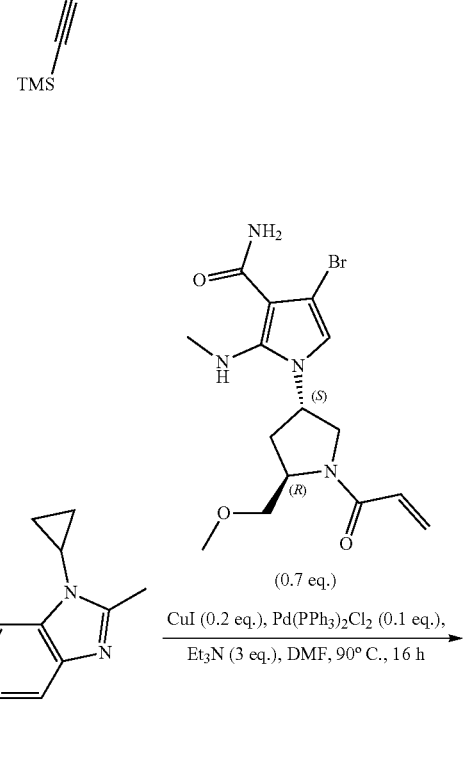

337

-continued

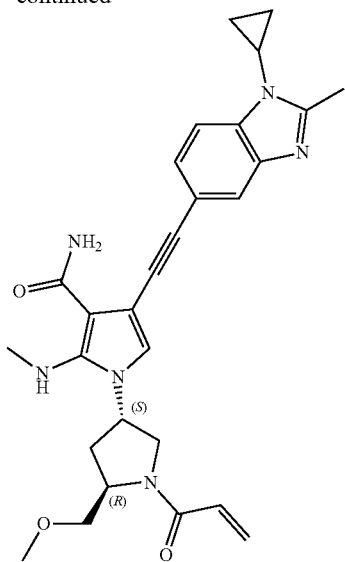

Step 1: N-cyclopropyl-4-iodo-2-nitroaniline

To a stirred mixture of 1-fluoro-4-iodo-2-nitrobenzene (10.00 g, 37.453 mmol) in Et$_3$N (29.15 mL, 288.10 mmol) was added aminocyclopropane (10.69 g, 187.27 mmol) at room temperature. The reaction mixture was stirred for 16 h at 80° C. under nitrogen atmosphere. The mixture was allowed to cool down to room temperature. The resulting mixture was quenched by the addition of sat. NaHCO$_3$ (aq.) (300 mL), extracted with EtOAc (3×200 mL). The combined organic layers were washed with brine (300 mL), dried over anhydrous Na$_2$SO$_4$ and filtered. The filtrate was concentrated under reduced pressure to afford N-cyclopropyl-4-iodo-2-nitroaniline (10 g, 87%) as a brown solid which was used in the next step without further purification. MS ESI calculated for C$_9$H$_9$IN$_2$O$_2$ [M+H]$^+$, 304.00, found 305.00.

Step 2: N1-cyclopropyl-4-iodobenzene-1,2-diamine

To a stirred mixture of N-cyclopropyl-4-iodo-2-nitroaniline (5.20 g, 17.10 mmol) in THF (1.00 mL) was added Zn (11.19 g, 171.00 mmol) and HCl (2.60 mL, 71.25 mmol) at room temperature. The reaction mixture was stirred for 2 h at 60° C., then 16 h at room temperature. The resulting mixture was filtered, the filter cake was washed with EtOAc (3×300 mL). The filtrate was concentrated under reduced pressure and dried to afford N$^1$-cyclopropyl-4-iodobenzene-1,2-diamine (5 g, crude) as a brown solid which was used in the next step without further purification. MS ESI calculated for C$_9$H$_{11}$IN$_2$ [M+H]$^+$, 274.95, found 274.95.

Step 3: 1-cyclopropyl-5-iodo-2-methyl-1,3-benzodiazole

To a stirred mixture of N$^1$-cyclopropyl-4-iodobenzene-1,2-diamine (0.20 g, 0.73 mmol) in methanol (2.00 mL) was added 1,1,1-trimethoxyethane (0.13 g, 1.09 mmol) at room temperature. The reaction mixture was stirred for 16 h at 70° C. The resulting mixture was allowed to cool down to room temperature. The resulting mixture was concentrated under reduced pressure. The residue was purified by silica gel column chromatography, eluted with PE/(EtOAc/EtOH(3:

338

1)) (1:1). The fractions contained desired product were combined and concentrated to afford 1-cyclopropyl-5-iodo-2-methyl-1,3-benzodiazole (1.4 g, 51%) as a yellow solid. MS ESI calculated for C$_{11}$H$_{11}$IN$_2$ [M+H]$^+$, 298.95, found 298.95.

Step 4: 1-cyclopropyl-2-methyl-5-[2-(trimethylsilyl)ethynyl]-1,3-benzodiazole

To a stirred mixture of 1-cyclopropyl-5-iodo-2-methyl-1,3-benzodiazole (0.70 g, 2.35 mmol) and CuI (89.44 mg, 0.47 mmol) in DMF (7.00 mL) were added Pd(PPh$_3$)$_2$Cl$_2$ (0.16 g, 0.24 mmol), trimethylsilylacetylene (98.84 mg, 1.01 mmol) and TEA (6.53 mL, 64.51 mmol). The reaction mixture was degassed with nitrogen for three times and stirred for 16 h at 80° C. The mixture was allowed to cool down to room temperature. The resulting mixture was quenched by the addition of Water (50 mL) at room temperature, extracted with EtOAc (3×50 mL). The combined organic layers were washed with brine (100 mL), dried over anhydrous Na$_2$SO$_4$ and filtered. The filtrate was concentrated under reduced pressure. The residue was purified by silica gel column chromatography, eluted with PE/(EtOAc/EtOH(3:1)) (1:1). The fractions contained desired product were combined and concentrated to afford 1-cyclopropyl-2-methyl-5-[2-(trimethylsilyl)ethynyl]-1,3-benzodiazole (0.50 g, 79%) as a brown solid. MS ESI calculated for C$_{16}$H$_{20}$N$_2$Si [M+H]$^+$, 269.10, found 269.10.

Step 5: 1-cyclopropyl-5-ethynyl-2-methyl-1,3-benzodiazole

To a stirred solution of 1-cyclopropyl-2-methyl-5-[2-(trimethylsilyl)ethynyl]-1,3-benzodiazole (0.50 g, 1.86 mmol) in THF (5.00 mL) was added TBAF (2.79 mL, 2.79 mmol) at 0° C. The reaction mixture was stirred for 16 h at room temperature. The resulting mixture was quenched by the addition of Water (50 mL) at room temperature. The resulting mixture was extracted with EtOAc (3×50 mL). The combined organic layers were washed with brine (3×50 mL), dried over anhydrous Na$_2$SO$_4$ and filtered. The filtrate was concentrated under reduced pressure. The residue was purified by silica gel column chromatography, eluted with PE/EtOAc (1:4). The fractions contained desired product were combined and concentrated to afford 1-cyclopropyl-5-ethynyl-2-methyl-1,3-benzodiazole (0.28 g, 76%) as a yellow solid. MS ESI calculated for C$_{13}$H$_{12}$N$_2$ [M+H]$^+$, 197.05, found 197.05.

Step 6: 3-[2-(1-cyclopropyl-2-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide To a stirred mixture of 3-bromo-1-[(3S,5R)-5-(methoxymethyl)-1-(prop-2-enoyl)pyrrolidin-3-yl]-5-(methylamino)pyrazole-4-carboxamide (0.17 g, 0.44 mmol) and 1-cyclopropyl-5-ethynyl-2-methyl-1,3-benzodiazole (0.13 g, 0.66 mmol) in DMF (2.00 mL) were added CuI (16.76 mg, 0.09 mmol), TEA (0.18 mL, 1.81 mmol) and Pd(PPh$_3$)$_2$Cl$_2$ (30.89 mg, 0.04 mmol) at room temperature. The reaction mixture was degassed with argon for three times and stirred for 16 h at 90° C. The mixture was allowed to cool down to room temperature. The residue was purified by reverse flash chromatography with the following conditions: column, C18 silica gel; mobile phase, ACN in water (0.1% NH$_4$HCO$_3$), 10% to 50% gradient in 20 min; detector, UV 254 nm to give crude product. Then the crude product was further purified by Prep-HPLC with the following conditions: Column: XBridge Prep C18 OBD Column, 19×150 mm 5 um; Mobile Phase A: Water (10 mM $NH_4HCO_3$), Mobile Phase B: ACN; Flow rate: 20 mL/min; Gradient: 40 B to 80 B in 4.3 min; 210/254 nm; RT1:4.02. The fractions contained desired product were combined and concentrated to afford 3-[2-(1-cyclopropyl-2-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (72.5 mg, 32%) as an off-white solid. MS ESI calculated for $C_{27}H_{31}N_7O_3$ [M+H]$^+$, 501.15, found 502.1; $^1$H NMR (400 MHz, DMSO-$d_6$) δ 7.76 (s, 1H), 7.61 (d, J=8.4 Hz, 1H), 7.44-7.35 (m, 2H), 6.91-6.58 (m, 2H), 6.21-6.18 (m, 1H), 5.69 (dd, J=10.3, 2.7 Hz, 1H), 5.29-5.18 (m, 1H), 4.56-4.36 (m, 1H), 4.10-4.01 (m, 1H), 3.91-3.83 (m, 1H), 3.61-3.58 (m, 1H), 3.51-3.43 (m, 2H), 3.12-3.02 (m, 3H), 2.94 (s, 3H), 2.62 (s, 3H), 2.48-2.43 (m, 1H), 2.36-2.27 (s, 2H), 1.25-1.14 (m, 2H), 1.13-0.97 (m, 2H).

Example 13: 1-((3S,5R)-1-acryloyl-5-(methoxymethyl)pyrrolidin-3-yl)-3-((1-cyclopropyl-1H-benzo[d]imidazol-5-yl)ethynyl)-5-(methylamino)-1H-pyrazole-4-carboxamide

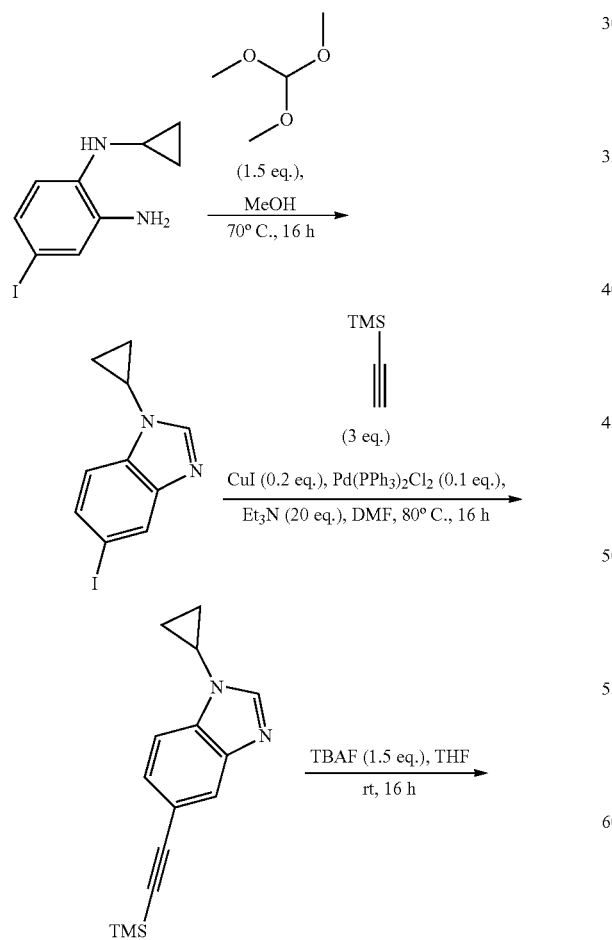

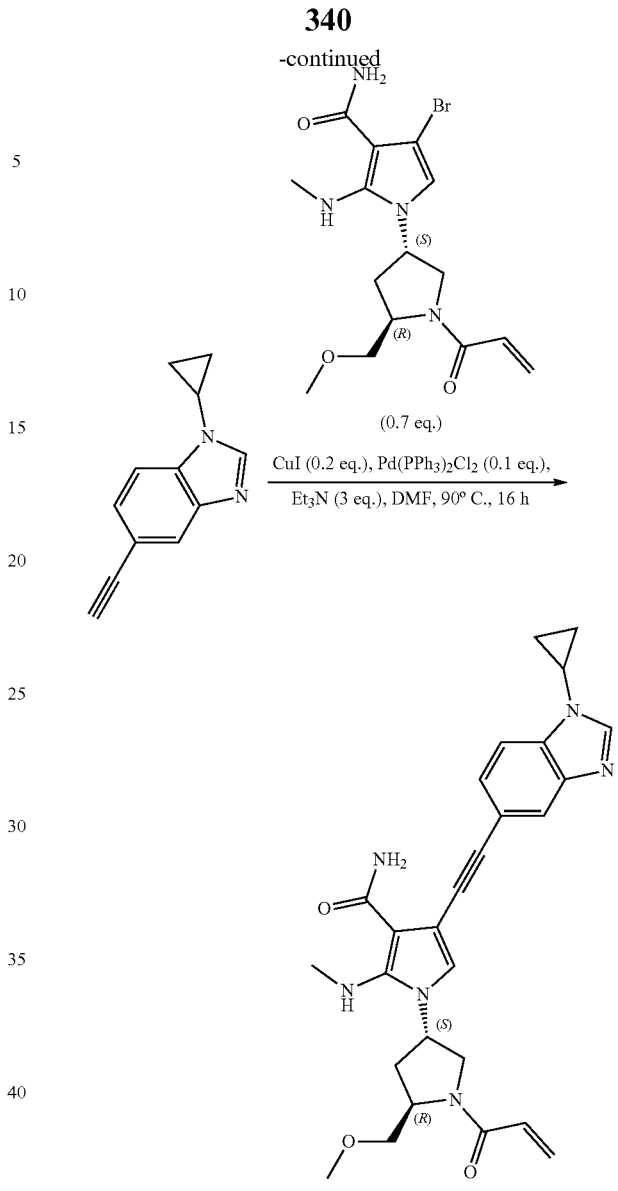

Step 1: 1-cyclopropyl-5-iodo-1,3-benzodiazole

To a stirred mixture of $N^1$-cyclopropyl-4-iodobenzene-1,2-diamine (2.50 g, 9.12 mmol) in methanol (30.00 mL) was added trimethyl orthoformate (1.45 g, 13.68 mmol) at room temperature. The reaction mixture was stirred for 16 h at 70° C. The mixture was allowed to cool down to room temperature. The resulting mixture was concentrated under reduced pressure. The residue was purified by silica gel column chromatography, eluted with PE/(EtOAc/EtOH) (3:1)) (1:1). The fractions contained desired product were combined and concentrated to afford 1-cyclopropyl-5-iodo-1,3-benzodiazole (1.2 g, 46%) as a yellow solid. MS ESI calculated for $C_{10}H_9IN_2$ [M+H]$^+$, 284.95, found 284.95.

Step 2: 1-cyclopropyl-5-[2-(trimethylsilyl)ethynyl]-1,3-benzodiazole

To a stirred mixture of 1-cyclopropyl-5-iodo-1,3-benzodiazole (0.70 g, 2.46 mmol) and CuI (93.85 mg, 0.49 mmol) in DMF (7.00 mL) were added Pd(PPh3)2Cl2 (0.17 g, 0.25 mmol), trimethylsilylacetylene (0.10 g, 1.06 mmol) and TEA (6.85 mL, 67.69 mmol) at room temperature. The reaction mixture was degassed with argon for three times and stirred for 16 h at 80° C. The reaction was quenched by the addition of Water (50 mL) at room temperature, extracted with EtOAc (3×50 mL). The combined organic layers were washed with brine (150 mL), dried over anhydrous $Na_2SO_4$ and filtered. The filtrate was concentrated under reduced pressure. The residue was purified by silica gel column chromatography, eluted with PE/(EtOAc/EtOH (3:1)) (1:1). The fractions contained desired product were combined and concentrated to afford 1-cyclopropyl-5-[2-(trimethylsilyl)ethynyl]-1,3-benzodiazole (0.58 g, 92%) as a brown oil. MS ESI calculated for $C_{15}H_{18}N_2Si$ $[M+H]^+$, 255.15, found 255.15.

Step 3: 1-cyclopropyl-5-ethynyl-1,3-benzodiazole

To a stirred solution of 1-cyclopropyl-5-[2-(trimethylsilyl)ethynyl]-1,3-benzodiazole (0.60 g, 2.36 mmol) in THF (6.00 mL) was added TBAF (3.54 mL, 3.54 mmol) at 0° C. The reaction mixture was stirred for 16 h at room temperature. The resulting mixture was quenched by the addition of Water (70 mL) at room temperature, extracted with EtOAc (3×70 mL). The combined organic layers were washed with brine (150 mL), dried over anhydrous $Na_2SO_4$ and filtered. The filtrate was concentrated under reduced pressure. The residue was purified by silica gel column chromatography, eluted with PE/EtOAc (1:4). The fractions contained desired product were combined and concentrated to afford 1-cyclopropyl-5-ethynyl-1,3-benzodiazole (0.26 g, 60%) as a yellow oil. MS ESI calculated for $C_{10}H_{12}N_2$ $[M+H]^+$, 183.05, found 183.05.

Step 4: 3-[2-(1-cyclopropyl-1,3-benzodiazol-5-yl) ethynyl]-1-[(3S,5R)-5-(methoxymethyl)-1-(prop-2-enoyl)pyrrolidin-3-yl]-5-(methylamino)pyrazole-4-carboxamide To a stirred mixture of 3-bromo-1-[(3S,5R)-5-(methoxymethyl)-1-(prop-2-enoyl)pyrrolidin-3-yl]-5-(methylamino)pyrazole-4-carboxamide (0.17 g, 0.44 mmol) and 1-cyclopropyl-5-ethynyl-1,3-benzodiazole (0.12 g, 0.66 mmol) in DMF (2.00 mL) were added CuI (16.76 mg, 0.09 mmol), TEA (0.18 mL, 1.81 mmol) and $Pd(PPh_3)_2Cl_2$ (30.89 mg, 0.04 mmol) at room temperature. The reaction mixture was degassed with argon for three times and stirred for 16 h at 90° C. The resulting mixture was allowed to cool down to room temperature. The residue was purified by reverse flash chromatography with the following conditions: column, C18 silica gel; mobile phase, ACN in water (0.1% $NH_4HCO_3$), 10% to 50% gradient in 20 min; detector, UV 254 nm. The fractions contained desired product were combined and concentrated. The residue was purified by reverse flash chromatography with the following conditions: Column: XBridge Prep C18 OBD Column, 19×150 mm 5 um; Mobile Phase A: Water (10 mmol/L $NH_4HCO_3$), Mobile Phase B: ACN; Flow rate: 20 mL/min; Gradient: 40 B to 80 B in 4.3 min; 210/254 nm; RT1: 4.02. The fractions contained desired product were combined and concentrated to afford 3-[2-(1-cyclopropyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (74.2 mg, 34%) as an off-white solid. MS ESI calculated for $C_{26}H_{29}N_7O_3$ $[M+H]^+$, 488.10, found 488.10. H-NMR (400 MHz, DMSO-$d_6$) δ 8.36 (s, 1H), 7.90 (s, 1H), 7.70 (d, J=8.3 Hz, 1H), 7.49 (d, J=8.7 Hz, 1H), 7.37 (s, 1H), 6.85-6.52 (m, 2H), 6.17 (dd, J=16.6, 2.6 Hz, 1H), 5.69 (dd, J=10.2, 2.6 Hz, 1H), 5.33-5.18 (m, 1H), 4.42-4.38 (m, 1H), 4.07-3.98 (m, 1H), 3.92-3.83 (m, 1H), 3.65-3.51 (m, 2H), 3.49-3.42-3.38 (m, 1H), 3.31-3.30 (m, 3H), 2.94 (t, J=5.1 Hz, 3H), 2.53-2.48 (m, 2H), 2.35-2.31 (m, 1H), 1.16-1.01 (m, 4H).

Example 14: 1-((3S,5R)-1-acryloyl-5-(methoxymethyl)pyrrolidin-3-yl)-3-((1-ethyl-1H-indazol-5-yl) ethynyl)-5-(methylamino)-1H-pyrazole-4-carboxamide To a stirred mixture of 3-bromo-1-[(3S,5R)-5-(methoxymethyl)-1-(prop-2-enoyl)pyrrolidin-3-yl]-5-(methylamino)pyrazole-4-carboxamide (0.18 g, 0.47 mmol), 1-ethyl-5-ethynylindazole (0.12 g, 0.70 mmol), CuI (17.75 mg, 0.10 mmol) and $Pd(PPh_3)_2Cl_2$ (32.71 mg, 0.05 mmol) in DMF (3.00 mL) was added TEA (0.19 mL, 1.92 mmol). The reaction mixture was degassed with nitrogen for three times and stirred for 16 h at 90° C. The resulting mixture was purified by reverse flash chromatography with the following conditions: column, C18 silica gel; mobile phase, $NH_4HCO_3$ in water, 25% to 40% gradient in 25 min; detector, UV 254 nm. The crude product was purified by Prep-HPLC with the following conditions Column: XBridge Prep C18 OBD Column, 19×150 mm 5 um; Mobile Phase A: Water (10 mmol/L NH$_4$HCO$_3$), Mobile Phase B: ACN; Flow rate: 20 mL/min; Gradient: 40 B to 60 B in 4.3 min; 210/254 nm; RT1:4.12. The fractions contained desired product were combined and concentrated to afford 3-[2-(1-ethylindazol-5-yl)ethynyl]-1-[(3S,5R)-5-(methoxymethyl)-1-(prop-2-enoyl)pyrrolidin-3-yl]-5-(methylamino)pyrazole-4-carboxamide (57.5 mg, 25%) as an off-white solid. MS ESI calculated for C$_{25}$H$_{29}$N$_7$O$_3$ [M+H]$^+$, 476.23, found 476.25. H-NMR (400 MHz, DMSO-d$_6$): δ 8.15-8.10 (m, 2H), 7.78 (d, J=8.6 Hz, 1H), 7.59-7.50 (m, 1H), 7.36 (s, 1H), 6.90-6.49 (m, 3H), 6.18 (d, J=16.6 Hz, 1H), 5.71 (d, J=10.4 Hz, 1H), 5.26 (s, 1H), 4.52-4.45 (m, 3H), 4.09-3.68 (m, 2H), 3.65-3.37 (m, 2H), 3.33-3.31 (m, 3H), 2.96 (t, J=4.5 Hz, 3H), 2.55-2.53 (m, 1H), 2.34-2.32 (m, 1H), 1.45-1.41 (m, 3H).

Example 15: 1-((3S,5R)-1-acryloyl-5-(methoxymethyl)pyrrolidin-3-yl)-3-((2-ethyl-2H-indazol-5-yl)ethynyl)-5-(methylamino)-1H-pyrazole-4-carboxamide

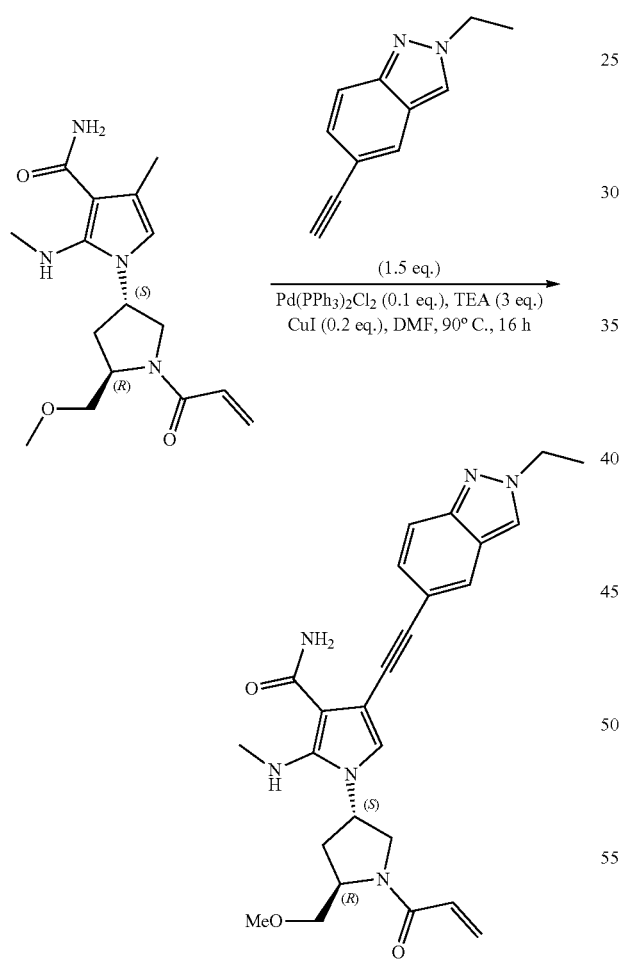

To a stirred mixture of 3-bromo-1-[(3S,5R)-5-(methoxymethyl)-1-(prop-2-enoyl)pyrrolidin-3-yl]-5-(methylamino)pyrazole-4-carboxamide (0.25 g, 0.65 mmol), 2-ethyl-5-ethynylindazole (0.16 g, 0.97 mmol), CuI (24.65 mg, 0.13 mmol) and Pd(PPh$_3$)$_2$Cl$_2$ (45.43 mg, 0.06 mmol) in DMF (2.50 mL) was added TEA (0.27 mL, 2.67 mmol). The reaction mixture was degassed with nitrogen for three times and stirred for 16 h at 90° C. The resulting mixture was diluted with water (40 mL) and extracted with EA (3×50 mL). The combined organic layers were washed with brine (2×100 mL), dried over anhydrous Na$_2$SO$_4$, filtered and concentrated under reduced pressure. The residue was purified by reverse flash chromatography with the following conditions: column, C18 silica gel; mobile phase, NH$_4$HCO$_3$ in water, 25% to 40% gradient in 25 min; detector, UV 254 nm. The fractions contained desired product were combined and concentrated. The residue was purified by Prep-HPLC with the following conditions Column: Xselect CSH OBD Column 30*150 mm 5 um, n; Mobile Phase A: Water (10 mmol/L NH$_4$HCO$_3$), Mobile Phase B: ACN; Flow rate: 30 mL/min; Gradient: 20 B to 60 B in 8 min; 210/254 nm; RT1: 7.78. The fractions contained desired product were combined and concentrated to afford 3-[2-(2-ethylindazol-5-yl)ethynyl]-1-[(3S,5R)-5-(methoxymethyl)-1-(prop-2-enoyl)pyrrolidin-3-yl]-5-(methylamino)pyrazole-4-carboxamide (71.4 mg, 23%) as an off-white solid. MS ESI calculated for C$_{25}$H$_{29}$N$_7$O$_3$ [M+H]$^+$, 476.23, found 476.20. H-NMR (400 MHz, DMSO-d$_6$): 8.50 (s, 1H), 8.03 (s, 1H), 7.70-7.62 (m, 1H), 7.32 (dd, J=8.9, 1.6 Hz, 2H), 6.88-6.47 (m, 3H), 6.19-6.17 (m, 1H), 5.71-5.68 (m, 1H), 5.27-5.23 (m, 1H), 4.52-4.48 (m, 3H), 4.06-3.41 (m, 4H), 3.30 (d, J=5.4 Hz, 3H), 2.95 (t, J=5.3 Hz, 3H), 2.64-2.61 (m, 1H), 2.35-2.31 (m, 1H), 1.55-1.52 (m, 3H).

Example 16: 1-((3S,5R)-1-acryloyl-5-(methoxymethyl)pyrrolidin-3-yl)-3-((1-ethyl-4,6-difluoro-2-methyl-1H-benzo[d]imidazol-5-yl)ethynyl)-5-(methylamino)-1H-pyrazole-4-carboxamide

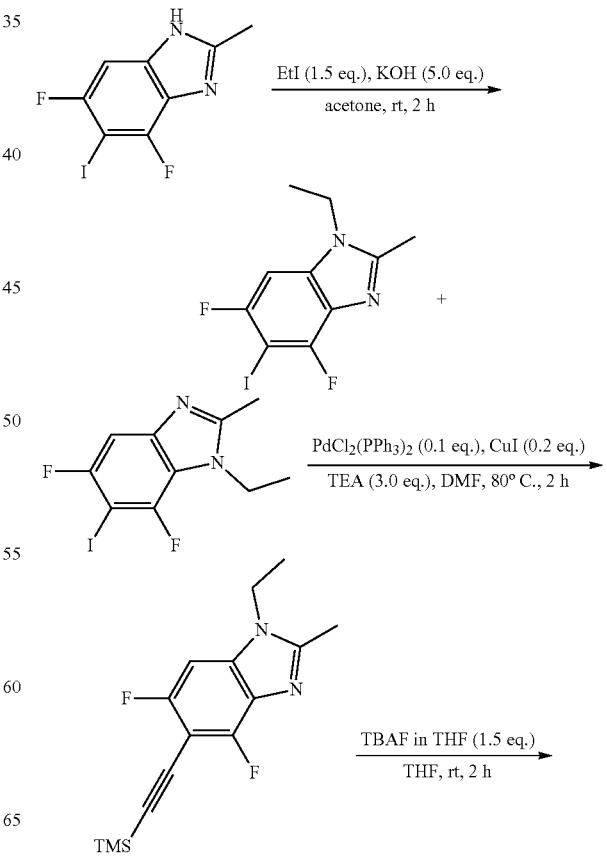

345

-continued

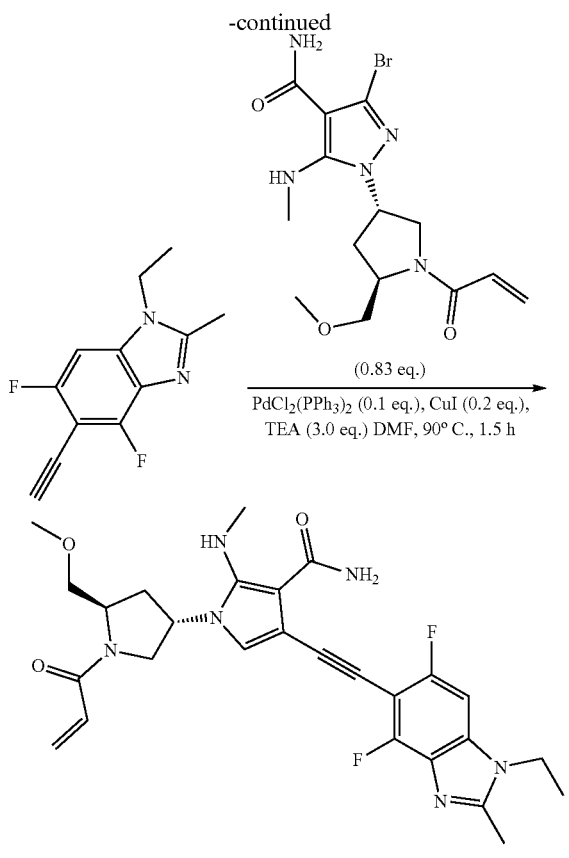

(0.83 eq.)
PdCl$_2$(PPh$_3$)$_2$ (0.1 eq.), CuI (0.2 eq.),
TEA (3.0 eq.) DMF, 90° C., 1.5 h

Step 1: 1-ethyl-4,6-difluoro-5-iodo-2-methyl-1,3-benzodiazole

To a stirred solution of 4,6-difluoro-5-iodo-2-methyl-1H-1, 3-benzodiazole (3.00 g, 10.20 mmol) and KOH (2.86 g, 51.01 mmol) in THF (45.00 mL) was added ethyl iodide (2.39 g, 15.30 mmol) dropwise at room temperature. The resulting mixture was stirred for 2 h at room temperature. The resulting mixture was extracted with EtOAc (3×500 mL). The combined organic layers were washed with brine (3×50 mL), dried over anhydrous Na$_2$SO$_4$ and filtered. The filtrate was concentrated under reduced pressure. The residue was purified by silica gel column chromatography, eluted with CH$_2$Cl$_2$/EtOAc (50-89%). The fractions contained desired product were combined and concentrated to afford 1-ethyl-4,6-difluoro-5-iodo-2-methyl-1,3-benzodiazole (1.20 g, 36%) as a yellow solid and 1-ethyl-5,7-difluoro-6-iodo-2-methyl-1,3-benzodiazole (1.00 g, 30%) as a yellow solid. MS ESI calculated for C$_{10}$H$_9$F$_2$IN$_2$ [M+H]$^+$, 322.97, found 323.09.

Step 2: 1-ethyl-4,6-difluoro-2-methyl-5-[2-(trimethylsilyl)ethynyl]-1,3-benzodiazole Into a 50 mL vial were added 1-ethyl-4,6-difluoro-5-iodo-2-methyl-1,3-benzodiazole (1.23 g, 3.82 mmol), trimethylsilylacetylene (1.13 g, 11.46 mmol), Pd(PPh$_3$)$_2$Cl$_2$ (0.27 g, 0.38 mmol), CuI (0.15 g, 0.76 mmol) and TEA (1.16 g, 11.46 mmol) in DMF (10.00 mL) at room temperature. The reaction mixture was degassed with argon for three times and stirred for 2 h at 80° C. The resulting mixture was allowed to cool down to room temperature. The resulting mixture was concentrated under reduced pressure. The residue was purified by silica gel column chromatography, eluted with PE/EtOAc (0-75%). The fractions contained desired product were combined and concentrated to afford 1-ethyl-4,6-difluoro-2-methyl-5-[2-(trimethylsilyl)ethynyl]-1,3-benzodiazole (1.1 g, 98%) as a yellow solid. MS ESI calculated for C$_{15}$H$_{18}$F$_2$N$_2$Si [M+H]$^+$, 293.12, found 293.40.

Step 3: 1-ethyl-5-ethynyl-4,6-difluoro-2-methyl-1,3-benzodiazole

To a stirred solution of 1-ethyl-4,6-difluoro-2-methyl-5-[2-(trimethylsilyl)ethynyl]-1,3-benzodiazole (1.20 g, 4.10 mmol) in THF (10.00 mL) was added TBAF (1.61 g, 6.16 mmol) in portions at room temperature. The reaction mixture was stirred for 2 h at room temperature. The resulting mixture was concentrated under reduced pressure. The residue was diluted with water (150 mL), extracted with EtOAc (3×150 mL). The combined organic layers were washed with water (3×100 mL), dried over anhydrous Na$_2$SO$_4$ and filtered. The filtrate was concentrated under reduced pressure. The residue was purified by silica gel column chromatography, eluted with PE/EtOAc (20-60%). The fractions contained desired product were combined and concentrated to afford 1-ethyl-5-ethynyl-4, 6-difluoro-2-methyl-1,3-benzodiazole (0.67 g, 74%) as a yellow solid. MS ESI calculated for C$_{15}$H$_{18}$F$_2$N$_2$Si [M+H]$^+$, 221.08, found 221.22.

Step 4: 3-[2-(1-ethyl-4,6-difluoro-2-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide Into a 25 mL vial were added 3-bromo-1-[(3S,5R)-5-(methoxymethyl)-1-(prop-2-enoyl)pyrrolidin-3-yl]-5-(methylamino)pyrazole-4-carboxamide (0.20 g, 0.52 mmol), 1-ethyl-5-ethynyl-4,6-difluoro-2-methyl-1,3-benzodiazole (0.14 g, 0.62 mmol), Pd(PPh$_3$)$_2$Cl$_2$ (36.34 mg, 0.05 mmol) and CuI (19.72 mg, 0.10 mmol) in DMF (4.00 mL) was added TEA (0.16 g, 1.55 mmol) at room temperature. The reaction mixture was degassed with argon for three times and stirred for 1.5 h at 90° C. The mixture was allowed to cool down to room temperature. The resulting mixture was extracted with EtOAc (3×100 mL). The combined organic layers were washed with water (3×50 mL), dried over anhydrous Na$_2$SO$_4$ and filtered. The filtrate was concentrated under reduced pressure. The residue was purified by silica gel column chromatography, eluted with CH$_2$Cl$_2$/MeOH (0-6%). The fractions contained desired product were combined and concentrated. The crude product (160 mg) was purified by Prep-HPLC with the following conditions Column: XBridge Prep C18 OBD Column, 19×150 mm 5 um; Mobile Phase A: Water (10 mmol/L NH$_4$HCO$_3$), Mobile Phase B: ACN; Flow rate: 20 mL/min; Gradient: 23 B to 43 B in 4.3 min; 210/254 nm; RT1: 4.02. The fractions contained desired product were combined and concentrated to afford 3-[2-(1-ethyl-4,6-difluoro-2-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (85.7 mg, 31%) as a white solid. MS ESI calculated for C$_{26}$H$_{29}$F$_2$N$_7$O$_3$ [M+H]$^+$, 512.21, found 526.56. 1H-NMR (400 MHz, DMSO-d$_6$) δ 7.60 (t, J=11.4 Hz, 2H), 6.83-6.50 (m, 3H), 6.19-6.16 (m, 1H), 5.71-5.68 (m, 1H), 5.29-5.25 (m, 1H), 4.46 (d, J=54.4 Hz, 1H), 4.24 (q, J=7.2 Hz, 2H), 4.07-3.71 (m, 2H), 3.66-3.41 (m, 2H), 3.30

(d, J=5.6 Hz, 3H), 2.96 (t, J=5.5 Hz, 3H), 2.70-2.60 (m, 1H), 2.57 (s, 3H), 2.37-2.25 (m, 1H), 1.29 (t, J=7.2 Hz, 3H).

Example 17: 1-((3S,5R)-1-acryloyl-5-(methoxymethyl)pyrrolidin-3-yl)-3-((4,6-difluoro-2-methyl-1H-benzo[d]imidazol-5-yl)ethynyl)-5-(methylamino)-1H-pyrazole-4-carboxamide

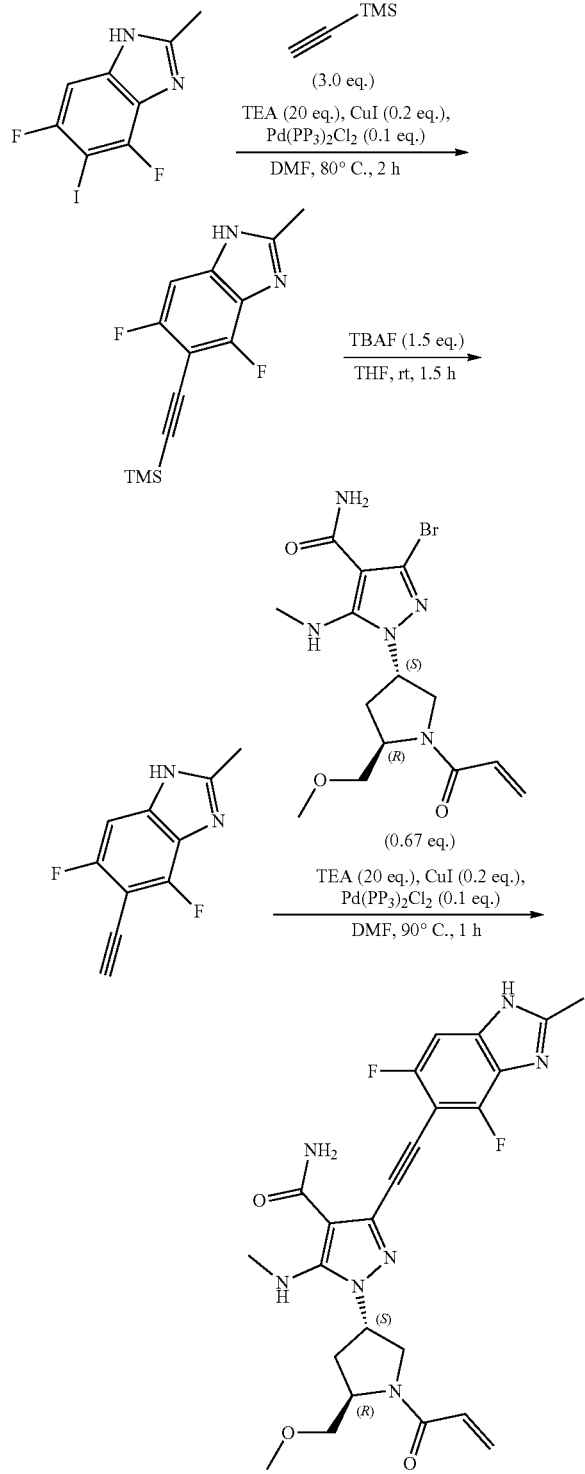

Step 1: 4,6-difluoro-2-methyl-5-[2-(trimethylsilyl)ethynyl]-1H-1,3-benzodiazole

To a stirred mixture of 4,6-difluoro-5-iodo-2-methyl-1H-1,3-benzodiazole (0.60 g, 2.04 mmol), trimethylsilylacetylene (0.60 g, 6.12 mmol), Pd(PPh$_3$)$_2$Cl$_2$ (0.14 g, 0.20 mmol) and CuI (77.72 mg, 0.41 mmol) in DMF (10.00 mL) was added TEA (4.13 g, 40.81 mmol). The reaction mixture was degassed with nitrogen for three times and stirred for 2 h at 80° C. The resulting mixture was diluted with water (50 mL). The resulting mixture was extracted with EtOAc (3×50 mL). The combined organic layers was dried over anhydrous Na$_2$SO$_4$ and filtered. The filtrate was concentrated under reduced pressure. The residue was purified by silica gel column chromatography, eluted with PE/EtOAc (1:4). The fractions contained desired product were combined and concentrated to afford 4,6-difluoro-2-methyl-5-[2-(trimethylsilyl)ethynyl]-1H-1,3-benzodiazole (0.40 g, 74%) as a brown semi-solid. MS ESI calculated for C$_{13}$H$_{14}$F$_2$N$_2$Si [M+H]$^+$, 265.09, found 265.10.

Step 2: 5-ethynyl-4,6-difluoro-2-methyl-1H-1,3-benzodiazole

Into a 25 mL round-bottom flask were added 4,6-difluoro-2-methyl-5-[2-(trimethylsilyl)ethynyl]-1H-1,3-benzodiazole (0.40 g, 1.51 mmol), TBAF (2.27 mL, 2.27 mmol) and THF (4.00 mL) at 0° C. The reaction mixture was stirred for 1.5 h at room temperature. The resulting mixture was concentrated under reduced pressure. The residue was purified by silica gel column chromatography, eluted with CH$_2$Cl$_2$/MeOH (10:1). The fractions contained desired product were combined and concentrated to afford 5-ethynyl-4,6-difluoro-2-methyl-1H-1,3-benzodiazole (0.22 g, 75%) as a light yellow solid. MS ESI calculated for C$_{10}$H$_6$F$_2$N$_2$ [M+H]$^+$, 193.05, found 193.15.

Step 3: 3-[2-(4,6-difluoro-2-methyl-1H-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide To a mixture of 3-bromo-1-[(3S,5R)-5-(methoxymethyl)-1-(prop-2-enoyl)pyrrolidin-3-yl]-5-(methylamino)pyrazole-4-carboxamide (0.20 g, 0.52 mmol) and 5-ethynyl-4,6-difluoro-2-methyl-1H-1,3-benzodiazole (0.15 g, 0.78 mmol) in DMF (4.00 mL) were added CuI (19.72 mg, 0.10 mmol), Pd(PPh$_3$)$_2$Cl$_2$ (36.34 mg, 0.05 mmol) and TEA (1.05 g, 10.34 mmol). The reaction mixture was degassed with argon for three times and stirred for 1 h at 90° C. The resulting mixture was filtered, the filter cake was washed with MeOH (3×10 mL). The filtrate was concentrated under reduced pressure. The residue was purified by reverse flash chromatography with the following conditions: column, C18 silica gel; mobile phase, ACN in water (10 mM NH$_4$HCO$_3$), 5% to 35% gradient in 30 min; detector, UV 220 nm. The crude product (150 mg) was purified by Prep-HPLC with the following conditions Column: SunFire Prep C18 OBD Column, 19×150 mm 5 um 10 nm; Mobile Phase A: Water (0.1% FA), Mobile Phase B: ACN; Flow rate: 20 mL/min; Gradient: 40 B to 80 B in 4.3 min; 210/254 nm; RT1:4.03. The fractions contained desired product were combined and concentrated to afford 3-[2-(4,6-difluoro-2-methyl-1H-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (43.3 mg, 16%) as a white solid. MS ESI calculated for C$_{24}$H$_{25}$F$_2$N$_7$O$_3$ [M+H]$^+$, 498.20, found 498.20. H-NMR (400 MHz, DMSO-d$_6$): δ 7.59 (s, 1H), 7.37 (d, J=9.1 Hz, 1H), 6.81-6.67 (m, 2H), 6.63-6.60 (m, 1H), 6.18-6.16 (m, 1H), 5.69-5.65 (m, 1H), 5.35-5.21 (m, 1H), 4.53-4.51 (m, 1H), 4.41-4.39 (m, 1H), 4.05-4.01 (m, 1H), 3.90-3.87 (m, 1H), 3.77-3.75 (m, 1H), 3.63-3.59 (m, 1H), 3.49-3.45 (m, 3H), 3.30 (d, J=5.6 Hz, 3H), 2.96 (t, J=5.5 Hz, 3H), 2.69-2.65 (m, 1H), 2.36-2.23 (m, 1H).

Example 18: 1-((3S,5R)-1-acryloyl-5-(methoxymethyl)pyrrolidin-3-yl)-3-((4,6-difluoro-1,2-dimethyl-1H-benzo[d]imidazol-5-yl)ethynyl)-5-(methylamino)-1H-pyrazole-4-carboxamide

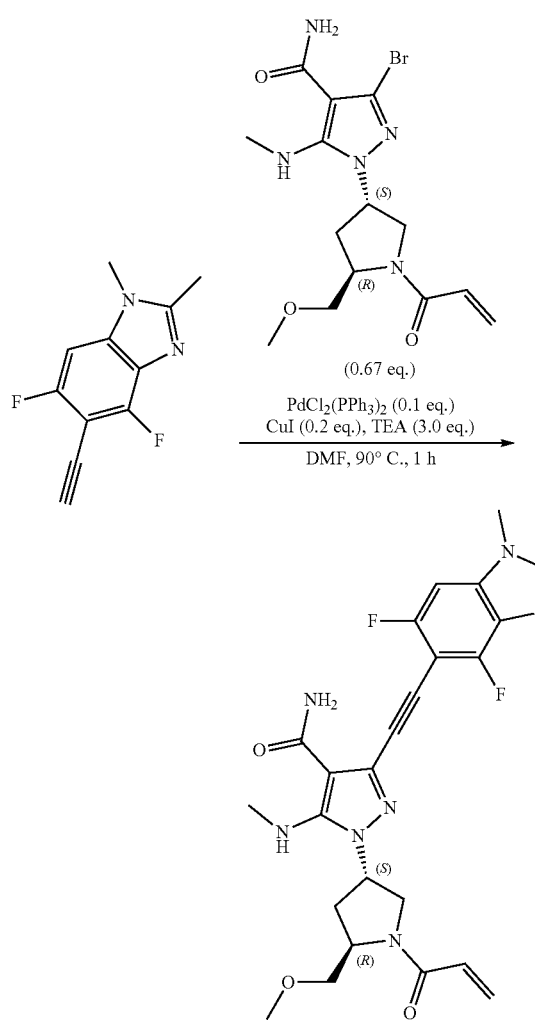

To a stirred mixture of 3-bromo-1-[(3S,5R)-5-(methoxymethyl)-1-(prop-2-enoyl)pyrrolidin-3-yl]-5-(methylamino)pyrazole-4-carboxamide (0.30 g, 0.78 mmol) in DMF (5.00 mL) were added 5-ethynyl-4,6-difluoro-1,2-dimethyl-1,3-benzodiazole (0.19 g, 0.93 mmol), Pd(PPh$_3$)$_2$Cl$_2$ (54.52 mg, 0.08 mmol), CuI (29.58 mg, 0.16 mmol) and TEA (0.24 g, 2.33 mmol) at room temperature. The reaction mixture was degassed with argon for three times and stirred for 1 h at 90° C. The mixture was allowed to cool down to room temperature. The resulting mixture was filtered; the filter cake was washed with DMF (3×3 mL). The residue was purified by reverse phase flash chromatography with the following conditions: Column: Spherical C18, 20-40 um, 180 g; Mobile Phase A: Water (NH$_4$HCO$_3$ 0.1 mM); Mobile Phase B: ACN; Flow rate: 90 mL/min; Gradient: 5%-5% B, 10 min, 25% B-60% B gradient in 20 min; Detector: 254 nm. The fractions containing the desired product were collected at 30% B and concentrated under reduced pressure to afford 3-[2-(4, 6-difluoro-1, 2-dimethyl-1, 3-benzodiazol-5-yl) ethynyl]-1-[(3S,5R)-5-(methoxymethyl)-1-(prop-2-enoyl) pyrrolidin-3-yl]-5-(methylamino) pyrazole-4-carboxamide as a white solid (83.7 mg, 21%) as a white solid. MS ESI calculated for C$_{25}$H$_{27}$F$_2$N$_7$O$_3$ [M+H]$^+$, 512.21, found 512.53. 1H-NMR (300 MHz, DMSO-d$_6$) δ 7.58 (d, J=9.3 Hz, 2H), 6.88-6.51 (m, 3H), 6.23-6.11 (m, 1H), 5.73-5.69 (m, 1H), 5.29-5.26 (m, 1H), 4.48 (d, J=41.7 Hz, 1H), 4.10-3.83 (m, 2H), 3.76 (s, 3H), 3.68-3.43 (m, 2H), 3.35-3.32 (m, 3H), 3.00-2.95 (m, 3H), 2.69-2.63 (m, 1H), 2.56 (s, 3H), 2.39-2.24 (m, 1H).

Example 19: 1-((3S,5R)-1-acryloyl-5-(methoxymethyl)pyrrolidin-3-yl)-3-((4,6-difluoro-1-methyl-1H-indazol-5-yl)ethynyl)-5-(methylamino)-1H-pyrazole-4-carboxamide

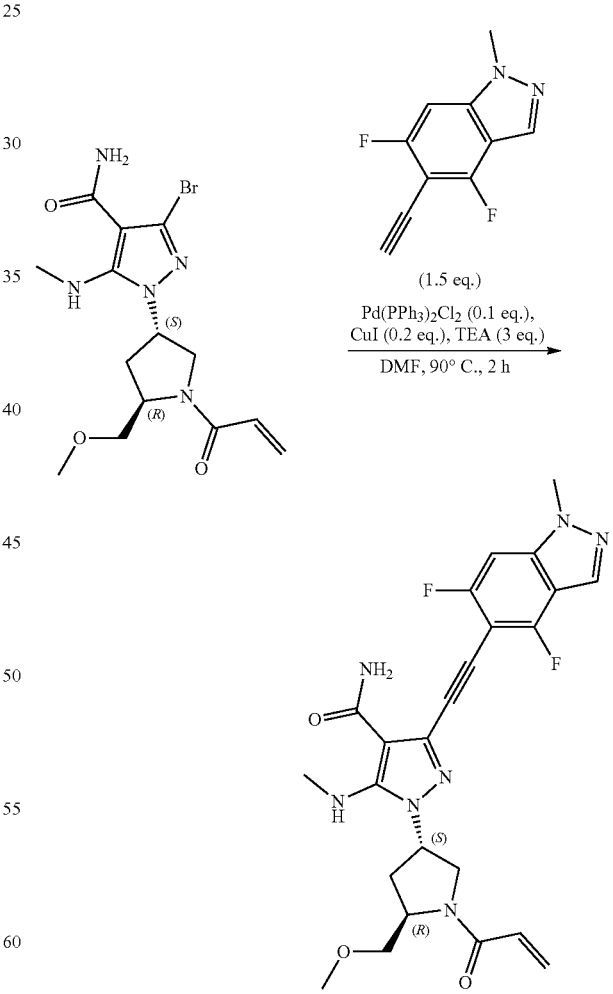

To a stirred mixture of 3-bromo-1-[(3S,5R)-5-(methoxymethyl)-1-(prop-2-enoyl)pyrrolidin-3-yl]-5-(methylamino)pyrazole-4-carboxamide (0.15 g, 0.39 mmol), 5-ethynyl-4,6-difluoro-1-methylindazole (0.11 g, 0.58 mmol), Pd(PPh3)2Cl2 (27.26 mg, 0.04 mmol) and CuI (14.79 mg, 0.08 mmol) in DMF (2.00 mL) was added TEA (0.12 g, 1.17 mmol). The reaction mixture was degassed with argon for three times and stirred for 2 h at 90° C. The resulting mixture was concentrated under reduced pressure. The residue was purified by reverse flash chromatography with the following conditions: column, C18 silica gel; mobile phase ACN, NH4HCO3 0.01 mmol in water, 25% to 40% gradient in 20 min; detector, UV 254 nm. The crude product was purified by Prep-HPLC with the following conditions Column: Atlantis Prep T3 OBD Column, 19*250 mm 10 u; Mobile Phase A: Water (0.1% FA), Mobile Phase B: ACN; Flow rate: 20 mL/min; Gradient: 25 B to 50 B in 6 min; 210/254 nm; RT1:5.56. The fractions contained desired product were combined and concentrated to afford 3-[2-(4,6-difluoro-1-methylindazol-5-yl)ethynyl]-1-[(3S,5R)-5-(methoxymethyl)-1-(prop-2-enoyl)pyrrolidin-3-yl]-5-(methylamino)pyrazole-4-carboxamide (27.5 mg, 14%) as a white solid. ESI calculated for $C_{24}H_{25}F_2N_7O_3$ [M+H]$^+$, 498.2; found 498.2. $^1$H NMR (400 MHz, DMSO-d$_6$) δ 8.33 (s, 1H), 7.72 (d, J=9.5 Hz, 1H), 7.57 (s, 1H), 6.91-6.53 (m, 3H), 6.17-5.92 (m, 1H), 5.69-5.45 (m, 1H), 5.41-5.18 (m, 1H), 4.54-4.34 (m, 1H), 4.06 (s, 3H), 3.88-3.65 (m, 1H), 3.63-3.59 (m, 1H), 3.55-3.39 (m, 2H), 3.31 (s, 3H), 2.98-2.94 (m, 3H), 2.62-2.43 (m, 1H), 2.30-1.96 (m, 1H).

Example 20: 1-((3S,5R)-1-acryloyl-5-(methoxymethyl)pyrrolidin-3-yl)-3-((4-fluoro-1,2-dimethyl-1H-benzo[d]imidazol-5-yl)ethynyl)-5-(methylamino)-1H-pyrazole-4-carboxamide

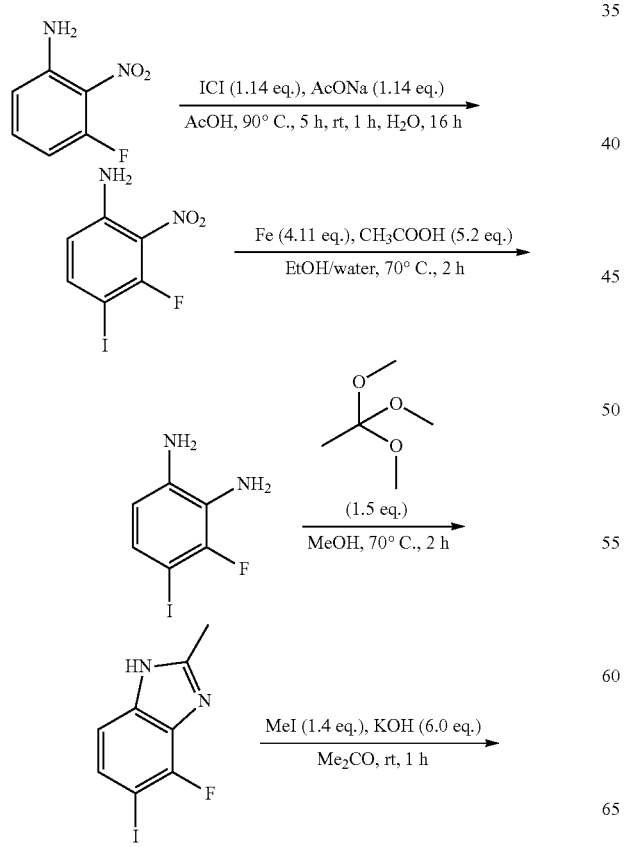

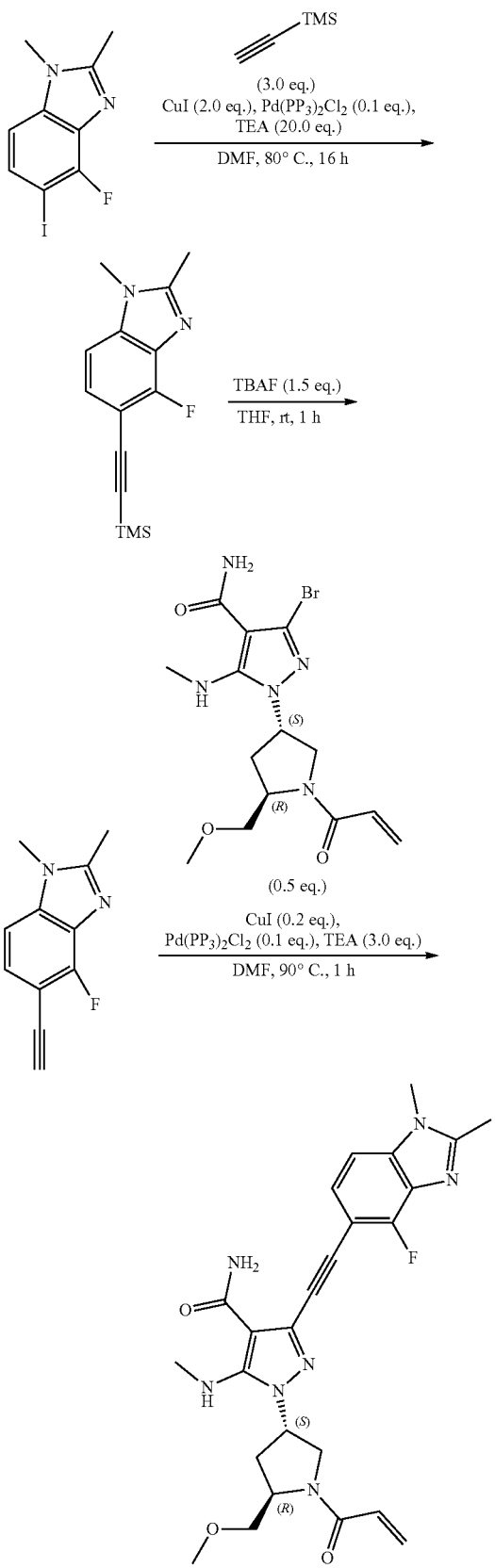

Step 1: 3-fluoro-4-iodo-2-nitroaniline

To a stirred solution of 3-fluoro-2-nitroaniline (14.50 g, 92.88 mmol) and NaOAc (8.69 g, 105.93 mmol) in AcOH (250.00 mL) was added ICl (17.19 g, 105.88 mmol) in AcOH (50.00 mL) dropwise at room temperature under nitrogen atmosphere. The reaction mixture was stirred for additional 5 h at 90° C., then stirred for 1 h at room temperature. To the above mixture was added water (300.00 mL) at room temperature, and was stirred for 16 h. The resulting mixture was filtered, the filter cake was washed with water (3×80 mL). The residue was purified by silica gel column chromatography, eluted with PE/EtOAc (4:1), the fractions contained desired product were combined and concentrated to afford 3-fluoro-4-iodo-2-nitroaniline (13.1 g, 50%) as an orange solid.

Step 2: 3-fluoro-4-iodobenzene-1,2-diamine

A mixture of Fe (10.66 g, 190.92 mmol) and $CH_3COOH$ (13.84 mL, 241.53 mmol) in EtOH (150.00 mL) and water (50.00 mL) was stirred for 0.5 h at 70° C. To the above mixture was added 3-fluoro-4-iodo-2-nitroaniline (13.10 g, 46.45 mmol) in portions at 70° C. The resulting mixture was stirred for additional 2 h at 70° C. The mixture was cooled. The resulting mixture was filtered, the filter cake was washed with EA (2×150 mL). The filtrate was concentrated under reduced pressure. The residue was added water (70 mL) and extracted with EA (3×100 mL). The combined organic layers were washed with Sat. NaCl (2×70 mL), dried over anhydrous $Na_2SO_4$ and filtered. The residue was concentrated to afford 3-fluoro-4-iodobenzene-1,2-diamine (11.2 g, 95.7%) as a brown solid which was used in the next step without further purification.

Step 3: 4-fluoro-5-iodo-2-methyl-1H-benzo[d]imidazole

To a stirred solution of 3-fluoro-4-iodobenzene-1,2-diamine (5.00 g, 19.84 mmol) in MeOH (50.00 mL) was added 1,1,1-trimethoxyethane (3.58 g, 29.79 mmol) dropwise at room temperature under nitrogen atmosphere. The reaction mixture was stirred for 2 h at 70° C. under nitrogen atmosphere. The resulting mixture was concentrated under reduced pressure. The residue was purified by silica gel column chromatography, eluted with PE/EtOAc (1:4), the fractions contained desired product were combined and concentrated to afford 4-fluoro-5-iodo-2-methyl-1H-benzo[d]imidazole (5.15 g, 94%) as a light yellow solid. MS ESI calculated for $C_8H_6FIN_2$ $[M+H]^+$, 276.96, found 276.95.

Step 4: 4-fluoro-5-iodo-1,2-dimethyl-1H-benzo[d]imidazole

To a stirred solution of 4-fluoro-5-iodo-2-methyl-1H-benzo[d]imidazole (2.35 g, 8.51 mmol) and KOH (2.87 g, 51.15 mmol) in acetone (25.00 mL) was added MeI (0.74 mL, 5.23 mmol) dropwise at room temperature under nitrogen atmosphere. The reaction mixture was stirred for 40 min. The resulting mixture was extracted with EtOAc (3×60 mL). The combined organic layers were washed with brine (3×50 mL), dried over anhydrous $Na_2SO_4$ and filtered. The filtrate was concentrated under reduced pressure. The residue was purified by silica gel column chromatography, eluted with $CH_2Cl_2$/MeOH (10:1), the fractions contained desired product were combined and concentrated to afford 4-fluoro-5-iodo-1,2-dimethyl-1H-benzo[d]imidazole (1.13 g, 45%) as an off-white solid. MS ESI calculated for $C_9H_8FIN_2$ $[M+H]^+$, 290.97, found 290.95.

Step 5: 4-fluoro-1,2-dimethyl-5-((trimethylsilyl)ethynyl)-1H-benzo[d]imidazole To a mixture of 4-fluoro-5-iodo-1,2-dimethyl-1H-benzo[d]imidazole (1.13 g, 3.89 mmol), trimethylsilylacetylene (1.15 g, 11.71 mmol), CuI (0.15 g, 0.78 mmol) and $Pd(PPh_3)_2Cl_2$ (0.27 g, 0.39 mmol) in DMF (12.00 mL) was added TEA (10.83 mL, 77.92 mmol). The reaction mixture was degassed with argon for three times and stirred for 16 h at 80° C. The resulting mixture was extracted with EtOAc (3×80 mL). The combined organic layers were washed with water (3×60 mL), dried over anhydrous $Na_2SO_4$ and filtered. The filtrate was concentrated under reduced pressure. The residue was purified by silica gel column chromatography, eluted with PE/EtOAc (1:2), the fractions contained desired product were combined and concentrated to afford 4-fluoro-1,2-dimethyl-5-((trimethylsilyl)ethynyl)-1H-benzo[d]imidazole (0.94 g, 92%) as a light yellow solid. MS ESI calculated for $C_{14}H_{17}FN_2Si$ $[M+H]^+$, 261.11, found 261.15.

Step 6: 5-ethynyl-4-fluoro-1,2-dimethyl-1H-benzo[d]imidazole

To a stirred solution of 4-fluoro-1,2-dimethyl-5-((trimethylsilyl)ethynyl)-1H-benzo[d]imidazole (0.84 g, 3.23 mmol) in THF (10.00 mL) was added TBAF (4.84 mL, 4.84 mmol) dropwise at 0° C. under nitrogen atmosphere. The reaction mixture was stirred for 1 h at room temperature. The resulting mixture was concentrated under reduced pressure. The residue was purified by silica gel column chromatography, eluted with PE/EtOAc (1:2), the fractions contained desired product were combined and concentrated to afford 5-ethynyl-4-fluoro-1,2-dimethyl-1H-benzo[d]imidazole (0.67 g, 99%) as an off-white solid. MS ESI calculated for $C_{11}H_9FN_2$ $[M+H]^+$, 189.07, found 189.20.

Step 7: 1-((3S,5R)-1-acryloyl-5-(methoxymethyl)pyrrolidin-3-yl)-3-((4-fluoro-1,2-dimethyl-1H-benzo[d]imidazol-5-yl)ethynyl)-5-(methylamino)-1H-pyrazole-4-carboxamide To a mixture of 3-bromo-1-[(3S,5R)-5-(methoxymethyl)-1-(prop-2-enoyl)pyrrolidin-3-yl]-5-(methylamino)pyrazole-4-carboxamide (0.2 g, 0.52 mmol), 5-ethynyl-4-fluoro-1,2-dimethyl-1H-benzo[d]imidazole (0.19 g, 1.04 mmol), CuI (19.72 mg, 0.10 mmol) and $Pd(PPh_3)_2Cl_2$ (36.34 mg, 0.05 mmol) in DMF (2.00 mL) was added TEA (0.22 mL, 1.58 mmol). The reaction mixture was degassed with argon for three times and stirred for 1 h at 90° C. The residue was purified by Prep-HPLC with the following conditions: Column: XBridge Prep OBD C18 Column, 19*250 mm, 5 um; Mobile Phase A: Water (10 mmol/L $NH_4HCO_3$), Mobile Phase B: ACN; Flow rate: 20 mL/min; Gradient: 25 B to 60 B in 5.8 min; 210/254 nm; RT1: 5.55, the fractions contained desired product were combined and concentrated to afford 1-((3S,5R)-1-acryloyl-5-(methoxymethyl)pyrrolidin-3-yl)-3-((4-fluoro-1,2-dimethyl-1H-benzo[d]imidazol-5-yl)ethynyl)-5-(methylamino)-1H-pyrazole-4-carboxamide (0.10 g, 39%) as an off-white solid. MS ESI calculated for $C_{25}H_{28}FN_7O_3$ $[M+H]^+$, 494.22, found 494.20. H NMR (400 MHz, DMSO-$d_6$) δ 7.43-7.38 (m, 3H), 6.76-6.56 (m, 3H), 6.19-6.14 (m, 1H), 5.70-5.67 (m, 1H), 5.28-5.26 (m, 1H), 4.53-4.39 (m, 1H), 3.79-3.75 (m, 5H), 3.62-3.44 (m, 2H), 3.32 (s, 3H), 2.97-2.94 (t, J=5.2 Hz, 3H), 2.58-2.52 (m, 4H), 2.32-2.27 (m, 1H).

Example 21: 1-((3S,5R)-1-acryloyl-5-(methoxymethyl)pyrrolidin-3-yl)-3-((1-ethyl-4-fluoro-2-methyl-1H-benzo[d]imidazol-5-yl)ethynyl)-5-(methylamino)-1H-pyrazole-4-carboxamide

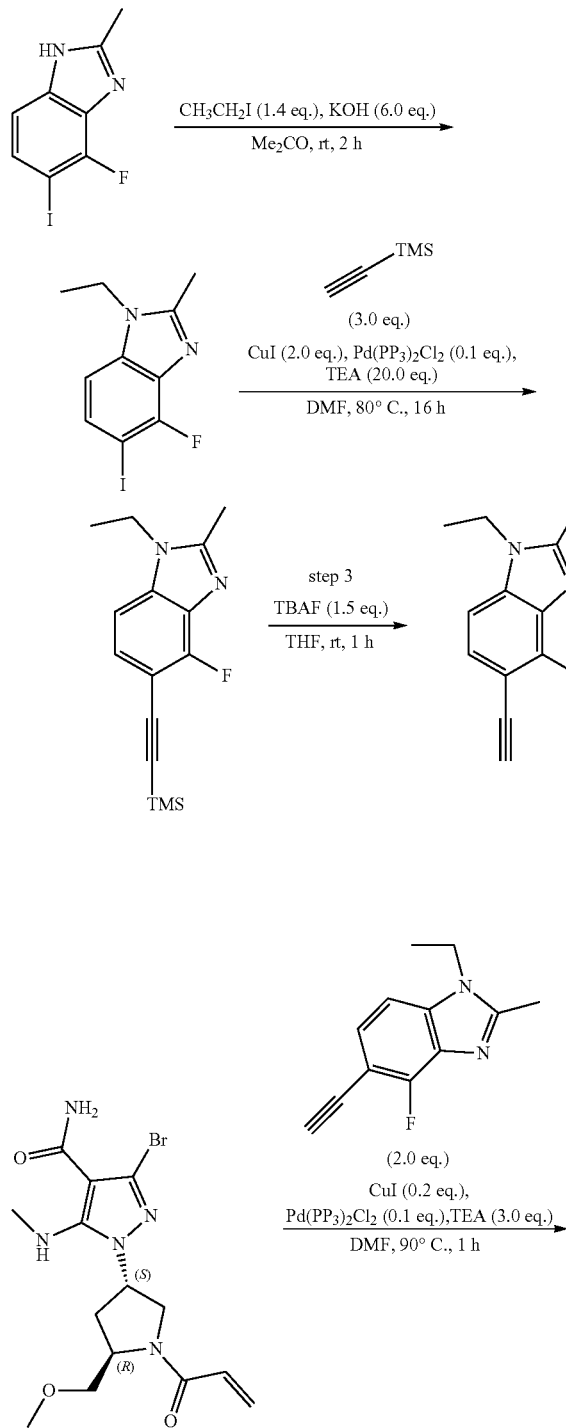

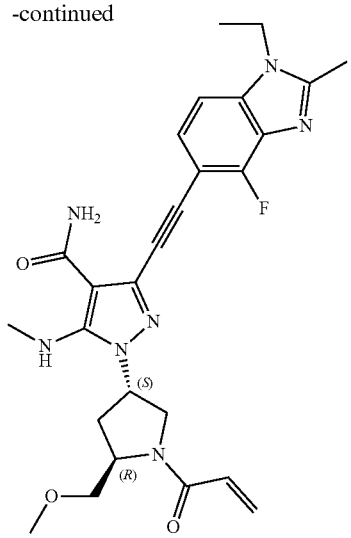

Step 1: 1-ethyl-4-fluoro-5-iodo-2-methyl-1H-benzo[d]imidazole

To a stirred solution of 4-fluoro-5-iodo-2-methyl-1H-1,3-benzodiazole (2.35 g, 8.51 mmol) and KOH (2.87 g, 51.08 mmol) in acetone (25.00 mL) was added ethyl iodide (1.86 g, 11.93 mmol) dropwise at room temperature under nitrogen atmosphere. The resulting mixture was stirred for 2 h at room temperature under nitrogen atmosphere. The resulting mixture was extracted with EtOAc (3×60 mL). The combined organic layers were washed with brine (3×50 mL), dried over anhydrous $Na_2SO_4$ and filtered. The filtrate was concentrated under reduced pressure. The residue was purified by silica gel column chromatography, eluted with $CH_2Cl_2$/EtOAc (1:1), the fractions contained desired product were combined and concentrated to afford 1-ethyl-4-fluoro-5-iodo-2-methyl-1H-benzo[d]imidazole (1.46 g, 56.4%) as an off-white solid. MS ESI calculated for $C_{10}H_{10}FIN_2$ $[M+H]^+$, 304.99, found 304.95.

Step 2: 1-ethyl-4-fluoro-2-methyl-5-((trimethylsilyl)ethynyl)-1H-benzo[d]imidazole To a mixture of 1-ethyl-4-fluoro-5-iodo-2-methyl-1H-benzo[d]imidazole (1.46 g, 4.80 mmol), trimethylsilylacetylene (1.41 g, 14.36 mmol), CuI (0.18 g, 0.96 mmol) and $Pd(PPh_3)_2Cl_2$ (0.34 g, 0.48 mmol) in DMF (15.00 mL) was added TEA (13.35 mL, 96.04 mmol). The reaction mixture was degassed with argon for three times and stirred for 16 h at 80° C. The resulting mixture was extracted with EtOAc (3×100 mL). The combined organic layers were washed with water (3×60 mL), dried over anhydrous $Na_2SO_4$ and filtered. The filtrate was concentrated under reduced pressure. The residue was purified by silica gel column chromatography, eluted with PE/EtOAc (1:2), the fractions contained desired product were combined and concentrated to afford 1-ethyl-4-fluoro-2-methyl-5-((trimethylsilyl)ethynyl)-1H-benzo[d]imidazole (1.0 g, 75%) as a light yellow solid. MS ESI calculated for $C_{15}H_{19}FN_2Si$ $[M+H]^+$, 275.13, found 275.15.

Step 3: 1-ethyl-5-ethynyl-4-fluoro-2-methyl-1H-benzo[d]imidazole

To a stirred solution of 1-ethyl-4-fluoro-2-methyl-5-((trimethylsilyl)ethynyl)-1H-benzo[d]imidazole (0.91 g, 3.32 mmol) in THF (10.00 mL) was added TBAF (4.97 mL, 4.97 mmol) dropwise at 0° C. under nitrogen atmosphere. The resulting mixture was stirred for 1 h at room temperature under nitrogen atmosphere. The resulting mixture was concentrated under reduced pressure. The residue was purified by silica gel column chromatography, eluted with PE/EtOAc (1:2), the fractions contained desired product were combined and concentrated to afford 1-ethyl-5-ethynyl-4-fluoro-2-methyl-1H-benzo[d]imidazole (0.68 g, 96%) as an off-white solid. MS ESI calculated for $C_{12}H_{11}FN_2$ [M+H]$^+$, 203.09, found 203.20.

Step 4: 1-((3S,5R)-1-acryloyl-5-(methoxymethyl)pyrrolidin-3-yl)-3-((1-ethyl-4-fluoro-2-methyl-1H-benzo[d]imidazol-5-yl)ethynyl)-5-(methylamino)-1H-pyrazole-4-carboxamide To a mixture of 3-bromo-1-[(3S,5R)-5-(methoxymethyl)-1-(prop-2-enoyl)pyrrolidin-3-yl]-5-(methylamino)pyrazole-4-carboxamide (0.2 g, 0.52 mmol), 1-ethyl-5-ethynyl-4-fluoro-2-methyl-1H-benzo[d]imidazole (0.21 g, 1.04 mmol), CuI (19.72 mg, 0.10 mmol) and Pd(PPh$_3$)$_2$Cl$_2$ (36.34 mg, 0.05 mmol) in DMF (2.00 mL) was added TEA (0.22 mL, 2.13 mmol). The reaction mixture was degassed with argon for three times and stirred for 1 h at 90° C. The resulting mixture was concentrated under reduced pressure. The residue was purified by Prep-HPLC with the following conditions: Column: XBridge Prep OBD C18 Column, 19*250 mm, 5 um; Mobile Phase A: Water (10 mmol/L NH$_4$HCO$_3$), Mobile Phase B: ACN; Flow rate: 20 mL/min; Gradient: 25 B to 60 B in 5.8 min; 210/254 nm; RT1: 5.56, the fractions contained desired product were combined and concentrated to afford 1-((3S,5R)-1-acryloyl-5-(methoxymethyl)pyrrolidin-3-yl)-3-((1-ethyl-4-fluoro-2-methyl-1H-benzo[d]imidazol-5-yl)ethynyl)-5-(methylamino)-1H-pyrazole-4-carboxamide (0.11 g, 41%) as an off-white solid. MS ESI calculated for $C_{26}H_{30}FN_7O_3$ [M+H]$^+$, 508.24, found 508.25. H NMR (400 MHz, DMSO-d$_6$) δ 7.48-7.38 (m, 3H), 6.79-6.56 (m, 3H), 6.19-6.14 (m, 1H), 5.70-5.67 (m, 1H), 5.30-5.24 (m, 1H), 4.53-4.40 (m, 1H), 4.28-4.23 (m, 2H), 4.08-3.72 (m, 2H), 3.66-3.41 (m, 2H), 3.32-3.29 (m, 3H), 2.96 (t, J=5.2 Hz, 3H), 2.60-2.56 (m, 4H), 2.33-2.29 (m, 1H), 1.30 (t, J=7.1 Hz, 3H).

Example 22: 1-((3S,5R)-1-acryloyl-5-(methoxymethyl)pyrrolidin-3-yl)-3-((3-ethyl-2-methyl-3H-imidazo[4,5-b]pyridin-6-yl)ethynyl)-5-(methylamino)-1H-pyrazole-4-carboxamide

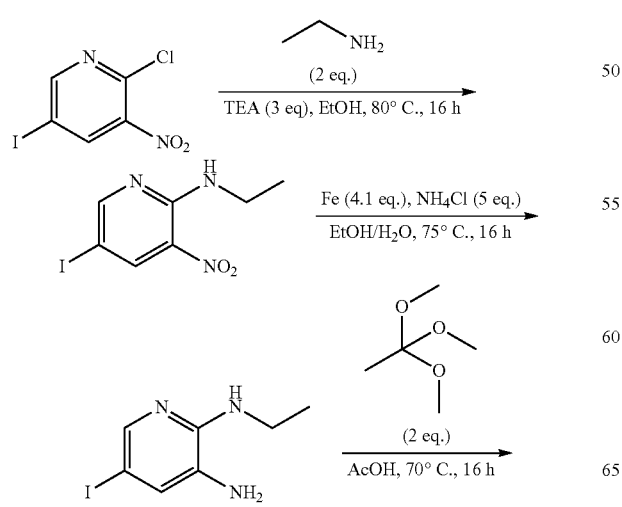

Step 1: N-ethyl-5-iodo-3-nitropyridin-2-amine

To a stirred mixture of 2-chloro-5-iodo-3-nitropyridine (3.10 g, 10.90 mmol) and ethylamine (0.98 g, 21.8 mmol) in EtOH (30.00 mL) was added TEA (3.31 g, 32.69 mmol) at room temperature under air atmosphere. The reaction mixture was stirred for 16 h at 80° C. The resulting mixture was concentrated under reduced pressure. The residue was diluted with water (300 mL), extracted with EA (3×250 mL). The combined organic layers were washed with Sat. NaCl (500 mL), dried over anhydrous $Na_2SO_4$ and filtered. The residue was concentrated to afford N-ethyl-5-iodo-3-nitropyridin-2-amine (3.5 g, 99%) as an orang solid which was used in the next step without further purification. ESI calculated for $C_7H_8IN_3O_2$ $[M+H]^+$, 293.9; found 294.

Step 2: N2-ethyl-5-iodopyridine-2,3-diamine

To a stirred mixture of N-ethyl-5-iodo-3-nitropyridin-2-amine (3.00 g, 10.24 mmol) and $NH_4Cl$ (2.74 g, 51.18 mmol) in EtOH (52.00 mL) and water (8 mL) was added Fe (2.29 g, 40.95 mmol) at room temperature. The reaction mixture was stirred for 16 h at 75° C. under air atmosphere. The resulting mixture was filtered, the filter cake was washed with EA (2×150 mL). The filtrate was concentrated under reduced pressure. The residue was diluted with water (200 mL) and extracted with EA (3×200 mL). The combined organic layers were washed with Sat. NaCl (500 mL), dried over anhydrous $Na_2SO_4$ and filtered. The resulting mixture was concentrated to afford N2-ethyl-5-iodopyridine-2,3-diamine (2.6 g, 96%) as a black solid which was used in the next step without further purification. MS ESI calculated for $C_7H_{10}IN_3$ $[M+H]^+$, 263.9; found 264.05.

Step 3: 3-ethyl-6-iodo-2-methylimidazo[4,5-b]pyridine

To a stirred mixture of $N_2$-ethyl-5-iodopyridine-2,3-diamine (2.20 g, 8.36 mmol) in $CH_3COOH$ (22.00 mL) was added 1,1,1-trimethoxyethane (2.01 g, 16.73 mmol) at room temperature under air atmosphere. The reaction mixture was stirred for 16 h at 70° C. The resulting mixture was concentrated under reduced pressure. The residue was diluted with EtOAc (100 mL). The mixture was basified to pH 8 with saturated $NaHCO_3$ (aq.). The resulting mixture was extracted with EtOAc (3×150 mL). The combined organic layers were washed with brine (200 mL), dried over anhydrous $Na_2SO_4$ and filtered. The filtrate was concentrated under reduced pressure. The residue was purified by silica gel column chromatography, eluted with $CH_2Cl_2$/MeOH (20:1). The fractions contained desired product were combined and concentrated to afford 3-ethyl-6-iodo-2-methylimidazo[4,5-b]pyridine (1.7 g, 70%) as a brown solid. MS ESI calculated for $C_9H_{10}IN_3$ $[M+H]^+$, 287.99; found 287.95.

Step 4: 3-ethyl-2-methyl-6-[2-(trimethylsilyl)ethynyl]imidazo[4,5-b]pyridine

To a stirred mixture of 3-ethyl-6-iodo-2-methylimidazo[4,5-b]pyridine (1.50 g, 5.23 mmol), trimethylsilylacetylene (1.54 g, 15.67 mmol), $Pd(PPh3)_2Cl_2$ (0.37 g, 0.52 mmol) and CuI (0.2 g, 1.05 mmol) in DMF (14.00 mL) was added TEA (10.57 g, 104.49 mmol). The reaction mixture was degassed with argon for three times and stirred for 2 h at 80° C. The residue was diluted with water (150 mL), extracted with EtOAc (3×150 mL). The combined organic layers were washed with brine (200 mL), dried over anhydrous $Na_2SO_4$ and filtered. The filtrate was concentrated under reduced pressure. The residue was purified by silica gel column chromatography, eluted with $CH_2Cl_2$/MeOH (20:1). The fractions contained desired product were combined and concentrated to afford 3-ethyl-2-methyl-6-[2-(trimethylsilyl)ethynyl]imidazo[4,5-b]pyridine (1.1 g, 81%) as a brown solid. MS ESI calculated for $C_{14}H_{19}N_3Si[M+H]^+$, 258.13; found 258.05.

Step 5: 3-ethyl-6-ethynyl-2-methylimidazo[4,5-b]pyridine

To a stirred mixture of 3-ethyl-2-methyl-6-[2-(trimethylsilyl)ethynyl]imidazo[4,5-b]pyridine (1.00 g, 3.89 mmol) in THF (10.00 mL) was added TBAF (1.52 g, 5.83 mmol) at room temperature under air atmosphere. The reaction mixture was stirred for 16 h at room temperature. The resulting mixture was concentrated under reduced pressure. The residue was diluted with water (100 mL), extracted with EtOAc (3×150 mL). The combined organic layers were washed with brine (200 mL), dried over anhydrous $Na_2SO_4$ and filtered. The filtrate was concentrated under reduced pressure. The residue was purified by silica gel column chromatography, eluted with $CH_2Cl_2$/MeOH (10:1). The fractions contained desired product were combined and concentrated to afford 3-ethyl-6-ethynyl-2-methylimidazo[4,5-b]pyridine (0.28 g, 38%) as a brown solid. MS ESI calculated for $C_{11}H_{11}N_3$ $[M+H]^+$, 186.1; found 186.15.

Step 6: 3-(2-[3-ethyl-2-methylimidazo[4,5-b]pyridin-6-yl]ethynyl)-1-[(3S,5R)-5-(methoxymethyl)-1-(prop-2-enoyl)pyrrolidin-3-yl]-5-(methylamino)pyrazole-4-carboxamide To a stirred mixture of 3-bromo-1-[(3S,5R)-5-(methoxymethyl)-1-(prop-2-enoyl)pyrrolidin-3-yl]-5-(methylamino)pyrazole-4-carboxamide (0.2 g, 0.52 mmol), 3-ethyl-6-ethynyl-2-methylimidazo[4,5-b]pyridine (0.14 g, 0.78 mmol), $Pd(PPh3)_2Cl_2$ (36.34 mg, 0.05 mmol) and CuI (19.72 mg, 0.1 mmol) in DMF (2.00 mL) was added TEA (0.16 g, 1.55 mmol) dropwise at room temperature. The reaction mixture was degassed with argon for three times and stirred for 2 h at 90° C. The residue was purified by reverse flash chromatography with the following conditions: column, C18 silica gel; mobile phase ACN, $NH_4HCO_3$ 0.01 mmol in water, 20% to 40% gradient in 20 min; detector, UV 254 nm. The fractions contained desired product were combined and concentrated. The residue was purified by Prep-HPLC with the following conditions Column: XBridge Prep C18 OBD Column, 19×150 mm 5 um; Mobile Phase A: Water (10 mmol/L $NH_4HCO_3$), Mobile Phase B: ACN; Flow rate: 20 mL/min; Gradient: 25 B to 55 B in 6 min; 210/254 nm; RT1: 5.53. The fractions contained desired product were combined and concentrated to afford 3-(2-[3-ethyl-2-methylimidazo[4,5-b]pyridin-6-yl]ethynyl)-1-[(3S,5R)-5-(methoxymethyl)-1-(prop-2-enoyl)pyrrolidin-3-yl]-5-(methylamino)pyrazole-4-carboxamide (59 mg, 23%) as a light yellow solid. MS ESI calculated for $C_{25}H_{30}N_8O_3$ $[M+H]^+$, 491.24; found 491.15. $^1H$ NMR (400 MHz, DMSO-$d_6$) δ 8.49 (d, J=1.9 Hz, 1H), 8.19-8.15 (m, 1H), 7.31 (s, 1H), 6.94-6.71 (m, 1H), 6.69-6.47 (m, 2H), 6.17-5.96 (m, 1H), 5.69-5.43 (m, 1H), 5.23-5.03 (m, 1H), 4.49-4.45 (m, 1H), 4.29 (q, J=7.3 Hz, 2H), 4.11-3.71 (m, 2H), 3.68-3.41 (m, 2H), 3.31 (d, J=5.4 Hz, 3H), 3.06-2.89 (m, 3H), 2.65-2.60 (m, 4H), 2.38-2.25 (m, 1H), 1.34 (t, J=7.2 Hz, 3H).

Example 23: 1-((3S,5R)-1-acryloyl-5-(methoxymethyl)pyrrolidin-3-yl)-3-((3-methyl-3H-imidazo[4,5-b]pyridin-6-yl)ethynyl)-5-(methylamino)-1H-pyrazole-4-carboxamide

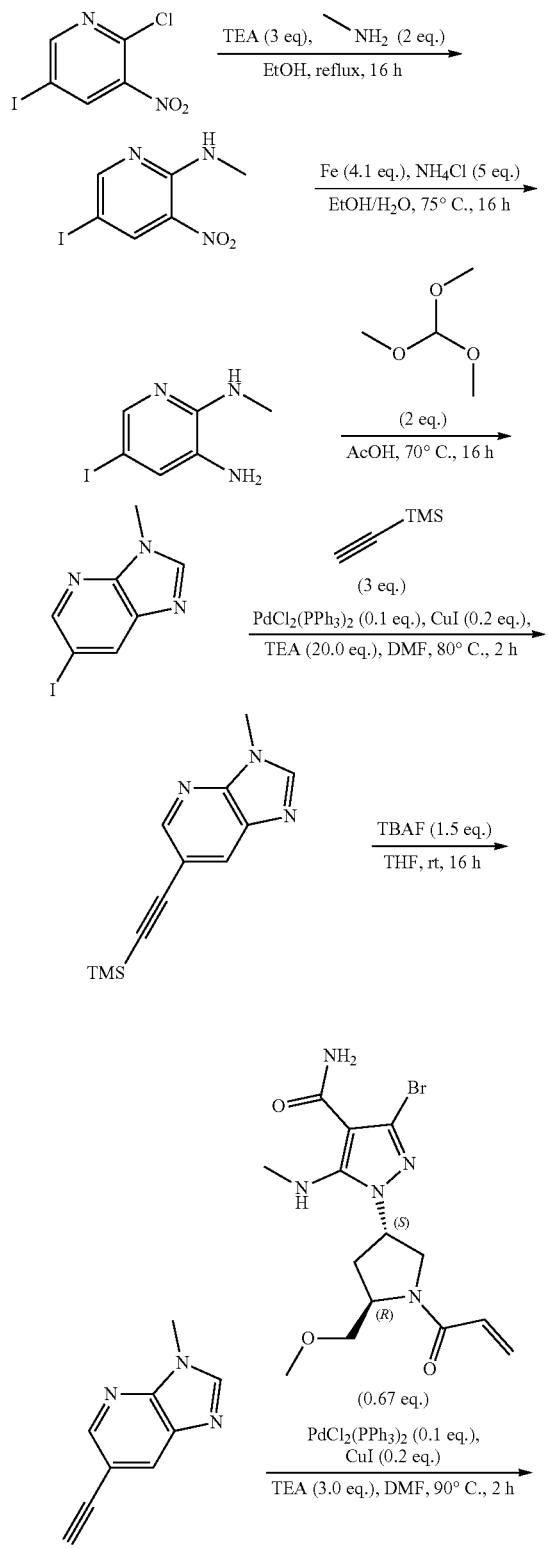

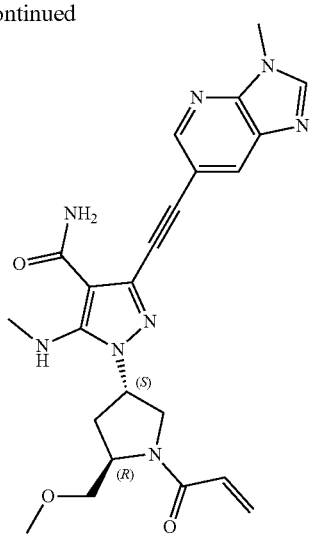

Step 1: 5-iodo-N-methyl-3-nitropyridin-2-amine

To a stirred mixture of 2-chloro-5-iodo-3-nitropyridine (3.00 g, 10.55 mmol) and methylamine (0.65 g, 21.09 mmol) in EtOH (30.00 mL) was added TEA (3.20 g, 31.64 mmol) at room temperature under air atmosphere. The reaction mixture was stirred for 16 h at 80° C. The resulting mixture was concentrated under reduced pressure. The residue was diluted with water (300 mL), extracted with EA (3×150 mL). The combined organic layers were washed with Sat. NaCl (500 mL), dried over anhydrous $Na_2SO_4$ and filtered. The filtrate was concentrated and dried to afford 5-iodo-N-methyl-3-nitropyridin-2-amine (2.9 g, 98%) as an orang solid which was used in the next step directly without further purification. ESI calculated for $C_6H_6IN_3O_2$ $[M+H]^+$, 279.95; found 279.95.

Step 2: 5-iodo-N2-methylpyridine-2,3-diamine

To a stirred mixture of 5-iodo-N-methyl-3-nitropyridin-2-amine (3.00 g, 10.75 mmol) and $NH_4Cl$ (2.88 g, 53.75 mmol) in EtOH (52.00 mL)/$H_2O$ (7.00 mL) was added Fe (2.40 g, 43.00 mmol) at room temperature under air atmosphere. The reaction mixture was stirred for 16 h at 75° C. The resulting mixture was filtered, the filter cake was washed with EA (2×150 mL). The filtrate was concentrated under reduced pressure. The residue was diluted with water (200 mL) and extracted with EA (3×200 mL). The combined organic layers were washed with Sat. NaCl (500 mL), dried over anhydrous $Na_2SO_4$ and filtered. The filtrate were combined and concentrated to afford 5-iodo-$N_2$-methylpyridine-2,3-diamine (1.7 g, 63%) as a black solid which was used in the next step directly without further purification. MS ESI calculated for $C_6H_8IN_3$ $[M+H]^+$, 249.98; found 250.0.

Step 3: 6-iodo-3-methylimidazo[4,5-b]pyridine

To a stirred mixture of 5-iodo-N2-methylpyridine-2,3-diamine (1.30 g, 5.22 mmol) in $CH_3COOH$ (13.00 mL) was added trimethyl orthoformate (1.11 g, 0.01 mmol) at room temperature under air atmosphere. The reaction mixture was stirred for 16 h at 70° C. under air atmosphere. The resulting mixture was concentrated under reduced pressure. The residue was diluted with EtOAc (100 mL). The mixture was basified to pH 8 with saturated NaHCO₃ (aq.). The resulting mixture was extracted with EtOAc (3×150 mL). The combined organic layers were washed with brine (200 mL), dried over anhydrous Na₂SO₄ and filtered. The filtrate was concentrated under reduced pressure. The residue was purified by silica gel column chromatography, eluted with CH₂Cl₂/MeOH (20:1). The fractions contained desired product were combined and concentrated to afford 6-iodo-3-methylimidazo[4,5-b]pyridine (0.85 g, 62%) as a brown solid. MS ESI calculated for C₇H₆IN₃ [M+H]⁺, 258.96; found 259.85.

Step 4: 3-methyl-6-[2-(trimethylsilyl)ethynyl]imidazo[4,5-b]pyridine

To a stirred mixture of 6-iodo-3-methylimidazo[4,5-b]pyridine (0.8 g, 3.08 mmol), trimethylsilylacetylene (0.9 g, 9.26 mmol), Pd(PPh3)2Cl2 (0.22 g, 0.31 mmol) and CuI (0.12 g, 0.62 mmol) in DMF (8.00 mL) was added TEA (6.25 g, 61.76 mmol) dropwise at room temperature. The reaction mixture was degassed with argon for three times and stirred for 2 h at 80° C. The residue was diluted with water (150 mL), extracted with EtOAc (3×150 mL). The combined organic layers were washed with brine (200 mL), dried over anhydrous Na2SO4 and filtered. The filtrate was concentrated under reduced pressure. The residue was purified by silica gel column chromatography, eluted with CH2Cl2/MeOH (10:1). The fractions contained desired product were combined and concentrated to afford 3-methyl-6-[2-(trimethylsilyl)ethynyl]imidazo[4,5-b]pyridine (0.70 g, 98%) as a brown solid. MS ESI calculated for C12H15N3Si [M+H]⁺, 230.1; found 230.0.

Step 5: 6-ethynyl-3-methylimidazo[4,5-b]pyridine

To a stirred mixture of 3-methyl-6-[2-(trimethylsilyl)ethynyl]imidazo[4,5-b]pyridine (0.56 g, 2.44 mmol) in THF (6.00 mL) was added TBAF (0.96 g, 3.66 mmol) at room temperature under air atmosphere. The reaction mixture was stirred for 16 h at room temperature. The resulting mixture was concentrated under reduced pressure. The residue was diluted with water (100 mL), extracted with EtOAc (3×150 mL). The combined organic layers were washed with brine (200 mL), dried over anhydrous Na2SO4 and filtered. The filtrate was concentrated under reduced pressure. The residue was purified by silica gel column chromatography, eluted with CH2Cl2/MeOH (10:1). The fractions contained desired product were combined and concentrated to afford 6-ethynyl-3-methylimidazo[4,5-b]pyridine (0.30 g, 78%) as a brown solid. MS ESI calculated for C9H7N3 [M+H]+, 158.06; found 158.10.

Step 6: 1-[(3S,5R)-5-(methoxymethyl)-1-(prop-2-enoyl)pyrrolidin-3-yl]-5-(methylamino)-3-(2-[3-methylimidazo[4,5-b]pyridin-6-yl]ethynyl)pyrazole-4-carboxamide To a stirred mixture of 3-bromo-1-[(3S,5R)-5-(methoxymethyl)-1-(prop-2-enoyl)pyrrolidin-3-yl]-5-(methylamino)pyrazole-4-carboxamide (0.2 g, 0.52 mmol), 6-ethynyl-3-methylimidazo[4,5-b]pyridine (0.12 g, 0.78 mmol), Pd(PPh₃)₂Cl₂ (36.34 mg, 0.05 mmol) and CuI (19.72 mg, 0.11 mmol) in DMF (2.00 mL) was added TEA (0.16 g, 1.55 mmol) dropwise at room temperature. The reaction mixture was degassed with argon for three times and stirred for 2 h at 90° C. The residue was purified by reverse flash chromatography with the following conditions: column, C18 silica gel; mobile phase ACN, NH₄HCO₃ 0.01 mmol in water, 20% to 40% gradient in 20 min; detector, UV 254 nm. The fractions contained desired product were combined and concentrated. The residue was purified by Prep-HPLC with the following conditions Column: SunFire Prep C18 OBD Column, 19×150 mm 5 um 10 nm; Mobile Phase A: Water (0.1% FA), Mobile Phase B: MeOH—HPLC; Flow rate: 20 mL/min; Gradient: 30 B to 50 B in 6 min; 210/254 nm; RT1: 5.68. The fractions contained desired product were combined and concentrated to afford 1-[(3S,5R)-5-(methoxymethyl)-1-(prop-2-enoyl)pyrrolidin-3-yl]-5-(methylamino)-3-(2-[3-methylimidazo[4,5-b]pyridin-6-yl]ethynyl)pyrazole-4-carboxamide (22.5 mg, 9%) as a light yellow solid. MS ESI calculated for C₂₃H₂₆N₈O₃ [M+H]⁺, 463.21; found 463.15. ¹H NMR (300 MHz, DMSO-d₆) δ 8.64-8.57 (m, 2H), 8.35 (d, J=1.8 Hz, 1H), 7.28 (s, 1H), 6.65-6.43 (m, 2H), 6.15-5.96 (m, 1H), 5.68-5.43 (m, 1H), 5.23-5.01 (m, 1H), 4.60-4.47 (m, 1H), 4.44-4.34 (m, 1H), 4.05-4.00 (m, 1H), 3.89-3.85 (m, 4H), 3.65-3.42 (m, 2H), 3.31-3.27 (m, 3H), 2.95-2.90 (m, 3H), 2.79-2.55 (m, 1H), 2.39-2.19 (m, 1H).

Example 24: 1-((3S,5R)-1-acryloyl-5-(methoxymethyl)pyrrolidin-3-yl)-3-((6-cyano-1-ethyl-2-methyl-1H-benzo[d]imidazol-5-yl)ethynyl)-5-(methylamino)-1H-pyrazole-4-carboxamide

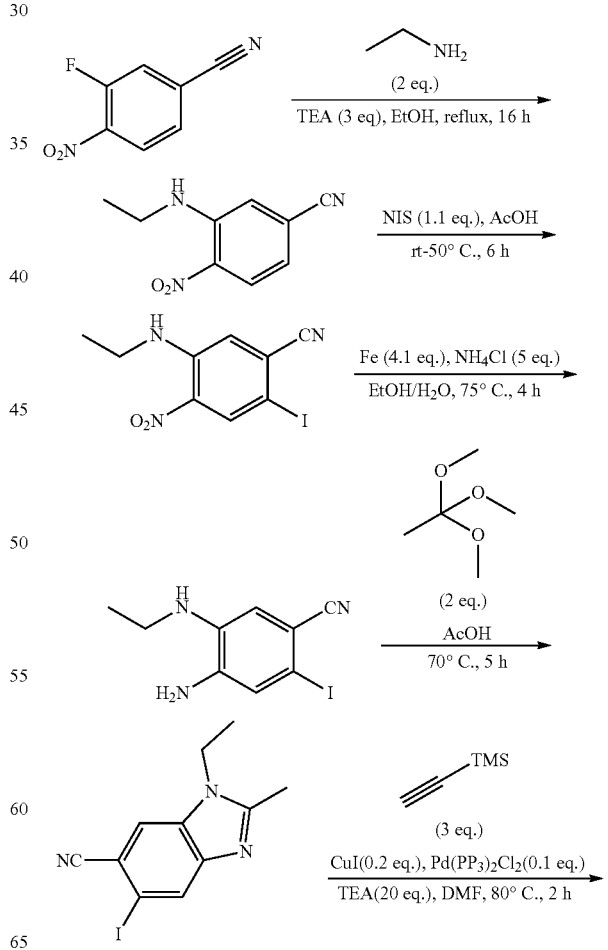

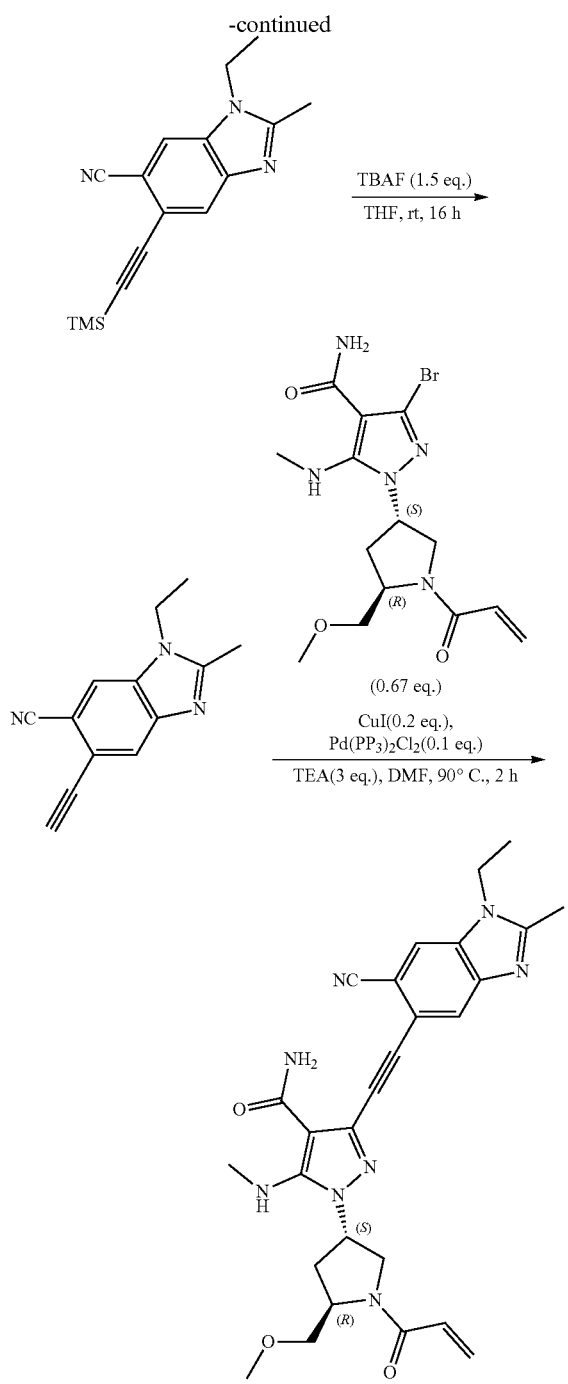

to afford 3-(ethylamino)-4-nitrobenzonitrile (11.5 g, 89%) which was used in the next step directly without further purification. H-NMR (400 MHz, Chloroform-d): δ 8.27 (d, J=8.7 Hz, 1H), 7.98 (s, 1H), 7.17 (d, J=1.7 Hz, 1H), 6.88 (dd, J=8.7, 1.7 Hz, 1H), 3.41-3.38 (m, 2H), 1.43 (t, J=7.2 Hz, 3H).

Step 2: 5-(ethylamino)-2-iodo-4-nitrobenzonitrile

To a stirred solution of 3-(ethylamino)-4-nitrobenzonitrile (12.50 g, 65.38 mmol) in AcOH (120.00 mL) was added NIS (16.18 g, 71.92 mmol) in portions at room temperature under nitrogen atmosphere. The reaction mixture was stirred for 6 h at 50° C. The resulting mixture was concentrated under reduced pressure. The residue was diluted with EtOAc (100 mL). The resulting mixture was basified to pH 8 with saturated $NaHCO_3$ (aq.) and extracted with EtOAc (3×500 mL). The combined organic layers were washed with brine (3×300 mL), dried over anhydrous $Na_2SO_4$ and filtered. The filtrate was concentrated under reduced pressure. The residue was purified by trituration with $CH_2Cl_2$/MeOH (50:1) (500 mL). The precipitated solids were collected by filtration and dried to afford 5-(ethylamino)-2-iodo-4-nitrobenzonitrile (13.9 g, 60%) as a reddish brown solid. MS ESI calculated for $C_9H_8IN_3O_2$ $[M–H]^-$, 315.97, found 315.90.

Step 3: 4-amino-5-(ethylamino)-2-iodobenzonitrile

To a stirred mixture of 5-(ethylamino)-2-iodo-4-nitrobenzonitrile (3.00 g, 9.46 mmol) and $NH_4Cl$ (2.53 g, 47.31 mmol) in EtOH (30.00 mL) and $H_2O$ (4.50 mL) was added Fe (2.11 g, 37.85 mmol). The reaction mixture was stirred for 4 h at 75° C. under nitrogen atmosphere. The resulting mixture was filtered, the filter cake was washed with EtOH (6×300 mL). The filtrate was concentrated under reduced pressure. The residue was diluted with water (300 mL), extracted with EtOAc (3×200 mL). The combined organic layers were washed with brine (300 mL), dried over anhydrous $Na_2SO_4$ and filtered. The filtrate was concentrated under reduced pressure. The crude product 4-amino-5-(ethylamino)-2-iodobenzonitrile (2.4 g, 79%) was used in the next step directly without further purification. MS ESI calculated for $C_9H_{10}N_3$ $[M–H]^-$, 285.99, found 286.00.

Step 4: 3-ethyl-6-iodo-2-methyl-1,3-benzodiazole-5-carbonitrile

To a stirred solution of 4-amino-5-(ethylamino)-2-iodobenzonitrile (3.50 g, 12.19 mmol) in AcOH (35.00 mL) was added 1,1,1-trimethoxyethane (2.93 g, 24.38 mmol) at room temperature under nitrogen atmosphere. The reaction mixture was stirred for 5 h at 70° C. The resulting mixture was concentrated under reduced pressure. The residue was diluted with EtOAc (100 mL). The mixture was basified to pH 8 with saturated $NaHCO_3$ (aq.). The resulting mixture was extracted with EtOAc (3×150 mL). The combined organic layers were washed with brine (200 mL), dried over anhydrous $Na_2SO_4$ and filtered. The filtrate was concentrated under reduced pressure. The residue was purified by silica gel column chromatography, eluted with $CH_2Cl_2$/MeOH (20:1). The fractions contained desired product were combined and concentrated to afford 3-ethyl-6-iodo-2-methyl-1,3-benzodiazole-5-carbonitrile (2.18 g, 54%) as an off-white solid. MS ESI calculated for $C_{11}H_{10}N_3$ $[M+H]^+$, 311.99, found 312.05.

Step 1: 3-(ethylamino)-4-nitrobenzonitrile

To a stirred mixture of 3-fluoro-4-nitrobenzonitrile (10.00 g, 60.20 mmol) and ethylamine (5.43 g, 120.40 mmol) in EtOH (90.00 mL) was added TEA (25.10 mL, 248.08 mmol) at room temperature under nitrogen atmosphere. The reaction mixture was stirred for 16 h at 50° C. The resulting mixture was concentrated under reduced pressure. The residue was diluted with NaHCO3 (300 mL). The resulting mixture was extracted with EtOAc (3×200 mL). The combined organic layers were washed with brine (300 mL), dried anhydrous Na2SO4 and filtered. The filtrate was concentrated under reduced pressure. The residue was dried

Step 5: 3-ethyl-2-methyl-6-[2-(trimethylsilyl)ethynyl]-1,3-benzodiazole-5-carbonitrile To a stirred mixture of 3-ethyl-6-iodo-2-methyl-1,3-benzodiazole-5-carbonitrile (2.18 g, 7.01 mmol), trimethylsilylacetylene (2.97 mL, 30.25 mmol), CuI (0.27 g, 1.40 mmol) and Pd(PPh$_3$)$_2$Cl$_2$ (0.49 g, 0.70 mmol) in DMF (22.00 mL) was added TEA (19.48 mL, 192.50 mmol). The reaction mixture was degassed with nitrogen for three times and stirred for 2 h at 80° C. The resulting mixture was diluted with water (100 mL) and extracted with EA (3×100 mL). The combined organic layers were washed with brine (2×100 mL), dried over anhydrous Na$_2$SO$_4$, filtered and concentrated under reduced pressure. The residue was purified by silica gel column chromatography, eluted with CH$_2$Cl$_2$/MeOH (25:1). The fractions contained desired product were combined and concentrated to afford 3-ethyl-2-methyl-6-[2-(trimethylsilyl)ethynyl]-1,3-benzodiazole-5-carbonitrile (2 g, 94%) as a brown solid. MS ESI calculated for C$_{16}$H$_{19}$N$_3$Si [M+H]$^+$, 282.13, found 282.15.

Step 6: 3-ethyl-6-ethynyl-2-methyl-1,3-benzodiazole-5-carbonitrile

To a stirred solution of 3-ethyl-2-methyl-6-[2-(trimethylsilyl)ethynyl]-1,3-benzodiazole-5-carbonitrile (1.00 g, 3.55 mmol) in THF (10.00 mL) was added TBAF (5.33 mL, 5.33 mmol) dropwise at 0° C. under nitrogen atmosphere. The reaction mixture was stirred for 16 h at room temperature. The resulting mixture was diluted with water (80 mL), extracted with EtOAc (3×100 mL). The combined organic layers were washed with brine (150 mL), dried over anhydrous Na$_2$SO$_4$ and filtered. The filtrate was concentrated under reduced pressure. The residue was purified by silica gel column chromatography, eluted with CH$_2$Cl$_2$/MeOH (25:1). The fractions contained desired product were combined and concentrated to afford 3-ethyl-6-ethynyl-2-methyl-1,3-benzodiazole-5-carbonitrile (0.70 g, 84%) as a yellow solid. MS ESI calculated for C$_{13}$H$_{11}$N$_3$ [M+H]$^+$, 210.10, found 210.20.

Step 7: 3-[2-(6-cyano-1-ethyl-2-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide To a stirred mixture of 3-bromo-1-[(3S,5R)-5-(methoxymethyl)-1-(prop-2-enoyl)pyrrolidin-3-yl]-5-(methylamino)pyrazole-4-carboxamide (0.20 g, 0.52 mmol), 3-ethyl-6-ethynyl-2-methyl-1,3-benzodiazole-5-carbonitrile (0.16 g, 0.78 mmol), CuI (19.72 mg, 0.10 mmol) and Pd(PPh$_3$)$_2$Cl$_2$ (36.34 mg, 0.05 mmol) in DMF (2.00 mL) was added TEA (0.22 mL, 2.13 mmol). The reaction mixture was degassed with argon for three times and stirred for 2 h at 90° C. The resulting mixture was concentrated under reduced pressure. The residue was purified by reverse flash chromatography with the following conditions: column, C18 silica gel; mobile phase, NH$_4$HCO$_3$ (10 mmol/L) in water, 10% to 50% gradient in 25 min; detector, UV 254 nm. The fractions contained desired product were combined and concentrated. The crude product was purified by Prep-HPLC with the following conditions Column: XBridge Prep OBD C18 Column, 19×250 mm, 5 um; Mobile Phase A: Water (10 mmol/L NH$_4$HCO$_3$), Mobile Phase B: ACN; Flow rate: 20 mL/min; Gradient: 25 B to 60 B in 5.8 min; 210/254 nm; RT1: 5.52. The fractions contained desired product were combined and concentrated to afford 3-[2-(6-cyano-1-ethyl-2-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (49.9 mg, 18%) as an off-white solid. MS ESI calculated for C$_{27}$H$_{30}$N$_8$O$_3$ [M+H]$^+$, 515.24, found 515.30. H-NMR (400 MHz, DMSO-d$_6$): δ 8.34 (d, J=1.3 Hz, 1H), 7.98 (d, J=0.5 Hz, 1H), 7.43 (s, 1H), 6.78-6.53 (m, 3H), 6.19-6.17 (m, 1H), 5.73-5.61 (m, 1H), 5.33-5.28 (m, 1H), 4.50-4.45 (m, 1H), 4.35-4.30 (m, 2H), 4.07-3.70 (m, 2H), 3.63-3.43 (m, 2H), 3.30 (s, 3H), 2.96-2.92 (m, 3H), 2.63 (s, 3H), 2.50-2.47 (m, 1H), 2.36-2.27 (m, 1H), 1.32 (t, J=7.2 Hz, 3H).

Example 25: 1-((3S,5R)-1-acryloyl-5-(methoxymethyl)pyrrolidin-3-yl)-3-((2-cyclopropyl-1-ethyl-1H-benzo[d]imidazol-5-yl)ethynyl)-5-(methylamino)-1H-pyrazole-4-carboxamide

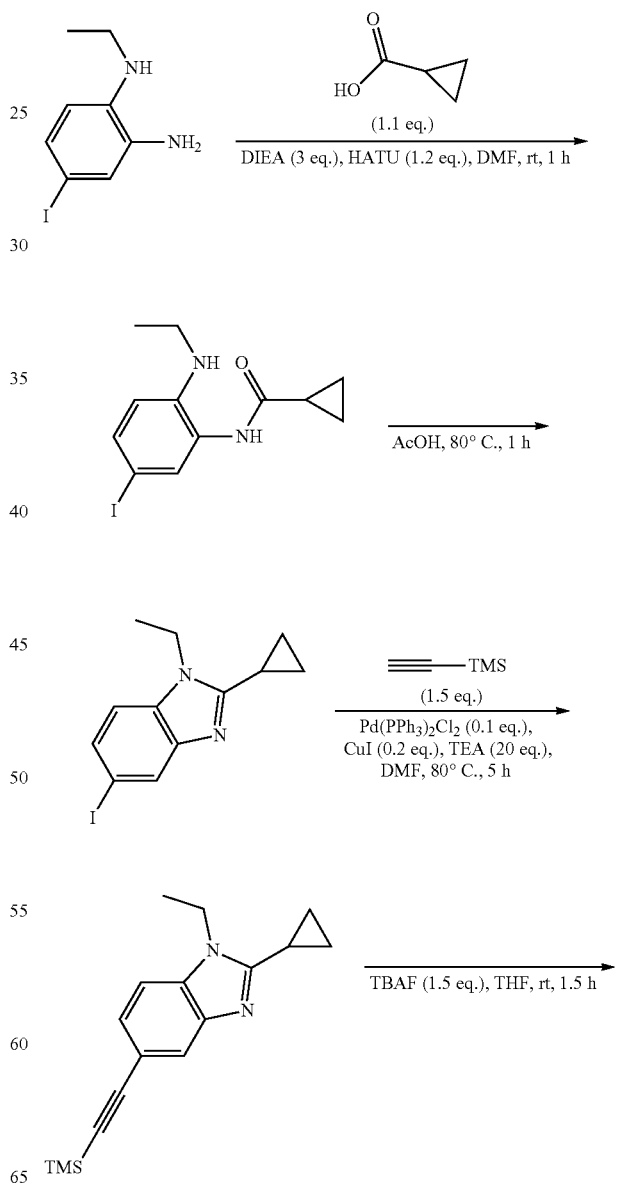

-continued

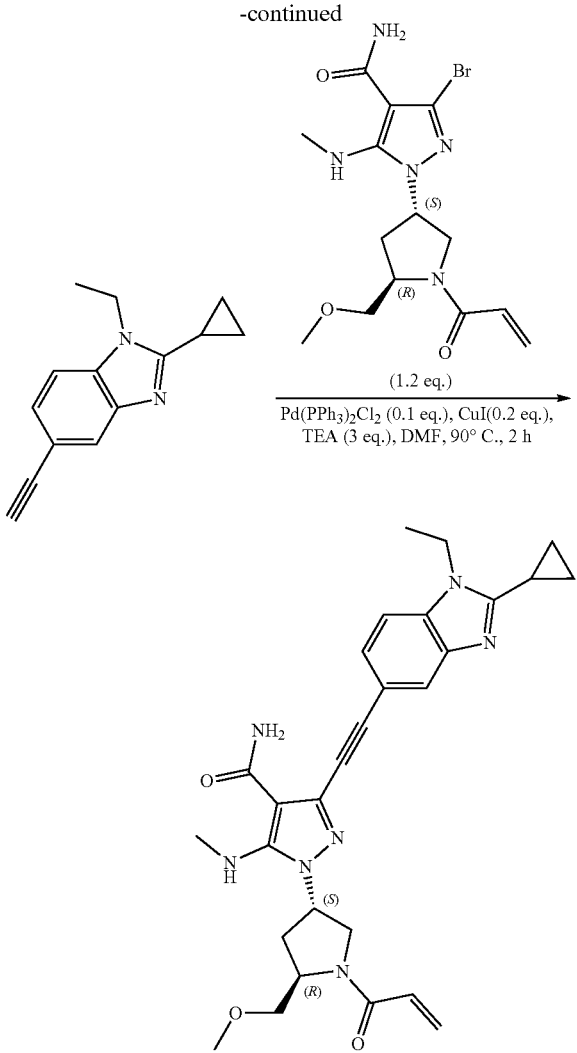

Step 1: N-[2-(ethylamino)-5-iodophenyl]cyclopropanecarboxamide

To a stirred mixture of cyclopropanecarboxylic acid (0.16 g, 1.91 mmol) and HATU (1.09 g, 2.86 mmol) in DMF (5.00 mL) was added N,N-diisopropylethylamine (0.74 g, 5.72 mmol) dropwise at room temperature. The reaction mixture was stirred for 10 min at room temperature. To the above mixture was added N1-ethyl-4-iodobenzene-1,2-diamine (0.50 g, 1.91 mmol) at room temperature. The resulting mixture was stirred for additional 1 h. The reaction was quenched with water (10 mL) and extracted with EtOAc (3×20 mL). The combined organic layers were washed with brine (3×10 mL), dried over anhydrous $Na_2SO_4$ and filtered. The filtrate was concentrated under reduced pressure to afford N-[2-(ethylamino)-5-iodophenyl]cyclopropanecarboxamide (0.50 g, 79%) as a dark grey solid which was used in the next step directly without further purification. ESI calculated for $C_{12}H_{15}IN_2O$ [M+H]$^+$, 331.02; found 331.05.

Step 2: 2-Cyclopropyl-1-ethyl-5-iodo-1,3-benzodiazole

A mixture of N-[2-(ethylamino)-5-iodophenyl]cyclopropanecarboxamide (0.90 g, 2.73 mmol) in acetic acid (9.00 mL) was stirred for 1 h at 80° C. The resulting mixture was allowed to cool down to room temperature and concentrated under reduced pressure. The residue was neutralized to pH=7 with saturated $NaHCO_3$ (aq.) and extracted with EtOAc (3×50 mL). The combined organic layers were washed with brine (3×50 mL), dried over anhydrous $Na_2SO_4$ and filtered. The resulting mixture was concentrated under reduced pressure. The residue was purified by silica gel column chromatography, eluted with PE/EtOAc (3:1). The fractions contained desired product were combined and concentrated to afford 2-cyclopropyl-1-ethyl-5-iodo-1,3-benzodiazole (0.61 g, 71%) as a brown semi-solid. MS ESI calculated for $C_{12}H_{13}IN_2$ [M+H]$^+$, 313.01; found 312.95.

Step 3: 2-Cyclopropyl-1-ethyl-5-[2-(trimethylsilyl)ethynyl]-1,3-benzodiazole To a mixture of 2-cyclopropyl-1-ethyl-5-iodo-1,3-benzodiazole (0.61 g, 1.95 mmol) and trimethylsilylacetylene (0.58 g, 5.86 mmol) in DMF (6.00 mL) were added $Pd(PPh_3)_2Cl_2$ (0.14 g, 0.19 mmol), CuI (74.43 mg, 0.39 mmol) and TEA (3.95 g, 39.08 mmol) at room temperature. The reaction mixture was degassed with nitrogen for three times and stirred for 5 h at 80° C. The mixture was allowed to cool down to room temperature. The resulting mixture was diluted with water (30 mL), extracted with EtOAc (3×50 mL). The combined organic layers were washed with brine (100 mL), dried over anhydrous $Na_2SO_4$ and filtered. The filtrate was concentrated under reduced pressure. The residue was purified by silica gel column chromatography, eluted with PE/EtOAc (3:1). The combined organic layers were washed with brine (300 mL), dried over anhydrous $Na_2SO_4$ and filtered. The filtrate was concentrated under reduced pressure to afford 2-cyclopropyl-1-ethyl-5-[2-(trimethylsilyl)ethynyl]-1,3-benzodiazole (0.54 g, 97%) as a light brown semi-solid. MS ESI calculated for $C_{17}H_{22}N_2Si$ [M+H]$^+$, 283.16; found 283.25.

Step 4: 2-Cyclopropyl-1-ethyl-5-ethynyl-1,3-benzodiazole

To a stirred solution of 2-cyclopropyl-1-ethyl-5-[2-(trimethylsilyl)ethynyl]-1,3-benzodiazole (0.54 g, 1.91 mmol) in THF (6.00 mL) was added TBAF (0.75 g, 2.88 mmol). The reaction mixture was stirred for 1.5 h at room temperature. The reaction was quenched by the addition of water (5 mL) at room temperature. The resulting mixture was extracted with EtOAc (3×10 mL). The combined organic layers were washed with brine (3×10 mL), dried over anhydrous $Na_2SO_4$. After filtration, the filtrate was concentrated under reduced pressure. The residue was purified by silica gel column chromatography, eluted with PE/EtOAc (3:1). The fractions contained desired product were combined and concentrated to afford 2-cyclopropyl-1-ethyl-5-ethynyl-1,3-benzodiazole (0.35 g, 87%) as a pink semi-solid. MS ESI calculated for $C_{14}H_{14}N_2$ [M+H]$^+$, 211.12; found 211.05.

Step 5: 3-[2-(2-Cyclopropyl-1-ethyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide To a mixture of 2-cyclopropyl-1-ethyl-5-ethynyl-1,3-benzodiazole (0.16 g, 0.76 mmol) and 3-bromo-1-[(3S,5R)-5-(methoxymethyl)-1-(prop-2-enoyl)pyrrolidin-3-yl]-5-(methylamino)pyrazole-4-carboxamide (0.35 g, 0.91 mmol) in DMF (2.00 mL) were added $Pd(PPh_3)_2Cl_2$ (53.41 mg, 0.07 mmol), CuI (28.98 mg, 0.15 mmol) and TEA (0.23 g, 2.28 mmol) at room temperature. The reaction mixture was degassed with argon for three times and stirred for 2 h at 90° C. The resulting mixture was allowed to cool down to room temperature. The resulting mixture was extracted with EtOAc (3×10 mL). The combined organic layers were washed with brine (3×10 mL), dried over anhydrous Na$_2$SO$_4$ and filtered. The filtrate was concentrated under reduced pressure. The residue was purified by silica gel column chromatography, eluted with PE/EtOAc (1:1). The crude product (150 mg) was purified by Prep-HPLC with the following conditions Column: XBridge Prep C18 OBD Column, 19×150 mm 5 um; Mobile Phase A: Water (10 mmol/L NH$_4$HCO$_3$), Mobile Phase B: ACN; Flow rate: 20 mL/min; Gradient: 15 B to 60 B in 4.3 min; 254 nm; RT1:4.02. The fractions contained desired product were combined and concentrated to afford 3-[2-(2-cyclopropyl-1-ethyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (75.8 mg, 19%) as an off-white solid. MS ESI calculated for C$_{28}$H$_{33}$N$_7$O$_3$ [M+H]$^+$, 516.26; found 516.15. $^1$H NMR (300 MHz, DMSO-d$_6$) δ 7.69 (d, J=1.4 Hz, 1H), 7.57 (d, J=8.3 Hz, 1H), 7.38-7.31 (m, 2H), 6.85-6.48 (m, 3H), 6.16 (d, J=16.6 Hz, 1H), 5.68 (d, J=10.3 Hz, 1H), 5.31-5.13 (m, 1H), 4.41-4.34 (m, 3H), 3.87-3.84 (m, 1H), 3.79-3.66 (m, 1H), 3.61-3.57 (m, 1H), 3.50-3.37 (m, 2H), 3.30-3.24 (m, 3H), 2.95-2.90 (m, 3H), 2.44-2.16 (m, 2H), 1.34 (t, J=7.1 Hz, 3H), 1.10-1.05 (m, 4H).

Example 26: 1-((3S,5R)-1-acryloyl-5-(methoxymethyl)pyrrolidin-3-yl)-3-(benzo[d]isoxazol-6-ylethynyl)-5-(methylamino)-1H-pyrazole-4-carboxamide

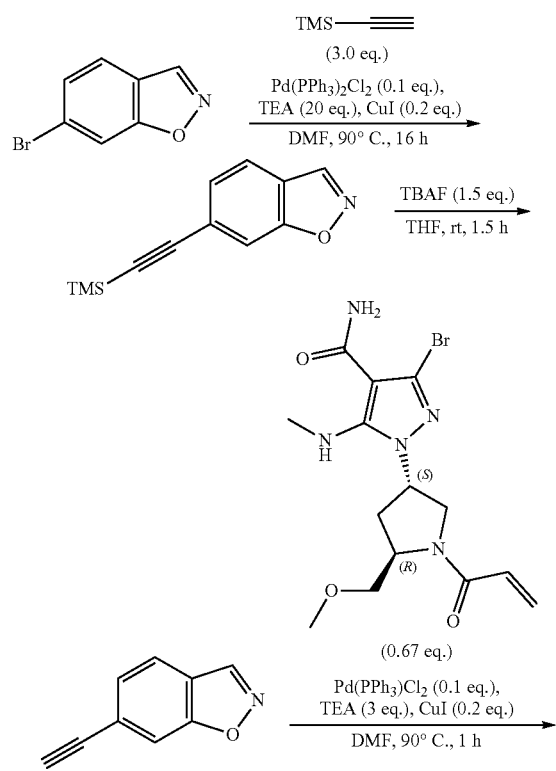

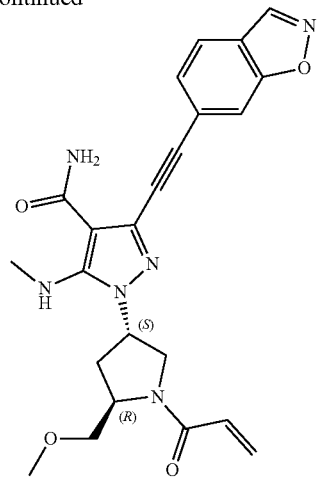

Step 1: 6-[2-(trimethylsilyl)ethynyl]-1,2-benzoxazole

To a mixture of 6-bromo-1,2-benzoxazole (2.00 g, 10.10 mmol), trimethylsilylacetylene (1.49 g, 15.15 mmol), CuI (0.38 g, 2.02 mmol) and Pd(PPh$_3$)$_2$Cl$_2$ (0.71 g, 1.01 mmol) in DMF (8.00 mL) was added TEA (20.44 g, 202.00 mmol). The reaction mixture was degassed with argon for three times and stirred for 16 h at 90° C. The resulting mixture was diluted with water (100 mL). The resulting mixture was extracted with EtOAc (3×150 mL). The combined organic layers were washed with water (3×100 mL), dried over anhydrous Na$_2$SO$_4$ and filtered. The filtrate was concentrated under reduced pressure. The residue was purified by silica gel column chromatography, eluted with PE/EtOAc (1:1). The fractions contained desired product were combined and concentrated to afford 6-[2-(trimethylsilyl)ethynyl]-1,2-benzoxazole (0.80 g, 36%) as a yellow semi-solid. MS ESI calculated for C$_{12}$H$_{13}$NOSi [M−H]$^-$, 214.09, found 214.15.

Step 2: 6-ethynyl-1,2-benzoxazole

To a stirred solution of 6-[2-(trimethylsilyl)ethynyl]-1,2-benzoxazole (0.80 g, 3.72 mmol) in THF (8.00 mL) was added TBAF (5.57 mL, 5.57 mmol) dropwise at 0° C. under air atmosphere. The reaction mixture was stirred for 1.5 h at room temperature. The resulting mixture was concentrated under reduced pressure. The residue was purified by silica gel column chromatography, eluted with PE/EtOAc (1:1). The fractions contained desired product were combined and concentrated to afford 6-ethynyl-1,2-benzoxazole (0.29 g, 54%) as a light brown solid. MS ESI calculated for C$_9$H$_5$NO [M−H]$^-$, 142.04, found 142.10.

Step 3: 3-[2-(1,2-benzoxazol-6-yl)ethynyl]-1-[(3S,5R)-5-(methoxymethyl)-1-(prop-2-enoyl)pyrrolidin-3-yl]-5-(methylamino)pyrazole-4-carboxamide To a stirred mixture of 3-bromo-1-[(3S,5R)-5-(methoxymethyl)-1-(prop-2-enoyl)pyrrolidin-3-yl]-5-(methylamino)pyrazole-4-carboxamide (0.20 g, 0.52 mmol) and 6-ethynyl-1,2-benzoxazole (0.12 g, 0.78 mmol) in DMF (2.00 mL) was added CuI (19.72 mg, 0.10 mmol), Pd(PPh$_3$)$_2$Cl$_2$ (36.34 mg, 0.05 mmol) and TEA (0.16 g, 1.55 mmol).

The reaction mixture was degassed with argon for three times and stirred for 1 h at 90° C. The resulting mixture was purified by reverse flash chromatography with the following conditions: column, C18 silica gel; mobile phase, ACN in water (10 mM NH₄HCO₃), 5% to 35% gradient in 30 min; detector, UV 220 nm. The crude product (150 mg) was purified by Prep-HPLC with the following conditions Column: XBridge Prep OBD C18 Column, 19*250 mm, 5 um; Mobile Phase A: Water (10 mmol/L NH₄HCO₃), Mobile Phase B: ACN; Flow rate: 20 mL/min; Gradient: 30 B to 60 B in 5.8 min; 210/254 nm; RT1:5.65. The fractions contained desired product were combined and concentrated to afford 3-[2-(1,2-benzoxazol-6-yl)ethynyl]-1-[(3S,5R)-5-(methoxymethyl)-1-(prop-2-enoyl)pyrrolidin-3-yl]-5-(methylamino)pyrazole-4-carboxamide (37.00 mg, 16%) as a white solid. MS ESI calculated for $C_{23}H_{24}N_6O_4$ [M+H]⁺, 449.19, found 449.25. H-NMR (400 MHz, DMSO-$d_6$): δ 7.67 (d, J=7.9 Hz, 1H), 7.34 (m, 1H), 7.08 (d, J=13.3 Hz, 2H), 6.71 (s, 1H), 6.58 (m, J=16.8, 10.3 Hz, 1H), 6.52 (d, J=5.7 Hz, 1H), 6.17 (d, J=16.6 Hz, 1H), 5.69 (d, J=10.0 Hz, 1H), 5.30-5.14 (m, 1H), 4.52 (s, 1H), 4.39 (s, 1H), 4.06-3.97 (m, 1H), 3.89-3.79 (m, 1H), 3.77-3.73 (m, 1H), 3.61-3.58 (m, 1H), 3.48-3.45 (m, 3H), 2.94 (s, 3H), 2.53-2.49 (m, 1H), 2.36-2.32 (m, 1H).

Example 27: 1-((3S,5R)-1-acryloyl-5-(methoxymethyl)pyrrolidin-3-yl)-3-((1-ethyl-2-(trifluoromethyl)-1H-benzo[d]imidazol-5-yl)ethynyl)-5-(methylamino)-1H-pyrazole-4-carboxamide

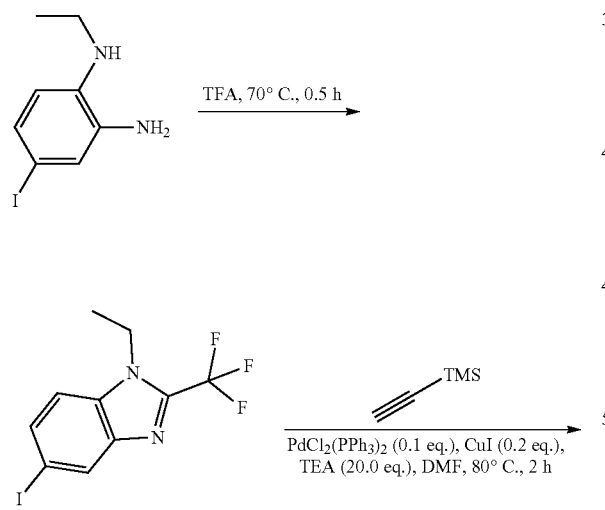

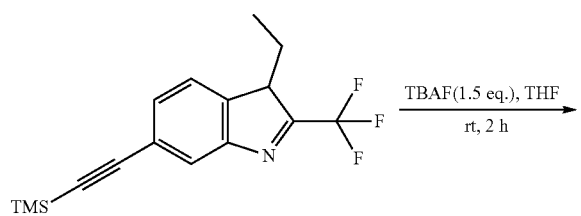

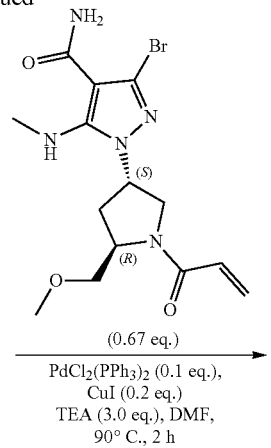

Step 1: 1-ethyl-5-iodo-2-(trifluoromethyl)-1H-benzo[d]imidazole

A solution of N¹-ethyl-4-iodobenzene-1,2-diamine (2.00 g, 7.63 mmol) in CF₃COOH was stirred for 0.5 h at 70° C. under nitrogen atmosphere. The resulting mixture was concentrated under reduced pressure. The residue was diluted with EA (50 mL), quenched by the addition of sat. NH₃HCO₃ (aq.) (50 mL) at room temperature. The resulting mixture was extracted with EtOAc (3×150 mL). The combined organic layers were washed with brine (300 mL), dried over anhydrous Na₂SO₄ and filtered. The resulting mixture was concentrated under reduced pressure. The residue was purified by silica gel column chromatography, eluted with PE/EtOAc (5:1). The fractions contained desired product were combined and concentrated to afford 1-ethyl-5-iodo-2-(trifluoromethyl)-1H-benzo[d]imidazole (2.5 g, 96%) as an off-white solid. ESI calculated for $C_{10}H_8F_3IN_2$ [M+H]⁺, 340.97; found 340.80.

Step 2: 3-ethyl-2-(trifluoromethyl)-6-((trimethylsilyl)ethynyl)-3H-indole

To a stirred mixture of 1-ethyl-5-iodo-2-(trifluoromethyl)-1H-benzo[d]imidazole (1.25 g, 3.68 mmol), Pd(PPh₃)₂Cl₂ (0.26 g, 0.37 mmol), CuI (0.14 g, 0.74 mmol)

and trimethylsilylacetylene (1.08 g, 11.03 mmol) in DMF was added TEA (7.44 g, 73.51 mmol). The reaction mixture was degassed with argon for three times and stirred for 2 h at 80° C. The resulting mixture was extracted with EtOAc (3×150 mL). The combined organic layers were washed with brine (200 mL), dried over anhydrous $Na_2SO_4$ and filtered. The resulting mixture was concentrated under reduced pressure. The residue was purified by silica gel column chromatography, eluted with PE/EtOAc (5:1). The fractions contained desired product were combined and concentrated to afford 3-ethyl-2-(trifluoromethyl)-6-((trimethylsilyl)ethynyl)-3H-indole (1.2 g, 96%) as a white solid. MS ESI calculated for $C_{16}H_{18}F_3NSi$ $[M+H]^+$, 310.12; found 310.25.

Step 3: 1-ethyl-5-ethynyl-2-(trifluoromethyl)-1H-benzo[d]imidazole

To a stirred solution of 3-ethyl-2-(trifluoromethyl)-6-((trimethylsilyl)ethynyl)-3H-indole (1.10 g, 3.54 mmol) in THF was added TBAF (1.39 g, 5.32 mmol) dropwise at 0° C. under nitrogen atmosphere. The reaction mixture was stirred for 2 h at room temperature. The resulting mixture was concentrated under reduced pressure. The residue was purified by silica gel column chromatography, eluted with PE/EtOAc (5:1). The fractions contained desired product were combined and concentrated to afford 1-ethyl-5-ethynyl-2-(trifluoromethyl)-1H-benzo[d]imidazole (0.83 g, 98%) as a light yellow solid. MS ESI calculated for $C_{12}H_9F_3N_2$ $[M+H]^+$, 239.07; found 239.15.

Step 4: 1-((3S,5R)-1-acryloyl-5-(methoxymethyl)pyrrolidin-3-yl)-3-((1-ethyl-2-(trifluoromethyl)-1H-benzo[d]imidazol-5-yl)ethynyl)-5-(methylamino)-1H-pyrazole-4-carboxamide To a stirred mixture of 1-ethyl-5-ethynyl-2-(trifluoromethyl)-1H-benzo[d]imidazole (0.17 g, 0.70 mmol), $Pd(PPh_3)_2Cl_2$ (32.71 mg, 0.05 mmol), CuI (17.75 mg, 0.09 mmol) and 1-((3S,5R)-1-acryloyl-5-(methoxymethyl)pyrrolidin-3-yl)-3-bromo-5-(methylamino)-1H-pyrazole-4-carboxamide (0.18 g, 0.47 mmol) in DMF was added TEA (0.14 g, 1.40 mmol). The reaction mixture was degassed with argon for three times and stirred for 2 h at 90° C. The resulting mixture was concentrated under reduced pressure. The residue was purified by reverse flash chromatography with the following conditions: column, C18 silica gel; mobile phase, $NH_4HCO_3$ in water, 10% to 50% gradient in 10 min; detector, UV 254 nm. The crude product was purified by Prep-HPLC with the following conditions Column: Xselect CSH OBD Column 30*150 mm 5 um, Mobile Phase A: Water (10 mmol/L $NH_4HCO_3$), Mobile Phase B: ACN; Flow rate: 30 mL/min; Gradient: 20 B to 60 B in 6 min; 210/254 nm; RT: 5.59. The fractions contained desired product were combined and concentrated to afford 1-((3S,5R)-1-acryloyl-5-(methoxymethyl)pyrrolidin-3-yl)-3-((1-ethyl-2-(trifluoromethyl)-1H-benzo[d]imidazol-5-yl)ethynyl)-5-(methylamino)-1H-pyrazole-4-carboxamide (97.3 mg, 38%) as a white solid. MS ESI calculated for $C_{26}H_{28}F_3N_7O_3$ $[M+H]^+$, 544.22; found 544.25. H-NMR (300 MHz, DMSO-$d_6$) δ 8.11 (s, 1H), 7.93 (d, J=8.6 Hz, 1H), 7.75-7.55 (m, 1H), 7.35 (s, 1H), 6.98-6.51 (m, 3H), 6.18 (d, J=16.6 Hz, 1H), 5.70 (d, J=10.4 Hz, 1H), 5.26 (s, 1H), 4.35-4.60 (m, 3H), 4.14-3.66 (m, 2H), 3.65-3.39 (m, 2H), 3.31-3.27 (m, 3H), 2.95 (t, J=4.4 Hz, 3H), 2.50-2.46 (m, 1H), 2.25-2.58 (m, 1H), 1.41 (t, J=7.1 Hz, 3H).

Example 28: 1-((3S,5R)-1-acryloyl-5-(methoxymethyl)pyrrolidin-3-yl)-3-((6-fluoro-1,2-dimethyl-1H-benzo[d]imidazol-5-yl)ethynyl)-5-(methylamino)-1H-pyrazole-4-carboxamide

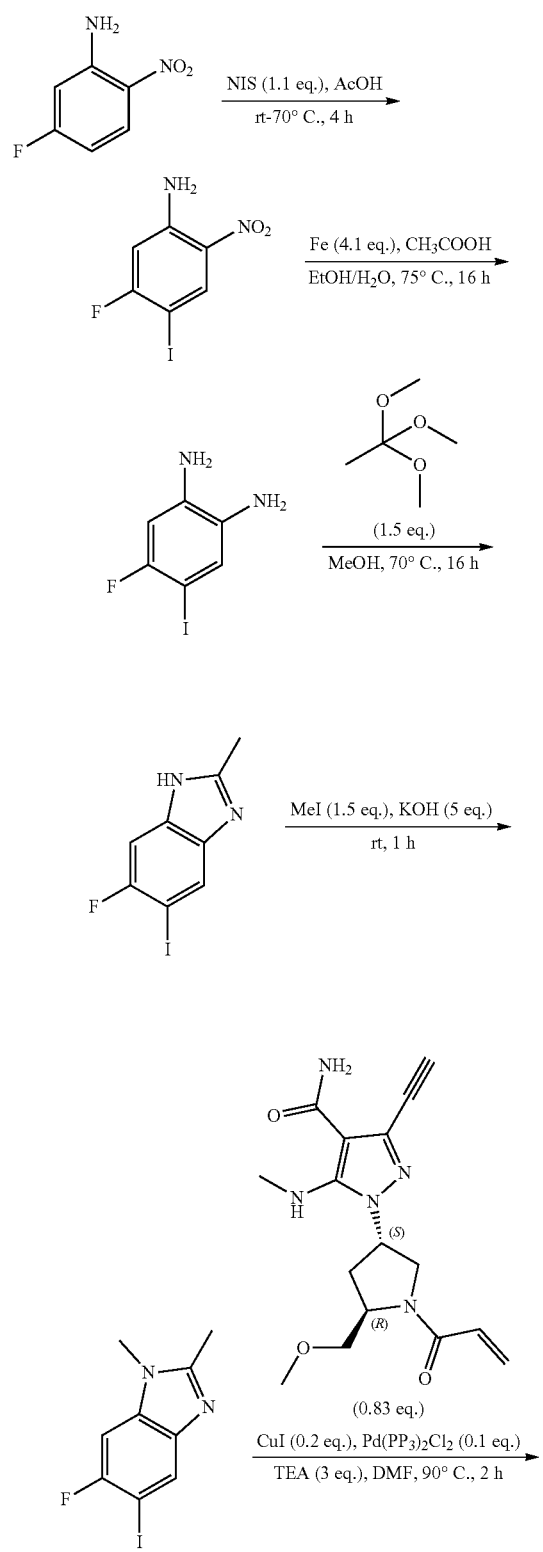

-continued

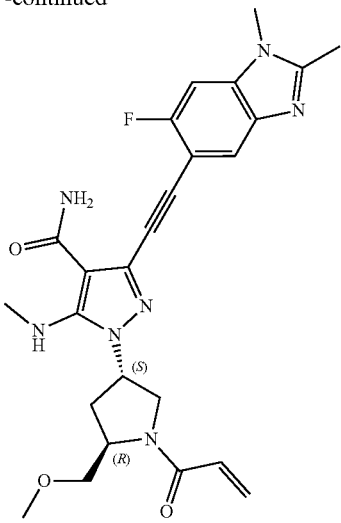

Step 1: 5-fluoro-4-iodo-2-nitroaniline

To a mixture of 5-fluoro-2-nitroaniline (15.00 g, 96.08 mmol) in AcOH (120.00 mL) was added NIS (22.70 g, 100.88 mmol). The reaction mixture was stirred for 4 h at 70° C. The resulting mixture was concentrated under reduced pressure. The residue was diluted with EtOAc (50 mL). The mixture was basified to pH 8 with saturated NaHCO$_3$ (aq.). The resulting mixture was extracted with EtOAc (3×200 mL). The combined organic layers were washed with brine (300 mL), dried over anhydrous Na$_2$SO$_4$ and filtered. The filtrate was concentrated under reduced pressure. The residue was purified by silica gel column chromatography, eluted with PE/EtOAc (9:1). The fractions contained desired product were combined and concentrated to afford 5-fluoro-4-iodo-2-nitroaniline (24 g, 79%) as a yellow solid. MS ESI calculated for C$_6$H$_4$FIN$_2$O$_2$ [M−H]$^-$, 280.93; found 281.00.

Step 2: 4-fluoro-5-iodobenzene-1,2-diamine

To a stirred mixture of 5-fluoro-4-iodo-2-nitroaniline (10.00 g, 35.46 mmol) and NH$_4$Cl (9.48 g, 177.29 mmol) in EtOH (100.00 mL) and H$_2$O (15.00 mL) was added Fe (8.12 g, 145.38 mmol). The reaction mixture was stirred for 16 h at 75° C. under nitrogen atmosphere. The resulting mixture was filtered, the filter cake was washed with ethanol (3×500 mL). The filtrate was concentrated under reduced pressure. The residue was diluted with water (200 mL). The resulting mixture was extracted with EtOAc (3×200 mL). The combined organic layers were washed with brine (500 mL), dried over anhydrous Na$_2$SO$_4$ and filtered. The filtrate was concentrated under reduced pressure and dried to afford 4-fluoro-5-iodobenzene-1,2-diamine (10 g, 89%) as a black solid which was used in the next step directly without further purification. MS ESI calculated for C$_6$H$_6$FIN$_2$ [M+H]$^+$, 252.96, found 253.00.

Step 3: 5-fluoro-6-iodo-2-methyl-3H-1,3-benzodiazole

To a solution of 4-fluoro-5-iodobenzene-1,2-diamine (3.17 g, 12.58 mmol) and in MeOH (30 mL) was added 1,1,1-trimethoxyethane (2.27 g, 18.87 mmol). The reaction mixture was stirred for overnight at 70° C. under nitrogen atmosphere. The resulting mixture was concentrated under reduced pressure. The residue was purified by silica gel column chromatography, eluted with CH$_2$Cl$_2$/MeOH (10:1). The fractions contained desired product were combined and concentrated to afford 5-fluoro-6-iodo-2-methyl-3H-1,3-benzodiazole (2.9 g, 83%) as a light yellow solid. MS ESI calculated for C$_8$H$_6$FIN$_2$ [M+H]$^+$, 276.96, found 277.00.

Step 4: 6-fluoro-5-iodo-1,2-dimethyl-1,3-benzodiazole

To a stirred mixture of 5-fluoro-6-iodo-2-methyl-3H-1,3-benzodiazole (1 g, 3.62 mmol) and KOH (1.01 g, 18.00 mmol) in acetone was added methyl iodide (0.36 mL) dropwise at 0° C. under nitrogen atmosphere. The reaction mixture was stirred for 1 h at room temperature. The resulting mixture was filtered, the filter cake was washed with ethyl acetate (3×10 mL). The filtrate was concentrated under reduced pressure. The residue was purified by silica gel column chromatography, eluted with CH$_2$Cl$_2$/MeOH (10:1). The fractions contained desired product were combined and concentrated. The residue was purified by Prep-SFC with the following conditions Column: CHIRALPAK IF, 5*25 cm, 5 um; Mobile Phase A: CO$_2$, Mobile Phase B: MeOH (0.1% 2 M NH$_3$-MEOH); Flow rate: 180 mL/min; Gradient: 40% B; 220 nm; RT1:5.22; RT2:6.2. The fractions contained desired product were combined and concentrated to afford 6-fluoro-5-iodo-1,2-dimethyl-1,3-benzodiazole (0.47 g, 44%) as an off-white solid. MS ESI calculated for C$_9$H$_8$FIN$_2$ [M+H]$^+$, 476.23, found 476.25.

Step 5: 3-[2-(6-fluoro-1,2-dimethyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide To a stirred mixture of 3-ethynyl-1-[(3S,5R)-5-(methoxymethyl)-1-(prop-2-enoyl)pyrrolidin-3-yl]-5-(methylamino)pyrazole-4-carboxamide (0.15 g, 0.45 mmol), 6-fluoro-5-iodo-1,2-dimethyl-1,3-benzodiazole (0.16 g, 0.54 mmol), Pd(PPh$_3$)$_2$Cl$_2$ (31.77 mg, 0.05 mmol) and CuI (17.24 mg, 0.09 mmol) in DMF (1.50 mL, 20.52 mmol) was added TEA (0.19 mL, 1.86 mmol). The reaction mixture was degassed with argon for three times and stirred for 2 h at 90° C. The residue was purified by Prep-HPLC with the following conditions Column: XBridge Prep OBD C18 Column, 19*250 mm, 5 um; Mobile Phase A: Water (10 mmol/L NH$_4$HCO$_3$), Mobile Phase B: ACN; Flow rate: 20 mL/min; Gradient: 50 B to 80 B in 4.3 min; 210/254 nm; RT1: 4.03. The fractions contained desired product were combined and concentrated. The crude product (70 mg) was purified by Prep-HPLC with the following conditions Column: XBridge Prep C18 OBD Column, 19×150 mm 5 um; Mobile Phase A: Water (10 mmol/L NH$_4$HCO$_3$), Mobile Phase B: ACN; Flow rate: 20 mL/min; Gradient: 25 B to 50 B in 4.3 min; 210/254 nm. The fractions contained product were combined and concentrated to afford 3-[2-(6-fluoro-1,2-dimethyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (58 mg, 25%) as an off-white solid. MS ESI calculated for C$_{25}$H$_{28}$FN$_7$O$_3$ [M+H]$^+$, 494.22, found 494.30. H-NMR (400 MHz, DMSO-d$_6$): δ 7.78 (dd, J=6.3, 1.2 Hz, 1H), 7.61 (d, J=9.9 Hz, 1H), 7.49 (s, 1H), 6.79-6.52 (m, 3H), 6.18-6.16 (m, 1H), 5.72-5.67 (m, 1H), 5.28-5.25 (m, 1H), 4.55-4.42 (m, 1H), 4.06-

3.56 (m, 5H), 3.52-3.42 (m, 2H), 3.35-3.28 (m, 3H), 2.99-2.93 (m, 3H), 2.53 (s, 3H), 2.49-2.43 (m, 1H), 2.35-2.27 (m, 1H).

Example 29: 1-((3S,5R)-1-acryloyl-5-(methoxymethyl)pyrrolidin-3-yl)-3-((1-ethyl-4,6-difluoro-1H-benzo[d]imidazol-5-yl)ethynyl)-5-(methylamino)-1H-pyrazole-4-carboxamide

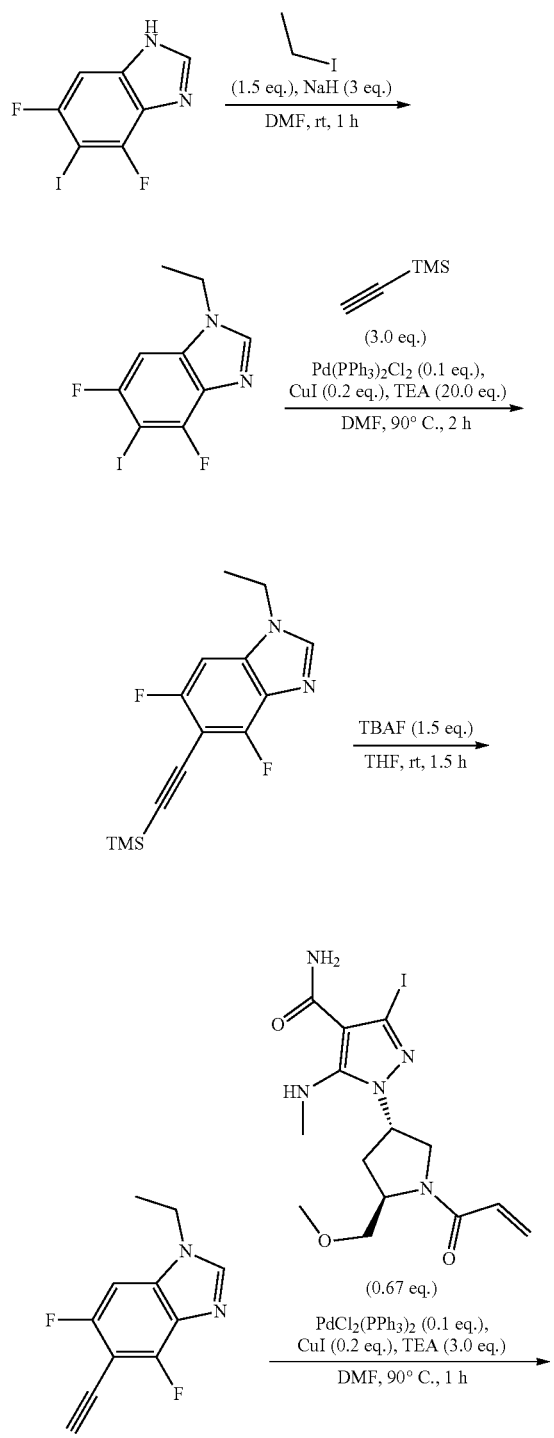

-continued

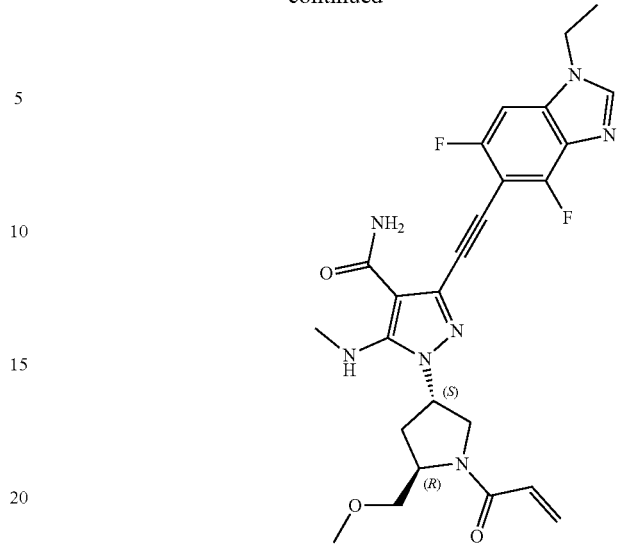

Step 1: 1-ethyl-4,6-difluoro-5-iodo-1,3-benzodiazole

To a solution of 4,6-difluoro-5-iodo-1H-1,3-benzodiazole (1.00 g, 0.004 mmol) in DMF was added sodium hydride (60% in oil, 0.26 g) at 0° C. The mixture was stirred for 15 min. To the above mixture was added ethyl iodide (1.67 g, 0.01 mmol). The reaction mixture was stirred for 1 h at rt. The resulting mixture was quenched by water and extracted with EA (3×50 mL). The combined organic layers was dried over anhydrous $Na_2SO_4$ and filtered. The filtrate was concentrated under reduced pressure. The residue was purified by silica gel column chromatography, eluted with $CH_2Cl_2$/EtOAc (5:1). The fractions contained desired product were combined and concentrated to afford 1-ethyl-4,6-difluoro-5-iodo-1,3-benzodiazole (0.4 g, 36%) as an off-white solid. MS ESI calculated for $C_9H_7F_2IN_2$ [M+H]$^+$, 308.96, found 308.90.

Step 2: 1-ethyl-4,6-difluoro-5-[2-(trimethylsilyl)ethynyl]-1,3-benzodiazole

To a mixture of 1-ethyl-4,6-difluoro-5-iodo-1,3-benzodiazole (0.40 g, 1.29 mmol), trimethylsilylacetylene (0.38 g, 3.90 mmol), CuI (49.46 mg, 0.26 mmol) and $Pd(PPh_3)_2Cl_2$ (91.14 mg, 0.13 mmol) in DMF (4.00 mL) was added TEA (2.63 g, 25.97 mmol). The reaction mixture was degassed with argon for three times and stirred for 2 h at 90° C. The resulting mixture was diluted with water (50 mL), extracted with EtOAc (3×50 mL). The combined organic layers were washed with water (3×30 mL), dried over anhydrous $Na_2SO_4$ and filtered. The filtrate was concentrated under reduced pressure. The residue was purified by silica gel column chromatography, eluted with PE/EtOAc (1:1). The fractions contained desired product were combined and concentrated to afford 1-ethyl-4,6-difluoro-5-[2-(trimethylsilyl)ethynyl]-1,3-benzodiazole (0.30 g, 83%) as a yellow oil. MS ESI calculated for $C_{10}H_6F_2N_2$ [M+H]$^+$, 279.11, found 279.25.

Step 3: 1-ethyl-5-ethynyl-4,6-difluoro-1,3-benzodiazole

To a stirred solution of 1-ethyl-4,6-difluoro-5-[2-(trimethylsilyl)ethynyl]-1,3-benzodiazole (0.30 g, 1.08 mmol) in THF (3.00 mL) was added TBAF (1.62 mL, 1.62 mmol) dropwise at 0° C. under air atmosphere. The reaction mixture was stirred for 1.5 h at room temperature. The resulting mixture was concentrated under reduced pressure. The residue was purified by silica gel column chromatography, eluted with PE/EtOAc (1:1). The fractions contained desired product were combined and concentrated to afford 1-ethyl-5-ethynyl-4,6-difluoro-1,3-benzodiazole (0.18 g, 81%) as a light yellow solid. MS ESI calculated for $C_{11}H_8F_2N_2$ [M+H]$^+$, 207.07, found 207.05.

Step 4: 3-[2-(1-ethyl-4,6-difluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide To a stirred mixture of 3-iodo-1-[(3S,5R)-5-(methoxymethyl)-1-(prop-2-enoyl)pyrrolidin-3-yl]-5-(methylamino)pyrazole-4-carboxamide (0.15 g, 0.35 mmol), 1-ethyl-5-ethynyl-4,6-difluoro-1,3-benzodiazole (0.14 g, 0.692 mmol), Pd(PPh$_3$)$_2$Cl$_2$ (24.30 mg, 0.04 mmol) and CuI (13.19 mg, 0.069 mmol) in DMF (2.00 mL) was added TEA (0.11 g, 1.04 mmol). The reaction mixture was degassed with argon for three times and stirred for 1 h at 90° C. The resulting mixture was purified by reverse flash chromatography with the following conditions: column, C18 silica gel; mobile phase, ACN in water (10 mM NH$_4$HCO$_3$), 5% to 35% gradient in 30 min; detector, UV 254 nm. The fractions contained desired product were combined and concentrated. The crude product (130 mg) was purified by Prep-HPLC with the following conditions Column: XBridge Prep OBD C18 Column, 19*250 mm, 5 um; Mobile Phase A: Water (10 mmol/L NH$_4$HCO$_3$), Mobile Phase B: ACN; Flow rate: 20 mL/min; Gradient: 30 B to 60 B in 5.8 min; 210/254 nm; RT1:5.56. The fractions contained desired product were combined and concentrated to afford 3-[2-(1-ethyl-4,6-difluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (91 mg, 51%) as a white solid. MS ESI calculated for $C_{25}H_{27}F_2N_7O_3$ [M+H]$^+$, 512.21, found 512.20. H-NMR (400 MHz, DMSO-d$_6$): δ 8.46 (s, 1H), 7.73-7.70 (m, 1H), 7.58 (s, 1H), 6.78-6.55 (m, 3H), 6.18-6.25 (m, 1H), 5.71-5.68 (m, 1H), 5.29-5.26 (m, 1H), 4.60-4.36 (m, 1H), 4.30 (q, J=7.3 Hz, 2H), 4.08-3.69 (m, 2H), 3.65-3.41 (m, 2H), 3.35-3.30 (m, 3H), 2.97 (t, J=5.3 Hz, 3H), 2.71-2.58 (m, 1H), 2.33-2.30 (m, 1H), 1.41 (t, J=7.2 Hz, 3H).

Example 30: 1-((3S,5R)-1-acryloyl-5-(methoxymethyl)pyrrolidin-3-yl)-3-((1-(difluoromethyl)-4,6-difluoro-1H-benzo[d]imidazol-5-yl)ethynyl)-5-(methylamino)-1H-pyrazole-4-carboxamide

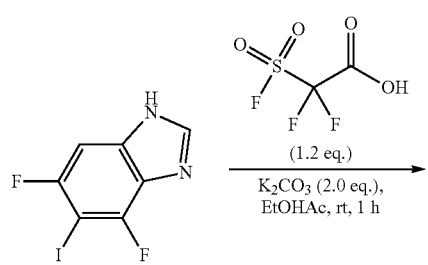

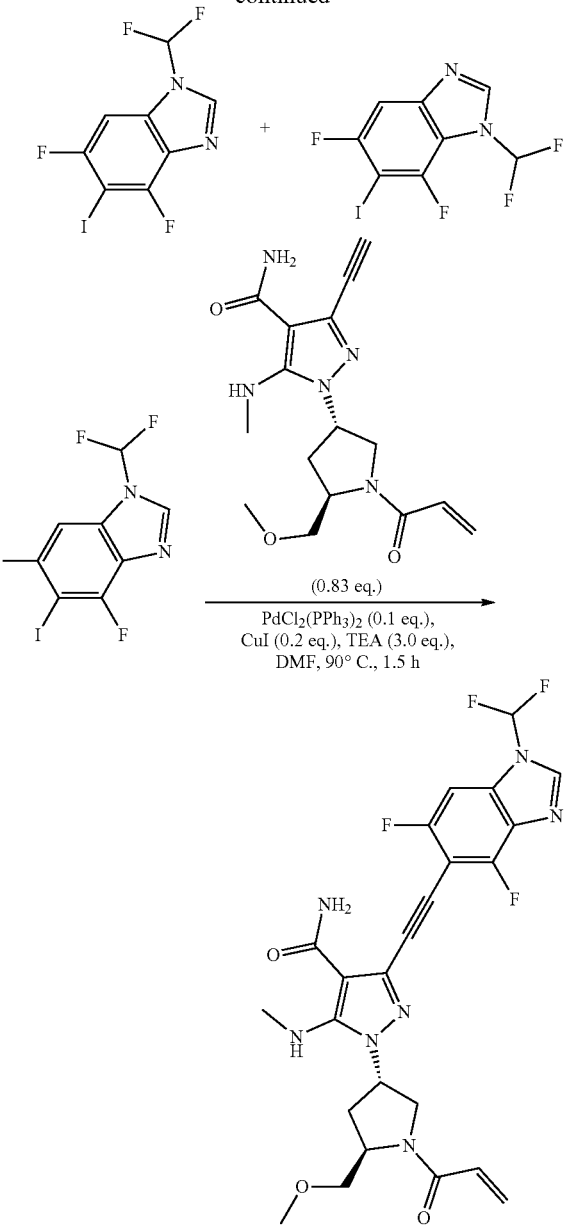

Step 1: 1-(difluoromethyl)-4,6-difluoro-5-iodo-1,3-benzodiazole

To a stirred solution of 4,6-difluoro-5-iodo-1H-1,3-benzodiazole (1.00 g, 3.57 mmol) in EA (8.00 mL) were added difluoro(sulfo)acetic acid (0.76 g, 4.28 mmol) and K$_2$CO$_3$ (1.48 g, 10.71 mmol) at room temperature. The reaction mixture was stirred at room temperature for 1 h. The resulting mixture was quenched by saturated aqueous sodium bicarbonate (30 mL). The organic layer was separated and the aqueous layer was extracted with EA (3×45 mL). The combined organic layers were washed with brine (2×45 mL), dried over anhydrous sodium sulfate and filtered. The filtrate was concentrated under reduced pressure. The residue was purified by silica gel column chromatography, eluted with EA in DCM (0-50%). The fractions contained desired product were combined and concentrated.

The crude product was further separated by Prep-Achiral-SFC with the following conditions Column: BEH 2-Ethlpyridine, 30*150 mm, 5 μm; Mobile Phase A: $CO_2$, Mobile Phase B: MeOH (0.1% 2 M $NH_3$-MeOH); Flow rate: 45 mL/min; Gradient: 10% B; Detector: UV 254 nm). The faster fractions (RT: 2.93 min) contained the desired product were combined and concentrated under reduced pressure to afford 1-(difluoromethyl)-4,6-difluoro-5-iodo-1,3-benzodiazole (0.45 g, 37%) as a white solid. The slower fractions (RT: 3.50 min) contained the desired product were combined and concentrated under reduced pressure to afford 1-(difluoromethyl)-5,7-difluoro-6-iodo-1,3-benzodiazole (0.15 g, 12%) as a white solid. MS ESI calculated for $C_8H_3F_4IN_2$ [M+H]$^+$, 330.93, found 330.95.

Step 2: 3-[2-[1-(difluoromethyl)-4,6-difluoro-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide To a stirred mixture of 1-(difluoromethyl)-4,6-difluoro-5-iodo-1,3-benzodiazole (0.18 g, 0.54 mmol) and 3-ethynyl-1-[(3S,5R)-5-(methoxymethyl)-1-(prop-2-enoyl)pyrrolidin-3-yl]-5-(methylamino)pyrazole-4-carboxamide (0.15 g, 0.45 mmol) in DMF (4.00 mL) were added Pd(PPh$_3$)$_2$Cl$_2$ (44.29 mg, 0.05 mmol), CuI (20.66 mg, 0.11 mmol) and TEA (0.16 g, 1.63 mmol). The reaction mixture was degassed with argon for three times and stirred for 1.5 h at 90° C. The resulting mixture was concentrated under reduced pressure. The residue was purified by silica gel column chromatography, eluted with MeOH in DCM (0-4.8%). The fractions contained desired product were combined and concentrated. The crude product was further purified by Prep-HPLC with the following conditions Column: XBridge Prep C18 OBD Column, 19×150 mm, 5 μm; Mobile Phase A: Water (10 mM NH$_4$HCO$_3$), Mobile Phase B: ACN; Flow rate: 20 mL/min; Gradient: 30% B to 60% B in 4.3 min; Detector: UV 210 & 254 nm; RT: 4.02 min. The fractions contained desired product were combined and concentrated under reduced pressure to afford 3-[2-[1-(difluoromethyl)-4,6-difluoro-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide (44.8 mg, 15%) as a white solid. MS ESI calculated for $C_{24}H_{23}F_4N_7O_3$ [M+H]$^+$, 534.18, found 534.25. H-NMR (400 MHz, d$_6$-DMSO) δ 8.79 (s, 1H), 8.11 (t, J=58.4 Hz, 1H), 7.75 (d, J=8.4 Hz, 1H), 7.56 (brs, 1H), 6.71-6.55 (m, 3H), 6.17 (d, J=16.9 Hz, 1H), 5.69 (d, J=10.3 Hz, 1H), 5.28 (s, 1H), 4.53-4.39 (m, 1H), 4.02-3.72 (m, 2H), 3.60-3.45 (m, 2H), 3.32 (s, 3H), 2.96 (s, 3H), 2.67-2.61 (m, 1H), 2.33-2.30 (m, 1H).

Example 31: 1-((3S,5R)-1-acryloyl-5-(methoxymethyl)pyrrolidin-3-yl)-3-((1-(difluoromethyl)-4,6-difluoro-2-methyl-1H-benzo[d]imidazol-5-yl)ethynyl)-5-(methylamino)-1H-pyrazole-4-carboxamide

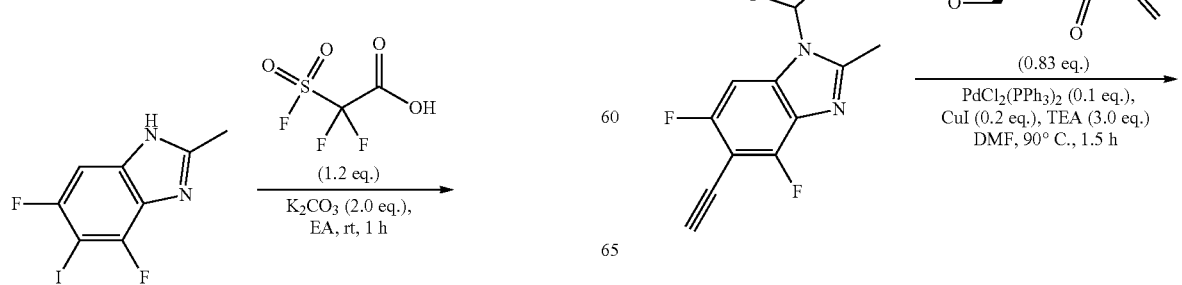

-continued

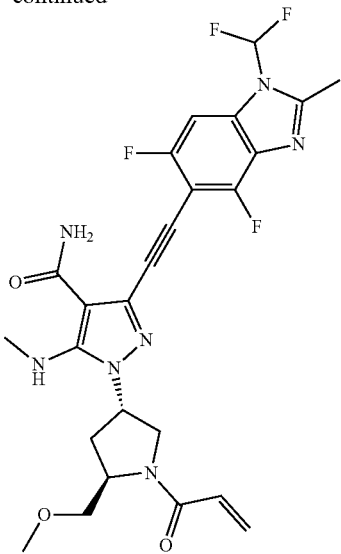

Step 1: 1-(difluoromethyl)-4,6-difluoro-5-iodo-2-methyl-1,3-benzodiazole

To a stirred solution of 4,6-difluoro-5-iodo-2-methyl-1H-1,3-benzodiazole (0.20 g, 0.68 mmol) and $K_2CO_3$ (0.19 g, 1.36 mmol) in EA (3.00 mL) was added difluoro(sulfo)acetic acid (0.15 g, 0.82 mmol) dropwise at 0° C. The reaction mixture was stirred for 1 h at ambient temperature. The resulting mixture was diluted with water (10 mL) and extracted with EA (3×10 mL). The combined organic layers were washed with brine (2×10 mL), dried over anhydrous $Na_2SO_4$ and filtered. The filtrate was concentrated under reduced pressure. The residue was purified by silica gel column chromatography, eluted with EA in PE (10-35%). The fractions contained desired product were combined and concentrated to afford 1-(difluoromethyl)-4,6-difluoro-5-iodo-2-methyl-1,3-benzodiazole (80 mg, 34%) as a light yellow solid. MS ESI calculated for $C_9H_5F_4IN_2$ $[M+H]^+$, 344.95, found 345.00.

Step 2: 1-(difluoromethyl)-4,6-difluoro-2-methyl-5-[2-(trimethylsilyl)ethynyl]-1,3-benzodiazole To a stirred mixture of 1-(difluoromethyl)-4,6-difluoro-5-iodo-2-methyl-1,3-benzodiazole (0.61 g, 1.77 mmol), trimethylsilylacetylene (0.52 g, 5.32 mmol), $PdCl_2(PPh_3)_2$ (0.12 g, 0.18 mmol) and CuI (67.53 mg, 0.36 mmol) in DMF (8.00 mL) was added TEA (0.36 g, 3.55 mmol). The reaction mixture was degassed with argon for three times and stirred for 2 h at 90° C. After cooling down to ambient temperature, the resulting mixture was diluted with water (20 mL) and extracted with EA (3×25 mL). The combined organic layers were washed with brine (2×30 mL), dried over anhydrous $Na_2SO_4$ and filtered. The filtrate was concentrated under reduced pressure. The residue was purified by silica gel column chromatography, eluted of EA in PE (20-50%). The fractions contained desired product were combined and concentrated under reduced pressure to afford 1-(difluoromethyl)-4,6-difluoro-2-methyl-5-[2-(trimethylsilyl)ethynyl]-1,3-benzodiazole (0.5 g, 89%) as a yellow solid. MS ESI calculated for $C_{14}H_{14}F_4N_2Si$ $[M+H]^+$, 315.09, found 315.15.

Step 3: 1-(difluoromethyl)-5-ethynyl-4,6-difluoro-2-methyl-1,3-benzodiazole

To a stirred solution of 1-(difluoromethyl)-4,6-difluoro-2-methyl-5-[2-(trimethylsilyl)ethynyl]-1,3-benzodiazole (0.50 g, 1.59 mmol) in THF (5.00 mL) was added TBAF (1.0 M in THF, 2.40 mL, 2.40 mmol) dropwise at 0° C. The reaction mixture was stirred for 2 h at ambient temperature under argon atmosphere. The resulting mixture was diluted with water (20 mL) and extracted with EA (3×20 mL). The combined organic layers were washed with brine (30 mL), dried over anhydrous $Na_2SO_4$ and filtered. The filtrate was concentrated under reduced pressure. The residue was purified by silica gel column chromatography, eluted with EA in PE (50-90%). The fractions contained desired product were combined and concentrated under reduced pressure to afford 1-(difluoromethyl)-5-ethynyl-4,6-difluoro-2-methyl-1,3-benzodiazole (0.33 g, 85%) as a yellow solid. MS ESI calculated for $C_{11}H_6F_4N_2$ $[M+H]^+$, 243.05, found 242.85.

Step 4: 3-[2-[1-(difluoromethyl)-4,6-difluoro-2-methyl-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide To a mixture of 3-iodo-1-[(3S,5R)-5-(methoxymethyl)-1-(prop-2-enoyl)pyrrolidin-3-yl]-5-(methylamino)pyrazole-4-carboxamide (0.13 g, 0.30 mmol), 1-(difluoromethyl)-5-ethynyl-4,6-difluoro-2-methyl-1,3-benzodiazole (87.20 mg, 0.36 mmol), $PdCl_2(PPh_3)_2$ (21.06 mg, 0.03 mmol) and CuI (11.43 mg, 0.06 mmol) in DMF (2.00 mL) was added TEA (60.73 mg, 0.60 mmol). The reaction mixture was degassed with argon for three times and stirred for 1.5 h at 90° C. After cooling down to ambient temperature, the resulting mixture was concentrated under reduced pressure. The residue was purified by silica gel column chromatography, eluting with MeOH in DCM (0-5.0%) to afford crude product. The crude product was further purified by Prep-HPLC with the following conditions Column: XBridge Prep C18 OBD Column, 19×150 mm 5 um; Mobile Phase A: Water (10 mM $NH_4HCO_3$), Mobile Phase B: ACN; Flow rate: 20 mL/min; Gradient: 25% B to 50% B in 4.3 min; Detector: UV 210 & 254 nm; RT: 4.02 min. The fractions contained desired product were combined and concentrated under reduced pressure to afford 3-[2-[1-(difluoromethyl)-4,6-difluoro-2-methyl-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide (86 mg, 52%) as a white solid. MS ESI calculated for $C_{25}H_{25}F_4N_7O_3$ $[M+H]^+$, 548.20, found 548.05. H NMR (400 MHz, $d_6$-DMSO) δ 8.11 (t, J=57.2 Hz, 1H), 7.67 (d, J=8.8 Hz, 1H), 7.56 (brs, 1H), 6.75-6.56 (m, 3H), 6.18-6.15 (m, 1H), 5.71-5.68 (m, 1H), 5.32-5.20 (m, 1H), 4.55-4.36 (m, 1H), 4.05-3.71 (m, 2H), 3.62-3.44 (m, 2H), 3.30 (d, J=5.7 Hz, 3H), 2.96 (t, J=5.5 Hz, 3H), 2.69 (s, 3H), 2.67-2.46 (m, 1H), 2.34-2.27 (m, 1H).

Example 32: 1-((3S,5R)-1-acryloyl-5-(methoxymethyl)pyrrolidin-3-yl)-3-((1-ethyl-6-fluoro-1H-benzo[d]imidazol-5-yl)ethynyl)-5-(methylamino)-1H-pyrazole-4-carboxamide

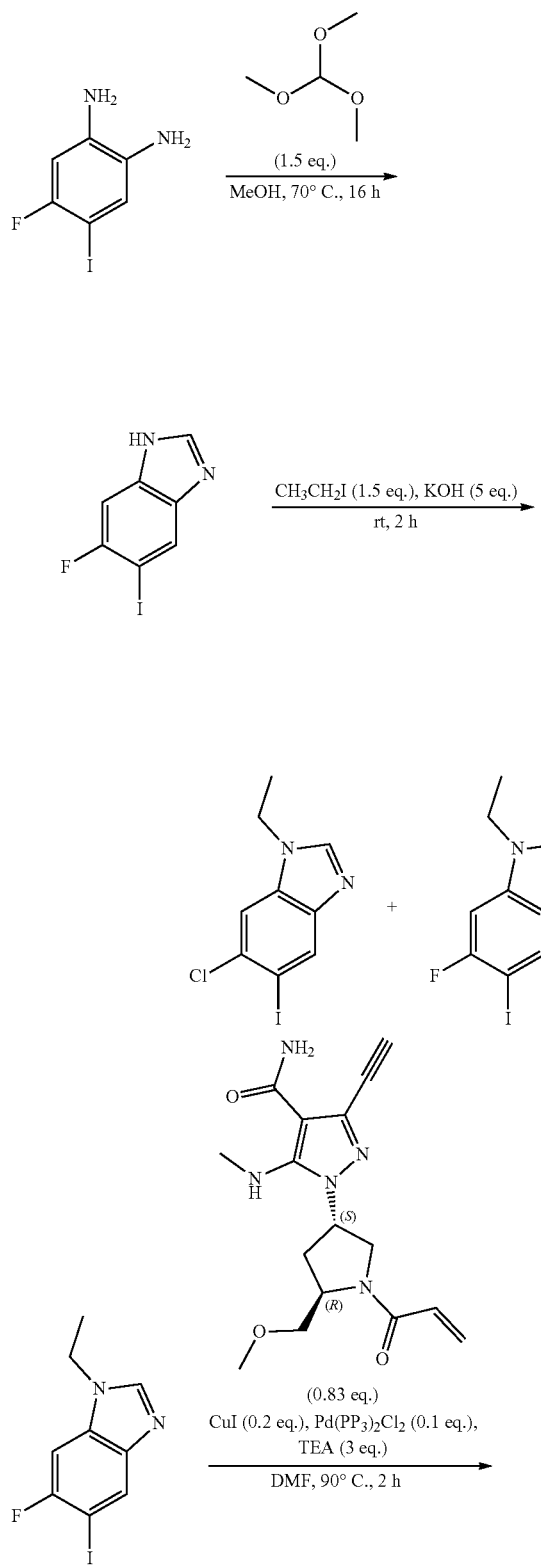

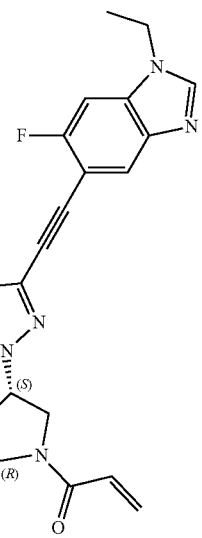

Step 1: 5-fluoro-6-iodo-3H-1,3-benzodiazole

To a solution of 4-fluoro-5-iodobenzene-1,2-diamine (3.17 g, 12.58 mmol) in MeOH (30 mL) was added trimethyl orthoformate (2.00 g, 18.85 mmol). The reaction mixture was stirred for overnight at 70° C. under nitrogen atmosphere. The resulting mixture was concentrated under reduced pressure. The residue was purified by silica gel column chromatography, eluted with $CH_2Cl_2$/MeOH (10:1). The fractions contained desired product were combined and concentrated to afford 5-fluoro-6-iodo-3H-1,3-benzodiazole (2.9 g, 88%) as a light brown solid. MS ESI calculated for $C_7H_4FIN_2$ [M+H]$^+$, 262.94; found 262.95.

Step 2: 1-ethyl-6-fluoro-5-iodo-1,3-benzodiazole

To a stirred solution of 5-fluoro-6-iodo-3H-1,3-benzodiazole (1.10 g, 4.20 mmol) and KOH (1.18 g, 20.99 mmol) in acetone (16.50 mL) was added iodoethane (0.50 mL, 3.23 mmol) dropwise at 0° C. under nitrogen atmosphere. The reaction mixture was stirred for 2 h at room temperature. The resulting mixture was diluted with water (100 mL), extracted with EtOAc (3×100 mL). The combined organic layers were washed with brine (100 mL), dried over anhydrous $Na_2SO_4$ and filtered. The filtrate was concentrated under reduced pressure. The residue was purified by silica gel column chromatography, eluted with $CH_2Cl_2$/MeOH (15:1). The fractions contained desired product were combined and concentrated to afford 1.4 g crude product. The crude product was purified by Prep-Achiral-SFC with the following conditions Column: CHIRAL ART Cellulose-SB, 3*25 cm, 5 um; Mobile Phase A: $CO_2$, Mobile Phase B: MeOH (0.1% 2M $NH_3$-MeOH); Flow rate: 100 mL/min; Gradient: 20% B; 220 nm; RT1: 3.7; RT2: 4.3; Injection Volume: 2 ml; Number Of Runs: 20;). The fractions contained desired product (last peak RT2: 4.3) were combined and concentrated to afford 1-ethyl-6-fluoro-5-iodo-1,3-benzodiazole (0.44 g, 32%) as a light brown solid.

Step 3: 3-[2-(1-ethyl-6-fluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide To a stirred mixture of 3-ethynyl-1-[(3S,5R)-5-(methoxymethyl)-1-(prop-2-enoyl)pyrrolidin-3-yl]-5-

(methylamino)pyrazole-4-carboxamide (0.18 g, 0.54 mmol), 1-ethyl-6-fluoro-5-iodo-1,3-benzodiazole (0.19 g, 0.65 mmol), Pd(PPh$_3$)$_2$Cl$_2$ (38.13 mg, 0.05 mmol) and CuI (20.69 mg, 0.11 mmol) in DMF (2.00 mL) was added TEA (0.23 mL, 2.24 mmol). The reaction mixture was degassed with argon for three times and stirred for 2 h at 90° C. The resulting mixture was concentrated under reduced pressure. The residue was purified by silica gel column chromatography, eluted with 6% MeOH in DCM. The fractions contained desired product were combined and concentrated. The crude product (200 mg) was purified by Prep-HPLC with the following conditions Column: XBridge Prep C18 OBD Column, 19×150 mm 5 um; Mobile Phase A: Water (10 mmol/L NH$_4$HCO$_3$), Mobile Phase B: ACN; Flow rate: 20 mL/min; Gradient: 25 B to 55 B in 4.3 min; 210/254 nm; RT1: 4.02. The fractions contained desired product were combined and concentrated to afford 3-[2-(1-ethyl-6-fluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (62.9 mg, 23%) as an off-white solid. MS ESI calculated for C$_{25}$H$_{28}$FN$_7$O$_3$ [M+H]$^+$, 494.22, found 494.25. H-NMR (400 MHz, DMSO-d$_6$): δ 8.41 (s, 1H), 7.95 (d, J=6.2 Hz, 1H), 7.76 (d, J=9.7 Hz, 1H), 7.49 (s, 1H), 6.87-6.49 (m, 3H), 6.19-6.17 (m, 1H), 5.75-5.65 (m, 1H), 5.29-5.25 (m, 1H), 4.50-4.45 (m, 1H), 4.28 (q, J=7.3 Hz, 2H), 4.07-3.44 (m, 3H), 3.35-3.29 (m, 3H), 2.96 (t, J=5.2 Hz, 3H), 2.47 (t, J=7.1 Hz, 1H), 2.45-2.44 (m, 1H), 2.35-2.24 (m, 1H), 1.41 (t, J=7.3 Hz, 3H).

Example 33: 1-((3S,5R)-1-acryloyl-5-(methoxymethyl)pyrrolidin-3-yl)-3-((6-chloro-1-ethyl-2-methyl-1H-benzo[d]imidazol-5-yl)ethynyl)-5-(methylamino)-1H-pyrazole-4-carboxamide

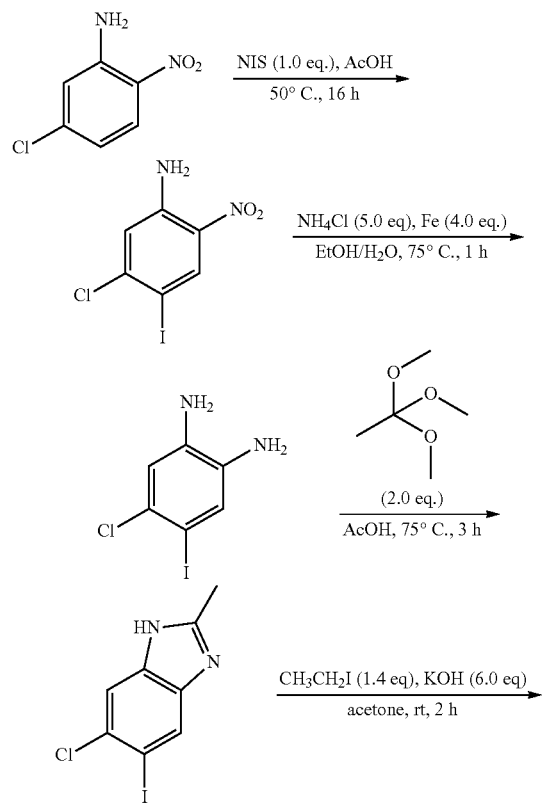

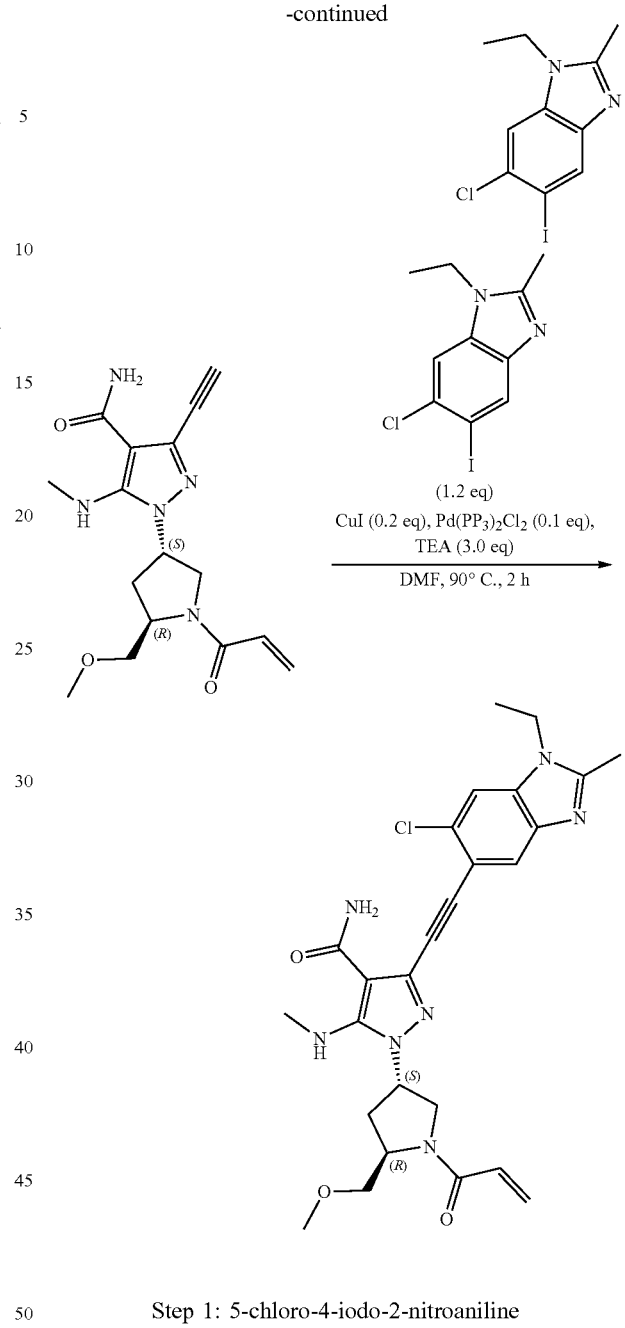

Step 1: 5-chloro-4-iodo-2-nitroaniline

To a mixture of 5-chloro-2-nitroaniline (5.00 g, 28.97 mmol) in AcOH (50.00 mL) was added NIS (6.52 g, 28.98 mmol). The reaction mixture was stirred for overnight at 50° C. under argon atmosphere. The resulting mixture was concentrated under reduced pressure. The residue was quenched by the addition of sat. NaHCO$_3$ (aq.) (100 mL) at room temperature. The resulting mixture was extracted with EtOAc (2×300 mL). The combined organic layers were washed with water (2×150 mL), dried over anhydrous Na$_2$SO$_4$. and filtered. The filtrate was concentrated under reduced pressure. The residue was purified by silica gel column chromatography, eluted with PE/EtOAc (6:1). The fractions contained desired product were combined and concentrated to afford 5-chloro-4-iodo-2-nitroaniline (7.6 g, 87%) as a light yellow solid. H-NMR (400 MHz, DMSO-d$_6$) δ 8.36 (s, 1H), 7.60 (s, 2H), 7.27 (s, 1H).

Step 2: 4-chloro-5-iodobenzene-1,2-diamine

To a mixture of Fe (5.61 g, 100.46 mmol) and 5-chloro-4-iodo-2-nitroaniline (7.50 g, 25.13 mmol) in EtOH (100.00 mL) and H₂O (25.00 mL) was added NH₄Cl (6.72 g, 125.63 mmol, 5.00 equiv). The reaction mixture was stirred for 1 h at 75° C. under argon atmosphere. The resulting mixture was filtered, the filter cake was washed with MeOH (3×100 mL). The filtrate was concentrated under reduced pressure. The resulting mixture was extracted with EA (2×200 mL). The combined organic layers were washed with EtOAc (2×200 mL), dried over anhydrous Na₂SO₄ and filtered. The filtrate was concentrated under reduced pressure to afford 4-chloro-5-iodobenzene-1,2-diamine (6.6 g, 97.83%) as a yellow solid which was used in the next step directly without further purification. MS ESI calculated for $C_6H_6ClIN_2$ [M+H]⁺, 268.93, found 268.85.

Step 3: 5-chloro-6-iodo-2-methyl-3H-1,3-benzodiazole

To a solution of 4-chloro-5-iodobenzene-1,2-diamine (3.50 g, 13.04 mmol) in AcOH (40.00 mL) was added 1,1,1-trimethoxyethane (3.33 mL, 26.05 mmol). The reaction mixture was stirred for 3 h at 75° C. under argon atmosphere. The residue was neutralized to pH 7 with saturated NaHCO₃ (aq.). The resulting mixture was extracted with EtOAc (2×200 mL). The combined organic layers were washed with water (2×100 mL), dried over anhydrous Na₂SO₄ and filtered. The filtrate was concentrated under reduced pressure. The residue was purified by silica gel column chromatography, eluted with DCM/MeOH (20/1). The fractions contained desired product were combined and concentrated to afford 5-chloro-6-iodo-2-methyl-3H-1,3-benzodiazole (3.2 g, 83%) as an off-white solid. MS ESI calculated for $C_8H_6ClIN_2$ [M+H]⁺, 292.93, found 292.95.

Step 4: 6-chloro-1-ethyl-5-iodo-2-methyl-1,3-benzodiazole

To a mixture of 5-chloro-6-iodo-2-methyl-3H-1,3-benzodiazole (3.20 g, 10.94 mmol) and KOH (3.68 g, 65.59 mmol) in acetone (40.00 mL) was added iodoethane (1.28 mL, 8.19 mmol). The reaction mixture was stirred for 2 h at room temperature under argon atmosphere. The resulting mixture was concentrated under reduced pressure. The residue was extracted with EtOAc (2×300 mL). The combined organic layers were washed with water (3×100 mL), dried over anhydrous Na₂SO₄ and filtered. The filtrate was concentrated under reduced pressure. The residue was purified by silica gel column chromatography, eluted with CH₂Cl₂/MeOH (10:1). The fractions contained desired product were combined and concentrated to afford 3.8 g of mixture. The crude product (2 g) was purified by Prep-SFC with the following conditions Column: CHIRALPAK IG, 5*25 cm, 10 um; Mobile Phase A: CO₂, Mobile Phase B: MeOH (0.1% 2M NH₃-MEOH); Flow rate: 200 mL/min; Gradient: 50% B; 220 nm; RT1: 5.99; RT2: 7.74; Injection Volume: 3 ml; Number Of Runs: 17. The fractions contained desired product were combined and concentrated to afford 6-chloro-1-ethyl-5-iodo-2-methyl-1,3-benzodiazole (0.80 g, 22%) as a light yellow solid. MS ESI calculated for $C_{10}H_{10}ClIN_2$ [M+H]⁺, 320.96, found 320.95.

Step 5: 3-[2-(6-chloro-1-ethyl-2-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide To a mixture of 3-ethynyl-1-[(3S,5R)-5-(methoxymethyl)-1-(prop-2-enoyl)pyrrolidin-3-yl]-5-(methylamino)pyrazole-4-carboxamide (0.15 g, 0.45 mmol), 6-chloro-1-ethyl-5-iodo-2-methyl-1,3-benzodiazole (0.17 g, 0.54 mmol), CuI (17.24 mg, 0.09 mmol) and Pd(PPh₃)₂Cl₂ (31.77 mg, 0.05 mmol) in DMF (1.50 mL) was added TEA (0.19 mL, 1.87 mmol). The reaction mixture was degassed with argon for three times and stirred for 2 h at 90° C. The resulting mixture was concentrated under reduced pressure. The residue was purified by Prep-HPLC with the following conditions Column: XBridge Prep C18 OBD Column, 19×150 mm 5 um; Mobile Phase A: Water (10 mmol/L NH₄HCO₃), Mobile Phase B: ACN; Flow rate: 20 mL/min; Gradient: 25 B to 50 B in 4.3 min; 210/254 nm; RT1:4.23. The fractions contained desired product were combined and concentrated to afford 3-[2-(6-chloro-1-ethyl-2-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (44.4 mg, 18.72%) as an off-white solid. MS ESI calculated for $C_{26}H_{30}ClN_7O_3$ [M+H]⁺, 292.93, found 292.95. H-NMR (400 MHz, DMSO-d₆) δ 7.92-7.84 (m, 2H), 7.51 (s, 1H), 6.86 (s, 1H), 6.77-6.55 (m, 2H), 6.22-6.13 (m, 1H), 5.73-5.65 (m, 1H), 5.33-5.21 (m, 1H), 4.58-4.36 (m, 1H), 4.30-4.20 (m, 2H), 4.08-3.70 (m, 2H), 3.65-3.42 (m, 2H), 3.33 (s, 1H), 3.31 (d, J=5.4 Hz, 3H), 3.00-2.93 (m, 3H), 2.56 (s, 3H), 2.31 (m, 1H), 1.29 (t, J=7.2 Hz, 3H).

Example 34: 1-((3S,5R)-1-acryloyl-5-(methoxymethyl)pyrrolidin-3-yl)-3-((4,6-difluoro-1-(2,2,2-trifluoroethyl)-1H-benzo[d]imidazol-5-yl)ethynyl)-5-(methylamino)-1H-pyrazole-4-carboxamide

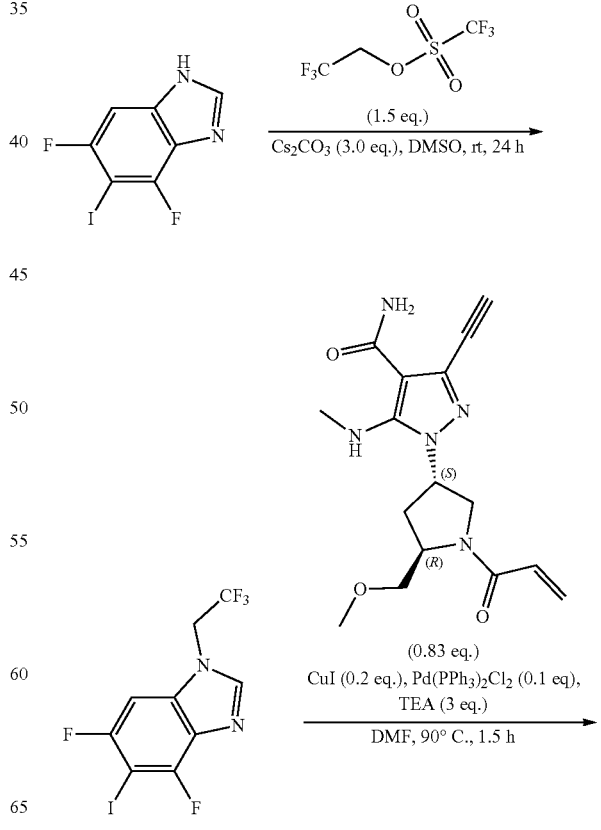

393

-continued

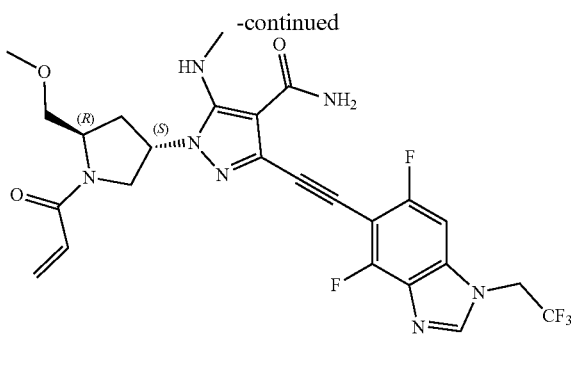

Step 1: 4,6-difluoro-5-iodo-1-(2,2,2-trifluoroethyl)-1,3-benzodiazole

To a stirred mixture of 4,6-difluoro-5-iodo-1H-1,3-benzodiazole (0.80 g, 2.86 mmol) and trifluoro(trifluoromethanesulfonylmethoxy)methane (0.99 g, 4.28 mmol) in DMSO (8.00 mL) was added $Cs_2CO_3$ (2.79 g, 8.57 mmol) at room temperature. The reaction mixture was stirred for 24 h. The reaction was quenched by the addition of water (10 mL) at room temperature. The resulting mixture was extracted with EtOAc (3×20 mL). The combined organic layers were washed with brine (3×20 mL), dried over anhydrous $Na_2SO_4$ and filtered. The filtrate was concentrated under reduced pressure. The residue was purified by SFC to afford 4,6-difluoro-5-iodo-1-(2,2,2-trifluoroethyl)-1,3-benzodiazole (0.32 g, 30%) as a light yellow solid. MS ESI calculated for $C_9H_4F_5IN_2$ [M+H]$^+$, 363.04, found 363.00.

Step 2: 3-[2-[4,6-difluoro-1-(2,2,2-trifluoroethyl)-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide To a stirred mixture of 3-ethynyl-1-[(3S,5R)-5-(methoxymethyl)-1-(prop-2-enoyl) pyrrolidin-3-yl]-5-(methylamino) pyrazole-4-carboxamide (0.15 g, 0.45 mmol), 4,6-difluoro-5-iodo-1-(2,2,2-trifluoroethyl)-1,3-benzodiazole (0.20 g, 0.54 mmol), Pd(PPh$_3$)$_2$Cl$_2$ (31.77 mg, 0.05 mmol) and CuI (17.24 mg, 0.09 mmol) in DMF (1.50 mL) were added TEA (0.14 g, 1.36 mmol). The reaction mixture was degassed with argon for three times and stirred for 1.5 h at 90° C. The resulting mixture was concentrated under reduced pressure. The residue was purified by Prep-HPLC Column: XBridge Prep C18 OBD Column, 19×150 mm 5 um; Mobile Phase A: Water (10 mmol/L NH$_4$HCO$_3$), Mobile Phase B: ACN; Flow rate: 20 mL/min; Gradient: 25 B to 55 B in 4.3 min; 210/254 nm; RT1: 4.12. The fractions contained desired product were combined and concentrated to afford 3-[2-[4,6-difluoro-1-(2,2,2-trifluoroethyl)-1,3-benzodiazol-5-yl] ethynyl]-1-[(3S,5R)-5-(methoxymethyl)-1-(prop-2-enoyl) pyrrolidin-3-yl]-5-(methylamino) pyrazole-4-carboxamide (0.10 g, 39%) as an off-white solid. MS ESI calculated for $C_{25}H_{24}F_5N_7O_3$ [M+H]$^+$, 566.19, found 566.20. $^1$H NMR (400 MHz, d$_6$-DMSO) δ 8.51 (s, 1H), 7.81 (d, J=9.1 Hz, 1H), 7.56 (s, 1H), 6.75-6.56 (m, 3H), 6.17 (d, J=16.6 Hz, 1H), 5.69 (d, J=9.5 Hz, 1H), 5.43-5.27 (m, 3H), 4.57-4.37 (m, 1H), 4.08-3.83 (m, 2H), 3.79-3.53 (m, 2H), 3.52-3.34 (m, 3H), 2.98-2.94 (m, 3H), 2.51 (m, 1H), 2.33-2.29 (m, 1H).

394

Example 35: 1-((3S,5R)-1-acryloyl-5-(methoxymethyl)pyrrolidin-3-yl)-3-((4,6-difluoro-2-methyl-1-(2,2,2-trifluoroethyl)-1H-benzo[d]imidazol-5-yl)ethynyl)-5-(methylamino)-1H-pyrazole-4-carboxamide

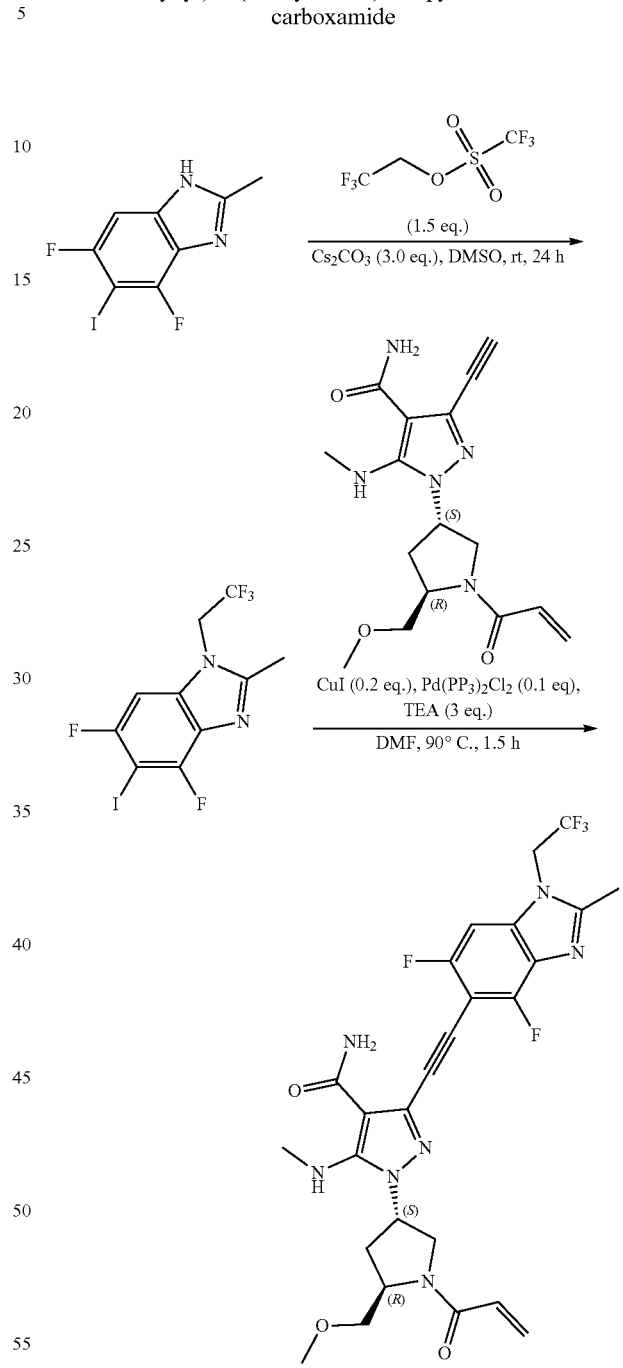

Step 1: Tert-butyl 2-(1,1-difluoroethyl)morpholine-4-carboxylate

To a stirred solution of 4,6-difluoro-5-iodo-2-methyl-1H-1,3-benzodiazole (1.00 g, 3.40 mmol) in DMSO (10.00 mL) was added trifluoro(trifluoromethanesulfonylmethoxy) methane (1.18 g, 5.10 mmol) and Cs$_2$CO$_3$ (3.32 g, 0.01 mmol) in portions at room temperature. The reaction mixture was stirred for 24 h at room temperature. The reaction was quenched by the addition of water (10 mL) at room temperature. The resulting mixture was extracted with EtOAc (3×20 mL). The combined organic layers were washed with brine (3×20 mL), dried over anhydrous $Na_2SO_4$ and filtered. The filtrate was concentrated under reduced pressure. The residue was purified by SFC Column: DAICEL DCpak P4VP (O2), 30*250 mm, 5 um; Mobile Phase A: $CO_2$, Mobile Phase B: MeOH (0.1% 2M $NH_3$-MeOH); Flow rate: 60 mL/min; Gradient: 18% B; 254 nm; RT2: 6.21; Injection Volume: 0.8 ml; Number of Runs: 15. The fractions contained desired product were combined and concentrated to afford 4,6-difluoro-5-iodo-2-methyl-1-(2,2,2-trifluoroethyl)-1,3-benzodiazole (0.42 g, 32%) as a light yellow solid. MS ESI calculated for $C_{10}H_6F_5IN_2$ [M+H]$^+$, 376.95, found 377.00.

Step 2: 3-[2-[4,6-Difluoro-2-methyl-1-(2,2,2-trifluoroethyl)-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide To a stirred mixture of 3-ethynyl-1-[(3S,5R)-5-(methoxymethyl)-1-(prop-2-enoyl)pyrrolidin-3-yl]-5-(methylamino)pyrazole-4-carboxamide (0.15 g, 0.45 mmol), 4,6-difluoro-5-iodo-2-methyl-1-(2,2,2-trifluoroethyl)-1,3-benzodiazole (0.20 g, 0.54 mmol), Pd(PPh$_3$)$_2$Cl$_2$ (31.77 mg, 0.05 mmol) and CuI (17.24 mg, 0.09 mmol) in DMF (1.50 mL) was added TEA (0.14 g, 1.36 mmol) at room temperature. The reaction mixture was degassed with argon for three times and stirred for 1.5 h at 90° C. The resulting mixture was concentrated under reduced pressure. The residue was purified by Prep-HPLC Column: XBridge Prep C18 OBD Column, 19×150 mm 5 um; Mobile Phase A: Water (10 mmol/L NH$_4$HCO$_3$), Mobile Phase B: ACN; Flow rate: 20 mL/min; Gradient: 25 B to 60 B in 4.3 min; 210/254 nm; RT1: 4.02. The fractions contained desired product were combined and concentrated to afford 3-[2-[4,6-difluoro-2-methyl-1-(2,2,2-trifluoroethyl)-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide (0.10 g, 37%) as an off-white solid. MS ESI calculated for $C_{26}H_{26}F_5N_7O_3$ [M+H]$^+$, 580.20, found 580.25. $^1$H NMR (400 MHz, DMSO-d$_6$) δ 7.70 (d, J=9.1 Hz, 1H), 7.55 (s, 1H), 6.86-6.49 (m, 3H), 6.19-6.14 (m, 1H), 5.71-5.67 (m, 1H), 5.42-5.19 (m, 3H), 4.62-4.35 (m, 1H), 4.08-3.70 (m, 2H), 3.65-3.42 (m, 2H), 3.33-3.27 (m, 3H), 2.96 (t, J=5.5 Hz, 3H), 2.60 (s, 3H), 2.52-2.48 (m, 1H), 2.37-2.25 (m, 1H).

Example 36: 3-[2-(3-ethyl-4-fluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide

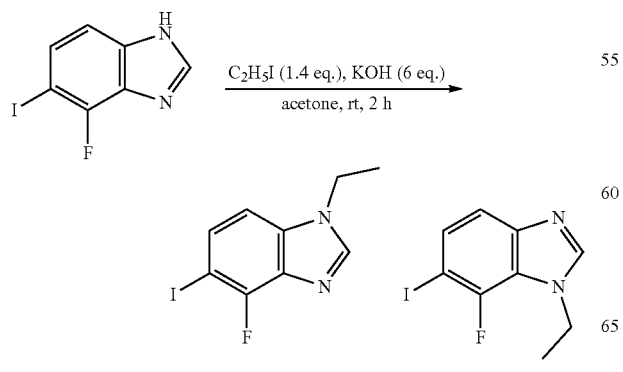

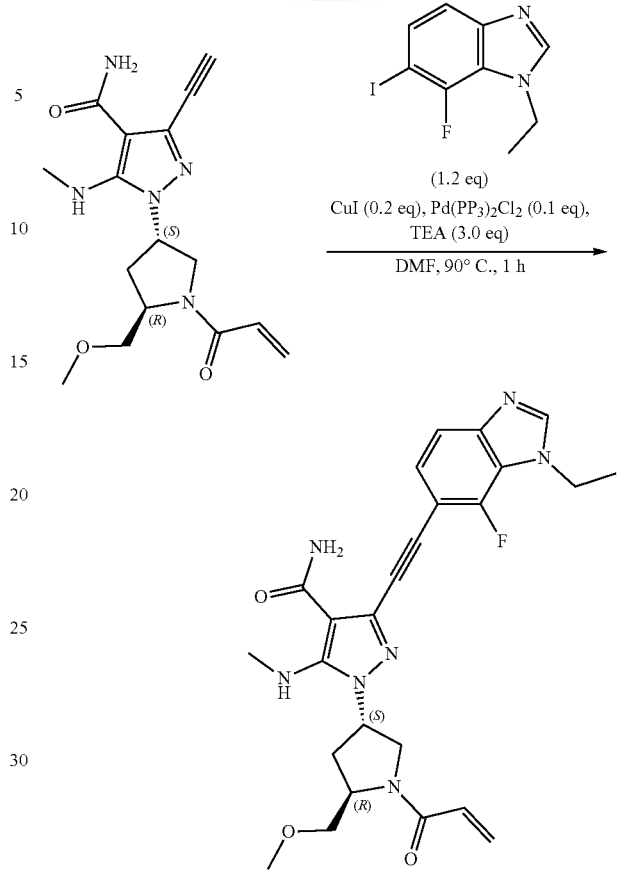

Step 1: 1-ethyl-4-fluoro-5-iodo-1,3-benzodiazole and 1-ethyl-7-fluoro-6-iodo-1,3-benzodiazole To a stirred mixture of 4-fluoro-5-iodo-1H-1,3-benzodiazole (2.00 g, 7.63 mmol) and KOH (2.57 g, 45.80 mmol) in acetone (20.00 mL) was added iodoethane (1.67 g, 10.69 mmol) at room temperature under air atmosphere. The reaction mixture was stirred for 2 h at room temperature. The resulting mixture was diluted with water (50 mL) and extracted with EA (3×70 mL). The combined organic layers were washed with brine (2×50 mL), dried over anhydrous Na$_2$SO$_4$ and filtered. The filtrate was concentrated under reduced pressure. The residue was purified by reverse flash chromatography with the following conditions: column, C18 silica gel; mobile phase, ACN in water (1 g/NH$_4$HCO$_3$), 25% to 55% gradient in 30 min; detector, UV 254 nm. The fraction contained desired product were combined and concentrated to afford 1-ethyl-4-fluoro-5-iodo-1,3-benzodiazole (0.80 g, 36%) as a yellow solid and 1-ethyl-7-fluoro-6-iodo-1,3-benzodiazole (0.78 g, 35%) as a yellow solid. PH-FNT-KIN-03-1434-1: MS ESI calculated for $C_9H_8FIN_2$ [M+H]$^+$, 290.97, found 290.99. PH-FNT-KIN-03-1300-1: MS ESI calculated for $C_9H_8FIN_2$ [M+H]$^+$, 290.97, found 290.95.

Step 2: 3-[2-(3-ethyl-4-fluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide To a stirred mixture of 3-ethynyl-1-[(3S,5R)-5-(methoxymethyl)-1-(prop-2-enoyl)pyrrolidin-3-yl]-5-

(methylamino)pyrazole-4-carboxamide (0.18 g, 0.54 mmol), 1-ethyl-7-fluoro-6-iodo-1,3-benzodiazole (0.19 g, 0.65 mmol), CuI (20.69 mg, 0.11 mmol) and Pd(pph₃)Cl₂ (44.36 mg, 0.05 mmol) in DMF (2.00 mL) was added TEA (0.23 mL, 2.24 mmol). The reaction mixture was degassed with argon for three times and stirred for 1 h at 90° C. The resulting mixture was concentrated under reduced pressure. The residue was purified by Prep-HPLC with the following conditions Column: XBridge Prep OBD C18 Column, 19*250 mm, 5 um; Mobile Phase A: Water (10 mmol/L NH₄HCO₃), Mobile Phase B: ACN; Flow rate: 20 mL/min; Gradient: 25 B to 60 B in 5.8 min; 210/254 nm; RT1: 5.57. The fractions contained desired product were combined and concentrated to afford 3-[2-(3-ethyl-4-fluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (85 mg, 31%) as an off-white solid. MS ESI calculated for $C_{25}H_{28}FN_7O_3$ [M+H]⁺, 494.22, found 494.25. H-NMR (400 MHz, DMSO-d₆) δ 8.42 (s, 1H), 7.64-7.29 (m, 3H), 6.93-6.46 (m, 3H), 6.17 (d, J=16.4 Hz, 1H), 5.74-5.65 (m, 1H), 5.33-5.20 (m, 1H), 4.62-4.30 (m, 3H), 4.07-3.71 (m, 2H), 3.65-3.41 (m, 2H), 3.32-3.28 (m, 1H), 3.03-2.92 (m, 3H), 2.51 (s, 3H), 2.35-2.30 (m, 1H), 1.47-1.44 (m, 3H).

Example 37: 3-[2-(1-ethyl-6-fluoro-2-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide

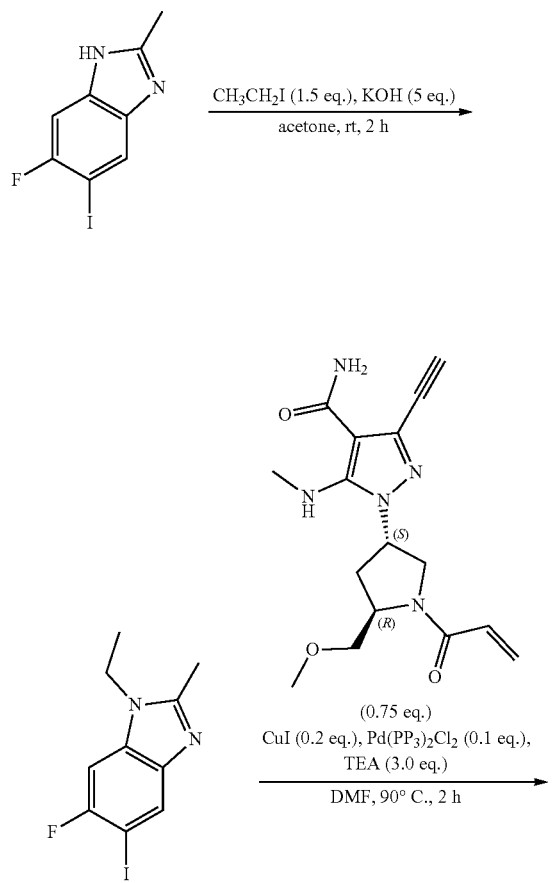

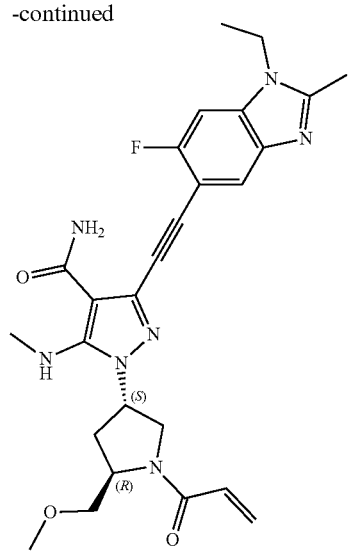

Step 1:
1-ethyl-6-fluoro-5-iodo-2-methyl-1,3-benzodiazole

To a stirred solution of 5-fluoro-6-iodo-2-methyl-3H-1,3-benzodiazole (1.1 g, 3.98 mmol) and KOH (1.12 g, 19.92 mmol) in acetone (16.50 mL) was added iodoethane (0.48 mL, 3.07 mmol) dropwise at 0° C. under nitrogen atmosphere. The reaction mixture was stirred for 2 h at room temperature. The resulting mixture was diluted with water (100 mL), extracted with EtOAc (3×100 mL). The combined organic layers were washed with brine (100 mL), dried over anhydrous Na₂SO₄ and filtered. The filtrate was concentrated under reduced pressure. The residue was purified by silica gel column chromatography, eluted with CH₂Cl₂/MeOH (15:1). The fractions contained desired product were combined and concentrated to afford 1.29 g crude product. The crude product was purified by Prep-Achiral-SFC with the following conditions Column: CHIRAL ART Cellulose-SB, 3*25 cm, 5 um; Mobile Phase A: CO₂, Mobile Phase B: MeOH (0.1% 2M NH₃-MeOH); Flow rate: 100 mL/min; Gradient: 20% B; 220 nm; RT1: 3.7; RT2: 4.3; Injection Volume: 2 ml; Number Of Runs: 20. The fractions contained desired product (slower peak RT2:4.3) were combined and concentrated to afford 1-ethyl-6-fluoro-5-iodo-2-methyl-1,3-benzodiazole (0.48 g, 35%) as a light brown solid. ¹H NMR (300 MHz, Chloroform-d) δ 8.02 (d, J=5.6 Hz, 1H), 7.05 (d, J=7.8 Hz, 1H), 4.11 (q, J=7.3 Hz, 2H), 2.60 (s, 3H), 1.40 (t, J=7.3 Hz, 3H)

Step 2: 3-[2-(1-ethyl-6-fluoro-2-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide To a stirred solution of 3-ethynyl-1-[(3S,5R)-5-(methoxymethyl)-1-(prop-2-enoyl)pyrrolidin-3-yl]-5-(methylamino)pyrazole-4-carboxamide (0.10 g, 0.31 mmol), 1-ethyl-6-fluoro-5-iodo-2-methyl-1,3-benzodiazole (0.14 g, 0.45 mmol), Pd(PPh3)₂Cl₂ (21.18 mg, 0.03 mmol) and CuI (11.49 mg, 0.06 mmol) in DMF (1.00 mL) was added TEA (91.61 mg, 0.91 mmol). The reaction mixture was degassed with argon for three times and stirred for 2 h at 90° C. The resulting mixture was purified by reverse flash chromatography with the following conditions: column, C18 silica gel; mobile phase ACN, NH$_4$HCO$_3$ 0.01 mmol in water, 25% to 40% gradient in 20 min; detector, UV 254 nm. The fractions contained desired product were combined and concentrated. The crude product was purified by Prep-HPLC with the following conditions Column: Atlantis Prep T3 OBD Column, 19*250 mm 10 u; Mobile Phase A: Water (0.1% FA), Mobile Phase B: MeOH—HPLC; Flow rate: 20 mL/min; Gradient: 15 B to 50 B in 6 min; 210/254 nm; RT1: 5.56. The fractions contained desired product were combined and concentrated to afford 3-[2-(1-ethyl-6-fluoro-2-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (32.8 mg, 21%) as a light yellow solid. ESI calculated for C$_{26}$H$_{30}$FN$_7$O$_3$ [M+H]$^+$, 508.23; found 508.25. $^1$H NMR (300 MHz, DMSO-d$_6$) δ 7.78 (d, J=6.3 Hz, 1H), 7.64 (d, J=9.9 Hz, 1H), 7.48 (d, J=8.0 Hz, 1H), 6.93-6.51 (m, 3H), 6.16-5.88 (m, 1H), 5.68-5.42 (m, 1H), 5.25-5.01 (m, 1H), 4.47-4.43 (m, 1H), 4.21 (q, J=7.2 Hz, 2H), 4.10-3.73 (m, 2H), 3.64-3.43 (m, 2H), 3.37-3.26 (m, 3H), 2.95 (d, J=4.3 Hz, 3H), 2.54 (s, 4H), 2.33-2.28 (m, 1H), 1.30-1.25 (m, 3H).

Example 38: 3-[2-(4-chloro-1-ethyl-2-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide

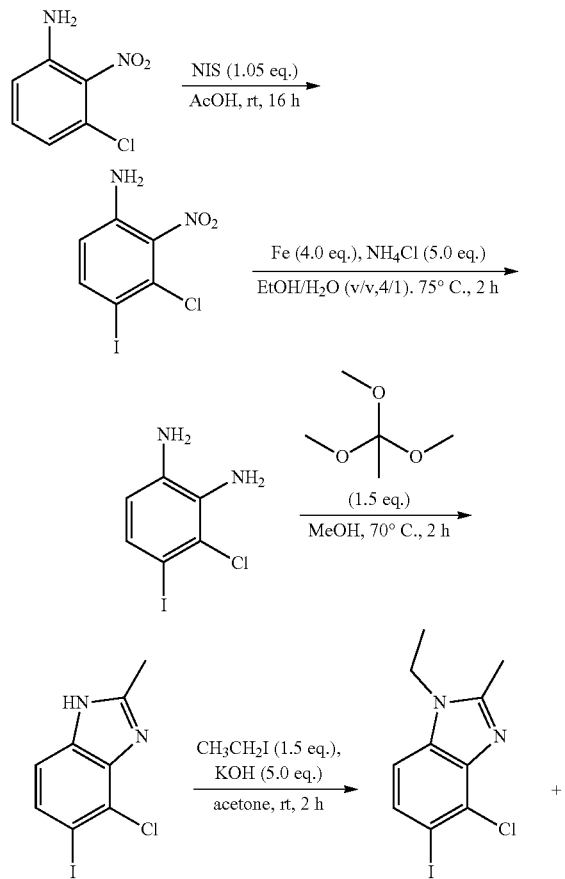

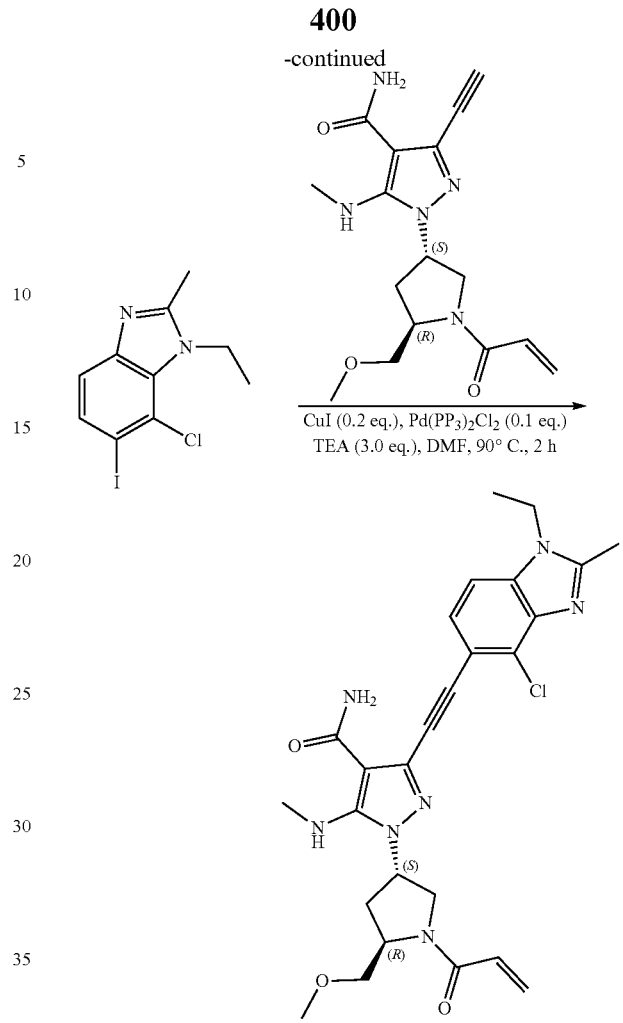

Step 1: 3-chloro-4-iodo-2-nitroaniline

To a stirred solution of 3-chloro-2-nitroaniline (5.00 g, 28.97 mmol) in AcOH (50.00 mL) was added NIS (6.84 g, 30.40 mmol) at room temperature. The resulting reaction was stirred for 16 h at room temperature. The resulting mixture was concentrated under reduced pressure. The residue was dissolved in water (50 mL). The mixture was extracted with EA (3×100 mL) and the combined organic layers was dried over anhydrous Na$_2$SO$_4$. After filtration, the filtrate was concentrated under reduced pressure to afford 3-chloro-4-iodo-2-nitroaniline (8.50 g, 98%) as an orange solid which was used in the next step directly without further purification. MS ESI calculated for C$_6$H$_4$ClIN$_2$O$_2$ [M−H]$^−$, 296.89, 297.90; found 297.00, 299.00.

Step 2: 3-chloro-4-iodobenzene-1,2-diamine

To a stirred mixture of 3-chloro-4-iodo-2-nitroaniline (1.00 g, 3.35 mmol) in EtOH (12.00 mL) and H$_2$O (3.00 mL) were added Fe (0.75 g, 13.43 mmol) and NH$_4$Cl (0.90 g, 16.75 mmol) at room temperature. The reaction mixture was stirred for 2 h at 75° C. The resulting mixture was allowed to cool down to room temperature. The resulting mixture was filtered, the filter cake was washed with EtOH (3×10 mL). The filtrate was concentrated under reduced pressure. The residue was dissolved in water (20 mL), extracted with EA (3×50 mL). The combined organic layers were washed with brine (3×10 mL), dried over anhydrous $Na_2SO_4$ and filtered. The filtrate was concentrated under reduced pressure to afford 3-chloro-4-iodobenzene-1,2-diamine (0.79 g, 87%) as a brown solid which was used in the next step directly without further purification. MS ESI calculated for $C_6H_6ClIN_2$ [M+H]$^+$, 268.93, 270.93; found 268.85, 270.85.

Step 3: 3-chloro-4-iodobenzene-1,2-diamine

To a stirred solution of 3-chloro-4-iodobenzene-1,2-diamine (0.79 g, 2.94 mmol) in MeOH (10.00 mL) was added 1,1,1-trimethoxyethane (0.53 g, 4.41 mmol) at room temperature. The reaction mixture was stirred for 2 h at 70° C. The resulting mixture was allowed to cool down to room temperature. The residue was purified by silica gel column chromatography, eluted with EA in PE (0-70%). The fractions contained desired product were combined and concentrated to afford 4-chloro-5-iodo-2-methyl-1H-1,3-benzodiazole (0.67 g, 77%) as a brown solid. MS ESI calculated for $C_8H_6ClIN_2$ [M+H]$^+$, 292.93, 294.93; found 292.80, 294.80.

Step 4: 4-chloro-1-ethyl-5-iodo-2-methyl-1,3-benzodiazole

To a stirred solution of 4-chloro-5-iodo-2-methyl-1H-1,3-benzodiazole (0.52 g, 1.77 mmol) in acetone (6.00 mL) were added ethyl iodide (0.42 g, 2.66 mmol) and KOH (0.50 g, 8.88 mmol) at room temperature. The reaction mixture was stirred for 2 h at room temperature. The resulting mixture was concentrated under reduced pressure. The residue was purified by silica gel column chromatography, eluted with 3% MeOH in DCM. The fractions contained desired product were combined and concentrated to afford 4-chloro-1-ethyl-5-iodo-2-methyl-1,3-benzodiazole (0.23 g, 40%) as an off-white solid. Also eluted 4% MeOH in DCM. The fractions contained desired product were combined and concentrated to afford 7-chloro-1-ethyl-6-iodo-2-methyl-1,3-benzodiazole (0.11 mg, 19%) as a yellow solid. MS ESI calculated for $C_{10}H_{10}ClIN_2$ [M+H]$^+$, 320.96, 322.96; found 320.85, 322.85.

Step 5: 3-[2-(4-chloro-1-ethyl-2-methyl-1,3-benzodiazol-5-yl)ethynyl]-1-[(3S,5R)-5-(methoxymethyl)-1-(prop-2-enoyl)pyrrolidin-3-yl]-5-(methylamino) pyrazole-4-carboxamide To a stirred mixture of 3-ethynyl-1-[(3S,5R)-5-(methoxymethyl)-1-(prop-2-enoyl)pyrrolidin-3-yl]-5-(methylamino)pyrazole-4-carboxamide (0.13 g, 0.39 mmol) and 4-chloro-1-ethyl-5-iodo-2-methyl-1,3-benzodiazole (0.15 g, 0.47 mmol) in DMF (3.00 mL) were added Pd(PPh$_3$)$_2$Cl$_2$ (27.54 mg, 0.03 mmol), CuI (14.94 mg, 0.07 mmol) and TEA (0.12 g, 1.17 mmol). The reaction mixture was degassed with argon for three times and stirred for 2 h at 90° C. The resulting mixture was concentrated under reduced pressure. The residue was purified by silica gel column chromatography, eluted with MeOH in DCM (0-6.0%). The fractions contained desired product were combined and concentrated. The crude product (0.15 g) was purified by Prep-HPLC with the following conditions Column: SunFire Prep C18 OBD Column, 19×150 mm 5 um 10 nm; Mobile Phase A: Water (0.1% FA), Mobile Phase B: ACN; Flow rate: 20 mL/min; Gradient: 20 B to 50 B in 4.3 min; 210/254 nm; RT1: 4.02 min. The fractions contained desired product were combined and concentrated to afford 3-[2-(4-chloro-1-ethyl-2-methyl-1,3-benzodiazol-5-yl)ethy- nyl]-1-[(3S,5R)-5-(methoxymethyl)-1-(prop-2-enoyl)pyrrolidin-3-yl]-5-(methylamino)pyrazole-4-carboxamide (49.30 mg, 23%) as an off-white solid. MS ESI calculated for $C_{26}H_{30}ClN_7O_3$ [M+H]$^+$, 524.22, 526.21; found 524.15.526.15. H-NMR (300 MHz, DMSO-d$_6$) δ 7.81-7.41 (m, 3H), 6.88 (s, 1H), 6.65 (d, J=12.3 Hz, 1H), 6.57 (d, J=12.8 Hz, 1H), 6.16 (d, J=16.6 Hz, 1H), 5.68 (d, J=10.4 Hz, 1H), 5.29-5.25 (m, 1H), 4.61-4.21 (m, 3H), 3.98-3.94 (m, 4H), 3.29 (d, J=3.8 Hz, 3H), 2.95 (d, J=3.1 Hz, 3H), 2.63-2.59 (m, 4H), 2.33-2.30 (m, 1H), 1.30 (t, J=7.0 Hz, 3H).

Example 39: 3-(2-[1-ethyl-2-methylimidazo[4,5-b] pyridin-5-yl]ethynyl)-1-[(3S,5R)-5-(methoxymethyl)-1-(prop-2-enoyl)pyrrolidin-3-yl]-5-(methylamino)pyrazole-4-carboxamide

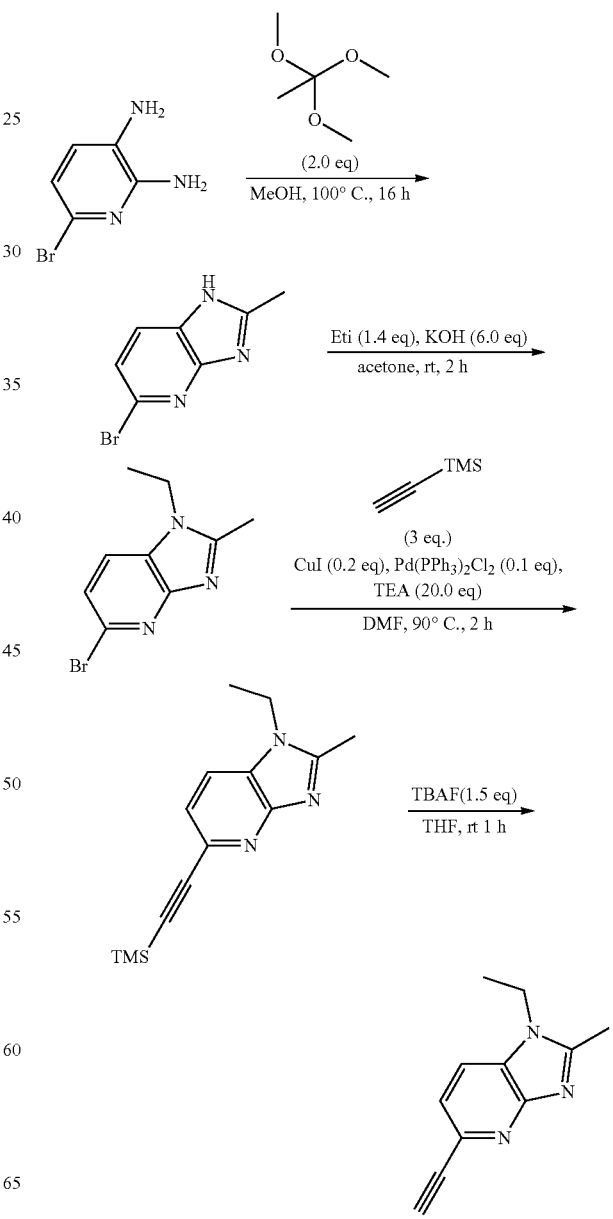

-continued

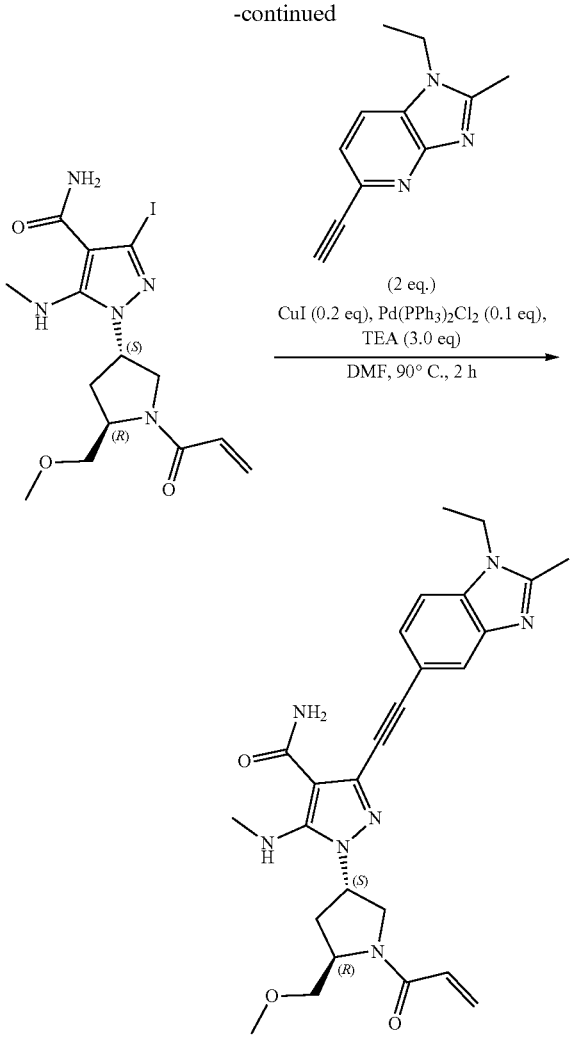

Step 1: 5-bromo-2-methyl-1H-imidazo[4,5-b]pyridine

To a solution of 6-bromopyridine-2,3-diamine (2.70 g, 14.36 mmol) in AcOH (30.00 mL) was added 1,1,1-trimethoxyethane (3.78 mL, 31.47 mmol). The reaction mixture was stirred for overnight at 100° C. under argon atmosphere. The resulting mixture was concentrated under reduced pressure. The residue was neutralized to pH 7 with saturated NaHCO₃ (aq.). The resulting mixture was extracted with EtOAc (2×200 mL). The combined organic layers were washed with water (2×100 mL), dried over anhydrous Na₂SO₄ and filtered. The filtrate was concentrated under reduced pressure. The residue was purified by silica gel column chromatography, eluted with DCM/MeOH (20/1). The fractions contained desired product were combined and concentrated to afford 5-bromo-2-methyl-1H-imidazo[4,5-b]pyridine (2.4 g, 78%) as an orange solid. MS ESI calculated for $C_7H_6BrN_3$ [M+H]⁺, 211.97, found 211.90.

Step 2: 5-bromo-1-ethyl-2-methylimidazo[4,5-b]pyridine

To a stirred mixture of 5-bromo-2-methyl-1H-imidazo[4,5-b]pyridine (2.40 g, 11.32 mmol) and KOH (3.81 g, 67.91 mmol) in acetone (25.00 mL) was added iodoethane (1.27 mL, 8.13 mmol). The reaction mixture was stirred for 2 h at room temperature under argon atmosphere. The resulting mixture was extracted with EtOAc (2×100 mL). The combined organic layers were washed with water (2×100 mL), dried over anhydrous Na₂SO₄ and filtered. The filtrate was concentrated under reduced pressure. The residue was purified by silica gel column chromatography, eluted with CH₂Cl₂/EtOAc (1:2). The fractions contained desired product were combined and concentrated to afford 5-bromo-1-ethyl-2-methylimidazo[4,5-b]pyridine (0.77 g, 28%) as a light yellow solid. MS ESI calculated for $C_9H_{10}BrN_3$ [M+H]⁺, 240.01, found 240.05.

Step 3: 1-ethyl-2-methyl-5-[2-(trimethylsilyl)ethynyl]imidazo[4,5-b]pyridine

To a mixture of 5-bromo-1-ethyl-2-methylimidazo[4,5-b]pyridine (0.72 g, 3.00 mmol), trimethylsilylacetylene (0.86 mL, 8.78 mmol), CuI (0.11 g, 0.60 mmol) and Pd(PPh₃)₂Cl₂ (0.21 g, 0.30 mmol) in DMF (10.00 mL) was added TEA (1.30 mL, 12.81 mmol). The reaction mixture was degassed with argon for three times and stirred for 2 h at 90° C. The resulting mixture was concentrated under reduced pressure. The residue was purified by silica gel column chromatography, eluted with PE/EA (1/1). The fractions contained desired product were combined and concentrated to afford 1-ethyl-2-methyl-5-[2-(trimethylsilyl)ethynyl]imidazo[4,5-b]pyridine (0.70 g, 90%) as a brown solid. MS ESI calculated for $C_{14}H_{19}N_3Si$ [M+H]⁺, 258.13, found 258.20.

Step 4: 1-ethyl-5-ethynyl-2-methylimidazo[4,5-b]pyridine

To a stirred solution of 1-ethyl-2-methyl-5-[2-(trimethylsilyl)ethynyl]imidazo[4,5-b]pyridine (0.70 g, 2.71 mmol) in THF (10.00 mL) were added TBAF (4.06 mL, 4.06 mmol) dropwise at 0° C. under argon atmosphere. The resulting mixture was stirred for 1 h at room temperature. The resulting mixture was concentrated under reduced pressure. The residue was purified by silica gel column chromatography, eluted with CH₂Cl₂/MeOH (20:1). The fractions contained desired product were combined and concentrated to afford 1-ethyl-5-ethynyl-2-methylimidazo[4,5-b]pyridine (0.34 g, 67%) as a light yellow solid. MS ESI calculated for $C_{11}H_{11}N_3$ [M+H]⁺, 186.10, found 186.25.

Step 5: 3-(2-[1-ethyl-2-methylimidazo[4,5-b]pyridin-5-yl]ethynyl)-1-[(3S,5R)-5-(methoxymethyl)-1-(prop-2-enoyl)pyrrolidin-3-yl]-5-(methylamino)pyrazole-4-carboxamide To a mixture of 3-iodo-1-[(3S,5R)-5-(methoxymethyl)-1-(prop-2-enoyl)pyrrolidin-3-yl]-5-(methylamino)pyrazole-4-carboxamide (0.15 g, 0.35 mmol), 1-ethyl-5-ethynyl-2-methylimidazo[4,5-b]pyridine (0.13 g, 0.69 mmol), CuI (13.19 mg, 0.07 mmol) and Pd(PPh₃)₂Cl₂ (24.30 mg, 0.04 mmol) in DMF (1.50 mL) was added TEA (0.14 mL, 1.01 mmol). The reaction mixture was degassed with argon for three times and stirred for 2 h at 90° C. The resulting mixture was concentrated under reduced pressure. The residue was purified by Prep-HPLC with the following conditions Column: XBridge Prep OBD C18 Column, 19*250 mm, 5 um; Mobile Phase A: Water (10 mmol/L NH₄HCO₃), Mobile Phase B: ACN; Flow rate: 20 mL/min; Gradient: 35 B to 60 B in 5.8 min; 210/254 nm; RT1: 5.56. The fractions contained desired product were combined and concentrated to afford 3-(2-[1-ethyl-2-methylimidazo[4,5-b]pyridin-5-yl]ethynyl)-1-[(3S,5R)-5-(methoxymethyl)-1-(prop-2-enoyl)pyrrolidin-3-yl]-5-(methylamino)pyrazole-4-carboxamide (43.7 mg, 25%) as an off-white solid. MS ESI calculated for $C_{25}H_{30}N_8O_3$ $[M+H]^+$, 491.24, found 491.25. H-NMR (400 MHz, DMSO-$d_6$) δ 8.04 (d, J=8.0 Hz, 1H), 7.54-7.48 (m, 2H), 6.90-6.52 (m, 3H), 6.17 (d, J=16.4 Hz, 1H), 5.69 (d, J=10.4 Hz, 1H), 5.29-5.25 (m, 1H), 4.60-4.32 (m, 1H), 4.33-4.24 (m, 2H), 4.09-3.70 (m, 2H), 3.66-3.40 (m, 2H), 3.32-3.27 (m, 1H), 2.99-2.94 (m, 3H), 2.63 (s, 3H), 2.55-2.52 (m, 3H), 2.34-2.30 (m, 1H), 1.42-1.18 (m, 3H).

Example 40: 3-[2-(6-fluoro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide

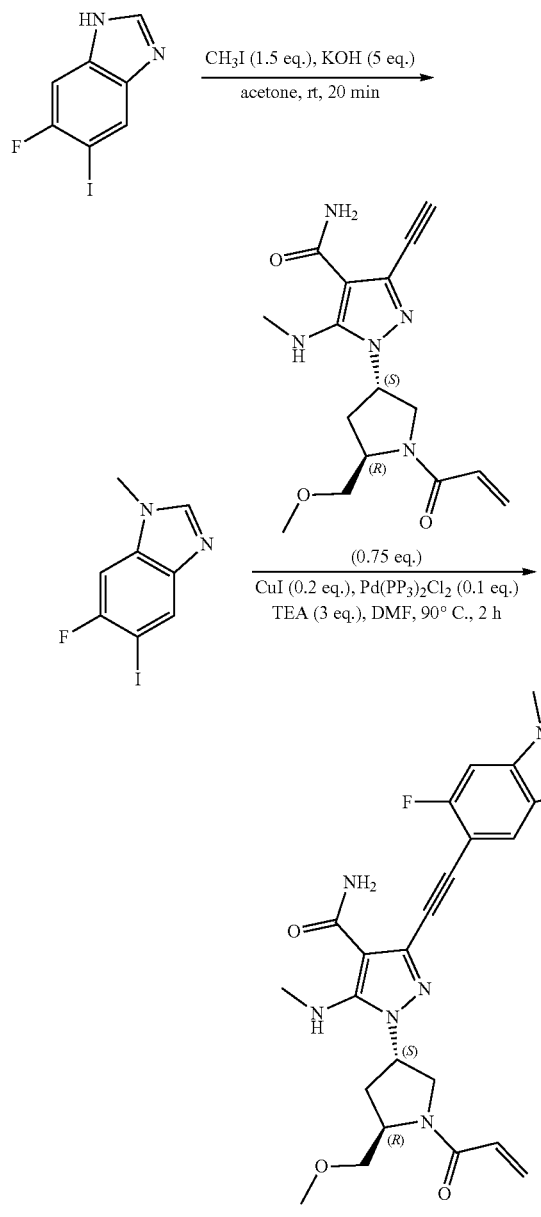

Step 1: 6-fluoro-5-iodo-1-methyl-1,3-benzodiazole

To a stirred mixture of 5-fluoro-6-iodo-3H-1,3-benzodiazole (0.1 g, 0.38 mmol) and KOH (0.11 g, 1.91 mmol) in acetone was added methyl iodide (0.04 mL) dropwise at 0° C. under nitrogen atmosphere. The reaction mixture was stirred for 20 min at room temperature under nitrogen atmosphere. The resulting mixture was filtered, the filter cake was washed with ethyl acetate (3×10 mL). The filtrate was concentrated under reduced pressure. The residue was purified by silica gel column chromatography, eluted with $CH_2Cl_2$/MeOH (10:1) to afford crude product. The crude product was purified by Prep-SFC with the following conditions Column: CHIRALPAK IF, 30*250 mm, 5 um; Mobile Phase A: $CO_2$, Mobile Phase B: MeOH (0.5% 2 M $NH_3$-MeOH)-HPLC; Flow rate: 80 mL/min; Gradient: 40% B; 220 nm; RT1: 3.8; RT2: 4.59; Injection Volume: 1 ml; Number Of Runs: 40. The fractions contained desired product were combined and concentrated to afford 6-fluoro-5-iodo-1-methyl-1,3-benzodiazole (0.44 g, 41%) as a white solid. ESI calculated for $C_8H_6FIN_2$ $[M+H]^+$, 277; found 277.

Step 2: 3-[2-(6-fluoro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide To a stirred mixture of 3-ethynyl-1-[(3S,5R)-5-(methoxymethyl)-1-(prop-2-enoyl)pyrrolidin-3-yl]-5-(methylamino)pyrazole-4-carboxamide (0.15 g, 0.45 mmol), 6-fluoro-5-iodo-1-methyl-1,3-benzodiazole (0.15 g, 0.54 mmol), Pd(PPh3)$_2$Cl$_2$ (31.77 mg, 0.04 mmol) and CuI (17.24 mg, 0.09 mmolv) in DMF (2.00 mL) was added TEA (0.14 g, 1.36 mmol) at room temperature. The reaction mixture was degassed with argon for three times and stirred for 2 h at 90° C. The resulting mixture was concentrated under reduced pressure. The residue was purified by silica gel column chromatography, eluted with $CH_2Cl_2$/MeOH (10:1). The fractions contained desired product were combined and concentrated. The crude product was purified by Prep-HPLC with the following conditions Column: XBridge Prep C18 OBD Column, 19×150 mm 5 um; Mobile Phase A: Water (10 mmol/L $NH_4HCO_3$), Mobile Phase B: ACN; Flow rate: 20 mL/min; Gradient: 20 B to 50 B in 4.3 min; 210/254 nm; RT1: 4.23. The fractions contained desired product were combined and concentrated to afford 3-[2-(6-fluoro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (43.6 mg, 20%) as a white solid. ESI calculated for $C_{24}H_{26}FN_7O_3$ $[M+H]^+$, 480.21; found 480.15. $^1$H NMR (300 MHz, DMSO-$d_6$) δ 8.30 (s, 1H), 7.93 (d, J=6.2 Hz, 1H), 7.68 (d, J=9.8 Hz, 1H), 7.45 (s, 1H), 6.84-6.50 (m, 3H), 6.16 (d, J=16.9 Hz, 1H), 5.73-5.63 (m, 1H), 5.27-5.23 (m, 1H), 4.49-4.42 (m, 1H), 4.16-3.92 (m, 1H), 3.86-3.80 (m, 6H), 3.65-3.36 (m, 3H), 2.95-2.73 (m, 4H), 2.41-2.15 (m, 1H).

Example 41: 3-[2-(4-fluoro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide

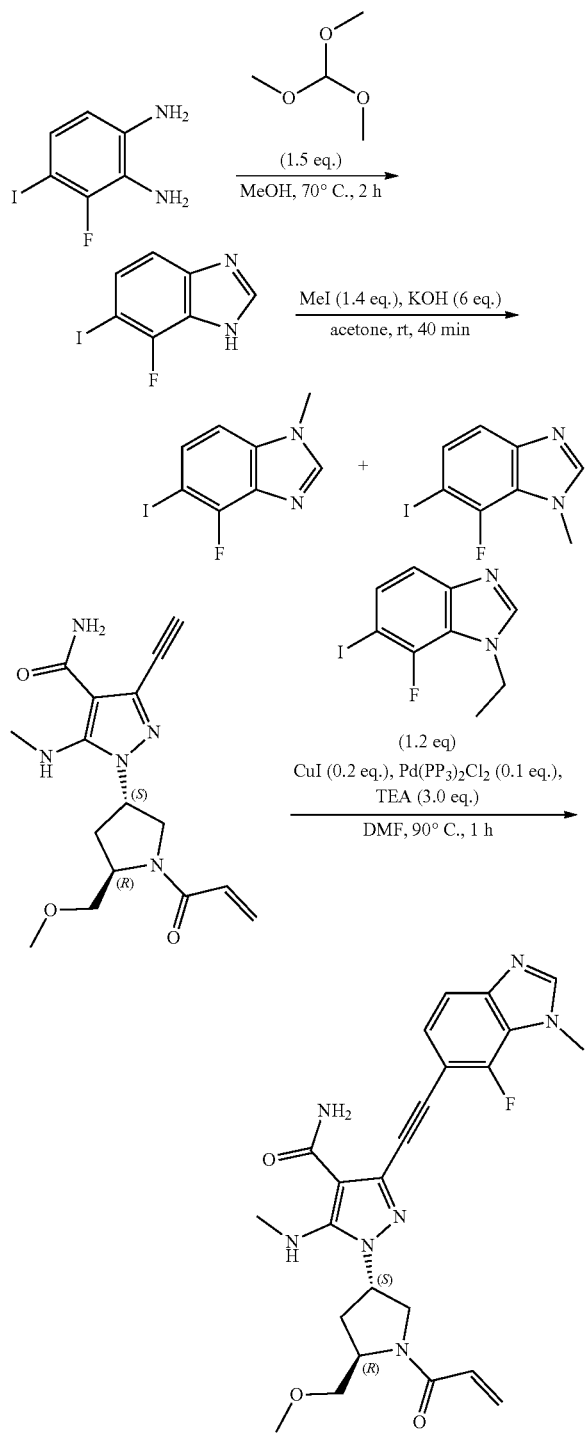

Step 1: 4-fluoro-5-iodo-1H-1,3-benzodiazole

To a stirred solution of 3-fluoro-4-iodobenzene-1,2-diamine (5.00 g, 19.84 mmol) in MeOH (50.00 mL) was added trimethyl orthoformate (3.16 g, 29.78 mmol) dropwise at room temperature under nitrogen atmosphere. The reaction mixture was stirred for 2 h at 70° C. under nitrogen atmosphere. The resulting mixture was concentrated under reduced pressure. The residue was purified by silica gel column chromatography, eluted with DCM/MeOH (10:1). The fractions contained desired product were combined and concentrated to afford 4-fluoro-5-iodo-1H-1,3-benzodiazole (4.6 g, 88%) as a light yellow solid. MS ESI calculated for $C_7H_4FIN_2$ [M+H]$^+$, 262.94, found 263.00.

Step 2: 4-fluoro-5-iodo-1-methyl-1,3-benzodiazole and 7-fluoro-6-iodo-1-methyl-1,3-benzodiazole To a stirred mixture of 4-fluoro-5-iodo-1H-1,3-benzodiazole (3.50 g, 13.36 mmol) and KOH (4.50 g, 80.21 mmol) in acetone (35.00 mL) was added $CH_3I$ (1.16 mL, 8.20 mmol) dropwise at room temperature. The reaction mixture was stirred for 40 min at room temperature. The resulting mixture was diluted with water (40 mL) and extracted with EA (3×70 mL). The combined organic layers were washed with brine (50 mL), dried over anhydrous $Na_2SO_4$, filtered and concentrated under reduced pressure. The residue was purified by reverse flash chromatography with the following conditions: column, C18 silica gel; mobile phase, ACN in water ($NH_4HCO_3$ 1 g/L), 20% to 50% gradient in 30 min; detector, UV 254 nm. The fractions contained desired product were combined and concentrated to afford 4-fluoro-5-iodo-1-methyl-1,3-benzodiazole (1.6 g, 43%) as an off-white solid and 7-fluoro-6-iodo-1-methyl-1,3-benzodiazole (1.57 g, 42%) as an off-white solid. MS ESI calculated for $C_8H_6FIN_2$ [M+H]$^+$, 276.96, found 277.00.

Step 3: 3-[2-(4-fluoro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide To a stirred mixture of 3-ethynyl-1-[(3S,5R)-5-(methoxymethyl)-1-(prop-2-enoyl)pyrrolidin-3-yl]-5-(methylamino)pyrazole-4-carboxamide (0.15 g, 0.45 mmol) and 4-fluoro-5-iodo-1-methyl-1,3-benzodiazole (0.16 g, 0.54 mmol), CuI (17.24 mg, 0.09 mmol), $Pd(PPh_3)_2Cl_2$ (31.77 mg, 0.045 mmol,) in DMF (2.00 mL) was added TEA (137.41 mg, 1.36 mmol). The reaction mixture was degassed with argon for three times and stirred for 1 h at 90° C. The mixture was allowed to cool down to room temperature and concentrated under reduced pressure. The residue was purified by silica gel column chromatography, eluted with DCM/MeOH (20:1) to afford ~110 mg product which was further purified was purified by Prep-HPLC with the following conditions: Column: XBridge Prep C18 OBD Column, 19×150 mm 5 um; Mobile Phase A: water (10 mmol/L $NH_4HCO_3$), Mobile Phase B: ACN; Flow rate: 20 mL/min; Gradient: 30 B to 60 B in 5.8 min; 210/254 nm; RT1:5.56. The fractions contained desired product were concentrated to afford 3-[2-(4-fluoro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (54.7 mg, 25%) as an off-white solid. MS ESI calculated for $C_{24}H_{26}FN_7O_3$, 479.21, found 480.10. H-NMR (400 MHz, DMSO-$d_6$) δ 8.32 (s, 1H), 7.53-7.36 (m, 3H), 6.76-6.56 (m, 3H), 6.20-6.14 (m, 1H), 5.71-5.67 (m, 1H), 5.31-5.20 (m, 1H), 4.54-4.30 (m, 1H), 4.04-3.59 (m, 5H), 3.50-3.45 (m, 2H), 3.27 (d, J=2.8 Hz, 3H), 2.96 (t, J=5.2 Hz, 3H), 2.52-2.47 (m, 1H), 2.34-2.36 (m, 1H).

Example 42: 3-[2-(2-cyclopropyl-1H-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide

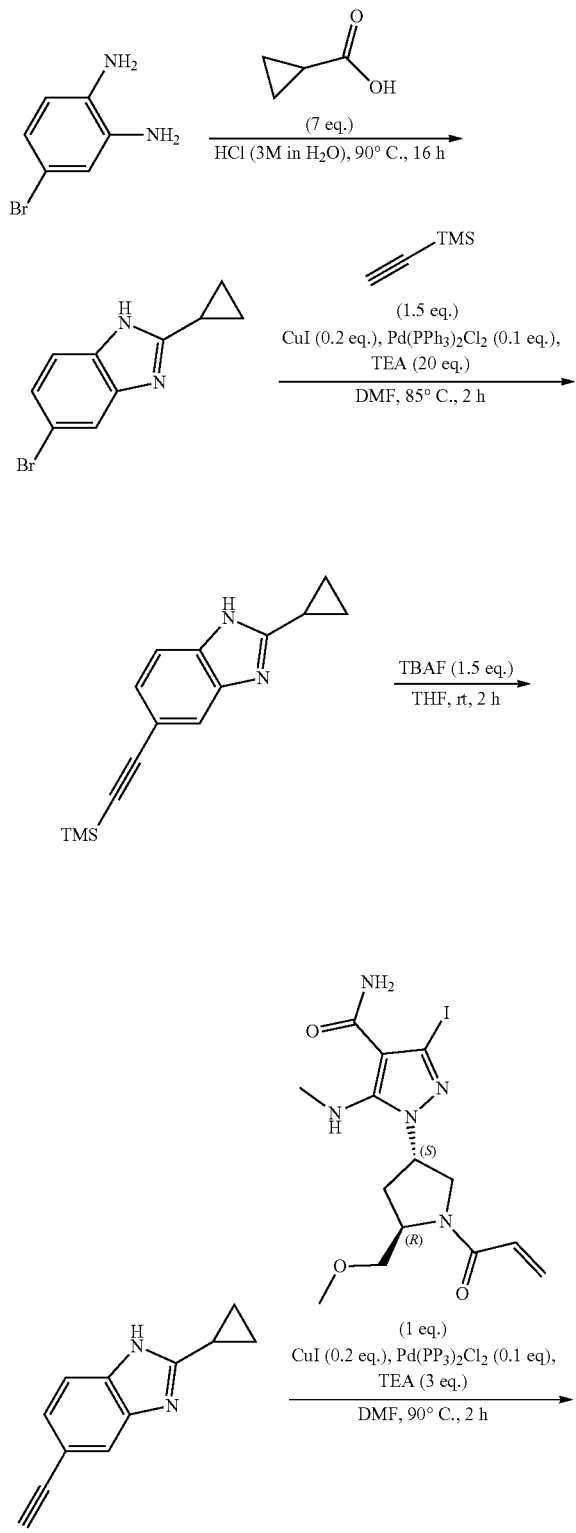

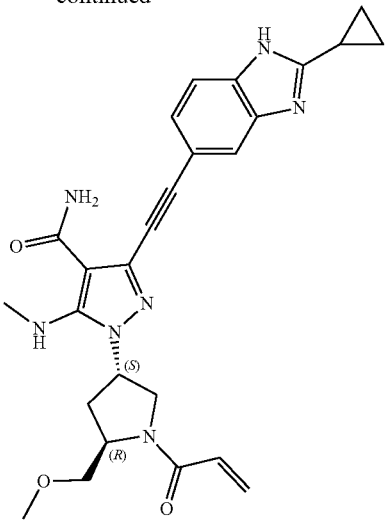

Step 1: 5-bromo-2-cyclopropyl-1H-benzo[d]imidazole

To a mixture of 4-bromobenzene-1,2-diamine (1.00 g, 5.35 mmol) in HCl (3.00 M in $H_2O$, 10.00 mL) was added cyclopropanecarboxylic acid (3.22 g, 37.43 mmol). The reaction mixture was stirred for 16 h at 90° C. under nitrogen atmosphere. The resulting mixture was neutralized to pH 7 with NaOH. The mixture was extracted with DCM (3×20 mL). The combined organic layers were washed with water (3×20 mL), dried over anhydrous $Na_2SO_4$ and filtered. The filtrate was concentrated under reduced pressure. The residue was purified by silica gel column chromatography, eluted with EA in PE (3:2). The fractions contained desired product were combined and concentrated under reduced pressure to afford 5-bromo-2-cyclopropyl-1H-1,3-benzodiazole (1.28 g, 100%) as a yellow solid. MS ESI calculated for $C_{10}H_9BrN_2$ [M+H]$^+$, 236.99, 238.99, found 236.90, 238.90.

Step 2: 2-cyclopropyl-5-((trimethylsilyl)ethynyl)-1H-benzo[d]imidazole

To a stirred solution of 5-bromo-2-cyclopropyl-1H-1,3-benzodiazole (1.32 g, 5.57 mmol) in DMF (10.00 mL) were added trimethylsilylacetylene (1.64 g, 16.71 mmol), Pd(PPh$_3$)$_2$Cl$_2$ (0.39 g, 0.56 mmol), CuI (0.21 g, 1.11 mmol) and TEA (1.69 g, 16.70 mmol) at room temperature. The reaction mixture was degassed with nitrogen for three times and stirred for 2 h at 85° C. The resulting mixture was diluted with water (100 mL), extracted with EA (3×100 mL). The combined organic layers were washed with brine (3×80 mL), dried over anhydrous $Na_2SO_4$ and filtered. The filtrate was concentrated under reduced pressure. The residue was purified by silica gel column chromatography, eluted with EA in PE (5:1). The fractions contained desired product were combined and concentrated under reduced pressure to afford 2-cyclopropyl-5-[2-(trimethylsilyl)ethynyl]-1H-1,3-benzodiazole (1.05 g, 74%) as a yellow solid. MS ESI calculated for $C_{15}H_{18}N_2Si$ [M+H]$^+$, 255.12; found 255.15.

Step 3: 2-cyclopropyl-5-ethynyl-1H-benzo[d]imidazole

To a mixture of 2-cyclopropyl-5-[2-(trimethylsilyl)ethynyl]-1H-1,3-benzodiazole (1.05 g, 4.13 mmol) in THF (10.00 mL) was added TBAF (1.62 g, 6.19 mmol). The reaction mixture was stirred for 2 h at room temperature. The resulting mixture was concentrated under reduced pressure. The residue was purified by silica gel column chromatography, eluted with EA in PE (5:1). The fractions contained desired product were combined and concentrated under reduced pressure to afford 2-cyclopropyl-5-ethynyl-1H-1,3-benzodiazole (0.60 g, 79%) as a brown solid. MS ESI calculated for $C_{12}H_{10}N_2$ [M+H]$^+$, 183.08; found 183.00.

Step 4: 3-[2-(2-cyclopropyl-1H-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide To a stirred mixture of 3-iodo-1-[(3S,5R)-5-(methoxymethyl)-1-(prop-2-enoyl)pyrrolidin-3-yl]-5-(methylamino)pyrazole-4-carboxamide (0.25 g, 0.58 mmol) and 2-cyclopropyl-5-ethynyl-1H-1,3-benzodiazole (0.11 g, 0.58 mmol) in DMF (2.00 mL) were added Pd(PPh$_3$)$_2$Cl$_2$ (40.50 mg, 0.06 mmol), CuI (21.98 mg, 0.12 mmol) and TEA (0.18 g, 1.73 mmol) at room temperature. The reaction mixture was degassed with argon for three times and stirred for 2 h at 90° C. The resulting mixture was concentrated under reduced pressure. The residue was purified by Prep-HPLC with the following conditions Column: XBridge Prep C18 OBD Column, 19×150 mm 5 um; Mobile Phase A: Water (10 mmol/L NH$_4$HCO$_3$), Mobile Phase B: ACN; Flow rate: 20 mL/min; Gradient: 25 B to 65 B in 5.8 min; 210/254 nm; RT1: 5.56 min. The fractions contained desired product were combined and concentrated under reduced pressure to afford 3-[2-(2-cyclopropyl-1H-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (44.20 mg, 15%) as a white solid. MS ESI calculated for $C_{26}H_{29}N_7O_3$ [M+H]$^+$, 488.23, found 488.15. $^1$H NMR (400 MHz, DMSO-d$_6$) δ 12.50 (s, 1H), 7.85-7.14 (m, 4H), 6.94-6.43 (m, 3H), 6.17 (d, J=16.6 Hz, 1H), 5.69 (d, J=10.2 Hz, 1H), 5.27-5.24 (m, 1H), 4.49-4.45 (m, 1H), 4.03-4.00 (m, 1H), 3.89-3.82 (m, 1H), 3.69-5.65 (m, 1H), 3.50-3.46 (m, 1H), 3.32-3.28 (m, 3H), 2.96-2.90 (m, 3H), 2.63-2.57 (m, 1H), 2.31-2.30 (m, 1H), 2.13-2.09 (m, 1H), 1.12-0.90 (m, 4H).

Example 43: 3-[2-(2-cyclopropyl-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide

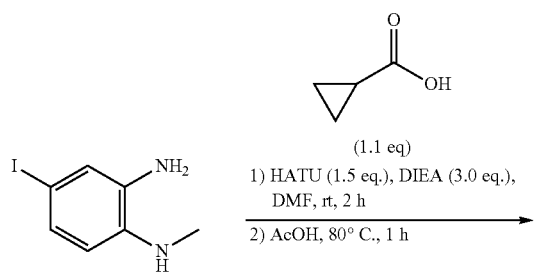

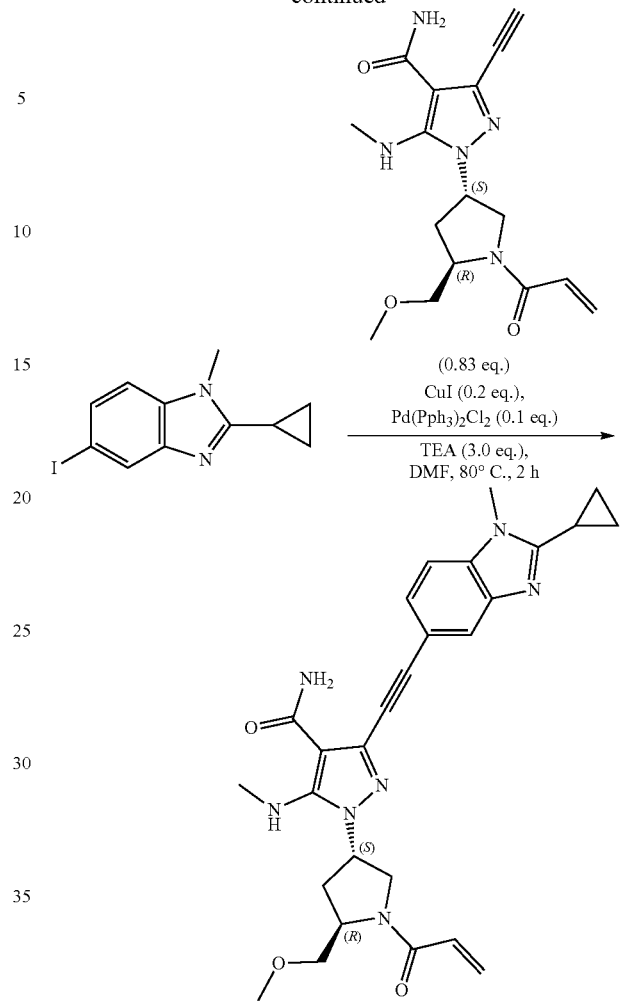

Step 1: 2-cyclopropyl-5-iodo-1-methyl-1,3-benzodiazole

To a stirred mixture of HATU (4.60 g, 12.09 mmol) and DIEA (3.13 g, 24.18 mmol) in DMF (10.00 mL) was added cyclopropanecarboxylic acid (0.76 g, 8.86 mmol). The reaction mixture was stirred for 30 min at room temperature. To the above mixture was added 4-iodo-N1-methylbenzene-1,2-diamine (2.00 g, 8.06 mmol). The resulting mixture was stirred for 2 h at room temperature. The final reaction mixture was added 50 ml H$_2$O. The resulting mixture was washed with 5×30 mL of EtOAc. The organic layers was dried over Na$_2$SO$_4$ and filtered. The filtrate was concentrated under reduced pressure. To the residue was added AcOH (20.00 mL). The resulting mixture was stirred for 1 h at 80° C. The resulting mixture was concentrated under reduced pressure. The residue was basified to pH 8 with saturated NaHCO$_3$, extracted with EA (4×150 mL), dried over anhydrous Na$_2$SO$_4$ and filtered. The filtrate was concentrated under reduced pressure. The residue was purified by silica gel column chromatography, eluted with EA in PE (0-50%). The fractions contained desired product were combined and concentrated to afford 2-cyclopropyl-5-iodo-1H-1,3-benzodiazole (2.1 g, 87%). MS ESI calculated for $C_{12}H_{12}IN$ [M+H]$^+$, 299.00, found 298.90.

Step 2: 3-[2-(2-cyclopropyl-1-methyl-1,3-benzodi-azol-5-yl)ethynyl]-1-[(3S,5R)-5-(methoxymethyl)-1-(prop-2-enoyl)pyrrolidin-3-yl]-5-(methylamino) pyrazole-4-carboxamide To a stirred mixture 2-cyclopropyl-5-iodo-1-methyl-1,3-benzodiazole (0.11 g, 0.36 mmol) and 3-ethynyl-1-[(3S,5R)-5-(methoxymethyl)-1-(prop-2-enoyl)pyrrolidin-3-yl]-5-(methylamino)pyrazole-4-carboxamide (0.10 g, 0.30 mmol) in DMF (2.00 mL) were added CuI (11.49 mg, 0.06 mmol) and Pd(PPh$_3$)$_2$Cl$_2$ (21.18 mg, 0.03 mmol). The reaction mixture was degassed with argon for three times and stirred for 2 h at 80° C. The resulting mixture was concentrated. The residue was purified by silica gel column chromatography, eluted with DCM/MeOH (0-10%) to afford the crude. The crude was purified by reverse flash chromatography with the following conditions: Column: SunFire Prep C18 OBD Column, 19×150 mm 5 um 10 nm; Mobile Phase A: Water (0.1% FA), Mobile Phase B: ACN; Flow rate: 20 mL/min; Gradient: 20 B to 30 B in 6 min; 210/254 nm; RT1: 5.58. The fractions contained desired product were combined and concentrated to afford 3-[2-(2-cyclopropyl-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (47.4 mg, 31%). MS ESI calculated for C$_{27}$H$_{31}$N$_7$O$_3$ [M+H]$^+$, 501.25, found 502.15. H NMR (300 MHz, DMSO-d$_6$) δ 7.74 (d, J=1.4 Hz, 1H), 7.63 (d, J=8.4 Hz, 1H), 7.49-7.26 (m, 2H), 6.77 (s, 1H), 6.71-6.46 (m, 2H), 6.17 (d, J=16.5 Hz, 1H), 5.70 (d, J=10.3 Hz, 1H), 5.39-5.12 (m, 1H), 4.47-4.39 (m, 1H), 4.13-3.95 (m, 1H), 3.93-3.85 (m, 4H), 3.77-3.72 (m, 1H), 3.57-3.52 (m, 2H), 3.33-3.28 (m, 3H), 2.97-2.92 (m, 3H), 2.35-2.32 (m, 2H), 1.21-1.02 (m, 4H).

Example 44: 1-[(3S,5R)-5-(methoxymethyl)-1-(prop-2-enoyl)pyrrolidin-3-yl]-3-[2-(3-methyl-1,2-benzoxazol-6-yl)ethynyl]-5-(methylamino)pyrazole-4-carboxamide

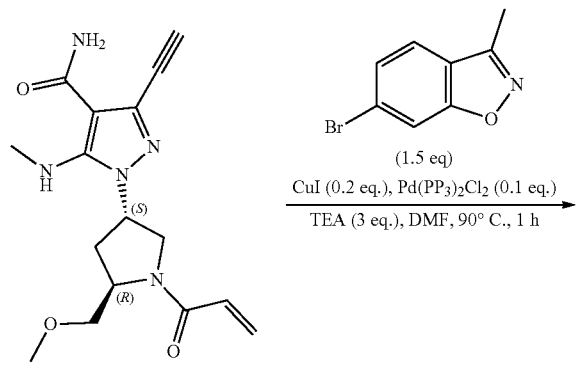

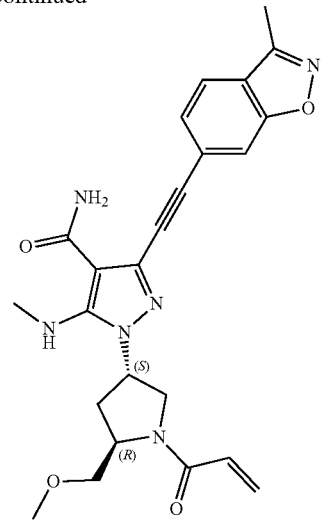

To a stirred mixture of 3-ethynyl-1-[(3S,5R)-5-(methoxymethyl)-1-(prop-2-enoyl)pyrrolidin-3-yl]-5-(methylamino)pyrazole-4-carboxamide (0.23 g, 0.69 mmol), 6-bromo-3-methyl-1,2-benzoxazole (0.22 g, 1.04 mmol), Pd(PPh$_3$)$_2$Cl$_2$ (48.72 mg, 0.07 mmol) and CuI (26.44 mg, 0.14 mmol) in DMF (2.50 mL) was added TEA (0.29 mL, 2.86 mmol). The reaction mixture was degassed with argon for three times and stirred for 1 h at 90° C. The resulting mixture was concentrated under reduced pressure. The residue was purified by silica gel column chromatography, eluted with 6% MeOH in DCM. The fractions contained desired product were combined and concentrated. The crude product (150 mg) was purified by Prep-HPLC with the following conditions Column: XBridge Prep C18 OBD Column, 19×150 mm 5 um; Mobile Phase A: Water (10 mmol/L NH$_4$HCO$_3$), Mobile Phase B: ACN; Flow rate: 20 mL/min; Gradient: 30 B to 60 B in 5.8 min; 210/254 nm; RT1: 5.56. The fractions contained desired product were combined and concentrated to afford 1-[(3S,5R)-5-(methoxymethyl)-1-(prop-2-enoyl)pyrrolidin-3-yl]-3-[2-(3-methyl-1,2-benzoxazol-6-yl)ethynyl]-5-(methylamino)pyrazole-4-carboxamide (44.9 mg, 13%) as an off-white solid. MS ESI calculated for C$_{24}$H$_{26}$N$_6$O$_4$ [M+H]$^+$, 463.20, found 463.20. H-NMR (400 MHz, DMSO-d$_6$): δ 8.04-7.90 (m, 2H), 7.56 (dd, J=8.2, 1.2 Hz, 1H), 7.29-7.23 (m, 1H), 6.94-6.42 (m, 3H), 6.19-6.25 (m, 1H), 5.71-5.67 (m, 1H), 5.26-5.23 (m, 1H), 4.56-4.33 (m, 1H), 4.06-3.67 (m, 2H), 3.64-3.39 (m, 2H), 3.32 (s, 3H), 2.97-2.90 (m, 3H), 2.58 (s, 3H), 2.45-2.41 (m, 1H), 2.35-2.26 (m, 1H).

Example 45: 3-[2-(2-cyclopropyl-1-ethyl-4,6-dif-luoro-1,3-benzodiazol-5-yl) ethynyl]-1-[(3S,5R)-5-(methoxymethyl)-1-(prop-2-enoyl) pyrrolidin-3-yl]-5-(methylamino) pyrazole-4-carboxamide

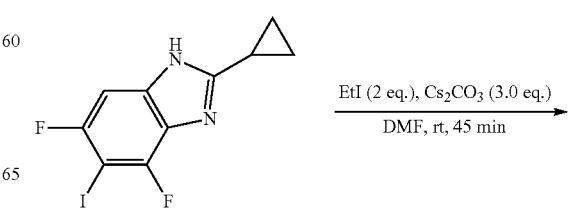

-continued

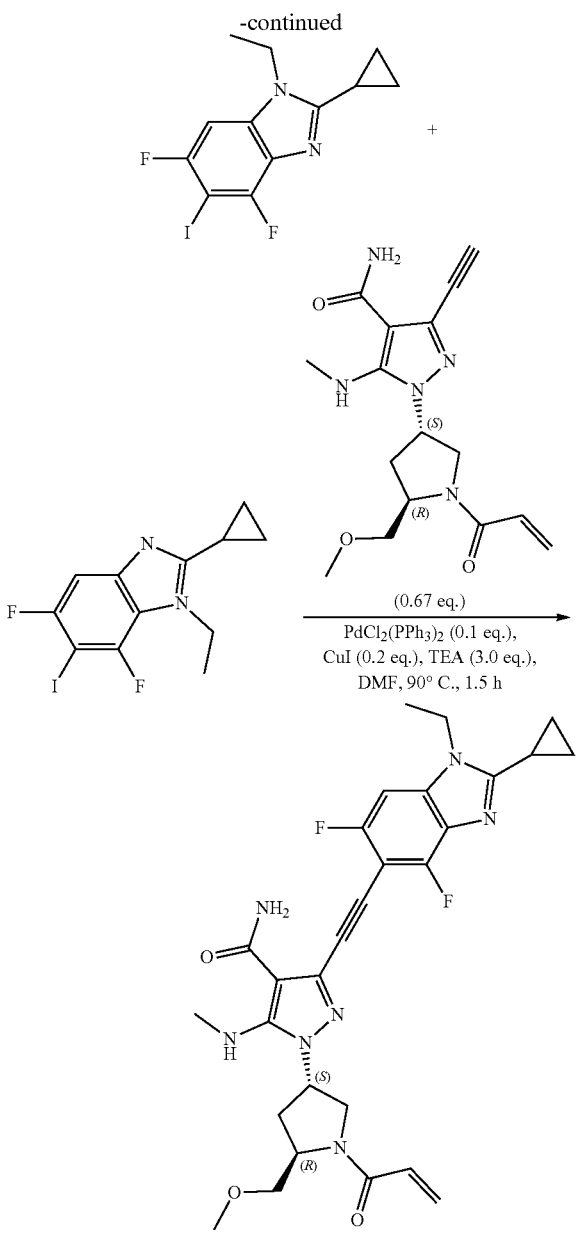

Step 1: 2-cyclopropyl-1-ethyl-4,6-difluoro-5-iodo-1,3-benzodiazole and 2-cyclopropyl-1-ethyl-5,7-difluoro-6-iodo-1,3-benzodiazole To a solution of 2-cyclopropyl-4,6-difluoro-5-iodo-1H-1,3-benzodiazole (1.50 g, 4.69 mmol) and iodoethane (1.46 g, 9.37 mmol) in DMF (15.00 mL) was added $Cs_2CO_3$ (4.58 g, 14.06 mmol) dropwise at room temperature. The reaction mixture was stirred for 45 min at room temperature. The resulting mixture was filtered, the filtrate was concentrated under reduced pressure. The residue was purified by reverse phase chromatography with the following conditions: Column: Spherical C18, 20-40 um, 300 g; Mobile Phase A: Water (10 mM $NH_4HCO_3$), Mobile Phase B: ACN; Flow rate: 50 mL/min; Gradient (B %): 5%~45% within 40 min, Detector: UV 254 & 220 nm. The fractions contained desired product were combined and concentrated to afford 2-cyclopropyl-1-ethyl-4,6-difluoro-5-iodo-1,3-benzodiazole (0.50 g, 31%) as a light yellow solid and 2-cyclopropyl-1-ethyl-5,7-difluoro-6-iodo-1,3-benzodiazole (0.37 g, 23%) as a light yellow solid. MS ESI calculated for $C_9H_9N_3O_2$ [M+H]$^+$, 348.99, found 348.85.

Step 2: 3-[2-(2-cyclopropyl-1-ethyl-4,6-difluoro-1,3-benzodiazol-5-yl) ethynyl]-1-[(3S,5R)-5-(methoxymethyl)-1-(prop-2-enoyl) pyrrolidin-3-yl]-5-(methylamino) pyrazole-4-carboxamide To a stirred mixture of 2-cyclopropyl-1-ethyl-4,6-difluoro-5-iodo-1,3-benzodiazole (0.21 g, 0.60 mmol), 3-ethynyl-1-[(3S,5R)-5-(methoxymethyl)-1-(prop-2-enoyl)pyrrolidin-3-yl]-5-(methylamino)pyrazole-4-carboxamide (0.14 g, 0.45 mmol), CuI (22.98 mg, 0.12 mmol) and Pd(PPh$_3$)$_2$Cl$_2$ (42.34 mg, 0.06 mmol) in DMF (2.00 mL) was added TEA (0.18 g, 1.81 mmol). The reaction mixture was degassed with argon for three times and stirred for 1.5 h at 90° C. The resulting mixture was concentrated under reduced pressure. The residue was purified by reverse phase chromatography with the following conditions: Column: Spherical C18, 20-40 um, 40 g; Mobile Phase A: Water (10 mM $NH_4HCO_3$), Mobile Phase B: ACN; Flow rate: 40 mL/min; Gradient (B %): 5%-45% within 45 min, Detector: UV 254 & 220 nm. The fractions contained desired product were combined and concentrated to afford 3-[2-(2-cyclopropyl-1-ethyl-4,6-difluoro-1,3-benzodiazol-5-yl)ethynyl]-1-[(3S,5R)-5-(methoxymethyl)-1-(prop-2-enoyl) pyrrolidin-3-yl]-5-(methylamino) pyrazole-4-carboxamide (84.1 mg, 25%) as an off-white solid. MS ESI calculated for $C_{28}H_{31}F_2N_7O_3$ [M+H]$^+$, 552.25; found 552.25. $^1$H NMR (300 MHz, d$_6$-DMSO) δ 7.66-7.52 (m, 2H), 6.83-6.52 (m, 3H), 6.19-6.15 (m, 1H), 5.71-5.68 (m, 1H), 5.30-5.27 (m, 1H), 4.58-4.32 (m, 3H), 3.90 (d, J=7.5 Hz, 2H), 3.66-3.41 (m, 2H), 3.34-3.26 (m, 4H), 2.99-2.95 (m, 3H), 2.30-2.25 (m, 2H), 1.35 (t, J=7.1 Hz, 3H), 1.16-1.03 (m, 4H).

Example 46: 3-[2-[4,6-difluoro-2-(trifluoromethyl)-1H-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide

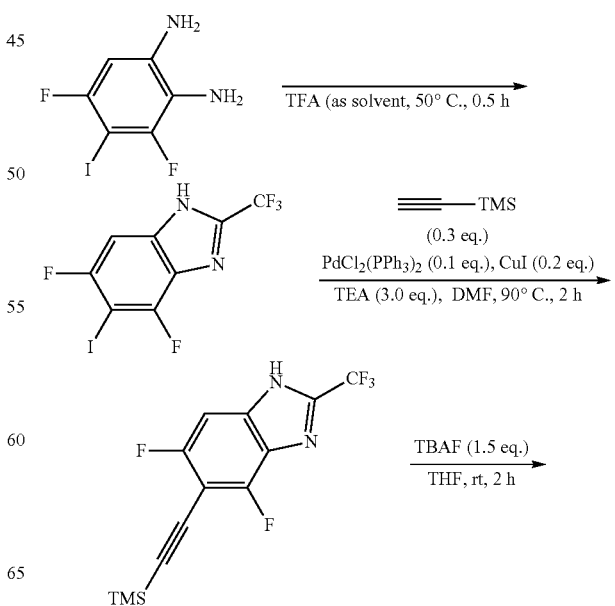

417
-continued

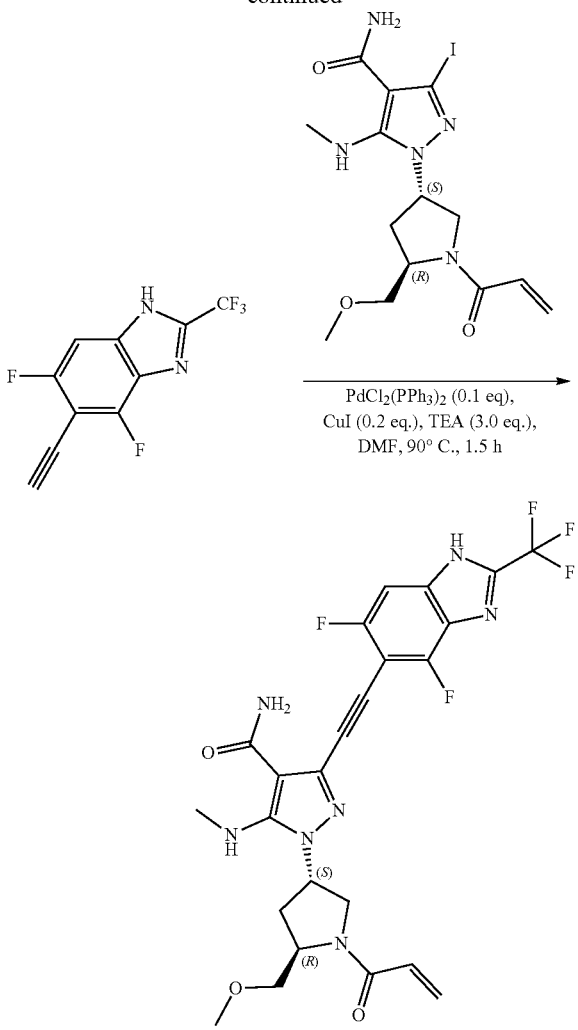

Step 1: 4,6-difluoro-5-iodo-2-(trifluoromethyl)-1H-1,3-benzodiazole

A solution of 3,5-difluoro-4-iodobenzene-1,2-diamine (5.50 g, 20.37 mmol) in trifluoroacetic acid (55 mL) was stirred at 50° C. for 30 min. The reaction liquid is mixed with saturated NaHCO$_3$ to basic solution at 0° C. The resulting mixture was poured into Sodium thiosulfate (550.0 mL) and extracted with EA (3×500.0 mL). The combined organic layers were washed with brine (2×300 mL), dried over anhydrous sodium sulfate and filtered. The filtrate was concentrated under reduced pressure. The residue was purified by reverse flash chromatography with the following conditions: Column: Spherical C18, 20-40 um, 40 g; Mobile Phase A: Water (10 mM NH$_4$HCO$_3$), Mobile Phase B: ACN; Flow rate: 40 mL/min; Gradient (B %): 0% hold 5 min, 5%-60% within 40 min; 60% hold 5 min, 60%~95% within 20 min, 95% hold 5 min; Detector: UV 254 & 210 nm; RT: 45 min). The fractions contained desired product were combined and concentrated to afford 4,6-difluoro-5-iodo-2-(trifluoromethyl)-1H-1,3-benzodiazole (1.3 g, 18%) as a light yellow solid. ESI calculated for C$_8$H$_2$F$_5$IN$_2$ [M+H]$^+$, 348.92; found 348.95.

418

Step 2: 4,6-Difluoro-2-(trifluoromethyl)-5-[2-(trimethylsilyl)ethynyl]-1H-1,3-benzodiazole To a stirred solution of 4,6-difluoro-5-iodo-2-(trifluoromethyl)-1H-1,3-benzodiazole (1.00 g, 2.87 mmol) in dimethylformamide (10 mL) were added trimethylsilylacetylene (0.85 g, 8.62 mmol), palladium chloride; bis(triphenylphosphine) (0.20 g, 0.28 mmol), copper(I) iodide (0.11 g, 0.57 mmol) and TEA (0.87 g, 8.62 mmol). The reaction mixture was degassed with argon for three times and stirred for 2 h at 90° C. After cooling down to ambient temperature, the resulting mixture was poured into water (100 mL) and extracted with EA (3×100 mL). The combined organic layers were washed with brine (2×100 mL), dried over anhydrous sodium sulfate and filtered. The filtrate was concentrated under reduced pressure. The residue was purified by silica gel column chromatography, eluted with 18% EA in PE. The fractions contained desired product were combined and concentrated to afford 4,6-difluoro-2-(trifluoromethyl)-5-[2-(trimethylsilyl)ethynyl]-1H-1,3-benzodiazole (0.40 g, 44%) as a light yellow solid. MS ESI calculated for C$_{13}$H$_{11}$F$_5$N$_2$Si [M+H]$^+$, 319.06; found 318.95.

Step 3: 5-Ethynyl-4,6-difluoro-2-(trifluoromethyl)-1H-1,3-benzodiazole

To a stirred solution of 4,6-difluoro-2-(trifluoromethyl)-5-[2-(trimethylsilyl)ethynyl]-1H-1,3-benzodiazole (0.38 mg, 1.19 mmol) in tetrahydrofuran (5 mL) was added TBAF (1.0 M in THF, 1.80 mL, 1.80 mmol) dropwise at 0° C. The reaction mixture was stirred at room temperature for 2 h. The resulting mixture was poured into sodium thiosulfate (10 mL) and extracted with EA (3×20 mL). The combined organic layers were washed with brine (2×10 mL), dried over anhydrous sodium sulfate and filtered. The filtrate was concentrated under reduced pressure. The residue was purified by Carbon eighteen gel column chromatography, eluted with ACN in H$_2$O (0~34%). The fractions contained desired product were combined and concentrated to afford 5-ethynyl-4,6-difluoro-2-(trifluoromethyl)-1H-1,3-benzodiazole (0.21 g, 71%) as a brown solid. MS ESI calculated for C$_{10}$H$_3$F$_5$N$_2$ [M+H]$^+$, 247.02; found 247.14.

Step 4: 3-[2-[4,6-difluoro-2-(trifluoromethyl)-1H-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide To a stirred mixture of 5-ethynyl-4,6-difluoro-2-(trifluoromethyl)-1H-1,3-benzodiazole (88.66 mg) and 3-iodo-1-[(3S,5R)-5-(methoxymethyl)-1-(prop-2-enoyl)pyrrolidin-3-yl]-5-(methylamino)pyrazole-4-carboxamide (0.13 g) in DMF (1.3 mL) were added Pd(PPh$_3$)$_2$Cl$_2$ (21.06 mg), CuI (11.4 mg) and TEA (91 mg). The reaction mixture was degassed with argon for three times and stirred for 1.5 h at 90° C. The resulting mixture was purified by reverse flash chromatography with the following conditions: column, C18 silica gel; mobile phase, ACN in water, 5% to 30% gradient in 30 min; detector, UV 210 nm. The fractions contained desired product were combined and concentrated. The crude product was purified by Prep-HPLC with the following conditions Column: XBridge Prep C18 OBD Column, 19×150 mm 5 um; Mobile Phase A: Water (10 mmoL/L NH$_4$HCO$_3$), Mobile Phase B: ACN; Flow rate: 20 mL/min; Gradient: 30 B to 60 B in 4.3 min; 210/254 nm; RT1: 4.23. The fractions contained desired product were combined and concentrated to afford 3-[2-[4,6-difluoro-2-(trifluoromethyl)-1H-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide (72 mg, 43%) as a white solid. MS ESI calculated for $C_{24}H_{22}F_5N_7O_3$ [M+H]$^+$, 552.17; found 552.48. $^1$H NMR (400 MHz, DMSO-d$_6$) δ 14.88 (s, 1H), 7.58 (brs, 2H), 6.76-6.59 (m, 3H), 6.19-6.14 (m, 1H), 5.71-5.66 (m, 1H), 5.30-5.25 (m, 1H), 4.48-4.44 (m, 1H), 3.99-3.96 (m, 2H), 3.59-3.44 (m, 2H), 3.31 (s, 3H), 2.96 (s, 3H), 2.67-2.60 (m, 1H), 2.32-2.28 (m, 1H).

Example 47: 3-[2-[1-(difluoromethyl)-4,6-difluoro-2-methyl-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide

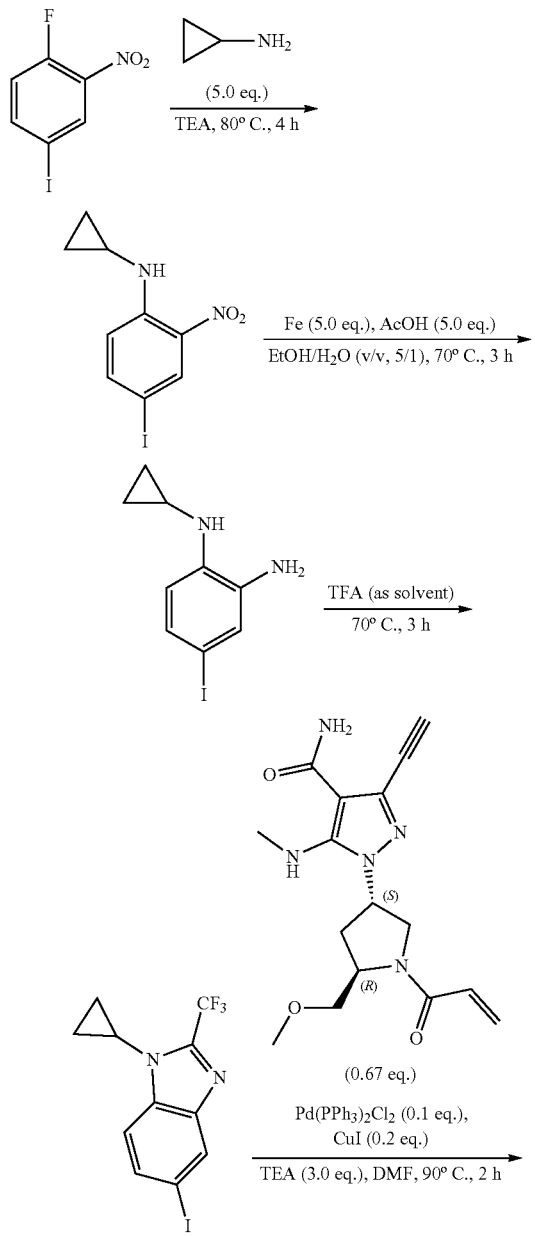

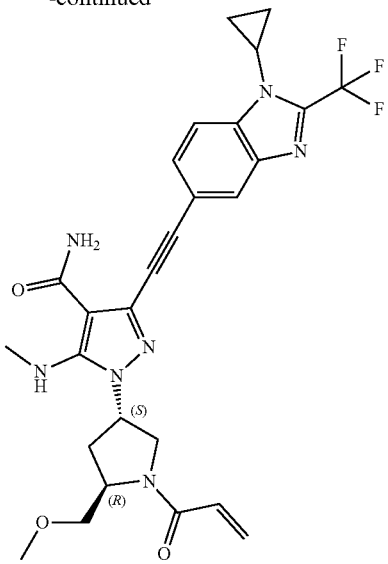

Step 1: N-cyclopropyl-4-iodo-2-nitroaniline

To a stirred mixture of 1-fluoro-4-iodo-2-nitrobenzene (5.00 g, 18.72 mmol) in Et$_3$N (14.58 mL, 144.05 mmol) was added aminocyclopropane (5.35 g, 93.63 mmol) at room temperature. The reaction mixture was stirred for 4 h at 80° C. under nitrogen atmosphere. The resulting mixture was cooled. Then the mixture was quenched with sat. NaHCO$_3$ (30 mL) and extracted with EA (3×50 mL). The combined organic layers were washed with brine (50 mL), dried over anhydrous Na$_2$SO$_4$ and filtered. The filtrate was concentrated under reduced pressure. The fractions contained desired product were combined and concentrated under reduced pressure to afford N-cyclopropyl-4-iodo-2-nitroaniline (5.80 g, crude) as a brown solid. MS ESI calculated for $C_9H_9IN_2O_2$ [M+H]$^+$, 304.97, found 304.90.

Step 2: N1-cyclopropyl-4-iodobenzene-1,2-diamine

To a stirred mixture of iron (5.51 g, 98.65 mmol) and AcOH (5.65 mL, 94.14 mmol) in EtOH (50.00 mL) and H$_2$O (10.00 mL) was added N-cyclopropyl-4-iodo-2-nitroaniline (6.00 g, 19.73 mmol) at 70° C. The resulting reaction was stirred for 3 h at 70° C. The resulting mixture was cooled. Then the mixture was filtered, the filter cake was washed with EA (2×100 mL). The filtrate was concentrated under reduced pressure. The resulting mixture was added water (50 mL) and extracted with EA (3×50 mL). The combined organic layers were washed with brine (2×50 mL), dried over anhydrous Na$_2$SO$_4$ and filtered. The filtrate was concentrated under reduced pressure. The residue was purified by silica gel column chromatography, eluted with EA in PE (20-50%). The fractions contained desired product were combined and concentrated under reduced pressure to afford N1-cyclopropyl-4-iodobenzene-1,2-diamine (3.90 g, 72%) as a brown solid. MS ESI calculated for $C_9H_{11}IN_2$ [M+H]$^+$, 275.11, found 275.05.

Step 3: 1-Cyclopropyl-5-iodo-2-(trifluoromethyl)-1,3-benzodiazole

A solution of N1-cyclopropyl-4-iodobenzene-1,2-diamine (2.00 g, 7.29 mmol) in TFA (15.00 mL) was stirred for 3 h at 70° C. The resulting solution was cooled and concentrated under reduced pressure. The residue was quenched with EA (30 mL) and basified to pH>7 with Sat. NaHCO₃. The mixture was extracted with EA (3×30 mL). The combined organic layers were washed with brine (20 mL), dried over anhydrous Na₂SO₄ and filtered. The filtrate was concentrated under reduced pressure. The residue was purified by silica gel column chromatography, eluted with EA in PE (0-20%). The fractions contained desired product were combined and concentrated to afford 1-cyclopropyl-5-iodo-2-(trifluoromethyl)-1,3-benzodiazole (0.60 g, 23%) as a white solid. MS ESI calculated for $C_{11}H_8F_3IN_2$ [M+H]⁺, 352.97, found 352.95.

Step 4: 3-[2-[1-(difluoromethyl)-4,6-difluoro-2-methyl-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide To a mixture of 3-ethynyl-1-[(3S,5R)-5-(methoxymethyl)-1-(prop-2-enoyl)pyrrolidin-3-yl]-5-(methylamino)pyrazole-4-carboxamide (0.15 g, 0.45 mmol) in DMF (3.00 mL) were added 1-cyclopropyl-5-iodo-2-(trifluoromethyl)-1,3-benzodiazole (0.16 g, 0.45 mmol), Pd(PPh₃)₂Cl₂ (31.77 mg, 0.04 mmol), CuI (17.24 mg, 0.09 mmol) and TEA (137.41 mg, 1.35 mmol). The reaction mixture was degassed with argon for three times and stirred for 2 h at 90° C. The residue was purified by silica gel column chromatography, eluting with MeOH in DCM (0-5%) to afford crude product. Then the crude product was further purified by Prep-HPLC with the following conditions Column: XBridge Prep C18 OBD Column, 19×150 mm 5 um; Mobile Phase A: Water (10 mM NH₄HCO₃), Mobile Phase B: ACN; Flow rate: 20 mL/min; Gradient: 35% B to 70% B in 5.8 min; 210/254 nm. The fractions contained desired product were combined and concentrated to afford 3-[2-[1-cyclopropyl-2-(trifluoromethyl)-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide (51 mg, 22%) as a white solid. MS ESI calculated for $C_{27}H_{28}F_3N_7O_3$ [M+H]⁺, 556.22, found 556.20. ¹H NMR (400 MHz, d₆-DMSO) δ 8.09 (s, 1H), 7.84 (d, J=8.6 Hz, 1H), 7.66-7.64 (m, 1H), 7.38 (brs, 1H), 6.92-6.96 (m, 3H), 6.17-6.14 (m, 1H), 5.69-5.67 (m, 1H), 5.30-5.19 (m, 1H), 4.57-4.52 (m, 1H), 3.91-3.83 (m, 1H), 3.78-3.72 (m, 1H), 3.67-3.58 (m, 2H), 3.53-3.41 (m, 1H), 3.32-3.28 (m, 3H), 2.98-2.92 (m, 3H), 2.49-2.45 (m, 1H), 2.36-2.24 (m, 1H), 1.31-1.12 (m, 4H).

Example 48: 3-(2-[3-Ethyl-2-methylimidazo[4,5-c]pyridin-6-yl]ethynyl)-1-[(3S,5R)-5-(methoxymethyl)-1-(prop-2-enoyl)pyrrolidin-3-yl]-5-(methylamino)pyrazole-4-carboxamide

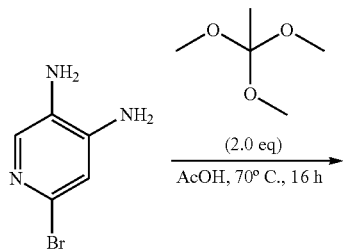

Step 1: 6-Bromo-2-methyl-3H-imidazo[4,5-c]pyridine

To a stirred solution of 6-bromopyridine-3,4-diamine (1.00 g, 5.32 mmol) in AcOH (10.00 mL) was added 1,1,1-trimethoxyethane (1.36 mL, 10.64 mmol). The reaction mixture was stirred for 16 h at 70° C. under argon atmosphere. The resulting mixture was concentrated under reduced pressure. The residue was neutralized to pH 7 with saturated NaHCO₃ (aq.). The resulting mixture was extracted with EtOAc (2×200 mL). The combined organic layers were washed with water (2×100 mL), dried over anhydrous Na₂SO₄ and filtered. The filtrate was concentrated under reduced pressure. The residue was purified by silica gel Column chromatography, eluted with DCM/MeOH (20/1). The fractions contained desired product were combined and concentrated to afford 6-bromo-2-methyl-3H-

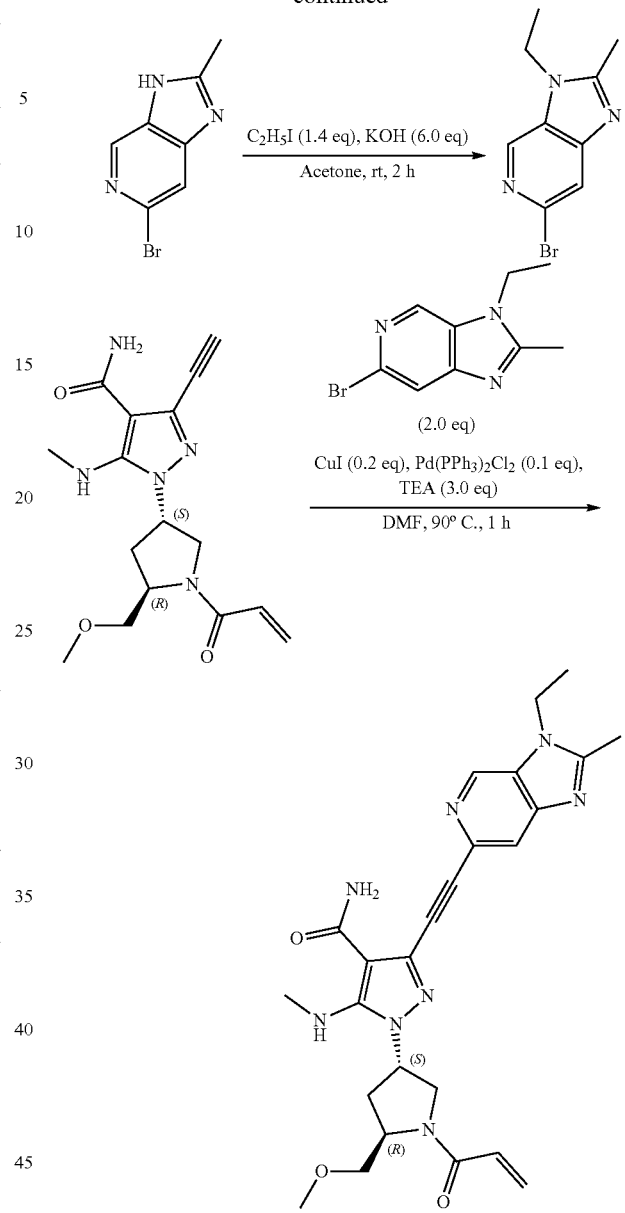

imidazo[4,5-c]pyridine (0.86 g, 75%) as a light yellow solid. MS ESI calculated for C₇H₆BrN₃ [M+H]⁺, 211.97, found 212.00.

Step 2: 6-Bromo-3-ethyl-2-methylimidazo[4,5-c]pyridine

To a stirred mixture of 6-bromo-2-methyl-3H-imidazo[4,5-c]pyridine (0.85 g, 4.01 mmol) and KOH (1.35 g, 24.06 mmol) in acetone (20.00 mL) was added ethyl iodide (0.45 mL, 5.63 mmol) dropwise at 0° C. The resulting mixture was stirred for 2 h at room temperature under argon atmosphere. The resulting mixture was extracted with EtOAc (2×200 mL). The combined organic layers were washed with water (2×100 mL), dried over anhydrous Na₂SO₄ and filtered. The filtrate was concentrated under reduced pressure. The residue was purified by silica gel Column chromatography, eluted with CH₂Cl₂/MeOH (20/1). The fractions contained desired product were combined and concentrated to afford 6-bromo-3-ethyl-2-methylimidazo[4,5-c]pyridine (0.32 g, 33%) as a light yellow solid. ¹H NMR (400 MHz, CDCl₃) δ 8.50 (d, J=0.8 Hz, 1H), 7.78 (d, J=0.8 Hz, 1H), 4.25 (q, J=7.2 Hz, 2H), 2.68 (s, 3H), 1.49 (t, J=7.2 Hz, 3H).

Step 3: 3-(2-[3-Ethyl-2-methylimidazo[4,5-c]pyridin-6-yl]ethynyl)-1-[(3S,5R)-5-(methoxymethyl)-1-(prop-2-enoyl)pyrrolidin-3-yl]-5-(methylamino)pyrazole-4-carboxamide To a stirred mixture of 3-ethynyl-1-[(3S,5R)-5-(methoxymethyl)-1-(prop-2-enoyl)pyrrolidin-3-yl]-5-(methylamino)pyrazole-4-carboxamide (0.18 g, 0.54 mmol), 6-bromo-3-ethyl-2-methylimidazo[4,5-c]pyridine (0.16 g, 0.65 mmol), CuI (20.69 mg, 0.11 mmol) and Pd(PPh₃)₂Cl₂ (38.13 mg, 0.05 mmol) in DMF (1.00 mL) was added TEA (0.24 mL, 1.73 mmol). The reaction mixture was degassed with argon for three times and stirred for 1 h at 90° C. The resulting mixture was concentrated under reduced pressure. The residue was purified by Prep-HPLC with the following conditions Column: SunFire Prep C18 OBD Column, 19×150 mm 5 μm 10 nm; Mobile Phase A: Water (0.1% FA), Mobile Phase B: MeOH; Flow rate: 20 mL/min; Gradient: 42 B to 56 B in 6 min; 210/254 nm; RT: 5.56 min. The fractions contained desired product were combined and concentrated to afford 3-(2-[3-ethyl-2-methylimidazo[4,5-c]pyridin-6-yl]ethynyl)-1-[(3S,5R)-5-(methoxymethyl)-1-(prop-2-enoyl)pyrrolidin-3-yl]-5-(methylamino)pyrazole-4-carboxamide (55.3 mg, 20%) as an off-white solid. MS ESI calculated for C₂₅H₃₀N₈O₃ [M+H]⁺, 491.24, found 491.15; ¹H NMR (400 MHz, DMSO-d₆) δ 9.00 (s, 1H), 7.93 (s, 1H), 7.47 (s, 1H), 7.01-6.46 (m, 3H), 6.17 (d, J=16.8 Hz, 1H), 5.69 (d, J=10.4 Hz, 1H), 5.34-5.20 (m, 1H), 4.65-4.25 (m, 3H), 4.09-3.47 (m, 5H), 3.48-3.42 (m, 3H), 2.96 (d, J=4.8 Hz, 3H), 2.64 (s, 3H), 2.37-2.25 (m, 1H), 1.36 (t, J=7.2 Hz, 3H).

Example 49: 3-[2-(2-Amino-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide

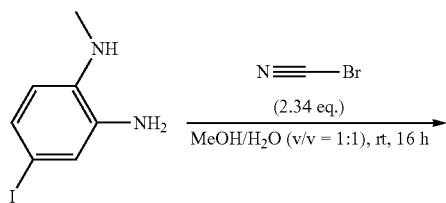

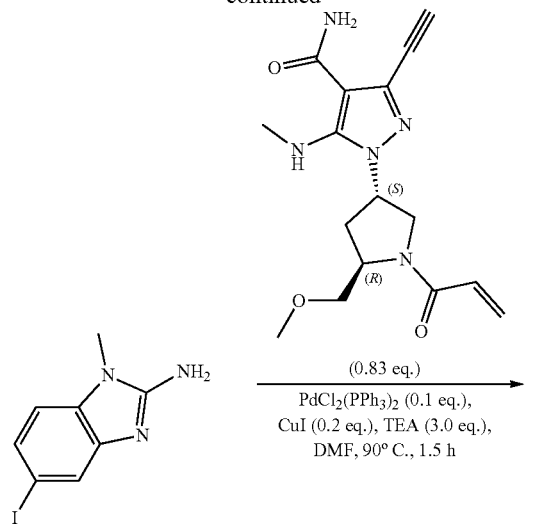

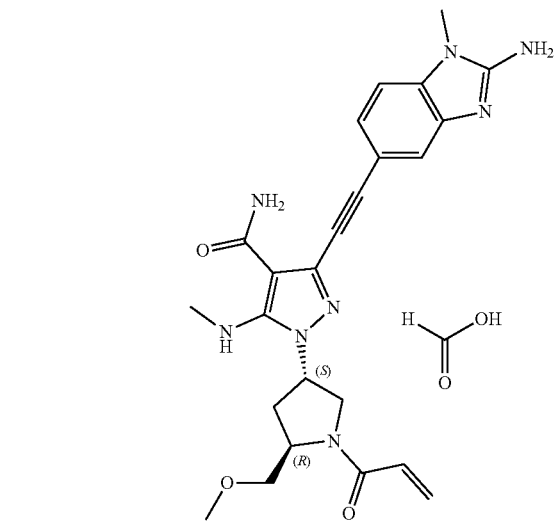

Step 1: 5-Iodo-1-methyl-1,3-benzodiazol-2-amine

To a stirred solution of 4-iodo-N1-methylbenzene-1,2-diamine (0.60 g, 2.42 mmol) in MeOH (6.00 mL) and H2O (6.00 mL) was added cyanogen bromide (0.60 g, 5.66 mmol). The reaction mixture was stirred for 16 h at room temperature. The resulting mixture was concentrated under reduced pressure. The residue was diluted with water (10 mL) and basified to pH 8 with NaHCO3 solid. The aqueous layer was extracted with EA (3×15 mL) and the combined organic layers was dried over anhydrous sodium sulfate and filtered. The filtrate was concentrated under reduced pressure. The residue was purified by silica gel Column chromatography, eluting with MeOH in DCM (0-5%). The fractions contained desired product were combined and concentrated under reduced pressure to afford 5-iodo-1-methyl-1,3-benzodiazol-2-amine (0.25 g, 38%). MS ESI calculated for C8H8IN3 [M+H]+, 273.98, found 274.00.

Step 2: 3-[2-(2-Amino-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide; formic acid To a stirred mixture of 3-ethynyl-1-[(3S,5R)-5-(methoxymethyl)-1-(prop-2-enoyl)pyrrolidin-3-yl]-5-(methylamino)pyrazole-4-carboxamide (0.13 g, 0.39 mmol), 5-iodo-1-methyl-1,3-benzodiazol-2-amine (0.13 g, 0.47 mmol), PdCl2(PPh3)2 (27.54 mg, 0.04 mmol) and CuI (14.94 mg, 0.08 mmol) in DMF (2.00 mL) was added TEA (0.12 g, 1.18 mmol). The reaction mixture was degassed with argon for three times and stirred for 1.5 h at 90° C. The resulting mixture was concentrated under reduced pressure. The residue was purified by silica gel Column chromatography, eluting with MeOH in DCM (0-5.0%) to afford crude product. Then the crude product was further purified by Prep-HPLC with the following conditions: Column: SunFire Prep C18 OBD Column, 19×150 mm 5 μm 10 nm; Mobile Phase A: Water (0.1% FA), Mobile Phase B: MeOH; Flow rate: 20 mL/min; Gradient: 30% B to 50% B in 6 min; 210/254 nm; RT: 5.56 min. The fractions contained desired product were combined and concentrated to afford 3-[2-(2-amino-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide; formic acid (30.7 mg, 15%) as a white solid. MS ESI calculated for C24H28N8O3 [M+H−FA]+, 477.24, found 477.25; 1H NMR (400 MHz, DMSO-d6) δ 8.14 (brs. 1H), 7.41-7.21 (m, 2H), 7.18-7.09 (m, 1H), 6.72 (m, 2H), 6.66-6.56 (m, 2H), 6.19-6.15 (m, 1H), 5.70-5.68 (m, 1H), 5.26-5.20 (m, 1H), 4.56-4.36 (m, 1H), 4.05-3.70 (m, 2H), 3.63-3.42 (m, 5H), 3.31-3.27 (m, 3H), 2.96-2.93 (m, 3H), 2.34-2.28 (m, 1H), 2.50-2.45 (m, 1H).

Example 50: 3-[2-(2-Cyclopropyl-4,6-difluoro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide

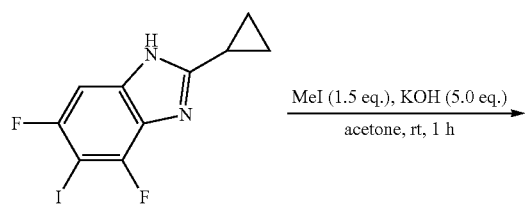

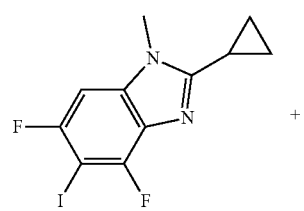

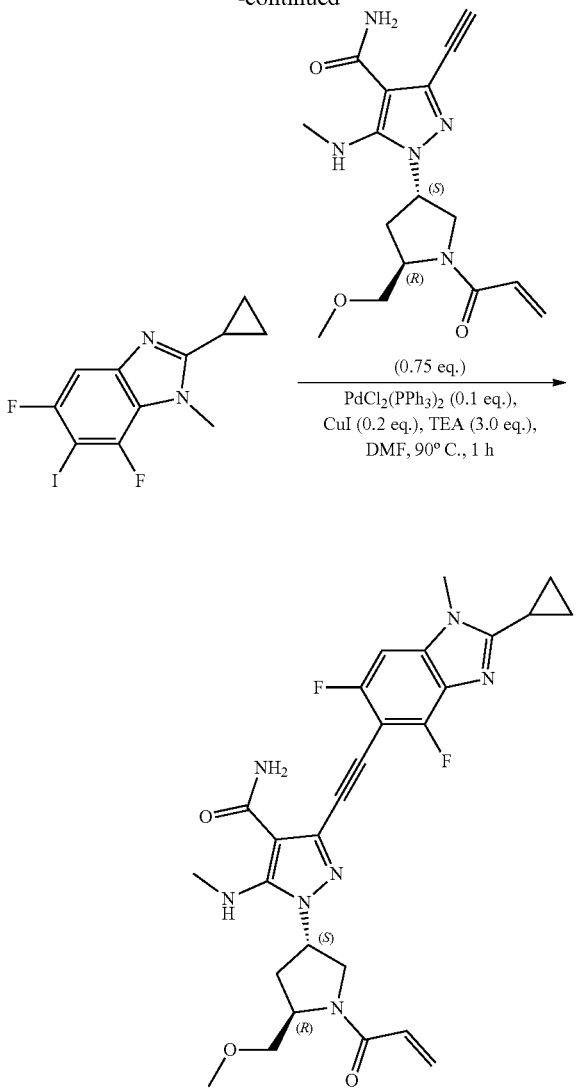

Step 1: 2-Cyclopropyl-4,6-difluoro-5-iodo-1-methyl-1,3-benzodiazole

To a stirred mixture of 2-cyclopropyl-4,6-difluoro-5-iodo-1H-1,3-benzodiazole (1.20 g, 3.75 mmol) and KOH (1.05 g, 18.75 mmol) in acetone (60.00 mL) was added MeI (1.06 g, 7.50 mmol) dropwise at 0° C. The reaction mixture was stirred for 1 h at room temperature. The resulting mixture was quenched with water (30 mL) at room temperature, extracted with EtOAc (3×60 mL). The combined organic layers were washed with brine (2×30 mL), dried over anhydrous Na2SO4 and filtered. The filtrate was concentrated under reduced pressure. The residue was purified by reverse phase flash with the following conditions Column: Spherical C18, 20-35 μm, 330 g; Mobile Phase A: water (10 mmol/L NH4HCO3), Mobile Phase B: ACN; Flow rate: 85 mL/min; Gradient: 0%-45% within 45 min, Detector: UV 254 & 220 nm; RT: 45 min. The fractions contained desired product were combined and concentrated to afford 2-cyclopropyl-4,6-difluoro-5-iodo-1-methyl-1,3-benzodiazole (0.33 g, 26%) as a light yellow solid. MS ESI calculated for C11H9F2IN2 [M+H]+, 334.98, found 335.00.

Step 2: 3-[2-(2-Cyclopropyl-4,6-difluoro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide To a stirred mixture of 2-cyclopropyl-4,6-difluoro-5-iodo-1-methyl-1,3-benzodiazole (0.14 g, 0.40 mmol) in DMF (2.00 mL) were added 3-ethynyl-1-[(3S,5R)-5-(methoxymethyl)-1-(prop-2-enoyl)pyrrolidin-3-yl]-5-(methylamino) pyrazole-4-carboxamide (0.10 g, 0.30 mmol), CuI (15.39 mg, 0.08 mmol), Pd(PPh3)2Cl2 (28.36 mg, 0.04 mmol) and TEA (0.12 g, 1.21 mmol). The reaction mixture was degassed with argon for three times and stirred for 1 h at 90° C. The resulting mixture was concentrated under reduced pressure. The residue was purified by reverse phase chromatography with the following conditions: Column: Spherical C18, 20-40 μm, 40 g; Mobile Phase A: water (10 mmol/L NH4HCO3), Mobile Phase B: ACN; Flow rate: 40 mL/min; Gradient: 20%~50% within 40 min; Detector: 254/220 nm; RT: 30 min. The fractions contained desired product were combined and concentrated to afford 3-[2-(2-cyclopropyl-4,6-difluoro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (61.3 mg, 28%) as an off-white solid. MS ESI calculated for C27H29F2N7O3 [M+H]+, 538.23, found 538.30; 1H NMR (300 MHz, DMSO-d6) δ 7.57 (d, J=9.2 Hz, 2H), 6.84-6.54 (m, 3H), 6.18-6.17 (m, 1H), 5.69-5.65 (m, 1H), 5.28-5.26 (m, 1H), 4.58-4.30 (m, 1H), 4.04-4.02 (m, 1H), 3.91-3.57 (m, 5H), 3.49-3.45 (m, 1H), 3.31 (d, J=4.0 Hz, 3H), 2.97-2.94 (m, 3H), 2.68-2.58 (m, 1H), 2.31-2.24 (m, 2H), 1.23-1.02 (m, 4H).

Example 51: 1-((3S,5R)-1-Acryloyl-5-(methoxymethyl)pyrrolidin-3-yl)-3-((2-cyclopropyl-4-fluoro-1-methyl-1H-benzo[d]imidazol-5-yl)ethynyl)-5-(methylamino)-1H-pyrazole-4-carboxamide

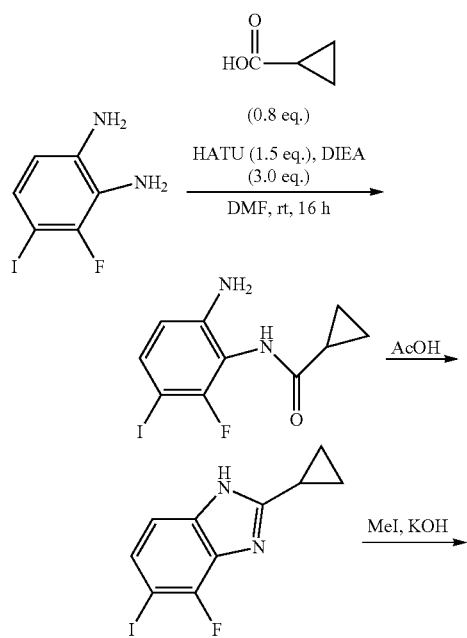

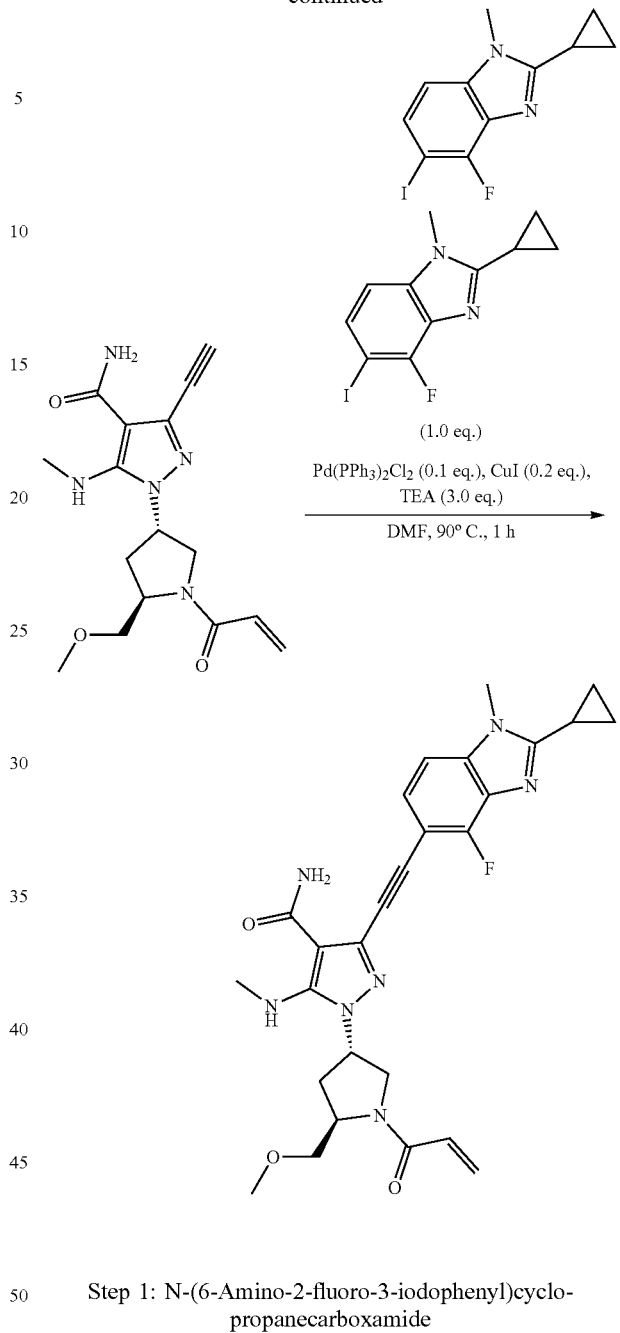

Step 1: N-(6-Amino-2-fluoro-3-iodophenyl)cyclopropanecarboxamide

To a stirred solution of 3-fluoro-4-iodobenzene-1,2-diamine (1.00 g, 3.97 mmol) and HATU (2.26 g, 5.95 mmol), DIEA (2.07 mL, 11.88 mmol) in DMF (7.00 mL) was added cyclopropanecarboxylic acid (0.17 g, 1.98 mmol) in DMF (3.00 mL) dropwise at room temperature under nitrogen atmosphere. The reaction mixture was stirred for 16 h. The resulting mixture was diluted with water (80 mL), extracted with EtOAc (3×80 mL). The combined organic layers were washed with brine (3×60 mL), dried over anhydrous Na2SO4 and filtered. The filtrate was concentrated under reduced pressure. The residue was purified by silica gel Column chromatography, eluted with PE/EtOAc (2/1). The fractions contained desired product were combined and concentrated to afford N-(6-amino-2-fluoro-3-iodophenyl)

cyclopropanecarboxamide (0.63 g, 50%) as a brown solid. MS ESI calculated for C10H10FIN2O [M+H]+, 320.98, found 321.05.

Step 2: 2-Cyclopropyl-4-fluoro-5-iodo-1H-benzo[d]imidazole

A solution of N-(6-amino-2-fluoro-3-iodophenyl)cyclopropanecarboxamide (0.63 g, 1.97 mmol) in AcOH (6.00 mL) was stirred for 5 h at 70° C. under nitrogen atmosphere. The resulting mixture was concentrated under reduced pressure. The residue was neutralized to pH 8 with saturated NaHCO3 (aq.). The resulting mixture was extracted with EtOAc (3×40 mL). The combined organic layers were washed with brine (3×30 mL), dried over anhydrous Na2SO4 and filtered. The filtrate was concentrated under reduced pressure. The residue was purified by silica gel Column chromatography, eluted with PE/EtOAc (1/1). The fractions contained desired product were combined and concentrated to afford 2-cyclopropyl-4-fluoro-5-iodo-1H-benzo[d]imidazole (0.41 g, 69%) as an off-white solid. MS ESI calculated for C10H8FIN2 [M+H]+, 302.97, found 302.95.

Step 3: 2-Cyclopropyl-4-fluoro-5-iodo-1-methyl-1H-benzo[d]imidazole

To a stirred mixture of 2-cyclopropyl-4-fluoro-5-iodo-1H-benzo[d]imidazole (0.38 g, 1.26 mmol) and KOH (0.42 g, 7.55 mmol) in acetone (5.00 mL) was added methyl iodide (0.25 g, 1.76 mmol) dropwise at 0° C. under nitrogen atmosphere. The reaction mixture was stirred for 40 min at room temperature. The resulting mixture was concentrated under reduced pressure. The residue was purified by reverse flash chromatography with the following conditions: Column, C18 silica gel; mobile phase A: Water (10 mmol/L NH4HCO3), Mobile Phase B: ACN; Gradient: 30 B to 60 B in 20 min; detector, UV 254 nm. The fractions contained desired product were combined and concentrated to afford 2-cyclopropyl-4-fluoro-5-iodo-1-methyl-1H-benzo[d]imidazole (0.14 g, 35%) as an off-white solid. MS ESI calculated for C11H10FIN2 [M+H]+, 316.99, found 316.95.

Step 4: 1-((3S,5R)-1-Acryloyl-5-(methoxymethyl)pyrrolidin-3-yl)-3-((2-cyclopropyl-4-fluoro-1-methyl-1H-benzo[d]imidazol-5-yl)ethynyl)-5-(methylamino)-1H-pyrazole-4-carboxamide To a stirred mixture of 3-ethynyl-1-[(3S,5R)-5-(methoxymethyl)-1-(prop-2-enoyl)pyrrolidin-3-yl]-5-(methylamino)pyrazole-4-carboxamide (0.13 g, 0.39 mmol), 2-cyclopropyl-4-fluoro-5-iodo-1-methyl-1H-benzo[d]imidazole (0.12 g, 0.38 mmol), CuI (14.83 mg, 0.08 mmol) and Pd(PPh3)2Cl2 (27.32 mg, 0.04 mmol) in DMF (1.50 mL) was added TEA (0.16 mL, 1.15 mmol). The reaction mixture was degassed with argon for three times and stirred for 1 h at 90° C. The resulting mixture was concentrated under reduced pressure. The residue was purified by Prep-HPLC with the following conditions: Column: XBridge Prep C18 OBD Column, 19×150 mm 5 μm; Mobile Phase A: Water (10 mmol/L NH4HCO3), Mobile Phase B: ACN; Flow rate: 20 mL/min; Gradient: 30 B to 60 B in 5.8 min; 210/254 nm; RT: 5.56 min. The fractions contained desired product were combined and concentrated to afford 1-((3S,5R)-1-acryloyl-5-(methoxymethyl)pyrrolidin-3-yl)-3-((2-cyclopropyl-4-fluoro-1-methyl-1H-benzo[d]imidazol-5-yl)ethynyl)-5-(methylamino)-1H-pyrazole-4-carboxamide (39.4 mg, 20%) as an off-white solid. MS ESI calculated for C27H30FN7O3 [M+H]+, 520.58, found 520.25; 1H NMR (400 MHz, DMSO-d6) δ 7.44-7.38 (m, 3H), 6.84-6.71 (m, 3H), 6.19-6.15 (m, 1H), 5.70-5.68 (m, 1H), 5.29-5.21 (m, 1H), 4.53 (d, J=54.3 Hz, 1H), 4.07-3.98 (m, 1H), 3.91-3.87 (m, 4H), 3.66-3.40 (m, 2H), 3.32-3.30 (m, 3H), 2.97 (t, J=5.2 Hz, 3H), 2.33-2.28 (m, 3H), 1.17-1.11 (m, 4H).

Example 52: 1-[(3 S,5R)-5-(Methoxymethyl)-1-(prop-2-enoyl) pyrrolidin-3-yl]-5-(methylamino)-3-[2-(quinolin-7-yl) ethynyl] pyrazole-4-carboxamide

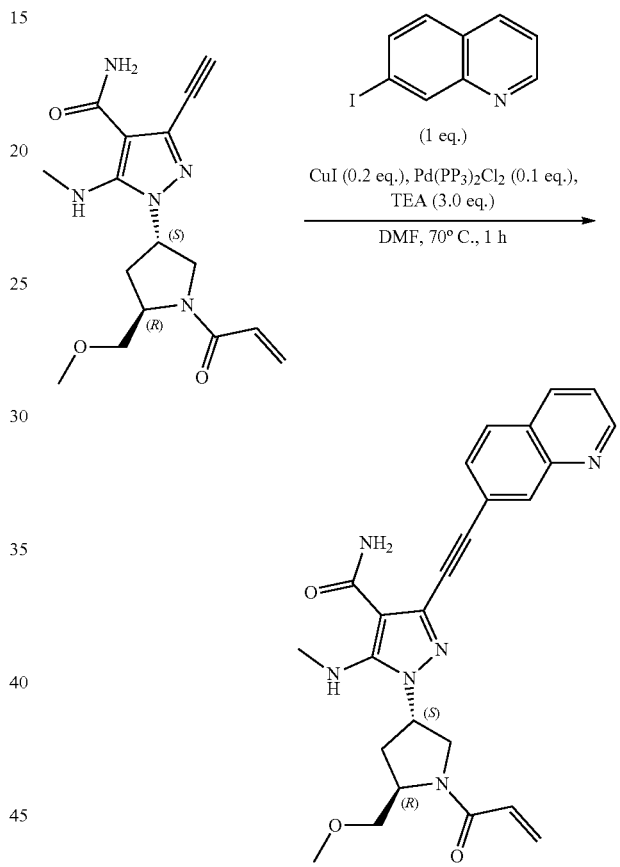

To a mixture of 7-iodoquinoline (0.1 g, 0.39 mmol), 3-ethynyl-1-[(3S,5R)-5-(methoxymethyl)-1-(prop-2-enoyl) pyrrolidin-3-yl]-5-(methylamino) pyrazole-4-carboxamide (0.13 g, 0.39 mmol), CuI (14.93 mg, 0.07 mmol) and Pd(PPh3)2Cl2 (27.52 mg, 0.04 mmol) in DMF (2.00 mL) was added TEA (0.12 g, 1.17 mmol). The reaction mixture was degassed with argon for three times and stirred for 1 h at 70° C. The resulting mixture was concentrated under reduced pressure. The residue was purified by reverse phase chromatography with the following conditions: Column: Spherical C18, 20-40 μm, 40 g; Mobile Phase A: Water (10 mM NH4HCO3), Mobile Phase B: ACN; Flow rate: 40 mL/min; Gradient: 15%-40% within 30 min, Detector: UV 254/220 nm; RT: 30 min. The fractions contained desired product were combined and concentrated to afford 1-[(3S, 5R)-5-(methoxymethyl)-1-(prop-2-enoyl) pyrrolidin-3-yl]-5-(methylamino)-3-[2-(quinolin-7-yl) ethynyl] pyrazole-4-carboxamide (0.10 g, 47%) as an off-white solid. MS ESI calculated for C25H26N6O3 [M+H]+, 459.21, found 459.20; 1H NMR (300 MHz, DMSO-d6) δ 8.98 (dd, J=4.2, 1.7 Hz, 1H), 8.46-8.37 (m, 1H), 8.24 (s, 1H), 8.06 (d, J=8.5 Hz, 1H), 7.73 (dd, J=8.5, 1.7 Hz, 1H), 7.60 (dd, J=8.3, 4.2 Hz, 1H), 7.37 (s, 1H), 6.92 (s, 1H), 6.80-6.48 (m, 2H), 6.18-6.15 (m, 1H), 5.73-5.68 (m, 1H), 5.30-5.21 (m, 1H), 4.49-4.45 (m 1H), 4.09-3.70 (m, 2H), 3.66-3.41 (m, 2H), 3.32 (d, J=3.6 Hz, 3H), 2.95-2.93 (m, 3H), 2.67-2.53 (m, 1H), 2.38-2.26 (m, 1H).

Example 53: 1-[(3S,5R)-5-(Methoxymethyl)-1-(prop-2-enoyl)pyrrolidin-3-yl]-5-(methylamino)-3-(2-[pyrazolo[1,5-a]pyrimidin-5-yl]ethynyl)pyrazole-4-carboxamide

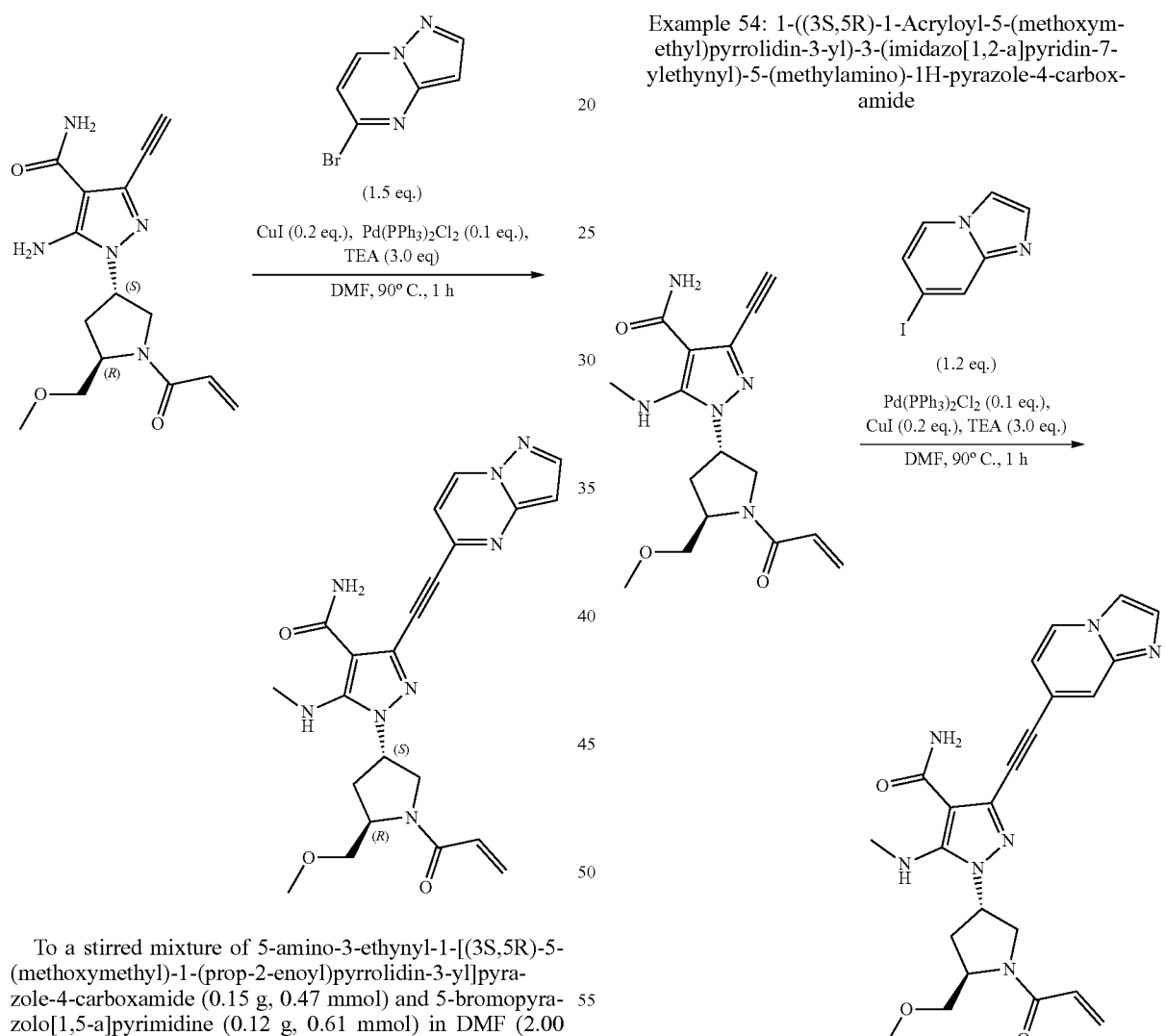

To a stirred mixture of 5-amino-3-ethynyl-1-[(3S,5R)-5-(methoxymethyl)-1-(prop-2-enoyl)pyrrolidin-3-yl]pyrazole-4-carboxamide (0.15 g, 0.47 mmol) and 5-bromopyrazolo[1,5-a]pyrimidine (0.12 g, 0.61 mmol) in DMF (2.00 mL) were added CuI (18.00 mg, 0.10 mmol), Pd(PPh3)2Cl2 (33.18 mg, 0.05 mmol) and TEA (0.14 g, 1.42 mmol) at room temperature. The reaction mixture was degassed with argon for three times and stirred for 1 h at 90° C. The resulting mixture was concentrated under reduced pressure. The residue was purified by silica gel Column chromatography, eluted with CH2Cl2/MeOH (0%-5%). The fractions contained desired product were combined and concentrated. The residue was purified by Prep-HPLC with the following conditions: Column: XBridge Prep C18 OBD Column, 19×150 mm 5 μm; Mobile Phase A: Water (10 mmol/L NH4HCO3), Mobile Phase B: ACN; Flow rate: 20 mL/min; Gradient: 35 B to 55 B in 6 min; 210/254 nm. The fractions contained desired product were combined and concentrated to afford 1-[(3S,5R)-5-(methoxymethyl)-1-(prop-2-enoyl) pyrrolidin-3-yl]-5-(methylamino)-3-(2-[pyrazolo[1,5-a]pyrimidin-5-yl]ethynyl)pyrazole-4-carboxamide (69.6 mg, 32%) as a yellow solid. MS ESI calculated for C22H24N8O3, 448.20, found 448.48; 1H NMR (400 MHz, DMSO-d6) δ 9.19 (dd, J=7.3, 1.0 Hz, 1H), 8.32 (d, J=2.4 Hz, 1H), 7.44 (s, 1H), 7.22 (dd, J=7.3, 3.6 Hz, 1H), 6.91-6.78 (m, 2H), 6.64-6.46 (m, 2H), 6.18-6.16 (m, 1H), 5.71-5.68 (m, 1H), 5.24-5.22 (m, 1H), 4.23-4.21 (m, 1H), 3.92-3.82 (m, 2H), 3.74-3.72 (m, 1H), 3.62-3.59 (m, 1H), 3.53-3.42 (m, 3H), 2.94 (t, J=5.3 Hz, 3H), 2.62-2.59 (m, 1H), 2.46-2.43 (m, 1H).

Example 54: 1-((3S,5R)-1-Acryloyl-5-(methoxymethyl)pyrrolidin-3-yl)-3-(imidazo[1,2-a]pyridin-7-ylethynyl)-5-(methylamino)-1H-pyrazole-4-carboxamide

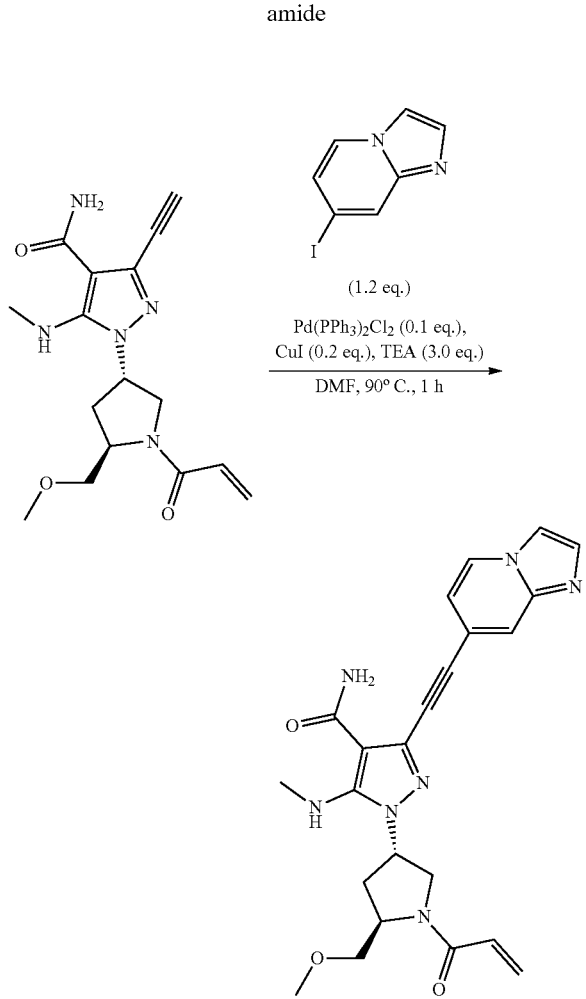

To a stirred mixture of 3-ethynyl-1-[(3S,5R)-5-(methoxymethyl)-1-(prop-2-enoyl)pyrrolidin-3-yl]-5-(methylamino)pyrazole-4-carboxamide (0.13 g, 0.39 mmol), 7-iodoimidazo[1,2-a]pyridine (0.12 g, 0.47 mmol), CuI (14.94 mg, 0.08 mmol) and Pd(PPh3)2Cl2 (27.54 mg, 0.04 mmol) in DMF (1.50 mL) was added TEA (0.16 mL, 1.15 mmol). The reaction mixture was degassed with argon for three times and stirred for 1 h at 90° C. The resulting mixture was diluted with water (20 mL), extracted with EA (3×20 mL). The combined organic layers were washed with brine (3×20 mL), dried over anhydrous Na2SO4 and filtered. The filtrate was concentrated under reduced pressure. The residue was purified by Prep-HPLC with the following conditions: Column: XBridge Prep C18 OBD Column, 19×150 mm 5 µm; Mobile Phase A: Water (10 mmol/L NH4HCO3), Mobile Phase B: ACN; Flow rate: 20 mL/min; Gradient: 30 B to 60 B in 6 min; 210/254 nm; RT: 5.56 min. The fractions contained desired product were combined and concentrated to afford 1-((3S,5R)-1-acryloyl-5-(methoxymethyl)pyrrolidin-3-yl)-3-(imidazo[1,2-a]pyridin-7-ylethynyl)-5-(methylamino)-1H-pyrazole-4-carboxamide (67.0 mg, 38%) as a light pink solid. MS ESI calculated for $C_{23}H_{25}N_7O_3$ [M+H]$^+$, 448.20, found 448.20; 1H NMR (400 MHz, DMSO-d6) δ 8.68 (s, 1H), 8.17-7.88 (m, 3H), 7.32 (s, 1H), 7.09-6.45 (m, 4H), 6.19-6.14 (m, 1H), 5.71-5.67 (m, 1H), 5.27-5.19 (m, 1H), 4.54-4.39 (m, 1H), 4.07-3.68 (m, 2H), 3.64-3.38 (m, 2H), 3.32 (s, 3H), 2.94 (t, J=5.1 Hz, 3H), 2.63-2.56 (m, 1H), 2.34-2.24 (m, 1H).

Example 55: 1-((3S,5R)-1-Acryloyl-5-(methoxymethyl)pyrrolidin-3-yl)-3-(imidazo[1,2-a]pyridin-6-ylethynyl)-5-(methylamino)-1H-pyrazole-4-carboxamide CuI (14.94 mg, 0.08 mmol) and Pd(PPh3)2Cl2 (27.54 mg, 0.04 mmol) in DMF (1.50 mL) was added TEA (0.16 mL, 1.15 mmol). The reaction mixture was degassed with argon for three times and stirred for 1 h at 90° C. The resulting mixture was diluted with water (20 mL), extracted with EA (3×20 mL). The combined organic layers were washed with brine (3×20 mL), dried over anhydrous Na2SO4 and filtered. The filtrate was concentrated under reduced pressure. The residue was purified by Prep-HPLC with the following conditions: Column: XBridge Prep C18 OBD Column, 19×150 mm 5 µm; Mobile Phase A: Water (10 mmol/L NH4HCO3), Mobile Phase B: ACN; Flow rate: 20 mL/min; Gradient: 25 B to 55 B in 6 min; 210/254 nm; RT: 5.52 min. The fractions contained desired product were combined and concentrated to afford 1-((3S,5R)-1-acryloyl-5-(methoxymethyl)pyrrolidin-3-yl)-3-(imidazo[1,2-a]pyridin-6-ylethynyl)-5-(methylamino)-1H-pyrazole-4-carboxamide (82.8 mg, 47%) as an off-white solid. MS ESI calculated for C23H25N7O3 [M+H]+, 448.20, found 448.10; 1H NMR (400 MHz, DMSO-d6) δ 9.16 (s, 1H), 8.41-7.39 (m, 3H), 7.35 (s, 2H), 7.02-6.42 (m, 3H), 6.19-6.13 (m, 1H), 5.71-5.67 (m, 1H), 5.29-5.17 (m, 1H), 4.54-4.39 (m, 1H), 4.13-3.65 (m, 2H), 3.64-3.40 (m, 2H), 3.30 (s, 3H), 2.94 (t, J=5.2 Hz, 3H), 2.69-2.54 (m, 1H), 2.36-2.23 (m, 1H).

Example 56: 1-[(3S,5R)-5-(Methoxymethyl)-1-(prop-2-enoyl)pyrrolidin-3-yl]-5-(methylamino)-3-(2-[pyrazolo[1,5-a]pyridin-5-yl]ethynyl)pyrazole-4-carboxamide

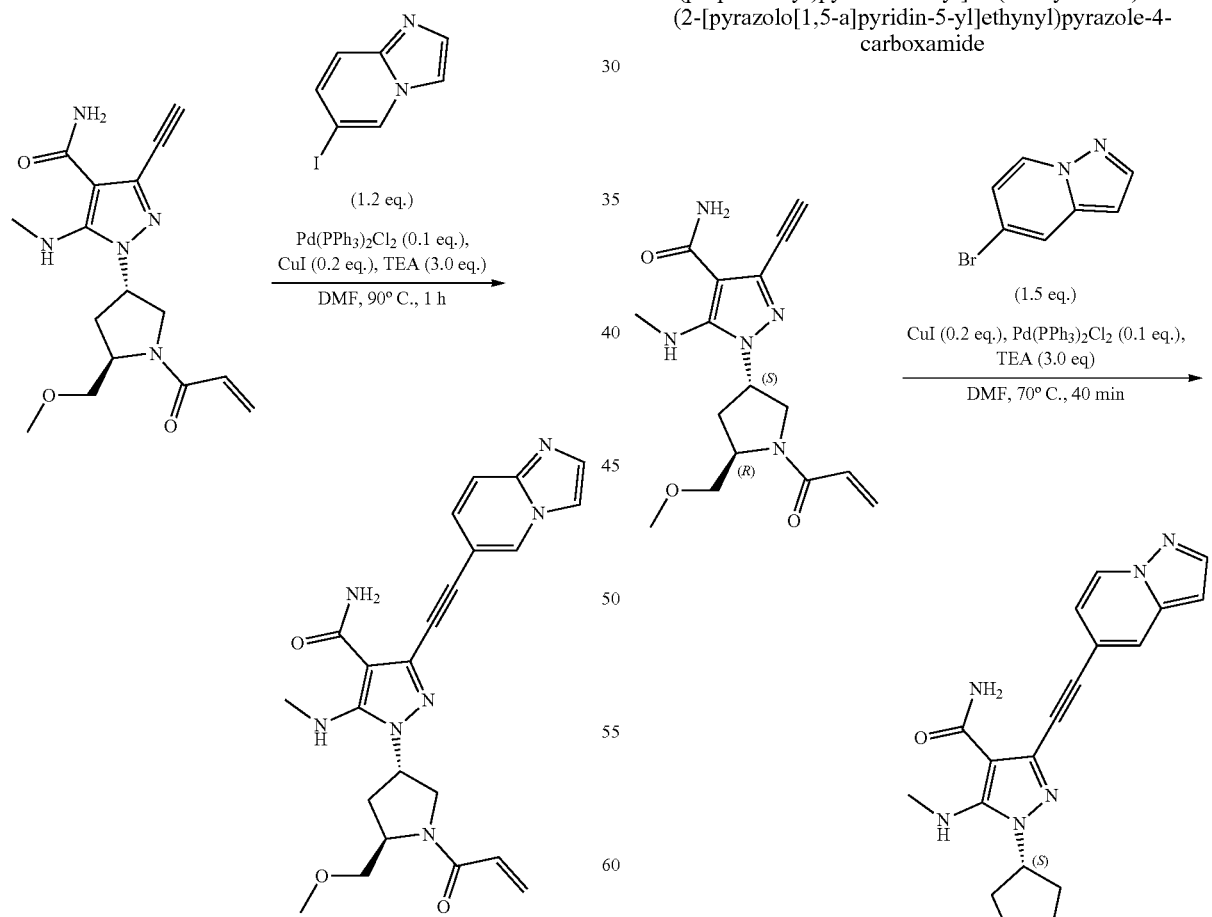

To a stirred mixture of 3-ethynyl-1-[(3S,5R)-5-(methoxymethyl)-1-(prop-2-enoyl)pyrrolidin-3-yl]-5-(methylamino)pyrazole-4-carboxamide (0.13 g, 0.39 mmol), 6-iodoimidazo[1,2-a]pyridine (0.11 g, 0.47 mmol), To a stirred mixture of 3-ethynyl-1-[(3S,5R)-5-(methoxymethyl)-1-(prop-2-enoyl)pyrrolidin-3-yl]-5-(methylamino)pyrazole-4-carboxamide (0.18 g, 0.54 mmol), 5-bromopyrazolo[1,5-a]pyridine (0.16 g, 0.82 mmol), Pd(PPh3)2Cl2 (38.13 mg, 0.05 mmol) and CuI (20.69 mg, 0.11 mmol) in DMF (2.00 mL) was added TEA (0.23 mL, 2.24 mmol). The reaction mixture was degassed with argon for three times and stirred for 40 min at 70° C. The resulting mixture was concentrated under reduced pressure. The residue was purified by silica gel Column chromatography, eluted with CH2Cl2/MeOH (10/1). The fractions contained desired product were combined and concentrated. The residue was purified by Prep-HPLC with the following conditions Column: XBridge Prep C18 OBD Column, 19×150 mm 5 µm; Mobile Phase A: Water (10 mmol/L NH4HCO3), Mobile Phase B: ACN; Flow rate: 20 mL/min; Gradient: 25 B to 55 B in 6 min; 210/254 nm; RT: 5.56 min. The fractions contained desired product were combined and concentrated to afford 1-[(3S,5R)-5-(methoxymethyl)-1-(prop-2-enoyl)pyrrolidin-3-yl]-5-(methylamino)-3-(2-[pyrazolo[1,5-a]pyridin-5-yl]ethynyl)pyrazole-4-carboxamide (66.6 mg, 27%) as an off-white solid. MS ESI calculated for C23H25N7O3 [M+H]+, 448.20, found 448.15; 1H NMR (400 MHz, DMSO-d6): δ 8.74 (d, J=7.3 Hz, 1H), 8.13-7.97 (m, 2H), 7.34-7.32 (m, 1H), 6.99-6.45 (m, 5H), 6.17 (d, J=16.5 Hz, 1H), 5.76-5.62 (m, 1H), 5.26-5.23 (m, 1H), 4.49-4.39 (m, 1H), 4.09-3.67 (m, 2H), 3.63-3.38 (m, 2H), 3.31 (d, J=4.1 Hz, 3H), 2.95 (d, J=4.7 Hz, 3H), 2.65-2.61 (m, 1H), 2.39-2.24 (m, 1H).

Example 57: 3-(2-[Imidazo[1,2-a]pyrimidin-6-yl]ethynyl)-1-[(3S,5R)-5-(methoxymethyl)-1-(prop-2-enoyl)pyrrolidin-3-yl]-5-(methylamino)pyrazole-4-carboxamide

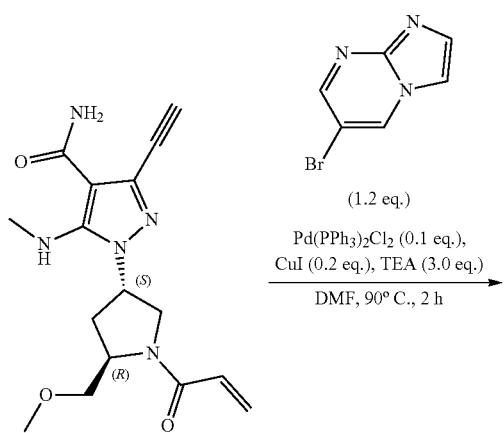

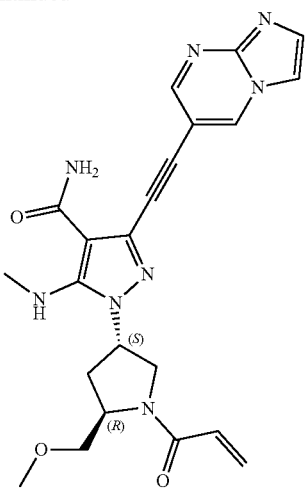

To a stirred mixture of 3-ethynyl-1-[(3S,5R)-5-(methoxymethyl)-1-(prop-2-enoyl)pyrrolidin-3-yl]-5-(methylamino)pyrazole-4-carboxamide (0.13 g, 0.39 mmol), 6-bromoimidazo[1,2-a]pyrimidine (93.22 mg, 0.47 mmol), Pd(PPh3)2Cl2 (27.54 mg, 0.04 mmol) and CuI (14.94 mg, 0.08 mmol) in DMF (1.50 mL) was added TEA (0.12 g, 1.18 mmol) at room temperature. The reaction mixture was degassed with argon for three times and stirred for 2 h at 90° C. The resulting mixture was filtered and the filtrate was concentrated under reduced pressure. The residue was purified by silica gel Column chromatography, eluted with CH2Cl2/MeOH (10/1). The fractions contained desired product were combined and concentrated. The residue was purified by Prep-HPLC with the following conditions Column: XBridge Prep C18 OBD Column, 19×150 mm 5 µm; Mobile Phase A: Water (10 mmol/L NH4HCO3), Mobile Phase B: ACN; Flow rate: 20 mL/min; Gradient: 30 B to 60 B in 5.8 min; 210/254 nm; RT: 5.56 min. The fractions contained desired product were combined and concentrated to afford 3-(2-[imidazo[1,2-a]pyrimidin-6-yl]ethynyl)-1-[(3S,5R)-5-(methoxymethyl)-1-(prop-2-enoyl)pyrrolidin-3-yl]-5-(methylamino)pyrazole-4-carboxamide (36.7 mg, 20%) as a white solid. MS ESI calculated for C22H24N8O3 [M+H]+, 449.20, found 449.15; 1H NMR (400 MHz, DMSO-d6) δ 9.37-9.36 (m, 1H), 8.66 (d, J=2.4 Hz, 1H), 7.94 (d, J=1.4 Hz, 1H), 7.91-7.76 (m, 1H), 7.48-6.80 (m, 2H), 6.77-6.47 (m, 2H), 6.17-5.96 (m, 1H), 5.69-5.43 (m, 1H), 5.25-5.23 (m, 1H), 4.63-4.34 (m, 1H), 4.11-3.71 (m, 2H), 3.67-3.38 (m, 2H), 3.30 (s, 3H), 2.96-2.93 (m, 3H), 2.71-2.54 (m, 1H), 2.44-2.24 (m, 1H).

Example 58: 3-(2-[Imidazo[1,2-a]pyrimidin-7-yl]ethynyl)-1-[(3S,5R)-5-(methoxymethyl)-1-(prop-2-enoyl)pyrrolidin-3-yl]-5-(methylamino)pyrazole-4-carboxamide

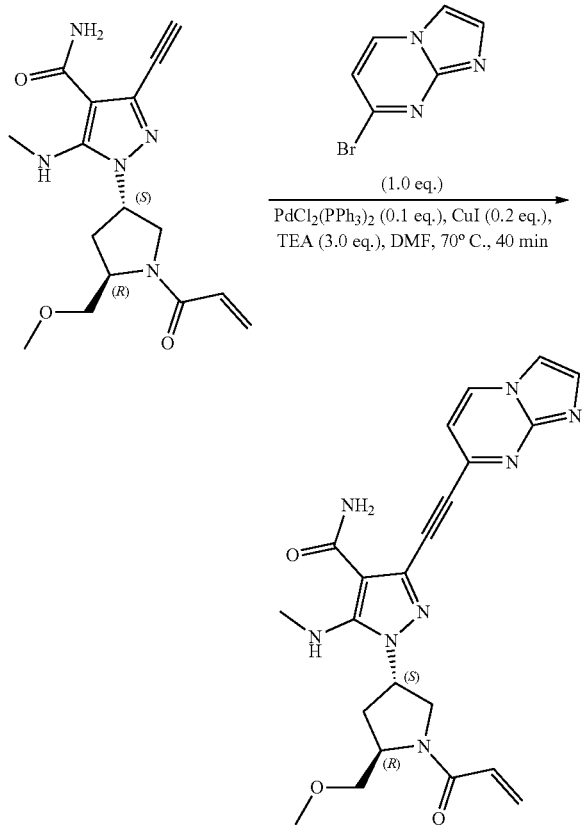

To a stirred mixture of 3-ethynyl-1-[(3S,5R)-5-(methoxymethyl)-1-(prop-2-enoyl)pyrrolidin-3-yl]-5-(methylamino)pyrazole-4-carboxamide (0.13 g, 0.39 mmol) and 7-bromoimidazo[1,2-a]pyrimidine (77.69 mg, 0.39 mmol) in DMF (2.50 mL) were added CuI (14.94 mg, 0.07 mmol), Pd(PPh3)2Cl2 (27.54 mg, 0.03 mmol) and TEA (0.12 g, 1.17 mmol) at room temperature. The reaction mixture was degassed with argon for three times and stirred for 40 min at 70° C. The resulting mixture was concentrated under reduced pressure. The residue was purified by silica gel Column chromatography, eluted with MeOH in DCM (0-7%). The fractions contained desired product were combined and concentrated to afford crude product. The crude product was purified by Prep-HPLC with the following conditions Column: XBridge Shield RP18 OBD Column, 30×150 mm, 5 μm; Mobile Phase A: Water (10 mmol/L NH4HCO3), Mobile Phase B: ACN; Flow rate: 30 mL/min; Gradient: 15 B to 50 B in 6 min; 210/254 nm; RT: 5.58 min. The fractions contained desired product were combined and concentrated to afford 3-(2-[imidazo[1,2-a]pyrimidin-7-yl]ethynyl)-1-[(3S,5R)-5-(methoxymethyl)-1-(prop-2-enoyl)pyrrolidin-3-yl]-5-(methylamino)pyrazole-4-carboxamide (62.1 mg, 34%) as a light yellow solid. MS ESI calculated for C22H24N8O3 [M+H]+, 449.20, found 449.10; 1H NMR (300 MHz, DMSO-d6) δ 9.02 (d, J=7.0 Hz, 1H), 8.00 (d, J=1.4 Hz, 1H), 7.85 (s, 1H), 7.60-7.11 (m, 2H), 7.08-6.32 (m, 3H), 6.28-6.07 (m, 1H), 5.68 (d, J=10.1 Hz, 1H), 5.23-5.20 (m, 1H), 4.54 (s, 1H), 4.08-3.66 (m, 2H), 3.25 (s, 3H), 3.65-3.40 (m, 2H), 2.93-2.91 (m, 3H), 2.75-2.56 (m, 1H), 2.38-2.22 (m, 1H).

Example 59: 3-[2-(1-Tert-butyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide

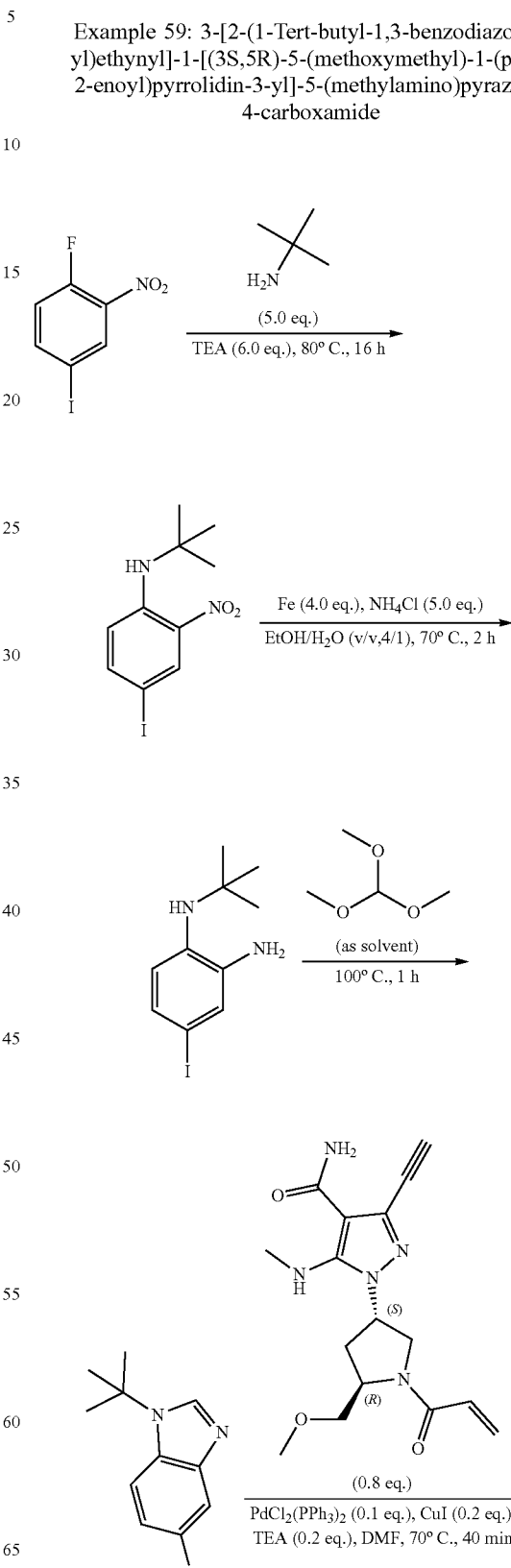

-continued

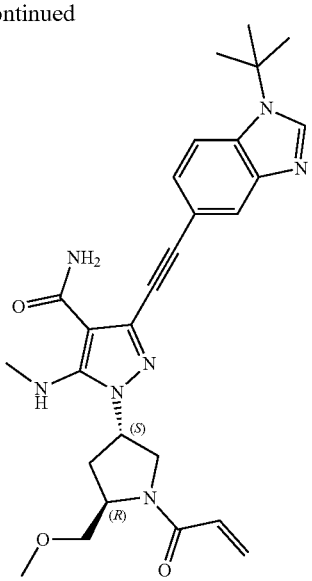

Step 1: N-Tert-butyl-4-iodo-2-nitroaniline

To a stirred solution of 1-fluoro-4-iodo-2-nitrobenzene (2.00 g, 7.49 mmol) in Et3N (4.55 g, 44.94 mmol) was added tert-butylamine (2.74 g, 37.46 mmol) at room temperature. The reaction mixture was stirred for 16 h at 80° C. The resulting mixture was cooled down to room temperature and concentrated under reduced pressure. The residue was dissolved in water (30 mL), extracted with EtOAc (3×50 mL). The combined organic layers was dried over anhydrous Na2SO4 and filtered. The filtrate was concentrated under reduced pressure to afford N-tert-butyl-4-iodo-2-nitroaniline (2.3 g, 95%) as an off-white solid which was used in the next step directly without further purification. MS ESI calculated for C10H13IN2O2 [M+H]+, 321.00, found 321.10.

Step 2: N1-Tert-butyl-4-iodobenzene-1,2-diamine

To a stirred mixture of N-tert-butyl-4-iodo-2-nitroaniline (2.30 g, 7.18 mmol) in EtOH (28.00 mL) and H2O (7.00 mL) were added Fe (1.60 g, 28.65 mmol) and NH4Cl (1.92 g, 35.92 mmol) at room temperature. The reaction mixture was stirred for 2 h at 70° C. The resulting mixture was filtered, the filter cake was washed with EtOH (3×70 mL). The filtrate was concentrated under reduced pressure. The residue was dissolved in water (50 mL). The resulting mixture was extracted with EtOAc (3×50 mL). The combined organic layers were washed with brine (30 mL), dried over anhydrous Na2SO4 and filtered. The filtrate was concentrated under reduced pressure to afford N1-tert-butyl-4-iodobenzene-1,2-diamine (2.1 g, crude) as a dark green solid which was used in the next step directly without further purification. MS ESI calculated for C10H15IN2 [M+H]+, 291.03, found 291.05.

Step 3: 1-Tert-butyl-5-iodo-1,3-benzodiazole

A solution of N1-tert-butyl-4-iodobenzene-1,2-diamine (1.90 g, 6.54 mmol) in trimethyl orthoformate (20.00 mL) was stirred for 1 h at 100° C. The resulting mixture was concentrated under reduced pressure. The residue was purified by silica gel Column chromatography, eluted with EA in PE (0-53%). The fractions contained desired product were combined and concentrated to afford 1-tert-butyl-5-iodo-1,3-benzodiazole (1.5 g, 76%) as a brown solid. MS ESI calculated for C11H13IN2 [M+H]+, 301.01, found 300.90.

Step 4: 3-[2-(1-Tert-butyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide To a stirred mixture of 3-ethynyl-1-[(3S,5R)-5-(methoxymethyl)-1-(prop-2-enoyl)pyrrolidin-3-yl]-5-(methylamino)pyrazole-4-carboxamide (0.13 g, 0.39 mmol) and 1-tert-butyl-5-iodo-1,3-benzodiazole (0.14 g, 0.47 mmol) in DMF (2.50 mL) were added Pd(PPh3)2Cl2 (27.54 mg, 0.03 mmol), CuI (14.94 mg, 0.08 mmol) and TEA (0.12 g, 1.17 mmol) at room temperature. The reaction mixture was degassed with argon for three times and stirred 40 min at 70° C. The resulting mixture was concentrated under reduced pressure. The residue was purified by silica gel Column chromatography, eluted with MeOH in DCM (0-6%) to afford crude product. The crude product was purified by reverse flash chromatography with the following conditions: Column, C18 silica gel; mobile phase, NH4HCO3 in water, 10% to 32% gradient in 10 min; detector, UV 254 nm. The fractions contained desired product were combined and concentrated to afford 3-[2-(1-tert-butyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (86.8 mg, 43%) as an off-white solid. MS ESI calculated for C27H33N7O3 [M+H]+, 504.26, found 504.15; 1H NMR (300 MHz, DMSO) δ 8.45 (s, 1H), δ 7.93-7.90 (m, 2H), 7.39 (d, J=8.6 Hz, 2H), 7.01-6.47 (m, 3H), 6.16 (d, J=16.7 Hz, 1H), 5.68 (d, J=10.4 Hz, 1H), δ 5.25 (s, 1H), 4.52-4.38 (m, 1H), 4.13-3.68 (m, 2H), 3.66-3.41 (m, 2H), 3.25 (s, 3H), 2.93-2.91 (m, 3H), 2.60 (m, 1H), 2.29-2.26 (m, 1H), 1.71 (s, J=3.4 Hz, 9H).

Example 60: 3-[2-[2-(Dimethylamino)-1-methyl-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide

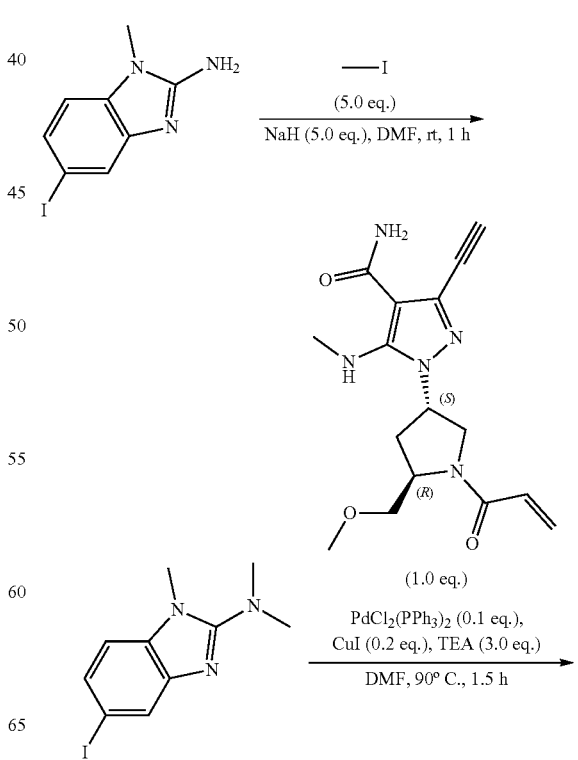

-continued

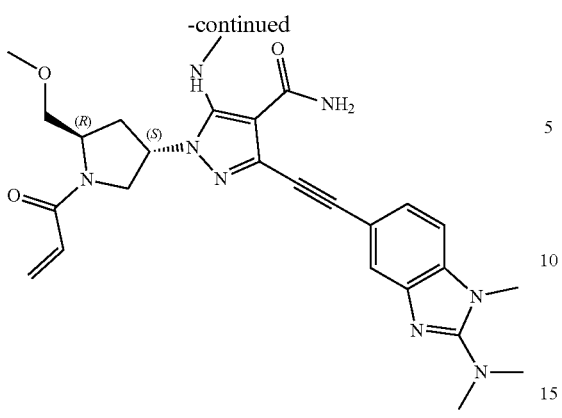

Step 1:
5-Iodo-N,N,1-trimethyl-1,3-benzodiazol-2-amine

To a stirred solution of 5-iodo-1-methyl-1,3-benzodiazol-2-amine (0.50 g, 1.83 mmol) in DMF (5.00 mL, 64.60 mmol) was added NaH (0.18 g, 7.32 mmol) in portions at room temperature. To the above mixture was added methyl iodide (1.30 g, 9.15 mmol) dropwise at room temperature. The reaction mixture was stirred for 1 h. To the resulting mixture was added H2O (100 mL). The resulting mixture was extracted with EtOAc (5×50 mL). The combined organic layers was dried over anhydrous Na2SO4 and filtered. The filtered was concentrated under reduced pressure. The residue was purified by silica gel Column chromatography, eluted with PE/EtOAc (0-50%). The fractions contained desired product were combined and concentrated to afford 5-iodo-N,N,1-trimethyl-1,3-benzodiazol-2-amine (0.40 g, 72%) as a light yellow solid. MS ESI calculated for C10H12IN3 [M+H]+, 302.01, found 301.95.

Step 2: 3-[2-[2-(Dimethylamino)-1-methyl-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide To a stirred mixture of 3-ethynyl-1-[(3S,5R)-5-(methoxymethyl)-1-(prop-2-enoyl)pyrrolidin-3-yl]-5-(methylamino)pyrazole-4-carboxamide (0.13 g, 0.39 mmol) and 5-iodo-N,N,1-trimethyl-1,3-benzodiazol-2-amine (0.14 g, 0.47 mmol) in DMF (2.00 mL) were added CuI (15.00 mg, 0.08 mmol), Pd(PPh$_3$)$_2$Cl$_2$ (27.50 mg, 0.04 mmol) and TEA (0.12 g). The reaction mixture was degassed with argon for three times and stirred for 1.5 h at 90° C. The resulting mixture was concentrated under reduced pressure. The residue was purified by silica gel Column chromatography, eluted with PE/EtOAc (0-10%) to afford the crude. The crude was purified by reverse phase chromatography with the following conditions: Column: Spherical C18, 20-40 μm, 40 g; Mobile Phase A: Water (10 mmol/L NH$_4$HCO$_3$); Mobile Phase B: ACN; Flow rate: 40 mL/min; 5%-60% within 60 min, Detector: UV 254 & 220 nm. The fractions contained desired product were combined and concentrated to afford 3-[2-[2-(dimethylamino)-1-methyl-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide (41.3 mg, 20%) as a white solid. MS ESI calculated for C$_{26}$H$_{32}$N$_8$O$_3$ [M+H]$^+$, 505.26, found 505.15; $^1$H NMR (300 MHz, DMSO-d$_6$) δ 7.54 (d, J=1.5 Hz, 1H), 7.38 (d, J=8.2 Hz, 2H), 7.26 (d, J=8.3 Hz, 1H), 6.85-6.50 (m, 3H), 6.18 (d, J=16.7 Hz, 1H), 5.70 (d, J=10.5 Hz, 1H), 5.26 (d, J=7.9 Hz, 1H), 4.53-4.38 (m, 1H), 4.10-3.69 (m, 2H), 3.66 (s, 3H), 3.54-3.41 (m, 2H), 3.33-3.30 (m, 3H), 2.97 (s, 9H), 2.60-2.58 (m, 1H), 2.30-2.28 (m, 1H).

Example 61: 3-[2-(2-Cyclopropyl-4,6-difluoro-1H-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide

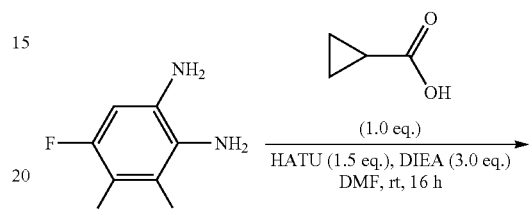

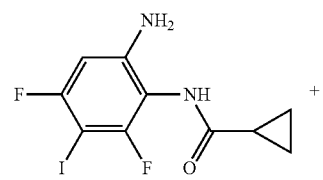

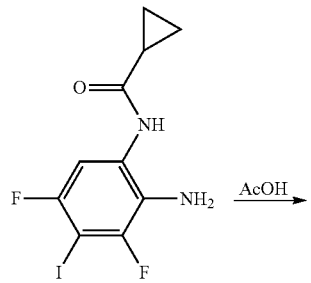

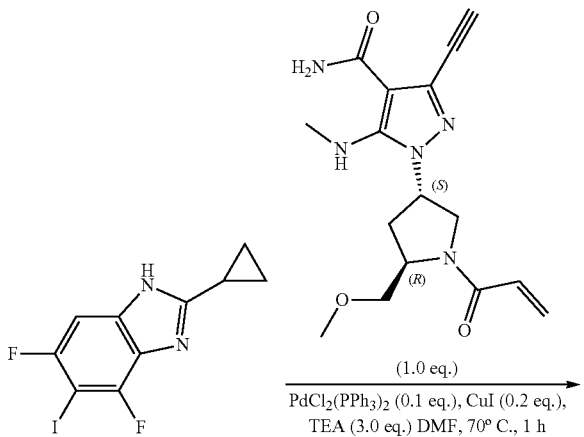

443

-continued

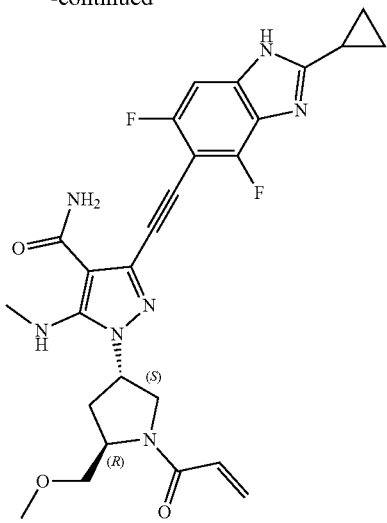

Step 1: N-(6-Amino-2,4-difluoro-3-iodophenyl) cyclopropanecarboxamide and N-(2-amino-3,5-difluoro-4-iodophenyl)cyclopropanecarboxamide To a solution of cyclopropanecarboxylic acid (1.91 g, 22.22 mmol) in DMF (30.00 mL) were added HATU (10.56 g, 27.77 mmol) and DIEA (7.18 g, 55.55 mmol) at room temperature. The reaction mixture was stirred for 30 min at room temperature. To the above mixture was added 3,5-difluoro-4-iodobenzene-1,2-diamine (5.00 g, 18.51 mmol) in DMF (20.00 mL). The resulting mixture was stirred for 16 h at room temperature. The resulting mixture was diluted with EA (100 mL), washed with water (3×50 mL). The combined organic layers were washed with brine (3×50 mL), dried over anhydrous $Na_2SO_4$ and filtered. The filtrate was concentrated under reduced pressure. The residue was purified by silica gel Column chromatography, eluted with EA in PE (0-20%). The fractions contained desired product were combined and concentrated to afford the mixture of N-(6-amino-2,4-difluoro-3-iodophenyl)cyclopropanecarboxamide and N-(2-amino-3,5-difluoro-4-iodophenyl)cyclopropanecarboxamide (4.0 g, 63%) as a yellow solid. MS ESI calculated for $C_{10}H_9F_2IN_2O$ [M+H]$^+$, 338.97, found 339.00.

Step 2: 2-Cyclopropyl-4,6-difluoro-5-iodo-1H-1,3-benzodiazole

A solution of N-(6-amino-2,4-difluoro-3-iodophenyl)cyclopropanecarboxamide and N-(2-amino-3,5-difluoro-4-iodophenyl)cyclopropanecarboxamide (5.00 g, 14.78 mmol) in AcOH (60.00 mL) was stirred for 24 h at 70° C. The resulting mixture was cooled down to room temperature and concentrated under reduced pressure. The residue was basified to PH 8 with saturated NaHCO3 (aq.). The resulting mixture was diluted with water (50 mL), extracted with EA (3×100 mL). The combined organic layers were washed with brine (3×50 mL), dried over anhydrous Na2SO4 and filtered. The filtrate was concentrated under reduced pressure. The residue was purified by silica gel Column chromatography, eluted with EA in PE (0-52%). The fractions contained desired product were combined and concentrated to afford 2-cyclopropyl-4,6-difluoro-5-iodo-1H-1,3-benzo-

444 diazole (2.2 g, 46%) as a yellow solid. MS ESI calculated for C10H7F2IN2 [M+H]+, 320.96, found. 320.85.

Step 3: 3-[2-(2-Cyclopropyl-4,6-difluoro-1H-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide To a stirred mixture of 2-cyclopropyl-4,6-difluoro-5-iodo-1H-1,3-benzodiazole (0.12 g, 0.38 mmol), 3-ethynyl-1-[(3S,5R)-5-(methoxymethyl)-1-(prop-2-enoyl)pyrrolidin-3-yl]-5-(methylamino)pyrazole-4-carboxamide (0.12 g, 0.38 mmol), Pd(PPh$_3$)$_2$Cl$_2$ (26.31 mg, 0.04 mmol) and CuI (14.28 mg, 0.08 mmol) in DMF (4.00 mL) was added TEA (0.13 g, 1.13 mmol) at room temperature. The reaction mixture was degassed with argon for three times and stirred for 1 h at 70° C. The resulting mixture was concentrated under reduced pressure. The residue was purified by silica gel Column chromatography, eluted with MeOH in CH$_2$Cl$_2$ (0-5%) to afford the crude product. The crude product was purified by reverse phase flash with the following conditions: Column: Spherical C18, 20~40 μm, 330 g; Mobile Phase A: Water (10 mmol/L NH$_4$HCO$_3$), Mobile Phase B: ACN; Flow rate: 65 mL/min; Gradient: 30%~40%, 20 min; Detector: 254 nm; RT: 20 min. The fractions contained desired product were combined and concentrated to afford 3-[2-(2-cyclopropyl-4,6-difluoro-1H-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (0.11 g, 55%) as an off-white solid. MS ESI calculated for $C_{26}H_{27}F_2N_7O_3$ [M+H]$^+$, 524.22, found. 524.15; $^1$H NMR (300 MHz, DMSO-d$_6$) δ 7.57 (s, 1H), 7.28 (d, J=9.2 Hz, 1H), 6.76-6.56 (m, 2H), 6.19-6.12 (m, 1H), 5.70-5.64 (m, 1H), 5.27-5.25 (m, 1H), 4.45-4.40 (m, 1H), 4.05-4.02 (m, 1H), 3.93-3.81 (m, 1H), 3.76-3.73 (m, 1H), 3.62-3.59 (m, 1H), 3.48-3.45 (m, 3H), 2.95 (t, J=3.0 Hz, 4H), 2.31-2.30 (m, 1H), 2.29-2.27 (m, 1H), 2.14-2.12 (m, 1H), 1.08-1.04 (m, 4H).

Example 62: 3-[2-(2-Cyclopropyl-6-fluoro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide

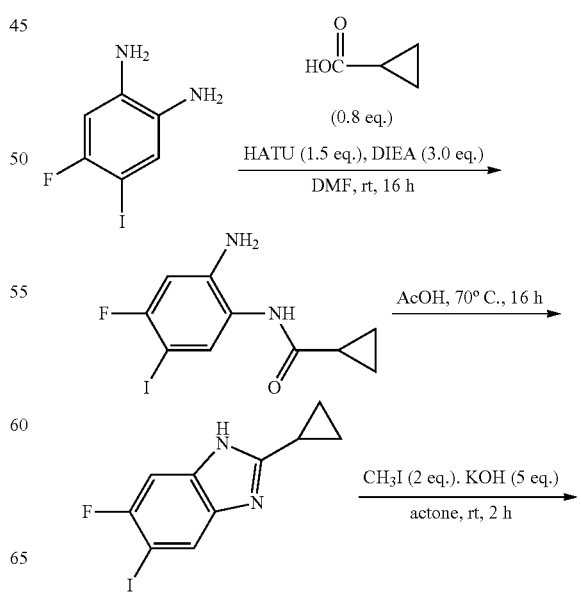

-continued

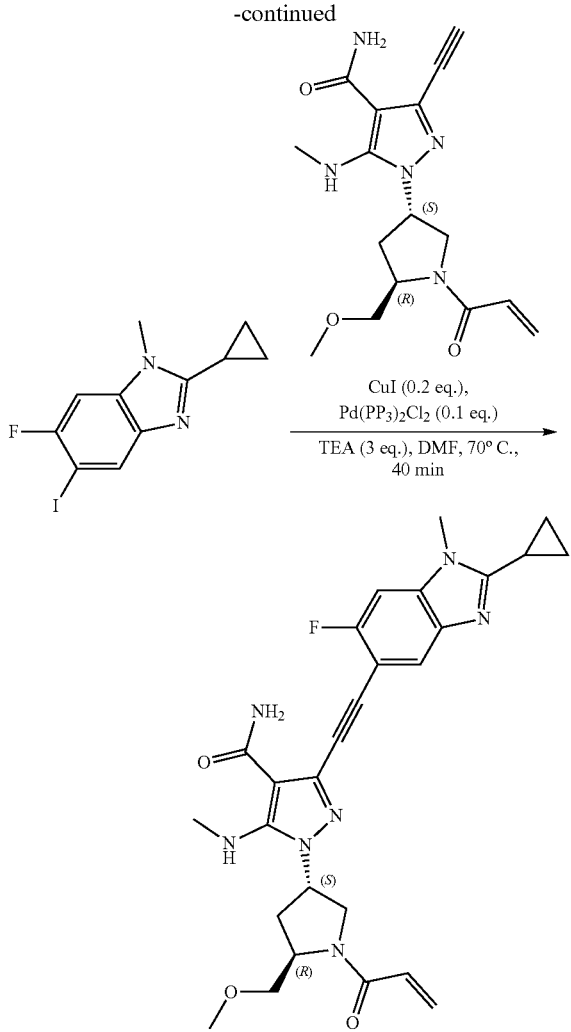

Step 1: N-(2-Amino-4-fluoro-5-iodophenyl)cyclopropanecarboxamide

To a stirred mixture of 4-fluoro-5-iodobenzene-1,2-diamine (2.00 g, 7.94 mmol), cyclopropanecarboxylic acid (0.34 g, 3.97 mmol) and HATU (4.53 g, 11.90 mmol) in DMF (20.00 mL) was added DIEA (3.30 mL). The reaction mixture was stirred for 16 h at room temperature under nitrogen atmosphere. The resulting mixture was diluted with water (80 mL), extracted with EtOAc (3×100 mL). The combined organic layers were washed with brine (150 mL), dried over anhydrous Na2SO4 and filtered. The filtrate was concentrated under reduced pressure. The residue was purified by silica gel Column chromatography, eluted with PE/EtOAc (5/1). The fractions contained desired product were combined and concentrated to afford N-(2-amino-4-fluoro-5-iodophenyl)cyclopropanecarboxamide (1.3 g, 51%) as a white solid. MS ESI calculated for $C_{10}H_{10}FIN_2O$ [M+H]$^+$, 320.98, found 321.00.

Step 2: 2-Cyclopropyl-6-fluoro-5-iodo-1H-benzo[d]imidazole

A mixture of N-(2-amino-4-fluoro-5-iodophenyl)cyclopropanecarboxamide (1.10 g) in AcOH (20 mL) was stirred for 16 h at 70° C. under nitrogen atmosphere. The resulting mixture was concentrated under reduced pressure. The residue was basified to pH 8 with saturated NaHCO₃. The resulting mixture was extracted with EtOAc (3×100 mL). The combined organic layers were washed with brine (3×50 mL), dried over anhydrous Na2SO4 and filtered. The filtrate was concentrated under reduced pressure. The residue was purified by silica gel Column chromatography, eluted with PE/EtOAc (1/1). The fractions contained desired product were combined and concentrated to afford 2-cyclopropyl-6-fluoro-5-iodo-1H-benzo[d]imidazole as a white solid. MS ESI calculated for C10H8FIN2 [M+H]+, 302.97, found 303.05.

Step 3: 2-Cyclopropyl-6-fluoro-5-iodo-1-methyl-1H-benzo[d]imidazole

To a stirred mixture of 2-cyclopropyl-6-fluoro-5-iodo-1H-benzo[d]imidazole (0.67 g, 2.22 mmol) and KOH (0.62 g, 11.09 mmol) in acetone (10.00 mL) was added CH3I (0.63 g, 4.44 mmol) dropwise at 0° C. under nitrogen atmosphere. The reaction mixture was stirred for 2 h at room temperature under nitrogen atmosphere. The resulting mixture was diluted with water (150 mL) and extracted with EtOAc (3×100 mL). The combined organic layers were washed with brine (3×50 mL), dried over anhydrous Na2SO4 and filtered. The filtrate was concentrated under reduced pressure. The residue was purified by silica gel Column chromatography, eluted with CH2Cl2/MeOH (10/1). The fractions contained desired product were combined and concentrated. The residue was purified by Prep-achiral-SFC with the following conditions Column: EnantioPak A1-5, 2.12×25 cm, 5 µm; Mobile Phase A: CO2, Mobile Phase B: MeOH (0.5% 2 M NH3-MeOH); Flow rate: 40 mL/min; Gradient: 35% B; 254 nm; RT1: 4.45 min; RT2: 5.09 min; Injection volume: 1 mL; Number of runs: 28. The fractions contained desired product were combined and concentrated to afford 2-cyclopropyl-6-fluoro-5-iodo-1-methyl-1H-benzo[d]imidazole (0.54 g, 32%) as an off-white solid. MS ESI calculated for C11H10FIN2 [M+H]+, 316.99, found 316.95.

Step 4: 3-[2-(2-Cyclopropyl-6-fluoro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide To a stirred mixture of 2-cyclopropyl-6-fluoro-5-iodo-1-methyl-1H-benzo[d]imidazole (47.70 mg, 0.15 mmol), 3-ethynyl-1-[(3S,5R)-5-(methoxymethyl)-1-(prop-2-enoyl)pyrrolidin-3-yl]-5-(methylamino)pyrazole-4-carboxamide (50 mg, 0.15 mmol), Pd(PPh3)2Cl2 (27.54 mg, 0.039 mmol) and CuI (5.75 mg, 0.03 mmol) in DMF (1.50 mL) was added TEA (0.06 mL, 0.62 mmol) dropwise at room temperature. The reaction mixture was degassed with argon for three times and stirred for 40 min at 70° C. The resulting mixture was diluted with water (50 mL), extracted with EtOAc (5×50 mL). The combined organic layers were washed with brine (3×30 mL), dried over anhydrous Na2SO4 and filtered. The filtrate was concentrated under reduced pressure. The residue was purified by silica gel Column chromatography, eluted with CH2Cl2/MeOH (10/1). The fractions contained desired product were combined and concentrated. The residue was purified by Prep-HPLC with the following conditions: Column: XBridge Prep C18 OBD Column, 19×150 mm 5 µm; Mobile Phase A: Water (10 mmol/L NH4HCO3), Mobile Phase B: ACN; Flow rate: 20 mL/min; Gradient: 30

B to 70 B in 5.8 min; 210/254 nm. The fractions contained desired product were combined and concentrated to afford the crude product. The crude product was purified by Prep-HPLC with the following conditions Column: XBridge Prep C18 OBD Column, 19×150 mm 5 μm; Mobile Phase A: Water (10 mmol/L NH4HCO3), Mobile Phase B: ACN; Flow rate: 20 mL/min; Gradient: 30 B to 70 B in 6 min; 210/254 nm. The fractions contained desired product were combined and concentrated to afford 3-[2-(2-cyclopropyl-6-fluoro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (9.1 mg, 11%) as a white solid. MS ESI calculated for C27H30FN7O3 [M+H]+, 520.24, found 520.25; 1H NMR (300 MHz, DMSO) δ 7.73 (d, J=6.3 Hz, 1H), 7.61 (d, J=9.8 Hz, 1H), 7.50 (s, 1H), 6.88-6.48 (m, 2H), 6.17 (d, J=16.6 Hz, 1H), 5.90-5.58 (m, 1H), 5.27 (s, 1H), 4.49-4.46 (m, 1H), 4.03-4.01 (m, 1H), 3.91-3.70 (m, 4H), 3.63-3.59 (m, 1H), 3.52-3.38 (m, 2H), 3.31 (s, 3H), 3.00-2.86 (m, 3H), 2.69-2.67 (m, 1H), 2.29-2.25 (m, 2H), 1.26-0.95 (m, 5H).

Example 63: 3-(2-[2-Cyclopropyl-3-methylimidazo[4,5-c]pyridin-6-yl]ethynyl)-1-[(3S,5R)-5-(methoxymethyl)-1-(prop-2-enoyl)pyrrolidin-3-yl]-5-(methylamino)pyrazole-4-carboxamide

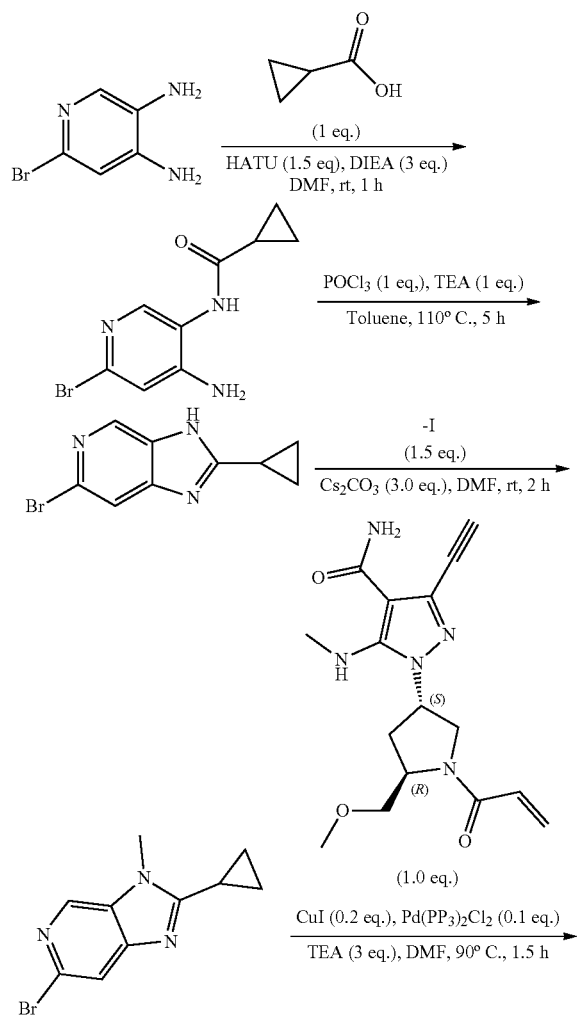

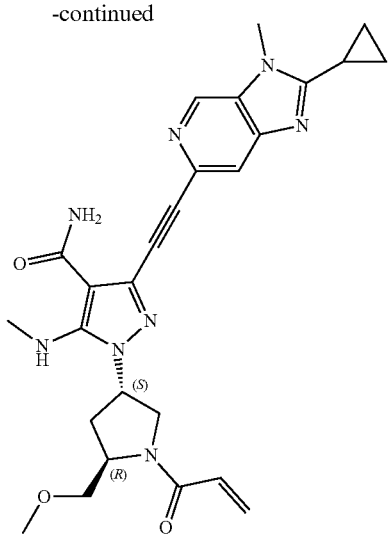

Step 1: N-(5-Amino-2-bromopyridin-4-yl)cyclopropanecarboxamide

To a stirred mixture of 6-bromopyridine-3,4-diamine (1.00 g, 5.31 mmol) and HATU (3.03 g, 7.98 mmol) in DMF (10.00 mL) was added DIEA (2.06 g, 15.96 mmol) dropwise at room temperature. The reaction mixture was stirred for 0.5 h. To the above mixture was added cyclopropanecarboxylic acid (0.46 g, 5.32 mmol) dropwise over 3 min. The reaction mixture was stirred for additional 1 h at room temperature. The resulting mixture was quenched by the addition of water (10 mL) at room temperature and extracted with EtOAc (3×20 mL). The combined organic layers were washed with brine (3×30 mL), dried over anhydrous Na2SO4 and filtered. The filtrate was concentrated under reduced pressure. The residue was purified by silica gel column chromatography, eluted with PE/EtOAc (1/1). The fractions contained desired product were combined and concentrated to afford N-(5-amino-2-bromopyridin-4-yl)cyclopropanecarboxamide (0.96 g, 70%) as a light yellow solid. MS ESI calculated for C9H10BrN3O [M+H]+, 256.00, 258.00, found 256.05, 258.05.

Step 2: 6-Bromo-2-cyclopropyl-3H-imidazo[4,5-c]pyridine

To a stirred solution of N-(5-amino-2-bromopyridin-4-yl)cyclopropanecarboxamide (1.20 g, 4.69 mmol) and TEA (0.47 g, 4.69 mmol) in toluene (12.00 mL) was added phosphorus oxychloride (0.72 g, 4.69 mmol) dropwise at room temperature. The reaction mixture was stirred for 5 h at 110° C. The resulting mixture was cooled down to room temperature and concentrated under reduced pressure. The residue was purified by silica gel Column chromatography, eluted with PE/EtOAc (1/3). The fractions contained desired product were combined and concentrated to afford 6-bromo-2-cyclopropyl-3H-imidazo[4,5-c]pyridine (0.71 g, 63%) as a light yellow solid. MS ESI calculated for C9H8BrN3 [M+H]+, 237.99, 239.99, found 238.05, 240.05.

Step 3: 6-Bromo-2-cyclopropyl-3-methylimidazo[4,5-c]pyridine

To a stirred mixture of 6-bromo-2-cyclopropyl-3H-imidazo[4,5-c]pyridine (0.71 g, 2.98 mmol) and Cs2CO3 (2.91 g, 8.94 mmol) in DMF (7.00 mL) was added methyl iodide (0.63 g, 4.47 mmol) dropwise at room temperature. The reaction mixture was stirred for 2 h at room temperature. The resulting mixture was filtered, the filter cake was washed with DMF (2 mL). the filtrate was purified by reverse flash chromatography with the following conditions: Column, C18 silica gel; mobile phase, ACN in water, 5% to 70% gradient in 30 min; detector, UV 254 nm. The fractions contained desired product were combined and concentrated to afford 6-bromo-2-cyclopropyl-3-methylimidazo[4,5-c]pyridine (0.13 g, 17%) as an off-white solid. MS ESI calculated for C10H10BrN3 [M+H]+, 252.01, 254.00, found 252.10, 254.10.

Step 4: 3-(2-[2-Cyclopropyl-3-methylimidazo[4,5-c]pyridin-6-yl]ethynyl)-1-[(3S,5R)-5-(methoxymethyl)-1-(prop-2-enoyl)pyrrolidin-3-yl]-5-(methylamino)pyrazole-4-carboxamide To a stirred mixture of 3-ethynyl-1-[(3S,5R)-5-(methoxymethyl)-1-(prop-2-enoyl)pyrrolidin-3-yl]-5-(methylamino) pyrazole-4-carboxamide (0.15 g, 0.43 mmol), 6-bromo-2-cyclopropyl-3-methylimidazo[4,5-c]pyridine (0.11 g, 0.44 mmol), Pd(PPh3)2Cl2 (30.71 mg, 0.04 mmol) and CuI (16.67 mg, 0.08 mmol) in DMF (2.00 mL) was added TEA (0.13 g, 1.31 mmol) at room temperature. The reaction mixture was degassed with argon for three times and stirred for 1.5 h at 90° C. The resulting mixture was cooled down to room temperature and concentrated under reduced pressure. The residue was purified by silica gel Column chromatography, eluted with PE/EtOAc (1/1). The fractions contained desired product were combined and concentrated, the residue was purified by Prep-HPLC with the following conditions Column: SunFire Prep C18 OBD Column, 19×150 mm 5 μm 10 nm; Mobile Phase A: water (0.1% FA), Mobile Phase B: MeOH; Flow rate: 20 mL/min; Gradient: 15 B to 35 B in 6 min; 210/254 nm; RT: 5.56 min. The fractions contained desired product were combined and concentrated to afford 3-(2-[2-cyclopropyl-3-methylimidazo[4,5-c]pyridin-6-yl]ethynyl)-1-[(3S,5R)-5-(methoxymethyl)-1-(prop-2-enoyl)pyrrolidin-3-yl]-5(methylamino) pyrazole-4-carboxamide (49.8 mg, 22%) as an off-white solid. MS ESI calculated for C26H30N8O3 [M+H]+, 503.24, found 503.20; 1H NMR (300 MHz, DMSO-d6) δ 8.88 (d, J=1.0 Hz, 1H), 7.81 (s, 1H), 7.46 (s, 1H), 6.86-6.52 (m, 3H), 6.17 (d, J=16.6 Hz, 1H), 5.70 (d, J=10.4 Hz, 1H), 5.27 (dd, J=13.6, 6.8 Hz, 1H), 4.40-4.05 (m, 1H), 3.98-3.96 (m, 4H), 3.92-3.82 (m, 1H), 3.79-3.56 (m, 1H), 3.53-3.41 (m, 2H), 3.31 (s, 3H), 2.98-2.95 (m, 3H), 2.36-2.29 (m, 2H), 1.27-1.01 (m, 4H).

Example 64: 1-[(3S,5R)-5-(Methoxymethyl)-1-(prop-2-enoyl) pyrrolidin-3-yl]-5-(methylamino)-3-[2-(quinoxalin-6-yl) ethynyl] pyrazole-4-carboxamide

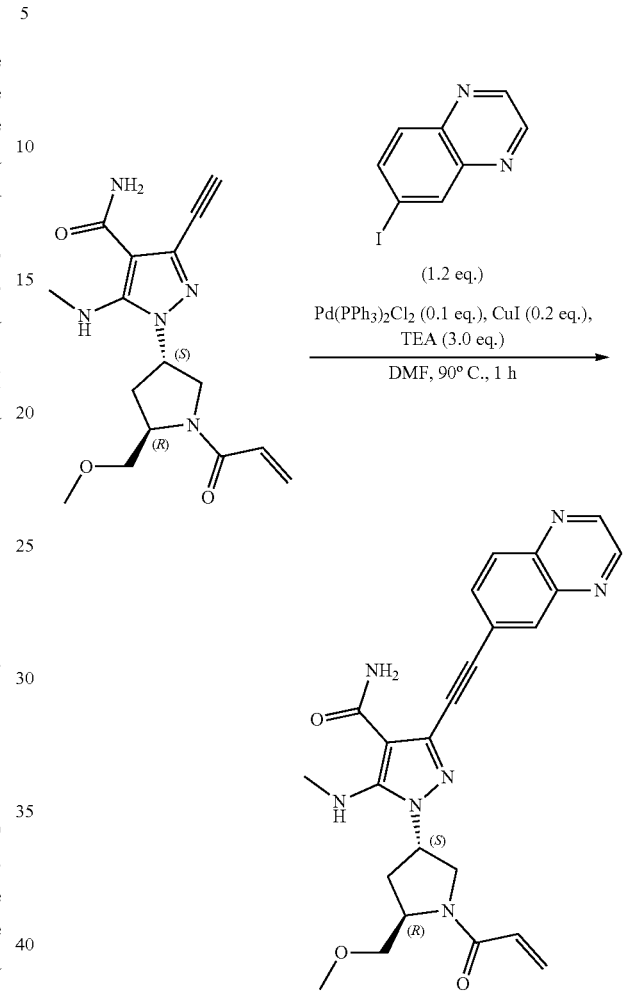

To a mixture of 6-iodoquinoxaline (0.12 g, 0.47 mmol), 3-ethynyl-1-[(3S,5R)-5-(methoxymethyl)-1-(prop-2-enoyl) pyrrolidin-3-yl]-5-(methylamino) pyrazole-4-carboxamide (0.13 g, 0.39 mmol), CuI (14.94 mg, 0.08 mmol) and Pd(PPh3)2Cl2 (27.54 mg, 0.04 mmol) in DMF (2.00 mL) was added TEA (0.12 g, 1.18 mmol). The reaction mixture was degassed with argon for three times and stirred for 1 h at 90° C. The resulting mixture was concentrated under reduced pressure. The residue was purified by reverse phase chromatography with the following conditions: Column: Spherical C18, 20-40 μm, 40 g; Mobile Phase A: Water (10 mmol/L NH4HCO3), Mobile Phase B: ACN; Flow rate: 40 mL/min; Gradient: 20%-40% within 40 min, Detector: UV 254/220 nm; RT: 30 min. The fractions contained desired product were combined and concentrated to afford 1-[(3S,5R)-5-(methoxymethyl)-1-(prop-2-enoyl) pyrrolidin-3-yl]-5-(methylamino)-3-[2-(quinoxalin-6-yl) ethynyl] pyrazole-4-carboxamide (91.4 mg, 51%) as an off-white solid. MS ESI calculated for C24H25N7O3 [M+H]+, 460.20, found 460.15; 1H NMR (300 MHz, DMSO-d6) δ 9.04-8.98 (m, 2H), 8.34 (d, J=1.7 Hz, 1H), 8.16 (d, J=8.7 Hz, 1H), 7.98 (dd, J=8.7, 1.9 Hz, 1H), 7.99-6.93 (m, 2H), 6.79-6.47 (m, 2H), 6.21-6.18 (m, 1H), 5.73-5.68 (m, 1H), 5.32-5.20 (m, 1H), 4.51-4.48 (m, 1H), 4.09-3.70 (m, 2H), 3.64-3.44 (m, 2H), 3.31 (s, 3H), 2.95-2.92 (m, 3H), 2.67-2.58 (m, 1H), 2.39-2.23 (m, 1H).

Example 65: 1-((3S,5R)-1-Acryloyl-5-(methoxymethyl)pyrrolidin-3-yl)-5-(methylamino)-3-((3-methylquinolin-7-yl)ethynyl)-1H-pyrazole-4-carboxamide

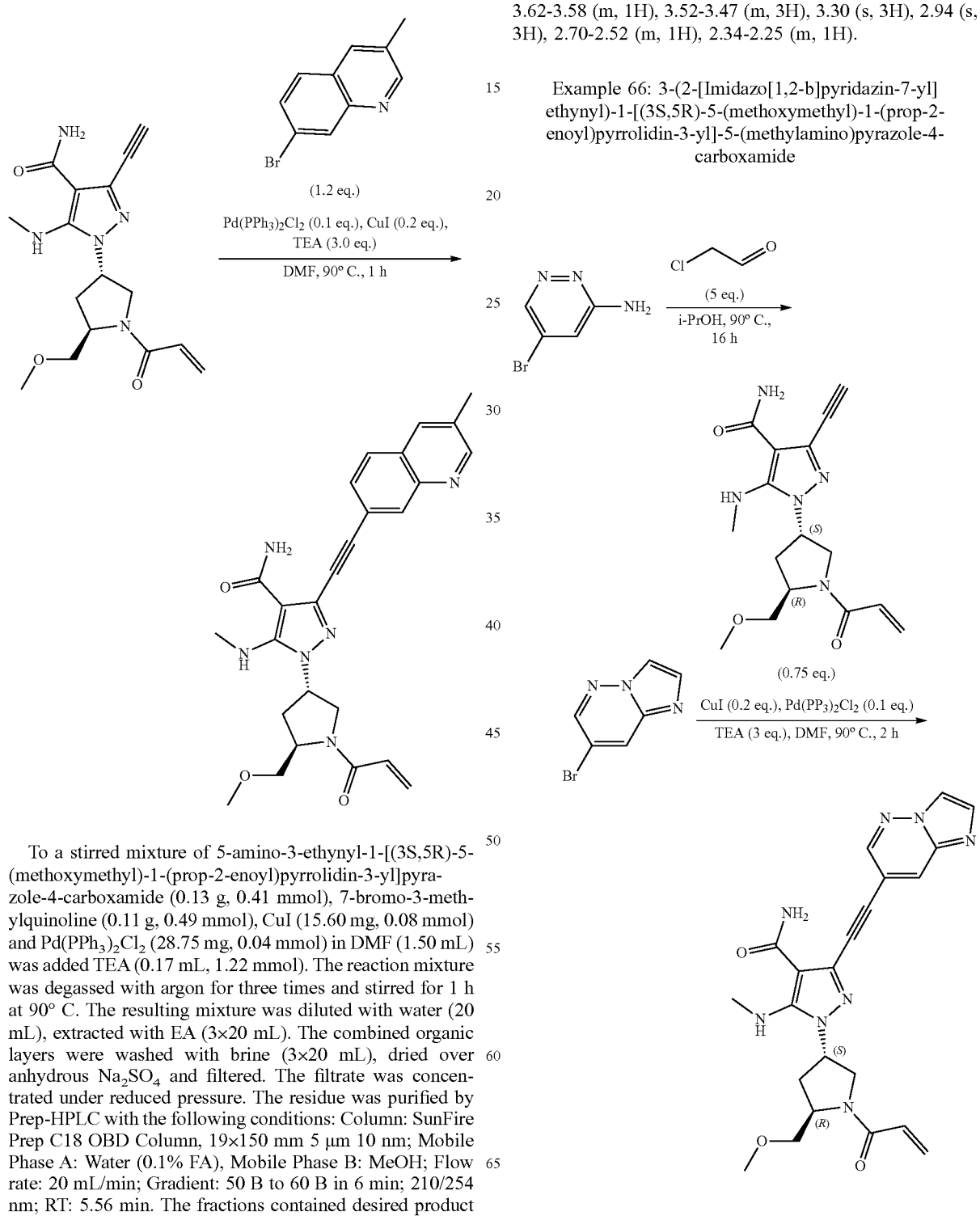

To a stirred mixture of 5-amino-3-ethynyl-1-[(3S,5R)-5-(methoxymethyl)-1-(prop-2-enoyl)pyrrolidin-3-yl]pyrazole-4-carboxamide (0.13 g, 0.41 mmol), 7-bromo-3-methylquinoline (0.11 g, 0.49 mmol), CuI (15.60 mg, 0.08 mmol) and Pd(PPh$_3$)$_2$Cl$_2$ (28.75 mg, 0.04 mmol) in DMF (1.50 mL) was added TEA (0.17 mL, 1.22 mmol). The reaction mixture was degassed with argon for three times and stirred for 1 h at 90° C. The resulting mixture was diluted with water (20 mL), extracted with EA (3×20 mL). The combined organic layers were washed with brine (3×20 mL), dried over anhydrous Na$_2$SO$_4$ and filtered. The filtrate was concentrated under reduced pressure. The residue was purified by Prep-HPLC with the following conditions: Column: SunFire Prep C18 OBD Column, 19×150 mm 5 μm 10 nm; Mobile Phase A: Water (0.1% FA), Mobile Phase B: MeOH; Flow rate: 20 mL/min; Gradient: 50 B to 60 B in 6 min; 210/254 nm; RT: 5.56 min. The fractions contained desired product were combined and concentrated to afford 1-((3S,5R)-1-acryloyl-5-(methoxymethyl)pyrrolidin-3-yl)-5-(methylamino)-3-((3-methylquinolin-7-yl)ethynyl)-1H-pyrazole-4-carboxamide (30.3 mg, 16%) as a yellow solid. MS ESI calculated for C$_{26}$H$_{28}$N$_6$O$_3$ [M+H]$^+$, 473.22, found 473.35; $^1$H NMR (400 MHz, DMSO-d$_6$) δ 8.87 (s, 1H), 8.23-8.19 (m, 2H), 7.99 (d, J=8.5 Hz, 1H), 7.71 (d, J=8.4 Hz, 1H), 7.37 (s, 1H), 6.90 (s, 1H), 6.76-6.69 (m, 1H), 6.63-6.56 (m, 1H), 6.20-6.14 (m, 1H), 5.72-5.68 (m, 1H), 5.30-5.19 (m, 1H), 4.66-4.30 (m, 1H), 4.13-3.80 (m, 2H), 3.76-3.68 (m, 1H), 3.62-3.58 (m, 1H), 3.52-3.47 (m, 3H), 3.30 (s, 3H), 2.94 (s, 3H), 2.70-2.52 (m, 1H), 2.34-2.25 (m, 1H).

Example 66: 3-(2-[Imidazo[1,2-b]pyridazin-7-yl]ethynyl)-1-[(3S,5R)-5-(methoxymethyl)-1-(prop-2-enoyl)pyrrolidin-3-yl]-5-(methylamino)pyrazole-4-carboxamide

453
Step 1: 7-Bromoimidazo[1,2-b]pyridazine

To a stirred solution of 5-bromopyridazin-3-amine (0.5 g, 2.87 mmol) in i-PrOH (5.50 mL) was added chloroacetaldehyde (2.37 mL, 12.07 mmol, 40%) dropwise at room temperature under argon atmosphere. The reaction mixture was stirred for 16 h at 90° C. under argon atmosphere. The resulting mixture was diluted with water (100 mL) and extracted with EtOAc (3×150 mL). The combined organic layers were washed with brine (200 mL), dried over anhydrous Na$_2$SO$_4$ and filtered. The filtrate was concentrated under reduced pressure. The residue was purified by silica gel Column chromatography, eluted with CH$_2$Cl$_2$/MeOH (10/1). The fractions contained desired product were combined and concentrated to afford 7-bromoimidazo[1,2-b]pyridazine (0.44 g, 78%) as a white solid. MS ESI calculated for C$_6$H$_4$BrN$_3$ [M+H]$^+$, 197.96, found 198.00.

Step 2: 3-(2-[Imidazo[1,2-b]pyridazin-7-yl]ethynyl)-1-[(3S,5R)-5-(methoxymethyl)-1-(prop-2-enoyl)pyrrolidin-3-yl]-5-(methylamino)pyrazole-4-carboxamide To a stirred mixture of 3-ethynyl-1-[(3S,5R)-5-(methoxymethyl)-1-(prop-2-enoyl)pyrrolidin-3-yl]-5-(methylamino)pyrazole-4-carboxamide (0.17 g, 0.51 mmol), 7-bromoimidazo[1,2-b]pyridazine (0.15 g, 0.77 mmol), Pd(PPh$_3$)$_2$Cl$_2$ (36.01 mg, 0.05 mmol) and CuI (19.54 mg, 0.10 mmol) in DMF (2.00 mL) was added TEA (0.21 mL, 2.11 mmol) at room temperature. The reaction mixture was degassed with argon for three times and stirred for 2 h at 90° C. The resulting mixture was diluted with water (30 mL) and extracted with EtOAc (3×30 mL). The combined organic layers were washed with brine (100 mL), dried over anhydrous Na$_2$SO$_4$ and filtered. The filtrate was concentrated under reduced pressure. The residue was purified by silica gel Column chromatography, eluted with CH$_2$Cl$_2$/MeOH (10/1). The fractions contained desired product were combined and concentrated. The residue was purified by Prep-HPLC with the following conditions Column: Atlantis Prep T3 OBD Column, 19×250 mm 10 p; Mobile Phase A: Water (0.1% FA), Mobile Phase B: ACN; Flow rate: 20 mL/min; Gradient: 25 B to 55 B in 6 min; 210/254 nm; RT: 5.56 min. The fractions contained desired product were combined and concentrated to afford 3-(2-[imidazo[1,2-b]pyridazin-7-yl]ethynyl)-1-[(3S,5R)-5-(methoxymethyl)-1-(prop-2-enoyl)pyrrolidin-3-yl]-5-(methylamino)pyrazole-4-carboxamide (37.7 mg, 16%) as a yellow solid. MS ESI calculated for C$_{22}$H$_{24}$N$_8$O$_3$ [M+H]$^+$, 449.20, found 449.20; $^1$H NMR (400 MHz, DMSO-d$_6$) δ 8.67 (d, J=2.0 Hz, 1H), 8.52-8.33 (m, 2H), 7.92 (d, J=1.2 Hz, 1H), 7.30 (s, 1H), 6.90 (s, 1H), 6.82-6.45 (m, 2H), 6.17-5.96 (m, 1H), 5.69-5.43 (m, 1H), 5.25-5.23 (m, 1H), 4.63-4.32 (m, 1H), 4.17-3.70 (m, 2H), 3.68-3.41 (m, 2H), 3.30 (d, J=5.5 Hz, 3H), 2.94-2.76 (m, 3H), 2.65-2.60 (m, 1H), 2.41-2.20 (m, 1H).

454
Example 67: 1-[(3S,5R)-5-(Methoxymethyl)-1-(prop-2-enoyl)pyrrolidin-3-yl]-5-(methylamino)-3-(2-[pyrazolo[1,5-a]pyridin-6-yl]ethynyl)pyrazole-4-carboxamide

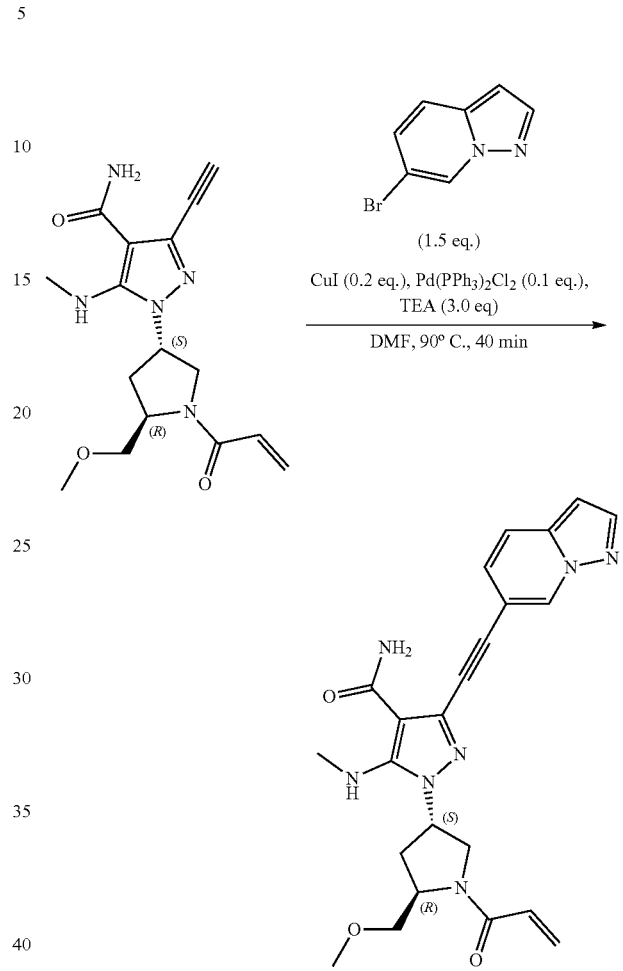

To a stirred mixture of 5-amino-3-ethynyl-1-[(3S,5R)-5-(methoxymethyl)-1-(prop-2-enoyl)pyrrolidin-3-yl]pyrazole-4-carboxamide (0.11 g, 0.35 mmol), 6-bromopyrazolo[1,5-a]pyridine (0.10 g, 0.52 mmol), Pd(PPh$_3$)$_2$Cl$_2$ (24.33 mg, 0.03 mmol) and CuI (13.20 mg, 0.07 mmol) in DMF (1.50 mL) was added TEA (0.14 mL, 1.01 mmol). The reaction mixture was degassed with argon for three times and stirred for 40 min at 90° C. The resulting mixture was concentrated under reduced pressure. The residue was purified by silica gel Column chromatography, eluted with 6% MeOH in DCM. The fractions contained desired product were combined and concentrated. The crude product was purified by Prep-HPLC with the following conditions Column: XBridge Prep C18 OBD Column, 19×150 mm 5 μm; Mobile Phase A: Water (10 mmol/L NH$_4$HCO$_3$), Mobile Phase B: ACN; Flow rate: 20 mL/min; Gradient: 25 B to 55 B in 6 min; 210/254 nm. The fractions contained desired product were combined and concentrated to afford 1-[(3S,5R)-5-(methoxymethyl)-1-(prop-2-enoyl)pyrrolidin-3-yl]-5-(methylamino)-3-(2-[pyrazolo[1,5-a]pyridin-6-yl]ethynyl)pyrazole-4-carboxamide (31.9 mg, 20%) as an off-white solid. MS ESI calculated for C$_{23}$H$_{25}$N$_7$O$_3$ [M+H]$^+$, 448.20, found 448.20; $^1$H NMR (400 MHz, DMSO-d$_6$): δ 9.14 (s, 1H), 8.12 (d, J=2.2 Hz, 1H), 7.78-7.70 (m, 1H), 7.30 (dd, J=9.2, 1.5 Hz, 2H), 6.88-6.48 (m, 4H), 6.22-6.13 (m, 1H), 5.73-5.68 (m, 1H), 5.26-5.22 (m, 1H), 4.55-4.38 (m, 1H), 4.10-3.68 (m, 2H), 3.64-3.39 (m, 2H), 3.33-3.30 (m, 3H), 2.95-2.94 (m, 3H), 2.53-2.51 (m, 1H), 2.39-2.35 (m, 1H).

Example 68: 1-((3S,5R)-1-Acryloyl-5-(methoxymethyl)pyrrolidin-3-yl)-3-((1-ethyl-4-fluoro-1H-benzo[d]imidazol-5-yl)ethynyl)-5-(methylamino)-1H-pyrazole-4-carboxamide

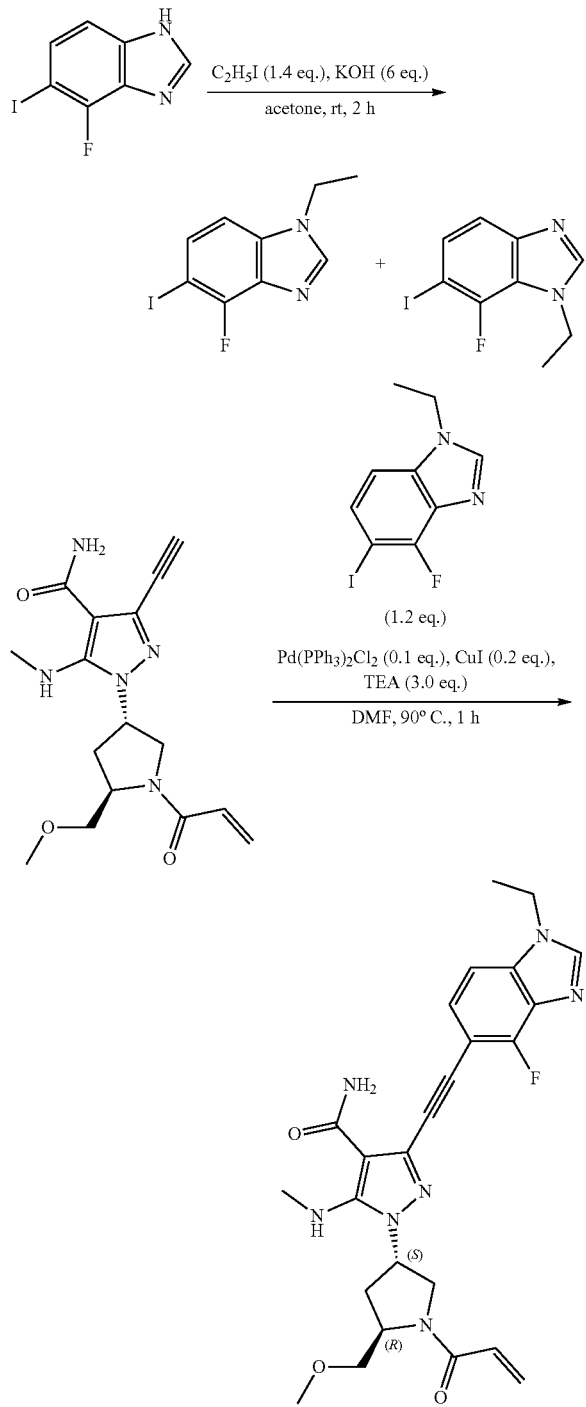

Step 1: 1-Ethyl-4-fluoro-5-iodo-1,3-benzodiazole and 1-ethyl-7-fluoro-6-iodo-1,3-benzodiazole To a stirred mixture of 4-fluoro-5-iodo-1H-1,3-benzodiazole (2.00 g, 7.63 mmol) and KOH (2.57 g, 45.80 mmol) in acetone (20.00 mL) was added iodoethane (1.67 g, 10.69 mmol) at room temperature. The reaction mixture was stirred for 2 h at room temperature. The resulting mixture was diluted with water (50 mL) and extracted with EA (3×70 mL). The combined organic layers were washed with brine (2×50 mL), dried over anhydrous $Na_2SO_4$ and filtered. The filtrate was concentrated under reduced pressure. The residue was purified by reverse flash chromatography with the following conditions: Column, C18 silica gel; mobile phase, ACN in water (10 mmol/L $NH_4HCO_3$), 25% to 55% gradient in 30 min; detector, UV 254 nm. The fraction contained desired product were combined and concentrated to afford 1-ethyl-4-fluoro-5-iodo-1,3-benzodiazole (0.80 g, 36%) as a yellow solid. MS ESI calculated for $C_9H_8FIN_2$ $[M+H]^+$, 290.97, found 290.99; And also afford 1-ethyl-7-fluoro-6-iodo-1,3-benzodiazole (0.78 g, 35%) as a yellow solid. MS ESI calculated for $C_9H_8FIN_2$ $[M+H]^+$, 290.97, found 290.95.

Step 2: 1-((3S,5R)-1-Acryloyl-5-(methoxymethyl)pyrrolidin-3-yl)-3-((1-ethyl-4-fluoro-1H-benzo[d]imidazol-5-yl)ethynyl)-5-(methylamino)-1H-pyrazole-4-carboxamide To a stirred mixture of 3-ethynyl-1-[(3S,5R)-5-(methoxymethyl)-1-(prop-2-enoyl)pyrrolidin-3-yl]-5-(methylamino)pyrazole-4-carboxamide (0.2 g, 0.60 mmol), 1-ethyl-4-fluoro-5-iodo-1,3-benzodiazole (0.21 g, 0.72 mmol), CuI (22.99 mg, 0.12 mmol) and $Pd(PPh_3)_2Cl_2$ (42.36 mg, 0.06 mmol) in DMF (2.00 mL) was added TEA (0.25 mL, 1.80 mmol). The reaction mixture was degassed with argon for three times and stirred for 1 h at 90° C. The resulting mixture was concentrated under reduced pressure. The residue was purified by Prep-HPLC with the following conditions: Column: Atlantis Prep T3 OBD Column, 19×250 mm 10 u; Mobile Phase A: Water (0.1% FA), Mobile Phase B: ACN; Flow rate: 20 mL/min; Gradient: 30 B to 50 B in 6 min; 210/254 nm; RT: 5.58 min. The fractions contained desired product were combined and concentrated to afford 1-((3S,5R)-1-acryloyl-5-(methoxymethyl)pyrrolidin-3-yl)-3-((1-ethyl-4-fluoro-1H-benzo[d]imidazol-5-yl)ethynyl)-5-(methylamino)-1H-pyrazole-4-carboxamide (60.0 mg, 20%) as a light pink solid. MS ESI calculated for $C_{25}H_{28}FN_7O_3$ $[M+H]^+$, 494.22, found 494.20; $^1H$ NMR (400 MHz, DMSO-$d_6$) δ 8.56 (s, 1H), 7.56-7.44 (m, 3H), 6.99-6.43 (m, 2H), 6.19-6.14 (m, 1H), 5.70-5.67 (m, 2H), 5.30-5.22 (m, 1H), 4.57-4.38 (m, 3H), 4.07-3.88 (m, 2H), 3.81-3.65 (m, 2H), 3.32 (s, 3H), 2.98 (s, 3H), 2.66-2.54 (m, 1H), 2.34-2.27 (m, 1H), 1.59-1.54 (m, 3H).

Example 69: 1-((3S,5R)-1-Acryloyl-5-(methoxymethyl)pyrrolidin-3-yl)-5-(methylamino)-3-((2-methylquinoxalin-6-yl)ethynyl)-1H-pyrazole-4-carboxamide

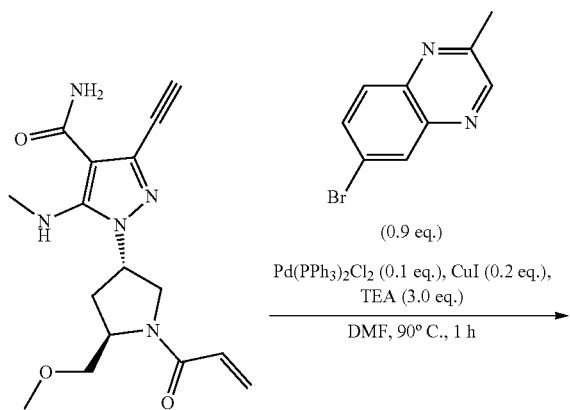

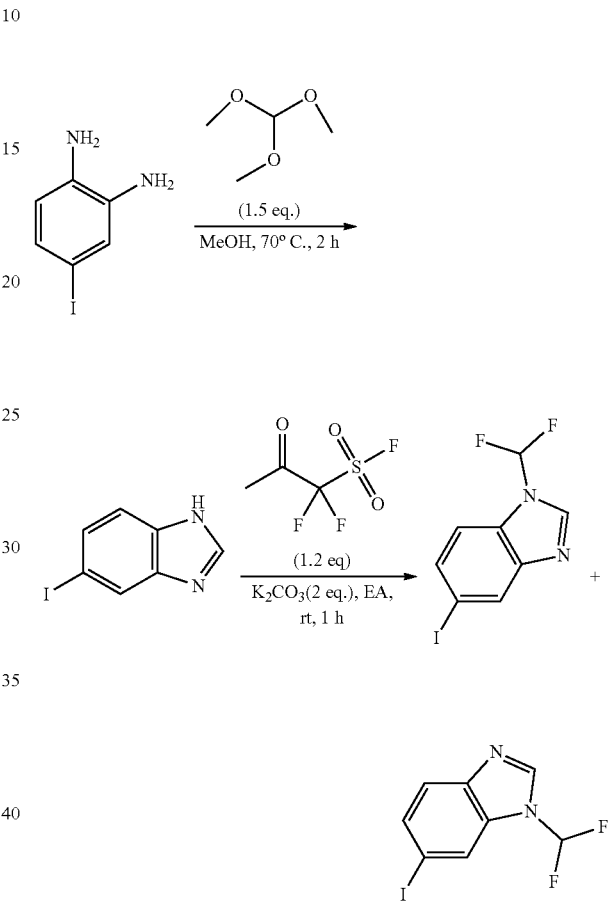

To a stirred mixture of 3-ethynyl-1-[(3S,5R)-5-(methoxymethyl)-1-(prop-2-enoyl)pyrrolidin-3-yl]-5-(methylamino)pyrazole-4-carboxamide (0.16 g, 0.48 mmol), 6-bromo-2-methylquinoxaline (96.94 mg, 0.44 mmol), CuI (18.39 mg, 0.10 mmol) and Pd(PPh$_3$)$_2$Cl$_2$ (33.89 mg, 0.05 mmol) in DMF (1.60 mL) was added TEA (0.20 mL, 1.99 mmol). The reaction mixture was degassed with argon for three times and stirred for 1 h at 90° C. The resulting mixture was concentrated under reduced pressure. The residue was purified by Prep-HPLC with the following conditions: Column: Atlantis Prep T3 OBD Column, 19×250 mm 10 u; Mobile Phase A: Water (0.1% FA), Mobile Phase B: ACN; Flow rate: 20 mL/min; Gradient: 25 B to 45 B in 6 min; 210/254 nm; RT: 5.56 min. The fractions contained desired product were combined and concentrated to afford 1-((3S,5R)-1-acryloyl-5-(methoxymethyl)pyrrolidin-3-yl)-5-(methylamino)-3-((2-methylquinoxalin-6-yl)ethynyl)-1H-pyrazole-4-carboxamide (39.1 mg, 17%) as a yellow solid. MS ESI calculated for C$_{25}$H$_{27}$N$_7$O$_3$ [M+H]$^+$, 474.22, found 474.15; $^1$H NMR (400 MHz, DMSO-d$_6$) δ 8.89 (s, 1H), 8.21 (s, 1H), 8.10 (d, J=8.6 Hz, 1H), 7.89 (dd, J=8.6, 1.8 Hz, 1H), 7.34 (s, 1H), 7.06-6.36 (m, 2H), 6.20-6.14 (m, 1H), 5.78-5.65 (m, 1H), 5.28-5.18 (m, 1H), 4.64-4.25 (m, 1H), 4.12-3.67 (m, 2H), 3.64-3.41 (m, 2H), 3.30 (s, 4H), 2.98-2.92 (m, 3H), 2.72 (s, 2H), 2.54 (s, 1H), 2.31-2.28 (m, 1H).

Example 70: 3-[2-[1-(Difluoromethyl)-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide

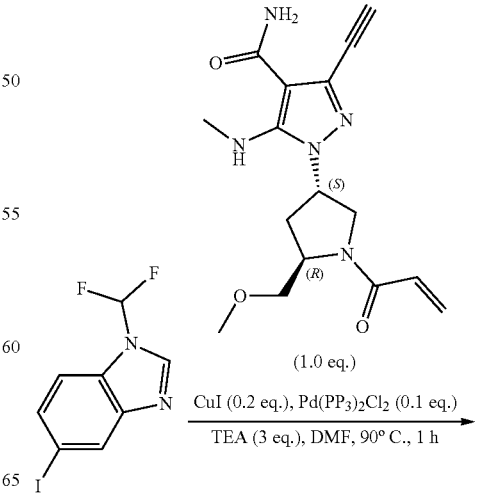

459

-continued

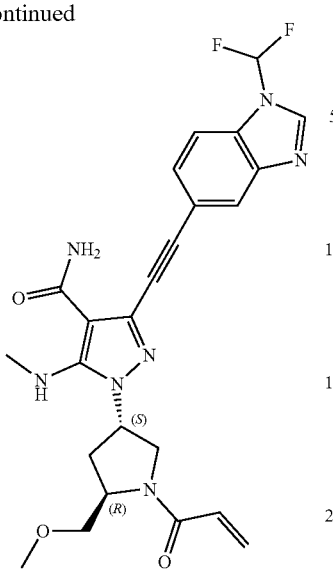

Step 1: 5-Iodo-1H-1,3-benzodiazole

To a stirred solution of 4-iodobenzene-1,2-diamine (5.00 g, 21.36 mmol) in MeOH (50.00 mL) was added trimethyl orthoformate (6.80 g, 0.06 mmol) dropwise at room temperature under nitrogen atmosphere. The reaction mixture was stirred for 2 h at 70° C. The resulting mixture was cooled down to room temperature and concentrated under reduced pressure. The residue was purified by silica gel Column chromatography, eluted with PE/EtOAc (0~50%). The fractions contained desired product were combined and concentrated to afford 5-iodo-1H-1,3-benzodiazole (5.5 g, 94%) as a dark yellow solid. MS ESI calculated for $C_7H_{11}IN_2$ $[M+H]^+$, 244.95, found 245.00.

Step 2: 1-(Difluoromethyl)-5-iodo-1,3-benzodiazole and 1-(difluoromethyl)-6-iodo-1,3-benzodiazole To a stirred mixture of 5-iodo-1H-1,3-benzodiazole (5.00 g, 20.49 mmol) and $K_2CO_3$ (5.66 g, 0.04 mmol) in EtOAc (50.00 mL) was added 1,1-difluoro-2-oxopropane-1-sulfonyl fluoride (4.33 g, 0.03 mmol) dropwise at room temperature under nitrogen atmosphere. The reaction mixture was stirred for 1 h at room temperature. The resulting mixture was filtered. The filter cake was washed with MeOH (3×100 mL). The filtrate was concentrated under reduced pressure. The residue was purified by silica gel Column chromatography, eluted with PE/EtOAc (0~50%). The fractions contained desired product were combined and concentrated. The crude product was purified by Prep-SFC with the following conditions Column: Chiralpak if, 30×250 mm, 5 μm; Mobile Phase A: $CO_2$, Mobile Phase B: MeOH (0.1% 2 M $NH_3$-MeOH); Flow rate: 50 mL/min; Gradient: 45% B; 220 nm; RT1: 6.2 min; RT2: 7.8 min; Injection volume: 0.5 mL; Number of runs: 60. The fractions contained desired product were combined and concentrated to afford 1-(difluoromethyl)-5-iodo-1,3-benzodiazole (1.78 g, 29%, assumed) as a yellow green solid and 1-(difluoromethyl)-6-iodo-1,3-benzodiazole (2.13 g, 35%, assumed) as a yellow green solid. MS ESI calculated for $C_8H_5F_2IN_2$ $[M+H]^+$, 295.04, found 295.00.

460

Step 3: 3-[2-[1-(Difluoromethyl)-1,3-benzodiazol-5-yl]ethynyl]-1-[(3S,5R)-5-(methoxymethyl)-1-(prop-2-enoyl) pyrrolidin-3-yl]-5-(methylamino) pyrazole-4-carboxamide To a stirred mixture of 1-(difluoromethyl)-5-iodo-1,3-benzodiazole (0.13 g, 0.45 mmol), 3-ethynyl-1-[(3S,5R)-5-(methoxymethyl)-1-(prop-2-enoyl) pyrrolidin-3-yl]-5-(methylamino) pyrazole-4-carboxamide (0.15 g, 0.45 mmol), $Pd(PPh_3)_2Cl_2$ (31.80 mg, 0.05 mmol) and CuI (17.25 mg, 0.09 mmol) in DMF (2.00 mL) was added TEA (0.14 g, 1.36 mmol) at room temperature. The reaction mixture was degassed with argon for three times and stirred for 2 h at 90° C. The resulting mixture was concentrated under reduced pressure. The residue was purified by silica gel Column chromatography, eluted with $CH_2Cl_2$/MeOH (10/1), The fractions contained desired product were combined and concentrated. The residue was purified by reverse flash chromatography with the following conditions: Column, C18 silica gel; mobile phase, ACN in water, 5% to 70% gradient in 30 min; detector, UV 254 nm. The fractions contained desired product were combined and concentrated to afford 3-[2-[1-(difluoromethyl)-1,3-benzodiazol-5-yl] ethynyl]-1-[(3S,5R)-5-(methoxymethyl)-1-(prop-2-enoyl) pyrrolidin-3-yl]-5-(methylamino) pyrazole-4-carboxamide (80.2 mg, 33%) as an off-white solid. MS ESI calculated for $C_{24}H_{25}F_2N_7O_3$ $[M+H]^+$, 498.51, found 498.20; $^1H$ NMR (400 MHz, DMSO-$d_6$) δ 8.71 (s, 1H), 8.29-7.93 (m, 2H), 7.80 (d, J=8.4 Hz, 1H), 7.61 (dd, J=8.4, 1.5 Hz, 1H), 7.35 (s, 1H), 6.85-6.57 (m, 3H), 6.19-6.15 (m, 1H), 5.69-5.66 (m, 1H), 5.27-5.24 (m, 1H), 4.58-4.36 (m, 1H), 4.04-3.70 (m, 2H), 3.63-3.42 (m, 2H), 3.30 (d, J=5.2 Hz, 3H), 2.94 (t, J=5.1 Hz, 3H), 2.68-2.42 (m, 1H), 2.32-2.28 (m, 1H).

Example 71: 1-((3S,5R)-1-Acryloyl-5-(methoxymethyl)pyrrolidin-3-yl)-3-((4-fluoro-1-methyl-1H-benzo[d]imidazol-5-yl)ethynyl)-5-(methylamino)-1H-pyrazole-4-carboxamide

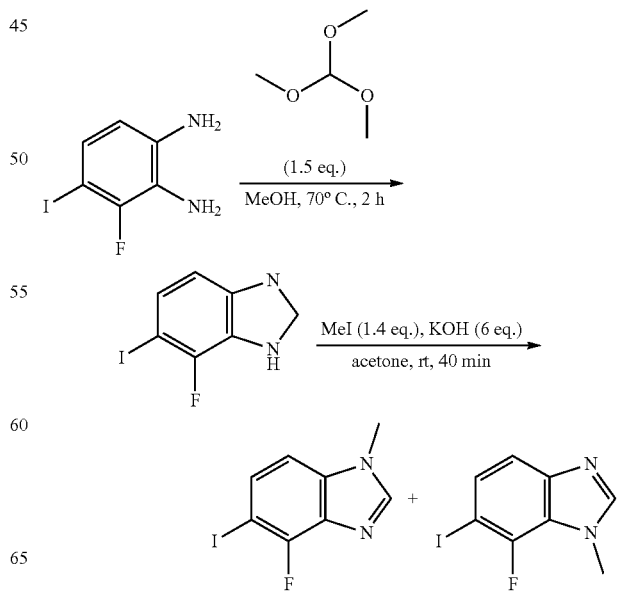

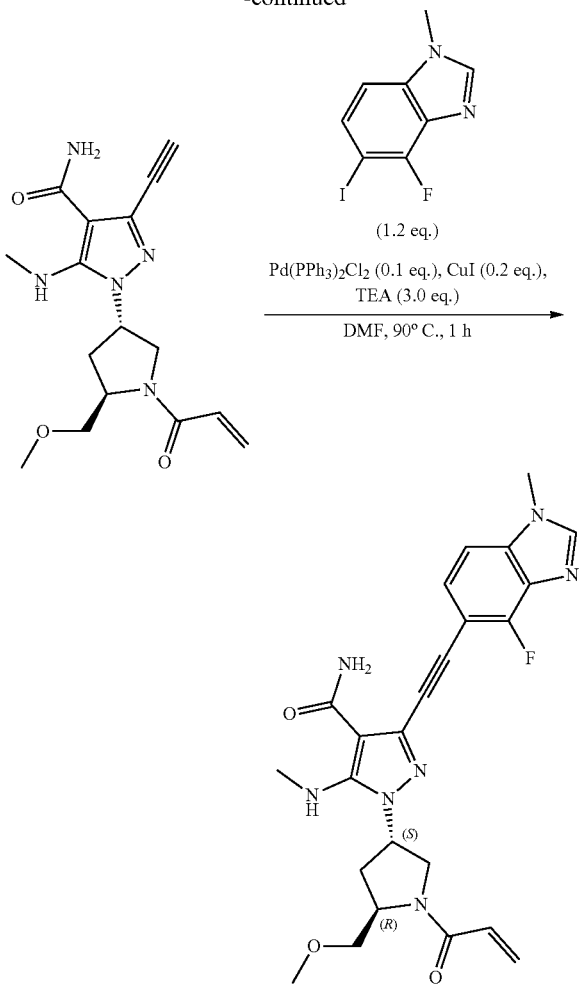

Step 1: 4-Fluoro-5-iodo-1H-1,3-benzodiazole

To a stirred solution of 3-fluoro-4-iodobenzene-1,2-diamine (5.00 g, 19.84 mmol) in MeOH (50.00 mL) was added trimethyl orthoformate (3.16 g, 29.78 mmol) dropwise at room temperature under nitrogen atmosphere. The reaction mixture was stirred for 2 h at 70° C. under nitrogen atmosphere. The resulting mixture was concentrated under reduced pressure. The residue was purified by silica gel Column chromatography, eluted with DCM/MeOH (10/1). The fractions contained desired product were combined and concentrated to afford 4-fluoro-5-iodo-1H-1,3-benzodiazole (4.6 g, 88%) as a light yellow solid. MS ESI calculated for $C_7H_4FIN_2$ [M+H]$^+$, 262.94, found 263.00.

Step 2: 4-Fluoro-5-iodo-1-methyl-1,3-benzodiazole and 7-fluoro-6-iodo-1-methyl-1,3-benzodiazole To a stirred mixture of 4-fluoro-5-iodo-1H-1,3-benzodiazole (3.50 g, 13.36 mmol) and KOH (4.50 g, 80.21 mmol) in acetone (35.00 mL) was added CH$_3$I (1.16 mL, 8.20 mmol) dropwise. The reaction mixture was stirred for 40 min at room temperature. The resulting mixture was diluted with water (40 mL) and extracted with EA (3×70 mL). The combined organic layers were washed with brine (50 mL), dried over anhydrous Na$_2$SO$_4$, filtered and concentrated under reduced pressure. The residue was purified by reverse flash chromatography with the following conditions: Column, C18 silica gel; mobile phase, ACN in water (10 mmol/L NH$_4$HCO$_3$), 20% to 50% gradient in 30 min; detector, UV 254 nm. The fractions contained desired product were combined and concentrated to afford 4-fluoro-5-iodo-1-methyl-1,3-benzodiazole (1.6 g, 43%) as an off-white solid. MS ESI calculated for $C_8H_6FIN_2$ [M+H]$^+$, 276.96, found 277.00. And also afford 7-fluoro-6-iodo-1-methyl-1,3-benzodiazole (1.57 g, 42%) as an off-white solid. MS ESI calculated for $C_8H_6FIN_2$ [M+H]$^+$, 276.96, found 277.00.

Step 3: 1-((3S,5R)-1-Acryloyl-5-(methoxymethyl) pyrrolidin-3-yl)-3-((4-fluoro-1-methyl-1H-benzo[d] imidazol-5-yl)ethynyl)-5-(methylamino)-1H-pyrazole-4-carboxamide To a stirred mixture of 3-ethynyl-1-[(3S,5R)-5-(methoxymethyl)-1-(prop-2-enoyl)pyrrolidin-3-yl]-5-(methylamino)pyrazole-4-carboxamide (0.2 g, 0.61 mmol), 4-fluoro-5-iodo-1-methyl-1,3-benzodiazole (0.2 g, 0.72 mmol), CuI (22.99 mg, 0.12 mmol) and Pd(PPh$_3$)$_2$Cl$_2$ (42.36 mg, 0.06 mmol) in DMF (2.00 mL) was added TEA (0.25 mL, 2.49 mmol). The reaction mixture was degassed with argon for three times and stirred for 1 h at 90° C. The residue was purified by Prep-HPLC with the following conditions: Column: XBridge Prep C18 OBD Column, 19×150 mm 5 μm; Mobile Phase A: Water (10 mmol/L NH$_4$HCO$_3$), Mobile Phase B: ACN; Flow rate: 20 mL/min; Gradient: 35 B to 60 B in 6 min; 210/254 nm; RT: 5.56 min. The fractions contained desired product were combined and concentrated to afford 1-((3S,5R)-1-acryloyl-5-(methoxymethyl)pyrrolidin-3-yl)-3-((4-fluoro-1-methyl-1H-benzo[d]imidazol-5-yl)ethynyl)-5-(methylamino)-1H-pyrazole-4-carboxamide (45.3 mg, 15%) as an off-white solid. MS ESI calculated for $C_{24}H_{26}FN_7O_3$ [M+H]$^+$, 480.53, found 480.20; $^1$H NMR (400 MHz, DMSO-d$_6$) δ 8.35 (s, 1H), 7.56-7.44 (m, 3H), 6.99-6.43 (m, 3H), 6.19-6.14 (m, 1H), 5.70-5.67 (m, 1H), 5.30-5.22 (m, 1H), 4.53-4.40 (m, 1H), 4.07-3.98 (m, 1H), 3.91-3.85 (m, 4H), 3.77-3.72 (m, 1H), 3.63-3.59 (m, 1H), 3.51-3.42 (m, 3H), 2.97-2.94 (m, 3H), 2.46-2.44 (m, 1H), 2.34-2.27 (m, 1H).

Example 72: 1-((3S,5R)-1-Acryloyl-5-(methoxymethyl)pyrrolidin-3-yl)-5-(methylamino)-3-((3-methylquinoxalin-6-yl)ethynyl)-1H-pyrazole-4-carboxamide

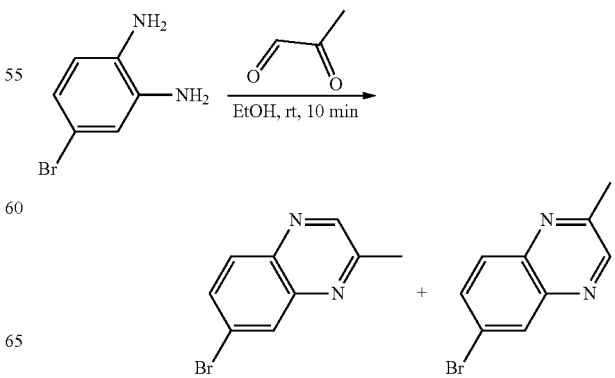

-continued

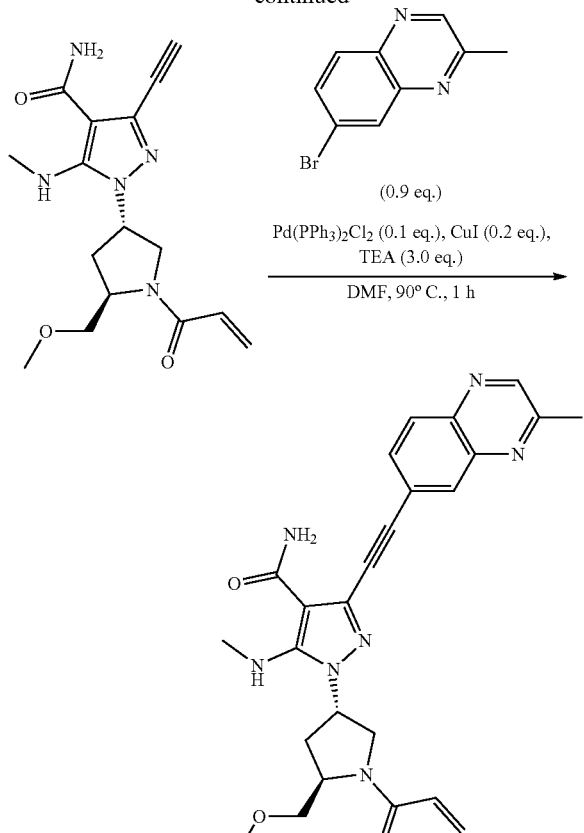

Step 1: 7-Bromo-2-methylquinoxaline and 6-bromo-2-methylquinoxaline

To a stirred solution of 4-bromobenzene-1,2-diamine (1.00 g, 5.35 mmol) in EtOH (10.00 mL) was added 2-oxo-propanal (4 mL, 40%) at room temperature under argon atmosphere. The reaction mixture was stirred for 10 min. The resulting mixture was extracted with EtOAc (3×300 mL). The combined organic layers were washed with brine (2×200 mL), dried over anhydrous $Na_2SO_4$ and filtered. The filtrate was concentrated under reduced pressure. The residue was purified by Prep-SFC with the following conditions Column: Chiralpak if, 30×250 mm, 5 μm; Mobile Phase A: $CO_2$, Mobile Phase B: IPA (0.5% 2 M $NH_3$-MeOH); Flow rate: 50 mL/min; Gradient: 20% B; 220 nm; RT1: 8.75 min; RT2: 10.62 min; Injection volume: 0.8 mL; Number of runs: 35. The fractions contained desired product were combined and concentrated to afford 7-bromo-2-methylquinoxaline (0.39 g, 33%) as a light brown solid. MS ESI calculated for $C_9H_7BrN_2$ $[M+H]^+$, 222.98, found 222.95. And also afford 6-bromo-2-methylquinoxaline (0.32 g, 27%) as a light brown solid. MS ESI calculated for $C_9H_7BrN_2$ $[M+H]^+$, 222.98, found 223.00.

Step 2: 1-((3S,5R)-1-Acryloyl-5-(methoxymethyl) pyrrolidin-3-yl)-5-(methylamino)-3-((3-methylqui-noxalin-6-yl)ethynyl)-1H-pyrazole-4-carboxamide To a stirred mixture of 3-ethynyl-1-[(3S,5R)-5-(methoxymethyl)-1-(prop-2-enoyl)pyrrolidin-3-yl]-5-(methylamino)pyrazole-4-carboxamide (0.16 g, 0.48 mmol), 7-bromo-2-methylquinoxaline (96.94 mg, 0.44 mmol), CuI (18.39 mg, 0.10 mmol) and $Pd(PPh_3)_2Cl_2$ (33.89 mg, 0.05 mmol) in DMF (1.60 mL) was added TEA (0.20 mL, 1.44 mmol). The reaction mixture was degassed with argon for three times and stirred for 1 h at 90° C. The resulting mixture was concentrated under reduced pressure. The residue was purified by Prep-HPLC with the following conditions: Column: Atlantis Prep T3 OBD Column, 19×250 mm 10 u; Mobile Phase A: Water (0.1% FA), Mobile Phase B: ACN; Flow rate: 20 mL/min; Gradient: 25 B to 55 B in 6 min; 210/254 nm. The fractions contained desired product were combined and concentrated to afford 1-((3S, 5R)-1-acryloyl-5-(methoxymethyl)pyrrolidin-3-yl)-5-(methylamino)-3-((3-methylquinoxalin-6-yl)ethynyl)-1H-pyrazole-4-carboxamide (52.2 mg, 23%) as a yellow solid. MS ESI calculated for $C_{25}H_{27}N_7O_3$ $[M+H]^+$, 474.22, found 474.20; $^1$H NMR (400 MHz, DMSO-$d_6$) δ 8.89 (s, 1H), 8.21 (s, 1H), 8.10 (d, J=8.6 Hz, 1H), 7.89-7.86 (m, 1H), 7.34 (s, 1H), 7.06-6.36 (m, 2H), 6.20-6.14 (m, 1H), 5.78-5.65 (m, 1H), 5.28-5.18 (m, 1H), 4.64-4.25 (m, 1H), 4.12-3.67 (m, 2H), 3.64-3.41 (m, 2H), 3.30 (s, 4H), 2.98-2.92 (m, 3H), 2.72 (s, 2H), 2.54 (s, 1H), 2.31-2.28 (m, 1H).

Example 73: 3-[2-[3-(Difluoromethyl)-1,3-benzodi-azol-5-yl]ethynyl]-1-[(3S,5R)-5-(methoxymethyl)-1-(prop-2-enoyl)pyrrolidin-3-yl]-5-(methylamino) pyrazole-4-carboxamide

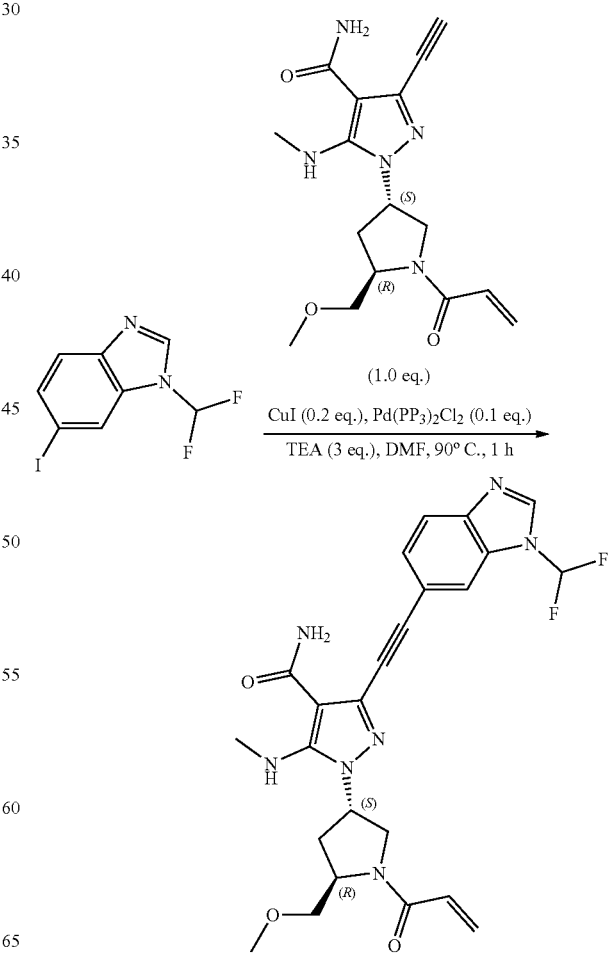

465

To a stirred mixture of 1-(difluoromethyl)-6-iodo-1,3-benzodiazole (0.13 g, 0.45 mmol), 3-ethynyl-1-[(3S,5R)-5-(methoxymethyl)-1-(prop-2-enoyl)pyrrolidin-3-yl]-5-(methylamino)pyrazole-4-carboxamide (0.15 g, 0.45 mmol), Pd(PPh$_3$)$_2$Cl$_2$ (31.77 mg, 0.05 mmol) and CuI (17.24 mg, 0.09 mmol) in DMF (2.00 mL) was added TEA (0.14 g, 1.36 mmol) at room temperature. The reaction mixture was degassed with argon for three times and stirred for 1 h at 90° C. The resulting mixture was concentrated under reduced pressure. The residue was purified by silica gel Column chromatography, eluted with CH$_2$Cl$_2$/MeOH (10/1). The fractions contained desired product were combined and concentrated. The residue was purified by reverse flash chromatography with the following conditions: Column, C18 silica gel; mobile phase, ACN in water, 5% to 70% gradient in 30 min; detector, UV 254 nm. The fractions contained desired product were combined and concentrated to afford 3-[2-[3-(difluoromethyl)-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide (88.3 mg) as an off-white solid. MS ESI calculated for C$_{24}$H$_{25}$F$_2$N$_7$O$_3$ [M+H]$^+$, 498.51, found 498.20; $^1$H NMR (400 MHz, DMSO-d$_6$) δ 8.73 (s, 1H), 8.30-7.94 (m, 2H), 7.84 (d, J=8.4 Hz, 1H), 7.56 (dd, J=8.4, 1.5 Hz, 1H), 7.36 (s, 1H), 6.85 (s, 1H), 6.77-6.49 (m, 2H), 6.19-6.15 (m, 1H), 5.71-5.68 (m, 1H), 5.25-5.23 (m, 1H), 4.57-4.37 (m, 1H), 4.08-3.67 (m, 2H), 3.61-3.41 (m, 2H), 3.30 (d, J=5.3 Hz, 3H), 2.94 (t, J=5.2 Hz, 3H), 2.66-2.41 (m, 1H), 2.33-2.98 (m, 1H).

Example 74: 1-[(3S,5R)-5-(Methoxymethyl)-1-(prop-2-enoyl)pyrrolidin-3-yl]-5-(methylamino)-3-[2-(4-methylquinolin-7-yl)ethynyl]pyrazole-4-carboxamide

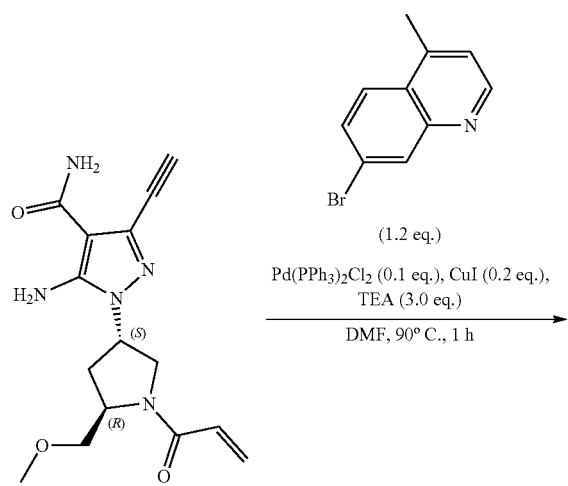

Pd(PPh$_3$)$_2$Cl$_2$ (0.1 eq.), CuI (0.2 eq.), TEA (3.0 eq.)
DMF, 90° C., 1 h

466
-continued

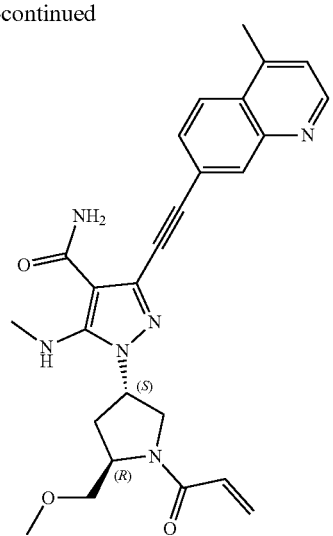

To a stirred mixture of 3-ethynyl-1-[(3S,5R)-5-(methoxymethyl)-1-(prop-2-enoyl)pyrrolidin-3-yl]-5-(methylamino)pyrazole-4-carboxamide (0.20 g, 0.60 mmol), 7-bromo-4-methylquinoline (0.16 g, 0.72 mmol), Pd(PPh$_3$)$_2$Cl$_2$ (42.36 mg, 0.06 mmol) and CuI (22.99 mg, 0.12 mmol) in DMF (2.00 mL) was added TEA (0.25 mL, 2.49 mmol). The reaction mixture was degassed with argon for three times and stirred for 1 h at 90° C. The resulting mixture was diluted with water (20 mL), extracted with EA (3×20 mL). The combined organic layers were washed with brine (3×20 mL), dried over anhydrous Na$_2$SO$_4$ and filtered. The filtrate was concentrated under reduced pressure. The residue was purified by silica gel Column chromatography, eluted with 6% MeOH in DCM. The fractions contained desired product were combined and concentrated. The residue was purified by Prep-HPLC with the following conditions: Column: SunFire Prep C18 OBD Column, 19×150 mm 5 μm 10 nm; Mobile Phase A: Water (0.05% TFA), Mobile Phase B: ACN; Flow rate: 20 mL/min; Gradient: 35 B to 60 B in 6 min; 210/254 nm; RT: 5.57 min. The fractions contained desired product were combined and concentrated to afford 1-[(3S,5R)-5-(methoxymethyl)-1-(prop-2-enoyl)pyrrolidin-3-yl]-5-(methylamino)-3-[2-(4-methylquinolin-7-yl)ethynyl]pyrazole-4-carboxamide (41.8 mg, 14%) as an off-white solid. MS ESI calculated for C$_{26}$H$_{28}$N$_6$O$_3$ [M+H]$^+$, 473.22, found 473.30; $^1$H NMR (400 MHz, DMSO-d$_6$): δ 8.82 (d, J=4.4 Hz, 1H), 8.26-8.07 (m, 2H), 7.74 (dd, J=8.6, 1.7 Hz, 1H), 7.44 (d, J=4.4 Hz, 2H), 6.91 (s, 1H), 6.78-6.47 (m, 2H), 6.19-6.15 (m, 1H), 5.72-5.68 (m, 1H), 5.26-5.24 (m, 1H), 4.50-4.45 (m, 1H), 4.08-3.68 (m, 2H), 3.64-3.40 (m, 2H), 3.31 (d, J=5.3 Hz, 3H), 2.95 (t, J=5.2 Hz, 3H), 2.75-2.54 (m, 4H), 2.35-2.25 (m, 1H).

Example 75: 1-[(3S,5R)-5-(Methoxymethyl)-1-(prop-2-enoyl)pyrrolidin-3-yl]-5-(methylamino)-3-(2-[3-methylimidazo[1,2-a]pyridin-7-yl] ethynyl) pyrazole-4-carboxamide

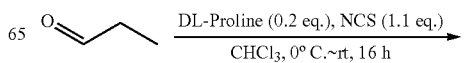

DL-Proline (0.2 eq.), NCS (1.1 eq.)
CHCl$_3$, 0° C.~rt, 16 h

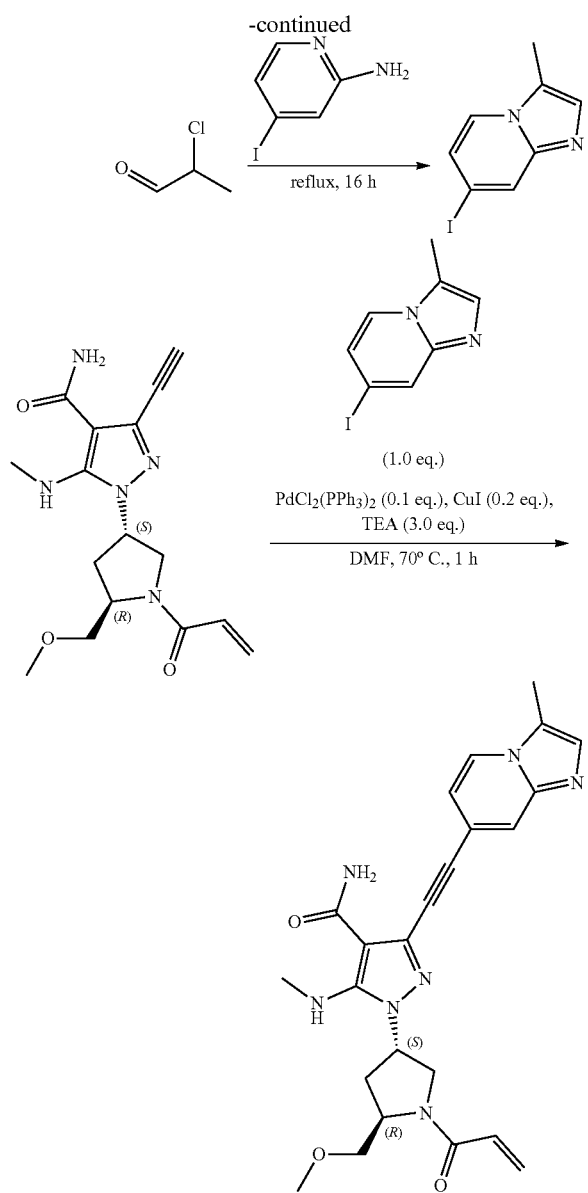

tions contained desired product were combined and concentrated to afford 7-iodo-3-methylimidazo[1,2-a]pyridine (80 mg, 1.43%) as a light yellow solid. MS ESI calculated for $C_8H_7IN_2$ [M+H]$^+$, 258.97, found 259.05; $^1$H NMR (400 MHz, CDCl$_3$) δ 8.04 (s, 1H), 7.65 (d, J=7.1 Hz, 1H), 7.38 (s, 1H), 7.10-7.07 (m, 1H), 2.47 (s, 3H)

Step 3: 1-[(3S,5R)-5-(Methoxymethyl)-1-(prop-2-enoyl) pyrrolidin-3-yl]-5-(methylamino)-3-(2-[3-methylimidazo[1,2-a] pyridin-7-yl] ethynyl)pyrazole-4-carboxamide To a stirred mixture of 7-iodo-3-methylimidazo[1,2-a] pyridine (0.10 g, 0.39 mmol), 3-ethynyl-1-[(3S,5R)-5-(methoxymethyl)-1-(prop-2-enoyl) pyrrolidin-3-yl]-5-(methylamino) pyrazole-4-carboxamide (0.13 g, 0.39 mmol), CuI (14.76 mg, 0.08 mmol) and Pd(PPh$_3$)$_2$Cl$_2$ (27.20 mg, 0.04 mmol) in DMF (2.00 mL) was added TEA (23.53 mg, 0.23 mmol). The reaction mixture was degassed with argon for three times and stirred for 1 h at 70° C. The resulting mixture was diluted with water (20 mL) and extracted with EA (3×20 mL). The combined organic layers were washed with brine (3×20 mL), dried over anhydrous Na$_2$SO$_4$ and filtered. The filtrate was concentrated under reduced pressure. The residue was purified by reverse phase chromatography with the following conditions: Column: Spherical C18, 20-40 μm, 40 g; Mobile Phase A: Water (10 mmol/L NH$_4$HCO$_3$), Mobile Phase B: ACN; Flow rate: 40 mL/min; Gradient: 5%-40% within 30 min, Detector: UV 254/220 nm; RT: 30 min. The fractions contained desired product were combined and concentrated to afford 1-[(3S,5R)-5-(methoxymethyl)-1-(prop-2-enoyl) pyrrolidin-3-yl]-5-(methylamino)-3-(2-[3-methylimidazo[1,2-a] pyridin-7-yl] ethynyl) pyrazole-4-carboxamide (67.4 mg, 37%) as an off-white solid. MS ESI calculated for $C_{24}H_{27}N_7O_3$ [M+H]$^+$, 462.22, found 462.15; $^1$H NMR (400 MHz, DMSO-d$_6$) δ 8.38 (s, 1H), 7.69-7.29 (m, 3H), 7.03 (d, J=7.0 Hz, 1H), 6.90-6.48 (m, 3H), 6.28-6.17 (m, 1H), 5.79-5.61 (m, 1H), 5.35-5.12 (m, 1H), 4.52-4.35 (m, 1H), 4.11-3.68 (m, 2H), 3.62-3.42 (m, 2H), 3.31 (s, 3H), 2.94 (t, J=5.2 Hz, 3H), 2.68-2.55 (m, 1H), 2.52-2.48 (m, 3H), 2.36-2.21 (m, 1H).

Example 76: 3-[2-[3-(Difluoromethyl)-6-fluoro-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide Step 1: 2-Chloropropanal To a stirred solution of propionaldehyde (2.50 g, 43.04 mmol) in CHCl$_3$ (25.00 mL) were added NCS (6.32 g, 47.35 mmol) and DL-Camphor sulfonic acid (2.00 g, 8.61 mmol) at 0° C. The reaction mixture was stirred for 16 h at room temperature. The precipitated solids were collected by filtration and washed with acetone (50 mL). The crude product 2-chloropropanal (0.85 g) was dried and used in the next step directly without further purification.

Step 2: 7-Iodo-3-methylimidazo[1,2-a]pyridine

To a stirred solution of 2-chloropropanal (0.85 g, crude) in acetone (50.00 mL) and CHCl$_3$ (25.00 mL) was added 4-iodopyridin-2-amine (2.02 g, 9.19 mmol). The reaction mixture was stirred for 16 h at 70° C. under air atmosphere. The resulting mixture was concentrated under reduced pressure. The residue was purified by silica gel Column chromatography, eluted with CH$_2$Cl$_2$/MeOH (10/1). The frac-

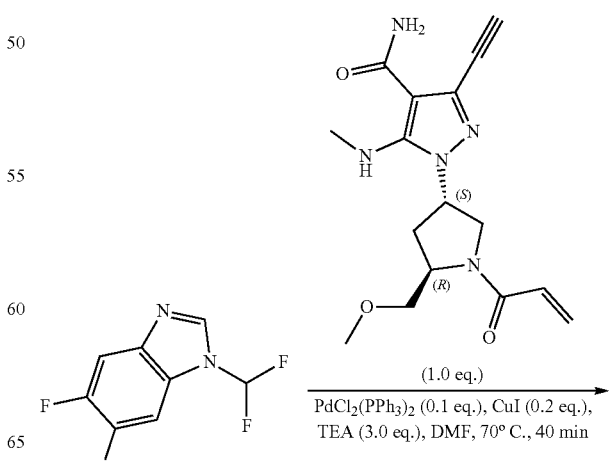

469
-continued

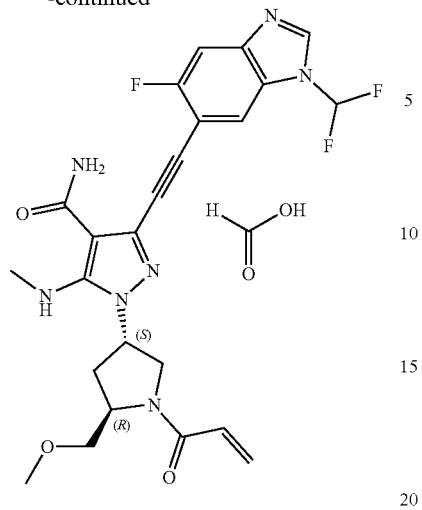

To a stirred solution of 1-(difluoromethyl)-5-fluoro-6-iodo-1,3-benzodiazole (0.10 g, 0.32 mmol), 3-ethynyl-1-[(3S,5R)-5-(methoxymethyl)-1-(prop-2-enoyl)pyrrolidin-3-yl]-5-(methylamino)pyrazole-4-carboxamide (0.11 g, 0.32 mmol), Pd(PPh$_3$)$_2$Cl$_2$ (22.49 mg, 0.03 mmol) and CuI (12.21 mg, 0.06 mmol) in DMF (4.00 mL) was added TEA (0.97 g, 0.96 mmol) dropwise at room temperature. The reaction mixture was degassed with argon for three times and stirred for 40 min at 70° C. The resulting mixture was cooled down and concentrated under reduced pressure. The residue was purified by silica gel Column chromatography, eluted with MeOH in DCM (0-5%) to afford the crude product. Then the crude product was purified by Prep-HPLC with the following conditions: Column: Sun-Fire Prep C18 OBD Column, 19×150 mm 5 µm 10 nm; Mobile Phase A: Water (0.1% FA), Mobile Phase B: ACN; Flow rate: 20 mL/min; Gradient: 30 B to 60 B in 6 min; 210/254 nm; RT: 5.55 min. The fractions contained desired product were combined and concentrated to afford 3-[2-[3-(difluoromethyl)-6-fluoro-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide; formic acid (0.79 g, 44%) as a white solid. MS ESI calculated for C$_{24}$H$_{24}$F$_3$N$_7$O$_3$ [M+H]$^+$, 516.19, found 516.15; $^1$H NMR (400 MHz, CDCl$_3$) δ 8.31 (s, 1H), 7.91-7.88 (m, 1H), 7.62 (d, J=9.4 Hz, 1H), 7.43 (t, J=60.0 Hz, 1H), 7.08 (brs, 1H), 6.53-6.40 (m, 2H), 5.75-5.72 (m, 1H), 5.57-5.27 (m, 1H), 4.62-4.41 (m, 1H), 4.13-4.02 (m, 2H), 3.92-3.90 (m, 1H), 3.53-3.42 (m, 1H), 3.39 (s, 3H), 3.09-3.03 (m, 4H), 2.75-2.68 (m, 1H), 2.36-2.31 (m, 1H).

Example 77: 3-[2-[1-(Difluoromethyl)-6-fluoro-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide

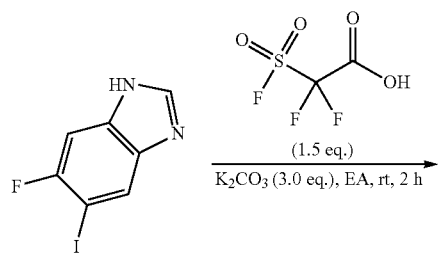

470
-continued

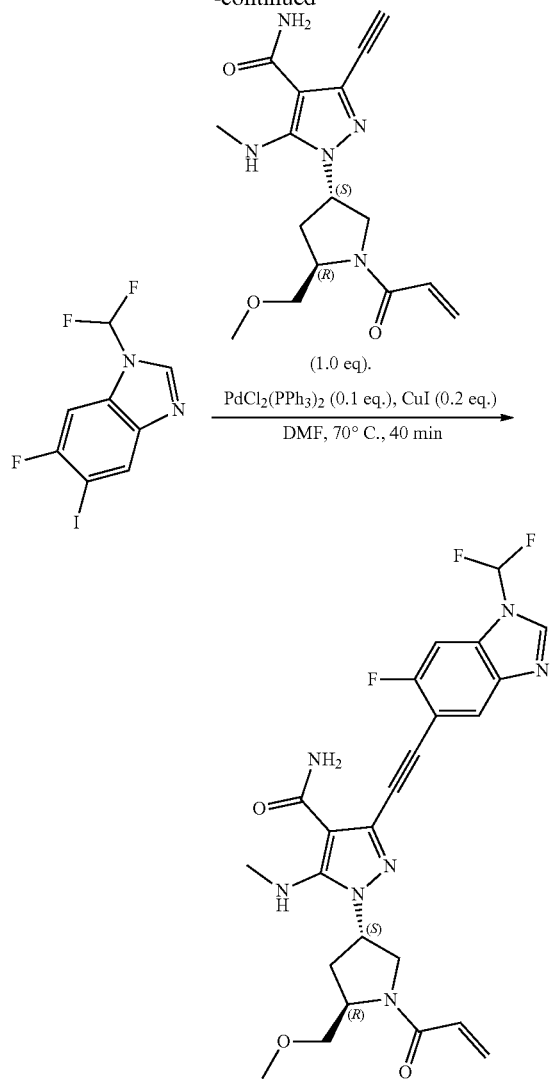

Step 1: 1-(Difluoromethyl)-6-fluoro-5-iodo-1,3-benzodiazole

To a stirred mixture of 5-fluoro-6-iodo-3H-1,3-benzodiazole (30.00 g, 114.49 mmol) and K$_2$CO$_3$ (47.47 g, 343.48 mmol) in EA (300.00 mL) was added 2-(fluorosulfonyl)acetic acid (30.58 g, 171.74 mmol) dropwise at room temperature. The reaction mixture was stirred for 2 h at room temperature. The resulting mixture was concentrated under reduce pressure. The residue was purified by silica gel Column chromatography, eluted with EA in PE (20-80%). The fractions contained desired product were combined and concentrated. The residue was purified by Prep-SFC with the following conditions Column: Chiralpak ig, 5×25 cm, 10 µm; Mobile Phase A: CO$_2$, Mobile Phase B: MeOH (0.1% 2 M NH$_3$-MeOH); Flow rate: 200 mL/min; Gradient: 30% B; 220 nm; RT1: 4.68 min; RT2: 6.32 min; Injection volume: 6 mL; Number of runs: 33. The fractions contained desired product were combined and concentrated to afford 1-(difluoromethyl)-6-fluoro-5-iodo-1,3-benzodiazole (9.9 g, 26%) as a light yellow solid. MS ESI calculated for C$_8$H$_4$F$_3$IN$_2$ [M+H]$^+$, 312.94, found 312.90; $^1$H NMR (400

MHz, CDCl₃) δ 8.24 (d, J=5.5 Hz, 1H), 8.10 (s, 1H), 7.39 (d, J=7.2 Hz, 1H), 7.34 (t, J=60.0 Hz, 1H).

Step 2: 3-[2-[1-(Difluoromethyl)-6-fluoro-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide To a stirred mixture of 1-(difluoromethyl)-6-fluoro-5-iodo-1,3-benzodiazole (2.82 g, 9.05 mmol), 3-ethynyl-1-[(3S,5R)-5-(methoxymethyl)-1-(prop-2-enoyl)pyrrolidin-3-yl]-5-(methylamino)pyrazole-4-carboxamide (3.00 g, 9.05 mmol), Pd(PPh₃)₂Cl₂ (0.64 g, 0.90 mmol) and CuI (0.34 g, 1.81 mmol) in DMF (60.00 mL) was added TEA (2.75 g, 27.16 mmol) dropwise at room temperature. The reaction mixture was degassed with argon for three times and stirred for 40 min at 70° C. The resulting mixture was cooled down and concentrated under reduced pressure. The residue was diluted with water (200 mL) and extracted with EA (3×200 mL). The combined organic layers were washed with brine (3×200 mL), dried over anhydrous Na₂SO₄ and filtered. The filtrate was concentrated under reduced pressure. The residue was purified by silica gel Column chromatography, eluted with MeOH in DCM (0-5%). Then the crude product was purified by Prep-HPLC with the following conditions: Column: Sun-Fire Prep C18 OBD Column, 19×150 mm 5 μm 10 nm; Mobile Phase A: Water (10 mmoL/L NH₄HCO₃), Mobile Phase B: ACN; Flow rate: 100 mL/min; Gradient: 25 B to 40 B in 30 min; 220/254 nm. The fractions contained desired product were combined and concentrated to afford 3-[2-[1-(difluoromethyl)-6-fluoro-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide (1.85 g, 39%) as a white solid. MS ESI calculated for C₂₄H₂₄F₃N₇O₃ [M+H]⁺, 516.19, found 516.10; ¹H NMR (400 MHz, CDCl₃) δ 8.28 (brs, 1H), 8.10 (brs, 1H), 7.47-7.40 (m, 1H), 7.34 (s, 1H), 7.05-6.69 (m, 1H), 6.31-6.33 (m, 2H), 5.73-5.69 (m, 1H), 5.63-5.25 (m, 2H), 4.51-4.42 (m, 1H), 4.23-3.84 (m, 3H), 3.63-3.41 (m, 1H), 3.37 (s, 3H), 3.07-2.98 (m, 4H), 2.76-2.68 (m, 1H), 2.42-2.30 (m, 1H).

Example 78: 3-[2-(1-Cyclopropyl-4,6-difluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide

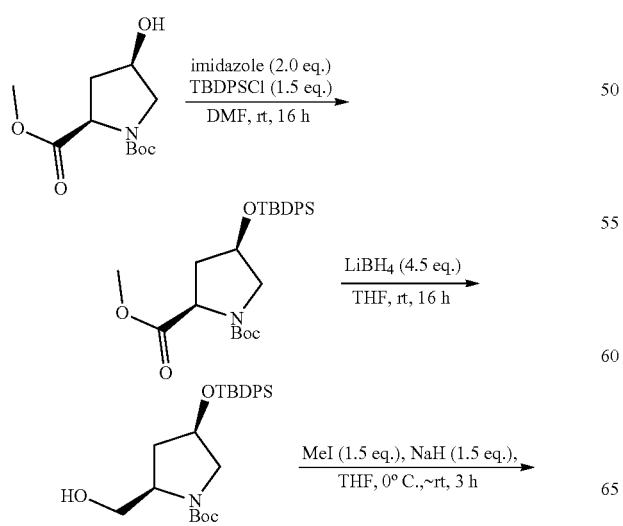

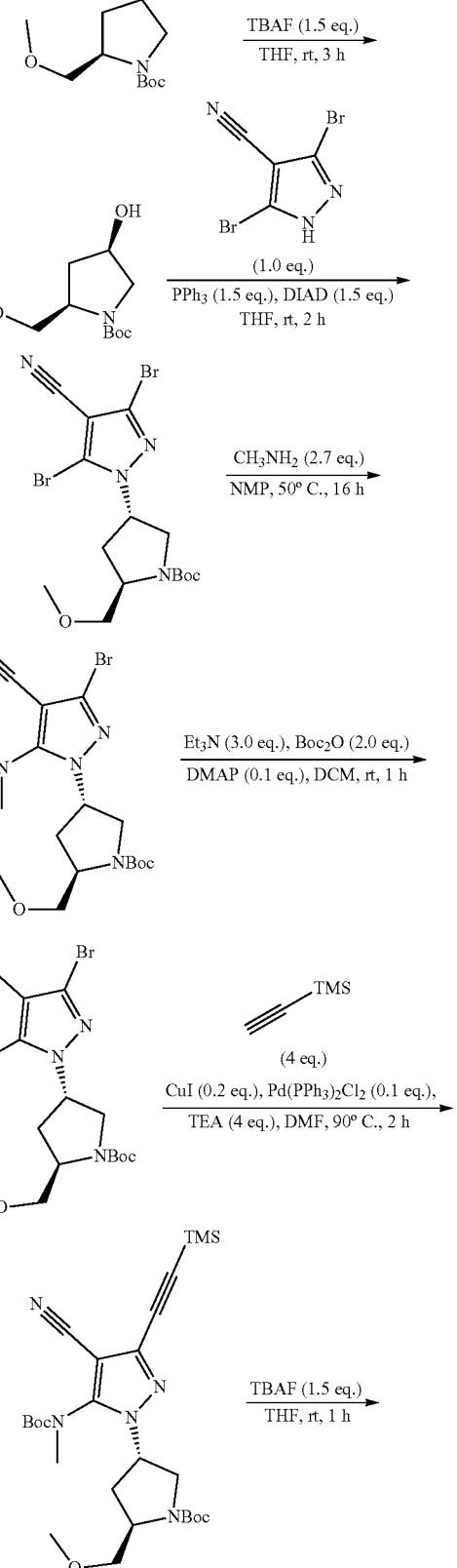

473
-continued
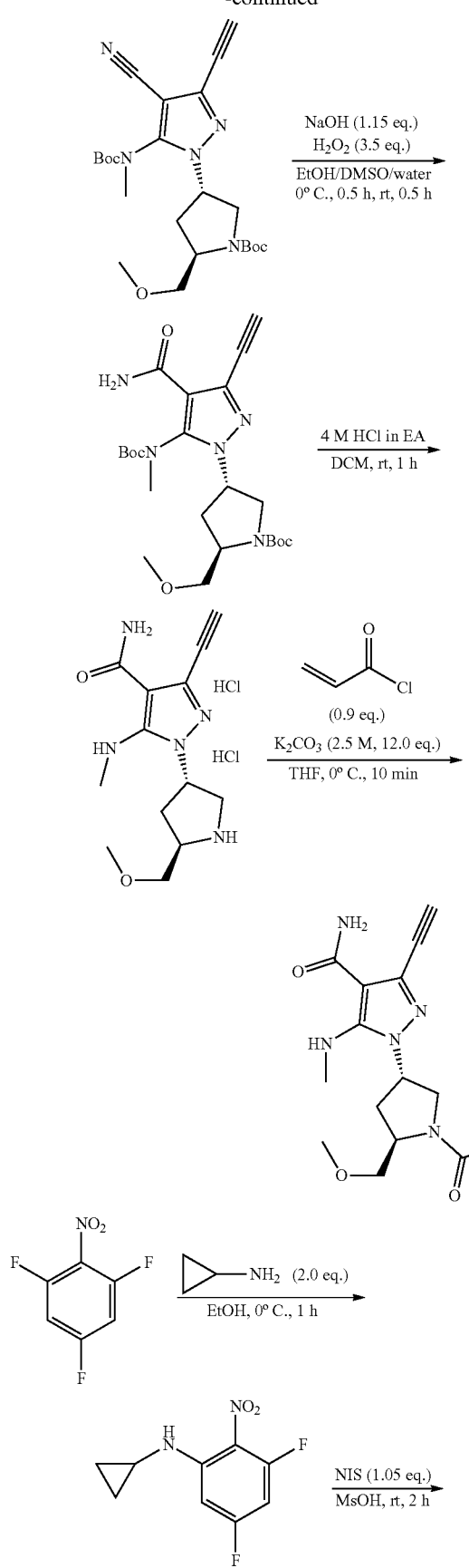
474
-continued
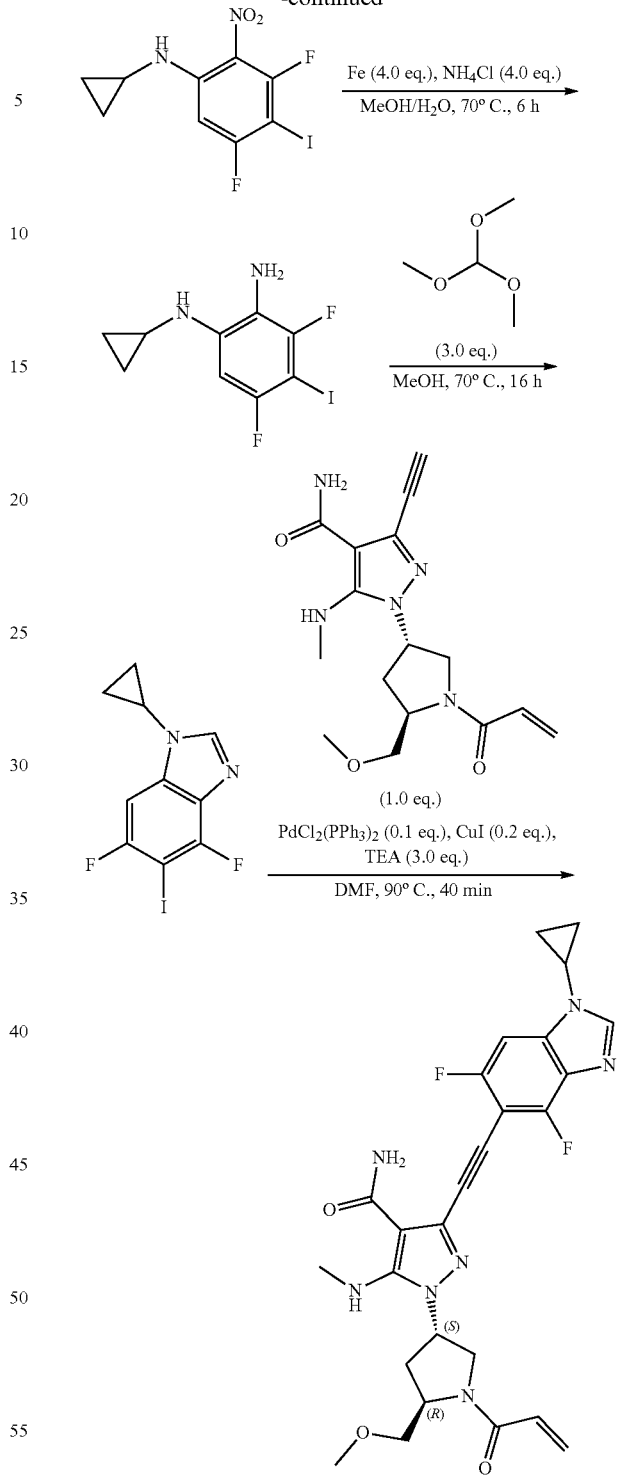
Step 1: 1-(Tert-butyl) 2-methyl (2R,4R)-4-((tert-butyldiphenylsilyl)oxy)pyrrolidine-1,2-dicarboxylate
To a stirred solution of 1-(tert-butyl) 2-methyl (2R,4R)-4-hydroxypyrrolidine-1,2-dicarboxylate (8.00 g, 32.62 mmol) and imidazole (4.44 g, 65.23 mmol) in DMF (80.00 mL) was added tert-butyl(chloro)diphenylsilane (13.45 g, 48.93 mmol) at 0° C. over 30 min. The reaction mixture was stirred for 16 h at room temperature. The resulting mixture was diluted with water (400 mL) and extracted with EA (3×300 mL). The combined organic layers was washed with brine (5×500 mL), dried over anhydrous $Na_2SO_4$ and filtered. The filtrate was concentrated under reduced pressure. The residue was purified by silica gel column chromatography, eluted with PE/EA (6/1). The fractions contained desired product were combined and concentrated to afford 1-(tert-butyl) 2-methyl (2R,4R)-4-((tert-butyldiphenylsilyl)oxy)pyrrolidine-1,2-dicarboxylate (14.20 g, 90%) as a colorless oil. MS ESI calculated for $C_{27}H_{37}NO_5Si$ [M+H]$^+$, 484.24, found 484.25.

Step 2: Tert-butyl (2R,4R)-4-[(tert-butyldiphenylsilyl)oxy]-2-(hydroxymethyl)pyrrolidine-1-carboxylate To a stirred solution of 1-(tert-butyl) 2-methyl (2R,4R)-4-((tert-butyldiphenylsilyl)oxy)pyrrolidine-1,2-dicarboxylate (30.00 g, 62.02 mmol) in THF (300.00 mL) was added $LiBH_4$ (6.08 g, 0.28 mol) in portions at 0° C. under nitrogen atmosphere. The reaction mixture was stirred for 16 h at room temperature under nitrogen atmosphere. The resulting mixture was acidified to pH 5 with HCl (1M) at 0° C. and then basified to pH 8 with saturated $NaHCO_3$ (aq.). The resulting mixture was extracted with EA (4×500 mL). The combined organic layers was dried over anhydrous $Na_2SO_4$ and filtered. The filtrate was concentrated under reduced pressure. The residue was purified by silica gel column chromatography, eluted with PE/EA (5/1). The fractions contained desired product were combined and concentrated to afford tert-butyl (2R,4R)-4-[(tert-butyldiphenylsilyl)oxy]-2-(hydroxymethyl)pyrrolidine-1-carboxylate (24.00 g, 85%) as a light yellow oil. MS ESI calculated for $C_{26}H_{37}NO_4Si$ [M+H]$^+$, 456.25, found 456.30.

Step 3: Tert-butyl (2R,4R)-4-[(tert-butyldiphenylsilyl)oxy]-2-(methoxymethyl)pyrrolidine-1-carboxylate To a suspension of NaH (0.20 g, 8.33 mmol) in THF (18 mL) was added a solution of tert-butyl (2R,4R)-4-[(tert-butyldiphenylsilyl)oxy]-2-(hydroxymethyl)pyrrolidine-1-carboxylate (2.50 g, 5.49 mmol) in THF (64.00 mL) slowly at 0° C. under nitrogen atmosphere. After stirred at 0° C. for 1 h, to the above mixture was added $CH_3I$ (1.17 g, 8.23 mmol) dropwise at 0° C. The reaction mixture was stirred for additional 3 h at room temperature. The resulting mixture was diluted with water (60 mL), and then extracted with EA (3×30 mL). The combined organic layers was dried over anhydrous $Na_2SO_4$ and filtered. The filtrate was concentrated under reduced pressure to afford tert-butyl (2R,4R)-4-[(tert-butyldiphenylsilyl)oxy]-2-(methoxymethyl)pyrrolidine-1-carboxylate (2.30 g, 89%) as a light yellow solid. MS ESI calculated for $C_{27}H_{39}NO_4Si$ [M+H]$^+$, 470.26, found 470.30.

Step 4: Tert-butyl (2R,4R)-4-hydroxy-2-(methoxymethyl)pyrrolidine-1-carboxylate

To a stirred solution of tert-butyl (2R,4R)-4-[(tert-butyldiphenylsilyl)oxy]-2-(methoxymethyl)pyrrolidine-1-carboxylate (46.30 g, 98.57 mmol) in THF (375.00 mL) was added tetra-n-butylammonium fluoride (1 M in THF) (146.70 mL, 0.14 mol) at 0° C. The reaction mixture was stirred at room temperature for 3 h. The resulting mixture was diluted with water (1 L) and extracted with EA (3×500 mL). The combined organic layers was dried over anhydrous $Na_2SO_4$ and filtered. The filtrate was concentrated under reduced pressure. The residue was purified by silica gel column chromatography, eluted with PE/EA (3/1). The fractions contained desired product were combined and concentrated to afford tert-butyl (2R,4R)-4-hydroxy-2-(methoxymethyl)pyrrolidine-1-carboxylate (16.60 g, 73%) as a light yellow oil. MS ESI calculated for $C_{11}H_{21}NO_4$ [M+H]$^+$, 232.15, found 232.20.

Step 5: Tert-butyl (2R)-4-(3,5-dibromo-4-cyanopyrazol-1-yl)-2-(methoxymethyl)pyrrolidine-1-carboxylate To a stirred solution of 3,5-dibromo-1H-pyrazole-4-carbonitrile (2.00 g, 7.97 mmol), tert-butyl (2R,4R)-4-hydroxy-2-(methoxymethyl)pyrrolidine-1-carboxylate (1.84 g, 7.97 mmol) and triphenylphosphine (3.14 g, 11.95 mmol) in THF (40.00 mL) was added diisopropyl azodicarboxylate (2.42 g, 11.95 mmol) dropwise at 0° C. under argon atmosphere. The reaction mixture was stirred for 2 h at room temperature. The resulting mixture was diluted with water (300 mL). The resulting mixture was extracted with EtOAc (3×200 mL). The combined organic layers was dried over anhydrous $Na_2SO_4$ and filtered. The filtrate was concentrated under reduced pressure. The residue was purified by silica gel column chromatography, eluted with PE/EtOAc (5/1). The fractions contained desired product were combined and concentrated to afford tert-butyl (2R)-4-(3,5-dibromo-4-cyanopyrazol-1-yl)-2-(methoxymethyl)pyrrolidine-1-carboxylate (3.50 g, 94%) as a dark yellow solid. MS ESI calculated for $C_{15}H_{20}Br_2N_4O_3$ [M+H−100]$^+$, 361.99, 363.99, 365.99; found 362.10, 364.10, 366.10.

Step 6: Tert-butyl (2S,4R)-4-[3-bromo-4-cyano-5-(methylamino)pyrazol-1-yl]-2-(methoxymethyl)pyrrolidine-1-carboxylate To a stirred solution of tert-butyl (2R)-4-(3,5-dibromo-4-cyanopyrazol-1-yl)-2-(methoxymethyl)pyrrolidine-1-carboxylate (1.00 g, 2.15 mmol) in NMP (10.00 mL) was added $CH_3NH_2$ (2.98 mL, 5.96 mmol) at room temperature under nitrogen atmosphere. The reaction mixture was stirred for 16 h at 50° C. under nitrogen atmosphere. The resulting mixture was diluted with water (30 mL) and extracted with EA (3×50 mL). The combined organic layers was washed with brine (3×20 mL), dried over anhydrous $Na_2SO_4$. After filtration, the filtrate was concentrated under reduced pressure. The residue was purified by silica gel column chromatography, eluted with PE/EA (3/1). The fractions contained desired product were combined and concentrated to afford tert-butyl (2S,4R)-4-[3-bromo-4-cyano-5-(methylamino)pyrazol-1-yl]-2-(methoxymethyl)pyrrolidine-1-carboxylate (0.67 g, 35%) as an off-white solid. MS ESI calculated for $C_{16}H_{24}BrN_5O_3$ [M+H−100]$^+$, 314.11, 316.11, found 314.10, 316.10.

Step 7: (2R,4S)-4-[3-bromo-5-[(tert-butoxycarbonyl)(methyl)amino]-4-cyanopyrazol-1-yl]-2-(methoxymethyl)pyrrolidine-1-carboxylate To a stirred solution of tert-butyl (2R,4S)-4-[3-bromo-4-cyano-5-(methylamino)pyrazol-1-yl]-2-(methoxymethyl) pyrrolidine-1-carboxylate (20.30 g, 49.00 mmol) in DCM (300.00 mL) were added $Boc_2O$ (20.97 mL, 98.01 mmol), DMAP (0.60 g, 4.90 mmol) and $Et_3N$ (20.43 mL, 0.14 mol) at 0° C. under nitrogen atmosphere. The reaction mixture was stirred for 1 h at room temperature. The resulting mixture was diluted with water (3×200 mL) and extracted with DCM (3×200 mL). The combined organic layers was washed with brine (3×100 mL). The organic layer was dried over anhydrous $Na_2SO_4$ and filtered. The filtrate was concentrated under reduced pressure. The residue was purified by silica gel column chromatography, eluted with PE/EA (1/1). The fractions contained desired product were combined and concentrated to afford (2R,4S)-4-[3-bromo-5-[(tert-butoxycarbonyl)(methyl)amino]-4-cyanopyrazol-1-yl]-2-(methoxymethyl)pyrrolidine-1-carboxylate (24.00 g, 95%) as an off-white solid. MS ESI calculated for $C_{21}H_{32}BrN_5O_5$ $[M+H]^+$, 514.16, 516.16, found 514.15, 516.15; $^1$H NMR (400 MHz, $CDCl_3$) δ 4.94-4.90 (m, 1H), 4.23-4.19 (m, 1H), 3.75-3.66 (m, 3H), 3.44-3.40 (m, 1H), 3.36 (s, 3H), 3.25 (s, 3H), 2.62-2.58 (m, 1H), 2.41-2.19 (m, 1H), 1.48 (s, 18H).

Step 8: Tert-butyl (2R,4S)-4-[5-[(tert-butoxycarbonyl)(methyl)amino]-4-cyano-3-[2-(trimethylsilyl)ethynyl]pyrazol-1-yl]-2-(methoxymethyl)pyrrolidine-1-carboxylate To a stirred mixture of (2R,4S)-4-[3-bromo-5-[(tert-butoxycarbonyl)(methyl)amino]-4-cyanopyrazol-1-yl]-2-(methoxymethyl)pyrrolidine-1-carboxylate (24.00 g, 46.65 mmol), CuI (1.78 g, 9.33 mmol), $Pd(PPh_3)_2Cl_2$ (3.27 g, 4.67 mmol) and trimethylsilylacetylene (19.78 mL, 0.20 mol) in DMF (240.00 mL) was added TEA (19.45 mL, 0.19 mol). The reaction mixture was degassed with nitrogen for three times and stirred for 2 h at 90° C. The resulting mixture was concentrated under reduced pressure. The residue was diluted with water (500 mL) and extracted with EA (4×500 mL). The combined organic layers was washed with brine (2×500 mL), dried over anhydrous $Na_2SO_4$, filtered and the filtrate was concentrated under reduced pressure. The residue was purified by silica gel column chromatography, eluted with PE/EA (2/1). The fractions contained desired product were combined and concentrated to afford tert-butyl (2R,4S)-4-[5-[(tert-butoxycarbonyl)(methyl)amino]-4-cyano-3-[2-(trimethylsilyl)ethynyl]pyrazol-1-yl]-2-(methoxymethyl)pyrrolidine-1-carboxylate (24.00 g, 96%) as a brown solid. MS ESI calculated for $C_{26}H_{41}N_5O_5Si$ $[M+H]^+$, 532.29, found 532.40; $^1$H NMR (400 MHz, $CDCl_3$) δ 4.93-4.89 (m, 1H), 4.23-4.17 (m, 1H), 3.68-3.52 (m, 3H), 3.42-3.37 (m, 1H), 3.35-3.33 (m, 3H), 3.25-3.20 (m, 3H), 2.63-2.58 (m, 1H), 2.33-2.13 (m, 1H), 1.46 (s, 18H), 0.27 (s, 9H).

Step 9: Tert-butyl (2R,4S)-4-[5-[(tert-butoxycarbonyl)(methyl)amino]-4-cyano-3-ethynylpyrazol-1-yl]-2-(methoxymethyl)pyrrolidine-1-carboxylate To a stirred solution of tert-butyl (2R,4S)-4-[5-[(tert-butoxycarbonyl)(methyl)amino]-4-cyano-3-[2-(trimethylsilyl)ethynyl]pyrazol-1-yl]-2-(methoxymethyl)pyrrolidine-1-carboxylate (24.00 g, 45.14 mmol) in THF (200.00 mL) was added TBAF (67.70 mL, 67.70 mmol, 1 M in THF) at 0° C. The reaction mixture was stirred for 1 h at room temperature. The resulting mixture was concentrated under reduced pressure. The residue was diluted with water (500 mL) and extracted with EA (3×500 mL). The combined organic layers was washed with brine (2×500 mL), dried over anhydrous $Na_2SO_4$, filtered and concentrated under reduced pressure. The residue was purified by silica gel column chromatography, eluted with PE/EA (2/1). The fractions contained desired product were combined and concentrated to afford tert-butyl (2R,4S)-4-[5-[(tert-butoxycarbonyl)(methyl)amino]-4-cyano-3-ethynylpyrazol-1-yl]-2-(methoxymethyl)pyrrolidine-1-carboxylate (17.40 g, 83%) as an off-white solid. MS ESI calculated for $C_{23}H_{33}N_5O_5$ $[M+H]^+$, 460.25, found 460.40; $^1$H NMR (400 MHz, $CDCl_3$) δ 4.93-4.89 (m, 1H), 4.22-4.18 (m, 1H), 3.84-3.46 (m, 3H), 3.42-3.37 (m, 1H), 3.37-3.31 (m, 4H), 3.24 (s, 3H), 2.62-2.59 (m, 1H), 2.28-2.24 (m, 1H), 1.46 (s, 18H).

Step 10: Tert-butyl (2R,4S)-4-[5-[(tert-butoxycarbonyl)(methyl)amino]-4-carbamoyl-3-ethynylpyrazol-1-yl]-2-(methoxymethyl)pyrrolidine-1-carboxylate To a stirred solution of tert-butyl (2R,4S)-4-[5-[(tert-butoxycarbonyl)(methyl)amino]-4-cyano-3-ethynylpyrazol-1-yl]-2-(methoxymethyl)pyrrolidine-1-carboxylate (17.40 g, 37.86 mmol) in DMSO (30.00 mL) and EtOH (150.00 mL) were added 0.5 M NaOH (87.09 mL, 43.54 mmol) and $H_2O_2$ (10.26 mL, 0.13 mol) at 0° C. The reaction mixture was stirred for 0.5 h at 0° C. Then the reaction mixture was warmed up to room temperature and stirred for another 0.5 h at room temperature. The resulting mixture was diluted with water (500 mL) and extracted with EA (3×500 mL). The combined organic layers was washed with brine (2×300 mL), dried over anhydrous $Na_2SO_4$, filtered and concentrated under reduced pressure. The residue was purified by silica gel column chromatography, eluted with PE/EA (1/2). The fractions contained desired product were combined and concentrated to afford tert-butyl (2R,4S)-4-[5-[(tert-butoxycarbonyl)(methyl)amino]-4-carbamoyl-3-ethynylpyrazol-1-yl]-2-(methoxymethyl)pyrrolidine-1-carboxylate (17.20 g, 95%) as an off-white solid. MS ESI calculated for $C_{23}H_{35}N_5O_6$ $[M+H]^+$, 478.26, found 478.25; $^1$H NMR (300 MHz, $CDCl_3$) 6.80-6.74 (m, 1H), 5.69-5.62 (m, 1H), 5.04-5.00 (m, 1H), 4.23-4.19 (m, 1H), 3.75-3.67 (m, 3H), 3.49-3.42 (m, 1H), 3.39-3.32 (m, 3H), 3.14 (s, 3H), 2.72-2.60 (m, 1H), 2.32-2.21 (m, 1H), 1.62-1.31 (m, 18H).

Step 11: 3-Ethynyl-1-[(3S,5R)-5-(methoxymethyl)pyrrolidin-3-yl]-5-(methylamino)pyrazole-4-carboxamide dihydrochloride To a stirred mixture of tert-butyl (2R,4S)-4-[5-[(tert-butoxycarbonyl)(methyl)amino]-4-carbamoyl-3-ethynylpyrazol-1-yl]-2-(methoxymethyl)pyrrolidine-1-carboxylate (17.20 g, 36.02 mmol) in DCM (170.00 mL) was added HCl (180.08 mL, 0.72 mol, 4 M in EA). The reaction mixture was stirred for 1 h at room temperature under argon atmosphere. The resulting mixture was concentrated and dried to afford 3-ethynyl-1-[(3S,5R)-5-(methoxymethyl)pyrrolidin-3-yl]-5-(methylamino)pyrazole-4-carboxamide dihydrochloride (12.50 g, crude) as an off-white solid which was used in the next step directly without further purification. MS ESI calculated for $C_{13}H_{21}Cl_2N_5O_2$ $[M+H-2HCl]^+$, 278.15, found 278.05.

Step 12: 3-Ethynyl-1-[(3S,5R)-5-(methoxymethyl)-1-(prop-2-enoyl)pyrrolidin-3-yl]-5-(methylamino)pyrazole-4-carboxamide To a stirred mixture of 3-ethynyl-1-[(3S,5R)-5-(methoxymethyl)pyrrolidin-3-yl]-5-(methylamino)pyrazole-4-carboxamide dihydrochloride (12.50 g, 35.69 mmol) and $K_2CO_3$ (172 mL, 0.43 mol, 2.5 M) in THF (250.00 mL) was added acryloyl chloride (2.89 g, 32.15 mmol) dropwise at 0° C. under argon atmosphere. The reaction mixture was stirred for 10 min at 0° C. The resulting mixture was diluted with water (500 mL) and extracted with EA (3×500 mL). The combined organic layers was washed with brine (2×300 mL), dried over anhydrous $Na_2SO_4$, filtered and concentrated under reduced pressure. The residue was purified by silica gel column chromatography, eluted with DCM/MeOH (10/1). The fractions contained desired product were combined and concentrated to afford 3-ethynyl-1-[(3S,5R)-5-(methoxymethyl)-1-(prop-2-enoyl)pyrrolidin-3-yl]-5-(methylamino)pyrazole-4-carboxamide (11.10 g, 84%) as an off-white solid. MS ESI calculated for $C_{16}H_{21}N_5O_3$ [M+H]$^+$, 332.16, found 332.20; $^1$H NMR (400 MHz, CDCl$_3$) δ 6.76 (s, 1H), 6.60-6.36 (m, 2H), 5.74-5.68 (m, 1H), 5.50-5.20 (m, 2H), 4.55-4.39 (m, 1H), 4.06-3.83 (m, 3H), 3.53-3.40 (m, 2H), 3.36-3.35 (m, 3H), 3.03-2.99 (m, 3H), 2.68-2.60 (m, 1H), 2.37-2.23 (m, 1H).

Step 13: N-cyclopropyl-3,5-difluoro-2-nitroaniline

To a stirred solution of 1,3,5-trifluoro-2-nitrobenzene (4.50 g, 25.41 mmol) in EtOH (45.00 mL) was added aminocyclopropane (2.90 g, 50.82 mmol) dropwise at 0° C. under nitrogen atmosphere. The reaction mixture was stirred for 1 h at 0° C. The resulting mixture was diluted with water (100 mL) and extracted with EA (3×100 mL). The combined organic layers was washed with brine (2×50 mL), dried over anhydrous $Na_2SO_4$ and filtered. The filtrate was concentrated under reduced pressure. The residue was purified by silica gel column chromatography, eluted with PE/EA (2/1). The fractions contained desired product were combined and concentrated to afford N-cyclopropyl-3,5-difluoro-2-nitroaniline (4.11 g, 85%) as a yellow solid. $^1$H NMR (400 MHz, CDCl$_3$) δ 7.64 (s, 1H), 6.80-6.74 (m, 1H), 6.30-6.27 (m, 1H), 2.59-2.54 (m, 1H), 1.01-0.83 (m, 2H), 0.76-0.61 (m, 2H).

Step 14: N-cyclopropyl-3,5-difluoro-4-iodo-2-nitroaniline

To a stirred mixture of N-cyclopropyl-3,5-difluoro-2-nitroaniline (4.11 g, 19.19 mmol) in methanesulfonic acid (45.00 mL) was added NIS (4.53 g, 20.15 mmol) in portions at 0° C. The reaction mixture was stirred for 2 h at room temperature. The resulting mixture was quenched with ice/water (100 mL) at 0° C. The resulting mixture was basified to pH 8 with sat. NaOH and extracted with EA (3×100 mL). The combined organic layers was washed with brine (3×100 mL), dried over anhydrous $Na_2SO_4$ and filtered. The filtrate was concentrated under reduced pressure. The residue was purified by silica gel column chromatography, eluted with PE/EA (1/1). The fractions contained desired product were combined and concentrated to afford N-cyclopropyl-3,5-difluoro-4-iodo-2-nitroaniline (4.50 g, 69%) a yellow solid. $^1$H NMR (400 MHz, CDCl$_3$) δ 7.53 (s, 1H), 6.90-6.88 (m, 1H), 2.57-2.54 (m, 1H), 1.07-0.85 (m, 2H), 0.83-0.58 (m, 2H).

Step 15: N1-cyclopropyl-3,5-difluoro-4-iodobenzene-1,2-diamine

To a stirred mixture of N-cyclopropyl-3,5-difluoro-4-iodo-2-nitroaniline (4.40 g, 12.94 mmol) and $NH_4Cl$ (2.77 g, 51.76 mmol) in EtOH (44.00 mL) and $H_2O$ (8.80 mL) was added Fe (2.89 g, 51.76 mmol). The reaction mixture was stirred at 70° C. for 6 h. The resulting mixture was diluted with water (150 mL) and extracted with EA (3×100 mL). The combined organic layers was washed with brine (2×50 mL), dried over anhydrous $Na_2SO_4$ and filtered. The filtrate was concentrated under reduced pressure to afford $N^1$-cyclopropyl-3,5-difluoro-4-iodobenzene-1,2-diamine (3.30 g, crude) as a brown oil which was used in the next step directly without further purification. MS ESI calculated for $C_9H_9F_2IN_2$ [M+H]$^+$, 310.98, found 311.00; $^1$H NMR (300 MHz, CDCl$_3$) δ 6.68-6.61 (m, 1H), 2.50-2.41 (m, 1H), 0.89-0.73 (m, 2H), 0.78-0.51 (m, 2H).

Step 16: 1-Cyclopropyl-4,6-difluoro-5-iodo-1,3-benzodiazole

To a stirred solution of $N^1$-cyclopropyl-3,5-difluoro-4-iodobenzene-1,2-diamine (3.30 g, 10.64 mmol) in MeOH (33.00 mL) was added trimethyl orthoformate (3.39 g, 31.92 mmol) at room temperature under nitrogen atmosphere. The reaction mixture was stirred for 16 h at 70° C. The resulting mixture was cooled down to room temperature and concentrated under reduced pressure. The residue was purified by silica gel column chromatography, eluted with PE/EA (1/2). The fractions contained desired product were combined and concentrated to afford 1-cyclopropyl-4,6-difluoro-5-iodo-1,3-benzodiazole (1.70 g, 50%) as a yellow solid. MS ESI calculated for $C_{10}H_7F_2IN_2$ [M+H]$^+$, 320.96, found 321.00; $^1$H NMR (300 MHz, CDCl$_3$) δ 7.91 (s, 1H), 7.22-7.18 (m, 1H), 3.41-3.36 (m, 1H), 1.31-1.02 (m, 4H).

Step 17: 3-[2-(1-Cyclopropyl-4,6-difluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide To a stirred solution of 1-cyclopropyl-4,6-difluoro-5-iodo-1,3-benzodiazole (0.97 g, 3.02 mmol), 3-ethynyl-1-[(3S,5R)-5-(methoxymethyl)-1-(prop-2-enoyl)pyrrolidin-3-yl]-5-(methylamino)pyrazole-4-carboxamide (1.00 g, 3.02 mmol), Pd(PPh$_3$)$_2$Cl$_2$ (0.21 g, 0.30 mmol) and CuI (0.11 g, 0.60 mmol) in DMF (15.00 mL) was added TEA (0.92 g, 9.05 mmol) dropwise at room temperature. The reaction mixture was degassed with argon for three times and stirred for 40 min at 90° C. The resulting mixture was cooled down to room temperature and concentrated under reduced pressure. The residue was purified by silica gel column chromatography, eluted with DCM/MeOH (10/1) to afford the crude product. Then the crude product was further purified by reverse phase flash with the following conditions: column: C18 silica gel; mobile phase: ACN in water (10 mmol/L NH$_3$HCO$_3$), 10% to 50% gradient in 30 min; detector: UV 254 nm. The fractions contained desired product were combined and concentrated to afford 3-[2-(1-cyclopropyl-4,6-difluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (0.51 g, 33%) as a white solid. MS ESI calculated for $C_{26}H_{27}F_2N_7O_3$ [M+H]$^+$, 524.21, found 524.35; $^1$H NMR (300 MHz, CDCl$_3$) δ 7.99 (s, 1H), 7.30-7.12 (m, 2H), 6.83 (brs, 1H), 6.67-6.32 (m, 1H), 5.84-5.73 (m, 1H), 5.64-5.12 (m, 2H), 4.71-4.38 (m, 1H), 4.25-3.84 (m, 3H), 3.60-3.33 (m, 5H), 3.20-3.08 (m, 3H), 2.86-2.70 (m, 1H), 2.37-2.31 (m, 1H), 1.40-0.89 (m, 4H).

Example 79: 3-[2-(6-Fluoro-1-methyl-1,3-benzodi-azol-5-yl)ethynyl]-5-(methylamino)-1-[(3S,5R)-1-(prop-2-enoyl)-5-[(trifluoromethoxy)methyl]pyrrolidin-3-yl]pyrazole-4-carboxamide

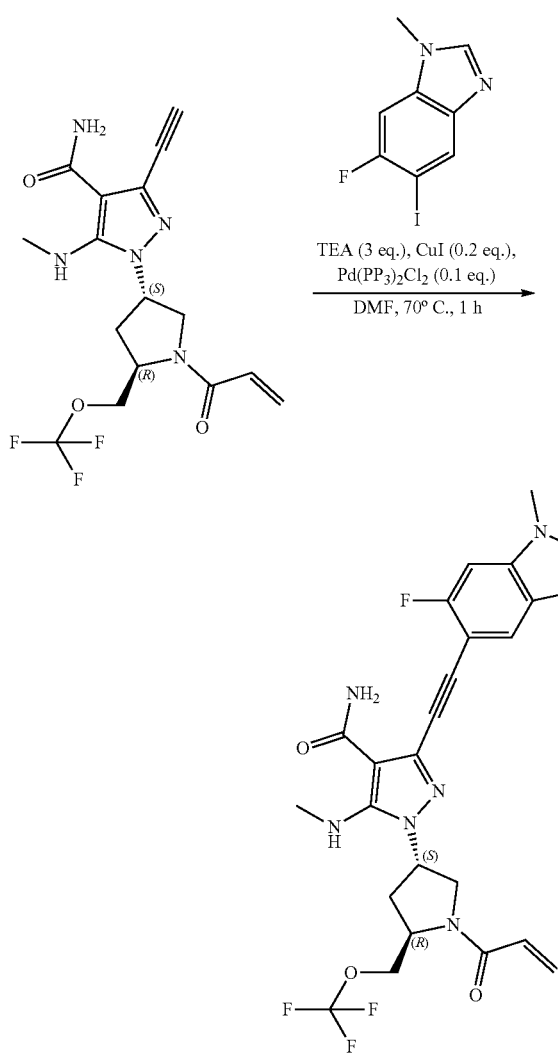

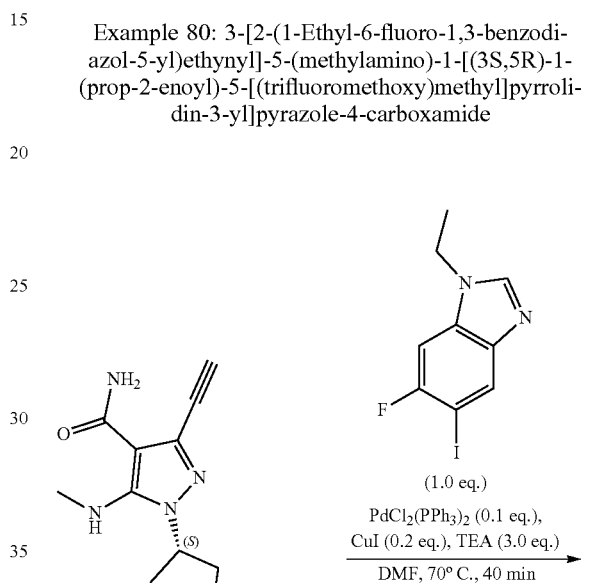

To a stirred mixture of 3-ethynyl-5-(methylamino)-1-[(3S,5R)-1-(prop-2-enoyl)-5-[(trifluoromethoxy)methyl]pyrrolidin-3-yl]pyrazole-4-carboxamide (2.50 g, 6.49 mmol), 6-fluoro-5-iodo-1-methyl-1,3-benzodiazole (1.79 g, 6.49 mmol), Pd(PPh$_3$)$_2$Cl$_2$ (0.46 g, 0.65 mmol) and CuI (0.25 g, 1.29 mmol) in DMF (25.00 mL) was added TEA (2.71 mL, 19.46 mmol). The reaction mixture was degassed with argon for three times and stirred for 1 h at 70° C. The resulting mixture was diluted with water (200 mL) and extracted with EA (3×200 mL). The combined organic layers were washed with brine (2×300 mL), dried over anhydrous Na$_2$SO$_4$ and filtered. The filtrate was concentrated under reduced pressure. The residue was purified by silica gel Column chromatography, eluted with 5% MeOH in DCM. The fractions contained desired product were combined and concentrated. The crude product was purified by Prep-HPLC with the following conditions: Column: XBridge Prep C18 OBD Column, Mobile Phase A: Water (10 mmol/L NH$_4$HCO$_3$), Mobile Phase B: ACN; Flow rate: 100 mL/min; Gradient: 15 B to 45 B in 30 min; 210/254 nm. The fractions contained desired product were combined and concentrated to afford 3-[2-(6-fluoro-1-methyl-1,3-benzodi-azol-5-yl)ethynyl]-5-(methylamino)-1-[(3S,5R)-1-(prop-2-enoyl)-5-[(trifluoromethoxy)methyl]pyrrolidin-3-yl]pyrazole-4-carboxamide (1.54 g, 44%) as an off-white solid. MS ESI calculated for C$_{24}$H$_{23}$F$_4$N$_7$O$_3$ [M+H]$^+$, 534.18, found 534.15; $^1$H NMR (400 MHz, DMSO-d$_6$): δ 8.35 (s, 1H), 7.96 (s, 1H), 7.71 (d, J=9.7 Hz, 1H), 7.49 (s, 1H), 6.81-6.55 (m, 3H), 6.20 (dd, J=16.7, 2.3 Hz, 1H), 5.78-5.68 (m, 1H), 5.31-5.21 (m, 1H), 4.83-4.37 (m, 2H), 4.28-4.24 (m, 1H), 4.03-3.98 (m, 2H), 3.85 (s, 3H), 3.02-2.94 (m, 3H), 2.76-2.54 (m, 1H), 2.38-2.31 (m, 1H).

Example 80: 3-[2-(1-Ethyl-6-fluoro-1,3-benzodi-azol-5-yl)ethynyl]-5-(methylamino)-1-[(3S,5R)-1-(prop-2-enoyl)-5-[(trifluoromethoxy)methyl]pyrrolidin-3-yl]pyrazole-4-carboxamide

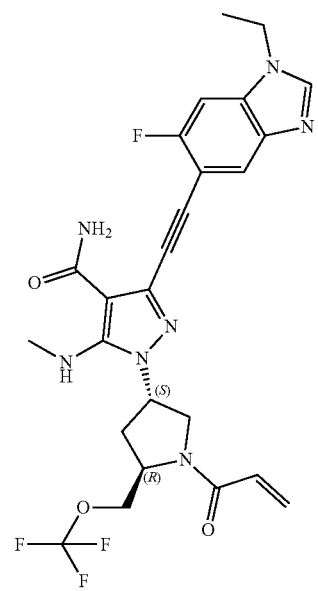

To a stirred mixture of 3-ethynyl-5-(methylamino)-1-[(3S,5R)-1-(prop-2-enoyl)-5-[(trifluoromethoxy)methyl]

pyrrolidin-3-yl]pyrazole-4-carboxamide (2.40 g, 6.22 mmol) and 1-ethyl-6-fluoro-5-iodo-1,3-benzodiazole (1.81 g, 6.24 mmol) in DMF (48.00 mL) were added Pd(PPh₃)₂Cl₂ (0.44 g, 0.62 mmol), CuI (0.24 g, 1.24 mmol) and TEA (1.89 g, 18.68 mmol) dropwise over 10 min under argon atmosphere. The reaction mixture was degassed with argon for three times and stirred for 40 min at 70° C. The resulting mixture was diluted with water (300 mL) and extracted with EA (3×200 mL). The combined organic layers were washed with brine (2×300 mL), dried over anhydrous Na₂SO₄ and filtered. The filtrate was concentrated under reduced pressure. The residue was purified by silica gel Column chromatography, eluted with MeOH/DCM (0-3%). The fractions contained desired product were combined and concentrated. The residue was purified by reverse flash chromatography with the following conditions: Column, C18 silica gel; mobile phase, NH₄HCO₃ (10 mmol/L) in water, 5% to 41% gradient in 30 min; detector, UV 254 nm. The fractions contained desired product were combined and concentrated to afford 3-[2-(1-ethyl-6-fluoro-1,3-benzodiazol-5-yl)ethynyl]-5-(methylamino)-1-[(3S,5R)-1-(prop-2-enoyl)-5-[(trifluoromethoxy)methyl]pyrrolidin-3-yl]pyrazole-4-carboxamide (1.50 g, 43%) as an off-white solid. MS ESI calculated for C₂₅H₂₅F₄N₇O₃ [M+H]⁺, 548.20, found 548.10; ¹H NMR (300 MHz, DMSO-d₆) δ 8.41 (s, 1H), 7.96 (d, J=6.3 Hz, 1H), 7.76 (d, J=9.8 Hz, 1H), 7.50 (s, 1H), 6.97-6.53 (m, 3H), 6.33-6.10 (m, 1H), 5.74 (d, J=10.2 Hz, 1H), 5.25 (d, J=6.7 Hz, 1H), 4.87-4.42 (m, 2H), 4.29-4.25 (m, 3H), 4.11-3.76 (m, 2H), 3.14-2.89 (m, 3H), 2.81-2.58 (m, 1H), 2.44-2.27 (m, 1H), 1.42 (t, J=7.2 Hz, 3H).

Example 81: 3-[2-[1-(Difluoromethyl)-6-fluoro-1,3-benzodiazol-5-yl]ethynyl]-5-(methylamino)-1-[(3S,5R)-1-(prop-2-enoyl)-5-[(trifluoromethoxy)methyl]pyrrolidin-3-yl]pyrazole-4-carboxamide

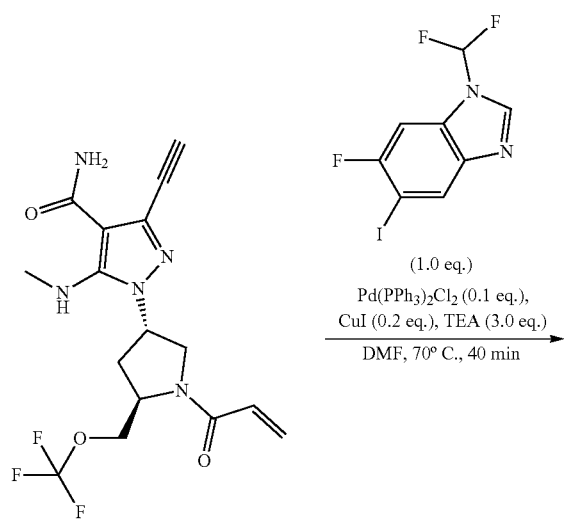

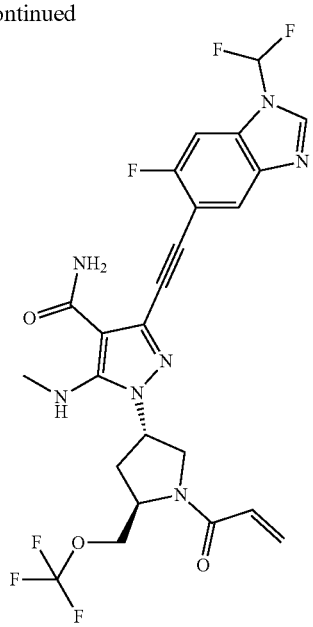

To a stirred mixture of 1-[(3S,5R)-5-[(1,1-difluoroethoxy)methyl]-1-(prop-2-enoyl)pyrrolidin-3-yl]-3-ethynyl-5-(methylamino)pyrazole-4-carboxamide (0.30 g, 0.78 mmol), 1-(difluoromethyl)-6-fluoro-5-iodo-1,3-benzodiazole (0.25 g, 0.78 mmol), Pd(PPh₃)₂Cl₂ (57.32 mg, 0.08 mmol) and CuI (31.11 mg, 0.16 mmol) in DMF (2.00 mL) was added TEA (0.25 g, 2.45 mmol). The reaction mixture was degassed with argon for three times and stirred for 40 min at 70° C. The resulting mixture was diluted with water (20 mL) and extracted with EA (3×20 mL). The combined organic layers were washed with brine (3×20 mL), dried over anhydrous Na₂SO₄ and filtered. The filtrate was concentrated under reduced pressure. The residue was purified by silica gel Column chromatography, eluted with MeOH/DCM (0-5%), the fractions contained desired product were combined and concentrated. Then the crude product was purified by Prep-HPLC with the following conditions: Column: Sun-Fire Prep C18 OBD Column, 19×150 mm 5 μm 10 nm; Mobile Phase A: Water (10 mmoL/L NH₄HCO₃), Mobile Phase B: ACN; Flow rate: 20 mL/min; Gradient: 25 B to 40 B in 30 min; 220/254 nm. The fractions contained desired product were combined and concentrated to afford 3-[2-[1-(difluoromethyl)-6-fluoro-1,3-benzodiazol-5-yl]ethynyl]-5-(methylamino)-1-[(3S,5R)-1-(prop-2-enoyl)-5-[(trifluoromethoxy)methyl]pyrrolidin-3-yl]pyrazole-4-carboxamide (0.33 g, 75%) as a white solid. MS ESI calculated for C₂₄H₂₁F₆N₇O₃ [M+H]⁺, 570.16, found 570.05; ¹H NMR (400 MHz, DMSO-d₆) δ 8.73 (s, 1H), 8.18-7.82 (m, 2H), 7.81-7.80 (m, 1H), 7.48 (s, 1H), 6.76-6.38 (m, 3H), 6.21-6.16 (m, 1H), 5.83-5.61 (m, 1H), 5.27-5.22 (m, 1H), 4.78-4.50 (m, 1H), 4.44-4.40 (m, 1H), 4.30-4.20 (m, 1H), 4.06-3.93 (m, 2H), 2.97-2.96 (m, 3H), 2.72-2.63 (m, 1H), 2.38-2.33 (m, 1H).

Example 82: 3-[2-(6-Chloro-1,2-dimethyl-1,3-ben-zodiazol-5-yl)ethynyl]-1-[(3S,5R)-5-(methoxymethyl)-1-(prop-2-enoyl)pyrrolidin-3-yl]-5-(methylamino)pyrazole-4-carboxamide

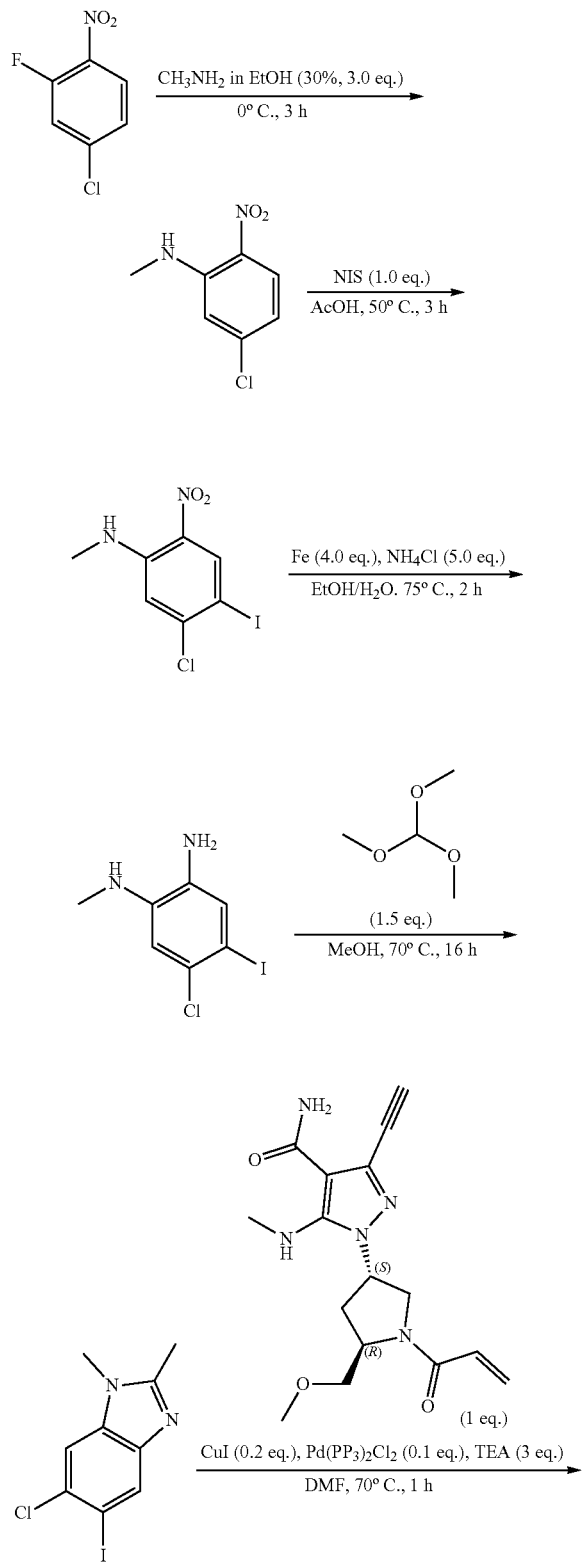

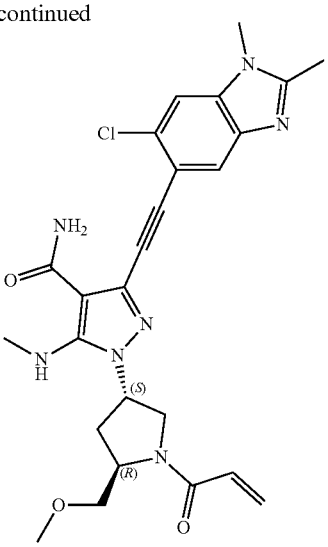

Step 1: 5-Chloro-N-methyl-2-nitroaniline

To a stirred solution of 4-chloro-2-fluoro-1-nitrobenzene (35.00 g, 199.38 mmol) in EtOH (350.00 mL) was added methylamine (61.92 g, 598.15 mmol, 30% in ethanol) dropwise at 0° C. under $N_2$ atmosphere. The reaction mixture was stirred for 3 h at 0° C. The resulting mixture was quenched with water (300 mL) at 0° C. The precipitated solids were collected by filtration and washed with water (3×300 mL). The filter cake was dried to afford 5-chloro-N-methyl-2-nitroaniline (36 g, 96%) as a yellow solid which was used in the next step directly without further purification. MS ESI calculated for $C_7H_7ClN_2O_2$ [M−H]⁻, 185.02, 187.02, found 185.00, 187.00; ¹H NMR (400 MHz, CDCl₃) δ 8.12-8.07 (m, 2H), 6.83 (d, J=2.2 Hz, 1H), 6.61 (dd, J=9.1, 2.1 Hz, 1H), 3.02 (d, J=5.1 Hz, 3H).

Step 2: 5-Chloro-4-iodo-N-methyl-2-nitroaniline

To a stirred mixture of 5-chloro-N-methyl-2-nitroaniline (42.00 g, 225.08 mmol) in CH₃COOH (420.00 mL) was added NIS (50.64 g, 225.08 mmol) at room temperature. The reaction mixture was stirred for 3 h at 50° C. The resulting mixture was cooled down and concentrated under reduced pressure. The residue was diluted with water (400 mL) and extracted with EA (3×500 mL). The combined organic layers were washed with water (2×300 mL), dried over anhydrous Na₂SO₄ and filtered. The filtrate was concentrated under reduced pressure. The residue was purified by silica gel Column chromatography, eluted with EA in PE (0-40%). The fractions contained desired product were combined and concentrated to afford 5-chloro-4-iodo-N-methyl-2-nitroaniline (70 g, 99%) as an orange solid. MS ESI calculated for $C_7H_6ClIN_2O_2$ [M−H]⁻, 310.92, 312.92, found 310.85, 312.85; ¹H NMR (400 MHz, CDCl₃) δ 8.74-8.52 (m, 1H), 7.99 (brs, 1H), 7.00 (d, J=1.8 Hz, 1H), 3.03 (d, J=4.7 Hz, 3H).

Step 3: 5-Chloro-4-iodo-N1-methylbenzene-1,2-diamine

To a stirred mixture of 5-chloro-4-iodo-N-methyl-2-nitroaniline (65.00 g, 208.01 mmol) and NH₄Cl (55.63 g, 1040.03 mmol) in EtOH (650.00 mL) and H₂O (130.00 mL)

was added Fe (46.46 g, 832.02 mmol). The reaction mixture was stirred for 2 h at 75° C. The resulting mixture was cooled down and filtered, the filter cake was washed with EA (2×100 mL). The filtrate was concentrated under reduced pressure. The residue was diluted with water (500 mL) and extracted with EA (3×600 mL). The combined organic layers were washed with brine (2×400 mL), dried over anhydrous $Na_2SO_4$ and filtered. The filtrate was concentrated and dried to afford 5-chloro-4-iodo-$N^1$-methylbenzene-1,2-diamine (60 g, crude) as a brown solid which was used in the next step directly without further purification. MS ESI calculated for $C_7H_8ClIN_2$ [M−H]⁻, 280.94, 282.94, found 281.00, 283.00; ¹H NMR (400 MHz, CDCl₃) δ 7.11 (s, 1H), 6.70 (s, 1H), 3.25 (brs, 3H), 2.84 (s, 3H).

Step 4: 6-Chloro-5-iodo-1,2-dimethyl-1H-benzo[d]imidazole

To a stirred solution of 5-chloro-4-iodo-$N^1$-methylbenzene-1,2-diamine (27.80 g, 98.40 mmol) in MeOH (280.00 mL) was added 1,1,1-trimethoxyethane (18.87 mL, 147.61 mmol). The reaction mixture was stirred for 16 h at 70° C. under argon atmosphere. The resulting mixture was concentrated under reduced pressure. The residue was purified by silica gel Column chromatography, eluted with $CH_2Cl_2$/MeOH (10/1). The fractions contained desired product were combined and concentrated to afford 6-chloro-5-iodo-1,2-dimethyl-1H-benzo[d]imidazole (28.1 g, 93%) as a brown solid. MS ESI calculated for $C_9H_8ClIN_2$ [M+H]⁺, 306.94, found 307.30; ¹H NMR (400 MHz, DMSO-$d_6$) δ 8.06 (s, 1H), 7.87 (s, 1H), 3.71 (s, 3H), 2.52 (s, 3H)

Step 5: 3-[2-(6-Chloro-1,2-dimethyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide To a stirred mixture of 3-ethynyl-1-[(3S,5R)-5-(methoxymethyl)-1-(prop-2-enoyl)pyrrolidin-3-yl]-5-(methylamino)pyrazole-4-carboxamide (2.00 g, 6.03 mmol), 6-chloro-5-iodo-1,2-dimethyl-1H-benzo[d]imidazole (1.85 g, 6.04 mmol), Pd(PPh₃)₂Cl₂ (0.42 g, 0.60 mmol) and CuI (0.23 g, 1.21 mmol) in DMF (20.00 mL) was added TEA (2.52 mL, 24.87 mmol) dropwise at room temperature. The reaction mixture was degassed with argon for three times and stirred for 1 h at 70° C. The resulting mixture was concentrated under reduced pressure. The residue was purified by silica gel Column chromatography, eluted with $CH_2Cl_2$/MeOH (10/1). The fractions contained desired product were combined and concentrated. The residue was purified by reverse flash chromatography with the following conditions: Column, C18 silica gel; mobile phase A: ACN, B: Water (10 mmol/L $NH_4HCO_3$), 10% to 40% gradient in 30 min; detector, UV 254 nm. The fractions contained desired product were combined and concentrated to afford 3-[2-(6-chloro-1,2-dimethyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (1.79 g, 58%) as a white solid. ESI calculated for $C_{25}H_{28}ClN_7O_3$ [M+H]⁺, 510.19, found 510.15; ¹H NMR (400 MHz, DMSO-$d_6$) δ 7.85 (d, J=1.5 Hz, 2H), 7.51 (s, 1H), 6.86 (s, 1H), 6.78-6.54 (m, 2H), 6.17-5.96 (m, 1H), 5.69-5.45 (m, 1H), 5.27-5.03 (m, 1H), 4.52-4.41 (m, 1H), 4.04-3.95 (m, 1H), 3.89-3.65 (m, 1H), 3.75 (s, 3H), 3.61-3.56 (m, 1H), 3.52-3.42 (m, 1H), 3.33-3.30 (m, 3H), 3.00-2.93 (m, 1H), 2.64-2.58 (m, 1H), 2.54 (s, 3H), 2.29-2.12 (m, 1H).

Example 83: 1-[(3S,5R)-5-(Methoxymethyl)-1-(prop-2-enoyl)pyrrolidin-3-yl]-5-(methylamino)-3-[2-(2-methylquinolin-7-yl)ethynyl]pyrazole-4-carboxamide

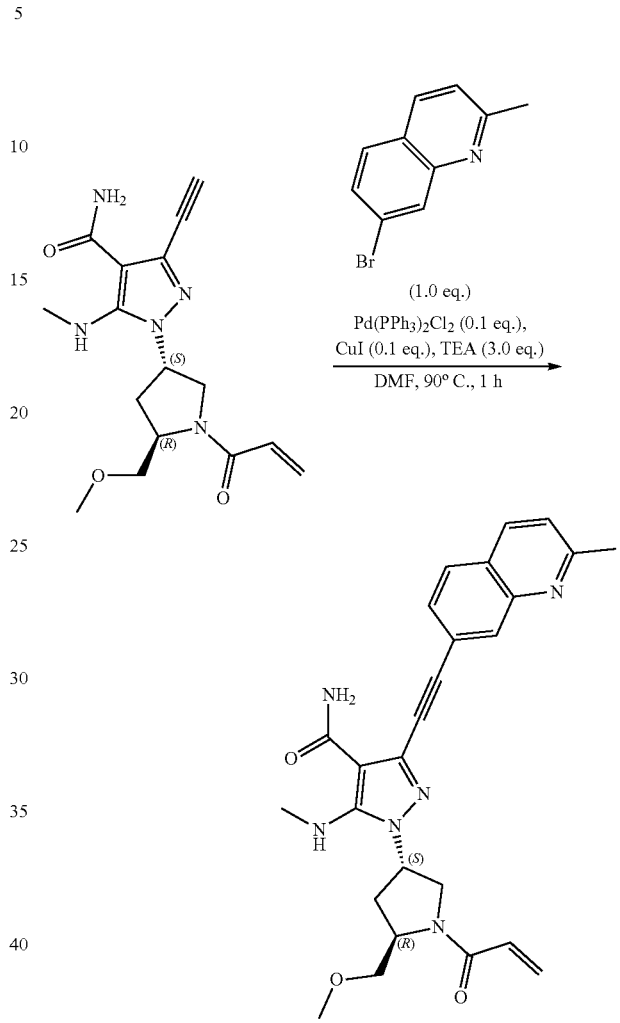

To a stirred mixture of 3-ethynyl-1-[(3S,5R)-5-(methoxymethyl)-1-(prop-2-enoyl)pyrrolidin-3-yl]-5-(methylamino)pyrazole-4-carboxamide (0.30 g, 0.9 mmol), 7-bromo-2-methylquinoline (0.20 g, 0.91 mmol), Pd(PPh₃)₂Cl₂ (63.54 mg, 0.09 mmol) and CuI (34.48 mg, 0.18 mmol) in DMF (2.00 mL) was added TEA (0.27 g, 2.72 mmol) dropwise at room temperature. The reaction mixture was degassed with argon for three times and stirred for 1 h at 90° C. The resulting mixture was concentrated under reduced pressure. The residue was purified by silica gel Column chromatography, eluted with $CH_2Cl_2$/MeOH (10/1). The fractions contained desired product were combined and concentrated. The residue was purified by reverse flash chromatography with the following conditions: Column, C18 silica gel; mobile phase ACN, Water (10 mmol/L, $NH_4HCO_3$), 10% to 40% gradient in 30 min; detector, UV 254 nm. The fractions contained desired product were combined and concentrated to afford 1-[(3S,5R)-5-(methoxymethyl)-1-(prop-2-enoyl)pyrrolidin-3-yl]-5-(methylamino)-3-[2-(2-methylquinolin-7-yl)ethynyl]pyrazole-4-carboxamide (0.15 g, 35%) as a white solid. MS ESI calculated for $C_{26}H_{28}N_6O_3$ [M+H]⁺, 473.20, found 473.25; ¹H NMR (300 MHz, DMSO-$d_6$) δ 8.28 (d, J=8.5 Hz, 1H), 8.10 (s, 1H), 7.98 (d, J=8.5 Hz, 1H), 7.63 (d, J=8.4 Hz, 1H), 7.47 (d, J=8.4 Hz, 1H), 7.36 (s, 1H), 6.86 (s, 1H), 6.72-6.67 (m, 1H), 6.64-6.52 (m, 1H), 6.16 (d, J=16.6 Hz, 1H), 5.68 (d, J=10.2 Hz, 1H), 5.25 (d, J=7.5 Hz, 1H), 4.47 (d, J=39.4 Hz, 1H), 4.02-3.96 (m, 1H), 3.86 (d, J=6.7 Hz, 1H), 3.64-3.55 (m, 1H), 3.53-3.40 (m, 1H), 3.30 (d, J=5.2 Hz, 3H), 2.94-2.75 (m, 3H), 2.69-2.65 (m, 4H), 2.33-2.30 (m, 1H).

Example 84: 3-[2-(4,6-Difluoro-1-methyl-1,3-benzodiazol-5-yl)ethynyl]-5-(methylamino)-1-[(3S,5R)-1-(prop-2-enoyl)-5-[(trifluoromethoxy)methyl]pyrrolidin-3-yl]pyrazole-4-carboxamide

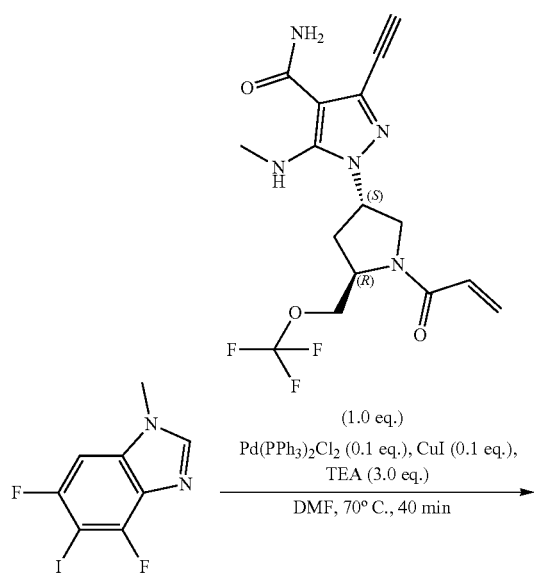

To a stirred mixture of 4,6-difluoro-5-iodo-1-methyl-1,3-benzodiazole (0.23 g, 0.78 mmol), 3-ethynyl-5-(methylamino)-1-[(3S,5R)-1-(prop-2-enoyl)-5-[(trifluoromethoxy)methyl]pyrrolidin-3-yl]pyrazole-4-carboxamide (0.30 g, 0.78 mmol), Pd(PPh$_3$)$_2$Cl$_2$ (54.90 mg, 0.08 mmol), CuI (29.79 mg, 0.16 mmol) in DMF (3.00 mL) was added TEA (0.24 g, 2.34 mmol) at room temperature. The reaction mixture was degassed with argon for three times and stirred for 40 min at 70° C. The resulting mixture was concentrated under reduced pressure. The residue was purified by silica gel Column chromatography, eluted with MeOH in DCM (0-4%) to afford the crude product. The crude product was purified by Prep-HPLC with the following conditions Column: XBridge Prep C18 OBD Column, 19×150 mm 5 μm; Mobile Phase A: Water (10 mmol/L NH$_4$HCO$_3$), Mobile Phase B: ACN; Flow rate: 20 mL/min; Gradient: 30 B to 60 B in 6.0 min; 210/254 nm; RT: 5.58. The fractions contained desired product were combined and concentrated to afford 3-[2-(4,6-difluoro-1-methyl-1,3-benzodiazol-5-yl)ethynyl]-5-(methylamino)-1-[(3S,5R)-1-(prop-2-enoyl)-5-[(trifluoromethoxy)methyl]pyrrolidin-3-yl]pyrazole-4-carboxamide (53.0 mg, 12%) as a white solid. MS ESI calculated for C$_{24}$H$_{22}$F$_5$N$_7$O$_3$ [M+H]$^+$, 552.17, found 551.90; $^1$H NMR (400 MHz, CDCl$_3$) δ 7.90 (s, 1H), 7.10-6.94 (m, 2H), 6.84 (s, 1H), 6.42 (d, J=6.1 Hz, 2H), 5.75 (t, J=6.1 Hz, 1H), 5.38-5.35 (m, 2H), 4.74-4.58 (m, 2H), 4.23-4.01 (m, 3H), 3.85 (s, 3H), 3.03 (s, 3H), 2.89-2.87 (m, 1H), 2.37-2.34 (m, 1H).

Example 85: 3-[2-(1-Ethyl-4,6-difluoro-1,3-benzodiazol-5-yl)ethynyl]-5-(methylamino)-1-[(3S,5R)-1-(prop-2-enoyl)-5-[(trifluoromethoxy)methyl]pyrrolidin-3-yl]pyrazole-4-carboxamide

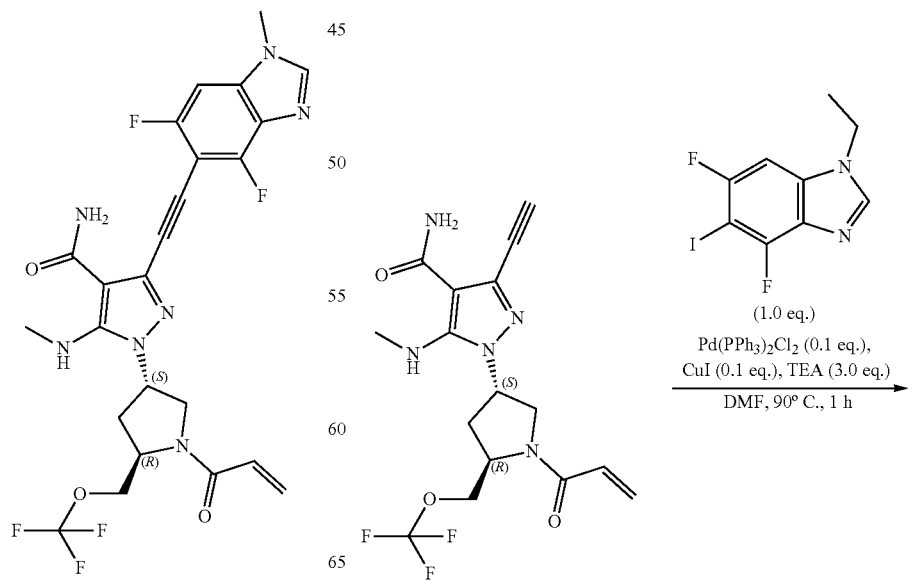

491
-continued

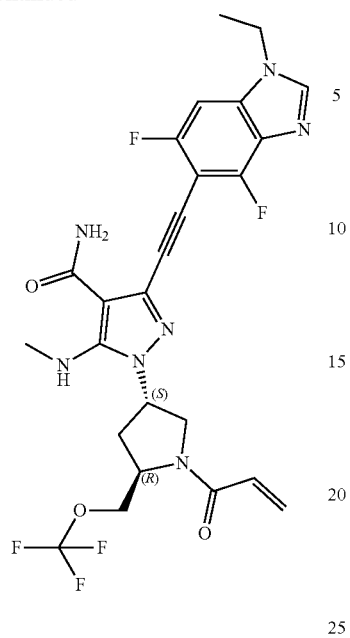

To a stirred solution of 1-ethyl-4,6-difluoro-5-iodo-1,3-benzodiazole (96.00 mg, 0.31 mmol) and 3-ethynyl-5-(methylamino)-1-[(3S,5R)-1-(prop-2-enoyl)-5-[(trifluoromethoxy)methyl]pyrrolidin-3-yl]pyrazole-4-carboxamide (0.12 g, 0.31 mmol) in DMF (3.00 mL) were added Pd(PPh$_3$)$_2$Cl$_2$ (21.87 mg, 0.03 mmol), CuI (11.87 mg, 0.06 mmol) and TEA (94.60 mg, 0.94 mmol) at room temperature. The reaction mixture was degassed with argon for three times and stirred for 1 h at 90° C. The resulting mixture was cooled down and concentrated under reduced pressure. The residue was purified by silica gel Column chromatography, eluted with CH$_2$Cl$_2$/MeOH (10/1). The fractions contained desired product were combined and concentrated. The residue was purified by reverse flash chromatography with the following conditions: Column, C18 silica gel; mobile phase, NH$_4$HCO$_3$ in water, 5% to 70% gradient in 30 min; detector, UV 254 nm. The fractions contained desired product were combined and concentrated to afford 3-[2-(1-ethyl-4,6-difluoro-1,3-benzodiazol-5-yl)ethynyl]-5-(methylamino)-1-[(3S,5R)-1-(prop-2-enoyl)-5-[(trifluoromethoxy)methyl]pyrrolidin-3-yl] pyrazole-4-carboxamide (64 mg, 36%) as an off-white solid. MS ESI calculated for C$_{25}$H$_{24}$F$_5$N$_7$O$_3$ [M+H]$^+$, 566.19, found 566.15; $^1$H NMR (400 MHz, CDCl$_3$) δ 8.10 (s, 1H), 7.05 (d, J=8.3 Hz, 2H), 6.52-6.42 (m, 2H), 5.77 (t, J=6.1 Hz, 1H), 5.53-5.16 (m, 2H), 4.71-4.58 (m, 2H), 4.30-4.03 (m, 5H), 3.05 (s, 3H), 2.90-2.85 (m, 1H), 2.39-2.35 (m, 1H), 1.59 (t, J=7.3 Hz, 3H).

492

Example 86: 3-[2-(6-Fluoro-1H-1,3-benzodiazol-5-yl)ethynyl]-5-(methylamino)-1-[(3S,5R)-1-(prop-2-enoyl)-5-[(trifluoromethoxy)methyl]pyrrolidin-3-yl] pyrazole-4-carboxamide

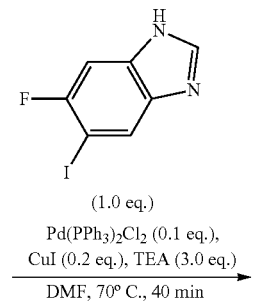

(1.0 eq.)
Pd(PPh$_3$)$_2$Cl$_2$ (0.1 eq.),
CuI (0.2 eq.), TEA (3.0 eq.)
———————————————
DMF, 70° C., 40 min

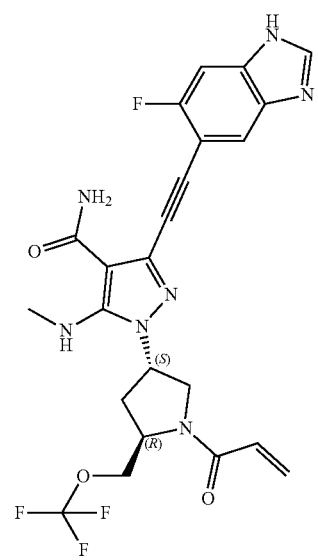

To a stirred mixture of 3-ethynyl-5-(methylamino)-1-[(3S,5R)-1-(prop-2-enoyl)-5-[(trifluoromethoxy)methyl]pyrrolidin-3-yl]pyrazole-4-carboxamide (0.15 g, 0.39 mmol), 5-fluoro-6-iodo-3H-1,3-benzodiazole (0.10 g, 0.39 mmol), Pd(PPh$_3$)$_2$Cl$_2$ (27.32 mg, 0.04 mmol), CuI (14.83 mg, 0.08 mmol) in DMF (4.5 mL) was added TEA (0.12 g, 1.17 mmol) at room temperature. The reaction mixture was degassed with argon for three times and stirred for 40 min at 70° C. The resulting mixture was concentrated under reduced pressure. The residue was purified by silica gel Column chromatography, eluted with MeOH in DCM (0-10%) to afford the crude product. The crude product was purified by Prep-HPLC with the following conditions Column: Atlantis HILIC OBD Column, 19×150 mm 5 μm; Mobile Phase A: Water (10 mmol/L NH$_4$HCO$_3$), Mobile Phase B: ACN; Flow rate: 20 mL/min; Gradient: 35 B to 70 B in 5.8 min; 210/254 nm; RT: 5.58 min. The fractions contained desired product were combined and concentrated to afford 3-[2-(6-fluoro-1H-1,3-benzodiazol-5-yl)ethynyl]-5-(methylamino)-1-[(3S,5R)-1-(prop-2-enoyl)-5-[(trifluoromethoxy)methyl]pyrrolidin-3-yl]pyrazole-4-carboxamide (33.3 mg, 16%) as an off-white solid. MS ESI calculated for $C_{23}H_{21}F_4N_7O_3$ [M+H]$^+$, 520.16, found 520.10; $^1$H NMR (400 MHz, CDCl$_3$) δ 8.15 (s, 1H), 7.82 (s, 1H), 7.42 (s, 1H), 7.12 (s, 1H), 6.86 (d, J=6.1 Hz, 1H), 6.53-6.33 (m, 2H), 5.76 (dd, J=7.3, 4.9 Hz, 1H), 5.40-5.32 (m, 2H), 4.71-4.55 (m, 2H), 4.19-3.92 (m, 3H), 3.03 (d, J=5.9 Hz, 3H), 2.97-2.73 (m, 1H), 2.39-2.35 (m, 1H).

Example 87: 3-[2-(6-Chloro-2-methyl-1H-1,3-benzodiazol-5-yl)ethynyl]-5-(methylamino)-1-[(3S,5R)-1-(prop-2-enoyl)-5-[(trifluoromethoxy)methyl]pyrrolidin-3-yl]pyrazole-4-carboxamide

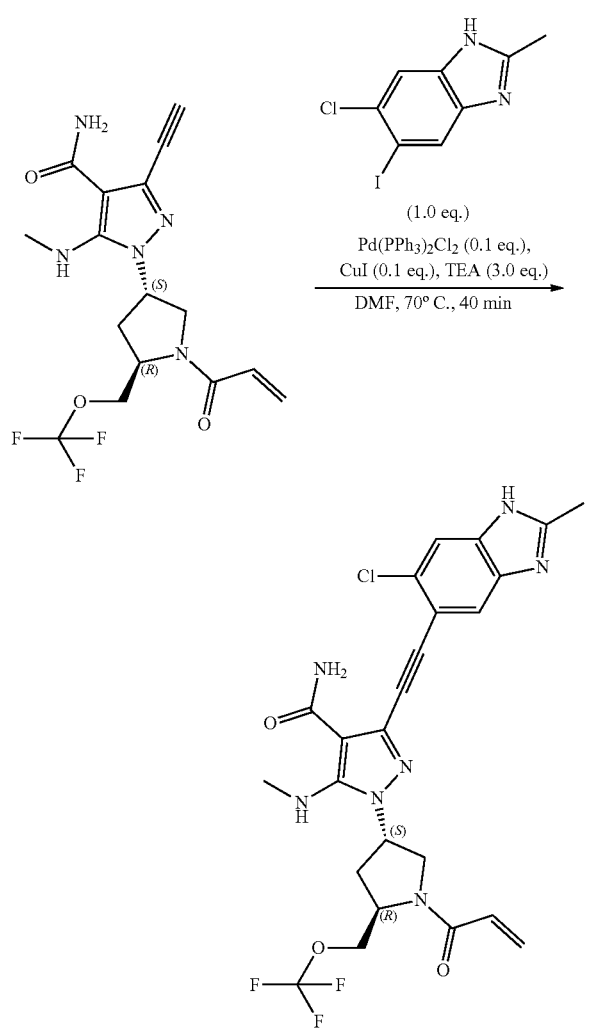

To a stirred mixture of 3-ethynyl-5-(methylamino)-1-[(3S,5R)-1-(prop-2-enoyl)-5-[(trifluoromethoxy)methyl] pyrrolidin-3-yl]pyrazole-4-carboxamide (0.15 g, 0.39 mmol), 5-chloro-6-iodo-2-methyl-3H-1,3-benzodiazole (0.11 g, 0.39 mmol), Pd(PPh$_3$)$_2$Cl$_2$ (27.32 mg, 0.04 mmol) and CuI (14.83 mg, 0.08 mmol) in DMF (1.50 mL, 19.38 mmol) was added TEA (0.16 mL, 1.17 mmol). The reaction mixture was degassed with argon for three times and stirred for 40 min at 70° C. The resulting mixture was concentrated under reduced pressure. The residue was purified by silica gel Column chromatography, eluted with 4% MeOH in DCM. The fractions contained desired product were combined and concentrated. The residue was purified by reverse flash chromatography with the following conditions: Column: XBridge Prep C18 OBD Column, 19×150 mm 5 μm; Mobile Phase A: Water (10 mmol/L NH$_4$HCO$_3$), Mobile Phase B: ACN; Flow rate: 20 mL/min; Gradient: 40 B to 60 B in 6 min; 210/254 nm; RT: 5.56 min. The fractions contained desired product were combined and concentrated to afford 3-[2-(6-chloro-2-methyl-1H-1,3-benzodiazol-5-yl)ethynyl]-5-(methylamino)-1-[(3S,5R)-1-(prop-2-enoyl)-5-[(trifluoromethoxy)methyl]pyrrolidin-3-yl]pyrazole-4-carboxamide (77.5 mg, 35%) as an off-white solid. MS ESI calculated for $C_{24}H_{23}ClF_3N_7O_3$ [M+H]$^+$, 550.15, found 550.10; $^1$H NMR (400 MHz, DMSO-d$_6$) δ 7.72 (d, J=37.9 Hz, 2H), 6.88-6.84 (m, 1H), 6.51-6.36 (m, 2H), 5.78-5.76 (m, 1H), 5.42-5.37 (m, 2H), 4.80-4.51 (m, 2H), 4.22-3.97 (m, 3H), 3.05 (d, J=5.9 Hz, 4H), 2.94-2.76 (m, 1H), 2.66 (brs, 3H), 2.40-2.35 (m, 1H).

Example 88: 3-[2-(6-Chloro-1-methyl-1,3-benzodiazol-5-yl)ethynyl]-1-[(3S,5R)-5-(methoxymethyl)-1-(prop-2-enoyl)pyrrolidin-3-yl]-5-(methylamino) pyrazole-4-carboxamide

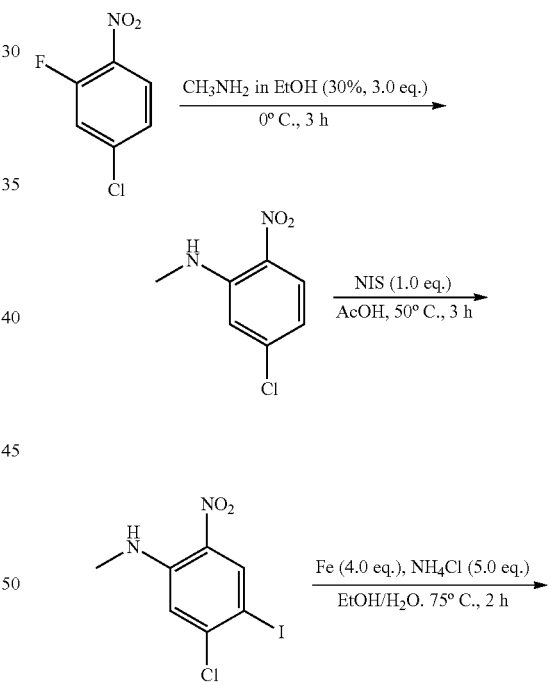

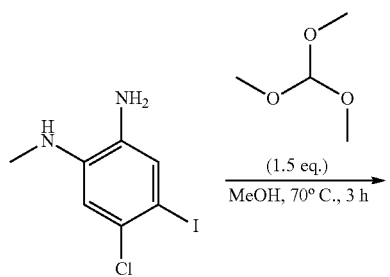

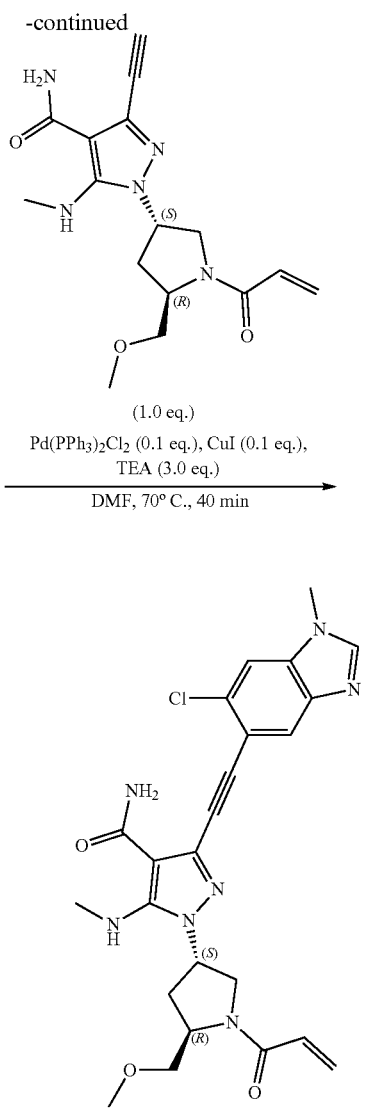

Step 1: 5-Chloro-N-methyl-2-nitroaniline

To a stirred solution of 4-chloro-2-fluoro-1-nitrobenzene (35.00 g, 199.38 mmol) in EtOH (350.00 mL) was added methylamine in ethanol (61.92 g, 598.15 mmol, 30% in ethanol) dropwise at 0° C. under $N_2$ atmosphere. The reaction mixture was stirred for 3 h. The resulting mixture was quenched with water (300 mL) at 0° C. The precipitated solids were collected by filtration and washed with water (3×300 mL). The filter cake was dried to afford 5-chloro-N-methyl-2-nitroaniline (36.00 g, 96%) as a yellow solid. MS ESI calculated for $C_7H_7ClN_2O_2$ [M−H]$^-$, 185.02, found 185.00; $^1$H NMR (400 MHz, CDCl$_3$) δ 8.12-8.07 (m, 2H), 6.83 (d, J=2.2 Hz, 1H), 6.61 (dd, J=9.1, 2.1 Hz, 1H), 3.02 (d, J=5.1 Hz, 3H).

Step 2: 5-Chloro-4-iodo-N-methyl-2-nitroaniline

To a stirred mixture of 5-chloro-N-methyl-2-nitroaniline (42.00 g, 225.08 mmol) in CH$_3$COOH (420.00 mL) was added NIS (50.64 g, 225.08 mmol) at room temperature. The reaction mixture was stirred for 3 h at 50° C. The resulting mixture was cooled down and concentrated under reduced pressure. The residue was diluted with water (400 mL) and extracted with EA (3×500 mL). The combined organic layers were washed with brine (2×300 mL), dried over anhydrous Na$_2$SO$_4$ and filtered. The filtrate was concentrated under reduced pressure. The residue was purified by silica gel Column chromatography, eluted with EA in PE (0-40%). The fractions contained desired product were combined and concentrated to afford 5-chloro-4-iodo-N-methyl-2-nitroaniline (70 g, 99%) as an orange solid. MS ESI calculated for $C_7H_6ClIN_2O_2$ [M−H]$^-$, 310.92, found 310.85; $^1$H NMR (400 MHz, CDCl$_3$) δ 8.74-8.52 (m, 1H), 7.99 (brs, 1H), 7.00 (d, J=1.8 Hz, 1H), 3.03 (d, J=4.7 Hz, 3H).

Step 3:
5-Chloro-4-iodo-N1-methylbenzene-1,2-diamine

To a stirred mixture of 5-chloro-4-iodo-N-methyl-2-nitroaniline (65.00 g, 208.01 mmol) and NH$_4$Cl (55.63 g, 1040.03 mmol) in EtOH (650.00 mL) and H$_2$O (130.00 mL) was added Fe (46.46 g, 832.02 mmol). The reaction mixture was stirred for 2 h at 75° C. The resulting mixture was cooled down and filtered, the filter cake was washed with EA (2×100 mL). The filtrate was concentrated under reduced pressure. The residue was diluted with water (500 mL) and extracted with EA (3×600 mL). The combined organic layers were washed with brine (2×400 mL), dried over anhydrous Na$_2$SO$_4$ and filtered, The filtrate was concentrated and dried to afford 5-chloro-4-iodo-N$^1$-methylbenzene-1,2-diamine (60 g, 99%) as a brown solid which was used in the next step directly without further purification. MS ESI calculated for $C_7H_8ClIN_2$ [M−H]$^-$, 280.94, found 281.00; $^1$H NMR (400 MHz, CDCl$_3$) δ 7.11 (s, 1H), 6.70 (s, 1H), 3.25 (brs, 3H), 2.84 (s, 3H).

Step 4: 6-Chloro-5-iodo-1-methyl-1,3-benzodiazole

To a stirred solution of 5-chloro-4-iodo-N$^1$-methylbenzene-1,2-diamine (60.00 g, 212.38 mmol) in MeOH (600.00 mL) was added trimethyl orthoformate (33.81 g, 318.57 mmol). The reaction mixture was stirred for 3 h at 70° C. The resulting mixture was concentrated under reduced pressure. The residue was purified by silica gel Column chromatography, eluted with EA in PE (50-100%). The fractions contained desired product were combined and concentrated to afford 6-chloro-5-iodo-1-methyl-1,3-benzodiazole (65 g, 90%) as a yellow solid. MS ESI calculated for $C_8H_6ClIN_2$ [M+H]$^+$, 292.93, found 292.95; $^1$H NMR (400 MHz, CDCl$_3$) δ 8.29 (s, 1H), 7.83 (s, 1H), 7.54 (s, 1H), 3.81 (s, 3H).

Step 5: 3-[2-(6-Chloro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide To a stirred mixture of 6-chloro-5-iodo-1-methyl-1,3-benzodiazole (0.33 g, 1.12 mmol), 3-ethynyl-1-[(3S,5R)-5-(methoxymethyl)-1-(prop-2-enoyl)pyrrolidin-3-yl]-5-(methylamino)pyrazole-4-carboxamide (0.37 g, 1.12 mmol), Pd(PPh$_3$)$_2$Cl$_2$ (78.37 mg, 0.11 mmol) and CuI (42.53 mg, 0.22 mmol) in DMF (5.00 mL) was added TEA (0.34 g, 3.35 mmol) dropwise at room temperature. The reaction mixture was degassed with argon for three times and stirred for 40 min at 70° C. The resulting mixture was cooled down and concentrated under reduced pressure. The residue was purified by silica gel Column chromatography, eluted with MeOH in DCM (0-5%) to afford the crude product. Then the crude product was purified by Prep-HPLC with the following conditions: Column: XBridge Prep C18 OBD Column, 19×150 mm 5 μm; Mobile Phase A: Water (10 mmol/L NH₄HCO₃), Mobile Phase B: ACN; Flow rate: 20 mL/min; Gradient: 35 B to 50 B in 6 min; 210/254 nm; RT: 5.58 min. The fractions contained desired product were combined and concentrated to afford 3-[2-(6-chloro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (0.21 g, 38%) as a white solid. MS ESI calculated for $C_{24}H_{26}ClN_7O_3$ [M+H]⁺, 496.18, found 496.05; ¹H NMR (400 MHz, CDCl₃) δ 8.10 (brs, 1H), 7.98 (brs, 1H), 7.51 (brs, 1H), 7.18 (brs, 1H), 6.81 (brs, 1H), 6.57-6.35 (m, 2H), 5.79-5.21 (m, 3H), 4.60-4.37 (m, 1H), 4.18-3.77 (m, 6H), 3.57-3.26 (m, 4H), 3.08-3.01 (m, 3H), 2.2.76-71 (m, 1H), 2.34-2.27 (m, 1H).

Example 89: 3-[2-(6-Chloro-1-ethyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide

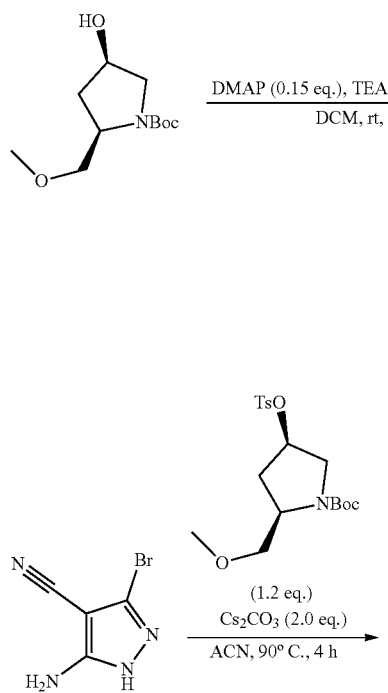

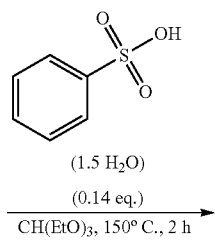

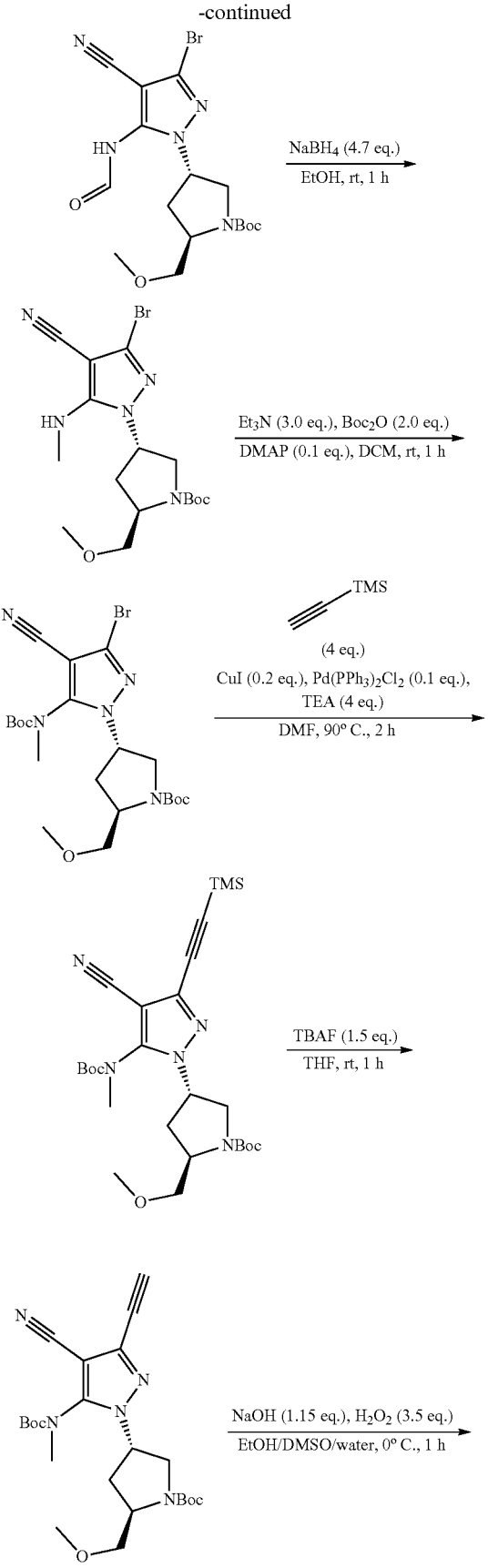

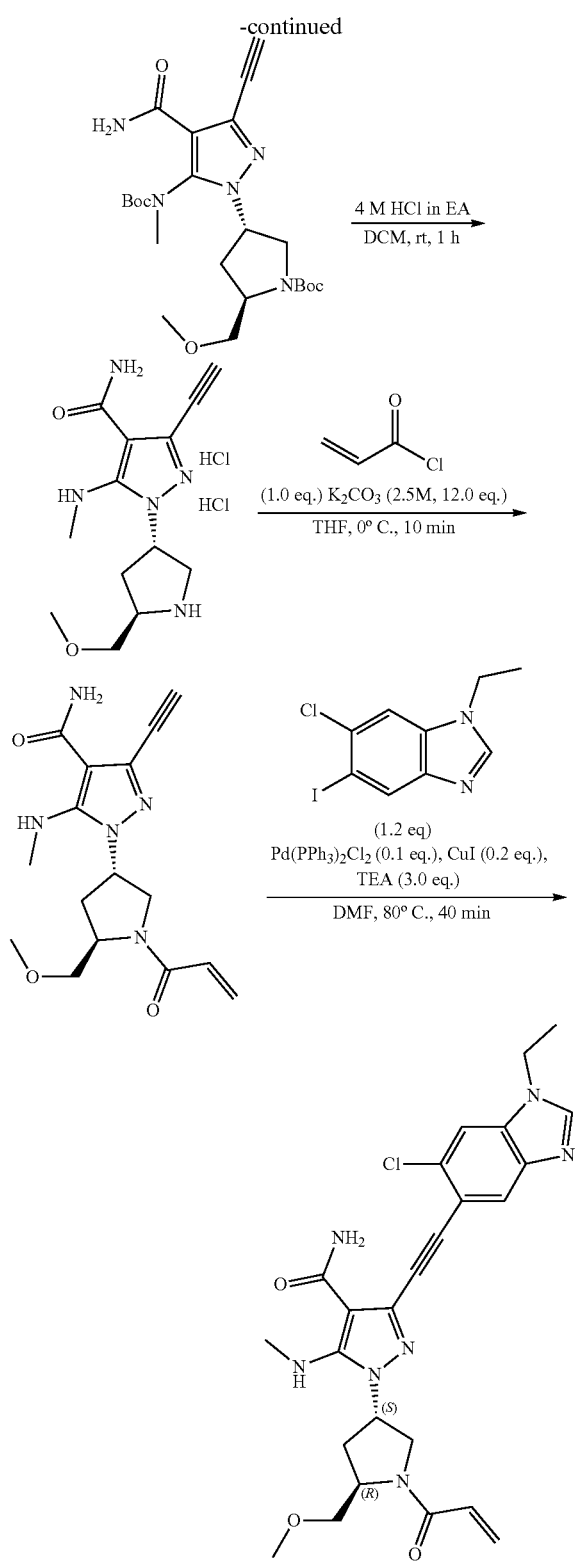

Step 1: Tert-butyl (2R,4R)-2-(methoxymethyl)-4-(tosyloxy)pyrrolidine-1-carboxylate To a stirred solution of tert-butyl (2R,4R)-4-hydroxy-2-(methoxymethyl)pyrrolidine-1-carboxylate (15.20 g, 65.72 mmol), TEA (18.27 mL, 131.44 mmol) and DMAP (1.21 g, 9.86 mmol) in DCM (150.00 mL) was added TsCl (18.79 g, 98.58 mmol) at 0° C. The reaction mixture was stirred for 16 h at room temperature under nitrogen atmosphere. The resulting mixture was diluted with water (80 mL) and extracted with DCM (3×150 mL). The combined organic layers were washed with brine (2×80 mL), dried over anhydrous $Na_2SO_4$ and filtered. The filtrate was concentrated under reduced pressure. The residue was purified by silica gel Column chromatography, eluted with 33% EA in PE. The fractions contained desired product were combined and concentrated to afford tert-butyl (2R,4R)-2-(methoxymethyl)-4-(tosyloxy)pyrrolidine-1-carboxylate (18.5 g, 73%) as a yellow oil. MS ESI calculated for $C_{18}H_{27}NO_6S$ [M+H]$^+$, 386.16, found 386.10; $^1$H NMR (400 MHz, CDCl$_3$) δ 7.88-7.72 (m, 2H), 7.38-7.35 (m, 2H), 5.04-5.48 (m, 1H), 3.99-3.95 (m, 1H), 3.65-3.61 (m, 2H), 3.39-3.26 (m, 5H), 2.46 (s, 3H), 2.25-2.23 (m, 1H), 2.18-2.15 (m, 1H), 1.44 (s, 9H).

Step 2: Tert-butyl (2R,4S)-4-(5-amino-3-bromo-4-cyano-1H-pyrazol-1-yl)-2-(methoxymethyl)pyrrolidine-1-carboxylate To a mixture of 3-amino-5-bromo-2H-pyrazole-4-carbonitrile (7.20 g, 38.50 mmol) and $Cs_2CO_3$ (25.09 g, 77.01 mmol) in ACN (190.00 mL) was added tert-butyl (2R,4R)-2-(methoxymethyl)-4-(tosyloxy)pyrrolidine-1-carboxylate (17.81 g, 46.20 mmol). The reaction mixture was stirred for 4 h at 90° C. The resulting mixture was cooled down to room temperature and filtered. The filter cake was washed with DCM (3×70 mL). The filtrate was concentrated under reduced pressure. The residue was purified by silica gel Column chromatography, eluted with 46% EA in PE. The fractions contained desired product were concentrated. The residue was purified by reverse phase-flash chromatography with the following conditions: Column, C18 silica gel; mobile phase, ACN in water (10 mmol/L NH$_4$HCO$_3$), 5% to 46% gradient in 30 min; detector, UV 254 nm. The fractions contained desired product were combined and concentrated to afford tert-butyl (2R,4S)-4-(5-amino-3-bromo-4-cyano-1H-pyrazol-1-yl)-2-(methoxymethyl)pyrrolidine-1-carboxylate (5 g, 32%) as an off-white solid. MS ESI calculated for $C_{15}H_{22}BrN_5O_3$ [M+H]$^+$, 400.09, 402.09, found 400.15, 402.15; $^1$H NMR (400 MHz, CDCl$_3$) δ 4.76-4.73 (m, 1H), 4.53-4.49 (m, 2H), 4.22-4.15 (m, 1H), 3.74-3.69 (m, 3H), 3.41-3.38 (m, 1H), 3.37 (s, 3H), 2.62-2.59 (m, 1H), 2.25-2.21 (m, 1H), 1.46 (s, 9H).

Step 3: Tert-butyl (2R,4S)-4-(3-bromo-4-cyano-5-formamido-1H-pyrazol-1-yl)-2-(methoxymethyl)pyrrolidine-1-carboxylate To a mixture of tert-butyl (2R,4S)-4-(5-amino-3-bromo-4-cyano-1H-pyrazol-1-yl)-2-(methoxymethyl)pyrrolidine-1-carboxylate (3.50 g, 8.74 mmol) in (diethoxymethoxy)ethane (70.00 mL) was added benzenesulfonic acid (0.23 g, 1.22 mmol). The reaction mixture was stirred for 2 h at 150° C. under nitrogen atmosphere. The resulting mixture was cooled down and concentrated under reduced pressure. The residue was diluted with water (50 mL). The resulting mixture was extracted with EA (3×150 mL). The combined organic layers were washed with brine (80 mL), dried over anhydrous $Na_2SO_4$ and filtered. The filtrate was concentrated and dried to afford tert-butyl (2R,4S)-4-(3-bromo-4-cyano-5-formamido-1H-pyrazol-1-yl)-2-(methoxymethyl) pyrrolidine-1-carboxylate (3.75 g, crude) as a yellow oil which was used in the next step directly without further purification. MS ESI calculated for $C_{16}H_{22}BrN_5O_4$ [M−H]⁻, 426.09, 428.09, found 426.15, 428.15.

Step 4: Tert-butyl (2R,4S)-4-(3-bromo-4-cyano-5-(methylamino)-1H-pyrazol-1-yl)-2-(methoxymethyl)pyrrolidine-1-carboxylate To a stirred solution of tert-butyl (2R,4S)-4-(3-bromo-4-cyano-5-formamido-1H-pyrazol-1-yl)-2-(methoxymethyl)pyrrolidine-1-carboxylate (3.75 g, 8.76 mmol) in EtOH (200.00 mL) was added NaBH₄ (1.56 g, 41.23 mmol) at 0° C. under nitrogen atmosphere. The reaction mixture was stirred for 1 h at room temperature. The resulting mixture was quenched with brine at 0° C. and extracted with EA (3×150 mL). The combined organic layers were washed with brine (70 mL), dried over anhydrous Na₂SO₄ and filtered. The filtrate was concentrated under reduced pressure. The residue was purified by silica gel Column chromatography, eluted with 62% EA in PE. The fractions contained desired product were combined and concentrated to afford tert-butyl (2R,4S)-4-(3-bromo-4-cyano-5-(methylamino)-1H-pyrazol-1-yl)-2-(methoxymethyl)pyrrolidine-1-carboxylate (3.3 g, 91%) as an off-white solid. MS ESI calculated for $C_{16}H_{24}BrN_5O_3$ [M−H]⁻, 412.11, 414.11, found 412.20, 414.20; ¹H NMR (400 MHz, CDCl₃): 4.64-4.61 (m, 1H), 4.43-4.20 (m, 2H), 3.71-3.63 (m, 3H), 3.40-3.37 (m, 1H), 3.36 (s, 3H), 3.21 (s, 3H), 2.62-2.58 (m, 1H), 2.22-2.17 (m, 1H), 1.46 (s, 9H).

Step 5: Tert-butyl (2R,4S)-4-[3-bromo-5-[(tert-butoxycarbonyl)(methyl)amino]-4-cyanopyrazol-1-yl]-2-(methoxymethyl)pyrrolidine-1-carboxylate To a stirred solution of tert-butyl (2R,4S)-4-[3-bromo-4-cyano-5-(methylamino)pyrazol-1-yl]-2-(methoxymethyl)pyrrolidine-1-carboxylate (20.30 g, 49.00 mmol) in DCM (300.00 mL) were added Boc₂O (20.97 mL, 98.01 mmol), DMAP (0.60 g, 4.90 mmol) and Et₃N (20.43 mL, 146.98 mmol) at 0° C. under nitrogen atmosphere. The reaction mixture was stirred for 1 h at rt. The resulting mixture was washed with water (3×200 mL) and brine (200 mL). The organic layer was dried over anhydrous Na₂SO₄ and filtered. The filtrate was concentrated under reduced pressure. The residue was purified by silica gel Column chromatography, eluted with 39% EA in PE. The fractions contained desired product were combined and concentrated to afford tert-butyl (2R,4S)-4-[3-bromo-5-[(tert-butoxycarbonyl)(methyl)amino]-4-cyanopyrazol-1-yl]-2-(methoxymethyl)pyrrolidine-1-carboxylate (24.0 g, 95%) as an off-white solid. MS ESI calculated for $C_{21}H_{32}BrN_5O_5$ [M+H]⁺, 516.16, found 516.15; ¹H NMR (400 MHz, CDCl₃) δ 4.94-4.90 (m, 1H), 4.23-4.19 (m, 1H), 3.75-3.66 (m, 3H), 3.44-3.40 (m, 1H), 3.36 (s, 3H), 3.25 (s, 3H), 2.62-2.58 (m, 1H), 2.41-2.19 (m, 1H), 1.48 (s, 18H).

Step 6: Tert-butyl (2R,4S)-4-[5-[(tert-butoxycarbonyl)(methyl)amino]-4-cyano-3-[2-(trimethylsilyl)ethynyl]pyrazol-1-yl]-2-(methoxymethyl)pyrrolidine-1-carboxylate To a stirred mixture of tert-butyl (2R,4S)-4-[3-bromo-5-[(tert-butoxycarbonyl)(methyl)amino]-4-cyanopyrazol-1-yl]-2-(methoxymethyl)pyrrolidine-1-carboxylate (24.00 g, 46.65 mmol), CuI (1.78 g, 9.33 mmol), Pd(PPh₃)₂Cl₂ (3.27 g, 4.67 mmol) and trimethylsilylacetylene (19.78 mL, 201.39 mmol) in DMF (240 mL) was added TEA (19.45 mL, 192.26 mmol) at room temperature. The reaction mixture was degassed with nitrogen for three times and stirred for 2 h at 90° C. The resulting mixture was concentrated under reduced pressure. The residue was diluted with water (500 mL) and extracted with EA (4×500 mL). The combined organic layers were washed with brine (2×500 mL), dried over anhydrous Na₂SO₄, filtered and concentrated under reduced pressure. The residue was purified by silica gel Column chromatography, eluted with 25% EA in PE. The fractions contained desired product were combined and concentrated to afford tert-butyl (2R,4S)-4-[5-[(tert-butoxycarbonyl)(methyl)amino]-4-cyano-3-[2-(trimethylsilyl)ethynyl]pyrazol-1-yl]-2-(methoxymethyl)pyrrolidine-1-carboxylate (24 g, 96%) as a brown solid. MS ESI calculated for $C_{26}H_{41}N_5O_5Si$ [M+H]⁺, 532.29, found 532.40; ¹H NMR (400 MHz, CDCl₃) δ 4.93-4.89 (m, 1H), 4.23-4.17 (m, 1H), 3.68-3.52 (m, 3H), 3.42-3.37 (m, 1H), 3.35-3.33 (m, 3H), 3.25-3.20 (m, 3H), 2.63-2.58 (m, 1H), 2.33-2.13 (m, 1H), 1.46 (s, 18H), 0.27 (s, 9H).

Step 7: Tert-butyl (2R,4S)-4-[5-[(tert-butoxycarbonyl)(methyl)amino]-4-cyano-3-ethynylpyrazol-1-yl]-2-(methoxymethyl)pyrrolidine-1-carboxylate To a stirred solution of tert-butyl (2R,4S)-4-[5-[(tert-butoxycarbonyl)(methyl)amino]-4-cyano-3-[2-(trimethylsilyl)ethynyl]pyrazol-1-yl]-2-(methoxymethyl)pyrrolidine-1-carboxylate (24.00 g, 45.14 mmol) in THF (200.00 mL) was added TBAF (67.70 mL, 67.70 mmol, 1 M in THF) at 0° C. The reaction mixture was stirred for 1 h at room temperature. The resulting mixture was concentrated under reduced pressure. The residue was diluted with water (500 mL) and extracted with EA (3×500 mL). The combined organic layers were washed with brine (2×500 mL), dried over anhydrous Na₂SO₄, filtered and concentrated under reduced pressure. The residue was purified by silica gel Column chromatography, eluted with 30% EA in PE. The fractions contained desired product were combined and concentrated to afford tert-butyl (2R,4S)-4-[5-[(tert-butoxycarbonyl)(methyl)amino]-4-cyano-3-ethynylpyrazol-1-yl]-2-(methoxymethyl)pyrrolidine-1-carboxylate (17.4 g, 83%) as an off-white solid. MS ESI calculated for $C_{23}H_{33}N_5O_5$ [M+H]⁺, 460.25, found 460.40; ¹H NMR (400 MHz, CDCl₃) δ 4.93-4.89 (m, 1H), 4.22-4.18 (m, 1H), 3.84-3.46 (m, 3H), 3.42-3.37 (m, 1H), 3.37-3.31 (m, 4H), 3.24 (s, 3H), 2.62-2.59 (m, 1H), 2.28-2.24 (m, 1H), 1.46 (s, 18H).

Step 8: Tert-butyl (2R,4S)-4-[5-[(tert-butoxycarbonyl)(methyl)amino]-4-carbamoyl-3-ethynylpyrazol-1-yl]-2-(methoxymethyl)pyrrolidine-1-carboxylate To a stirred solution of tert-butyl (2R,4S)-4-[5-[(tert-butoxycarbonyl)(methyl)amino]-4-cyano-3-ethynylpyrazol-1-yl]-2-(methoxymethyl)pyrrolidine-1-carboxylate (17.4 g, 37.86 mmol) in DMSO (30.00 mL) and EtOH (150.00 mL) were added 0.5 M NaOH (87.09 mL, 43.54 mmol) and H₂O₂ (10.26 mL, 132.14 mmol) at 0° C. The reaction mixture was stirred for 0.5 h at 0° C. and 0.5 h at room temperature. The resulting mixture was diluted with water (500 mL) and extracted with EA (3×500 mL). The combined organic layers were washed with brine (2×300 mL), dried over anhydrous Na₂SO₄, filtered and concentrated under reduced pressure. The residue was purified by silica gel Column chromatography, eluted with 65% EA in PE. The fractions contained desired product were combined and concentrated to afford tert-butyl (2R,4S)-4-[5-[(tert-butoxycarbonyl)(methyl)amino]-4-carbamoyl-3-ethynylpyrazol-1-yl]-2-(methoxymethyl)pyrrolidine-1-carboxylate (17.2 g, 95%) as an off-white solid. MS ESI calculated for $C_{23}H_{35}N_5O_6$ [M+H]$^+$, 478.26, found 478.25; $^1$H NMR (300 MHz, CDCl$_3$) 6.80 (brs, 1H), 5.67 (brs, 1H), 5.04-5.00 (m, 1H), 4.23-4.19 (m, 1H), 3.75-3.67 (m, 3H), 3.49-3.42 (m, 1H), 3.39-3.32 (m, 3H), 3.14 (s, 3H), 2.72-2.60 (m, 1H), 2.32-2.21 (m, 1H), 1.62-1.31 (m, 18H).

Step 9: 3-Ethynyl-1-[(3S,5R)-5-(methoxymethyl) pyrrolidin-3-yl]-5-(methylamino)pyrazole-4-carboxamide dihydrochloride To a stirred mixture of tert-butyl (2R,4S)-4-[5-[(tert-butoxycarbonyl)(methyl)amino]-4-carbamoyl-3-ethynylpyrazol-1-yl]-2-(methoxymethyl)pyrrolidine-1-carboxylate (17.2 g, 36.02 mmol) in DCM (170.00 mL) was added HCl (180.08 mL, 720.32 mmol, 4 M in EA). The reaction mixture was stirred for 1 h at room temperature under argon atmosphere. The resulting mixture was concentrated and dried to afford 3-ethynyl-1-[(3S,5R)-5-(methoxymethyl) pyrrolidin-3-yl]-5-(methylamino)pyrazole-4-carboxamide dihydrochloride (12.5 g, 99%) as an off-white solid which was used in the next step directly without further purification. MS ESI calculated for $C_{13}H_{21}Cl_2N_5O_2$ [M+H−2 HCl]$^+$, 278.15, found 278.05.

Step 10: 3-Ethynyl-1-[(3S,5R)-5-(methoxymethyl)-1-(prop-2-enoyl)pyrrolidin-3-yl]-5-(methylamino) pyrazole-4-carboxamide To a stirred mixture of 3-ethynyl-1-[(3S,5R)-5-(methoxymethyl)pyrrolidin-3-yl]-5-(methylamino)pyrazole-4-carboxamide dihydrochloride (12.50 g, 35.69 mmol) and K$_2$CO$_3$ (172 mL, 430 mmol, 2.5 M) in THF (250.00 mL) was added acryloyl chloride ((2.91 mL, 32.15 mmol) in THF (15.00 mL) dropwise at 0° C. under argon atmosphere. The reaction mixture was stirred for 10 min at 0° C. The resulting mixture was diluted with water (500 mL) and extracted with EA (3×500 mL). The combined organic layers were washed with brine (2×300 mL), dried over anhydrous Na$_2$SO$_4$, filtered and concentrated under reduced pressure. The residue was purified by silica gel Column chromatography, eluted with 5% DCM in MeOH. The fractions contained desired product were combined and concentrated to afford 3-ethynyl-1-[(3S,5R)-5-(methoxymethyl)-1-(prop-2-enoyl) pyrrolidin-3-yl]-5-(methylamino)pyrazole-4-carboxamide (11.1 g, 84%) as an off-white solid. MS ESI calculated for $C_{16}H_{21}N_5O_3$ [M+H]$^+$, 332.16, found 332.20; $^1$H NMR (400 MHz, CDCl$_3$) δ 6.76 (s, 1H), 6.60-6.36 (m, 2H), 5.74-5.68 (m, 1H), 5.50-5.20 (m, 2H), 4.55-4.39 (m, 1H), 4.06-3.83 (m, 3H), 3.53-3.40 (m, 2H), 3.36-3.35 (m, 3H), 3.03-2.99 (m, 3H), 2.68-2.60 (m, 1H), 2.37-2.23 (m, 1H).

Step 11: 3-[2-(6-Chloro-1-ethyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide To a stirred mixture of 3-ethynyl-1-[(3S,5R)-5-(methoxymethyl)-1-(prop-2-enoyl)pyrrolidin-3-yl]-5-(methylamino)pyrazole-4-carboxamide (0.45 g, 1.36 mmol) and 6-chloro-1-ethyl-5-iodo-1,3-benzodiazole (0.50 g, 1.63 mmol) in DMF (5.00 mL) was added CuI (51.73 mg, 0.27 mmol), Pd(PPh$_3$)$_2$Cl$_2$ (95.32 mg, 0.14 mmol) and TEA (0.41 g, 4.07 mmol) dropwise at room temperature. The reaction mixture was degassed with argon for three times and stirred for 40 min at 80° C. The resulting mixture was concentrated under reduced pressure. The residue was purified by silica gel Column chromatography, eluted with CH$_2$Cl$_2$/MeOH (0-10%) to afford the crude product. The crude product was purified by reverse flash chromatography with the following conditions: Column: XBridge Prep C18 OBD Column, 5×25 cm 5 μm; Mobile Phase A: Water (10 mmol/L NH$_4$HCO$_3$), Mobile Phase B: ACN; Flow rate: 40 mL/min; Gradient: 5 B to 55 B in 60 min; 210/254 nm. The fractions contained desired product were combined and concentrated to afford 3-[2-(6-chloro-1-ethyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (0.35 g, 50%) as an off-white solid. MS ESI calculated for $C_{25}H_{28}ClN_7O_3$ [M+H]$^+$, 510.19, found 510.10; $^1$H NMR (300 MHz, CDCl$_3$) δ 8.02-7.96 (m, 2H), 7.21 (s, 1H), 6.83 (d, J=6.2 Hz, 1H), 6.47-6.37 (m, 2H), 5.72 (dd, J=8.2, 4.2 Hz, 1H), 5.62-5.31 (m, 2H), 4.60-4.56 (m, 1H), 4.28-4.24 (m, 2H), 4.19-4.02 (m, 2H), 3.94-3.89 (m, 1H), 3.42-3.36 (m, 4H), 3.10-3.04 (m, 3H), 2.76-2.73 (m, 1H), 2.46-2.26 (m, 1H), 1.59-1.55 (m, 3H).

Example 90: 3-[2-(6-Fluoro-1H-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide

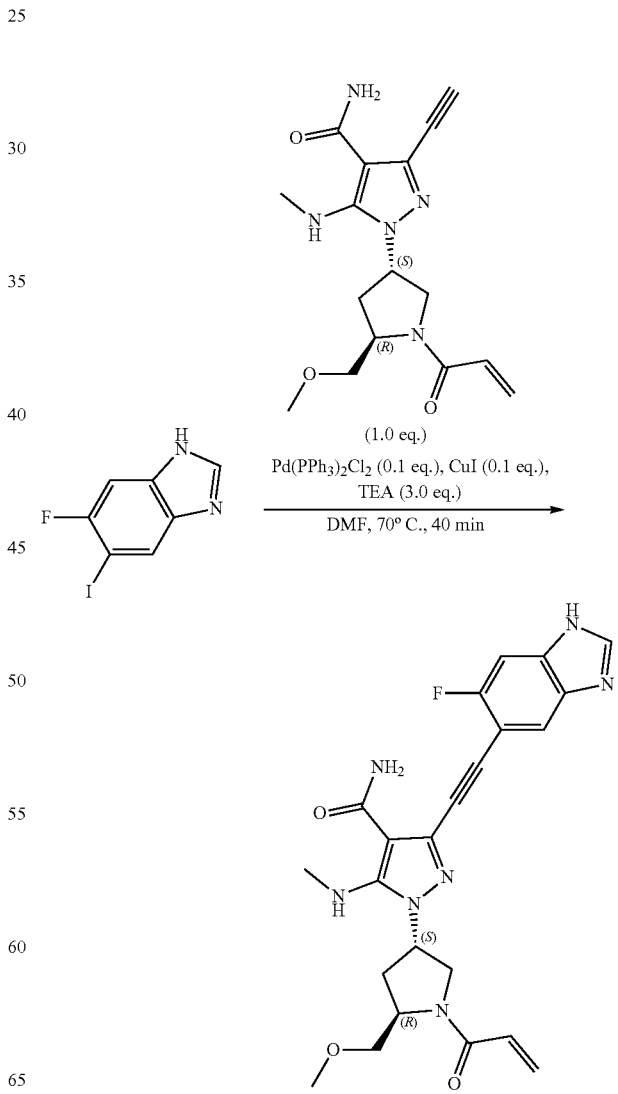

To a stirred mixture of 3-ethynyl-1-[(3S,5R)-5-(methoxymethyl)-1-(prop-2-enoyl)pyrrolidin-3-yl]-5-(methylamino)pyrazole-4-carboxamide (0.20 g, 0.60 mmol), 5-fluoro-6-iodo-3H-1,3-benzodiazole (0.19 g, 0.72 mmol), Pd(PPh$_3$)$_2$Cl$_2$ (42.36 mg, 0.06 mmol), CuI (22.99 mg, 0.12 mmol) in DMF (4.00 mL) was added TEA (0.18 g, 1.81 mmol) dropwise at room temperature. The reaction mixture was degassed with argon for three times and stirred for 40 min at 70° C. The resulting mixture was concentrated under reduced pressure. The residue was purified by silica gel Column chromatography, eluted with MeOH in DCM (0-5%) to afford the crude product. The crude product was purified by Prep-HPLC with the following conditions: Column: XBridge Prep C18 OBD Column, 19×150 mm 5 μm; Mobile Phase A: Water (10 mmol/L NH$_4$HCO$_3$), Mobile Phase B: ACN; Flow rate: 20 mL/min; Gradient: 5 B to 50 B in 5.8 min; 210/254 nm; RT: 5.75 min. The fractions contained desired product were combined and concentrated to afford 3-[2-(6-fluoro-1H-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (69.60 mg, 24%) as an off-white solid. MS ESI calculated for C$_{23}$H$_{24}$FN$_7$O$_3$ [M+H]$^+$, 466.19, found 466.05; $^1$H NMR (400 MHz, CDCl$_3$) δ 11.35 (d, J=184.5 Hz, 1H), 8.17 (s, 1H), 7.69 (d, J=73.3 Hz, 1H), 7.17 (s, 1H), 6.88-6.70 (m, 1H), 6.57-6.25 (m, 2H), 5.74 (d, J=10.9 Hz, 1H), 5.66-5.15 (m, 2H), 4.70-4.38 (m, 1H), 4.15-4.07 (m, 2H), 3.90 (d, J=9.2 Hz, 1H), 3.60-3.17 (m, 5H), 3.06-3.01 (m, 3H), 2.76-2.68 (m, 1H), 2.35-2.07 (m, 1H).

Example 91: 3-[2-(6-Fluoro-2-methyl-1H-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide

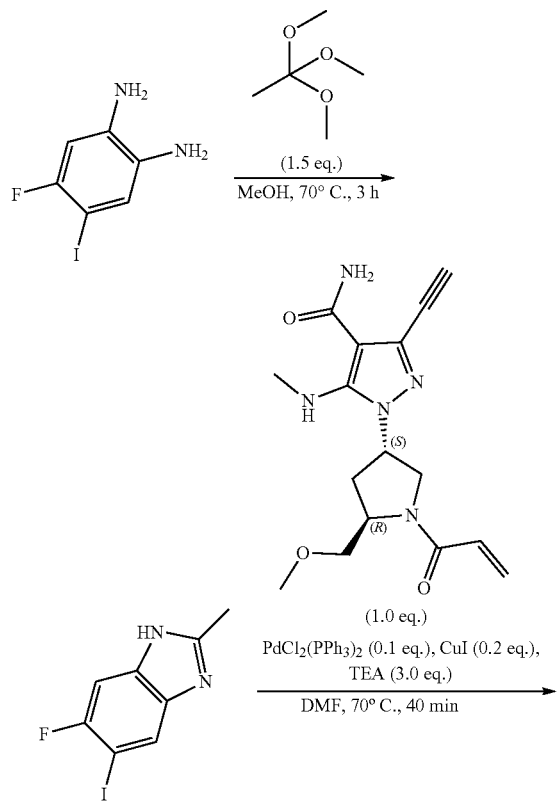

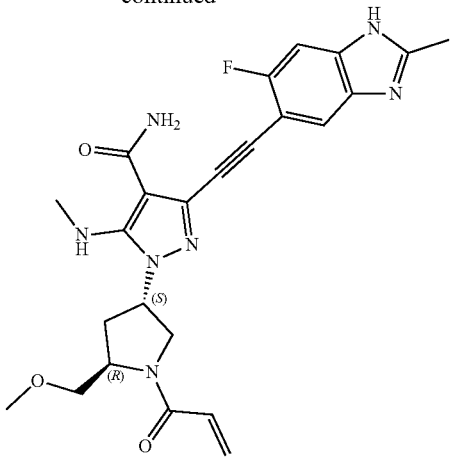

Step 1:
5-Fluoro-6-iodo-2-methyl-3H-1,3-benzodiazole

To a stirred solution of 4-fluoro-5-iodobenzene-1,2-diamine (5.00 g, 19.84 mmol) in MeOH (50.00 mL) was added 1,1,1-trimethoxyethane (3.58 g, 29.76 mmol) at room temperature. The reaction mixture was stirred for 3 h at 70° C. under argon atmosphere. The resulting mixture was cooled down and concentrated under reduced pressure. The residue was purified by silica gel Column chromatography, eluted with EA in PE (0-80%). The fractions contained desired product were combined and concentrated to afford 5-fluoro-6-iodo-2-methyl-3H-1,3-benzodiazole (4.96 g, 90%) as a brown semi-solid. MS ESI calculated for C$_8$H$_6$FN$_2$ [M+H]$^+$, 276.96, found 276.85; H NMR (400 MHz, CDCl$_3$) δ 7.89 (d, J=5.3 Hz, 1H), 7.30 (s, 1H), 2.64 (s, 3H).

Step 2: 3-[2-(6-Fluoro-2-methyl-1H-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide To a stirred solution of 3-ethynyl-1-[(3S,5R)-5-(methoxymethyl)-1-(prop-2-enoyl)pyrrolidin-3-yl]-5-(methylamino)pyrazole-4-carboxamide (0.20 g, 0.60 mmol), 5-fluoro-6-iodo-2-methyl-3H-1,3-benzodiazole (0.18 g, 0.66 mmol), Pd(PPh$_3$)$_2$Cl$_2$ (42.36 mg, 0.06 mmol) and CuI (22.99 mg, 0.12 mmol) in DMF (6.00 mL) was added TEA (0.18 g, 1.81 mmol) at room temperature under argon atmosphere. The reaction mixture was degassed with argon for three times and stirred for 40 minutes at 70° C. The resulting mixture was concentrated under reduced pressure. The residue was purified by silica gel Column chromatography, eluted with CH$_2$Cl$_2$/MeOH (10/1). The fractions contained desired product were combined and concentrated. The crude product was purified by reverse flash chromatography with the following conditions: Column: XBridge Prep C18 OBD Column, 19×150 mm 5 μm; Mobile Phase A: Water (10 mmol/L NH$_4$HCO$_3$), Mobile Phase B: ACN; Flow rate: 20 mL/min; Gradient: 5 B to 50 B in 5.8 min; 210/254 nm; RT: 5.58 min. The fractions contained desired product were combined and concentrated to afford 3-[2-(6-fluoro-2-methyl-1H-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (0.12 g, 40%) as an off-white solid. MS ESI calculated for C$_{24}$H$_{26}$FN$_7$O$_3$

[M+H]+, 480.22, found 480.10; 1H NMR (400 MHz, CDCl3) δ 7.67-7.58 (m, 1H), 7.27 (d, J=23.5 Hz, 1H), 7.18 (s, 1H), 6.83-6.81 (m, 1H), 6.62-6.35 (m, 2H), 5.78-5.72 (m, 1H), 5.55-5.26 (m, 2H), 4.58-4.45 (m, 1H), 4.18-4.10 (m, 1H), 4.08-3.95 (m, 1H), 3.90-3.85 (m, 1H), 3.45-3.42 (m, 1H), 3.39-3.35 (m, 3H), 3.04-3.01 (m, 3H), 2.79-2.62 (m, 1H), 2.65 (s, 3H), 2.45-2.29 (m, 1H).

Example 92: 3-[2-(6-Chloro-1H-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide

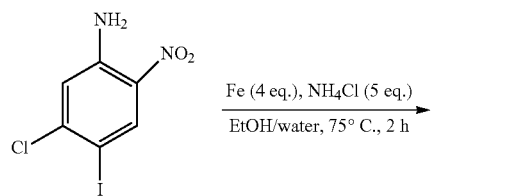

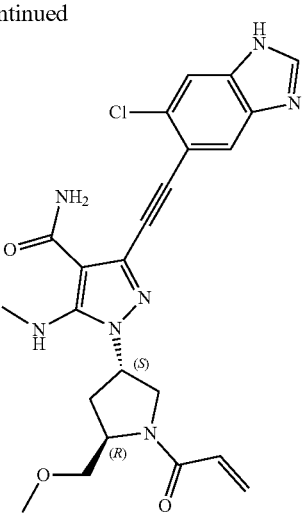

Step 1: 4-Chloro-5-iodobenzene-1,2-diamine

To a stirred mixture of 5-chloro-4-iodo-2-nitroaniline (3.00 g, 10.05 mmol) and Fe (0.22 g, 4.01 mmol) in EtOH (10.50 mL) and H2O (1.50 mL) was added NH4Cl (0.27 g, 5.01 mmol) at room temperature. The reaction mixture was stirred for 2 h at 75° C. The resulting mixture was filtered, the filter cake was washed with EtOH (3×200 mL). The filtrate was concentrated under reduced pressure. The residue was diluted with water (300 mL) and extracted with EtOAc (3×200 mL). The combined organic layers were washed with brine (2×300 mL), dried over anhydrous Na2SO4 and filtered. The filtrate was concentrated under reduced pressure. The residue was purified by silica gel Column chromatography, eluted with 50% PE in EA. The fractions contained desired product were combined and concentrated to afford 4-chloro-5-iodobenzene-1,2-diamine (1.13 g, 41%) as a light yellow solid. MS ESI calculated for C6H6ClIN2 [M+H]+, 268.93, found 268.90; 1H NMR (400 MHz, CDCl3) δ 7.11 (s, 1H), 6.80 (s, 1H).

Step 2: 5-Chloro-6-iodo-3H-1,3-benzodiazole

To a stirred mixture of 4-chloro-5-iodobenzene-1,2-diamine (1.00 g, 3.73 mmol) in MeOH (15.00 mL) was added trimethyl orthoformate (0.59 g, 5.59 mmol). The reaction mixture was stirred for 16 h at 75° C., The resulting mixture was concentrated under reduced pressure. The residue was purified by silica gel Column chromatography, eluted with 5% MeOH in DCM. The fractions contained desired product were combined and concentrated to afford 5-chloro-6-iodo-3H-1,3-benzodiazole (0.66 g, 63%) as a light brown solid. MS ESI calculated for C7H4Cl1IN2 [M+H]+, 278.91, found 278.95.

Step 3: 3-[2-(6-Chloro-1H-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide To a stirred mixture of 3-ethynyl-1-[(3S,5R)-5-(methoxymethyl)-1-(prop-2-enoyl) pyrrolidin-3-yl]-5-

(methylamino) pyrazole-4-carboxamide (0.24 g, 0.72 mmol), 5-chloro-6-iodo-3H-1,3-benzodiazole (0.20 g, 0.72 mmol), CuI (27.20 mg, 0.14 mmol) and Pd(PPh$_3$)$_2$Cl$_2$ (50.41 mg, 0.07 mmol) in DMF (2.00 mL) was added TEA (0.40 mL, 2.88 mmol) at room temperature. The reaction mixture was degassed with argon for three times and stirred for 1 h at 70° C. The resulting mixture was concentrated under reduced pressure. The residue was purified by silica gel Column chromatography, eluted with 6% MeOH in DCM. The fractions contained desired product were combined and concentrated. The crude product was purified by Prep-HPLC with the following conditions: Column: X Bridge Prep C18 OBD Column, 19×150 mm 5 µm; Mobile Phase A: Water (10 mmol/L NH$_4$HCO$_3$), Mobile Phase B: ACN; Flow rate: 20 mL/min; Gradient: 35 B to 70 B in 5.8 min, 210/254 nm; RT: 5.58 min. The fractions contained desired product were combined and concentrated to afford 3-[2-(6-chloro-1H-1,3-benzodiazol-5-yl)ethynyl]-1-[(3S,5R)-5-(methoxymethyl)-1-(prop-2-enoyl)pyrrolidin-3-yl]-5-(methylamino) pyrazole-4-carboxamide (0.20 g, 57%) as a brown solid. MS ESI calculated for C$_{23}$H$_{24}$ClN$_7$O$_3$ [M+H]$^+$, 482.16, found 482.05; $^1$H NMR (300 MHz, DMSO-d$_6$) δ 12.84 (s, 1H), 8.41 (s, 1H), 7.91 (d, J=37.6 Hz, 2H), 7.52 (s, 1H), 7.04-6.49 (m, 3H), 6.18 (d, J=16.6 Hz, 1H), 5.87-5.62 (m, 1H), 5.39-5.19 (m, 1H), 4.49-4.45 (m, 1H), 4.07-3.56 (m, 4H), 3.34-3.29 (m, 3H), 2.97-2.94 (m, 3H), 2.56-2.54 (m, 1H), 2.33-2.29 (m, 1H).

Example 93: 3-[2-[6-Chloro-3-(difluoromethyl)-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide

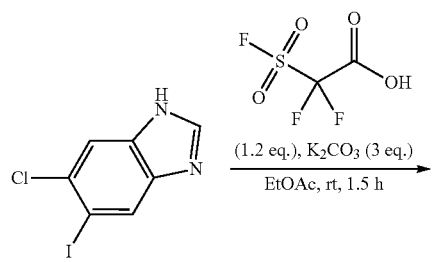

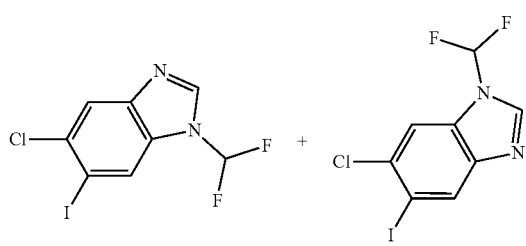

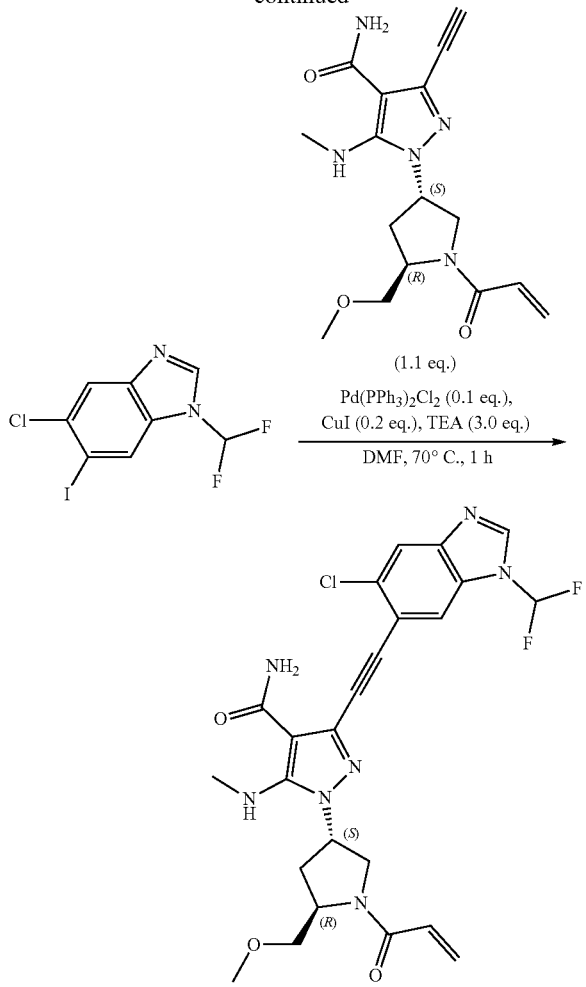

Step 1: 5-Chloro-1-(difluoromethyl)-6-iodo-1,3-benzodiazole and 6-chloro-1-(difluoromethyl)-5-iodo-1,3-benzodiazole To a stirred mixture of 5-chloro-6-iodo-3H-1,3-benzodiazole (3.20 g, 11.49 mmol) and K$_2$CO$_3$ (4.76 g, 34.47 mmol) in EA (32.00 mL) was added difluoro(sulfo)acetic acid (2.46 g, 13.79 mmol) dropwise at 0° C. under nitrogen atmosphere. The reaction mixture was stirred for 1.5 h at room temperature. The resulting mixture was concentrated under reduced pressure. The residue was purified by silica gel Column chromatography, eluted with 39% EA in PE. The fractions contained desired product were combined and concentrated. The crude product was purified by Prep-SFC with the following conditions Column: Chiralpak AD-H, 5×25 cm, 5 µm; Mobile Phase A: CO$_2$, Mobile Phase B: MeOH (0.1% 2 M NH$_3$-MeOH); Flow rate: 200 mL/min; Gradient: 50% B, 220 nm; RT1: 4.98 min; RT2: 6.49 min; Injection volume: 2.5 mL; Number of runs: 20. The faster peak contained desired product were combined and concentrated to afford 5-chloro-1-(difluoromethyl)-6-iodo-1,3-benzodiazole (0.97 g, 24%) as an off-white solid. MS ESI calculated for C$_8$H$_4$ClF$_2$IN$_2$ [M+H]$^+$, 328.91, found 328.95; $^1$H NMR (400 MHz, CDCl$_3$) δ 8.14 (s, 1H), 8.09 (s, 1H), 7.96 (s, 1H), 7.28 (t, J=60.1 Hz, 1H).

The slower peak contained desired product were combined and concentrated to afford 6-chloro-1-(difluoromethyl)-5-iodo-1,3-benzodiazole (0.99 g, 24%) as an off-white solid. MS ESI calculated for $C_8H_4ClF_2IN_2$ [M+H]$^+$, 328.91, found 328.95; $^1$H NMR (400 MHz, CDCl$_3$) δ 8.35 (s, 1H), 8.08 (s, 1H), 7.78 (s, 1H), 7.29 (t, J=60.1 Hz, 1H).

Step 2: 3-[2-[6-Chloro-3-(difluoromethyl)-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide To a stirred mixture of 5-chloro-1-(difluoromethyl)-6-iodo-1,3-benzodiazole (0.3 g, 0.91 mmol), 3-ethynyl-1-[(3S,5R)-5-(methoxymethyl)-1-(prop-2-enoyl)pyrrolidin-3-yl]-5-(methylamino)pyrazole-4-carboxamide (0.33 g, 1.01 mmol), CuI (34.79 mg, 0.18 mmol) and Pd(PPh$_3$)$_2$Cl$_2$ (64.10 mg, 0.09 mmol) in DMF (6.00 mL) was added TEA (0.38 mL, 3.76 mmol). The reaction mixture was degassed with argon for three times and stirred for 1 h at 70° C. The resulting mixture was diluted with EtOAc (300 mL), washed with water (3×100 mL), dried over anhydrous Na$_2$SO$_4$ and filtered. The filtrate was concentrated under reduced pressure. The residue was purified by Prep-HPLC with the following conditions: Column: XBridge Prep C18 OBD Column, 19×150 mm 5 μm; Mobile Phase A: Water (10 mmol/L NH$_4$HCO$_3$), Mobile Phase B: ACN; Flow rate: 20 mL/min; Gradient: 35 B to 70 B in 5.8 min; 210 nm; RT: 5.58 min. The fractions contained desired product were combined and concentrated to afford 3-[2-[6-chloro-3-(difluoromethyl)-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide (0.30 g, 62%) as an off-white solid. MS ESI calculated for $C_{24}H_{24}ClF_2N_7O_3$ [M+H]$^+$, 532.16, found 532.20; $^1$H NMR (400 MHz, CDCl$_3$) δ 8.22 (s, 1H), 7.98 (d, J=8.0 Hz, 1H), 7.93 (d, J=2.0 Hz, 1H), 7.34 (s, 1H), 7.16 (s, 1H), 6.59-6.36 (m, 2H), 5.78-5.70 (m, 1H), 5.61-5.26 (m, 2H), 4.65-4.35 (m, 1H), 4.15-3.96 (m, 2H), 3.94-3.83 (m, 1H), 3.55-3.42 (m, 1H), 3.39 (d, J=5.6 Hz, 3H), 3.05 (d, J=14.2 Hz, 3H), 2.78-2.66 (m, 1H), 2.45-2.29 (m, 1H).

Example 94: 3-[2-[6-Chloro-1-(difluoromethyl)-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide

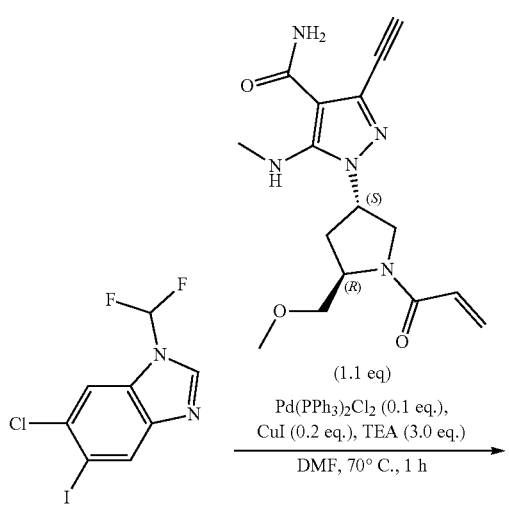

(1.1 eq)
Pd(PPh$_3$)$_2$Cl$_2$ (0.1 eq.),
CuI (0.2 eq.), TEA (3.0 eq.)
DMF, 70° C., 1 h

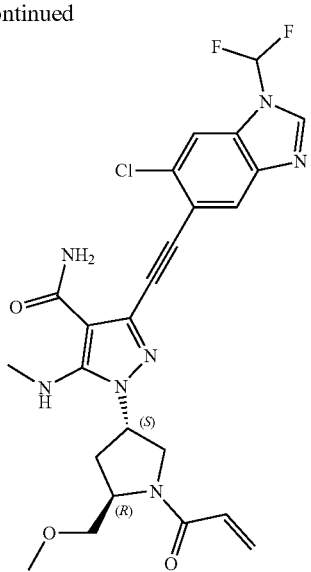

To a stirred mixture of 6-chloro-1-(difluoromethyl)-5-iodo-1,3-benzodiazole (0.3 g, 0.91 mmol), 3-ethynyl-1-[(3S,5R)-5-(methoxymethyl)-1-(prop-2-enoyl)pyrrolidin-3-yl]-5-(methylamino)pyrazole-4-carboxamide (0.33 g, 1.01 mmol), CuI (34.79 mg, 0.18 mmol) and Pd(PPh$_3$)$_2$Cl$_2$ (64.10 mg, 0.09 mmol) in DMF (6.00 mL) was added TEA (0.38 mL, 3.76 mmol). The reaction mixture was degassed with argon for three times and stirred for 1 h at 70° C. The resulting mixture was diluted with EtOAc (300 mL), washed with water (3×100 mL), dried over anhydrous Na$_2$SO$_4$ and filtered. The filtrate was concentrated under reduced pressure. The residue was purified by Prep-HPLC with the following conditions: Column: Atlantis HILIC OBD Column, 19×150 mm×5 μm; Mobile Phase A: Water (10 mmol/L NH$_4$HCO$_3$), Mobile Phase B: ACN; Flow rate: 20 mL/min; Gradient: 35 B to 70 B in 5.8 min; 210/254 nm. The fractions contained desired product were combined and concentrated to afford 3-[2-[6-chloro-1-(difluoromethyl)-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide (0.23 g, 47%) as an off-white solid. MS ESI calculated for $C_{24}H_{24}ClF_2N_7O_3$ [M+H]$^+$, 532.16 found 532.20; $^1$H NMR (400 MHz, CDCl$_3$) δ 8.33-8.09 (m, 2H), 7.79 (s, 1H), 7.50-7.31 (m, 1H), 7.23-7.06 (m, 1H), 6.57-6.38 (m, 2H), 5.77-5.70 (m, 1H), 5.61-5.25 (m, 2H), 4.63-4.39 (m, 1H), 4.17-4.00 (m, 2H), 3.95-3.85 (m, 1H), 3.55-3.43 (m, 1H), 3.40-3.39 (m, 3H), 3.07-3.04 (m, 3H), 2.79-2.67 (m, 1H), 2.45-2.28 (m, 1H).

Example 95: 3-[2-[6-Chloro-3-(difluoromethyl)-2-methyl-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide

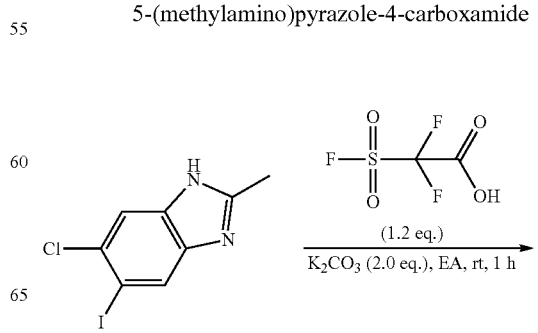

(1.2 eq.)
K$_2$CO$_3$ (2.0 eq.), EA, rt, 1 h

-continued

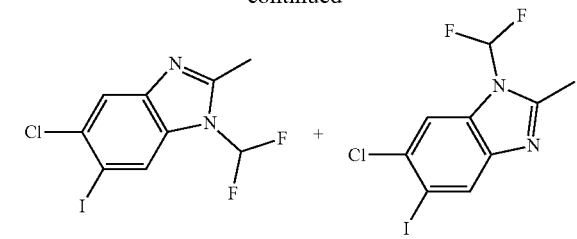

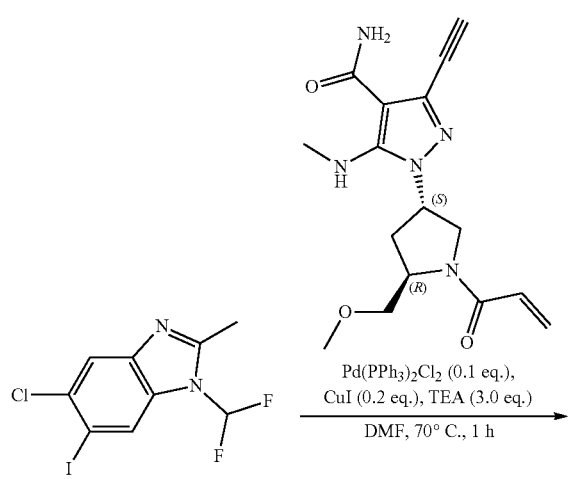

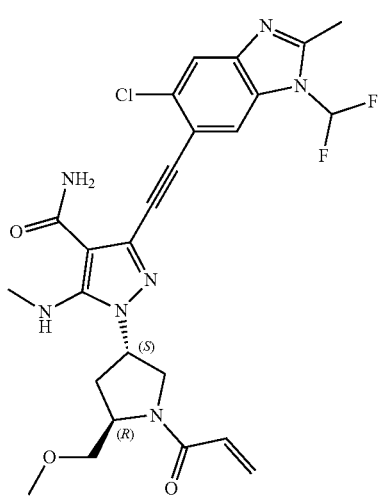

Step 1: 5-Chloro-1-(difluoromethyl)-6-iodo-2-methyl-1H-benzo[d]imidazole and 6-chloro-1-(difluoromethyl)-5-iodo-2-methyl-1H-benzo[d]imidazole To a stirred mixture of 5-chloro-6-iodo-2-methyl-3H-1,3-benzodiazole (0.30 g, 1.03 mmol) and $K_2CO_3$ (0.28 g, 2.05 mmol) in EtOAc (5.00 mL) was added difluoro(sulfo)acetic acid (0.22 g, 1.23 mmol) at 0° C. The reaction mixture was stirred for 1 h at room temperature. The resulting mixture was concentrated under reduced pressure. The residue was purified by silica gel Column chromatography, eluted with $CH_2Cl_2$/MeOH (10/1) to afford the crude product. The crude product (1.8 g) was purified by Prep-SFC with the following conditions Column: Chiralpak IG, 5×25 cm, 10 μm; Mobile Phase A: $CO_2$, Mobile Phase B: MeOH (0.1% 2 M $NH_3$-MeOH); Flow rate: 200 mL/min; Gradient: 50% B; 220 nm; RT1: 4.1 min; RT2: 9.07 min; Injection volume: 4.8 mL; Number of runs: 10. The faster peak contained desired product were combined and concentrated to afford 6-chloro-1-(difluoromethyl)-5-iodo-2-methyl-1H-benzo[d]imidazole (0.82 g, 35%) as a white solid. $^1H$ NMR (300 MHz, $CDCl_3$) δ 8.19 (s, 1H), 7.72 (s, 1H), 7.48-7.00 (m, 1H), 2.71 (s, 3H).

The slower peak contained desired product were combined and concentrated to afford 5-chloro-1-(difluoromethyl)-6-iodo-2-methyl-1H-benzo[d]imidazole (0.85 g, 36%) as a white solid. $^1H$ NMR (300 MHz, $CDCl_3$) δ 8.07 (s, 1H), 7.82 (s, 1H), 7.45-6.95 (m, 1H), 2.71 (s, 3H).

Step 2: 3-[2-[6-Chloro-3-(difluoromethyl)-2-methyl-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide To a stirred mixture of 5-chloro-1-(difluoromethyl)-6-iodo-2-methyl-1,3-benzodiazole (0.3 g, 0.88 mmol), 3-ethynyl-1-[(3S,5R)-5-(methoxymethyl)-1-(prop-2-enoyl)pyrrolidin-3-yl]-5-(methylamino)pyrazole-4-carboxamide (0.32 g, 0.96 mmol), CuI (33.36 mg, 0.18 mmol) and $Pd(PPh_3)_2Cl_2$ (61.48 mg, 0.09 mmol) in DMF (6.00 mL) was added TEA (0.37 mL, 3.61 mmol). The reaction mixture was degassed with argon for three times and stirred for 1 h at 70° C. The resulting mixture was diluted with EtOAc (300 mL), washed with water (3×100 mL), dried over anhydrous $Na_2SO_4$ and filtered. The filtrate was concentrated under reduced pressure. The residue was purified by Prep-HPLC with the following conditions: Column: XBridge Prep C18 OBD Column, 19×150 mm×5 μm; Mobile Phase A: Water (10 mmol/L $NH_4HCO_3$), Mobile Phase B: ACN; Flow rate: 20 mL/min; Gradient: 25 B to 60 B in 5.8 min; 210 nm; RT: 5.58 min; The fractions contained desired product were combined and concentrated to afford 3-[2-[6-chloro-3-(difluoromethyl)-2-methyl-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide (0.27 g, 56%) as an off-white solid. MS ESI calculated for $C_{25}H_{26}ClF_2N_7O_3$ $[M+H]^+$, 546.18, found 546.25; $^1H$ NMR (400 MHz, $CDCl_3$) δ 7.91 (d, J=8.0 Hz, 1H), 7.78 (d, J=1.6 Hz, 1H), 7.16 (d, J=17.2 Hz, 1H), 6.59-6.36 (m, 2H), 5.78-5.70 (m, 1H), 5.60-5.20 (m, 2H), 4.62-4.38 (m, 1H), 4.15-3.96 (m, 2H), 3.94-3.86 (m, 1H), 3.55-3.42 (m, 1H), 3.39 (d, J=5.2 Hz, 3H), 3.05 (d, J=14.4 Hz, 3H), 2.75 (s, 3H), 2.78-2.66 (m, 1H), 2.45-2.28 (m, 1H).

Example 96: 3-[2-[6-Chloro-1-(difluoromethyl)-2-methyl-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide

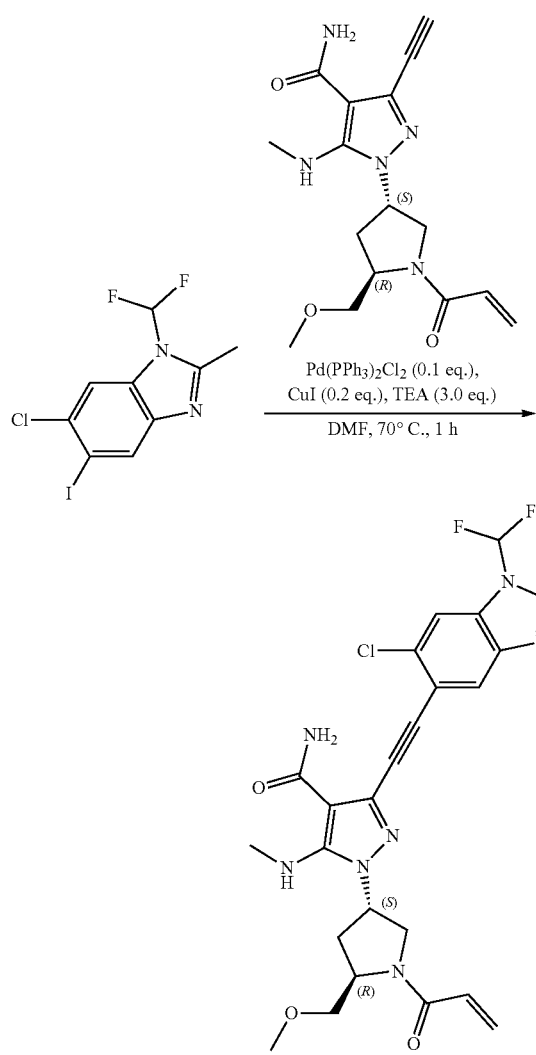

To a stirred mixture of 6-chloro-1-(difluoromethyl)-5-iodo-2-methyl-1,3-benzodiazole (0.3 g, 0.88 mmol), 3-ethynyl-1-[(3S,5R)-5-(methoxymethyl)-1-(prop-2-enoyl)pyrrolidin-3-yl]-5-(methylamino)pyrazole-4-carboxamide (0.32 g, 0.96 mmol), CuI (33.36 mg, 0.18 mmol) and Pd(PPh$_3$)$_2$Cl$_2$ (61.48 mg, 0.09 mmol) in DMF (6.00 mL) was added TEA (0.37 mL, 3.61 mmol). The reaction mixture was degassed with argon for three times and stirred for 1 h at 70° C. The resulting mixture was diluted with EtOAc (300 mL), washed with water (3×100 mL), dried over anhydrous Na$_2$SO$_4$ and filtered. The filtrate was concentrated under reduced pressure. The residue was purified by Prep-HPLC with the following conditions: Column: XBridge Prep C18 OBD Column, 19×150 mm×5 μm; Mobile Phase A: Water (10 mmol/L NH$_4$HCO$_3$), Mobile Phase B: ACN; Flow rate: 20 mL/min; Gradient: 25 B to 60 B in 5.8 min; 210/254 nm; RT: 5.58 min. The fractions contained desired product were combined and concentrated to afford 3-[2-[6-chloro-1-(difluoromethyl)-2-methyl-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide (0.25 g, 52%) as an off-white solid. MS ESI calculated for C$_{25}$H$_{26}$ClF$_2$N$_7$O$_3$ [M+H]$^+$, 546.18, found 546.25; $^1$H NMR (400 MHz, CDCl$_3$) δ 7.99 (d, J=5.2 Hz, 1H), 7.69 (s, 1H), 7.14 (s, 1H), 6.59-6.36 (m, 2H), 5.77-5.69 (m, 1H), 5.59-5.26 (m, 2H), 4.63-4.36 (m, 1H), 4.17-3.99 (m, 2H), 3.95-3.85 (m, 1H), 3.55-3.42 (m, 1H), 3.39 (d, J=5.2 Hz, 3H), 3.05 (d, J=15.2 Hz, 3H), 2.74 (s, 3H), 2.74-2.66 (m, 1H), 2.44-2.28 (m, 1H).

Example 97: 3-[2-(4,6-Difluoro-1-methyl-1,2,3-benzotriazol-5-yl)ethynyl]-1-[(3S,5R)-5-(methoxymethyl)-1-(prop-2-enoyl)pyrrolidin-3-yl]-5-(methylamino)pyrazole-4-carboxamide

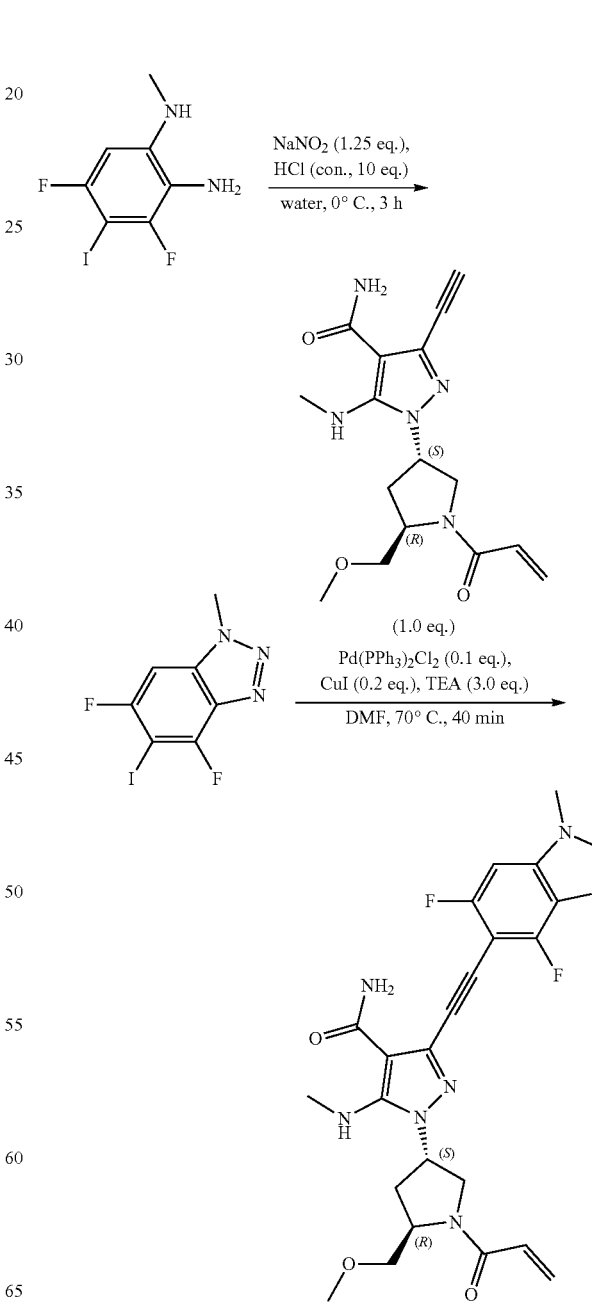

Step 1: 4,6-Difluoro-5-iodo-1-methyl-1H-benzo[d][1,2,3]triazole

To a stirred solution of 3,5-difluoro-4-iodo-$N^1$-methyl-benzene-1,2-diamine (0.54 g, 1.90 mmol) in con. HCl (1.58 mL, 19.01 mmol) and $H_2O$ (6.32 mL) was added $NaNO_2$ (0.16 g, 2.39 mmol) in water (2 mL) dropwise at 0° C. The reaction mixture was stirred for 3 h at 0° C. The resulting mixture was neutralized to pH 7 with saturated KOH (0.5 M). The resulting mixture was washed with water (3×5 mL). The precipitated solids were collected by filtration, washed with water (3×10 mL) and dried to afford 4,6-difluoro-5-iodo-1-methyl-1H-benzo[d][1,2,3]triazole (0.36 g, 64%) as a brown solid. MS ESI calculated for $C_7H_4F_2IN_3$ $[M+H]^+$, 295.94, found 296.00; $^1H$ NMR (400 MHz, $CDCl_3$) δ 7.11 (s, 1H), 4.31 (s, 3H).

Step 2: 3-[2-(4,6-Difluoro-1-methyl-1,2,3-benzotriazol-5-yl)ethynyl]-1-[(3S,5R)-5-(methoxymethyl)-1-(prop-2-enoyl)pyrrolidin-3-yl]-5-(methylamino)pyrazole-4-carboxamide To a stirred solution of 4,6-difluoro-5-iodo-1-methyl-1H-benzo[d][1,2,3]triazole (0.2 g, 0.67 mmol) and 3-ethynyl-1-[(3S,5R)-5-(methoxymethyl)-1-(prop-2-enoyl)pyrrolidin-3-yl]-5-(methylamino)pyrazole-4-carboxamide (0.18 g, 0.56 mmol) in DMF (2.00 mL, 25.84 mmol) were added $Pd(PPh_3)_2Cl_2$ (47.58 mg, 0.07 mmol), CuI (25.82 mg, 0.13 mmol) and TEA (0.20 g, 2.03 mmol) dropwise at room temperature. The reaction mixture was degassed with argon for three times and stirred for 40 min at 70° C. The resulting mixture was concentrated under reduced pressure. The residue was purified by silica gel Column chromatography, eluted with $CH_2Cl_2$/MeOH (0-10%) to afford the crude. The crude product was purified by reverse flash chromatography with the following conditions: Column: XBridge Prep C18 OBD Column, 19×150 mm 5 μm; Mobile Phase A: Water (10 mmol/L $NH_4HCO_3$), Mobile Phase B: ACN; Flow rate: 40 mL/min; Gradient: 5 B to 35 B in 30 min; 210/254 nm. The fractions contained desired product were combined and concentrated to afford 3-[2-(4,6-difluoro-1-methyl-1,2,3-benzotriazol-5-yl)ethynyl]-1-[(3S,5R)-5-(methoxymethyl)-1-(prop-2-enoyl)pyrrolidin-3-yl]-5-(methylamino)pyrazole-4-carboxamide (55.5 mg, 16%) as a white solid. MS ESI calculated for $C_{23}H_{24}F_2N_8O_3$ $[M+H]^+$, 499.19, found 499.10; $^1H$ NMR (300 MHz, $CDCl_3$) δ 7.13 (d, J=7.4 Hz, 1H), 6.45 (d, J=8.8 Hz, 2H), 5.73 (m, 1H), 5.59-5.22 (m, 2H), 4.58-4.45 (m, 1H), 4.32 (s, 3H), 4.11-4.09 (m, 2H), 3.92-3.89 (m, 1H), 3.50-3.48 (m, 1H), 3.39 (d, J=3.9 Hz, 3H), 3.06 (d, J=11.3 Hz, 3H), 2.72-3.69 (m, 1H), 2.33-2.30 (m, 1H).

Example 98: 3-[2-(6-Chloro-2-methyl-1H-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide

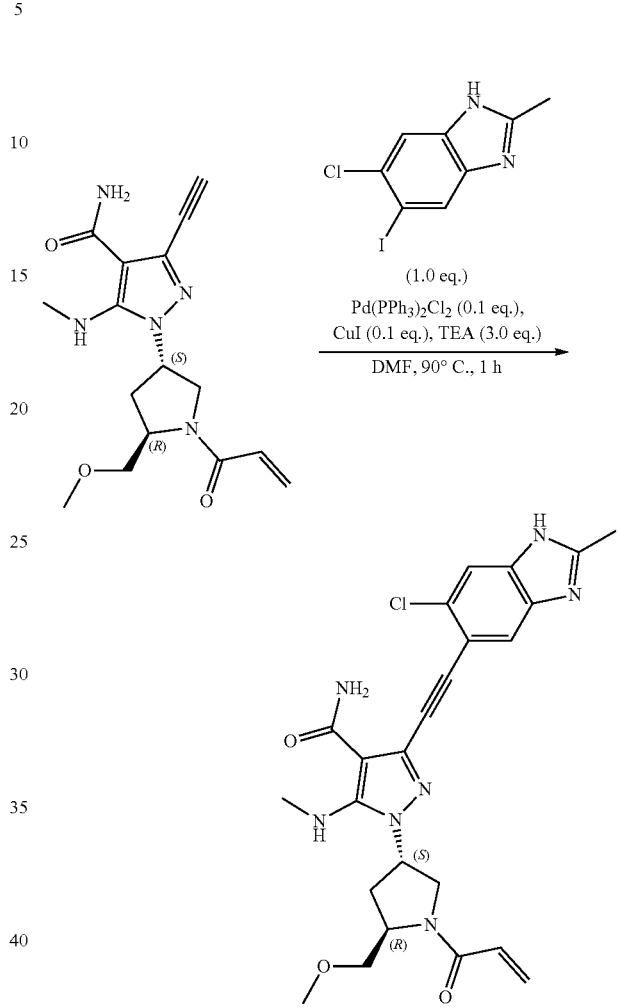

To a stirred solution of 3-ethynyl-1-[(3S,5R)-5-(methoxymethyl)-1-(prop-2-enoyl)pyrrolidin-3-yl]-5-(methylamino)pyrazole-4-carboxamide (0.15 g, 0.45 mmol), 5-chloro-6-iodo-2-methyl-3H-1,3-benzodiazole (0.13 g, 0.45 mmol), $Pd(PPh_3)_2Cl_2$ (31.77 mg, 0.05 mmol) and CuI (17.24 mg, 0.09 mmol) in DMF (0.50 mL) was added TEA (0.14 g, 1.36 mmol) dropwise at room temperature. The reaction mixture was degassed with argon for three times and stirred for 1 h at 90° C. The resulting mixture was concentrated under reduced pressure. The residue was purified by silica gel Column chromatography, eluted with $CH_2Cl_2$/MeOH (10/1). The fractions contained desired product were combined and concentrated. The crude product was purified by Prep-HPLC with the following conditions: Column: XBridge Prep C18 OBD Column, 19×150 mm 5 μm; Mobile Phase A: Water (10 mmol/L $NH_4HCO_3$), Mobile Phase B: ACN; Flow rate: 20 mL/min; Gradient: 30 B to 60 B in 5.8 min; 210/254 nm; RT: 5.8 min. The fractions contained desired product were combined and concentrated to afford 3-[2-(6-chloro-2-methyl-1H-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (0.11 g, 50%) as a white solid. MS ESI calculated for $C_{24}H_{26}ClN_7O_3$ [M+H]$^+$, 496.20, found 496.10; $^1$H NMR (400 MHz, DMSO-d$_6$) δ 12.67 (s, 1H), 7.82 (s, 1H), 7.70 (s, 1H), 7.53 (s, 1H), 6.86 (s, 1H), 6.76-6.46 (m, 2H), 6.17-5.86 (m, 1H), 5.70-5.46 (m, 1H), 5.28-4.96 (m, 1H), 4.59-4.34 (m, 1H), 4.06-3.74 (m, 2H), 3.65-3.40 (m, 2H), 3.31 (s, 3H), 2.96 (t, J=5.1 Hz, 3H), 2.66-2.57 (m, 1H), 2.51 (s, 3H), 2.36-2.27 (m, 1H).

Example 99: 3-[2-(6-Chloro-1-ethyl-4-fluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide

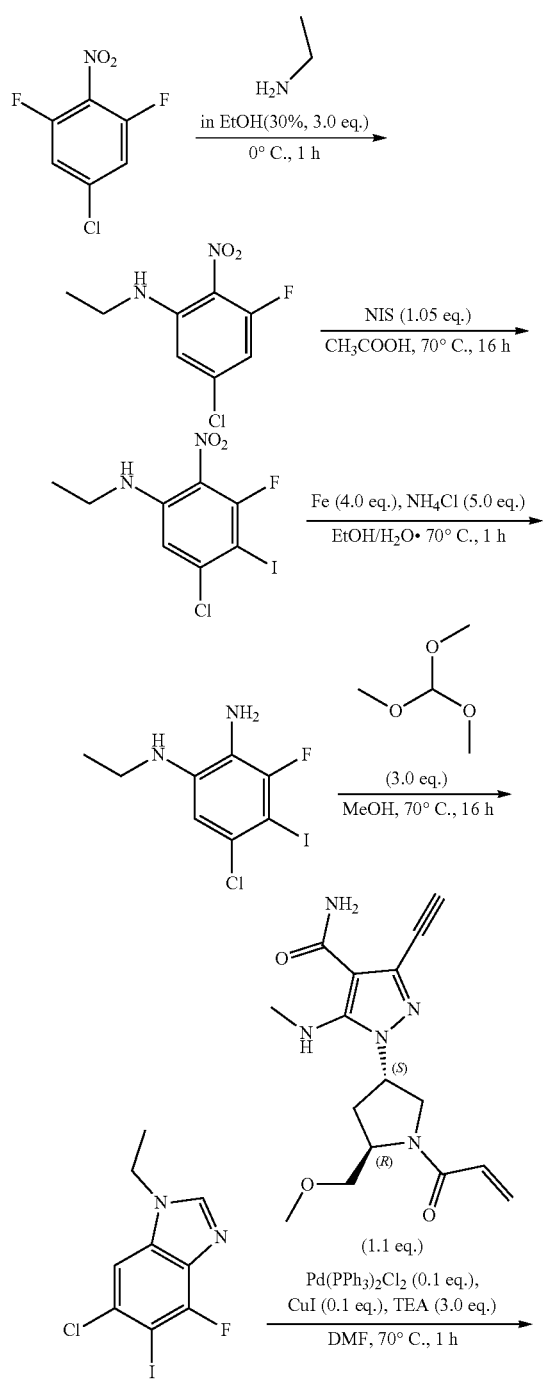

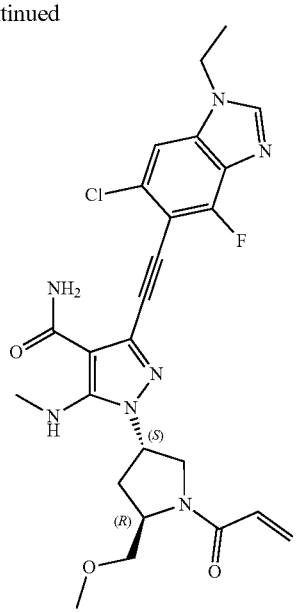

Step 1: 5-Chloro-N-ethyl-3-fluoro-2-nitroaniline

To a stirred solution of 5-chloro-1,3-difluoro-2-nitrobenzene (4.50 g, 23.25 mmol) in EtOH (90.00 mL) was added ethylamine in EtOH (13.27 mL, 294.33 mmol, 30%) dropwise at 0° C. under argon atmosphere. The reaction mixture was stirred for additional 1 h at 0° C. The resulting mixture was diluted with water (100 mL) and filtered, the filter cake was washed with water (3×100 mL). The filter cake was dried to afford 5-chloro-N-ethyl-3-fluoro-2-nitroaniline (5.0 g, 98%) as a red solid which was used in the next step directly without further purification. MS ESI calculated for $C_8H_8ClFN_2O_2$ [M+H]$^+$, 219.03, found 219.10.

Step 2: 5-Chloro-N-ethyl-3-fluoro-4-iodo-2-nitroaniline

To a stirred solution of 5-chloro-N-ethyl-3-fluoro-2-nitroaniline (5.00 g, 22.87 mmol) in AcOH (100.00 mL) was added and NIS (5.40 g, 24.00 mmol). The reaction mixture was stirred for 16 h at 70° C. under argon atmosphere. The resulting mixture was concentrated under reduced pressure. The residue was neutralized to pH 7 with saturated NaHCO$_3$ (aq.). The resulting mixture was extracted with EtOAc (3×500 mL). The combined organic layers were washed with water (3×200 mL), dried over anhydrous Na$_2$SO$_4$ and filtered. The filtrate was concentrated under reduced pressure. The residue was purified by silica gel Column chromatography, eluted with 15% EA in PE. The fractions contained desired product were combined and concentrated to afford 5-chloro-N-ethyl-3-fluoro-4-iodo-2-nitroaniline (7.5 g, 95%) as a red solid. MS ESI calculated for $C_8H_7ClFIN_2O_2$ [M−H]$^-$, 342.92, found 342.90; $^1$H NMR (400 MHz, CDCl$_3$) δ 7.12 (s, 1H), 6.85 (d, J=2.0 Hz, 1H), 3.35-3.23 (m, 2H), 1.37 (t, J=7.2 Hz, 3H).

Step 3: 5-Chloro-N1-ethyl-3-fluoro-4-iodobenzene-1,2-diamine

To a stirred mixture of 5-chloro-N-ethyl-3-fluoro-4-iodo-2-nitroaniline (7.30 g, 21.19 mmol) and NH$_4$Cl (5.67 g, 106.00 mmol) in EtOH (80.00 mL) and H₂O (20.00 mL) was added Fe (4.73 g, 84.70 mmol). The reaction mixture was stirred for 1 h at 70° C. under argon atmosphere. The resulting mixture was filtered, the filter cake was washed with EtOAc (3×400 mL). The combined organic layers were washed with water (4×200 mL), dried over anhydrous Na₂SO₄ and filtered. The filtrate was concentrated under reduced pressure to afford 5-chloro-N¹-ethyl-3-fluoro-4-iodobenzene-1,2-diamine (6.8 g, 96%) as a red oil which was used in the next step directly without further purification. MS ESI calculated for C₈H₉ClFIN₂ [M+H]⁺, 314.95, found 314.90.

Step 4:
6-Chloro-1-ethyl-4-fluoro-5-iodo-1,3-benzodiazole

To a stirred solution of 5-chloro-N¹-ethyl-3-fluoro-4-iodobenzene-1,2-diamine (3.00 g, 9.54 mmol) in MeOH (60.00 mL) was added trimethyl orthoformate (3.13 mL, 28.61 mmol). The reaction mixture was stirred for 16 h at 70° C. under argon atmosphere. The resulting mixture was concentrated under reduced pressure. The residue was purified by silica gel Column chromatography, eluted with PE/EtOAc (1/2). The fractions contained desired product were combined and concentrated to afford 6-chloro-1-ethyl-4-fluoro-5-iodo-1,3-benzodiazole (2.3 g, 74%) as a green solid. MS ESI calculated for C₉H₇ClFIN₂ [M+H]⁺, 324.93, found 324.95; ¹H NMR (400 MHz, CDCl₃) δ 7.91 (s, 1H), 7.44 (d, J=1.2 Hz, 1H), 4.22 (q, J=7.2 Hz, 2H), 1.57 (t, J=7.2 Hz, 3H).

Step 5: 3-[2-(6-Chloro-1-ethyl-4-fluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide To a stirred mixture of 6-chloro-1-ethyl-4-fluoro-5-iodo-1,3-benzodiazole (0.3 g, 0.92 mmol), 3-ethynyl-1-[(3S,5R)-5-(methoxymethyl)-1-(prop-2-enoyl)pyrrolidin-3-yl]-5-(methylamino)pyrazole-4-carboxamide (0.34 g, 1.02 mmol), CuI (35.21 mg, 0.19 mmol) and Pd(PPh₃)₂Cl₂ (64.89 mg, 0.09 mmol) in DMF (6.00 mL) was added TEA (0.39 mL, 3.81 mmol). The reaction mixture was degassed with argon for three times and stirred for 1 h at 70° C. The resulting mixture was diluted with EtOAc (300 mL), washed with water (3×100 mL), dried over anhydrous Na₂SO₄ and filtered. The filtrate was concentrated under reduced pressure. The residue was purified by Prep-HPLC with the following conditions: Column: XBridge Prep C18 OBD Column, 19×150 mm 5 μm; Mobile Phase A: Water (10 mmol/L NH₄HCO₃), Mobile Phase B: ACN; Flow rate: 20 mL/min; Gradient: 15 B to 50 B in 6 min; 210/254 nm; RT: 5.75 min. The fractions contained desired product were combined and concentrated to afford 3-[2-(6-chloro-1-ethyl-4-fluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (0.20 g, 42%) as an off-white solid. MS ESI calculated for C₂₅H₂₇ClFN₇O₃ [M+H]⁺, 528.18, found 528.25; ¹H NMR (400 MHz, CDCl₃) δ 7.98 (s, 1H), 7.35 (s, 1H), 7.14 (s, 1H), 6.57-6.36 (m, 2H), 5.82-5.67 (m, 1H), 5.56-5.25 (m, 2H), 4.63-4.39 (m, 1H), 4.31-4.19 (m, 2H), 4.19-4.07 (m, 1H), 4.07-3.97 (m, 1H), 4.00-3.87 (m, 1H), 3.55-3.42 (m, 1H), 3.39 (d, J=5.2 Hz, 3H), 3.04 (d, J=15.6 Hz, 3H), 2.79-2.67 (m, 1H), 2.43-2.26 (m, 1H), 1.58 (t, J=7.2 Hz, 3H).

Example 100: 3-[2-(6-Chloro-4-fluoro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide

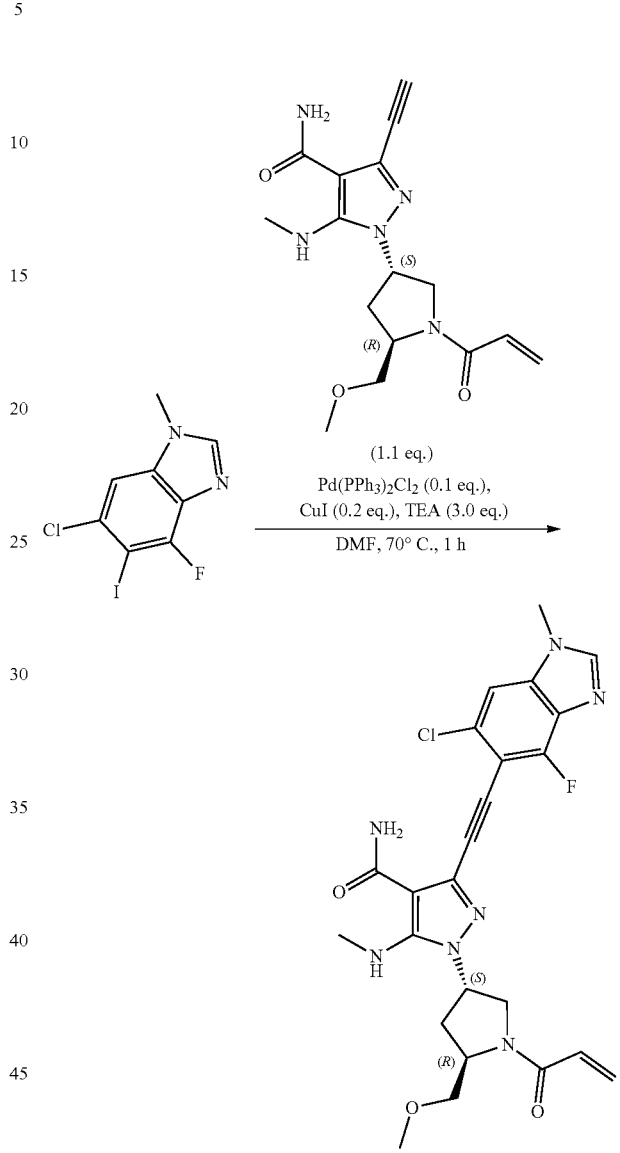

To a stirred mixture of 6-chloro-4-fluoro-5-iodo-1-methyl-1,3-benzodiazole (0.5 g, 1.13 mmol, 70%), 3-ethynyl-1-[(3S,5R)-5-(methoxymethyl)-1-(prop-2-enoyl)pyrrolidin-3-yl]-5-(methylamino)pyrazole-4-carboxamide (0.41 g, 1.24 mmol), CuI (42.94 mg, 0.23 mmol) and Pd(PPh₃)₂Cl₂ (79.12 mg, 0.11 mmol) in DMF (5.00 mL) was added TEA (0.50 mL, 4.94 mmol). The reaction mixture was degassed with argon for three times and stirred for 1 h at 70° C. The resulting mixture was diluted with EtOAc (300 mL), washed with water (3×100 mL), dried over anhydrous Na₂SO₄ and filtered. The filtrate was concentrated under reduced pressure. The residue was purified by Prep-HPLC with the following conditions Column: SunFire Prep C18 OBD Column, 19×150 mm×5 μm 10 nm; Mobile Phase A: Water (0.1% FA), Mobile Phase B: ACN; Flow rate: 20 mL/min; Gradient: 25 B to 45 B in 8 min; 254/210 nm; RT: 6.5 min. The fractions contained desired product were combined and concentrated to afford 3-[2-(6-chloro-4- fluoro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (0.20 g, 34%) as an off-white solid. MS ESI calculated for $C_{24}H_{25}ClFN_7O_3$ [M+H]$^+$, 514.17, found 514.20; $^1$H NMR (400 MHz, CDCl$_3$) δ 8.07 (s, 1H), 7.43 (s, 1H), 7.11 (s, 1H), 6.80 (s, 1H), 6.46 (d, J=11.2 Hz, 2H), 5.73 (d, J=9.2 Hz, 1H), 5.61-5.19 (m, 2H), 4.66-4.37 (m, 1H), 4.20-3.99 (m, 2H), 3.92 (s, 4H), 3.55-3.43 (m, 1H), 3.39 (d, J=4.8 Hz, 3H), 3.06 (d, J=15.6 Hz, 3H), 2.77-2.67 (m, 1H), 2.39-2.30 (m, 1H).

Example 101: 3-[2-(6,7-Difluoro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide

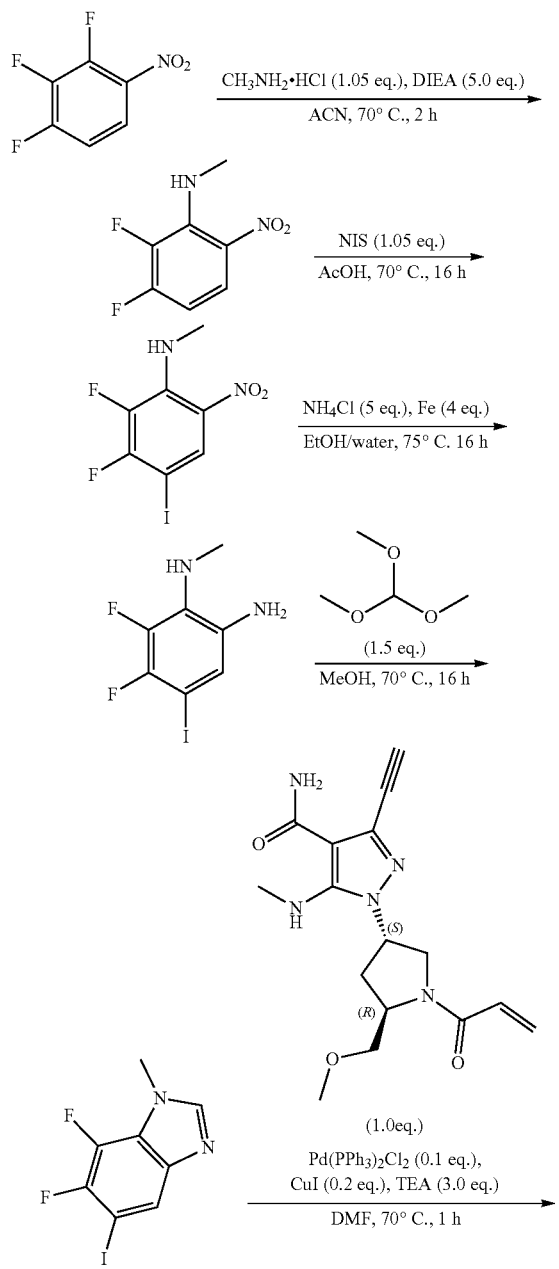

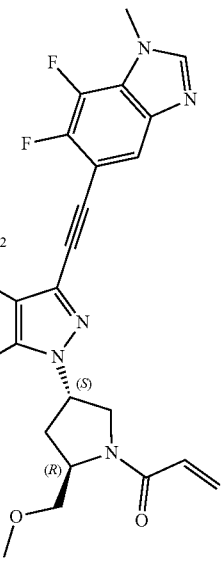

Step 1: 2,3-Difluoro-N-methyl-6-nitroaniline

To a stirred mixture of 1,2,3-trifluoro-4-nitrobenzene (3.00 g, 16.94 mmol) in ACN (30.00 mL) was added CH$_3$NH$_2$HCl (1.20 g, 17.78 mmol) and DIEA (14.75 mL) at rt. The reaction mixture was stirred for 2 h at 70° C. under nitrogen atmosphere. The resulting mixture was concentrated under reduced pressure. The residue was diluted with water (100 mL) and extracted with EA (3×100 mL). The combined organic layers were washed with brine (2×150 mL), dried over anhydrous Na$_2$SO$_4$ and filtered. The filtrate was concentrated under reduced pressure to afford 2,3-difluoro-N-methyl-6-nitroaniline (3 g, 94%) as a light yellow solid which was used in the next step directly without further purification. $^1$H NMR (300 MHz, CDCl$_3$) δ 7.99-7.95 (m, 1H), 6.46-6.44 (m, 1H), 3.29 (d, J=7.5 Hz, 3H).

Step 2: 2,3-Difluoro-4-iodo-N-methyl-6-nitroaniline

To a stirred mixture of 2,3-difluoro-N-methyl-6-nitroaniline (3.23 g, 17.16 mmol) in AcOH (30.00 mL) was added and NIS (4.06 g, 18.04 mmol). The reaction mixture was stirred for 16 h at 70° C. under nitrogen atmosphere. The resulting mixture was concentrated under reduce pressure. The residue was neutralized to pH 7 with saturated NaHCO$_3$ (aq.). The resulting mixture was diluted with water (150 mL) and extracted with EA (3×150 mL). The combined organic layers were washed with brine (2×150 mL), dried over anhydrous Na$_2$SO$_4$ and filtered. The filtrate was concentrated under reduced pressure. The residue was purified by silica gel Column chromatography, eluted with 25% DCM in PE. The fractions contained desired product were combined and concentrated to afford 2,3-difluoro-4-iodo-N-methyl-6-nitroaniline (3.66 g, 67%) as a yellow solid. MS ESI calculated for $C_7H_5F_2IN_2O_2$ [M+H]$^+$, 315.03, found 315.00; $^1$H NMR (300 MHz, CDCl$_3$) δ 8.38 (dd, J=6.3, 2.4 Hz, 1H), 7.98 (s, 1H), 3.29 (dd, J=7.5, 5.5 Hz, 3H).

Step 3: 5,6-Difluoro-4-iodo-N1-methylbenzene-1,2-diamine

To a stirred mixture of 2,3-difluoro-4-iodo-N-methyl-6-nitroaniline (0.50 g, 1.59 mmol) and NH$_4$Cl (0.43 g, 7.96 mmol) in EtOH (8.75 ml) and water (1.25 ml) was added Fe (0.36 g, 6.36 mmol). The reaction mixture was stirred for 16 h at 75° C. The resulting mixture was cooled down and filtered, the filter cake was washed with EtOH (3×150 mL). The filtrate was concentrated under reduced pressure. The residue was diluted with water (100 mL) and extracted with EA (3×100 mL). The combined organic layers were washed with brine (150 mL), dried over anhydrous $Na_2SO_4$ and filtered. The filtrate was concentrated under reduced pressure to afford 5,6-difluoro-4-iodo-$N^1$-methylbenzene-1,2-diamine (0.22 g, 48%) as a yellow solid which was used in the next step directly without further purification. MS ESI calculated for $C_7H_7F_2IN_2$ $[M+H]^+$, 284.96, found 285.00.

Step 4:
6,7-Difluoro-5-iodo-1-methyl-1,3-benzodiazole

To a stirred solution of 5,6-difluoro-4-iodo-$N^1$-methyl-benzene-1,2-diamine (0.22 g, 0.77 mmol) in MeOH (2.20 mL) was added trimethyl orthoformate (0.12 g, 1.16 mmol). The reaction mixture was stirred for 16 h at 70° C. under argon atmosphere. The resulting mixture was concentrated under reduce pressure. The residue was purified by silica gel Column chromatography, eluted with 8% MeOH in DCM. The fractions contained desired product were combined and concentrated to afford 6,7-difluoro-5-iodo-1-methyl-1,3-benzodiazole (0.20 g, 87%) as a light brown solid. MS ESI calculated for $C_8H_5F_2IN_2$ $[M+H]^+$, 295.04, found 294.95; $^1H$ NMR (300 MHz, $CDCl_3$) δ 8.44 (s, 1H), 8.11-8.04 (m, 1H), 4.14 (s, 3H).

Step 5: 3-[2-(6,7-Difluoro-1-methyl-1,3-benzodi-azol-5-yl)ethynyl]-1-[(3S,5R)-5-(methoxymethyl)-1-(prop-2-enoyl)pyrrolidin-3-yl]-5-(methylamino) pyrazole-4-carboxamide To a stirred mixture of 3-ethynyl-1-[(3S,5R)-5-(methoxymethyl)-1-(prop-2-enoyl)pyrrolidin-3-yl]-5-(methylamino)pyrazole-4-carboxamide (0.15 g, 0.45 mmol), 6,7-difluoro-5-iodo-1-methyl-1,3-benzodiazole (0.13 g, 0.45 mmol), CuI (17.24 mg, 0.09 mmol) and $Pd(PPh_3)_2Cl_2$ (31.77 mg, 0.04 mmol) in DMF (1.50 mL) was added TEA (0.19 mL, 1.86 mmol). The reaction mixture was degassed with argon for three times and stirred for 1 h at 70° C. The resulting mixture was concentrated under reduce pressure. The residue was purified by silica gel Column chromatography, eluted with 8% MeOH in DCM. The fractions contained desired product were combined and concentrated. The crude product was purified by Prep-HPLC with the following conditions: Column: XBridge Prep C18 OBD Column, 19×150 mm 5 µm; Mobile Phase A: Water (10 mmol/L $NH_4HCO_3$), Mobile Phase B: ACN; Flow rate: 20 mL/min; Gradient: 10 B to 50 B in 5.8 min, 254 nm; RT: 5.85 min. The fractions contained desired product were combined and concentrated to afford 3-[2-(6,7-difluoro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (75.0 mg, 33%) as a white solid. MS ESI calculated for $C_{24}H_{25}F_2N_7O_3$ $[M+H]^+$, 498.20, found 498.15; $^1H$ NMR (300 MHz, DMSO-$d_6$) δ 8.33 (s, 1H), 7.80 (d, J=5.2 Hz, 1H), 7.45 (s, 1H), 6.81-6.49 (m, 3H), 6.16 (d, J=16.5 Hz, 1H), 5.82-5.53 (m, 1H), 5.25-5.20 (m, 1H), 4.46-4.32 (m, 1H), 3.99-3.95 (m, 4H), 3.92-3.75 (m, 1H), 3.47-3.42 (m, 2H), 3.31 (s, 3H), 2.95-2.91 (m, 3H), 2.46-2.43 (m, 1H), 2.31-2.29 (m, 1H).

Example 102: 3-[2-(1,3-Benzothiazol-2-yl)ethynyl]-1-[(3S,5R)-5-(methoxymethyl)-1-(prop-2-enoyl) pyrrolidin-3-yl]-5-(methylamino)pyrazole-4-carboxamide

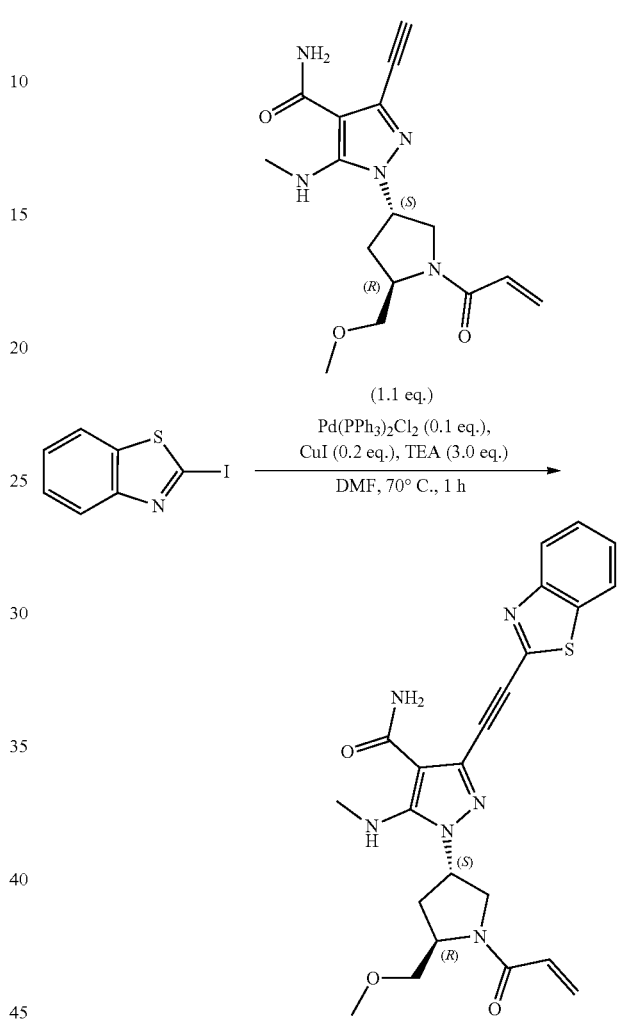

To a stirred mixture of 2-iodo-1,3-benzothiazole (0.3 g, 1.15 mmol), 3-ethynyl-1-[(3S,5R)-5-(methoxymethyl)-1-(prop-2-enoyl)pyrrolidin-3-yl]-5-(methylamino)pyrazole-4-carboxamide (0.42 g, 1.26 mmol), CuI (43.77 mg, 0.23 mmol) and $Pd(PPh_3)_2Cl_2$ (80.65 mg, 0.12 mmol) in DMF (6.00 mL) was added TEA (0.48 mL, 4.74 mmol). The reaction mixture was degassed with argon for three times and stirred for 1 h at 70° C. The resulting mixture was diluted with EtOAc (300 mL), washed with water (3×100 mL), dried over anhydrous $Na_2SO_4$ and filtered. The filtrate was concentrated under reduced pressure. The residue was purified by reverse flash chromatography with the following conditions: Column, C18 silica gel; mobile phase, ACN in water, 15% to 45% gradient in 40 min; detector, UV 254 nm. The fractions contained desired product were combined and concentrated to afford 3-[2-(1,3-benzothiazol-2-yl)ethynyl]-1-[(3S,5R)-5-(methoxymethyl)-1-(prop-2-enoyl)pyrrolidin-3-yl]-5-(methylamino)pyrazole-4-carboxamide (0.30 g, 56%) as a light yellow solid. MS ESI calculated for $C_{23}H_{24}N_6O_3S$ $[M+H]^+$, 465.16, found 465.25; $^1H$ NMR (400 MHz, CDCl₃) δ 8.15-8.08 (m, 1H), 7.95-7.88 (m, 1H), 7.62-7.46 (m, 2H), 6.91-6.82 (m, 1H), 6.76 (s, 1H), 6.60-6.38 (m, 2H), 5.82-5.73 (m, 1H), 5.61-5.21 (m, 2H), 4.64-4.40 (m, 1H), 4.16-3.98 (m, 2H), 3.95-3.89 (m, 1H), 3.55-3.44 (m, 1H), 3.39 (d, J=4.8 Hz, 3H), 3.06 (m, 3H), 2.77-2.63 (m, 1H), 2.46-2.30 (m, 1H).

Example 103: 3-[2-(1,3-Benzothiazol-5-yl)ethynyl]-1-[(3S,5R)-5-(methoxymethyl)-1-(prop-2-enoyl)pyrrolidin-3-yl]-5-(methylamino)pyrazole-4-carboxamide

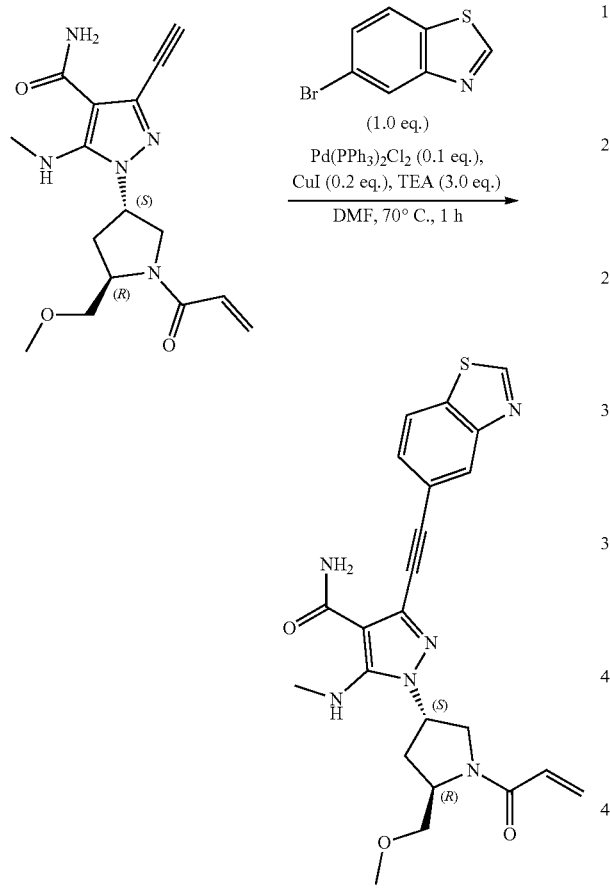

To a stirred mixture of 5-bromo-1,3-benzothiazole (64.60 mg, 0.30 mmol), 3-ethynyl-1-[(3S,5R)-5-(methoxymethyl)-1-(prop-2-enoyl) pyrrolidin-3-yl]-5-(methylamino) pyrazole-4-carboxamide (0.10 g, 0.30 mmol), Pd(PPh₃)₂Cl₂ (21.18 mg, 0.03 mmol) and CuI (11.49 mg, 0.06 mmol) in DMF (3.00 mL) was added TEA (91.61 mg, 0.91 mmol) at room temperature. The reaction mixture was degassed with argon for three times and stirred for 1 h at 70° C. under argon atmosphere. The resulting mixture was cooled down to room temperature and concentrated under reduced pressure. The residue was purified by silica gel Column chromatography, eluted with CH₂Cl₂/MeOH (10/1). The fractions contained desired product were combined and concentrated. The crude product was purified by Prep-HPLC with the following conditions: Column: XBridge Prep C18 OBD Column, 19×150 mm 5 μm; Mobile Phase A: Water (10 mmol/L NH₄HCO₃, Mobile Phase B: ACN; Flow rate: 20 mL/min; Gradient: 10 B to 50 B in 5.8 min; 210/254 nm; RT: 5.59 min. The fractions contained desired product were combined and concentrated to afford 3-[2-(1,3-benzothiazol-5-yl)ethynyl]-1-[(3S,5R)-5-(methoxymethyl)-1-(prop-2-enoyl)pyrrolidin-3-yl]-5-(methylamino)pyrazole-4-carboxamide (0.05 g, 32%) as an off-white solid. MS ESI calculated for $C_{23}H_{24}N_6O_3S$ [M+H]⁺, 465.16, found 465.05; ¹H NMR (300 MHz, CDCl₃) δ 9.09 (s, 1H), 8.34 (s, 1H), 7.99 (d, J=8.3 Hz, 1H), 7.63 (d, J=8.4 Hz, 1H), 6.82 (s, 2H), 6.49-6.40 (m, 2H), 5.73 (dd, J=8.2, 4.4 Hz, 1H), 5.53 (s, 2H), 4.58-4.45 (m, 1H), 4.08-4.05 (m, 2H), 3.92-3.89 (m, 1H), 3.56-3.42 (m, 1H), 3.39-3.36 (m, 3H), 3.06-3.03 (m, 3H), 2.73-2.70 (m, 1H), 2.33-2.30 (m, 1H).

Example 104: 3-(2-[Imidazo[1,2-a]pyridin-2-yl]ethynyl)-1-[(3S,5R)-5-(methoxymethyl)-1-(prop-2-enoyl)pyrrolidin-3-yl]-5-(methylamino)pyrazole-4-carboxamide

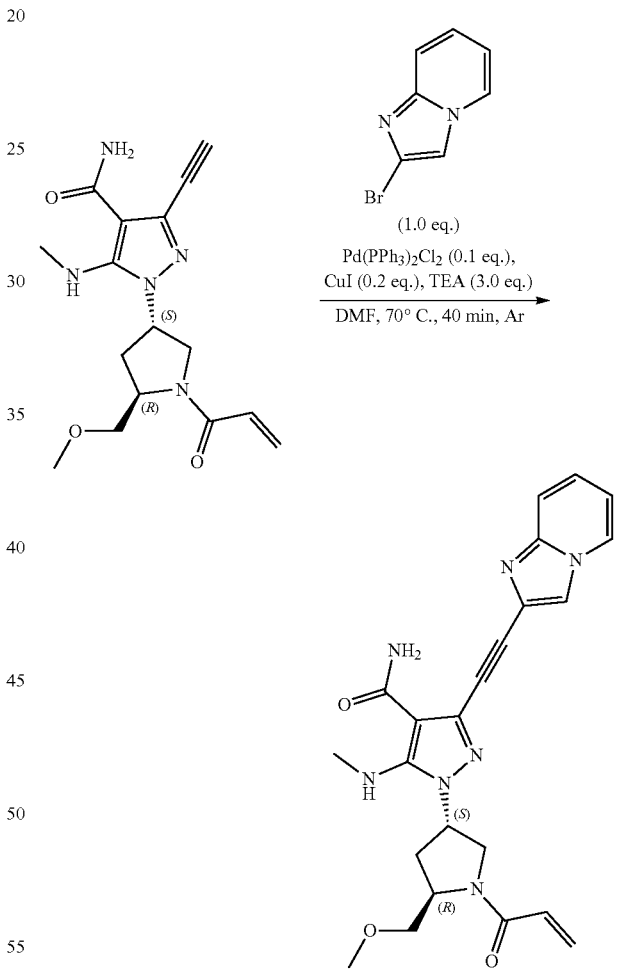

To a stirred mixture of 3-ethynyl-1-[(3S,5R)-5-(methoxymethyl)-1-(prop-2-enoyl)pyrrolidin-3-yl]-5-(methylamino)pyrazole-4-carboxamide (0.30 g, 0.90 mmol), 2-bromoimidazo[1,2-a]pyridine (0.18 g, 0.91 mmol), Pd(PPh₃)₂Cl₂ (63.54 mg, 0.09 mmol) and CuI (34.48 mg, 0.18 mmol) in DMF (4.00 mL) was added TEA (0.27 g, 2.72 mmol). The reaction mixture was degassed with argon for three times and stirred for 40 min at 70° C. The resulting mixture was concentrated under reduced pressure. The residue was purified by silica gel Column chromatography, eluted with MeOH in DCM (0-5%) to afford the crude product. The crude product was purified by Prep-HPLC with the following conditions: Column: SunFire Prep C18 OBD Column, 19×150 mm 5 μm 10 nm; Mobile Phase A: Water (0.1% FA), Mobile Phase B: ACN; Flow rate: 20 mL/min; Gradient: 5 B to 50 B in 5.8 min; 210/254 nm; RT: 5.58 min. The fractions contained desired product were combined and concentrated to afford 3-(2-[imidazo[1,2-a]pyridin-2-yl]ethynyl)-1-[(3S,5R)-5-(methoxymethyl)-1-(prop-2-enoyl)pyrrolidin-3-yl]-5-(methylamino)pyrazole-4-carboxamide (17.90 mg, 4%) as an orange solid. MS ESI calculated for $C_{23}H_{25}N_7O_3$ [M+H]$^+$, 448.20, found 448.10; $^1$H NMR (400 MHz, CDCl$_3$) δ 8.12 (d, J=6.8 Hz, 1H), 7.87 (s, 1H), 7.62 (d, J=9.2 Hz, 1H), 7.26 (d, J=8.3 Hz, 1H), 7.01 (s, 1H), 6.89 (d, J=6.8 Hz, 1H), 6.82-6.64 (m, 1H), 6.59-6.36 (m, 2H), 5.73-5.70 (m, 1H), 5.57-5.24 (m, 2H), 4.65-4.38 (m, 1H), 4.17-3.97 (m, 2H), 3.92-3.88 (m, 1H), 3.53-3.44 (m, 1H), 3.39 (d, J=4.1 Hz, 3H), 3.06-3.01 (m, 3H), 2.72-2.66 (m, 1H), 2.34-2.29 (m, 1H).

Example 105: 1-((3S,5R)-1-Acryloyl-5-(methoxymethyl)pyrrolidin-3-yl)-3-((3-cyanoimidazo[1,2-a]pyridin-2-yl)ethynyl)-5-(methylamino)-1H-pyrazole-4-carboxamide

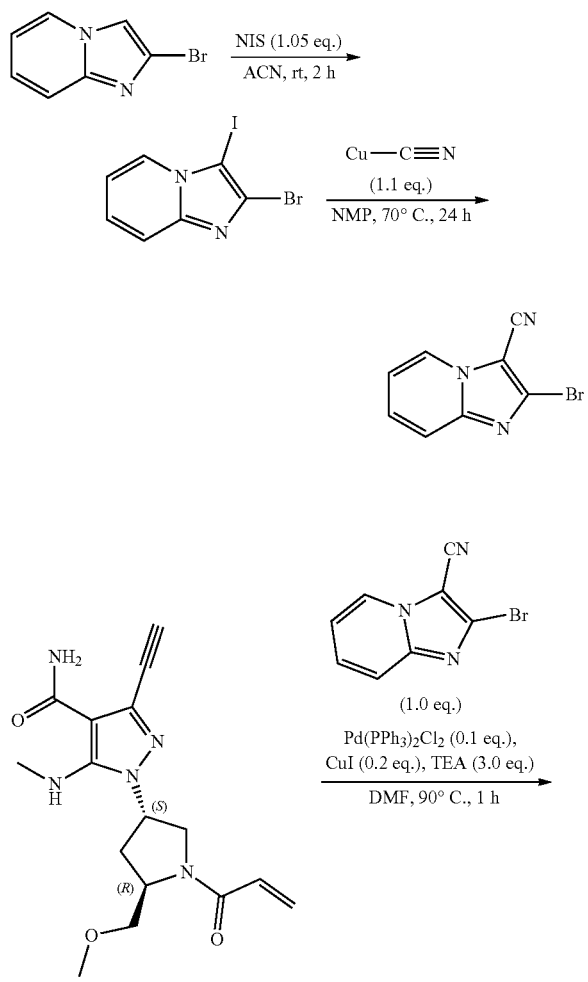

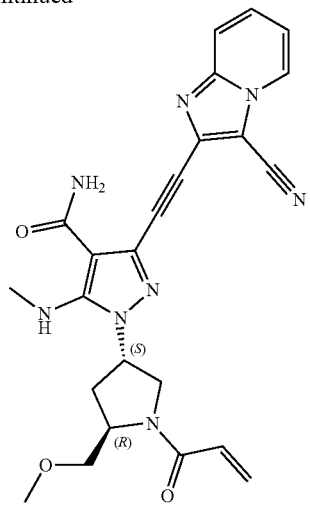

Step 1: 2-Bromo-3-iodoimidazo[1,2-a]pyridine

To a stirred solution of 2-bromoimidazo[1,2-a]pyridine (1.60 g, 8.12 mmol) in ACN (16.00 mL) was added NIS (1.92 g, 8.53 mmol) in portions at room temperature under nitrogen atmosphere. The reaction mixture was stirred for 2 h at room temperature. The resulting mixture was concentrated under reduced pressure. The residue was purified by silica gel Column chromatography, eluted with CH$_2$Cl$_2$/MeOH (10/1), the fractions contained desired product were combined and concentrated to afford 2-bromo-3-iodoimidazo[1,2-a]pyridine (2.3 g, 87%) as a brown solid. MS ESI calculated for $C_7H_4BrIN_2$ [M+H]$^+$, 322.86, 324.86, found 322.85, 324.85; $^1$H NMR (400 MHz, CDCl$_3$) δ 8.10-8.07 (m, 1H), 7.61-7.52 (m, 1H), 7.31-7.23 (m, 1H), 6.98-6.96 (m, 1H).

Step 2: 2-Bromoimidazo[1,2-a]pyridine-3-carbonitrile

To a stirred solution of 2-bromo-3-iodoimidazo[1,2-a]pyridine (1.00 g, 3.09 mmol) in NMP (10 mL) was added cuprous cyanide (0.31 g, 3.46 mmol) in portions at room temperature under nitrogen atmosphere. The reaction mixture was stirred for 24 h at 70° C. The resulting mixture was quenched by the addition of edta disodium salt dihydrate (120.00 mL, 0.32 mol) at room temperature and diluted with EtOAc (150 mL). The resulting mixture was stirred for additional 2 h at room temperature. The resulting mixture was extracted with EtOAc (3×100 mL). The combined organic layers were washed with brine (3×80 mL), dried over anhydrous Na$_2$SO$_4$ and filtered. The filtrate was concentrated under reduced pressure. The residue was purified by silica gel Column chromatography, eluted with CH$_2$Cl$_2$/MeOH (10/1). The fractions contained desired product were combined and concentrated to afford 2-bromoimidazo[1,2-a]pyridine-3-carbonitrile (0.14 g, 20%) as an off-white solid. MS ESI calculated for $C_8H_4BrN_3$ [M+H]$^+$, 221.96, 223.96, found 222.00, 224.00; $^1$H NMR (400 MHz, CDCl$_3$) δ 8.33-8.30 (m, 1H), 7.75-7.71 (m, 1H), 7.53-7.48 (m, 1H), 7.18-7.15 (m, 1H).

531

Step 3: 1-((3S,5R)-1-Acryloyl-5-(methoxymethyl) pyrrolidin-3-yl)-3-((3-cyanoimidazo[1,2-a]pyridin-2-yl)ethynyl)-5-(methylamino)-1H-pyrazole-4-carboxamide To a stirred mixture of 3-ethynyl-1-[(3S,5R)-5-(methoxymethyl)-1-(prop-2-enoyl)pyrrolidin-3-yl]-5-(methylamino)pyrazole-4-carboxamide (0.19 g, 0.57 mmol), 2-bromoimidazo[1,2-a]pyridine-3-carbonitrile (0.13 g, 0.57 mmol), CuI (0.02 g, 0.12 mmol) and Pd(PPh$_3$)$_2$Cl$_2$ (0.04 g, 0.05 mmol) in DMF (2.00 mL) was added TEA (0.24 mL, 1.72 mmol). The reaction mixture was degassed with argon for three times and stirred for 1 h at 90° C. The resulting mixture was diluted with water (20 mL), extracted with EA (3×20 mL). The combined organic layers were washed with brine (3×20 mL), dried over anhydrous Na$_2$SO$_4$ and filtered. The filtrate was concentrated under reduced pressure. The residue was purified by Prep-HPLC with the following conditions: Column: XBridge Prep C18 OBD Column, 19×150 mm 5 μm; Mobile Phase A: Water (10 mmol/L NH$_4$HCO$_3$), Mobile Phase B: ACN; Flow rate: 20 mL/min; Gradient: 25 B to 50 B in 6 min; 210/254 nm; RT: 5.58 min. The fractions contained desired product were combined and concentrated to afford 1-((3S,5R)-1-acryloyl-5-(methoxymethyl)pyrrolidin-3-yl)-3-((3-cyanoimidazo[1,2-a]pyridin-2-yl)ethynyl)-5-(methylamino)-1H-pyrazole-4-carboxamide (87.8 mg, 32%) as an off-white solid. MS ESI calculated for C$_{24}$H$_{24}$N$_8$O$_3$ [M+H]$^+$, 473.20, found 473.15; $^1$H NMR (400 MHz, DMSO-d$_6$) δ 8.68-8.65 (m, 1H), 7.86-7.82 (m, 1H), 7.69-7.64 (m, 1H), 7.49 (s, 1H), 7.33-7.29 (m, 1H), 6.97-6.40 (m, 3H), 6.18-7.15 (m, 1H), 5.69-5.66 (m, 1H), 5.28-5.23 (m, 1H), 4.48-4.44 (m, 1H), 4.13-3.67 (m, 2H), 3.66-3.41 (m, 2H), 3.31 (s, 3H), 2.94 (t, J=5.6 Hz, 3H), 2.64-2.61 (m, 1H), 2.34-2.25 (m, 1H).

Example 106: 1-[(3S,5R)-5-(Methoxymethyl)-1-(prop-2-enoyl)pyrrolidin-3-yl]-5-(methylamino)-3-(2-[[1,2,4]triazolo[1,5-a]pyridin-6-yl]ethynyl)pyrazole-4-carboxamide

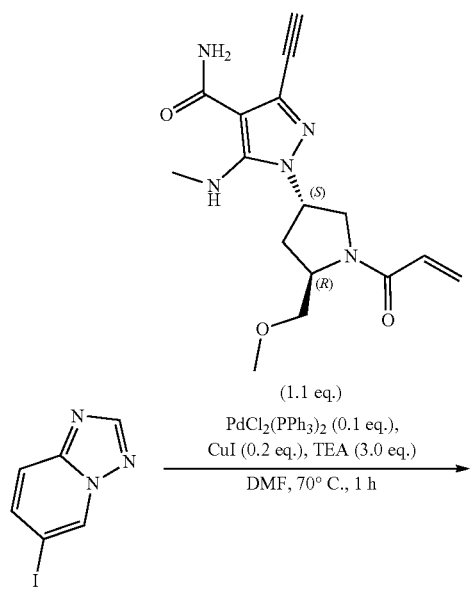

532

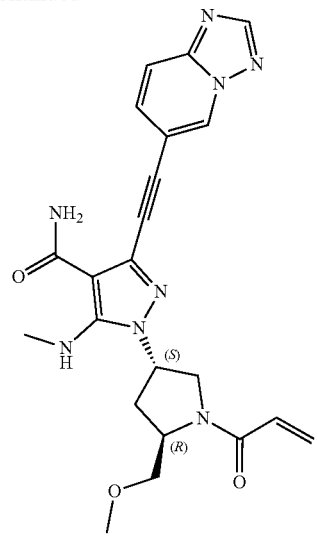

To a stirred mixture of 6-iodo-[1,2,4]triazolo[1,5-a]pyridine (0.15 g, 0.61 mmol), 3-ethynyl-1-[(3S,5R)-5-(methoxymethyl)-1-(prop-2-enoyl)pyrrolidin-3-yl]-5-(methylamino)pyrazole-4-carboxamide (0.22 g, 0.67 mmol), CuI (23.32 mg, 0.12 mmol) and Pd(PPh$_3$)$_2$Cl$_2$ (42.97 mg, 0.06 mmol) in DMF (2.00 mL) was added TEA (0.26 mL, 2.52 mmol). The reaction mixture was degassed with argon for three times and stirred for 1 h at 70° C. The resulting mixture was diluted with EtOAc (300 mL), washed with water (3×100 mL), dried over anhydrous Na$_2$SO$_4$ and filtered. The filtrate was concentrated under reduced pressure. The residue was purified by Prep-HPLC with the following conditions: Column: XBridge Prep C18 OBD Column, 19×150 mm 5 μm; Mobile Phase A: Water (10 mmol/L NH$_4$HCO$_3$), Mobile Phase B: ACN; Flow rate: 20 mL/min; Gradient: 15 B to 50 B in 6 min, 210/254 nm; RT: 5.8 min. The fractions contained desired product were combined and concentrated to afford 1-[(3S,5R)-5-(methoxymethyl)-1-(prop-2-enoyl)pyrrolidin-3-yl]-5-(methylamino)-3-(2-[[1,2,4]triazolo[1,5-a]pyridin-6-yl]ethynyl)pyrazole-4-carboxamide (0.11 g, 40%) as an off-white solid. MS ESI calculated for C$_{22}$H$_{24}$N$_8$O$_3$ [M+H]$^+$, 449.20, found 449.30; $^1$H NMR (400 MHz, CDCl$_3$) δ 8.86 (s, 1H), 8.44 (s, 1H), 7.85-7.78 (m, 1H), 7.65 (dd, J=9.2, 1.6 Hz, 1H), 6.64 (s, 1H), 6.59-6.37 (m, 2H), 5.80-5.69 (m, 1H), 5.61-5.23 (m, 2H), 4.66-4.35 (m, 1H), 4.14-3.95 (m, 2H), 3.95-3.89 (m, 1H), 3.55-3.42 (m, 1H), 3.39 (d, J=5.2 Hz, 3H), 3.06 (d, J=14.6 Hz, 3H), 2.76-2.64 (m, 1H), 2.46-2.29 (m, 1H).

Example 107: 1-[(3S,5R)-5-(Methoxymethyl)-1-(prop-2-enoyl)pyrrolidin-3-yl]-5-(methylamino)-3-(2-[[1,2,4]triazolo[1,5-a]pyridin-7-yl]ethynyl)pyrazole-4-carboxamide

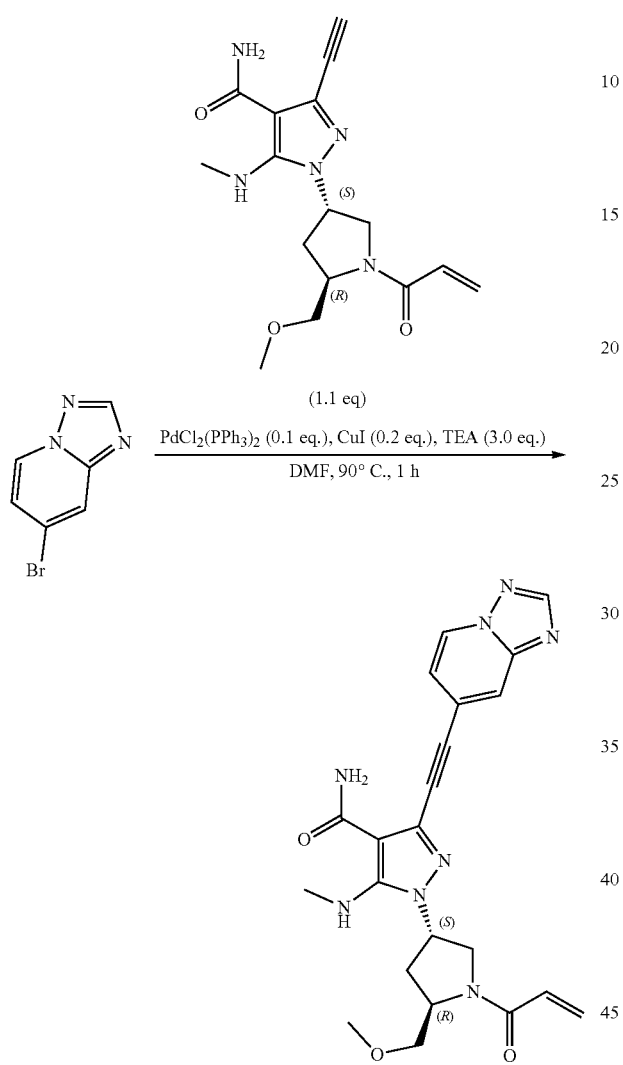

To a stirred mixture of 7-bromo-[1,2,4]triazolo[1,5-a]pyridine (0.15 g, 0.76 mmol), 3-ethynyl-1-[(3S,5R)-5-(methoxymethyl)-1-(prop-2-enoyl)pyrrolidin-3-yl]-5-(methylamino)pyrazole-4-carboxamide (0.27 g, 0.83 mmol), CuI (28.85 mg, 0.15 mmol) and Pd(PPh$_3$)$_2$Cl$_2$ (53.17 mg, 0.08 mmol) in DMF (2.00 mL) was added TEA (0.32 mL, 3.12 mmol). The reaction mixture was degassed with argon for three times and stirred for 1 h at 90° C. The resulting mixture was diluted with EtOAc (300 mL), washed with water (3×100 mL), dried over anhydrous Na$_2$SO$_4$ and filtered. The filtrate was concentrated under reduced pressure. The residue was purified by Prep-HPLC with the following conditions: Column: Atlantis HILIC OBD Column, 19×150 mm×5 μm; Mobile Phase A: Water (10 mmol/L NH$_4$HCO$_3$), Mobile Phase B: ACN; Flow rate: 20 mL/min; Gradient: 15 B to 50 B in 6 min; 210/254 nm; RT: 5.8 min. The fractions contained desired product were combined and concentrated to afford 1-[(3S,5R)-5-(methoxymethyl)-1-(prop-2-enoyl)pyrrolidin-3-yl]-5-(methylamino)-3-(2-[[1,2,4]triazolo[1,5-a]pyridin-7-yl]ethynyl)pyrazole-4-carboxamide (0.14 g, 40%) as an off-white solid. MS ESI calculated for C$_{22}$H$_{24}$N$_8$O$_3$ [M+H]$^+$, 449.20, found 449.10; $^1$H NMR (400 MHz, CDCl$_3$) δ 8.62 (d, J=7.2 Hz, 1H), 8.44 (s, 1H), 7.98 (s, 1H), 7.16 (dd, J=7.2, 1.2 Hz, 1H), 6.88-6.57 (m, 1H), 6.53-6.38 (m, 2H), 5.78-5.69 (m, 1H), 5.62-5.22 (m, 2H), 4.68-4.36 (m, 1H), 4.14-4.03 (m, 2H), 4.02-3.88 (m, 1H), 3.57-3.43 (m, 1H), 3.39 (d, J=5.2 Hz, 3H), 3.06 (d, J=14.4 Hz, 3H), 2.76-2.64 (m, 1H), 2.46-2.29 (m, 1H).

Example 108: 3-[2-(1,3-Benzoxazol-5-yl)ethynyl]-1-[(3S,5R)-5-(methoxymethyl)-1-(prop-2-enoyl)pyrrolidin-3-yl]-5-(methylamino)pyrazole-4-carboxamide

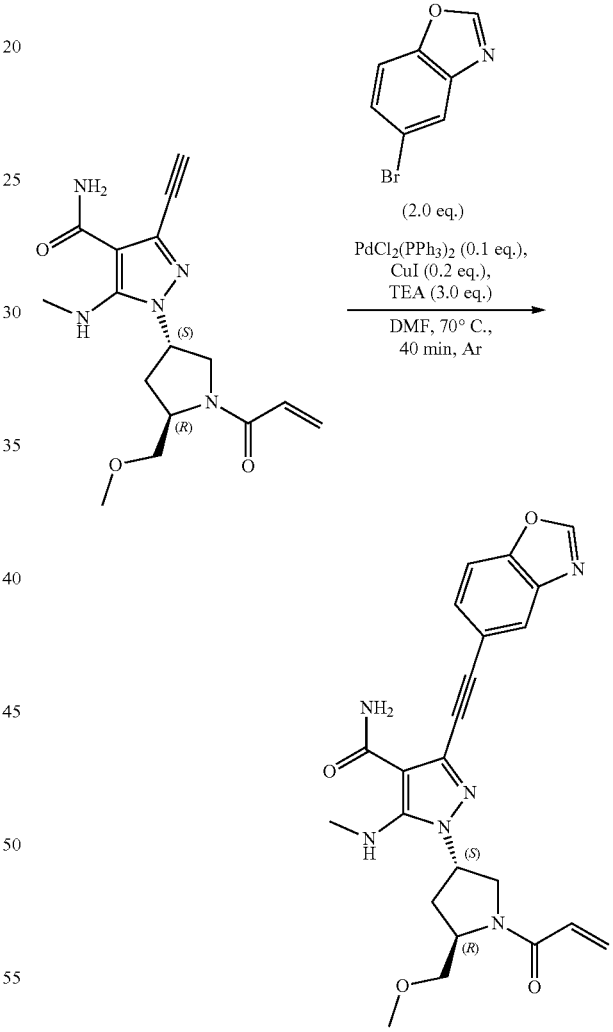

To a stirred solution of 3-ethynyl-1-[(3S,5R)-5-(methoxymethyl)-1-(prop-2-enoyl)pyrrolidin-3-yl]-5-(methylamino)pyrazole-4-carboxamide (0.12 g, 0.36 mmol), 5-bromo-1,3-benzoxazole (0.14 g, 0.72 mmol), Pd(PPh$_3$)$_2$Cl$_2$ (25.42 mg, 0.04 mmol) and CuI (13.79 mg, 0.07 mmol) in DMF (0.50 mL) was added TEA (0.11 g, 1.08 mmol) dropwise at room temperature. The reaction mixture was degassed with argon for three times and stirred for 40 minutes at 70° C. The resulting mixture was concentrated under reduced pressure. The residue was purified by silica gel Column chromatography, eluted with CH$_2$Cl$_2$/MeOH (10/1). The fractions contained desired product were combined and concentrated. The crude product was purified by Prep-HPLC with the following conditions: Column: XBridge Prep C18 OBD Column, 19×150 mm 5 µm; Mobile Phase A: Water (10 mmol/L NH$_4$HCO$_3$), Mobile Phase B: ACN; Flow rate: 20 mL/min; Gradient: 35 B to 55 B in 6 min; 210/254 nm. The fractions contained desired product were combined and concentrated to afford 3-[2-(1,3-benzoxazol-5-yl)ethynyl]-1-[(3S,5R)-5-(methoxymethyl)-1-(prop-2-enoyl)pyrrolidin-3-yl]-5-(methylamino)pyrazole-4-carboxamide (14.50 mg, 9%) as a white solid. MS ESI calculated for C$_{23}$H$_{24}$N$_6$O$_4$ [M+H]$^+$, 449.20, found 449.15; $^1$H NMR (300 MHz, CDCl$_3$) δ 8.16 (s, 1H), 7.99 (s, 1H), 7.60 (d, J=1.2 Hz, 2H), 6.78 (d, J=6.3 Hz, 2H), 6.57-6.26 (m, 2H), 5.70-5.51 (m, 1H), 5.49-4.45 (m, 2H), 4.56-4.45 (m, 1H), 4.15-3.96 (m, 2H), 3.90-3.67 (m, 1H), 3.59-3.28 (m, 4H), 3.04-2.87 (m, 3H), 2.78-2.59 (m, 1H), 2.34-2.12 (m, 1H).

Example 109: 5-[(Cyclopropylmethyl)amino]-3-[2-(1-ethyl-4,6-difluoro-1,3-benzodiazol-5-yl)ethynyl]-1-[(3S,5R)-5-(methoxymethyl)-1-(prop-2-enoyl)pyrrolidin-3-yl]pyrazole-4-carboxamide

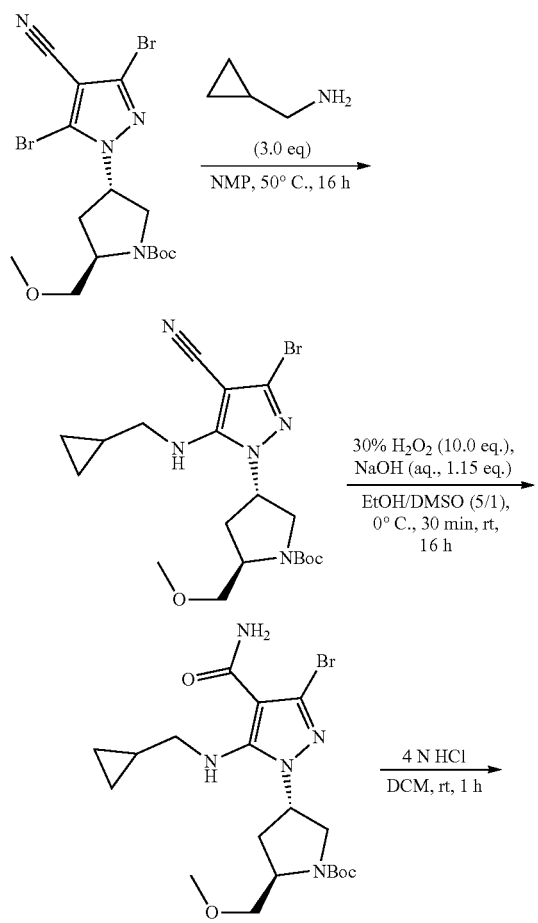

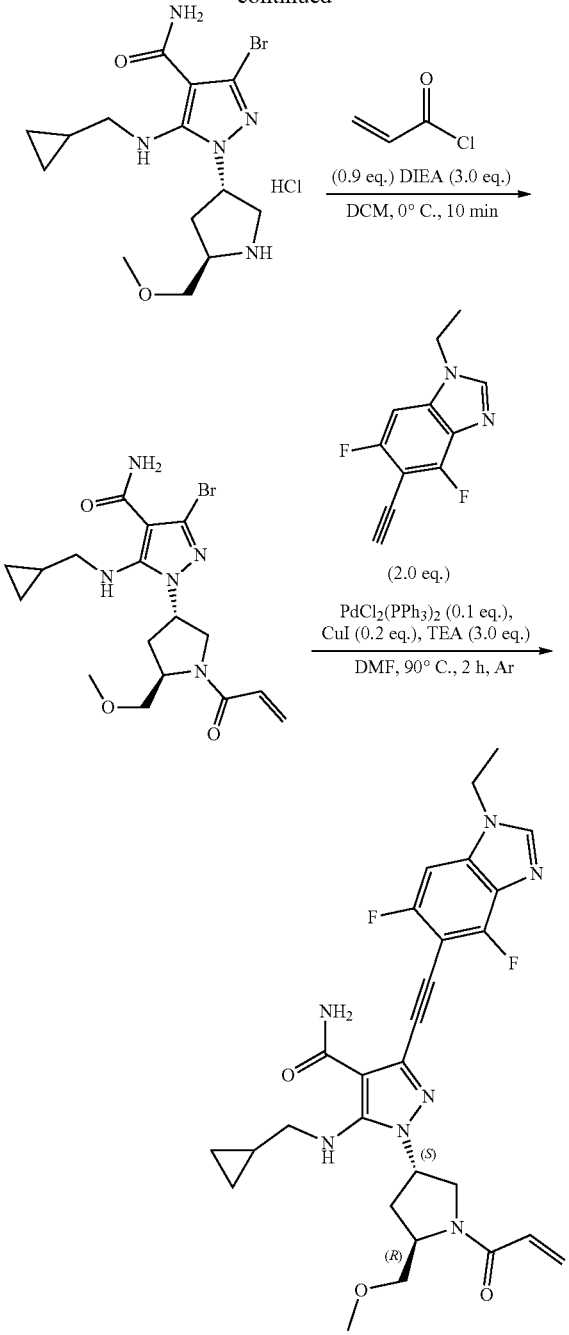

Step 1: Tert-butyl (2R,4S)-4-[3-bromo-4-cyano-5-[(cyclopropylmethyl)amino]pyrazol-1-yl]-2-(methoxymethyl)pyrrolidine-1-carboxylate To a stirred mixture of tert-butyl (2R,4S)-4-(3,5-dibromo-4-cyanopyrazol-1-yl)-2-(methoxymethyl)pyrrolidine-1-carboxylate (1.00 g, 2.15 mmol) in NMP (10.00 mL) was added 1-cyclopropylmethanamine (0.46 g, 6.46 mmol). The reaction mixture was stirred for 16 h at 50° C. The resulting mixture was poured into water (50 mL) and extracted with EtOAc (3×50 mL). The combined organic layers were washed with water (4×30 mL), dried over anhydrous Na$_2$SO$_4$ and filtrated. The filtrate was concentrated under reduced pressure to afford tert-butyl (2R,4S)-4-[3-bromo-4-cyano-5-[(cyclopropylmethyl)amino]pyrazol-1-yl]-2-(methoxymethyl)pyrrolidine-1-carboxylate (1.0 g, 99%) as a yellow oil which was used in the next step directly without further purification. MS ESI calculated for $C_{19}H_{28}BrN_5O_3$ [M+H−56]$^+$, 398.14, 400.14. found 398.20, 400.20; $^1$H NMR (400 MHz, CDCl$_3$) δ 6.40 (s, 1H), 4.99-4.93 (m, 1H), 4.72 (s, 1H), 4.26-4.14 (m, 2H), 3.78-3.56 (m, 4H), 3.47-3.30 (m, 2H), 2.59 (s, 1H), 2.25 (s, 1H), 2.06 (s, 1H), 1.28 (m, 9H), 1.20-1.09 (m, 1H), 0.72-0.58 (m, 2H), 0.32 (m, 2H).

Step 2: Tert-butyl (2R,4S)-4-[3-bromo-4-carbamoyl-5-[(cyclopropylmethyl)amino]pyrazol-1-yl]-2-(methoxymethyl)pyrrolidine-1-carboxylate To a stirred solution of tert-butyl (2R,4S)-4-[3-bromo-4-cyano-5-[(cyclopropylmethyl)amino]pyrazol-1-yl]-2-(methoxymethyl)pyrrolidine-1-carboxylate (1.00 g, 2.20 mmol) in EtOH (10.00 mL) and DMSO (2.00 mL) were added NaOH (0.5 M in water) (0.10 mL, 2.53 mmol) and H$_2$O$_2$ (1.71 mL, 22.01 mmol, 30%) dropwise at 0° C. The reaction mixture was stirred for 30 min at 0° C. and 16 h at room temperature. The resulting mixture was diluted with water (20 mL) and extracted with EA (3×20 mL). The combined organic layers were washed with water (2×20 mL), dried over anhydrous Na$_2$SO$_4$ and filtered. The filtrate was concentrated under reduced pressure. The residue was purified by silica gel Column chromatography, eluted with EA in PE (20-70%). The fractions contained desired product were combined and concentrated to afford tert-butyl (2R,4S)-4-[3-bromo-4-carbamoyl-5-[(cyclopropylmethyl)amino]pyrazol-1-yl]-2-(methoxymethyl)pyrrolidine-1-carboxylate (0.80 g, 77%) as a yellow solid. MS ESI calculated for $C_{19}H_{30}BrN_5O_4$ [M+H]$^+$, 472.15, 474.15, found 472.10, 474.10; $^1$H NMR (400 MHz, CDCl$_3$) δ 6.69 (d, J=100.4 Hz, 2H), 6.06-5.29 (m, 1H), 5.13 (brs, 1H), 4.24-4.04 (m, 1H), 3.79-3.62 (m, 3H), 3.48-3.28 (m, 3H), 3.05-3.02 (m, 2H), 2.59-2.56 (m, 1H), 2.32-1.98 (m, 1H), 1.59-1.38 (m, 9H), 1.37-1.01 (m, 2H), 0.58-0.52 (m, 2H), 0.29-0.25 (m, 2H).

Step 3: 3-Bromo-5-[(cyclopropylmethyl)amino]-1-[(3S,5R)-5-(methoxymethyl)pyrrolidin-3-yl]pyrazole-4-carboxamide hydrochloride To a stirred solution of tert-butyl (2R,4S)-4-[3-bromo-4-carbamoyl-5-[(cyclopropylmethyl)amino]pyrazol-1-yl]-2-(methoxymethyl)pyrrolidine-1-carboxylate (0.80 g, 1.69 mmol) in DCM (8.00 mL) was added HCl (4 M in EA) (4.00 mL) dropwise at 0° C. The reaction mixture was stirred for 1 h at room temperature. The resulting mixture was concentrated under reduced pressure to afford 3-bromo-5-[(cyclopropylmethyl)amino]-1-[(3S,5R)-5-(methoxymethyl)pyrrolidin-3-yl]pyrazole-4-carboxamide hydrochloride (0.70 g, 99%) as a yellow solid which was used in the next step directly without further purification. MS ESI calculated for $C_{14}H_{22}BrN_5O_2$ [M+H]$^+$, 372.10, 374.10, found 372.15, 374.15; $^1$H NMR (400 MHz, CD$_3$OD) δ 5.51-5.32 (m, 1H), 4.36-4.25 (m, 2H), 3.81-3.68 (m, 3H), 3.67-3.55 (m, 1H), 3.47 (s, 3H), 3.18-3.05 (m, 2H), 2.41-2.39 (m, 2H), 2.04 (s, 2H), 1.20-1.18 (m, 1H), 1.16-1.02 (m, 1H), 0.63-0.52 (m, 2H), 0.32-0.24 (m, 2H).

Step 4: 1-[(2R,4S)-4-[4-(1-Aminoethenyl)-3-bromo-5-[(cyclopropylmethyl)amino]pyrazol-1-yl]-2-(methoxymethyl)pyrrolidin-1-yl]prop-2-en-1-one To a stirred solution of 3-bromo-5-[(cyclopropylmethyl)amino]-1-[(3S,5R)-5-(methoxymethyl)pyrrolidin-3-yl]pyrazole-4-carboxamide hydrochloride (0.35 g, 0.86 mmol) and DIEA (0.33 g, 2.57 mmol) in DCM (4.00 mL) was added acryloyl chloride (69.75 mg, 0.77 mmol) dropwise at 0° C. under N$_2$ atmosphere. The reaction mixture was stirred for 10 min at 0° C. The resulting mixture was quenched with water (8 mL) and extracted with EA (3×10 mL). The combined organic layers were washed with water (20 mL), dried over anhydrous Na$_2$SO$_4$ and filtered. The filtrate was concentrated under reduced pressure. The residue was purified by silica gel Column chromatography, eluted with MeOH in DCM (0-10%). The fractions contained desired product were combined and concentrated to afford 1-[(2R,4S)-4-[4-(1-aminoethenyl)-3-bromo-5-[(cyclopropylmethyl)amino]pyrazol-1-yl]-2-(methoxymethyl)pyrrolidin-1-yl]prop-2-en-1-one (0.20 g, 55%) as a white solid. MS ESI calculated for $C_{17}H_{24}BrN_5O_3$ [M+H]$^+$, 426.11, 428.11, found 426.20, 428.20; $^1$H NMR (400 MHz, CDCl$_3$) δ 6.57 (s, 1H), 6.42-6.41 (m, 2H), 5.73-5.71 (m, 1H), 5.43-5.30 (m, 1H), 4.54-4.50 (m, 1H), 3.98 (d, J=8.2 Hz, 2H), 3.95-3.80 (m, 1H), 3.52-3.40 (m, 1H), 3.18-3.08 (m, 4H), 3.12-2.98 (m, 2H), 2.62-2.20 (m, 2H), 1.27-1.12 (m, 2H), 0.68-0.54 (m, 2H), 0.36-0.24 (m, 2H).

Step 5: 5-[(Cyclopropylmethyl)amino]-3-[2-(1-ethyl-4,6-difluoro-1,3-benzodiazol-5-yl)ethynyl]-1-[(3S,5R)-5-(methoxymethyl)-1-(prop-2-enoyl)pyrrolidin-3-yl]pyrazole-4-carboxamide To a stirred solution of 3-bromo-5-[(cyclopropylmethyl)amino]-1-[(3S,5R)-5-(methoxymethyl)-1-(prop-2-enoyl)pyrrolidin-3-yl]pyrazole-4-carboxamide (0.15 g, 0.35 mmol), 1-ethyl-5-ethynyl-4,6-difluoro-1,3-benzodiazole (0.15 g, 0.70 mmol), CuI (13.40 mg, 0.07 mmol) and Pd(PPh$_3$)$_2$Cl$_2$ (24.70 mg, 0.04 mmol) in DMF (4.00 mL) was added TEA (0.11 g, 1.06 mmol). The reaction mixture was degassed with argon for three times and stirred for 2 h at 90° C. The resulting mixture was cooled down and concentrated under reduced pressure. The residue was purified by silica gel Column chromatography, eluted with MeOH in DCM (0-5%) to afford the crude product. Then the crude product was purified by Prep-HPLC with the following conditions: Column: X-Bridge Prep C18 OBD Column, 19×150 mm 5 μm; Mobile Phase A: Water (10 mmol/L NH$_4$HCO$_3$), Mobile Phase B: ACN; Flow rate: 20 mL/min; Gradient: 10 B to 50 B in 5.8 min, 210/254 nm; RT: 5.58 min. The fractions contained desired product were combined and concentrated to afford 5-[(cyclopropylmethyl)amino]-3-[2-(1-ethyl-4,6-difluoro-1,3-benzodiazol-5-yl)ethynyl]-1-[(3S,5R)-5-(methoxymethyl)-1-(prop-2-enoyl)pyrrolidin-3-yl]pyrazole-4-carboxamide (43.4 mg, 22%) as a white solid. MS ESI calculated for $C_{28}H_{31}F_2N_7O_3$ [M+H]$^+$, 552.25, found 552.20; $^1$H NMR (400 MHz, CDCl$_3$) δ 8.05 (s, 1H), 7.04 (d, J=8.2 Hz, 2H), 6.66-6.34 (m, 2H), 5.72-5.69 (m, 1H), 5.54-5.17 (m, 2H), 4.64-4.36 (m, 1H), 4.25-4.24 (m, 2H), 4.09-4.06 (m, 2H), 3.92-3.91 (m, 1H), 3.58-3.44 (m, 1H), 3.39 (d, J=5.0 Hz, 3H), 3.22-2.90 (m, 2H), 2.84-2.63 (m, 1H), 2.41-2.30 (m, 1H), 1.71-1.59 (m, 4H), 1.25-1.06 (m, 1H), 0.65-0.61 (m, 2H), 0.33-0.29 (m, 2H).

Example 110: 3-[2-[1-(Difluoromethyl)-4,6-difluoro-2-methyl-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide

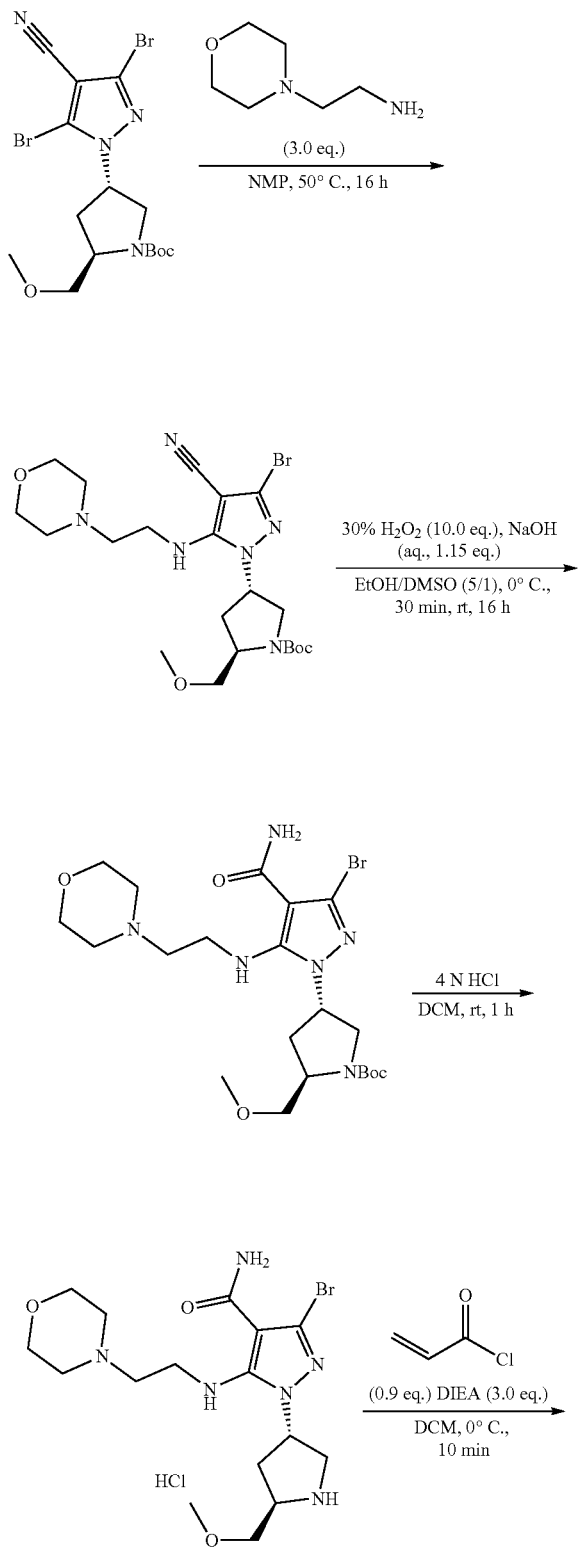

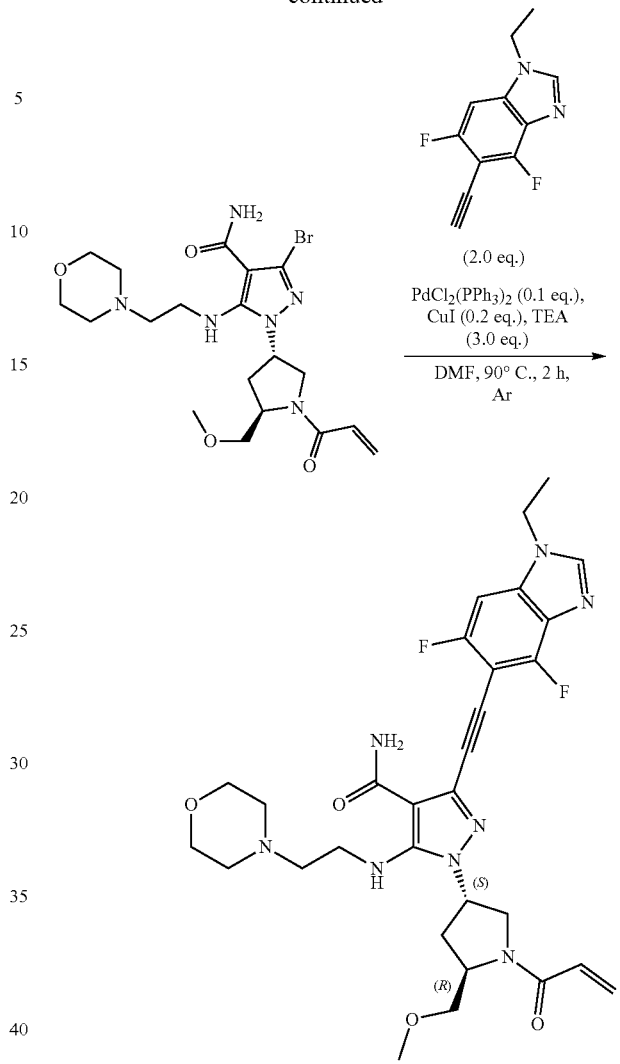

Step 1: Tert-butyl (2R,4S)-4-(3-bromo-4-cyano-5-[[2-(morpholin-4-yl)ethyl]amino]pyrazol-1-yl)-2-(methoxymethyl)pyrrolidine-1-carboxylate To a stirred mixture of tert-butyl (2R,4S)-4-(3,5-dibromo-4-cyanopyrazol-1-yl)-2-(methoxymethyl)pyrrolidine-1-carboxylate (1.00 g, 2.15 mmol) in NMP (10.00 mL) was added N-aminoethylmorpholine (0.84 g, 6.46 mmol). The reaction mixture was stirred for 16 h at 50° C. The resulting mixture was poured into water (100 mL) and extracted with EA (3×150 mL). The combined organic layers were washed with brine (2×200 mL), dried over anhydrous $Na_2SO_4$ and filtrated. The filtrate was concentrated under reduced pressure to afford tert-butyl (2R,4S)-4-(3-bromo-4-cyano-5-[[2-(morpholin-4-yl)ethyl]amino]pyrazol-1-yl)-2-(methoxymethyl)pyrrolidine-1-carboxylate (1.1 g, 99%) as a yellow oil which was used in the next step directly without further purification. MS ESI calculated for $C_{21}H_{33}BrN_6O_4$ [M+H]$^+$, 513.17, 515.17, found 513.25, 515.25; $^1$H NMR (400 MHz, CDCl$_3$) δ 6.37 (s, 1H), 5.32 (s, 1H), 5.02-5.00 (m, 1H), 4.73 (s, 1H), 4.16 (d, J=7.2 Hz, 1H), 3.83-3.56 (m, 7H), 3.52-3.40 (m, 2H), 2.89-2.83 (m, 3H), 2.79-2.50 (m, 2H), 2.40-2.38 (m, 3H), 2.33-2.19 (m, 1H), 2.10-1.99 (m, 1H), 1.32-1.29 (m, 9H).

Step 2: Tert-butyl (2R,4S)-4-(3-bromo-4-formyl-5-[[2-(morpholin-4-yl)ethyl]amino]pyrazol-1-yl)-2-(methoxymethyl)pyrrolidine-1-carboxylate To a stirred solution of tert-butyl (2R,4S)-4-(3-bromo-4-methyl-5-[[2-(morpholin-4-yl)ethyl]amino]pyrazol-1-yl)-2-(methoxymethyl)pyrrolidine-1-carboxylate (0.95 g, 1.89 mmol) in EtOH (10.00 mL) and DMSO (2.00 mL) were added NaOH (0.5 M in water) (86.97 mg, 2.17 mmol) and $H_2O_2$ (1.47 mL, 43.17 mmol, 30%) dropwise at 0° C. The reaction mixture was stirred for 30 min at 0° C. and 16 h at room temperature. The resulting mixture was diluted with water (200 mL) and extracted with EA (3×150 mL). The combined organic layers were washed with water (2×200 mL), dried over anhydrous $Na_2SO_4$ and filtered. The filtrate was concentrated under reduced pressure. The residue was purified by silica gel Column chromatography, eluted with EA in PE (50-100%). The fractions contained desired product were combined and concentrated to afford tert-butyl (2R,4S)-4-(3-bromo-4-formyl-5-[[2-(morpholin-4-yl)ethyl]amino]pyrazol-1-yl)-2-(methoxymethyl)pyrrolidine-1-carboxylate (0.65 g, 66%) as a white solid. MS ESI calculated for $C_{21}H_{35}BrN_6O_5$ [M+H]$^+$, 531.19, 533.19, found 531.20, 533.20; $^1$H NMR (400 MHz, CDCl$_3$) δ 7.09-6.96 (m, 1H), 6.59 (s, 1H), 5.48 (s, 1H), 5.25-5.03 (m, 1H), 4.16 (s, 1H), 3.78-2.75 (m, 5H), 3.56 (s, 1H), 3.50 (s, 2H), 3.45-3.37 (m, 1H), 3.38-3.34 (m, 3H), 3.31 (d, J=8.1 Hz, 2H), 2.64-2.60 (m, 2H), 2.70-2.50 (m, 3H), 2.24-2.21 (m, 1H), 1.79-1.75 (m, 1H), 1.46-1.48 (m, 9H).

Step 3: 3-Bromo-1-[(3S,5R)-5-(methoxymethyl)pyrrolidin-3-yl]-5-[[2-(morpholin-4-yl)ethyl]amino]pyrazole-4-carboxamide hydrochloride To a stirred mixture of tert-butyl (2R,4S)-4-(3-bromo-4-carbamoyl-5-[[2-(morpholin-4-yl)ethyl]amino]pyrazol-1-yl)-2-(methoxymethyl)pyrrolidine-1-carboxylate (0.65 g, 1.22 mmol) in DCM (6.00 mL) was added HCl (4 M in EA) (3.00 mL) dropwise at 0° C. The reaction mixture was stirred for 1 h at room temperature. The resulting mixture was concentrated under reduced pressure to afford 3-bromo-1-[(3S,5R)-5-(methoxymethyl)pyrrolidin-3-yl]-5-[[2-(morpholin-4-yl)ethyl]amino]pyrazole-4-carboxamide hydrochloride (0.60 g, 99%) as a yellow solid which was used in the next step directly without further purification. MS ESI calculated for $C_{16}H_{27}BrN_6O_3$ [M+H]$^+$, 431.13, 433.13, found 431.15, 433.15; $^1$H NMR (400 MHz, CD$_3$OD) δ 5.51 (s, 1H), 5.42 (s, 1H), 4.35-4.32 m, 1H), 4.08 (d, J=13.0 Hz, 2H), 4.00-3.90 (m, 2H), 3.84-3.81 (m, 1H), 3.77-3.71 (m, 2H), 3.69-3.58 (m, 4H), 3.61-3.53 (m, 2H), 3.47 (s, 3H), 3.41-3.34 (m, 2H), 3.26-3.22 (m, 2H), 2.52-2.34 (m, 2H), 2.04-2.02 (m, 1H), 1.34-1.16 (m, 1H).

Step 4: 3-[2-[1-(Difluoromethyl)-4,6-difluoro-2-methyl-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide To a stirred mixture of 3-bromo-1-[(3S,5R)-5-(methoxymethyl)pyrrolidin-3-yl]-5-[[2-(morpholin-4-yl)ethyl]amino]pyrazole-4-carboxamide hydrochloride (0.60 g, 1.28 mmol) and DIEA (0.67 mL, 5.18 mmol) in DCM (6.00 mL) was added acryloyl chloride (0.11 g, 1.15 mmol) dropwise at 0° C. under $N_2$ atmosphere. The reaction mixture was stirred for 10 min at 0° C. The resulting mixture was quenched with water (8 mL) and extracted with EA (3×20 mL). The combined organic layers were washed with brine (20 mL), dried over anhydrous $Na_2SO_4$ and filtered. The filtrate was concentrated under reduced pressure. The residue was purified by silica gel Column chromatography, eluted with MeOH in DCM (0-5%). The fractions contained desired product were combined and concentrated to afford 3-bromo-1-[(3S,5R)-5-(methoxymethyl)-1-(prop-2-enoyl)pyrrolidin-3-yl]-5-[[2-(morpholin-4-yl)ethyl]amino]pyrazole-4-carboxamide (0.37 g, 59%) as a yellow solid. MS ESI calculated for $C_{19}H_{29}BrN_6O_4$ [M+H]$^+$, 485.14, 487.14, found 485.20, 487.20; $^1$H NMR (300 MHz, CDCl$_3$) δ 7.10 (s, 1H), 6.60-6.38 (m, 2H), 5.75-5.72 (m, 1H), 5.39-5.35 (m, 1H), 4.55 (d, J=9.2 Hz, 1H), 3.99 (d, J=8.3 Hz, 2H), 3.95-3.81 (m, 1H), 3.78-3.74 (m, 4H), 3.49-3.45 (m, 1H), 3.46-3.27 (m, 5H), 2.66-2.64 (m, 2H), 2.70-2.54 (m, 1H), 2.54-2.51 (m, 4H), 2.32-2.19 (m, 1H), 1.30-1.28 (m, 1H).

Step 5: 3-[2-(1-Ethyl-4,6-difluoro-1,3-benzodiazol-5-yl)ethynyl]-1-[(3S,5R)-5-(methoxymethyl)-1-(prop-2-enoyl)pyrrolidin-3-yl]-5-[[2-(morpholin-4-yl)ethyl]amino]pyrazole-4-carboxamide To a stirred solution of 3-bromo-1-[(3S,5R)-5-(methoxymethyl)-1-(prop-2-enoyl)pyrrolidin-3-yl]-5-[[2-(morpholin-4-yl)ethyl]amino]pyrazole-4-carboxamide (0.19 g, 0.39 mmol), 1-ethyl-5-ethynyl-4,6-difluoro-1,3-benzodiazole (0.16 g, 0.78 mmol), CuI (14.91 mg, 0.08 mmol) and Pd(PPh$_3$)$_2$Cl$_2$ (27.48 mg, 0.04 mmol) in DMF (4.00 mL) was added TEA (0.12 g, 1.17 mmol) dropwise at room temperature. The reaction mixture was degassed with argon for three times and stirred for 2 h at 90° C. The resulting mixture was cooled down and concentrated under reduced pressure. The residue was purified by silica gel Column chromatography, eluted with MeOH in DCM (0-5%) to afford the crude product. Then the crude product was purified by Prep-HPLC with the following conditions: Column: X-Bridge Prep C18 OBD Column, 19×150 mm 5 μm; Mobile Phase A: Water (10 mmoL/L NH$_4$HCO$_3$), Mobile Phase B: ACN; Flow rate: 20 mL/min; Gradient: 25 B to 50 B in 6 min, 210/254 nm; RT: 5.58 min. The fractions contained desired product were combined and concentrated to afford 3-[2-(1-ethyl-4,6-difluoro-1,3-benzodiazol-5-yl)ethynyl]-1-[(3S,5R)-5-(methoxymethyl)-1-(prop-2-enoyl)pyrrolidin-3-yl]-5-[[2-(morpholin-4-yl)ethyl]amino]pyrazole-4-carboxamide (84.6 mg, 35%) as a white solid. MS ESI calculated for $C_{30}H_{36}F_2N_8O_4$ [M+H]$^+$, 611.28, found 611.25; $^1$H NMR (300 MHz, CDCl$_3$) δ 7.94 (s, 1H), 7.15-6.96 (m, 2H), 6.81 (d, J=45.9 Hz, 1H), 6.57-6.37 (m, 2H), 5.71-5.68 (m, 1H), 5.50-5.19 (m, 2H), 4.64-4.38 (m, 1H), 4.20-4.16 (m, 2H), 4.15-3.84 (m, 3H), 3.79-3.74 (m, 4H), 3.50-3.47 (m, 1H), 3.37-3.32 (m, 5H), 2.79-2.58 (m, 3H), 2.55-2.51 (m, 4H), 2.43-2.21 (m, 1H), 1.60-1.54 (m, 3H).

Example 111: 3-[2-(1-Ethyl-4,6-difluoro-1,3-benzo-diazol-5-yl)ethynyl]-1-[(3S,5R)-5-(methoxymethyl)-1-(prop-2-enoyl)pyrrolidin-3-yl]-5-[[3-(morpholin-4-yl)propyl]amino]pyrazole-4-carboxamide

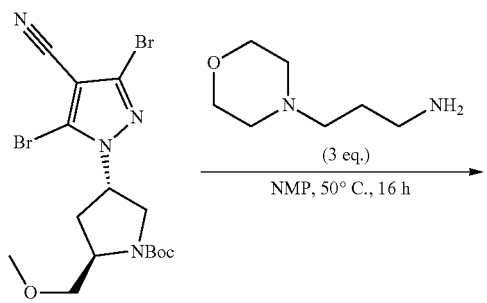

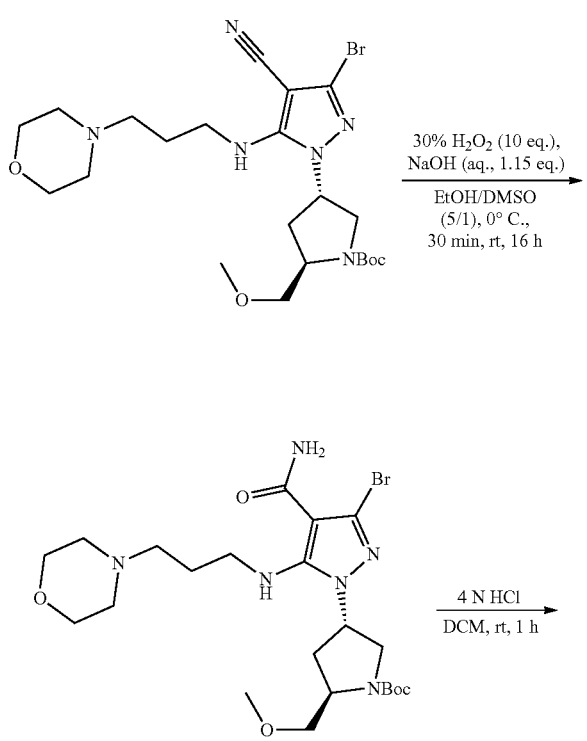

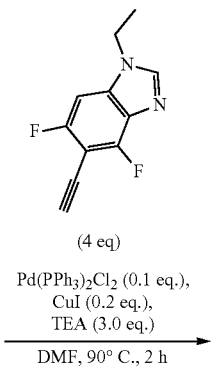

Step 1: Tert-butyl (2R,4S)-4-(3-bromo-4-cyano-5-[[3-(morpholin-4-yl)propyl]amino]pyrazol-1-yl)-2-(methoxymethyl)pyrrolidine-1-carboxylate To a stirred mixture of tert-butyl (2R,4S)-4-(3,5-dibromo-4-cyanopyrazol-1-yl)-2-(methoxymethyl)pyrrolidine-1-carboxylate (1.00 g, 2.15 mmol) in NMP (10.00 mL) was added 4-morpholinepropanamine (0.93 g, 6.46 mmol) dropwise at room temperature. The reaction mixture was stirred for 16 h at 50° C. The resulting mixture was poured into water (100 mL) and extracted with EA (3×50 mL). The combined organic layers were washed with brine (2×100 mL), dried over anhydrous Na2SO4, filtrated and concentrated under reduced pressure to afford tert-butyl (2R,4S)-4-(3-bromo-4-cyano-5-[[3-(morpholin-4-yl)propyl]amino]pyrazol-1-yl)-2-(methoxymethyl)pyrrolidine-1-carboxylate (1.0 g, 88%) as a yellow oil which was used in the next step directly without further purification. MS ESI calculated for $C_{22}H_{35}BrN_6O_4$ [M+H]$^+$, 526.19, found 527.25; $^1$H NMR (400 MHz, CDCl$_3$) δ 6.50 (s, 1H), 3.75-3.70 (m, 5H), 3.63-3.58 (m, 5H), 3.38-3.34 (m, 5H), 2.40-2.35 (m, 8H), 2.00-1.75 (m, 2H), 1.46 (s, 9H).

Step 2: Tert-butyl (2R,4S)-4-(3-bromo-4-carbamoyl-5-[[3-(morpholin-4-yl)propyl]amino]pyrazol-1-yl)-2-(methoxymethyl)pyrrolidine-1-carboxylate To a stirred solution of tert-butyl (2R,4S)-4-(3-bromo-4-cyano-5-[[3-(morpholin-4-yl)propyl]amino]pyrazol-1-yl)-2-(methoxymethyl)pyrrolidine-1-carboxylate (1.00 g, 1.90 mmol) in EtOH (10.00 mL) and DMSO (2.00 mL) were added NaOH (0.5 M in water) (4.36 mL, 2.18 mmol) and $H_2O_2$ (0.64 g, 18.96 mmol, 30%) dropwise at 0° C. The reaction mixture was stirred for 30 min at 0° C. and 16 h at room temperature. The resulting mixture was diluted with water (100 mL) and extracted with EA (3×100 mL). The combined organic layers were washed with brine (100 mL), dried over anhydrous $Na_2SO_4$ and filtered. The filtrate was concentrated under reduced pressure. The residue was purified by silica gel Column chromatography, eluted with MeOH in DCM (0-5%). The fractions contained desired product were combined and concentrated to afford tert-butyl (2R,4S)-4-(3-bromo-4-carbamoyl-5-[[3-(morpholin-4-yl)propyl]amino]pyrazol-1-yl)-2-(methoxymethyl)pyrrolidine-1-carboxylate (1 g, 97%) as a yellow solid. MS ESI calculated for $C_{22}H_{37}BrN_6O_5$ [M+H]$^+$, 545.20, 547.20, found 545.25, 547.25; $^1$H NMR (400 MHz, CDCl$_3$) δ 6.74 (s, 1H), 6.59 (s, 1H), 6.44 (s, 1H), 4.18 (d, J=18.4 Hz, 1H), 3.73-3.69 (m, 5H), 3.49 (s, 1H), 3.42-3.34 (m, 1H), 3.37 (s, 3H), 3.29-3.25 (m, 2H), 2.86-2.82 (m, 2H), 2.47-2.43 (m, 5H), 2.39-2.31 (m, 1H), 2.25-2.18 (m, 1H), 2.08-1.96 (m, 1H), 1.84-1.76 (m, 2H), 1.47 (s, 9H).

Step 3: 3-Bromo-1-[(3S,5R)-5-(methoxymethyl)pyrrolidin-3-yl]-5-[[3-(morpholin-4-yl)propyl]amino]pyrazole-4-carboxamide hydrochloride To a stirred solution of tert-butyl (2R,4S)-4-(3-bromo-4-carbamoyl-5-[[3-(morpholin-4-yl)propyl]amino]pyrazol-1-yl)-2-(methoxymethyl)pyrrolidine-1-carboxylate (1.00 g, 1.83 mmol) in DCM (10.00 mL) was added HCl (4 M in EA) (5.00 mL) dropwise at 0° C. The reaction mixture was stirred for 1 h at room temperature. The resulting mixture was concentrated under reduced pressure to afford 3-bromo-1-[(3S,5R)-5-(methoxymethyl)pyrrolidin-3-yl]-5-[[3-(morpholin-4-yl)propyl]amino]pyrazole-4-carboxamide hydrochloride (0.8 g, 91%) as a yellow solid which was used in the next step directly without further purification. MS ESI calculated for $C_{17}H_{29}BrN_6O_3$ [M+H]$^+$, 445.15, 447.15, found 445.20, 447.20; $^1$H NMR (300 MHz, CDCl$_3$) δ 6.37 (s, 1H), 5.57 (s, 3H), 5.30 (s, 1H), 4.99-4.95 (m, 1H), 4.12-4.09 (m, 1H), 3.45-3.42 (m, 2H), 2.90-2.85 (m, 2H), 2.56-2.51 (m, 1H), 2.08-2.05 (m, 1H), 2.07-2.02 (m, 5H), 1.27-1.21 (m, 10H).

Step 4: 3-Bromo-1-[(3S,5R)-5-(methoxymethyl)-1-(prop-2-enoyl)pyrrolidin-3-yl]-5-[[3-(morpholin-4-yl)propyl]amino]pyrazole-4-carboxamide To a stirred mixture of 3-bromo-1-[(3S,5R)-5-(methoxymethyl)pyrrolidin-3-yl]-5-[[3-(morpholin-4-yl)propyl]amino]pyrazole-4-carboxamide hydrochloride (0.80 g, 1.66 mmol) and DIEA (0.64 g, 4.98 mmol) in DCM (10.00 mL) was added acryloyl chloride (5.97 mL, 1.45 mmol, 0.25 M in DCM) dropwise at 0° C. under $N_2$ atmosphere. The reaction mixture was stirred for 10 min at 0° C. The resulting mixture was diluted with water (50 mL) and extracted with EA (3×50 mL). The combined organic layers were washed with water (100 mL), dried over anhydrous $Na_2SO_4$ and filtered. The filtrate was concentrated under reduced pressure. The residue was purified by silica gel Column chromatography, eluted with MeOH in DCM (0-10%). The fractions contained desired product were combined and concentrated to afford 3-bromo-1-[(3S,5R)-5-(methoxymethyl)-1-(prop-2-enoyl)pyrrolidin-3-yl]-5-[[3-(morpholin-4-yl)propyl]amino]pyrazole-4-carboxamide (0.25 g, 30%) as an off-white solid. MS ESI calculated for $C_{20}H_{31}BrN_6O_4$ [M+H]$^+$, 499.16, found 499.30; $^1$H NMR (400 MHz, CDCl$_3$) δ 6.83-6.81 (m, 2H), 6.71 (s, 1H), 5.39-5.26 (m, 2H), 5.15-5.12 (m, 1H), 4.53-4.50 (m, 2H), 4.39 (s, 1H), 3.97-3.92 (m, 4H), 3.95-3.78 (m, 3H), 3.66-3.62 (m, 1H), 3.51-3.39 (m, 3H), 3.10-3.08 (m, 1H), 2.25-2.22 (m, 2H), 1.85-1.82 (m, 4H), 1.43-1.41 (m, 2H), 1.25-1.22 (m, 2H).

Step 5: 3-[2-(1-Ethyl-4,6-difluoro-1,3-benzodiazol-5-yl)ethynyl]-1-[(3S,5R)-5-(methoxymethyl)-1-(prop-2-enoyl)pyrrolidin-3-yl]-5-[[3-(morpholin-4-yl)propyl]amino]pyrazole-4-carboxamide To a stirred solution of 3-bromo-1-[(3S,5R)-5-(methoxymethyl)-1-(prop-2-enoyl)pyrrolidin-3-yl]-5-[[3-(morpholin-4-yl)propyl]amino]pyrazole-4-carboxamide (0.15 g, 0.30 mmol), 1-ethyl-5-ethynyl-4,6-difluoro-1,3-benzodiazole (0.12 g, 0.60 mmol), Pd(PPh$_3$)$_2$Cl$_2$ (21.08 mg, 0.03 mmol) and CuI (11.44 mg, 0.06 mmol) in DMF (5.00 mL) was added TEA (91.18 mg, 0.90 mmol) dropwise at room temperature. The reaction mixture was degassed with argon for three times and stirred for 2 h at 90° C. The resulting mixture was cooled down and concentrated under reduced pressure. The residue was purified by silica gel Column chromatography, eluted with MeOH in DCM (0-10%) to afford the crude product. Then the crude product was purified by Prep-HPLC with the following conditions: Column: X-Bridge Prep C18 OBD Column, 19×150 mm 5 μm; Mobile Phase A: Water (10 mmoL/L NH$_4$HCO$_3$), Mobile Phase B: ACN; Flow rate: 20 mL/min; Gradient: 20 B to 50 B in 6 min; 210/254 nm. The fractions contained desired product were combined and concentrated to afford 3-[2-(1-ethyl-4,6-difluoro-1,3-benzodiazol-5-yl)ethynyl]-1-[(3S,5R)-5-(methoxymethyl)-1-(prop-2-enoyl)pyrrolidin-3-yl]-5-[[3-(morpholin-4-yl)propyl]amino]pyrazole-4-carboxamide (68 mg, 36%) as an off-white solid. MS ESI calculated for $C_{31}H_{38}F_2N_8O_4$ [M+H]$^+$, 625.30, found 625.25; $^1$H NMR (300 MHz, CDCl$_3$) δ 7.94 (s, 1H), 7.13-6.93 (m, 2H), 6.63-6.60 (m, 1H), 6.50-6.30 (m, 2H), 5.71-5.68 (m, 1H), 5.50-5.12 (m, 2H), 4.62-4.35 (m, 1H), 4.20-4.18 (m, 2H), 4.10-3.94 (m, 2H), 3.89-3.85 (m, 1H), 3.71-3.68 (m, 4H), 3.53-3.40 (m, 1H), 3.38-3.17 (m, 5H), 3.01-2.63 (m, 1H), 2.46 (d, J=6.5 Hz, 6H), 2.30-2.25 (m, 1H), 1.84-1.80 (m, 2H), 1.67 (s, 3H).

Example 112: 3-[2-(1-Ethyl-4,6-difluoro-1,3-benzodiazol-5-yl)ethynyl]-5-[[2-(morpholin-4-yl)ethyl]amino]-1-[(3S)-1-(prop-2-enoyl)pyrrolidin-3-yl]pyrazole-4-carboxamide

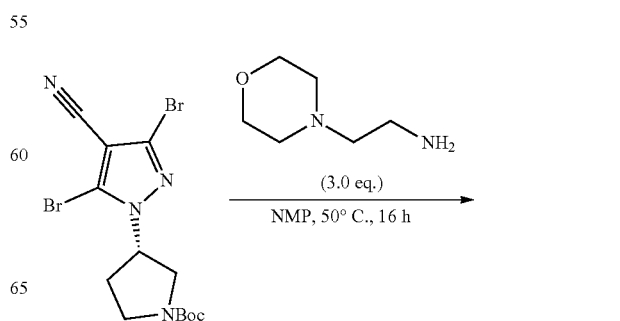

547
-continued

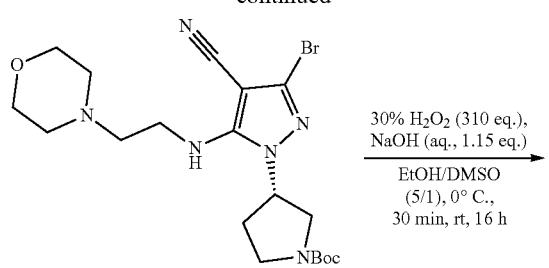

30% H₂O₂ (310 eq.),
NaOH (aq., 1.15 eq.)
———————→
EtOH/DMSO
(5/1), 0° C.,
30 min, rt, 16 h

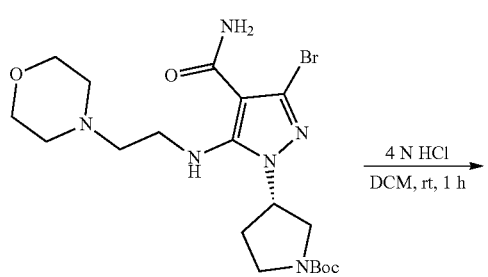

4 N HCl
————→
DCM, rt, 1 h

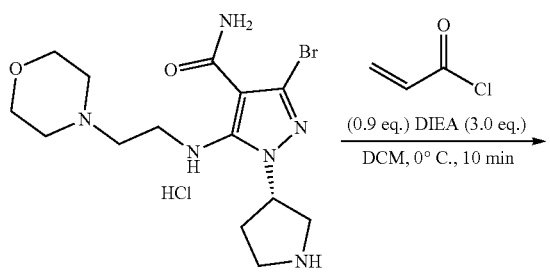

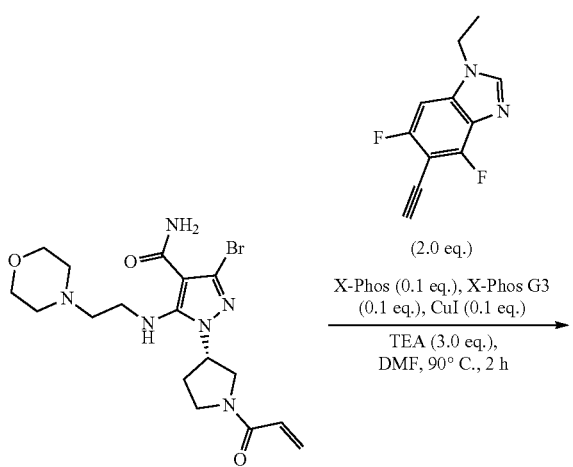

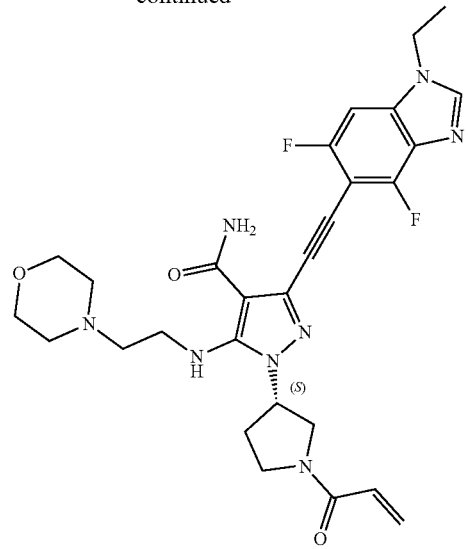

(2.0 eq.)
X-Phos (0.1 eq.), X-Phos G3
(0.1 eq.), CuI (0.1 eq.)
—————————————→
TEA (3.0 eq.),
DMF, 90° C., 2 h 548
-continued Step 1: Tert-butyl (3S)-3-(3-bromo-4-cyano-5-[[2-(morpholin-4-yl)ethyl]amino]pyrazol-1-yl)pyrrolidine-1-carboxylate To a stirred mixture of tert-butyl (3S)-3-(3,5-dibromo-4-cyanopyrazol-1-yl)pyrrolidine-1-carboxylate (1.00 g, 2.380 mmol) in NMP (10.00 mL) was added N-aminoethylmorpholine (0.93 g, 7.14 mmol) dropwise at room temperature. The reaction mixture was stirred for 16 h at 50° C. under argon atmosphere. The resulting mixture was diluted with water (30 mL), extracted with ethyl acetate (5×30 mL), dried over anhydrous Na₂SO₄ and filtered. The filtrate was concentrated under reduced pressure to afford tert-butyl (3S)-3-(3-bromo-4-cyano-5-[[2-(morpholin-4-yl)ethyl]amino] pyrazol-1-yl)pyrrolidine-1-carboxylate (1 g, 78%) as a light yellow oil which was used in the next step directly without further purification. MS ESI calculated for $C_{19}H_{29}BrN_6O_3$ [M+H]$^+$, 469.15, found 469.15.

Step 2: Tert-butyl (3S)-3-(3-bromo-4-carbamoyl-5-[[2-(morpholin-4-yl)ethyl]amino]pyrazol-1-yl)pyrrolidine-1-carboxylate To a stirred solution of tert-butyl (2R,4S)-4-[3-bromo-4-cyano-5-[(cyclopropylmethyl)amino]pyrazol-1-yl]-2-(methoxymethyl)pyrrolidine-1-carboxylate (1.00 g, 2.20 mmol) in EtOH (10.00 mL) and DMSO (2.00 mL) were added NaOH (0.5 M in water) (0.11 mL, 2.70 mmol) and H₂O₂ (1.82 mL, 53.50 mmol, 30%) dropwise at 0° C. The reaction mixture was stirred for 30 min at 0° C. and 16 h at room temperature. The resulting mixture was diluted with water (20 mL) and extracted with EA (3×20 mL). The combined organic layers were washed with water (2×20 mL), dried over anhydrous Na₂SO₄ and filtered. The filtrate was concentrated under reduced pressure. The residue was purified by silica gel Column chromatography, eluted with EA in PE (20-70%). The fractions contained desired product were combined and concentrated to afford tert-butyl (3S)-3-(3-bromo-4-carbamoyl-5-[[2-(morpholin-4-yl)ethyl] amino]pyrazol-1-yl)pyrrolidine-1-carboxylate (0.37 g, 32%) as a yellow solid. MS ESI calculated for $C_{21}H_{35}BrN_6O_5$ [M+H]$^+$, 487.16, 489.16, found 487.15, 489.15; $^1$H NMR (400 MHz, CDCl₃) δ 6.92 (s, 1H), 6.55 (d, J=45.4 Hz, 1H), 5.49 (s, 1H), 5.09-4.81 (m, 1H), 3.92-3.67 (m, 8H), 3.56-3.41 (m, 1H), 3.29-3.27 (m, 2H), 3.00 (s, 1H), 2.59-2.54 (m, 7H), 2.28-2.25 (m, 1H), 1.50-1.47 (m, 9H), 1.29-1.25 (m, 2H).

Step 3: 3-Bromo-5-[[2-(morpholin-4-yl)ethyl]amino]-1-[(3S)-pyrrolidin-3-yl]pyrazole-4-carboxamide hydrochloride To a stirred solution of tert-butyl (3S)-3-(3-bromo-4-carbamoyl-5-[[2-(morpholin-4-yl)ethyl]amino]pyrazol-1-yl)pyrrolidine-1-carboxylate (0.36 g, 0.74 mmol) in DCM (4.00 mL) was added HCl (4 M in EA) (2.00 mL) dropwise at 0° C. The reaction mixture was stirred for 1 h at room temperature. The resulting mixture was concentrated under reduced pressure to afford 3-bromo-5-[[2-(morpholin-4-yl)ethyl]amino]-1-[(3S)-pyrrolidin-3-yl]pyrazole-4-carboxamide hydrochloride (0.32 g, 99%) as a light yellow solid which was used in the next step directly without further purification. MS ESI calculated for $C_{14}H_{23}BrN_6O_2$ [M+H]$^+$, 387.16, 389.16, found 387.15, 389.15; $^1$H NMR (400 MHz, CD$_3$OD) δ 5.51 (s, 2H), 5.45-5.39 (m, 1H), 4.17-3.89 (m, 3H), 3.86-3.69 (m, 2H), 3.73-3.65 (m, 1H), 3.65 (d, J=1.9 Hz, 1H), 3.65-3.57 (m, 1H), 3.61-3.54 (m, 1H), 3.57-3.48 (m, 1H), 3.41-3.36 (m, 2H), 3.30-3.18 (m, 2H), 2.70-2.65 (m, 1H), 2.59-2.56 (m, 1H), 2.37-2.31 (m, 1H), 2.06-2.03 (m, 1H), 1.64-1.61 (m, 1H), 1.33-1.16 (m, 1H).

Step 4: 3-Bromo-5-[[2-(morpholin-4-yl)ethyl]amino]-1-[(3S)-1-(prop-2-enoyl)pyrrolidin-3-yl]pyrazole-4-carboxamide To a stirred solution of 3-bromo-5-[[2-(morpholin-4-yl)ethyl]amino]-1-[(3S)-pyrrolidin-3-yl]pyrazole-4-carboxamide hydrochloride (0.32 g, 0.75 mmol) and DIEA (0.39 mL, 3.05 mmol) in DCM (4.00 mL) was added acryloyl chloride (61.52 mg, 0.68 mmol) dropwise at 0° C. under N$_2$ atmosphere. The reaction mixture was stirred for 10 min at 0° C. The resulting mixture was diluted with water (10 mL) and extracted with EA (3×20 mL). The combined organic layers were washed with water (20 mL), dried over anhydrous Na$_2$SO$_4$ and filtered. The filtrate was concentrated under reduced pressure. The residue was purified by silica gel Column chromatography, eluted with MeOH in DCM (0-10%). The fractions contained desired product were combined and concentrated to afford 3-bromo-5-[[2-(morpholin-4-yl)ethyl]amino]-1-[(3S)-1-(prop-2-enoyl)pyrrolidin-3-yl]pyrazole-4-carboxamide (0.20 g, 60%) as a yellow solid. MS ESI calculated for $C_{17}H_{25}BrN_6O_3$ [M+H]$^+$, 441.12, 443.12, found 441.25, 443.25; $^1$H NMR (300 MHz, CDCl$_3$) δ 6.96 (d, J=6.1 Hz, 1H), 6.58-6.41 (m, 1H), 6.45-6.36 (m, 1H), 5.79-5.67 (m, 1H), 5.46 (s, 1H), 5.04-4.93 (m, 1H), 4.11-3.83 (m, 3H), 3.88-3.51 (s, 1H), 3.31 (d, J=6.0 Hz, 2H), 2.68-2.65 (m, 2H), 2.64-2.62 (m, 1H), 2.55-2.52 (m, 4H), 2.52-2.28 (m, 1H), 1.60-1.57 (m, 1H), 1.49-1.46 (m, 1H), 1.28-1.27 (m, 1H), 1.26-1.24 (m, 1H), 0.93-0.82 (m, 1H).

Step 5: 3-[2-(1-Ethyl-4,6-difluoro-1,3-benzodiazol-5-yl)ethynyl]-5-[[2-(morpholin-4-yl)ethyl]amino]-1-[(3S)-1-(prop-2-enoyl)pyrrolidin-3-yl]pyrazole-4-carboxamide To a stirred mixture of 3-bromo-5-[[2-(morpholin-4-yl)ethyl]amino]-1-[(3S)-1-(prop-2-enoyl)pyrrolidin-3-yl]pyrazole-4-carboxamide (0.10 g, 0.23 mmol), 1-ethyl-5-ethynyl-4,6-difluoro-1,3-benzodiazole (93.44 mg, 0.45 mmol), CuI (4.32 mg, 0.02 mmol), X-Phos Pd G3 (19.18 mg, 0.02 mmol) and X-Phos (10.80 mg, 0.02 mmol) in DMF (2.00 mL) was added TEA (68.79 mg, 0.68 mmol) dropwise at room temperature. The reaction mixture was degassed with argon for three times and stirred for 2 h at 90° C. The resulting mixture was cooled down and concentrated under reduced pressure. The residue was purified by silica gel Column chromatography, eluted with MeOH in DCM (0-5%) to afford the crude product. Then the crude product was purified by Prep-HPLC with the following conditions: Column: X-Bridge Prep C18 OBD Column, 19×150 mm 5 μm; Mobile Phase A: Water (10 mmol/L NH$_4$HCO$_3$), Mobile Phase B: ACN; Flow rate: 20 mL/min; Gradient: 15 B to 50 B in 6 min. The fractions contained desired product were combined and concentrated to afford 3-[2-(1-ethyl-4,6-difluoro-1,3-benzodiazol-5-yl)ethynyl]-5-[[2-(morpholin-4-yl)ethyl]amino]-1-[(3S)-1-(prop-2-enoyl)pyrrolidin-3-yl]pyrazole-4-carboxamide (30.4 mg, 23%) as a white solid. MS ESI calculated for $C_{28}H_{32}F_2N_8O_3$ [M+H]$^+$, 567.26, found 567.25; $^1$H NMR (400 MHz, CDCl$_3$) δ 7.96 (s, 1H), 7.21-6.95 (m, 2H), 6.76 (d, J=7.0 Hz, 1H), 6.62-6.33 (m, 2H), 5.79-5.65 (m, 1H), 5.44 (s, 1H), 5.10-5.07 (m, 1H), 4.25-4.20 (m, 2H), 4.17-3.86 (m, 3H), 3.78-3.76 (m, 5H), 3.31-3.27 (m, 2H), 2.83-2.27 (m, 8H), 1.60-1.56 (m, 2H), 1.33-1.27 (m, 1H).

Example 113: 3-[2-(6-Chloro-7-fluoro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide

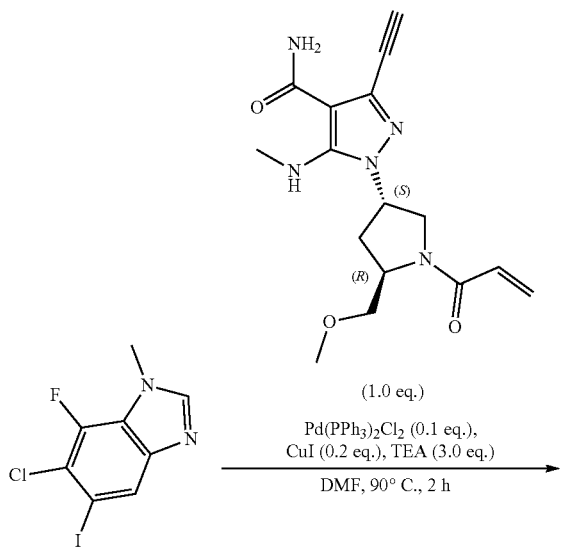

-continued

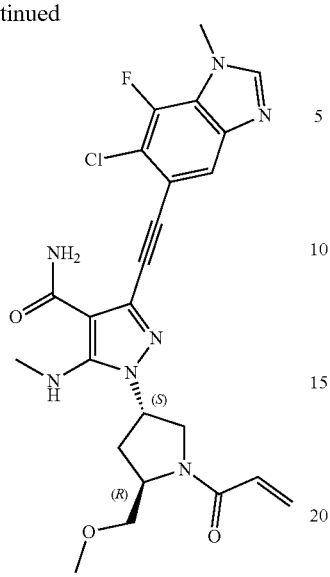

To a stirred mixture of 3-ethynyl-1-[(3S,5R)-5-(methoxymethyl)-1-(prop-2-enoyl)pyrrolidin-3-yl]-5-(methylamino)pyrazole-4-carboxamide (0.15 g, 0.45 mmol), 6-chloro-7-fluoro-5-iodo-1-methyl-1,3-benzodiazole (0.14 g, 0.45 mmol), CuI (17.24 mg, 0.09 mmol) and Pd(PPh₃)₂Cl₂ (31.77 mg, 0.04 mmol) in DMF (2.00 mL) was added TEA (0.14 g, 1.36 mmol). The reaction mixture was degassed with argon for three times and stirred for 2 h at 90° C. The resulting mixture was cooled down and concentrated under reduced pressure. The residue was purified by silica gel Column chromatography, eluted with MeOH in DCM (0-5%) to afford the crude product. Then the crude product was purified by Prep-HPLC with the following conditions: Column: X-Bridge Prep C18 OBD Column, 19×150 mm 5 µm; Mobile Phase A: Water (10 mmol/L NH₄HCO₃), Mobile Phase B: ACN; Flow rate: 20 mL/min; Gradient: 20 B to 50 B in 6 min. The fractions contained desired product were combined and concentrated to afford 3-[2-(6-chloro-7-fluoro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (70.1 mg, 30%) as a white solid. MS ESI calculated for $C_{24}H_{25}ClFN_7O_3$ [M+H]⁺, 514.17, found 514.15; ¹H NMR (300 MHz, CDCl₃) δ 7.89 (d, J=10.6 Hz, 2H), 7.11 (s, 1H), 6.83 (d, J=6.1 Hz, 1H), 6.56-6.35 (m, 2H), 5.72 (m, 1H), 5.61-5.46 (m, 2H), 4.60-4.57 (m, 1H), 4.18-3.88 (m, 6H), 3.41-3.58 (m, 1H), 3.56-3.45 (m, 3H), 3.02-2.98 (m, 3H), 2.81-2.64 (m, 1H), 2.41-2.35 (m, 1H).

Example 114: 3-[2-(1,3-Benzoxazol-2-yl)ethynyl]-1-[(3S,5R)-5-(methoxymethyl)-1-(prop-2-enoyl)pyrrolidin-3-yl]-5-(methylamino)pyrazole-4-carboxamide

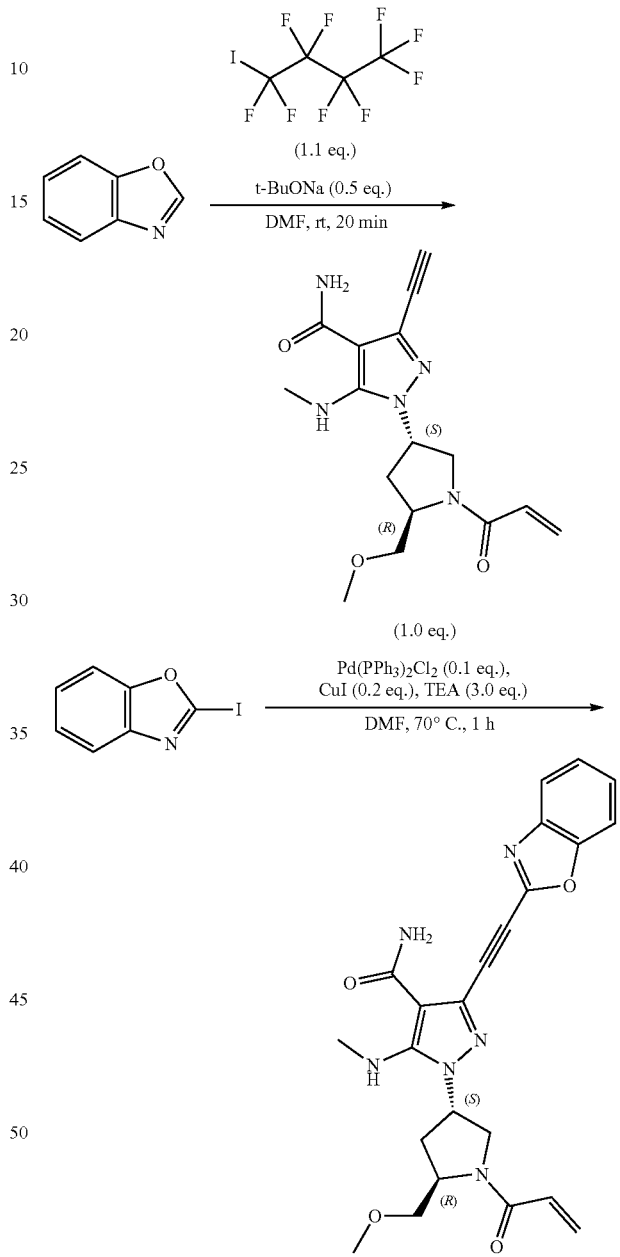

Step 1: 2-Iodo-1,3-benzoxazole

To a stirred solution of benzoxazole (1 g, 8.40 mmol) in DMF (42.00 mL) were added 1,1,1,2,2,3,3,4,4-nonafluoro-4-iodobutane (1.59 mL, 9.24 mmol) and sodium 2-methylpropan-2-olate (0.40 g, 4.16 mmol) at room temperature. The reaction mixture was stirred for 20 min at room temperature. The resulting mixture was poured into water and extracted with EA (3×70 mL). The combined organic layers were washed with brine (5×50 mL), dried over anhydrous Na₂SO₄, filtered and concentrated under reduced pressure. The residue was purified by silica gel Column chromatography, eluted with 8% EA in PE. The fractions contained desired product were combined and concentrated to afford 2-iodo-1,3-benzoxazole (1.88 g, 91%) as a white solid. MS ESI calculated for C₇H₄INO [M+H]⁺, 245.93, found 245.95; ¹H NMR (400 MHz, CDCl₃) δ 7.74-7.68 (m, 1H), 7.57-7.52 (m, 1H), 7.35-7.28 (m, 2H).

Step 2: 3-[2-(1,3-Benzoxazol-2-yl)ethynyl]-1-[(3S,5R)-5-(methoxymethyl)-1-(prop-2-enoyl)pyrrolidin-3-yl]-5-(methylamino)pyrazole-4-carboxamide To a stirred mixture of 2-iodo-1,3-benzoxazole (0.11 g, 0.45 mmol), 3-ethynyl-1-[(3S,5R)-5-(methoxymethyl)-1-(prop-2-enoyl)pyrrolidin-3-yl]-5-(methylamino)pyrazole-4-carboxamide (0.15 g, 0.45 mmol), Pd(PPh₃)₂Cl₂ (31.51 mg, 0.05 mmol) and CuI (17.10 mg, 0.09 mmol) in DMF (1 mL) was added TEA (0.19 mL, 1.85 mmol). The reaction mixture was degassed with argon for three times and stirred for 1 h at 70° C. The resulting mixture was diluted with water (15 mL) and extracted with EA (3×30 mL). The combined organic layers were washed with brine (5×20 mL), dried over anhydrous Na₂SO₄ and filtered. The filtrate was concentrated under reduced pressure. The residue was purified by silica gel Column chromatography, eluted with CH₂Cl₂/MeOH (10/1). The fractions contained desired product were combined and concentrated. The crude product was purified by Prep-HPLC with the following conditions: Column: XBridge Prep C18 OBD Column, 19×150 mm 5 μm; Mobile Phase A: Water (10 mmol/L NH₄HCO₃), Mobile Phase B: ACN; Flow rate: 20 mL/min; Gradient: 15 B to 50 B in 6 min; 210/254 nm; RT: 5.75 min. The fractions contained desired product were combined and concentrated to afford 3-[2-(1,3-Benzoxazol-2-yl)ethynyl]-1-[(3S,5R)-5-(methoxymethyl)-1-(prop-2-enoyl)pyrrolidin-3-yl]-5-(methylamino)pyrazole-4-carboxamide (0.07 g, 36%) as an off-white solid. MS ESI calculated for C₂₃H₂₄N₆O₄ [M+H]⁺, 448.47, found 448.19; ¹H NMR (400 MHz, CDCl₃) δ 7.81-7.79 (m, 1H), 7.58 (d, J=7.6 Hz, 1H), 7.50-7.41 (m, 2H), 6.86 (s, 1H), 6.68-6.44 (m, 2H), 5.76-5.72 (m, 1H), 5.56-5.52 (m, 2H), 4.60-4.58 (m, 1H), 4.41-3.91 (m, 3H), 3.54-3.39 (m, 4H), 3.07 (d, J=15.2 Hz, 3H), 2.98-2.65 (m, 1H), 2.37-2.32 (m, 1H).

Example 115: 3-[2-(6-Fluoro-1,3-benzoxazol-5-yl)ethynyl]-1-[(3S,5R)-5-(methoxymethyl)-1-(prop-2-enoyl)pyrrolidin-3-yl]-5-(methylamino)pyrazole-4-carboxamide

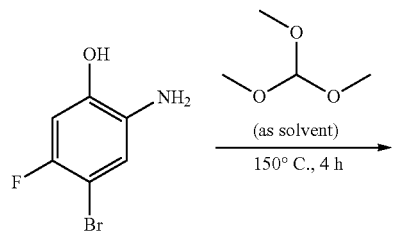

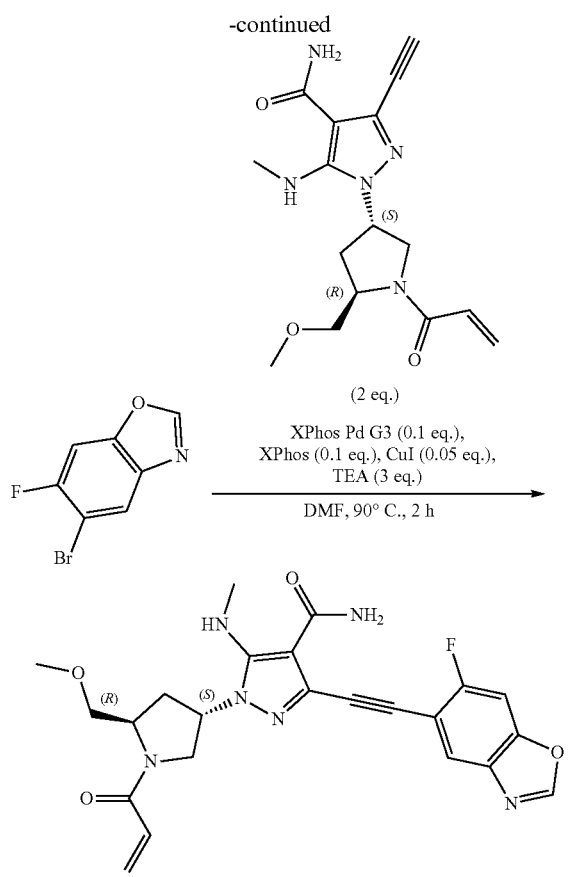

Step 1: 5-Bromo-6-fluoro-1,3-benzoxazole

A solution of 2-amino-4-bromo-5-fluorophenol (1.70 g, 8.25 mmol) in trimethyl orthoformate (17.00 mL) was stirred for 4 h at 150° C. The resulting mixture was concentrated under reduced pressure. The residue was purified by silica gel Column chromatography, eluted with 8% EA in PE. The fractions contained desired product were combined and concentrated to afford 5-bromo-6-fluoro-1,3-benzoxazole (1.4 g, 78%) as a light pink solid. MS ESI calculated for C₇H₃BrFNO [M+H]⁺, 215.94, found 215.95; ¹H NMR (400 MHz, CDCl₃) δ 8.10 (s, 1H), 8.00 (d, J=6.3 Hz, 1H), 7.41 (d, J=7.4 Hz, 1H).

Step 2: 3-[2-(6-Fluoro-1,3-benzoxazol-5-yl)ethynyl]-1-[(3S,5R)-5-(methoxymethyl)-1-(prop-2-enoyl)pyrrolidin-3-yl]-5-(methylamino)pyrazole-4-carboxamide To a stirred mixture of 5-bromo-6-fluoro-1,3-benzoxazole (0.05 g, 0.23 mmol), 3-ethynyl-1-[(3S,5R)-5-(methoxymethyl)-1-(prop-2-enoyl)pyrrolidin-3-yl]-5-(methylamino)pyrazole-4-carboxamide (0.08 g, 0.23 mmol), XPhos Pd G₃ (39.20 mg, 0.05 mmol), XPhos (22 mg, 0.05 mmol) and CuI (2.20 mg, 0.01 mmol) in DMF (0.50 mL) was added TEA (0.10 mL, 0.95 mmol) dropwise at room temperature. The reaction mixture was degassed with argon for three times and stirred for 2 h at 90° C. The resulting mixture was diluted with water (15 mL) and extracted with EA (3×30 mL). The combined organic layers were washed with water (5×20 mL), dried over anhydrous Na₂SO₄ and filtered. The filtrate was concentrated under reduced pressure. The residue was purified by silica gel Column chromatography, eluted with CH$_2$Cl$_2$/MeOH (10/1). The fractions contained desired product were combined and concentrated. The crude product was purified by Prep-HPLC with the following conditions: Column: XBridge Prep C$_{18}$ OBD Column, 19×150 mm 5 µm; Mobile Phase A: Water (10 mmol/L NH$_4$HCO$_3$), Mobile Phase B: ACN; Flow rate: 20 mL/min; Gradient: 15 B to 50 B in 6 min; 210/254 nm; RT: 5.75 min. The fractions contained desired product were combined and concentrated to afford 3-[2-(6-fluoro-1,3-benzoxazol-5-yl)ethynyl]-1-[(3S,5R)-5-(methoxymethyl)-1-(prop-2-enoyl)pyrrolidin-3-yl]-5-(methylamino)pyrazole-4-carboxamide (0.07 g, 31%) as an off-white solid. MS ESI calculated for C$_{23}$H$_{23}$FN$_6$O$_4$ [M+H]$^+$, 466.47, found 466.18; $^1$H NMR (400 MHz, CDCl$_3$) δ 8.16 (s, 1H), 8.01 (t, J=16 Hz, 1H), 7.42 (d, J=8 Hz, 1H), 7.00 (s, 1H), 6.53-6.40 (m, 2H), 5.75-5.71 (m, 1H), 5.57-5.51 (m, 1H), 5.40-5.31 (m, 1H), 4.59-4.57 (m, 1H), 4.13-4.01 (m, 2H), 3.93-3.90 (m, 1H), 3.53-3.44 (m, 1H), 3.40 (d, J=4 Hz, 3H), 3.07-3.03 (m, 3H), 2.76-2.68 (m, 1H), 2.35-2.30 (m, 1H).

Example 116: 3-[2-(1-Ethyl-4,6-difluoro-1,3-benzodiazol-5-yl)ethynyl]-5-[(2-hydroxyethyl)amino]-1-[(3S,5R)-5-(methoxymethyl)-1-(prop-2-enoyl)pyrrolidin-3-yl]pyrazole-4-carboxamide

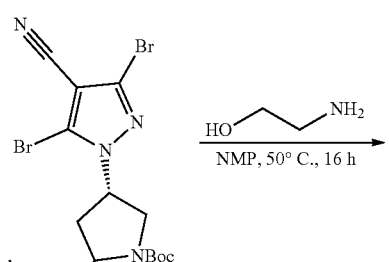

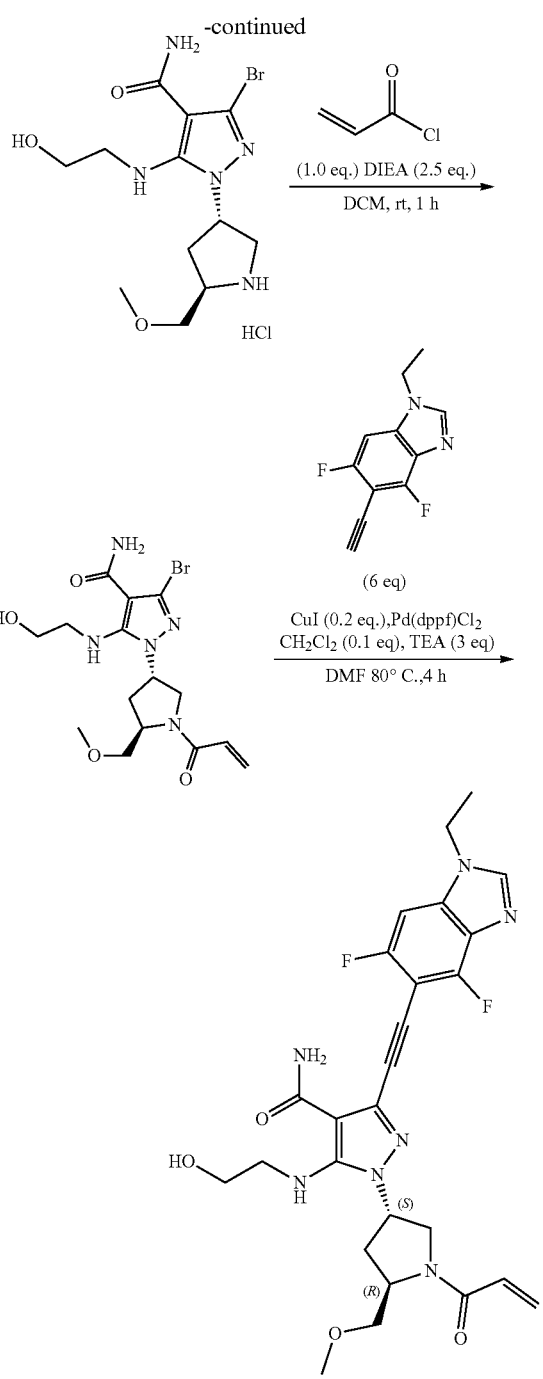

Step 1: Tert-butyl (2R,4S)-4-[3-bromo-4-cyano-5-[(2-hydroxyethyl)amino]pyrazol-1-yl]-2-(methoxymethyl)pyrrolidine-1-carboxylate To a stirred solution of tert-butyl (2R,4S)-4-(3,5-dibromo-4-cyanopyrazol-1-yl)-2-(methoxymethyl)pyrrolidine-1-carboxylate (1.00 g, 2.15 mmol) in NMP (10.00 mL, 0.10 mol) was added ethanolamine (0.39 g, 6.46 mmol). The reaction mixture was stirred for 16 h at 50° C. The resulting mixture was diluted with water (300 mL), extracted with EtOAc (3×300 mL), dried over anhydrous Na$_2$SO$_4$ and filtered. The filtrate was concentrated under reduced pressure to afford tert-butyl (2R,4S)-4-[3-bromo-4-cyano-5-[(2-hydroxyethyl)

amino]pyrazol-1-yl]-2-(methoxymethyl)pyrrolidine-1-carboxylate (0.95 g, crude) which was used in the next step directly without further purification. MS ESI calculated for $C_{17}H_{28}BrN_5O_5$ [M+H]$^+$, 444.12, found 444.20.

Step 2: Tert-butyl (2R,4S)-4-[3-bromo-4-carbamoyl-5-[(2-hydroxyethyl)amino]pyrazol-1-yl]-2-(methoxymethyl)pyrrolidine-1-carboxylate To a stirred solution tert-butyl (2R,4S)-4-[3-bromo-4-cyano-5-[(2-hydroxyethyl)amino]pyrazol-1-yl]-2-(methoxymethyl)pyrrolidine-1-carboxylate (0.95 g, 2.15 mmol) in DMSO (2.00 mL, 28.15 mmol) and EtOH (10.00 mL, 0.17 mol) was added $H_2O_2$ (1.67 mL, 71.68 mmol, 30%) and NaOH (4.95 mL, 2.47 mmol, 0.5 M) dropwise at 0° C. The reaction mixture was stirred for 30 min at 0° C. and 16 h at room temperature. The resulting mixture was diluted with water (300 mL), extracted with EtOAc (3×300 mL), dried over anhydrous $Na_2SO_4$ and filtered. The filtrate was concentrated under reduced pressure. The residue was purified by silica gel Column chromatography, eluted with PE/EtOAc (0-50%). The fractions contained desired product were combined and concentrated to afford tert-butyl (2R,4S)-4-[3-bromo-4-carbamoyl-5-[(2-hydroxyethyl)amino] pyrazol-1-yl]-2-(methoxymethyl)pyrrolidine-1-carboxylate (0.65 g, 65%) as an off-white oil. MS ESI calculated for $C_{17}H_{28}BrN_5O_5$ [M+H]$^+$, 462.13, found 462.15.

Step 3: 3-Bromo-5-[(2-hydroxyethyl)amino]-1-[(3S,5R)-5-(methoxymethyl)pyrrolidin-3-yl]pyrazole-4-carboxamide To a stirred solution of tert-butyl (2R,4S)-4-[3-bromo-4-carbamoyl-5-[(2-hydroxyethyl)amino]pyrazol-1-yl]-2-(methoxymethyl)pyrrolidine-1-carboxylate (0.65 g, 1.40 mmol) in DCM (7.00 mL) was added HCl (4 M in EA) (7.73 mL, 30.93 mmol) dropwise at 0° C. The reaction mixture was stirred for 1 h at room temperature. The resulting mixture was concentrated under reduced pressure to afford 3-bromo-5-[(2-hydroxyethyl)amino]-1-[(3S,5R)-5-(methoxymethyl)pyrrolidin-3-yl]pyrazole-4-carboxamide (0.5 g, crude) which was used in the next step directly without further purification. MS ESI calculated for $C_{12}H_{20}BrN_5O_3$ [M+H–HCl]$^+$, 362.07, found 362.10.

Step 4: 3-Bromo-5-[(2-hydroxyethyl)amino]-1-[(3S,5R)-5-(methoxymethyl)-1-(prop-2-enoyl)pyrrolidin-3-yl]pyrazole-4-carboxamide To a stirred mixture of 3-bromo-5-[(2-hydroxyethyl)amino]-1-[(3S,5R)-5-(methoxymethyl)pyrrolidin-3-yl]pyrazole-4-carboxamide (0.5 g, 1.38 mmol) and DIEA (0.60 mL, 4.65 mmol) in DCM (5.00 mL) was added acryloyl chloride (5.02 mL, 1.25 mmol) dropwise at 0° C. The reaction mixture was stirred for 1 h at room temperature. The resulting mixture was quenched with $H_2O$ (1 mL) and concentrated under reduced pressure. The residue was purified by silica gel Column chromatography, eluted with $CH_2Cl_2$/MeOH (0-10%). The fractions contained desired product were combined and concentrated to afford 3-bromo-5-[(2-hydroxyethyl)amino]-1-[(3S,5R)-5-(methoxymethyl)-1-(prop-2-enoyl)pyrrolidin-3-yl]pyrazole-4-carboxamide (0.55 g, 95%) as an off-white oil. MS ESI calculated for $C_{15}H_{22}BrN_5O_4$ [M+H]$^+$, 416.09, found 416.15; $^1$H NMR (300 MHz, CDCl$_3$) δ 6.73 (s, 1H), 6.57-6.33 (m, 2H), 5.71-5.68 (m, 1H), 5.31 (s, 2H), 4.03-3.81 (m, 2H), 3.68-3.62 (m, 5H), 3.42-3.31 (m, 4H), 3.11-3.08 (m, 3H).

Step 5: 3-[2-(1-Ethyl-4,6-difluoro-1,3-benzodiazol-5-yl)ethynyl]-5-[(2-hydroxyethyl)amino]-1-[(3S,5R)-5-(methoxymethyl)-1-(prop-2-enoyl)pyrrolidin-3-yl]pyrazole-4-carboxamide To a stirred mixture of 3-bromo-5-[(2-hydroxyethyl)amino]-1-[(3S,5R)-5-(methoxymethyl)-1-(prop-2-enoyl)pyrrolidin-3-yl]pyrazole-4-carboxamide (0.19 g, 0.45 mmol), 1-ethyl-5-ethynyl-4,6-difluoro-1,3-benzodiazole (0.56 g, 2.73 mmol), CuI (17.39 mg, 0.09 mmol) and Pd(dppf)Cl$_2$·CH$_2$Cl$_2$ (37.18 mg, 0.05 mmol) in DMF (6.00 mL) was added TEA (0.14 g, 1.36 mmol) dropwise at room temperature. The reaction mixture was degassed with argon for three times and stirred for 4 h at 80° C. The resulting mixture was concentrated under reduced pressure. The residue was purified by silica gel Column chromatography, eluted with $CH_2Cl_2$/MeOH (0-10%) to afford the crude. The crude was purified by reverse flash chromatography with the following conditions: Column: XBridge Prep C18 OBD Column, 19×150 mm 5 μm; Mobile Phase A: Water (10 mmol/L NH$_4$HCO$_3$), Mobile Phase B: ACN; Flow rate: 20 mL/min; Gradient: 5 B to 40 B in 6 min; 210/254 nm; RT: 5.58 min. The fractions contained desired product were combined and concentrated to afford 3-[2-(1-ethyl-4,6-difluoro-1,3-benzodiazol-5-yl)ethynyl]-5-[(2-hydroxyethyl)amino]-1-[(3S,5R)-5-(methoxymethyl)-1-(prop-2-enoyl)pyrrolidin-3-yl]pyrazole-4-carboxamide (62.2 mg, 25%) as a white solid. MS ESI calculated for $C_{26}H_{29}F_2N_7O_4$ [M+H]$^+$, 542.22, found 542.20; $^1$H NMR (300 MHz, DMSO-d$_6$) δ 8.46 (s, 1H), 7.72 (d, J=9.2 Hz, 1H), 7.59 (s, 1H), 6.81-6.51 (m, 3H), 6.18 (d, J=16.8 Hz, 1H), 5.70-5.65 (m, 1H), 5.34-5.23 (m, 1H), 4.90-4.88 (m, 1H), 4.48 (d, J=41.8 Hz, 1H), 4.31 (q, J=7.2 Hz, 2H), 4.04-4.01 (m, 1H), 3.86 (m, 2H), 3.61-3.43 (m, 4H), 2.46-2.41 (m, 1H), 2.33-2.30 (m, 1H), 1.42 (t, J=7.2 Hz, 3H).

Example 117: 3-[2-(1-Ethyl-4,6-difluoro-1,3-benzodiazol-5-yl)ethynyl]-5-[(2-methoxyethyl)amino]-1-[(3S,5R)-5-(methoxymethyl)-1-(prop-2-enoyl)pyrrolidin-3-yl]pyrazole-4-carboxamide

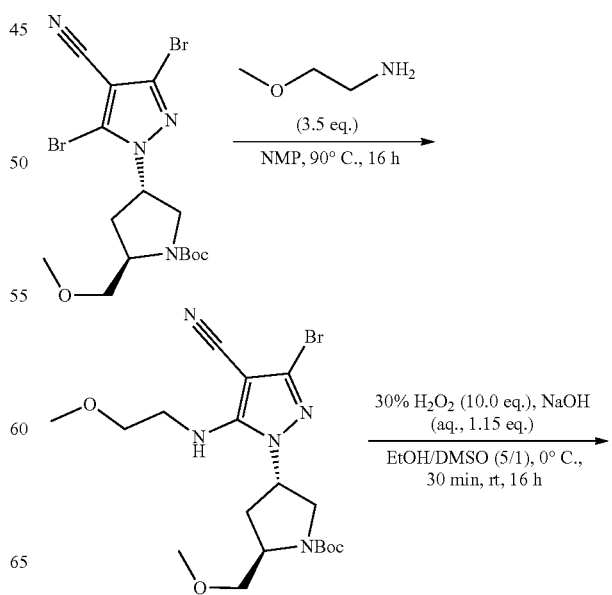

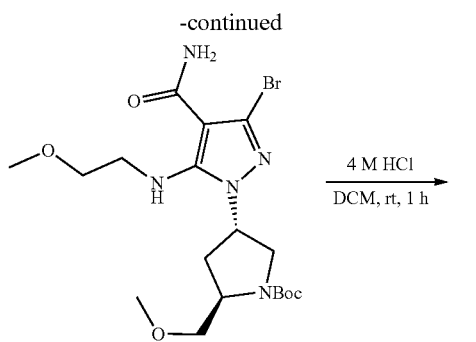

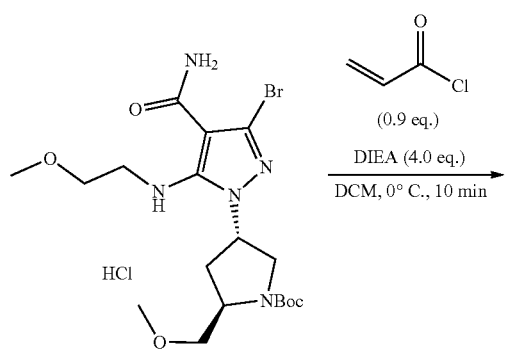

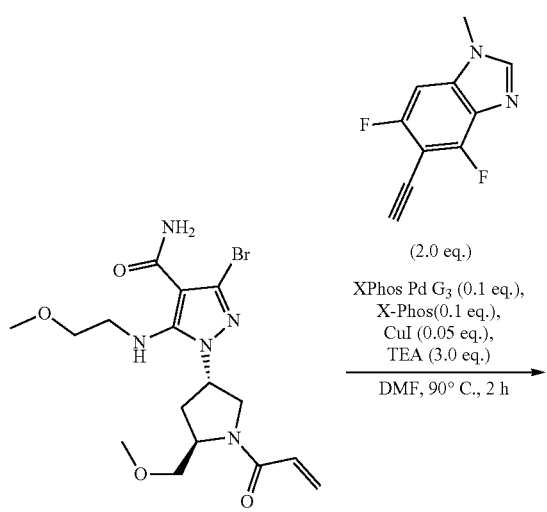

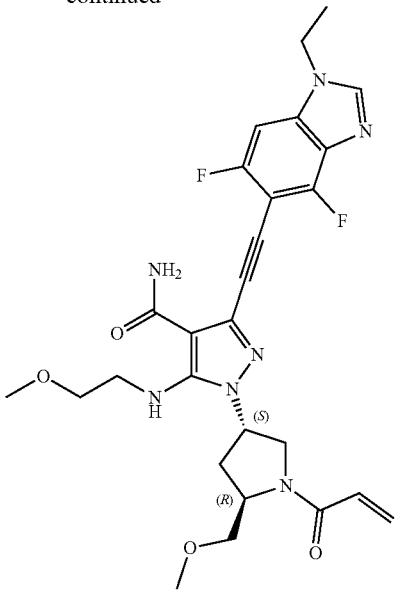

Step 1: Tert-butyl (2R,4S)-4-[3-bromo-4-cyano-5-[(2-methoxyethyl)amino]pyrazol-1-yl]-2-(methoxymethyl)pyrrolidine-1-carboxylate To a stirred solution of tert-butyl (2R,4S)-4-(3,5-dibromo-4-cyanopyrazol-1-yl)-2-(methoxymethyl)pyrrolidine-1-carboxylate (1.00 g, 2.15 mmol) in NMP (10.00 mL) was added ethanamine 2-methoxy (0.57 g, 7.58 mmol). The reaction mixture was stirred for 16 h at 90° C. The resulting mixture was cooled down, diluted with water (30 mL) and extracted with EtOAc (3×30 mL). The combined organic layers were washed with brine (3×30 mL), dried over anhydrous $Na_2SO_4$ and filtered. The filtrate was concentrated under reduced pressure to afford tert-butyl (2R,4S)-4-[3-bromo-4-cyano-5-[(2-methoxyethyl)amino]pyrazol-1-yl]-2-(methoxymethyl)pyrrolidine-1-carboxylate (0.98 g, 99%) as a yellow oil which was used in the next step directly without further purification. MS ESI calculated for $C_{18}H_{28}BrN_5O_4$ [M+H−56]$^+$, 402.13, 404.13, found 401.95, 403.95; $^1$H NMR (300 MHz, CDCl$_3$) δ 6.37 (s, 1H), 4.99-4.96 (m, 1H), 4.14-4.12 (m, 1H), 3.78-3.66 (m, 4H), 3.62-3.59 (m, 2H), 3.45-3.59 (m, 7H), 2.66-2.63 (m, 1H), 2.19-2.15 (m, 1H), 1.29 (s, 9H).

Step 2: Tert-butyl (2R,4S)-4-[3-bromo-4-carbamoyl-5-[(2-methoxyethyl)amino]pyrazol-1-yl]-2-(methoxymethyl)pyrrolidine-1-carboxylate To a stirred solution of tert-butyl (2R,4S)-4-[3-bromo-4-cyano-5-[(2-methoxyethyl)amino]pyrazol-1-yl]-2-(methoxymethyl)pyrrolidine-1-carboxylate (0.98 g, 2.13 mmol) and NaOH (98.34 mg, 2.45 mmol, 0.5 M) in EtOH (10.00 mL) and DMSO (2.00 mL) was added $H_2O_2$ (0.72 g, 21.38 mmol, 30%) dropwise at 0° C. The reaction mixture was stirred for 30 min at 0° C. and 16 h at room temperature. The resulting mixture was diluted with water (30 mL) and extracted with EtOAc (3×30 mL). The combined organic layers were washed with brine (3×30 mL), dried over anhydrous $Na_2SO_4$ and filtered. The filtrate was concentrated under reduced pressure. The residue was purified by silica gel Column chromatography, eluted with EA in PE (0-64%). The fractions contained desired product were combined and concentrated to afford tert-butyl (2R,4S)-4-[3-bromo-4-carbamoyl-5-[(2-methoxyethyl)amino]pyrazol-1-yl]-2-(methoxymethyl)pyrrolidine-1-carboxylate (0.72 g, 70%) as an off-white solid. MS ESI calculated for $C_{18}H_{30}BrN_5O_5$ [M+H]$^+$, 420.15, 422.15, found, 419.95, 421.95; $^1$H NMR (300 MHz, CDCl$_3$) δ 6.57 (s, 1H), 5.17 (s, 1H), 4.15 (s, 1H), 3.87-3.45 (m, 5H), 3.40-3.35 (m, 8H), 2.62-2.59 (m, 1H), 2.23-2.21 (m, 1H), 1.66-1.10 (m, 9H).

Step 3: 3-Bromo-5-[(2-methoxyethyl)amino]-1-[(3S,5R)-5-(methoxymethyl)pyrrolidin-3-yl]pyrazole-4-carboxamide hydrochloride To a stirred solution of tert-butyl (2R,4S)-4-[3-bromo-4-carbamoyl-5-[(2-methoxyethyl)amino]pyrazol-1-yl]-2-(methoxymethyl)pyrrolidine-1-carboxylate (0.72 g, 1.51 mmol) in DCM (8.00 mL) was added HCl (gas) in 1,4-dioxane (8.00 mL, 140.14 mmol, 4 M) dropwise at 0° C. The reaction mixture was stirred for 1 h at room temperature. The resulting mixture was concentrated under reduced pressure to afford 3-bromo-5-[(2-methoxyethyl)amino]-1-[(3S,5R)-5-(methoxymethyl)pyrrolidin-3-yl]pyrazole-4-carboxamide hydrochloride (0.61 g, 98%) as an off-white solid which was used in the next step directly without further purification. MS ESI calculated for $C_{13}H_{22}BrN_5O_3$ [M+H]$^+$, 376.10, 378.10, found 376.10, 378.10.

Step 4: 3-Bromo-5-[(2-methoxyethyl)amino]-1-[(3S,5R)-5-(methoxymethyl)-1-(prop-2-enoyl)pyrrolidin-3-yl]pyrazole-4-carboxamide 4-chloro-1-ethyl-5-iodo-2-methyl-1,3-benzodiazole To a stirred solution of 3-bromo-5-[(2-methoxyethyl)amino]-1-[(3S,5R)-5-(methoxymethyl)pyrrolidin-3-yl]pyrazole-4-carboxamide hydrochloride (0.51 g, 1.23 mmol) in DCM (6.00 mL) were added DIEA (0.63 g, 4.94 mmol) and acryloyl chloride (4.45 mL, 1.11 mmol) dropwise at 0° C. under nitrogen atmosphere. The reaction mixture was diluted with water (30 mL) and extracted with CH$_2$Cl$_2$ (3×30 mL). The combined organic layers were washed with brine (30 mL), dried over anhydrous Na$_2$SO$_4$ and filtered. The filtrate was concentrated under reduced pressure. The residue was purified by silica gel Column chromatography, eluted with MeOH in DCM (0-4%). The fractions contained desired product were combined and concentrated to afford 3-bromo-5-[(2-methoxyethyl)amino]-1-[(3S,5R)-5-(methoxymethyl)-1-(prop-2-enoyl)pyrrolidin-3-yl]pyrazole-4-carboxamide (0.47 g, 88%) as an off-white solid. MS ESI calculated for $C_{16}H_{24}BrN_5O_4$ [M+H]$^+$, 430.11, 432.11, found 430.20, 432.20; $^1$H NMR (300 MHz, CDCl$_3$) δ 6.92 (s, 1H), 6.56-6.33 (m, 2H), 5.72-5.69 (m, 1H), 5.55-5.11 (m, 2H), 4.69-4.29 (m, 1H), 4.06-3.77 (m, 3H), 3.57 (q, J=5.6 Hz, 2H), 3.51-3.28 (m, 9H), 2.72-2.50 (m, 1H), 2.46-2.14 (m, 1H).

Step 5: 3-[2-(1-Ethyl-4,6-difluoro-1,3-benzodiazol-5-yl)ethynyl]-5-[(2-methoxyethyl)amino]-1-[(3S,5R)-5-(methoxymethyl)-1-(prop-2-enoyl)pyrrolidin-3-yl]pyrazole-4-carboxamide To a stirred solution of 3-bromo-5-[(2-methoxyethyl)amino]-1-[(3S,5R)-5-(methoxymethyl)-1-(prop-2-enoyl)pyrrolidin-3-yl]pyrazole-4-carboxamide (0.15 g, 0.34 mmol) and 1-ethyl-5-ethynyl-4,6-difluoro-1,3-benzodiazole (0.14 g, 0.69 mmol) in DMF (2.50 mL) were added XPhos Pd G$_3$ (29.51 mg, 0.04 mmol), X-Phos (16.62 mg, 0.03 mmol), CuI (3.32 mg, 0.01 mmol) and TEA (0.10 g, 1.04 mmol) dropwise at room temperature. The reaction mixture was degassed with argon for three times and stirred for 2 h at 90° C. The resulting mixture was cooled and concentrated under reduced pressure. The residue was purified by silica gel Column chromatography, eluted with MeOH in DCM (0-4%) to afford crude product. The crude product was purified by Prep-HPLC with the following conditions: Column: XBridge Prep Phenyl OBD Column, 19×150 mm 5 μm 13 nm; Mobile Phase A: Water (10 mmol/L NH$_4$HCO$_3$), Mobile Phase B: ACN; Flow rate: 20 mL/min; Gradient: 25 B to 50 B in 6 min, 210/254 nm; RT: 5.58 min. The fractions contained desired product were combined and concentrated to afford 3-[2-(1-ethyl-4,6-difluoro-1,3-benzodiazol-5-yl)ethynyl]-5-[(2-methoxyethyl)amino]-1-[(3S,5R)-5-(methoxymethyl)-1-(prop-2-enoyl)pyrrolidin-3-yl]pyrazole-4-carboxamide (99.4 mg, 50%) as an off-white solid. MS ESI calculated for $C_{27}H_{31}F_2N_7O_4$ [M+H]$^+$, 556.25, found 556.20; $^1$H NMR (300 MHz, CDCl$_3$) δ 7.96 (s, 1H), 7.06-7.02 (m, 2H), 6.76 (s, 1H), 6.62-6.33 (m, 2H), 5.72 (dd, J=7.9, 4.5 Hz, 1H), 5.62-5.24 (m, 2H), 4.66-4.38 (m, 1H), 4.22 (q, J=7.3 Hz, 2H), 4.08-4.42 (m, 2H), 3.89-3.85 (m, 1H), 3.61 (q, J=5.8 Hz, 2H), 3.54-3.29 (m, 9H), 3.01-2.61 (m, 1H), 2.33-2.30 (m, 1H), 1.57 (t, J=7.3 Hz, 3H).

Example 118: 5-[(Cyclopropylmethyl)amino]-3-[2-(1-ethyl-4,6-difluoro-1,3-benzodiazol-5-yl)ethynyl]-1-[(3S)-1-(prop-2-enoyl)pyrrolidin-3-yl]pyrazole-4-carboxamide

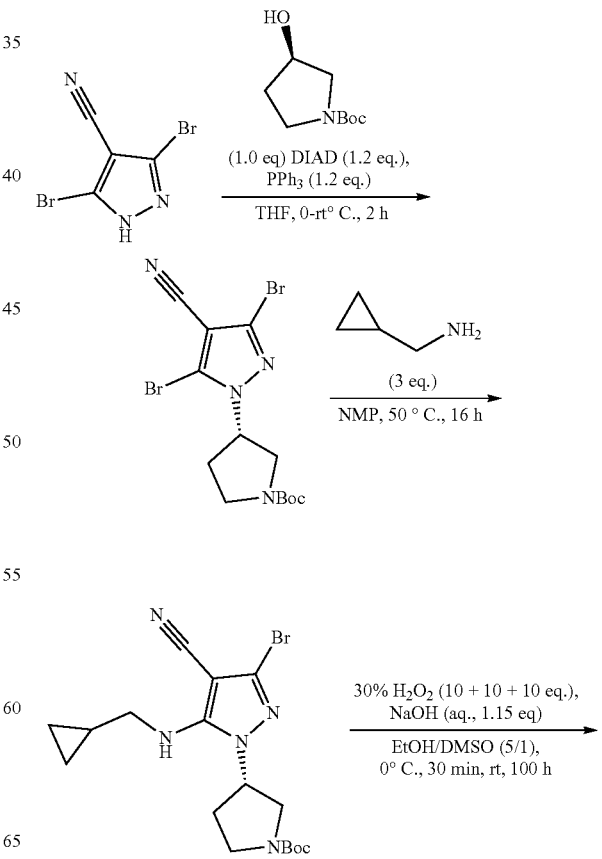

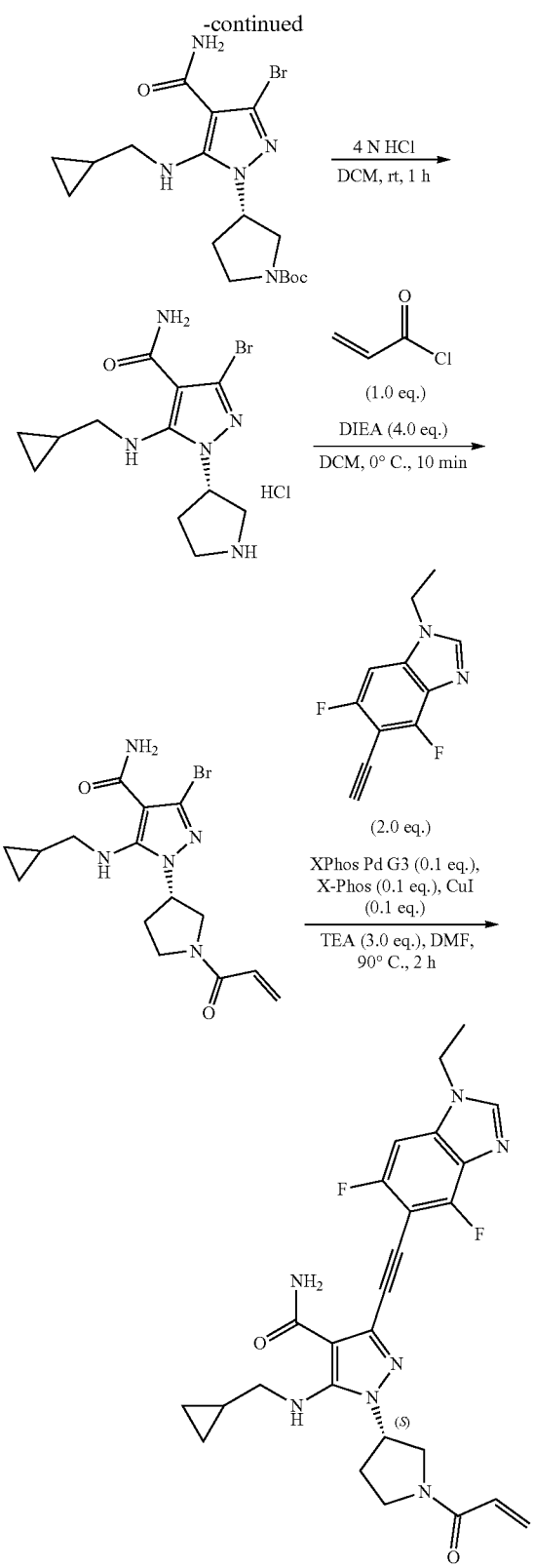

Step 1: Tert-butyl (3S)-3-(3,5-dibromo-4-cyanopyrazol-1-yl)pyrrolidine-1-carboxylate To a stirred solution of 3,5-dibromo-1H-pyrazole-4-carbonitrile (6.90 g, 27.50 mmol) and tert-butyl (3R)-3-hydroxypyrrolidine-1-carboxylate (5.15 g, 27.50 mmol) in THF (120.00 mL) were added PPh$_3$ (8.66 g, 33.00 mmol) and DIAD (6.67 g, 33.00 mmol) dropwise at 0° C. under nitrogen atmosphere. The reaction mixture was stirred for 2 h at room temperature. The resulting mixture was concentrated under reduced pressure. The residue was diluted with water (100 mL) and extracted with EtOAc (3×150 mL). The combined organic layers were washed with brine (100 mL), dried over anhydrous Na$_2$SO$_4$ and filtered. The filtrate was concentrated under reduced pressure. The residue was purified by silica gel Column chromatography, eluted with EA in PE (0-21%). The fractions contained desired product were combined and concentrated to afford tert-butyl (3S)-3-(3,5-dibromo-4-cyanopyrazol-1-yl)pyrrolidine-1-carboxylate (11.4 g, 98%) as an off-white solid. MS ESI calculated for C$_{13}$H$_{16}$Br$_2$N$_4$O$_2$ [M+H−56]$^+$, 362.96, 364.96, found 362.90, 364.90; $^1$H NMR (400 MHz, CDCl$_3$) δ 6.37-6.35 (m, 1H), 50.5-4.92 (m, 1H), 3.78-3.73 (m, 2H), 3.52-3.49 (m, 1H), 2.70-2.16 (m, 1H), 1.69-1.68 (m, 1H), 1.48-1.26 (m, 9H).

Step 2: Tert-butyl (3S)-3-[3-bromo-4-cyano-5-[(cyclopropylmethyl)amino]pyrazol-1-yl]pyrrolidine-1-carboxylate To a stirred mixture of tert-butyl (3S)-3-(3,5-dibromo-4-cyanopyrazol-1-yl)pyrrolidine-1-carboxylate (50.00 mg, 0.12 mmol) in NMP (0.5 mL) was added 1-cyclopropylmethanamine (16.93 mg, 0.24 mmol) dropwise at room temperature. The reaction mixture was stirred for 16 h at 50° C. under argon atmosphere. The resulting mixture was diluted with water (100 mL) and extracted with EtOAc (3×100 mL). The combined organic layers were washed with brine (8×50 mL), dried over anhydrous Na$_2$SO$_4$ and filtered. The filtrate was concentrated under reduced pressure to afford tert-butyl (3S)-3-[3-bromo-4-cyano-5-[(cyclopropylmethyl)amino]pyrazol-1-yl]pyrrolidine-1-carboxylate (0.90 g, 92%) as a yellow oil which was used in the next step directly without further purification. MS ESI calculated for C$_{17}$H$_{24}$BrN$_5$O$_2$ [M−H]$^-$, 408.11, found 408.00.

Step 3: Tert-butyl (3S)-3-[3-bromo-4-carbamoyl-5-[(cyclopropylmethyl)amino]pyrazol-1-yl]pyrrolidine-1-carboxylate To a stirred mixture of tert-butyl (3S)-3-[3-bromo-4-cyano-5-[(cyclopropylmethyl)amino]pyrazol-1-yl]pyrrolidine-1-carboxylate (0.85 g, 2.07 mmol) in EtOH (7.00 mL) and DMSO (1.40 mL) were added NaOH (0.10 g, 2.38 mmol, 0.5 M) and H$_2$O$_2$ (2.35 g, 20.72 mmol, 30%) dropwise at 0° C. under nitrogen atmosphere. The reaction mixture was stirred for 0.5 h at 0° C. and 100 h at room temperature under nitrogen atmosphere. The resulting mixture was quenched by the addition of water (10 mL) at 0° C. and extracted with EtOAc (3×20 mL). The combined organic layers were washed with brine (3×50 mL), dried over anhydrous Na$_2$SO$_4$ and filtered. The filtrate was concentrated under reduced pressure. The residue was purified by silica gel Column chromatography, eluted with PE/EtOAc (1/2). The fractions contained desired product were combined and concentrated. The residue was purified by reverse flash chromatography with the following conditions: Column, C18 silica gel; mobile phase, MeCN in water (10 mmol/L, NH$_4$HCO$_3$), 10% to 50% gradient in 30 min; detector, UV 254 nm. The fractions contained desired product were combined and concentrated to afford tert-butyl (3S)-3-[3-bromo-4-carbamoyl-5-[(cyclopropylmethyl)amino]pyrazol-1-yl]pyrrolidine-1-carboxylate (0.18 g, 20%)

as an off-white semi-solid. MS ESI calculated for C₁₇H₂₆BrN₅O₃ [M+H]⁺, 428.13, found 428.15; ¹H NMR (400 MHz, CDCl₃) δ 6.76 (s, 1H), 6.61 (s, 1H), 4.83 (d, J=7.8 Hz, 1H), 3.69-3.65 (m, 1H), 3.47-3.45 (m, 1H), 3.05 (t, J=6.6 Hz, 2H), 2.52 (s, 1H), 2.19-2.07 (m, 1H), 1.64 (s, 2H), 1.49 (s, 9H), 1.28-1.26 (m, 1H), 1.09 (s, 1H), 0.64-0.57 (m, 2H), 0.27-0.25 (m, 2H).

Step 4: 3-Bromo-5-[(cyclopropylmethyl)amino]-1-[(3S)-pyrrolidin-3-yl]pyrazole-4-carboxamide hydrochloride To a stirred mixture of tert-butyl (3S)-3-[3-bromo-4-carbamoyl-5-[(cyclopropylmethyl)amino]pyrazol-1-yl]pyrrolidine-1-carboxylate (0.18 g, 0.42 mmol) in DCM (2.00 mL) was added HCl (4 M in EtOAc) (2.00 mL) dropwise at 0° C. The reaction mixture was stirred for 1 h at room temperature. The resulting mixture was concentrated under reduced pressure to afford 3-bromo-5-[(cyclopropylmethyl)amino]-1-[(3S)-pyrrolidin-3-yl]pyrazole-4-carboxamide hydrochloride (0.20 g, 99%) as an off-white solid which was used in the next step directly without further purification. MS ESI calculated for C₁₂H₁₈BrN₅O [M+H]⁺, 328.07, 330.07, found 328.00, 330.00.

Step 5: 3-Bromo-5-[(cyclopropylmethyl)amino]-1-[(3S)-1-(prop-2-enoyl)pyrrolidin-3-yl]pyrazole-4-carboxamide To a stirred mixture of 3-bromo-5-[(cyclopropylmethyl)amino]-1-[(3S)-pyrrolidin-3-yl]pyrazole-4-carboxamide hydrochloride (0.18 g, 0.49 mmol) and DIEA (28.35 mg, 0.22 mmol) in DCM (4.50 mL) was added acryloyl chloride (1.82 mL, 0.45 mmol) dropwise at 0° C. The reaction mixture was stirred for 10 min at 0° C. under nitrogen atmosphere. The resulting mixture was quenched with water (10 mL) at 0° C. and extracted with CH₂Cl₂ (3×10 mL). The combined organic layers was dried over anhydrous Na₂SO₄ and filtered. The filtrate was concentrated under reduced pressure. The residue was purified by silica gel Column chromatography, eluted with CH₂Cl₂/MeOH (10/1). The fractions contained desired product were combined and concentrated to afford 3-bromo-5-[(cyclopropylmethyl)amino]-1-[(3S)-1-(prop-2-enoyl)pyrrolidin-3-yl]pyrazole-4-carboxamide (0.15 g, 79%) as a light yellow solid. MS ESI calculated for C₁₅H₂₀BrN₅O₂ [M+H]⁺, 382.09, found 382.00.

Step 6: 5-[(Cyclopropylmethyl)amino]-3-[2-(1-ethyl-4,6-difluoro-1,3-benzodiazol-5-yl)ethynyl]-1-[(3S)-1-(prop-2-enoyl)pyrrolidin-3-yl]pyrazole-4-carboxamide To a stirred mixture of 3-bromo-5-[(cyclopropylmethyl)amino]-1-[(3S)-1-(prop-2-enoyl)pyrrolidin-3-yl]pyrazole-4-carboxamide (0.15 g, 0.39 mmol) and 1-ethyl-5-ethynyl-4,6-difluoro-1,3-benzodiazole (0.16 mg, 0.78 mmol) in DMF (4.00 mL) were added X-Phos (18.71 mg, 0.04 mmol), XPhos Pd G3 (33.21 mg, 0.04 mmol), CuI (7.47 mg, 0.04 mmol) and TEA (0.12 g, 1.18 mmol) dropwise at room temperature. The reaction mixture was degassed with argon for three times and stirred for 2 h at 90° C. The resulting mixture was cooled down and concentrated under reduced pressure. The residue was purified by silica gel Column chromatography, eluted with CH₂Cl₂/MeOH (10/1). The fractions contained desired product were combined and concentrated. The residue was purified by reverse flash chromatography with the following conditions: Column: SunFire Prep C18 OBD Column, 19×150 mm 5 μm 10 nm; Mobile Phase A: Water (0.05% FA), Mobile Phase B: ACN; Flow rate: 20 mL/min; Gradient: 25 B to 50 B in 6 min; 210/254 nm; RT: 5.58 min. The fractions contained desired product were combined and concentrated to afford 5-[(cyclopropylmethyl)amino]-3-[2-(1-ethyl-4,6-difluoro-1,3-benzodiazol-5-yl)ethynyl]-1-[(3S)-1-(prop-2-enoyl)pyrrolidin-3-yl]pyrazole-4-carboxamide (80.6 mg, 39%) as an off-white solid. MS ESI calculated for C₂₆H₂₇F₂N₇O₂ [M+H]⁺, 508.32, found 508.30; ¹H NMR (300 MHz, CDCl₃) δ 7.97 (s, 1H), 7.23-6.98 (m, 2H), 6.61-6.37 (m, 3H), 5.80-5.68 (m, 1H), 5.45 (s, 1H), 5.01 (dd, J=13.2, 6.8 Hz, 1H), 4.32-3.83 (m, 5H), 3.75-3.68 (m, 1H), 3.05 (q, J=6.9 Hz, 2H), 2.84-2.50 (m, 1H), 2.37 (s, 1H), 1.58 (t, J=7.3 Hz, 3H), 1.12 (s, 1H), 0.67-0.57 (m, 2H), 0.29-0.27 (m, 2H).

Example 119: 3-[2-(1-Ethyl-4,6-difluoro-1,3-benzodiazol-5-yl)ethynyl]-5-[(2-methoxyethyl)amino]-1-[(3S)-1-(prop-2-enoyl)pyrrolidin-3-yl]pyrazole-4-carboxamide

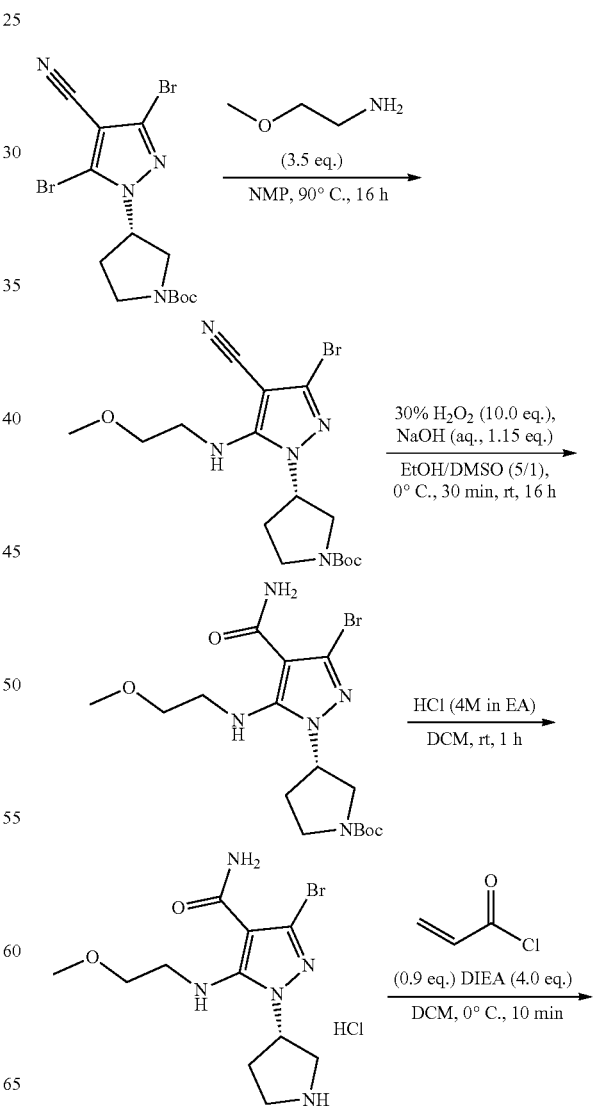

-continued

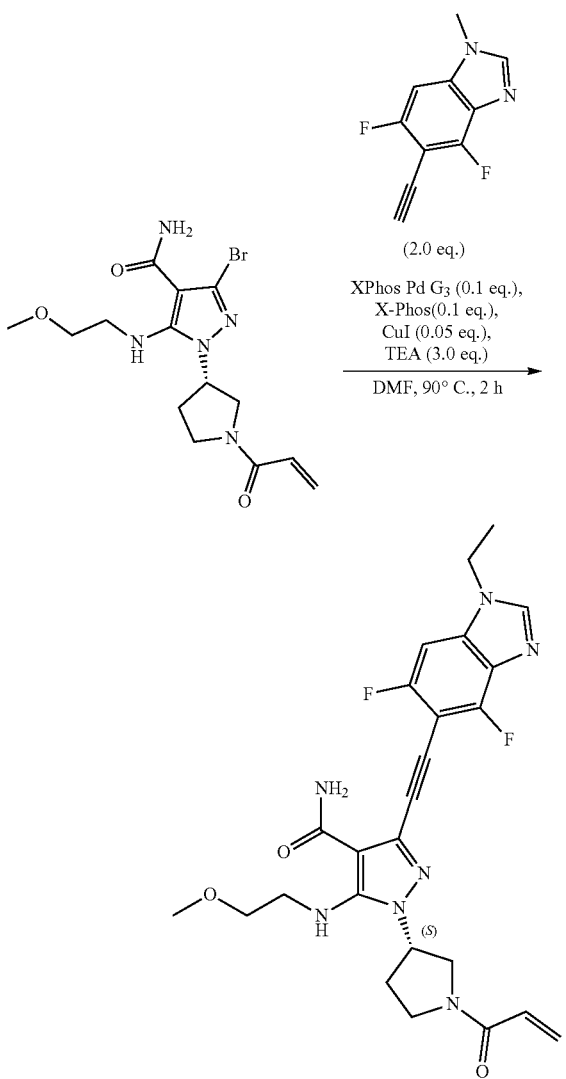

Step 1: Tert-butyl (3S)-3-[3-bromo-4-cyano-5-[(2-methoxyethyl)amino]pyrazol-1-yl]pyrrolidine-1-carboxylate To a stirred solution of tert-butyl (3S)-3-(3,5-dibromo-4-cyanopyrazol-1-yl)pyrrolidine-1-carboxylate (1.00 g, 2.38 mmol) in NMP (10.00 mL) was added 2-methoxyethan-1-amine (0.63 g, 8.38 mmol). The reaction mixture was stirred for 16 h at 90° C. The resulting mixture was cooled down, diluted with water (30 mL) and extracted with EtOAc (3×30 mL). The combined organic layers were washed with brine (3×30 mL), dried over anhydrous $Na_2SO_4$ and filtered. The filtrate was concentrated under reduced pressure to afford tert-butyl (3S)-3-[3-bromo-4-cyano-5-[(2-methoxyethyl)amino]pyrazol-1-yl]pyrrolidine-1-carboxylate (0.98 g, 99%) as a yellow oil which was used in the next step directly without further purification. MS ESI calculated for $C_{16}H_{24}BrN_5O_3$ [M+H−56]⁺, 358.11, 360.11, found 357.95, 359.95; ¹H NMR (300 MHz, CDCl₃) δ 6.41 (s, 1H), 4.99-4.95 (m, 1H), 4.78-4.05 (m, 2H), 3.86-3.57 (m, 5H), 3.43 (s, 3H), 2.62-1.98 (m, 2H), 1.29 (s, 9H).

Step 2: Tert-butyl (3S)-3-[3-bromo-4-carbamoyl-5-[(2-methoxyethyl)amino]pyrazol-1-yl]pyrrolidine-1-carboxylate To a stirred solution of tert-butyl (3S)-3-[3-bromo-4-cyano-5-[(2-methoxyethyl)amino]pyrazol-1-yl]pyrrolidine-1-carboxylate (0.98 g, 2.36 mmol) and NaOH (0.11 g, 2.72 mmol, 0.5 M) in EtOH (10.00 mL) and DMSO (2.00 mL) was added $H_2O_2$ (0.80 g, 23.65 mmol, 30%) dropwise at 0° C. The reaction mixture was stirred for 30 min at 0° C. and 16 h at room temperature. The resulting mixture was diluted with water (30 mL) and extracted with EtOAc (3×30 mL). The combined organic layers were washed with brine (3×30 mL), dried over anhydrous $Na_2SO_4$ and filtered. The filtrate was concentrated under reduced pressure. The residue was purified by silica gel Column chromatography, eluted with EA in PE (0-82%). The fractions contained desired product were combined and concentrated to afford tert-butyl (3S)-3-[3-bromo-4-carbamoyl-5-[(2-methoxyethyl)amino]pyrazol-1-yl]pyrrolidine-1-carboxylate (0.55 g, 53%) as an off-white solid. MS ESI calculated for $C_{16}H_{26}BrN_5O_4$ [M+H]⁺, 432.12, 434.12, found 432.15, 434.15.

Step 3: 3-Bromo-5-[(2-methoxyethyl)amino]-1-[(3S)-pyrrolidin-3-yl]pyrazole-4-carboxamide hydrochloride To a stirred solution of tert-butyl (3S)-3-[3-bromo-4-carbamoyl-5-[(2-methoxyethyl)amino]pyrazol-1-yl]pyrrolidine-1-carboxylate (0.55 g, 1.27 mmol) in DCM (6.00 mL) was added HCl (gas) in 1,4-dioxane (6.00 mL, 105.10 mmol) dropwise at 0° C. The reaction mixture was stirred for 1 h at room temperature. The resulting mixture was concentrated under reduced pressure to afford 3-bromo-5-[(2-methoxyethyl)amino]-1-[(3S)-pyrrolidin-3-yl]pyrazole-4-carboxamide hydrochloride (0.47 g, 99%) as an off-white solid which was used in the next step directly without further purification. MS ESI calculated for $C_{11}H_{18}BrN_5O_2$ [M+H]⁺, 332.07, 334.07, found 332.00, 334.00.

Step 4: 3-Bromo-5-[(2-methoxyethyl)amino]-1-[(3S)-1-(prop-2-enoyl)pyrrolidin-3-yl]pyrazole-4-carboxamide To a stirred solution of 3-bromo-5-[(2-methoxyethyl)amino]-1-[(3S)-pyrrolidin-3-yl]pyrazole-4-carboxamide hydrochloride (0.41 g, 1.11 mmol) in DCM (6.00 mL) were added DIEA (0.57 g, 4.44 mmol) and acryloyl chloride (4.00 mL, 1.00 mmol) dropwise at 0° C. under nitrogen atmosphere. The reaction mixture was diluted with water (30 mL) and extracted with $CH_2Cl_2$ (3×30 mL). The combined organic layers were washed with brine (30 mL), dried over anhydrous $Na_2SO_4$ and filtered. The filtrate was concentrated under reduced pressure. The residue was purified by silica gel Column chromatography, eluted with MeOH in DCM (0-4%). The fractions contained desired product were combined and concentrated to afford 3-bromo-5-[(2-methoxyethyl)amino]-1-[(3S)-1-(prop-2-enoyl)pyrrolidin-3-yl]pyrazole-4-carboxamide (0.37 g, 86%) as an off-white solid. MS ESI calculated for $C_{14}H_{20}BrN_5O_3$ [M+H]⁺, 386.08, 388.08, found 386.10, 388.10; ¹H NMR (300 MHz, CDCl₃) δ 6.61 (s, 1H), 6.54-6.32 (m, 2H), 5.79-5.69 (m, 1H), 5.51 (s, 1H), 5.21-4.93 (m, 1H), 4.13-3.84 (m, 3H), 3.79-3.50 (m, 3H), 3.48-3.15 (m, 5H), 2.68-2.48 (m, 1H), 2.45-2.25 (m, 1H).

Step 5: 3-[2-(1-Ethyl-4,6-difluoro-1,3-benzodiazol-5-yl)ethynyl]-5-[(2-methoxyethyl)amino]-1-[(3S)-1-(prop-2-enoyl)pyrrolidin-3-yl]pyrazole-4-carboxamide To a stirred solution of 3-bromo-5-[(2-methoxyethyl)amino]-1-[(3S)-1-(prop-2-enoyl)pyrrolidin-3-yl]pyrazole-4-carboxamide (0.15 g, 0.38 mmol) and 1-ethyl-5-ethynyl-4,6-difluoro-1,3-benzodiazole (0.16 g, 0.77 mmol) in DMF (2.50 mL) were added XPhos Pd $G_3$ (32.87 mg, 0.03 mmol), X-Phos (18.51 mg, 0.03 mmol), CuI (3.70 mg, 0.01 mmol) and TEA (0.11 g, 1.16 mmol) dropwise at room temperature. The reaction mixture was degassed with argon for three times and stirred for 2 h at 90° C. The resulting mixture was cooled down and concentrated under reduced pressure. The residue was purified by silica gel Column chromatography, eluted with MeOH in DCM (0-5%) to afford crude product. The crude product was purified by Prep-HPLC with the following conditions: Column: XBridge Prep Phenyl OBD Column, 19×150 mm 5 μm 13 nm; Mobile Phase A: Water (10 mmol/L $NH_4HCO_3$), Mobile Phase B: ACN; Flow rate: 20 mL/min; Gradient: 25 B to 50 B in 6 min, 210/254 nm; RT: 5.58 min. The fractions contained desired product were combined and concentrated to afford 3-[2-(1-ethyl-4,6-difluoro-1,3-benzodiazol-5-yl)ethynyl]-5-[(2-methoxyethyl)amino]-1-[(3S)-1-(prop-2-enoyl)pyrrolidin-3-yl]pyrazole-4-carboxamide (86.3 mg, 43%) as an off-white solid. MS ESI calculated for $C_{25}H_{27}F_2N_7O_3$ $[M+H]^+$, 512.21, found 512.15; $^1H$ NMR (300 MHz, $CDCl_3$) δ 7.97 (s, 1H), 7.23-6.97 (m, 2H), 6.65-6.26 (m, 2H), 5.86-5.66 (m, 1H), 5.47 (s, 1H), 5.27-4.98 (m, 1H), 4.23 (q, J=7.3 Hz, 2H), 4.16-3.86 (m, 3H), 3.84-3.65 (m, 1H), 3.65-3.53 (m, 2H), 3.48-3.24 (m, 5H), 2.77-2.51 (m, 1H), 2.40-2.35 (m, 1H), 1.58 (t, J=7.3 Hz, 3H).

Example 120: 3-[2-(1-Ethyl-4,6-difluoro-1,3-benzodiazol-5-yl)ethynyl]-5-[[3-(morpholin-4-yl)propyl]amino]-1-[(3S)-1-(prop-2-enoyl)pyrrolidin-3-yl]pyrazole-4-carboxamide

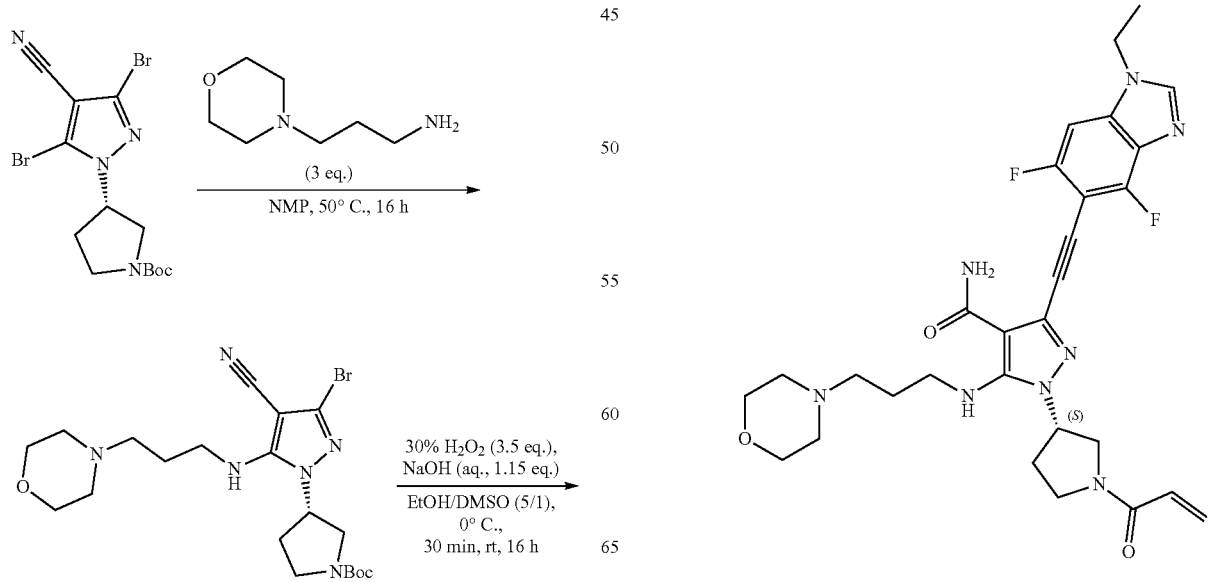

Step 1: Tert-butyl (3S)-3-(3-bromo-4-cyano-5-[[3-(morpholin-4-yl)propyl]amino]pyrazol-1-yl)pyrrolidine-1-carboxylate To a stirred mixture of tert-butyl (3S)-3-(3,5-dibromo-4-cyanopyrazol-1-yl)pyrrolidine-1-carboxylate (1.00 g, 2.38 mmol) in NMP (10.00 mL) was added 4-morpholinepropanamine (1.03 g, 7.14 mmol) dropwise at room temperature. The reaction mixture was stirred for 16 h at 50° C. under argon atmosphere. The resulting mixture was poured into water (100 mL) and extracted with EA (3×50 mL). The combined organic layers were washed with brine (2×100 mL), dried over anhydrous $Na_2SO_4$, filtrated and concentrated under reduced pressure to afford tert-butyl (3S)-3-(3-bromo-4-cyano-5-[[3-(morpholin-4-yl)propyl]amino]pyrazol-1-yl)pyrrolidine-1-carboxylate (1.0 g, 87%) as a light yellow oil which was used in the next step directly without further purification. MS ESI calculated for $C_{20}H_{31}BrN_6O_3$ [M+H]$^+$, 483.16, found 483.30.

Step 2: Tert-butyl (3S)-3-(3-bromo-4-carbamoyl-5-[[3-(morpholin-4-yl)propyl]amino]pyrazol-1-yl)pyrrolidine-1-carboxylate To a stirred solution of tert-butyl (3S)-3-(3-bromo-4-cyano-5-[[3-(morpholin-4-yl)propyl]amino]pyrazol-1-yl)pyrrolidine-1-carboxylate (0.75 g, 1.55 mmol) and NaOH (0.5 M in water) (3.57 mL, 1.78 mmol) in DMSO (1.60 mL) and EtOH (8.00 mL) was added $H_2O_2$ (1.20 mL, 51.51 mmol, 30%) dropwise at 0° C. The reaction mixture was stirred for 30 min at 0° C. and 16 h at room temperature. The resulting mixture was diluted with water (100 mL) and extracted with EA (3×100 mL). The combined organic layers were washed with brine (100 mL), dried over anhydrous $Na_2SO_4$ and filtered. The filtrate was concentrated under reduced pressure. The residue was purified by silica gel Column chromatography, eluted with MeOH in DCM (0-5%). The fractions contained desired product were combined and concentrated to afford tert-butyl (3S)-3-(3-bromo-4-carbamoyl-5-[[3-(morpholin-4-yl)propyl]amino]pyrazol-1-yl)pyrrolidine-1-carboxylate (0.48 g, 62%) as an off-white oil. MS ESI calculated for $C_{20}H_{33}BrN_6O_4$ [M+H]$^+$, 501.17, found 501.25.

Step 3: 3-Bromo-5-[[3-(morpholin-4-yl)propyl]amino]-1-[(3S)-pyrrolidin-3-yl]pyrazole-4-carboxamide hydrochloride To a stirred solution of tert-butyl (3S)-3-(3-bromo-4-carbamoyl-5-[[3-(morpholin-4-yl)propyl]amino]pyrazol-1-yl)pyrrolidine-1-carboxylate (0.48 mg, 0.96 mmol) in DCM (5.00 mL) was added HCl (4 M in EA) (5.00 mL) dropwise at 0° C. under nitrogen atmosphere. The reaction mixture was stirred for 1 h at room temperature. The resulting mixture was concentrated under reduced pressure to afford 3-bromo-5-[[3-(morpholin-4-yl)propyl]amino]-1-[(3S)-pyrrolidin-3-yl]pyrazole-4-carboxamide hydrochloride (0.4 g, 95%) as a yellow solid which was used in the next step directly without further purification. MS ESI calculated for $C_{15}H_{26}BrClN_6O_2$ [M+H]$^+$, 401.12, found 401.15; $^1$H NMR (400 MHz, CD$_3$OD) δ 5.49 (s, 1H), 5.37 (d, J=6.5 Hz, 2H), 4.09-4.05 (m, 1H), 3.88-3.72 (m, 4H), 3.74-3.71 (m, 2H), 3.68-3.63 (m, 1H), 3.62-3.59 (m, 2H), 3.49-3.45 (m, 1H), 3.42-3.33 (m, 4H), 3.17-3.15 (m, 1H), 2.66-2.55 (m, 1H), 2.34-2.26 (m, 1H), 2.10-2.08 (m, 2H), 2.02-2.19 (m, 1H).

Step 4: 3-Bromo-5-[[3-(morpholin-4-yl)propyl]amino]-1-[(3S)-1-(prop-2-enoyl)pyrrolidin-3-yl]pyrazole-4-carboxamide To a stirred solution of 3-bromo-5-[[3-(morpholin-4-yl)propyl]amino]-1-[(3S)-pyrrolidin-3-yl]pyrazole-4-carboxamide hydrochloride (0.40 g, 0.91 mmol) and DIEA (0.35 g, 2.741 mmol) in DCM (4.00 mL) was added acryloyl chloride (3.29 mL, 0.82 mmol, 0.25 M in DCM) dropwise at 0° C. The reaction mixture was stirred for 10 min at 0° C. under argon atmosphere. The resulting mixture was diluted with water (20 mL) and extracted with EA (3×20 mL). The combined organic layers were washed with brine (20 mL), dried over anhydrous $Na_2SO_4$ and filtered. The filtrate was concentrated under reduced pressure. The residue was purified by silica gel Column chromatography, eluted with MeOH in DCM (0-10%). The fractions contained desired product were combined and concentrated to afford 3-bromo-5-[[3-(morpholin-4-yl)propyl]amino]-1-[(3S)-1-(prop-2-enoyl)pyrrolidin-3-yl]pyrazole-4-carboxamide (0.2 g, 48%) as a white solid. MS ESI calculated for $C_{18}H_{27}BrN_6O_3$ [M+H]$^+$, 457.13, found 457.15; $^1$H NMR (400 MHz, CDCl$_3$) δ 6.64 (s, 2H), 6.43-6.35 (m, 1H), 5.76-5.66 (m, 1H), 5.45 (s, 1H), 4.99 (m, 1H), 4.04 (d, J=6.9 Hz, 1H), 4.03-3.98 (m, 1H), 3.98-3.95 (m, 1H), 3.96-3.85 (m, 1H), 3.85-3.81 (m, 4H), 3.69-3.66 (m, 3H), 1.93 (s, 3H), 1.56-1.46 (m, 4H), 1.26-1.23 (m, 2H), 0.90-0.81 (m, 1H).

Step 5: 3-[2-(1-Ethyl-4,6-difluoro-1,3-benzodiazol-5-yl)ethynyl]-5-[[3-(morpholin-4-yl)propyl]amino]-1-[(3S)-1-(prop-2-enoyl)pyrrolidin-3-yl]pyrazole-4-carboxamide To a stirred mixture of 3-bromo-5-[[3-(morpholin-4-yl)propyl]amino]-1-[(3S)-1-(prop-2-enoyl)pyrrolidin-3-yl]pyrazole-4-carboxamide (0.15 g, 0.33 mmol), 1-ethyl-5-ethynyl-4,6-difluoro-1,3-benzodiazole (0.14 g, 0.66 mmol), X-Phos (15.70 mg, 0.03 mmol), XPhos Pd G3 (27.88 mg, 0.03 mmol) and CuI (6.27 mg, 0.03 mmol) in DMF (4.00 mL) was added TEA (0.10 g, 0.99 mmol) dropwise at room temperature. The reaction mixture was degassed with argon for three times and stirred for 2 h at 90° C. The resulting mixture was cooled down and concentrated under reduced pressure. The residue was purified by silica gel Column chromatography, eluted with MeOH in DCM (0-10%) to afford the crude product. Then the crude product was purified by Prep-HPLC with the following conditions: Column: X-Bridge Prep C18 OBD Column, 19×150 mm 5 μm; Mobile Phase A: Water (10 mmol/L NH$_4$HCO$_3$), Mobile Phase B: ACN; Flow rate: 20 mL/min; Gradient: 15 B to 50 B in 5.8 min, 210/254 nm. The fractions contained desired product were combined and concentrated to afford 3-[2-(1-ethyl-4,6-difluoro-1,3-benzodiazol-5-yl)ethynyl]-5-[[3-(morpholin-4-yl)propyl]amino]-1-[(3S)-1-(prop-2-enoyl)pyrrolidin-3-yl]pyrazole-4-carboxamide (30.2 mg, 16%) as an off-white solid. MS ESI calculated for $C_{29}H_{34}F_2N_8O_3$ [M+H]$^+$, 581.27, found 581.30; $^1$H NMR (300 MHz, CDCl$_3$) δ 7.94 (s, 1H), 7.20-6.93 (m, 2H), 6.58-6.31 (m, 3H), 5.83-5.65 (m, 1H), 5.41 (s, 1H), 5.05-5.00 (m, 1H), 4.26-4.21 (m, 2H), 4.12-3.87 (m, 3H), 3.72-3.69 (m, 5H), 3.26-3.24 (m, 2H), 2.78-2.57 (m, 1H), 2.46-2.44 (m, 7H), 1.85-1.75 (m, 2H), 1.66 (s, 3H).

573

Example 121: 1-((3S,5R)-1-Acryloyl-5-(methoxymethyl)pyrrolidin-3-yl)-3-((7-fluoro-1-methyl-1H-benzo[d]imidazol-5-yl)ethynyl)-5-(methylamino)-1H-pyrazole-4-carboxamide

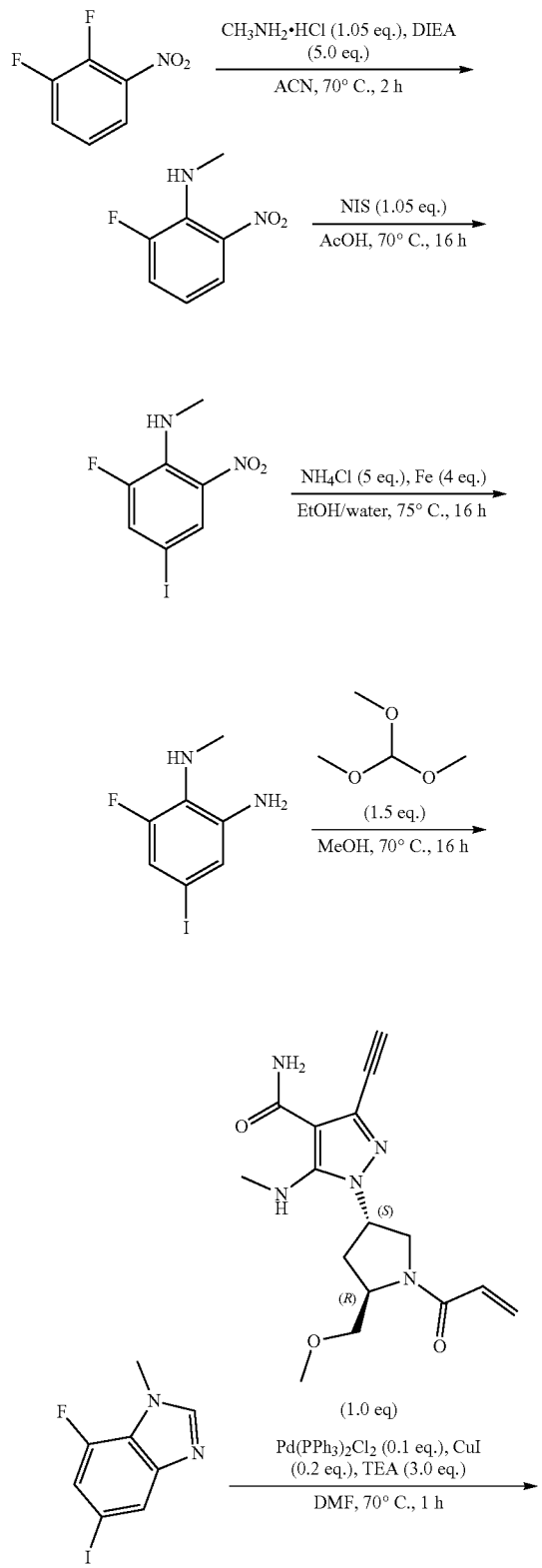

574
-continued

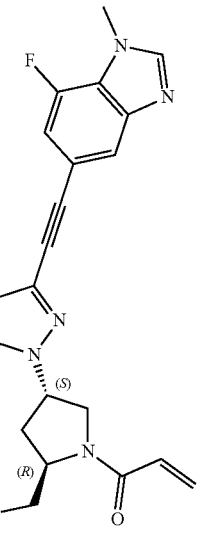

Step 1: 2-Fluoro-N-methyl-6-nitroaniline

To a stirred mixture of 1,2-difluoro-3-nitrobenzene (1.00 g, 6.28 mmol) in ACN (9.00 mL) were added CH$_3$NH$_2$HCl (0.45 g, 6.66 mmol) and DIEA (5.47 mL, 42.35 mmol). The reaction mixture was stirred for 2 h at 70° C. The resulting mixture was cooled down and concentrated under reduced pressure. The residue was diluted with water (20 mL) and extracted with EA (3×20 mL). The combined organic layers were washed with brine (3×20 mL), dried over anhydrous Na$_2$SO$_4$ and filtered. The filtrate was concentrated under reduced pressure to afford 2-fluoro-N-methyl-6-nitroaniline (0.98 g, crude) as a yellow solid which was used in the next step directly without further purification. $^1$H NMR (300 MHz, CDCl$_3$) δ 7.94-7.83 (m, 2H), 7.21-7.14 (m, 1H), 6.59-6.52 (m, 1H), 3.27-3.23 (m, 3H).

Step 2: 2-Fluoro-4-iodo-N-methyl-6-nitroaniline

To a stirred solution of 2-fluoro-N-methyl-6-nitroaniline (0.96 g, 5.6 mmol) in AcOH (9.60 mL) was added NIS (1.33 g, 5.92 mmol) at 70° C. The reaction mixture was stirred for 16 h at 70° C. under nitrogen atmosphere. The resulting mixture was concentrated under reduced pressure. The residue was diluted with water (100 mL), adjusted to pH 8 with NaHCO$_3$ and extracted with EtOAc (3×100 mL). The combined organic layers were washed with brine (3×100 mL), dried over anhydrous Na$_2$SO$_4$ and filtered. The filtrate was concentrated under reduced pressure. The residue was purified by silica gel Column chromatography, eluted with 17% DCM in PE. The fractions contained desired product were combined and concentrated to afford 2-fluoro-4-iodo-N-methyl-6-nitroaniline (1.48 g, 88%) as a yellow solid. $^1$H NMR (300 MHz, CDCl$_3$) δ 8.26 (s, 1H), 7.87 (s, 1H), 7.44-7.39 (m, 1H), 3.25-3.23 (m, 3H)

Step 3: 6-Fluoro-4-iodo-N1-methylbenzene-1,2-diamine

To a stirred mixture of 2-fluoro-4-iodo-N-methyl-6-nitroaniline (0.80 g, 2.70 mmol) and Fe (0.60 g, 10.80 mmol) in EtOH (14.00 mL) and water (2.00 mL) was added NH$_4$Cl (0.72 g, 13.51 mmol). The reaction mixture was stirred for 16 h at 75° C. The resulting mixture was cooled and filtered, the filter cake was washed with EtOH (3×50 mL). The filtrate was concentrated under reduced pressure. The residue was diluted with water (50 mL) and extracted with EA (3×50 mL). The combined organic layers were washed with brine (3×50 mL), dried over anhydrous $Na_2SO_4$ and filtered. The filtrate was concentrated under reduced pressure to afford 6-fluoro-4-iodo-$N^1$-methylbenzene-1,2-diamine (0.69 g, crude) as a brown solid which was used in the next step directly without further purification. MS ESI calculated for $C_7H_8FIN_2$ [M+H]$^+$, 266.98, found 266.95.

Step 4: 7-Fluoro-5-iodo-1-methyl-1,3-benzodiazole

To a stirred mixture of 6-fluoro-4-iodo-$N^1$-methylbenzene-1,2-diamine (0.69 g, 2.60 mmol) in MeOH (7.00 mL) was added trimethyl orthoformate (0.41 g, 3.90 mmol). The reaction mixture was stirred for 16 h at 70° C. The resulting mixture was concentrated under reduced pressure. The residue was purified by silica gel Column chromatography, eluted with 8% MeOH in DCM. The fractions contained desired product were combined and concentrated to afford 7-fluoro-5-iodo-1-methyl-1,3-benzodiazole (0.20 g, 87%) as a light brown solid. MS ESI calculated for $C_8H_6FIN_2$ [M+H]$^+$, 276.96, found 277.00; $^1$H NMR (300 MHz, CDCl$_3$) δ 7.92 (d, J=1.3 Hz, 1H), 7.73 (s, 1H), 7.34-7.21 (m, 1H), 4.00 (s, 3H).

Step 5: 1-((3S,5R)-1-Acryloyl-5-(methoxymethyl) pyrrolidin-3-yl)-3-((7-fluoro-1-methyl-1H-benzo[d] imidazol-5-yl)ethynyl)-5-(methylamino)-1H-pyrazole-4-carboxamide To a stirred mixture of 7-fluoro-5-iodo-1-methyl-1,3-benzodiazole (0.12 g, 0.45 mmol), 3-ethynyl-1-[(3S,5R)-5-(methoxymethyl)-1-(prop-2-enoyl) pyrrolidin-3-yl]-5-(methylamino) pyrazole-4-carboxamide (0.15 g, 0.45 mmol), CuI (17.24 mg, 0.09 mmol) and Pd(PPh$_3$)$_2$Cl$_2$ (31.77 mg, 0.04 mmol) in DMF (1.2 mL) was added TEA (0.19 mL, 1.86 mmol) at room temperature. The reaction mixture was degassed with argon for three times and stirred for 1 h at 70° C. The resulting mixture was concentrated under reduced pressure. The residue was purified by silica gel Column chromatography, eluted with 8% MeOH in DCM. The fractions contained desired product were combined and concentrated. The crude product was purified by Prep-HPLC with the following conditions: Column: XBridge Prep C18 OBD Column, 19×150 mm 5 μm; Mobile Phase A: Water (10 mmol/L NH$_4$HCO$_3$), Mobile Phase B: ACN; Flow rate: 20 mL/min; Gradient: 20 B to 50 B in 5.8 min, 210/254 nm. The fractions contained desired product were combined and concentrated to afford 1-((3S,5R)-1-acryloyl-5-(methoxymethyl)pyrrolidin-3-yl)-3-((7-fluoro-1-methyl-1H-benzo[d] imidazol-5-yl)ethynyl)-5-(methylamino)-1H-pyrazole-4-carboxamide (79.6 mg, 36%) as an off-white solid. MS ESI calculated for $C_{24}H_{26}FN_7O_3$ [M+H]$^+$, 480.21, found 480.30; $^1$H NMR (300 MHz, DMSO-d$_6$) δ 8.36 (s, 1H), 7.75 (d, J=1.2 Hz, 1H), 7.39-7.18 (m, 2H), 6.65-6.61 (m, 2H), 6.21-6.11 (m, 1H), 5.68-5.65 (m, 1H), 5.32-5.15 (m, 1H), 4.46-4.32 (m, 1H), 4.00-3.97 (m, 3H), 3.92-3.46 (m, 4H), 3.29 (m, 3H), 2.94 (d, J=3.1 Hz, 3H), 2.43-2.41 (m, 1H), 2.31-2.27 (m, 1H).

Example 122: 3-(2-[7-Fluoro-[1,2,4]triazolo[1,5-a] pyridin-6-yl]ethynyl)-1-[(3S,5R)-5-(methoxymethyl)-1-(prop-2-enoyl)pyrrolidin-3-yl]-5-(methylamino)pyrazole-4-carboxamide

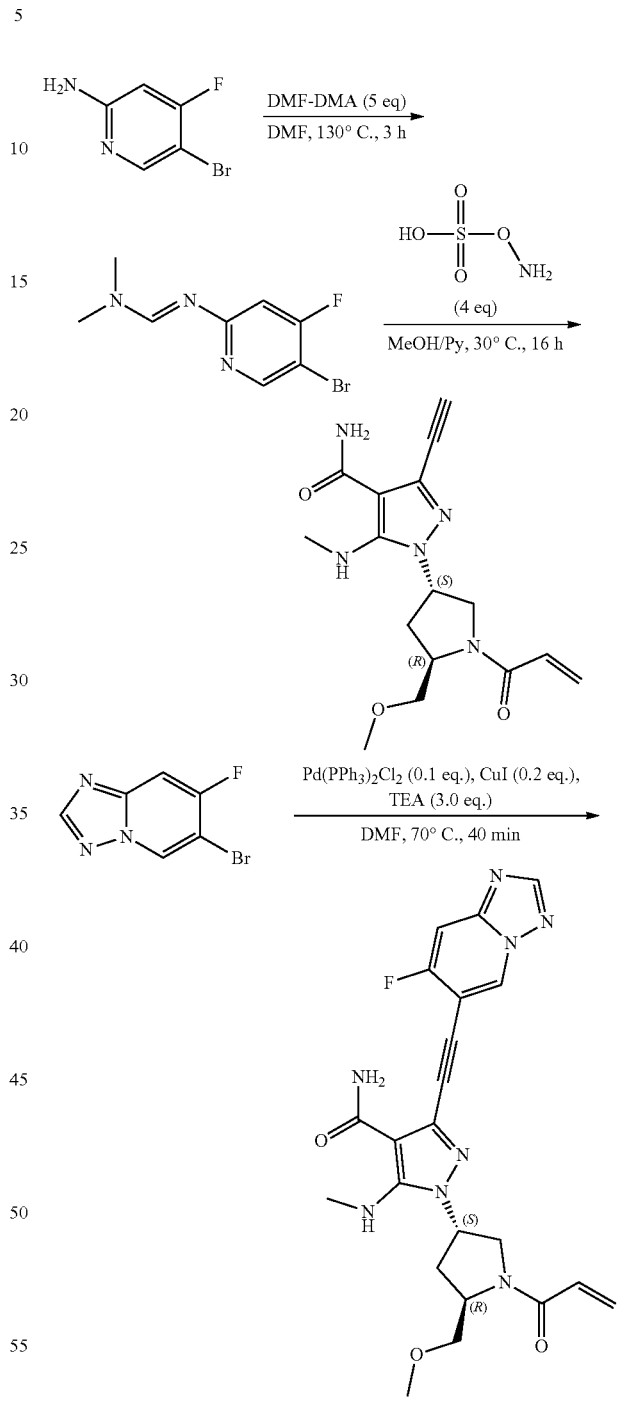

Step 1: (E)-N'-(5-Bromo-4-fluoropyridin-2-yl)-N,N-dimethylmethanimidamide

To a stirred solution of 5-bromo-4-fluoropyridin-2-amine (3.00 g, 15.70 mmol) in DMF (10.00 mL) was added DMF-DMA (9.36 g, 78.53 mmol) at room temperature. The reaction mixture was stirred for 3 h at 130° C. under argon atmosphere. The resulting mixture was concentrated under reduced pressure. The residue was purified by silica gel column chromatography, eluted with PE/EA (2/1). The fractions contained desired product were combined and concentrated to afford (E)-N'-(5-bromo-4-fluoropyridin-2-yl)-N,N-dimethylmethanimidamide (3 g, 77%) as a white solid. MS ESI calculated for $C_8H_9BrFN_3$ [M+H]$^+$, 246.00, found 246.05; $^1$H NMR (400 MHz, CDCl$_3$) δ 8.44 (s, 1H), 8.27 (d, J=9.7 Hz, 1H), 6.70 (d, J=10.1 Hz, 1H), 3.11-2.95 (m, 6H).

Step 2: 6-Bromo-7-fluoro-[1,2,4]triazolo[1,5-a]pyridine

To a stirred solution of (E)-N'-(5-bromo-4-fluoropyridin-2-yl)-N,N-dimethyl methanimidamide (3.00 g, 12.19 mmol) in MeOH (60.00 mL) and Pyridine (4.82 g, 60.95 mmol) was added aminooxysulfonic acid (5.51 g, 48.76 mmol) at 0° C. The reaction mixture was stirred for 16 h at 30° C. under nitrogen atmosphere. The resulting mixture was concentrated under reduced pressure. The residue was purified by silica gel column chromatography, eluted with PE/EA (2/1). The fractions contained desired product were combined and concentrated to afford 6-bromo-7-fluoro-[1,2,4]triazolo[1,5-a]pyridine (0.47 g, 17%) as a white solid. MS ESI calculated for $C_6H_3BrFN_3$ [M+H]$^+$, 215.95, 217.95, found 216.00, 218.00; $^1$H NMR (400 MHz, DMSO-d$_6$) δ 9.61-9.23 (m, 1H), 8.55 (s, 1H), 8.02 (d, J=8.9 Hz, 1H).

Step 3: 3-(2-[7-Fluoro-[1,2,4]triazolo[1,5-a]pyridin-6-yl]ethynyl)-1-[(3S,5R)-5-(methoxymethyl)-1-(prop-2-enoyl)pyrrolidin-3-yl]-5-(methylamino)pyrazole-4-carboxamide To a stirred solution of 3-ethynyl-1-[(3S,5R)-5-(methoxymethyl)-1-(prop-2-enoyl)pyrrolidin-3-yl]-5-(methylamino)pyrazole-4-carboxamide (0.2 g, 0.60 mmol), 6-bromo-7-fluoro-[1,2,4]triazolo[1,5-a]pyridine (0.13 g, 0.60 mmol), Pd(PPh$_3$)$_2$Cl$_2$ (42.36 mg, 0.06 mmol) and CuI (22.99 mg, 0.12 mmol) in DMF (2.00 mL) was added TEA (0.18 g, 1.81 mmol) dropwise at room temperature. The reaction mixture was degassed with argon for three times and stirred for 40 min at 70° C. The resulting mixture was concentrated under reduced pressure. The residue was purified by silica gel column chromatography, eluted with CH$_2$Cl$_2$/MeOH (10/1). The fractions contained desired product were combined and concentrated. The crude product was purified by Prep-HPLC with the following conditions: Column: XBridge Prep C18 OBD Column, 19×150 mm 5 µm; Mobile Phase A: Water (10 mmol/L NH$_4$HCO$_3$), Mobile Phase B: ACN; Flow rate: 20 mL/min; Gradient: 35 B to 55 B in 6 min; 210/254 nm. The fractions contained desired product were combined and concentrated to afford 3-(2-[7-fluoro-[1,2,4]triazolo[1,5-a]pyridin-6-yl]ethynyl)-1-[(3S,5R)-5-(methoxymethyl)-1-(prop-2-enoyl)pyrrolidin-3-yl]-5-(methylamino)pyrazole-4-carboxamide (89.4 mg, 31%) as a white solid. MS ESI calculated for $C_{22}H_{23}FN_6O_3$ [M+H]$^+$, 467.20, found 467.20; $^1$H NMR (400 MHz, CDCl$_3$) δ 8.87 (d, J=6.1 Hz, 1H), 8.41 (s, 1H), 7.51 (d, J=8.8 Hz, 1H), 7.12-6.52 (m, 1H), 6.50-6.35 (m, 2H), 5.85-5.65 (m, 1H), 5.61-5.25 (m, 2H), 4.65-4.34 (m, 1H), 4.23-3.85 (m, 3H), 3.55-3.42 (m, 1H), 3.39 (d, J=5.5 Hz, 3H), 3.06 (d, J=14.2 Hz, 3H), 2.96-2.61 (m, 1H), 2.38-2.13 (m, 1H).

Example 123: 3-[2-(1-Ethyl-4,6-difluoro-1,3-benzodiazol-5-yl)ethynyl]-5-[(2-hydroxyethyl)amino]-1-[(3S)-1-(prop-2-enoyl)pyrrolidin-3-yl]pyrazole-4-carboxamide

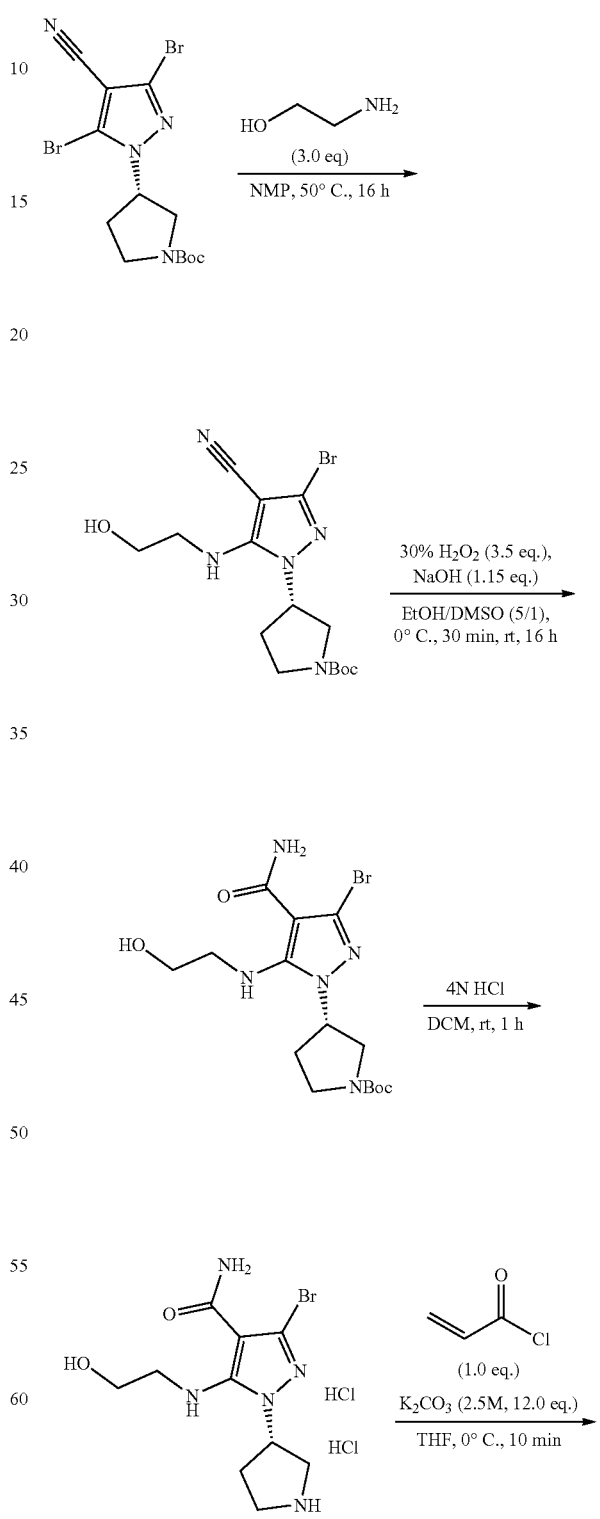

-continued

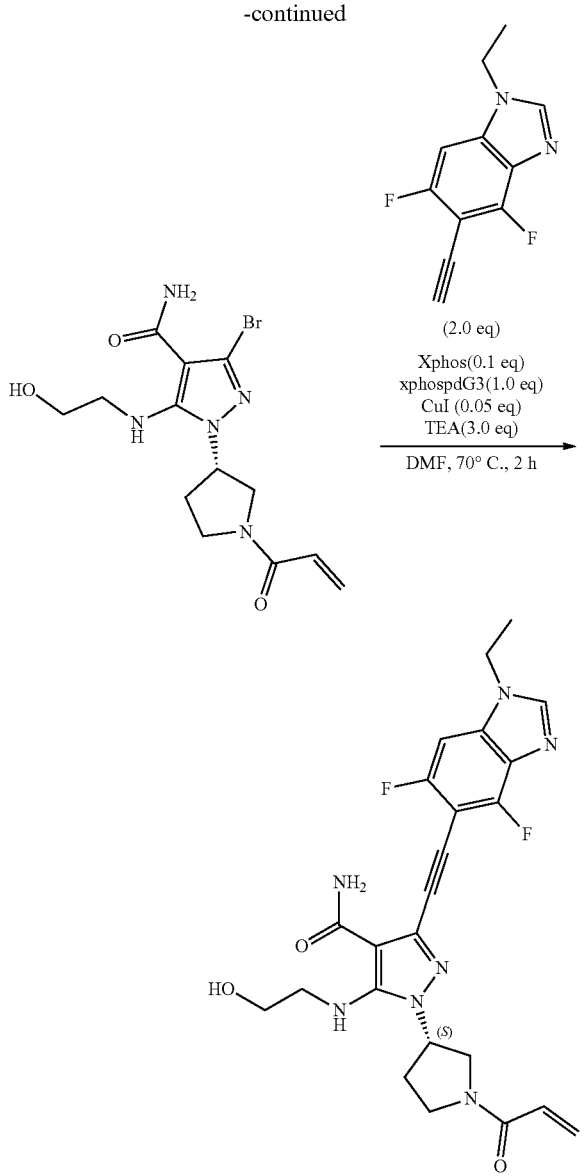

Step 1: Tert-butyl (3S)-3-[3-bromo-4-cyano-5-[(2-hydroxyethyl)amino]pyrazol-1-yl]pyrrolidine-1-carboxylate To a stirred solution of tert-butyl (3S)-3-(3,5-dibromo-4-cyanopyrazol-1-yl) pyrrolidine-1-carboxylate (3.00 g, 7.14 mmol) in NMP (30.00 mL) was added ethanolamine (1.32 g, 21.64 mmol) dropwise. The reaction mixture was stirred for 16 h at 50° C. under argon atmosphere. The resulting mixture was cooled down and concentrated under reduced pressure. The residue was diluted with water (200 mL) and extracted with EA (3×200 mL). The combined organic layers were washed with brine (400 mL), dried over anhydrous $Na_2SO_4$ and filtered. The filtrate was concentrated under reduced pressure to afford tert-butyl (3S)-3-[3-bromo-4-cyano-5-[(2-hydroxyethyl)amino]pyrazol-1-yl]pyrrolidine-1-carboxylate (3.03 g, crude) as a light yellow oil which was used in the next step directly without further purification. MS ESI calculated for $C_{15}H_{22}BrN_5O_3$ $[M+H]^+$, 400.09, found 400.10; $^1$H-NMR (300 MHz, $CDCl_3$) δ 6.44 (s, 1H), 5.03-4.99 (m, 2H), 4.31-3.39 (m, 5H), 2.66-2.20 (m, 2H), 2.07 (s, 1H), 1.48 (s, 2H) 1.28 (d, J=6.2 Hz, 9H).

Step 2: Tert-butyl (3S)-3-[3-bromo-4-carbamoyl-5-[(2-hydroxyethyl)amino]pyrazol-1-yl]pyrrolidine-1-carboxylate To a stirred solution of tert-butyl (3S)-3-[3-bromo-4-cyano-5-[(2-hydroxyethyl)amino]pyrazol-1-yl]pyrrolidine-1-carboxylate (1.50 g, 3.75 mmol) in EtOH (15.00 mL) and DMSO (3.00 mL) were added NaOH (8.61 mL, 4.31 mmol, 0.5 M) and $H_2O_2$ (0.90 mL, 13.31 mmol, 30%) at 0° C. The reaction mixture was stirred for 30 min at 0° C. and 16 h at room temperature. The resulting mixture was diluted with water (100 mL) and extracted with DCM (3×100 mL). The combined organic layers were washed with brine (2×100 mL), dried over anhydrous $Na_2SO_4$ and filtered. The filtrate was concentrated under reduced pressure. The residue was purified by silica gel column chromatography, eluted with PE/(EA:EtOH (3:1)). The fractions contained desired product were combined and concentrated to afford tert-butyl (3S)-3-[3-bromo-4-carbamoyl-5-[(2-hydroxyethyl)amino] pyrazol-1-yl]pyrrolidine-1-carboxylate (0.58 g, 37%) as a light yellow solid. MS ESI calculated for $C_{15}H_{24}BrN_5O_4$ $[M+H]^+$, 416.10, found 416.15; $^1$H-NMR (300 MHz, $CDCl_3$) δ 6.77 (s, 1H), 5.68 (s, 1H), 4.90 (t, J=7.4 Hz, 1H), 4.18-3.59 (m, 5H), 3.52-3.18 (m, 3H), 2.55-2.16 (m, 2H), 2.06 (d, J=10.9 Hz, 1H), 1.47 (s, 9H), 1.26 (t, J=7.2 Hz, 1H).

Step 3: 3-Bromo-5-[(2-hydroxyethyl)amino]-1-[(3S)-pyrrolidin-3-yl]pyrazole-4-carboxamidedihydrochloride To a stirred solution of tert-butyl (3S)-3-[3-bromo-4-carbamoyl-5-[(2-hydroxyethyl)amino]pyrazol-1-yl]pyrrolidine-1-carboxylate (0.58 g, 1.38 mmol) in DCM (10 mL) was added HCl (6 mL, 4 M in EA) at 0° C. The reaction mixture was stirred for 1 h at rt. The resulting mixture was concentrated under reduced pressure to afford 3-bromo-5-[(2-hydroxyethyl)amino]-1-[(3S)-pyrrolidin-3-yl]pyrazole-4-carboxamide dihydrochloride (0.72 g, crude) which was used in the next step directly without further purification. MS ESI calculated for $C_{10}H_{16}BrN_5O_2$ $[M+H]^+$, 318.18, found 318.15.

Step 4: 3-Bromo-5-[(2-hydroxyethyl)amino]-1-[(3S)-1-(prop-2-enoyl)pyrrolidin-3-yl]pyrazole-4-carboxamide (EB2000269-024)

To a stirred mixture of 3-bromo-5-[(2-hydroxyethyl)amino]-1-[(3S)-pyrrolidin-3-yl]pyrazole-4-carboxamide dihydrochloride (0.54 g, 1.38 mmol) and $K_2CO_3$ (2.28 g, 16.54 mmol) in THF (5.50 mL) was added acryloyl chloride (6.66 mL, 16.66 mmol, 2.5 M) in THF (10.00 mL) dropwise at 0° C. under argon atmosphere. The reaction mixture was stirred for 10 min at 0° C. under argon atmosphere. The resulting mixture was diluted with water (80 mL) and extracted with DCM (3×80 mL). The combined organic layers were washed with brine (2×50 mL), dried over anhydrous $Na_2SO_4$ and filtered. The filtrate was concentrated under reduced pressure. The residue was purified by silica gel column chromatography, eluted with 8% MeOH in DCM. The fractions contained desired product were combined and concentrated to afford 3-bromo-5-[(2-hydroxyethyl)amino]-1-[(3S)-1-(prop-2-enoyl)pyrrolidin-3-yl]pyrazole-4-carboxamide (0.32 g, 62%) as a white solid. MS ESI calculated for $C_{13}H_{18}BrN_5O_3$ $[M+H]^+$, 372.22, found 372.10; $^1$H-NMR (300 MHz, CDCl$_3$) δ 6.78 (s, 1H), 6.58-6.37 (m, 2H), 5.81-5.58 (m, 2H), 5.04 (dd, J=14.7, 7.3 Hz, 1H), 4.13-3.56 (m, 7H), 3.29 (d, J=4.7 Hz, 2H), 2.72-2.34 (m, 3H).

Step 5: 3-[2-(1-Ethyl-4,6-difluoro-1,3-benzodiazol-5-yl)ethynyl]-5-[(2-hydroxyethyl)amino]-1-[(3S)-1-(prop-2-enoyl)pyrrolidin-3-yl]pyrazole-4-carboxamide To a stirred mixture of 3-bromo-5-[(2-hydroxyethyl) amino]-1-[(3S)-1-(prop-2-enoyl) pyrrolidin-3-yl]pyrazole-4-carboxamide (0.18 g, 0.47 mmol), 1-ethyl-5-ethynyl-4,6-difluoro-1,3-benzodiazole (0.19 g, 0.94 mmol), CuI (4.48 mg, 0.02 mmol), X-Phos (22.41 mg, 0.05 mmol) and XPhos Pd G3 (39.80 mg, 0.05 mmol) in DMF (1.75 mL) was added TEA (0.20 mL, 1.94 mmol). The reaction mixture was degassed with argon for three times and stirred for 2 h at 70° C. The resulting mixture was concentrated under reduced pressure. The residue was purified by silica gel column chromatography, eluted with 8% MeOH in DCM. The fractions contained desired product were combined and concentrated. The crude product was purified by Prep-HPLC with the following conditions: Column: X Bridge Prep C18 OBD Column, 19×150 mm 5 μm; Mobile Phase A: Water (10 mmol/L NH$_4$HCO$_3$), Mobile Phase B: ACN; Flow rate: 20 mL/min; Gradient: 35 B to 70 B in 5.8 min, 210/254 nm; RT: 5.58 min. The fractions contained desired product were combined and concentrated to afford 3-[2-(1-ethyl-4,6-difluoro-1,3-benzodiazol-5-yl)ethynyl]-5-[(2-hydroxyethyl) amino]-1-[(3S)-1-(prop-2-enoyl)pyrrolidin-3-yl]pyrazole-4-carboxamide (79.6 mg, 34%) as a white solid. MS ESI calculated for C$_{24}$H$_{25}$F$_2$N$_7$O$_3$ [M+H]$^+$ 498.20, found 498.25; $^1$H-NMR (400 MHz, DMSO-d$_6$) δ 8.45 (s, 1H), 7.76-7.42 (m, 2H), 6.87-6.52 (m, 3H), 6.17-6.15 (m, 1H), 5.70-5.68 (m, 1H), 5.28-5.07 (m, 1H), 4.87-4.82 (m, 1H), 4.30 (q, J=7.3 Hz, 2H), 3.86-3.81 (m, 2H), 3.79-3.63 (m, 2H), 3.56-3.51 (m, 2H), 3.33-3.27 (m, 2H), 2.36-2.31 (m, 2H), 1.41 (t, J=7.2 Hz, 3H).

Example 124: 3-[2-(6-Chloro-1-cyclopropyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide

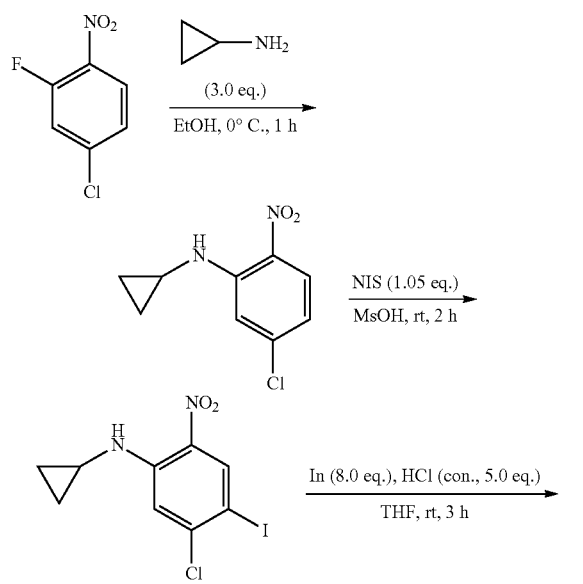

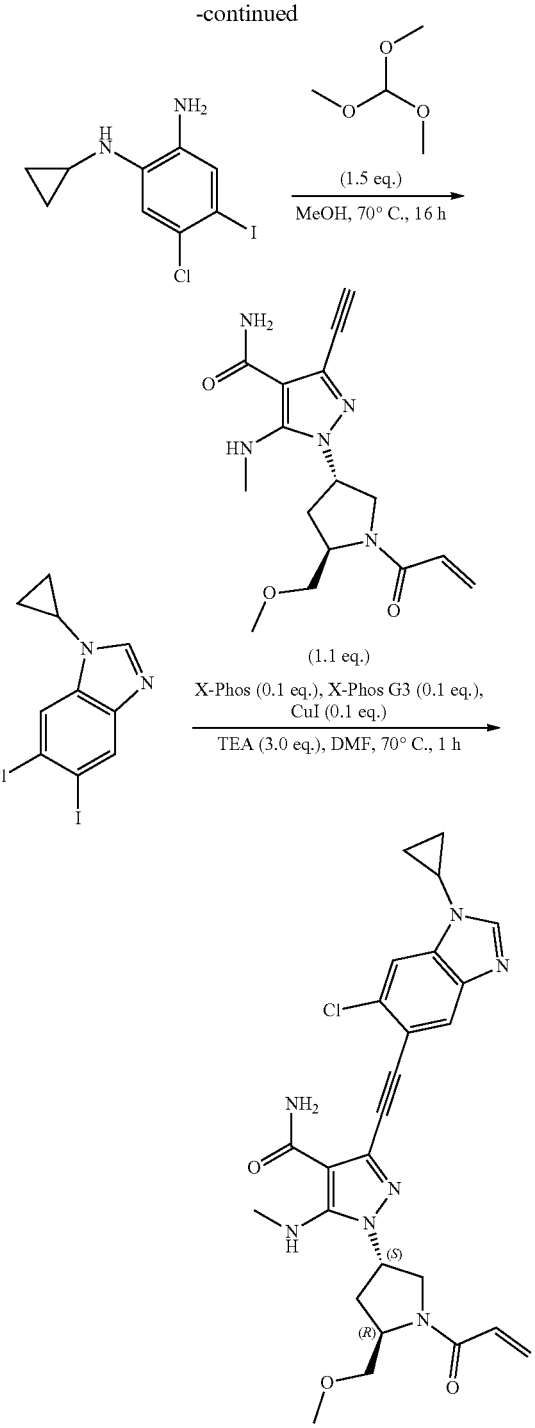

Step 1: 5-Chloro-N-cyclopropyl-2-nitroaniline

To a stirred solution of 4-chloro-2-fluoro-1-nitrobenzene (10.00 g, 56.97 mmol) in EtOH (100.00 mL) was added aminocyclopropane (9.76 g, 170.90 mmol) dropwise at 0° C. The resulting mixture was stirred for 1 h at 0° C. The resulting mixture was filtered, the filter cake was washed with water (3×100 mL) and dried to afford 5-chloro-N-cyclopropyl-2-nitroaniline (12 g, 99%) as a yellow solid which was used in the next step directly without further purification. MS ESI calculated for C$_9$H$_9$ClN$_2$O$_2$ [M+H]$^+$, 213.04, 215.04, found 213.10, 215.10; $^1$H NMR (400 MHz, CDCl$_3$) δ 8.13 (s, 1H), 8.12 (d, J=9.1 Hz, 1H), 7.32 (d, J=2.2 Hz, 1H), 6.68 (dd, J=9.1, 2.2 Hz, 1H), 2.62-2.56 (m, 1H), 1.04-0.93 (m, 2H), 0.74-0.66 (m, 2H).

Step 2:
5-Chloro-N-cyclopropyl-4-iodo-2-nitroaniline

To a stirred mixture of 5-chloro-N-cyclopropyl-2-nitroaniline (12.00 g, 56.44 mmol) in methanesulfonic acid (60 mL) was added NIS (13.33 g, 59.26 mmol) in portions at 0° C. The reaction mixture was stirred for 2 h at room temperature. The resulting mixture was quenched with ice/water (100 mL) at 0° C., adjusted to pH 8 with NaOH and extracted with EtOAc (3×100 mL). The combined organic layers were washed with brine (3×100 mL), dried over anhydrous Na$_2$SO$_4$ and filtered. The filtrate was concentrated under reduced pressure. The residue was purified by silica gel Column chromatography, eluted with PE/EA. The fractions contained desired product were combined and concentrated to afford 5-chloro-N-cyclopropyl-4-iodo-2-nitroaniline (10 g, 52%) as an orange solid. MS ESI calculated for C$_9$H$_8$ClN$_2$O$_2$ [M−H]−, 336.93, 338.93, found 336.90, 338.85; $^1$H NMR (300 MHz, CDCl$_3$) δ 8.60 (s, 1H), 8.03 (s, 1H), 7.47 (s, 1H), 2.62-2.51 (m, 1H), 1.07-0.87 (m, 2H), 0.81-0.64 (m, 2H).

Step 3:
5-Chloro-N1-cyclopropyl-4-iodobenzene-1,2-diamine

To a stirred mixture of 5-chloro-N-cyclopropyl-4-iodo-2-nitroaniline (9.00 g, 26.59 mmol) and In (24.42 g, 212.68 mmol) in THF (60.00 mL) was added con. HCl (11.08 mL, 132.96 mmol) dropwise at 0° C. The reaction mixture was stirred for 3 h at room temperature under nitrogen atmosphere. The resulting mixture was concentrated under reduced pressure. The residue was purified by silica gel Column chromatography, eluted with PE/EtOAc (1/1). The fractions contained desired product were combined and concentrated to afford 5-chloro-N$^1$-cyclopropyl-4-iodobenzene-1,2-diamine (3 g, 36%) as a light brown solid. MS ESI calculated for C$_9$H$_{10}$ClIN$_2$ [M+H]$^+$, 308.96, 310.96, found 308.95, 310.95.

Step 4:
6-Chloro-1-cyclopropyl-5-iodo-1,3-benzodiazole

To a stirred solution of 5-chloro-N$^1$-cyclopropyl-4-iodobenzene-1,2-diamine (3.00 g, 9.72 mmol) in MeOH (30.00 mL) was added trimethyl orthoformate (1.55 g, 14.58 mmol). The reaction mixture was stirred for 16 h at 70° C. The resulting mixture was cooled down and concentrated under reduced pressure. The residue was purified by silica gel Column chromatography, eluted with PE/EtOAc (1/1). The fractions contained desired product were combined and concentrated to afford 6-chloro-1-cyclopropyl-5-iodo-1,3-benzodiazole (0.90 g, 29%) as a light brown solid. MS ESI calculated for C$_{10}$H$_8$ClIN$_2$ [M+H]$^+$, 318.95, 320.95, found 318.95, 320.95; $^1$H NMR (300 MHz, CDCl$_3$) δ 8.30 (s, 1H), 7.92 (s, 1H), 7.74 (s, 1H), 3.39-3.33 (m, 1H), 1.24-1.18 (m, 2H), 1.10-1.01 (m, 2H).

Step 5: 3-[2-(6-Chloro-1-cyclopropyl-1,3-benzodiazol-5-yl)ethynyl]-1-[(3S,5R)-5-(methoxymethyl)-1-(prop-2-enoyl)pyrrolidin-3-yl]-5-(methylamino) pyrazole-4-carboxamide To a stirred mixture of 6-chloro-1-cyclopropyl-5-iodo-1,3-benzodiazole (50.00 mg, 0.16 mmol) and 3-ethynyl-1-[(3S,5R)-5-(methoxymethyl)-1-(prop-2-enoyl)pyrrolidin-3-yl]-5-(methylamino)pyrazole-4-carboxamide (57.22 mg, 0.17 mmol) in DMF (1.50 mL) were added XPhos Pd G3 (13.29 mg, 0.02 mmol), XPhos Pd G3 (13.29 mg, 0.02 mmol), CuI (2.99 mg, 0.02 mmol) and TEA (47.65 mg, 0.47 mmol). The reaction mixture was degassed with argon for three times and stirred for 1 h at 70° C. The resulting mixture was cooled down and concentrated under reduced pressure. The residue was purified by silica gel Column chromatography, eluted with CH$_2$Cl$_2$/MeOH (10/1) to afford crude. The crude product was purified by Prep-HPLC with the following conditions: Column: SunFire Prep C18 OBD Column, 19×150 mm 5 μm 10 nm; Mobile Phase A: Water (10 mmol/L, NH$_4$HCO$_3$), Mobile Phase B: ACN; Flow rate: 20 mL/min; Gradient: 25 B to 50 B in 6 min; 210/254 nm; RT: 5.58 min. The fractions contained desired product were combined and concentrated to afford 3-[2-(6-chloro-1-cyclopropyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (41.5 mg, 50%) as an off-white solid. MS ESI calculated for C$_{26}$H$_{28}$ClN$_7$O$_3$ [M+H]$^+$, 522.19, found 522.25; $^1$H NMR (400 MHz, CDCl$_3$) δ 8.07 (d, J=5.9 Hz, 2H), 7.68 (s, 1H), 7.20 (s, 1H), 6.82 (s, 1H), 6.59-6.36 (m, 2H), 5.73-5.70 (m, 1H), 5.57-5.40 (m, 2H), 4.59-4.45 (m, 1H), 4.17-3.95 (m, 2H), 3.93-3.89 (m, 1H), 3.50-3.36 (m, 5H), 3.06 (s, 3H), 2.79-2.67 (m, 1H), 2.34-2.31 (m, 1H), 1.28-1.17 (m, 2H), 1.19-1.05 (m, 2H).

Example 125: 3-[2-(1-Ethyl-6,7-difluoro-1,3-benzodiazol-5-yl)ethynyl]-1-[(3S,5R)-5-(methoxymethyl)-1-(prop-2-enoyl)pyrrolidin-3-yl]-5-(methylamino) pyrazole-4-carboxamide

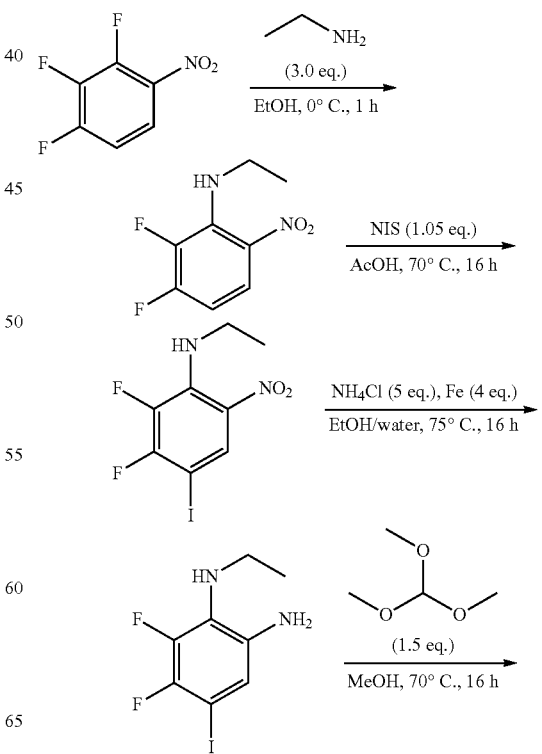

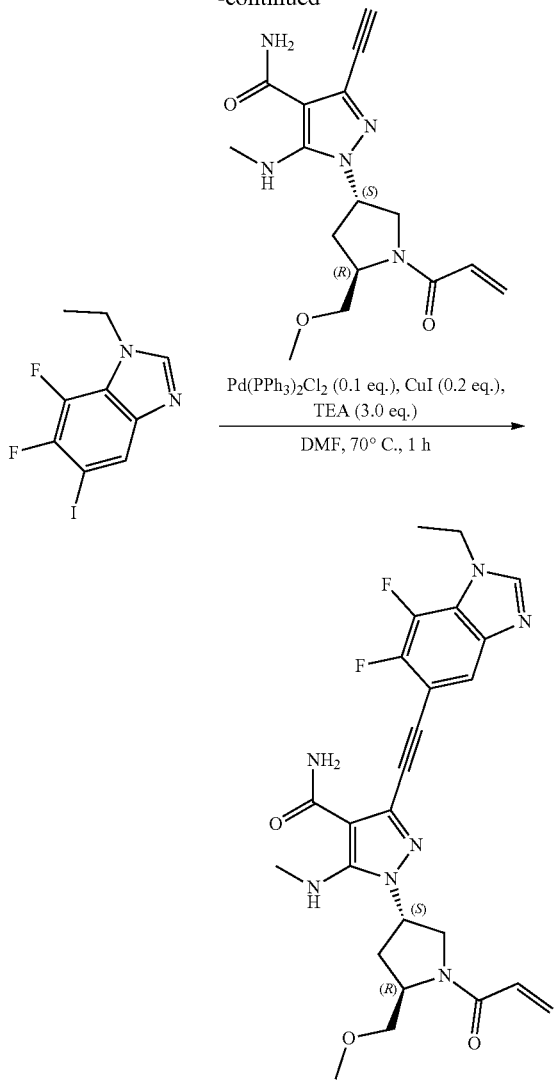

Step 1: N-Ethyl-2,3-difluoro-6-nitroaniline

To a solution of 1,2,3-trifluoro-4-nitrobenzene (5 g, 28.23 mmol) in EtOH (40 mL) was added ethylamine (3.82 g, 84.70 mmol). The reaction mixture was stirred for 1 h 0° C. The precipitated solids were collected by filtration and washed with water (4×100 mL) and dried to afford N-ethyl-2,3-difluoro-6-nitroaniline (5.3 g, 92%) as a yellow solid which was used in the next step directly without further purification. MS ESI calculated for $C_{25}H_{24}ClN_7O_2$ [M–H]−, 201.06, found 201.05; $^1$H NMR (300 MHz, CDCl$_3$) δ 8.00-7.92 (m, J=9.8, 5.6, 2.3 Hz, 2H), 6.53-6.39 (m, 1H), 3.71-3.62 (m, 4.7 Hz, 2H), 1.36-1.24 (m, 0.9 Hz, 3H).

Step 2: N-Ethyl-2,3-difluoro-4-iodo-6-nitroaniline

To a stirred mixture of N-ethyl-2,3-difluoro-6-nitroaniline (5.30 g, 26.21 mmol) in AcOH (53 mL) was added NIS (6.20 g, 103.24 mmol). The reaction mixture was stirred for 16 h at 70° C. under nitrogen reduced. The resulting mixture was concentrated under reduced pressure. The residue was basified to pH 8 with sat. NaHCO$_3$ (aq.) (100 mL) at room temperature. The resulting mixture was extracted with EtOAc (2×300 mL). The combined organic layers were washed with water (2×150 mL), dried over anhydrous Na$_2$SO$_4$ and filtered. The filtrate was concentrated under reduced pressure. The residue was purified by silica gel Column chromatography, eluted with CH$_2$Cl$_2$/PE (6/1). The fractions contained desired product were combined and concentrated to afford N-ethyl-2,3-difluoro-4-iodo-6-nitroaniline (7.3 g, 84%) as a light yellow solid. MS ESI calculated for $C_8H_7F_2IN_2O_2$ [M–H]−, 326.95, found 326.70; $^1$H NMR (300 MHz, CDCl$_3$) δ 8.39 (dd, J=6.3, 2.4 Hz, 1H), 7.92 (s, 1H), 3.74-3.59 (m, 2H), 1.39-1.22 (m, 3H).

Step 3: N1-Ethyl-5,6-difluoro-4-iodobenzene-1,2-diamine

To a stirred mixture of N-ethyl-2,3-difluoro-4-iodo-6-nitroaniline (2.00 g, 6.09 mmol) and NH$_4$Cl (1.63 g, 30.47 mmol) in EtOH (20.00 mL) and water (4.00 mL) was added Fe (1.36 g, 24.35 mmol). The reaction mixture was stirred for 16 h at 75° C. The resulting mixture was filtered, the filter cake was washed with EtOAc (3×100 mL). The filtrate was concentrated under reduced pressure. The residue was dissolved in water (200 mL), extracted with EA (3×100 mL). The combined organic layers were washed brine (3×100 mL), dried over anhydrous Na$_2$SO$_4$, filtered and concentrated under reduced pressure to afford $N^1$-ethyl-5,6-difluoro-4-iodobenzene-1,2-diamine (1.7 g, 93%) as a dark grey semi-solid which was used in the next step directly without further purification. MS ESI calculated for $C_8H_9F_2IN_2$ [M–H]−, 296.98, found 296.95.

Step 4: 1-Ethyl-6,7-difluoro-5-iodo-1,3-benzodiazole

To a stirred solution of $N^1$-ethyl-5,6-difluoro-4-iodobenzene-1,2-diamine (1.70 g, 5.70 mmol) in MeOH (17.00 mL) was added trimethyl orthoformate (0.91 g, 8.55 mmol) at room temperature. The reaction mixture was stirred for 16 h at 70° C. The resulting mixture was concentrated under reduced pressure. The residue was purified by silica gel Column chromatography, eluted with PE/EtOAc (1/1). The fractions contained desired product were combined and concentrated to afford 1-ethyl-6,7-difluoro-5-iodo-1,3-benzodiazole (1.3 g, 73%) as a brown yellow solid. MS ESI calculated for $C_9H_7F_2IN_2$ [M+H]+, 308.96, found 309.00; $^1$H NMR (400 MHz, CDCl$_3$) δ 7.95 (dd, J=4.5, 1.7 Hz, 1H), 7.88 (s, 1H), 4.38 (q, J=7.3 Hz, 2H), 1.58 (t, J=7.3 Hz, 3H).

Step 5: 3-[2-(1-Ethyl-6,7-difluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide To a stirred mixture of 1-ethyl-6,7-difluoro-5-iodo-1,3-benzodiazole (0.13 g, 0.45 mmol), 3-ethynyl-1-[(3S,5R)-5-(methoxymethyl)-1-(prop-2-enoyl)pyrrolidin-3-yl]-5-(methylamino)pyrazole-4-carboxamide (0.15 g, 0.45 mmol), Pd(PPh$_3$)$_2$Cl$_2$ (31.77 mg, 0.04 mmol) and CuI (17.24 mg, 0.09 mmol) in DMF (3 mL) was added TEA (0.13 g, 1.35 mmol) dropwise at room temperature. The reaction mixture was degassed with argon for three times and stirred for 1 h at 70° C. The resulting mixture was concentrated under reduced pressure. The residue was purified by silica gel Column chromatography, eluted with CH$_2$Cl$_2$/MeOH (10/1). The fractions contained desired product were combined and concentrated. The crude product was purified by reverse flash chromatography with the following conditions:

Column: XBridge Prep C18 OBD Column, 19×150 mm 5 µm; Mobile Phase A: Water (10 mmol/L NH$_4$HCO$_3$), Mobile Phase B: ACN; Flow rate: 20 mL/min; Gradient: 20 B to 50 B in 6 min, 210/254 nm. The fractions contained desired product were combined and concentrated to afford 3-[2-(1-ethyl-6,7-difluoro-1,3-benzodiazol-5-yl)ethynyl]-1-[(3S, 5R)-5-(methoxymethyl)-1-(prop-2-enoyl)pyrrolidin-3-yl]-5-(methylamino)pyrazole-4-carboxamide (0.12 g, 53%) as a white solid. MS ESI calculated for C$_{25}$H$_{27}$F$_2$N$_7$O$_3$ [M+H]$^+$, 512.21, found 512.20; $^1$H NMR (400 MHz, CDCl$_3$) δ 7.92 (d, J=82.3 Hz, 2H), 6.83-6.81 (m, 2H), 6.54-6.36 (m, 2H), 5.70-5.69 (m, 1H), 5.52-5.49 (m, 1H), 5.42-5.40 (m, 1H), 4.56 (d, J=9.0 Hz, 1H), 4.39-4.33 (m, 2H), 4.10 (t, J=9.1 Hz, 1H), 4.06-3.96 (m, 1H), 3.90-3.88 (m, 1H), 3.53-3.40 (m, 1H), 3.37-3.35 (m, 3H), 3.03-3.01 (m, 3H), 2.76-2.64 (m, 1H), 2.30-2.28 (m, 1H), 1.5-1.55 (m, 3H).

Example 126: 3-[2-(6-Chloro-1-ethyl-7-fluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide

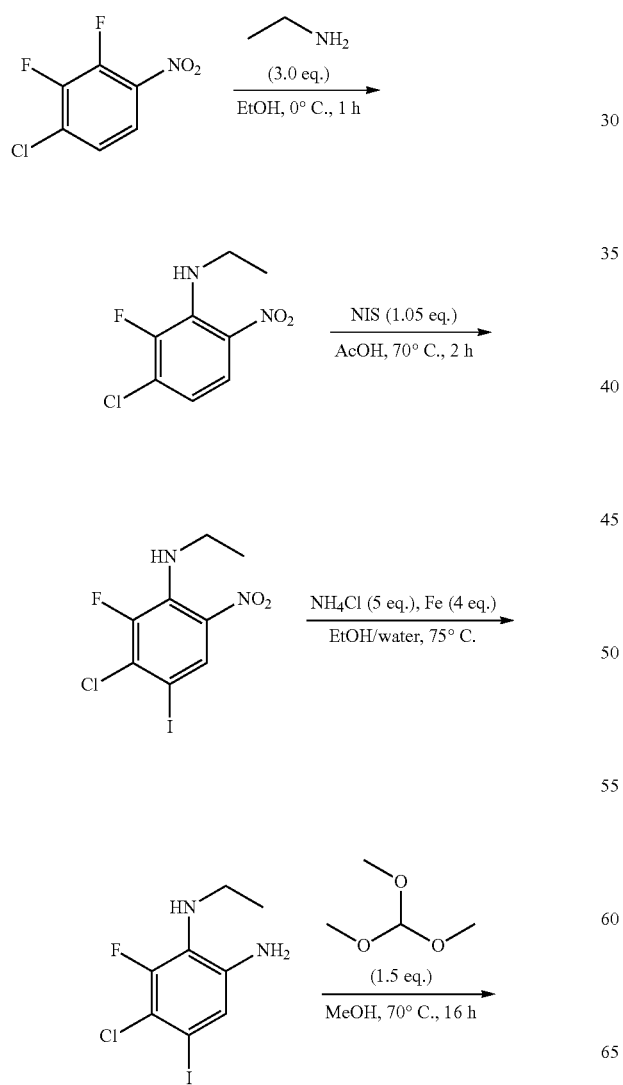

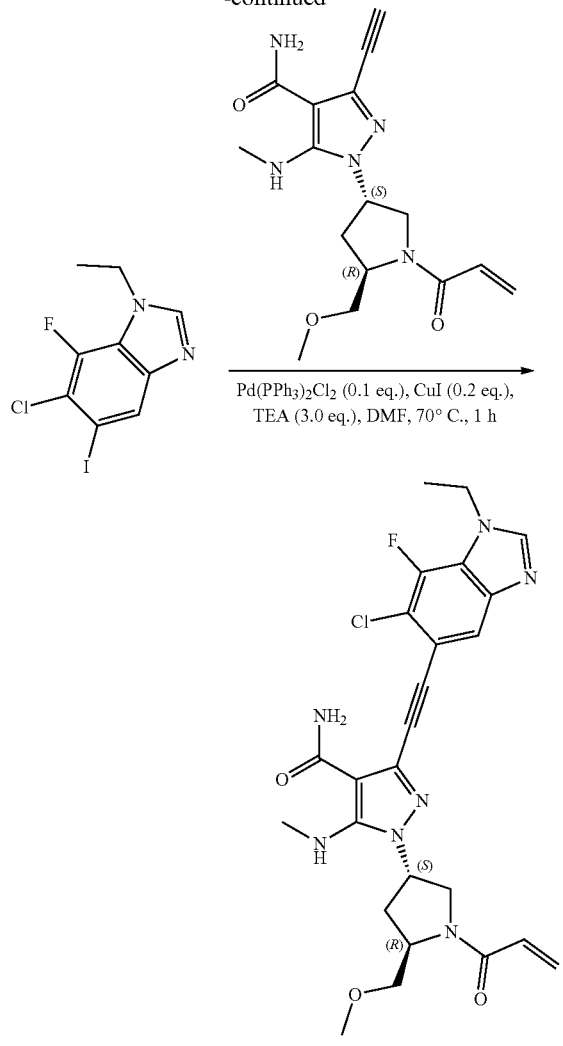

Step 1: 3-Chloro-N-ethyl-2-fluoro-6-nitroaniline

To a stirred solution of 1-chloro-2,3-difluoro-4-nitrobenzene (3.30 g, 17.05 mmol) in EtOH (25.00 mL) was added ethylamine in EtOH (7.69 g, 51.15 mmol, 30%) dropwise at 0° C. under nitrogen atmosphere. The reaction mixture was stirred for 1 h at 0° C. under nitrogen atmosphere. The resulting mixture was filtered, the filter cake was washed with water (3×50 mL). The filter cake was dried to afford 3-chloro-N-ethyl-2-fluoro-6-nitroaniline (3.4 g, 91%) as a yellow solid which was used in the next step directly without further purification. MS ESI calculated for C$_8$H$_8$ClFN$_2$O$_2$ [M+H]$^+$, 219.03, found 219.05; $^1$H NMR (400 MHz, CDCl$_3$) δ 7.93 (dd, J=9.4, 2.0 Hz, 1H), 6.64 (dd, J=9.4, 6.5 Hz, 1H), 3.72-3.61 (m, 2H), 1.33 (t, J=7.2 Hz, 3H).

Step 2: 3-Chloro-N-ethyl-2-fluoro-4-iodo-6-nitroaniline

To a stirred solution of 3-chloro-N-ethyl-2-fluoro-6-nitroaniline (3.40 g, 15.55 mmol) in AcOH (34.00 mL) was added NIS (4.02 g, 17.88 mmol) in portions at room temperature under nitrogen atmosphere. The reaction mixture was stirred for 2 h at 70° C. under nitrogen atmosphere.

589

The resulting mixture was concentrated under reduced pressure. The residue was diluted with EtOAc (100 mL). The resulting mixture was basified to pH 8 with saturated NaHCO$_3$ (aq.) and extracted with EtOAc (2×150 mL). The combined organic layers were washed with brine (100 mL), dried over anhydrous Na$_2$SO$_4$ and filtered. The filtrate was concentrated under reduced pressure. The residue was purified by silica gel column chromatography, eluted with PE/DCM (4/1). The fractions contained desired product were combined and concentrated to afford 3-chloro-N-ethyl-2-fluoro-4-iodo-6-nitroaniline (5 g, 93%) as a yellow solid. MS ESI calculated for C$_8$H$_7$ClFIN$_2$O$_2$ [M+H]$^+$, 345.51, found 345.00; $^1$H NMR (300 MHz, CDCl$_3$) δ 8.45 (d, J=2.1 Hz, 1H), 7.84 (s, 1H), 3.65 (s, 2H), 1.33 (t, J=7.2 Hz, 3H).

Step 3: 5-Chloro-N1-ethyl-6-fluoro-4-iodobenzene-1,2-diamine

To a stirred mixture of 5-chloro-N-ethyl-3-fluoro-4-iodo-2-nitroaniline (5.00 g, 14.51 mmol) and NH$_4$Cl (3.88 g, 72.56 mmol) in EtOH (50.00 mL) and water (10.00 mL) was added Fe (3.24 g, 58.05 mmol) in portions at room temperature. The reaction mixture was stirred for 16 h at 75° C. under nitrogen atmosphere. The resulting mixture was filtered, the filter cake was washed with EtOAc (3×150 mL). The filtrate was diluted with water (100 mL). The resulting mixture was extracted with EtOAc (3×200 mL). The combined organic layers were washed with brine (3×80 mL), dried over anhydrous Na$_2$SO$_4$ and filtered. The filtrate was concentrated under reduced pressure to afford 5-chloro-N$^1$-ethyl-6-fluoro-4-iodobenzene-1,2-diamine (4.5 g, 98%) as a brown solid which was used in the next step directly without further purification. MS ESI calculated for C$_8$H$_9$ClFIN$_2$ [M+H]$^+$, 314.95, found 315.00.

Step 4: 6-Chloro-1-ethyl-7-fluoro-5-iodo-1H-benzo[d]imidazole

To a stirred solution of 5-chloro-N$^1$-ethyl-6-fluoro-4-iodobenzene-1,2-diamine (4.50 g, 14.31 mmol) in MeOH (45.00 mL) was added trimethyl orthoformate (2.28 g, 21.46 mmol) dropwise at room temperature under nitrogen atmosphere. The reaction mixture was stirred for 16 h at 70° C. under nitrogen atmosphere. The resulting mixture was concentrated under reduced pressure The residue was purified by silica gel column chromatography, eluted with CH$_2$Cl$_2$/MeOH (10/1). The fractions contained desired product were combined and concentrated to afford 6-chloro-1-ethyl-7-fluoro-5-iodo-1H-benzo[d]imidazole (4 g, 86%) as a brown solid. MS ESI calculated for C$_9$H$_7$ClFIN$_2$ [M+H]$^+$, 324.93, found 325.00; $^1$H NMR (400 MHz, CDCl$_3$) δ 8.11 (d, J=1.2 Hz, 1H), 7.84 (s, 1H), 4.36 (q, J=7.2 Hz, 2H), 1.57-1.54 (m, 3H).

Step 5: 3-[2-(6-Chloro-1-ethyl-7-fluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide To a stirred solution of 6-chloro-1-ethyl-7-fluoro-5-iodo-1,3-benzodiazole (0.15 g, 0.45 mmol), 3-ethynyl-1-[(3S,5R)-5-(methoxymethyl)-1-(prop-2-enoyl)pyrrolidin-3-yl]-5-(methylamino)pyrazole-4-carboxamide (0.15 g, 0.45 mmol), Pd(PPh$_3$)$_2$Cl$_2$ (31.75 mg, 0.05 mmol) and CuI (17.23 mg, 0.09 mmol) in DMF (1.50 mL) was added TEA (0.19 mL, 1.86 mmol) dropwise at room temperature. The reaction mixture was degassed with argon for three times and stirred

590 for 1 h at 70° C. The resulting mixture was diluted with water (150 mL) and extracted with EA (3×50 mL). The combined organic layers were washed with water (5×30 mL), dried over anhydrous Na$_2$SO$_4$ and filtered. The filtrate was concentrated under reduced pressure. The residue was purified by silica gel column chromatography, eluted with CH$_2$Cl$_2$/MeOH (10/1). The fractions contained desired product were combined and concentrated. Then the crude product was purified by Prep-HPLC with the following conditions: Column: XBridge Prep C18 OBD Column, 19×150 mm 5 μm; Mobile Phase A: Water (10 mmol/L NH$_4$HCO$_3$), Mobile Phase B: ACN; Flow rate: 20 mL/min; Gradient: 15 B to 50 B in 6 min; 210/254 nm; RT: 5.75 min. The fractions contained desired product were combined and concentrated to afford 3-[2-(6-chloro-1-ethyl-7-fluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (0.1 g, 43%) as a white solid. MS ESI calculated for C$_{25}$H$_{27}$ClFN$_7$O$_3$ [M+H]$^+$, 528.18, found 528.30; $^1$H-NMR (400 MHz, CDCl$_3$) δ 7.95 (d, J=12 Hz, 2H), 7.29-6.53 (m, 1H), 6.51-6.43 (m, 2H), 5.75-5.71 (m, 1H), 5.56-5.41 (m, 2H), 4.60-4.37 (m, 3H), 4.16-3.90 (m, 3H), 3.53-3.39 (m, 4H), 3.05 (d, J=16 Hz, 3H), 2.78-2.29 (m, 2H), 1.62-1.57 (m, 4H).

Example 127: 3-[2-(6,7-Difluoro-1,2-dimethyl-1,3-benzodiazol-5-yl)ethynyl]-1-[(3S,5R)-5-(methoxymethyl)-1-(prop-2-enoyl) pyrrolidin-3-yl]-5-(methylamino) pyrazole-4-carboxamide

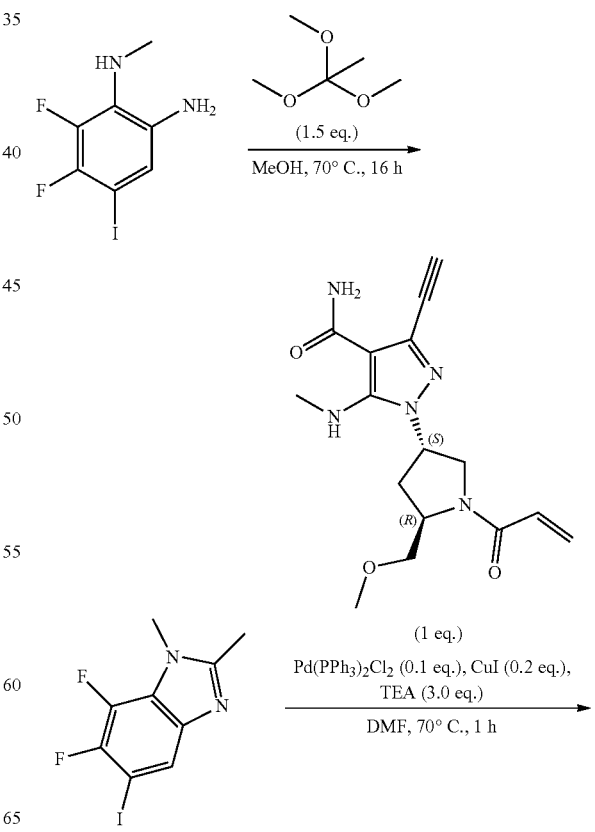

-continued

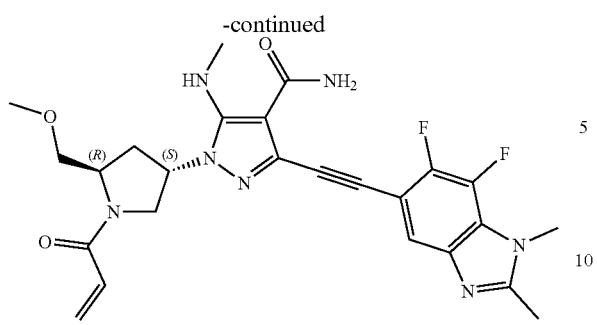

Step 1: 6,7-Difluoro-5-iodo-1,2-dimethyl-1H-benzo[d]imidazole

To a stirred solution of 5,6-difluoro-4-iodo-$N^1$-methyl-benzene-1,2-diamine (1.64 g, 5.77 mmol) in MeOH (18.00 mL) was added 1,1,1-trimethoxyethane (1.04 g, 8.66 mmol) at room temperature. The reaction mixture was stirred for 16 h at 70° C. The resulting mixture was concentrated under reduced pressure. The residue was purified by silica gel Column chromatography, eluted with $CH_2Cl_2$/MeOH (10/1). The fractions contained desired product were combined and concentrated to afford 6,7-difluoro-5-iodo-1,2-dimethyl-1H-benzo[d]imidazole (1.88 g, 82%) as a brown solid. ESI calculated for $C_9H_7F_2IN_2$ [M+H]$^+$, 308.96, found 309.10.

Step 2: 3-[2-(6,7-Difluoro-1,2-dimethyl-1,3-benzodiazol-5-yl)ethynyl]-1-[(3S,5R)-5-(methoxymethyl)-1-(prop-2-enoyl) pyrrolidin-3-yl]-5-(methylamino) pyrazole-4-carboxamide To a stirred solution of 6,7-difluoro-5-iodo-1,2-dimethyl-1,3-benzodiazole (0.15 g, 0.49 mmol), 3-ethynyl-1-[(3S,5R)-5-(methoxymethyl)-1-(prop-2-enoyl) pyrrolidin-3-yl]-5-(methylamino) pyrazole-4-carboxamide (0.16 g, 0.49 mmol), Pd(PPh$_3$)$_2$Cl$_2$ (34.18 mg, 0.05 mmol), and CuI (18.55 mg, 0.10 mmol) in DMF (1.50 mL) was added TEA (0.20 mL, 2.01 mmol) dropwise at room temperature. The reaction mixture was degassed with argon for three times and stirred for 1 h at 70° C. The resulting mixture was diluted with EA (100 mL), washed with water (3×30 mL) and brine (50 mL), dried over anhydrous Na$_2$SO$_4$ and filtered. The filtrate was concentrated under reduced pressure. The residue was purified by silica gel Column chromatography, eluted with CH$_2$Cl$_2$/MeOH (10/1). The fractions contained desired product were combined and concentrated. The crude product was purified by Prep-HPLC with the following conditions: Column: XBridge Prep C18 OBD Column, 19×150 mm 5 µm; Mobile Phase A: Water (10 mmol/L NH$_4$HCO$_3$), Mobile Phase B: ACN; Flow rate: 20 mL/min; Gradient: 15 B to 50 B in 6 min; 210/254 nm; RT: 5.75 min. The fractions contained desired product were combined and concentrated to afford 3-[2-(6,7-difluoro-1,2-dimethyl-1,3-benzodiazol-5-yl)ethynyl]-1-[(3S,5R)-5-(methoxymethyl)-1-(prop-2-enoyl) pyrrolidin-3-yl]-5-(methylamino) pyrazole-4-carboxamide (58.5 mg, 23%) as a white solid. MS ESI calculated for $C_{25}H_{27}F_2N_7O_3$ [M+H]$^+$, 511.53, found 511.21; $^1$H NMR (400 MHz, CDCl$_3$) δ 7.66 (d, J=4 Hz, 1H), 7.02 (s, 1H), 6.85 (s, 1H), 6.53-6.43 (m, 2H), 5.74-5.71 (m, 1H), 5.55-5.50 (m, 1H), 5.38-5.3 (m, 1H), 4.57-4.45 (m, 1H), 4.14-3.97 (m, 2H), 3.93 (s, 3H), 3.92-3.90 (m, 1H), 3.53-3.44 (m, 1H), 3.39-3.35 (m, 3H), 3.07-3.03 (m, 3H), 2.76-2.68 (m, 1H), 2.64 (s, 3H), 2.34-2.31 (m, 1H).

Example 128: 3-[2-(6-Chloro-7-fluoro-1,2-dimethyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide

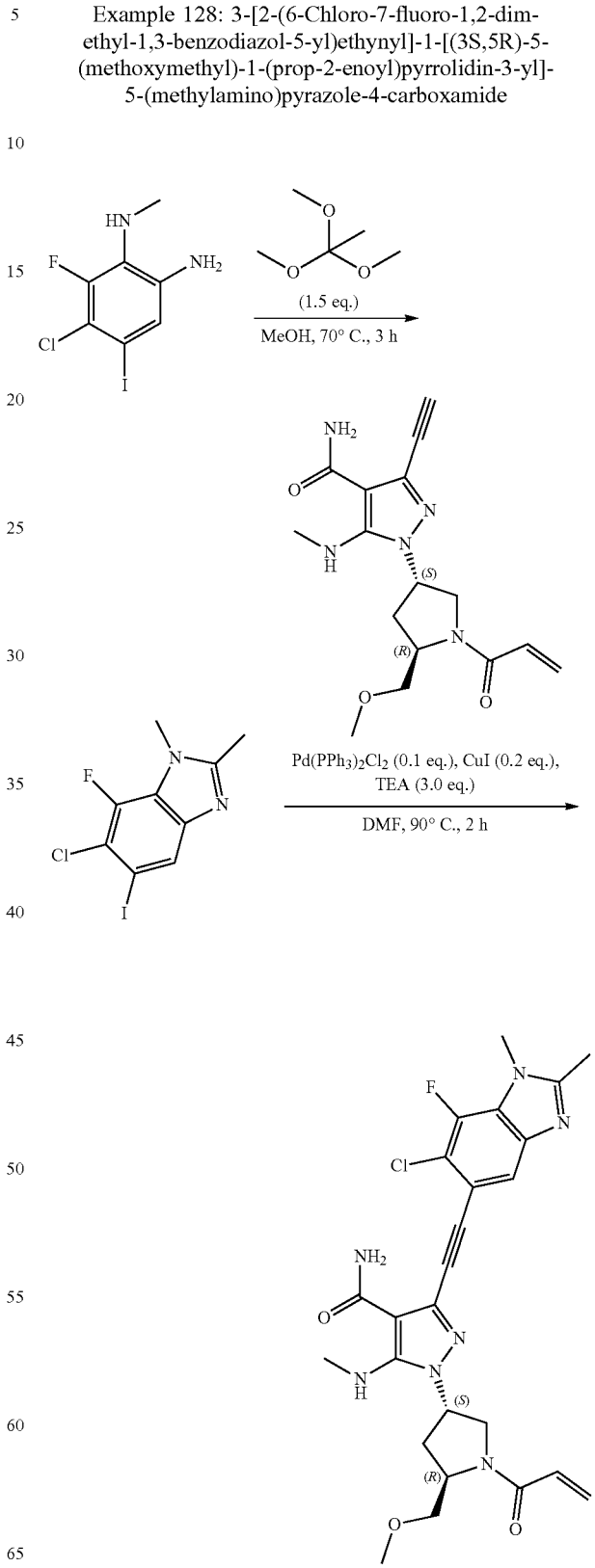

Step 1: 6-Chloro-7-fluoro-5-iodo-1,2-dimethyl-1,3-benzodiazole

To a solution of 5-chloro-6-fluoro-4-iodo-N¹-methylbenzene-1,2-diamine (1.50 g, 4.99 mmol) in MeOH (60.00 mL) was added 1,1,1-trimethoxyethane (1.80 g, 14.98 mmol) at room temperature. The reaction mixture was stirred for 3 h at 70° C. The resulting mixture was concentrated under reduced pressure. The residue was diluted with EA (50 mL), washed with water (2×25 mL), dried over anhydrous Na₂SO₄ and filtered. The filtrate was concentrated under reduced pressure. The residue was purified by silica gel Column chromatography, eluted with EA in PE (40-100%). The fractions contained desired product were combined and concentrated to afford 6-chloro-7-fluoro-5-iodo-1,2-dimethyl-1,3-benzodiazole (0.24 g, 15%) as a yellow solid. MS ESI calculated for C₉H₇ClFIN₂ [M+H]⁺, 324.93, found 324.95; ¹H NMR (400 MHz, CDCl₃) δ 7.96 (d, J=1.2 Hz, 1H), 3.92-3.85 (m, 3H), 2.59 (s, 3H).

Step 2: 3-[2-(6-Chloro-7-fluoro-1,2-dimethyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide To a stirred solution of 6-chloro-7-fluoro-5-iodo-1,2-dimethyl-1,3-benzodiazole (0.15 g, 0.45 mmol), 3-ethynyl-1-[(3S,5R)-5-(methoxymethyl)-1-(prop-2-enoyl)pyrrolidin-3-yl]-5-(methylamino)pyrazole-4-carboxamide (0.15 g, 0.45 mmol), Pd(PPh₃)₂Cl₂ (31.77 mg, 0.05 mmol) and CuI (17.24 mg, 0.09 mmol) in DMF (4.00 mL) was added TEA (0.14 g, 1.36 mmol) dropwise at room temperature. The reaction mixture was degassed with argon for three times and stirred for 2 h at 90° C. The resulting mixture was cooled down and concentrated under reduced pressure. The residue was purified by silica gel Column chromatography, eluted with MeOH in DCM (0-5%) to afford the crude product. Then the crude product was purified by Prep-HPLC with the following conditions: Column: SunFire Prep C18 OBD Column, 19×150 mm 5 μm 10 nm; Mobile Phase A: Water (0.1% FA), Mobile Phase B: ACN; Flow rate: 20 mL/min; Gradient: 25 B to 50 B in 5.8 min. The fractions contained desired product were combined and concentrated to afford 3-[2-(6-chloro-7-fluoro-1,2-dimethyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (50.1 mg, 21%) as a white solid. MS ESI calculated for C₂₅H₂₇ClFN₇O₃ [M+H]⁺, 528.18, found 528.20; ¹H NMR (400 MHz, CDCl₃) δ 7.78 (s, 1H), 7.19-6.61 (m, 2H), 6.63-6.29 (m, 2H), 5.80-5.54 (m, 1H), 4.57-4.51 (m, 1H), 4.24-3.83 (m, 6H), 3.57-3.32 (m, 4H), 3.11-2.96 (m, 3H), 2.81-2.58 (m, 4H), 2.41-2.21 (m, 1H).

Example 129: 3-[2-(6-Chloro-1-ethyl-1,3-benzodiazol-5-yl)ethynyl]-1-[(3S,5R)-1-(2-fluoroprop-2-enoyl)-5-(methoxymethyl)pyrrolidin-3-yl]-5-(methylamino)pyrazole-4-carboxamide

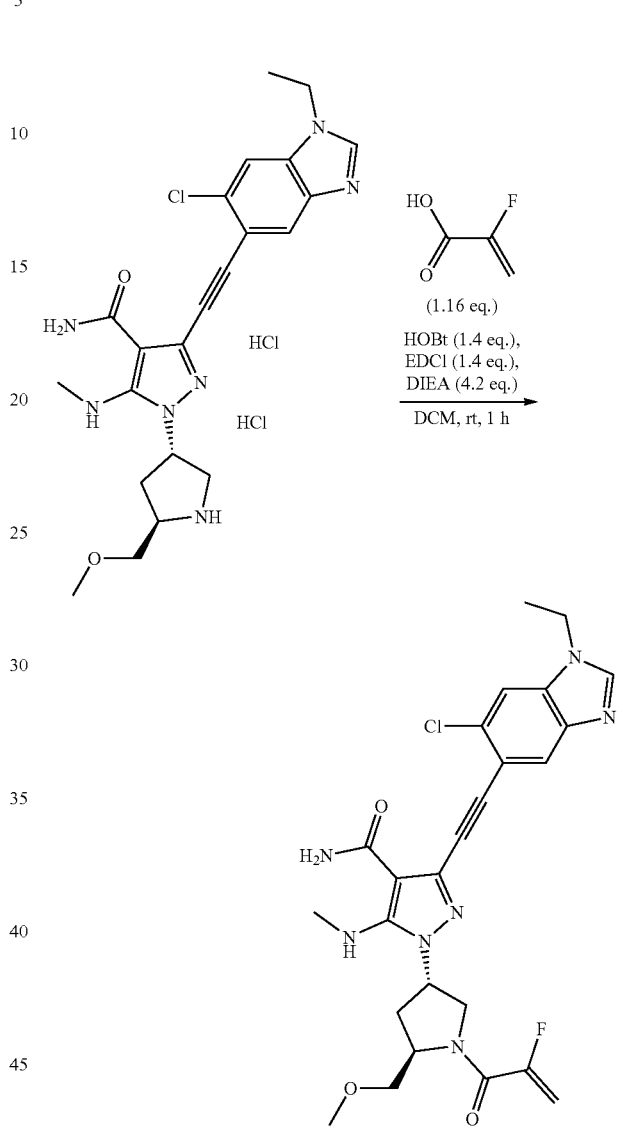

To a stirred mixture of 3-[2-(6-chloro-1-ethyl-1,3-benzodiazol-5-yl)ethynyl]-1-[(3S,5R)-5-(methoxymethyl)pyrrolidin-3-yl]-5-(methylamino)pyrazole-4-carboxamide (90.00 mg, 0.20 mmol), 2-fluoroprop-2-enoic acid (20.62 mg, 0.23 mmol), HOBT (37.34 mg, 0.28 mmol) and EDCI (52.98 mg, 0.28 mmol) in DCM (2.00 mL) was added DIEA (0.11 g, 0.83 mmol) dropwise at 0° C. The reaction mixture was stirred for 1 h at room temperature under argon atmosphere. The resulting mixture was diluted with water (40 mL) and extracted with CH₂Cl₂ (3×30 mL). The combined organic layers were washed with brine (2×20 mL), dried over anhydrous Na₂SO₄ and filtered. The filtrate was concentrated under reduced pressure. The residue was purified by Prep-HPLC with the following conditions: Column: XBridge Prep C18 OBD Column, 19×150 mm 5 μm; Mobile Phase A: Water (10 mmol/L NH₄HCO₃), Mobile Phase B: ACN; Flow rate: 20 mL/min; Gradient: 14 B to 55 B in 6 min; 210/254 nm; RT: 5.8 min. The fractions contained desired product were combined and concentrated to afford 3-[2-(6-chloro-1-ethyl-1,3-benzodiazol-5-yl)ethynyl]-1-[(3S,5R)-1-(2-fluoroprop-2-enoyl)-5-(methoxymethyl)pyrrolidin-3-yl]-5-(methylamino)pyrazole-4-carboxamide (50.1 mg, 47%) as a white solid. MS ESI calculated for $C_{25}H_{27}ClFN_7O_3$ [M+H]$^+$, 528.18, found 528.20; $^1$H NMR (400 MHz, DMSO-d$_6$) δ 8.52 (s, 1H), 8.02 (d, J=5.3 Hz, 2H), 7.49 (s, 1H), 6.86 (s, 1H), 5.54-5.15 (m, 3H), 4.53-4.42 (m, 1H), 4.32-4.29 (m, 2H), 4.00-3.89 (m, 2H), 3.54-3.49 (m, 2H), 3.30 (s, 3H), 2.95 (s, 3H), 2.45-2.41 (m, 1H), 2.34-2.31 (m, 1H), 1.42 (t, J=7.2 Hz, 3H).

Example 130: 3-(2-[6-Fluoro-[1,2,4]triazolo[1,5-a]pyridin-7-yl]ethynyl)-1-[(3S,5R)-5-(methoxymethyl)-1-(prop-2-enoyl)pyrrolidin-3-yl]-5-(methylamino)pyrazole-4-carboxamide

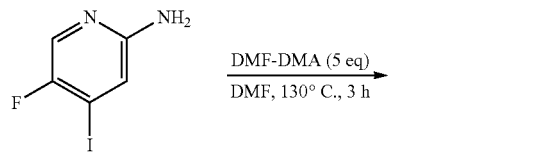

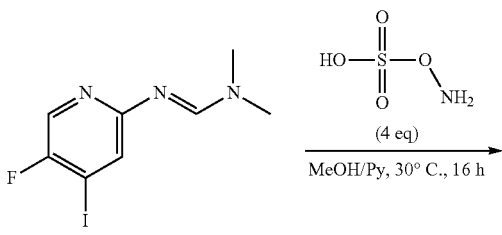

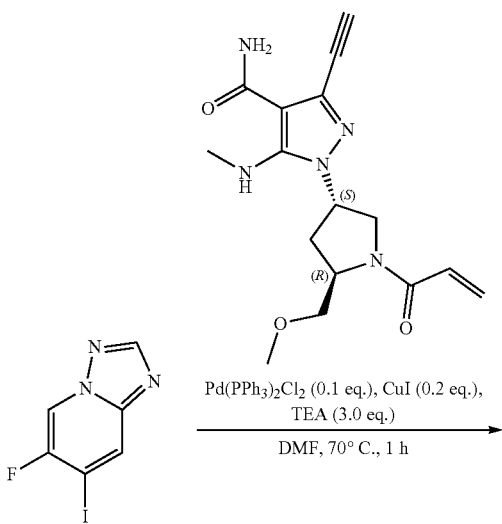

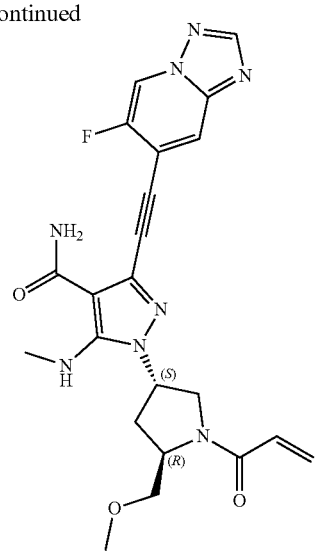

Step 1: (E)-N-(5-Fluoro-4-iodopyridin-2-yl)-N,N-dimethylmethanimidamide

To a stirred solution of 5-fluoro-4-iodopyridin-2-amine (2.4 g, 10.25 mmol) in DMF (24.40 mL) was added DMF-DMA (6.8 mL, 51.08 mmol) at room temperature under nitrogen atmosphere. The reaction mixture was stirred for 3 h at 130° C. The resulting mixture was concentrated under reduced pressure. The residue was purified by silica gel Column chromatography, eluted with PE/EA (2/1). The fractions contained desired product were combined and concentrated to afford (E)-N-(5-fluoro-4-iodopyridin-2-yl)-N,N-dimethylmethanimidamide (2.86 g, 95%) as a light yellow oil. MS ESI calculated for $C_8H_9FIN_3$ [M+H]$^+$, 293.99, found 294.35; $^1$H NMR (300 MHz, CDCl$_3$) δ 8.36 (s, 1H), 7.98 (s, 1H), 7.45 (d, J=4.5 Hz, 1H), 3.12 (d, J=3.8 Hz, 6H).

Step 2: 6-Fluoro-7-iodo-[1,2,4]triazolo[1,5-a]pyridine

To a stirred solution of (E)-N-(5-fluoro-4-iodopyridin-2-yl)-N,N-dimethylmethanimidamide (2.86 g, 9.76 mmol) and aminooxysulfonic acid (4.41 g, 39.03 mmol) in MeOH (28.60 mL) was added Pyridine (3.93 mL, 49.65 mmol) dropwise at 0° C. under nitrogen atmosphere. The reaction mixture was stirred for 16 h at room temperature. The resulting mixture was concentrated under reduced pressure. The residue was purified by Prep-TLC (CH$_2$Cl$_2$/MeOH 10/1). The fractions contained desired product were combined and concentrated to afford 6-fluoro-7-iodo-[1,2,4]triazolo[1,5-a]pyridine (0.30 g, 11%) as a light yellow solid. MS ESI calculated for $C_6H_3FIN_3$ [M+H]$^+$, 263.94, found 264.00; $^1$H NMR (300 MHz, CDCl$_3$) δ 8.56 (d, J=2.4 Hz, 1H), 8.38 (s, 1H), 8.30 (d, J=5.7 Hz, 1H).

Step 3: 3-(2-[6-Fluoro-[1,2,4]triazolo[1,5-a]pyridin-7-yl]ethynyl)-1-[(3S,5R)-5-(methoxymethyl)-1-(prop-2-enoyl)pyrrolidin-3-yl]-5-(methylamino)pyrazole-4-carboxamide To a stirred solution of 1-((3S,5R)-1-acryloyl-5-(methoxymethyl)pyrrolidin-3-yl)-3-ethynyl-5-(methylamino)-1H-pyrazole-4-carboxamide (0.15 g, 0.45 mmol), 6-fluoro-7-iodo-[1,2,4]triazolo[1,5-a]pyridine (0.12 g, 0.45 mmol), Pd(PPh$_3$)$_2$Cl$_2$ (31.59 mg, 0.05 mmol) and CuI (17.14 mg, 0.09 mmol) in DMF (2.00 mL) was added TEA (0.14 g, 1.35 mmol) at room temperature. The reaction mixture was degassed with argon for three times and stirred for 1 h at 70° C. The resulting mixture was cooled down and concentrated under reduced pressure. The residue was purified by silica gel Column chromatography, eluted with CH$_2$Cl$_2$/MeOH (10/1). The fractions contained desired product were combined and concentrated to afford crude. The crude product was purified by reverse phase flash with the following conditions Column: C18 spherical Column, 20-35 μm; Mobile Phase A: Water (10 mmol/L NH$_4$HCO$_3$), Mobile Phase B: ACN; Flow rate: 40 mL/min; Gradient: 5 B to 50 B in 20 min. The fractions contained desired product were combined and concentrated to afford 3-(2-[6-fluoro-[1,2,4]triazolo[1,5-a]pyridin-7-yl]ethynyl)-1-[(3S,5R)-5-(methoxymethyl)-1-(prop-2-enoyl)pyrrolidin-3-yl]-5-(methylamino)pyrazole-4-carboxamide (39.6 mg, 44%) as an off-white solid. MS ESI calculated for C$_{22}$H$_{23}$FN$_8$O$_3$ [M+H]$^+$, 467.19, found 467.15; $^1$H NMR (400 MHz, CDCl$_3$) δ 8.66 (s, 1H), 8.45 (s, 1H), 8.02 (s, 1H), 6.79-6.70 (m, 2H), 6.55-6.38 (m, 2H), 5.80-5.69 (m, 1H), 5.60-5.44 (m, 2H), 4.63-4.55 (m, 1H), 4.18-3.87 (m, 3H), 3.55-3.34 (m, 4H), 3.12-3.03 (m, 3H), 2.76-2.63 (m, 1H), 2.39-2.29 (m, 1H).

Example 131: 3-[2-(6-Fluoro-1,3-benzothiazol-5-yl)ethynyl]-1-[(3S,5R)-5-(methoxymethyl)-1-(prop-2-enoyl)pyrrolidin-3-yl]-5-(methylamino)pyrazole-4-carboxamide

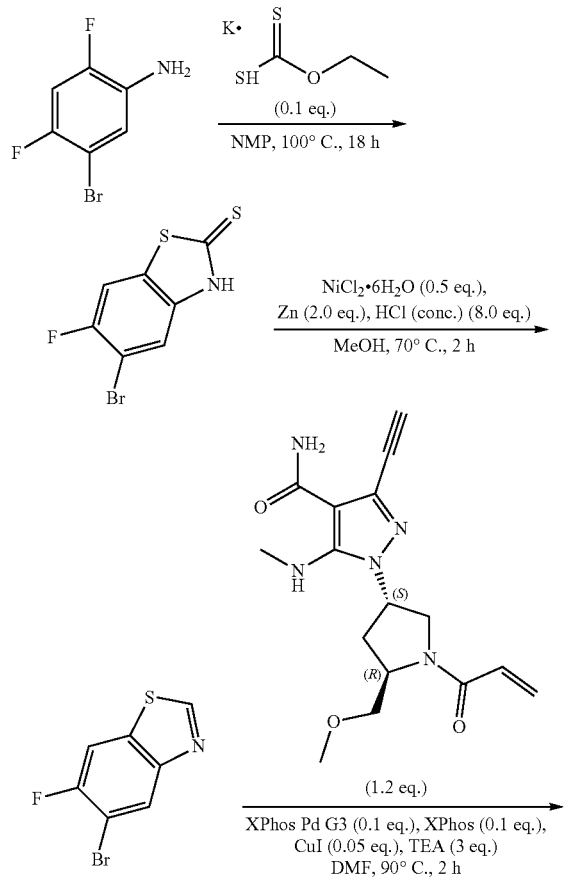

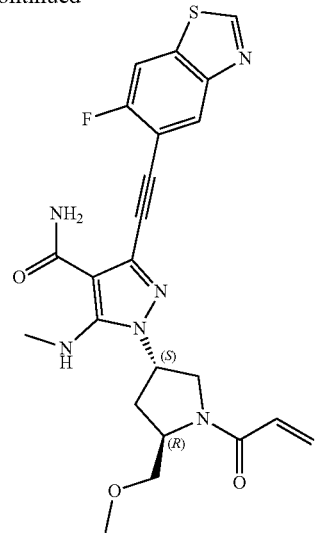

Step 1:
5-Bromo-6-fluoro-3H-1,3-benzothiazole-2-thione

To a solution of 5-bromo-2,4-difluoroaniline (0.50 g, 2.404 mmol) in NMP (5.00 mL) was added ethoxy(potassiosulfanyl)methanethione (0.46 g, 2.885 mmol) at room temperature. The reaction mixture was stirred for 18 h at 100° C. The resulting mixture was diluted with EtOAc (10.00 mL). The residue was washed with water (3×10 mL). The combined organic layers were washed with brine (2×10 mL), dried over anhydrous Na$_2$SO$_4$ and filtered. The filtrate was concentrated under reduced pressure to afford 5-bromo-6-fluoro-3H-1,3-benzothiazole-2-thione (0.5 g, 78%) as a pink solid. MS ESI calculated for C$_7$H$_3$BrFNS$_2$ [M–H]$^-$, 261.89, 263.89; found 262.00, 264.00; $^1$H-NMR (300 MHz, CDCl$_3$) δ 11.41 (s, 1H), 7.25 (d, J=7.5 Hz, 2H).

Step 2: 5-Bromo-6-fluoro-1,3-benzothiazole

To a solution of 5-bromo-6-fluoro-3H-1,3-benzothiazole-2-thione (2.60 g, 9.84 mmol), Zn (3.22 g, 49.22 mmol) and NiCl$_2$·6H$_2$O (2.46 g, 10.34 mmol) in MeOH (26.00 mL) were added con. HCl (20.00 mL) dropwise at room temperature under argon atmosphere. The reaction mixture was stirred for 2 h at 70° C. under argon atmosphere. The resulting mixture was filtered, the filter cake was washed with EtOAc (200.00 mL). The filtrate was concentrated under reduced pressure. The residue was diluted with water (200.00 mL) and basified to pH 9 with saturated NaHCO$_3$ (aq.). The resulting mixture was extracted with EtOAc (3×200 mL). The combined organic layers were washed with brine (300 mL), dried over anhydrous Na$_2$SO$_4$ and filtered. The filtrate was concentrated under reduced pressure. The residue was purified by silica gel column chromatography, eluted with EA in PE (0-50%). The fractions contained desired product were combined and concentrated to afford 5-bromo-6-fluoro-1,3-benzothiazole (0.41 g, 17%) as a yellow solid. $^1$H NMR (300 MHz, CDCl$_3$) δ 8.90 (s, 1H), 8.27 (d, J=6.1 Hz, 1H), 7.64 (d, J=7.7 Hz, 1H).

Step 3: 3-[2-(6-Fluoro-1,3-benzothiazol-5-yl)ethynyl]-1-[(3S,5R)-5-(methoxymethyl)-1-(prop-2-enoyl)pyrrolidin-3-yl]-5-(methylamino)pyrazole-4-carboxamide To a solution of 5-bromo-6-fluoro-1,3-benzothiazole (0.15 g, 0.64 mmol,) XPhos Pd G3 (54.71 mg, 0.07 mmol), X-Phos (30.81 mg, 0.06 mmol), CuI (6.15 mg, 0.03 mmol) and 3-ethynyl-1-[(3S,5R)-5-(methoxymethyl)-1-(prop-2-enoyl)pyrrolidin-3-yl]-5-(methylamino)pyrazole-4-carboxamide (0.26 g, 0.77 mmol) in DMF (4.50 mL) was added TEA (0.20 g, 1.94 mmol) dropwise at room temperature. The reaction mixture was degassed with argon for three times and stirred for 2 h at 90° C. The resulting mixture was concentrated under reduced pressure. The residue was purified by silica gel column chromatography, eluted with MeOH in DCM (0-10%) to afford the crude product. The crude product was purified by reverse phase flash with the following conditions: Column: Spherical C18, 20-40 μm, 40 g; Mobile Phase A: Water (10 mmol/mL NH$_4$HCO$_3$); Mobile Phase B: ACN; Flow rate: 60 mL/min; Gradient: 5%-35% within 30 min; Detector: UV 254/220 nm; RT: 48 min. The fractions contained desired product were combined and concentrated to afford 3-[2-(6-fluoro-1,3-benzothiazol-5-yl)ethynyl]-1-[(3S,5R)-5-(methoxymethyl)-1-(prop-2-enoyl)pyrrolidin-3-yl]-5-(methylamino)pyrazole-4-carboxamide (95.2 mg, 30%) as a white solid. MS ESI calculated for C$_{23}$H$_{23}$FN$_6$O$_3$S [M+H]$^+$, 483.15; found 483.10; $^1$H-NMR (300 MHz, CDCl$_3$) δ 9.05 (s, 1H), 8.34 (d, J=6.1 Hz, 1H), 7.74 (d, J=8.6 Hz, 1H), 7.04 (s, 1H), 6.59-6.36 (m, 2H), 5.75-5.71 (m, 1H), 5.63-5.24 (m, 2H), 4.69-4.37 (m, 1H), 4.19-3.91 (m, 3H), 3.53-3.44 (m, 1H), 3.39 (d, J=3.6 Hz, 3H), 3.06 (d, J=11.2 Hz, 3H), 2.77-2.62 (m, 1H), 2.36-2.30 (m, 1H).

Example 132: 1-((3S,5R)-1-Acryloyl-5-(methoxymethyl)pyrrolidin-3-yl)-3-((6-fluoroimidazo[1,2-a]pyridin-7-yl)ethynyl)-5-(methylamino)-1H-pyrazole-4-carboxamide

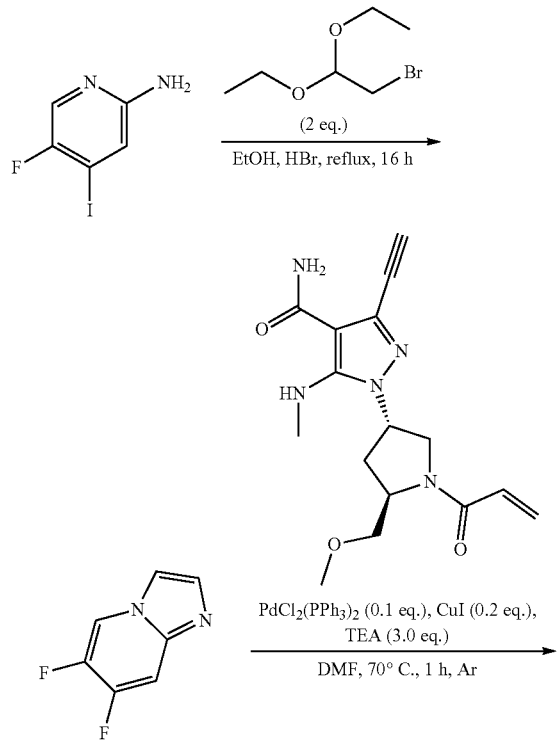

Step 1: 6-Fluoro-7-iodoimidazo[1,2-a]pyridine

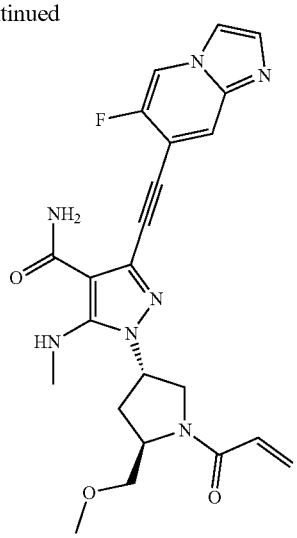

To a stirred mixture of 5-fluoro-4-iodopyridin-2-amine (0.10 g, 0.42 mmol) and 2-bromo-1,1-diethoxyethane (0.17 g, 0.84 mmol) in EtOH (0.50 mL) was added HBr (0.05 mL) dropwise at 0° C. The resulting mixture was stirred for 16 h at 80° C. The resulting mixture was cooled down to room temperature. The resulting mixture was quenched with NaHCO$_3$ (aq.) and extracted with EtOAc (3×60 mL). The combined organic layers were washed with brine (40 mL), dried over anhydrous Na$_2$SO$_4$ and filtered. The filtrate was concentrated under reduced pressure. The residue was purified by silica gel Column chromatography, eluted with PE/(EtOAc:EtOH (3:1)) (1/3). The fractions contained desired product were combined and concentrated to afford 6-fluoro-7-iodoimidazo[1,2-a]pyridine (1.78 g, 81%) as a brown solid. ESI calculated for C$_7$H$_4$FIN$_2$ [M+H]$^+$, 262.94, found 262.90; $^1$H NMR (400 MHz, CDCl$_3$) δ 8.12 (dd, J=10.0, 4.4 Hz, 2H), 7.69 (s, 1H), 7.62 (s, 1H).

Step 2: 1-((3S,5R)-1-Acryloyl-5-(methoxymethyl)pyrrolidin-3-yl)-3-((6-fluoroimidazo[1,2-a]pyridin-7-yl)ethynyl)-5-(methylamino)-1H-pyrazole-4-carboxamide To a stirred mixture of 6-fluoro-7-iodoimidazo[1,2-a]pyridine (0.12 g, 0.45 mmol), 3-ethynyl-1-[(3S,5R)-5-(methoxymethyl)-1-(prop-2-enoyl)pyrrolidin-3-yl]-5-(methylamino)pyrazole-4-carboxamide (0.15 g, 0.45 mmol), CuI (17.24 mg, 0.09 mmol) and Pd(PPh$_3$)$_2$Cl$_2$ (31.77 mg, 0.05 mmol) in DMF (1.5 mL) was added TEA (0.14 g, 1.36 mmol) dropwise at room temperature. The reaction mixture was degassed with argon for three times and stirred for 1 h at 70° C. The resulting mixture was concentrated under reduced pressure. The residue was purified by silica gel Column chromatography, eluted with CH$_2$Cl$_2$/MeOH (10/1) to afford the crude product. The crude product was purified by Prep-HPLC with the following conditions: Column: SunFire Prep C18 OBD Column, 19×150 mm 5 μm 10 nm; Mobile Phase A: Water (0.1% FA), Mobile Phase B: ACN; Flow rate: 20 mL/min; Gradient: 25 B to 50 B in 6 min; 210/254 nm; RT: 5.58 min. The fractions contained desired product were combined and concentrated to afford 1-((3S,5R)-1-acryloyl-5-(methoxymethyl)pyrrolidin-3-yl)-

3-((6-fluoroimidazo[1,2-a]pyridin-7-yl)ethynyl)-5-(methylamino)-1H-pyrazole-4-carboxamide (0.15 g, 73%) as a light yellow solid. MS ESI calculated for $C_{23}H_{24}FN_7O_3$ [M+H]$^+$, 466.19, found 466.30; $^1$H NMR (300 MHz, CDCl$_3$) δ 8.29-8.15 (m, 1H), 7.99 (d, J=6.3 Hz, 1H), 7.83 (s, 1H), 7.73 (d, J=6.6 Hz, 1H), 6.89-6.70 (m, 2H), 6.55-6.36 (m, 2H), 5.73 (dd, J=8.0, 4.3 Hz, 1H), 5.61-5.22 (m, 2H), 4.65-4.35 (m, 1H), 4.20-3.81 (m, 3H), 3.60-3.30 (m, 4H), 3.06 (d, J=10.6 Hz, 3H), 2.61-2.78 (m, 1H), 2.35-2.30 (m, 1H).

Example 133: 3-[2-(6-Chloro-4-fluoro-1,2-dimethyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide

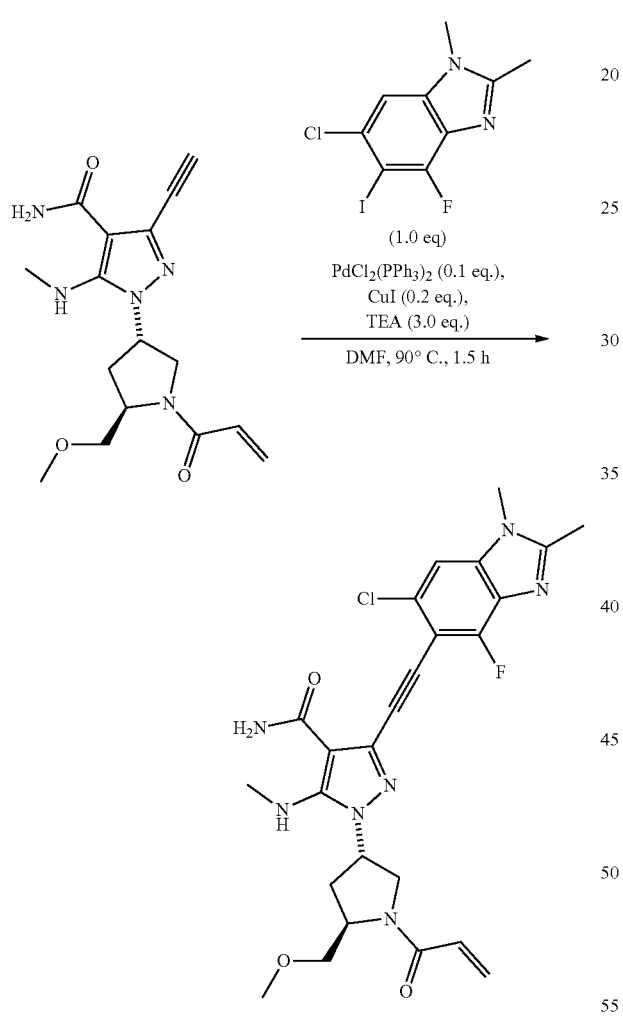

To a stirred mixture of 3-ethynyl-1-[(3S,5R)-5-(methoxymethyl)-1-(prop-2-enoyl)pyrrolidin-3-yl]-5-(methylamino)pyrazole-4-carboxamide (0.20 g, 0.60 mmol), CuI (22.99 mg, 0.12 mmol), Pd(PPh$_3$)$_2$Cl$_2$ (42.36 mg, 0.06 mmol) and 6-chloro-4-fluoro-5-iodo-1,2-dimethyl-1,3-benzodiazole (0.22 g, 0.66 mmol) in DMF (2 mL) was added TEA (0.25 mL, 1.81 mmol) dropwise at room temperature. The reaction mixture was degassed with argon for three times and stirred for 1.5 h at 90° C. The resulting mixture was diluted with water (150 mL) and extracted with EtOAc (3×100 mL). The combined organic layers were washed with brine (3×50 mL), dried over anhydrous Na$_2$SO$_4$ and filtered. The filtrate was concentrated under reduced pressure. The residue was purified by silica gel column chromatography, eluted with CH$_2$Cl$_2$/MeOH (10/1) to afford the crude product. The crude product was purified by Prep-HPLC with the following conditions: Column: XBridge Prep C18 OBD Column, 19×150 mm 5 μm; Mobile Phase A: Water (10 mmol/L NH$_4$HCO$_3$), Mobile Phase B: ACN; Flow rate: 20 mL/min; Gradient: 20 B to 50 B in 6 min; 210/254 nm; RT: 5.58 min. The fractions contained desired product were combined and concentrated to afford 3-[2-(6-chloro-4-fluoro-1,2-dimethyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (60.0 mg, 18%) as a white solid. MS ESI calculated for $C_{25}H_{27}ClFN_7O_3$ [M+H]$^+$, 528.18; found 528.30; $^1$H NMR (300 MHz, DMSO-d$_6$) δ 7.80 (s, 1H), 7.58 (s, 1H), 6.95-6.49 (m, 3H), 6.18 (d, J=16.6 Hz, 1H), 5.70 (d, J=10.2 Hz, 1H), 5.50-5.00 (m, 1H), 4.47-4.35 (m, 1H), 4.13-3.98 (m, 1H), 3.97-3.82 (m, 1H), 3.77-3.74 (m, 3H), 3.62 (m, 1H), 3.47-3.42 (m, 1H), 3.38-3.27 (m, 3H), 2.98-2.95 (m, 3H), 2.57 (d, J=1.2 Hz, 3H), 2.53-2.49 (m, 1H), 2.33-2.29 (m, 1H).

Example 134: 3-[2-(6-Chloro-1,3-benzothiazol-5-yl)ethynyl]-1-[(3S,5R)-5-(methoxymethyl)-1-(prop-2-enoyl)pyrrolidin-3-yl]-5-(methylamino)pyrazole-4-carboxamide

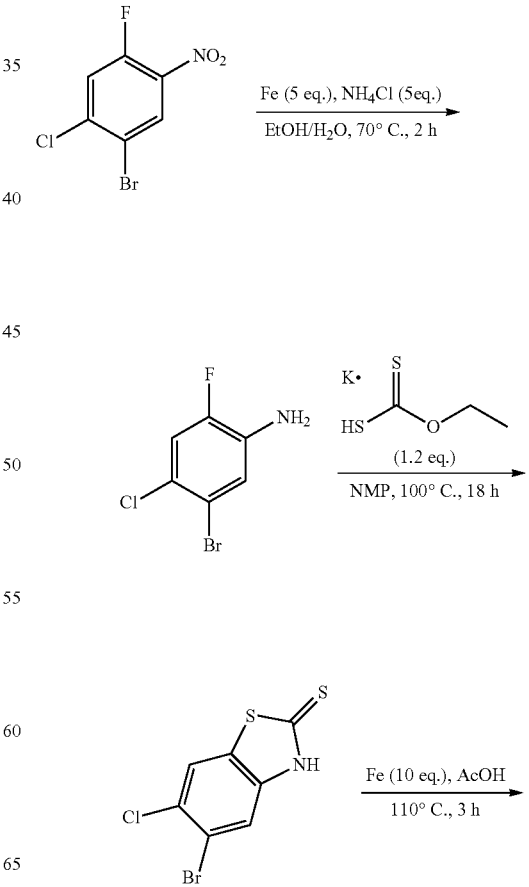

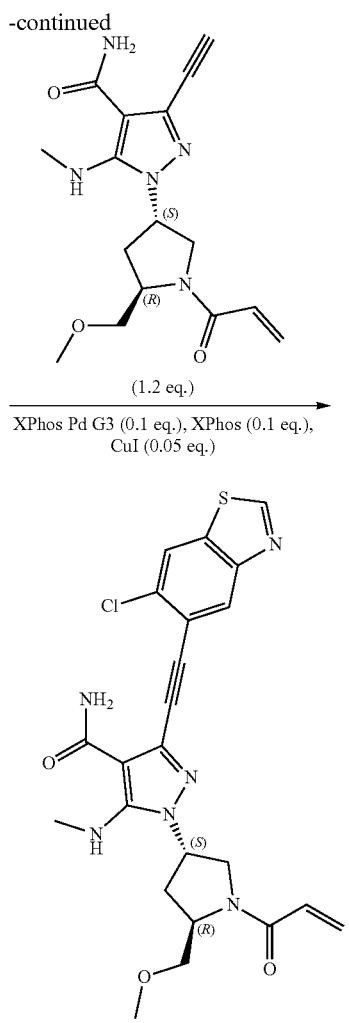

Step 1: 5-Bromo-4-chloro-2-fluoroaniline

To a solution of 1-bromo-2-chloro-4-fluoro-5-nitrobenzene (1.00 g, 3.93 mmol) in EtOH (10.00 mL) and H$_2$O (2 mL) were added Fe (1.10 g, 19.65 mmol) and NH$_4$Cl (1.05 g, 19.65 mmol) at room temperature. The reaction mixture was stirred for 2 h at 70° C. The resulting mixture was filtered, the filter cake was washed with EA (3×150 mL). The filtrate was concentrated under reduced pressure. The residue was diluted with water (200 mL). The resulting mixture was extracted with EtOAc (3×150 mL). The combined organic layers were washed with brine (300 mL), dried over anhydrous Na$_2$SO$_4$ and filtered. The filtrate was concentrated under reduced pressure to afford 5-bromo-4-chloro-2-fluoroaniline (0.7 g, 79%) as a light yellow solid which was used in the next step directly without further purification. MS ESI calculated for C$_6$H$_4$BrClFN [M+H]$^+$, 223.92, 225.92, found 223.95, 225.95; $^1$H-NMR (400 MHz, CDCl$_3$) δ 7.12 (d, J=10.5 Hz, 1H), 7.04 (d, J=8.7 Hz, 1H).

Step 2: 5-Bromo-6-chloro-3H-1,3-benzothiazole-2-thione

To a solution of 5-bromo-4-chloro-2-fluoroaniline (0.7 g, 3.12 mmol) in NMP (10.00 mL) was added ethoxy(potassiosulfanyl)methanethione (0.60 g, 3.74 mmol) at room temperature. The reaction mixture was stirred for 18 h at 100° C. The resulting mixture was diluted with EtOAc (150 mL) and washed with water (3×100 mL). The combined organic layers were washed with brine (200 mL), dried over anhydrous Na$_2$SO$_4$ and filtered. The filtrate was concentrated under reduced pressure. The residue was purified by silica gel column chromatography, eluted with EA in PE (0-100%). The fractions contained desired product were combined and concentrated to afford 5-bromo-6-chloro-3H-1,3-benzothiazole-2-thione (0.8 g, 91%) as an off-white solid. MS ESI calculated for C$_7$H$_3$BrClNS$_2$ [M−H]$^-$, 277.86, 279.86, found 277.95, 279.95; $^1$H NMR (400 MHz, CDCl$_3$) δ 17.81 (s, 1H), 8.05 (s, 1H), 7.54 (s, 1H).

Step 3: 5-Bromo-6-chloro-1,3-benzothiazole

To a solution of 5-bromo-6-chloro-3H-1,3-benzothiazole-2-thione (0.5 g, 1.78 mmol) in AcOH (20.00 mL) was added Fe (1.00 g, 17.82 mmol) at room temperature. The reaction mixture was stirred for 3 h at 110° C. The resulting mixture was filtered; the filter cake was washed with EA (150.00 mL). The filtrate was concentrated under reduced pressure. The residue was basified to pH 9 with saturated NaHCO$_3$ (aq.). The resulting mixture was extracted with EtOAc (3×150 mL). The combined organic layers were washed with brine (300 mL), dried over anhydrous Na$_2$SO$_4$ and filtered. The filtrate was concentrated under reduced pressure. The residue was purified by silica gel column chromatography, eluted with EA in PE (0-80%). The fractions contained desired product were combined and concentrated to afford 5-bromo-6-chloro-1,3-benzothiazole (0.28 g, 64%) as a white solid. $^1$H NMR (400 MHz, CDCl$_3$) δ 9.02 (s, 1H), 8.43 (s, 1H), 8.09 (s, 1H).

Step 4: 3-[2-(6-Chloro-1,3-benzothiazol-5-yl)ethynyl]-1-[(3S,5R)-5-(methoxymethyl)-1-(prop-2-enoyl)pyrrolidin-3-yl]-5-(methylamino)pyrazole-4-carboxamide To a solution of 5-bromo-6-chloro-1,3-benzothiazole (0.15 g, 0.60 mmol) and 3-ethynyl-1-[(3S,5R)-5-(methoxymethyl)-1-(prop-2-enoyl)pyrrolidin-3-yl]-5-(methylamino)pyrazole-4-carboxamide (0.24 g, 0.73 mmol) in DMF (4.5 mL) were added X-Phos (28.77 mg, 0.06 mmol), XPhos Pd G3 (51.09 mg, 0.06 mmol), CuI (5.75 mg, 0.03 mmol) and TEA (0.18 g, 1.81 mmol) dropwise at room temperature. The reaction mixture was degassed with argon for three times and stirred for 2 h at 90° C. The resulting mixture was concentrated under reduced pressure. The residue was purified by silica gel column chromatography, eluted with MeOH in DCM (0-5%) to afford the crude product. The crude product was purified by Prep-HPLC with the following conditions: Column: Spherical C18, 20-40 μm, 40 g Mobile Phase A: Water (10 mmol/mL NH$_4$HCO$_3$), Mobile Phase B: ACN; Flow rate: 50 mL/min; Gradient: 5%-34% within 30 min; Detector: UV 254/220 nm; RT: 50 min. The fractions contained desired product were combined and concentrated to afford 3-[2-(6-chloro-1,3-benzothiazol-5-yl)ethynyl]-1-[(3S,5R)-5-(methoxymethyl)-1-(prop-2-enoyl)pyrrolidin-3-yl]-5-(methylamino)pyrazole-4-carboxamide (72.30 mg, 23%) as a white solid. MS ESI calculated for C$_{23}$H$_{23}$ClN$_6$O$_3$S [M+H]$^+$, 499.12, 501.12, found 499.10, 501.10; $^1$H-NMR (400 MHz, CDCl$_3$) δ 9.06 (d, J=1.6 Hz, 1H), 8.41 (d, J=5.5 Hz, 1H), 8.06 (d, J=2.3 Hz, 1H), 7.12 (s, 1H), 6.88-6.70 (m, 1H), 6.54-6.32 (m, 2H), 5.74-5.50 (m, 1H), 5.59-5.24 (m, 2H), 4.59-4.57 (m, 1H), 4.15-3.99 (m, 2H), 3.93-3.90 (m, 1H), 3.56-3.44 (m, 1H), 3.39-3.36 (m, 3H), 3.07-3.02 (m, 3H), 2.74-2.68 (m, 1H), 2.35-2.30 (m, 1H).

Example 135: 3-[2-(1-Cyclopropyl-6-fluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide

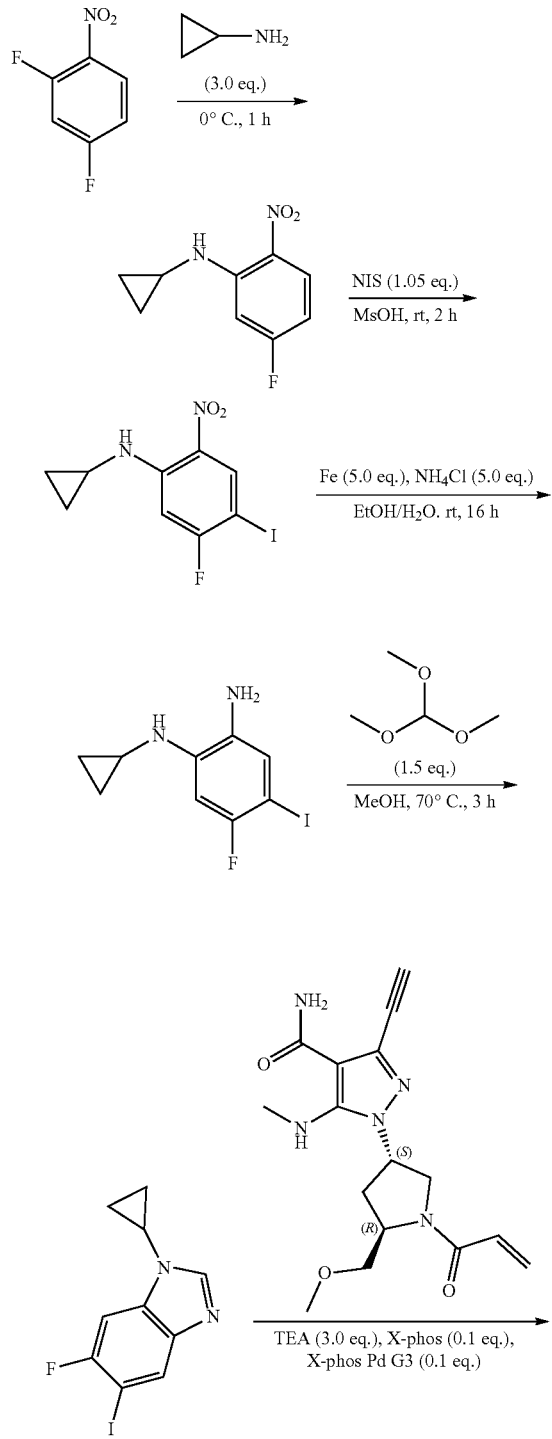

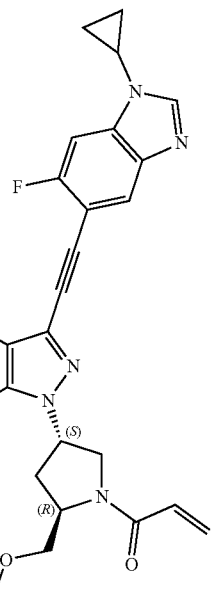

Step 1: N-cyclopropyl-5-fluoro-2-nitroaniline

To a stirred solution of 2,4-difluoro-1-nitrobenzene (20 g, 125.71 mmol) in EtOH (200.00 mL) was added aminocyclopropane (21.53 g, 377.14 mmol) dropwise at 0° C. The reaction mixture was stirred for 1 h at 0° C. The resulting mixture was diluted with H2O (400 mL) and filtered. The filter cake was washed with H2O (3×200 mL). The filter cake was dried under reduced pressure to afford N-cyclopropyl-5-fluoro-2-nitroaniline (25.5 g, crude) as a yellow solid which was used in the next step directly without further purification. MS ESI calculated for C9H9FN2O2 [M+H]+, 197.06, found 196.95.

Step 2: N-cyclopropyl-5-fluoro-4-iodo-2-nitroaniline

To a stirred solution of N-cyclopropyl-5-fluoro-2-nitroaniline (25.5 g, 129.98 mmol) in methanesulfonic acid (100 mL) was added NIS (30.71 g, 136.48 mmol) at 0° C. The reaction mixture was stirred for 2 h at room temperature. The resulting mixture was diluted with water (500 mL) and extracted with EtOAc (3×300 mL). The combined organic layers was washed with brine (500 mL), dried over anhydrous Na2SO4 and filtered. The filtrate was concentrated under reduced pressure. The residue was purified by silica gel column chromatography, eluted with EA in PE (0-10%). The fractions contained desired product were combined and concentrated to afford N-cyclopropyl-5-fluoro-4-iodo-2-nitroaniline (27 g, 64%) as a black solid. MS ESI calculated for C9H8FIN2O2 [M+H]+, 322.96, found, 322.95.

Step 3: N1-cyclopropyl-5-fluoro-4-iodobenzene-1,2-diamine

To a stirred mixture of N-cyclopropyl-5-fluoro-4-iodo-2-nitroaniline (27.0 g, 83.83 mmol) and NH4Cl (22.42 g, 419.16 mmol) in EtOH (150 mL) and H2O (150 mL) was added Fe (23.41 g, 419.16 mmol) at room temperature. The reaction mixture was stirred for 16 h at room temperature. The resulting mixture was filtered. The filter cake was washed with MeOH (3×100 mL). The filtrate was concentrated under reduced pressure to afford N1-cyclopropyl-5-fluoro-4-iodobenzene-1,2-diamine (23 g, crude) as a light brown solid which was used in the next step directly without further purification. MS ESI calculated for C9H10FIN2 [M+H]+, 292.99, found 292.95.

Step 4:
1-Cyclopropyl-6-fluoro-5-iodo-1,3-benzodiazole

To a stirred solution of N1-cyclopropyl-5-fluoro-4-iodobenzene-1,2-diamine (23 g, 78.74 mmol) in MeOH (230 mL) was added trimethyl orthoformate (25.07 mL, 236.22 mmol) at room temperature under argon atmosphere. The reaction mixture was stirred for 3 h at 70° C. The resulting mixture was concentrated under reduced pressure. The residue was purified by silica gel column chromatography, eluted with EA in PE (50%-100%). The fractions contained desired product were combined and concentrated to afford 1-cyclopropyl-6-fluoro-5-iodo-1,3-benzodiazole (8 g, 34%) as a yellow solid. MS ESI calculated for C10H8FIN2 [M+H]+, 302.97, found 302.85. 1H NMR (400 MHz, CDCl3) δ 8.15 (d, J=5.6 Hz, 1H), 7.92 (s, 1H), 7.32 (d, J=7.6 Hz, 1H), 3.36-3.31 (m, 1H), 1.26-1.13 (m, 2H), 1.15-1.01 (m, 2H).

Step 5: 3-[2-(1-Cyclopropyl-6-fluoro-1,3-benzodiazol-5-yl)ethynyl]-1-[(3S,5R)-5-(methoxymethyl)-1-(prop-2-enoyl)pyrrolidin-3-yl]-5-(methylamino) pyrazole-4-carboxamide To a stirred solution of 3-ethynyl-1-[(3S,5R)-5-(methoxymethyl)-1-(prop-2-enoyl)pyrrolidin-3-yl]-5-(methylamino)pyrazole-4-carboxamide (0.77 g, 2.32 mmol) and 1-cyclopropyl-6-fluoro-5-iodo-1,3-benzodiazole (0.70 g, 2.32 mmol) in DMF (20 mL) were added XPhos (0.11 g, 0.23 mmol), X-Phos Pd G3 (0.20 g, 0.23 mmol), CuI (44.13 mg, 0.23 mmol) at room temperature under nitrogen atmosphere. To the above mixture was added TEA (0.10 g, 0.99 mmol) dropwise over 1 min at room temperature. The reaction mixture was degassed with nitrogen for three times and stirred for 1 h at 90° C. The resulting mixture was cooled down to room temperature. The residue was purified by silica gel column chromatography, eluted with CH2Cl2/MeOH (10/1) to afford crude product. The crude product was further purified by reverse flash chromatography with the following conditions: column, C18 silica gel; mobile phase, ACN in water, 10% to 50% gradient in 30 min; detector, UV 254 nm. The fractions contained desired product were combined and concentrated to afford 3-[2-(1-cyclopropyl-6-fluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide (0.63 g, 52%) as an off-white solid. MS ESI calculated for C26H28FN7O3 [M+H]+, 506.23; found 506.20. 1H NMR (300 MHz, DMSO-d6) δ 8.38 (s, 1H), 7.97 (d, J=6.3 Hz, 1H), 7.66 (d, J=9.5 Hz, 1H), 7.50 (s, 1H), 6.92-6.45 (m, 3H), 6.24-6.13 (m, 1H), 5.70 (dd, J=10.2, 2.7 Hz, 1H), 5.30-5.26 (m, 1H), 4.48-4.42 (m, 1H), 4.05-4.01 (m, 1H), 3.91-3.87 (m, 1H), 3.66-3.43 (m, 3H), 3.32 (d, J=3.9 Hz, 3H), 2.98-2.91 (m, 3H), 2.68-2.62 (m, 1H), 2.33-2.28 (m, 1H), 1.13-1.03 (m, 4H).

Example 136: 3-[2-(1-Cyclopropyl-6-fluoro-1,3-benzodiazol-5-yl)ethynyl]-5-(methylamino)-1-[(3S)-1-(prop-2-enoyl)pyrrolidin-3-yl]pyrazole-4-carboxamide

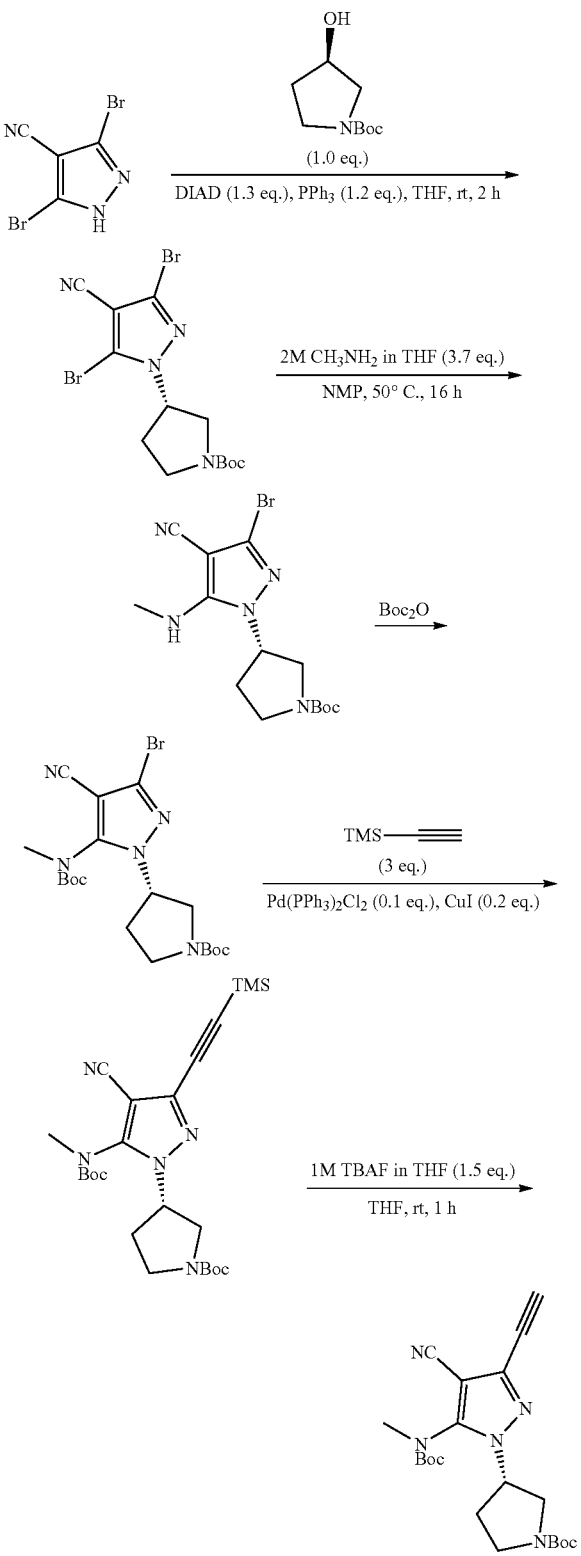

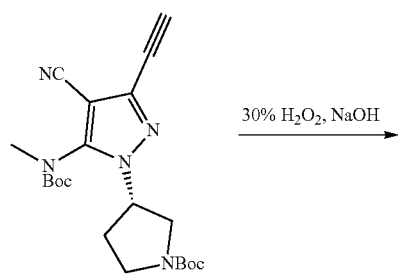

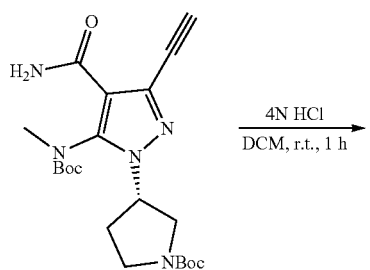

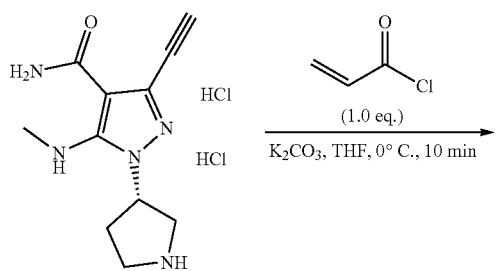

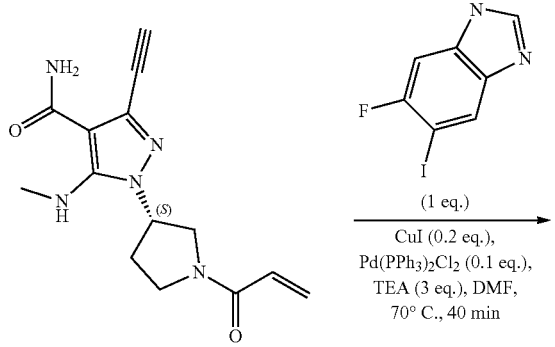

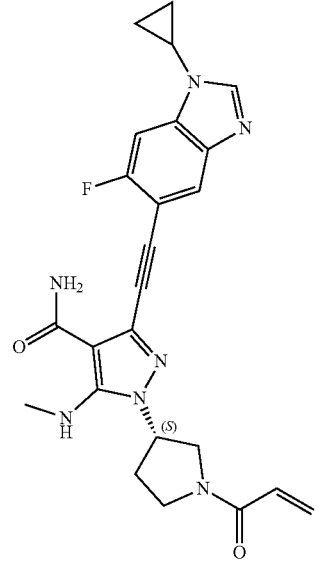

Step 1: Tert-butyl(3S)-3-(3,5-dibromo-4-cyanopyrazol-1-yl)pyrrolidine-1-carboxylate To a stirred solution of 3,5-dibromo-1H-pyrazole-4-carbonitrile (5 g, 19.93 mmol) and tert-butyl(R)-3-hydroxypyrrolidine-1-carboxylate (4.48 g, 23.91 mmol) in THF (100 mL) was added PPh3 (7.84 g, 29.89 mmol) and DIAD (6.04 g, 29.89 mmol) dropwise at 0° C. under argon atmosphere. The reaction mixture was degassed with argon for three times and stirred for 2 h at room temperature. The resulting mixture was concentrated under reduced pressure. The residue was purified by silica gel column chromatography, eluted with PE/EA (2/1). The fractions contained desired product were combined and concentrated to afford tert-butyl (3S)-3-(3,5-dibromo-4-cyanopyrazol-1-yl)pyrrolidine-1-carboxylate (8 g, 95%) as a white solid. MS ESI calculated for C13H16Br2N4O2 [M+H−56]+, 362.96, 364.96, 366.96, found 362.95, 364.95, 366.95; 1H NMR (400 MHz, CDCl3) δ 3.90-3.31 (m, 4H), 2.52-2.26 (m, 2H), 2.09-2.00 (m, 1H), 1.46 (s, 9H).

Step 2: Tert-butyl(3S)-3-[3-bromo-4-cyano-5-(methylamino)pyrazol-1-yl]pyrrolidine-1-carboxylate To a stirred solution of tert-butyl(3S)-3-(3,5-dibromo-4-cyanopyrazol-1-yl)pyrrolidine-1-carboxylate (9 g, 21.42 mmol) in NMP (90 mL) was added CH3NH2 in THF (2.46 g, 79.26 mmol) at room temperature. The reaction mixture was stirred for 16 h at 50° C. The resulting mixture was concentrated under reduced pressure. The residue was purified by reverse flash chromatography with the following conditions: column, C18 silica gel; mobile phase, MeCN in water (NH4HCO3), 30% to 60% gradient in 30 min; detector, UV 254 nm. The fractions contained desired product were combined and concentrated to afford tert-butyl(3S)-3-[3-bromo-4-cyano-5-(methylamino)pyrazol-1-yl]pyrrolidine-1-carboxylate (2.7 g, 34%) as a white solid. MS ESI calculated for C14H20BrN5O2 [M−H]−, 368.08, 370.08, found 368.10, 370.10; 1H NMR (400 MHz, CDCl3) δ 5.11 (s, 1H), 4.53-4.33 (m, 1H), 3.76-3.60 (m, 2H), 3.58 (d, J=9.9 Hz, 1H), 3.51-3.36 (m, 1H), 3.18 (s, 3H), 2.49-2.45 (m, 1H), 2.24-1.96 (m, 1H), 1.46 (s, 9H).

Step 3: Tert-butyl(3S)-3-{3-bromo-5-[(tert-butoxycarbonyl)(methyl)amino]-4-cyanopyrazol-1-yl}pyrrolidine-1-carboxylate To a stirred solution of tert-butyl(3S)-3-[3-bromo-4-cyano-5-(methylamino)pyrazol-1-yl]pyrrolidine-1-carboxylate (6.3 g, 17.01 mmol) and TEA (2.58 g, 25.52 mmol) in DCM (60 mL) were added DMAP (0.21 g, 1.70 mmol) and Boc2O (7.43 g, 34.03 mmol) dropwise at room temperature. The reaction mixture was stirred for 1 h at room temperature. The resulting mixture was concentrated under reduced pressure. The residue was purified by silica gel column chromatography, eluted with PE/EA (2/1). The fractions contained desired product were combined and concentrated to afford tert-butyl(3S)-3-{3-bromo-5-[(tert-butoxycarbonyl)(methyl)amino]-4-cyanopyrazol-1-yl}pyrrolidine-1-carboxylate (7.60 g, 94%) as a white solid. MS ESI calculated for C19H28BrN5O4 [M+H]$^+$, 470.13, 472.13, found 470.25, 472.25; 1H NMR (400 MHz, CDCl3) δ 3.72-3.62 (m, 3H), 3.52-3.26 (m, 2H), 3.21 (s, 3H), 2.47-2.16 (m, 2H), 1.44 (s, 18H).

Step 4: Tert-butyl(3S)-3-{5-[(tert-butoxycarbonyl)(methyl)amino]-4-cyano-3-[2-(trimethylsilyl)ethynyl]pyrazol-1-yl}pyrrolidine-1-carboxylate To a stirred solution of tert-butyl(3S)-3-{3-bromo-5-[(tert-butoxycarbonyl)(methyl)amino]-4-cyanopyrazol-1-yl}pyrrolidine-1-carboxylate (7 g, 14.88 mmol), Pd(PPh3)2Cl2 (1.04 g, 1.48 mmol) and CuI (0.57 g, 2.97 mmol) in DMF (70 mL) were added TEA (6.21 mL, 44.64 mmol) and trimethylsilylacetylene (4.39 g, 44.64 mmol) dropwise at room temperature. The reaction mixture was degassed with argon for three times and stirred for 2 h at 90° C. The resulting mixture was concentrated under reduced pressure. The residue was purified by silica gel column chromatography, eluted with PE/EA (2/1). The fractions contained desired product were combined and concentrated to afford tert-butyl (3S)-3-{5-[(tert-butoxycarbonyl)(methyl)amino]-4-cyano-3-[2-(trimethylsilyl)ethynyl]pyrazol-1-yl}pyrrolidine-1-carboxylate (7 g, 96%) as a brown solid. MS ESI calculated for C24H37N5O4Si [M+H]+, 488.26, found 488.35; 1H NMR (300 MHz, CDCl3) δ 3.68-3.33 (m, 4H), 3.22-2.96 (m, 3H), 2.64-1.90 (m, 3H), 1.44 (s, 18H), 0.27 (s, 9H).

Step 5: Tert-butyl(3S)-3-{5-[(tert-butoxycarbonyl)(methyl)amino]-4-cyano-3-ethynylpyrazol-1-yl}pyrrolidine-1-carboxylate To a stirred solution of tert-butyl(3S)-3-{5-[(tert-butoxycarbonyl)(methyl)amino]-4-cyano-3-[2-(trimethylsilyl)ethynyl]pyrazol-1-yl}pyrrolidine-1-carboxylate (7.00 g, 14.35 mmol) in THF (70 mL) was added TBAF (21.53 mL, 21.53 mmol, 1 M in THF) at room temperature. The reaction mixture was stirred for 1 h at room temperature. The resulting mixture was concentrated under reduced pressure. The residue was purified by silica gel column chromatography, eluted with PE/EA (3/1). The fractions contained desired product were combined and concentrated to afford tert-butyl(3S)-3-{5-[(tert-butoxycarbonyl)(methyl)amino]-4-cyano-3-ethynylpyrazol-1-yl}pyrrolidine-1-carboxylate (4.30 g, 72%) as a white solid. MS ESI calculated for C21H29N5O4 [M+H]+, 416.22, found 416.30; 1H NMR (400 MHz, CDCl3) δ 3.77-3.73 (m, 2H), 3.60-3.50 (m, 1H), 3.51-3.47 (m, 2H), 3.38 (s, 1H), 3.23 (s, 3H), 2.43-2.39 (m, 1H), 2.32-2.28 (m, 1H), 1.46 (s, 18H).

Step 6: Tert-butyl(3S)-3-{5-[(tert-butoxycarbonyl)(methyl)amino]-4-carbamoyl-3-ethynylpyrazol-1-yl}pyrrolidine-1-carboxylate To a stirred solution of tert-butyl(3S)-3-{5-[(tert-butoxycarbonyl)(methyl)amino]-4-cyano-3-ethynylpyrazol-1-yl}pyrrolidine-1-carboxylate (3.70 g, 8.90 mmol) and NaOH (20.48 mL, 10.24 mmol, 0.5 M) in EtOH (30 mL) and DMSO (6 mL) was added H2O2 (0.73 mL, 31.16 mmol, 30%) dropwise at 0° C. The reaction mixture was stirred for 30 min at 0° C. then 40 min at room temperature. The resulting mixture was concentrated under reduced pressure. The residue was purified by silica gel column chromatography, eluted with CH2Cl2/MeOH (10/1). The fractions contained desired product were combined and concentrated to afford tert-butyl(3S)-3-{5-[(tert-butoxycarbonyl)(methyl)amino]-4-carbamoyl-3-ethynylpyrazol-1-yl}pyrrolidine-1-carboxylate (3.30 g, 85%) as a white solid. MS ESI calculated for C21H31N5O5 [M+H]$^+$, 434.24, found 434.50; 1H NMR (300 MHz, CDCl3) δ 6.81 (brs, 1H), 6.16 (brs, 1H), 4.86-4.82 (m, 1H), 3.74-3.69 (m, 2H), 3.51-3.45 (m, 1H), 3.45-3.40 (m, 1H), 3.12 (s, 3H), 2.98-2.93 (m, 2H), 2.27-2.22 (m, 1H), 1.53-1.29 (m, 18H)

Step 7: 3-Ethynyl-5-(methylamino)-1-[(3S)-pyrrolidin-3-yl]pyrazole-4-carboxamide dihydrochloride To a stirred mixture of tert-butyl(3S)-3-{5-[(tert-butoxycarbonyl)(methyl)amino]-4-carbamoyl-3-ethynylpyrazol-1-yl}pyrrolidine-1-carboxylate (3.00 g, 6.92 mmol) in DCM (30 mL) was added HCl (gas) in 1,4-dioxane (15 mL) dropwise at room temperature. The resulting mixture was stirred for 1 h at room temperature. The resulting mixture was filtered. The filter cake was washed with DCM (3×20 mL) and dried to afford 3-ethynyl-5-(methylamino)-1-[(3S)-pyrrolidin-3-yl]pyrazole-4-carboxamide dihydrochloride (2.30 g, crude) as an off-white solid. MS ESI calculated for C11H17Cl2N5O [M+H]+, 306.08, found 306.60.

Step 8: 3-Ethynyl-5-(methylamino)-1-[(3S)-1-(prop-2-enoyl)pyrrolidin-3-yl]pyrazole-4-carboxamide To a stirred solution of 3-ethynyl-5-(methylamino)-1-[(3S)-pyrrolidin-3-yl]pyrazole-4-carboxamide dihydrochloride (2.20 g, 7.18 mmol) and K2CO3 (34.49 mL, 86.22 mmol, 2.5 M) in THF (22 mL) was added acryloyl chloride (0.59 g, 6.46 mmol) dropwise at 0° C. The reaction mixture was stirred for 10 min at 0° C. The resulting mixture was diluted with water (50 mL) and extracted with EtOAc (3×50 mL). The combined organic layers was washed with brine (150 mL), dried over anhydrous Na2SO4, filtered and concentrated under reduced pressure. The residue was purified by silica gel column chromatography, eluted with CH2Cl2/MeOH (10/1). The fractions contained desired product were combined and concentrated to afford 3-ethynyl-5-(methylamino)-1-[(3S)-1-(prop-2-enoyl)pyrrolidin-3-yl]pyrazole-4-carboxamide (1.20 g, 58%) as a white solid. MS ESI calculated for C14H17N5O2 [M+H]$^+$, 288.14, found 288.05; 1H NMR (400 MHz, DMSO-d6) δ 6.69-6.47 (m, 2H), 6.15-5.96 (m, 1H), 5.68-5.42 (m, 1H), 5.24-5.01 (m, 1H), 4.57-4.21 (m, 1H), 3.88-3.65 (m, 3H), 3.62-3.50 (m, 1H), 2.52-2.48 (m, 4H), 2.41-2.20 (m, 2H).

613

Step 9: 3-[2-(1-Cyclopropyl-6-fluoro-1,3-benzodiazol-5-yl)ethynyl]-5-(methylamino)-1-[(3S)-1-(prop-2-enoyl)pyrrolidin-3-yl]pyrazole-4-carboxamide To a stirred mixture of 3-ethynyl-5-(methylamino)-1-[(3S)-1-(prop-2-enoyl)pyrrolidin-3-yl]pyrazole-4-carboxamide (0.13 g, 0.45 mmol), 1-cyclopropyl-6-fluoro-5-iodo-1,3-benzodiazole (0.13 g, 0.45 mmol), Pd(PPh3)2Cl2 (31.76 mg, 0.04 mmol) and CuI (17.23 mg, 0.09 mmol) in DMF (1.5 mL) was added TEA (0.13 g, 1.35 mmol) dropwise at room temperature under argon atmosphere. The reaction mixture was degassed with argon for three times and stirred for 40 min at 70° C. The resulting mixture was concentrated under reduced pressure. The residue was purified by silica gel column chromatography, eluted with CH2Cl2/MeOH (10/1) to afford the crude product which was purified by Prep-HPLC with the following conditions: Column: XBridge Prep C18 OBD Column, 19×150 mm 5 m; Mobile Phase A: water (10 mmol/L NH4HCO3), Mobile Phase B: ACN; Flow rate: 20 mL/min; Gradient: 20 B to 50 B in 6 min; 210/254 nm; RT: 5.58 min; The fractions contained desired product were combined and concentrated to afford 3-[2-(1-cyclopropyl-6-fluoro-1,3-benzodiazol-5-yl)ethynyl]-5-(methylamino)-1-[(3S)-1-(prop-2-enoyl)pyrrolidin-3-yl]pyrazole-4-carboxamide (0.10 g, 50%) as a white solid. MS ESI calculated for C24H24FN7O2 [M+H]+, 462.20, found 462.15; 1H NMR (300 MHz, DMSO-d6) δ 8.37 (s, 1H), 7.98-7.75 (m, 1H), 7.65-7.51 (m, 1H), 7.49 (s, 1H), 6.92-6.51 (m, 3H), 6.25-6.11 (m, 1H), 5.70-5.42 (m, 1H), 5.19-4.96 (m, 1H), 4.14-3.44 (m, 5H), 2.97-2.54 (m, 3H), 2.36-1.96 (m, 2H), 1.18-1.00 (m, 4H).

Example 137: 1-[(3S,5R)-1-(but-2-ynoyl)-5-(methoxymethyl)pyrrolidin-3-yl]-3-[2-(1-ethyl-4,6-difluoro-1,3-benzodiazol-5-yl)ethynyl]-5-(methylamino)pyrazole-4-carboxamide

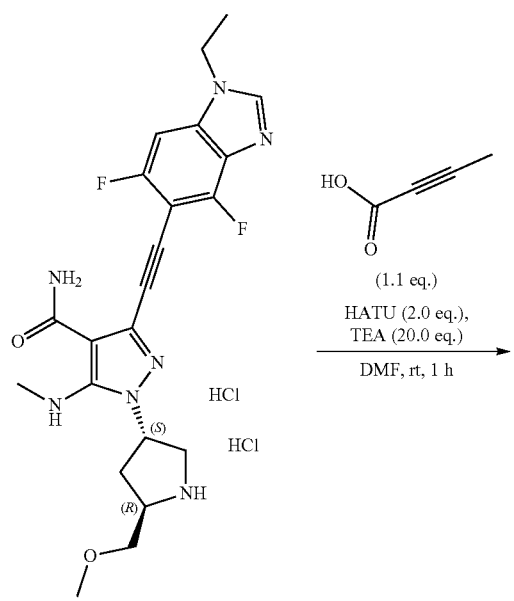

614

-continued

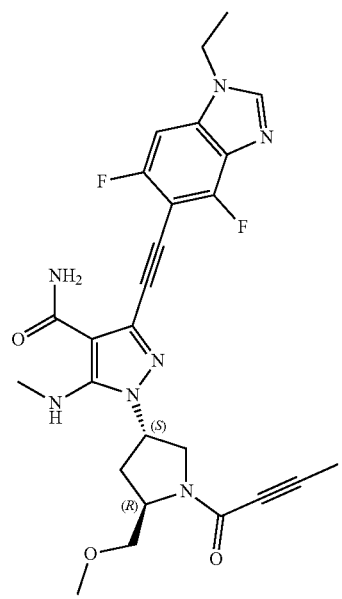

1-[(3S,5R)-1-(but-2-ynoyl)-5-(methoxymethyl)pyrrolidin-3-yl]-3-[2-(1-ethyl-4,6-difluoro-1,3-benzodiazol-5-yl)ethynyl]-5-(methylamino)pyrazole-4-carboxamide. MS ESI calculated for C26H27F2N7O3 [M+H]+, 524.21, found 524.35; 1H NMR (300 MHz, CD3OD) δ 8.33 (s, 1H), 7.45 (d, J=8.9 Hz, 1H), 5.48-5.34 (m, 1H), 4.64-4.49 (m, 1H), 4.35-4.30 (m, 2H), 4.12-3.68 (m, 3H), 3.68-3.58 (m, 1H), 3.43-3.40 (m, 1H), 3.42-3.39 (m, 3H), 3.04-3.01 (m, 3H), 2.84-2.61 (m, 1H), 2.47-2.43 (m, 1H), 2.06-2.03 (m, 3H), 1.53 (t, J=7.3 Hz, 3H).

Example 138: 1-((3S,5R)-1-acryloyl-5-((methoxy-d3)methyl)pyrrolidin-3-yl)-3-((6-chloro-1-ethyl-1H-benzo[d]imidazol-5-yl)ethynyl)-5-(methylamino)-1H-pyrazole-4-carboxamide

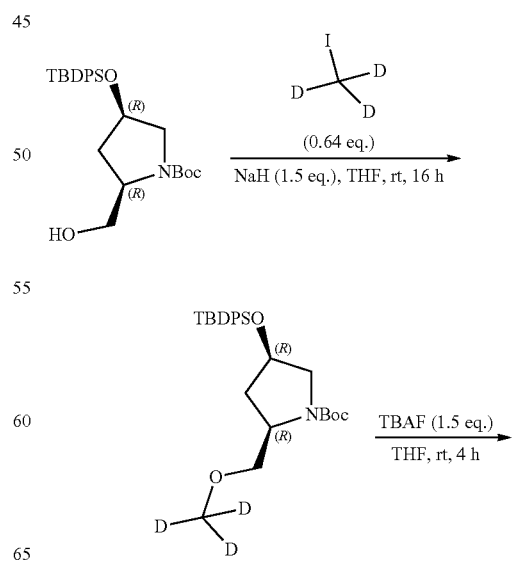

615
-continued
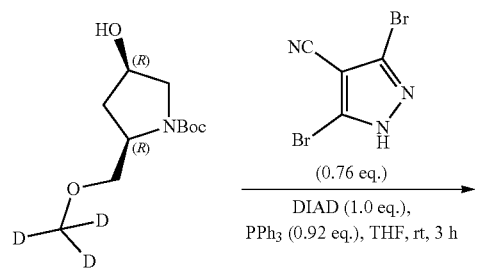
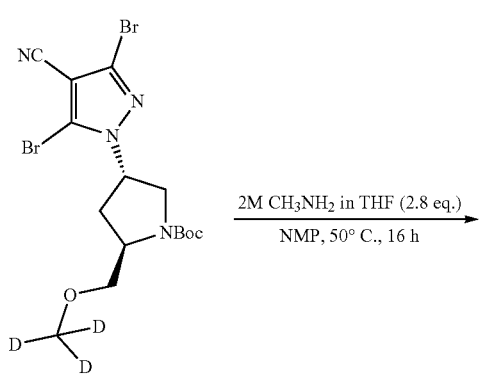
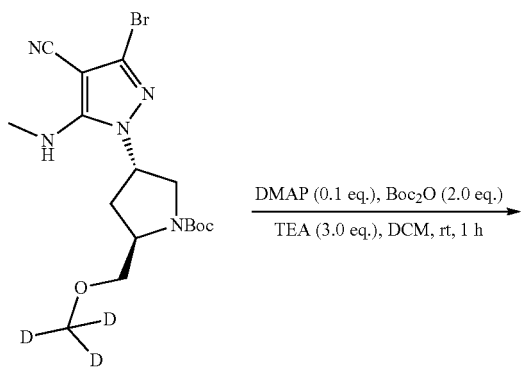
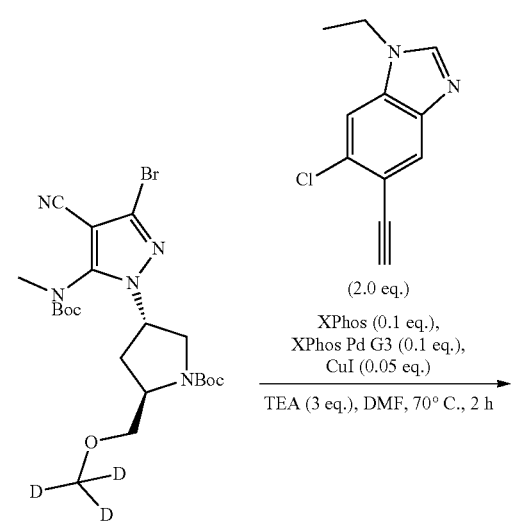
616
-continued
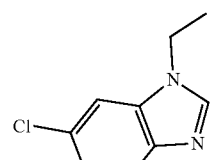
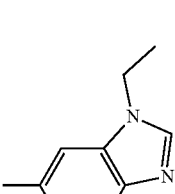
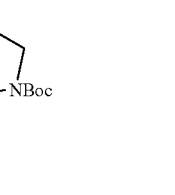

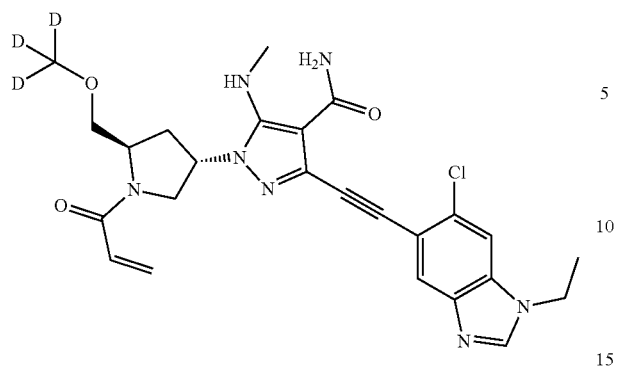
1-((3S,5R)-1-acryloyl-5-((methoxy-d₃)methyl)pyrrolidin-3-yl)-3-((6-chloro-1-ethyl-1H-benzo[d]imidazol-5-yl)ethynyl)-5-(methylamino)-1H-pyrazole-4-carboxamide. MS ESI calculated for C$_{25}$H$_{25}$D$_3$ClN$_7$O$_3$ [M+H]$^+$, 531.21, found 531.25; $^1$H NMR (400 MHz, CDCl$_3$) δ 8.10 (d, J=5.1 Hz, 1H), 8.00 (s, 1H), 7.51 (s, 1H), 6.82 (s, 1H), 6.57-6.36 (m, 2H), 5.72 (dd, J=8.6, 3.6 Hz, 1H), 5.59-5.25 (m, 2H), 4.57-4.45 (m, 1H), 4.29-3.87 (m, 4H), 3.55-3.42 (m, 1H), 3.09-2.95 (m, 3H), 2.73-2.69 (m, 1H), 2.36-2.31 (m, 1H), 1.58-1.50 (m, 3H).
Example 139: 3-[2-(6-Fluoro-1-methyl-1,3-benzodiazol-5-yl)ethynyl]-5-(methylamino)-1-[(3S)-1-(prop-2-enoyl)pyrrolidin-3-yl]pyrazole-4-carboxamide
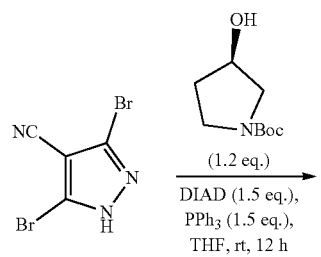
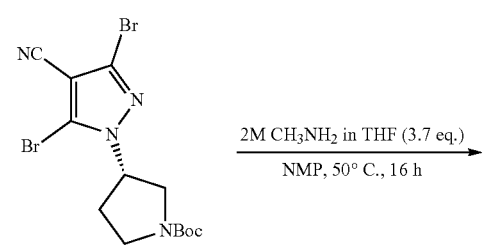
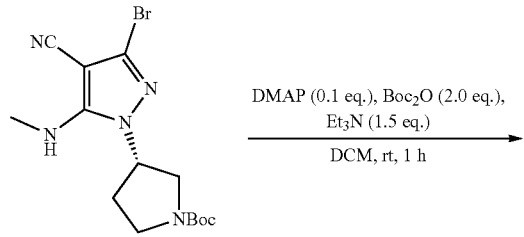
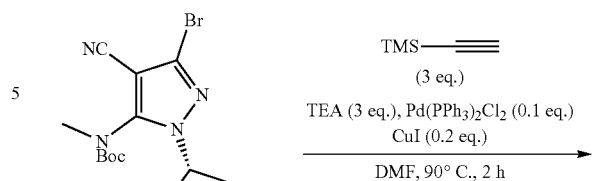
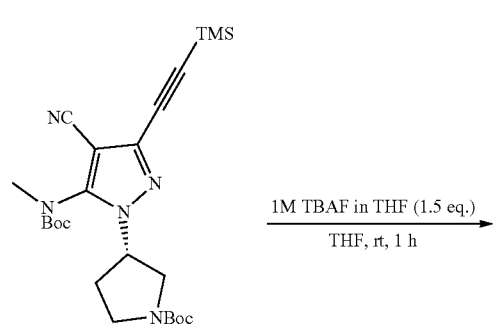
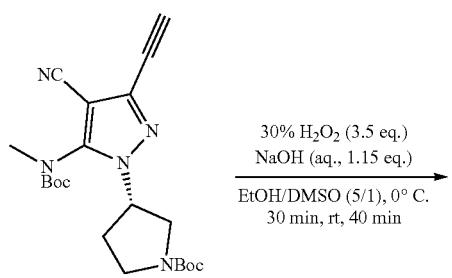
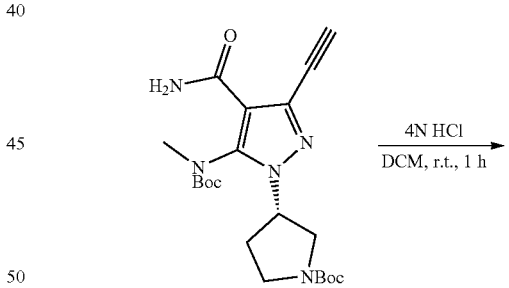
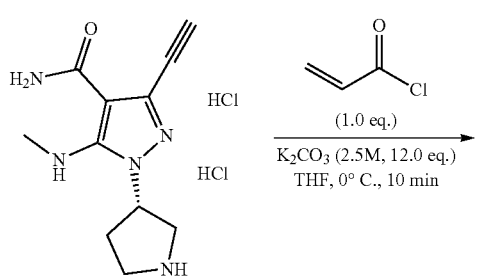

619
-continued

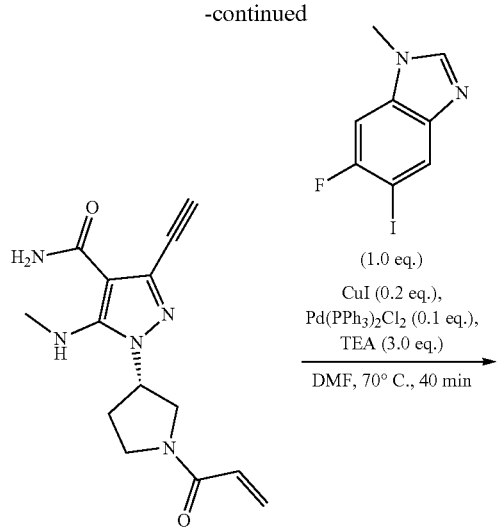
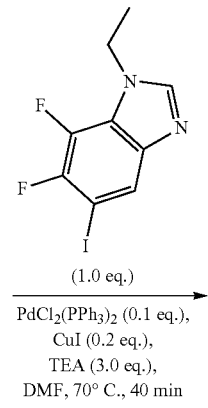

(1.0 eq.)
CuI (0.2 eq.),
Pd(PPh₃)₂Cl₂ (0.1 eq.),
TEA (3.0 eq.)
DMF, 70° C., 40 min 3-[2-(6-fluoro-1-methyl-1,3-benzodiazol-5-yl)ethynyl]-5-(methylamino)-1-[(3S)-1-(prop-2-enoyl)pyrrolidin-3-yl]pyrazole-4-carboxamide MS ESI calculated for $C_{22}H_{22}FN_7O_2$ [M+H]⁺, 436.20, found 436.20; ¹H NMR (400 MHz, DMSO-d₆) δ 8.31 (s, 1H), 7.96-7.73 (m, 1H), 7.68 (d, J=9.7 Hz, 1H), 7.48 (s, 1H), 6.80 (s, 1H), 6.68 (d, J=6.1, 4.6 Hz, 1H), 6.68-6.54 (m, 1H), 6.17-5.89 (m, 1H), 5.69-5.43 (m, 2.4 Hz, 1H), 5.25-5.08 (m, 1H), 4.10-3.99 (m, 1H), 3.92-3.83 (m, 1H), 3.84 (s, 3H), 3.82-3.71 (m, 1H), 3.73-3.50 (m, 1H), 2.96-2.73 (m, 3H), 2.40-2.35 (m, 1H), 2.29-2.10 (m, 1H).

620

Example 140: 3-[2-(1-Ethyl-6,7-difluoro-1,3-benzodiazol-5-yl)ethynyl]-5-(methylamino)-1-[(3S)-1-(prop-2-enoyl)pyrrolidin-3-yl]pyrazole-4-carboxamide

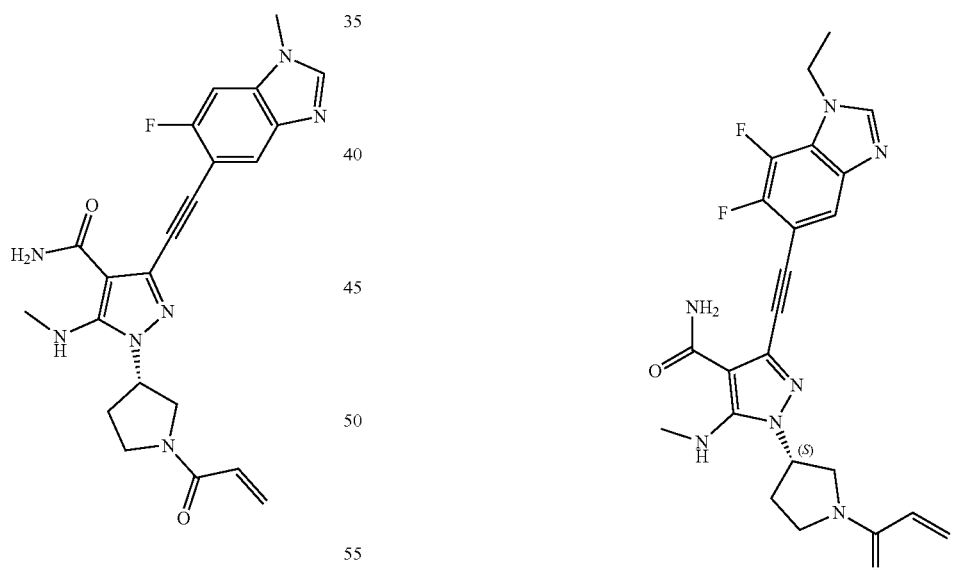

3-[2-(1-ethyl-6,7-difluoro-1,3-benzodiazol-5-yl)ethynyl]-5-(methylamino)-1-[(3S)-1-(prop-2-enoyl)pyrrolidin-3-yl]pyrazole-4-carboxamide. MS ESI calculated for $C_{23}H_{23}F_2N_7O_2$ [M+H]⁺, 468.20, found 468.10; ¹H NMR (300 MHz, DMSO) δ 8.44 (s, 1H), 7.85 (d, J=5.3 Hz, 1H), 7.47 (s, 1H), 6.92-6.55 (m, 3H), 6.25-6.12 (m, 1H), 5.71-5.62 (m, 1H), 5.18-5.12 (m, 1H), 4.40 (q, J=7.2 Hz, 2H), 4.12-3.60 (m, 4H), 2.97-2.92 (m, 3H), 2.42-2.24 (m, 2H), 1.47 (t, J=7.2 Hz, 3H).

Example 141: 3-[2-(6-Chloro-1-ethyl-7-fluoro-1,3-benzodiazol-5-yl)ethynyl]-5-(methylamino)-1-[(3S)-1-(prop-2-enoyl)pyrrolidin-3-yl]pyrazole-4-carboxamide

Example 142: 3-[2-(6-Chloro-7-fluoro-1-methyl-1,3-benzodiazol-5-yl)ethynyl]-5-(methylamino)-1-[(3S)-1-(prop-2-enoyl)pyrrolidin-3-yl]pyrazole-4-carboxamide

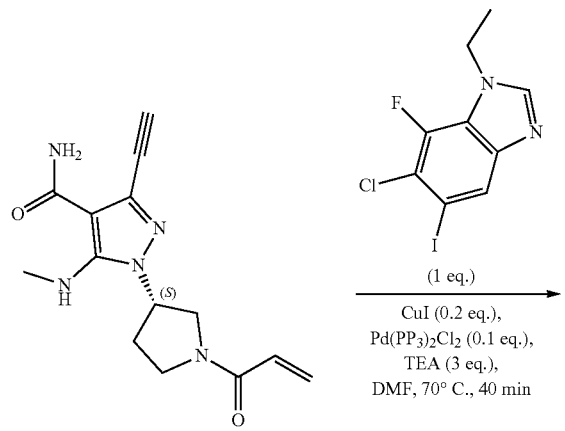

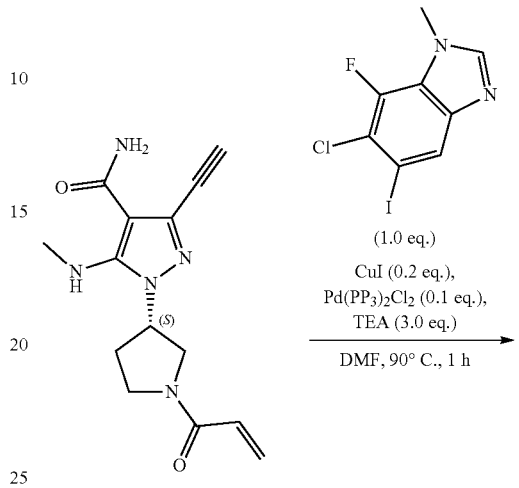

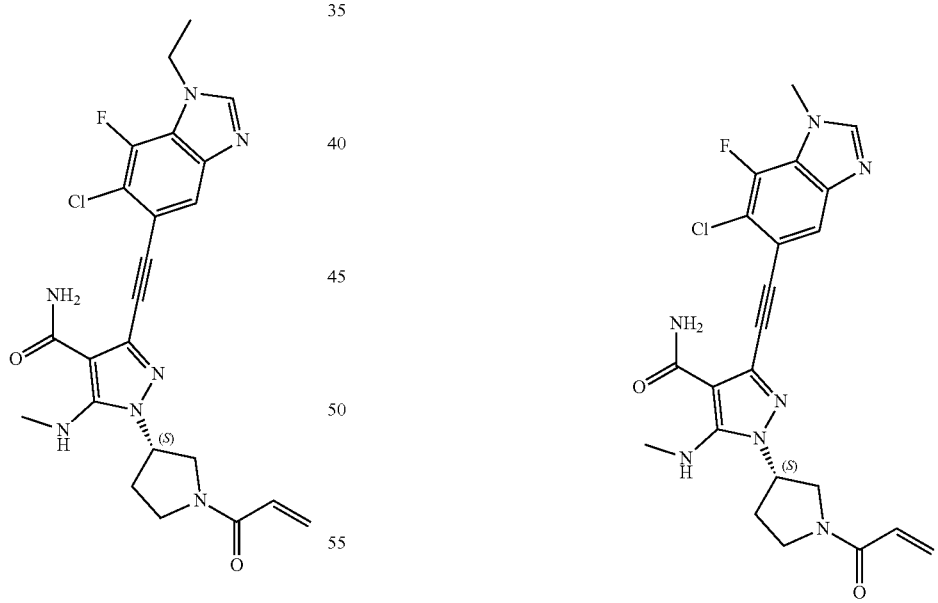

3-[2-(6-chloro-1-ethyl-7-fluoro-1,3-benzodiazol-5-yl)ethynyl]-5-(methylamino)-1-[(3S)-1-(prop-2-enoyl)pyrrolidin-3-yl]pyrazole-4-carboxamide. MS ESI calculated for $C_{23}H_{23}ClFN_7O_2$ [M+H]$^+$, 484.20, found 484.05; $^1$H NMR (400 MHz, DMSO-d$_6$) δ 8.46 (d, J=1.2 Hz, 1H), 7.93 (d, J=1.6 Hz, 1H), 7.49 (s, 1H), 6.85 (s, 1H), 6.71-6.55 (m, 2H), 6.17-5.96 (m, 1H), 5.70-5.46 (m, 1H), 5.25-5.08 (m, 1H), 4.39-4.12 (m, 2H), 3.92-3.50 (m, 4H), 2.96-2.64 (m, 3H), 2.41-2.21 (m, 1H), 2.34-2.26 (m, 1H), 1.45 (m, 3H).

3-[2-(6-chloro-7-fluoro-1-methyl-1,3-benzodiazol-5-yl)ethynyl]-5-(methylamino)-1-[(3S)-1-(prop-2-enoyl)pyrrolidin-3-yl]pyrazole-4-carboxamide. MS ESI calculated for $C_{22}H_{21}ClFN_7O_2$ [M+H]$^+$, 470.14, found 470.10; $^1$H NMR (400 MHz, DMSO) δ 8.38 (s, 1H), 7.92 (s, 1H), 7.48 (s, 1H), 6.85 (s, 1H), 6.69-6.57 (m, 2H), 6.20-6.14 (m, 1H), 5.73-5.67 (m, 1H), 5.22-5.10 (m, 1H), 4.06-3.83 (m, 5H), 3.76-3.33 (m, 2H), 2.97 (s, 3H), 2.43-2.38 (m, 1H), 2.32-2.30 (m, 1H).

623

Example 143: 3-[2-(1-Ethyl-6-fluoro-1,3-benzodiazol-5-yl)ethynyl]-5-(methylamino)-1-[(3S)-1-(prop-2-enoyl)pyrrolidin-3-yl]pyrazole-4-carboxamide

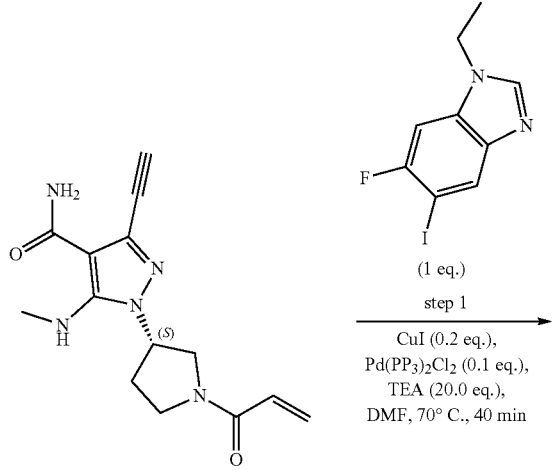

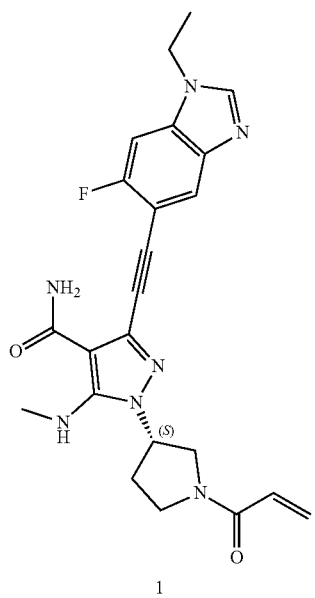

3-[2-(1-ethyl-6-fluoro-1,3-benzodiazol-5-yl)ethynyl]-5-(methylamino)-1-[(3S)-1-(prop-2-enoyl)pyrrolidin-3-yl]pyrazole-4-carboxamide. MS ESI calculated for $C_{23}H_{24}FN_7O_2$ [M+H]$^+$, 450.20, found 450.15; $^1$H NMR (300 MHz, DMSO-d$_6$) δ 8.41 (s, 1H), 7.97-7.77 (m, 1H), 7.76-7.56 (m, 1H), 7.49 (s, 1H), 6.81 (s, 1H), 6.70 (s, 1H), 6.74-6.54 (m, 1H), 6.25-6.11 (m, 1H), 5.71-5.43 (m, 1H), 5.18-4.96 (m, 1H), 4.29 (q, J=7.3 Hz, 2H), 4.12-3.51 (m, 4H), 2.97-2.69 (m, 3H), 2.45-2.27 (m, 2H), 1.42-1.23 (m, 3H).

624

Example 144: 3-[2-(6-Chloro-1-methyl-1,3-benzodiazol-5-yl)ethynyl]-5-(methylamino)-1-[(3S)-1-(prop-2-enoyl)pyrrolidin-3-yl]pyrazole-4-carboxamide

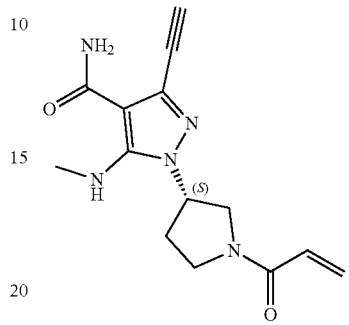
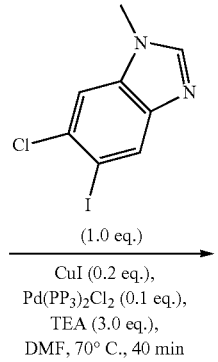

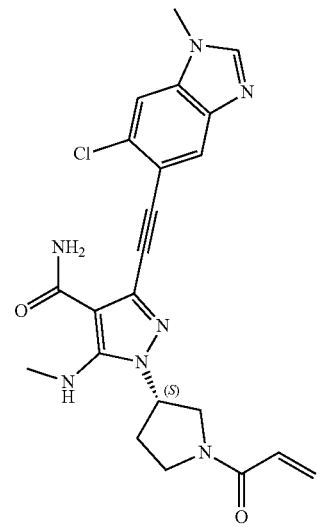

3-[2-(6-chloro-1-methyl-1,3-benzodiazol-5-yl)ethynyl]-5-(methylamino)-1-[(3S)-1-(prop-2-enoyl)pyrrolidin-3-yl]pyrazole-4-carboxamide. MS ESI calculated for $C_{22}H_{22}ClN_7O_2$ [M+H]$^+$, 452.16, found 452.15; $^1$H NMR (300 MHz, DMSO) δ 8.36 (s, 1H), 8.04 (s, 1H), 7.95 (s, 1H), 7.51 (s, 1H), 6.88 (s, 1H), 6.78-6.54 (m, 2H), 6.18-6.13 (m, 1H), 5.70-5.65 (m, 1H), 5.18-5.13 (m, 1H), 3.87-3.81 (m, 4H), 3.85-3.49 (m, 3H), 2.97-2.93 (m, 3H), 2.38-2.32 (m, 2H).

Example 145: 3-[2-(6,7-Difluoro-1-methyl-1,3-benzodiazol-5-yl)ethynyl]-5-(methylamino)-1-[(3S)-1-(prop-2-enoyl)pyrrolidin-3-yl]pyrazole-4-carboxamide

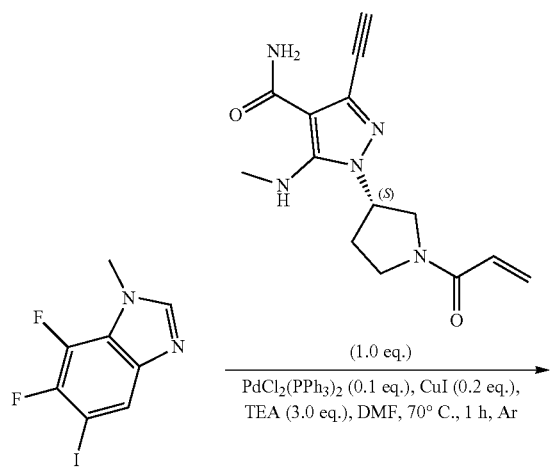

3-[2-(6,7-difluoro-1-methyl-1,3-benzodiazol-5-yl)ethynyl]-5-(methylamino)-1-[(3S)-1-(prop-2-enoyl)pyrrolidin-3-yl]pyrazole-4-carboxamide. MS ESI calculated for $C_{22}H_{21}F_2N_7O_2$ [M+H]$^+$, 454.17, found 454.15; $^1$H NMR (300 MHz, DMSO-$d_6$) δ 8.35 (s, 1H), 7.83 (d, J=5.2 Hz, 1H), 7.47 (s, 1H), 6.71-6.57 (m, 3H), 6.21-6.14 (m, 1H), 5.74-5.67 (m, 1H), 5.22-5.13 (m, 1H), 4.07 (s, 3H), 3.91-3.58 (m, 4H), 2.97-2.92 (m, 3H), 2.52-2.28 (m, 2H).

Example 147: 3-[2-(6-Chloro-1-cyclopropyl-7-fluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide

627
-continued

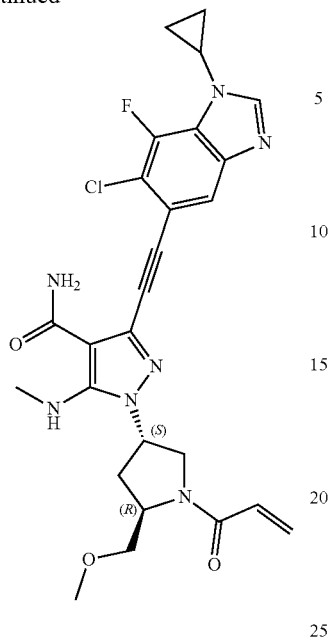

3-[2-(6-chloro-1-cyclopropyl-7-fluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide. MS ESI calculated for $C_{26}H_{27}ClFN_7O_3$ [M+H]$^+$, 540.18, found 540.30; $^1$H NMR (300 MHz, CDCl$_3$) δ 8.01 (brs, 1H), 7.12 (brs, 1H), 6.83 (brs, 1H), 6.67-6.33 (m, 2H), 5.77-5.71 (m, 1H), 5.65-5.21 (m, 2H), 4.66-4.38 (m, 1H), 4.26-3.83 (m, 2H), 3.73-3.28 (m, 6H), 3.05-3.01 (m, 3H), 2.89-2.57 (m, 1H), 2.36-2.31 (m, 1H), 1.44-0.97 (m, 4H).

Example 148: 3-[2-(6-Fluoro-1-methyl-1,3-benzodiazol-5-yl)ethynyl]-1-[(3S,5R)-5-(fluoromethyl)-1-(prop-2-enoyl)pyrrolidin-3-yl]-5-(methylamino)pyrazole-4-carboxamide

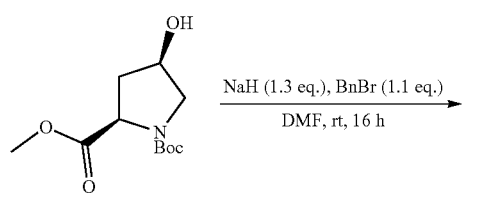
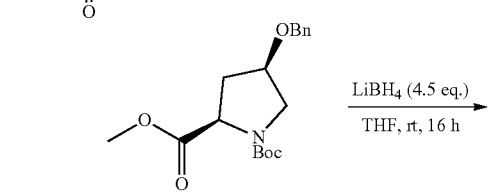
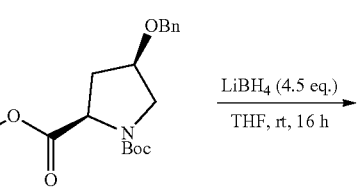
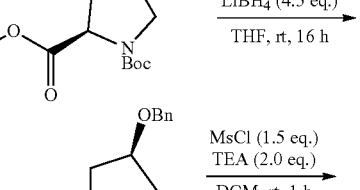
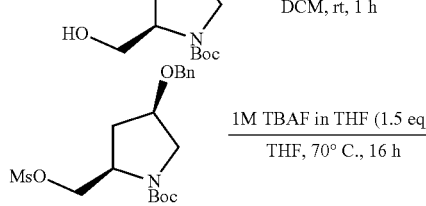

628
-continued

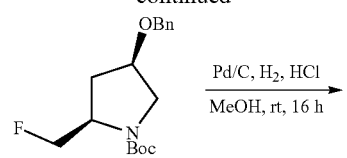
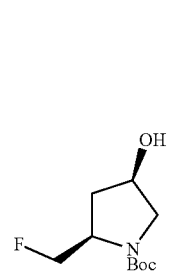 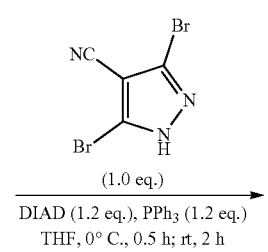
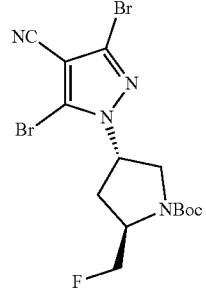 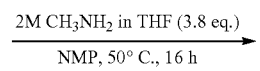
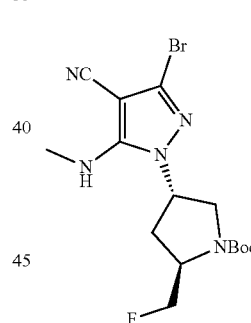 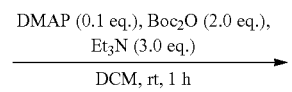
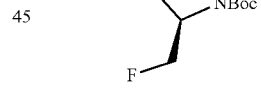
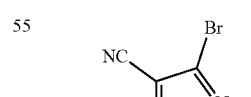 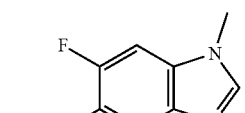
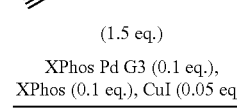

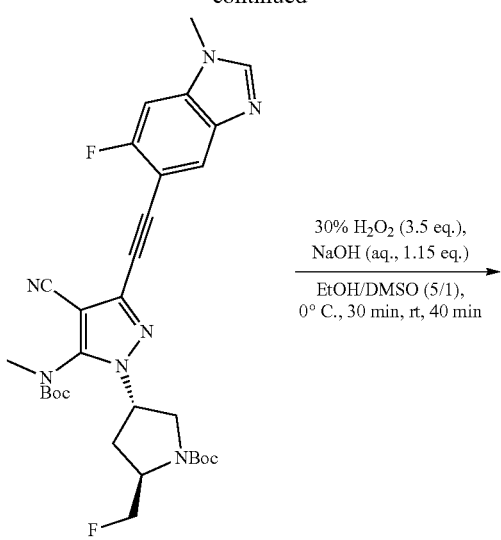

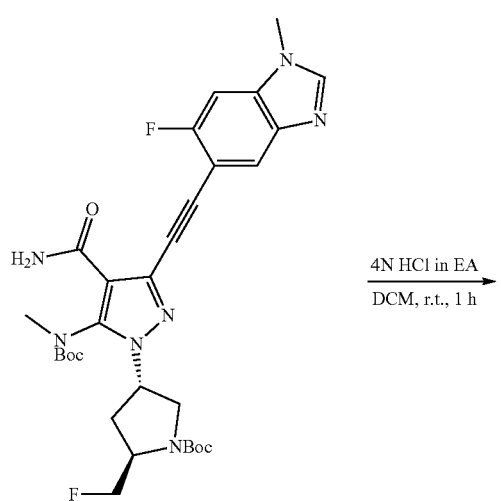

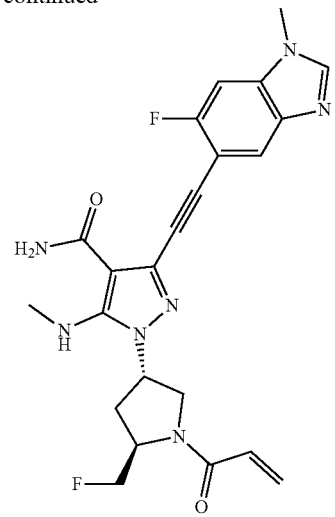

3-[2-(6-fluoro-1-methyl-1,3-benzodiazol-5-yl)ethynyl]-1-[(3S,5R)-5-(fluoromethyl)-1-(prop-2-enoyl)pyrrolidin-3-yl]-5-(methylamino)pyrazole-4-carboxamide. MS ESI calculated for $C_{23}H_{23}F_2N_7O_2$ [M+H]$^+$, 468.19, found 468.25; $^1$H NMR (300 MHz, CDCl$_3$) δ 7.98 (d, J=6.3 Hz, 1H), 7.91 (s, 1H), 7.14 (d, J=9.0 Hz, 2H), 6.80-6.78 (m, 1H), 6.43 (d, J=2.1 Hz, 1H), 6.41 (s, 1H), 5.76-5.72 (m, 1H), 5.43-5.40 (m, 1H), 5.37-5.29 (m, 1H), 5.05-4.85 (m, 1H), 4.68-4.40 (m, 2H), 4.17-4.04 (m, 2H), 3.84 (s, 3H), 3.03 (d, J=6.0 Hz, 3H), 2.89-2.78 (m, 1H), 2.43-2.46 (m, 1H).

Example 149: 1-[(3S,5R)-5-(Methoxymethyl)-1-(prop-2-enoyl)pyrrolidin-3-yl]-5-(methylamino)-3-[2-(4,6,7-trifluoro-1,2-dimethyl-1,3-benzodiazol-5-yl)ethynyl]pyrazole-4-carboxamide

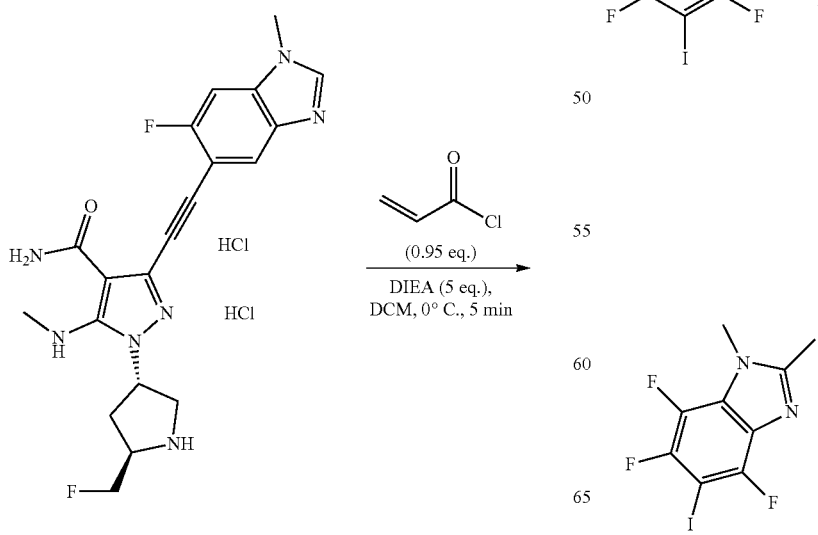

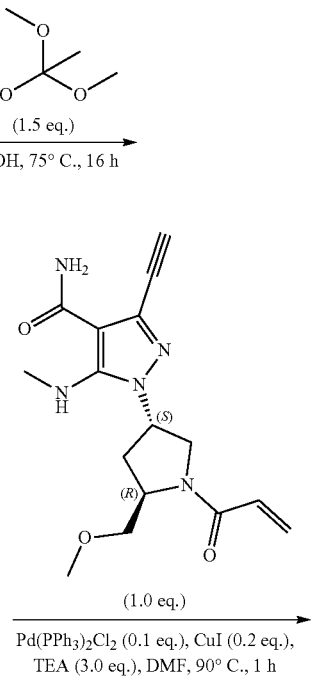

-continued

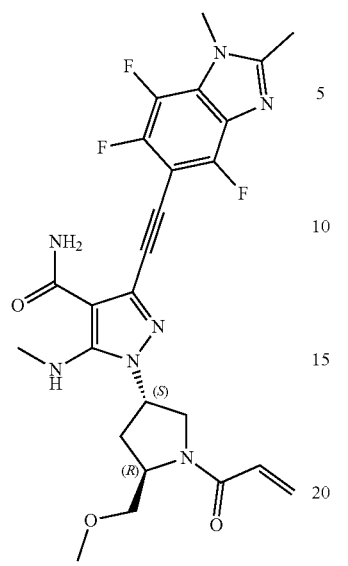

1-[(3S,5R)-5-(methoxymethyl)-1-(prop-2-enoyl)pyrrolidin-3-yl]-5-(methylamino)-3-[2-(4,6,7-trifluoro-1,2-dimethyl-1,3-benzodiazol-5-yl)ethynyl]pyrazole-4-carboxamide. MS ESI calculated for $C_{25}H_{26}F_3N_7O_3$ [M+H]$^+$, 530.20, found 530.20; $^1$H NMR (400 MHz, CDCl$_3$) δ 7.05-6.98 (m, 1H), 6.89-6.82 (m, 1H), 6.49-6.41 (m, 2H), 5.78-5.72 (m, 1H), 5.56-5.32 (m, 2H), 4.58-4.32 (m, 1H), 4.18-4.01 (m, 2H), 3.98-3.91 (m, 4H), 3.54-3.45 (m, 1H), 3.38 (s, 3H), 3.09-2.99 (m, 3H), 2.79-2.71 (m, 1H), 2.61 (s, 3H), 2.39-2.31 (m, 1H).

Example 150: 3-[2-(1-Cyclopropyl-6-fluoro-2-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide

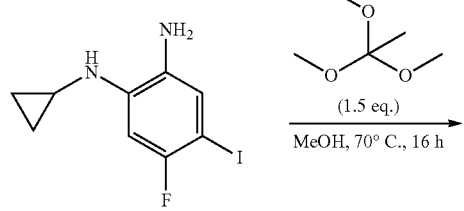

-continued

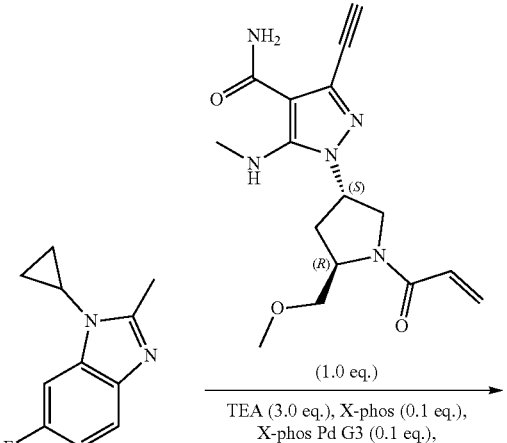

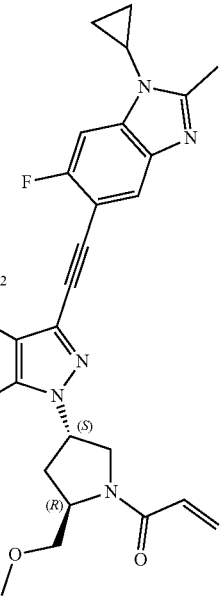

3-[2-(1-cyclopropyl-6-fluoro-2-methyl-1,3-benzodiazol-5-yl) ethynyl]-1-[(3S,5R)-5-(methoxymethyl)-1-(prop-2-enoyl)pyrrolidin-3-yl]-5-(methylamino)pyrazole-4-carboxamide. MS ESI calculated for $C_{27}H_{30}FN_7O_3$ [M+H]$^+$, 520.25, found 520.30; $^1$H NMR (400 MHz, CDCl$_3$) δ 7.87 (s, 1H), 7.16 (s, 1H), 6.83 (d, J=6.0 Hz, 1H), 6.58-6.35 (m, 2H), 5.72-5.68 (m, 1H), 5.58-5.22 (m, 2H), 4.56 (d, J=8.9 Hz, 1H), 4.12-4.03 (m, 2H), 3.91-3.85 (m, 1H), 3.54-3.41 (m, 1H), 3.38 (d, J=4.4 Hz, 3H), 3.20-3.15 (m, 1H), 3.05-3.01 (m, 3H), 2.80-2.48 (m, 3H), 2.31-2.26 (m, 1H), 1.29-1.27 (m, 2H), 1.11-1.02 (m, 2H).

Example 151: 3-[2-(1-Cyclopropyl-6,7-difluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide

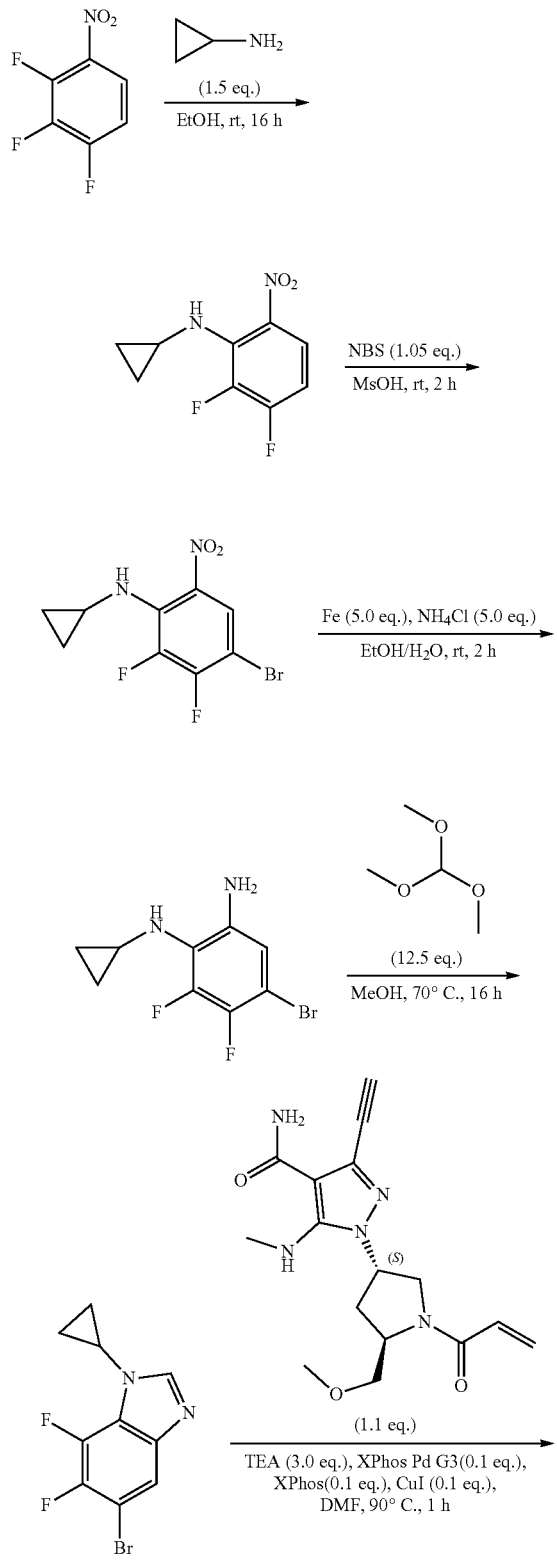

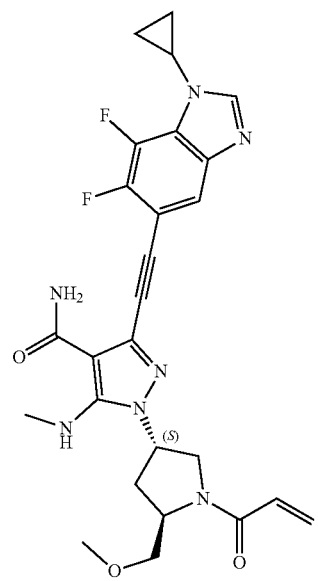

3-[2-(1-cyclopropyl-6,7-difluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide. MS ESI calculated for $C_{26}H_{27}F_2N_7O_3$ $[M+H]^+$, 524.21, found 524.30; $^1$H NMR (400 MHz, CDCl$_3$) δ 7.94 (s, 1H), 7.75 (d, J=5.0 Hz, 1H), 7.05-6.95 (m, 1H), 6.85-6.82 (m, 1H), 6.55-6.39 (m, 2H), 5.72-5.68 (m, 1H), 5.53-5.45 (m, 1H), 5.41-5.26 (m, 1H), 4.58 (d, J=9.1 Hz, 1H), 4.16-3.87 (m, 3H), 3.73-3.52 (m, 1H), 3.55-3.42 (m, 1H), 3.39 (d, J=4.6 Hz, 3H), 3.05 (d, J=15.5 Hz, 3H), 2.83-2.62 (m, 1H), 2.45-2.26 (m, 1H), 1.28-1.08 (m, 4H).

Example 152: 1-[(3S,5R)-5-(Methoxymethyl)-1-(prop-2-enoyl)pyrrolidin-3-yl]-5-(methylamino)-3-[2-(4,6,7-trifluoro-1-methyl-1,3-benzodiazol-5-yl)ethynyl]pyrazole-4-carboxamide

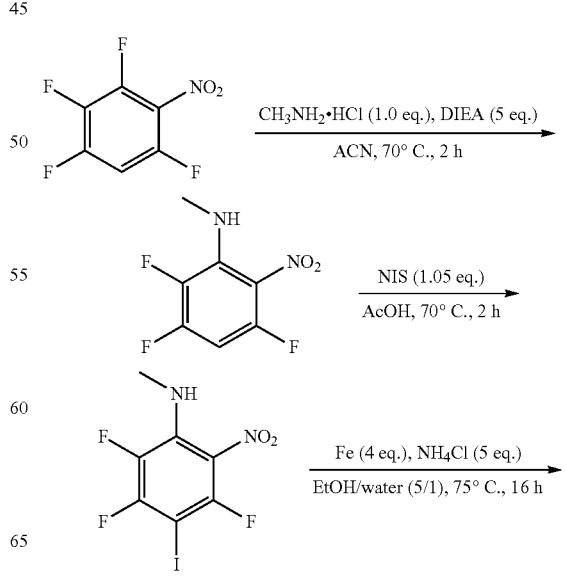

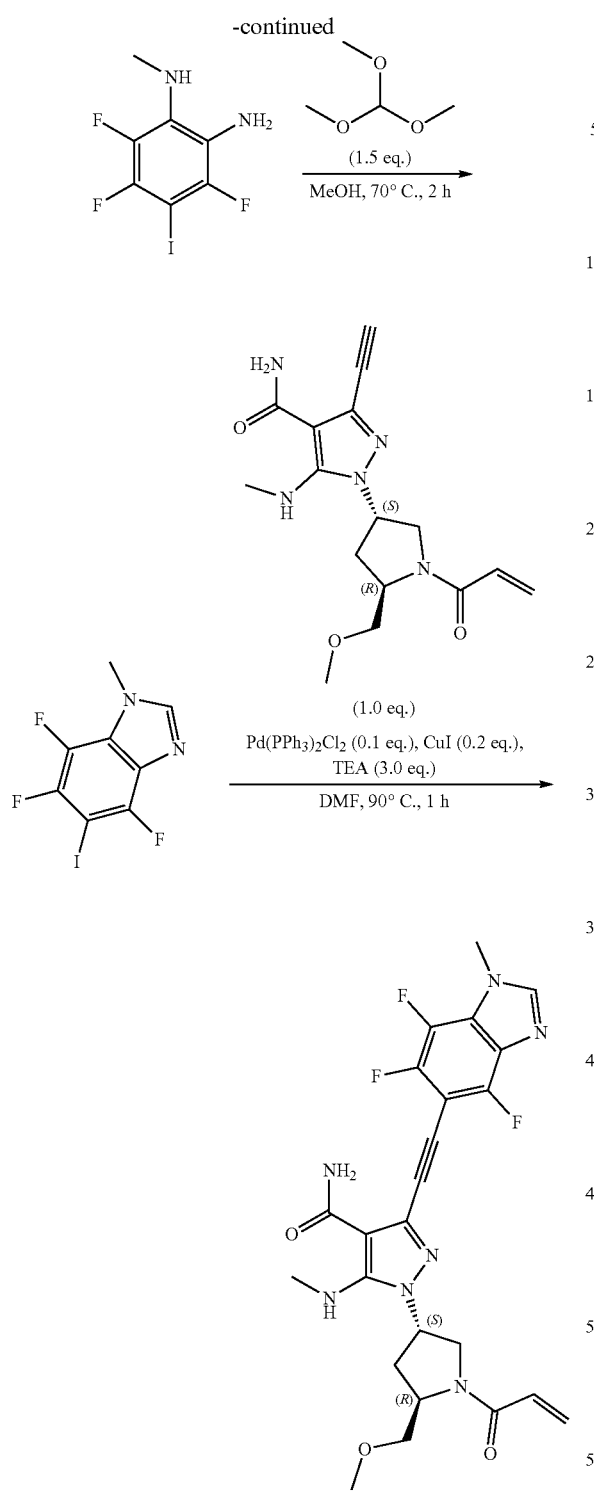
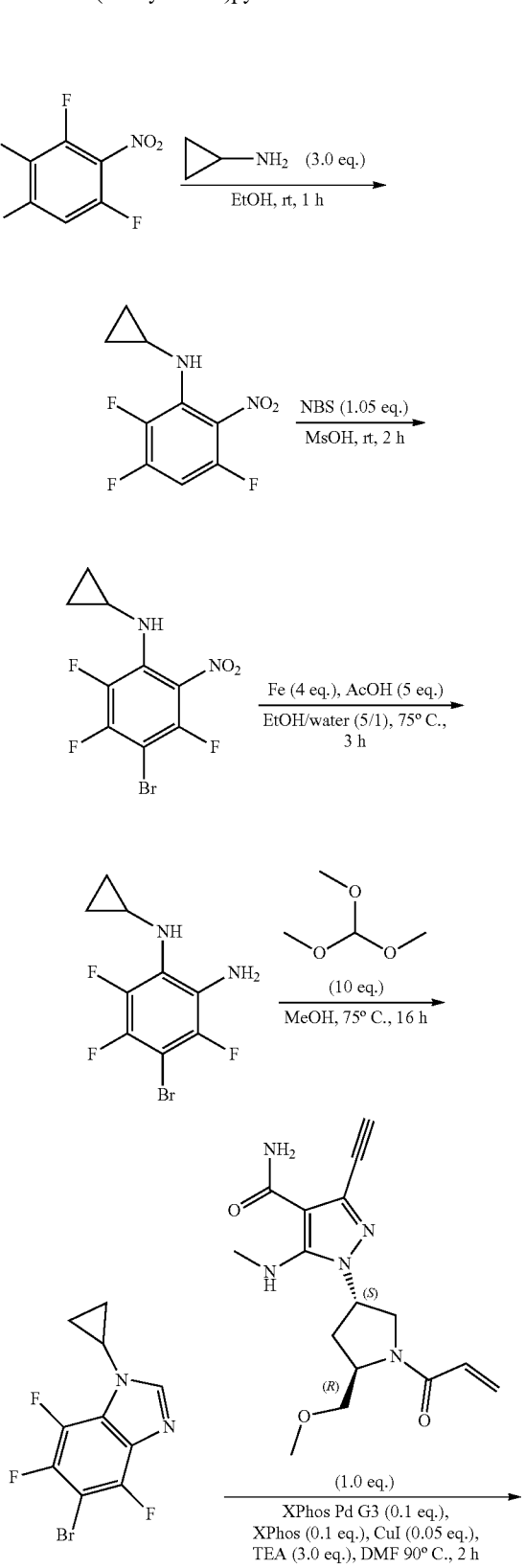

Example 153: 3-[2-(1-Cyclopropyl-4,6,7-trifluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide 1-[(3S,5R)-5-(methoxymethyl)-1-(prop-2-enoyl)pyrrolidin-3-yl]-5-(methylamino)-3-[2-(4,6,7-trifluoro-1-methyl-1,3-benzodiazol-5-yl)ethynyl]pyrazole-4-carboxamide. MS ESI calculated for $C_{24}H_{24}F_3N_7O_3$ [M+H]$^+$, 516.19, found 516.10; $^1$H NMR (400 MHz, CDCl$_3$) δ 7.86 (s, 1H), 6.99 (s, 1H), 6.57-6.39 (m, 2H), 5.74-5.71 (m, 1H), 5.54-5.42 (m, 2H), 4.59-4.56 (m, 1H), 4.15-4.02 (m, 6H), 3.53-3.44 (m, 1H), 3.39 (d, J=4 Hz, 3H), 3.05 (d, J=12 Hz, 3H), 2.76-2.68 (m, 1H), 2.42-2.30 (m, 1H).

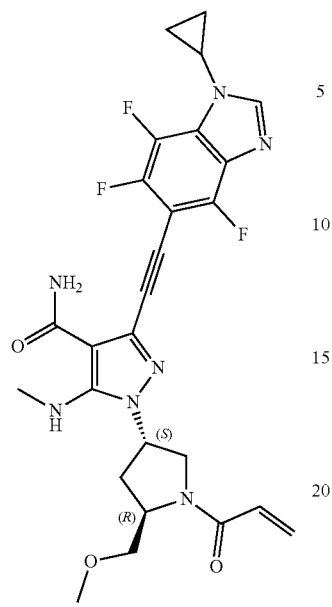

3-[2-(1-cyclopropyl-4,6,7-trifluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide. MS ESI calculated for $C_{26}H_{26}F_3N_7O_3$ [M+H]$^+$, 542.20, found 542.20; $^1$H NMR (400 MHz, CDCl$_3$) δ 7.92 (s, 1H), 6.99 (s, 1H), 6.50-6.41 (m, 2H), 5.72-5.69 (m, 1H), 5.55-5.48 (m, 1H), 5.48-5.24 (m, 1H), 4.61-4.39 (m, 1H), 4.08-4.01 (m, 2H), 3.99-3.39 (m, 1H), 3.62-3.60 (m, 1H), 3.54-3.42 (m, 1H), 3.39 (d, J=5.0 Hz, 3H), 3.05 (d, J=15.8 Hz, 3H), 2.81-2.63 (m, 1H), 2.39-2.26 (m, 1H), 1.32-1.23 (m, 2H), 1.22-1.12 (m, 2H).

Example 154: 1-[(3S,5R)-5-[(Difluoromethoxy)methyl]-1-(prop-2-enoyl)pyrrolidin-3-yl]-3-[2-(1-ethyl-6,7-difluoro-1,3-benzodiazol-5-yl)ethynyl]-5-(methylamino)pyrazole-4-carboxamide

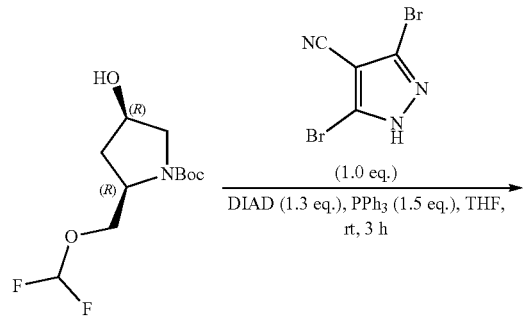

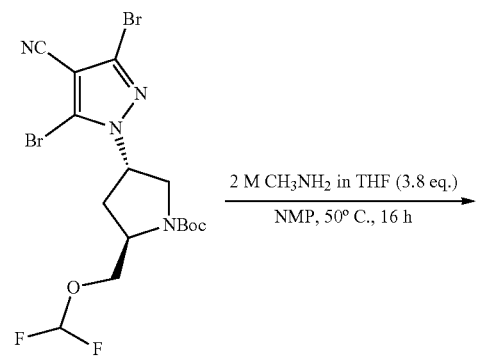

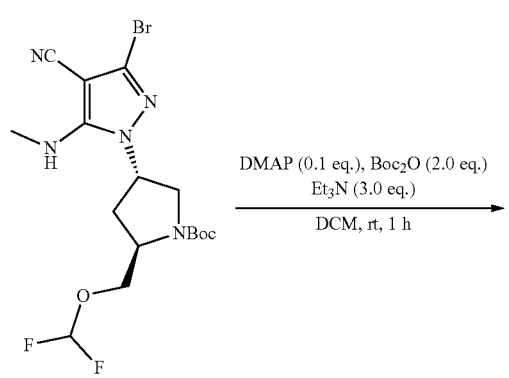

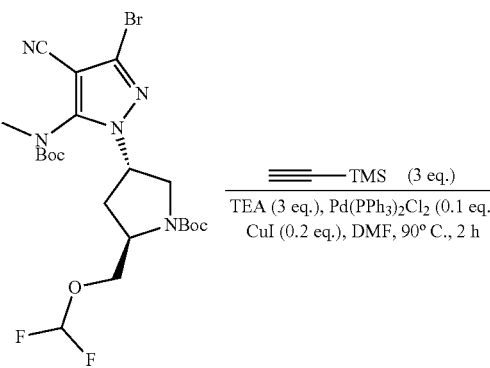

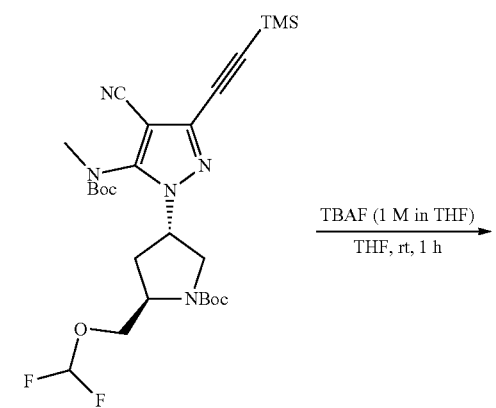

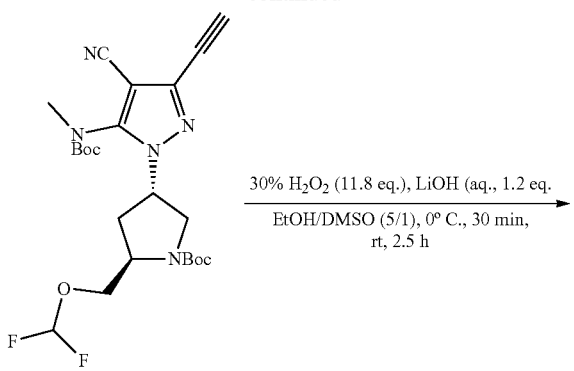

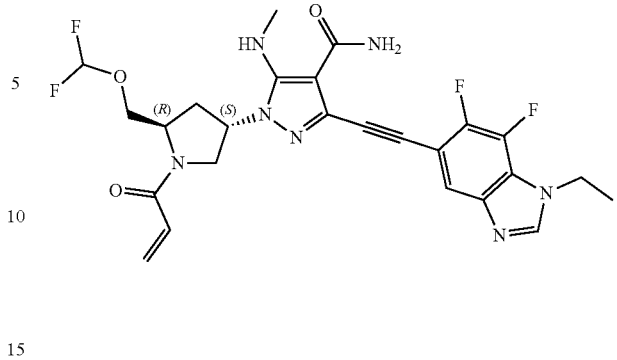

1-[(3S,5R)-5-[(difluoromethoxy)methyl]-1-(prop-2-enoyl)pyrrolidin-3-yl]-3-[2-(1-ethyl-6,7-difluoro-1,3-benzodiazol-5-yl)ethynyl]-5-(methylamino)pyrazole-4-carboxamide. MS ESI calculated for $C_{25}H_{25}F_4N_7O_3$ [M+H]$^+$, 548.20, found 548.15; $^1$H NMR (400 MHz, CDCl$_3$) δ 7.91 (s, 1H), 7.76-7.45 (m, 1H), 7.02 (s, 1H), 6.82-6.43 (m, 1H), 6.52-6.34 (m, 3H), 5.80-5.70 (m, 1H), 5.51-5.28 (m, 2H), 4.68-4.61 (m, 1H), 4.46-4.33 (m, 3H), 4.09-3.98 (m, 2H), 3.94-3.74 (m, 1H), 3.04-2.96 (m, 3H), 2.83-2.63 (m, 1H), 2.41-2.32 (m, 1H), 1.57-1.32 (m, 3H).

Example 155: 3-[2-(1-Cyclopropyl-1,3-benzodiazol-5-yl)ethynyl]-1-[(3S,5R)-5-[(difluoromethoxy)methyl]-1-(prop-2-enoyl)pyrrolidin-3-yl]-5-(methylamino)pyrazole-4-carboxamide

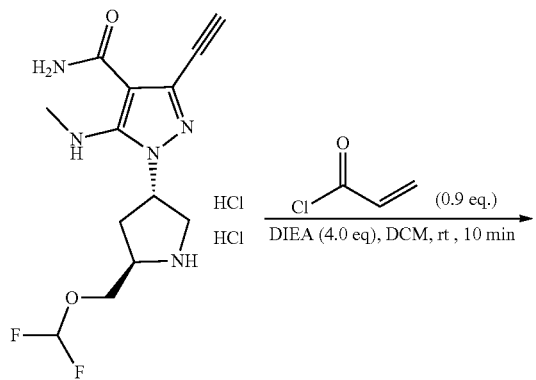

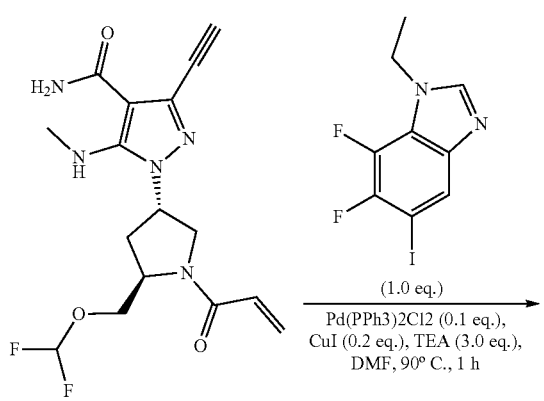

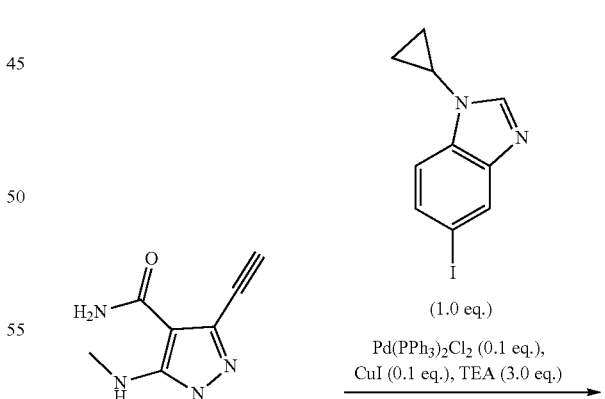

641

-continued

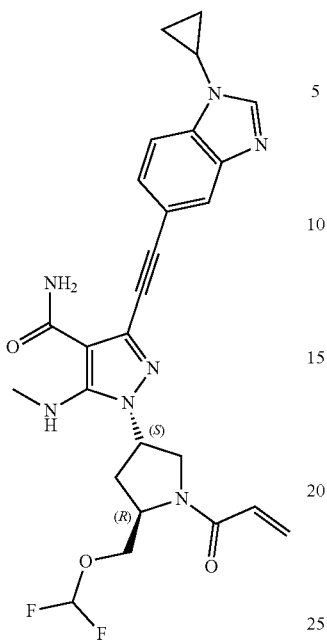

3-[2-(1-cyclopropyl-1,3-benzodiazol-5-yl)ethynyl]-1-[(3S,5R)-5-[(difluoromethoxy)methyl]-1-(prop-2-enoyl)pyrrolidin-3-yl]-5-(methylamino)pyrazole-4-carboxamide. MS ESI calculated for $C_{26}H_{27}F_2N_7O_3$ [M+H]$^+$, 524.21, found 524.20; $^1$H NMR (400 MHz, CDCL$_3$) δ 8.04 (d, J=96.4 Hz, 2H), 7.48 (d, J=8.0 Hz, 1H), 6.94-6.92 (m, 1H), 6.77 (d, J=6.2 Hz, 1H), 6.56-5.97 (m, 3H), 5.79-5.69 (m, 1H), 5.40-5.38 (m, 1H), 4.68-4.60 (m, 1H), 4.41 (dd, J=10.3, 3.1 Hz, 1H), 4.13-4.12 (m, 1H), 4.04-4.01 (m, 1H), 3.93-3.92 (m, 1H), 3.40 (s, 1H), 3.03-2.98 (m, 3H), 2.83-2.37 (m, 1H), 2.41-2.31 (m, 1H), 1.20-1.18 (m, 2H), 1.07-1.05 (m, 2H).

Example 156: 1-((3S,5R)-1-Acryloyl-5-((difluoromethoxy)methyl)pyrrolidin-3-yl)-3-((1-cyclopropyl-4,6-difluoro-1H-benzo[d]imidazol-5-yl)ethynyl)-5-(methylamino)-1H-pyrazole-4-carboxamide

642

-continued 1-((3S,5R)-1-acryloyl-5-((difluoromethoxy)methyl)pyrrolidin-3-yl)-3-((1-cyclopropyl-4,6-difluoro-1H-benzo[d]imidazol-5-yl)ethynyl)-5-(methylamino)-1H-pyrazole-4-carboxamide. MS ESI calculated for $C_{26}H_{25}F_4N_7O_3$ [M+H]$^+$, 560.20; found 560.15; $^1$H NMR (400 MHz, CDCl$_3$) δ 7.95 (s, 1H), 7.27 (s, 1H), 7.16 (d, J=8.2 Hz, 1H), 7.05 (s, 1H), 6.88-6.00 (m, 3H), 5.74-5.71 (m, 1H), 5.56-5.01 (m, 2H), 4.63 (d, J=9.2 Hz, 1H), 4.42 (d, J=10.3, 3.2 Hz, 1H), 4.14 (d, J=9.8, 8.0 Hz, 1H), 4.04 (d, J=9.9, 8.1 Hz, 1H), 3.94 (dd, J=10.4, 2.3 Hz, 1H), 3.38-3.35 (m, 1H), 3.03 (s, 3H), 2.84-2.81 (m, 1H), 2.37-2.35 (m, 1H), 1.28-1.14 (m, 2H), 1.11-1.03 (m, 2H).

Example 157: 3-[2-(1-Ethyl-4,6,7-trifluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide

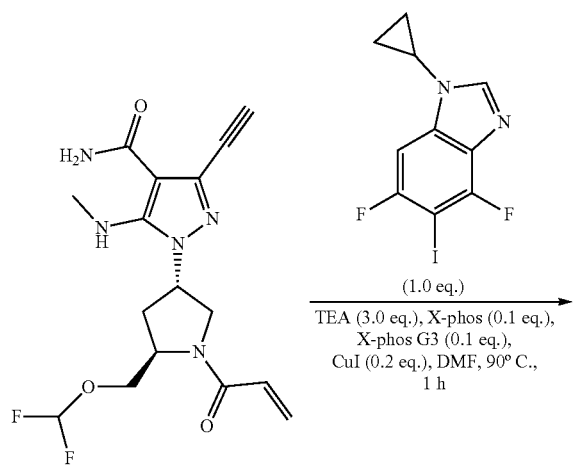

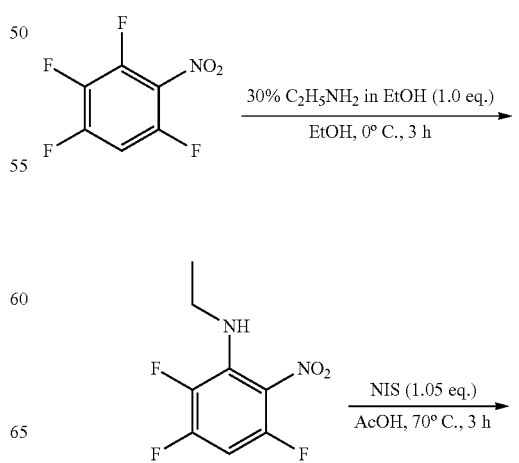

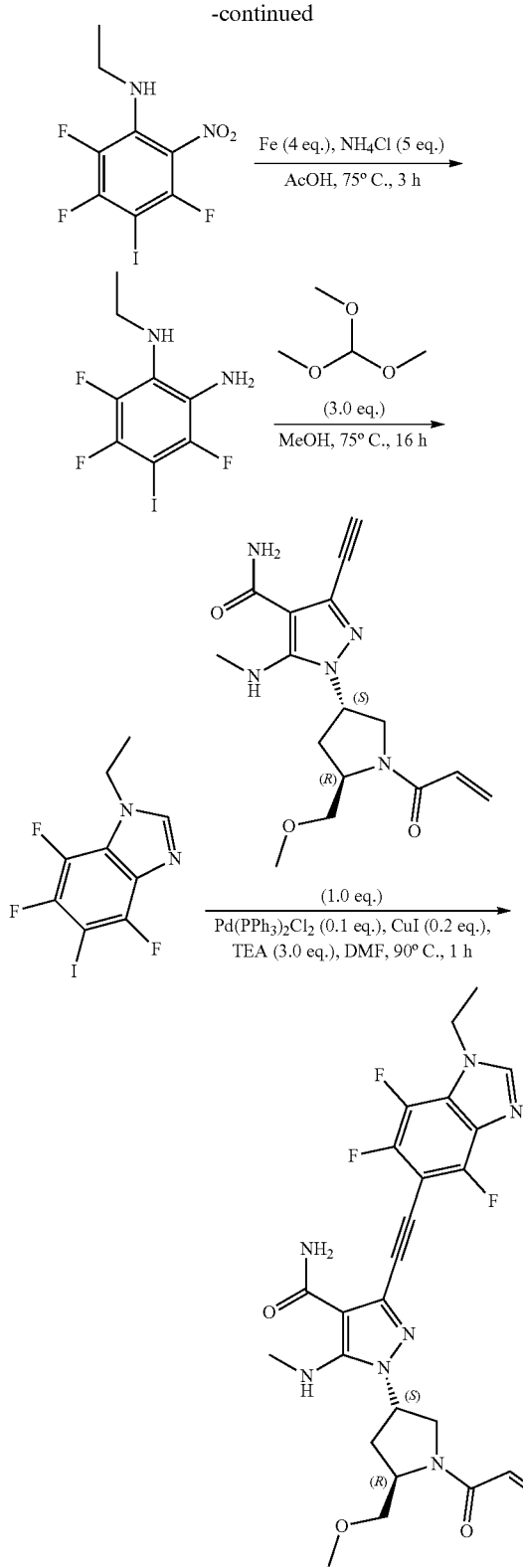

2H), 4.57 (d, J=9.0 Hz, 1H), 4.41 (q, J=7.2 Hz, 2H), 4.12 (d, J=8.7 Hz, 1H), 4.07-3.97 (m, 1H), 3.93-3.90 (m, 1H), 3.56-3.41 (m, 1H), 3.39 (d, J=5.1 Hz, 3H), 3.05 (d, J=15.7 Hz, 3H), 2.77-2.66 (m, 1H), 2.34-2.29 (m, 1H), 1.60 (t, J=7.3 Hz, 3H).

Example 158: 3-[2-(1-Cyclopropyl-6,7-difluoro-1,3-benzodiazol-5-yl)ethynyl]-1-[(3S,5S)-5-methyl-1-(prop-2-enoyl)pyrrolidin-3-yl]-5-(methylamino)pyrazole-4-carboxamide

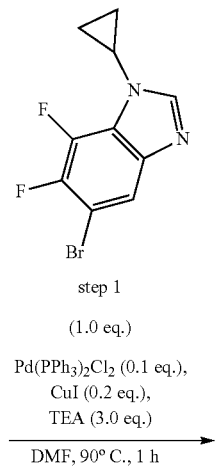

step 1

(1.0 eq.)

Pd(PPh$_3$)$_2$Cl$_2$ (0.1 eq.), CuI (0.2 eq.), TEA (3.0 eq.)

DMF, 90° C., 1 h

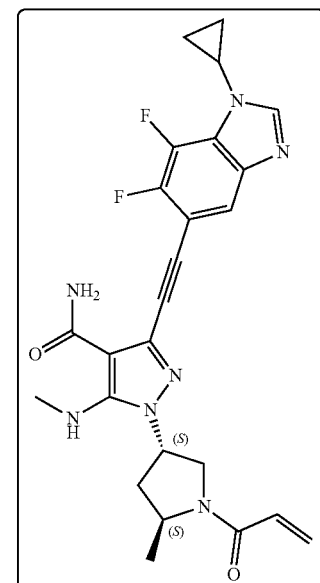

3-[2-(1-ethyl-4,6,7-trifluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide. MS ESI calculated for C$_{25}$H$_{26}$F$_3$N$_7$O$_3$ [M+H]$^+$, 530.20, found 530.25; $^1$H NMR (400 MHz, CDCl$_3$) δ 7.92 (s, 1H), 6.99 (s, 1H), 6.63-6.32 (m, 2H), 5.80-5.70 (m, 1H), 5.57-5.25 (m, 3-[2-(1-cyclopropyl-6,7-difluoro-1,3-benzodiazol-5-yl)ethynyl]-1-[(3S,5S)-5-methyl-1-(prop-2-enoyl)pyrrolidin-3-yl]-5-(methylamino)pyrazole-4-carboxamide. MS ESI calculated for C$_{25}$H$_{25}$F$_2$N$_7$O$_2$ [M+H]$^+$, 494.50, found 494.20; $^1$H NMR (400 MHz, CDCl$_3$) δ 7.95 (s, 1H), 7.74 (s, 1H), 7.02 (s, 1H), 6.59-6.40 (m, 1H), 6.40-6.29 (m, 1H), 5.80-5.59 (m, 1H), 5.40 (s, 1H), 5.13-4.96 (m, 1H), 4.52-4.32 (m, 1H), 4.16-3.93 (m, 2H), 3.61-3.46 (m, 1H), 3.01-2.96 (m, 3H), 2.87-2.66 (m, 1H), 2.07-1.85 (m, 1H), 1.35-1.27 (m, 3H), 1.26-1.21 (m, 2H), 1.18-1.12 (m, 2H).

Example 159: 3-[2-(1-Cyclopropyl-4,6-difluoro-1,3-benzodiazol-5-yl)ethynyl]-1-[(3S,5S)-5-methyl-1-(prop-2-enoyl)pyrrolidin-3-yl]-5-(methylamino)pyrazole-4-carboxamide

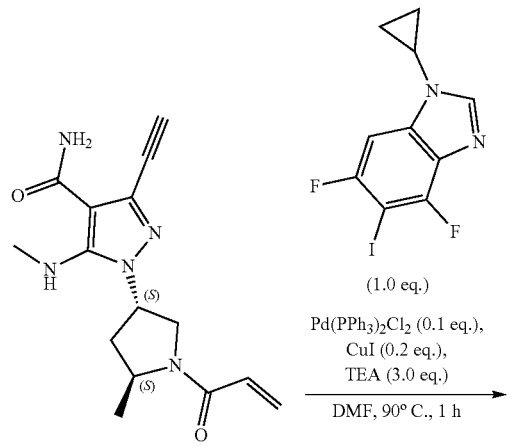

3-[2-(1-cyclopropyl-4,6-difluoro-1,3-benzodiazol-5-yl)ethynyl]-1-[(3S,5S)-5-methyl-1-(prop-2-enoyl)pyrrolidin-3-yl]-5-(methylamino)pyrazole-4-carboxamide. MS ESI calculated for $C_{25}H_{25}F_2N_7O_2$ [M+H]$^+$, 494.20, found 494.25; $^1$H NMR (400 MHz, CDCl$_3$) δ 7.97 (s, 1H), 7.17 (d, J=4 Hz, 1H), 7.09 (s, 1H), 6.58-6.40 (m, 2H), 5.76-5.69 (m, 1H), 5.43 (s, 1H), 5.18-5.10 (m, 1H), 4.58-4.49 (m, 1H), 4.15-4.00 (m, 2H), 3.43-3.35 (m, 1H), 3.07-3.02 (m, 3H), 2.87-2.79 (m, 1H), 2.80-2.03 (m, 1H), 1.37 (d, J=4 Hz, 3H), 1.28-1.21 (m, 2H), 1.11-1.06 (m, 2H).

Example 161: 1-((3S,5R)-1-Acryloyl-5-((difluoromethoxy)methyl)pyrrolidin-3-yl)-3-((1-cyclopropyl-6-fluoro-1H-benzo[d]imidazol-5-yl)ethynyl)-5-(methylamino)-1H-pyrazole-4-carboxamide

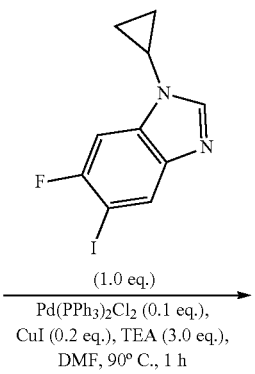

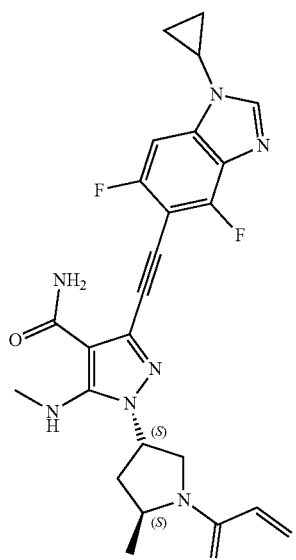

1-((3S,5R)-1-acryloyl-5-((difluoromethoxy)methyl)pyrrolidin-3-yl)-3-((1-cyclopropyl-6-fluoro-1H-benzo[d]imidazol-5-yl)ethynyl)-5-(methylamino)-1H-pyrazole-4-carboxamide. MS ESI calculated for $C_{26}H_{26}F_3N_7O_3$ [M+H]$^+$, 542.20, found 542.20; $^1$H NMR (400 MHz, CDCl$_3$) δ 7.99 (s, 2H), 7.33 (d, J=9.1 Hz, 1H), 7.13 (s, 1H), 6.83 (d, J=6.3 Hz, 1H), 6.53-6.40 (m, 2H), 6.23 (s, 1H), 5.82-5.71 (m, 1H), 5.57-5.33 (m, 2H), 4.66 (d, J=9.1 Hz, 1H), 4.44 (dd, J=10.4, 3.1 Hz, 1H), 4.24-3.81 (m, 3H), 3.39-3.34 (m, 1H), 3.05 (d, J=5.8 Hz, 3H), 2.85 (dt, J=12.7, 9.6 Hz, 1H), 2.38 (dd, J=13.1, 7.2 Hz, 1H), 1.22 (q, J=6.5, 5.9 Hz, 2H), 1.09-1.01 (m, 2H).

647

Example 162: 3-[2-(6-Chloro-1-cyclopropyl-1,3-benzodiazol-5-yl)ethynyl]-1-[(3S,5R)-5-(difluoromethyl)-1-(prop-2-enoyl)pyrrolidin-3-yl]-5-(methylamino)pyrazole-4-carboxamide

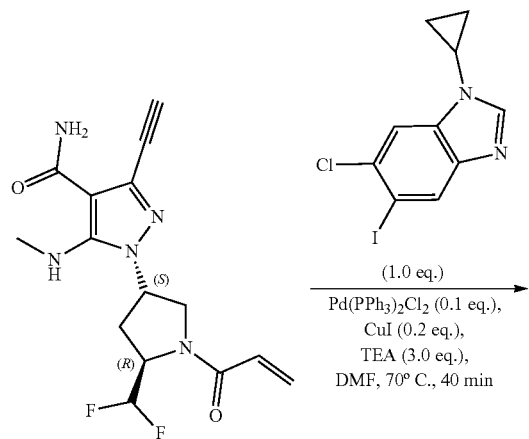

3-[2-(6-chloro-1-cyclopropyl-1,3-benzodiazol-5-yl)ethynyl]-1-[(3S,5R)-5-(difluoromethyl)-1-(prop-2-enoyl)pyrrolidin-3-yl]-5-(methylamino)pyrazole-4-carboxamide. MS ESI calculated for $C_{25}H_{24}ClF_2N_7O_2$ [M+H]$^+$, 528.16, found 528.20; $^1$H NMR (400 MHz, CDCl$_3$) δ 8.06 (d, J=22.6 Hz, 2H), 7.68 (s, 1H), 7.20 (s, 1H), 6.81 (s, 1H), 6.53-6.37 (m, 2H), 6.32-6.28 (m, 1H), 5.80-5.75 (m, 1H), 5.41-5.28 (m, 2H), 4.70-4.65 (m, 1H), 4.20-4.15 (m, 1H), 4.06-4.02 (m, 1H), 3.40-3.32 (m, 1H), 3.05 (s, 3H), 2.82-2.69 (m, 1H), 2.64-2.58 (m, 1H), 1.30-1.19 (m, 2H), 1.15-1.05 (m, 2H).

648

Example 163: 3-[2-(1-Cyclopropyl-4,6-difluoro-1,3-benzodiazol-5-yl)ethynyl]-1-[(3S,5R)-5-(difluoromethyl)-1-(prop-2-enoyl)pyrrolidin-3-yl]-5-(methylamino)pyrazole-4-carboxamide

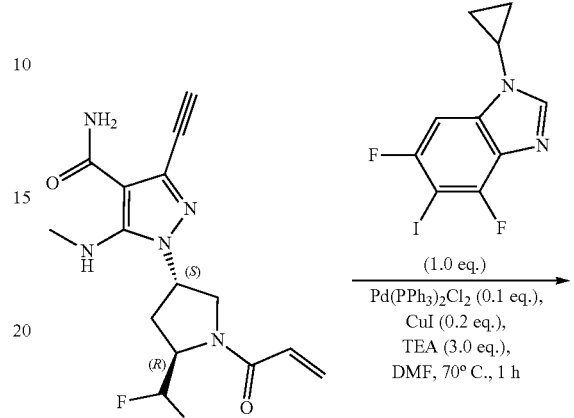

3-[2-(1-cyclopropyl-4,6-difluoro-1,3-benzodiazol-5-yl)ethynyl]-1-[(3S,5R)-5-(difluoromethyl)-1-(prop-2-enoyl)pyrrolidin-3-yl]-5-(methylamino)pyrazole-4-carboxamide. MS ESI calculated for $C_{25}H_{23}F_4N_7O_2$ [M+H]$^+$, 530.18, found 530.25; $^1$H NMR (400 MHz, CDCl$_3$) δ 7.97 (s, 1H), 7.18 (d, J=8.2 Hz, 1H), 7.07 (s, 1H), 6.52-6.37 (m, 2H), 6.34-6.13 (m, 1H), 5.80 (dd, J=8.6, 3.6 Hz, 1H), 5.45 (s, 1H), 5.32-5.31 (m, 1H), 4.70 (dd, J=28.9, 9.0 Hz, 1H), 4.20-4.17 (m, 1H), 4.06-4.03 (m, 1H), 3.41-3.37 (m, 1H), 3.05-3.02 (m, 3H), 2.75-2.70 (m, 1H), 2.63-2.60 (m, 1H), 1.29-1.17 (m, 2H), 1.17-1.05 (m, 2H).

Example 164: 1-((3S,5R)-1-Acryloyl-5-methylpyrrolidin-3-yl)-3-((1-cyclopropyl-6-fluoro-1H-benzo[d]imidazol-5-yl)ethynyl)-5-(methylamino)-1H-pyrazole-4-carboxamide
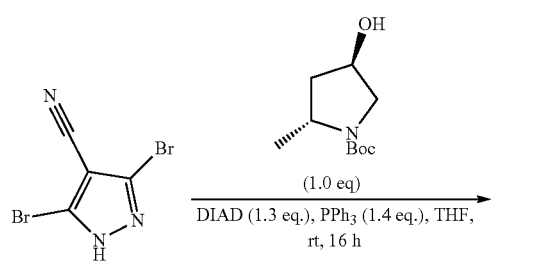
DIAD (1.3 eq.), PPh₃ (1.4 eq.), THF, rt, 16 h
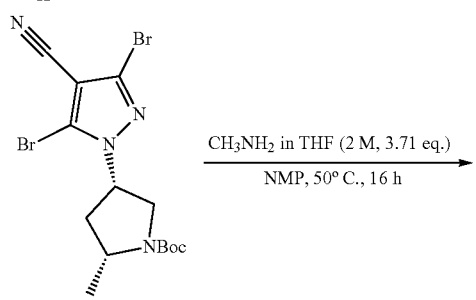
CH₃NH₂ in THF (2 M, 3.71 eq.)
NMP, 50° C., 16 h
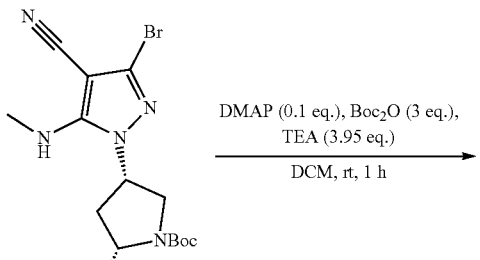
DMAP (0.1 eq.), Boc₂O (3 eq.), TEA (3.95 eq.)
DCM, rt, 1 h
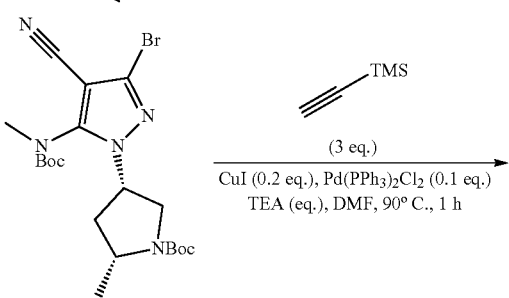
CuI (0.2 eq.), Pd(PPh₃)₂Cl₂ (0.1 eq.)
TEA (eq.), DMF, 90° C., 1 h
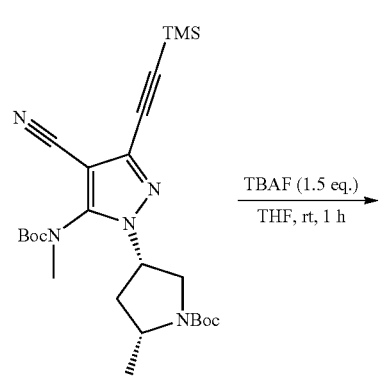
TBAF (1.5 eq.)
THF, rt, 1 h
-continued
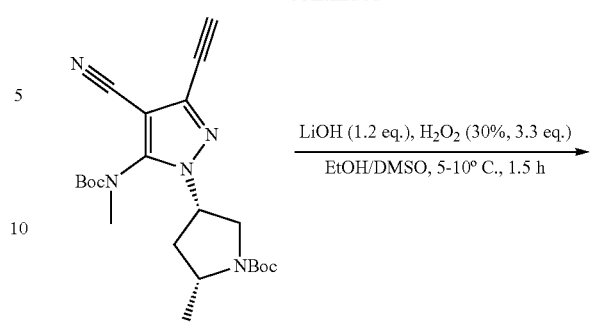
LiOH (1.2 eq.), H₂O₂ (30%, 3.3 eq.)
EtOH/DMSO, 5-10° C., 1.5 h
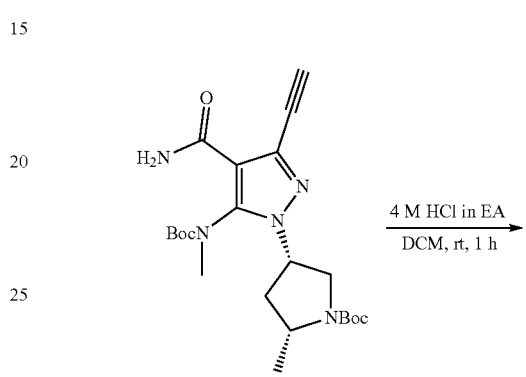
4 M HCl in EA
DCM, rt, 1 h
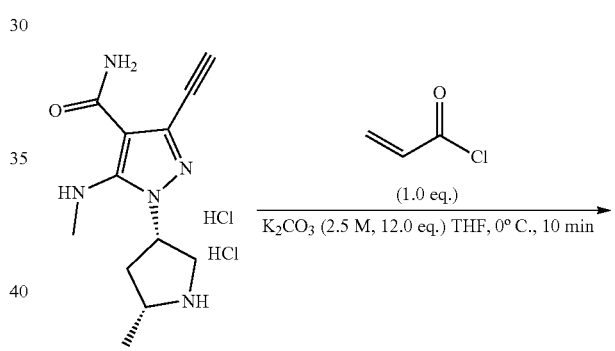
K₂CO₃ (2.5 M, 12.0 eq.) THF, 0° C., 10 min
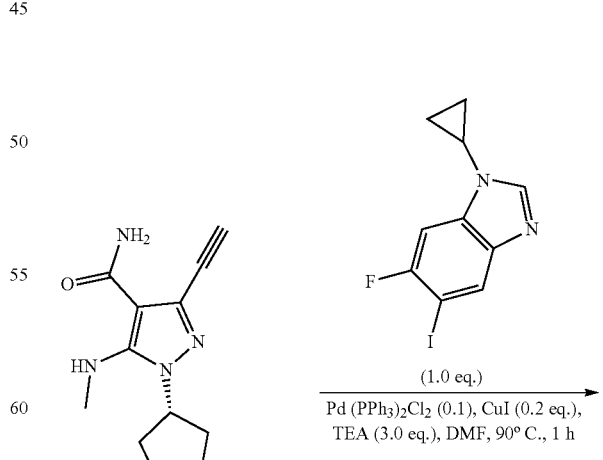
Pd(PPh₃)₂Cl₂ (0.1), CuI (0.2 eq.), TEA (3.0 eq.), DMF, 90° C., 1 h

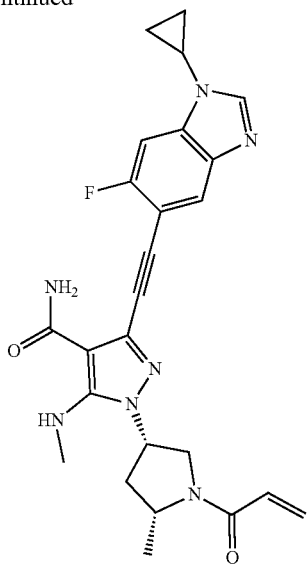

Step 1: Tert-butyl (2R,4S)-4-(3,5-dibromo-4-cyano-pyrazol-1-yl)-2-methylpyrrolidine-1-carboxylate To a stirred solution of 3,5-dibromo-1H-pyrazole-4-carbonitrile (21.19 g, 84.47 mmol), tert-butyl(2R,4R)-4-hydroxy-2-methylpyrrolidine-1-carboxylate (17 g, 84.47 mmol) and PPh3 (33.23 g, 0.12 mol) in THF (170.00 mL) was added DIAD (22.20 g, 0.11 mol) dropwise at 0° C. The reaction mixture was degassed with nitrogen for three times and stirred for 16 h at room temperature. The resulting mixture was concentrated under reduced pressure. The residue was purified by silica gel column chromatography, eluted with PE/EA (4/1). The fractions contained desired product were combined and concentrated to afford tert-butyl (2R,4S)-4-(3,5-dibromo-4-cyanopyrazol-1-yl)-2-methylpyrrolidine-1-carboxylate (42.70 g, 87%) as an off-white solid. MS ESI calculated for C14H18Br2N4O2 [M+H−56]+, 376.98, 378.98, 380.98, found 376.80, 378.80, 380.80; 1H NMR (400 MHz, CDCl3) δ 5.06-4.80 (m, 2H), 4.07 (d, J=51.2 Hz, 1H), 3.88-3.47 (m, 1H), 2.64-2.53 (m, 1H), 2.28 (s, 1H), 1.44-1.33 (m, 3H), 1.29 (s, 9H).

Step 2: Tert-butyl (2S,4S)-4-[3-bromo-4-cyano-5-(methylamino)pyrazol-1-yl]-2-methylpyrrolidine-1-carboxylate To a stirred solution of tert-butyl (2R,4S)-4-(3,5-dibromo-4-cyanopyrazol-1-yl)-2-methylpyrrolidine-1-carboxylate (44.65 g, 0.10 mol) in NMP (10.00 mL) was added CH3NH2 (0.19 L, 0.39 mol, 2 M in THF). The reaction mixture was stirred for 16 h at 50° C. under nitrogen atmosphere. The resulting mixture was concentrated under reduced pressure. The residue was purified by reverse phase chromatography with the following conditions: column: Spherical C18, 20-40 m, 330 g; Mobile Phase A: water (10 mmol/L NH4HCO3), Mobile Phase B: ACN; Flow rate: 80 mL/min; Gradient (B %): 30%~60% within 30 min; Detector: UV 254/210 nm. The fractions contained desired product were combined and concentrated to afford tert-butyl (2S,4S)-4-[3-bromo-4-cyano-5-(methylamino)pyrazol-1-yl]-2-methylpyrrolidine-1-carboxylate (24.30 g, 58%) as an off-white solid. MS ESI calculated for $C_{15}H_{22}BrN_5O_2$ [M+H−56]+, 328.10, 330.09, found 328.00, 330.00; 1H NMR (400 MHz, CDCl3) δ 4.89 (s, 1H), 4.37-4.24 (m, 1H), 3.98-3.88 (m, 1H), 3.91-3.80 (m, 1H), 3.40-3.35 (m, 1H), 3.18 (d, J=5.1 Hz, 3H), 2.44-2.39 (m, 1H), 2.37-2.24 (m, 1H), 1.46 (s, 9H), 1.35 (d, J=6.2 Hz, 3H).

Step 3: Tert-butyl (2R,4S)-4-{3-bromo-5-[(tert-butoxycarbonyl)(methyl)amino]-4-cyanopyrazol-1-yl}-2-methylpyrrolidine-1-carboxylate To a stirred solution of tert-butyl (2R,4S)-4-[3-bromo-4-cyano-5-(methylamino)pyrazol-1-yl]-2-methylpyrrolidine-1-carboxylate (24.30 g, 63.24 mmol) and DMAP (0.77 g, 6.32 mmol) in DCM (243.00 mL) were added TEA (35.16 mL, 0.25 mol) and Boc2O (41.40 g, 0.19 mol) dropwise at 0° C. under nitrogen atmosphere. The reaction mixture was stirred for 1 h at room temperature under nitrogen atmosphere. The resulting mixture was concentrated under reduced pressure. The residue was purified by silica gel column chromatography, eluted with PE/EA (4/1). The fractions contained desired product were combined and concentrated to afford tert-butyl (2R,4S)-4-{3-bromo-5-[(tert-butoxycarbonyl)(methyl)amino]-4-cyanopyrazol-1-yl}-2-methylpyrrolidine-1-carboxylate (26.80 g, 78%) as an off-white solid. MS ESI calculated for C20H30BrN5O4 [M+H−56]+, 428.15, 430.15, found 428.10, 430.10; 1H NMR (400 MHz, CDCl3) δ 4.53-4.45 (m, 1H), 3.96 (s, 2H), 3.56-3.48 (m, 1H), 3.23 (s, 3H), 2.51-2.44 (m, 1H), 2.23 (s, 1H), 1.47 (s, 18H), 1.42-1.36 (m, 3H).

Step 4: Tert-butyl (2R,4S)-4-{5-[(tert-butoxycarbonyl)(methyl)amino]-4-cyano-3-[2-(trimethylsilyl)ethynyl]pyrazol-1-yl}-2-methylpyrrolidine-1-carboxylate To a stirred mixture of tert-butyl (2R,4S)-4-{3-bromo-5-[(tert-butoxycarbonyl)(methyl)amino]-4-cyanopyrazol-1-yl}-2-methylpyrrolidine-1-carboxylate (26.80 g, 55.33 mmol), Pd(PPh3)2Cl2 (3.88 g, 5.53 mmol) and CuI (2.11 g, 11.07 mmol) in DMF (268.00 mL) were added TEA (23.07 mL, 0.16 mol) and trimethylsilylacetylene (23.46 mL, 0.16 mol) at room temperature under nitrogen atmosphere. The reaction mixture was degassed with nitrogen for three times and stirred for 1 h at 90° C. The resulting mixture was concentrated under reduced pressure. The residue was purified by silica gel column chromatography, eluted with 23% EA in PE. The fractions contained desired product were combined and concentrated tert-butyl (2R,4S)-4-{5-[(tert-butoxycarbonyl)(methyl)amino]-4-cyano-3-[2-(trimethylsilyl)ethynyl]pyrazol-1-yl}-2-methylpyrrolidine-1-carboxylate (22.30 g, 72%) as a brown solid. MS ESI calculated for C25H39N5O4Si [M+H]+, 502.28, found 502.35; 1H NMR (400 MHz, CDCl3) δ 4.53-4.46 (m, 1H), 3.98-3.92 (m, 2H), 3.68-3.41 (m, 1H), 3.24 (d, J=4.4 Hz, 3H), 2.49 (s, 1H), 2.30-2.25 (m, 1H), 1.48-1.45 (m, 18H), 1.41 (d, J=5.9 Hz, 3H), 0.30 (s, 9H).

Step 5: Tert-butyl (2R,4S)-4-{5-[(tert-butoxycarbonyl)(methyl)amino]-4-cyano-3-ethynylpyrazol-1-yl}-2-methylpyrrolidine-1-carboxylate To a stirred solution of tert-butyl (2R,4S)-4-{5-[(tert-butoxycarbonyl)(methyl)amino]-4-cyano-3-[2-(trimethylsilyl)ethynyl]pyrazol-1-yl}-2-methylpyrrolidine-1-carboxylate (22.30 g, 44.45 mmol) in THF (223.00 mL) was added 1 M TBAF in THF (66.67 mL, 66.67 mmol,) at 0° C. under nitrogen atmosphere. The reaction mixture was stirred for 1 h at room temperature. The resulting mixture was concentrated under reduced pressure. The residue was purified by silica gel column chromatography, eluted with 25% EA in PE. The fractions contained desired product were combined and concentrated to afford tert-butyl (2R,4S)-4-{5-[(tert-butoxycarbonyl)(methyl)amino]-4-cyano-3-ethynylpyrazol-1-yl}-2-methylpyrrolidine-1-carboxylate (14.30 g, 67%) as an off-white solid. MS ESI calculated for C22H31N5O4 [M+H−112]+, 318.24, found 318.05; 1H NMR (400 MHz, CDCl3) δ 4.56-4.51 (m, 1H), 3.99-3.95 (m, 2H), 3.74-3.44 (m, 1H), 3.39-3.32 (m, 1H), 3.25 (s, 3H), 2.63-2.39 (m, 1H), 2.38-2.14 (m, 1H), 1.54-1.49 (m, 18H), 1.40 (d, J=7.0 Hz, 3H).

Step 6: Tert-butyl (2R,4S)-4-{5-[(tert-butoxycarbonyl)(methyl)amino]-4-carbamoyl-3-ethynylpyrazol-1-yl}-2-methylpyrrolidine-1-carboxylate To a stirred solution of tert-butyl (2R,4S)-4-{5-[(tert-butoxycarbonyl)(methyl)amino]-4-cyano-3-ethynylpyrazol-1-yl}-2-methylpyrrolidine-1-carboxylate (14.30 g, 33.29 mmol) in EtOH (235.00 mL) and DMSO (47.00 mL) were added 0.5 M LiOH (79.90 mL, 39.95 mmol) and $H_2O_2$ (30%, 9.05 mL, 0.11 mol) at 0° C. The reaction mixture was stirred for 1.5 h at 5-10° C. The resulting mixture was quenched with sat. Na2SO3 (aq.) (2.5 M) at 0° C. The resulting mixture was diluted with water (500 mL) and extracted with EA (3×500 mL). The combined organic layers was washed with brine (5×300 mL), dried over anhydrous Na2SO4, filtered and concentrated under reduced pressure. The residue was purified by silica gel column chromatography, eluted with 63% EA in PE. The fractions contained desired product were combined and concentrated to afford tert-butyl (2R,4S)-4-{5-[(tert-butoxycarbonyl)(methyl)amino]-4-carbamoyl-3-ethynylpyrazol-1-yl}-2-methylpyrrolidine-1-carboxylate (16.50 g, 88%) as a light yellow solid. MS ESI calculated for C22H33N5O5 [M+H−156]+, 292.25, found 292.25; 1H NMR (400 MHz, CDCl3) δ 6.84 (s, 1H), 5.68 (s, 1H), 4.77-4.68 (m, 1H), 4.07-3.37 (m, 4H), 3.08-3.02 (m, 6H), 2.48-2.42 (m, 1H), 1.87 (s, 1H), 1.58-1.32 (m, 18H).

Step 7: 3-Ethynyl-5-(methylamino)-1-[(3S,5R)-5-methylpyrrolidin-3-yl]pyrazole-4-carboxamide dihydrochloride To a stirred mixture of tert-butyl (2R,4S)-4-{5-[(tert-butoxycarbonyl)(methyl)amino]-4-carbamoyl-3-ethynylpyrazol-1-yl}-2-methylpyrrolidine-1-carboxylate (16.50 g, 36.87 mmol) in DCM (165.00 mL) was added 4 M HCl in EA (165.00 mL, 0.66 mol). The reaction mixture was stirred for 1 h at room temperature. The precipitated solids were collected by filtration and washed with CH2Cl2 (3×50 mL). The filter cake was dried to afford 3-ethynyl-5-(methylamino)-1-[(3S,5R)-5-methylpyrrolidin-3-yl]pyrazole-4-carboxamide dihydrochloride (9.50 g, 68%) as a light yellow solid which was used in the next step directly without further purification. MS ESI calculated for C12H19Cl2N5O [M+H−2HCl]+, 248.14, found 248.05.

Step 8: 3-Ethynyl-1-[(3S,5R)-5-methyl-1-(prop-2-enoyl)pyrrolidin-3-yl]-5-(methylamino)pyrazole-4-carboxamide To a stirred mixture of 3-ethynyl-5-(methylamino)-1-[(3S,5R)-5-methylpyrrolidin-3-yl]pyrazole-4-carboxamide dihydrochloride (2.50 g, 7.81 mmol) and acryloyl chloride (0.71 g, 7.81 mmol) in THF (25.00 mL) was added 2.5 M K2CO3 (37.47 mL, 93.68 mmol) dropwise at 0° C. under nitrogen atmosphere. The resulting mixture was stirred for 10 min at 0° C. under nitrogen atmosphere. The resulting mixture was washed with 3×50 mL of water. The resulting mixture was extracted with EA (3×100 mL). The combined organic layers was washed with brine (2×50 mL), dried over anhydrous Na2SO4. After filtration, the filtrate was concentrated under reduced pressure. The residue was purified by silica gel column chromatography, eluted with CH2Cl2/MeOH (20/1). The fractions contained desired product were combined and concentrated to afford 3-ethynyl-1-[(3S,5R)-5-methyl-1-(prop-2-enoyl)pyrrolidin-3-yl]-5-(methylamino)pyrazole-4-carboxamide (2.40 g, 96%) as a white solid. MS ESI calculated for C15H19N5O2 [M+H]+, 302.15, found 302.10; 1H NMR (400 MHz, CDCl3) δ 6.81 (s, 1H), 6.54-6.42 (m, 1H), 6.41-6.30 (m, 1H), 5.84-5.64 (m, 1H), 5.42 (s, 1H), 4.86-4.81 (m, 1H), 4.50-3.76 (m, 3H), 3.48 (d, J=4.2 Hz, 1H), 2.98 (s, 3H), 2.74-2.54 (m, 1H), 2.52-2.28 (m, 1H), 1.45 (d, J=6.2 Hz, 3H).

Step 9: 1-((3S,5R)-1-Acryloyl-5-methylpyrrolidin-3-yl)-3-((1-cyclopropyl-6-fluoro-1H-benzo[d]imidazol-5-yl)ethynyl)-5-(methylamino)-1H-pyrazole-4-carboxamide To a stirred mixture of 3-ethynyl-1-[(3S,5R)-5-methyl-1-(prop-2-enoyl)pyrrolidin-3-yl]-5-(methylamino)pyrazole-4-carboxamide (0.25 g, 0.83 mmol), Pd(PPh3)2Cl2 (58.23 mg, 0.08 mmol), 1-cyclopropyl-6-fluoro-5-iodo-1,3-benzodiazole (0.25 g, 0.83 mmol) and CuI (31.60 mg, 0.17 mmol) in DMF (5.00 mL) was added TEA (0.35 mL, 2.49 mmol). The reaction mixture was degassed with argon for three timed and stirred for 1 h at 90° C. The resulting mixture was washed with 3×20 mL of water. The resulting mixture was extracted with EA (3×50 mL). The combined organic layers was washed with brine (3×20 mL), dried over anhydrous Na2SO4. After filtration, the filtrate was concentrated under reduced pressure. The residue was purified by silica gel column chromatography, eluted with CH2Cl2/MeOH (10/1) to afford the crude product which was further purified by reverse flash chromatography with the following conditions: column: C18 silica gel; mobile phase: ACN in water (10 mmol/L NH4HCO3), 40% to 60% gradient in 20 min; detector: UV 254 nm. The fractions contained desired product were combined and concentrated to afford 1-((3S,5R)-1-acryloyl-5-methylpyrrolidin-3-yl)-3-((1-cyclopropyl-6-fluoro-1H-benzo[d]imidazol-5-yl)ethynyl)-5-(methylamino)-1H-pyrazole-4-carboxamide (0.14 g, 36%) as a white solid. MS ESI calculated for C25H26FN7O2 [M+H]+, 476.21, found 476.20; 1H NMR (400 MHz, CDCl3) δ 8.08-7.86 (m, 2H), 7.42-7.24 (m, 1H), 7.15 (s, 1H), 6.68 (s, 1H), 6.59-6.27 (m, 2H), 5.83-5.64 (m, 1H), 5.50 (s, 1H), 4.83 (q, J=8.5 Hz, 1H), 4.57-3.80 (m, 3H), 3.39-3.32 (m, 1H), 2.99 (d, J=5.6 Hz, 3H), 2.77-2.26 (m, 2H), 1.48 (d, J=6.2 Hz, 3H), 1.29-1.16 (m, 2H), 1.14-0.98 (m, 2H).

Example 165: 3-[2-(1-Cyclopropyl-4,6-difluoro-1,3-benzodiazol-5-yl)ethynyl]-1-[(3S,5R)-5-methyl-1-(prop-2-enoyl)pyrrolidin-3-yl]-5-(methylamino)pyrazole-4-carboxamide

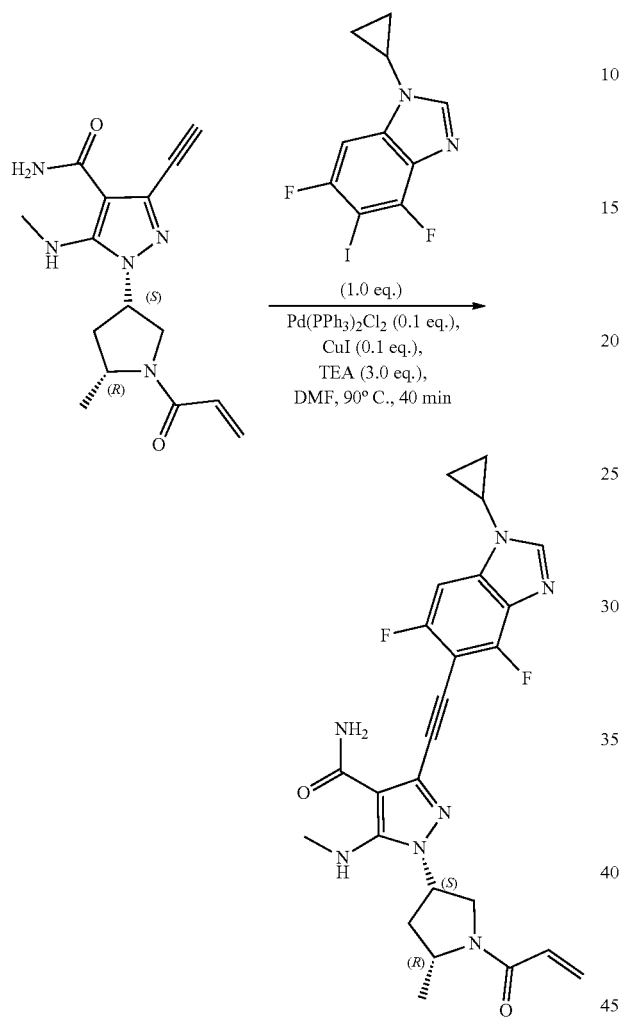

To a stirred solution of 3-ethynyl-1-[(3S,5R)-5-methyl-1-(prop-2-enoyl)pyrrolidin-3-yl]-5-(methylamino)pyrazole-4-carboxamide (0.30 g, 0.99 mmol), 1-cyclopropyl-4,6-difluoro-1,3-benzodiazole (0.19 g, 0.99 mmol), Pd(PPh3)2Cl2 (69.88 mg, 0.10 mmol) and CuI (37.92 mg, 0.20 mmol) in DMF (5.00 mL) was added TEA (0.42 mL, 2.98 mmol). The reaction mixture was degassed with argon for three times and stirred for 40 min at 90° C. The resulting mixture was cooled and concentrated under vacuum. The residue was purified by silica gel column chromatography, eluted with DCM/MeOH (10/1) to afford the crude product which was further purified by reverse phase flash with the following conditions: column, C18 silica gel; Mobile Phase A: water (10 mmol/L NH4HCO3), Mobile Phase B: ACN; Gradient: 20 B to 50 B in 30 min; 210/254 nm. The fractions contained desired product were combined and concentrated under reduced pressure to afford 3-[2-(1-cyclopropyl-4,6-difluoro-1,3-benzodiazol-5-yl)ethynyl]-1-[(3S,5R)-5-methyl-1-(prop-2-enoyl)pyrrolidin-3-yl]-5-(methylamino)pyrazole-4-carboxamide (0.10 g, 21%) as a white solid. MS ESI calculated for C25H25F2N7O2 [M+H]+, 494.20, found 494.10; 1H NMR (400 MHz, CDCl3) δ 7.97 (s, 1H), 7.26-6.99 (m, 2H), 6.68 (s, 1H), 6.58-6.29 (m, 2H), 5.82-5.61 (m, 1H), 5.43 (s, 1H), 4.92-4.77 (m, 1H), 4.56-4.09 (m, 2H), 4.09-3.80 (m, 1H), 3.48-3.36 (m, 1H), 3.00 (d, J=5.5 Hz, 3H), 2.83-2.29 (m, 2H), 1.49 (d, J=6.2 Hz, 3H), 1.32-1.25 (m, 2H), 1.19-1.05 (m, 2H).

Example 166: 1-((3S,5R)-1-Acryloyl-5-methylpyrrolidin-3-yl)-3-((6-chloro-1-cyclopropyl-1H-benzo[d]imidazol-5-yl)ethynyl)-5-(methylamino)-1H-pyrazole-4-carboxamide

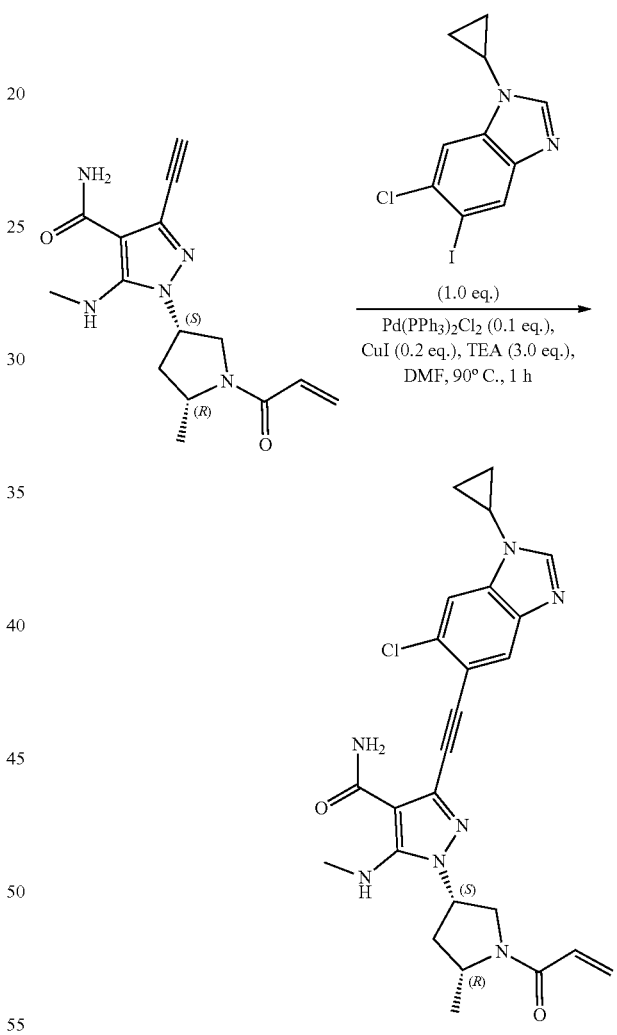

1-((3S,5R)-1-acryloyl-5-methylpyrrolidin-3-yl)-3-((6-chloro-1-cyclopropyl-1H-benzo[d]imidazol-5-yl)ethynyl)-5-(methylamino)-1H-pyrazole-4-carboxamide. MS ESI calculated for $C_{25}H_{26}ClN_7O_2$ [M+H]$^+$, 492.18, found 492.25; $^1$H NMR (400 MHz, CDCl$_3$) δ 8.10 (s, 1H), 8.02 (s, 1H), 7.68 (s, 1H), 7.22 (s, 1H), 6.67 (s, 1H), 6.54-6.36 (m, 2H), 5.81-5.67 (m, 1H), 5.45 (s, 1H), 4.84 (p, J=8.6, 7.9 Hz, 1H), 4.57-4.10 (m, 2H), 4.09-3.79 (m, 1H), 3.46-3.40 (m, 1H), 3.00 (s, 3H), 2.76-2.30 (m, 2H), 1.49 (d, J=6.2 Hz, 3H), 1.31-1.19 (m, 2H), 1.13-1.04 (m, 2H).

Example 167: 5-Amino-3-[2-(1-cyclopropyl-6-fluoro-1,3-benzodiazol-5-yl)ethynyl]-1-[(3S,5R)-5-(methoxymethyl)-1-(prop-2-enoyl)pyrrolidin-3-yl]pyrazole-4-carboxamide

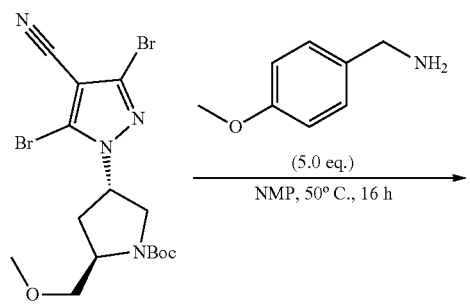

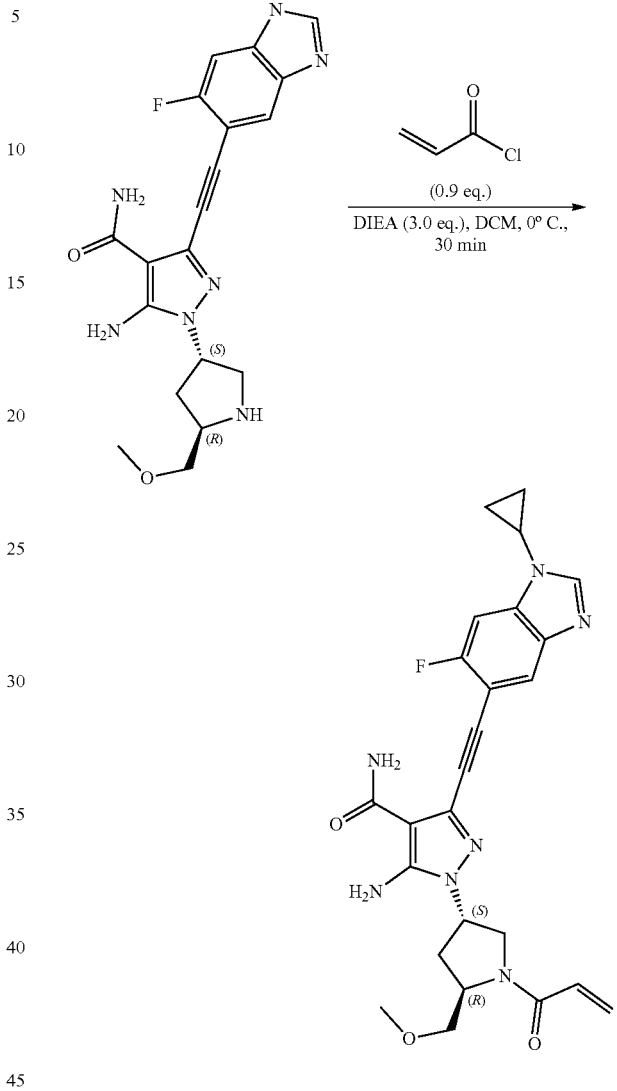

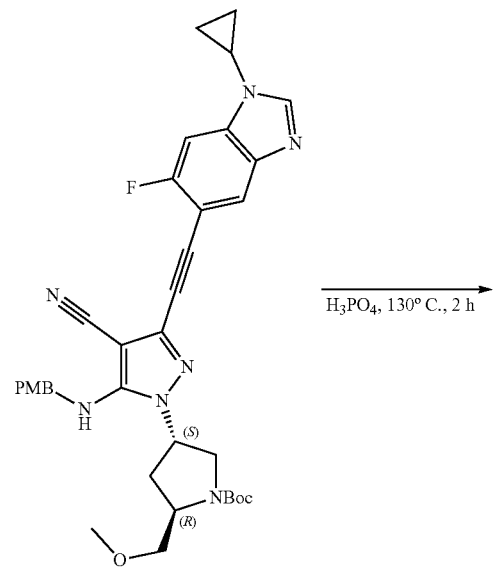

Step 1: Tert-butyl (2R,4S)-4-(3-bromo-4-cyano-5-((4-methoxybenzyl)amino)-1H-pyrazol-1-yl)-2-(methoxymethyl)pyrrolidine-1-carboxylate To a stirred solution of tert-butyl (2R,4S)-4-(3,5-dibromo-4-cyanopyrazol-1-yl)-2-(methoxymethyl)pyrrolidine-1-carboxylate (1.00 g, 2.15 mmol) and (4-methoxyphenyl)methanamine (1.48 g, 10.77 mmol) in NMP (10.00 mL) at room temperature under nitrogen atmosphere. The resulting mixture was stirred for 16 h at 50° C. under nitrogen atmosphere. The residue was purified by reverse flash chromatography with the following conditions: column: C18 silica gel; mobile phase: MeOH in water (10 mmol/L NH4HCO3), 10% to 50% gradient in 10 min; detector: UV 210 nm. The fractions contained desired product were combined and concentrated to afford tert-butyl (2R,4S)-4-(3-bromo-4-cyano-5-((4-methoxybenzyl)amino)-1H-pyrazol-1-yl)-2-(methoxymethyl)pyrrolidine-1-carboxylate (0.70 g, 62%) as an off-white solid. MS ESI calculated for C23H30BrN5O4 [M+H]+, 520.15, 522.15; found 520.15, 522.15; 1H NMR (400 MHz, CDCl3) δ 7.28-7.10 (d, J=1.8 Hz, 1H), 6.90-6.86

(m, 1H), 3.80-3.78 (s, 1H), 3.39-3.34 (m, 6H), 2.82-2.80 (d, J=0.8 Hz, 9H), 2.34-2.31 (t, J=8.1 Hz, 6H), 2.05-1.96 (m, 6H).

Step 2: Tert-butyl (2R,4S)-4-{4-cyano-3-[2-(1-cyclopropyl-6-fluoro-1,3-benzodiazol-5-yl)ethynyl]-5-{[(4-methoxyphenyl)methyl]amino}pyrazol-1-yl}-2-(methoxymethyl)pyrrolidine-1-carboxylates To a stirred mixture of tert-butyl (2R,4S)-4-(3-bromo-4-cyano-5-((4-methoxybenzyl)amino)-1H-pyrazol-1-yl)-2-(methoxymethyl)pyrrolidine-1-carboxylate (1.00 g, 1.92 mmol), Pd(PPh3)2Cl2 (0.13 g, 0.19 mmol), K2CO3 (0.80 g, 5.76 mmol), CuI (73.19 mg, 0.38 mmol) and TBAI (1.06 g, 2.88 mmol) in DMF (10.00 mL) was added 1-cyclopropyl-5-ethynyl-6-fluoro-1,3-benzodiazole (0.46 g, 2.30 mmol). The reaction mixture was degassed with argon for three times and stirred for 2 h at 100° C. The resulting mixture was cooled down and concentrated under vacuum. The residue was purified by silica gel column chromatography, eluted with DCM/MeOH (10/1). The fractions contained desired product were combined and concentrated under reduced pressure to afford tert-butyl (2R,4S)-4-{4-cyano-3-[2-(1-cyclopropyl-6-fluoro-1,3-benzodiazol-5-yl)ethynyl]-5-{[(4-methoxyphenyl)methyl]amino}pyrazol-1-yl}-2-(methoxymethyl)pyrrolidine-1-carboxylates (0.60 g, 48%) as a yellow solid. MS ESI calculated for C35H38FN7O4 [M+H]+, 640.30, found 640.55.

Step 3: 5-Amino-3-[2-(1-cyclopropyl-6-fluoro-1,3-benzodiazol-5-yl)ethynyl]-1-[(3S,5R)-5-(methoxymethyl)pyrrolidin-3-yl]pyrazole-4-carboxamide A solution of tert-butyl (2R,4S)-4-{4-cyano-3-[2-(1-cyclopropyl-6-fluoro-1,3-benzodiazol-5-yl)ethynyl]-5-{[(4-methoxyphenyl)methyl]amino}pyrazol-1-yl}-2-(methoxymethyl)pyrrolidine-1-carboxylates (0.60 g, 0.94 mmol) in H3PO4 (2.00 mL) was stirred for 2 h at 130° C. The reaction mixture was diluted with ice water (20 mL). The resulting mixture was extracted with EA (3×20 mL). The combined organic layers was washed with water (2×10 mL), dried over anhydrous Na2SO4. After filtration, the filtrate was concentrated under reduced pressure. The residue was purified by silica gel column chromatography, eluted with DCM/MeOH (15/1). The fractions contained desired product were combined and concentrated under reduced pressure to afford 5-amino-3-[2-(1-cyclopropyl-6-fluoro-1,3-benzodiazol-5-yl)ethynyl]-1-[(3S,5R)-5-(methoxymethyl)pyrrolidin-3-yl]pyrazole-4-carboxamide (0.26 g, 63%) as a yellow solid. MS ESI calculated for C22H24FN7O2 [M+H]+, 438.20, found 438.25.

Step 4: 5-Amino-3-[2-(1-cyclopropyl-6-fluoro-1,3-benzodiazol-5-yl)ethynyl]-1-[(3S,5R)-5-(methoxymethyl)-1-(prop-2-enoyl)pyrrolidin-3-yl]pyrazole-4-carboxamide To a stirred solution of 5-amino-3-[2-(1-cyclopropyl-6-fluoro-1,3-benzodiazol-5-yl)ethynyl]-1-[(3S,5R)-5-(methoxymethyl)pyrrolidin-3-yl]pyrazole-4-carboxamide (0.26 g, 0.59 mmol) in DCM (4.00 mL) and DIEA (0.31 mL, 1.78 mmol) was added acryloyl chloride (48.41 mg, 0.53 mmol) dropwise at 0° C. The reaction mixture was stirred for 30 min at 0° C. The resulting mixture was cooled down and concentrated under vacuum. The residue was purified by reverse phase flash with the following conditions: column: C18 silica gel; mobile phase: ACN in water (10 mmol/L NH4HCO3), 10% to 50% gradient in 30 min; detector: UV 254 nm. The fractions contained desired product were combined and concentrated under reduced pressure to afford 5-amino-3-[2-(1-cyclopropyl-6-fluoro-1,3-benzodiazol-5-yl)ethynyl]-1-[(3S,5R)-5-(methoxymethyl)-1-(prop-2-enoyl)pyrrolidin-3-yl]pyrazole-4-carboxamide (0.13 g, 44%) as a white solid. MS ESI calculated for C25H26FN7O3 [M+H]+, 492.21, found 492.15; 1H NMR (400 MHz, CDCl3) δ 7.98 (brs, 2H), 7.33 (d, J=9.1 Hz, 1H), 7.09 (s, 1H), 6.61-6.29 (m, 2H), 5.83-5.37 (m, 4H), 5.23-4.83 (m, 1H), 4.65-4.29 (m, 1H), 4.13-3.81 (m, 3H), 3.61-3.29 (m, 5H), 3.09-2.61 (m, 1H), 2.38-2.36 (m, 1H), 1.32-1.00 (m, 4H).

Example 168: 5-Amino-3-[2-(1-cyclopropyl-6-fluoro-1,3-benzodiazol-5-yl)ethynyl]-1-[(3S)-1-(prop-2-enoyl)pyrrolidin-3-yl]pyrazole-4-carboxamide

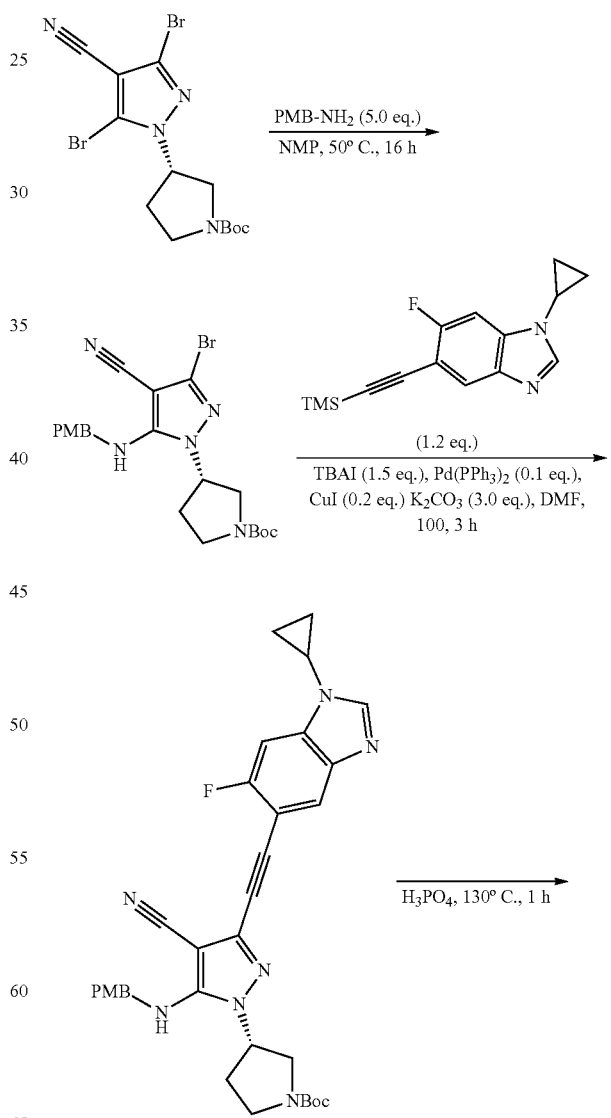

-continued

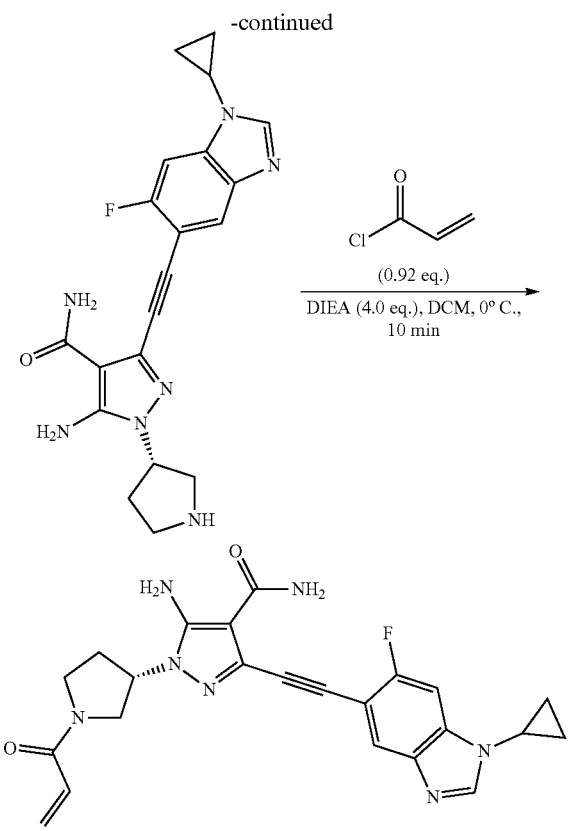

Step 1: Tert-butyl-(3S)-3-(3-bromo-4-cyano-5-{[(4-methoxyphenyl)methyl]amino}pyrazol-1-yl)pyrrolidine-1-carboxylate To a stirred solution of tert-butyl (3S)-3-(3,5-dibromo-4-cyanopyrazol-1-yl)pyrrolidine-1-carboxylate (5.00 g, 11.90 mmol) in NMP (50.00 mL) was added (4-methoxyphenyl)methanamine (8.16 g, 59.51 mmol) at room temperature. The reaction mixture was stirred for 16 h at 50° C. The resulting mixture was diluted with EA (50.00 mL). The residue was washed with water (3×30 mL). The combined organic layers was washed with brine (2×30 mL), dried over anhydrous Na2SO4. After filtration, the filtrate was concentrated under reduced pressure. The residue was purified by silica gel column chromatography, eluted with 35% EA in PE. The fractions contained desired product were combined and concentrated to afford tert-butyl (3S)-3-(3-bromo-4-cyano-5-{[(4-methoxyphenyl)methyl]amino}pyrazol-1-yl) pyrrolidine-1-carboxylate (4.80 g, 84%) as a light yellow oil. MS ESI calculated for C13H16Br2N4O2 [M+H−100]+, 376.12, found 376.15.

Step 2: Tert-butyl (3S)-3-{4-cyano-3-[2-(1-cyclopropyl-6-fluoro-1,3-benzodiazol-5-yl)ethynyl]-5-{[(4-methoxyphenyl)methyl]amino}pyrazol-1-yl}pyrrolidine-1-carboxylate To a stirred solution of tert-butyl (3S)-3-(3-bromo-4-cyano-5-{[(4-methoxyphenyl)methyl]amino}pyrazol-1-yl) pyrrolidine-1-carboxylate (2.00 g, 4.19 mmol) and 1-cyclopropyl-6-fluoro-5-[2-(trimethylsilyl)ethynyl]-1,3-benzodiazole (1.37 g, 5.04 mmol) in DMF (20.00 mL) were added 2.5 M K2CO3 (1.74 g, 12.59 mmol), TBAI (2.33 g, 6.29 mmol), CuI (0.16 g, 0.84 mmol) and Pd(PPh3)2Cl2 (0.29 g, 0.42 mmol). The reaction mixture was degassed with argon for three times and stirred for 3 h at 100° C. The resulting mixture was concentrated under reduced pressure. The residue was purified by silica gel column chromatography, eluted with 4% MeOH in DCM to afford the crude product which was further purified by reverse phase flash with the following conditions: column: Spherical C18, 20-40 m, 40 g; Mobile Phase A: water (10 mmol/L NH4HCO3); Mobile Phase B: ACN; Flow rate: 60 mL/min; Gradient (B %): 0% to 46% within 35 min; Detector: UV 254/220 nm. The fractions were combined and concentrated under reduced pressure to afford tert-butyl (3S)-3-{4-cyano-3-[2-(1-cyclopropyl-6-fluoro-1,3-benzodiazol-5-yl)ethynyl]-5-{[(4-methoxyphenyl)methyl]amino}pyrazol-1-yl}pyrrolidine-1-carboxylate (1.36 g, 54%) as a light yellow solid. MS ESI calculated for C33H34FN7O3 [M+H]+ 596.27; found 596.35; 1H NMR (400 MHz, CDCl3) δ 7.96-7.93 (m, 2H), 7.38-7.30 (m, 3H), 6.90 (d, J=8.2 Hz, 2H), 4.71 (s, 1H), 3.82 (s, 3H), 3.78-3.61 (m, 3H), 3.49-3.32 (m, 2H), 3.26 (s, 2H), 2.49-2.19 (m, 1H), 1.46 (s, 9H), 1.22-1.19 (m, 2H), 1.09-1.05 (m, 2H), 1.03-0.98 (m, 2H).

Step 3: (S)-5-Amino-3-((1-cyclopropyl-6-fluoro-1H-benzo[d]imidazol-5-yl)ethynyl)-1-(pyrrolidin-3-yl)-1H-pyrazole-4-carboxamide A solution of tert-butyl (3S)-3-{4-cyano-3-[2-(1-cyclopropyl-6-fluoro-1,3-benzodiazol-5-yl)ethynyl]-5-{[(4-methoxyphenyl)methyl]amino}pyrazol-1-yl}pyrrolidine-1-carboxylate (0.55 g, 0.92 mmol) in H3PO4 (5.50 mL) was stirred for 1 h at 130° C. The residue was basified to pH 8 with NaOH (aq.). The residue was purified by reverse phase flash with the following conditions: column: Spherical C18, 20-40 m, 40 g; Mobile Phase A: water (10 mmol/L NH4HCO3), Mobile Phase B: ACN; Flow rate: 60 mL/min; Gradient (B %): 0% hold 5 min, 5% to 22% within 10 min, 22% hold 5 min, 22% to 45% within 20 min, 45% hold 3 min, 45% to 95% within 2 min, 95% hold 5 min; Detector: UV 254/210 nm. The fractions were combined and concentrated under reduced pressure to afford (S)-5-amino-3-((1-cyclopropyl-6-fluoro-1H-benzo[d]imidazol-5-yl)ethynyl)-1-(pyrrolidin-3-yl)-1H-pyrazole-4-carboxamide (0.27 g, 73%) as a light green solid. MS ESI calculated for C20H20FN7O [M+H]+, 394.17, found 394.10; 1H NMR (400 MHz, CDCl3) δ 8.11-8.01 (m, 1H), 8.00-7.89 (m, 2H), 7.31 (d, J=8.9 Hz, 1H), 6.83 (d, J=9.4 Hz, 1H), 5.30 (s, 1H), 4.89 (s, 1H), 3.39-3.36 (m, 1H), 2.98 (s, 1H), 2.90 (s, 1H), 2.14 (s, 1H), 1.69 (s, 2H), 1.46 (s, 1H), 1.32-1.13 (m, 2H), 1.11-0.99 (m, 4H).

Step 4: 5-Amino-3-[2-(1-cyclopropyl-6-fluoro-1,3-benzodiazol-5-yl)ethynyl]-1-[(3S)-1-(prop-2-enoyl)pyrrolidin-3-yl]pyrazole-4-carboxamide To a stirred solution of (S)-5-amino-3-((1-cyclopropyl-6-fluoro-1H-benzo[d]imidazol-5-yl)ethynyl)-1-(pyrrolidin-3-yl)-1H-pyrazole-4-carboxamide (0.27 g, 0.68 mmol) and DIEA (0.35 g, 2.72 mmol) in DCM (10.00 mL) was added acryloyl chloride (2.50 mL, 0.62 mmol) dropwise at 0° C. under nitrogen atmosphere. The reaction mixture was stirred for 10 min at 0° C. under nitrogen atmosphere. The reaction was quenched with water (10 mL) at 0° C. The resulting mixture was extracted with EA (3×30 mL). The combined organic layers was washed with brine (2×20 mL), dried over anhydrous Na2SO4. After filtration, the filtrate was concentrated under reduced pressure. The residue was purified by silica gel column chromatography, eluted with 6% MeOH in DCM to afford the crude product which was further purified by reverse phase chromatography with the following conditions: column: Spherical C18, 20-40 m, 40 g; Mobile Phase A: water (10 mmol/L NH4HCO3), Mobile Phase B: ACN; Flow rate: 60 mL/min; Gradient (B %): 5% to 35% within 30 min; Detector: UV 254/210 nm. The collected fractions were combined and concentrated under reduced pressure to afford 5-amino-3-[2-(1-cyclopropyl-6-fluoro-1,3-benzodiazol-5-yl)ethynyl]-1-[(3S)-1-(prop-2-enoyl)pyrrolidin-3-yl]pyrazole-4-carboxamide (64.30 mg, 21%) as a white solid. MS ESI calculated for C23H22FN7O2 [M+H]+, 448.18, found 448.30; 1H NMR (400 MHz, CDCl3) δ 7.98 (d, J=6.6 Hz, 2H), 7.32 (d, J=9.0 Hz, 1H), 7.10 (s, 1H), 6.55-6.34 (m, 2H), 5.81-5.58 (m, 3H), 5.43 (s, 1H), 4.76-4.72 (m, 1H), 4.11-3.90 (m, 3H), 3.84-3.60 (m, 1H), 3.39-3.35 (m, 1H), 2.85-2.53 (m, 1H), 2.47-2.28 (m, 1H), 1.24-1.19 (m, 2H), 1.13-1.01 (m, 2H).

Example 169: 1-((3S,5S)-1-Acryloyl-5-methylpyrrolidin-3-yl)-3-((1-cyclopropyl-6-fluoro-1H-benzo[d]imidazol-5-yl)ethynyl)-5-(methylamino)-1H-pyrazole-4-carboxamide

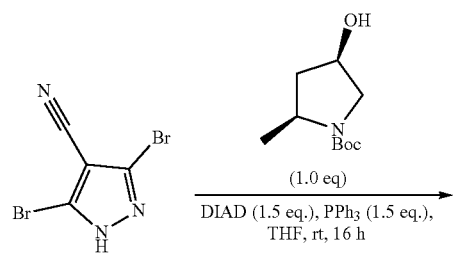

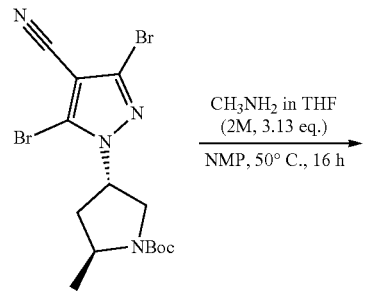

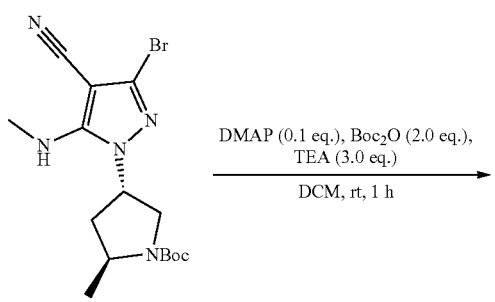

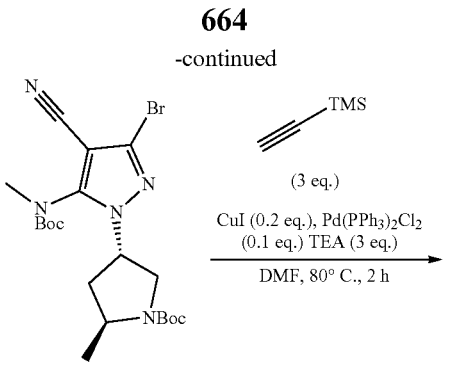

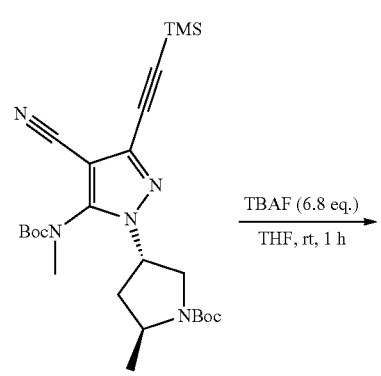

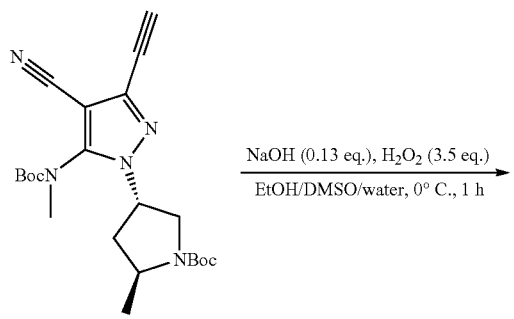

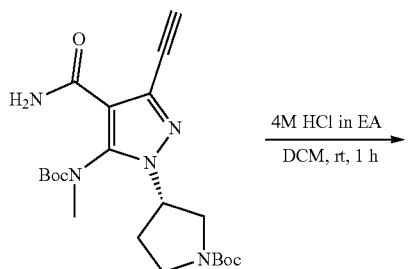

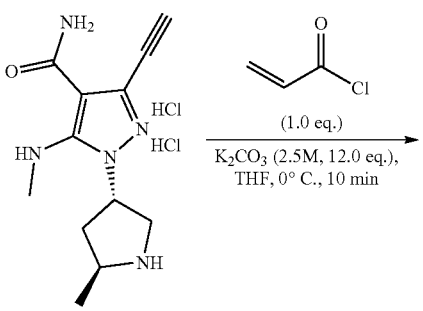

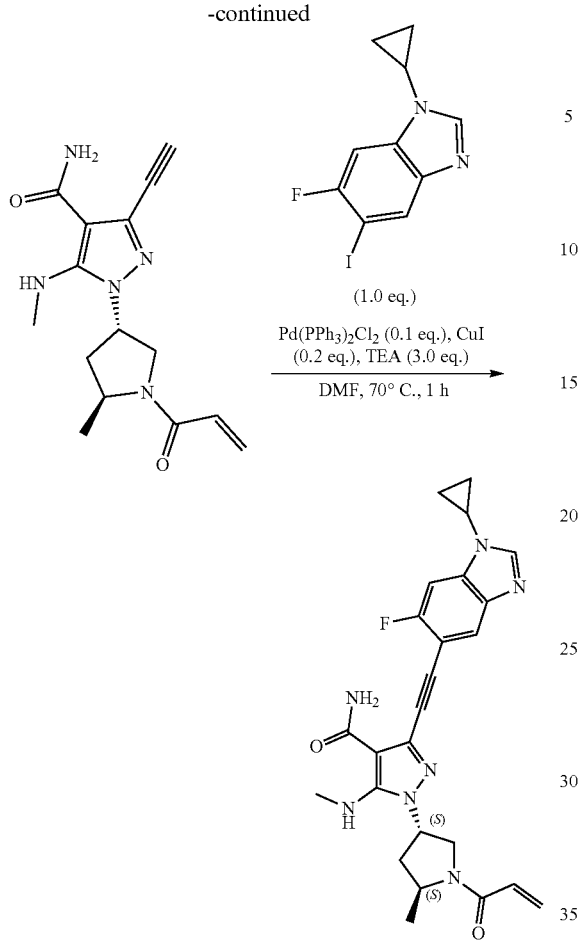

1-((3S,5S)-1-acryloyl-5-methylpyrrolidin-3-yl)-3-((1-cyclopropyl-6-fluoro-1H-benzo[d]imidazol-5-yl)ethynyl)-5-(methylamino)-1H-pyrazole-4-carboxamide. MS ESI calculated for $C_{25}H_{26}FN_7O_2$ [M+H]$^+$, 476.21, found 476.25; $^1$H NMR (400 MHz, DMSO-d$_6$) δ 8.36 (s, 1H), 7.95 (d, J=6.2 Hz, 1H), 7.63 (d, J=9.4 Hz, 1H), 7.47 (s, 1H), 6.81 (s, 1H), 6.72-6.50 (m, 2H), 6.19-6.16 (m, 1H), 5.70-5.67 (m, 1H), 5.24-5.21 (m, 1H), 4.53-4.27 (m, 1H), 3.99-3.96 (m, 1H), 3.82 (d, J=6.8 Hz, 1H), 3.57-3.47 (m, 1H), 2.96 (dd, J=5.7, 1.2 Hz, 3H), 2.76-2.54 (m, 1H), 2.24-1.94 (m, 1H), 1.26 (dd, J=6.5, 2.3 Hz, 3H), 1.15-1.00 (m, 4H).

Example 170: 3-[2-(1-Cyclopropyl-6-fluoro-1,3-benzodiazol-5-yl)ethynyl]-1-[(3S,5R)-5-(difluoromethyl)-1-(prop-2-enoyl)pyrrolidin-3-yl]-5-(methylamino)pyrazole-4-carboxamide

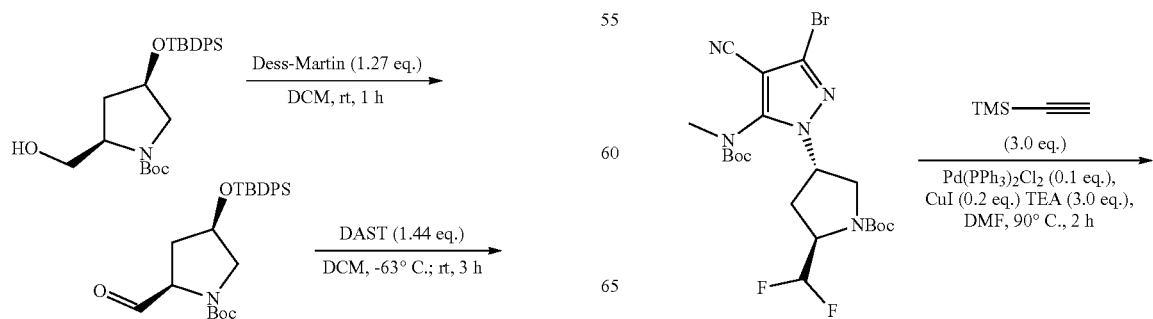

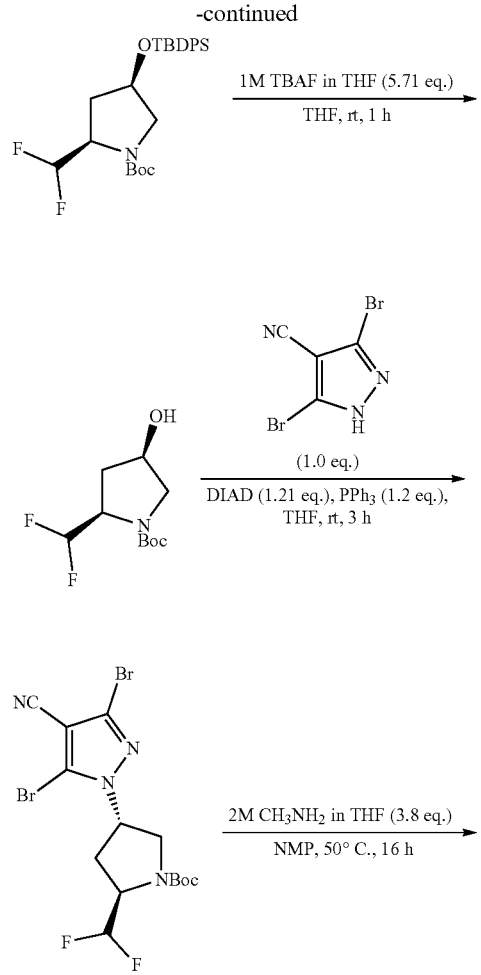

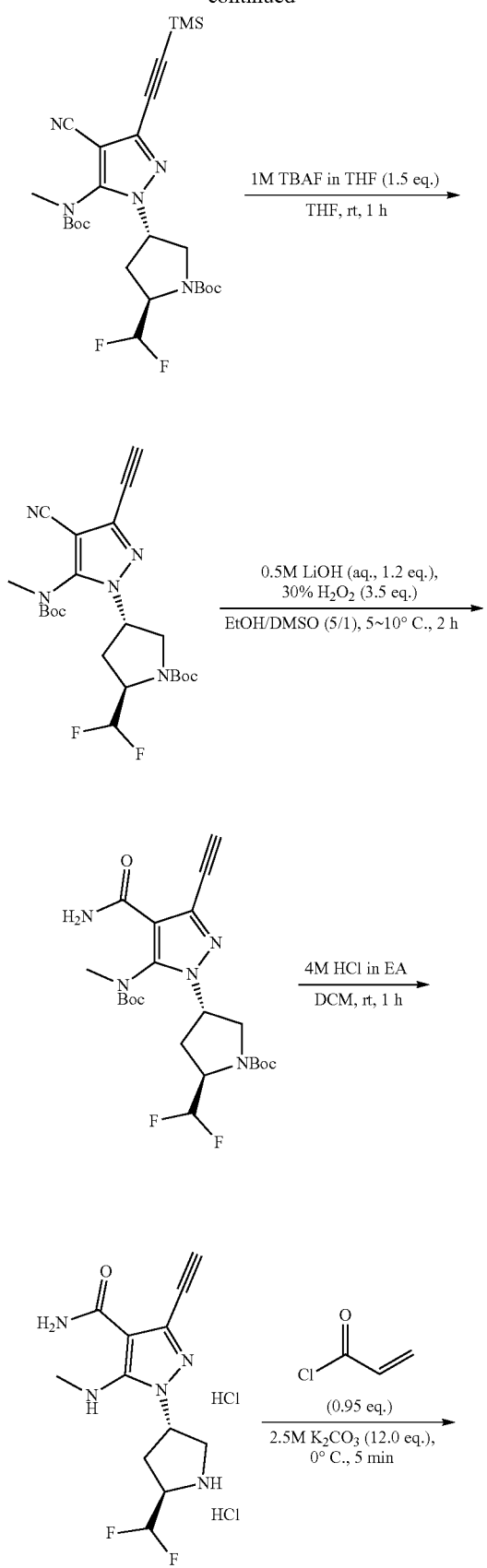
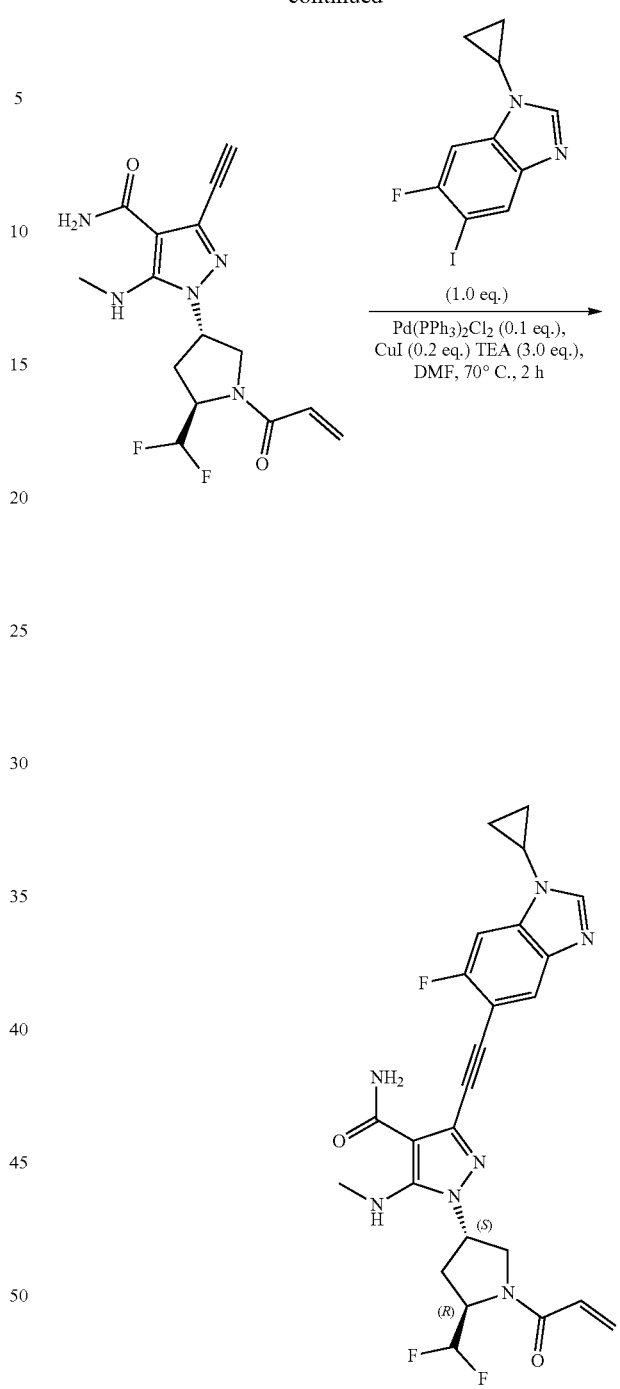
3-[2-(1-cyclopropyl-6-fluoro-1,3-benzodiazol-5-yl)ethynyl]-1-[(3S,5R)-5-(difluoromethyl)-1-(prop-2-enoyl)pyrrolidin-3-yl]-5-(methylamino)pyrazole-4-carboxamide. MS ESI calculated for $C_{25}H_{24}F_3N_7O_2$ [M+H]$^+$, 512.19, found 512.05; $^1$H NMR (400 MHz, CDCl$_3$) δ 8.01 (s, 1H), 7.98 (d, J=6.0 Hz, 1H), 7.33 (d, J=9.2 Hz, 1H), 7.13 (s, 1H), 6.82 (s, 1H), 6.50-6.17 (m, 3H), 5.82-5.79 (m, 1H), 5.42-5.30 (m, 2H), 4.75-4.65 (m, 1H), 4.21-4.17 (m, 1H), 4.09-4.04 (m, 1H), 3.41-3.37 (m, 1H), 3.05 (s, 3H), 2.79-2.71 (m, 1H), 2.66-2.63 (m, 1H), 1.25-1.20 (m, 2H), 1.10-1.06 (m, 2H).

Example 171: 3-[2-(1-Cyclopropyl-6,7-difluoro-1,3-benzodiazol-5-yl)ethynyl]-5-(methylamino)-1-[(3S)-1-(prop-2-enoyl)pyrrolidin-3-yl]pyrazole-4-carboxamide

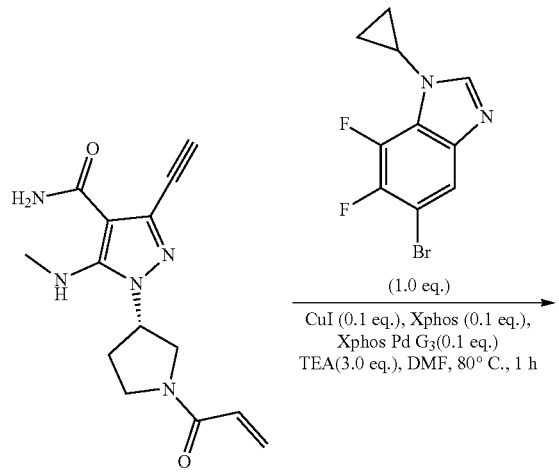

3-[2-(1-cyclopropyl-6,7-difluoro-1,3-benzodiazol-5-yl)ethynyl]-5-(methylamino)-1-[(3S)-1-(prop-2-enoyl)pyrrolidin-3-yl]pyrazole-4-carboxamide. MS ESI calculated for $C_{24}H_{23}F_2N_7O_2$ [M+H]$^+$, 480.19, found 480.25; $^1$H NMR (400 MHz, CDCl$_3$) δ 7.93 (d, J=1.6 Hz, 1H), 7.78-7.72 (m, 1H), 7.04 (s, 1H), 6.74-6.68 (m, 1H), 6.58-6.35 (m, 2H), 5.77-5.68 (m, 1H), 5.50 (s, 1H), 5.13-4.97 (m, 1H), 4.14-4.04 (m, 3H), 3.83-3.53 (m, 2H), 3.02 (t, J=5.6 Hz, 3H), 2.80-2.55 (m, 1H), 2.45-2.40 (m, 1H), 1.26-1.23 (m, 2H), 1.17-1.13 (m, 2H).

Example 172: 3-((1-Cyclopropyl-6-fluoro-1H-benzo[d]imidazol-5-yl)ethynyl)-1-(1-(2-fluoroacryloyl)azetidin-3-yl)-5-(methylamino)-1H-pyrazole-4-carboxamide

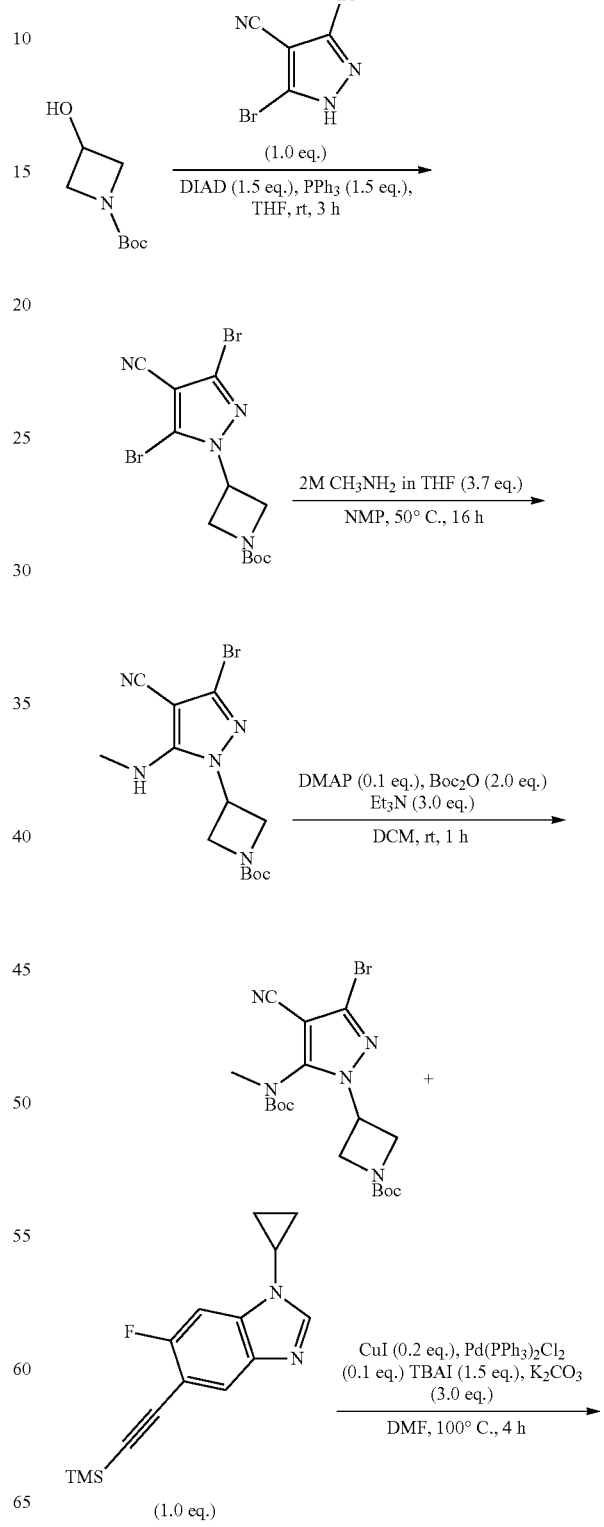

671

-continued

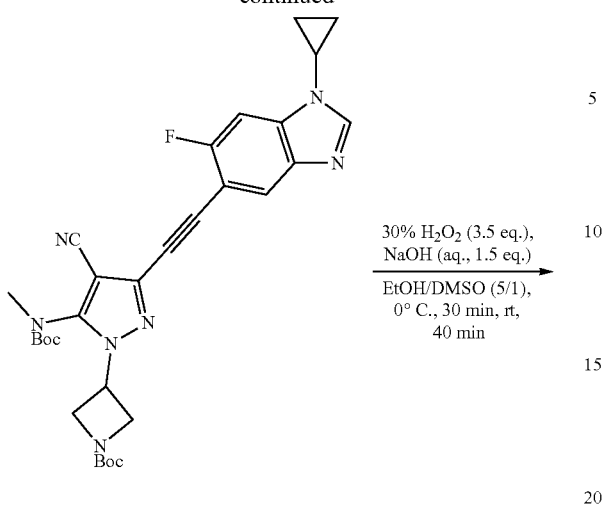

30% H₂O₂ (3.5 eq.),
NaOH (aq., 1.5 eq.)
———————————→
EtOH/DMSO (5/1),
0° C., 30 min, rt,
40 min

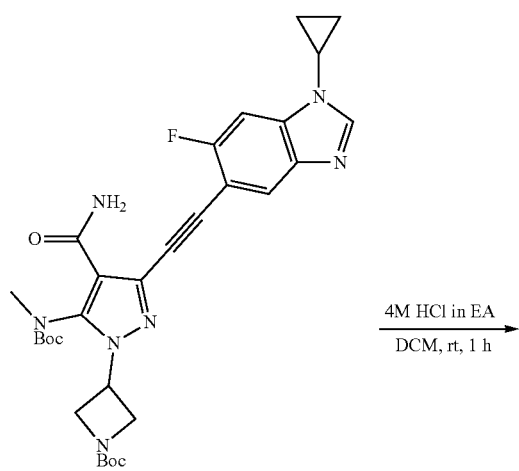

4M HCl in EA
——————→
DCM, rt, 1 h

672

-continued

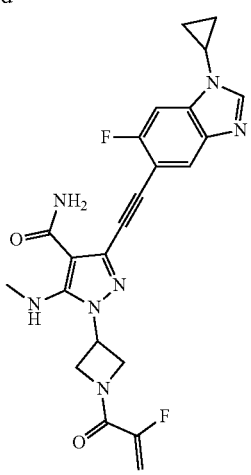

3-((1-cyclopropyl-6-fluoro-1H-benzo[d]imidazol-5-yl) ethynyl)-1-(1-(2-fluoroacryloyl)azetidin-3-yl)-5-(methylamino)-1H-pyrazole-4-carboxamide. MS ESI calculated for $C_{23}H_{21}F_2N_7O_2$ [M+H]⁺, 466.17, found 466.05; ¹H NMR (400 MHz, CDCl₃) δ 7.98 (d, J=4.7 Hz, 2H), 7.31 (d, J=9.1 Hz, 1H), 7.13 (s, 1H), 6.71 (q, J=6.0 Hz, 1H), 5.76-5.50 (m, 2H), 5.29-5.21 (m, 1H), 5.16-5.00 (m, 2H), 4.79 (s, 1H), 4.65 (dd, J=11.4, 5.8 Hz, 1H), 4.53 (t, J=9.7 Hz, 1H), 3.39-3.35 (m, 1H), 2.95 (d, J=5.8 Hz, 3H), 1.20 (d, J=7.2 Hz, 2H), 1.06 (s, 2H).

Example 173: 3-((1-Cyclopropyl-4,6-difluoro-1H-benzo[d]imidazol-5-yl)ethynyl)-1-(1-(2-fluoroacryloyl)azetidin-3-yl)-5-(methylamino)-1H-pyrazole-4-carboxamide

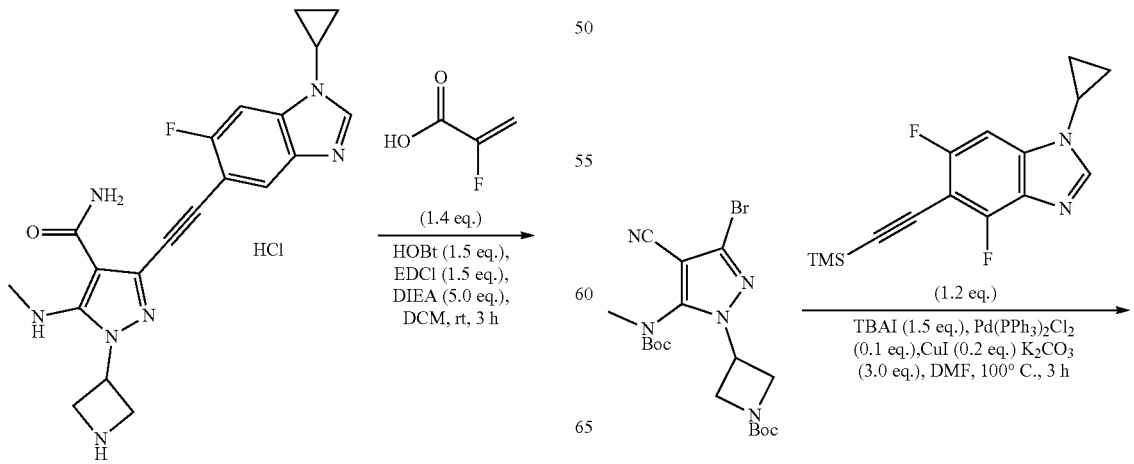

673
-continued

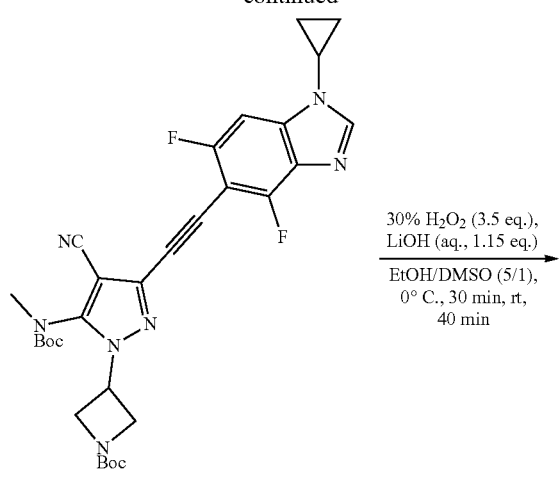

30% H₂O₂ (3.5 eq.),
LiOH (aq., 1.15 eq.)
———————————→
EtOH/DMSO (5/1),
0° C., 30 min, rt,
40 min

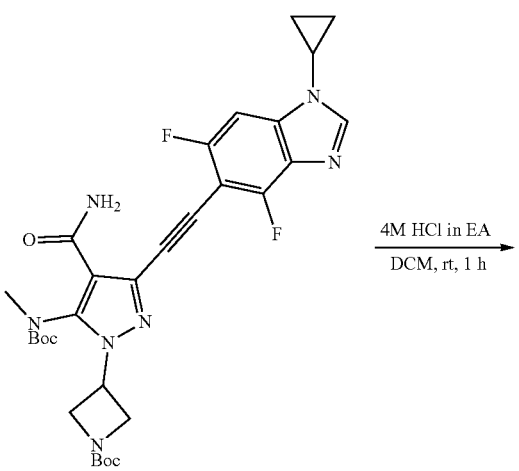

4M HCl in EA
————————→
DCM, rt, 1 h

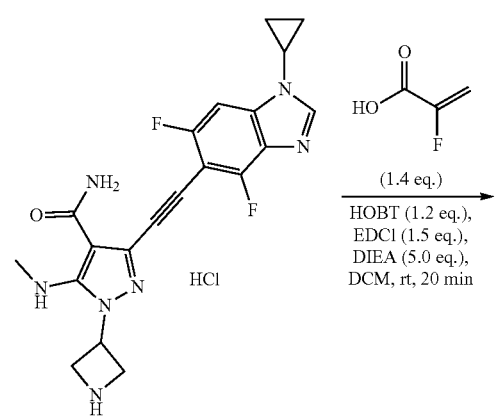

(1.4 eq.)
HOBT (1.2 eq.),
EDCl (1.5 eq.),
DIEA (5.0 eq.),
DCM, rt, 20 min
———————————→

674
-continued

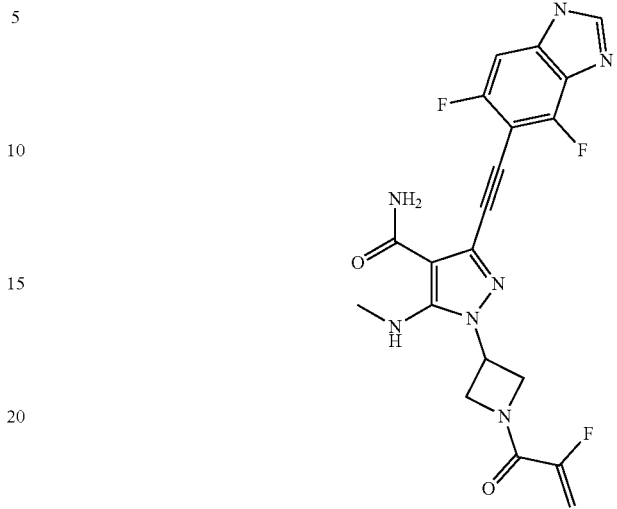

Step 1: Tert-butyl 3-{5-[(tert-butoxycarbonyl)
(methyl)amino]-4-cyano-3-[2-(1-cyclopropyl-4,6-
difluoro-1,3-benzodiazol-5-yl)ethynyl]pyrazol-1-
yl}azetidine-1-carboxylate To a stirred solution of tert-butyl 3-{3-bromo-5-[(tert-butoxycarbonyl)(methyl)amino]-4-cyanopyrazol-1-yl}azetidine-1-carboxylate (1.50 g, 3.29 mmol) and 1-cyclopropyl-4,6-difluoro-5-[2-(trimethylsilyl)ethynyl]-1,3-benzodiazole (1.15 g, 3.94 mmol) in DMF (20.00 mL) were added K2CO3 (1.36 g, 9.86 mmol), TBAI (1.82 g, 4.93 mmol), CuI (0.13 g, 0.65 mmol) and Pd(PPh3)2Cl2 (0.23 g, 0.32 mmol) at room temperature under nitrogen atmosphere. The reaction mixture was degassed with nitrogen for three times and stirred for 3 h at 100° C. The resulting mixture was concentrated under reduced pressure. The residue was purified by silica gel column chromatography, eluted with 58% EA in PE. The fractions contained desired product were combined and concentrated to afford tert-butyl 3-{5-[(tert-butoxycarbonyl)(methyl)amino]-4-cyano-3-[2-(1-cyclopropyl-4,6-difluoro-1,3-benzodiazol-5-yl)ethynyl]pyrazol-1-yl}azetidine-1-carboxylate (1.20 g, 61%) as a light yellow solid. MS ESI calculated for C30H33F2N7O4 [M+H]+, 594.26, found 594.34; 1H NMR (400 MHz, CDCl3) δ 8.02 (s, 1H), 7.19 (d, J=8.0 Hz, 1H), 4.91 (s, 1H), 4.54 (s, 1H), 4.32 (t, J=7.8 Hz, 3H), 3.43-3.39 (m, 1H), 3.29 (s, 3H), 1.48 (s, 18H), 1.29-1.23 (m, 2H), 1.13-1.06 (m, 2H).

Step 2: Tert-butyl 3-{5-[(tert-butoxycarbonyl)
(methyl)amino]-4-carbamoyl-3-[2-(1-cyclopropyl-4,
6-difluoro-1,3-benzodiazol-5-yl)ethynyl]pyrazol-1-
yl}azetidine-1-carboxylate To a stirred solution of tert-butyl 3-{5-[(tert-butoxycarbonyl)(methyl)amino]-4-cyano-3-[2-(1-cyclopropyl-4,6-difluoro-1,3-benzodiazol-5-yl)ethynyl]pyrazol-1-yl}azetidine-1-carboxylate (0.60 g, 1.01 mmol) and 30% H2O2 (0.36 mL, 3.53 mmol) in EtOH (10.00 mL) and DMSO (2.00 mL) was added LiOH (2.32 mL, 1.16 mmol) dropwise at 0° C. under nitrogen atmosphere. The reaction mixture was stirred for 30 min at 0° C. and 40 min at room temperature under nitrogen atmosphere. The resulting mixture was diluted with EA (10.00 mL). The residue was washed with water (3×5 mL). The combined organic layers were washed with brine (2×5 mL), dried over anhydrous Na2SO4. After filtration, the filtrate was concentrated under reduced pressure. The residue was purified by silica gel column chromatography, eluted with MeOH in DCM (0-3%). The fractions contained desired product were combined and concentrated to afford tert-butyl 3-{5-[(tert-butoxycarbonyl)(methyl)amino]-4-carbamoyl-3-[2-(1-cyclopropyl-4,6-difluoro-1,3-benzodiazol-5-yl)ethynyl]pyrazol-1-yl}azetidine-1-carboxylate (0.49 g, 78%) as a light yellow solid. MS ESI calculated for C30H35F2N7O5 [M+H]+, 612.27, found 612.35.

Step 3: 1-(Azetidin-3-yl)-3-[2-(1-cyclopropyl-4,6-difluoro-1,3-benzodiazol-5-yl)ethynyl]-5-(methylamino)pyrazole-4-carboxamide hydrochloride To a stirred solution of tert-butyl 3-{5-[(tert-butoxycarbonyl)(methyl)amino]-4-carbamoyl-3-[2-(1-cyclopropyl-4,6-difluoro-1,3-benzodiazol-5-yl)ethynyl]pyrazol-1-yl}azetidine-1-carboxylate (0.46 g, 0.79 mmol) in DCM (10.00 mL) was added HCl (4 M in EA) (10.00 mL) dropwise at 0° C. under nitrogen atmosphere. The reaction mixture was stirred for 1 h at room temperature under nitrogen atmosphere. The resulting mixture was concentrated under reduced pressure to afford 1-(azetidin-3-yl)-3-[2-(1-cyclopropyl-4,6-difluoro-1,3-benzodiazol-5-yl)ethynyl]-5-(methylamino)pyrazole-4-carboxamide hydrochloride (0.32 g, crude) as a light yellow solid. MS ESI calculated for C20H20ClF2N7O [M+H−HCl]+, 412.16, found 412.10.

Step 4: 3-((1-Cyclopropyl-4,6-difluoro-1H-benzo[d]imidazol-5-yl)ethynyl)-1-(1-(2-fluoroacryloyl)azetidin-3-yl)-5-(methylamino)-1H-pyrazole-4-carboxamide To a stirred solution of 1-(azetidin-3-yl)-3-[2-(1-cyclopropyl-4,6-difluoro-1,3-benzodiazol-5-yl)ethynyl]-5-(methylamino)pyrazole-4-carboxamide hydrochloride (0.33 g, 0.67 mmol) and 2-fluoroprop-2-enoic acid (85.38 mg, 0.94 mmol) in DCM (6.00 mL) was added HOBT (0.14 g, 1.02 mmol), EDCI (0.20 g, 1.02 mmol) and DIEA (0.43 g, 3.38 mmol) dropwise at 0° C. The reaction mixture was stirred for 20 min at room temperature. The residue was purified by silica gel column chromatography, eluted with MeOH in DCM (0-4%) to afford the crude product which was further purified by reverse phase flash with the following conditions: Column: Spherical C18, 20-40 m, 40 g; Mobile Phase A: water (10 mmol/L NH4HCO3), Mobile Phase B: ACN; Flow rate: 60 mL/min; Gradient: 5B to 35B in 30 min; Detector: UV 254/210 nm. The fractions contained desired product were combined and concentrated to afford 3-((1-cyclopropyl-4,6-difluoro-1H-benzo[d]imidazol-5-yl)ethynyl)-1-(1-(2-fluoroacryloyl)azetidin-3-yl)-5-(methylamino)-1H-pyrazole-4-carboxamide (84.80 mg, 25%) as a white solid. MS ESI calculated for C23H20F3N7O2 [M+H]+, 484.16, found 484.15; 1H NMR (400 MHz, CDCl3) δ 7.97 (s, 1H), 7.19 (d, J=8.2 Hz, 1H), 7.10 (s, 1H), 6.72 (s, 1H), 5.74 (d, J=3.1 Hz, 1H), 5.67-5.40 (m, 1H), 5.33-5.26 (m, 1H), 5.17-4.98 (m, 2H), 4.81 (s, 1H), 4.68-4.66 (m, 1H), 4.55 (t, J=9.6 Hz, 1H), 3.40-3.36 (m, 1H), 2.96 (s, 3H), 1.30-1.20 (m, 2H), 1.15-1.06 (m, 2H).

Example 174: 1-((3S,5R)-1-Acryloyl-5-(hydroxymethyl)pyrrolidin-3-yl)-3-((1-cyclopropyl-6-fluoro-1H-benzo[d]imidazol-5-yl)ethynyl)-5-(methylamino)-1H-pyrazole-4-carboxamide

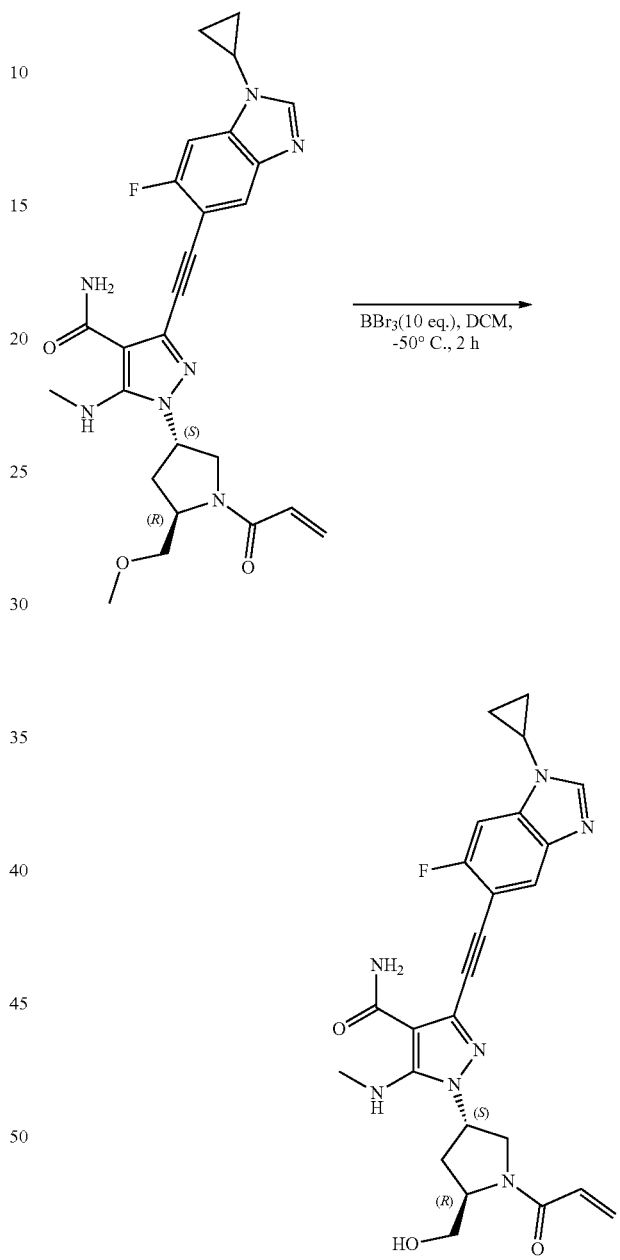

1-((3S,5R)-1-Acryloyl-5-(hydroxymethyl)pyrrolidin-3-yl)-3-((1-cyclopropyl-6-fluoro-1H-benzo[d]imidazol-5-yl)ethynyl)-5-(methylamino)-1H-pyrazole-4-carboxamide. MS ESI calculated for C25H26FN7O3 [M+H]+, 492.21, found 492.10; 1H NMR (400 MHz, DMSO-d6) δ 8.37 (s, 1H), 7.96-7.76 (m, 1H), 7.65 (d, J=9.4 Hz, 1H), 7.50 (s, 1H), 6.77 (d, J=18.5 Hz, 1H), 6.73-6.53 (m, 2H), 6.17-5.95 (m, 1H), 5.69-5.36 (m, 1H), 5.30-5.08 (m, 1H), 5.04-4.83 (m, 1H), 4.34-4.19 (m, 1H), 4.09-3.74 (m, 2H), 3.71-3.44 (m, 3H), 2.96-2.72 (m, 3H), 2.63-2.57 (m, 1H), 2.40-2.26 (m, 1H), 1.14-1.08 (m, 2H), 1.08-1.02 (m, 2H).

Example 175: Tert-butyl 3-[2-(1-cyclopropyl-6-fluoro-1,3-benzodiazol-5-yl)ethynyl]-5-(methylamino)-1-[1-(prop-2-enoyl)azetidin-3-yl]pyrazole-4-carboxamide

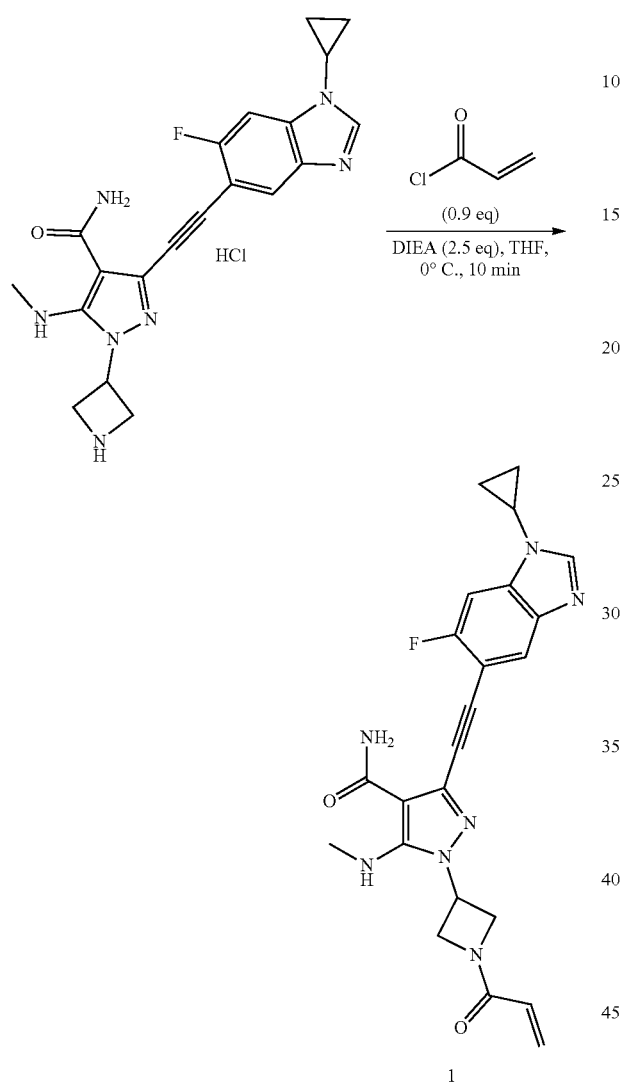

To a stirred mixture of 1-(azetidin-3-yl)-3-[2-(1-cyclopropyl-6-fluoro-1,3-benzodiazol-5-yl)ethynyl]-5-(methylamino)pyrazole-4-carboxamide hydrochloride (0.18 g, 0.42 mmol) and DIEA (0.13 g, 1.05 mmol) in THF (1.80 mL) was added acryloyl chloride (34.30 mg, 0.37 mmol) dropwise at 0° C. The reaction mixture was stirred for 10 min at 0° C. under nitrogen atmosphere. The resulting mixture was concentrated under reduced pressure. The residue was purified by silica gel column chromatography, eluted with DCM/MeOH (10/1) to afford crude product which was further purified by reverse phase flash with the following conditions: Column: YMC-Actus Triart C18 ExRS, 30 mm×150 mm, 5 m; Mobile Phase A: water (10 mmol/L NH4HCO3), Mobile Phase B: ACN; Flow rate: 60 mL/min; Gradient: 25 B to 45 B in 8 min, 254 nm; RT1: 8 min. The fractions contained desired product were combined and concentrated to afford 3-[2-(1-cyclopropyl-6-fluoro-1,3-benzodiazol-5-yl)ethynyl]-5-(methylamino)-1-[1-(prop-2-enoyl)azetidin-3-yl]pyrazole-4-carboxamide (19.90 mg, 10%) as an off-white solid. MS ESI calculated for C23H22FN7O2 [M+H]+, 448.18, found 448.05; 1H NMR (300 MHz, CDCl3) δ 8.01 (d, J=5.3 Hz, 2H), 7.34 (d, J=8.9 Hz, 1H), 6.44-6.35 (m, 1H), 6.25-6.21 (m, 1H), 5.76-5.71 (m, 1H), 5.29 (s, 1H), 4.98 (s, 1H), 4.67-4.46 (m, 3H), 3.44-3.36 (m, 1H), 2.97 (d, J=5.2 Hz, 3H), 2.03 (s, 1H), 1.33-1.15 (m, 3H), 1.09 (s, 2H).

Example 176: 1-((3S,5R)-1-Acryloyl-5-(fluoromethyl)pyrrolidin-3-yl)-3-((1-cyclopropyl-6-fluoro-1H-benzo[d]imidazol-5-yl)ethynyl)-5-(methylamino)-1H-pyrazole-4-carboxamide

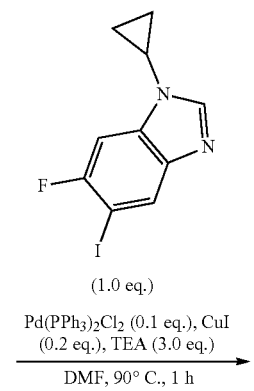

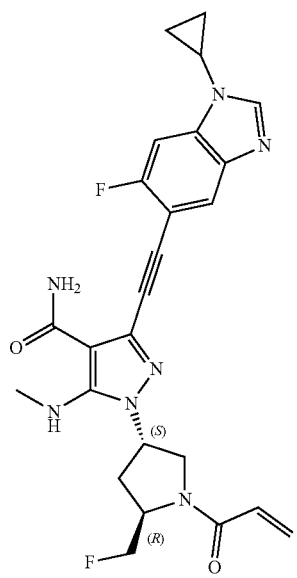

1-((3S,5R)-1-acryloyl-5-(fluoromethyl)pyrrolidin-3-yl)-3-((1-cyclopropyl-6-fluoro-1H-benzo[d]imidazol-5-yl)ethynyl)-5-(methylamino)-1H-pyrazole-4-carboxamide. MS ESI calculated for $C_{25}H_{25}F_2N_7O_2$ [M+H]+, 494.20, found 494.45; 1H NMR (400 MHz, DMSO-d6) δ 8.56 (s, 1H), 7.72 (t, J=102.6 Hz, 3H), 7.14-6.42 (m, 3H), 6.23-6.14 (m, 1H), 5.71-5.64 (m, 1H), 5.26-5.18 (m, 1H), 4.89-4.34 (m, 3H), 4.17-3.67 (m, 2H), 3.51 (s, 1H), 2.96 (d, J=5.2 Hz, 3H), 2.79-2.64 (m, 1H), 2.39-2.37 (m, 1H), 1.20-0.95 (m, 4H).

Example 177: 1-((3S,5R)-1-Acryloyl-5-(methoxymethyl)pyrrolidin-3-yl)-3-((4,6-difluoro-1H-benzo[d]imidazol-5-yl)ethynyl)-5-(methylamino)-1H-pyrazole-4-carboxamide Example 178: 1-((3S,5R)-1-Acryloyl-5-(fluoromethyl)pyrrolidin-3-yl)-3-((1-cyclopropyl-1H-benzo[d]imidazol-5-yl)ethynyl)-5-(methylamino)-1H-pyrazole-4-carboxamide

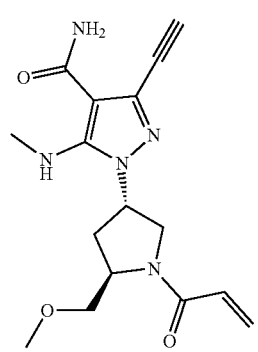
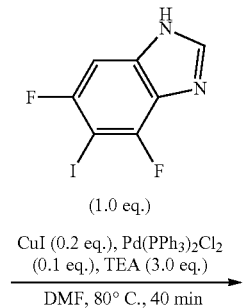
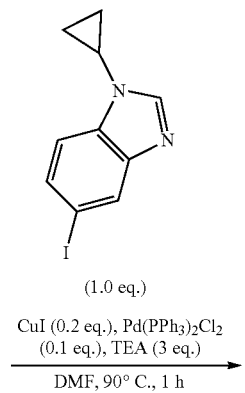
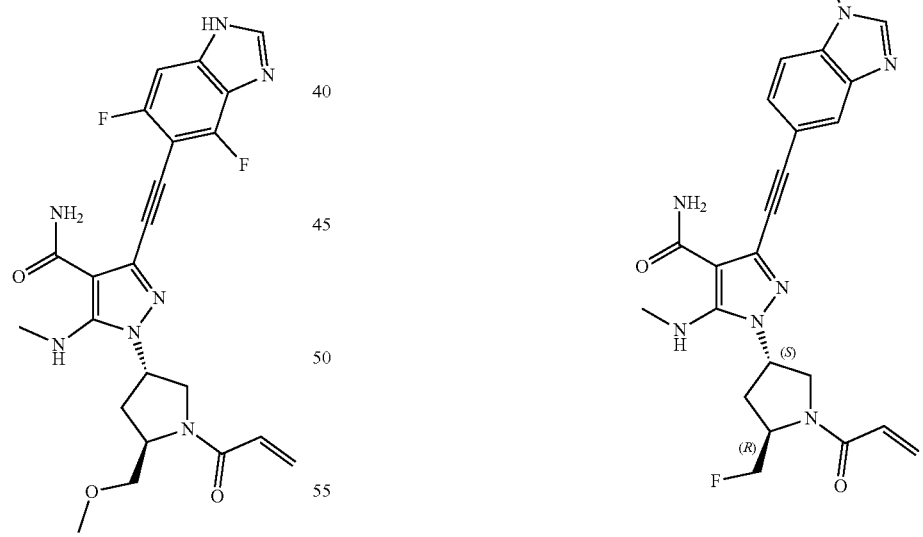

1-((3S,5R)-1-acryloyl-5-(methoxymethyl)pyrrolidin-3-yl)-3-((4,6-difluoro-1H-benzo[d]imidazol-5-yl)ethynyl)-5-(methylamino)-1H-pyrazole-4-carboxamide. MS ESI calculated for $C_{23}H_{23}F_2N_7O_3$ [M+H]$^+$, 484.18, found 484.30; $^1$H NMR (400 MHz, DMSO-d$_6$) δ 13.07 (s, 1H) 8.41 (s, 1H), 7.66-7.30 (m, 2H), 6.86-6.41 (m, 3H), 6.17-6.02 (m, 1H), 5.69-5.56 (m, 1H), 5.28-5.16 (m, 1H), 4.58-4.35 (m, 1H), 4.09-3.71 (m, 2H), 3.66-3.43 (m, 2H), 3.38-3.25 (m, 3H), 2.97-3.20 (m, 3H), 2.63-2.51 (m, 1H), 2.37-2.25 (m, 1H).

1-((3S,5R)-1-acryloyl-5-(fluoromethyl)pyrrolidin-3-yl)-3-((1-cyclopropyl-1H-benzo[d]imidazol-5-yl)ethynyl)-5-(methylamino)-1H-pyrazole-4-carboxamide. MS ESI calculated for $C_{25}H_{26}FN_7O_2$ [M+H]$^+$, 476.21, found 476.15; $^1$H NMR (400 MHz, CDCl$_3$) δ 8.11 (s, 2H), 7.52 (d, J=4 Hz, 1H), 6.96 (s, 1H), 6.78 (s, 1H), 6.47-6.44 (m, 2H), 5.79-5.74 (m, 1H), 5.39-5.34 (m, 2H), 5.05-4.91 (m, 1H), 4.69-4.44 (m, 2H), 4.20-4.07 (m, 2H), 3.44 (s, 1H), 3.08-1.82 (m, 3H), 1.44-1.39 (m, 1H), 1.37-1.25 (m, 1H), 1.24 (d, J=4 Hz, 2H), 1.10 (s, 2H).

Example 179: 1-((3S,5R)-1-Acryloyl-5-(fluoromethyl)pyrrolidin-3-yl)-3-((1-cyclopropyl-4,6-difluoro-1H-benzo[d]imidazol-5-yl)ethynyl)-5-(methylamino)-1H-pyrazole-4-carboxamide Example 180: 3-[2-(1-Cyclopropyl-6-fluoro-1,3-benzodiazol-5-yl)ethynyl]-1-[(3S,5S)-5-(fluoromethyl)-1-(prop-2-enoyl)pyrrolidin-3-yl]-5-(methylamino)pyrazole-4-carboxamide

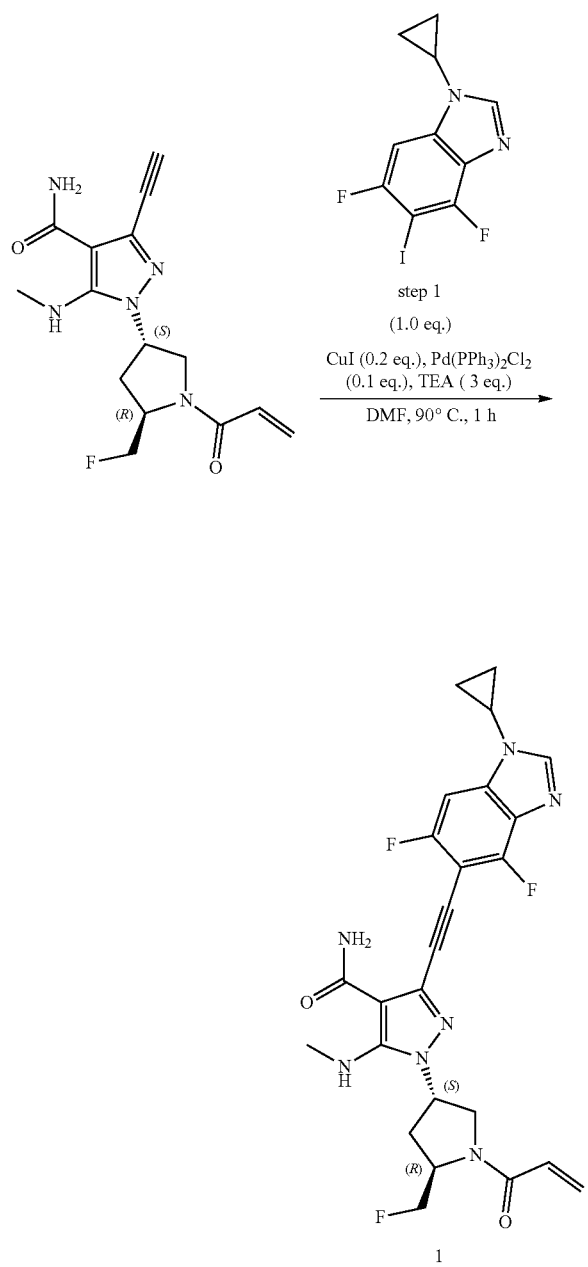

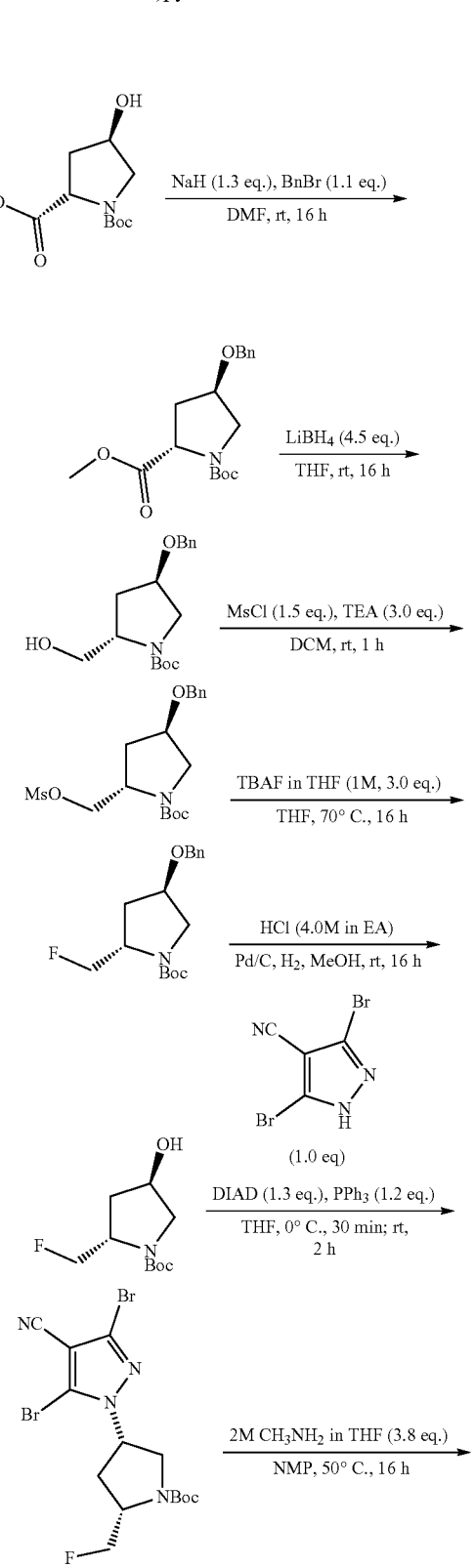

1-((3S,5R)-1-acryloyl-5-(fluoromethyl)pyrrolidin-3-yl)-3-((1-cyclopropyl-4,6-difluoro-1H-benzo[d]imidazol-5-yl)ethynyl)-5-(methylamino)-1H-pyrazole-4-carboxamide. MS ESI calculated for $C_{25}H_{24}F_3N_7O_2$ [M+H]$^+$, 512.19, found 512.35; $^1$H NMR (400 MHz, CDCl$_3$) δ 8.00 (s, 1H), 7.19-7.08 (m, 2H), 6.50-6.41 (m, 2H), 5.86-5.74 (m, 1H), 5.41-5.19 (m, 2H), 5.06-4.90 (dd, J=4, 4 Hz, 1H), 4.68-4.44 (m, 2H), 4.19-4.14 (m, 1H), 4.14-4.06 (m, 1H), 3.43-3.73 (m, 1H), 3.06 (s, 3H), 2.90-2.82 (m, 1H), 2.44-2.39 (m, 1H), 1.27-1.23 (m, 2H), 1.12-1.07 (m, 2H).

683
-continued

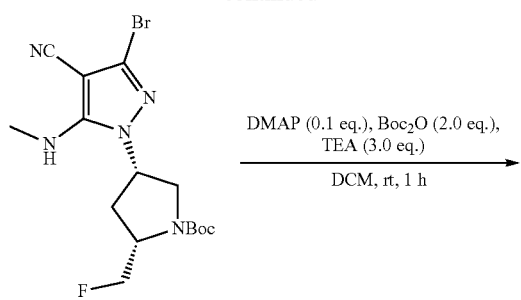 [SMILES: CNc1c(C#N)c(Br)nn1[C@H]1C[C@@H](CF)N(C(=O)OC(C)(C)C)C1]

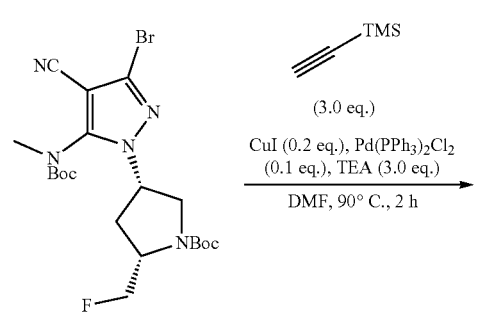

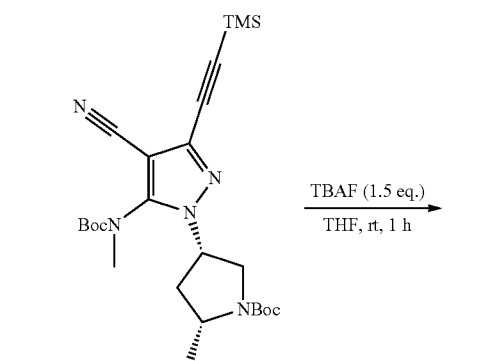

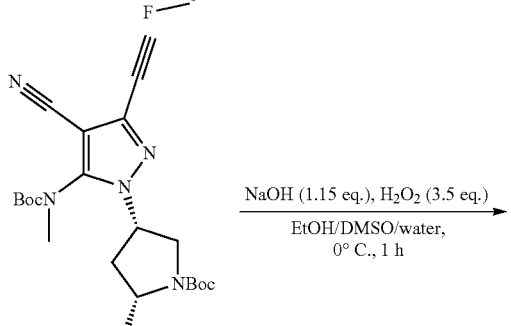

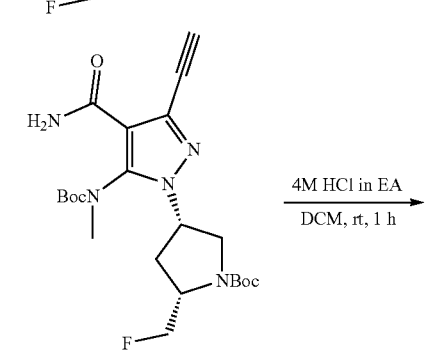

684
-continued

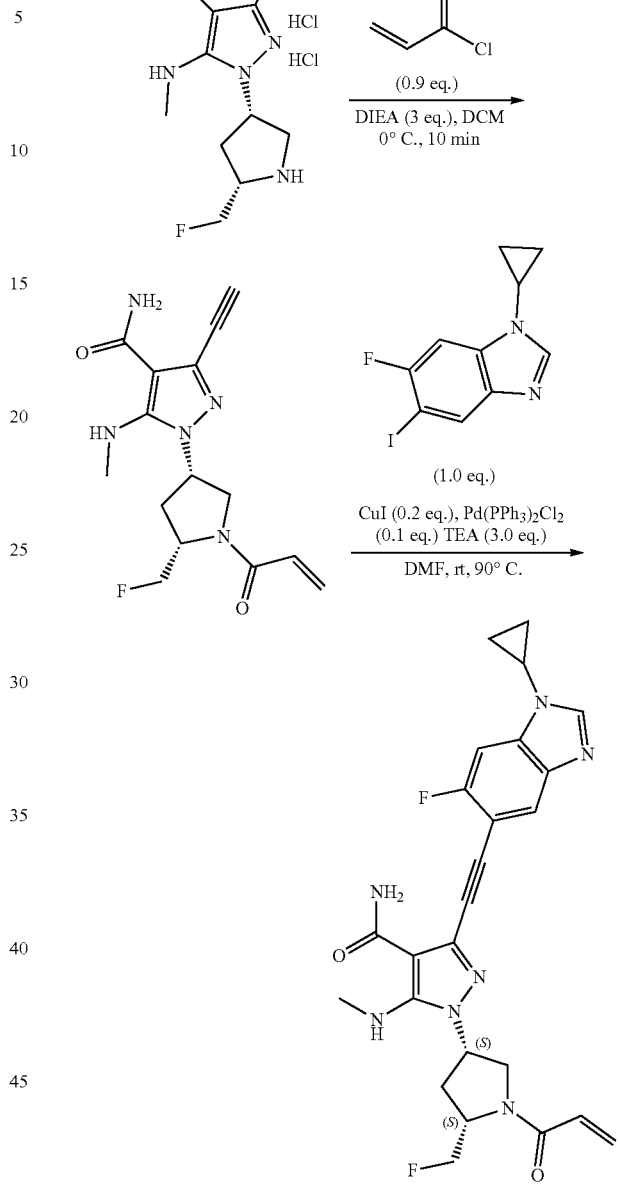

Step 1: 1-(Tert-butyl) 2-methyl (2S,4R)-4-(benzyloxy)pyrrolidine-1,2-dicarboxylate To a stirred solution of 1-(tert-butyl) 2-methyl (2S,4R)-4-hydroxypyrrolidine-1,2-dicarboxylate (30.00 g, 0.12 mol) and BnBr (23.01 g, 0.13 mol) in DMF (300.00 mL) was added NaH (60% in mineral oil) (6.36 g, 0.16 mol) in portions at 0° C. under nitrogen atmosphere. The reaction mixture was stirred for 16 h at room temperature under nitrogen atmosphere. The resulting mixture was diluted with water (100 mL) at 0° C. and extracted with EA (3×300 mL). The combined organic layers was washed with water (2×100 mL), dried over anhydrous Na2SO4. After filtration, the filtrate was concentrated under reduced pressure to afford 1-(tert-butyl) 2-methyl (2S,4R)-4-(benzyloxy)pyrrolidine-1, 2-dicarboxylate (40.00 g, 97%) as a yellow oil. MS ESI calculated for C18H25NO5 [M+H]+, 336.17, found, 336.20.

Step 2: Tert-butyl (2S,4R)-4-(benzyloxy)-2-(hydroxymethyl)pyrrolidine-1-carboxylate To a stirred solution of 1-(tert-butyl) 2-methyl (2S,4R)-4-(benzyloxy)pyrrolidine-1,2-dicarboxylate (40.00 g, 0.12 mol) in THF (400.00 mL) was added LiBH4 (11.69 g, 0.53 mol) in portions at 0° C. under nitrogen atmosphere. The reaction mixture was stirred for 16 h at room temperature under nitrogen atmosphere. The resulting mixture was added water (200 mL) and quenched with NH4Cl (400 mL) at 0° C. The aqueous layers was extracted with EA (3×500 mL). The combined organic layers was washed with water (2×400 mL), dried over anhydrous Na2SO4. After filtration, the filtrate was concentrated under reduced pressure. The residue was purified by silica gel column chromatography, eluted with EA in PE (50-100%). The fractions contained desired product were combined and concentrated under reduced pressure to afford tert-butyl (2S,4R)-4-(benzyloxy)-2-(hydroxymethyl)pyrrolidine-1-carboxylate (23.00 g, 62%) as a yellow oil. MS ESI calculated for C17H25NO4 [M+H−100]+, 208.18, found 208.05; 1H NMR (400 MHz, DMSO-d6) δ 7.62-7.19 (m, 5H), 4.72-4.56 (m, 1H), 4.46 (d, J=4.3 Hz, 2H), 4.32-4.09 (m, 2H), 3.39-3.10 (m, 4H), 2.04 (d, J=19.8 Hz, 2H), 1.40 (s, 9H).

Step 3: Tert-butyl (2S,4R)-4-(benzyloxy)-2-[(methanesulfonyloxy)methyl]pyrrolidine-1-carboxylate To a stirred solution of tert-butyl (2S,4R)-4-(benzyloxy)-2-(hydroxymethyl)pyrrolidine-1-carboxylate (22.00 g, 71.57 mmol) and TEA (29.84 mL, 0.21 mol) in DCM (220.00 mL) was added MsCl (8.31 mL, 0.11 mol) in dropwise at 0° C. under nitrogen atmosphere. The reaction mixture was stirred for 1.5 h at room temperature under nitrogen atmosphere. The resulting mixture was diluted with water at 0° C. (100 mL). The aqueous layer was extracted with DCM (3×300 mL). The combined organic layers were washed with water (2×200 mL), dried over anhydrous Na2SO4. After filtration, the filtrate was concentrated under reduced pressure to afford tert-butyl (2S,4R)-4-(benzyloxy)-2-[(methanesulfonyloxy) methyl]pyrrolidine-1-carboxylate (27.00 g, 97%) as a yellow oil. MS ESI calculated for C18H27NO6S [M+H−100]+, 286.16, found 286.05.

Step 4: Tert-butyl (2S,4R)-4-(benzyloxy)-2-(fluoromethyl)pyrrolidine-1-carboxylate To a stirred solution of tert-butyl (2S,4R)-4-(benzyloxy)-2-[(methanesulfonyloxy) methyl]pyrrolidine-1-carboxylate (27.00 g, 70.04 mmol) in THF (270.00 mL) was added TBAF (54.94 g, 0.21 mol) dropwise at room temperature. The reaction mixture was stirred for 16 h at 70° C. The resulting mixture was cooled down and concentrated under reduced pressure. The residue was purified by silica gel column chromatography, eluted with EA in PE (0-50%). The fractions contained desired product were combined and concentrated under reduced pressure to afford tert-butyl (2S,4R)-4-(benzyloxy)-2-(fluoromethyl)pyrrolidine-1-carboxylate (18.00 g, 83%) as a white solid. MS ESI calculated for C17H24FNO3 [M+H−100]+, 210.17, found 210.20; 1H NMR (400 MHz, CDCl3) δ 7.42-7.35 (m, 1H), 7.35-7.28 (m, 4H), 4.70-4.65 (m, 3H), 4.48-4.33 (m, 1H), 4.16 (d, J=33.1 Hz, 2H), 3.67-3.39 (m, 2H), 2.28-2.12 (m, 2H), 1.49 (s, 9H).

Step 5: Tert-butyl (2S,4R)-2-(fluoromethyl)-4-hydroxypyrrolidine-1-carboxylate A stirred solution of tert-butyl (2S,4R)-4-(benzyloxy)-2-(fluoromethyl)pyrrolidine-1-carboxylate (18.00 g, 58.18 mmol) and Pd/C (10% wt in water) (3.71 g, 3.49 mmol) in MeOH (180.00 mL) was added 4 M HCl in EA (1.80 mL, 31.53 mmol) dropwise at room temperature. The reaction mixture was stirred for 16 h at room temperature under hydrogen atmosphere. The resulting mixture was filtered, the filter cake was washed with MeOH (2×100 mL). The filtrate was concentrated under reduced pressure. The residue was purified by silica gel column chromatography, eluted with EA in PE (30-80%). The fractions contained desired product were combined and concentrated under reduced pressure to afford tert-butyl (2S,4R)-2-(fluoromethyl)-4-hydroxypyrrolidine-1-carboxylate (12.00 g, 94%) as an off-white oil. MS ESI calculated for C10H18FNO3 [M+H−56]+, 164.13, found 164.05; 1H NMR (400 MHz, CDCl3) δ 4.75-4.35 (m, 3H), 4.13 (d, J=17.8 Hz, 1H), 3.48 (d, J=10.9 Hz, 2H), 2.25-2.00 (m, 3H), 1.49 (s, 9H).

Step 6: Tert-butyl (2S,4S)-4-(3,5-dibromo-4-cyanopyrazol-1-yl)-2-(fluoromethyl)pyrrolidine-1-carboxylate To a stirred solution of 3,5-dibromo-1H-pyrazole-4-carbonitrile (11.44 g, 45.61 mmol) and tert-butyl (2S,4R)-2-(fluoromethyl)-4-hydroxypyrrolidine-1-carboxylate (10.00 g, 45.60 mmol) in THF (100.00 mL) was added PPh3 (14.36 g, 54.73 mmol) at room temperature under nitrogen atmosphere. The reaction mixture was stirred for 30 min at room temperature under nitrogen atmosphere. To the above mixture was added DIAD (11.99 g, 59.29 mmol) dropwise at 0° C. The reaction mixture was stirred for another 2 h at room temperature. The resulting mixture was diluted with water (100 mL) at 0° C. and extracted with EA (3×300 mL). The combined organic layers was washed with water (2×100 mL), dried over anhydrous Na2SO4. After filtration, the filtrate was concentrated under reduced pressure to afford tert-butyl (2S,4S)-4-(3,5-dibromo-4-cyanopyrazol-1-yl)-2-(fluoromethyl)pyrrolidine-1-carboxylate (20.00 g, 97%) as an off-white oil. MS ESI calculated for C14H17Br2FN4O2 [M+H−56]+, 394.97, 396.97, 398.97, found 394.90, 396.90, 398.90; 1H NMR (400 MHz, CDCl3) δ 6.50-6.45 (m, 1H), 5.15-4.87 (m, 2H), 4.78-4.65 (m, 1H), 4.27-3.94 (m, 1H), 3.63 (s, 1H), 2.72-2.65 (m, 1H), 1.29 (s, 9H).

Step 7: Tert-butyl (2S,4S)-4-[3-bromo-4-cyano-5-(methylamino)pyrazol-1-yl]-2-(fluoromethyl)pyrrolidine-1-carboxylate To a stirred mixture of tert-butyl (2S,4S)-4-(3,5-dibromo-4-cyanopyrazol-1-yl)-2-(fluoromethyl)pyrrolidine-1-carboxylate (20.00 g, 44.23 mmol,) in NMP (100.00 mL) was added CH3NH2 (1 M in THF) (84.05 mL, 0.17 mol). The reaction mixture was stirred for 16 h at 50° C. The residue was purified by reverse flash chromatography with the following conditions: column: C18 silica gel; mobile phase A: 10 mmol/L NH4HCO3 in water, mobile phase B: ACN, 20B to 80B gradient in 30 min; detector: UV 254 nm. The fractions contained desired product were combined and concentrated to afford tert-butyl (2S,4S)-4-[3-bromo-4-cyano-5-(methylamino)pyrazol-1-yl]-2-(fluoromethyl)pyrrolidine-1-carboxylate (15.00 g, 84%) as a yellow solid. MS ESI calculated for C15H21BrFN5O2 [M+H]+, 402.09, 404.09, found 402.15, 404.15; 1H NMR (400 MHz, CDCl3)

δ 4.95-4.85 (m, 1H), 4.78-4.65 (m, 1H), 4.58-4.35 (m, 2H), 4.15-3.96 (m, 2H), 3.43 (d, J=14.1 Hz, 1H), 3.42-3.25 (m, 3H), 2.89-2.51 (m, 1H), 2.65-2.36 (m, 1H), 1.47 (s, 9H).

Step 8: Tert-butyl (2S,4S)-4-{3-bromo-5-[(tert-butoxycarbonyl)(methyl)amino]-4-cyanopyrazol-1-yl}-2-(fluoromethyl)pyrrolidine-1-carboxylate To a stirred solution of tert-butyl (2S,4S)-4-[3-bromo-4-cyano-5-(methylamino)pyrazol-1-yl]-2-(fluoromethyl)pyrrolidine-1-carboxylate (15.00 g, 37.29 mmol), Et3N (15.55 mL, 0.11 mol) and DMAP (0.46 g, 3.73 mmol) in DCM (150.00 mL) was added Boc2O (16.28 g, 74.58 mmol) dropwise at 0° C. under nitrogen atmosphere. The reaction mixture was stirred for 1 h at room temperature. The resulting mixture was added water (100 mL) and extracted with DCM (3×300 mL). The combined organic layers was washed with water (2×200 mL), dried over anhydrous Na2SO4. After filtration, the filtrate was concentrated under reduced pressure to afford tert-butyl (2S,4S)-4-{3-bromo-5-[(tert-butoxycarbonyl)(methyl)amino]-4-cyanopyrazol-1-yl}-2-(fluoromethyl)pyrrolidine-1-carboxylate (16.00 g, 85%) as a white solid. MS ESI calculated for C20H29BrFN5O4 [M+H-112]+, 390.14, 392.14, found 389.95, 391.95; 1H NMR (400 MHz, CDCl3) δ 4.87-4.45 (m, 3H), 4.28-4.16 (m, 2H), 3.62-3.56 (m, 1H), 3.33-3.21 (m, 3H), 2.67-2.56 (m, 2H), 1.54 (s, 18H).

Step 9: Tert-butyl (2S,4S)-4-{5-[(tert-butoxycarbonyl)(methyl)amino]-4-cyano-3-[2-(trimethylsilyl)ethynyl]pyrazol-1-yl}-2-(fluoromethyl)pyrrolidine-1-carboxylate To a stirred solution of tert-butyl (2S,4S)-4-{3-bromo-5-[(tert-butoxycarbonyl)(methyl)amino]-4-cyanopyrazol-1-yl}-2-(fluoromethyl)pyrrolidine-1-carboxylate (8.00 g, 15.92 mmol), trimethylsilylacetylene (4.69 g, 47.77 mmol), Pd(PPh3)2Cl2 (1.12 g, 1.59 mmol) and CuI (0.61 g, 3.18 mmol) in DMF (80.00 mL) was added TEA (6.64 mL, 47.77 mmol). The reaction mixture was degassed with argon for three times and stirred for 2 h at 90° C. The resulting mixture was cooled and concentrated under vacuum. The residue was purified by silica gel column chromatography, eluted with EA in PE (10-50%). The fractions contained desired product were combined and concentrated to afford tert-butyl (2S,4S)-4-{5-[(tert-butoxycarbonyl)(methyl)amino]-4-cyano-3-[2-(trimethylsilyl)ethynyl]pyrazol-1-yl}-2-(fluoromethyl)pyrrolidine-1-carboxylate (7.40 g, 89%) as a white solid. MS ESI calculated for C25H38FN5O4Si [M+H]+, 520.27, found 520.45; 1H NMR (400 MHz, CDCl3) δ 4.74-4.51 (m, 3H), 4.42-4.91 (m, 2H), 3.61-3.49 (m, 1H), 3.24 (s, 3H), 2.53 (d, J=36.9 Hz, 2H), 1.47 (s, 18H), 0.30 (s, 9H).

Step 10: Tert-butyl (2S,4S)-4-{5-[(tert-butoxycarbonyl)(methyl)amino]-4-cyano-3-ethynylpyrazol-1-yl}-2-(fluoromethyl)pyrrolidine-1-carboxylate To a stirred solution of tert-butyl (2S,4S)-4-{5-[(tert-butoxycarbonyl)(methyl)amino]-4-cyano-3-[2-(trimethylsilyl)ethynyl]pyrazol-1-yl}-2-(fluoromethyl)pyrrolidine-1-carboxylate (7.40 g, 14.24 mmol) in THF (74.00 mL) was added TBAF (5.58 mL, 21.36 mmol) dropwise at 0° C. The reaction mixture was stirred for 1 h at room temperature. The residue was purified by silica gel column chromatography, eluted with EA in PE (20-90%). The fractions contained desired product were combined and concentrated to afford tert-butyl (2S,4S)-4-{5-[(tert-butoxycarbonyl)(methyl)amino]-4-cyano-3-ethynylpyrazol-1-yl}-2-(fluoromethyl)pyrrolidine-1-carboxylate (4.70 g, 73%) as a yellow solid. MS ESI calculated for C22H30FN5O [M+H]+, 448.23, found 448.20.

Step 11: Tert-butyl (2S,4S)-4-{5-[(tert-butoxycarbonyl)(methyl)amino]-4-carbamoyl-3-ethynylpyrazol-1-yl}-2-(fluoromethyl)pyrrolidine-1-carboxylate To a stirred solution of tert-butyl (2S,4S)-4-{5-[(tert-butoxycarbonyl)(methyl)amino]-4-cyano-3-ethynylpyrazol-1-yl}-2-(fluoromethyl)pyrrolidine-1-carboxylate (2.50 g, 5.58 mmol) and NaOH (1 M in water) (6.42 mL, 6.42 mmol) in DMSO (2.50 mL) and EtOH (25.00 mL) was added H2O2 (30% in water) (0.46 mL, 19.55 mmol) dropwise at 0° C. The reaction mixture was stirred for 1 h at 0° C. The resulting mixture was diluted with water (25 mL) and extracted with EA (3×50 mL). The combined organic layers was washed with water (2×25 mL), dried over anhydrous Na2SO4. After filtration, the filtrate was concentrated under reduced pressure. The residue was purified by silica gel column chromatography, eluted with EA in PE (50-100%). The fractions contained desired product were combined and concentrated to afford tert-butyl (2S,4S)-4-{5-[(tert-butoxycarbonyl)(methyl)amino]-4-carbamoyl-3-ethynylpyrazol-1-yl}-2-(fluoromethyl)pyrrolidine-1-carboxylate (2.40 g, 92%) as a white solid. MS ESI calculated for C22H32FN5O5 [M+H]+, 466.24, found, 466.20.

Step 12: 3-Ethynyl-1-[(3S,5S)-5-(fluoromethyl)pyrrolidin-3-yl]-5-(methylamino)pyrazole-4-carboxamide dihydrochloride To a stirred solution of tert-butyl (2S,4S)-4-{5-[(tert-butoxycarbonyl)(methyl)amino]-4-carbamoyl-3-ethynylpyrazol-1-yl}-2-(fluoromethyl)pyrrolidine-1-carboxylate (2.30 g, 4.94 mmol) in DCM (10.00 mL) was added HCl (4 M in EA) (10.00 mL, 0.17 mol) dropwise at 0° C. The reaction mixture was stirred for 1 h at room temperature. The resulting mixture was concentrated under reduced pressure to afford 3-ethynyl-1-[(3S,5S)-5-(fluoromethyl)pyrrolidin-3-yl]-5-(methylamino)pyrazole-4-carboxamide dihydrochloride (1.48 g, crude) as a yellow solid. MS ESI calculated for C12H16FN5O [M+H−2 HCl]+, 266.13, found 266.15.

Step 13: 3-Ethynyl-1-[(3S,5S)-5-(fluoromethyl)-1-(prop-2-enoyl)pyrrolidin-3-yl]-5-(methylamino)pyrazole-4-carboxamide To a stirred solution of 3-ethynyl-1-[(3S,5S)-5-(fluoromethyl)pyrrolidin-3-yl]-5-(methylamino)pyrazole-4-carboxamide dihydrochloride (1.48 g, 4.90 mmol) and DIEA (2.56 mL, 14.71 mmol) in DCM (23.00 mL) was added acryloyl chloride (0.40 g, 4.42 mmol) dropwise at 0° C. under nitrogen atmosphere. The reaction mixture was stirred for 10 min at 0° C. The resulting mixture was added water (20 mL) and extracted with EA (3×50 mL). The combined organic layers was washed with brine (1×20 mL), dried over anhydrous Na2SO4. After filtration, the filtrate was concentrated under reduced pressure. The residue was purified by silica gel column chromatography, eluted with MeOH in DCM (0-5%). The fractions contained desired product were combined and concentrated to afford 3-ethynyl-1-[(3S,5S)-5-(fluoromethyl)-1-(prop-2-enoyl)pyrrolidin-3-yl]-5-(methylamino)pyrazole-4-carboxamide (1.30 g, 83%) as a yellow solid. MS ESI calculated for C15H18FN5O2 [M+H]+, 320.14, found 320.10.

Step 14: 3-[2-(1-Cyclopropyl-6-fluoro-1,3-benzodiazol-5-yl)ethynyl]-1-[(3S,5S)-5-(fluoromethyl)-1-(prop-2-enoyl)pyrrolidin-3-yl]-5-(methylamino)pyrazole-4-carboxamide To a stirred mixture of 3-ethynyl-1-[(3S,5S)-5-(fluoromethyl)-1-(prop-2-enoyl)pyrrolidin-3-yl]-5-(methylamino)pyrazole-4-carboxamide (0.30 g, 0.94 mmol), 1-cyclopropyl-6-fluoro-5-iodo-1,3-benzodiazole (0.29 g, 0.94 mmol), CuI (35.78 mg, 0.18 mmol) and Pd(PPh3)2Cl2 (65.94 mg, 0.09 mmol) in DMF (9.30 mL) was added TEA (0.28 g, 2.77 mmol). The reaction mixture was degassed with nitrogen for three times and stirred for 1 h at 90° C. The resulting solution was concentrated under reduced pressure. The residue was purified by silica gel column chromatography, eluted with CH2Cl2/MeOH (10/1) to afford crude product which was further purified by reverse flash chromatography with the following conditions: column: C18 silica gel; mobile phase: ACN in water (10 mmol/L NH4HCO3), 5% to 70% gradient in 30 min; detector: UV 254 nm. The fractions contained desired product were combined and concentrated to afford 3-[2-(1-cyclopropyl-6-fluoro-1,3-benzodiazol-5-yl)ethynyl]-1-[(3S,5S)-5-(fluoromethyl)-1-(prop-2-enoyl)pyrrolidin-3-yl]-5-(methylamino)pyrazole-4-carboxamide (95.90 mg, 20%) as an off-white solid. MS ESI calculated for C25H25F2N7O2 [M+H]+, 494.21, found 494.35; 1H NMR (400 MHz, CDCl3) δ 8.01 (d, J=6.7 Hz, 2H), 7.34 (d, J=8.9 Hz, 1H), 7.15 (s, 1H), 6.68 (s, 1H), 6.43 (d, J=8.4 Hz, 2H), 5.77 (m, 1H), 5.39 (s, 1H), 4.96-4.87 (m, 1H), 4.82 (d, J=23.0 Hz, 1H), 4.77-4.60 (m, 1H), 4.51 (s, 1H), 4.21-4.07 (m, 1H), 3.43-3.37 (m, 1H), 3.01 (s, 3H), 2.81 (q, J=10.3 Hz, 1H), 2.59 (s, 1H), 1.30-1.16 (m, 2H), 1.09 (q, J=3.9, 3.4 Hz, 2H).

Example 181: 3-[2-(1-Cyclopropyl-4,6-difluoro-1,3-benzodiazol-5-yl)ethynyl]-1-[(3S,5S)-5-(fluoromethyl)-1-(prop-2-enoyl)pyrrolidin-3-yl]-5-(methylamino)pyrazole-4-carboxamide

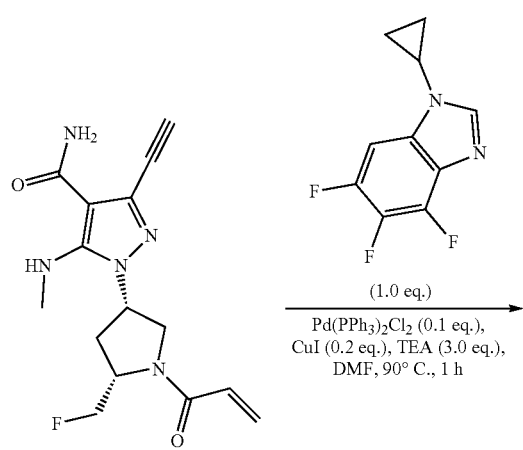

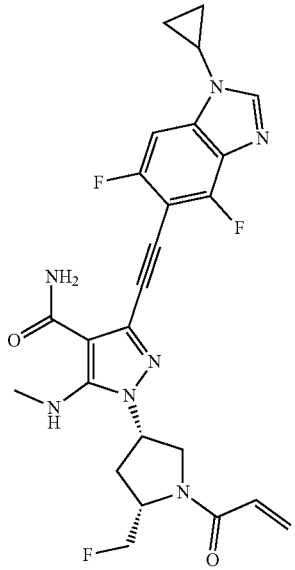

To a stirred solution of 3-ethynyl-1-[(3S,5S)-5-(fluoromethyl)-1-(prop-2-enoyl)pyrrolidin-3-yl]-5-(methylamino)pyrazole-4-carboxamide (0.25 g, 0.78 mmol), 1-cyclopropyl-4,6-difluoro-5-iodo-1,3-benzodiazole (0.25 g, 0.78 mmol), CuI (29.82 mg, 0.16 mmol) and Pd(PPh3)2Cl2 (54.95 mg, 0.08 mmol) in DMF (2.50 mL, 32.30 mmol) was added TEA (0.24 g, 2.35 mmol). The reaction mixture was degassed with nitrogen for three times and stirred for 1 h at 90° C. The resulting mixture was concentrated under reduced pressure. The residue was purified by silica gel column chromatography, eluted with DCM/MeOH (10/1) to afford the crude product which was further purified by reverse flash chromatography with the following conditions: column: C18 silica gel; mobile phase: ACN in water, 5% to 35% gradient in 40 min; detector: UV 254 nm. The fractions contained desired product were combined and concentrated to afford 3-[2-(1-cyclopropyl-4,6-difluoro-1,3-benzodiazol-5-yl)ethynyl]-1-[(3S,5S)-5-(fluoromethyl)-1-(prop-2-enoyl)pyrrolidin-3-yl]-5-(methylamino)pyrazole-4-carboxamide (91.70 mg, 22%) as a white solid. MS ESI calculated for C25H24F3N7O2 [M+H]+, 512.19, found 512.10; 1H NMR (400 MHz, CDCl3) δ 7.98 (s, 1H), 7.19 (d, J=8.3 Hz, 1H), 7.10 (s, 1H), 6.65-6.36 (m, 2H), 5.79-5.73 (m, 1H), 5.43 (s, 1H), 5.00-4.59 (m, 3H), 4.58-4.44 (m, 1H), 4.12-4.07 (m, 1H), 3.42-3.38 (m, 1H), 3.01 (s, 3H), 2.87-2.44 (m, 2H), 1.30-1.21 (m, 2H), 1.21-1.05 (m, 2H).

Example 182: 3-((1-Cyclopropyl-6-fluoro-1H-benzo[d]imidazol-5-yl)ethynyl)-1-((3S,5R)-5-(methoxymethyl)-1-propioloylpyrrolidin-3-yl)-5-(methylamino)-1H-pyrazole-4-carboxamide

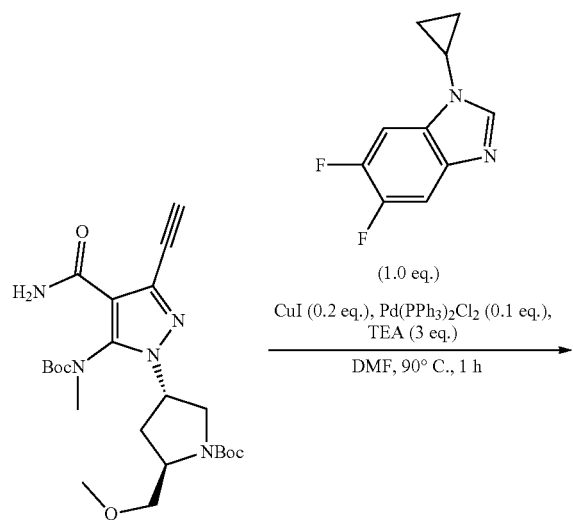

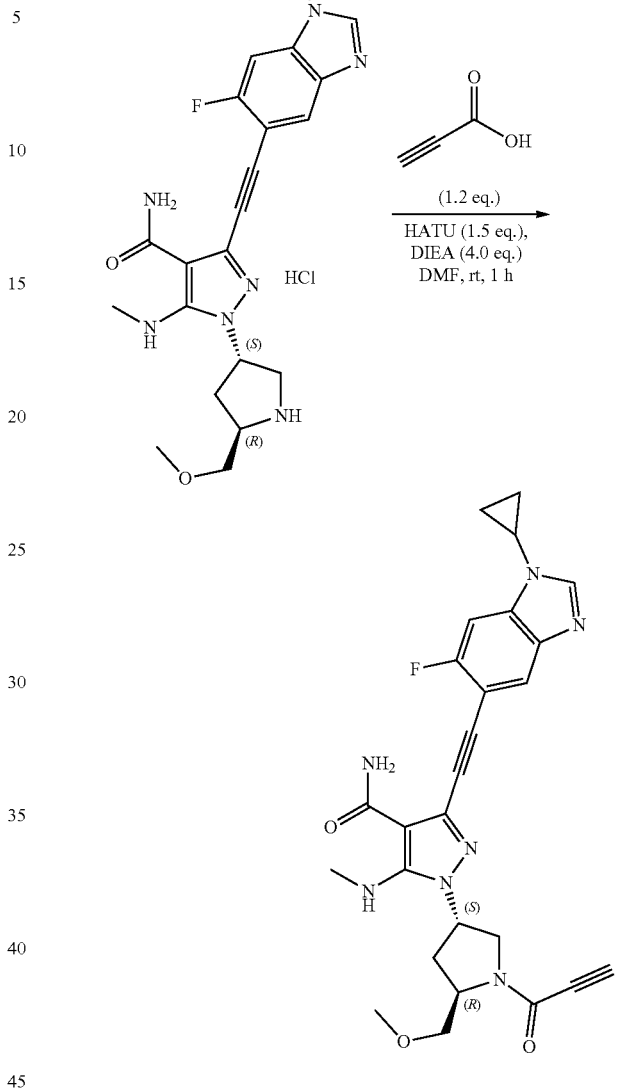

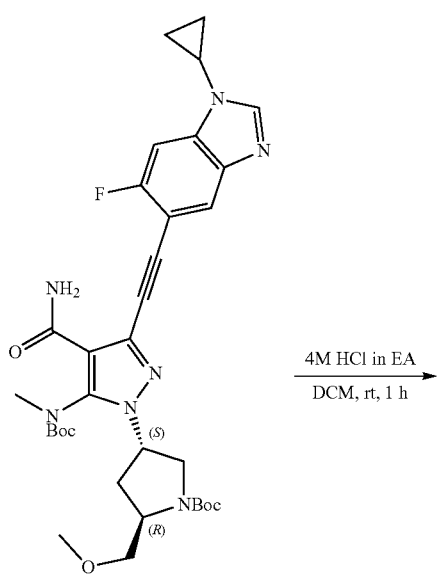

Step 1: Tert-butyl (2R,4S)-4-(5-((tert-butoxycarbonyl)(methyl)amino)-4-carbamoyl-3-((1-cyclopropyl-6-fluoro-1H-benzo[d]imidazol-5-yl)ethynyl)-1H-pyrazol-1-yl)-2-(methoxymethyl)pyrrolidine-1-carboxylate To a stirred mixture of tert-butyl (2R,4S)-4-{5-[(tert-butoxycarbonyl)(methyl)amino]-4-carbamoyl-3-ethynylpyrazol-1-yl}-2-(methoxymethyl)pyrrolidine-1-carboxylate (2.00 g, 4.18 mmol), CuI (0.16 g, 0.83 mmol), Pd(PPh$_3$)$_2$Cl$_2$ (0.29 g, 0.41 mmol) and 1-cyclopropyl-6-fluoro-5-iodo-1,3-benzodiazole (1.27 g, 4.18 mmol) in DMF (20.00 mL) was added TEA (1.75 mL, 12.56 mmol). The reaction mixture was degassed with nitrogen for three times and stirred for 1 h at 90° C. The resulting mixture was allowed to cool down to room temperature and concentrated under reduced pressure. The residue was purified by silica gel column chromatography, eluted with DCM/MeOH (10/1). The fractions contained desired product were combined and concentrated to afford tert-butyl (2R,4S)-4-(5-((tert-butoxycarbonyl)(methyl)amino)-4-carbamoyl-3-((1-cyclopropyl-6-fluoro-1H-benzo[d]imidazol-5-yl)ethynyl)-1H-pyrazol-1-yl)-2-(methoxymethyl)pyrrolidine-1-carboxylate (2.20 g, 80%) as an off-white solid. MS ESI calculated for $C_{33}H_{42}FN_7O_6$ [M+H]$^+$, 652.32, found 652.85; $^1$H NMR (400 MHz, CDCl$_3$) δ 10.42 (s, 1H), 8.11-7.91 (m, 2H), 7.33 (d, J=8.9 Hz, 1H), 5.52 (s, 1H), 5.07 (s, 1H), 4.23 (s, 1H), 3.90-3.50 (m, 3H), 3.38 (s, 1H), 3.19-3.12 (m, 6H), 2.66 (s, 1H), 2.29 (s, 1H), 1.82 (s, 1H), 1.48 (t, J=7.4 Hz, 18H), 1.28-1.17 (m, 2H), 1.11-0.79 (m, 2H).

Step 2: 3-((1-Cyclopropyl-6-fluoro-1H-benzo[d]imidazol-5-yl)ethynyl)-1-((3S,5R)-5-(methoxymethyl)pyrrolidin-3-yl)-5-(methylamino)-1H-pyrazole-4-carboxamide hydrochloride To a stirred mixture of tert-butyl (2R,4S)-4-(5-((tert-butoxycarbonyl)(methyl)amino)-4-carbamoyl-3-((1-cyclopropyl-6-fluoro-1H-benzo[d]imidazol-5-yl)ethynyl)-1H-pyrazol-1-yl)-2-(methoxymethyl)pyrrolidine-1-carboxylate (2.20 g, 3.37 mmol) in DCM (11.00 mL) was added 4 M HCl in EA (22.00 mL) dropwise at 0° C. under nitrogen atmosphere. The reaction mixture was stirred for 1 h at room temperature under nitrogen atmosphere. The precipitated solids were collected by filtration and washed with DCM (3×20 mL). The crude product 3-((1-cyclopropyl-6-fluoro-1H-benzo[d]imidazol-5-yl)ethynyl)-1-((3S,5R)-5-(methoxymethyl)pyrrolidin-3-yl)-5-(methylamino)-1H-pyrazole-4-carboxamide hydrochloride (1.60 g, crude) as an off-white was used in the next step directly without further purification. MS ESI calculated for $C_{23}H_{27}ClFN_7O_2$ [M+H–HCl]$^+$, 452.21, found 452.30.

Step 3: 3-((1-Cyclopropyl-6-fluoro-1H-benzo[d]imidazol-5-yl)ethynyl)-1-((3S,5R)-5-(methoxymethyl)-1-propioloylpyrrolidin-3-yl)-5-(methylamino)-1H-pyrazole-4-carboxamide To a stirred mixture of 3-((1-cyclopropyl-6-fluoro-1H-benzo[d]imidazol-5-yl)ethynyl)-1-((3S,5R)-5-(methoxymethyl)pyrrolidin-3-yl)-5-(methylamino)-1H-pyrazole-4-carboxamide hydrochloride (0.30 g, 0.61 mmol) and HATU (0.35 g, 0.92 mmol) in DMF (3.00 mL) were added DIEA (0.43 mL, 2.46 mmol) and propiolic acid (50.85 mg, 0.73 mmol) dropwise at 0° C. under nitrogen atmosphere. The reaction mixture was stirred for 1 h at room temperature under nitrogen atmosphere. The resulting mixture was concentrated under reduced pressure. The residue was purified by silica gel column chromatography, eluted with DCM/MeOH (10/1) to afford crude product which was further purified by reverse flash chromatography with the following conditions: column: C18 silica gel; mobile phase: ACN in water (10 mmol/L NH$_4$HCO$_3$), 10% to 50% gradient in 30 min; detector: UV 254 nm. The fractions contained desired product were combined and concentrated to afford 3-((1-cyclopropyl-6-fluoro-1H-benzo[d]imidazol-5-yl)ethynyl)-1-((3S,5R)-5-(methoxymethyl)-1-propioloylpyrrolidin-3-yl)-5-(methylamino)-1H-pyrazole-4-carboxamide (71.50 mg, 23%) as an off-white solid. MS ESI calculated for $C_{26}H_{26}FN_7O_3$ [M+H]$^+$, 504.21, found 504.20; $^1$H NMR (400 MHz, CDCl$_3$) δ 8.01 (s, 2H), 7.36 (s, 1H), 7.11 (s, 1H), 6.80 (s, 1H), 5.50-5.32 (m, 2H), 4.51-4.47 (m, 1H), 4.25-4.06 (m, 1H), 4.05-3.84 (m, 1H), 3.69-3.63 (m, 1H), 3.44-3.35 (m, 5H), 3.10-2.99 (m, 4H), 2.97-2.69 (m, 1H), 2.39-2.35 (m, 1H), 1.21-1.19 (m, 2H), 1.06 (s, 2H).

Example 183: 1-((3S,5R)-1-(But-2-ynoyl)-5-(methoxymethyl)pyrrolidin-3-yl)-3-((1-cyclopropyl-6-fluoro-1H-benzo[d]imidazol-5-yl)ethynyl)-5-(methylamino)-1H-pyrazole-4-carboxamide

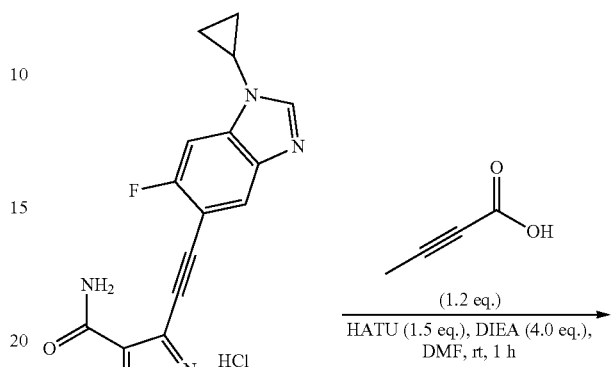

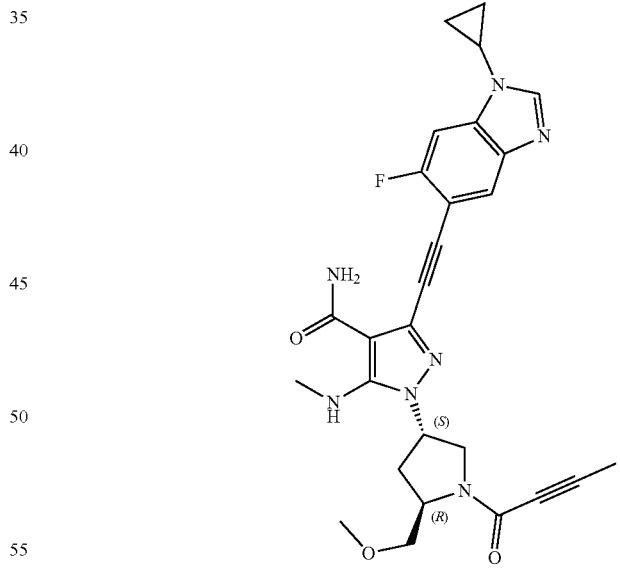

1-((3S,5R)-1-(But-2-ynoyl)-5-(methoxymethyl)pyrrolidin-3-yl)-3-((1-cyclopropyl-6-fluoro-1H-benzo[d]imidazol-5-yl)ethynyl)-5-(methylamino)-1H-pyrazole-4-carboxamide. MS ESI calculated for $C_{27}H_{28}FN_7O_3$ [M+H]$^+$, 518.22, found 518.30; $^1$H NMR (400 MHz, CDCl$_3$) δ 8.02-7.93 (m, 2H), 7.31-7.26 (m, 1H), 7.11 (s, 1H), 6.80 (s, 1H), 5.49-5.31 (m, 1H), 4.49-4.43 (m, 1H), 4.21-4.02 (m, 1H), 4.02-3.81 (m, 1H), 3.65-3.62 (m, 1H), 3.43-3.32 (m, 5H), 3.02 (d, J=16.6 Hz, 3H), 2.93-2.66 (m, 1H), 2.36-2.33 (m, 1H), 2.02 (s, 1H), 1.98 (s, 2H), 1.21-1.18 (m, 2H), 1.15-1.02 (m, 2H).

Example 184: 3-[2-(1-Cyclopropyl-4,6-difluoro-1,3-benzodiazol-5-yl)ethynyl]-1-[(3S,5R)-5-(methoxymethyl)-1-(prop-2-ynoyl)pyrrolidin-3-yl]-5-(methylamino)pyrazole-4-carboxamide Example 185: 1-[(3S,5R)-1-(But-2-ynoyl)-5-(methoxymethyl)pyrrolidin-3-yl]-3-[2-(1-cyclopropyl-4,6-difluoro-1,3-benzodiazol-5-yl)ethynyl]-5-(methylamino)pyrazole-4-carboxamide

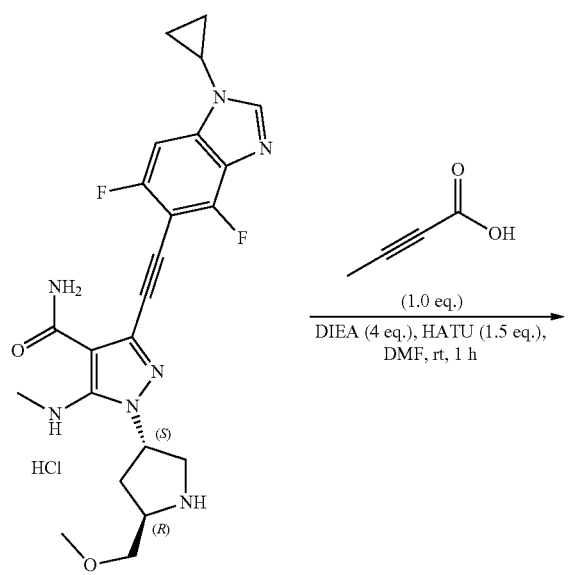

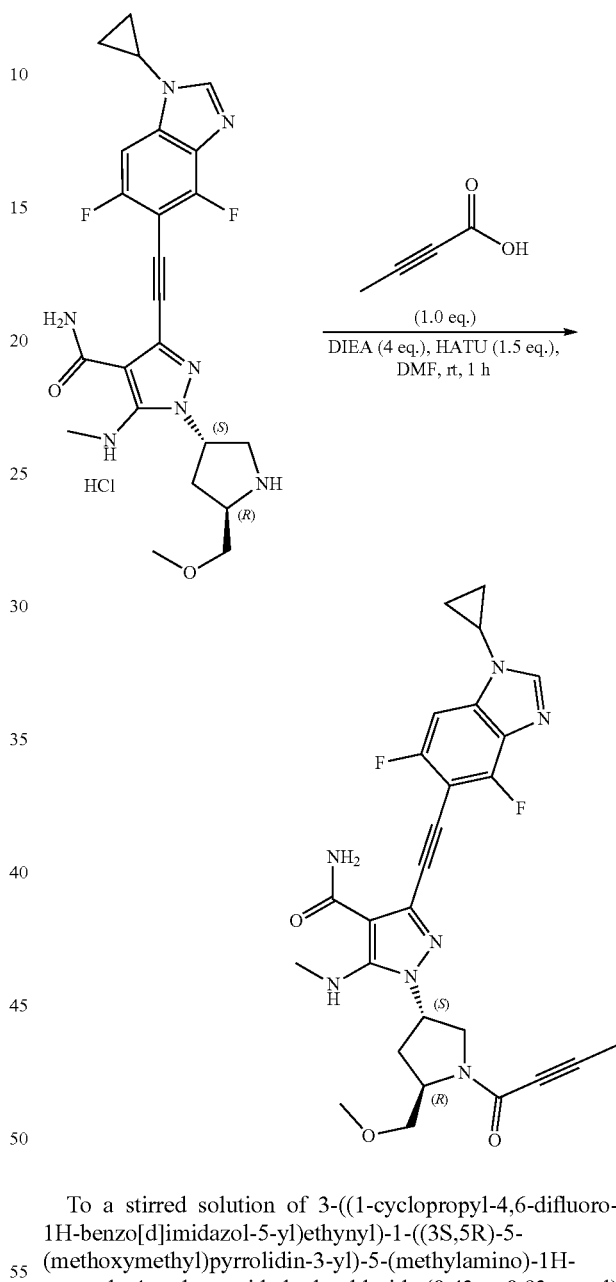

3-[2-(1-cyclopropyl-4,6-difluoro-1,3-benzodiazol-5-yl)ethynyl]-1-[(3S,5R)-5-(methoxymethyl)-1-(prop-2-ynoyl)pyrrolidin-3-yl]-5-(methylamino)pyrazole-4-carboxamide. MS ESI calculated for $C_{26}H_{25}F_2N_7O_3$ [M+H]$^+$, 522.20, found 522.35; $^1$H NMR (400 MHz, CDCl$_3$) δ 7.96 (d, J=4 Hz, 1H), 7.19-7.16 (m, 1H), 7.08 (s, 1H), 6.85-6.73 (m, 1H), 5.49-5.35 (m, 2H), 4.59-4.48 (m, 1H), 4.26-4.21 (m, 1H), 4.07-4.02 (m, 1H), 3.80-3.78 (m, 1H), 3.60-3.57 (m, 1H), 3.44-3.36 (m, 4H), 3.09-3.01 (m, 4H), 2.98-2.76 (m, 1H), 2.42-2.33 (m, 1H), 1.28-1.22 (m, 2H), 1.11-1.07 (m, 2H).

To a stirred solution of 3-((1-cyclopropyl-4,6-difluoro-1H-benzo[d]imidazol-5-yl)ethynyl)-1-((3S,5R)-5-(methoxymethyl)pyrrolidin-3-yl)-5-(methylamino)-1H-pyrazole-4-carboxamide hydrochloride (0.43 g, 0.93 mmol) in DMF (4.37 mL) were added 2-butynoic acid (78.25 mg, 0.93 mmol), HATU (0.53 g, 1.39 mmol) and DIEA (0.62 mL, 3.55 mmol) dropwise at 0° C. under nitrogen atmosphere. The reaction mixture was stirred for 1 h at room temperature. The resulting mixture was concentrated under reduced pressure. The residue was purified by silica gel column chromatography, eluted with DCM/MeOH (10/1) to afford the crude product which was further purified by Prep-HPLC with the following conditions: Column: XBridge Shield RP18 OBD Column, 30×150 mm, 5 m; Mobile Phase A: water (10 mmol/L NH$_4$HCO$_3$), Mobile Phase B: ACN; Flow rate: 60 mL/min; Gradient: 28% B to 45% B in 8 min; 254/210 nm; RT1: 6.65 min. The fractions contained desired product were combined and concentrated to afford 1-[(3S,5R)-1-(but-2-ynoyl)-5-(methoxymethyl)pyrrolidin-3-yl]-3-[2-(1-cyclopropyl-4,6-difluoro-1,3-benzodiazol-5-yl)ethynyl]-5-(methylamino)pyrazole-4-carboxamide (0.14 g, 28%) as a white solid. MS ESI calculated for $C_{27}H_{27}F_2N_7O_3$ [M+H]$^+$, 536.21, found 536.15; $^1$H NMR (400 MHz, CDCl$_3$) δ 7.97 (s, 1H), 7.19-7.16 (m, 1H), 7.08 (s, 1H), 5.49-5.32 (m, 2H), 4.55-4.45 (m, 1H), 4.20-3.99 (m, 1H), 3.93-3.86 (m, 1H), 3.77-3.56 (m, 1H), 3.43-3.40 (m, 2H), 3.37 (s, 3H), 3.06 (s, 3H), 2.96-2.74 (m, 1H), 2.39-2.30 (m, 1H). 2.00 (s, 3H), 1.27-1.22 (m, 2H), 1.11-1.07 (m, 2H).

Example 186: 3-[2-(1-Cyclopropyl-4,6-difluoro-1,3-benzodiazol-5-yl)ethynyl]-5-(methylamino)-1-[(3S)-1-(prop-2-enoyl)pyrrolidin-3-yl]pyrazole-4-carboxamide

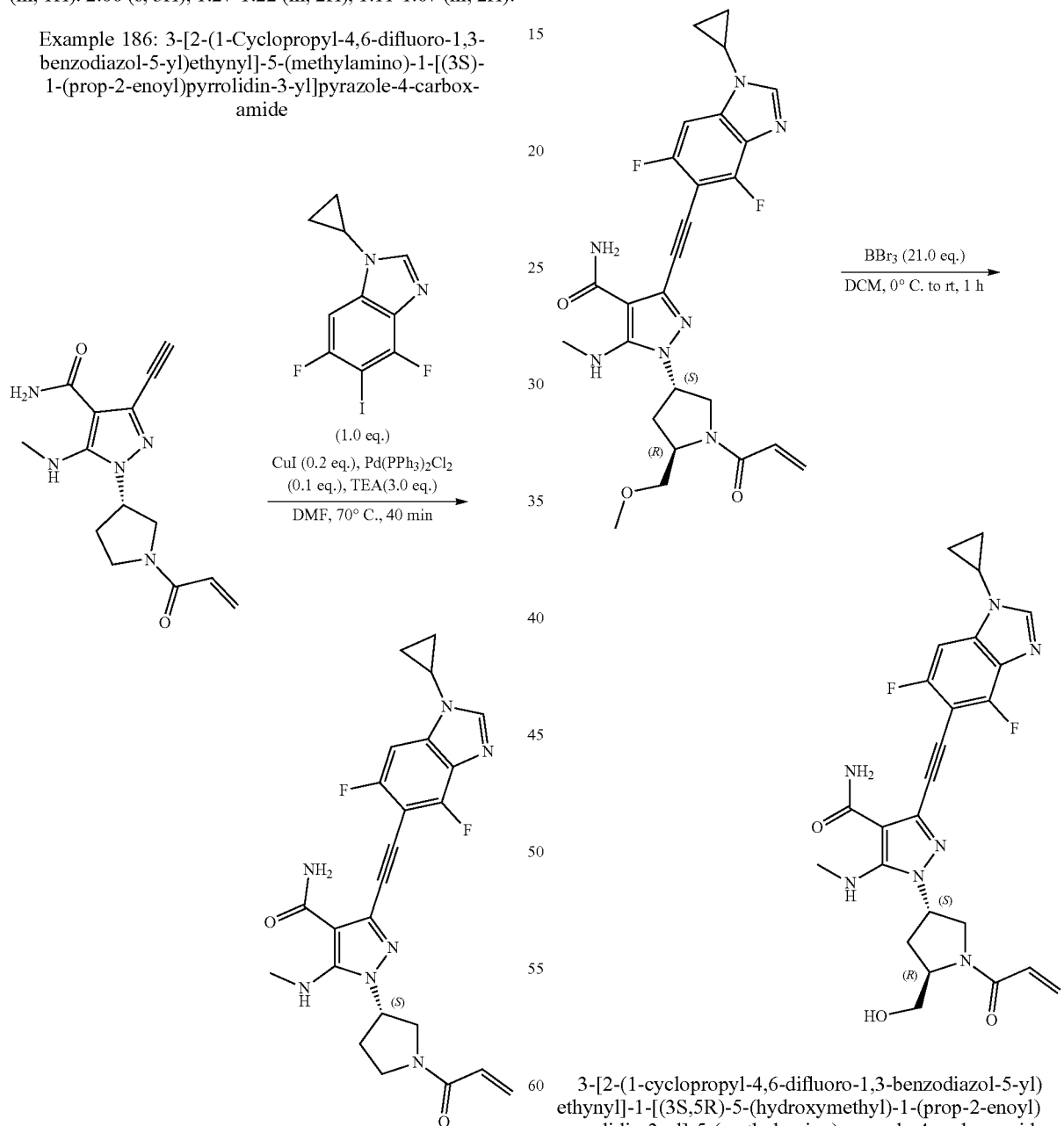

3-[2-(1-cyclopropyl-4,6-difluoro-1,3-benzodiazol-5-yl)ethynyl]-5-(methylamino)-1-[(3S)-1-(prop-2-enoyl)pyrrolidin-3-yl]pyrazole-4-carboxamide. MS ESI calculated for $C_{24}H_{23}F_2N_7O_2$ [M+H]$^+$, 480.49, found 480.35; $^1$H NMR (400 MHz, DMSO-d$_6$) δ 8.41-8.39 (s, 1H), 7.58-7.50 (d, J=8.8 Hz, 2H), 6.80-6.54 (m, 3H), 6.17-6.10 (m, 1H), 5.77-5.65 (m, 1H), 5.24-5.09 (m, 1H), 4.09-3.80 (m, 2H), 3.78-3.69 (m, 1H), 3.68-3.49 (m, 2H), 2.97-2.90 (m, 3H), 2.42-2.40 (m, 1H), 2.32-2.30 (m, 1H), 1.17-1.04 (m, 4H).

Example 187: 3-[2-(1-Cyclopropyl-4,6-difluoro-1,3-benzodiazol-5-yl)ethynyl]-1-[(3S,5R)-5-(hydroxymethyl)-1-(prop-2-enoyl)pyrrolidin-3-yl]-5-(methylamino)pyrazole-4-carboxamide 3-[2-(1-cyclopropyl-4,6-difluoro-1,3-benzodiazol-5-yl)ethynyl]-1-[(3S,5R)-5-(hydroxymethyl)-1-(prop-2-enoyl)pyrrolidin-3-yl]-5-(methylamino)pyrazole-4-carboxamide. MS ESI calculated for $C_{25}H_{25}F_2N_7O_3$ [M+H]$^+$, 510.20, found 510.15; $^1$H NMR (400 MHz, DMSO-d$_6$) δ 8.42 (s, 1H), 7.59 (d, J=8.8 Hz, 2H), 6.80-6.54 (m, 3H), 6.17-6.05 (m, 1H), 5.68 (m, 1H), 5.31-5.24 (m, 1H), 5.02-4.93 (m, 1H), 4.34-4.22 (m, 1H), 4.09-4.05 (m, 1H), 3.94-3.73 (m, 1H), 3.68-3.54 (m, 1H), 3.59-3.47 (m, 2H), 3.29-2.96 (m, 3H), 2.68-2.53 (m, 1H), 2.48-2.25 (m, 1H), 1.22-1.01 (m, 4H).

Example 188: 3-[2-(1-Cyclopropyl-6-fluoro-1,3-benzodiazol-5-yl)ethynyl]-5-(methylamino)-1-[1-(prop-2-ynoyl)pyrrolidin-3-yl]pyrazole-4-carboxamide

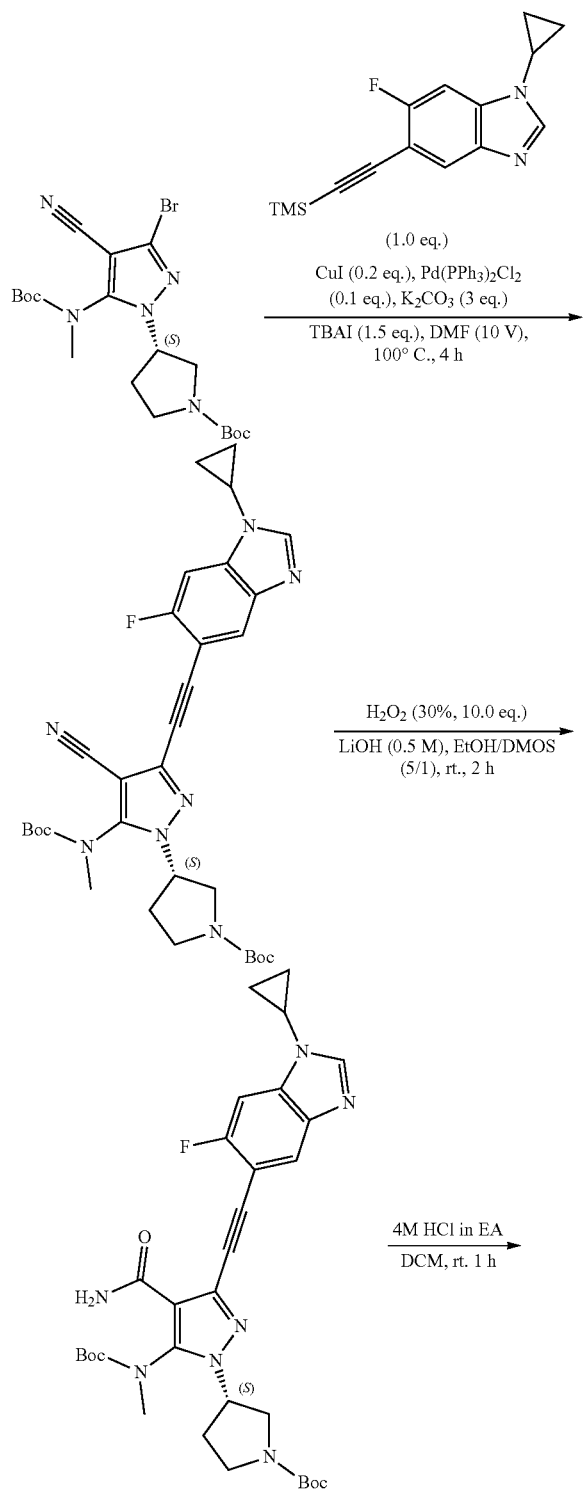

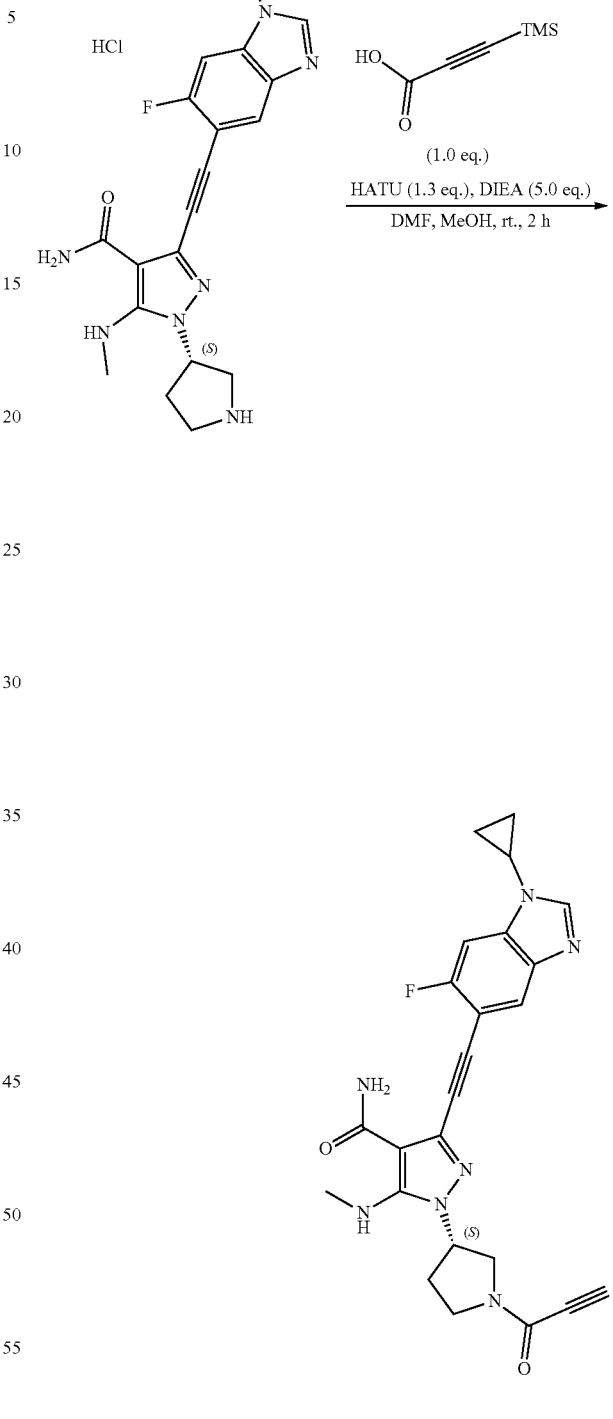

3-[2-(1-cyclopropyl-6-fluoro-1,3-benzodiazol-5-yl)ethynyl]-5-(methylamino)-1-[1-(prop-2-ynoyl)pyrrolidin-3-yl]pyrazole-4-carboxamide. MS ESI calculated for $C_{24}H_{22}FN_7O_2$ [M+H]$^+$, 460.18, found 460.15; $^1$H NMR (400 MHz, CDCl$_3$) δ 8.28 (d, J=12.8 Hz, 1H), 8.05 (s, 1H), 7.37 (d, J=8.6 Hz, 1H), 7.10 (s, 1H), 5.43 (s, 1H), 5.07 (s, 1H), 4.21-4.01 (m, 2H), 3.81 (d, J=90.7 Hz, 2H), 3.45 (s, 1H), 3.10 (d, J=15.7 Hz, 1H), 3.02 (d, J=11.0 Hz, 3H), 2.68 (s, 1H), 2.42 (s, 1H), 1.29-1.24 (m, 2H), 1.14 (s, 2H).

701

Example 189: 5-Amino-3-[2-(1-cyclopropyl-4,6-difluoro-1,3-benzodiazol-5-yl)ethynyl]-1-[(3S,5R)-5-(methoxymethyl)-1-(prop-2-enoyl)pyrrolidin-3-yl]pyrazole-4-carboxamide

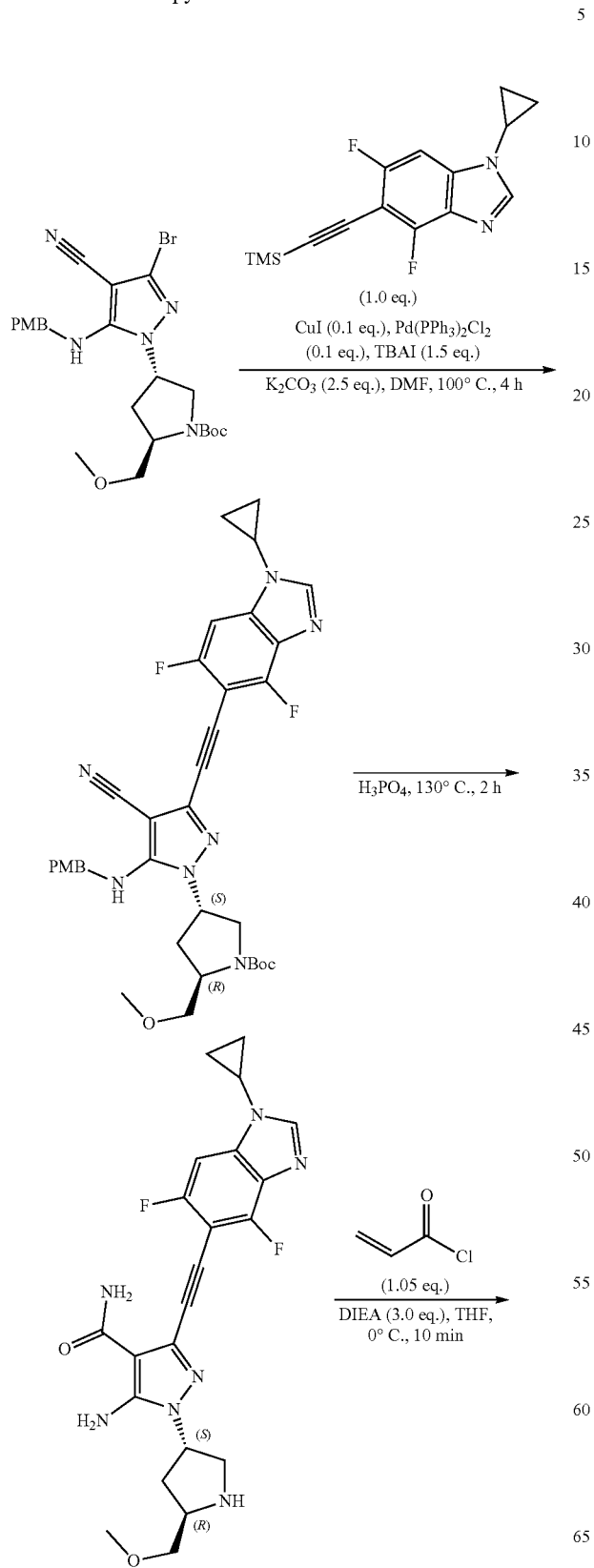

702

-continued

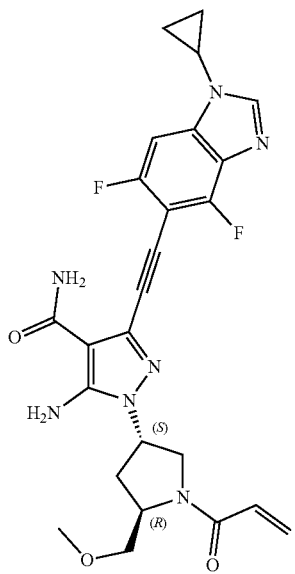

5-amino-3-[2-(1-cyclopropyl-4,6-difluoro-1,3-benzodiazol-5-yl)ethynyl]-1-[(3S,5R)-5-(methoxymethyl)-1-(prop-2-enoyl)pyrrolidin-3-yl]pyrazole-4-carboxamide. MS ESI calculated for $C_{25}H_{25}F_2N_7O_3$ [M+H]$^+$, 510.20, found 510.10; $^1$H NMR (400 MHz, DMSO-d$_6$) δ 8.42 (s, 1H), 7.59 (d, J=8.8 Hz, 1H), 7.45 (s, 1H), 6.78-6.65 (m, 2H), 6.57-6.48 (m, 1H), 6.16-6.07 (m, 1H), 5.69-5.61 (m, 1H), 5.12 (q, J=8.6, 7.9 Hz, 1H), 4.56-4.34 (m, 1H), 4.00-3.65 (m, 2H), 3.57-3.48 (m, 2H), 3.42 (d, J=5.7 Hz, 1H), 3.37-3.32 (m, 3H), 2.51-2.42 (m, 1H), 2.31-2.22 (m, 1H), 1.17-1.03 (m, 4H).

Example 190: 5-Amino-3-[2-(1-cyclopropyl-4,6-difluoro-1,3-benzodiazol-5-yl)ethynyl]-1-[(3S)-1-(prop-2-enoyl)pyrrolidin-3-yl]pyrazole-4-carboxamide

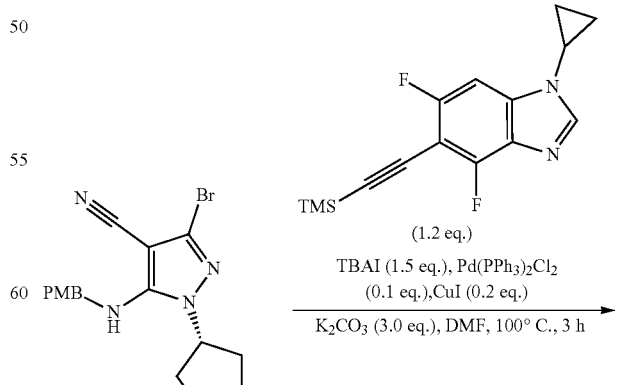

-continued
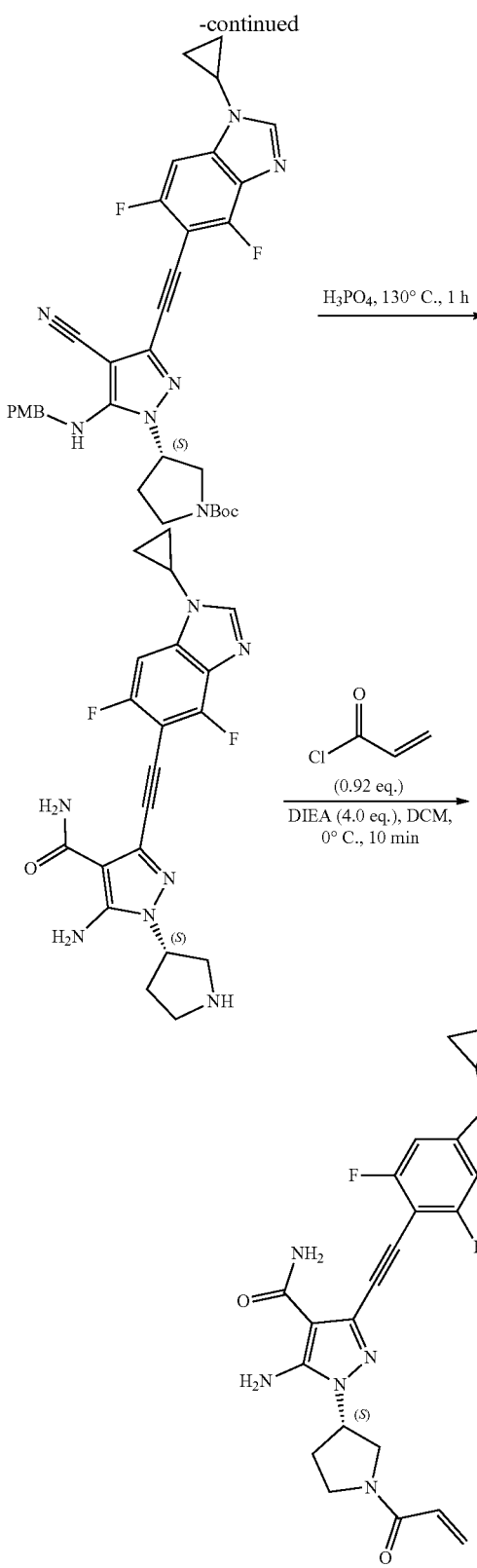
1H), 7.45 (s, 1H), 6.72-6.53 (m, 4H), 6.19-6.14 (m, 1H), 5.72-5.66 (m, 1H), 4.05-4.93 (m, 1H), 4.09-3.74 (m, 2H), 3.71-3.48 (m, 3H), 2.45-2.33 (m, 1H), 2.28-2.25 (m, 1H), 1.16-1.02 (m, 4H).
Example 191: 3-[2-(6-Chloro-1-ethyl-1,3-benzodiazol-5-yl)ethynyl]-1-[(3S,5R)-5-(hydroxymethyl)-1-(prop-2-enoyl)pyrrolidin-3-yl]-5-(methylamino)pyrazole-4-carboxamide
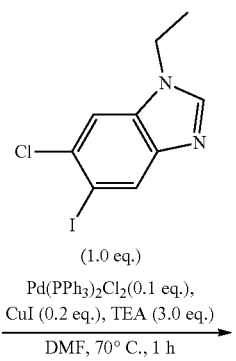
5-amino-3-[2-(1-cyclopropyl-4,6-difluoro-1,3-benzodiazol-5-yl)ethynyl]-1-[(3S)-1-(prop-2-enoyl)pyrrolidin-3-yl]pyrazole-4-carboxamide. MS ESI calculated for $C_{23}H_{21}F_2N_7O_2$ [M+H]$^+$, 466.17, found 466.35; $^1$H NMR (400 MHz, DMSO-d$_6$) δ 8.42 (s, 1H), 7.59 (d, J=8.9 Hz,

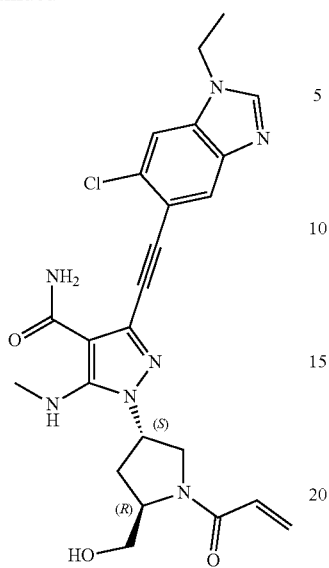
3-[2-(6-chloro-1-ethyl-1,3-benzodiazol-5-yl)ethynyl]-1-[(3S,5R)-5-(hydroxymethyl)-1-(prop-2-enoyl)pyrrolidin-3-yl]-5-(methylamino)pyrazole-4-carboxamide. MS ESI calculated for $C_{24}H_{26}ClN_7O_3$ [M+H]$^+$, 496.18, found 496.35; $^1$H NMR (400 MHz, CDCl$_3$) δ 8.43 (s, 1H), 8.01 (d, J=4 Hz, 2H), 7.49 (s, 1H), 6.86 (s, 1H), 6.75-6.57 (m, 2H), 6.20-6.14 (m, 1H), 5.71-5.67 (m, 1H), 5.38-5.24 (m, 1H), 5.10 (t, J=12 Hz, 1H), 4.95 (t, J=12.6 Hz, 3H), 4.38 (d, J=4 Hz, 2H), 4.33-4.28 (m, 2H), 3.92-3.76 (m, 3H), 3.71-3.66 (m, 1H), 3.55-3.49 (m, 1H), 1.41 (t, J=12 Hz, 3H).
Example 192: 3-[2-(6-Chloro-1-ethyl-1,3-benzodiazol-5-yl)ethynyl]-5-(methylamino)-1 [1-(prop-2-enoyl)azetidin-3-yl]pyrazole-4-carboxamide
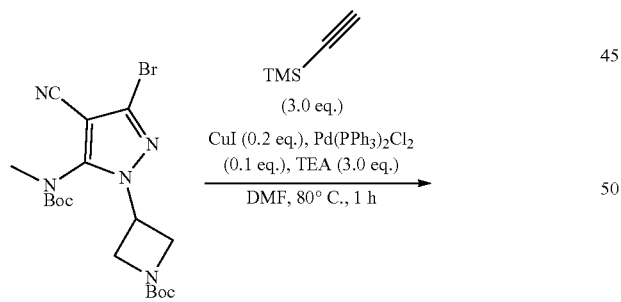
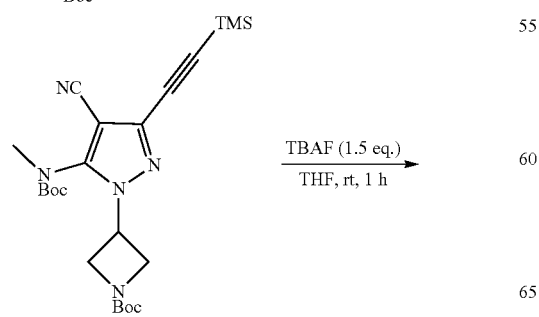
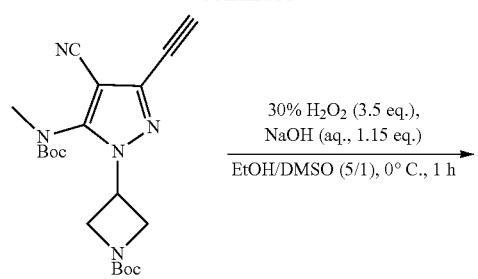
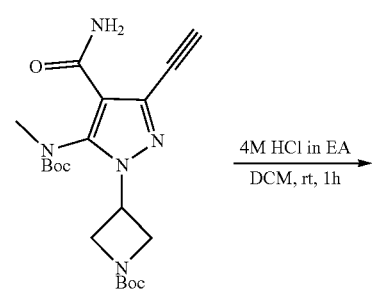
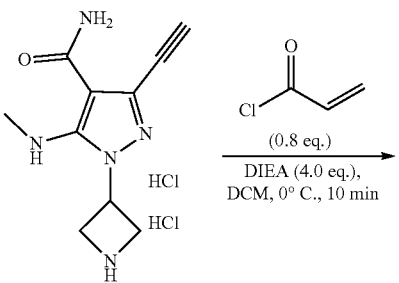

-continued

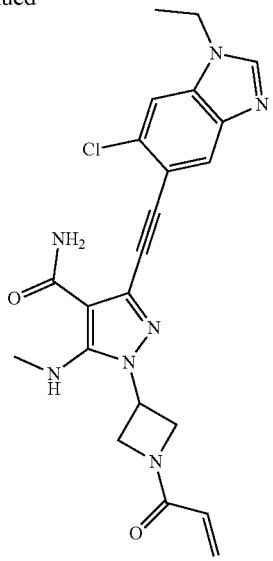

Step 1: Tert-butyl 3-(5-((tert-butoxycarbonyl) (methyl)amino)-4-cyano-3-((trimethylsilyl)ethynyl)-1H-pyrazol-1-yl)azetidine-1-carboxylate To a stirred mixture of tert-butyl 3-{3-bromo-5-[(tert-butoxycarbonyl)(methyl)amino]-4-cyanopyrazol-1-yl}azetidine-1-carboxylate (2.80 g, 6.13 mmol), Pd(PPh$_3$)$_2$Cl$_2$ (0.43 g, 0.61 mmol) and CuI (0.23 g, 1.21 mmol) in DMF (28.00 mL) were added TEA (2.56 mL, 18.42 mmol) and trimethylsilylacetylene (1.81 g, 18.41 mmol) at room temperature. The reaction mixture was degassed with nitrogen for three times and stirred for 1 h at 80° C. The resulting mixture was concentrated under reduced pressure. The residue was purified by silica gel column chromatography, eluted with PE/EA (2/1). The fractions contained desired product were combined and concentrated to afford tert-butyl 3-(5-((tert-butoxycarbonyl)(methyl)amino)-4-cyano-3-((trimethylsilyl)ethynyl)-1H-pyrazol-1-yl)azetidine-1-carboxylate (2.90 g, 94%) as a light yellow solid. MS ESI calculated for C$_{23}$H$_{35}$N$_5$O$_4$Si [M+H–112]$^+$, 362.25, found 362.00; $^1$H NMR (400 MHz, CDCl$_3$) δ 4.85 (s, 1H), 4.47 (s, 1H), 4.28 (d, J=7.9 Hz, 3H), 3.23 (s, 3H), 1.46 (d, J=3.0 Hz, 18H), 0.29 (s, 9H).

Step 2: Tert-butyl 3-(5-((tert-butoxycarbonyl) (methyl)amino)-4-cyano-3-ethynyl-1H-pyrazol-1-yl) azetidine-1-carboxylate To a stirred solution of tert-butyl 3-(5-((tert-butoxycarbonyl)(methyl)amino)-4-cyano-3-((trimethylsilyl)ethynyl)-1H-pyrazol-1-yl)azetidine-1-carboxylate (2.84 g, 5.99 mmol) in THF (19.88 mL) was added TBAF (8.99 mL, 8.99 mmol) dropwise at room temperature under nitrogen atmosphere. The reaction mixture was stirred for 1 h at room temperature under nitrogen atmosphere. The residue was purified by silica gel column chromatography, eluted with PE/EA (2/1). The fractions contained desired product were combined and concentrated to afford tert-butyl 3-(5-((tert-butoxycarbonyl)(methyl)amino)-4-cyano-3-ethynyl-1H-pyrazol-1-yl)azetidine-1-carboxylate (2.00 g, 83%) as an off-white solid. MS ESI calculated for C$_{20}$H$_{27}$N$_5$O$_4$ [M+H–56]$^+$, 346.21, found 346.10.

Step 3: Tert-butyl 3-(5-((tert-butoxycarbonyl) (methyl)amino)-4-carbamoyl-3-ethynyl-1H-pyrazol-1-yl)azetidine-1-carboxylate To a stirred solution of tert-butyl 3-(5-((tert-butoxycarbonyl)(methyl)amino)-4-cyano-3-ethynyl-1H-pyrazol-1-yl) azetidine-1-carboxylate (2 g, 4.98 mmol) in EtOH (20.00 mL) and DMSO (4.0 mL) were added H$_2$O$_2$ (30%) (1.35 mL, 17.43 mmol) and 0.5 M NaOH (11.46 mL, 5.73 mmol) dropwise at 0° C. under nitrogen atmosphere. Then the reaction mixture was stirred for 1 h at 0° C. The resulting mixture was extracted with EtOAc (3×100 mL). The combined organic layers was washed with brine (3×50 mL), dried over anhydrous Na$_2$SO$_4$. After filtration, the filtrate was concentrated under reduced pressure. The residue was purified by silica gel column chromatography, eluted with DCM/EA (2/1), the fractions contained desired product were combined and concentrated to afford tert-butyl 3-(5-((tert-butoxycarbonyl)(methyl)amino)-4-carbamoyl-3-ethynyl-1H-pyrazol-1-yl)azetidine-1-carboxylate (2.00 g, 95%) as an off-white solid. MS ESI calculated for C$_{20}$H$_{29}$N$_5$O$_5$ [M+H]$^+$, 420.22, found 420.20.

Step 4: 1-(Azetidin-3-yl)-3-ethynyl-5-(methylamino)pyrazole-4-carboxamide dihydrochloride To a stirred solution of tert-butyl 3-(5-((tert-butoxycarbonyl)(methyl)amino)-4-carbamoyl-3-ethynyl-1H-pyrazol-1-yl)azetidine-1-carboxylate (2.10 g, 4.51 mmol) in DCM (10.00 mL) was added 4 M HCl in EA (20.00 mL) dropwise at 0° C. under nitrogen atmosphere. The reaction mixture was stirred for 1 h at room temperature under nitrogen atmosphere. The precipitated solids were collected by filtration and washed with DCM (3×50 mL). The crude product 1-(azetidin-3-yl)-3-ethynyl-5-(methylamino)pyrazole-4-carboxamide dihydrochloride (0.77 g, crude) was used in the next step directly without further purification. MS ESI calculated for C$_{10}$H$_{15}$Cl$_2$N$_5$O [M+H–2HCl]$^+$, 220.07, found 220.25.

Step 5: 3-Ethynyl-5-(methylamino)-1-[1-(prop-2-enoyl)azetidin-3-yl]pyrazole-4-carboxamide To a stirred solution of 1-(azetidin-3-yl)-3-ethynyl-5-(methylamino)pyrazole-4-carboxamide dihydrochloride (0.77 g, 1.85 mmol) in DCM (10.00 mL) were added acryloyl chloride (5.90 mL, 1.48 mmol) and DIEA (1.29 mL, 7.38 mmol) dropwise at 0° C. under nitrogen atmosphere. The reaction mixture was stirred for 10 min at 0° C. under nitrogen atmosphere. The resulting mixture was diluted with water (30.00 mL) and extracted with EA (3×50 mL). The combined organic layers was washed with brine (3×20 mL), dried over anhydrous Na$_2$SO$_4$. After filtration, the filtrate was concentrated under reduced pressure. The residue was purified by silica gel column chromatography, eluted with CH$_2$Cl$_2$/MeOH (10/1). The fractions contained desired product were combined and concentrated to afford 3-ethynyl-5-(methylamino)-1-[1-(prop-2-enoyl)azetidin-3-yl] pyrazole-4-carboxamide (0.30 g, 60%) as a white solid. MS ESI calculated for C$_{13}$H$_{15}$N$_5$O$_2$ [M+H]$^+$, 274.12, found 274.10; $^1$H NMR (400 MHz, Chloroform-d) δ 6.80 (s, 2H), 6.45-6.29 (m, 1H), 6.34-6.17 (m, 2H), 6.14-6.02 (m, 1H), 4.56 (s, 3H), 4.03-3.88 (m, 1H), 3.85-3.65 (m, 1H), 3.50 (d, J=2.7 Hz, 1H), 2.95 (s, 3H).

Step 6: 3-[2-(6-Chloro-1-ethyl-1,3-benzodiazol-5-yl)ethynyl]-5-(methylamino)-1-[1-(prop-2-enoyl)azetidin-3-yl]pyrazole-4-carboxamide To a stirred mixture of 3-ethynyl-5-(methylamino)-1-[1-(prop-2-enoyl)azetidin-3-yl]pyrazole-4-carboxamide (80.00 mg, 0.29 mmol), 6-chloro-1-ethyl-5-iodo-1,3-benzodiazole (89.73 mg, 0.29 mmol), CuI (11.15 mg, 0.06 mmol) and Pd(PPh$_3$)$_2$Cl$_2$ (20.55 mg, 0.03 mmol) in DMF (2.00 mL) was added TEA (0.12 mL, 0.88 mmol). The reaction mixture was degassed with nitrogen for three times and stirred for 1 h at 90° C. The resulting mixture was diluted with water (20.00 mL). The resulting mixture was extracted with EA (3×50 mL). The combined organic layers were washed with brine (3×30 mL), dried over anhydrous Na$_2$SO$_4$. After filtration, the filtrate was concentrated under reduced pressure. The residue was purified by silica gel column chromatography, eluted with CH$_2$Cl$_2$/MeOH (10/1) to afford the crude product which was further purified by Prep-HPLC with the following conditions: Column: Xselect CSH OBD Column 30×150 mm 5 m; Mobile Phase A: water (0.1% FA), Mobile Phase B: ACN; Flow rate: 60 mL/min; Gradient: 20% B to 30% B in 8 min; Wave Length: 220 nm; RT1: 6.62 min. The fractions contained desired product were combined and concentrated to afford 3-[2-(6-chloro-1-ethyl-1,3-benzodiazol-5-yl)ethynyl]-5-(methylamino)-1-[1-(prop-2-enoyl)azetidin-3-yl]pyrazole-4-carboxamide (28.10 mg, 21%) as a white solid. MS ESI calculated for C$_{22}$H$_{22}$ClN$_7$O$_2$ [M+H]$^+$, 452.15, found 452.35; $^1$H NMR (400 MHz, DMSO-d$_6$) δ 8.43 (s, 1H), 8.06 (s, 1H), 8.01 (s, 1H), 7.52 (s, 1H), 6.87 (s, 1H), 6.83-6.67 (m, 1H), 6.45-6.29 (m, 1H), 6.24-6.09 (m, 1H), 5.80-5.68 (m, 1H), 5.51-5.39 (m, 1H), 4.73-4.52 (m, 2H), 4.47-4.22 (m, 4H), 2.91 (d, J=5.7 Hz, 3H), 1.41 (t, J=7.2 Hz, 3H).

Example 193: 3-[2-(1-Cyclopropyl-4,6-difluoro-1,3-benzodiazol-5-yl)ethynyl]-5-(methylamino)-1-[1-(prop-2-enoyl)azetidin-3-yl]pyrazole-4-carboxamide

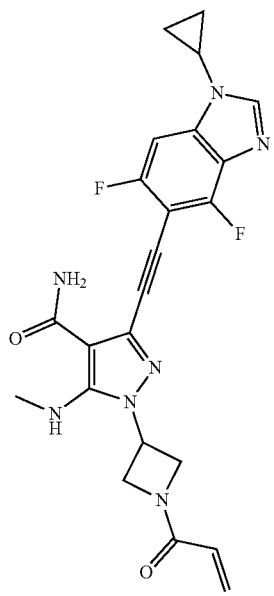

3-[2-(1-cyclopropyl-4,6-difluoro-1,3-benzodiazol-5-yl)ethynyl]-5-(methylamino)-1-[1-(prop-2-enoyl)azetidin-3-yl]pyrazole-4-carboxamide. MS ESI calculated for C$_{23}$H$_{21}$F$_2$N$_7$O$_2$ [M+H]$^+$, 466.17, found 466.40; $^1$H NMR (400 MHz, DMSO-d$_6$) δ 8.43 (s, 1H), 7.60 (d, J=8.7 Hz, 2H), 6.76 (q, J=6.8, 6.2 Hz, 2H), 6.46-6.23 (m, 1H), 6.24-6.07 (m, 1H), 5.79-5.65 (m, 1H), 5.51-5.34 (m, 1H), 4.72-4.56 (m, 2H), 4.39 (t, J=9.2 Hz, 1H), 4.37-4.23 (m, 1H), 3.61-3.46 (m, 1H), 2.91 (d, J=5.7 Hz, 3H), 1.17-1.03 (m, 4H).

Example 194: 5-Amino-3-[2-(6-chloro-1-ethyl-1,3-benzodiazol-5-yl)ethynyl]-1-[(3S,5R)-5-(hydroxymethyl)-1-(prop-2-enoyl)pyrrolidin-3-yl]pyrazole-4-carboxamide

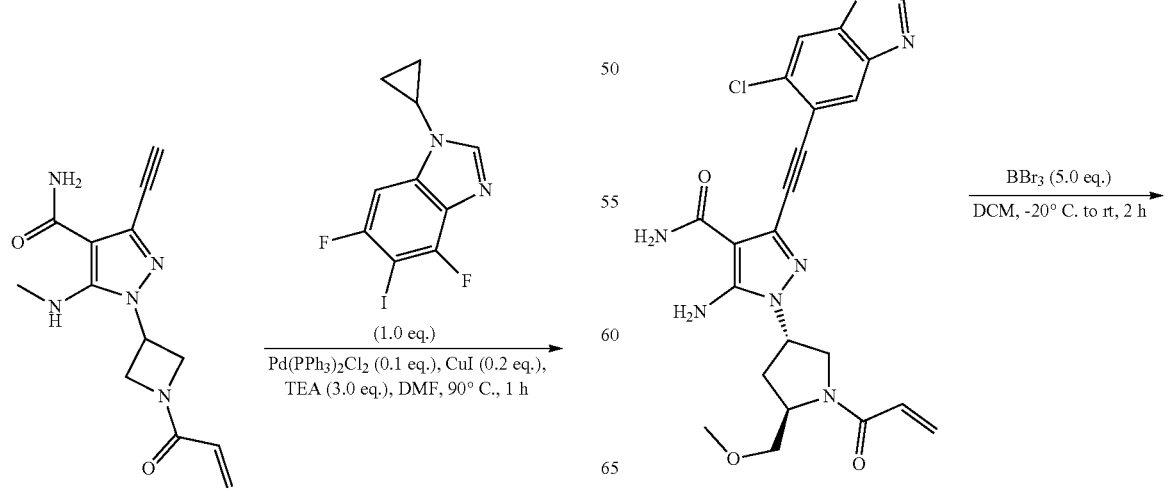

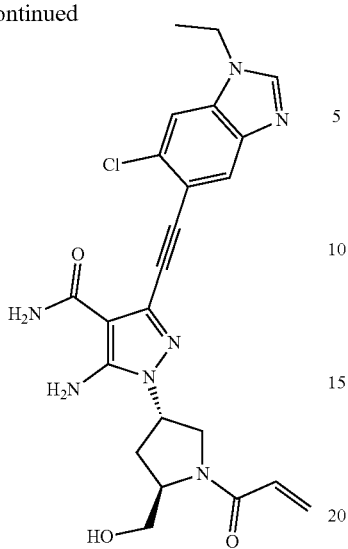

To a solution of 5-amino-3-[2-(6-chloro-1-ethyl-1,3-benzodiazol-5-yl)ethynyl]-1-[(3S,5R)-5-(methoxymethyl)-1-(prop-2-enoyl)pyrrolidin-3-yl]pyrazole-4-carboxamide (0.44 g, 0.89 mmol) in DCM (22.00 mL) was added BBr$_3$ (1.11 g, 4.44 mmol) dropwise at −20° C. The reaction mixture was allowed to warm to room temperature and stirred for 2 h. The resulting mixture was quenched with NaHCO$_3$ (aq.). and concentrated under reduced pressure. The residue product was purified by reverse phase flash with the following conditions: C18 silica gel; mobile phase: ACN in water (10 mmol/L NH$_4$HCO$_3$), 5% to 70% gradient in 30 min; detector: UV 254 nm. The fractions contained desired product were combined and concentrated to afford 5-amino-3-[2-(6-chloro-1-ethyl-1,3-benzodiazol-5-yl)ethynyl]-1-[(3S,5R)-5-(hydroxymethyl)-1-(prop-2-enoyl)pyrrolidin-3-yl]pyrazole-4-carboxamide (0.18 g, 42%) as an off-white solid. MS ESI calculated for C$_{23}$H$_{24}$ClN$_7$O$_3$ [M+H]$^+$, 482.17, found 482.30; $^1$H NMR (400 MHz, DMSO-d$_6$) δ 8.43 (s, 1H), 8.01 (d, J=6.2 Hz, 2H), 7.35 (s, 1H), 6.96-6.46 (m, 4H), 6.22-6.12 (m, 1H), 5.69-5.67 (m, 1H), 5.14-5.05 (m, 1H), 4.89-4.88 (m, 1H), 4.33-4.27 (m, 3H), 4.01-3.66 (m, 2H), 3.58-3.55 (m, 1H), 3.55-3.45 (m, 1H), 2.48-2.11 (m, 2H), 1.41 (t, J=7.2 Hz, 3H).

Example 195: 3-[2-(6-Chloro-1-cyclopropyl-1,3-benzodiazol-5-yl)ethynyl]-1-[(3S,5R)-5-(hydroxymethyl)-1-(prop-2-enoyl)pyrrolidin-3-yl]-5-(methylamino)pyrazole-4-carboxamide

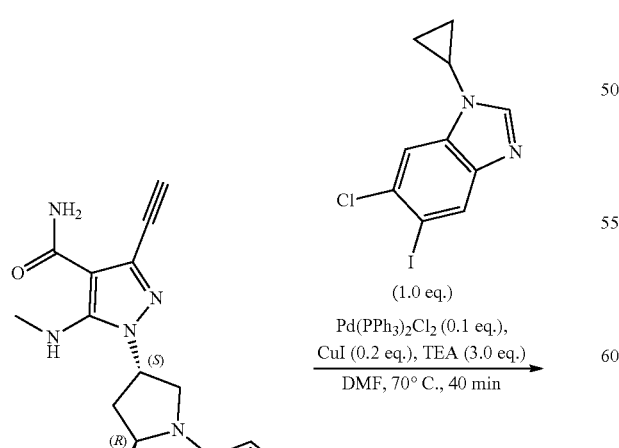

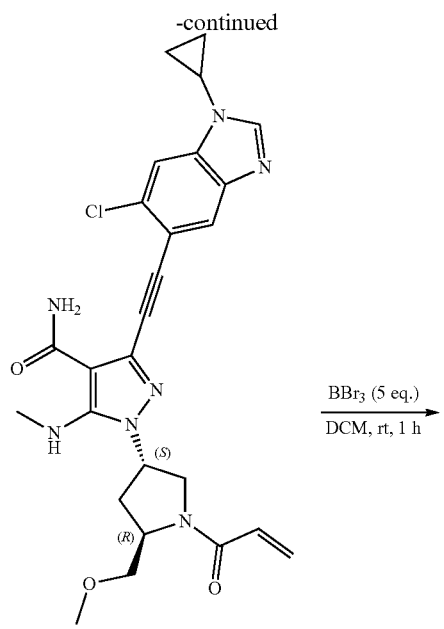

3-[2-(6-chloro-1-cyclopropyl-1,3-benzodiazol-5-yl)ethynyl]-1-[(3S,5R)-5-(hydroxymethyl)-1-(prop-2-enoyl)pyrrolidin-3-yl]-5-(methylamino)pyrazole-4-carboxamide. MS ESI calculated for C$_{25}$H$_{26}$ClN$_7$O$_3$ [M+H]$^+$, 508.18, found 508.10; $^1$H NMR (400 MHz, CDCl$_3$) δ 8.08 (d, J=13.3 Hz, 2H), 7.68 (s, 1H), 7.20 (s, 1H), 6.57-6.40 (m, 2H), 5.78-5.66 (m, 1H), 5.52-5.21 (m, 2H), 4.55 (d, J=73.4 Hz, 1H), 4.23-4.12 (m, 1H), 4.10-3.94 (m, 2H), 3.73-3.62 (m, 1H), 3.41-3.28 (m, 1H), 3.03 (s, 3H), 2.81-2.66 (m, 1H), 2.21-2.13 (m, 1H), 1.29-1.18 (m, 2H), 1.18-1.06 (m, 2H).

Example 196: 5-Amino-3-[2-(6-chloro-1-ethyl-1,3-benzodiazol-5-yl)ethynyl]-1-[(3S,5R)-5-(methoxymethyl)-1-(prop-2-enoyl)pyrrolidin-3-yl]pyrazole-4-carboxamide Example 197: 3-[2-(6-Chloro-1-cyclopropyl-1,3-benzodiazol-5-yl)ethynyl]-5-(methylamino)-1-[1-(prop-2-enoyl)azetidin-3-yl]pyrazole-4-carboxamide

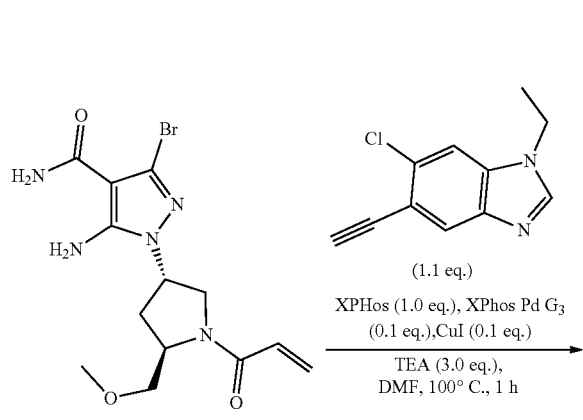

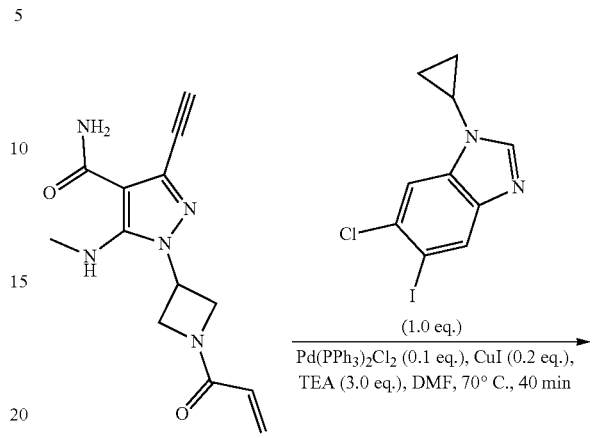

5-amino-3-[2-(6-chloro-1-ethyl-1,3-benzodiazol-5-yl)ethynyl]-1-[(3S,5R)-5-(methoxymethyl)-1-(prop-2-enoyl)pyrrolidin-3-yl]pyrazole-4-carboxamide. MS ESI calculated for $C_{24}H_{26}ClN_7O_3$ [M+H]$^+$, 496.19, found 496.15; $^1$H NMR (400 MHz, CDCl$_3$) δ 8.10 (d, J=4.6 Hz, 1H), 7.98 (s, 1H), 7.51 (s, 1H), 7.16 (s, 1H), 6.46-6.42 (m, 2H), 5.73-5.70 (m, 1H), 5.64 (s, 2H), 5.46 (s, 1H), 5.08-5.03 (m, 1H), 4.59 (d, J=9.1 Hz, 1H), 4.25-4.20 (m, 2H), 4.09-3.83 (m, 3H), 3.51-3.46 (m, 1H), 3.39 (s, 3H), 2.69 (m, 1H), 2.36-2.31 (m, 1H), 1.58 (t, J=7.3 Hz, 3H).

3-[2-(6-chloro-1-cyclopropyl-1,3-benzodiazol-5-yl)ethynyl]-5-(methylamino)-1-[1-(prop-2-enoyl)azetidin-3-yl]pyrazole-4-carboxamide. MS ESI calculated for $C_{23}H_{22}ClN_7O_2$ [M+H]$^+$, 464.15, found 464.35; $^1$H NMR (400 MHz, CDCl$_3$) δ 8.23 (s, 1H), 7.88 (s, 1H), 7.23-7.09 (m, 1H), 6.72 (s, 1H), 6.48-6.27 (m, 1H), 6.30-6.13 (m, 1H), 5.75-5.72 (m, 1H), 5.42 (s, 1H), 5.33-5.20 (m, 1H), 4.99 (d, J=8.1 Hz, 1H), 4.63-4.52 (m, 3H), 3.41 (s, 1H), 2.97 (s, 3H), 1.26 (t, J=7.4 Hz, 2H), 1.11 (s, 2H).

Example 198: 3-[2-(1-Cyclopropyl-6-fluoro-1,3-benzodiazol-5-yl)ethynyl]-1-[(3S,5R)-5-(hydroxymethyl)-1-(prop-2-ynoyl)pyrrolidin-3-yl]-5-(methylamino)pyrazole-4-carboxamide

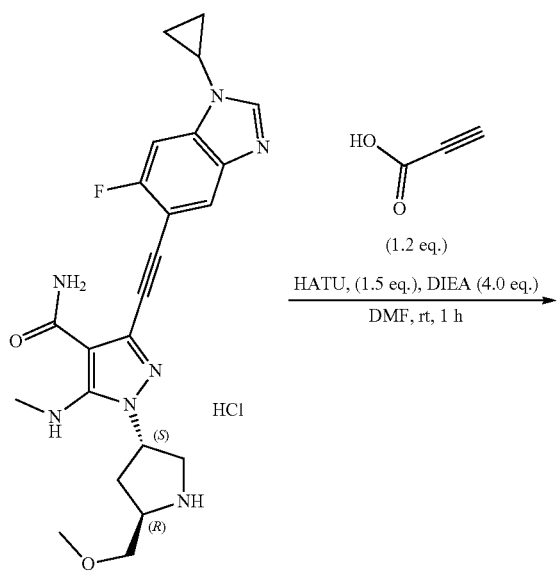
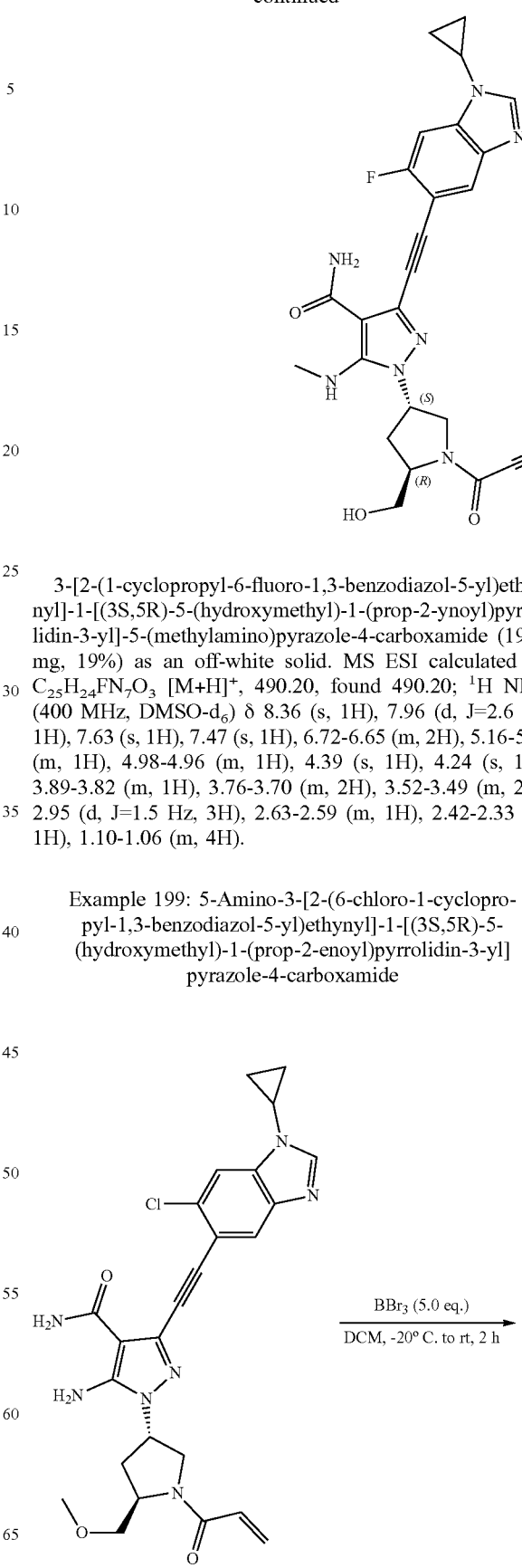

3-[2-(1-cyclopropyl-6-fluoro-1,3-benzodiazol-5-yl)ethynyl]-1-[(3S,5R)-5-(hydroxymethyl)-1-(prop-2-ynoyl)pyrrolidin-3-yl]-5-(methylamino)pyrazole-4-carboxamide (19.30 mg, 19%) as an off-white solid. MS ESI calculated for $C_{25}H_{24}FN_7O_3$ [M+H]$^+$, 490.20, found 490.20; $^1$H NMR (400 MHz, DMSO-d$_6$) δ 8.36 (s, 1H), 7.96 (d, J=2.6 Hz, 1H), 7.63 (s, 1H), 7.47 (s, 1H), 6.72-6.65 (m, 2H), 5.16-5.13 (m, 1H), 4.98-4.96 (m, 1H), 4.39 (s, 1H), 4.24 (s, 1H), 3.89-3.82 (m, 1H), 3.76-3.70 (m, 2H), 3.52-3.49 (m, 2H), 2.95 (d, J=1.5 Hz, 3H), 2.63-2.59 (m, 1H), 2.42-2.33 (m, 1H), 1.10-1.06 (m, 4H).

Example 199: 5-Amino-3-[2-(6-chloro-1-cyclopropyl-1,3-benzodiazol-5-yl)ethynyl]-1-[(3S,5R)-5-(hydroxymethyl)-1-(prop-2-enoyl)pyrrolidin-3-yl]pyrazole-4-carboxamide

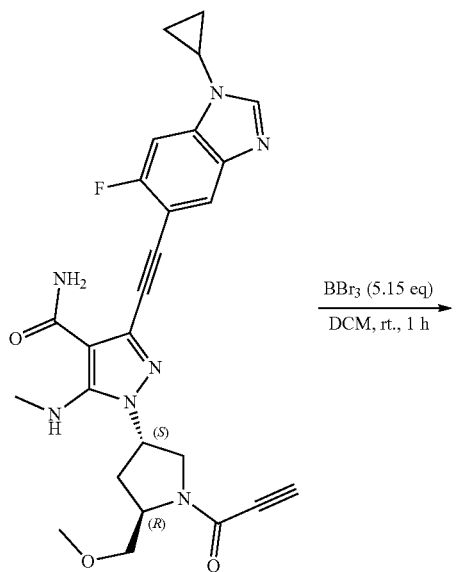

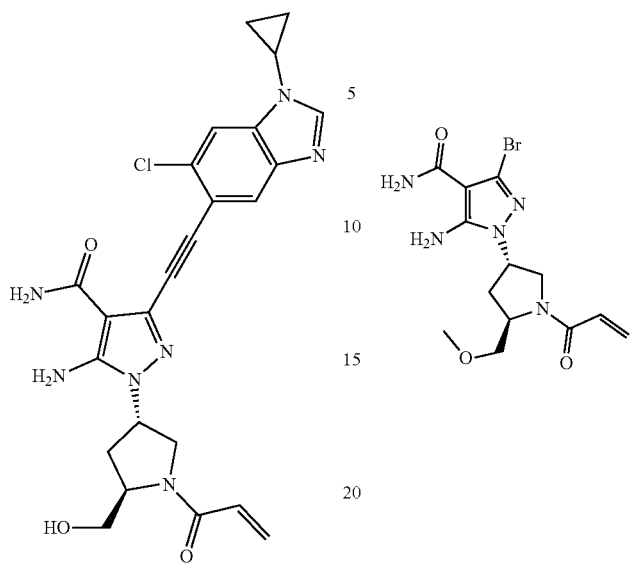

5-amino-3-[2-(6-chloro-1-cyclopropyl-1,3-benzodiazol-5-yl)ethynyl]-1-[(3S,5R)-5-(hydroxymethyl)-1-(prop-2-enoyl)pyrrolidin-3-yl]pyrazole-4-carboxamide. MS ESI calculated for $C_{24}H_{24}ClN_7O_3$ [M+H]$^+$, 494.16, found 494.15; $^1$H NMR (400 MHz, DMSO-$d_6$) δ 8.39 (s, 1H), 8.02 (s, 1H), 7.88 (s, 1H), 7.35 (s, 1H), 6.84-6.45 (m, 4H), 6.18-6.14 (m, 1H), 5.69-5.67 (m, 1H), 5.20-4.85 (m, 2H), 4.38-4.28 (m, 1H), 4.03-3.66 (m, 2H), 3.56-3.51 (m, 2H), 3.48 (d, J=5.2 Hz, 1H), 2.44-2.27 (m, 2H), 1.17-1.02 (m, 4H).

Example 200: 5-Amino-3-[2-(6-chloro-1-cyclopropyl-1,3-benzodiazol-5-yl)ethynyl]-1-[(3S,5R)-5-(methoxymethyl)-1-(prop-2-enoyl)pyrrolidin-3-yl]pyrazole-4-carboxamide

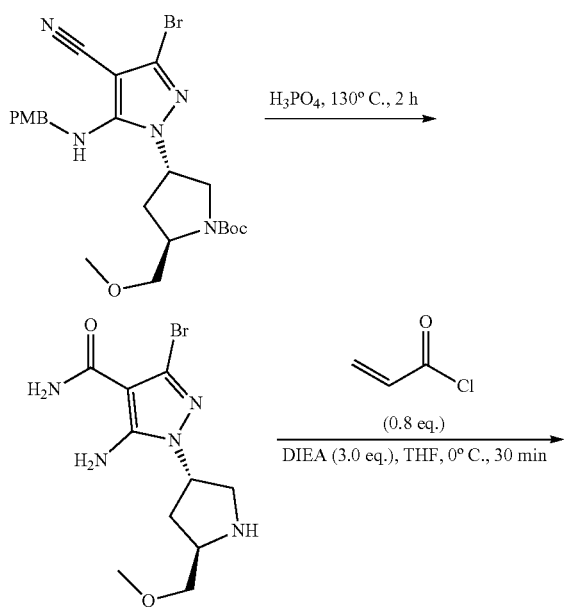

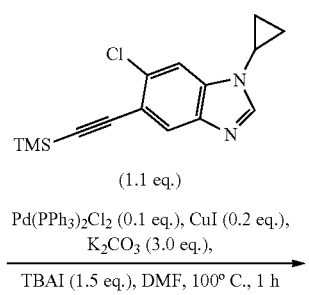

(1.1 eq.)

Pd(PPh$_3$)$_2$Cl$_2$ (0.1 eq.), CuI (0.2 eq.), K$_2$CO$_3$ (3.0 eq.),

TBAI (1.5 eq.), DMF, 100° C., 1 h 5-amino-3-[2-(6-chloro-1-cyclopropyl-1,3-benzodiazol-5-yl)ethynyl]-1-[(3S,5R)-5-(methoxymethyl)-1-(prop-2-enoyl)pyrrolidin-3-yl]pyrazole-4-carboxamide. MS ESI calculated for $C_{25}H_{26}ClN_7O_3$ [M+H]$^+$, 508.19, found 508.35; $^1$H NMR (400 MHz, CDCl$_3$) δ 8.05 (d, J=27.4 Hz, 2H), 7.67 (s, 1H), 7.16 (s, 1H), 6.51-6.36 (m, 2H), 5.75-5.72 (m, 1H), 5.60 (s, 2H), 5.44 (s, 1H), 5.09-5.05 (m, 1H), 4.60 (d, J=8.9 Hz, 1H), 4.06 (d, J=8.2 Hz, 2H), 3.99-3.86 (m, 1H), 3.54-3.50 (m, 1H), 3.39 (s, 4H), 2.72-2.65 (m, 1H), 2.47-2.29 (m, 1H), 1.25-1.20 (m, 2H), 1.10-1.06 (m, 2H).

Example 201: 5-Amino-3-[2-(1-cyclopropyl-4,6-difluoro-1,3-benzodiazol-5-yl)ethynyl]-1-[(3S,5R)-5-(hydroxymethyl)-1-(prop-2-enoyl)pyrrolidin-3-yl]pyrazole-4-carboxamide Example 202: 5-Amino-3-[2-(1-cyclopropyl-6-fluoro-1,3-benzodiazol-5-yl)ethynyl]-1-[1-(prop-2-enoyl)azetidin-3-yl]pyrazole-4-carboxamide

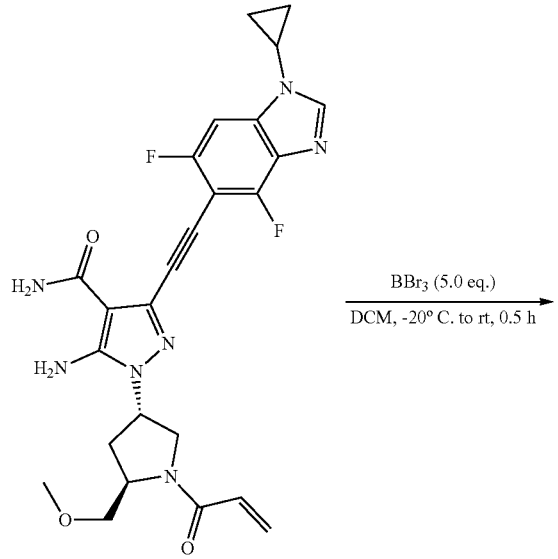
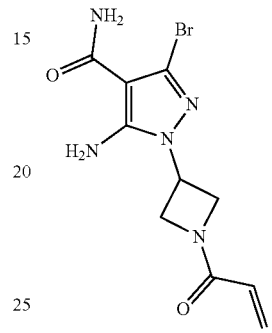
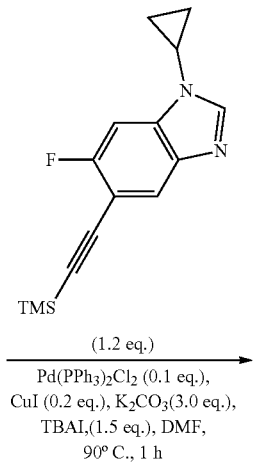

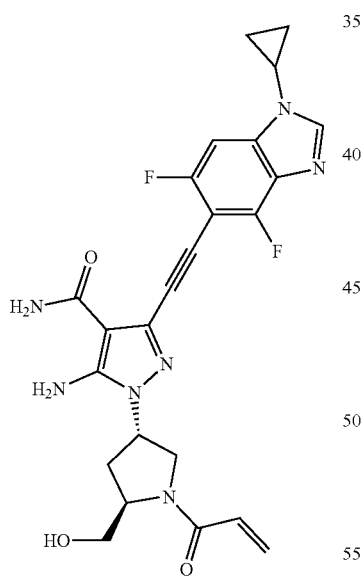
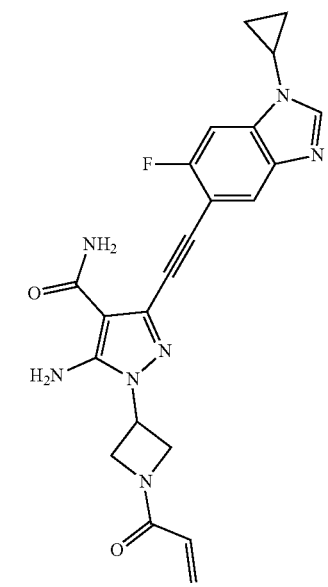

5-amino-3-[2-(1-cyclopropyl-4,6-difluoro-1,3-benzodiazol-5-yl)ethynyl]-1-[(3S,5R)-5-(hydroxymethyl)-1-(prop-2-enoyl)pyrrolidin-3-yl]pyrazole-4-carboxamide. MS ESI calculated for $C_{24}H_{23}F_2N_7O_3$ [M+H]$^+$, 496.19, found 496.15; $^1$H NMR (300 MHz, DMSO-d$_6$) δ 8.43 (s, 1H), 7.61 (d, J=8.8 Hz, 1H), 7.47 (s, 1H), 6.70 (s, 3H), 6.59-6.53 (m, 1H), 6.17 (d, J=16.6 Hz, 1H), 5.69 (d, J=10.4 Hz, 1H), 5.13 (s, 2H), 4.32 (d, J=15.6 Hz, 1H), 3.98-3.71 (m, 2H), 3.59-3.40 (m, 3H), 2.43 (d, J=57.7 Hz, 2H), 1.11 (t, J=7.7 Hz, 4H).

5-amino-3-[2-(1-cyclopropyl-6-fluoro-1,3-benzodiazol-5-yl)ethynyl]-1-[1-(prop-2-enoyl)azetidin-3-yl]pyrazole-4-carboxamide. MS ESI calculated for $C_{22}H_{20}FN_7O_2$ [M+H]$^+$, 434.17, found 434.14; $^1$H NMR (300 MHz, DMSO-d$_6$) δ 8.38 (s, 1H), 8.01 (d, J=6.4 Hz, 1H), 7.66 (d, J=9.5 Hz, 1H), 7.40 (s, 1H), 6.66 (s, 3H), 6.43-6.39 (m, 1H), 6.23-6.11 (m, 1H), 5.79-5.67 (m, 1H), 5.29 (s, 1H), 4.65 (t, J=8.6 Hz, 1H), 4.52 (t, J=7.7 Hz, 1H), 4.35 (t, J=9.3 Hz, 1H), 4.21 (t, J=7.5 Hz, 1H), 3.54 (d, J=6.3 Hz, 1H), 1.16-1.00 (m, 4H).

721

Example 203: 3-((1-Cyclopropyl-6-fluoro-1H-benzo[d]imidazol-5-yl)ethynyl)-1-((3S,5R)-1-(4-hydroxy-4-methylpent-2-ynoyl)-5-(methoxymethyl)pyrrolidin-3-yl)-5-(methylamino)-1H-pyrazole-4-carboxamide

722

Example 204: 3-[2-(1-Cyclopropyl-6-fluoro-1,3-benzodiazol-5-yl)ethynyl]-1-{1-[(2E)-4-(dimethylamino)but-2-enoyl]azetidin-3-yl}-5-(methylamino)pyrazole-4-carboxamide

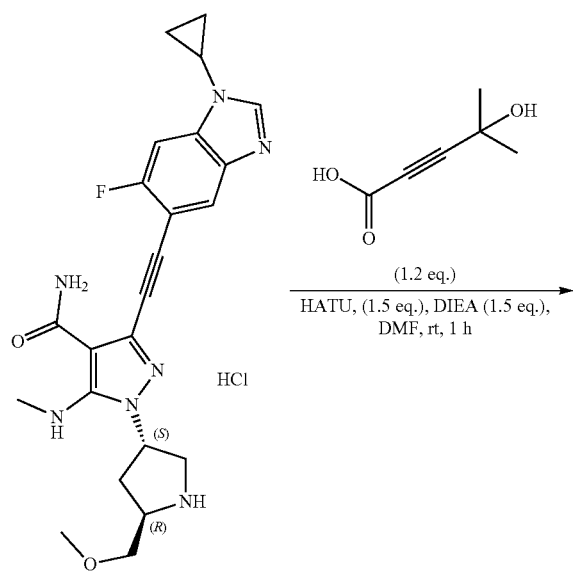

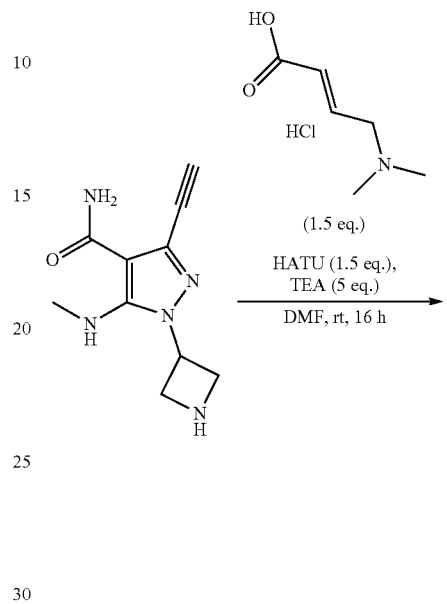

3-((1-cyclopropyl-6-fluoro-1H-benzo[d]imidazol-5-yl)ethynyl)-1-((3S,5R)-1-(4-hydroxy-4-methylpent-2-ynoyl)-5-(methoxymethyl)pyrrolidin-3-yl)-5-(methylamino)-1H-pyrazole-4-carboxamide (44.40 mg, 30%) as a white solid. MS ESI calculated for $C_{29}H_{32}FN_7O_4$ [M+H]$^+$, 562.25, found 562.45; $^1$H NMR (400 MHz, CDCl$_3$) δ 8.02 (d, J=50.8 Hz, 2H), 7.33 (s, 1H), 7.11 (s, 1H), 6.79 (s, 1H), 5.63-5.24 (m, 1H), 4.62-4.39 (m, 2H), 4.22-3.98 (m, 2H), 3.88 (d, J=9.6 Hz, 1H), 3.70-3.50 (m, 1H), 3.40 (d, J=13.5 Hz, 5H), 3.03 (d, J=10.3 Hz, 3H), 2.94-2.70 (m, 1H), 2.40-2.25 (m, 1H), 1.60 (d, J=12.3 Hz, 6H), 1.35-0.97 (m, 4H).

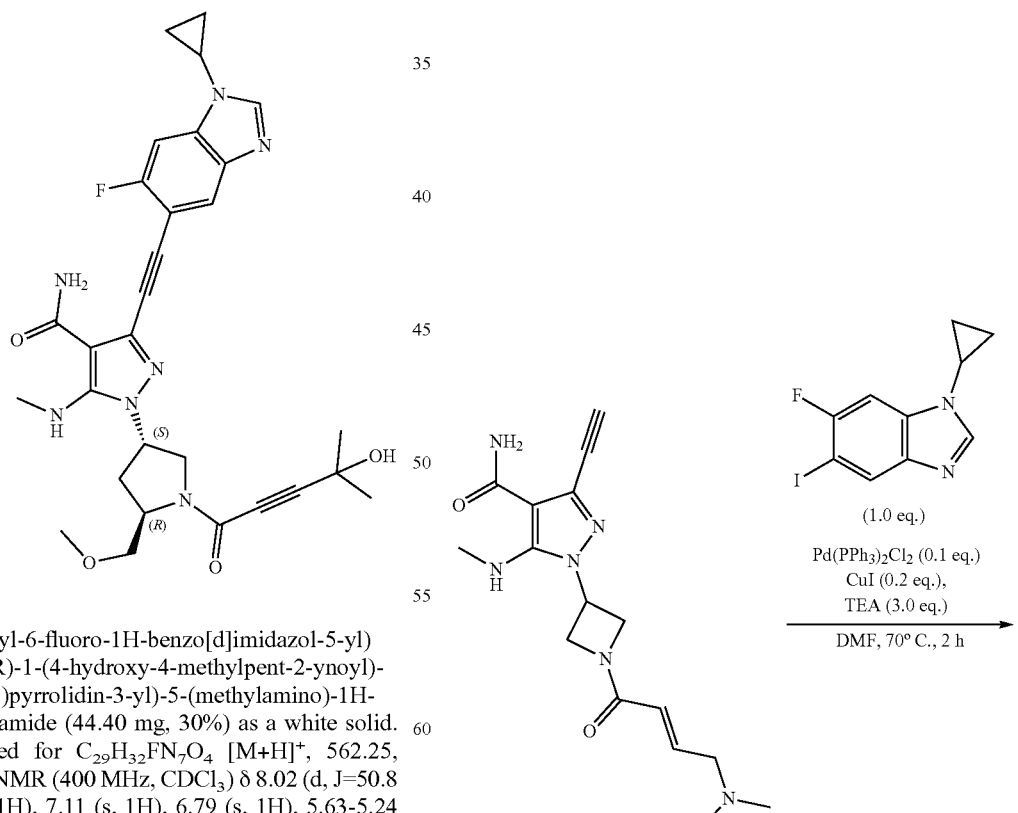

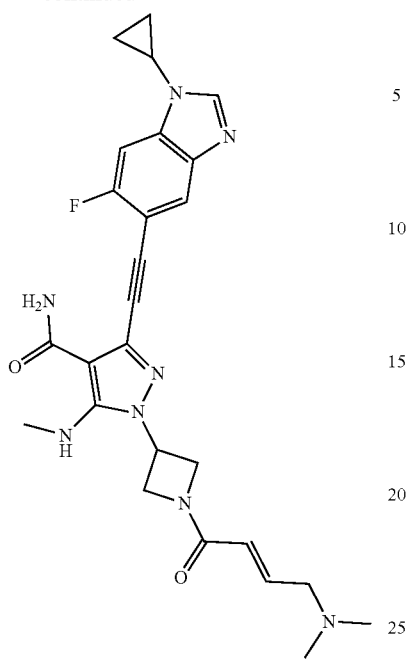

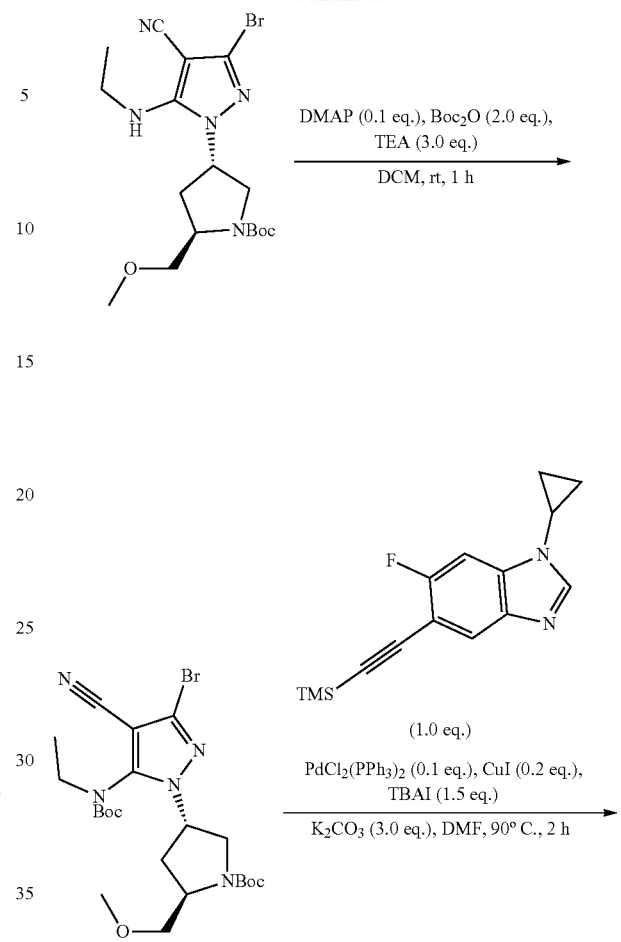

3-[2-(1-cyclopropyl-6-fluoro-1,3-benzodiazol-5-yl)ethynyl]-1-{1-[(2E)-4-(dimethylamino)but-2-enoyl]azetidin-3-yl}-5-(methylamino)pyrazole-4-carboxamide. MS ESI calculated for $C_{26}H_{29}FN_8O_2$ [M+H]$^+$, 505.24, found 505.40; $^1$H NMR (400 MHz, CDCl$_3$) δ 7.98 (d, J=4.8 Hz, 2H), 7.26 (s, 1H), 7.12 (s, 1H), 6.92-6.85 (m, 1H), 6.75-6.67 (m, 1H), 6.46 (s, 1H), 5.36 (s, 1H), 5.33-5.22 (m, 1H), 4.95 (t, J=7.4 Hz, 1H), 4.72 (t, J=8.5 Hz, 1H), 4.61 (t, J=8.3 Hz, 1H), 4.51 (t, J=9.4 Hz, 1H), 3.50 (s, 2H), 3.37-3.32 (m, 1H), 2.95 (d, J=5.9 Hz, 3H), 2.61 (s, 6H), 1.28-1.16 (m, 2H), 1.10-1.02 (m, 2H).

Example 205: 1-((3S,5R)-1-Acryloyl-5-(methoxymethyl)pyrrolidin-3-yl)-3-((1-cyclopropyl-6-fluoro-1H-benzo[d]imidazol-5-yl)ethynyl)-5-(ethylamino)-1H-pyrazole-4-carboxamide

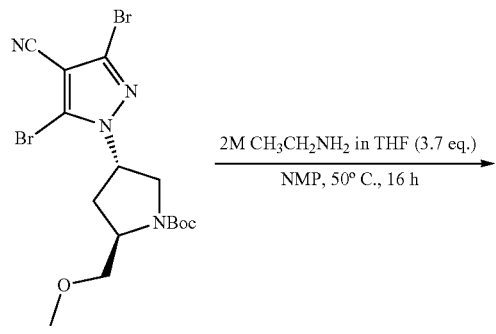

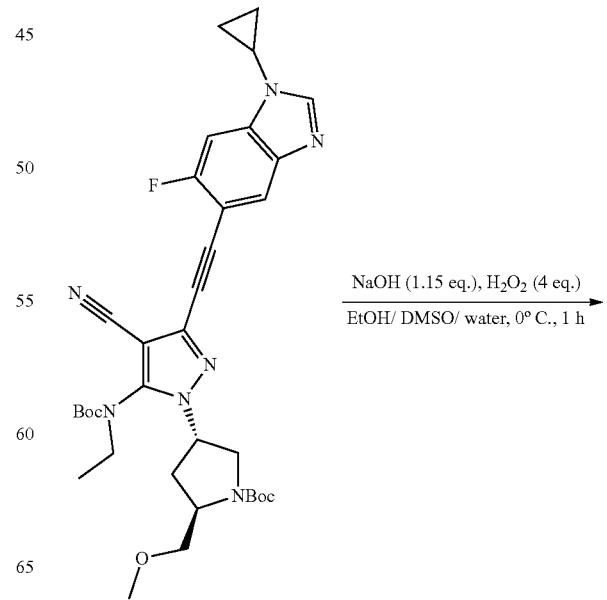

725
-continued

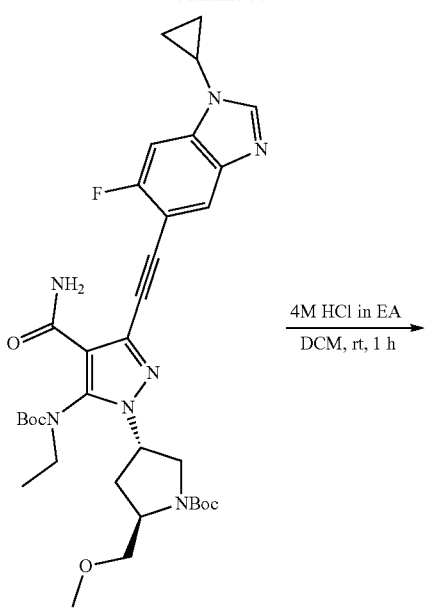

4M HCl in EA
DCM, rt, 1 h

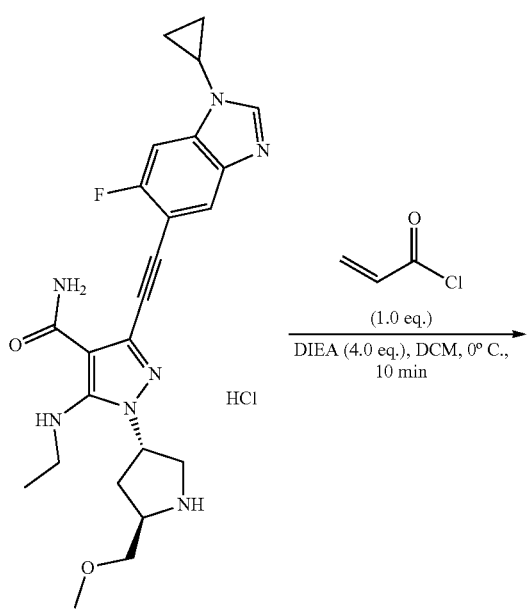

726
-continued

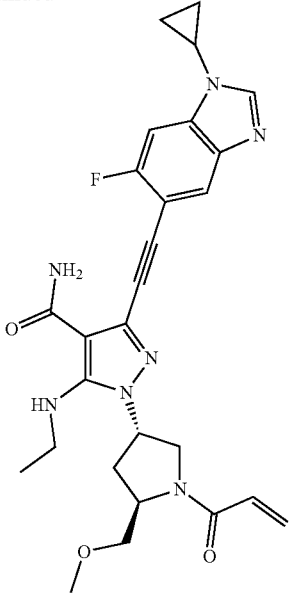

Step 1: Tert-butyl (2R,4S)-4-[3-bromo-4-cyano-5-(ethylamino)pyrazol-1-yl]-2-(methoxymethyl)pyrrolidine-1-carboxylate To a stirred solution of tert-butyl(2R,4S)-4-(3,5-dibromo-4-cyanopyrazol-1-yl)-2-(methoxymethyl)pyrrolidine-1-carboxylate (5.00 g, 10.77 mmol) in NMP (10.00 mL) was added ethylamine solution 2.0 M in THF (19.98 mL, 39.96 mmol) dropwise at room temperature under nitrogen atmosphere. The reaction mixture was stirred for 16 h at 50° C. under nitrogen atmosphere. The residue was purified by reverse flash chromatography with the following conditions: column: C18 silica gel; mobile phase: ACN in water (10 mmol/L $NH_4HCO_3$), 25% to 40% gradient in 20 min; detector: UV 254 nm. The fractions contained desired product were combined and concentrated to afford tert-butyl (2R,4S)-4-[3-bromo-4-cyano-5-(ethylamino)pyrazol-1-yl]-2-(methoxymethyl)pyrrolidine-1-carboxylate (3.80 g, 82%) as a light yellow oil. MS ESI calculated for $C_{17}H_{26}BrN_5O_3$ [M+H]$^+$, 428.12, 430.12, found 428.20, 430.20.

Step 2: Tert-butyl(2R,4S)-4-{3-bromo-5-[(tert-butoxycarbonyl)(ethyl)amino]-4-cyanopyrazol-1-yl}-2-(methoxymethyl)pyrrolidine-1-carboxylate To a stirred solution of tert-butyl(2R,4S)-4-[3-bromo-4-cyano-5-(ethylamino)pyrazol-1-yl]-2-(methoxymethyl)pyrrolidine-1-carboxylate (3.69 g, 8.61 mmol) and TEA (2.62 g, 25.84 mmol) in DCM (37.00 mL) were added Boc$_2$O (3.76 g, 17.23 mmol) and DMAP (0.11 g, 0.86 mmol) in portions at 0° C. under nitrogen atmosphere. The reaction mixture was stirred for 1 h at room temperature under nitrogen atmosphere. The resulting mixture was concentrated under reduced pressure. The residue was purified by silica gel column chromatography, eluted with PE/EA (1/2). The fractions contained desired product were combined and concentrated to afford tert-butyl (2R,4S)-4-{3-bromo-5-[(tert-butoxycarbonyl)(ethyl)amino]-4-cyanopyrazol-1-yl}-2-(methoxymethyl)pyrrolidine-1-carboxylate (2.30 g, 50%) as a yellow oil. MS ESI calculated for $C_{22}H_{34}BrN_5O_5$ [M+H]$^+$, 528.17, 530.17, found 528.20, 530.20.

Step 3: Tert-butyl (2R,4S)-4-(5-((tert-butoxycarbonyl)(ethyl)amino)-4-cyano-3-((1-cyclopropyl-6-fluoro-1H-benzo[d]imidazol-5-yl)ethynyl)-1H-pyrazol-1-yl)-2-(methoxymethyl)pyrrolidine-1-carboxylate To a stirred mixture of tert-butyl(2R,4S)-4-{3-bromo-5-[(tert-butoxycarbonyl)(ethyl)amino]-4-cyanopyrazol-1-yl}-2-(methoxymethyl)pyrrolidine-1-carboxylate (2.07 g, 3.91 mmol), 1-cyclopropyl-6-fluoro-5-[2-(trimethylsilyl)ethynyl]-1,3-benzodiazole (1.28 g, 4.70 mmol), CuI (0.15 g, 0.78 mmol), Pd(PPh$_3$)$_2$Cl$_2$ (0.27 g, 0.39 mmol) and K$_2$CO$_3$ (1.62 g, 11.75 mmol) in DMF (20.00 mL) was added TBAI (2.17 g, 5.87 mmol). The reaction mixture was degassed with nitrogen for three times and stirred for 2 h at 90° C. The resulting mixture was diluted with water (30 mL) and extracted with EA (3×30 mL). The combined organic layers was washed with brine (3×10 mL), dried over anhydrous Na$_2$SO$_4$, filtered and concentrated under reduced pressure. The residue was purified by silica gel column chromatography, eluted with 4% MeOH in DCM. The fractions contained desired product were combined and concentrated to afford tert-butyl (2R,4S)-4-(5-((tert-butoxycarbonyl)(ethyl)amino)-4-cyano-3-((1-cyclopropyl-6-fluoro-1H-benzo[d]imidazol-5-yl)ethynyl)-1H-pyrazol-1-yl)-2-(methoxymethyl)pyrrolidine-1-carboxylate (1.70 g, 67%) as a dark yellow solid. MS ESI calculated for C$_{34}$H$_{42}$FN$_7$O$_5$ [M+H]$^+$, 648.32, found 648.70; $^1$H NMR (400 MHz, CDCl$_3$) δ 8.02 (s, 1H), 7.67-7.63 (m, 1H), 7.55-7.52 (m, 1H), 7.46-7.41 (m, 1H), 5.00 (s, 1H), 4.22 (s, 1H), 3.70-3.69 (m, 1H), 3.35 (d, J=8.8 Hz, 4H), 2.95 (s, 1H), 2.88 (s, 1H), 2.71 (s, 1H), 2.62 (s, 1H), 2.32 (s, 1H), 2.21 (s, 1H), 1.47 (d, J=4.3 Hz, 21H), 1.19 (d, J=2.3 Hz, 2H), 1.14-1.01 (m, 2H).

Step 4: Tert-butyl (2R,4S)-4-(5-((tert-butoxycarbonyl)(ethyl)amino)-4-carbamoyl-3-((1-cyclopropyl-6-fluoro-1H-benzo[d]imidazol-5-yl)ethynyl)-1H-pyrazol-1-yl)-2-(methoxymethyl)pyrrolidine-1-carboxylate To a stirred solution of tert-butyl (2R,4S)-4-(5-((tert-butoxycarbonyl)(ethyl)amino)-4-cyano-3-((1-cyclopropyl-6-fluoro-1H-benzo[d]imidazol-5-yl)ethynyl)-1H-pyrazol-1-yl)-2-(methoxymethyl)pyrrolidine-1-carboxylat (1.53 g, 2.36 mmol) in DMSO (2.60 mL) and EtOH (12.70 mL) were added NaOH (0.11 g, 2.71 mmol) and H$_2$O$_2$ (30%) (0.32 g, 9.44 mmol) at 0° C. The reaction mixture was stirred for 1 h at 0° C. Then the reaction mixture was warmed up to 25° C. and stirred for another 0.5 h at room temperature. The resulting mixture was diluted with water (10 mL) and extracted with EA (3×10 mL). The combined organic layers was washed with brine (5×10 mL), dried over anhydrous Na$_2$SO$_4$, filtered and concentrated under reduced pressure. The residue was purified by silica gel column chromatography, eluted with 65% EtOH in EA. The fractions contained desired product were combined and concentrated to afford tert-butyl (2R,4S)-4-(5-((tert-butoxycarbonyl)(ethyl)amino)-4-carbamoyl-3-((1-cyclopropyl-6-fluoro-1H-benzo[d]imidazol-5-yl)ethynyl)-1H-pyrazol-1-yl)-2-(methoxymethyl)pyrrolidine-1-carboxylate (0.96 g, 61%) as a dark yellow solid. MS ESI calculated for C$_{34}$H$_{44}$FN$_7$O$_6$ [M+H–100]$^+$, 566.33, found 566.35; $^1$H NMR (400 MHz, CDCl$_3$) δ 8.04 (s, 1H), 7.99 (s, 1H), 7.35 (d, J=8.7 Hz, 1H), 7.19 (s, 1H), 5.62 (s, 1H), 5.20 (s, 2H), 4.23 (s, 1H), 4.04-4.01 (m, 1H), 3.72 (d, J=9.0 Hz, 2H), 3.49 (s, 1H), 2.85 (s, 1H), 2.62 (s, 3H), 2.58 (s, 1H), 2.30 (s, 1H), 2.22 (s, 1H), 1.59-1.41 (m, 13H), 1.37 (d, J=3.3 Hz, 8H), 1.15-1.03 (m, 2H), 0.92-0.81 (m, 2H).

Step 5: 3-((1-Cyclopropyl-6-fluoro-1H-benzo[d]imidazol-5-yl)ethynyl)-5-(ethylamino)-1-((3S,5R)-5-(methoxymethyl)pyrrolidin-3-yl)-1H-pyrazole-4-carboxamide hydrochloride To a stirred solution of tert-butyl (2R,4S)-4-(5-((tert-butoxycarbonyl)(ethyl)amino)-4-carbamoyl-3-((1-cyclopropyl-6-fluoro-1H-benzo[d]imidazol-5-yl)ethynyl)-1H-pyrazol-1-yl)-2-(methoxymethyl)pyrrolidine-1-carboxylate (0.50 g, 0.75 mmol) and DCM (5.00 mL) in 4 M HCl (g) in EA (4.17 mL, 16.68 mmol) was stirred for 1 h at room temperature under argon atmosphere. The resulting mixture was concentrated under reduced pressure. The residue was purified by trituration with DCM/PE (1/5, 500 mL) to afford 3-((1-cyclopropyl-6-fluoro-1H-benzo[d]imidazol-5-yl)ethynyl)-5-(ethylamino)-1-((3S,5R)-5-(methoxymethyl)pyrrolidin-3-yl)-1H-pyrazole-4-carboxamide hydrochloride (0.61 g, crude) as a light yellow solid. MS ESI calculated for C$_{24}$H$_{28}$FN$_7$O$_2$ [M+H]$^+$, 466.23, found 466.35.

Step 6: 1-((3S,5R)-1-Acryloyl-5-(methoxymethyl)pyrrolidin-3-yl)-3-((1-cyclopropyl-6-fluoro-1H-benzo[d]imidazol-5-yl)ethynyl)-5-(ethylamino)-1H-pyrazole-4-carboxamide To a stirred mixture of 3-((1-cyclopropyl-1H-benzo[d]imidazol-5-yl)ethynyl)-5-(ethylamino)-1-((3S,5R)-5-(methoxymethyl)pyrrolidin-3-yl)-1H-pyrazole-4-carboxamide hydrochloride (0.20 g, 0.43 mmol) and 2.5 M K$_2$CO$_3$ (0.71 mL, 5.13 mmol) was added acryloyl chloride (38.88 mg, 0.43 mmol) in THF (0.40 mL) dropwise at 0° C. The reaction mixture was stirred for 10 min at 0° C. The resulting mixture was extracted with EA (3×10 mL). The combined organic layers was washed with brine (2×5 mL), dried over anhydrous Na$_2$SO$_4$. After filtration, the filtrate was concentrated under reduced pressure. The residue was purified by silica gel column chromatography, eluted with CH$_2$Cl$_2$/MeOH (20/1). The fractions contained desired product were combined and concentrated to afford 1-((3S,5R)-1-acryloyl-5-(methoxymethyl)pyrrolidin-3-yl)-3-((1-cyclopropyl-6-fluoro-1H-benzo[d]imidazol-5-yl)ethynyl)-5-(ethylamino)-1H-pyrazole-4-carboxamide (74.50 mg, 33%) as an off-white solid. MS ESI calculated for C$_{27}$H$_{30}$FN$_7$O$_3$ [M+H]$^+$, 520.24, found 520.20; $^1$H NMR (400 MHz, CDCl$_3$) δ 8.10-7.84 (m, 2H), 7.31 (d, J=9.0 Hz, 1H), 7.11 (s, 1H), 6.85-6.07 (m, 3H), 5.76-5.66 (m, 1H), 5.87-4.90 (m, 2H), 4.56 (d, J=9.1 Hz, 1H), 4.04 (m, 3H), 3.52-3.40 (m, 1H), 3.37 (d, J=3.9 Hz, 4H), 3.35-3.21 (m, 2H), 2.70-2.30 (m, 2H), 1.30 (t, J=7.2 Hz, 3H), 1.21-1.02 (m, 4H).

729

Example 206: 5-Amino-3-[2-(1-cyclopropyl-6-fluoro-2-methyl-1,3-benzodiazol-5-yl)ethynyl]-1-[(3S,5R)-5-(methoxymethyl)-1-(prop-2-enoyl)pyrrolidin-3-yl]pyrazole-4-carboxamide

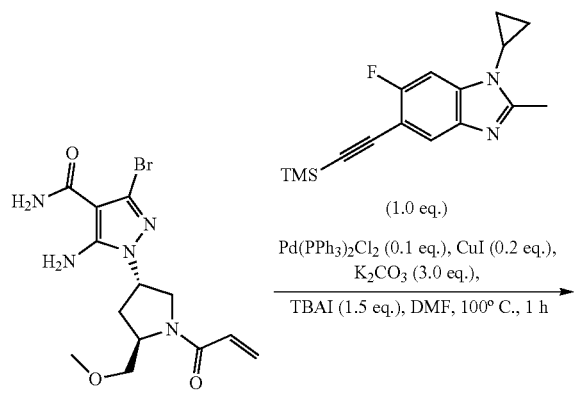

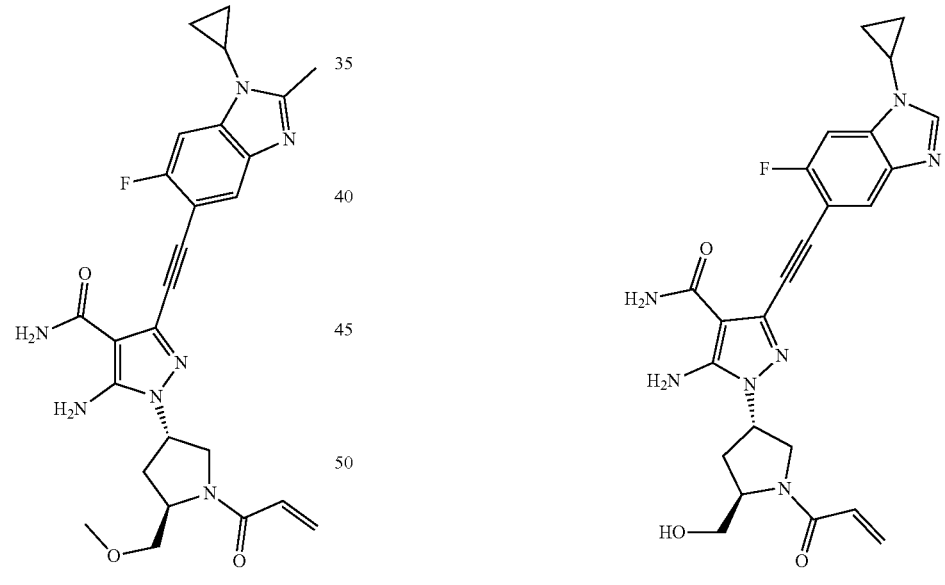

5-amino-3-[2-(1-cyclopropyl-6-fluoro-2-methyl-1,3-benzodiazol-5-yl)ethynyl]-1-[(3S,5R)-5-(methoxymethyl)-1-(prop-2-enoyl)pyrrolidin-3-yl]pyrazole-4-carboxamide. MS ESI calculated for $C_{26}H_{28}FN_7$ [M+H]$^+$, 506.55, found 506.40; $^1$H NMR (400 MHz, CDCL$_3$) δ 7.90-7.85 (m, 1H), 7.40-7.32 (m, 1H), 7.10-7.07 (s, 1H), 6.61-6.35 (m, 2H), 5.80-5.74 (m, 1H), 5.50 (m, 3H), 5.10-4.88 (m, 1H), 4.65-4.42 (m, 1H), 4.10-3.93 (m, 2H), 3.90-3.89 (m, 1H), 3.56-3.45 (m, 1H), 3.40-3.35 (m, 3H), 3.32-3.30 (s, 1H), 3.02-2.75 (m, 3H), 2.68-2.58 (m, 1H), 2.40-2.39 (m, 1H), 1.42-1.23 (m, 2H), 1.20-1.13 (s, 2H).

730

Example 207: 5-Amino-3-[2-(1-cyclopropyl-6-fluoro-1,3-benzodiazol-5-yl)ethynyl]-1-[(3S,5R)-5-(hydroxymethyl)-1-(prop-2-enoyl)pyrrolidin-3-yl]pyrazole-4-carboxamide

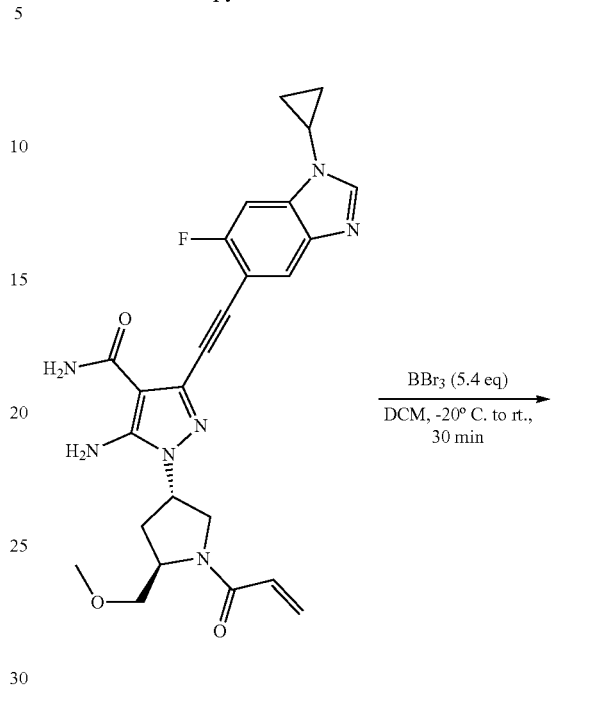

5-amino-3-[2-(1-cyclopropyl-6-fluoro-1,3-benzodiazol-5-yl)ethynyl]-1-[(3S,5R)-5-(hydroxymethyl)-1-(prop-2-enoyl)pyrrolidin-3-yl]pyrazole-4-carboxamide (79.60 mg, 45%) as an off-white solid. MS ESI calculated for $C_{24}H_{24}FN_7O_3$ [M+H]$^+$, 478.20, found, 478.35; $^1$H NMR (400 MHz, DMSO-d$_6$) δ 8.36 (s, 1H), 7.96 (d, J=6.5 Hz, 1H), 7.65 (d, J=9.4 Hz, 1H), 7.34 (s, 1H), 7.05-6.37 (m, 4H), 6.18-6.14 (m, 1H), 5.69-5.67 (m, 1H), 5.13-5.11 (m, 1H), 5.06-4.88 (m, 1H), 4.32 (d, J=19.2 Hz, 1H), 4.05-3.84 (m, 2H), 3.75-3.50 (m, 3H), 2.39 (s, 2H), 1.12-1.09 (m, 2H), 1.06 (t, J=4.4 Hz, 2H).

Example 208: 5-Amino-3-[2-(6-chloro-1-cyclopropyl-1,3-benzodiazol-5-yl)ethynyl]-1-[1-(prop-2-enoyl)azetidin-3-yl]pyrazole-4-carboxamide

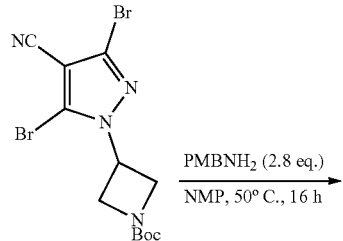

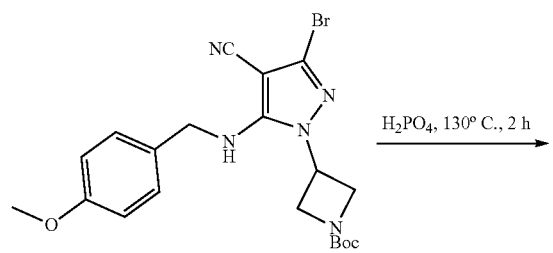

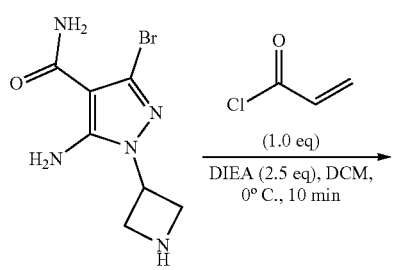

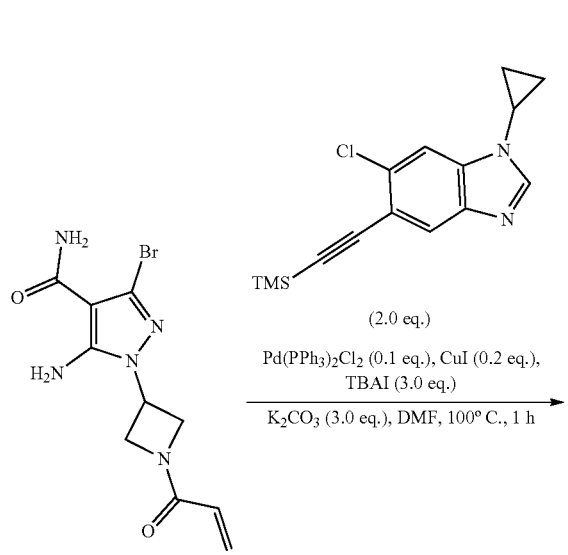

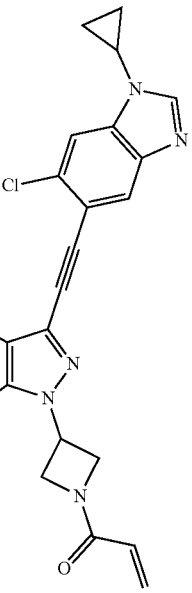

5-amino-3-[2-(6-chloro-1-cyclopropyl-1,3-benzodiazol-5-yl)ethynyl]-1-[1-(prop-2-enoyl)azetidin-3-yl]pyrazole-4-carboxamide (64.20 mg, 55%) as an off-white solid. MS ESI calculated for $C_{22}H_{20}ClN_7O_2$ [M+H]$^+$, 450.14, found 450.30; $^1$H NMR (400 MHz, DMSO-d$_6$) δ 8.40 (s, 1H), 8.07 (s, 1H), 7.89 (s, 1H), 7.39 (s, 1H), 6.74 (s, 1H), 6.64 (s, 2H), 6.43-6.39 (m, 1H), 6.16-6.10 (m, 1H), 5.72-5.68 (m, 1H), 5.32-5.21 (m, 1H), 4.65 (t, J=8.6 Hz, 1H), 4.51 (t, J=7.2 Hz, 1H), 4.35 (t, J=9.3 Hz, 1H), 4.23-4.12 (m, 1H), 3.68-3.54 (m, 1H), 1.13-0.99 (m, 4H).

Example 209: 5-Amino-3-[2-(6-chloro-1-ethyl-1,3-benzodiazol-5-yl)ethynyl]-1-[1-(prop-2-enoyl)azetidin-3-yl]pyrazole-4-carboxamide

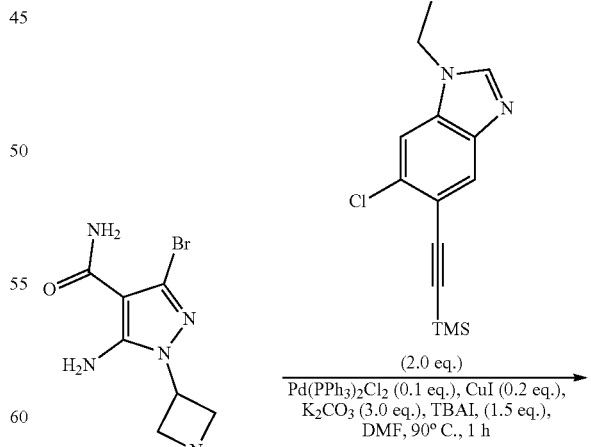

733

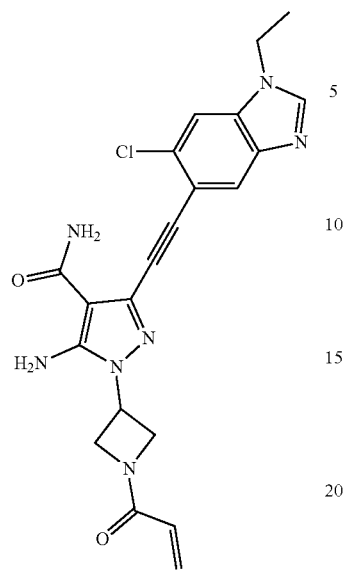

5-amino-3-[2-(6-chloro-1-ethyl-1,3-benzodiazol-5-yl)ethynyl]-1-[1-(prop-2-enoyl)azetidin-3-yl]pyrazole-4-carboxamide. MS ESI calculated for $C_{21}H_{20}ClN_7O_2$ [M+H]$^+$, 438.14, found 438.05; $^1$H NMR (400 MHz, DMSO-d$_6$) δ 8.43 (s, 1H), 8.06 (s, 1H), 8.01 (s, 1H), 7.38 (s, 1H), 6.75 (s, 1H), 6.64 (s, 2H), 6.42-6.33 (m, 1H), 6.22-6.16 (m, 1H), 5.65-5.72 (m, 1H), 5.28 (q, J=7.6, 6.6 Hz, 1H), 4.63 (d, J=8.5 Hz, 1H), 4.53-4.46 (m, 1H), 4.31 (q, J=7.3 Hz, 3H), 4.22 (d, J=5.6 Hz, 1H), 1.42 (t, J=7.2 Hz, 3H).

Example 210: 5-Amino-3-[2-(1-cyclopropyl-4,6-difluoro-1,3-benzodiazol-5-yl)ethynyl]-1-[1-(prop-2-enoyl)azetidin-3-yl]pyrazole-4-carboxamide

734

5-amino-3-[2-(1-cyclopropyl-4,6-difluoro-1,3-benzodiazol-5-yl)ethynyl]-1-[1-(prop-2-enoyl)azetidin-3-yl]pyrazole-4-carboxamide. MS ESI calculated for $C_{22}H_{19}F_2N_7O_2$ [M+H]$^+$, 452.16, found 452.35; $^1$H NMR (400 MHz, DMSO-d$_6$) δ 8.42 (s, 1H), 7.60 (d, J=8.8 Hz, 1H), 7.48 (s, 1H), 6.67 (s, 3H), 6.43-6.38 (m, 1H), 6.16-6.12 (m, 1H), 5.74-5.71 (m, 1H), 5.32-5.25 (m, 1H), 4.64 (m, 1H), 4.56-4.52 (m, 1H), 4.35 (t, J=9.2 Hz, 1H), 4.27-4.21 (m, 1H), 3.57-3.52 (m, 1H), 1.19-1.02 (m, 4H).

Example 211: 5-Amino-3-[2-(1-cyclopropyl-6-fluoro-1,3-benzodiazol-5-yl)ethynyl]-1-[(3S,5R)-5-[(difluoromethoxy)methyl]-1-(prop-2-enoyl)pyrrolidin-3-yl]pyrazole-4-carboxamide

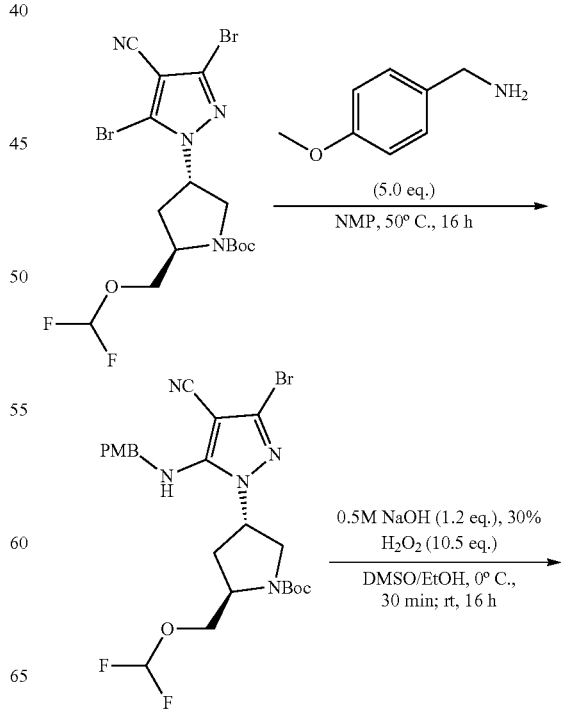

735
-continued

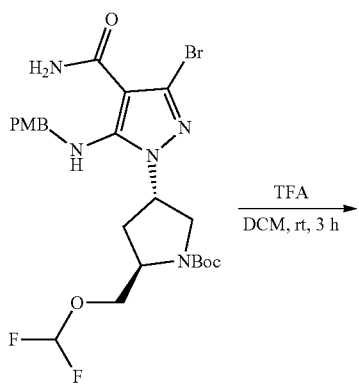

TFA
―――――→
DCM, rt, 3 h

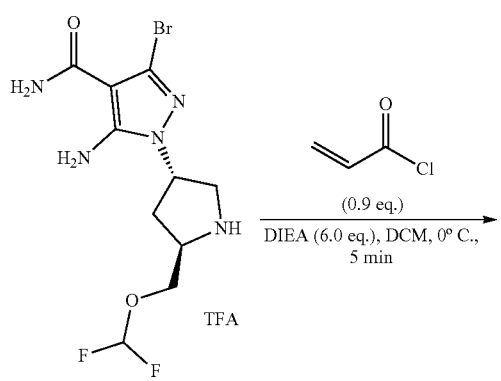

736
-continued

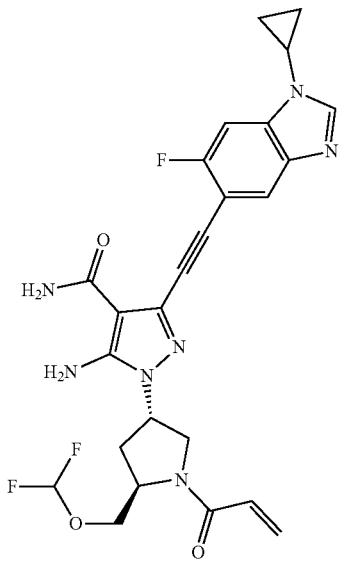

5-amino-3-[2-(1-cyclopropyl-6-fluoro-1,3-benzodiazol-5-yl)ethynyl]-1-[(3S,5R)-5-[(difluoromethoxy)methyl]-1-(prop-2-enoyl)pyrrolidin-3-yl]pyrazole-4-carboxamide. MS ESI calculated for $C_{25}H_{24}F_3N_7O_3$ [M+H]$^+$, 528.19, found 528.40; $^1$H NMR (400 MHz, CDCl$_3$) δ 8.08 (s, 2H), 7.48 (s, 1H), 7.07 (s, 1H), 6.60-5.98 (m, 3H), 5.76 (t, J=6.1 Hz, 1H), 5.48 (d, J=58.1 Hz, 3H), 4.96 (q, J=8.0 Hz, 1H), 4.68 (d, J=9.2 Hz, 1H), 4.53-4.36 (m, 1H), 4.09-4.06 (m, 2H), 3.98 (d, J=9.9 Hz, 1H), 3.41 (s, 1H), 2.84-2.72 (m, 1H), 2.49-2.31 (m, J=13.0, 7.1 Hz, 1H), 1.24 (d, J=6.7 Hz, 2H), 1.09 (s, 2H).

Example 212: 5-Amino-3-[2-(1-cyclopropyl-1,3-benzodiazol-5-yl)ethynyl]-1-[(3S,5R)-5-[(difluoromethoxy)methyl]-1-(prop-2-enoyl)pyrrolidin-3-yl]pyrazole-4-carboxamide

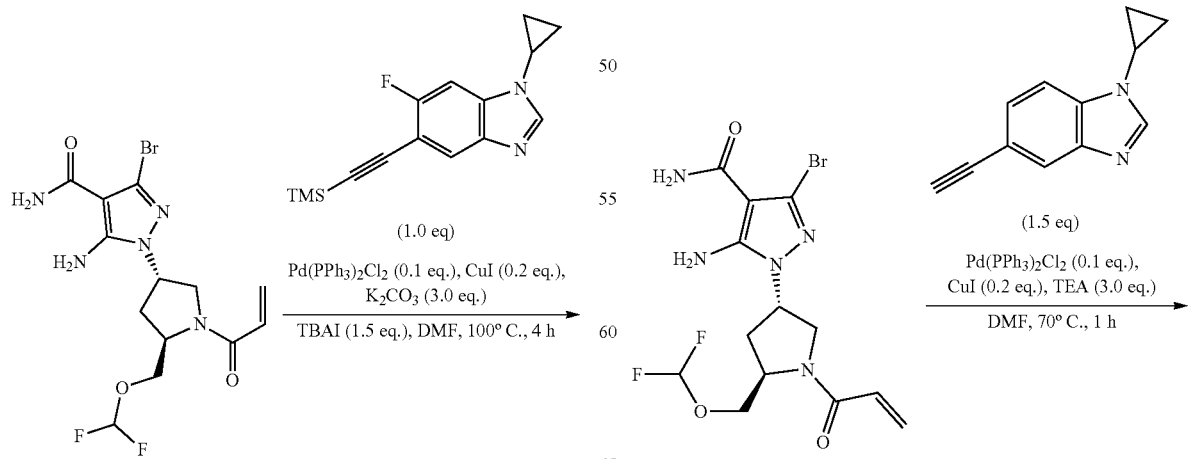

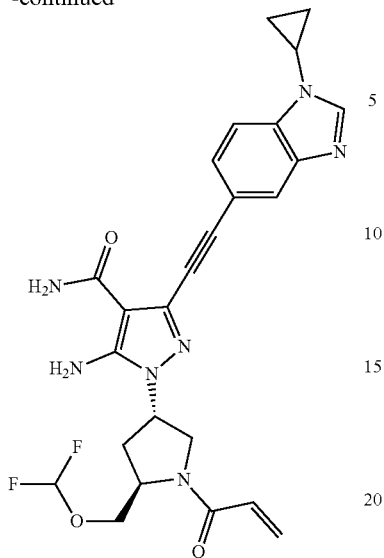
5-amino-3-[2-(1-cyclopropyl-1,3-benzodiazol-5-yl)ethynyl]-1-[(3S,5R)-5-[(difluoromethoxy)methyl]-1-(prop-2-enoyl)pyrrolidin-3-yl]pyrazole-4-carboxamide. MS ESI calculated for $C_{25}H_{25}F_2N_7O_3$ [M+H]$^+$, 510.20, found 510.35; $^1$H NMR (400 MHz, CDCl$_3$) δ 8.11 (s, 1H), 8.03 (s, 1H), 7.63-7.51 (m, 2H), 6.90 (s, 1H), 6.54-6.40 (m, 2H), 6.26 (s, 1H), 5.75 (t, J=6.1 Hz, 1H), 5.48 (d, J=51.1 Hz, 3H), 5.02-4.93 (m, 1H), 4.68 (d, J=9.0 Hz, 1H), 4.51-4.36 (m, 1H), 4.14-3.84 (m, 3H), 3.52-3.34 (m, 1H), 2.84-2.72 (m, 1H), 2.51-2.31 (m, 1H), 1.29-1.17 (m, 2H), 1.20-1.07 (m, 2H).
Example 213: 3-[2-(1-Cyclopropyl-6-fluoro-1,3-benzodiazol-5-yl)ethynyl]-5-(methylamino)-1-{[1-(prop-2-enoyl)azetidin-3-yl]methyl}pyrazole-4-carboxamide
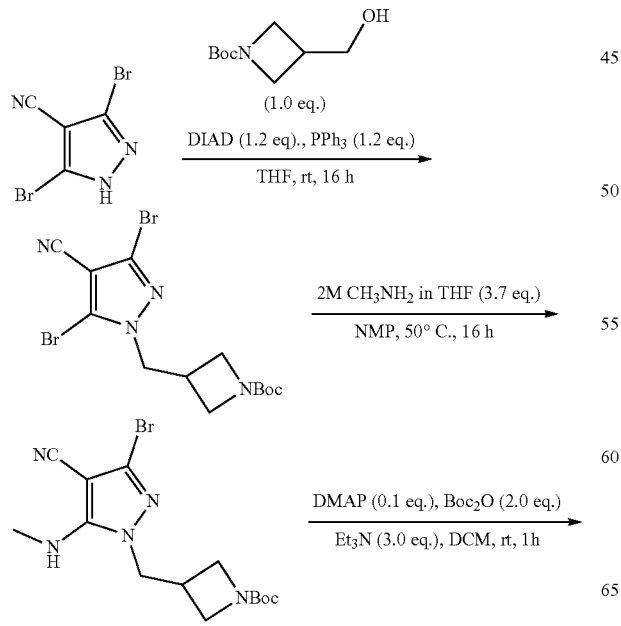
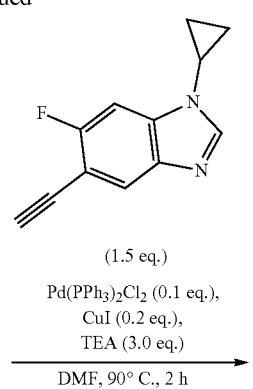
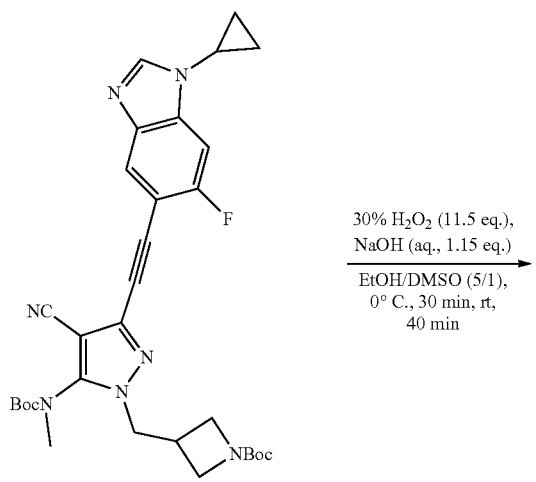
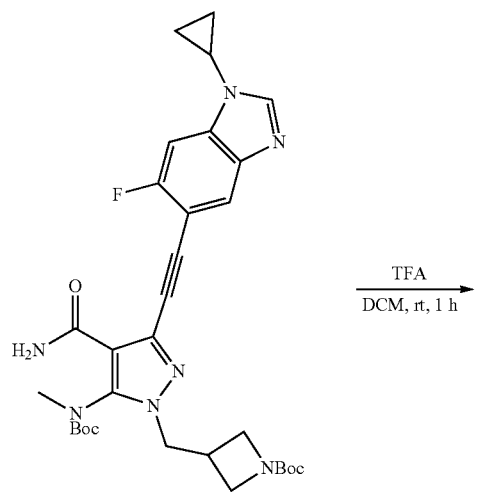

739
-continued
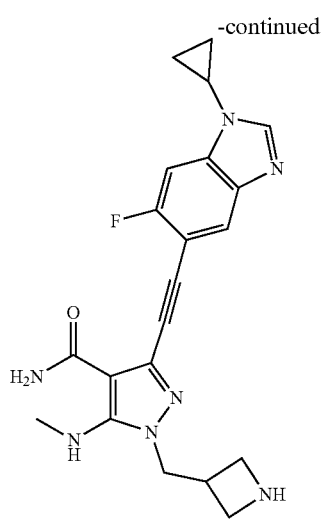
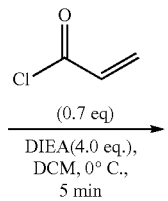
3-[2-(1-cyclopropyl-6-fluoro-1,3-benzodiazol-5-yl)ethy-nyl]-5-(methylamino)-1-{[1-(prop-2-enoyl)azetidin-3-yl]methyl}pyrazole-4-carboxamide. MS ESI calculated for $C_{24}H_{24}FN_7O_2$ [M+H]+, 462.20, found 462.30; 1H NMR (400 MHz, CDCl3) δ 8.01-7.96 (m, 2H), 7.33 (d, J=8 Hz, 1H), 7.12 (s, 1H), 6.76 (s, 1H), 6.39-6.34 (m, 1H), 6.24-6.16 (m, 1H), 5.71-5.68 (m, 1H), 5.36 (s, 1H), 4.40-4.34 (m, 3H), 4.28-4.23 (m, 1H), 4.19-4.15 (m, 1H), 3.93-3.89 (m, 1H), 3.42-3.37 (m, 1H), 3.33-3.29 (m, 1H), 3.02 (s, 3H), 1.25-1.18 (m, 2H), 1.11-1.07 (m, 2H).
740
Example 214: 5-Amino-3-[2-(6-chloro-1-cyclopropyl-2-methyl-1,3-benzodiazol-5-yl)ethynyl]-1-[(3S,5R)-5-(methoxymethyl)-1-(prop-2-enoyl)pyrrolidin-3-yl]pyrazole-4-carboxamide
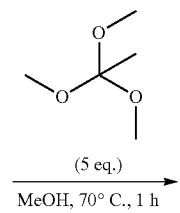
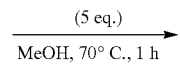
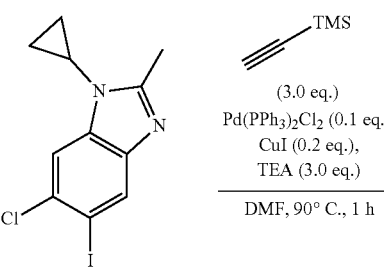
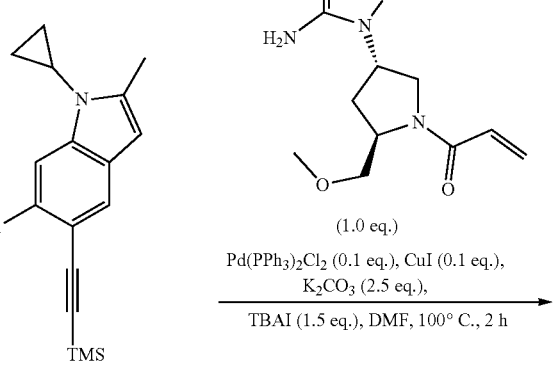

741
-continued

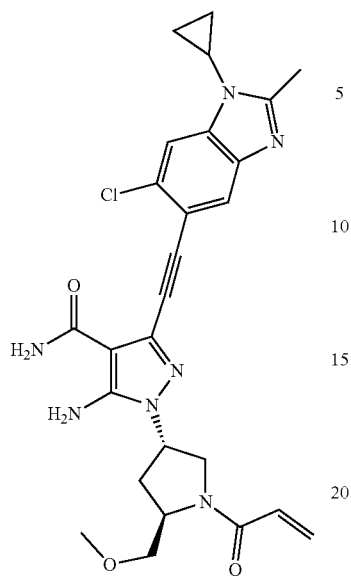

5-amino-3-[2-(6-chloro-1-cyclopropyl-2-methyl-1,3-benzodiazol-5-yl)ethynyl]-1-[(3S,5R)-5-(methoxymethyl)-1-(prop-2-enoyl)pyrrolidin-3-yl]pyrazole-4-carboxamide. MS ESI calculated for $C_{26}H_{28}ClN_7O_3$ [M+H]$^+$, 522.19, found 522.15; $^1$H NMR (400 MHz, CDCl$_3$) δ 7.92 (d, J=5.0 Hz, 1H), 7.56 (s, 1H), 7.20 (s, 1H), 6.58-6.35 (m, 2H), 5.76-5.62 (m, 3H), 5.55 (s, 1H), 5.17-4.88 (m, 1H), 4.62-4.37 (m, 1H), 4.11-3.94 (m, 2H), 3.89-3.80 (m, 1H), 3.47-3.39 (m, 1H), 3.38 (d, J=2.0 Hz, 3H), 3.22-3.14 (m, 1H), 2.68 (s, 4H), 2.37-2.28 (m, 1H), 1.29-1.20 (m, 2H), 1.11-1.03 (m, 2H).

Example 215: 5-Amino-3-[2-(1-cyclopropyl-4,6-difluoro-1,3-benzodiazol-5-yl)ethynyl]-1-[(3S,5R)-5-[(difluoromethoxy)methyl]-1-(prop-2-enoyl)pyrrolidin-3-yl]pyrazole-4-carboxamide

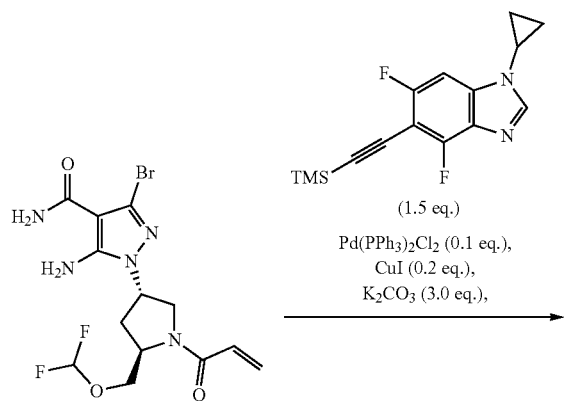

742
-continued

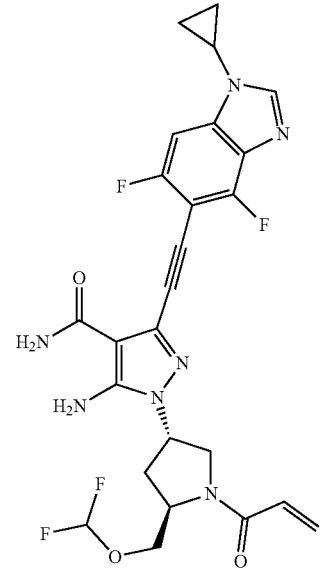

5-amino-3-[2-(1-cyclopropyl-4,6-difluoro-1,3-benzodiazol-5-yl)ethynyl]-1-[(3S,5R)-5-[(difluoromethoxy)methyl]-1-(prop-2-enoyl)pyrrolidin-3-yl]pyrazole-4-carboxamide. MS ESI calculated for $C_{25}H_{23}F_4N_7O_3$ [M+H]$^+$, 546.18, found 546.15; $^1$H NMR (400 MHz, CDCl$_3$) δ 7.97-7.80 (s, 1H), 7.19-7.18 (m, 1H), 7.10-6.90 (m, 1H), 6.44-6.40 (m, 2H), 6.30-6.10 (m, 1H), 5.83-5.70 (m, 1H), 5.60-5.49 (m, 3H), 4.95-4.90 (m, 1H), 4.70-4.68 (m, 1H), 4.42-4.40 (m, 1H), 4.17-3.93 (m, 3H), 3.39-3.30 (m, 1H), 2.85-2.71 (m, 1H), 2.39-2.35 (m, 1H), 1.25-1.20 (m, 2H), 1.10-1.05 (m, 2H).

Example 216: 3-[2-(1-Cyclopropyl-6-fluoro-1,3-benzodiazol-5-yl)ethynyl]-5-(cyclopropylamino)-1-[(3S,5R)-5-(methoxymethyl)-1-(prop-2-enoyl)pyrrolidin-3-yl]pyrazole-4-carboxamide

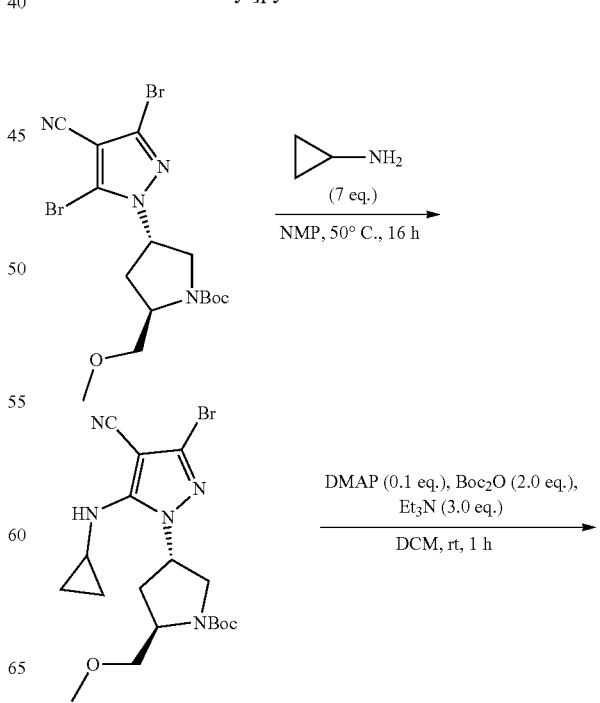

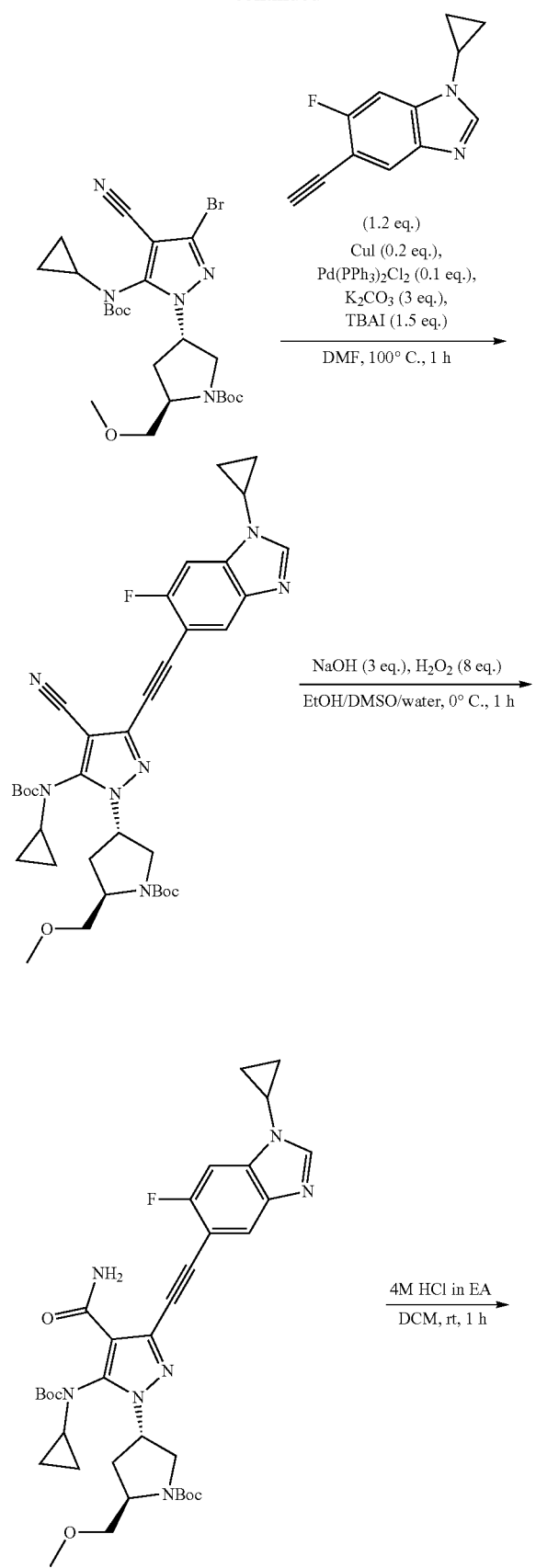
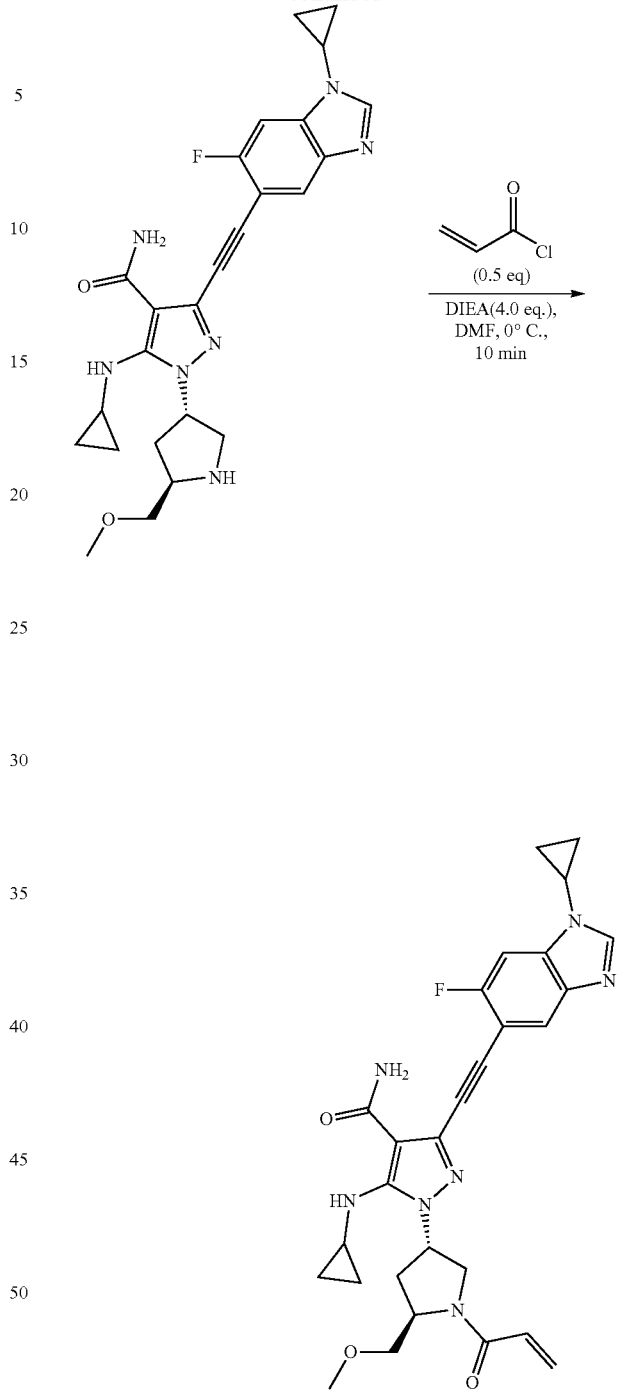
3-[2-(1-cyclopropyl-6-fluoro-1,3-benzodiazol-5-yl)ethynyl]-5-(cyclopropylamino)-1-[(3S,5R)-5-(methoxymethyl)-1-(prop-2-enoyl)pyrrolidin-3-yl]pyrazole-4-carboxamide.
MS ESI calculated for $C_{29}H_{30}FN_6O_3$ [M+H]$^+$, 532.24, found 532.45; $^1$H NMR (400 MHz, CDCl$_3$) δ 7.97 (d, J=5.8 Hz, 2H), 7.40 (d, J=2.3 Hz, 1H), 7.34 (d, J=8.5 Hz, 1H), 7.10 (s, 1H), 6.56-6.39 (m, 2H), 6.15-5.84 (m, 1H), 5.76-5.69 (m, 1H), 5.34 (s, 1H), 4.59-4.57 (m, 1H), 4.13-3.99 (m, 2H), 3.91-3.87 (m, 1H), 3.54-3.44 (m, 1H), 3.36 (d, J=10.4 Hz, 4H), 3.01-2.74 (m, 2H), 2.35-2.32 (m, 1H), 1.24-1.16 (m, 2H), 1.09-1.05 (m, 2H), 0.94-0.83 (m, 2H), 0.81-0.73 (m, 2H).

745
Example 217: 3-[2-(1-cyclopropyl-6-fluoro-1,3-benzodiazol-5-yl)ethynyl]-1-[(3S,5R)-5-(2-hydroxy-propan-2-yl)-1-(prop-2-enoyl)pyrrolidin-3-yl]-5-(methylamino)pyrazole-4-carboxamide
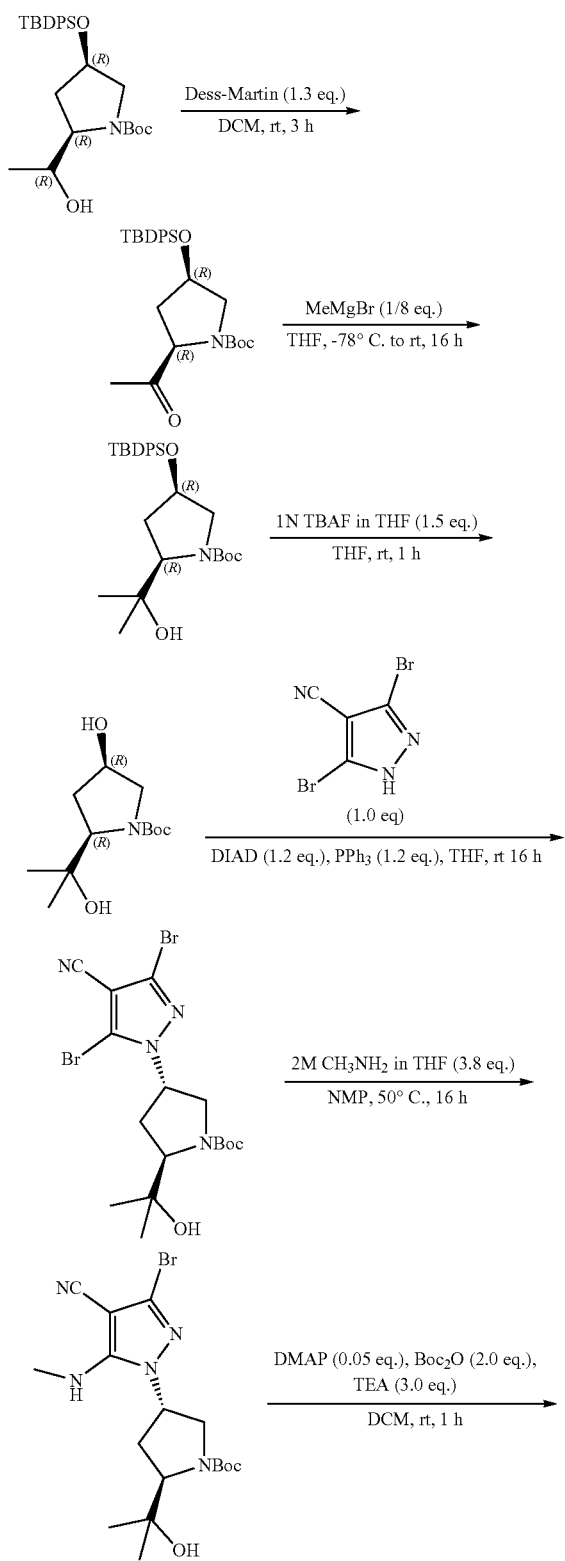
746
-continued
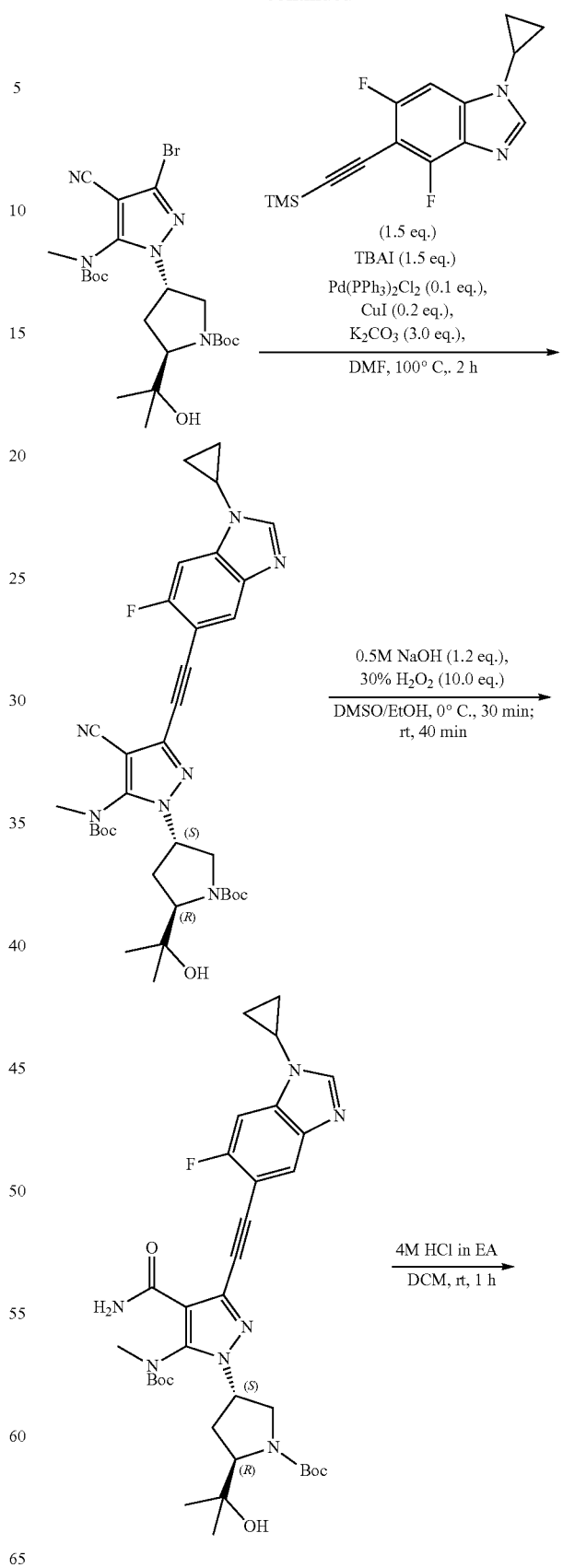

-continued

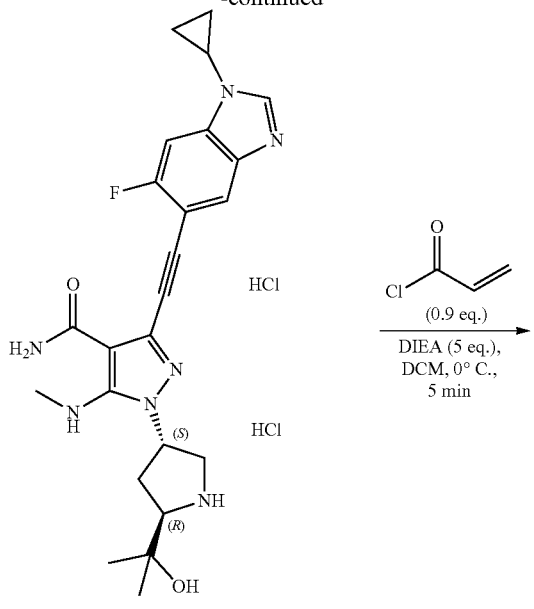

3-[2-(1-cyclopropyl-6-fluoro-1,3-benzodiazol-5-yl)ethynyl]-1-[(3S,5R)-5-(2-hydroxypropan-2-yl)-1-(prop-2-enoyl)pyrrolidin-3-yl]-5-(methylamino)pyrazole-4-carboxamide. MS ESI calculated for $C_{27}H_{30}FN_7O_3$ [M+H]$^+$, 520.24, found 520.20; $^1$H NMR (400 MHz, CDCl$_3$) δ 8.36 (s, 1H), 7.95 (d, J=4.6 Hz, 1H), 7.64 (d, J=4.9 Hz, 1H), 7.47 (s, 1H), 6.72-6.59 (m, 3H), 6.18-6.13 (m, 1H), 5.71-5.68 (m, 1H), 5.41-5.35 (m, 1H), 4.96 (s, 1H), 4.40-4.31 (m, 1H), 4.19-4.15 (m, 3H), 4.09-3.49 (m, 3H), 2.48-2.35 (m, 2H), 1.17-1.03 (m, 10H).

Example 218: 3-[2-(1-Cyclopropyl-6-fluoro-1,3-benzodiazol-5-yl)ethynyl]-1-[(3S,5R)-5-[(1R)-1-hydroxyethyl]-1-(prop-2-enoyl)pyrrolidin-3-yl]-5-(methylamino)pyrazole-4-carboxamide

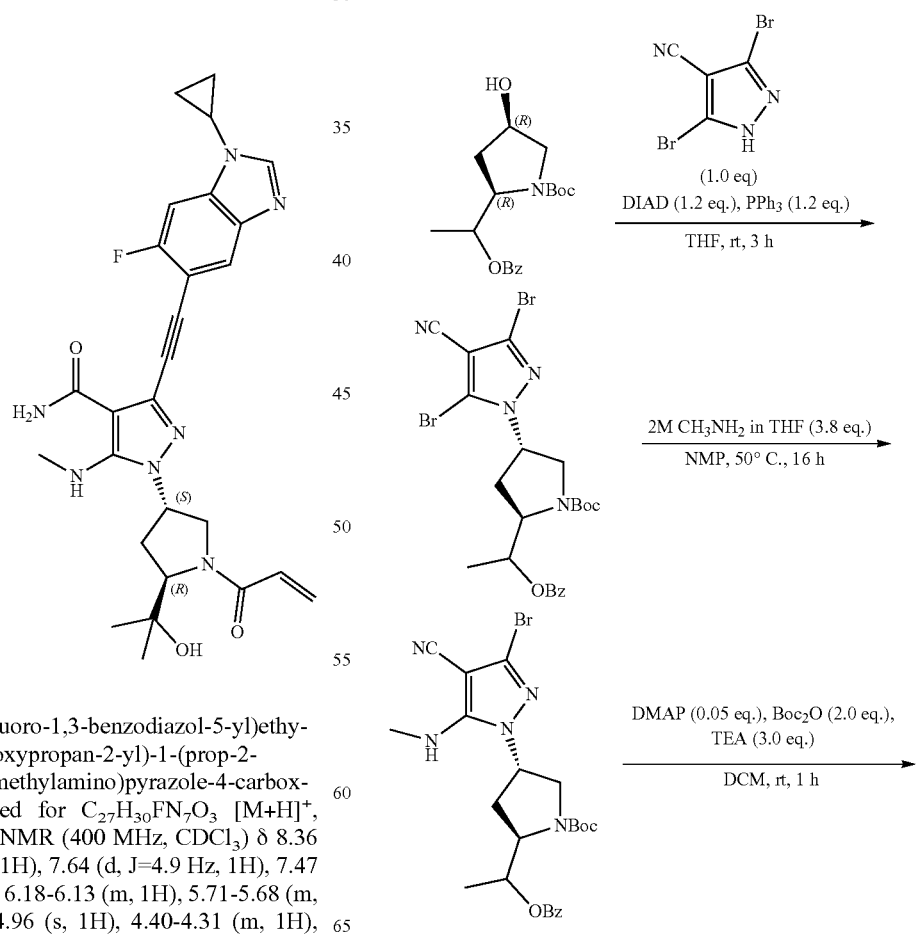

749
-continued

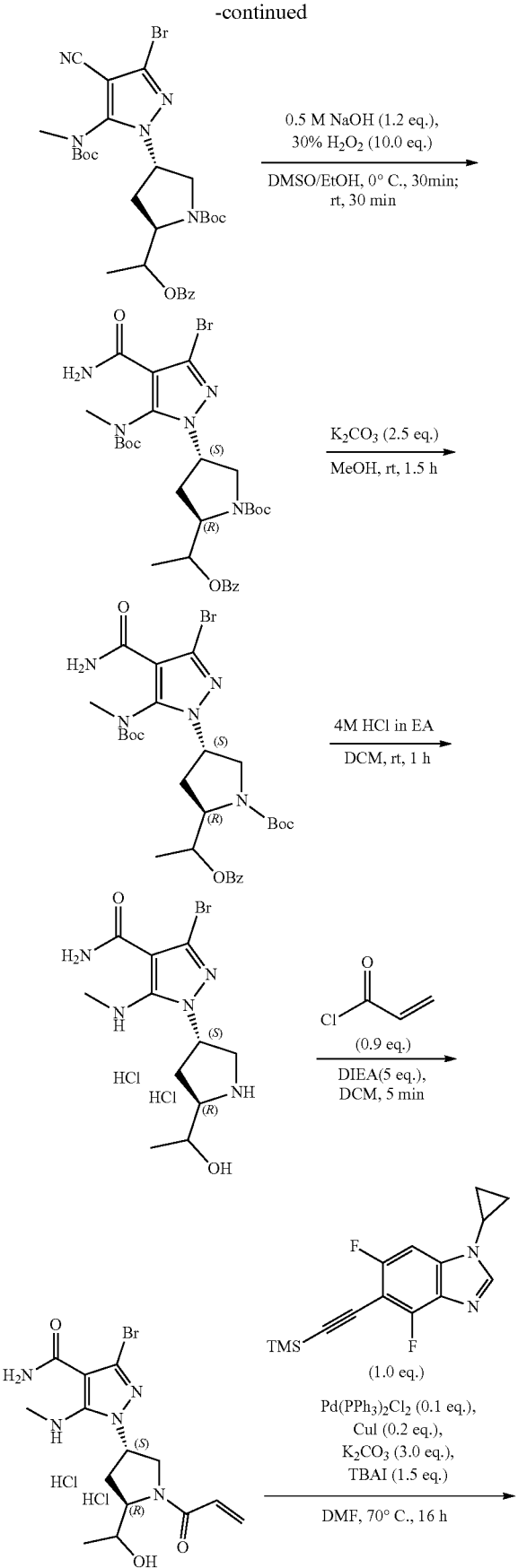

750
-continued

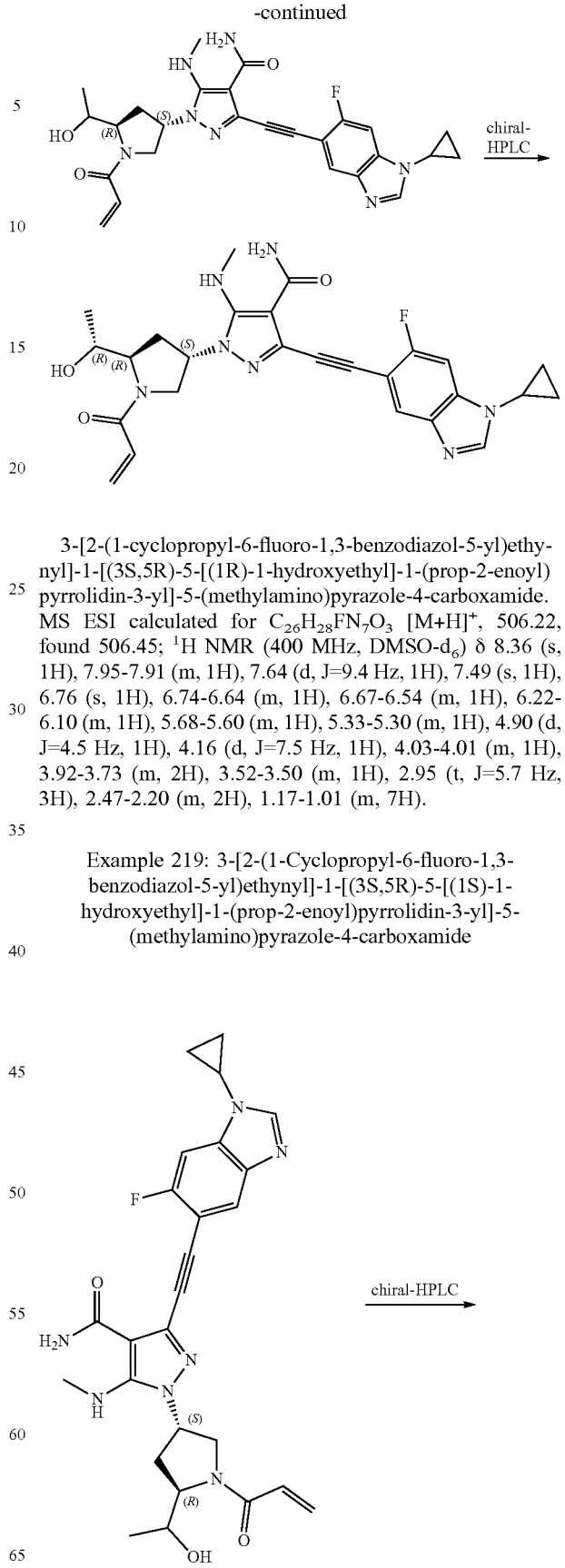

3-[2-(1-cyclopropyl-6-fluoro-1,3-benzodiazol-5-yl)ethynyl]-1-[(3S,5R)-5-[(1R)-1-hydroxyethyl]-1-(prop-2-enoyl)pyrrolidin-3-yl]-5-(methylamino)pyrazole-4-carboxamide. MS ESI calculated for $C_{26}H_{28}FN_7O_3$ [M+H]$^+$, 506.22, found 506.45; $^1$H NMR (400 MHz, DMSO-d$_6$) δ 8.36 (s, 1H), 7.95-7.91 (m, 1H), 7.64 (d, J=9.4 Hz, 1H), 7.49 (s, 1H), 6.76 (s, 1H), 6.74-6.64 (m, 1H), 6.67-6.54 (m, 1H), 6.22-6.10 (m, 1H), 5.68-5.60 (m, 1H), 5.33-5.30 (m, 1H), 4.90 (d, J=4.5 Hz, 1H), 4.16 (d, J=7.5 Hz, 1H), 4.03-4.01 (m, 1H), 3.92-3.73 (m, 2H), 3.52-3.50 (m, 1H), 2.95 (t, J=5.7 Hz, 3H), 2.47-2.20 (m, 2H), 1.17-1.01 (m, 7H).

Example 219: 3-[2-(1-Cyclopropyl-6-fluoro-1,3-benzodiazol-5-yl)ethynyl]-1-[(3S,5R)-5-[(1S)-1-hydroxyethyl]-1-(prop-2-enoyl)pyrrolidin-3-yl]-5-(methylamino)pyrazole-4-carboxamide 751 -continued

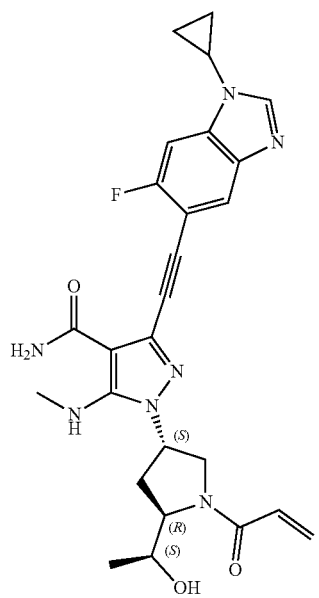

3-[2-(1-cyclopropyl-6-fluoro-1,3-benzodiazol-5-yl)ethynyl]-1-[(3S,5R)-5-[(1S)-1-hydroxyethyl]-1-(prop-2-enoyl)pyrrolidin-3-yl]-5-(methylamino)pyrazole-4-carboxamide. MS ESI calculated for $C_{26}H_{28}FN_7O_3$ [M+H]$^+$, 506.22, found 506.40; $^1$H NMR (400 MHz, DMSO-d$_6$) δ 8.36 (s, 1H), 7.95-7.90 (m, 1H), 7.64 (d, J=9.4 Hz, 1H), 7.48 (s, 1H), 6.88-6.50 (m, 3H), 6.14-6.10 (m, 1H), 5.66-5.62 (m, 1H), 5.33-5.18 (m, 1H), 4.99 (d, J=19.8 Hz, 1H), 4.50-4.17 (m, 1H), 3.99-3.96 (m, 2H), 3.70-3.69 (m, 1H), 3.52-3.50 (m, 1H), 2.98-2.92 (m, 3H), 2.44-2.24 (m, 2H), 1.15-0.98 (m, 7H).

Example 220: 1-((3S,5R)-1-Acryloyl-5-((R)-1-hydroxyethyl)pyrrolidin-3-yl)-3-((6-chloro-1-cyclopropyl-2-methyl-1H-benzo[d]imidazol-5-yl)ethynyl)-5-(methylamino)-1H-pyrazole-4-carboxamide

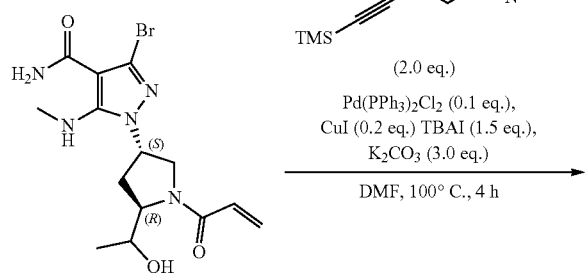

752 -continued

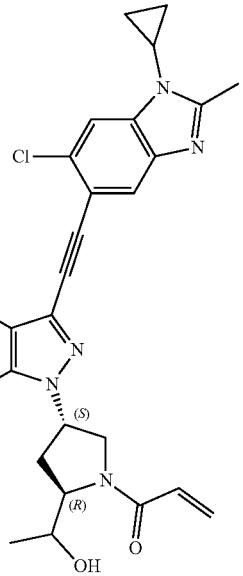

CHIRAL HPLC →

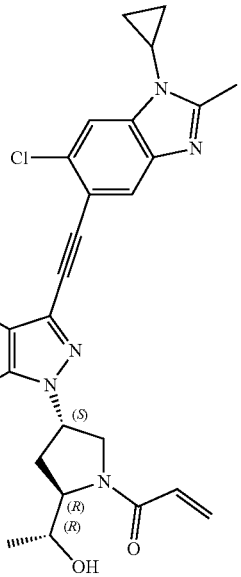

1-((3S,5R)-1-Acryloyl-5-((R)-1-hydroxyethyl)pyrrolidin-3-yl)-3-((6-chloro-1-cyclopropyl-2-methyl-1H-benzo[d]imidazol-5-yl)ethynyl)-5-(methylamino)-1H-pyrazole-4-carboxamide. MS ESI calculated for $C_{27}H_{30}ClN_7O_3$ [M+H]$^+$, 536.21, found 536.35; $^1$H NMR (400 MHz, DMSO-d$_6$) δ 7.86 (s, 1H), 7.71 (s, 1H), 7.53 (s, 1H), 6.94-6.78 (m, 1H), 6.77-6.53 (m, 2H), 6.20-6.08 (m, 1H), 5.73-5.65 (m, 1H), 5.44-5.28 (m, 1H), 5.06-5.00 (m, 1H), 4.36-3.66 (m, 3H), 3.33 (s, 2H), 2.95 (m, 3H), 2.60 (s, 3H), 2.54-2.18 (m, 2H), 1.28-1.16 (m, 2H), 1.09-1.04 (m, 5H).

Example 221: 1-((3S,5R)-1-Acryloyl-5-((S)-1-hydroxyethyl)pyrrolidin-3-yl)-3-((6-chloro-1-cyclopropyl-2-methyl-1H-benzo[d]imidazol-5-yl)ethynyl)-5-(methylamino)-1H-pyrazole-4-carboxamide

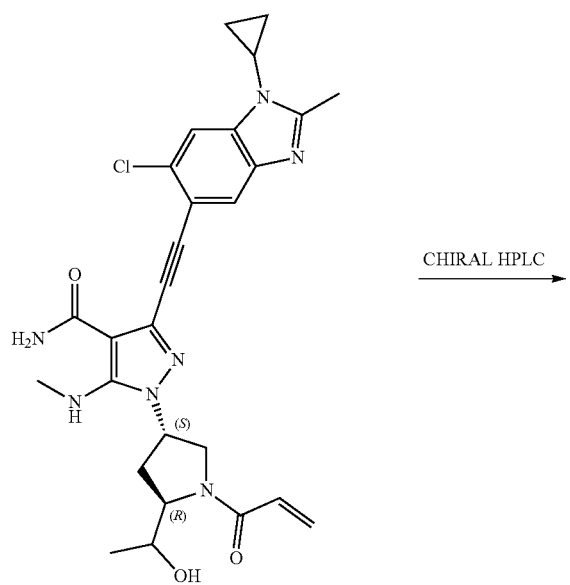

CHIRAL HPLC →

The racemic product (0.30 g) was purified by Prep-SFC with the following conditions: Column: CHIRAL ART Cellulose-SC, 2×25 cm, 5 μm; Mobile Phase A: Hex:DCM=1:1 (0.5% 2M NH₃-MeOH), Mobile Phase B: EtOH; Flow rate: 20 mL/min; Gradient: 50% B to 50% B in 12 min; Wave length: 220/254 nm; RT2: 10.04 min; Sample solvent: EtOH:DCM=1:1; Injection Volume: 0.3 mL; RT2: 10.04 min. The fractions contained desired product were combined and concentrated to afford 1-((3S,5R)-1-acryloyl-5-((S)-1-hydroxyethyl)pyrrolidin-3-yl)-3-((6-chloro-1-cyclopropyl-2-methyl-1H-benzo[d]imidazol-5-yl)ethynyl)-5-(methylamino)-1H-pyrazole-4-carboxamide (0.12 g, 35%) as a white solid. MS ESI calculated for $C_{27}H_{30}ClN_7O_3$ [M+H]⁺, 536.21, found 536.45; ¹H NMR (400 MHz, DMSO-d₆) δ 7.85 (s, 1H), 7.71 (s, 1H), 7.51 (s, 1H), 6.99-6.50 (m, 3H), 6.20-6.13 (m, 1H), 5.70-5.62 (m, 1H), 5.31-5.19 (m, 1H), 5.03-4.95 (m, 1H), 4.50-4.20 (m, 1H), 4.06-3.95 (m, 2H), 3.75-3.66 (m, 1H), 3.40-3.34 (m, 1H), 3.02-2.95 (m, 3H), 2.60 (s, 3H), 2.37-2.30 (m, 2H), 1.25-1.18 (m, 2H), 1.11-0.99 (m, 5H).

Example 222: 3-[2-(6-Chloro-1-cyclopropyl-1,3-benzodiazol-5-yl)ethynyl]-1-[(3S,5R)-5-[(1R)-1-hydroxyethyl]-1-(prop-2-enoyl)pyrrolidin-3-yl]-5-(methylamino)pyrazole-4-carboxamide

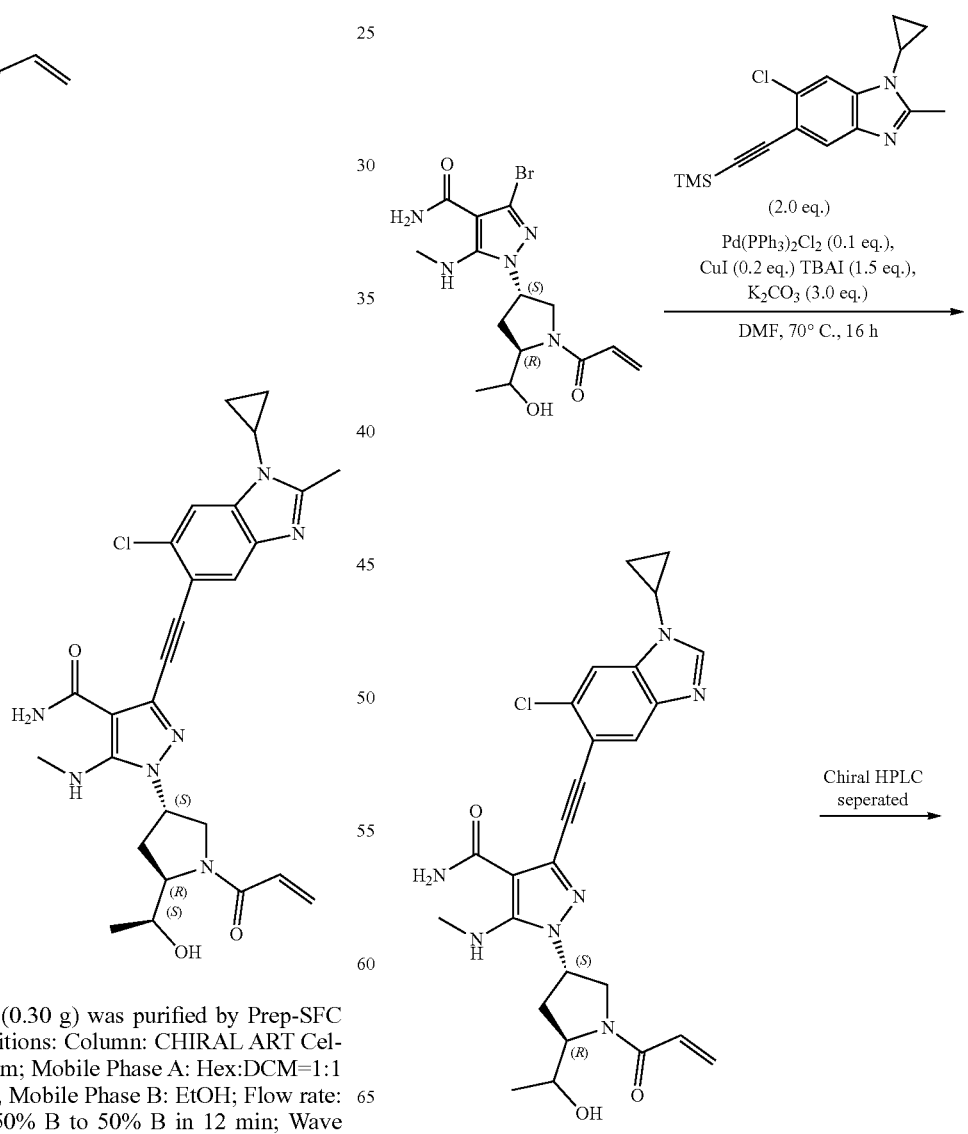

755
-continued

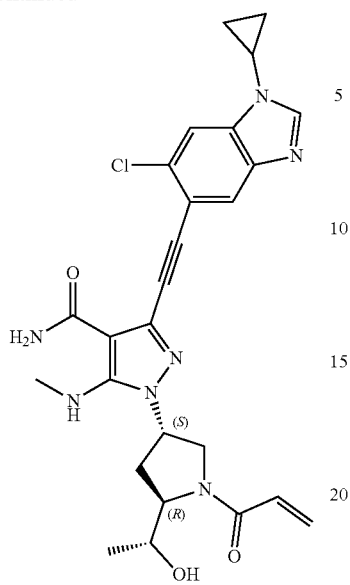

3-[2-(6-chloro-1-cyclopropyl-1,3-benzodiazol-5-yl)ethynyl]-1-[(3S,5R)-5-[(1R)-1-hydroxyethyl]-1-(prop-2-enoyl)pyrrolidin-3-yl]-5-(methylamino)pyrazole-4-carboxamide. MS ESI calculated for $C_{26}H_{28}ClN_7O_3$ [M+H]$^+$, 522.19, found 522.15; $^1$H NMR (400 MHz, CDCl$_3$) δ 8.39 (s, 1H), 8.02 (s, 1H), 7.88 (s, 1H), 7.49 (s, 1H), 6.84 (s, 1H), 6.72-6.57 (m, 2H), 6.21-6.13 (m, 1H), 5.71-5.66 (m, 1H), 5.39-5.32 (m, 1H), 5.09-4.89 (m, 1H), 4.27-4.16 (m, 1H), 3.92-3.76 (m, 2H), 3.57-3.52 (m, 1H), 2.96 (t, J=12 Hz, 3H), 2.39-2.09 (m, 3H), 1.15-1.04 (m, 7H).

Example 223: 3-[2-(6-Chloro-1-cyclopropyl-1,3-benzodiazol-5-yl)ethynyl]-1-[(3S,5R)-5-[(1S)-1-hydroxyethyl]-1-(prop-2-enoyl)pyrrolidin-3-yl]-5-(methylamino)pyrazole-4-carboxamide 756
-continued

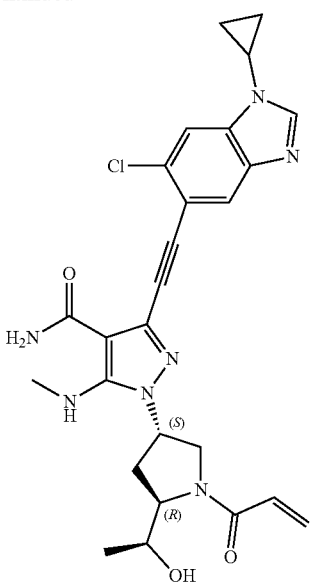

3-[2-(6-chloro-1-cyclopropyl-1,3-benzodiazol-5-yl)ethynyl]-1-[(3S,5R)-5-[(1S)-1-hydroxyethyl]-1-(prop-2-enoyl)pyrrolidin-3-yl]-5-(methylamino)pyrazole-4-carboxamide. MS ESI calculated for $C_{26}H_{28}ClN_7O_3$ [M+H]$^+$, 522.19, found 522.20; $^1$H NMR (400 MHz, CDCl$_3$) δ 8.41 (s, 1H), 8.03 (s, 1H), 7.89 (s, 1H), 7.52 (s, 1H), 6.87-6.57 (m, 3H), 6.15 (d, J=10 Hz, 1H), 5.71-5.64 (m, 1H), 5.28 (s, 1H), 5.04-4.97 (m, 1H), 4.43-4.30 (m, 1H), 4.05-3.97 (m, 2H), 3.74-3.68 (m, 1H), 3.55 (s, 1H), 2.97-2.95 (m, 3H), 2.51 (s, 1H), 2.35 (s, 1H), 1.13-1.01 (m, 7H).

Example 224: 3-[2-(1-Cyclopropyl-6-fluoro-2-methyl-1,3-benzodiazol-5-yl)ethynyl]-1-[(3S,5R)-5-[(1R)-1-hydroxyethyl]-1-(prop-2-enoyl)pyrrolidin-3-yl]-5-(methylamino)pyrazole-4-carboxamide

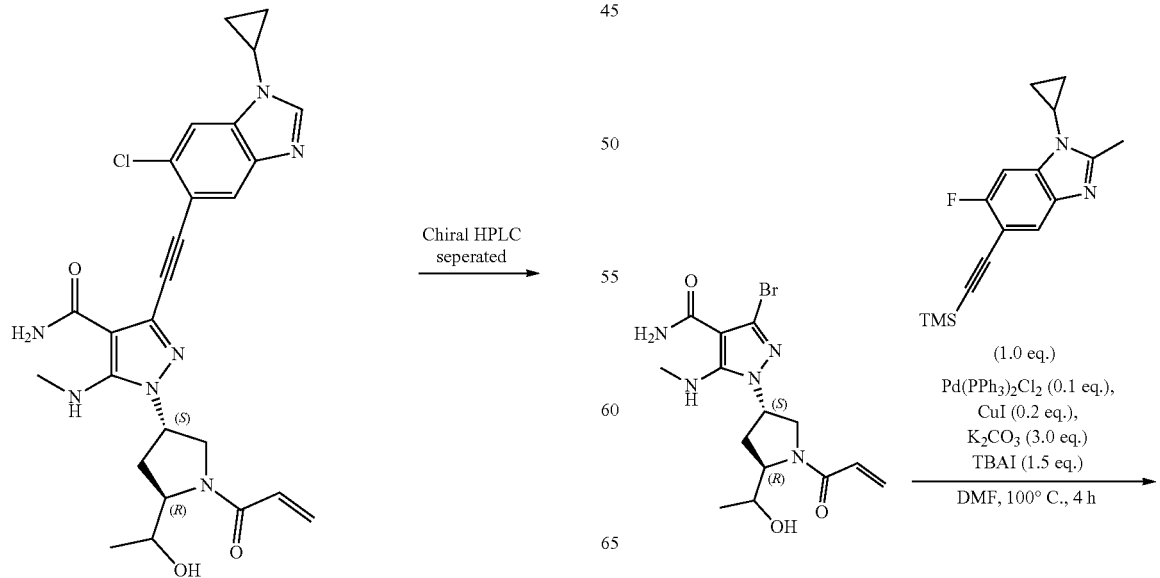

757

-continued

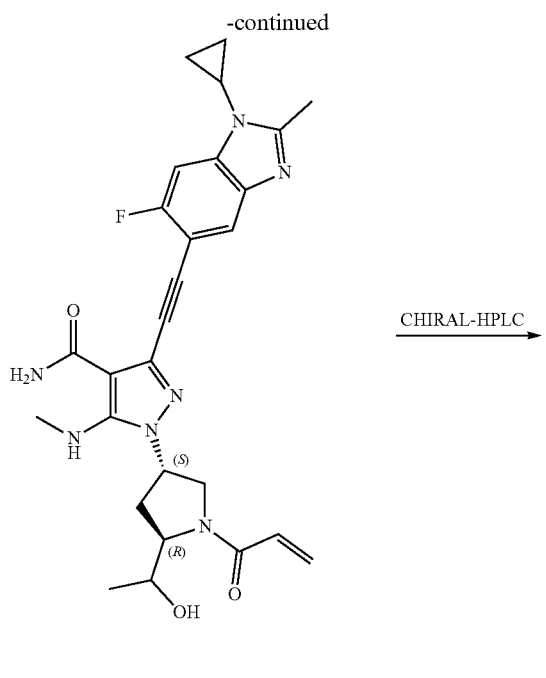

→ CHIRAL-HPLC →

Example 225: 3-[2-(1-Cyclopropyl-6-fluoro-2-methyl-1,3-benzodiazol-5-yl)ethynyl]-1-[(3S,5R)-5-[(1S)-1-hydroxyethyl]-1-(prop-2-enoyl)pyrrolidin-3-yl]-5-(methylamino)pyrazole-4-carboxamide

→ CHIRAL-HPLC →

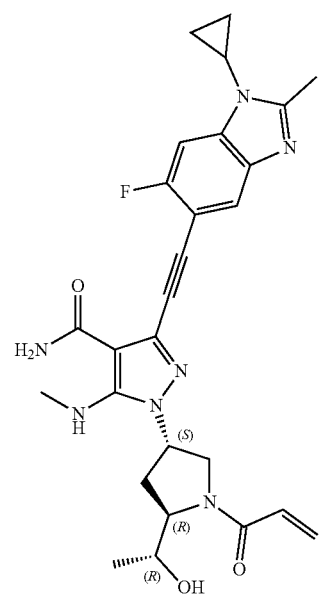

3-[2-(1-cyclopropyl-6-fluoro-2-methyl-1,3-benzodiazol-5-yl)ethynyl]-1-[(3S,5R)-5-[(1R)-1-hydroxyethyl]-1-(prop-2-enoyl)pyrrolidin-3-yl]-5-(methylamino)pyrazole-4-carboxamide. MS ESI calculated for $C_{27}H_{30}FN_7O_3$. [M+H]$^+$, 520.24, found 520.25; $^1$H NMR (400 MHz, DMSO-$d_6$) δ 7.79 (d, J=6.4 Hz, 1H), 7.50 (d, J=9.6 Hz, 2H), 6.78-6.54 (m, 3H), 6.23-6.11 (m, 1H), 5.73-5.61 (m, 1H), 5.41-5.29 (m, 1H), 5.06-4.89 (m, 1H), 4.33-3.70 (m, 4H), 2.95 (t, J=5.7 Hz, 3H), 2.59 (s, 3H), 2.46 (s, 3H), 1.25-1.11 (m, 2H), 1.11-1.02 (m, 5H).

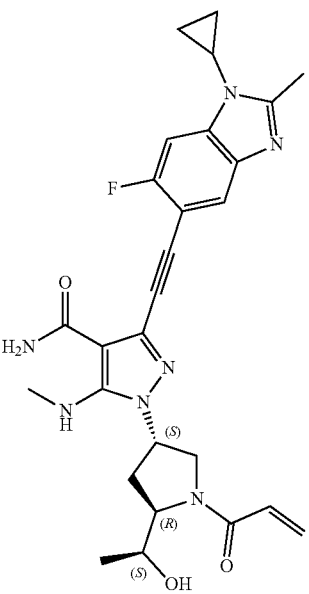

3-[2-(1-cyclopropyl-6-fluoro-2-methyl-1,3-benzodiazol-5-yl)ethynyl]-1-[(3S,5R)-5-[(1S)-1-hydroxyethyl]-1-(prop-2-enoyl)pyrrolidin-3-yl]-5-(methylamino)pyrazole-4-carboxamide. MS ESI calculated for $C_{27}H_{30}FN_7O_3$ [M+H]$^+$, 520.24, found 520.60; $^1$H NMR (400 MHz, DMSO-$d_6$) δ 7.78 (d, J=6.3 Hz, 1H), 7.49 (d, J=9.7 Hz, 2H), 6.83-6.54 (m, 3H), 6.15 (d, J=17.0 Hz, 1H), 5.72-5.61 (m, 1H), 5.31-5.20 (m, 1H), 5.01-4.94 (m, 1H), 4.48-4.24 (m, 1H), 4.06-3.90 (m, 2H), 3.79-3.68 (m, 1H), 3.01-2.89 (m, 3H), 2.59 (s, 3H), 2.49 (s, 1H), 2.40-2.29 (m, 1H), 1.25-1.12 (m, 2H), 1.12-1.05 (m, 2H), 1.03 (s, 3H).

Example 226: 3-[2-(6-Chloro-1-cyclopropyl-1,3-benzodiazol-5-yl)ethynyl]-1-[(3S,5R)-1-(4-hydroxy-4-methylpent-2-ynoyl)-5-(methoxymethyl)pyrrolidin-3-yl]-5-(methylamino)pyrazole-4-carboxamide

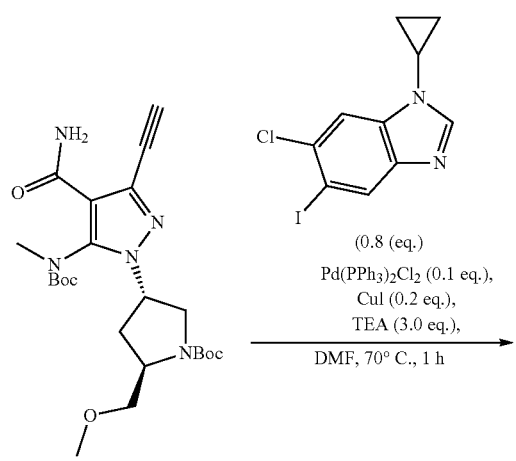

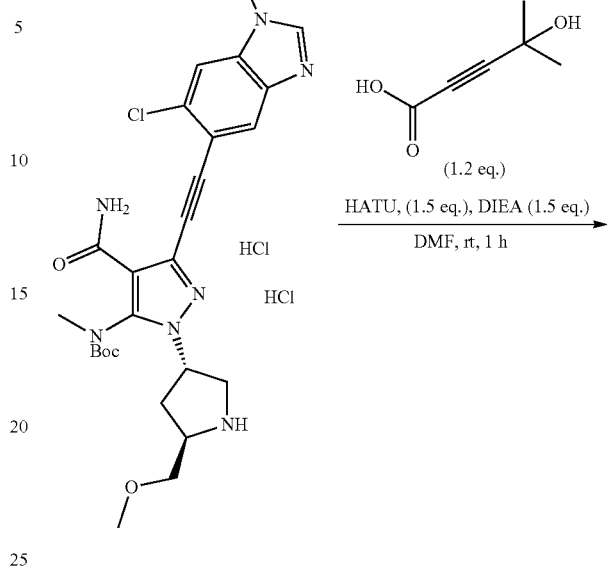

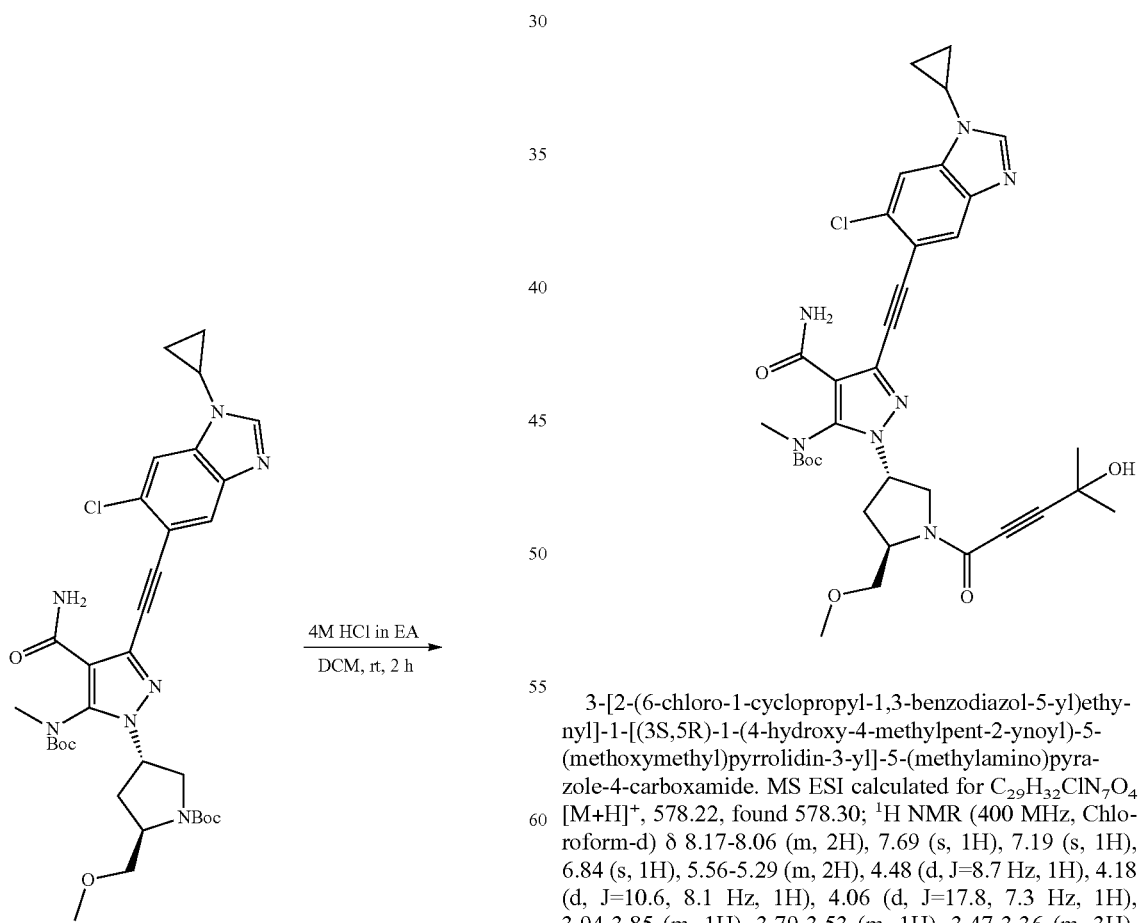

3-[2-(6-chloro-1-cyclopropyl-1,3-benzodiazol-5-yl)ethynyl]-1-[(3S,5R)-1-(4-hydroxy-4-methylpent-2-ynoyl)-5-(methoxymethyl)pyrrolidin-3-yl]-5-(methylamino)pyrazole-4-carboxamide. MS ESI calculated for $C_{29}H_{32}ClN_7O_4$ [M+H]$^+$, 578.22, found 578.30; $^1$H NMR (400 MHz, Chloroform-d) δ 8.17-8.06 (m, 2H), 7.69 (s, 1H), 7.19 (s, 1H), 6.84 (s, 1H), 5.56-5.29 (m, 2H), 4.48 (d, J=8.7 Hz, 1H), 4.18 (d, J=10.6, 8.1 Hz, 1H), 4.06 (d, J=17.8, 7.3 Hz, 1H), 3.94-3.85 (m, 1H), 3.79-3.53 (m, 1H), 3.47-3.36 (m, 3H), 3.04 (d, J=14.9 Hz, 3H), 2.86-2.74 (m, 1H), 2.17 (s, 2H), 1.60 (d, J=13.1 Hz, 6H), 1.30-1.21 (m, 2H), 1.15-1.07 (m, 2H).

Example 227: 3-[2-(1-Cyclopropyl-6-fluoro-2-methyl-1,3-benzodiazol-5-yl)ethynyl]-1-[(3S,5R)-1-(4-hydroxy-4-methylpent-2-ynoyl)-5-(methoxymethyl)pyrrolidin-3-yl]-5-(methylamino)pyrazole-4-carboxamide

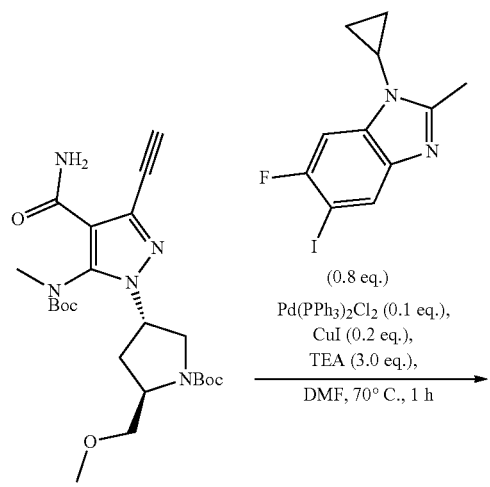

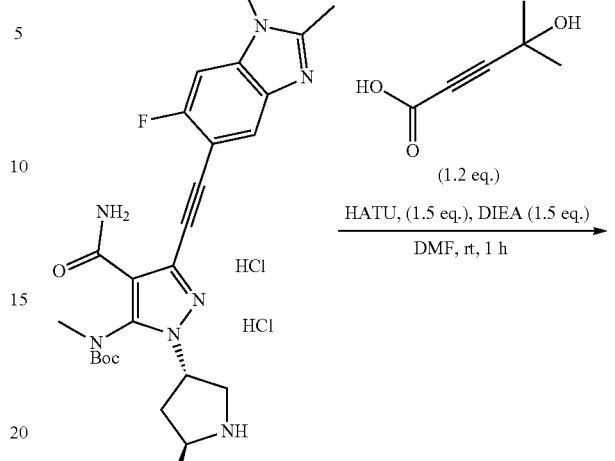

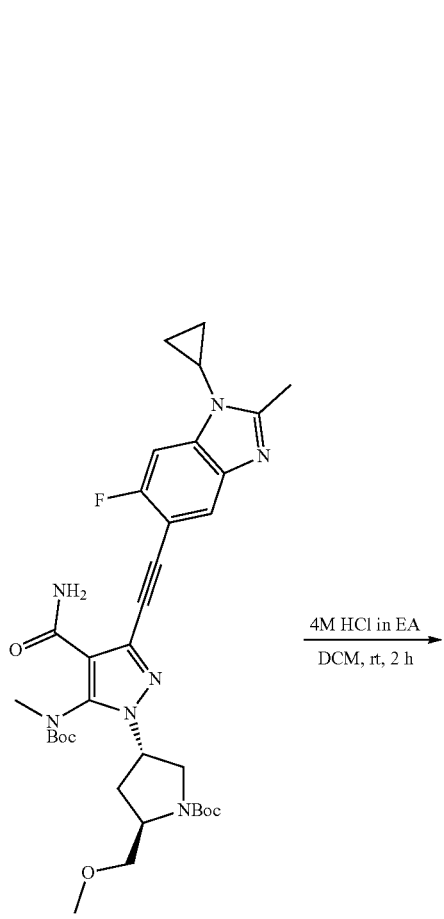

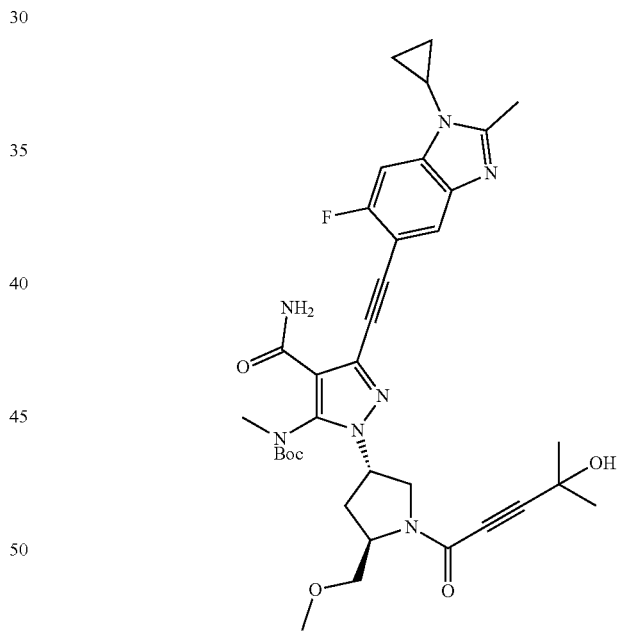

3-[2-(1-cyclopropyl-6-fluoro-2-methyl-1,3-benzodiazol-5-yl)ethynyl]-1-[(3S,5R)-1-(4-hydroxy-4-methylpent-2-ynoyl)-5-(methoxymethyl)pyrrolidin-3-yl]-5-(methylamino)pyrazole-4-carboxamide. MS ESI calculated for $C_{30}H_{34}FN_7O_4$ [M+H]$^+$, 576.27, found 576.30; $^1$H NMR (400 MHz, Chloroform-d) δ 7.82 (t, J=7.4 Hz, 1H), 7.13 (s, 1H), 6.82 (d, J=5.9 Hz, 1H), 5.50-5.30 (m, 2H), 4.47 (d, J=8.8 Hz, 1H), 4.21-4.12 (m, 1H), 4.12-4.01 (m, 1H), 3.92-3.83 (m, 1H), 3.73-3.59 (m, 1H), 3.40 (d, J=13.0 Hz, 3H), 3.29 (s, 1H), 3.09-2.96 (m, 3H), 2.75 (d, J=4.2 Hz, 3H), 2.43-2.28 (m, 2H), 1.60 (d, J=14.8 Hz, 6H), 1.35-1.25 (m, 2H), 1.10 (s, 2H).

Example 228: 3-[2-(6-Chloro-1-cyclopropyl-2-methyl-1,3-benzodiazol-5-yl)ethynyl]-1-[(3S,5R)-1-(4-hydroxy-4-methylpent-2-ynoyl)-5-(methoxymethyl)pyrrolidin-3-yl]-5-(methylamino)pyrazole-4-carboxamide

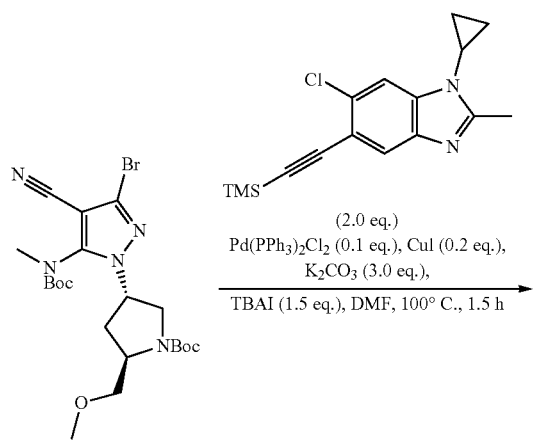

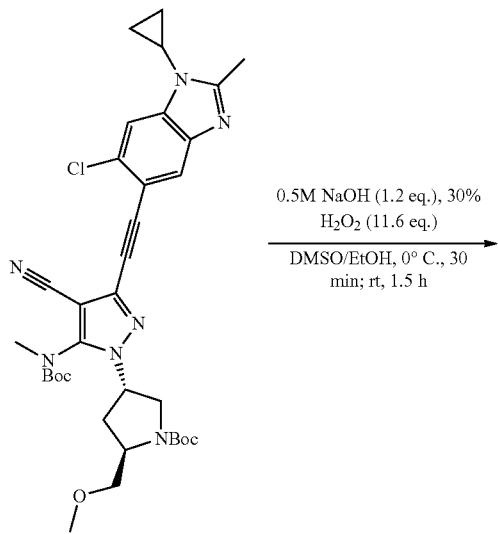

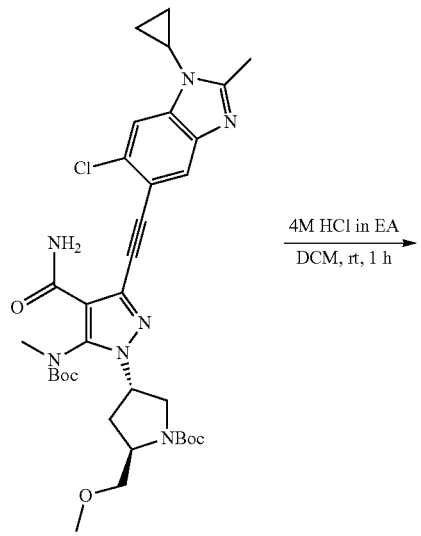

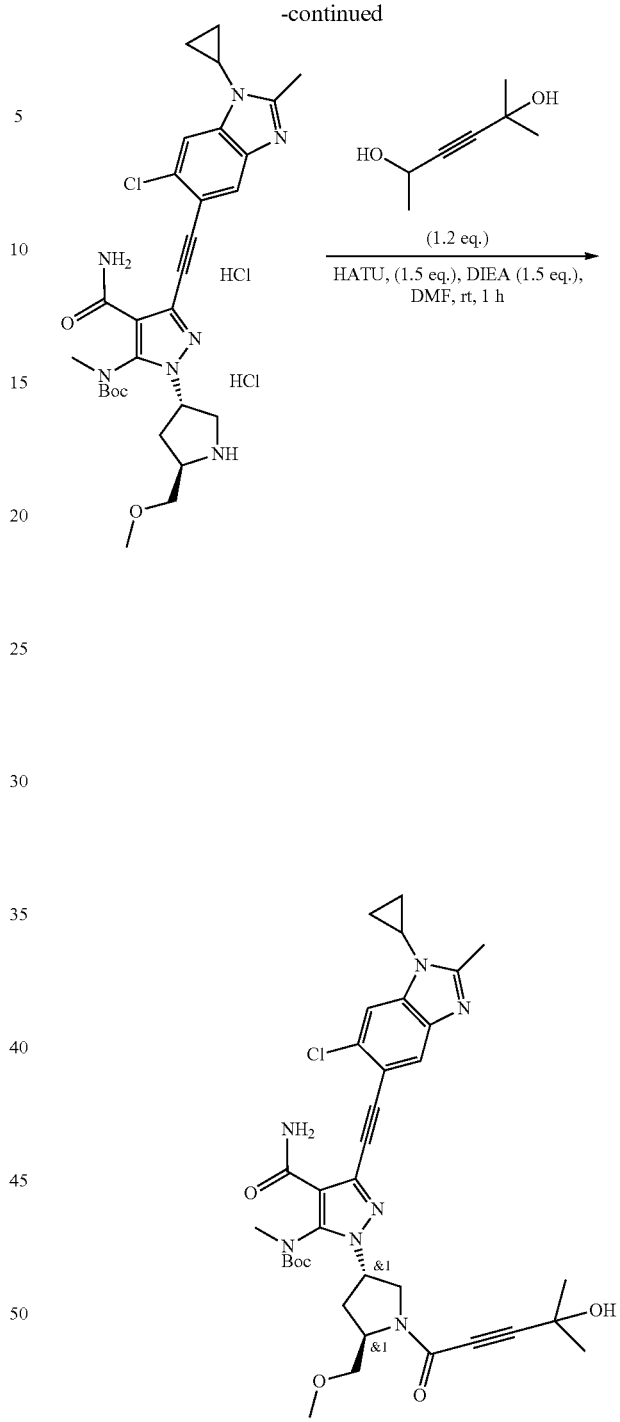

3-[2-(6-chloro-1-cyclopropyl-2-methyl-1,3-benzodiazol-5-yl)ethynyl]-1-[(3S,5R)-1-(4-hydroxy-4-methylpent-2-ynoyl)-5-(methoxymethyl)pyrrolidin-3-yl]-5-(methylamino)pyrazole-4-carboxamide. MS ESI calculated for $C_{30}H_{34}ClN_7O_4$ [M+H]$^+$, 592.24, found 592.30; $^1$H NMR (400 MHz, CDCl$_3$) δ 7.93 (s, 1H), 7.57 (s, 1H), 7.28 (s, 1H), 6.83 (s, 1H), 5.48-5.35 (m, 2H), 4.52-4.43 (m, 1H), 4.18-4.13 (m, 2H), 3.77-3.74 (m, 1H), 3.70-3.54 (m, 1H), 3.42-3.38 (m, 1H), 3.23 (s, 2H), 3.06-3.01 (m, 1H), 2.69 (s, 4H), 2.46 (s, 3H), 2.40-2.30 (m, 2H), 1.61-1.58 (m, 6H), 1.31-1.29 (m, 2H), 1.08 (s, 2H).

Example 230: 1-((3S,5R)-1-Acryloyl-5-(methoxymethyl)pyrrolidin-3-yl)-3-((1-cyclobutyl-6-fluoro-1H-benzo[d]imidazol-5-yl)ethynyl)-5-(methylamino)-1H-pyrazole-4-carboxamide

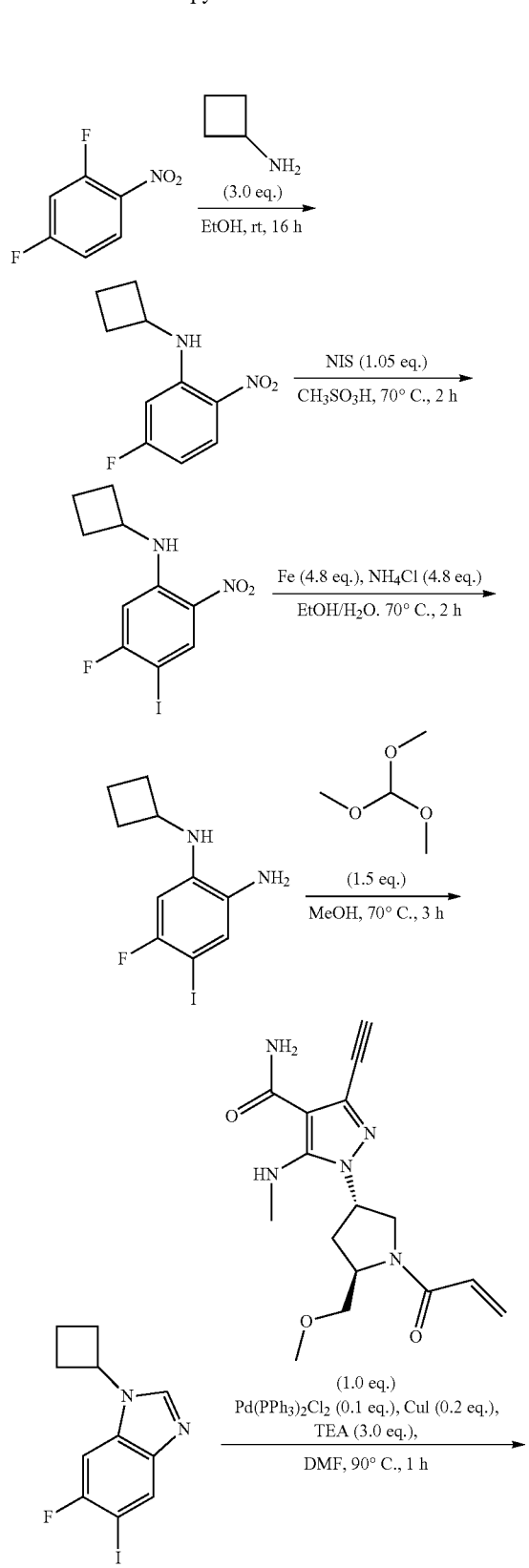

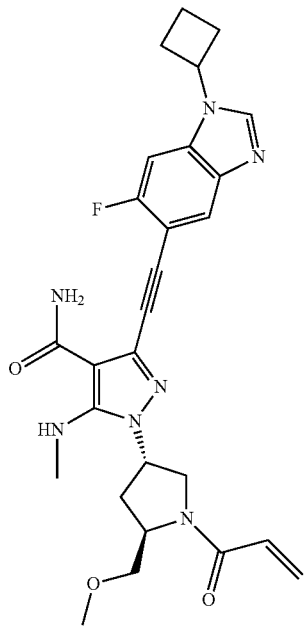

1-((3S,5R)-1-Acryloyl-5-(methoxymethyl)pyrrolidin-3-yl)-3-((1-cyclobutyl-6-fluoro-1H-benzo[d]imidazol-5-yl)ethynyl)-5-(methylamino)-1H-pyrazole-4-carboxamide. MS ESI calculated for $C_{27}H_{30}FN_7O_3$ [M+H]$^+$, 520.24, found 520.25; $^1$H NMR (400 MHz, CDCl$_3$) δ 8.13 (d, J=25.1 Hz, 1H), 8.00 (d, J=5.9 Hz, 1H), 7.17 (d, J=9.4 Hz, 2H), 6.81 (s, 1H), 6.61-6.32 (m, 2H), 5.75-5.68 (m, 1H), 5.61 (s, 1H), 5.57-5.22 (m, 1H), 4.85-6.78 (m, 1H), 4.64-4.37 (m, 1H), 4.15-4.09 (m, 1H), 4.06-4.00 (m, 1H), 3.94-3.87 (m, 1H), 3.56-3.42 (m, 1H), 3.38 (d, J=4.4 Hz, 3H), 3.04 (d, J=15.5 Hz, 3H), 2.79-2.62 (m, 3H), 2.58-2.50 (m, 2H), 2.38-2.30 (m, 1H), 2.09-2.01 (m, 2H).

Example 231: 1-((3S,5R)-1-Acryloyl-5-(methoxymethyl)pyrrolidin-3-yl)-3-((1-cyclobutyl-6-fluoro-2-methyl-1H-benzo[d]imidazol-5-yl)ethynyl)-5-(methylamino)-1H-pyrazole-4-carboxamide

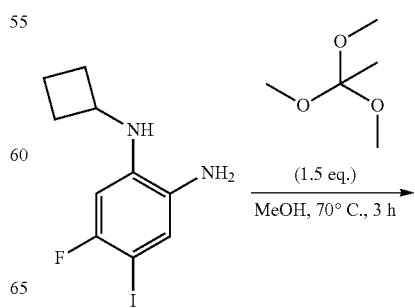

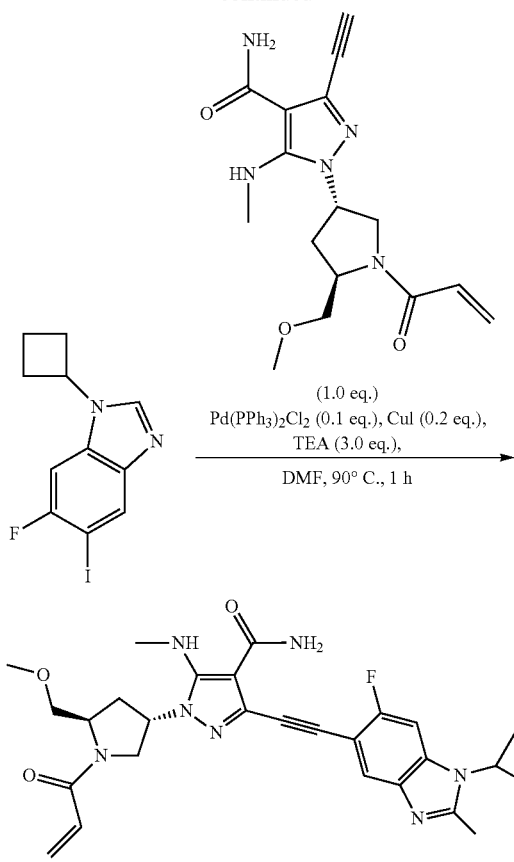

1-((3S,5R)-1-acryloyl-5-(methoxymethyl)pyrrolidin-3-yl)-3-((1-cyclobutyl-6-fluoro-2-methyl-1H-benzo[d]imidazol-5-yl)ethynyl)-5-(methylamino)-1H-pyrazole-4-carboxamide. MS ESI calculated for $C_{28}H_{32}FN_7O_3$ [M+H]$^+$, 534.26, found 534.40; $^1$H NMR (400 MHz, CDCl$_3$) δ 7.88 (d, J=6.2 Hz, 1H), 7.34 (d, J=10.3 Hz, 1H), 7.13 (s, 1H), 6.84 (d, J=6.3 Hz, 1H), 6.44 (d, J=7.9 Hz, 2H), 5.78-5.67 (m, 1H), 5.59-5.46 (m, 1H), 5.33 (d, J=26.1 Hz, 1H), 4.89-4.82 (m, 1H), 4.57 (d, J=8.9 Hz, 1H), 4.15-4.10 (m, 1H), 4.06-4.00 (m, 1H), 3.92 (d, J=9.8 Hz, 1H), 3.57-3.43 (m, 1H), 3.39 (d, J=3.9 Hz, 3H), 3.13-2.98 (m, 3H), 2.92-2.70 (m, 3H), 2.65 (s, 5H), 2.44-2.25 (m, 1H), 2.09-2.01 (m, 2H).

Example 232: 3-[2-(6-Chloro-1-cyclobutyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide

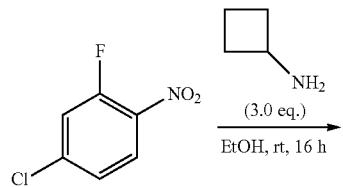

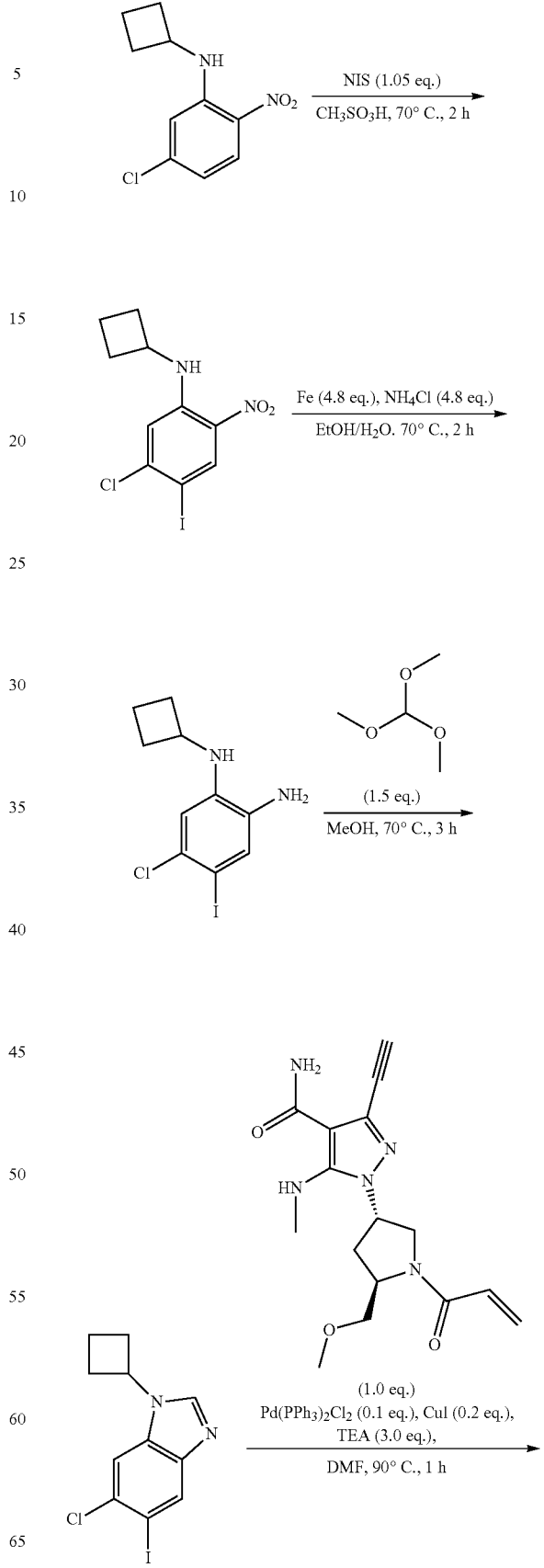

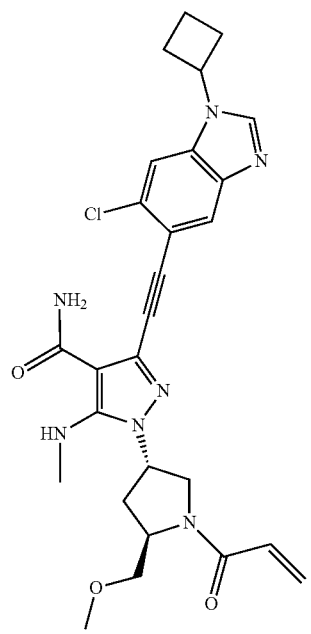

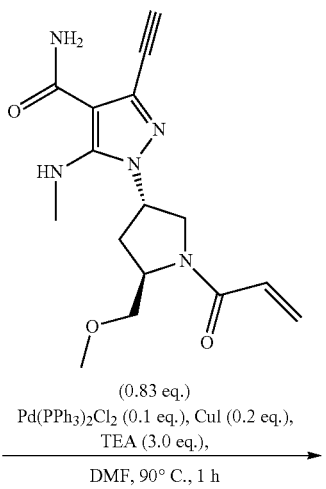

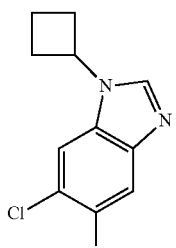

3-[2-(6-chloro-1-cyclobutyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide. MS ESI calculated for $C_{27}H_{30}ClN_7O_3$ [M+H]$^+$, 536.21, found 536.15; $^1$H NMR (400 MHz, CDCl$_3$) δ 8.10 (s, 2H), 7.72-7.67 (m, 1H), 7.21 (s, 1H), 6.83 (s, 1H), 6.57-6.39 (m, 2H), 5.73-5.70 (m, 1H), 5.56-5.48 (m, 1H), 5.36-5.28 (m, 1H), 4.85-4.77 (m, 1H), 4.57 (d, J=12 Hz, 1H), 4.15-3.96 (m, 2H), 3.93-3.90 (m, 1H), 3.52-3.38 (m, 4H), 3.07-2.97 (m, 3H), 2.77-2.66 (m, 3H), 2.61-2.51 (m, 2H), 2.41-2.29 (m, 1H), 2.11-2.02 (m, 2H).

Example 233: 1-((3S,5R)-1-Acryloyl-5-(methoxymethyl)pyrrolidin-3-yl)-3-((6-chloro-1-cyclobutyl-2-methyl-1H-benzo[d]imidazol-5-yl)ethynyl)-5-(methylamino)-1H-pyrazole-4-carboxamide

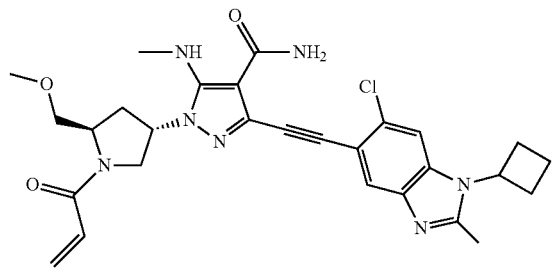

1-((3S,5R)-1-acryloyl-5-(methoxymethyl)pyrrolidin-3-yl)-3-((6-chloro-1-cyclobutyl-2-methyl-1H-benzo[d]imidazol-5-yl)ethynyl)-5-(methylamino)-1H-pyrazole-4-carboxamide. MS ESI calculated for $C_{28}H_{32}ClN_7O_3$ [M+H]$^+$, 550.23, found 550.30; $^1$H NMR (400 MHz, Methanol-d$_4$) δ 7.93-7.90 (s, 1H), 7.86-7.70 (m, 1H), 6.71-6.70 (m, 1H), 6.32-6.20 (m, 1H), 5.78-5.70 (m, 1H), 5.44-5.30 (m, 1H), 5.07-5.01 (m, 1H), 4.69-4.52 (m, 1H), 4.16-4.04 (m, 2H), 3.95-3.78 (m, 1H), 3.56-3.50 (m, 1H), 3.41-3.40 (in. 3H), 3.04-3.01 (m, 3H), 2.84-2.80 (m, 2H), 2.75-2.57 (m, 6H), 2.46-2.40 (m, 1H), 2.15-1.98 (in, 2H).

Example 234: 3-{2-[6-Fluoro-1-(oxetan-3-yl)-1,3-benzodiazol-5-yl]ethynyl}-1-[(3,5R)-5-(methoxymethyl)-1-(prop-2-enoyl)pyrrolidin-3-yl]-5-(methylamino)pyrazole-4-carboxamide

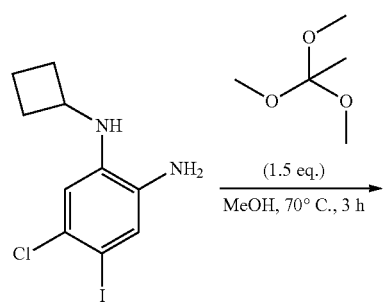

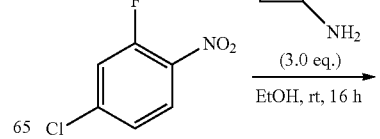

771
-continued

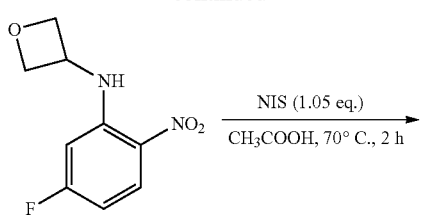

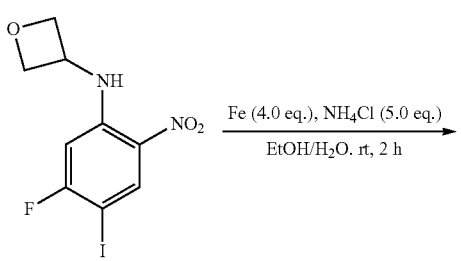

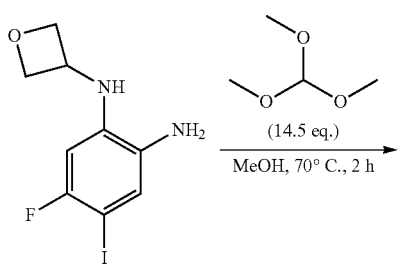

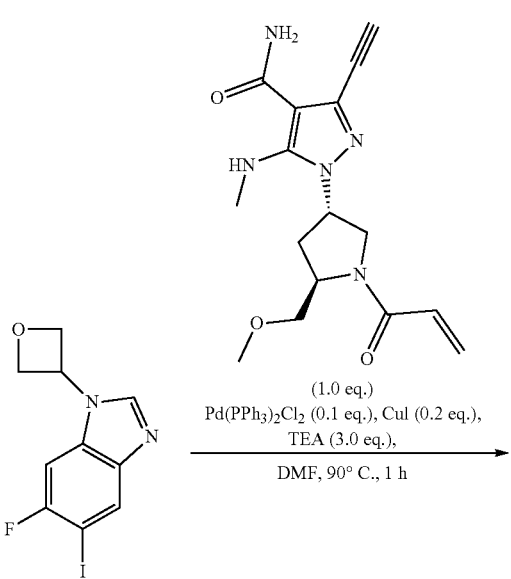

772
-continued

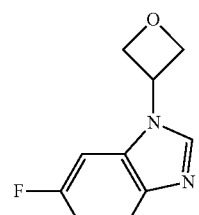

3-{2-[6-fluoro-1-(oxetan-3-yl)-1,3-benzodiazol-5-yl]ethynyl}-1-[(3S,5R)-5-(methoxymethyl)-1-(prop-2-enoyl)pyrrolidin-3-yl]-5-(methylamino)pyrazole-4-carboxamide. MS ESI calculated for $C_{26}H_{28}FN_7O_4$ [M+H]$^+$, 522.22, found 522.25; $^1$H NMR (400 MHz, CDCl$_3$) δ 8.13 (s, 1H), 8.04 (s, 1H), 7.57 (d, J=8.40 Hz, 1H), 7.10 (s, 1H), 6.83 (s, 1H), 6.55-6.35 (m, 2H), 5.74-5.70 (m, 1H), 5.54-5.50 (m, 2H), 5.48-5.26 (m, 3H), 5.10-5.07 (m, 2H), 4.56 (d, J=8.40 Hz, 1H), 4.14-4.10 (m, 1H), 4.09-4.02 (m, 1H), 3.93-3.90 (m, 1H), 3.53-3.40 (m, 1H), 3.37 (d, J=4.40 Hz, 3H), 3.04 (d, J=14.40 Hz, 3H), 2.70-2.68 (m, 1H), 2.42-2.25 (m, 1H).

Example 235: 3-{2-[6-Fluoro-2-methyl-1-(oxetan-3-yl)-1,3-benzodiazol-5-yl]ethynyl}-1-[(3S,5R)-5-(methoxymethyl)-1-(prop-2-enoyl)pyrrolidin-3-yl]-5-(methylamino)pyrazole-4-carboxamide

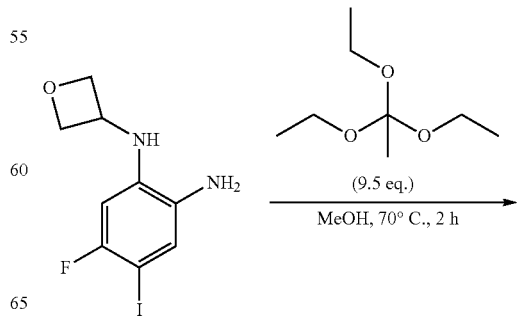

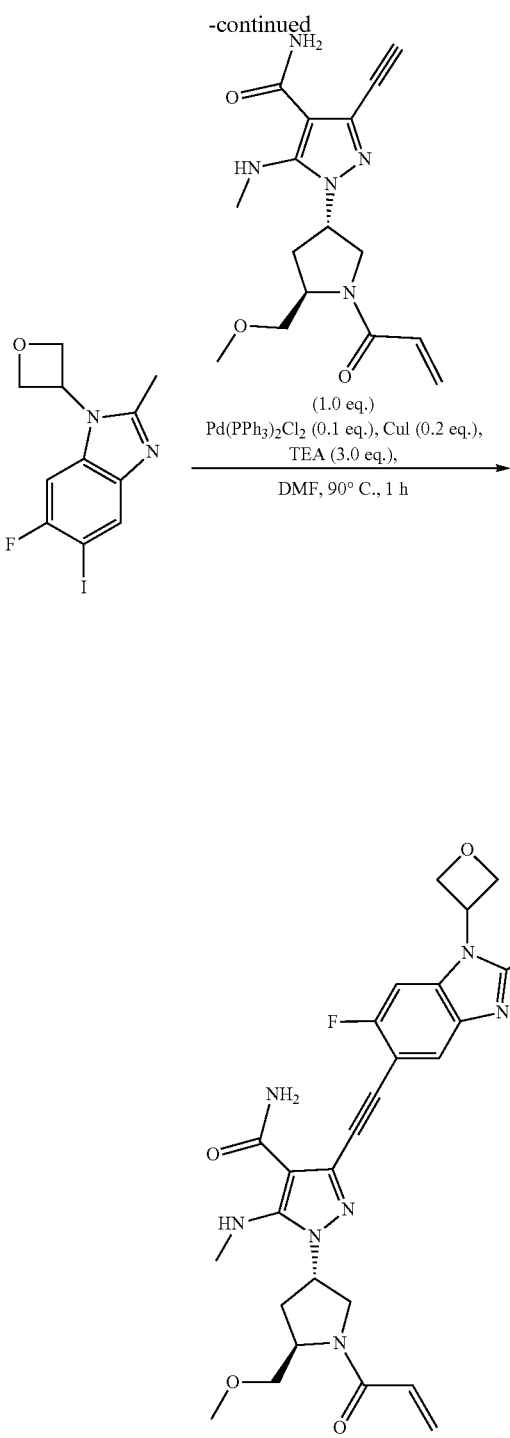

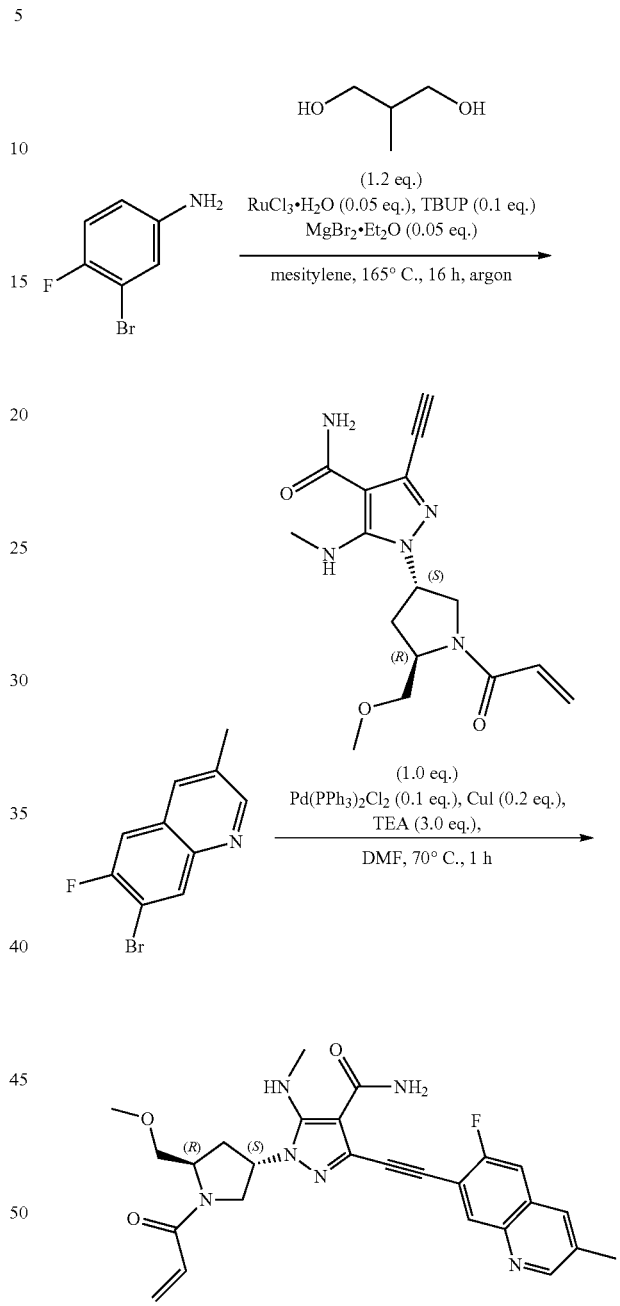

Example 236: 3-[2-(6-Fluoro-3-methylquinolin-7-yl)ethynyl]-1-[(3S,5R)-5-(methoxymethyl)-1-(prop-2-enoyl)pyrrolidin-3-yl]-5-(methylamino)pyrazole-4-carboxamide 3-{2-[6-fluoro-2-methyl-1-(oxetan-3-yl)-1,3-benzodiazol-5-yl]ethynyl}-1-[(3S,5R)-5-(methoxymethyl)-1-(prop-2-enoyl)pyrrolidin-3-yl]-5-(methylamino)pyrazole-4-carboxamide. MS ESI calculated for $C_{27}H_{30}FN_7O_4$ [M+H]$^+$, 536.23, found 536.65; $^1$H NMR (400 MHz, CDCl$_3$) δ 7.93-7.88 (m, 2H), 7.09 (s, 1H), 6.83 (s, 1H), 6.58-6.33 (m, 2H), 5.75-5.70 (m, 1H), 5.54-5.50 (m, 2H), 5.31-5.27 (m, 3H), 5.19-5.11 (m, 2H), 4.60-4.37 (m, 1H), 4.15-4.10 (m, 1H), 4.06-4.02 (m, 1H), 3.94-3.90 (m, 1H), 3.53-3.41 (m, 1H), 3.40-3.38 (m, 3H), 3.08-2.95 (m, 3H), 2.78-2.57 (m, 4H), 2.43-2.26 (m, 1H).

3-[2-(6-fluoro-3-methylquinolin-7-yl)ethynyl]-1-[(3S,5R)-5-(methoxymethyl)-1-(prop-2-enoyl)pyrrolidin-3-yl]-5-(methylamino)pyrazole-4-carboxamide. MS ESI calculated for $C_{26}H_{27}FN_6O_3$ [M+H]$^+$, 491.21, found 491.30; $^1$H NMR (400 MHz, Chloroform-d) δ 8.78 (s, 1H), 8.36 (d, J=6.7 Hz, 1H), 7.90 (s, 1H), 7.43 (d, J=9.5 Hz, 1H), 7.16-6.98 (m, 1H), 6.84 (s, 1H), 6.56-6.36 (m, 2H), 5.71-5.68 (m, 1H), 5.58-5.45 (m, 1H), 5.41 (s, 1H), 4.56 (d, J=9.0 Hz, 1H), 4.11 (t, J=9.1 Hz, 1H), 4.09-3.96 (m, 1H), 4.00-3.87 (m, 1H), 3.58-3.42 (m, 1H), 3.37 (d, J=4.8 Hz, 3H), 3.08-3.00 (m, 3H), 2.77-2.65 (m, 1H), 2.55 (s, 3H), 2.44-2.27 (m, 1H).

Example 237: 1-((3S,5R)-1-Acryloyl-5-(methoxymethyl)pyrrolidin-3-yl)-3-((6-fluoro-1-isopropyl-1H-benzo[d]imidazol-5-yl)ethynyl)-5-(methylamino)-1H-pyrazole-4-carboxamide

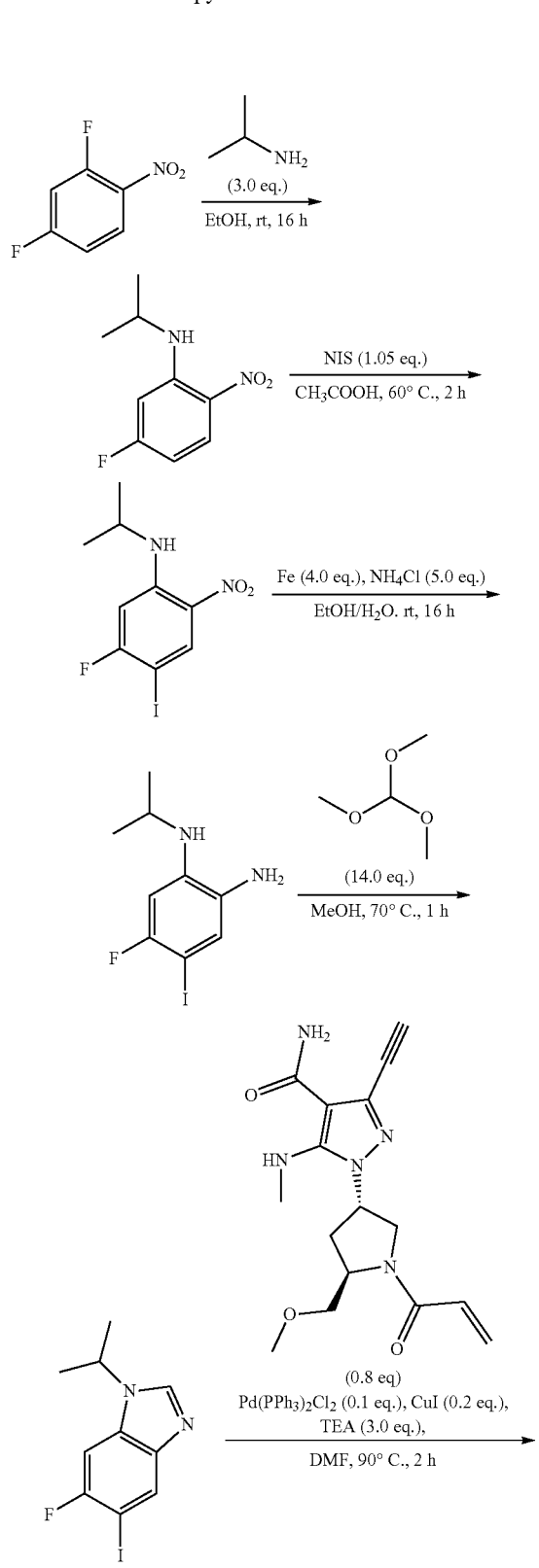

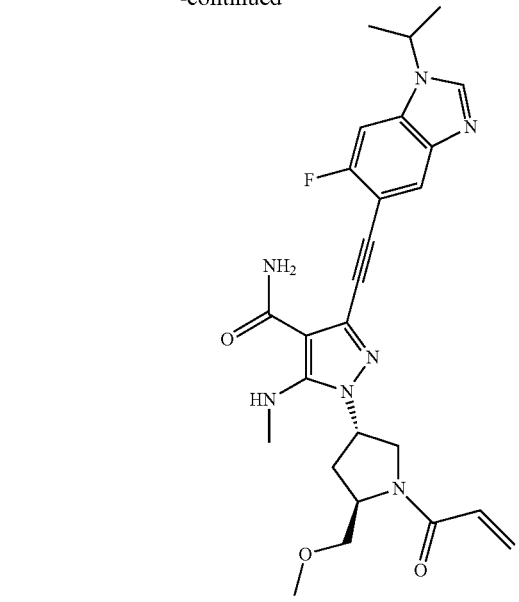

1-((3S,5R)-1-Acryloyl-5-(methoxymethyl)pyrrolidin-3-yl)-3-((6-fluoro-1-isopropyl-1H-benzo[d]imidazol-5-yl)ethynyl)-5-(methylamino)-1H-pyrazole-4-carboxamide. MS ESI calculated for $C_{26}H_{30}FN_7O_3$ [M+H]$^+$, 508.60, found 508.40; $^1$H NMR (400 MHz, CDCl$_3$) δ 8.09 (d, J=42.0 Hz, 2H), 7.18 (d, J=40.0 Hz, 2H), 6.78 (d, J=46.0 Hz, 1H), 6.54-6.39 (m, 2H), 5.72 (dd, J=8.5, 3.8 Hz, 1H), 5.53-5.24 (m, 2H), 4.60 (dd, J=16.4, 8.4 Hz, 2H), 4.18-4.09 (m, 2H), 3.92 (dd, J=9.7, 2.9 Hz, 1H), 3.53-3.37 (m, 4H), 3.05 (d, J=15.5 Hz, 3H), 2.78-2.66 (m, 1H), 2.38-2.34 (m, 1H), 1.66 (d, J=6.7 Hz, 6H).

Example 238: 3-{2-[6-Fluoro-1-(1-methylcyclopropyl)-1,3-benzodiazol-5-yl]ethynyl}-1-[(3S,5R)-5-(methoxymethyl)-1-(prop-2-enoyl)pyrrolidin-3-yl]-5-(methylamino)pyrazole-4-carboxamide

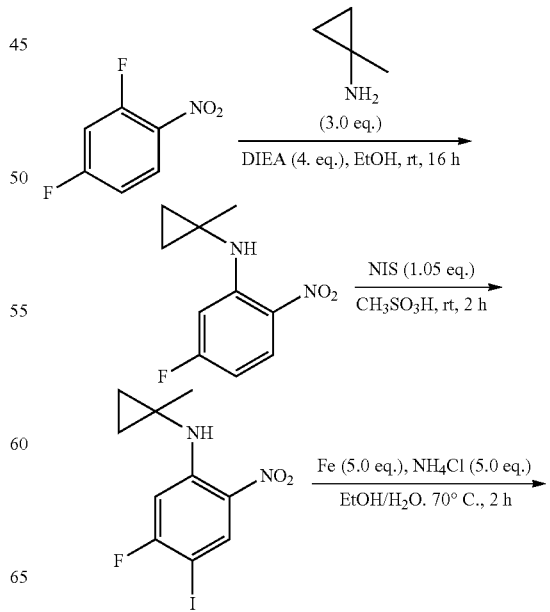

-continued

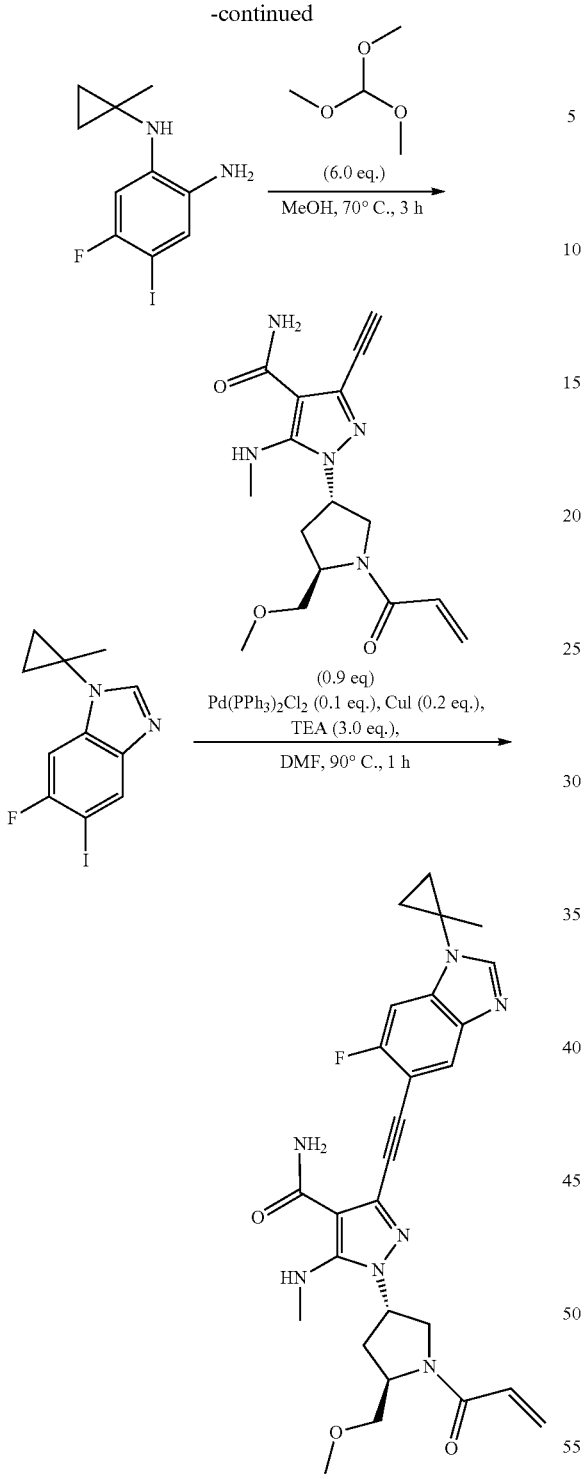

3-{2-[6-fluoro-1-(1-methylcyclopropyl)-1,3-benzodiazol-5-yl]ethynyl}-1-[(3S,5R)-5-(methoxymethyl)-1-(prop-2-enoyl)pyrrolidin-3-yl]-5-(methylamino)pyrazole-4-carboxamide. MS ESI calculated for $C_{27}H_{30}FN_7O_3$ [M+H]$^+$, 520.24, found 520.35; $^1$H NMR (400 MHz, DMSO-d$_6$) δ 8.43-8.41 (s, 1H), 7.96-7.95 (m, 1H), 7.74-7.59 (m, 1H), 7.52-7.50 (m, 1H), 6.87-6.53 (m, 3H), 6.17-6.16 (m, 1H), 5.69-5.67 (m, 1H), 5.28-5.20 (m, 1H), 4.59-4.35 (m, 1H), 4.06-3.74 (m, 2H), 3.68-3.43 (m, 2H), 3.31-3.30 (m, 3H), 2.96-2.94 (m, 3H), 2.63-2.62 (m, 1H), 2.30-2.28 (m, 1H), 1.55-1.52 (s, 3H), 1.19-1.17 (m, 2H), 1.11-1.00 (m, 2H).

Example 239: 1-((3S,5R)-1-Acryloyl-5-(methoxymethyl)pyrrolidin-3-yl)-3-((1-(1-cyanocyclopropyl)-6-fluoro-1H-benzo[d]imidazol-5-yl)ethynyl)-5-(methylamino)-1H-pyrazole-4-carboxamide

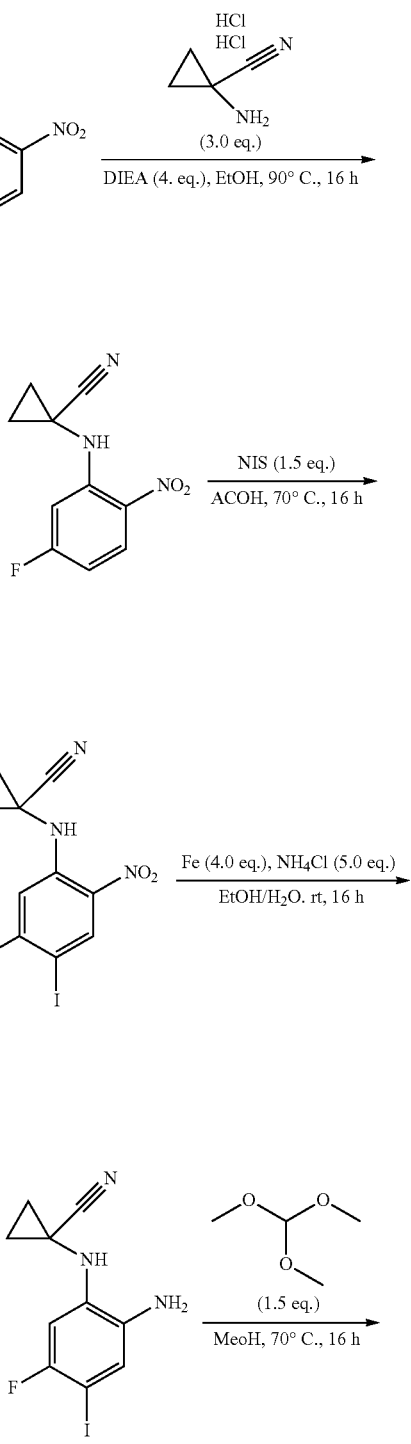

779

-continued

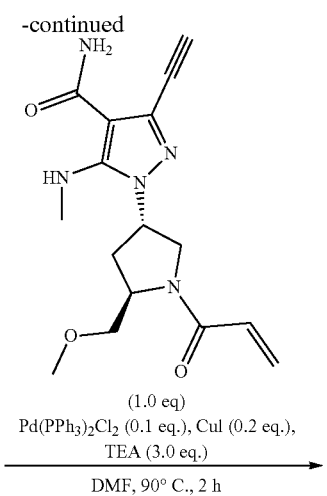

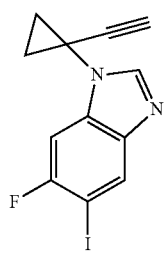

(1.0 eq)
Pd(PPh3)2Cl2 (0.1 eq.), CuI (0.2 eq.),
TEA (3.0 eq.)
———————————————→
DMF, 90° C., 2 h

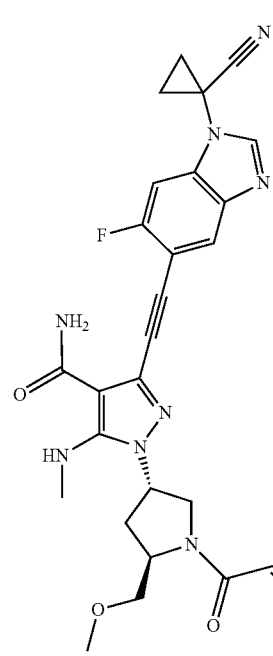

1-((3S,5R)-1-acryloyl-5-(methoxymethyl)pyrrolidin-3-yl)-3-((1-(1-cyanocyclopropyl)-6-fluoro-1H-benzo[d]imidazol-5-yl)ethynyl)-5-(methylamino)-1H-pyrazole-4-carboxamide. MS ESI calculated for $C_{27}H_{27}FN_8O_3$ [M+H]$^+$, 531.22, found 531.30; $^1$H NMR (400 MHz, Chloroform-d) δ 8.02 (s, 2H), 7.37 (d, J=8.6 Hz, 1H), 7.02 (d, J=16.9 Hz, 1H), 6.76 (dd, J=45.9, 6.1 Hz, 1H), 6.57-6.35 (m, 2H), 5.70 (dd, J=8.4, 3.9 Hz, 1H), 5.60-5.14 (m, 2H), 4.48 (d, J=54.9 Hz, 1H), 4.12-3.99 (m, 2H), 3.90 (dd, J=9.6, 2.9 Hz, 1H), 3.52-3.31 (m, 4H), 3.03 (dd, J=15.3, 5.9 Hz, 3H), 2.76-2.64 (m, 1H), 2.40-2.28 (m, 1H), 2.05-1.92 (m, 2H), 1.84-1.72 (m, 2H).

780

Example 240: 5-Amino-3-[2-(1-cyclopropyl-6-fluoro-1,3-benzodiazol-5-yl)ethynyl]-1-[(3S,5R)-5-[(1R)-1-hydroxyethyl]-1-(prop-2-enoyl)pyrrolidin-3-yl]pyrazole-4-carboxamide

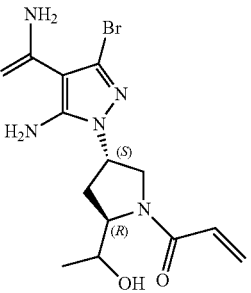

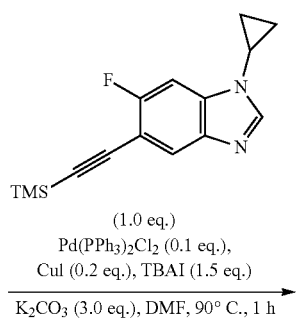

(1.0 eq.)
Pd(PPh3)2Cl2 (0.1 eq.),
CuI (0.2 eq.), TBAI (1.5 eq.)
———————————————→
K2CO3 (3.0 eq.), DMF, 90° C., 1 h

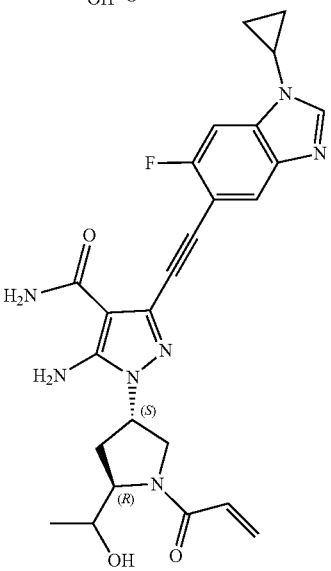

CHIRAL-SFC
———————→

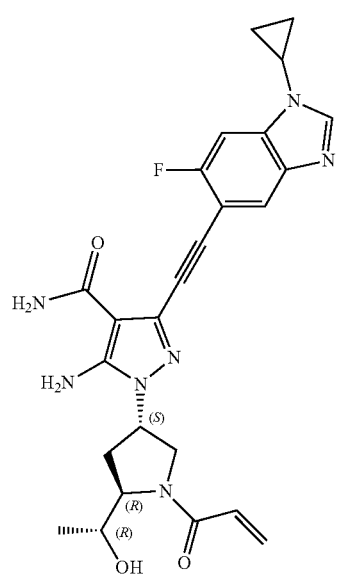

5-amino-3-[2-(1-cyclopropyl-6-fluoro-1,3-benzodiazol-5-yl)ethynyl]-1-[(3S,5R)-5-[(1R)-1-hydroxyethyl]-1-(prop-2-enoyl)pyrrolidin-3-yl]pyrazole-4-carboxamide. MS ESI calculated for $C_{25}H_{26}FN_7O_3$ [M+H]$^+$, 492.21, found 492.35; $^1$H NMR (400 MHz, DMSO-d$_6$) δ 8.38 (s, 1H), 8.00-7.93 (m, 1H), 7.65 (d, J=9.20 Hz, 1H), 7.37 (s, 1H), 6.77-6.49 (m, 4H), 6.18-6.10 (m, 1H), 5.69-5.84 (m, 1H), 5.14-4.66 (m, 2H), 4.32-4.11 (m, 1H), 3.97-3.77 (m, 2H), 3.67-3.62 (m, 1H), 3.53-3.49 (m, 1H), 2.41-2.36 (m, 1H), 2.29-2.22 (m, 1H), 1.10-1.03 (m, 7H).

Example 241: 5-Amino-3-[2-(1-cyclopropyl-6-fluoro-1,3-benzodiazol-5-yl)ethynyl]-1-[(3S,5R)-5-[(1S)-1-hydroxyethyl]-1-(prop-2-enoyl)pyrrolidin-3-yl]pyrazole-4-carboxamide lulose-SC, 2×25 cm, 5 m; Mobile Phase A: Hex (0.5% 2 M NH$_3$-MeOH)-HPLC, Mobile Phase B: MeOH:EtOH=1:1—HPLC; Flow rate: 20 mL/min; Gradient: 50% B to 50% B in 25 min; Wave Length: 220/254 nm; RT2: 22.72 min; Sample Solvent: MeOH:DCM=1:1; Injection Volume: 0.4 mL; The fractions contained desired product were combined and concentrated to afford 5-amino-3-[2-(1-cyclopropyl-6-fluoro-1,3-benzodiazol-5-yl)ethynyl]-1-[(3S,5R)-5-[(1S)-1-hydroxyethyl]-1-(prop-2-enoyl)pyrrolidin-3-yl]pyrazole-4-carboxamide (47.60 mg, 18%) as an off-white solid. MS ESI calculated for $C_{25}H_{26}FN_7O_3$ [M+H]$^+$, 492.21, found 492.30; $^1$H NMR (400 MHz, DMSO-d$_6$) δ 8.36 (s, 1H), 7.96 (d, J=6.40 Hz, 1H), 7.64 (d, J=10.40 Hz, 1H), 7.37 (s, 1H), 6.85-6.51 (m, 4H), 6.20-6.06 (m, 1H), 5.72-5.59 (m, 1H), 5.14-4.87 (m, 2H), 4.46-4.18 (m, 1H), 4.11-3.77 (m, 2H), 3.72-3.58 (m, 1H), 3.54-3.48 (m, 1H), 2.48-2.38 (m, 1H), 2.30 (s, 1H), 1.15-0.99 (m, 7H).

Example 242: 5-Amino-3-[2-(6-chloro-1-cyclopropyl-1,3-benzodiazol-5-yl)ethynyl]-1-[(3S,5R)-5-[(1R)-1-hydroxyethyl]-1-(prop-2-enoyl)pyrrolidin-3-yl]pyrazole-4-carboxamide

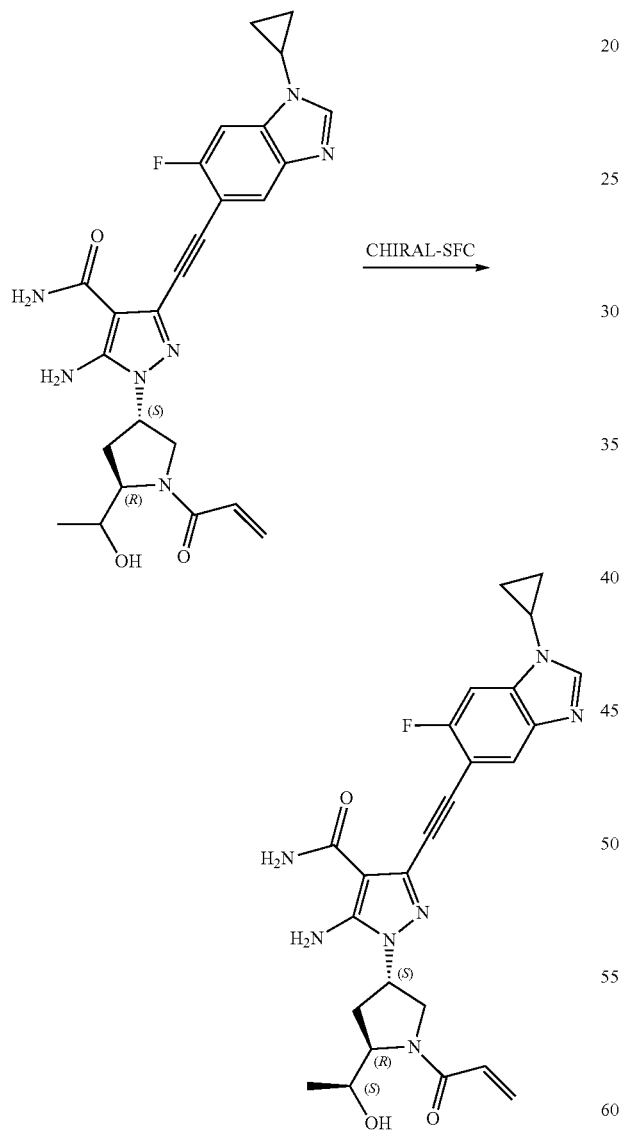

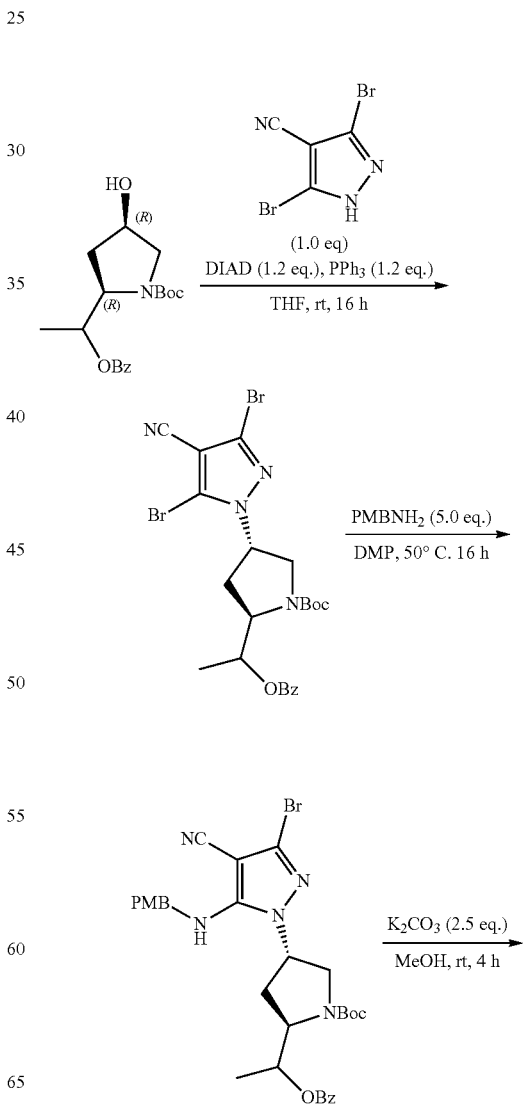

The racemic product 1-((3S,5R)-1-acryloyl-5-(1-hydroxyethyl)pyrrolidin-3-yl)-5-amino-3-((1-cyclopropyl-6-fluoro-1H-benzo[d]imidazol-5-yl)ethynyl)-1H-pyrazole-4-carboxamide (0.10 g) was purified by Prep-CHIRAL-HPLC with the following conditions Column: CHIRAL ART Cel-

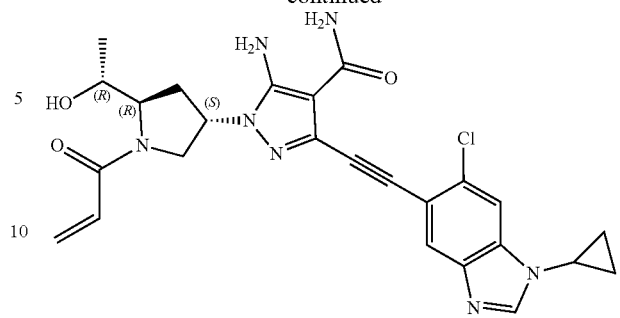
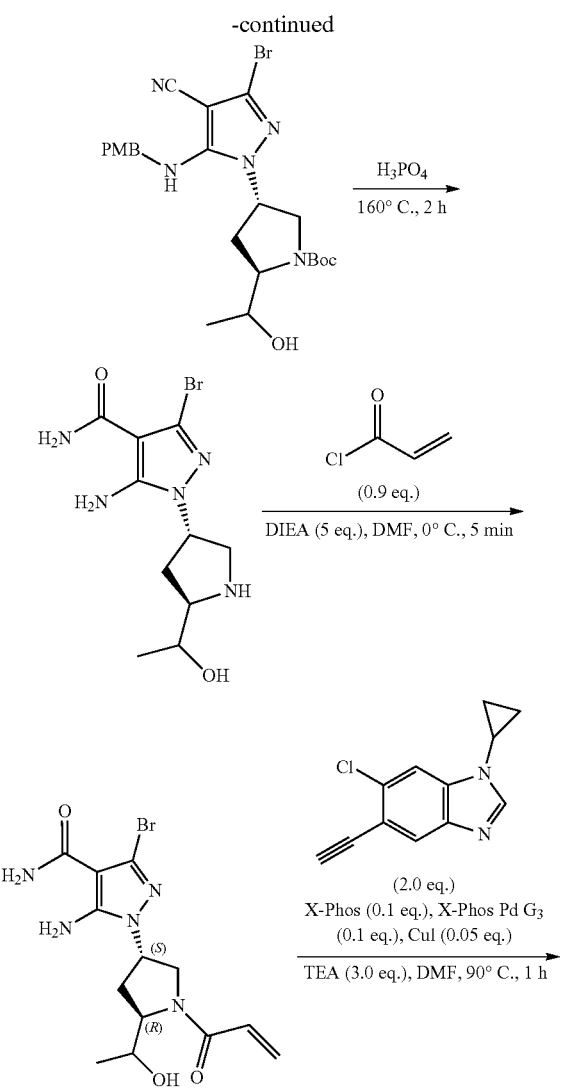
5-amino-3-[2-(6-chloro-1-cyclopropyl-1,3-benzodiazol-5-yl)ethynyl]-1-[(3S,5R)-5-[(1R)-1-hydroxyethyl]-1-(prop-2-enoyl)pyrrolidin-3-yl]pyrazole-4-carboxamide. MS ESI calculated for $C_{25}H_{26}ClN_7O_3$ [M+H]$^+$, 508.18, found 508.40; $^1$H NMR (400 MHz, CDCl$_3$) δ 8.40 (s, 1H), 8.00 (s, 1H), 7.90 (s, 1H), 6.71-6.51 (m, 1H), 6.19-6.11 (m, 1H), 5.72-5.57 (m, 1H), 5.03 (s, 1H), 4.27-4.14 (m, 1H), 3.90-3.64 (m, 3H), 3.54-3.50 (m, 1H), 2.41-2.26 (m, 2H), 1.13-1.03 (m, 7H).
Example 243: 5-Amino-3-[2-(6-chloro-1-cyclopropyl-1,3-benzodiazol-5-yl)ethynyl]-1-[(3S,5R)-5-[(1S)-1-hydroxyethyl]-1-(prop-2-enoyl)pyrrolidin-3-yl]pyrazole-4-carboxamide
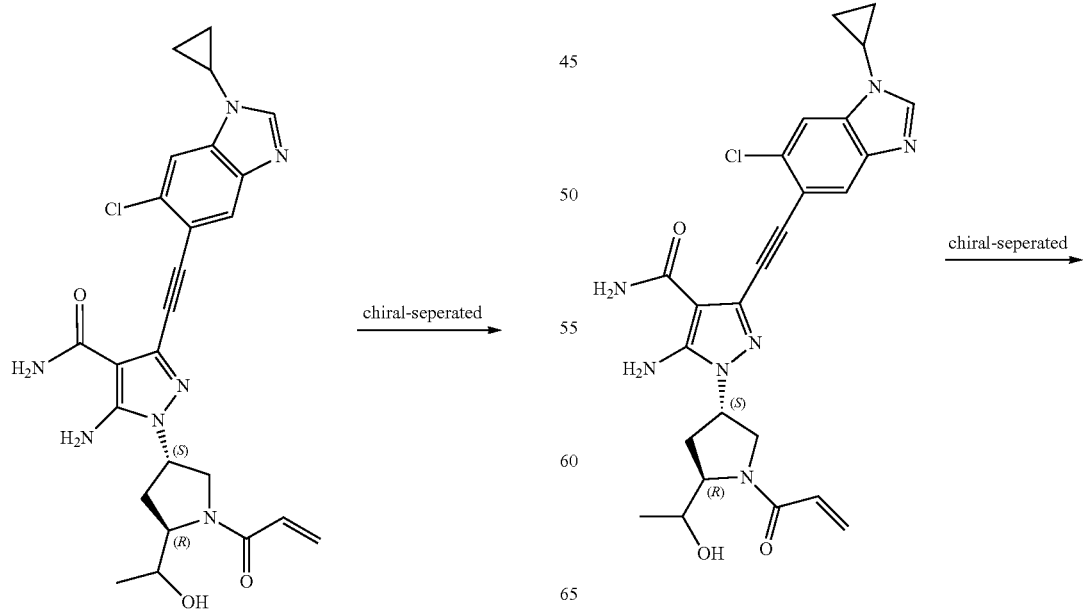

785
-continued

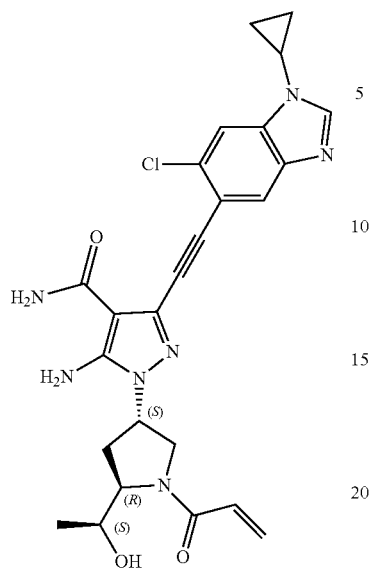

5-amino-3-[2-(6-chloro-1-cyclopropyl-1,3-benzodiazol-5-yl)ethynyl]-1-[(3S,5R)-5-[(1S)-1-hydroxyethyl]-1-(prop-2-enoyl)pyrrolidin-3-yl]pyrazole-4-carboxamide. MS ESI calculated for $C_{25}H_{26}ClN_7O_3$ [M+H]$^+$, 508.18, found 508.40; $^1$H NMR (400 MHz, CDCl$_3$) δ 8.40 (s, 1H), 8.01 (s, 1H), 7.90 (s, 1H), 6.80-6.51 (m, 1H), 6.16-6.10 (m, 1H), 5.71-5.63 (m, 1H), 5.05 (s, 1H), 4.41 (s, 1H), 4.05-3.84 (m, 2H), 3.55-3.50 (m, 1H), 2.67-2.47 (m, 1H), 2.45-2.25 (m, 2H), 1.14-1.08 (m, 4H), 1.06-1.01 (m, 3H).

Example 244: 1-((3S,5R)-1-Acryloyl-5-((R)-1-hydroxyethyl)pyrrolidin-3-yl)-5-amino-3-((6-chloro-1-cyclopropyl-2-methyl-1H-benzo[d]imidazol-5-yl)ethynyl)-1H-pyrazole-4-carboxamide

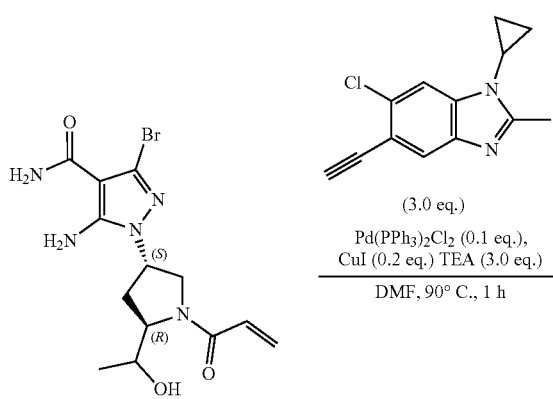

786
-continued

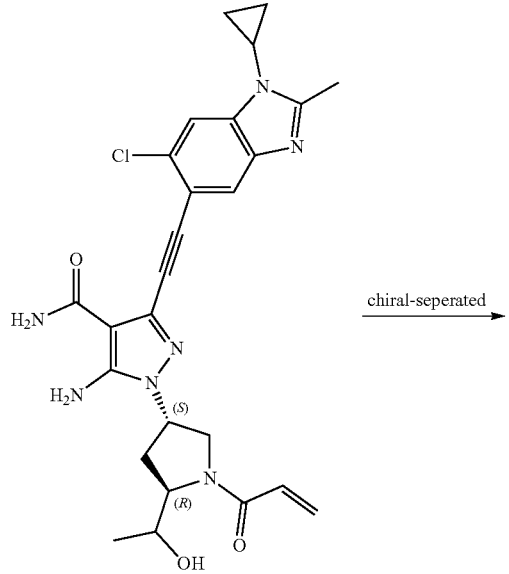

chiral-seperated

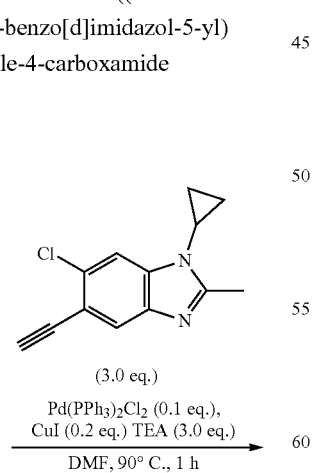

1-((3S,5R)-1-acryloyl-5-((R)-1-hydroxyethyl)pyrrolidin-3-yl)-5-amino-3-((6-chloro-1-cyclopropyl-2-methyl-1H-benzo[d]imidazol-5-yl)ethynyl)-1H-pyrazole-4-carboxamide. MS ESI calculated for $C_{26}H_{28}ClN_7O_3$ [M+H]$^+$, 522.19, found 522.25; $^1$H NMR (400 MHz, Chloroform-d) δ 7.91 (s, 1H), 7.55 (s, 1H), 7.14 (s, 1H), 6.56-6.27 (m, 2H), 5.94-5.49 (m, 3H), 5.11 (s, 1H), 4.52-3.86 (m, 4H), 3.36-3.06 (m, 1H), 2.69-2.65 (m, 3H), 2.56 (d, J=11.6 Hz, 1H), 2.38 (t, J=9.7 Hz, 1H), 1.31-1.18 (m, 6H), 1.07 (s, 2H).

787

Example 245: 1-((3S,5R)-1-Acryloyl-5-((S)-1-hydroxyethyl)pyrrolidin-3-yl)-5-amino-3-((6-chloro-1-cyclopropyl-2-methyl-1H-benzo[d]imidazol-5-yl)ethynyl)-1H-pyrazole-4-carboxamide

788

Example 246: 5-Amino-3-[2-(1-cyclopropyl-6-fluoro-2-methyl-1,3-benzodiazol-5-yl)ethynyl]-1-[(3S,5R)-5-[(1R)-1-hydroxyethyl]-1-(prop-2-enoyl)pyrrolidin-3-yl]pyrazole-4-carboxamide

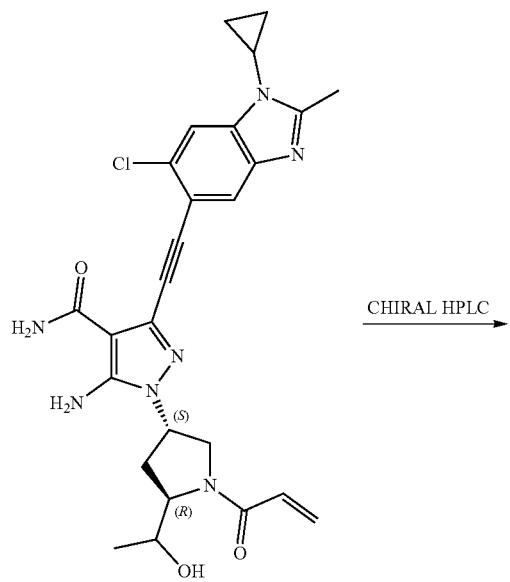

CHIRAL HPLC →

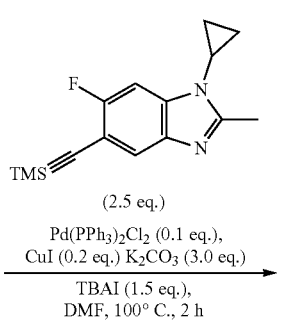

(2.5 eq.)
Pd(PPh₃)₂Cl₂ (0.1 eq.),
CuI (0.2 eq.) K₂CO₃ (3.0 eq.)
TBAI (1.5 eq.),
DMF, 100° C., 2 h
→

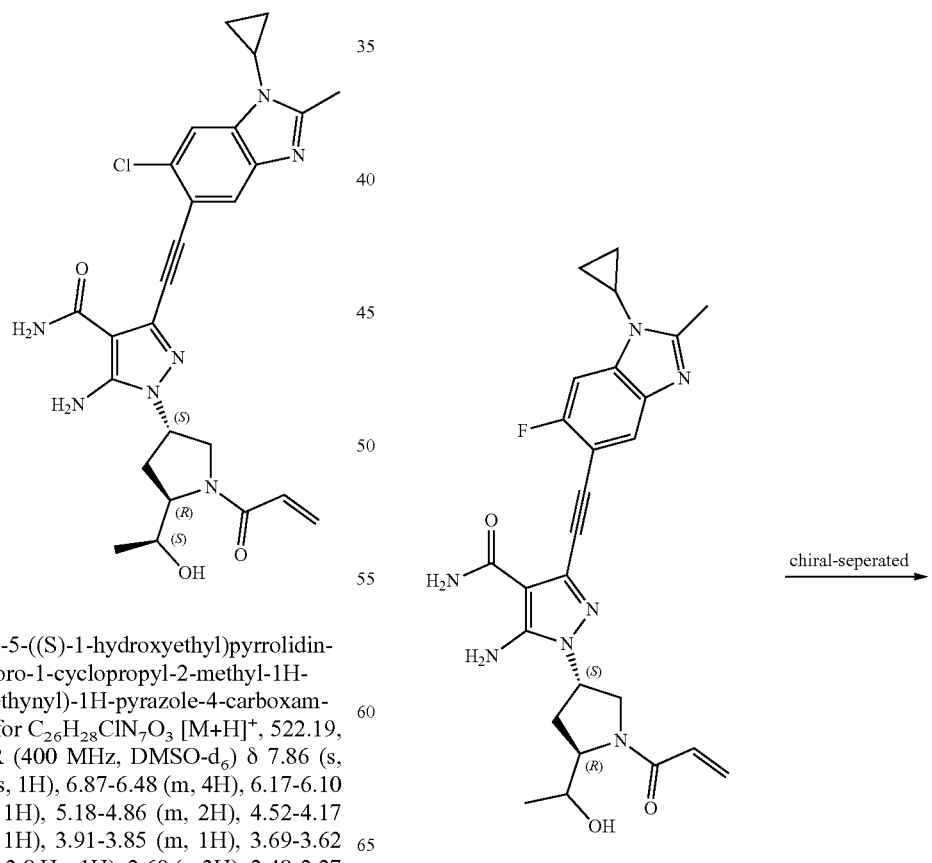

chiral-seperated →

1-((3S,5R)-1-acryloyl-5-((S)-1-hydroxyethyl)pyrrolidin-3-yl)-5-amino-3-((6-chloro-1-cyclopropyl-2-methyl-1H-benzo[d]imidazol-5-yl)ethynyl)-1H-pyrazole-4-carboxamide. MS ESI calculated for $C_{26}H_{28}ClN_7O_3$ [M+H]⁺, 522.19, found 522.20; ¹H NMR (400 MHz, DMSO-$d_6$) δ 7.86 (s, 1H), 7.72 (s, 1H), 7.38 (s, 1H), 6.87-6.48 (m, 4H), 6.17-6.10 (m, 1H), 5.69-5.62 (m, 1H), 5.18-4.86 (m, 2H), 4.52-4.17 (m, 1H), 4.06-3.98 (m, 1H), 3.91-3.85 (m, 1H), 3.69-3.62 (m, 1H), 3.35 (dd, J=7.1, 3.8 Hz, 1H), 2.60 (s, 3H), 2.48-2.27 (m, 2H), 1.26-1.15 (m, 2H), 1.14-0.96 (m, 5H).

789

-continued

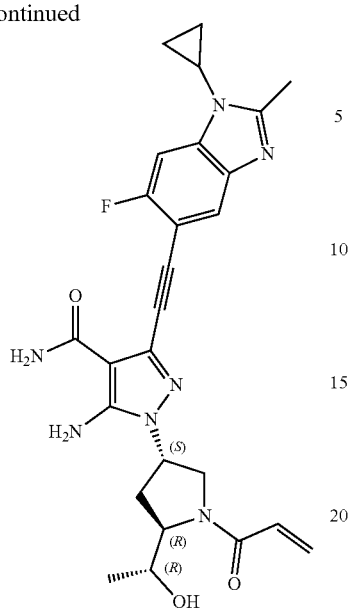

5-amino-3-[2-(1-cyclopropyl-6-fluoro-2-methyl-1,3-benzodiazol-5-yl)ethynyl]-1-[(3S,5R)-5-[(1R)-1-hydroxyethyl]-1-(prop-2-enoyl)pyrrolidin-3-yl]pyrazole-4-carboxamide. MS ESI calculated for C$_{26}$H$_{28}$FN$_7$O$_3$ [M+H]$^+$, 506.22, found 506.35; $^1$H NMR (400 MHz, CDCl$_3$) δ 7.83 (d, J=4 Hz, 1H), 7.25 (s, 1H), 7.09 (s, 1H), 6.50-6.38 (m, 2H), 5.75-5.72 (m, 3H), 5.68 (s, 1H), 5.53 (s, 1H), 4.47-4.38 (m, 2H), 4.15-4.04 (m, 2H), 2.39 (s, 1H), 2.71 (s, 3H), 2.63-2.55 (m, 1H), 2.39 (s, 1H), 2.30-2.26 (m, 2H), 2.24-2.21 (m, 3H), 1.08 (s, 2H).

Example 247: 5-Amino-3-[2-(1-cyclopropyl-6-fluoro-2-methyl-1,3-benzodiazol-5-yl)ethynyl]-1-[(3S,5R)-5-[(1S)-1-hydroxyethyl]-1-(prop-2-enoyl)pyrrolidin-3-yl]pyrazole-4-carboxamide

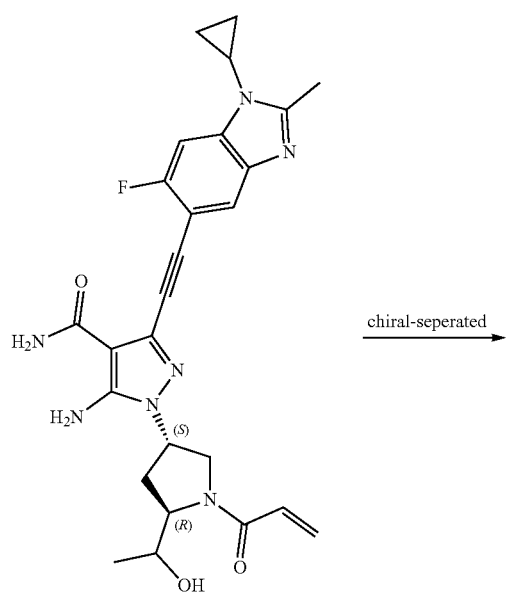

790

-continued

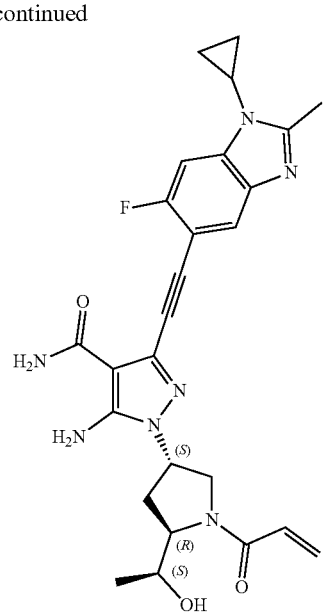

5-amino-3-[2-(1-cyclopropyl-6-fluoro-2-methyl-1,3-benzodiazol-5-yl)ethynyl]-1-[(3S,5R)-5-[(1S)-1-hydroxyethyl]-1-(prop-2-enoyl)pyrrolidin-3-yl]pyrazole-4-carboxamide. MS ESI calculated for C$_{26}$H$_{28}$FN$_7$O$_3$ [M+H]$^+$, 506.22, found 506.35; $^1$H NMR (400 MHz, CDCl$_3$) δ 7.82 (d, J=4 Hz, 1H), 7.26-7.23 (m, 1H), 7.11 (s, 1H), 6.45-6.40 (m, 2H), 5.79-5.73 (m, 1H), 5.73 (s, 2H), 5.68 (s, 1H), 5.50 (s, 1H), 4.86-4.68 (m, 1H), 4.52-4.45 (m, 1H), 4.15-4.12 (m, 1H), 4.05-4.01 (m, 1H), 3.91-3.84 (m, 1H), 3.28-3.21 (m, 1H), 2.76-2.69 (m, 4H), 2.31-2.15 (m, 1H), 1.32-1.21 (m, 4H), 1.09-1.05 (m, 2H).

Example 248: 3-{2-[6-Chloro-1-(oxetan-3-yl)-1,3-benzodiazol-5-yl]ethynyl}-1-[(3S,5R)-5-(methoxymethyl)-1-(prop-2-enoyl)pyrrolidin-3-yl]-5-(methylamino)pyrazole-4-carboxamide

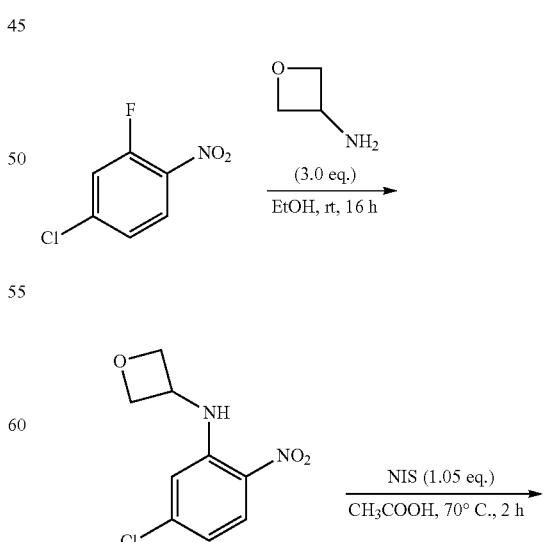

791
-continued

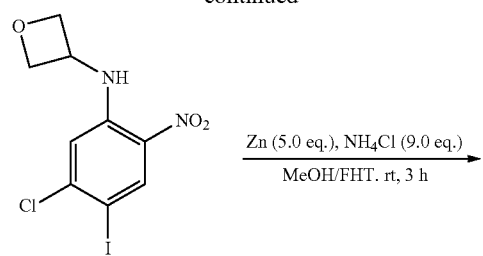

Zn (5.0 eq.), NH₄Cl (9.0 eq.)
MeOH/FHT. rt, 3 h
→

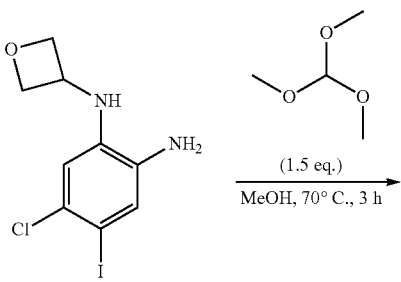

(1.5 eq.)
MeOH, 70° C., 3 h
→

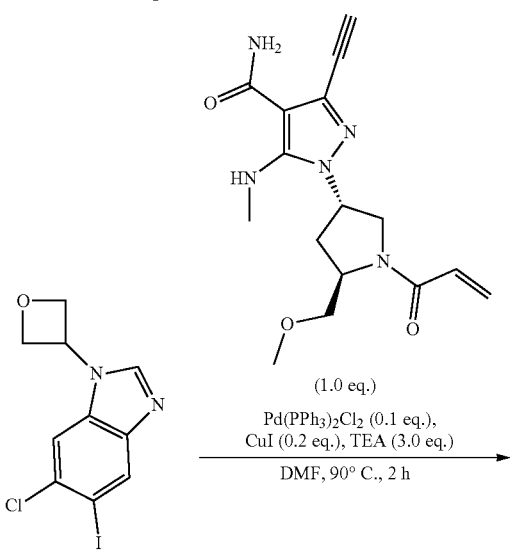

(1.0 eq.)
Pd(PPh₃)₂Cl₂ (0.1 eq.),
CuI (0.2 eq.), TEA (3.0 eq.)
DMF, 90° C., 2 h
→

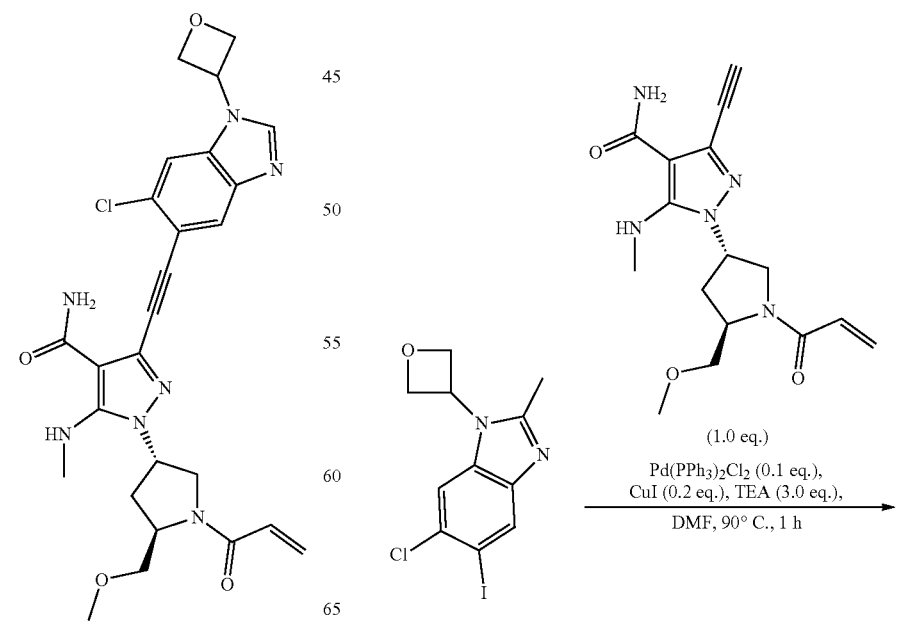

792

3-{2-[6-chloro-1-(oxetan-3-yl)-1,3-benzodiazol-5-yl]ethynyl}-1-[(3S,5R)-5-(methoxymethyl)-1-(prop-2-enoyl)pyrrolidin-3-yl]-5-(methylamino)pyrazole-4-carboxamide. MS ESI calculated for $C_{26}H_{28}ClN_7O_4$ [M+H]⁺, 538.19, found 538.25; ¹H NMR (400 MHz, Chloroform-d) δ 8.12 (d, J=5.1 Hz, 2H), 7.88 (d, J=4.6 Hz, 1H), 7.20-7.15 (m, 1H), 6.83 (s, 1H), 6.55-6.35 (m, 2H), 5.76-5.67 (m, 1H), 5.51-5.48 (m, 2H), 5.45 (s, 1H), 5.27 (t, J=7.6 Hz, 2H), 5.08-5.01 (m, 2H), 4.56 (d, J=9.0 Hz, 1H), 4.11 (t, J=9.1 Hz, 1H), 4.06-3.94 (m, 1H), 3.90-3.87 (m, 1H), 3.57-3.41 (m, 1H), 3.37 (d, J=5.2 Hz, 3H), 3.03 (d, J=15.6 Hz, 3H), 2.78-2.65 (m, 1H), 2.34-2.31 (m, 1H).

Example 249: 3-{2-[6-Chloro-2-methyl-1-(oxetan-3-yl)-1,3-benzodiazol-5-yl]ethynyl}-1-[(3S,5R)-5-(methoxymethyl)-1-(prop-2-enoyl)pyrrolidin-3-yl]-5-(methylamino)pyrazole-4-carboxamide

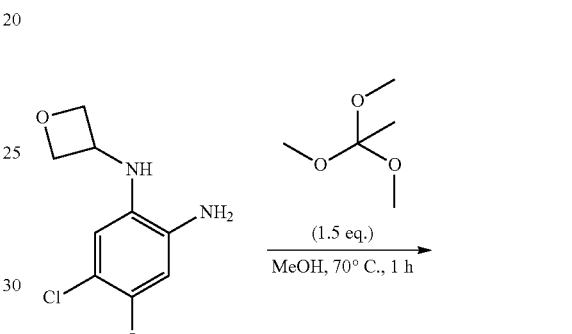

(1.5 eq.)
MeOH, 70° C., 1 h
→

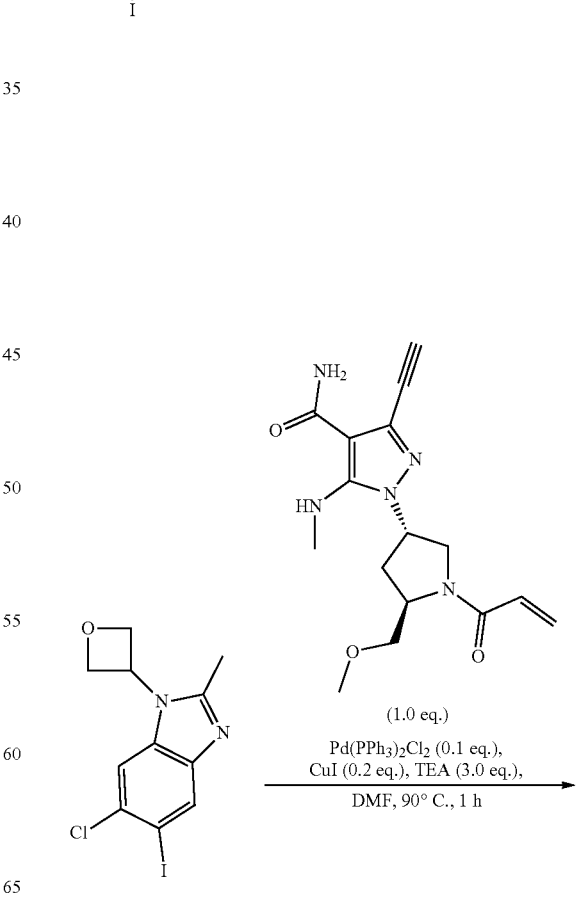

(1.0 eq.)
Pd(PPh₃)₂Cl₂ (0.1 eq.),
CuI (0.2 eq.), TEA (3.0 eq.),
DMF, 90° C., 1 h
→

793

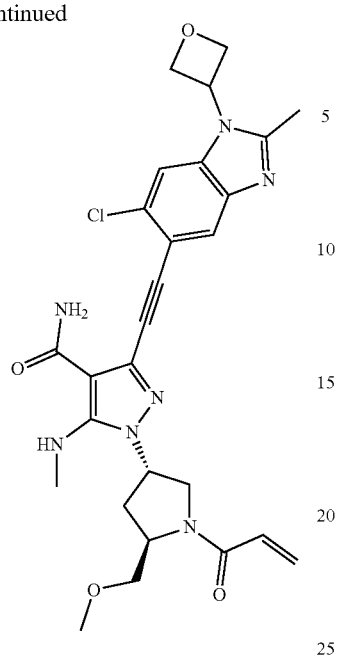

3-{2-[6-chloro-2-methyl-1-(oxetan-3-yl)-1,3-benzodiazol-5-yl]ethynyl}-1-[(3S,5R)-5-(methoxymethyl)-1-(prop-2-enoyl)pyrrolidin-3-yl]-5-(methylamino)pyrazole-4-carboxamide. MS ESI calculated for $C_{27}H_{30}ClN_7O_4$ [M+H]$^+$, 552.20, found 552.25; $^1$H NMR (400 MHz, Chloroform-d) δ 8.13 (d, J=3.0 Hz, 1H), 7.99 (d, J=5.8 Hz, 1H), 7.22 (s, 1H), 6.83 (d, J=6.0 Hz, 1H), 6.55-6.35 (m, 2H), 5.71-5.65 (m, 1H), 5.58-5.44 (m, 2H), 5.26 (t, J=7.7 Hz, 2H), 5.17-5.10 (m, 2H), 4.56 (d, J=9.1 Hz, 1H), 4.10-4.05 (m, 1H), 4.03 (t, J=9.3 Hz, 1H), 3.90-3.84 (m, 1H), 3.55-3.40 (m, 1H), 3.37 (d, J=5.0 Hz, 3H), 3.03-2.94 (m, 3H), 2.78-2.65 (m, 1H), 2.60 (s, 3H), 2.34-2.28 (m, 1H).

Example 250: 3-[2-(1-Cyclopropyl-6-fluoro-1,3-benzodiazol-5-yl)ethynyl]-5-[(2-hydroxyethyl)amino]-1-[(3S,5R)-5-(methoxymethyl)-1-(prop-2-enoyl)pyrrolidin-3-yl]pyrazole-4-carboxamide

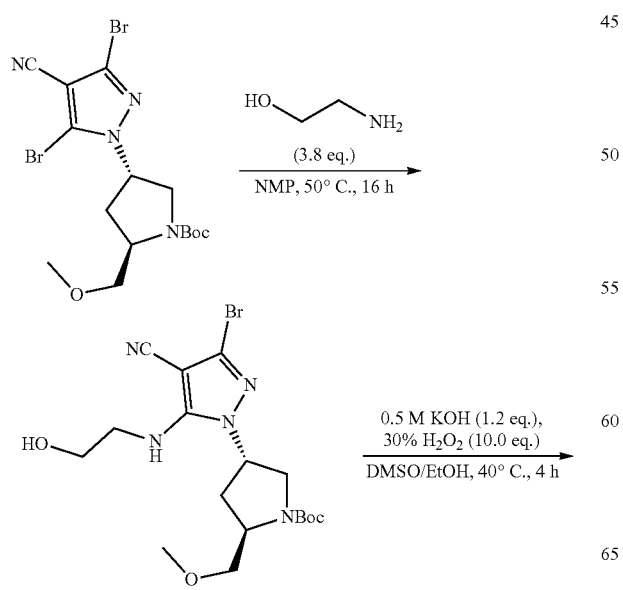

794

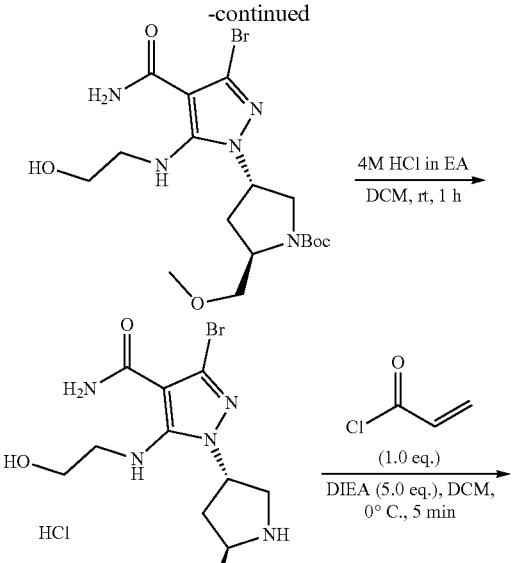

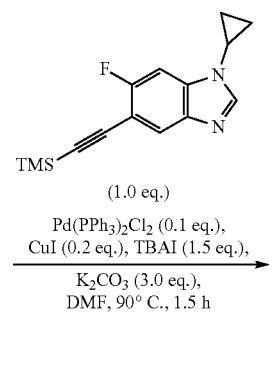

3-[2-(1-cyclopropyl-6-fluoro-1,3-benzodiazol-5-yl)ethynyl]-5-[(2-hydroxyethyl)amino]-1-[(3S,5R)-5-(methoxymethyl)-1-(prop-2-enoyl)pyrrolidin-3-yl]pyrazole-4-carboxamide. MS ESI calculated for $C_{27}H_{30}FN_7O_4$ [M+H]$^+$, 536.24, found 536.50; $^1$H NMR (400 MHz, CDCl$_3$) δ 8.02-7.94 (m, 2H), 7.32 (d, J=9.20 Hz, 2H), 6.53-6.37 (m, 2H), 5.88-5.21 (m, 4H), 4.58 (d, J=9.20 Hz, 1H), 4.07-3.81 (m, 3H), 3.71-3.41 (m, 4H), 3.39-3.22 (m, 6H), 2.73-2.61 (m, 1H), 2.40-2.24 (m, 1H), 1.21-1.07 (m, 2H), 1.06 (d, J=7.20 Hz, 2H).

Example 251: 3-[2-(1-Cyclopropyl-4,6-difluoro-1,3-benzodiazol-5-yl)ethynyl]-5-[(2-hydroxyethyl)amino]-1-[(3S,5R)-5-(methoxymethyl)-1-(prop-2-enoyl)pyrrolidin-3-yl]pyrazole-4-carboxamide Example 252: 3-[2-(1-Cyclopropyl-6-fluoro-2-methyl-1,3-benzodiazol-5-yl)ethynyl]-5-[(2-hydroxyethyl)amino]-1-[(3S,5R)-5-(methoxymethyl)-1-(prop-2-enoyl)pyrrolidin-3-yl]pyrazole-4-carboxamide

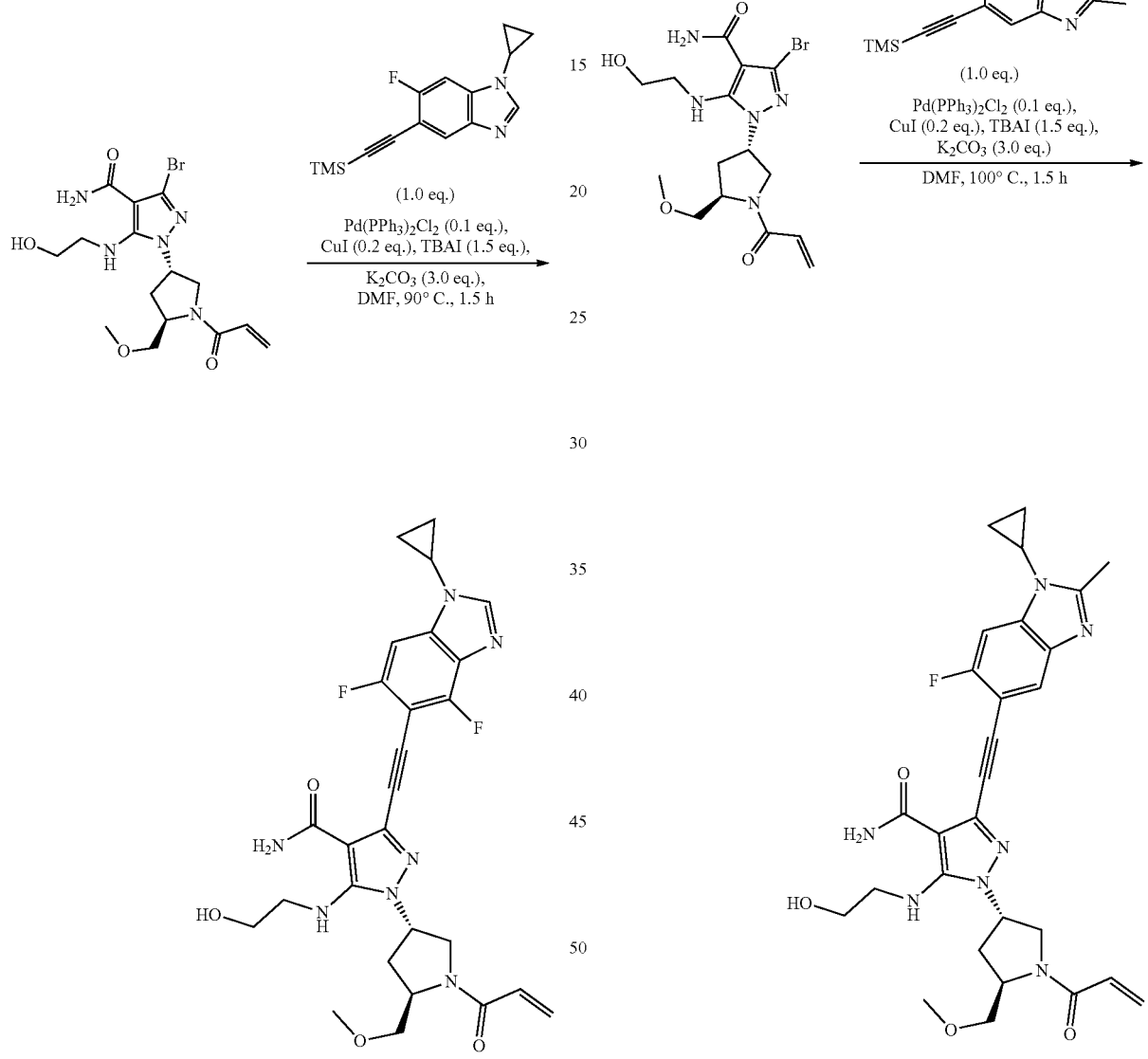

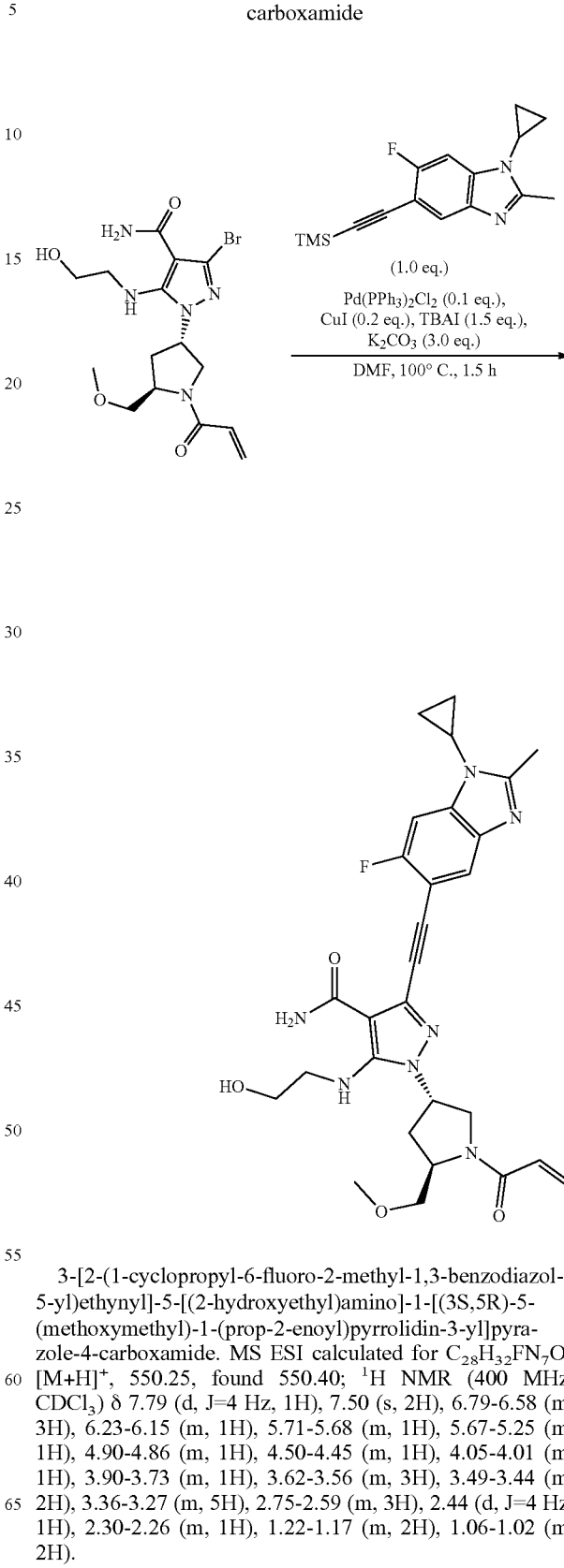

3-[2-(1-cyclopropyl-4,6-difluoro-1,3-benzodiazol-5-yl)ethynyl]-5-[(2-hydroxyethyl)amino]-1-[(3S,5R)-5-(methoxymethyl)-1-(prop-2-enoyl)pyrrolidin-3-yl]pyrazole-4-carboxamide. MS ESI calculated for $C_{27}H_{29}F_2N_7O_4$ [M+H]$^+$, 554.22, found 554.25; $^1$H NMR (400 MHz, CDCl$_3$) δ 7.99 (s, 1H), 7.17 (d, J=8.00 Hz, 1H), 6.56-6.38 (m, 2H), 5.76-5.67 (m, 2H), 5.48-5.39 (m, 1H), 4.62-4.39 (m, 1H), 4.03 (d, J=8.10 Hz, 2H), 3.88-3.85 (m, 1H), 3.67 (s, 2H), 3.52-3.42 (m, 1H), 3.38 (d, J=3.20 Hz, 4H), 3.32 (s, 2H), 2.96-2.60 (m, 1H), 2.39-2.25 (m, 1H), 1.25-1.20 (m, 2H), 1.08 (s, 2H).

3-[2-(1-cyclopropyl-6-fluoro-2-methyl-1,3-benzodiazol-5-yl)ethynyl]-5-[(2-hydroxyethyl)amino]-1-[(3S,5R)-5-(methoxymethyl)-1-(prop-2-enoyl)pyrrolidin-3-yl]pyrazole-4-carboxamide. MS ESI calculated for $C_{28}H_{32}FN_7O_4$ [M+H]$^+$, 550.25, found 550.40; $^1$H NMR (400 MHz, CDCl$_3$) δ 7.79 (d, J=4 Hz, 1H), 7.50 (s, 2H), 6.79-6.58 (m, 3H), 6.23-6.15 (m, 1H), 5.71-5.68 (m, 1H), 5.67-5.25 (m, 1H), 4.90-4.86 (m, 1H), 4.50-4.45 (m, 1H), 4.05-4.01 (m, 1H), 3.90-3.73 (m, 1H), 3.62-3.56 (m, 3H), 3.49-3.44 (m, 2H), 3.36-3.27 (m, 5H), 2.75-2.59 (m, 3H), 2.44 (d, J=4 Hz, 1H), 2.30-2.26 (m, 1H), 1.22-1.17 (m, 2H), 1.06-1.02 (m, 2H).

Example 253: 1-((3S,5R)-1-Acryloyl-5-(methoxymethyl)pyrrolidin-3-yl)-3-((6-chloro-1-cyclopropyl-2-methyl-1H-benzo[d]imidazol-5-yl)ethynyl)-5-((2-hydroxyethyl)amino)-1H-pyrazole-4-carboxamide Example 254: 3-[2-(6-Fluoro-2H-1,3-benzodioxol-5-yl)ethynyl]-1-[(3S,5R)-5-(methoxymethyl)-1-(prop-2-enoyl)pyrrolidin-3-yl]-5-(methylamino)pyrazole-4-carboxamide

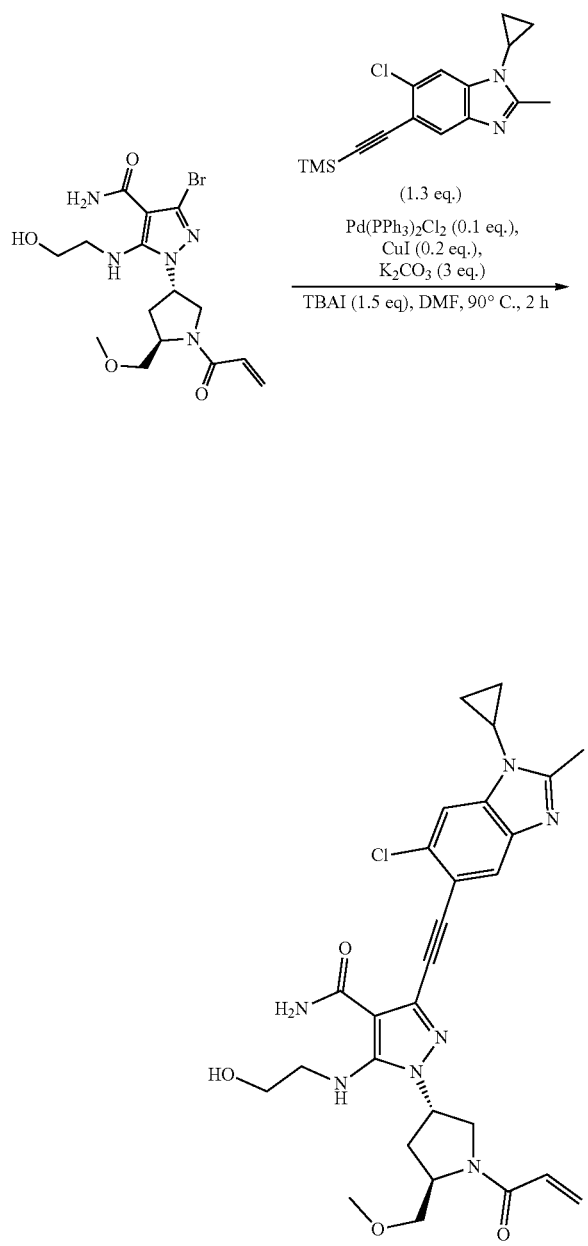

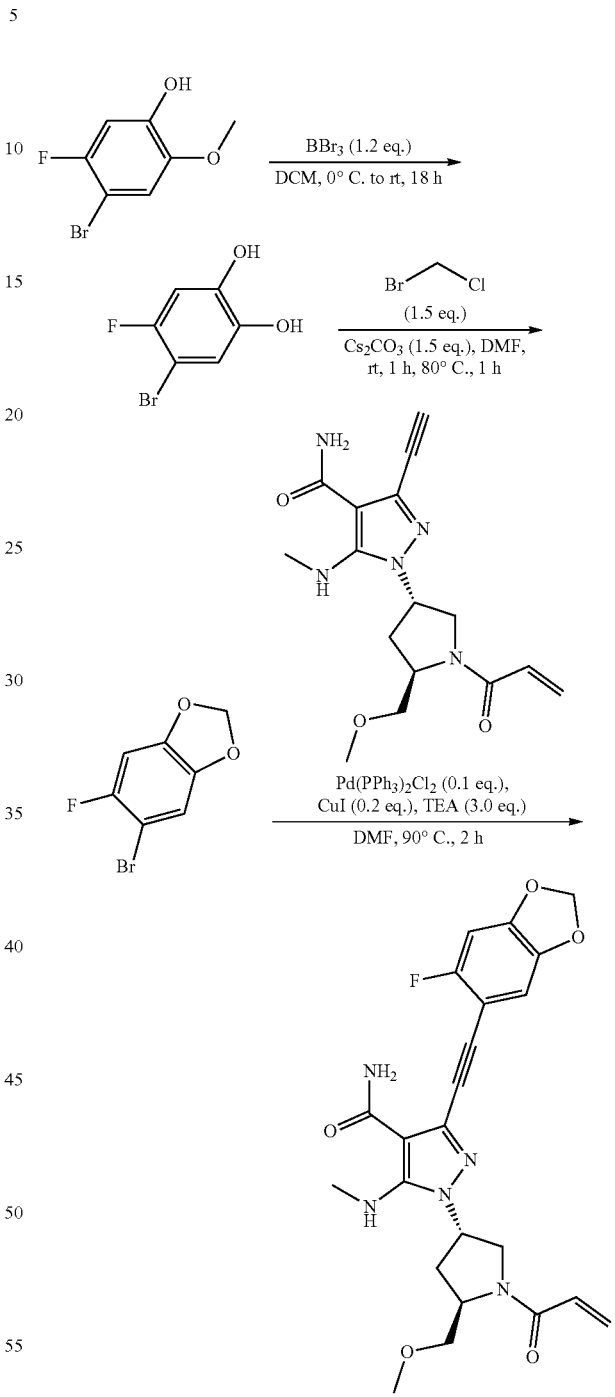

1-((3S,5R)-1-acryloyl-5-(methoxymethyl)pyrrolidin-3-yl)-3-((6-chloro-1-cyclopropyl-2-methyl-1H-benzo[d]imidazol-5-yl)ethynyl)-5-((2-hydroxyethyl)amino)-1H-pyrazole-4-carboxamide. MS ESI calculated for $C_{28}H_{32}ClN_7O_4$ [M+H]$^+$, 566.22, found 566.35; $^1$H NMR (400 MHz, CDCl$_3$) δ 7.93 (d, J=5.6 Hz, 1H), 7.58 (s, 1H), 7.44 (s, 1H), 6.44-6.42 (m, 2H), 5.86-5.70 (m, 2H), 5.60 (s, 1H), 5.48-5.44 (m, 1H), 4.61-4.58 (m, 1H), 4.06-3.95 (m, 2H), 3.87 (dd, J=9.8, 3.2 Hz, 1H), 3.66 (s, 2H), 3.47-3.42 (m, 1H), 3.38 (d, J=2.5 Hz, 3H), 3.31 (s, 2H), 3.21-3.16 (m, 1H), 2.95-2.68 (m, 4H), 2.32-2.30 (m, 1H), 1.29-1.25 (m, 2H), 1.10-1.02 (m, 2H).

3-[2-(6-fluoro-2H-1,3-benzodioxol-5-yl)ethynyl]-1-[(3S,5R)-5-(methoxymethyl)-1-(prop-2-enoyl)pyrrolidin-3-yl]-5-(methylamino)pyrazole-4-carboxamide. MS ESI calculated for $C_{23}H_{24}FN_5O_5$ [M+H]$^+$, 470.18, found 470.20; $^1$H NMR (400 MHz, Chloroform-d) δ 6.91 (d, J=5.8 Hz, 1H), 6.80 (d, J=6.2 Hz, 1H), 6.64 (d, J=8.7 Hz, 1H), 6.52-6.34 (m, 2H), 6.03 (s, 2H), 5.70-5.68 (m, 1H), 5.48-5.46 (m, 1H), 5.29 (s, 1H), 4.55 (d, J=9.0 Hz, 1H), 4.07 (t, J=8.9 Hz, 1H), 4.00 (t, J=9.1 Hz, 1H), 3.89-3.85 (m, 1H), 3.52-3.40 (m, 1H), 3.36 (d, J=4.6 Hz, 3H), 3.01-2.98 (m, 3H), 2.69-2.62 (m, 1H), 2.29-2.21 (m, 1H), 1.26 (s, 1H).

Example 256: 3-[2-(3-Chloro-6-fluoroquinolin-7-yl)ethynyl]-1-[(3S,5R)-5-(methoxymethyl)-1-(prop-2-enoyl)pyrrolidin-3-yl]-5-(methylamino)pyrazole-4-carboxamide

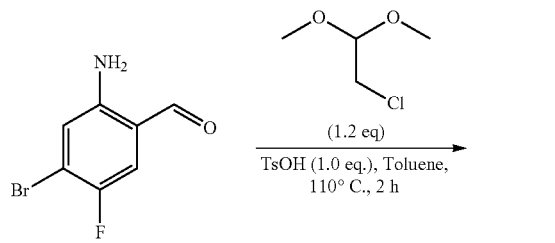

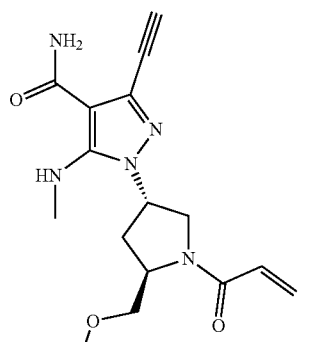

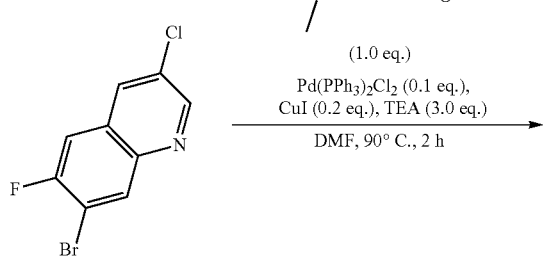

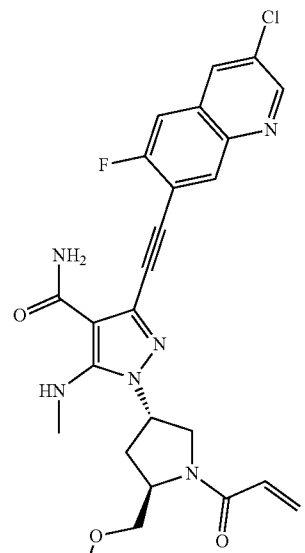

3-[2-(3-chloro-6-fluoroquinolin-7-yl)ethynyl]-1-[(3S,5R)-5-(methoxymethyl)-1-(prop-2-enoyl)pyrrolidin-3-yl]-5-(methylamino)pyrazole-4-carboxamide. MS ESI calculated for $C_{25}H_{24}ClFN_6O_3$ [M+H]$^+$, 511.16, found 511.15; $^1$H NMR (400 MHz, Chloroform-d) δ 8.82 (d, J=2.3 Hz, 1H), 8.32 (t, J=5.5 Hz, 1H), 8.08 (d, J=2.4 Hz, 1H), 7.44 (d, J=9.4 Hz, 1H), 6.96 (s, 1H), 6.84 (s, 1H), 6.58-6.36 (m, 2H), 5.72-5.70 (m, 1H), 5.58-5.45 (m, 1H), 5.39 (s, 1H), 4.57 (d, J=9.0 Hz, 1H), 4.10 (t, J=8.9 Hz, 1H), 4.09-3.97 (m, 1H), 4.00-3.87 (m, 1H), 3.54-3.41 (m, 1H), 3.37 (d, J=5.0 Hz, 3H), 3.04 (d, J=15.2 Hz, 3H), 2.70-2.68 (m, 1H), 2.35-2.31 (m, 1H).

Example 257: 1-((3S,5R)-1-Acryloyl-5-(methoxymethyl)pyrrolidin-3-yl)-3-((6-fluoro-3-methylimidazo[1,2-a]pyridin-7-yl)ethynyl)-5-(methylamino)-1H-pyrazole-4-carboxamide

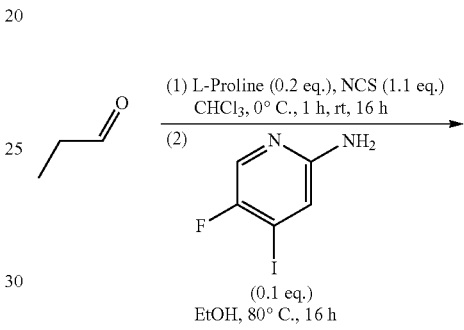

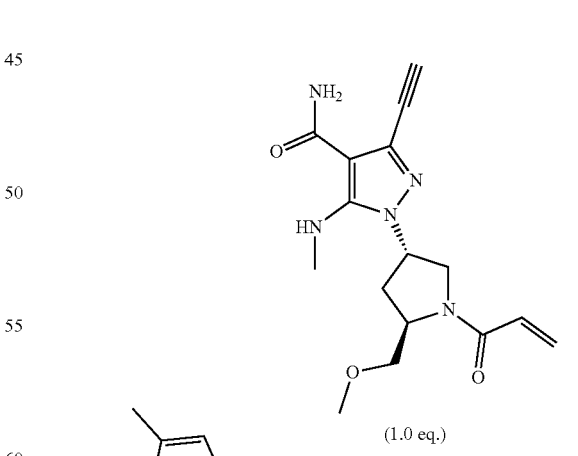

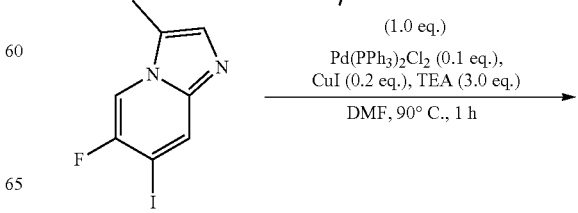

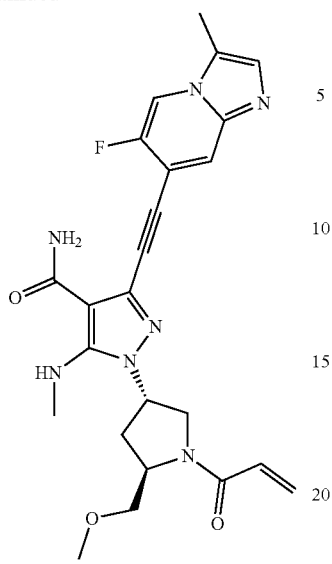

1-((3S,5R)-1-Acryloyl-5-(methoxymethyl)pyrrolidin-3-yl)-3-((6-fluoro-3-methylimidazo[1,2-a]pyridin-7-yl)ethynyl)-5-(methylamino)-1H-pyrazole-4-carboxamide. MS ESI calculated for $C_{24}H_{26}FN_7O_3$ [M+H]$^+$, 480.21, found 480.55; $^1$H NMR (400 MHz, Chloroform-d) δ 6.92-6.85 (m, 2H), 6.42 (d, J=8.2 Hz, 2H), 5.71 (s, 1H), 5.51 (s, 1H), 5.30 (s, 1H), 4.62-4.35 (m, 1H), 4.16-3.96 (m, 2H), 3.90 (d, J=9.5 Hz, 1H), 3.51 (s, 1H), 3.45 (s, 1H), 3.43 (s, 1H), 3.37 (d, J=4.6 Hz, 4H), 3.09-3.00 (m, 3H), 2.70 (d, J=10.8 Hz, 1H), 2.32 (s, 1H).

Example 258: 3-[2-(6-Chloro-3-methylquinolin-7-yl)ethynyl]-1-[(3S,5R)-5-(methoxymethyl)-1-(prop-2-enoyl)pyrrolidin-3-yl]-5-(methylamino)pyrazole-4-carboxamide

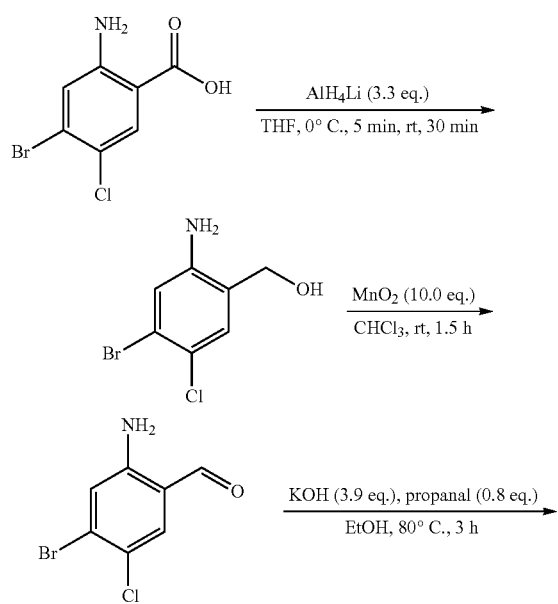

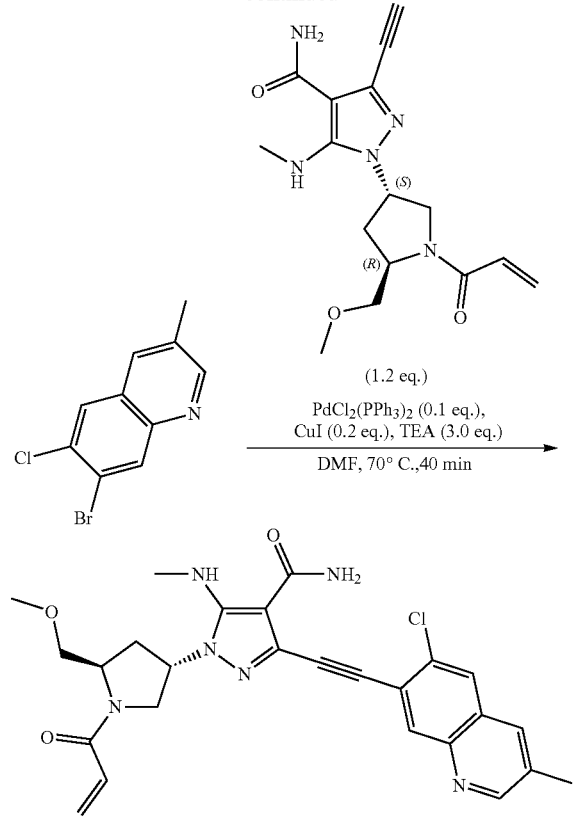

3-[2-(6-Chloro-3-methylquinolin-7-yl)ethynyl]-1-[(3S,5R)-5-(methoxymethyl)-1-(prop-2-enoyl)pyrrolidin-3-yl]-5-(methylamino)pyrazole-4-carboxamide. MS ESI calculated for $C_{26}H_{27}ClN_6O_3$ [M+H]$^+$, 507.18, found 507.50; $^1$H NMR (400 MHz, DMSO-d$_6$) δ 8.86 (d, J=2.1 Hz, 1H), 8.31 (s, 1H), 8.20 (s, 1H), 8.14 (s, 1H), 7.54 (s, 1H), 6.90 (s, 1H), 6.78-6.55 (m, 2H), 6.17-6.13 (m, 1H), 5.70-5.60 (m, 1H), 5.28-5.18 (m, 1H), 4.64-4.31 (m, 1H), 4.09-3.67 (m, 2H), 3.63-3.42 (m, 2H), 3.31 (s, 3H), 2.96-2.86 (m, 3H), 2.62-2.52 (m, 1H), 2.50-2.40 (m, 3H), 2.34-2.25 (m, 1H).

Example 259: 3-[2-(1-Cyclopropyl-6-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide

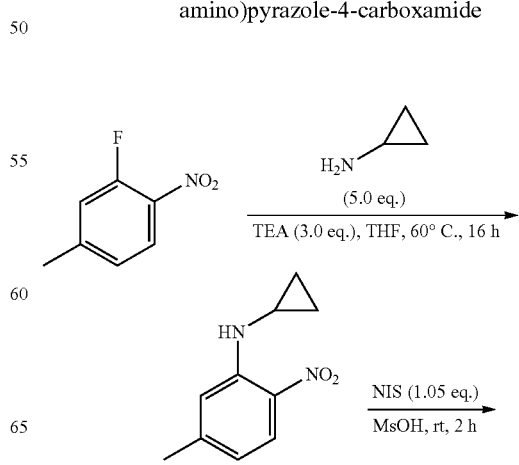

-continued

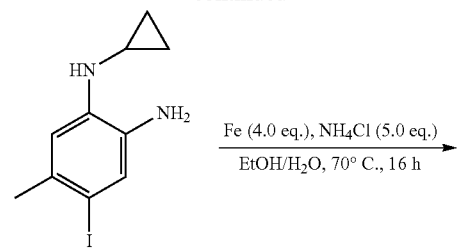

Fe (4.0 eq.), NH₄Cl (5.0 eq.)
EtOH/H₂O, 70° C., 16 h

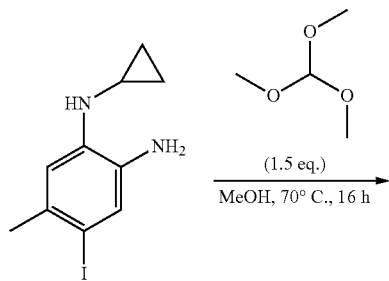

(1.5 eq.)
MeOH, 70° C., 16 h

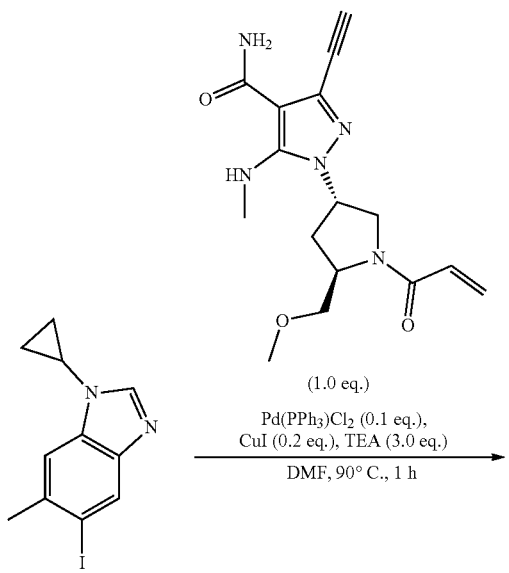

(1.0 eq.)
Pd(PPh₃)₂Cl₂ (0.1 eq.),
CuI (0.2 eq.), TEA (3.0 eq.)
DMF, 90° C., 1 h

3-[2-(1-cyclopropyl-6-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide. MS ESI calculated for $C_{27}H_{31}N_7O_3$ [M+H]⁺, 502.25, found 502.30; ¹H NMR (400 MHz, CDCl₃) δ 8.25 (s, 1H), 7.83 (s, 1H), 7.58 (s, 1H), 7.38 (s, 1H), 6.81-6.59 (m, 3H), 6.20-6.15 (m, 1H), 5.71-5.67 (m, 1H), 5.29-5.21 (m, 1H), 4.54-4.40 (m, 1H), 4.05-3.72 (m, 2H), 3.63-3.45 (m, 3H), 3.20 (s, 3H), 2.95 (t, J=12 Hz, 3H), 2.65-2.45 (m, 3H), 2.32-2.26 (m, 1H), 1.13-1.07 (m, 2H), 1.05-1.01 (m, 2H).

Example 260: 1-((3S,5R)-1-acryloyl-5-(methoxymethyl)pyrrolidin-3-yl)-3-((7-fluoro-2,3-dihydro-1H-benzo[d]pyrrolo[1,2-a]imidazol-6-yl)ethynyl)-5-(methylamino)-1H-pyrazole-4-carboxamide

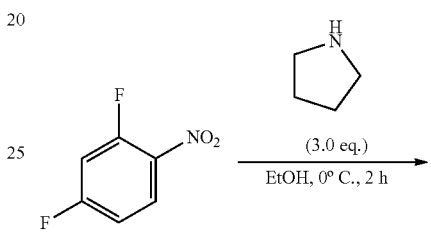

(3.0 eq.)
EtOH, 0° C., 2 h

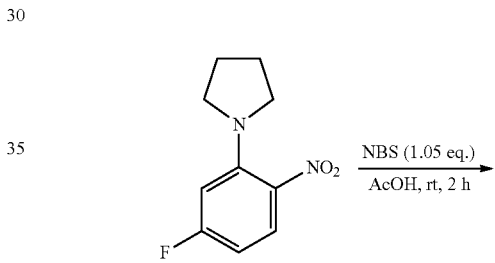

NBS (1.05 eq.)
AcOH, rt, 2 h

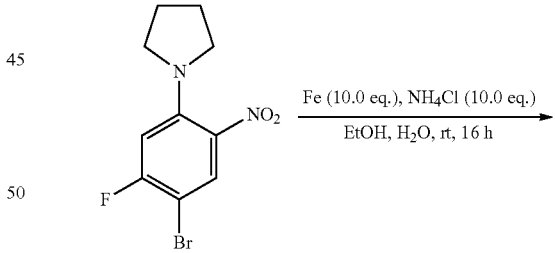

Fe (10.0 eq.), NH₄Cl (10.0 eq.)
EtOH, H₂O, rt, 16 h

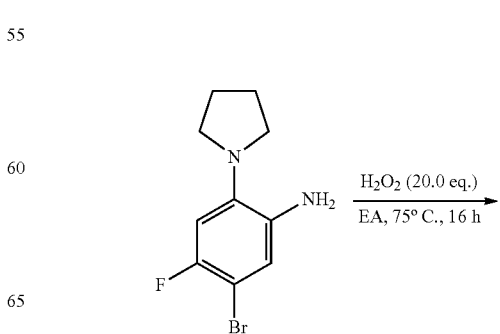

H₂O₂ (20.0 eq.)
EA, 75° C., 16 h

-continued

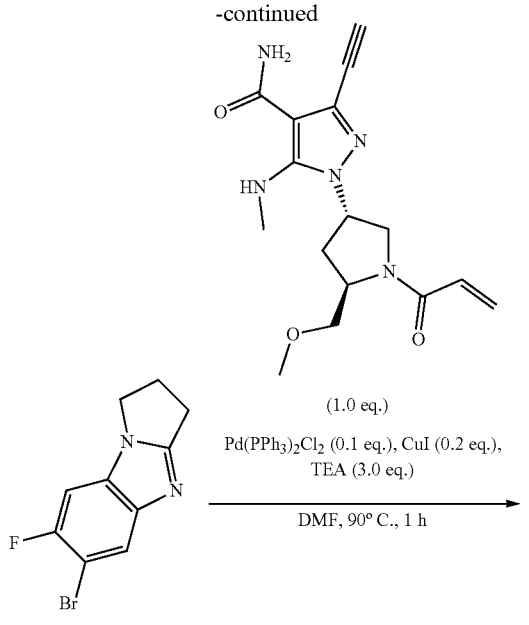

1-((3S,5R)-1-acryloyl-5-(methoxymethyl)pyrrolidin-3-yl)-3-((7-fluoro-2,3-dihydro-1H-benzo[d]pyrrolo[1,2-a]imidazol-6-yl)ethynyl)-5-(methylamino)-1H-pyrazole-4-carboxamide. MS ESI calculated for $C_{26}H_{28}FN_7O_3$ [M+H]$^+$, 506.22, found 506.40; $^1$H NMR (400 MHz, CDCl$_3$) δ 7.81 (s, 1H), 7.58-7.47 (m, 2H), 6.78-6.56 (m, 3H), 6.20-6.14 (m, 1H), 5.71-5.67 (m, 1H), 5.32-5.21 (m, 1H), 4.55-4.40 (m, 1H), 4.14-4.11 (m, 2H), 4.06-3.72 (m, 2H), 3.63-3.60 (m, 2H), 3.50-3.45 (m, 3H), 2.96 (t, J=12 Hz, 5H), 2.66-2.60 (m, 2H), 2.46 (d, J=8 Hz, 1H), 2.33-2.29 (m, 1H).

Example 261: 3-(2-{6-Chloro-3-cyclopropylimidazo[1,2-a]pyridin-7-yl}ethynyl)-1-[(3S,5R)-5-(methoxymethyl)-1-(prop-2-enoyl)pyrrolidin-3-yl]-5-(methylamino)pyrazole-4-carboxamide

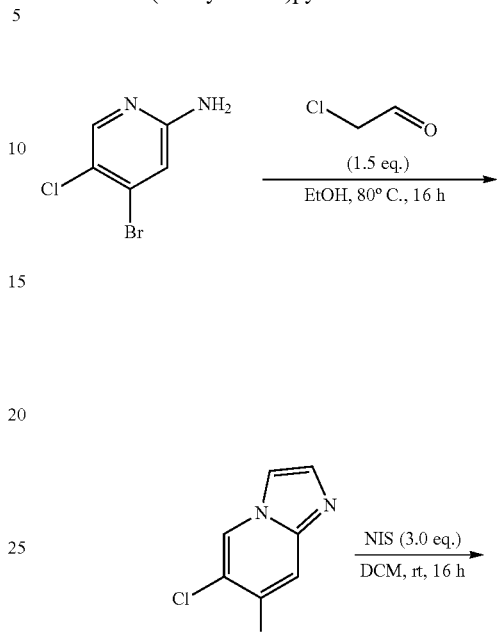

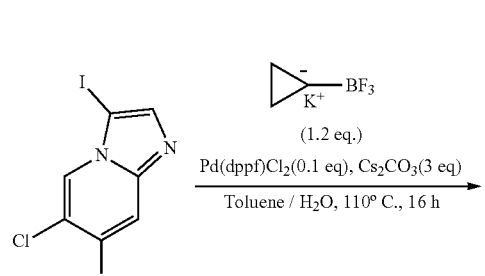

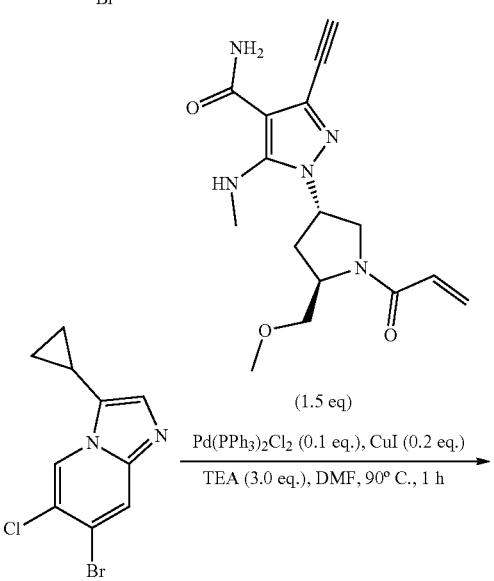

-continued

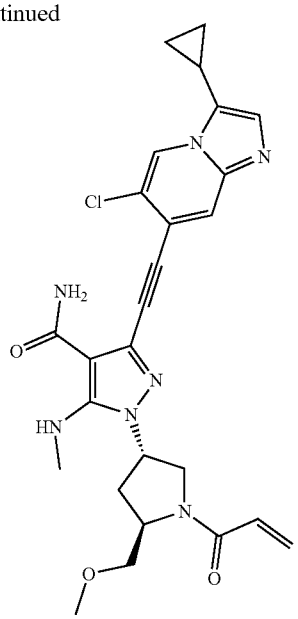

Step 1: 7-Bromo-6-chloroimidazo[1,2-a]pyridine

A solution of 4-bromo-5-chloropyridin-2-amine (3.00 g, 14.46 mmol) and chloroacetaldehyde (4.26 g, 21.69 mmol) in EtOH (30.00 mL) was stirred for 16 h at 80° C. under nitrogen atmosphere. The resulting mixture was concentrated under reduced pressure. The residue was purified by silica gel column chromatography, eluted with DCM/MeOH (10/1). The fractions contained desired product were combined and concentrated to afford 7-bromo-6-chloroimidazo [1,2-a]pyridine (2.50 g, 74%) as a yellow solid. MS ESI calculated for $C_7H_4BrClN_2$ [M+H]$^+$, 231.48, 233.48, found 231.00, 233.00.

Step 2: 7-Bromo-6-chloro-3-iodoimidazo[1,2-a] pyridine

To a stirred solution of 7-bromo-6-chloroimidazo[1,2-a] pyridine (2.10 g, 9.07 mmol) in DCM (21.00 mL) was added NIS (6.12 g, 27.21 mmol) in portions at room temperature under nitrogen atmosphere. The reaction mixture was stirred for 16 h at room temperature under nitrogen atmosphere. The resulting mixture was diluted with water (70 mL) and extracted with EA (2×100 mL). The combined organic layers was washed with water (2×100 mL), dried over anhydrous $Na_2SO_4$. After filtration, the filtrate was concentrated under reduced pressure. The residue was purified by silica gel column chromatography, eluted with DCM/MeOH (5/1). The fractions contained desired product were combined and concentrated to afford 7-bromo-6-chloro-3-iodoimidazo[1,2-a]pyridine (1.80 g, 55%) as an off-white solid. MS ESI calculated for $C_7H_3BrClIN_2$ [M+H]$^+$, 356.82, 358.82, found 356.90, 358.70.

Step 3: 7-Bromo-6-chloro-3-cyclopropylimidazo[1, 2-a]pyridine

To a stirred solution of 7-bromo-6-chloro-3-iodoimidazo [1,2-a]pyridine (0.76 g, 2.12 mmol) and potassium 1-(trifluoro-lambda4-boranyl)cyclopropan-1-ide (0.37 g, 2.55 mmol) in toluene (7.00 mL) and water (0.70 mL) were added $Cs_2CO_3$ (2.08 g, 6.38 mmol) and $Pd(dppf)Cl_2$ (0.15 g, 0.21 mmol). The reaction mixture was irradiated with microwave radiation for 16 h at 110° C. The resulting mixture was concentrated under reduced pressure. The residue was purified by silica gel column chromatography, eluted with PE/EA (5/1). The fractions contained desired product were combined and concentrated to afford 7-bromo-6-chloro-3-cyclopropylimidazo[1,2-a]pyridine (35.00 mg, 6%) as a brown solid. MS ESI calculated for $C_{10}H_8BrClN_2$ [M+H]$^+$, 270.96, 272.95, found 270.90, 272.90.

Step 4: 3-(2-{6-Chloro-3-cyclopropylimidazo[1,2-a] pyridin-7-yl}ethynyl)-1-[(3S,5R)-5-(methoxymethyl)-1-(prop-2-enoyl)pyrrolidin-3-yl]-5-(methylamino)pyrazole-4-carboxamide To a stirred solution of 7-bromo-6-chloro-3-cyclopropylimidazo[1,2-a]pyridine (35.00 mg, 0.12 mmol) and 3-ethynyl-1-[(3S,5R)-5-(methoxymethyl)-1-(prop-2-enoyl)pyrrolidin-3-yl]-5-(methylamino)pyrazole-4-carboxamide (64.07 mg, 0.19 mmol) and $Pd(PPh_3)_2Cl_2$ (9.05 mg, 0.01 mmol) and CuI (4.91 mg, 0.02 mmol) in DMF (0.50 mL) was added TEA (39.13 mg, 0.38 mmol). The reaction mixture was degassed with nitrogen for three times and stirred for 1 h at 90° C. The resulting mixture was concentrated under reduced pressure. The residue was purified by silica gel column chromatography, eluted with DCM/MeOH (5/1). The fractions contained desired product were combined and concentrated to afford the crude product which was further purified by reverse flash chromatography with the following conditions: column: C18 silica gel; mobile phase: ACN in water (10 mmol/L $NH_4HCO_3$), 10% to 50% gradient in 10 min; detector: UV 254 nm. The fractions contained desired product were combined and concentrated to afford 3-(2-{6-chloro-3-cyclopropylimidazo[1,2-a]pyridin-7-yl}ethynyl)-1-[(3S,5R)-5-(methoxymethyl)-1-(prop-2-enoyl)pyrrolidin-3-yl]-5-(methylamino)pyrazole-4-carboxamide (32.40 mg, 48%) as an off-white solid. MS ESI calculated for $C_{26}H_{28}ClN_7O_3$ [M+H]$^+$, 522.19, found 522.25; $^1$H NMR (400 MHz, Chloroform-d) δ 8.90-8.12 (s, 1H), 7.10-6.90 (m, 2H), 6.60-6.44 (m, 2H), 5.80-5.73 (s, 1H), 5.63-5.53 (s, 1H), 5.41-5.31 (s, 1H), 4.67-4.42 (m, 1H), 4.19-3.87 (m, 3H), 3.60-3.44 (m, 1H), 3.40-3.39 (m, 3H), 3.17-3.06 (m, 4H), 2.80-2.72 (m, 1H), 2.49-2.24 (m, 1H), 1.22-1.20 (s, 2H), 0.85-0.78 (s, 2H).

Example 262: 3-(2-{3-Cyano-6-fluoroimidazo[1,2-a]pyridin-7-yl}ethynyl)-1-[(3S,5R)-5-(methoxymethyl)-1-(prop-2-enoyl)pyrrolidin-3-yl]-5-(methylamino)pyrazole-4-carboxamide

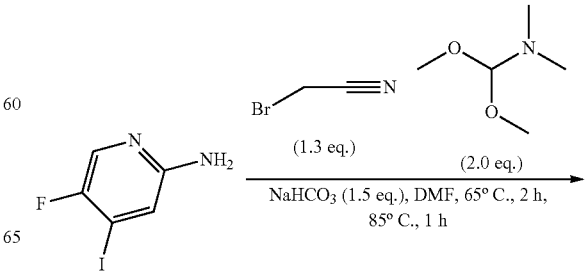

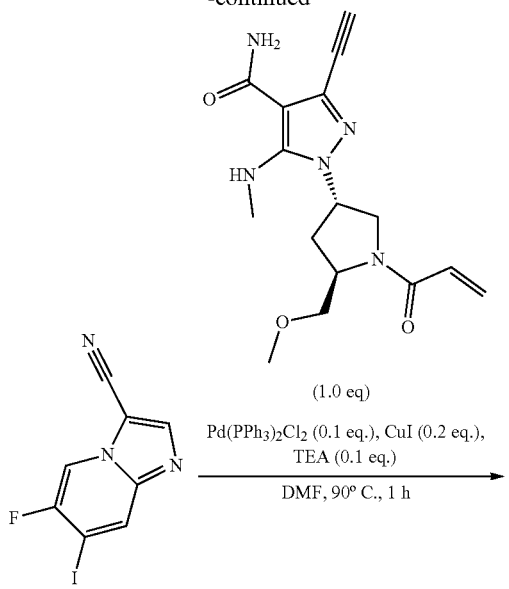
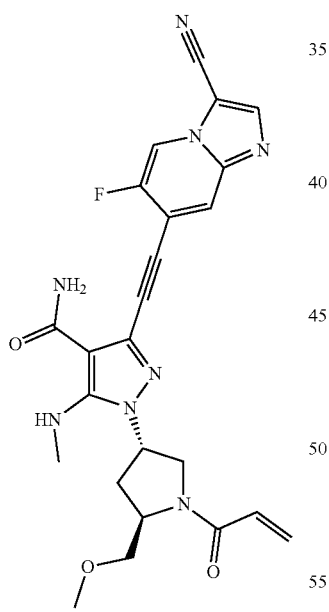
3-(2-{3-cyano-6-fluoroimidazo[1,2-a]pyridin-7-yl}ethynyl)-1-[(3S,5R)-5-(methoxymethyl)-1-(prop-2-enoyl)pyrrolidin-3-yl]-5-(methylamino)pyrazole-4-carboxamide. MS ESI calculated for $C_{24}H_{23}FN_8O_3$ [M+H]$^+$, 491.19, found 491.35; $^1$H NMR (400 MHz, CDCl$_3$) δ 9.15 (s, 1H), 8.57 (s, 1H), 8.31-8.29 (m, 1H), 7.52 (s, 1H), 6.65-6.55 (m, 3H), 6.19 (d, J=16.4 Hz, 1H), 5.70 (d, J=2.4 Hz, 1H), 5.28-5.26 (m, 1H), 4.41-4.03 (m, 1H), 3.90-3.58 (m, 2H), 3.60-3.58 (m, 2H), 3.31 (s, 3H), 2.96 (s, 3H), 2.59 (m, 1H), 2.20-2.39 (m, 1H).
Example 263: 3-(2-{3-Cyanopyrazolo[1,5-a]pyridin-6-yl}ethynyl)-1-[(3S,5R)-5-(methoxymethyl)-1-(prop-2-enoyl)pyrrolidin-3-yl]-5-(methylamino)pyrazole-4-carboxamide
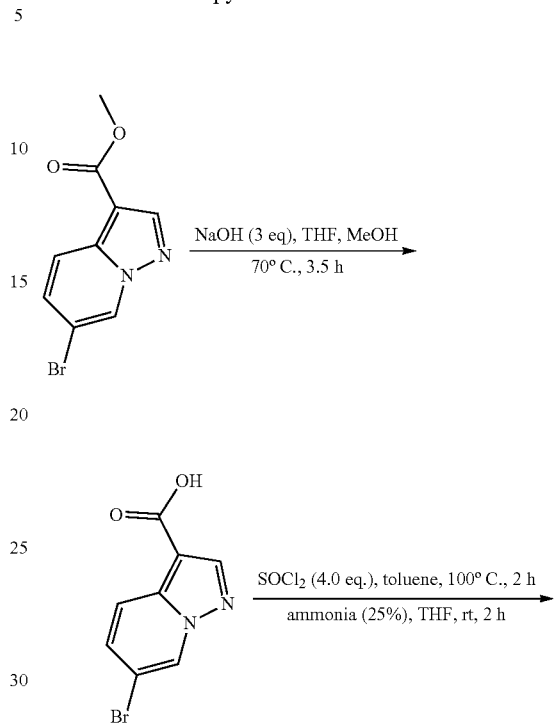
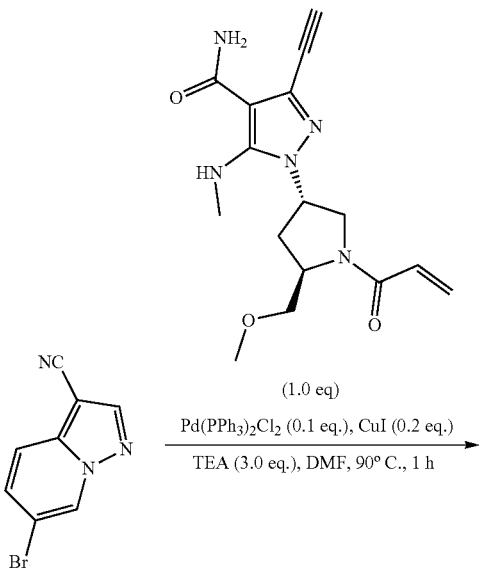

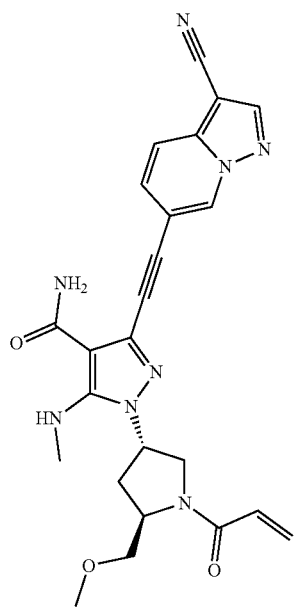 [SMILES: C=CC(=O)N1C[C@@H](n2nc(C#Cc3ccc4c(C#N)cnn4c3)c(C(N)=O)c2NC)C[C@@H]1COC]
3-(2-{3-cyanopyrazolo[1,5-a]pyridin-6-yl}ethynyl)-1-[(3S,5R)-5-(methoxymethyl)-1-(prop-2-enoyl)pyrrolidin-3-yl]-5-(methylamino)pyrazole-4-carboxamide. MS ESI calculated for $C_{24}H_{24}N_8O_3$ [M+H]$^+$, 473.20, found 473.25; $^1$H NMR (400 MHz, DMSO-d$_6$) δ 9.43 (s, 1H), 8.76 (s, 1H), 8.00 (dd, J=9.1, 1.0 Hz, 1H), 7.73 (dd, J=9.1, 1.5 Hz, 1H), 7.32 (s, 1H), 6.87 (s, 1H), 6.73 (dd, J=16.7, 10.3 Hz, 2H), 6.20-6.14 (m, 1H), 5.76-5.70 (m, 1H), 5.29-5.23 (m, 1H), 4.54 (s, 1H), 4.03-3.60 (m, 2H), 3.42-3.53 (m, 2H), 3.32 (s, 3H), 2.95-2.89 (m, 3H), 2.52-2.45 (m, 1H), 2.32 (s, 1H).
Example 264: 3-[2-(3,6-Difluoroquinolin-7-yl)ethynyl]-1-[(3S,5R)-5-(methoxymethyl)-1-(prop-2-enoyl)pyrrolidin-3-yl]-5-(methylamino)pyrazole-4-carboxamide
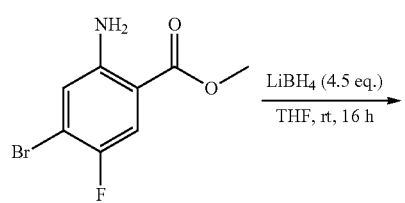
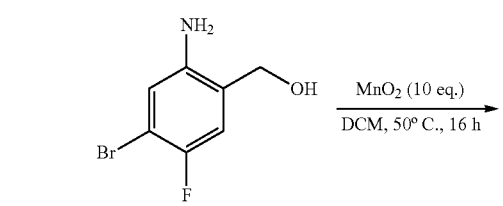
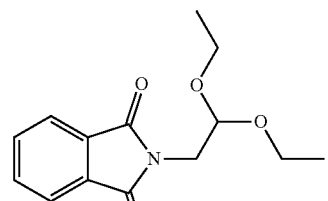
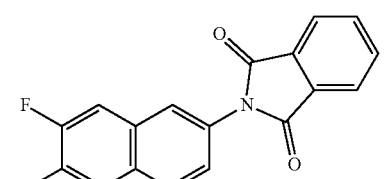
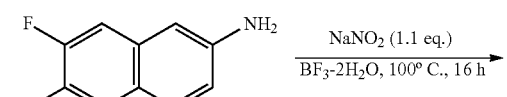
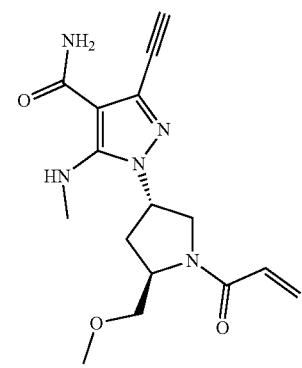

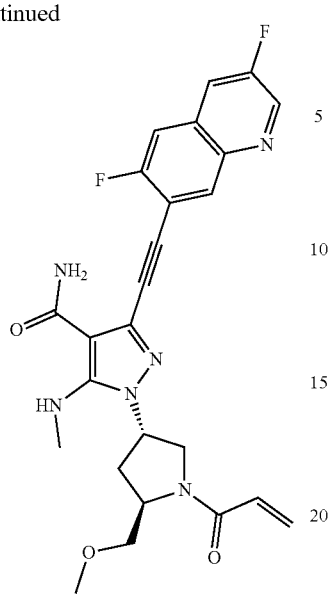

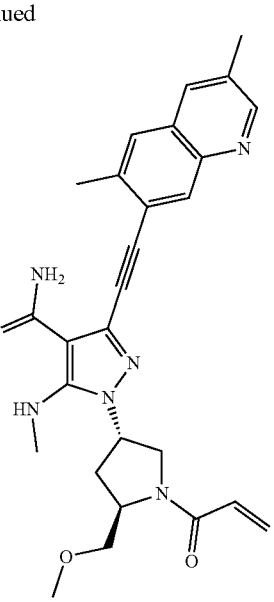

3-[2-(3,6-difluoroquinolin-7-yl)ethynyl]-1-[(3S,5R)-5-(methoxymethyl)-1-(prop-2-enoyl)pyrrolidin-3-yl]-5-(methylamino)pyrazole-4-carboxamide. MS ESI calculated for $C_{25}H_{24}F_2N_6O_3$ [M+H]$^+$, 495.19, found 495.30. $^1$H NMR (400 MHz, Chloroform-d) δ 8.84 (d, J=2.7 Hz, 1H), 8.38 (d, J=6.6 Hz, 1H), 7.75 (d, J=2.7 Hz, 1H), 7.50 (d, J=9.6 Hz, 1H), 6.86 (d, J=6.1 Hz, 2H), 6.49-6.41 (m, 2H), 5.73-5.64 (m, 1H), 5.60-5.37 (m, 2H), 4.59 (d, J=9.0 Hz, 1H), 4.14-4.02 (m, 2H), 3.92-3.62 (m, 1H), 3.50-3.44 (m, 1H), 3.39 (d, J=5.0 Hz, 3H), 3.08 (d, J=5.8 Hz, 3H), 2.79-2.68 (m, 1H), 2.45-2.31 (m, 1H).

Example 265: 3-[2-(3,6-Dimethylquinolin-7-yl)ethynyl]-1-[(3S,5R)-5-(methoxymethyl)-1-(prop-2-enoyl)pyrrolidin-3-yl]-5-(methylamino)pyrazole-4-carboxamide 3-[2-(3,6-dimethylquinolin-7-yl)ethynyl]-1-[(3S,5R)-5-(methoxymethyl)-1-(prop-2-enoyl)pyrrolidin-3-yl]-5-(methylamino)pyrazole-4-carboxamide. MS ESI calculated for $C_{27}H_{30}N_6O_3$ [M+H]$^+$, 487.24, found 487.30; $^1$H NMR (400 MHz, Chloroform-d) δ 8.76 (d, J=2.2 Hz, 1H), 8.28 (d, J=3.7 Hz, 1H), 7.86 (s, 1H), 7.60 (s, 1H), 7.03-6.72 (m, 2H), 6.60-6.43 (m, 2H), 5.78-5.70 (m, 1H), 5.57-5.46 (m, 1H), 5.35 (d, J=27.2 Hz, 1H), 4.67-4.42 (m, 1H), 4.13-4.10 (m, 1H), 4.08-3.98 (m, 1H), 3.92-3.58 (m, 1H), 3.50-3.42 (m, 1H), 3.39 (d, J=4.6 Hz, 3H), 3.07 (d, J=5.8 Hz, 3H), 2.80-2.69 (m, 1H), 2.67 (d, J=3.7 Hz, 3H), 2.54 (s, 3H), 2.33-2.28 (m, 1H).

Example 266: 1-((3S,5R)-1-Acryloyl-5-(methoxymethyl)pyrrolidin-3-yl)-3-((6-fluoro-4-methylcinnolin-7-yl)ethynyl)-5-(methylamino)-1H-pyrazole-4-carboxamide

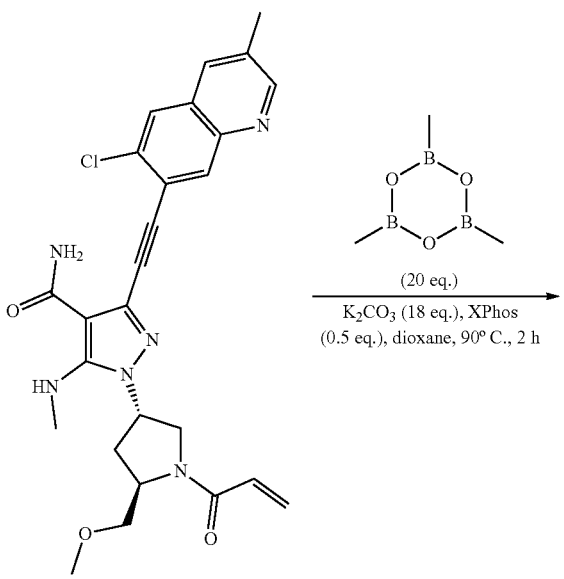

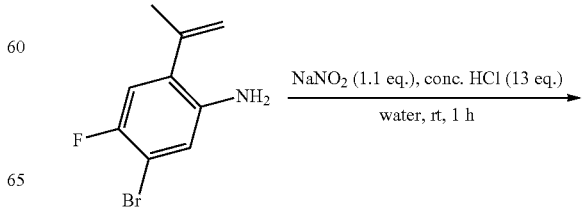

815

-continued

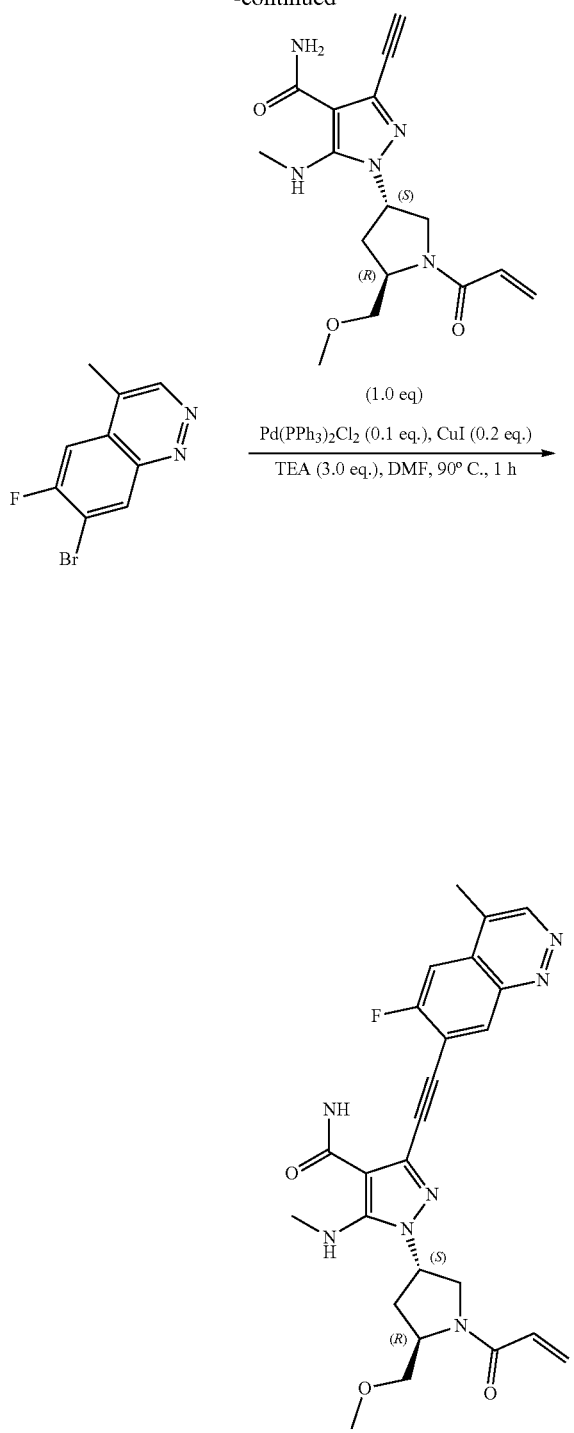

1-((3S,5R)-1-acryloyl-5-(methoxymethyl)pyrrolidin-3-yl)-3-((6-fluoro-4-methylcinnolin-7-yl)ethynyl)-5-(methylamino)-1H-pyrazole-4-carboxamide. MS ESI calculated for $C_{25}H_{26}FN_7O_3$ [M+H]$^+$, 492.21, found 492.35; $^1$H NMR (400 MHz, DMSO-d$_6$) δ 9.28 (s, 1H), 8.82 (dd, J=7.0, 2.6 Hz, 1H), 8.12 (d, J=10.3 Hz, 1H), 7.49 (s, 1H), 6.90 (s, 1H), 6.79-6.54 (m, 2H), 6.20-6.15 (m, 1H), 5.72-5.69 (m, 1H), 5.32-5.23 (m, 1H), 4.65-4.33 (m, 1H), 4.11-3.70 (m, 2H), 3.61 (dd, J=9.4, 5.2 Hz, 1H), 3.55-3.41 (m, 2H), 3.30 (s, 3H), 2.96 (t, J=5.1 Hz, 3H), 2.66 (s, 3H), 2.38-2.27 (m, 1H).

816

Example 267: 3-[2-(6-Chloro-3-fluoroquinolin-7-yl)ethynyl]-1-[(3S,5R)-5-(methoxymethyl)-1-(prop-2-enoyl)pyrrolidin-3-yl]-5-(methylamino)pyrazole-4-carboxamide

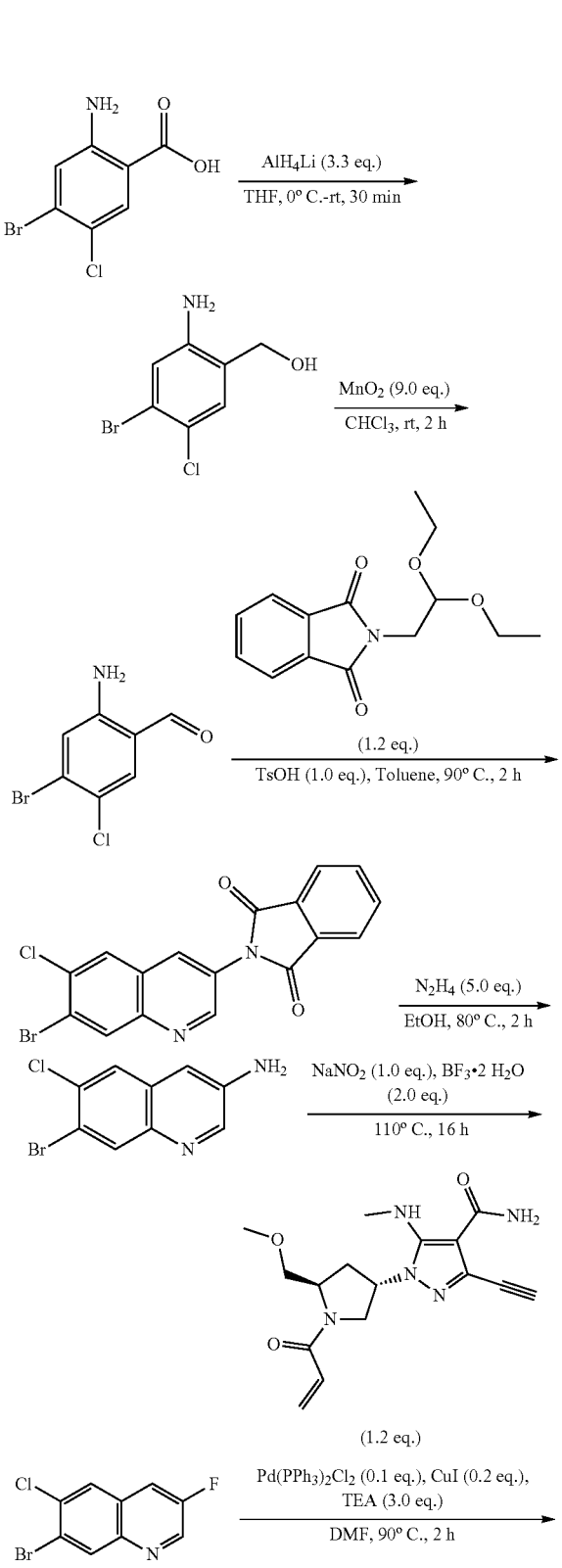

817
-continued

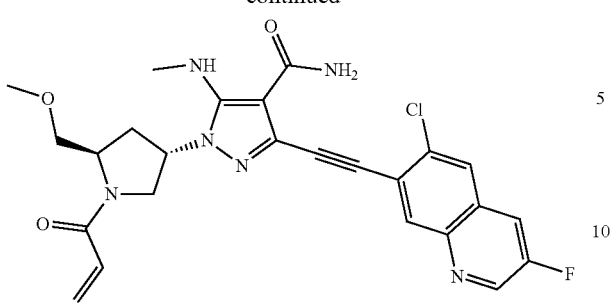

3-[2-(6-chloro-3-fluoroquinolin-7-yl)ethynyl]-1-[(3S,5R)-5-(methoxymethyl)-1-(prop-2-enoyl)pyrrolidin-3-yl]-5-(methylamino)pyrazole-4-carboxamide. MS ESI calculated for $C_{25}H_{24}ClFN_6O_3$ [M+H]$^+$, 511.16, found 511.20; $^1$H NMR (400 MHz, Chloroform-d) δ 8.84 (d, J=2.8 Hz, 1H), 8.41 (d, J=6.3 Hz, 1H), 7.87 (d, J=2.1 Hz, 1H), 7.69-7.56 (m, 1H), 7.06 (s, 1H), 6.83 (d, J=6.1 Hz, 1H), 6.54-6.40 (m, 1H), 6.44-6.35 (m, 1H), 5.76-5.67 (m, 1H), 5.57-5.51 (m, 1H), 5.40 (s, 1H), 4.57 (d, J=9.0 Hz, 1H), 4.16-3.97 (m, 2H), 4.00-3.87 (m, 1H), 3.54-3.41 (m, 1H), 3.37 (d, J=5.2 Hz, 3H), 3.04-2.91 (m, 3H), 2.71-2.65 (m, 1H), 2.35-2.28 (m, 1H).

Example 268: 1-((3S,5R)-1-acryloyl-5-(methoxymethyl)pyrrolidin-3-yl)-3-((6-chloro-4-methylcinnolin-7-yl)ethynyl)-5-(methylamino)-1H-pyrazole-4-carboxamide

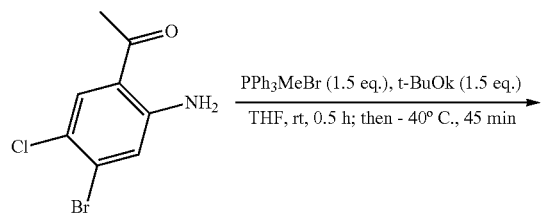

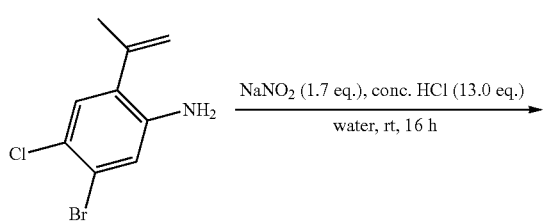

818
-continued

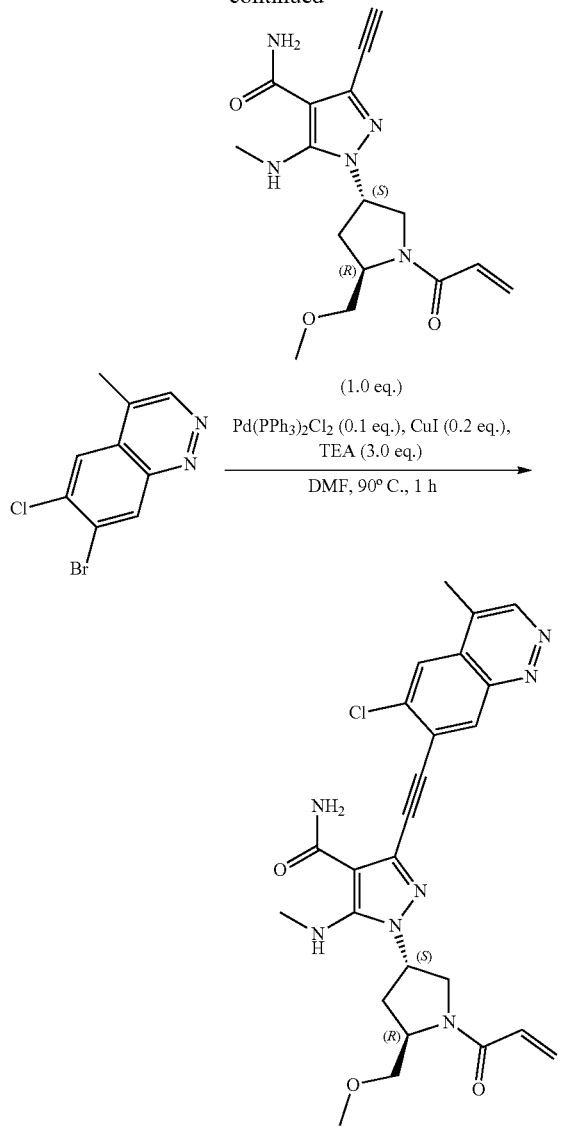

Step 1: 5-Bromo-4-chloro-2-(prop-1-en-2-yl)aniline

To a stirred mixture of methyltriphenylphosphanium bromide (2.16 g, 6.04 mmol) in THF (10.00 mL) was added t-BuOK (0.68 g, 6.04 mmol) in portions at 0° C. under nitrogen atmosphere. After stirred for 30 min at room temperature, 1-(2-amino-4-bromo-5-chlorophenyl)ethanone (1.00 g, 4.02 mmol) in THF (5.00 mL) was added dropwise at 0° C. under nitrogen atmosphere. The reaction mixture was stirred for 45 min at -40° C. The resulting mixture was quenched with water at -40° C. and extracted with EA (3×80 mL). The combined organic layers was washed with brine (60 mL), dried over anhydrous Na2SO4, filtered and concentrated under reduced pressure. The residue was purified by silica gel column chromatography, eluted with PE/DCM (4/1). The fractions contained desired product were combined and concentrated to afford 5-bromo-4-chloro-2-(prop-1-en-2-yl)aniline (0.10 g, 10%) as a yellow oil. MS ESI calculated for C9H9BrClN [M+H]+, 245.96, 247.96, found 246.05, 248.05.

Step 2: 7-Bromo-6-chloro-4-methylcinnoline

To a stirred mixture of 5-bromo-4-chloro-2-(prop-1-en-2-yl)aniline (0.10 g, 0.43 mmol) and conc.HCl (0.46 mL, 5.54 mmol) in water (0.46 mL) was added NaNO2 (0.36 mL, 2 M) dropwise at room temperature. The reaction mixture was stirred for 16 h at room temperature. The resulting mixture was diluted with water (10 mL) and extracted with EA (3×30 mL). The combined organic layers was washed with brine (2×30 mL), dried over anhydrous Na2SO4, filtered and concentrated under reduced pressure. The residue was purified by silica gel column chromatography, eluted with PE/EA (1/1). The fractions contained desired product were combined and concentrated to afford 7-bromo-6-chloro-4-methylcinnoline (90.00 mg, 82%) as a yellow solid. MS ESI calculated for C9H6BrClN2 [M+H]+, 256.94, 258.94, found 257.00, 259.00; 1H NMR (400 MHz, CDCl3) δ 9.19 (s, 1H), 8.86 (s, 1H), 8.12 (s, 1H), 2.68 (s, 3H).

Step 3: 1-((3S,5R)-1-acryloyl-5-(methoxymethyl)pyrrolidin-3-yl)-3-((6-chloro-4-methylcinnolin-7-yl)ethynyl)-5-(methylamino)-1H-pyrazole-4-carboxamide To a stirred mixture of 7-bromo-6-chloro-4-methylcinnoline (80.00 mg, 0.31 mmol), 3-ethynyl-1-[(3S,5R)-5-(methoxymethyl)-1-(prop-2-enoyl)pyrrolidin-3-yl]-5-(methylamino)pyrazole-4-carboxamide (0.10 g, 0.31 mmol), Pd(PPh3)2Cl2 (21.80 mg, 0.03 mmol) and CuI (11.83 mg, 0.06 mmol) in DMF (1.00 mL) was added TEA (94.31 mg, 0.93 mmol) at room temperature. The reaction mixture was degassed with argon for three times and stirred for 1 h at 90° C. The resulting mixture was concentrated under reduced pressure. The residue was purified by silica gel column chromatography, eluted with CH2Cl2/MeOH (10/1) to afford the crude product. The crude product (120 mg) was purified by Prep-HPLC with the following conditions: Column: XBridge Prep OBD C18 Column, 30×150 mm, 5 □m; Mobile Phase A: water (10 mmol/L NH4HCO3), Mobile Phase B: ACN; Flow rate: 60 mL/min; Gradient: 25% B to 35% B in 8 min; Wave length: 254 nm; RT: 8 min. The fractions contained desired product were combined and concentrated to afford 1-((3S,5R)-1-acryloyl-5-(methoxymethyl)pyrrolidin-3-yl)-3-((6-chloro-4-methylcinnolin-7-yl)ethynyl)-5-(methylamino)-1H-pyrazole-4-carboxamide (76.50 mg, 48%) as a white solid. MS ESI calculated for C25H26ClN7O3 [M+H]+, 508.18, found 508.20; 1H NMR (400 MHz, DMSO-d6) δ 9.32 (s, 1H), 8.81 (s, 1H), 8.46 (s, 1H), 7.50 (s, 1H), 6.94 (s, 1H), 6.78-6.50 (m, 2H), 6.23-6.15 (m, 1H), 5.74-5.67 (m, 1H), 5.30-5.24 (m, 1H), 4.63-4.33 (m, 1H), 4.05 (dd, J=10.6, 7.4 Hz, 1H), 3.97-3.83 (m, 1H), 3.81-3.57 (m, 1H), 3.47 (dd, J=9.6, 4.0 Hz, 1H), 3.32 (s, 3H), 2.96 (t, J=5.1 Hz, 3H), 2.69 (s, 3H), 2.62 (t, J=10.5 Hz, 1H), 2.33 (d, J=4.5 Hz, 1H).

Example 269: 3-(2-{3-Cyanoimidazo[1,2-a]pyridin-7-yl}ethynyl)-1-[(3S,5R)-5-(methoxymethyl)-1-(prop-2-enoyl)pyrrolidin-3-yl]-5-(methylamino)pyrazole-4-carboxamide

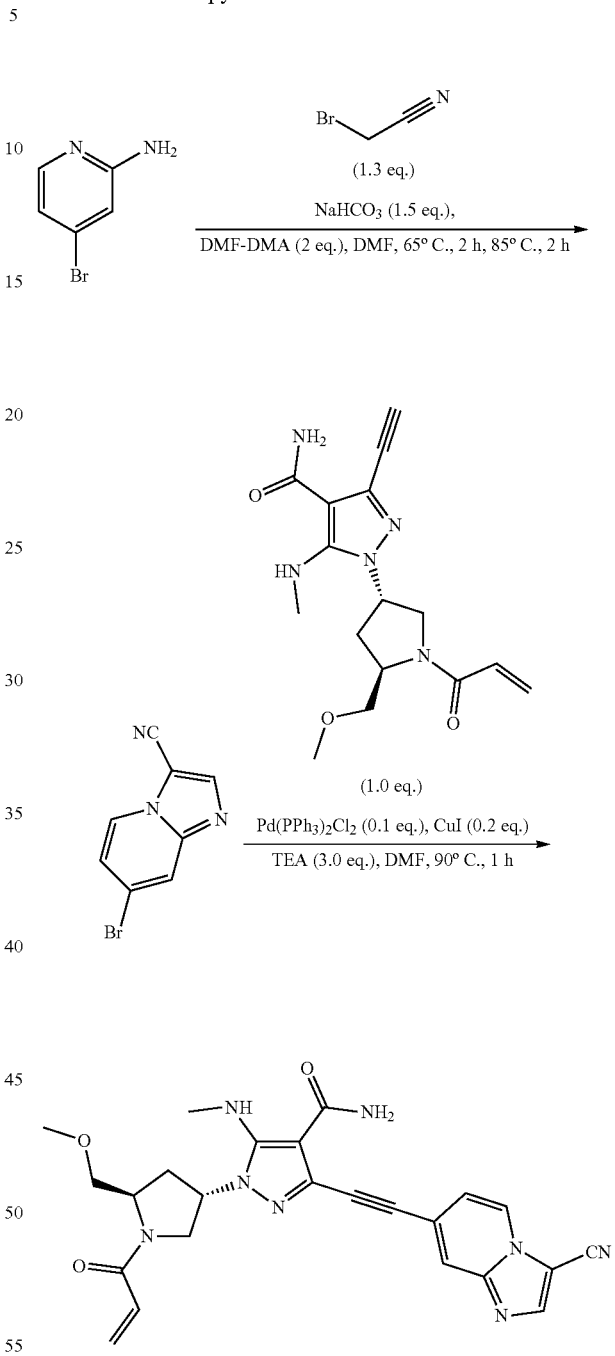

3-(2-{3-cyanoimidazo[1,2-a]pyridin-7-yl}ethynyl)-1-[(3S,5R)-5-(methoxymethyl)-1-(prop-2-enoyl)pyrrolidin-3-yl]-5-(methylamino)pyrazole-4-carboxamide. MS ESI calculated for $C_{24}H_{24}N_8O_3$ [M+H]+, 473.20, found 473.05; 1H NMR (400 MHz, CDCl3) δ 8.50 (s, 1H), 8.01 (s, 1H), 7.23 (d, J=6.9 Hz, 1H), 6.77 (d, J=47.9 Hz, 1H), 6.64-6.37 (m, 2H), 5.75-5.71 (m, 1H), 5.57-5.28 (m, 2H), 4.62-4.40 (m, 1H), 4.09-4.04 (m, 2H), 3.93-3.90 (m, 1H), 3.56-3.43 (m, 1H), 3.39 (d, J=5.3 Hz, 3H), 3.12-3.03 (m, 3H), 2.76-2.64 (m, 1H), 2.44-2.32 (m, 1H).

Example 270: 1-((3S,5R)-1-acryloyl-5-(methoxymethyl)pyrrolidin-3-yl)-3-((3-cyano-4-methoxypyrazolo[1,5-a]pyridin-6-yl)ethynyl)-5-(methylamino)-1H-pyrazole-4-carboxamide

Example 271: 3-(2-{1-[(1S)-2,2-Difluorocyclopropyl]-6-fluoro-1,3-benzodiazol-5-yl}ethynyl)-1-[(3S,5R)-5-(methoxymethyl)-1-(prop-2-enoyl)pyrrolidin-3-yl]-5-(methylamino)pyrazole-4-carboxamide

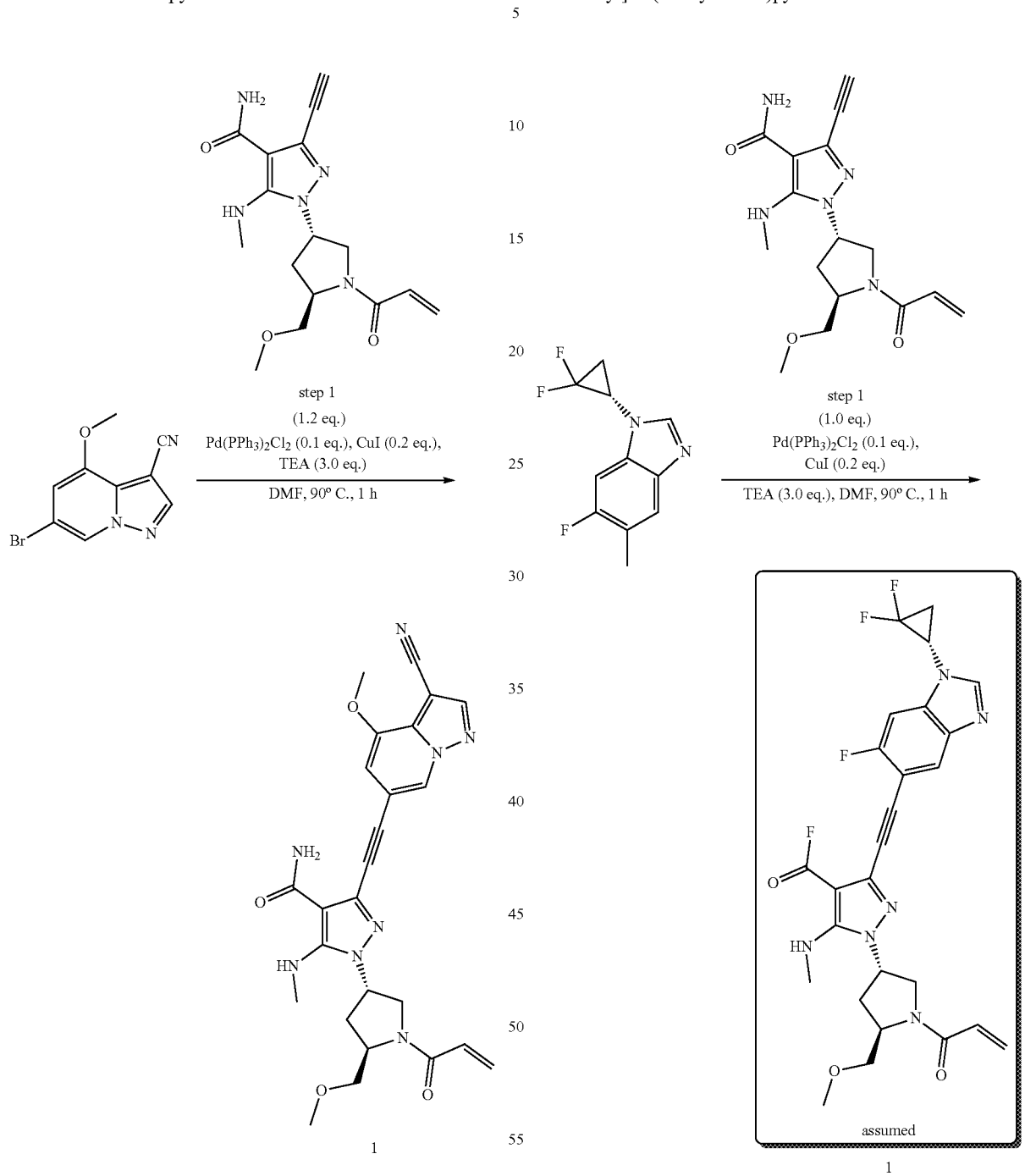

1-((3S,5R)-1-acryloyl-5-(methoxymethyl)pyrrolidin-3-yl)-3-((3-cyano-4-methoxypyrazolo[1,5-a]pyridin-6-yl)ethynyl)-5-(methylamino)-1H-pyrazole-4-carboxamide. MS ESI calculated for $C_{22}H_{29}FN_4O_5$ [M+H]$^+$, 503.21, found 503.35; $^1$H NMR (400 MHz, Chloroform-d) δ 8.43 (d, J=1.1 Hz, 1H), 8.24 (s, 1H), 6.83 (s, 1H), 6.75 (d, J=1.1 Hz, 1H), 6.56-6.37 (m, 2H), 5.73 (dd, J=7.5, 4.8 Hz, 1H), 5.52 (m, 2H), 4.59 (d, J=8.9 Hz, 1H), 4.07 (s, 5H), 4.02-3.87 (m, 1H), 3.55-3.33 (m, 4H), 3.09 (d, J=5.7 Hz, 3H), 2.69 (m, 1H), 2.37 (m, 1H).

To a stirred mixture of (S)-1-(2,2-difluorocyclopropyl)-6-fluoro-5-iodo-1H-benzo[d]imidazole (80 mg, 0.23 mmol) and 3-ethynyl-1-[(3S,5R)-5-(methoxymethyl)-1-(prop-2-enoyl)pyrrolidin-3-yl]-5-(methylamino)pyrazole-4-carboxamide (78.42 mg, 0.23 mmol) in DMF (0.50 mL) were added Pd(PPh$_3$)$_2$Cl$_2$ (16.61 mg, 0.02 mmol), CuI (9.01 mg, 0.04 mmol) and TEA (71.84 mg, 0.71 mmol). The reaction mixture was degassed with argon for three times and stirred for 1 h at 90 C. The resulting mixture was concentrated under reduced pressure. The residue was purified by silica gel column chromatography, eluted with CH$_2$Cl$_2$/MeOH (10/1) to afford the crude product which was further purified by Prep-HPLC with the following conditions: Column: XBridge Prep OBD C18 Column, 30×150 mm, 5 m; Mobile Phase A: water (10 mmol/L NH$_4$HCO$_3$), Mobile Phase B: ACN; Flow rate: 60 mL/min; Gradient: 28% B to 38% B in 8 min, 38% B; Wave Length: 254 nm; RT1: 7.17 min. The fractions contained desired product were combined and concentrated to afford 3-(2-{1-[(1S)-2,2-difluorocyclopropyl]-6-fluoro-1,3-benzodiazol-5-yl}ethynyl)-1-[(3S,5R)-5-(methoxymethyl)-1-(prop-2-enoyl)pyrrolidin-3-yl]-5-(methylamino)pyrazole-4-carboxamide (stereochemistry arbitrarily assigned) (71.20 mg, 55%) as an off-white solid. MS ESI calculated for C$_{26}$H$_{26}$F$_3$N$_7$O$_3$ [M+H]$^+$, 542.50, found 542.55; $^1$H NMR (400 MHz, CDCl$_3$) δ 8.04 (s, 2H), 7.26 (d, J=10.0 Hz, 2H), 6.59-6.36 (m, 2H), 5.77-5.68 (m, 1H), 5.59-5.46 (m, 1H), 5.41-5.28 (m, 1H), 4.58 (d, J=8.9 Hz, 1H), 4.08-4.02 (m, 2H), 3.97-3.92 (m, 2H), 3.55-3.42 (m, 1H), 3.39 (d, J=4.5 Hz, 3H), 3.05 (d, J=15.2 Hz, 3H), 2.79-2.66 (m, 1H), 2.44-2.25 (m, 2H), 2.09-2.04 (m, 1H).

Example 272: 3-{2-[1-((R)-2,2-difluorocyclopropyl)-6-fluoro-1,3-benzodiazol-5-yl]ethynyl}-1-[(3S,5R)-5-(methoxymethyl)-1-(prop-2-enoyl)pyrrolidin-3-yl]-5-(methylamino)pyrazole-4-carboxamide

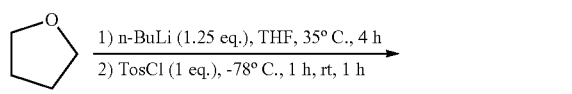

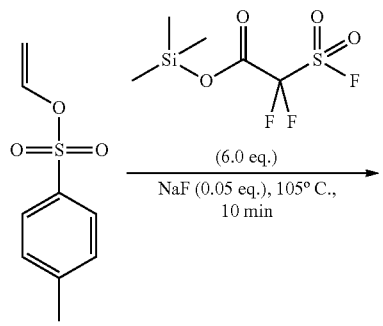

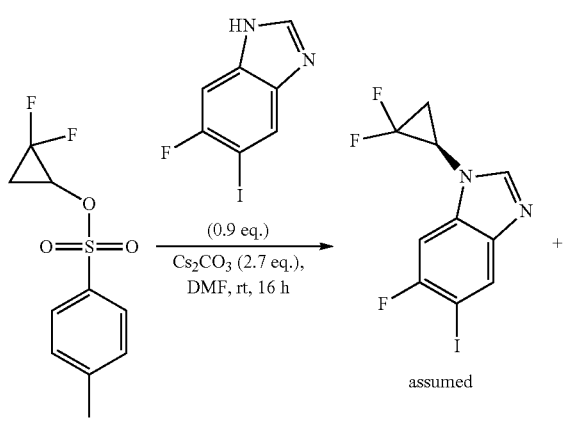

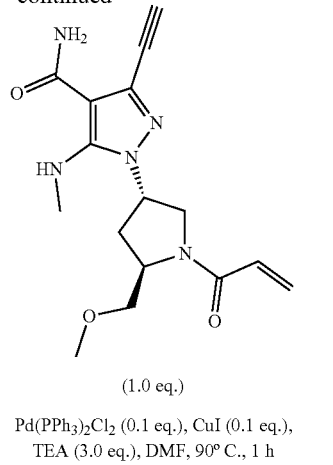

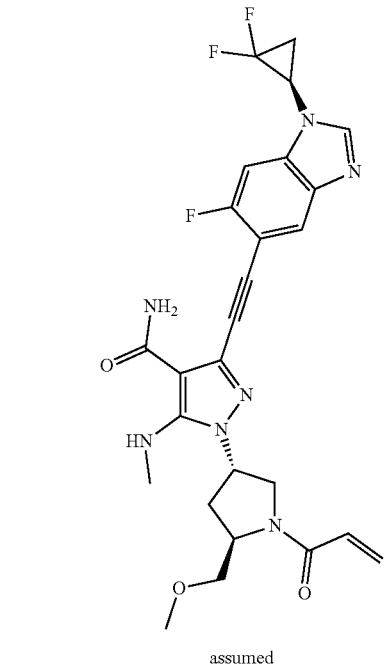 [SMILES: C=CC(=O)N1C[C@@H](n2nc(C#Cc3cc4ncn([C@@H]5CC5(F)F)c4cc3F)c(C(N)=O)c2NC)C[C@@H]1COC]

Step 1: Vinyl 4-methylbenzenesulfonate

A solution of n-BuLi (13.00 mL, 32.77 mmol) in THF (40.00 mL) was stirred for 4 h at 35° C. under nitrogen atmosphere. Then to the above mixture was added a solution of P-toluenesulfonyl chloride (5.00 g, 26.23 mmol) in THF (13.00 mL) dropwise over 30 min at −78° C. The reaction mixture was stirred for 1 h at −78° C. and another 1 h at room temperature. The resulting mixture was quenched by addition of water (50 mL) and extracted with MTBE (3×50 mL). The combined organic layers was dried over Na$_2$SO$_4$ and filtered. The filtrate was concentrated under reduced pressure. The residue was purified by silica gel column chromatography, eluted with PE. The fractions contained desired product were combined and concentrated to afford vinyl 4-methylbenzenesulfonate (3.40 g, 65%) as a colorless oil. MS ESI calculated for $C_9H_{10}O_3S$ [M−H]−, 197.04, found 196.90; $^1H$ NMR (400 MHz, $CDCl_3$) δ 7.89-7.74 (m, 2H), 7.43-7.33 (m, 2H), 6.62 (dd, J=13.6, 5.9 Hz, 1H), 4.90 (dd, J=13.5, 2.5 Hz, 1H), 4.70 (dd, J=5.9, 2.5 Hz, 1H).

Step 2: 2,2-Difluorocyclopropyl 4-methylbenzenesulfonate

To a stirred mixture of NaF (59.31 mg, 1.41 mmol) and vinyl 4-methylbenzenesulfonate (2.80 g, 14.12 mmol) was added trimethylsilyl 2,2-difluoro-2-sulfoacetate (21.21 g, 84.74 mmol) dropwise at room temperature under nitrogen atmosphere. The reaction mixture was stirred for 10 min at 105° C. under nitrogen atmosphere. The resulting mixture was purified by silica gel column chromatography, eluted with PE/EA (12/1). The fractions contained desired product were combined and concentrated to afford 2,2-difluorocyclopropyl 4-methylbenzenesulfonate (1.70 g, 48%) as a light yellow solid; $^1H$ NMR (400 MHz, $CDCl_3$) δ 7.89-7.80 (m, 2H), 7.45-7.37 (m, 2H), 4.30-4.24 (m, 1H), 2.50 (s, 3H), 1.82-1.58 (m, 2H).

Step 3: 1-(2,2-Difluorocyclopropyl)-6-fluoro-5-iodo-1,3-benzodiazole & 1-(2,2-difluorocyclopropyl)-5-fluoro-6-iodo-1,3-benzodiazole To a stirred solution of 2,2-difluorocyclopropyl 4-methylbenzenesulfonate (0.42 g, 1.68 mmol) and $Cs_2CO_3$ (1.49 g, 4.58 mmol) in DMF (5.00 mL) was added 5-fluoro-6-iodo-3H-1,3-benzodiazole (0.40 g, 1.53 mmol) at room temperature. The reaction mixture was stirred for 16 h at room temperature. The resulting mixture was filtered, the filter cake was washed with DMF (2×20 mL). The filtrate was concentrated under reduced pressure. The residue was purified by reverse flash chromatography with the following conditions: column: C18 silica gel; mobile phase, ACN in water ($NH_4HCO_3$, 10 mmol/L), 10% to 50% gradient in 40 min; detector: UV 254 nm to afford the crude product (360 mg) which was further purified by Prep-HPLC with the following conditions: Column: CHIRALPAK ID, 2×25 cm, 5 m; Mobile Phase A: Hex (0.5% 2 M $NH_3$-MeOH)-HPLC, Mobile Phase B: MeOH:EtOH=1:1—HPLC; Flow rate: 20 mL/min; Gradient: 20% B to 20% B in 15 min; Wave Length: 220/254 nm; RT1: 7.08 min; RT2: 11.51 min; Sample Solvent: MeOH:DCM=1:1. The faster peak (RT1: 7.08 min) was combined and concentrated to afford 1-[(1R)-2,2-difluorocyclopropyl]-6-fluoro-5-iodo-1,3-benzodiazole (80.00 mg, 15%) as a light yellow solid. MS ESI calculated for $C_{10}H_6F_3IN_2$ [M+H]+, 338.85, found 338.85; $^1H$ NMR (400 MHz, $CDCl_3$) δ 8.20 (d, J=5.5 Hz, 1H), 7.95 (d, J=1.7 Hz, 1H), 7.23 (d, J=7.3 Hz, 1H), 3.95-3.88 (m, 1H), 2.34-2.25 (m, 1H), 2.09-1.96 (m, 1H). The slower peak (RT1: 11.51 min) was combined and concentrated to afford 1-[(1S)-2,2-difluorocyclopropyl]-6-fluoro-5-iodo-1,3-benzodiazole (90.00 mg, 17%) as a light yellow solid. MS ESI calculated for $C_{10}H_6F_3IN_2$ [M+H]+, 338.85, found 338.85; $^1H$ NMR (400 MHz, $CDCl_3$) δ 8.21 (d, J=5.5 Hz, 1H), 7.97 (t, J=1.7 Hz, 1H), 7.23 (d, J=7.3 Hz, 1H), 3.95-3.88 (m, 1H), 2.34-3.25 (m, 1H), 2.07-1.99 (m, 1H).

Step 4: 3-{2-[1-((R)-2,2-difluorocyclopropyl)-6-fluoro-1,3-benzodiazol-5-yl]ethynyl}-1-[(3S,5R)-5-(methoxymethyl)-1-(prop-2-enoyl)pyrrolidin-3-yl]-5-(methylamino)pyrazole-4-carboxamide To a stirred mixture of 1-[(1R)-2,2-difluorocyclopropyl]-6-fluoro-5-iodo-1,3-benzodiazole (80.00 mg, 0.24 mmol), 3-ethynyl-1-[(3S,5R)-5-(methoxymethyl)-1-(prop-2-enoyl)pyrrolidin-3-yl]-5-(methylamino)pyrazole-4-carboxamide (78.42 mg, 0.24 mmol), $Pd(PPh_3)_2Cl_2$ (16.61 mg, 0.02 mmol) and CuI (4.51 mg, 0.02 mmol) in DMF (2.00 mL) was added TEA (71.84 mg, 0.71 mmol) dropwise at room temperature. The reaction mixture was degassed with nitrogen for three times and stirred for 1 h at 90° C. The resulting mixture was concentrated under reduced pressure. The residue was purified by silica gel column chromatography, eluted with $CH_2Cl_2$/MeOH (10/1) to afford the crude product (100 mg) which was further purified by reverse flash chromatography with the following conditions: column, C18 silica gel; mobile phase: ACN in water (10 mmol/L $NH_4HCO_3$), 5% to 70% gradient in 40 min; detector: UV 254 nm. The fractions contained desired product were combined and concentrated to afford 3-{2-[1-((R)-(2,2-difluorocyclopropyl)-6-fluoro-1,3-benzodiazol-5-yl]ethynyl}-1-[(3S,5R)-5-(methoxymethyl)-1-(prop-2-enoyl)pyrrolidin-3-yl]-5-(methylamino)pyrazole-4-carboxamide (stereochemistry arbitrarily assigned) (45.30 mg, 35%) as an off-white solid. MS ESI calculated for $C_{26}H_{26}F_3N_7O_3$ [M+H]+, 542.21, found 542.30; $^1H$ NMR (400 MHz, $CDCl_3$) δ 8.04 (s, 2H), 7.29 (s, 1H), 7.09 (s, 1H), 6.86-6.67 (m, 1H), 6.57-6.37 (m, 2H), 5.72 (dd, J=8.5, 4.0 Hz, 1H), 5.59-5.08 (m, 1H), 4.61-4.36 (m, 1H), 4.09-4.01 (m, 2H), 3.96-3.90 (m, 2H), 3.55-3.42 (m, 1H), 3.39 (d, J=4.4 Hz, 3H), 3.05 (dd, J=15.4, 5.8 Hz, 3H), 2.76-2.71 (m, 1H), 2.32 (dd, J=12.4, 7.0 Hz, 2H), 2.05 (d, J=14.0 Hz, 1H).

Example 273: 3-{2-[3-(Difluoromethyl)-6-fluoroquinolin-7-yl]ethynyl}-1-[(3S,5R)-5-(methoxymethyl)-1-(prop-2-enoyl)pyrrolidin-3-yl]-5-(methylamino)pyrazole-4-carboxamide

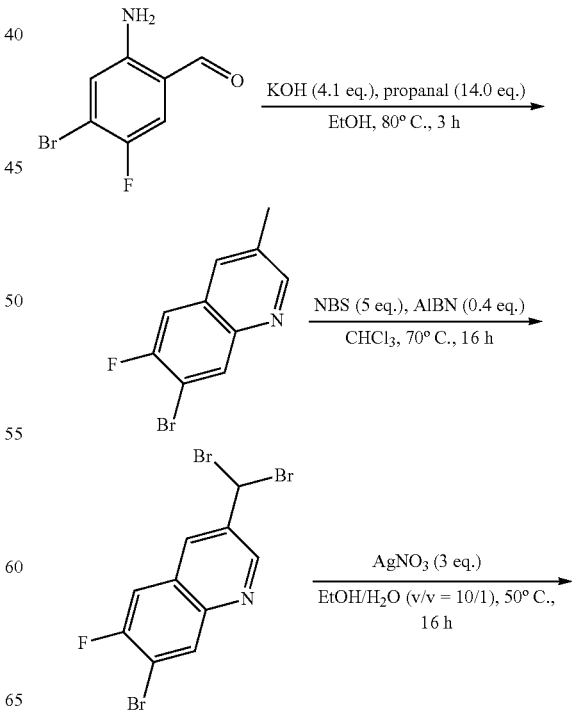

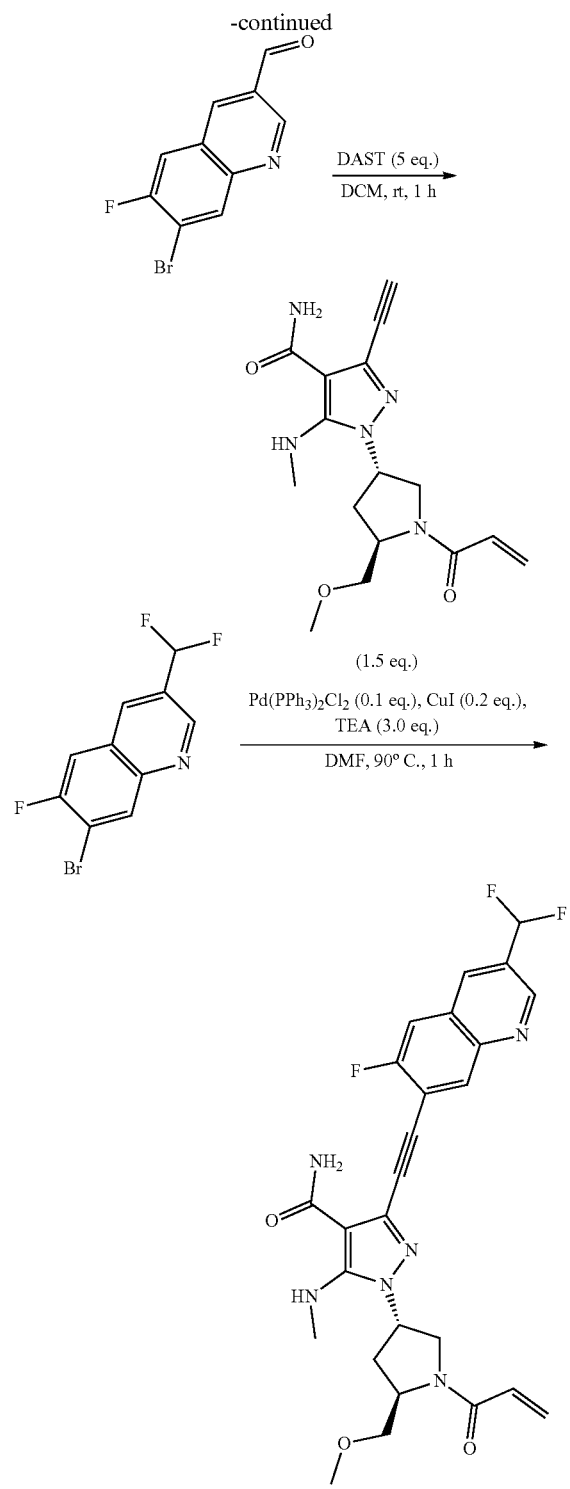

3-{2-[3-(difluoromethyl)-6-fluoroquinolin-7-yl]ethynyl}-1-[(3S,5R)-5-(methoxymethyl)-1-(prop-2-enoyl)pyrrolidin-3-yl]-5-(methylamino)pyrazole-4-carboxamide. MS ESI calculated for $C_{26}H_{25}F_3N_6O_3$ [M+H]+, 527.19, found 527.35; $^1$H NMR (400 MHz, Chloroform-d) δ 9.08-9.04 (m, 1H), 8.43 (d, J=6.4 Hz, 1H), 8.27 (s, 1H), 7.60 (d, J=9.2 Hz, 1H), 7.02 (d, J=23.0 Hz, 1H), 6.94-6.78 (m, 2H), 6.52-6.34 (m, 2H), 5.74-5.65 (m, 1H), 5.54-5.51 (m, 1H), 5.48-5.29 (m, 1H), 4.65-4.41 (m, 1H), 4.17-3.98 (m, 2H), 3.93-3.54 (m, 1H), 3.47-3.44 (m, 1H), 3.40 (d, J=5.1 Hz, 3H), 3.07-2.84 (m, 3H), 2.78-2.67 (m, 1H), 2.34-2.29 (m, 1H).

Example 274: 3-[2-(6-Fluoro-4-methylquinolin-7-yl)ethynyl]-1-[(3S,5R)-5-(methoxymethyl)-1-(prop-2-enoyl)pyrrolidin-3-yl]-5-(methylamino)pyrazole-4-carboxamide

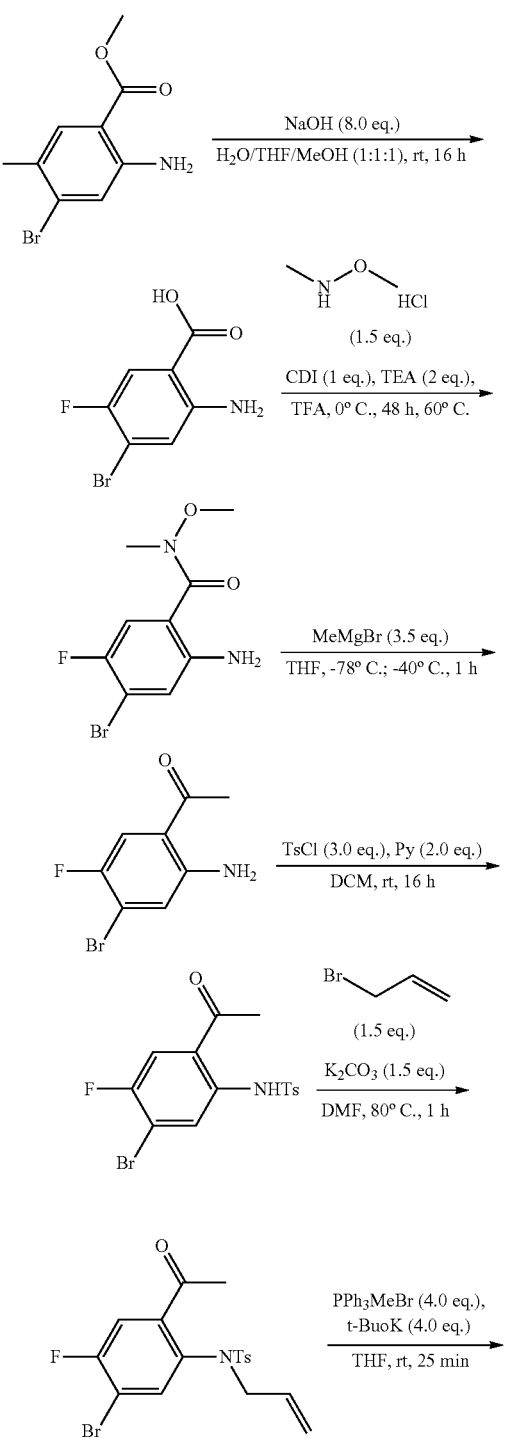

-continued

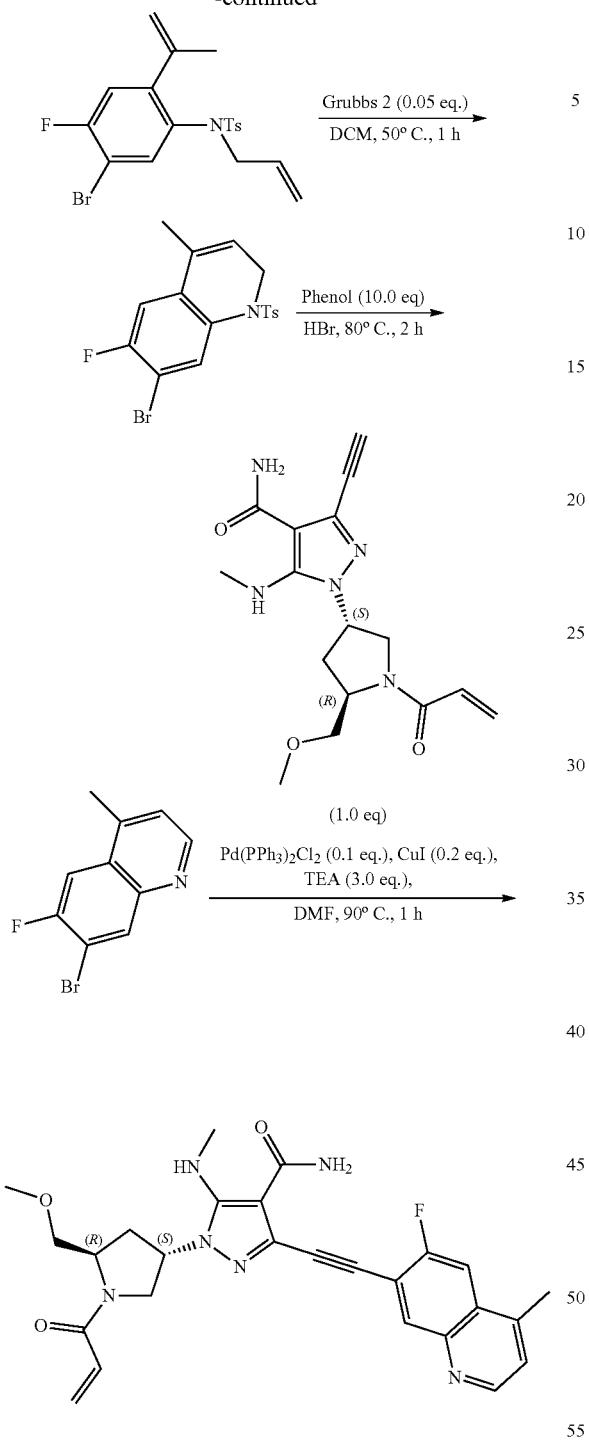

3-[2-(6-fluoro-4-methylquinolin-7-yl)ethynyl]-1-[(3S,5R)-5-(methoxymethyl)-1-(prop-2-enoyl)pyrrolidin-3-yl]-5-(methylamino)pyrazole-4-carboxamide. MS ESI calculated for $C_{26}H_{27}FN_6O_3$ [M+H]$^+$, 491.21, found 491.25; $^1$H NMR (400 MHz, DMSO-d$_6$) δ 8.81 (d, J=4.4 Hz, 1H), 8.33 (d, J=6.3 Hz, 1H), 8.01 (d, J=10.9 Hz, 1H), 7.47 (d, J=4.4 Hz, 2H), 6.86 (s, 1H), 6.77-6.53 (m, 2H), 6.17 (dd, J=16.7, 2.5 Hz, 1H), 5.69 (dd, J=10.4, 2.8 Hz, 1H), 5.29-5.24 (m, 1H), 4.63-4.31 (m, 1H), 4.10-3.68 (m, 2H), 3.61 (dd, J=9.3, 5.2 Hz, 1H), 3.53-3.41 (m, 1H), 3.31 (d, J=4.7 Hz, 3H), 2.96 (t, J=5.2 Hz, 3H), 2.67 (s, 3H), 2.32 (s, 1H).

Example 275: 1-((3S,5R)-1-Acryloyl-5-(methoxymethyl)pyrrolidin-3-yl)-3-((1-methyl-1H-indazol-4-yl)ethynyl)-5-(methylamino)-1H-pyrazole-4-carboxamide

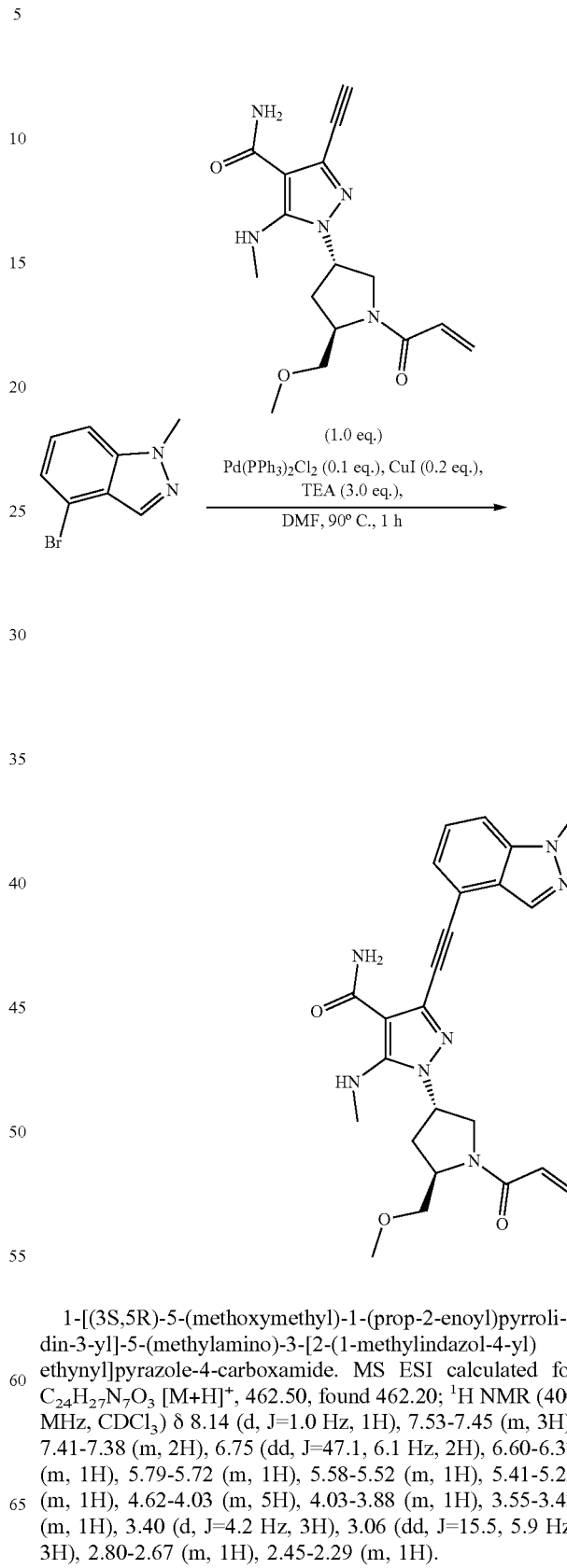

1-[(3S,5R)-5-(methoxymethyl)-1-(prop-2-enoyl)pyrrolidin-3-yl]-5-(methylamino)-3-[2-(1-methylindazol-4-yl)ethynyl]pyrazole-4-carboxamide. MS ESI calculated for $C_{24}H_{27}N_7O_3$ [M+H]$^+$, 462.50, found 462.20; $^1$H NMR (400 MHz, CDCl$_3$) δ 8.14 (d, J=1.0 Hz, 1H), 7.53-7.45 (m, 3H), 7.41-7.38 (m, 2H), 6.75 (dd, J=47.1, 6.1 Hz, 2H), 6.60-6.37 (m, 1H), 5.79-5.72 (m, 1H), 5.58-5.52 (m, 1H), 5.41-5.22 (m, 1H), 4.62-4.03 (m, 5H), 4.03-3.88 (m, 1H), 3.55-3.43 (m, 1H), 3.40 (d, J=4.2 Hz, 3H), 3.06 (dd, J=15.5, 5.9 Hz, 3H), 2.80-2.67 (m, 1H), 2.45-2.29 (m, 1H).

Example 276: 3-[2-(1-Cyclopropylindazol-4-yl)ethynyl]-1-[(3S,5R)-5-(methoxymethyl)-1-(prop-2-enoyl)pyrrolidin-3-yl]-5-(methylamino)pyrazole-4-carboxamide

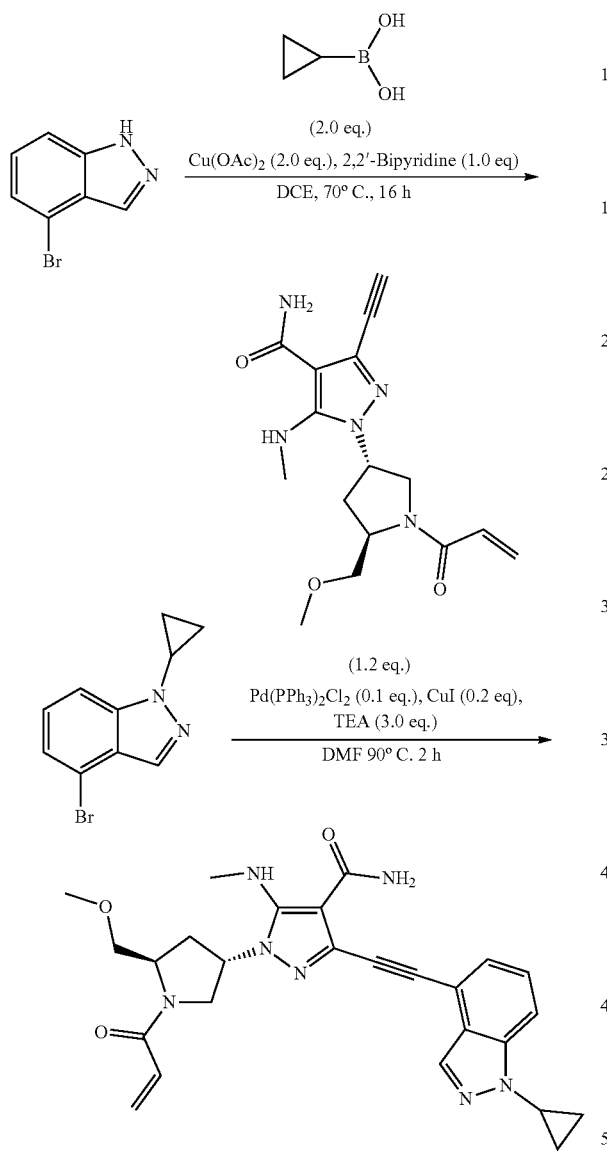

Step 1: 4-Bromo-1-cyclopropylindazole

To a stirred mixture of 4-bromo-1H-indazole (2.00 g, 10.15 mmol), cyclopropylboronic acid (1.74 g, 20.30 mmol), 2,2'-Bipyridine (1.59 g, 10.15 mmol) in DCE (100.00 mL) was added Cu(OAc)$_2$ (3.69 g, 20.30 mmol) at room temperature under air atmosphere. The reaction mixture was stirred for 16 h at 70° C. under air atmosphere. The resulting mixture was diluted with water (50 mL) and extracted with DCM (3×100 mL). The combined organic layers was washed with brine (2×50 mL), dried over anhydrous Na$_2$SO$_4$, filtered and concentrated under reduced pressure. The residue was purified by silica gel column chromatography, eluted with PE/EA (4/1). The fractions contained desired product were combined and concentrated to afford 4-bromo-1-cyclopropylindazole (0.80 g, 33%) as a colorless oil. MS ESI calculated for C$_{10}$H$_9$BrN$_2$ [M+H]$^+$, 236.99, 238.99, found 237.00, 239.00; $^1$H NMR (400 MHz, Chloroform-d) δ 7.94 (d, J=0.9 Hz, 1H), 7.54-7.50 (m, 1H), 7.34-7.18 (m, 2H), 3.64-3.55 (m, 1H), 1.30-1.12 (m, 4H).

Step 2: 3-[2-(1-Cyclopropylindazol-4-yl)ethynyl]-1-[(3S,5R)-5-(methoxymethyl)-1-(prop-2-enoyl)pyrrolidin-3-yl]-5-(methylamino)pyrazole-4-carboxamide To a stirred mixture of 4-bromo-1-cyclopropylindazole (0.10 g, 0.42 mmol) and 3-ethynyl-1-[(3S,5R)-5-(methoxymethyl)-1-(prop-2-enoyl)pyrrolidin-3-yl]-5-(methylamino)pyrazole-4-carboxamide (0.16 g, 0.50 mmol) in DMF (1.00 mL) were added Pd(PPh$_3$)$_2$Cl$_2$ (29.60 mg, 0.04 mmol), CuI (16.06 mg, 0.08 mmol) and TEA (0.12 g, 1.26 mmol). The reaction mixture was degassed with nitrogen for three times and stirred for 2 h at 90° C. The resulting mixture was concentrated under vacuum. The residue was purified by silica gel column chromatography, eluted with DCM/MeOH (20/1) to afford the crude product which was further purified by Prep-HPLC with the following conditions: Column: XSelect CSH Prep C18 OBD Column, 19×250 mm, 5 m; Mobile Phase A: water (10 mmol/L NH$_4$HCO$_3$), Mobile Phase B: DCM:EtOH=9:1-HPLC; Flow rate: 25 mL/min; Gradient: 57% B to 57% B in 20 min, 57% B; Wave Length: 254 nm; RT1: 15.2 min. The fractions contained desired product were combined and concentrated to afford 3-[2-(1-cyclopropylindazol-4-yl)ethynyl]-1-[(3S,5R)-5-(methoxymethyl)-1-(prop-2-enoyl)pyrrolidin-3-yl]-5-(methylamino)pyrazole-4-carboxamide (36.50 mg, 17%) as a white solid. MS ESI calculated for C$_{26}$H$_{29}$N$_7$O$_3$ [M+H]$^+$, 488.23, found 488.25; $^1$H NMR (400 MHz, Chloroform-d) δ 8.07 (d, J=1.0 Hz, 1H), 7.71-7.63 (m, 1H), 7.43-7.34 (m, 2H), 6.79 (d, J=6.1 Hz, 1H), 6.57-6.34 (m, 2H), 5.70-5.67 (m, 1H), 5.51-5.46 (m, 1H), 5.34 (s, 1H), 4.56 (d, J=9.1 Hz, 1H), 4.11-4.09 (m, 1H), 4.09-3.96 (m, 1H), 4.00-3.86 (m, 1H), 3.61-3.59 (m, 1H), 3.53-3.40 (m, 1H), 3.37 (d, J=4.2 Hz, 3H), 3.03-2.96 (m, 3H), 2.77-2.65 (m, 1H), 2.35-2.31 (m, 1H), 1.29-1.14 (m, 5H).

Example 277: 3-(2-{Imidazo[1,5-a]pyridin-8-yl}ethynyl)-1-[(3S,5R)-5-(methoxymethyl)-1-(prop-2-enoyl)pyrrolidin-3-yl]-5-(methylamino)pyrazole-4-carboxamide

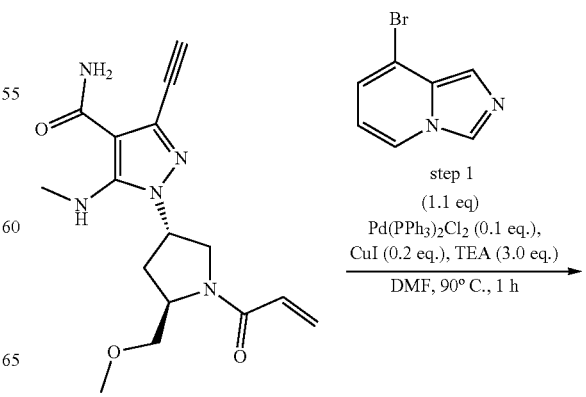

-continued

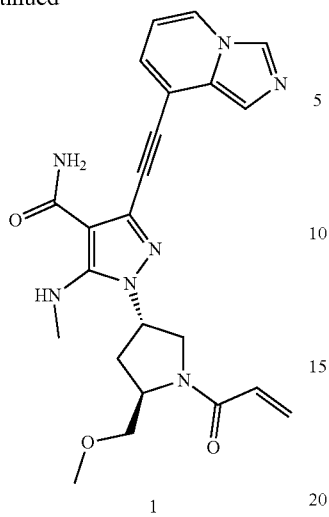

1

To a stirred solution of 3-ethynyl-1-[(3S,5R)-5-(methoxymethyl)-1-(prop-2-enoyl)pyrrolidin-3-yl]-5-(methylamino)pyrazole-4-carboxamide (0.15 g, 0.45 mmol) and 8-bromoimidazo[1,5-a]pyridine (98.11 mg, 0.49 mmol) in DMF (1.50 mL) were added Pd(PPh$_3$)$_2$Cl$_2$ (31.77 mg, 0.04 mmol) and CuI (17.24 mg, 0.09 mmol) and TEA (0.14 g, 1.35 mmol). The reaction mixture was degassed with nitrogen for three times and stirred for 1 h at 90° C. The resulting mixture was concentrated under reduced pressure. The residue was purified by silica gel column chromatography, eluted with DCM/MeOH (5/1) to afford the crude product. The crude product (150 mg) was purified by Prep-HPLC with the following conditions: Column: XBridge Shield RP18 OBD Column, 19×250 mm, 10 m; Mobile Phase A: water (10 mmol/L NH$_4$HCO$_3$), Mobile Phase B: MeOH—HPLC; Flow rate: 25 mL/min; Gradient: 50% B to 55% B in 8 min, 55% B; Wave Length: 254 nm; RT1: 6.7 min. The fractions contained desired product were combined and concentrated to afford 3-(2-{imidazo[1,5-a]pyridin-8-yl}ethynyl)-1-[(3S,5R)-5-(methoxymethyl)-1-(prop-2-enoyl)pyrrolidin-3-yl]-5-(methylamino)pyrazole-4-carboxamide (60.90 mg, 30%) as a light yellow solid. MS ESI calculated for C$_{23}$H$_{25}$N$_7$O$_3$ [M+H]$^+$, 448.49, found 448.25; $^1$H NMR (400 MHz, DMSO-d$_6$) δ 8.61-8.37 (m, 2H), 7.48-7.45 (s, 2H), 7.14-7.40 (m, 1H), 6.92-6.90 (s, 1H), 6.78-6.55 (m, 2H), 6.51-6.38 (m, 1H), 6.17-6.16 (m, 1H), 5.69-6.68 (m, 1H), 5.23-5.22 (m, 1H), 4.60-4.36 (m, 1H), 4.08-3.70 (m, 2H), 3.65-3.40 (m, 2H), 3.35-3.33 (m, 3H), 2.93-2.92 (m, 3H), 2.69-2.54 (m, 1H), 2.31-2.30 (m, 1H).

Example 278: 3-(2-{Imidazo[1,5-a]pyridin-5-yl}ethynyl)-1-[(3S,5R)-5-(methoxymethyl)-1-(prop-2-enoyl)pyrrolidin-3-yl]-5-(methylamino)pyrazole-4-carboxamide

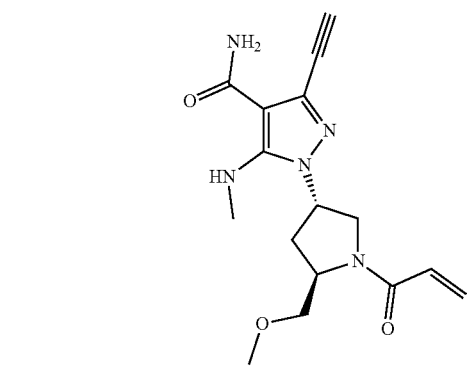

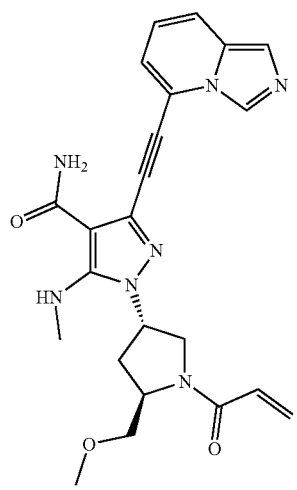

3-(2-{imidazo[1,5-a]pyridin-5-yl}ethynyl)-1-[(3S,5R)-5-(methoxymethyl)-1-(prop-2-enoyl)pyrrolidin-3-yl]-5-(methylamino)pyrazole-4-carboxamide. MS ESI calculated for C$_{23}$H$_{25}$N$_7$O$_3$ [M+H]$^+$, 448.20, found 448.15; $^1$H NMR (400 MHz, CDCl$_3$) δ 8.75-8.63 (s, 1H), 7.73 (d, J=9.2 Hz, 1H), 7.71 (s, 1H), 7.15 (s, 2H), 7.13-7.12 (m, 1H), 6.87-6.84 (m, 1H), 6.62-6.55 (m, 1H), 6.19-6.13 (m, 2H), 5.70 (d, J=4.0 Hz, 1H), 5.23-5.21 (m, 1H), 4.01 (m, 1H), 3.86-3.81 (m, 2H), 3.57-3.55 (m, 1H), 3.51-3.50 (m, 1H), 3.44 (s, 3H), 2.89 (s, 3H), 2.55-2.53 (m, 1H), 2.33-2.30 (m, 1H).

Example 279: 3-(2-{6-Chloro-1-[(1R)-2,2-difluoro-cyclopropyl]-1,3-benzodiazol-5-yl}ethynyl)-1-[(3S,5R)-5-(methoxymethyl)-1-(prop-2-enoyl)pyrrolidin-3-yl]-5-(methylamino)pyrazole-4-carboxamide
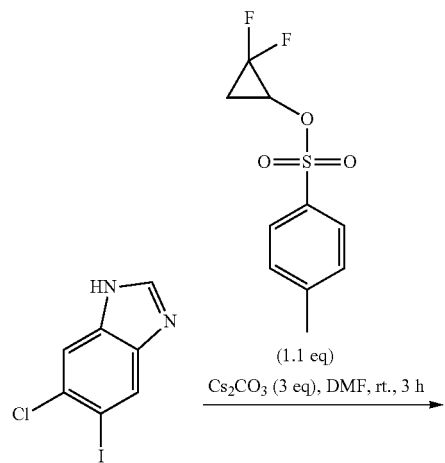
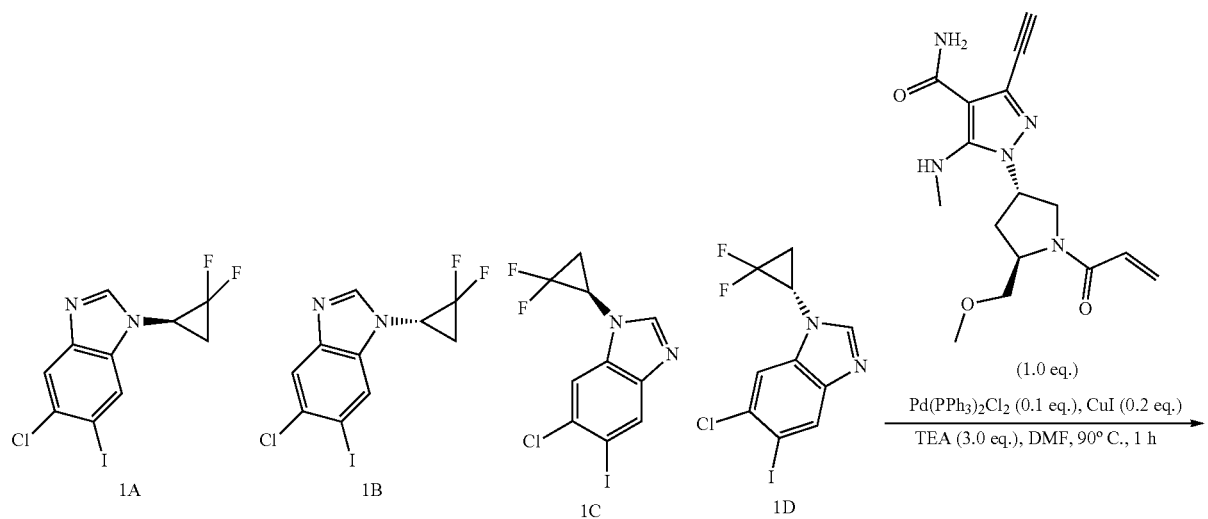

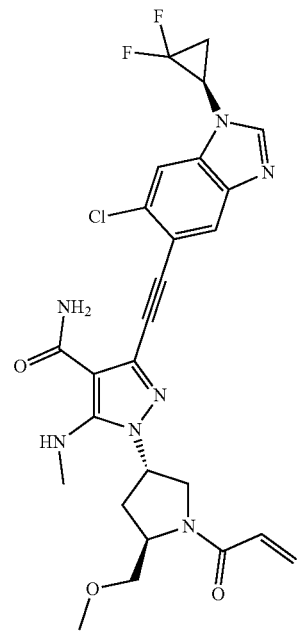

assumed

Step 1: (R)-5-chloro-1-(2,2-difluorocyclopropyl)-6-iodo-1H-benzo[d]imidazole & (S)-5-chloro-1-(2,2-difluorocyclopropyl)-6-iodo-1H-benzo[d]imidazole & (R)-6-chloro-1-(2,2-difluorocyclopropyl)-5-iodo-1H-benzo[d]imidazole & (S)-6-chloro-1-(2,2-difluorocyclopropyl)-5-iodo-1H-benzo[d]imidazole To a stirred mixture of 5-chloro-6-iodo-3H-1,3-benzodiazole (0.45 g, 1.61 mmol) and 2,2-difluorocyclopropyl 4-methylbenzenesulfonate (0.44 g, 1.77 mmol) in DMF (2.00 mL) was added $Cs_2CO_3$ (1.58 g, 4.84 mmol) in portions at room temperature under nitrogen atmosphere. The reaction mixture was stirred for 3 h at room temperature under nitrogen atmosphere. The resulting mixture was filtered, the filtrate was purified by reverse flash chromatography with the following conditions: column, C18 silica gel; mobile phase, ACN in water (10 mmol/L $NH_4HCO_3$), 10% to 50% gradient in 30 mi; detector: UV 254 nm to afford 6-chloro-1-(2,2-difluorocyclopropyl)-5-iodo-1,3-benzodiazole (320 mg). The crude product was purified by Prep-PLC with the following conditions: Column: CHIRALPAK IG, 2×25 cm, 5 m; Mobile Phase A: Hex (0.5% 2 M $NH_3$-MeOH)—HPLC, Mobile Phase B: MeOH:EtOH=1:1—HPLC; Flow rate: 20 mL/min; Gradient: 15% B to 15% B in 17 min; Wave Length: 220/254 nm; RT1: 11.40 min, RT2: 13.65 min; Sample Solvent: MeOH:DCM=1:1; Injection Volume: 0.3 mL. The faster peak contained desired product were combined and concentrated to afford (R)-5-chloro-1-(2,2-difluorocyclopropyl)-6-iodo-1H-benzo[d]imidazole (30.20 mg, 6%) as an off-white solid, MS ESI calculated for $C_{10}H_6ClF_2IN_2$ [M+H]$^+$, 355.50, found 354.80; $^1$H NMR (400 MHz, CDCl$_3$) δ 7.96 (s, 1H), 7.92 (d, J=1.4 Hz, 2H), 3.90-3.82 (m, 1H), 2.29-2.24 (m, 1H), 2.12-2.03 (m, 1H). And (S)-5-chloro-1-(2,2-difluorocyclopropyl)-6-iodo-1H-benzo[d]imidazole (40.10 mg, 7%) as an off-white solid, MS ESI calculated for $C_{10}H_6ClF_2IN_2$ [M+H]$^+$, 355.50, found 354.80; $^1$H NMR (400 MHz, CDCl$_3$) δ 7.97 (s, 1H), 7.93 (s, 2H), 3.96-3.85 (m, 1H), 2.29-2.23 (m, 1H), 2.02-1.98 (m, 1H).

The slower peak contained desired product were combined and concentrated to afford (R)-6-chloro-1-(2,2-difluorocyclopropyl)-5-iodo-1H-benzo[d]imidazole (39.89 mg, 7%) as an off-white solid, MS ESI calculated for $C_{10}H_6ClF_2IN_2$ [M+H]$^+$, 355.50, found, 354.80; $^1$H NMR (400 MHz, CDCl$_3$) δ 8.35-8.29 (m, 1H), 7.96-7.72 (m, 1H), 7.65-7.60 (m, 1H), 3.93-3.89 (m, 1H), 2.36-2.22 (m, 1H), 2.02 (ddt, J=14.4, 10.0, 5.3 Hz, 1H). And (S)-6-chloro-1-(2,2-difluorocyclopropyl)-5-iodo-1H-benzo[d]imidazole (39.62 mg, 7%) as an off-white solid. MS ESI calculated for $C_{10}H_6ClF_2IN_2$ [M+H]$^+$, 355.50, found 354.80; $^1$H NMR (400 MHz, CDCl$_3$) δ 8.29 (s, 1H), 7.91 (d, J=1.7 Hz, 1H), 7.60 (s, 1H), 3.94-3.90 (m, 1H), 2.29-2.26 (m, 1H), 2.08-1.95 (m, 1H).

Step 2: 3-(2-{6-Chloro-1-[(1R)-2,2-difluorocyclopropyl]-1,3-benzodiazol-5-yl}ethynyl)-1-[(3S,5R)-5-(methoxymethyl)-1-(prop-2-enoyl)pyrrolidin-3-yl]-5-(methylamino)pyrazole-4-carboxamide To a stirred solution of (R)-6-chloro-1-(2,2-difluorocyclopropyl)-5-iodo-1H-benzo[d]imidazole (40 mg, 0.11 mmol) and 3-ethynyl-1-[(3S,5R)-5-(methoxymethyl)-1-(prop-2-enoyl)pyrrolidin-3-yl]-5-(methylamino)pyrazole-4-carboxamide (37.39 mg, 0.11 mmol) in DMF (0.40 mL) were added Pd(PPh$_3$)$_2$Cl$_2$ (7.92 mg, 0.01 mmol) and TEA (34.25 mg, 0.34 mmol). The reaction mixture was degassed with argon for three times and stirred for 1 h at 90° C. The resulting mixture was concentrated under reduced pressure. The residue was purified by silica gel column chromatography, eluted with CH$_2$Cl$_2$/MeOH (10/1) to afford the crude product which was further purified by Prep-HPLC with the following conditions: Column: XBridge Prep OBD C18 Column, 30×150 mm, 5 m; Mobile Phase A: water (10 mmol/L NH$_4$HCO$_3$), Mobile Phase B: ACN; Flow rate: 60 mL/min; Gradient: 28% B to 38% B in 8 min, 38% B; Wave Length: 254 nm; RT1: 7 min. The fractions contained desired product were combined and concentrated to afford 3-(2-{6-chloro-1-[(1R)-2,2-difluorocyclopropyl]-1,3-benzodiazol-5-yl}ethynyl)-1-[(3S,5R)-5-(methoxymethyl)-1-(prop-2-enoyl)pyrrolidin-3-yl]-5-(methylamino)pyrazole-4-carboxamide (stereochemistry arbitrarily assigned) (20.40 mg, 32%) as an off-white solid. MS ESI calculated for C$_{26}$H$_{26}$ClF$_2$N$_7$O$_3$ [M+H]$^+$, 558.18, found, 558.20; $^1$H NMR (400 MHz, CDCl$_3$) δ 8.12 (d, J=4.9 Hz, 2H), 7.59 (s, 1H), 6.60-6.36 (m, 2H), 5.73 (dd, J=8.7, 3.6 Hz, 1H), 5.59-5.46 (m, 1H), 5.43-5.28 (m, 2H), 4.58 (d, J=8.9 Hz, 1H), 4.17-3.88 (m, 4H), 3.55-3.43 (m, 1H), 3.39 (d, J=4.8 Hz, 3H), 3.05 (d, J=15.2 Hz, 3H), 2.79-2.67 (m, 1H), 2.39-2.34 (m, 2H), 2.08-2.03 (m, 1H).

Example 280: 3-(2-{6-Chloro-1-[(1S)-2,2-difluorocyclopropyl]-1,3-benzodiazol-5-yl}ethynyl)-1-[(3S,5R)-5-(methoxymethyl)-1-(prop-2-enoyl)pyrrolidin-3-yl]-5-(methylamino)pyrazole-4-carboxamide

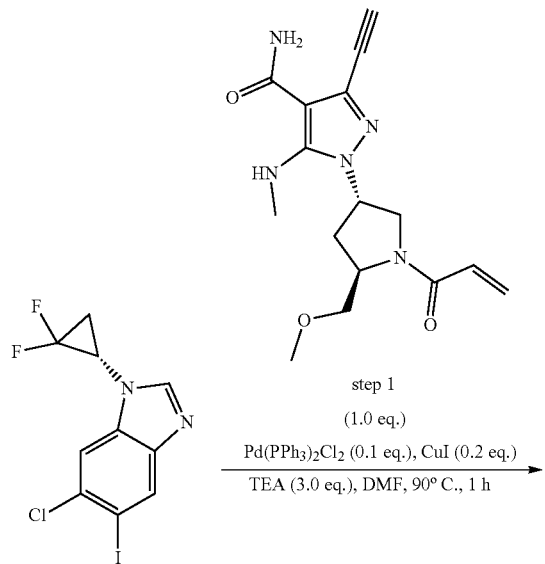

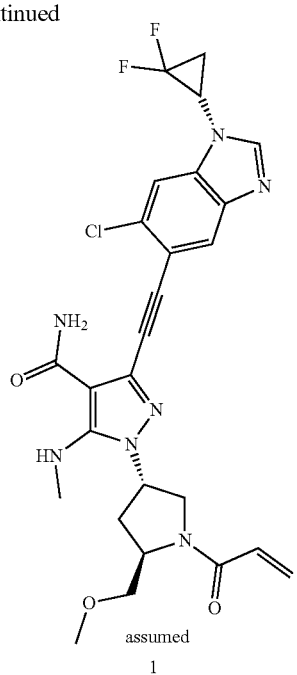

To a stirred solution of 6-chloro-1-[(1S)-2,2-difluorocyclopropyl]-5-iodo-1,3-benzodiazole (48.00 mg, 0.13 mmol), 3-ethynyl-1-[(3S,5R)-5-(methoxymethyl)-1-(prop-2-enoyl) pyrrolidin-3-yl]-5-(methylamino)pyrazole-4-carboxamide (44.87 mg, 0.13 mmol), Pd(PPh$_3$)$_2$Cl$_2$ (9.50 mg, 0.01 mmol) and CuI (5.16 mg, 0.03 mmol) in DMF (1.00 mL) was added TEA (41.10 mg, 0.41 mmol). The reaction mixture was degassed with nitrogen for three times and stirred for 1 h at 90° C. The resulting mixture was concentrated under reduced pressure. The residue was purified by silica gel column chromatography, eluted with DCM/MeOH (10/1) to afford the crude product which was further purified by reverse phase flash with the following conditions: Column: XBridge Prep OBD C18 Column, 30×150 mm, 5 m; Mobile Phase A: water (10 mmol/L NH$_4$HCO$_3$), Mobile Phase B: ACN; Flow rate: 60 mL/min; Gradient: 30% B to 35% B in 8 min, Wave Length: 254 nm. The fractions contained desired product were combined and concentrated to afford 3-(2-{6-chloro-1-[(1S)-2,2-difluorocyclopropyl]-1,3-benzodiazol-5-yl}ethynyl)-1-[(3S,5R)-5-(methoxymethyl)-1-(prop-2-enoyl)pyrrolidin-3-yl]-5-(methylamino)pyrazole-4-carboxamide (stereochemistry arbitrarily assigned) (10.70 mg, 14%) as a white solid. MS ESI calculated for C$_{26}$H$_{26}$ClF$_2$N$_7$O$_3$ [M+H]$^+$, 558.18, found 558.25; $^1$H NMR (400 MHz, CDCl$_3$) δ 8.13 (s, 1H), 8.03 (s, 1H), 7.59 (s, 1H), 7.17 (s, 1H), 6.83 (d, J=6.7 Hz, 1H), 6.44 (d, J=9.0 Hz, 2H), 5.73-5.71 (m, 1H), 5.57-5.48 (m, 1H), 5.36 (s, 1H), 4.58 (d, J=9.0 Hz, 1H), 4.15-4.04 (m, 2H), 3.93 (s, 2H), 3.60-3.31 (m, 4H), 3.07-3.02 (m, 3H), 2.77-2.72 (m, 1H), 2.34 (s, 2H), 2.04 (t, J=6.8 Hz, 1H).

Example 281: 3-[2-(6-chloro-4-methylquinolin-7-yl)ethynyl]-1-[(3S,5R)-5-(methoxymethyl)-1-(prop-2-enoyl)pyrrolidin-3-yl]-5-(methylamino)pyrazole-4-carboxamide

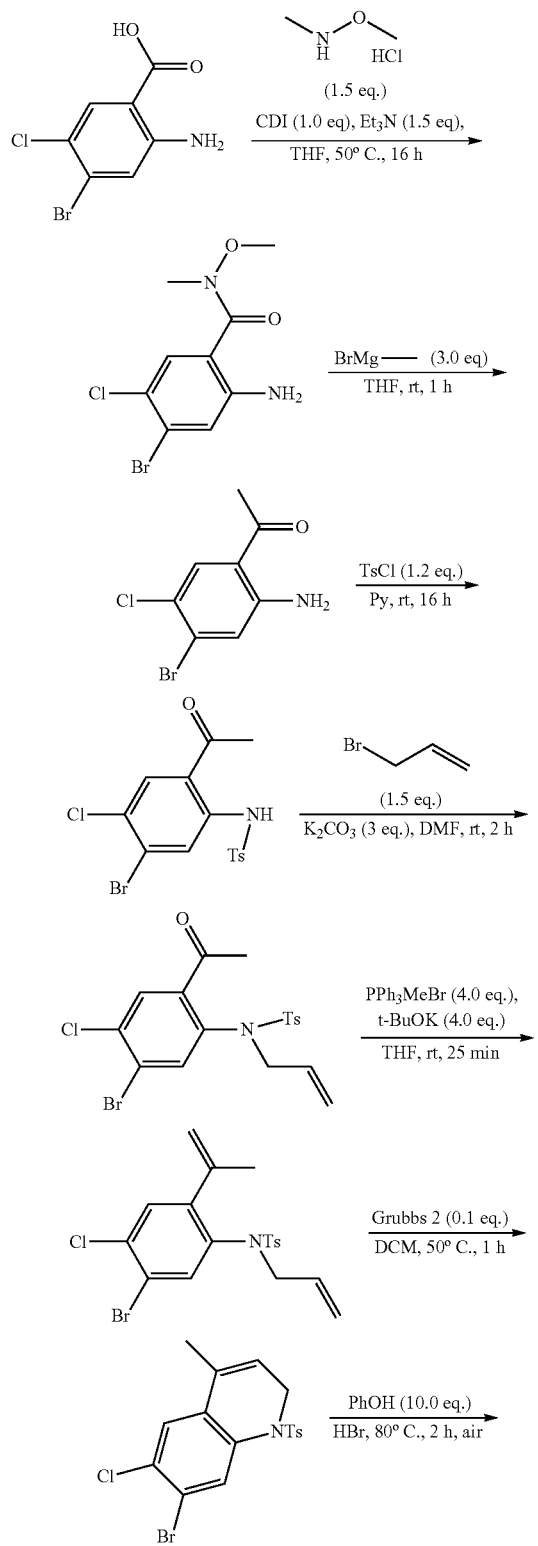

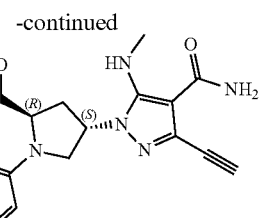

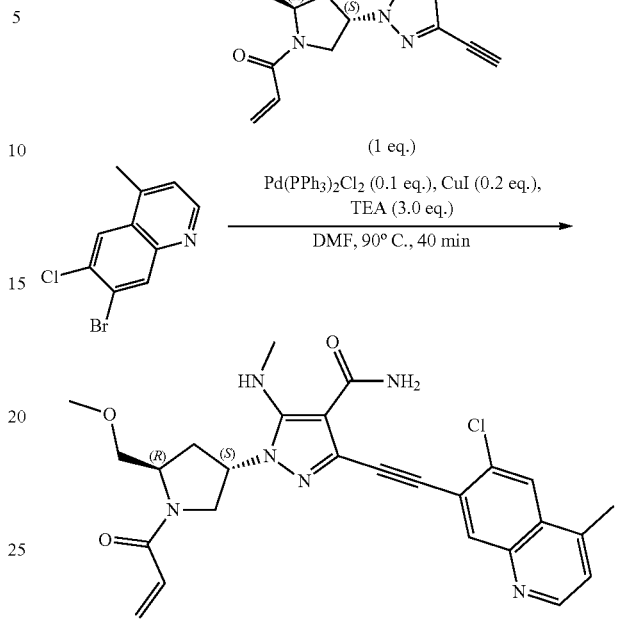

3-[2-(6-chloro-4-methylquinolin-7-yl)ethynyl]-1-[(3S,5R)-5-(methoxymethyl)-1-(prop-2-enoyl)pyrrolidin-3-yl]-5-(methylamino)pyrazole-4-carboxamide. MS ESI calculated for $C_{26}H_{27}ClN_6O_3$ [M+H]$^+$, 507.18, found 507.25; $^1$H NMR (400 MHz, CDCl$_3$) δ 8.84 (s, 1H), 8.44 (s, 1H), 8.09 (s, 1H), 7.32 (s, 1H), 7.12 (s, 1H), 6.85 (s, 1H), 6.48-6.40 (m, 2H), 5.85-5.73 (m, 1H), 5.57-5.32 (m, 2H), 4.59 (d, J=9.0 Hz, 1H), 4.22-4.10 (m, 2H), 3.93 (d, J=8.5 Hz, 1H), 3.47 (d, J=9.6 Hz, 1H), 3.40 (d, J=4.6 Hz, 3H), 3.20-3.06 (m, 3H), 2.71 (s, 4H), 2.50-2.34 (m, 1H).

Example 282: 1-((3S,5R)-1-Acryloyl-5-(methoxymethyl)pyrrolidin-3-yl)-3-((6-fluoro-3,4-dimethylquinolin-7-yl)ethynyl)-5-(methylamino)-1H-pyrazole-4-carboxamide

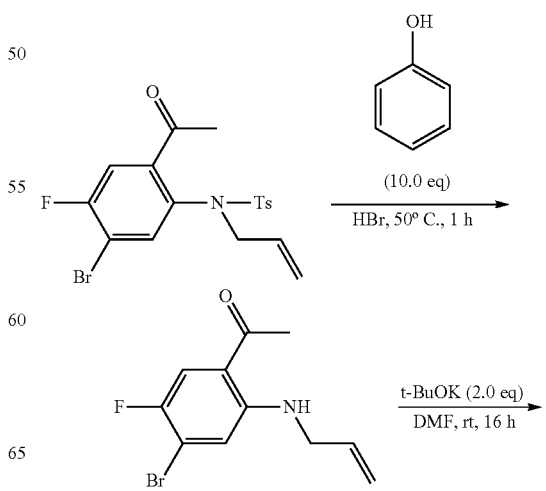

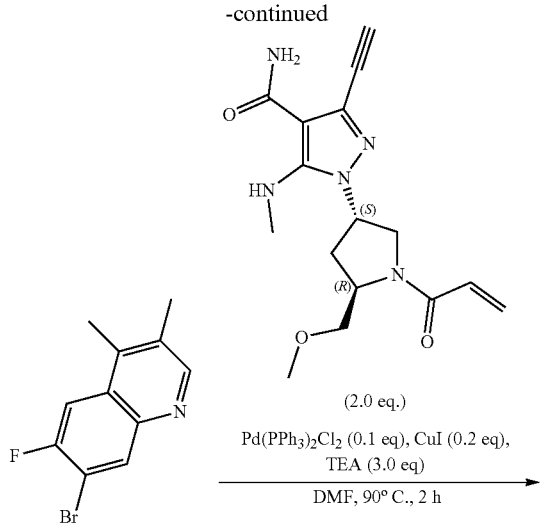

Step 1: 1-[4-Bromo-5-fluoro-2-(prop-2-en-1-ylamino)phenyl]ethanone

To a stirred mixture of N-(2-acetyl-5-bromo-4-fluorophenyl)-N-allyl-4-methylbenzenesulfonamide (0.50 g, 1.17 mmol) in HBr (5.00 mL) was added phenol (1.10 g, 11.73 mmol) at room temperature under nitrogen atmosphere. The reaction mixture was stirred for 1 h at 50° C. under nitrogen atmosphere. The resulting mixture was concentrated under vacuum. The residue was purified by silica gel column chromatography, eluted with PE/EA (5/1). The fractions contained desired product were combined and concentrated to afford 1-[4-bromo-5-fluoro-2-(prop-2-en-1-ylamino)phenyl]ethanone (0.24 g, 75%) as a yellow solid. MS ESI calculated for $C_{11}H_{11}BrFNO$ [M+H]$^+$, 272.00, 274.00, found 271.90, 273.90; $^1$H NMR (400 MHz, Chloroform-d) δ 8.85 (s, 1H), 7.49 (d, J=9.6 Hz, 1H), 6.88 (d, J=5.7 Hz, 1H), 5.93 (m, 1H), 5.35-5.15 (m, 2H), 3.86 (m, 2H), 2.57 (s, 3H).

Step 2: 7-bromo-6-fluoro-3,4-dimethylquinoline

To a stirred mixture of 1-[4-bromo-5-fluoro-2-(prop-2-en-1-ylamino)phenyl]ethanone (0.20 g, 0.74 mmol) in DMF (7.00 mL) was added t-BuOK (0.17 g, 1.47 mmol) in portions at room temperature under nitrogen atmosphere. The reaction mixture was stirred for 16 h at room temperature under nitrogen atmosphere. The residue was purified by reverse flash chromatography with the following conditions: column: C18 silica gel; mobile phase: ACN in water (10 mmol/L $NH_4HCO_3$), 30% to 70% gradient in 25 min; detector: UV 254 nm. The fractions contained desired product were combined and concentrated to afford 7-bromo-6-fluoro-3,4-dimethylquinoline (63.00 mg, 34%) as a yellow solid. MS ESI calculated for $C_{11}H_9BrFN$ [M+H]$^+$, 253.99, 255.99. found 253.65, 255.65.

Step 3. 1-((3S,5R)-1-Acryloyl-5-(methoxymethyl)pyrrolidin-3-yl)-3-((6-fluoro-3,4-dimethylquinolin-7-yl)ethynyl)-5-(methylamino)-1H-pyrazole-4-carboxamide To a stirred mixture of 7-bromo-6-fluoro-3,4-dimethylquinoline (50.00 mg, 0.20 mmol) and 1-((3S,5R)-1-acryloyl-5-(methoxymethyl)pyrrolidin-3-yl)-3-ethynyl-5-(methylamino)-1H-pyrazole-4-carboxamide (0.13 g, 0.40 mmol) in DMF (0.50 mL) was added Pd(PPh$_3$)$_2$Cl$_2$ (13.81 mg, 0.02 mmol), CuI (7.50 mg, 0.04 mmol) TEA (59.73 mg, 0.59 mmol) at room temperature under nitrogen atmosphere. The reaction mixture was degassed with nitrogen for three times and stirred for 2 h at 90° C. The resulting mixture was concentrated under vacuum. The residue was purified by silica gel column chromatography, eluted with DCM/MeOH (10/1) to afford the crude product which was further purified by Prep-HPLC with the following conditions: Column: XBridge Shield RP18 OBD Column, 30×150 mm, 5 m; Mobile Phase A: water (10 mmol/L $NH_4HCO_3$), Mobile Phase B: ACN; Flow rate: 60 mL/min; Gradient: 34% B to 44% B in 10 min, 44% B; Wave Length: 220 nm; RT1: 9 min. The fractions contained desired product were combined and concentrated to afford 1-((3S,5R)-1-acryloyl-5-(methoxymethyl)pyrrolidin-3-yl)-3-((6-fluoro-3,4-dimethylquinolin-7-yl)ethynyl)-5-(methylamino)-1H-pyrazole-4-carboxamide (25.50 mg, 25%) as an off-white solid. MS ESI calculated for $C_{27}H_{29}FN_6O_3$ [M+H]$^+$, 505.23, found 505.35; $^1$H NMR (400 MHz, Chloroform-d) δ 8.71 (s, 1H), 8.30 (d, J=7.1 Hz, 1H), 7.67 (d, J=11.1 Hz, 1H), 7.07 (s, 1H), 6.86 (d, J=6.0 Hz, 1H), 6.60-6.37 (m, 2H), 5.73 (m, 1H), 5.62-5.20 (m, 2H), 4.58 (d, J=9.0 Hz, 1H), 4.18-3.88 (m, 3H), 3.56-3.43 (m, 1H), 3.39 (d, J=4.7 Hz, 3H), 3.06 (dd, J=15.7, 5.9 Hz, 3H), 2.80-2.67 (m, 1H), 2.58 (s, 3H), 2.50 (s, 3H), 2.37 (m, 1H).

Example 283: 3-(2-{3-Cyclopropyl-6-fluoroimidazo[1,2-a]pyridin-7-yl}ethynyl)-1-[(3S,5R)-5-(methoxymethyl)-1-(prop-2-enoyl)pyrrolidin-3-yl]-5-(methylamino)pyrazole-4-carboxamide Example 284: 3-(2-{3-Cyclopropyl-4-methoxypyrazolo[1,5-a]pyridin-6-yl}ethynyl)-1-[(3S,5R)-5-(methoxymethyl)-1-(prop-2-enoyl)pyrrolidin-3-yl]-5-(methylamino)pyrazole-4-carboxamide

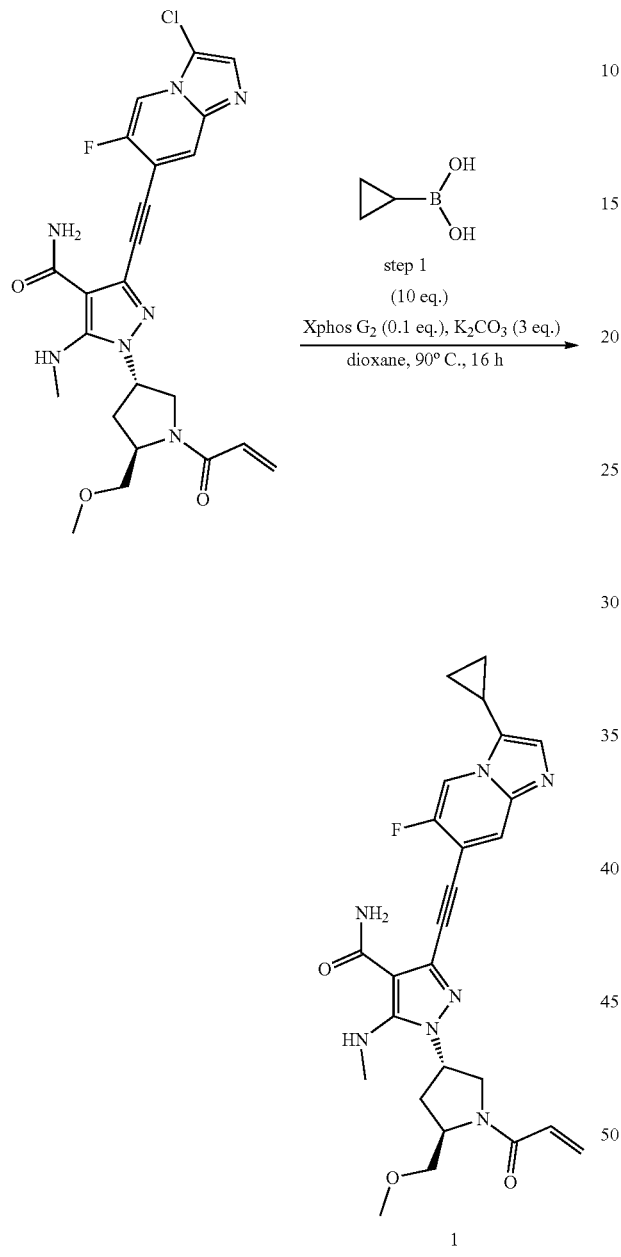

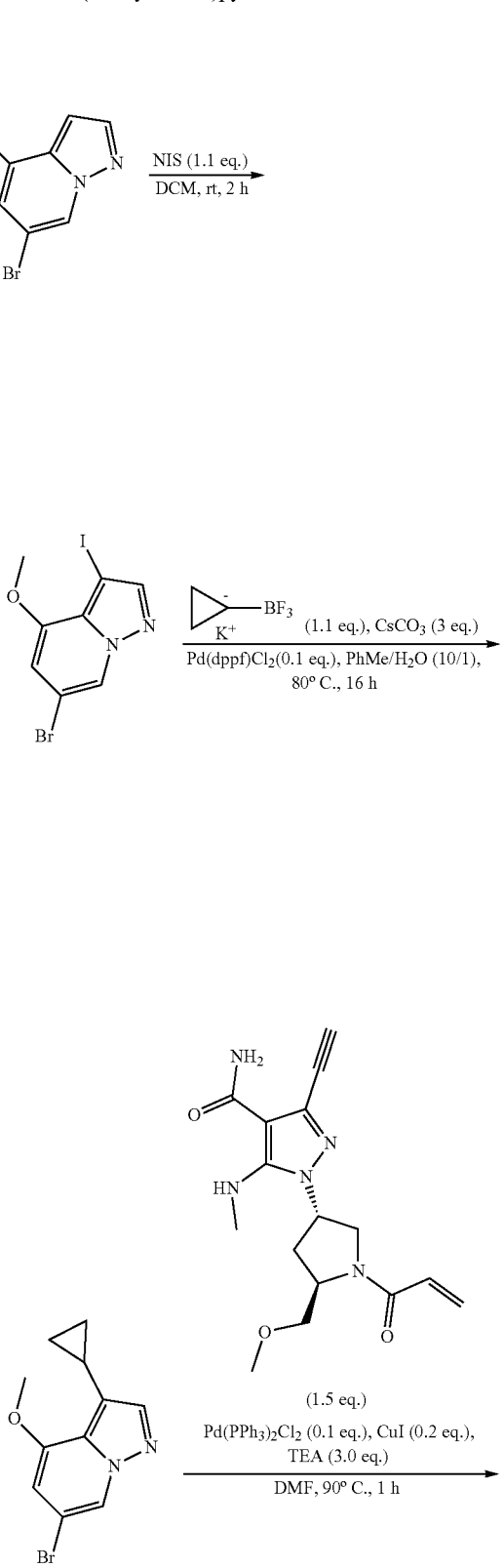

3-(2-{3-cyclopropyl-6-fluoroimidazo[1,2-a]pyridin-7-yl}ethynyl)-1-[(3S,5R)-5-(methoxymethyl)-1-(prop-2-enoyl)pyrrolidin-3-yl]-5-(methylamino)pyrazole-4-carboxamide. MS ESI calculated for $C_{26}H_{28}FN_7O_3$ [M+H]$^+$, 506.22, found 506.25; $^1$H NMR (400 MHz, CDCl$_3$) δ 6.88-6.70 (m, 2H), 6.44 (d, J=8.6 Hz, 2H), 5.85-5.73 (m, 1H), 5.52 (d, J=9.6 Hz, 1H), 5.33 (s, 1H), 4.60-4.43 (m, 1H), 4.20-4.06 (m, 2H), 3.93 (d, J=9.7 Hz, 1H), 3.50 (d, J=22.2 Hz, 1H), 3.39 (s, 3H), 3.05 (d, J=15.1 Hz, 3H), 2.75-2.65 (m, 1H), 2.45-2.33 (m, 1H), 1.96 (s, 1H), 1.14 (d, J=7.5 Hz, 2H), 0.77 (s, 2H).

847
-continued

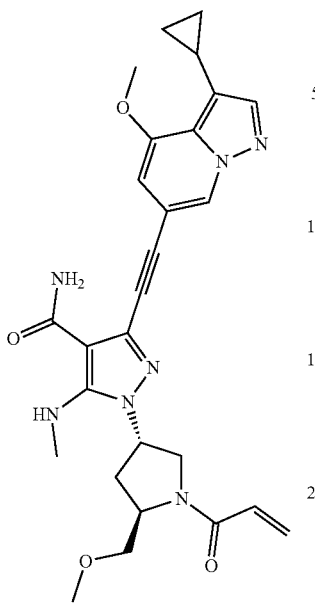

3-(2-{3-cyclopropyl-4-methoxypyrazolo[1,5-a]pyridin-6-yl}ethynyl)-1-[(3S,5R)-5-(methoxymethyl)-1-(prop-2-enoyl)pyrrolidin-3-yl]-5-(methylamino)pyrazole-4-carboxamide. MS ESI calculated for $C_{27}H_{31}N_7O_4$ [M+H]$^+$, 518.24, found 518.40; $^1$H NMR (400 MHz, Chloroform-d) δ 8.30 (s, 1H), 7.55 (s, 1H), 6.75 (s, 1H), 6.57-6.40 (m, 2H), 6.35 (s, 1H), 5.72-5.64 (m, 1H), 5.55-5.28 (m, 2H), 4.58 (d, J=8.9 Hz, 1H), 4.16-3.90 (m, 6H), 3.50-3.41 (m, 1H), 3.39 (d, J=4.5 Hz, 3H), 3.06 (d, J=14.2 Hz, 3H), 2.71-2.48 (m, 1H), 2.44-2.30 (m, 2H), 1.01-0.95 (m, 2H), 0.73-0.63 (m, 2H).

Example 285: 1-((3S,5R)-1-Acryloyl-5-(methoxymethyl)pyrrolidin-3-yl)-3-((7-chloro-2,3-dihydro-1H-benzo[d]pyrrolo[1,2-a]imidazol-6-yl)ethynyl)-5-(methylamino)-1H-pyrazole-4-carboxamide

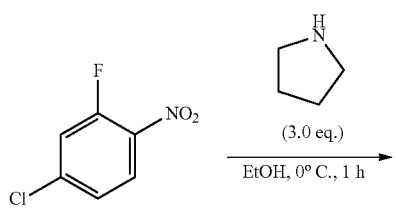

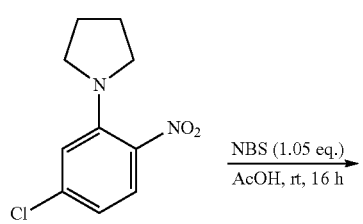

848
-continued

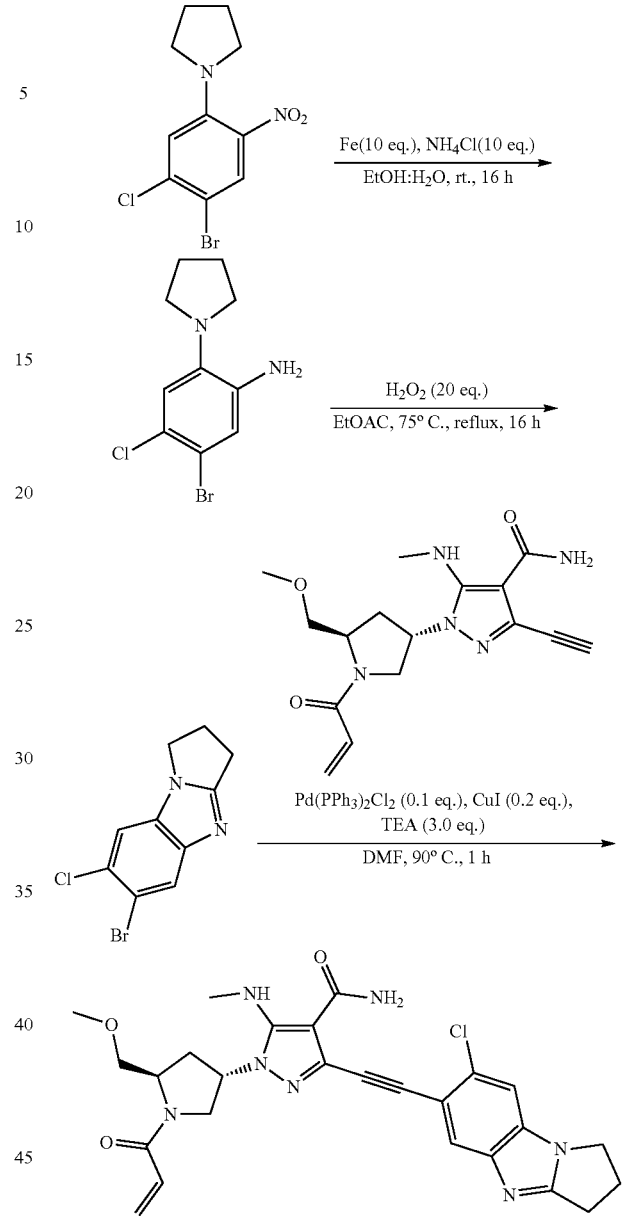

Step 1: 1-(5-Chloro-2-nitrophenyl) pyrrolidine

To a stirred solution of 4-chloro-2-fluoro-1-nitrobenzene (3.30 g, 18.80 mmol) in EtOH (30 mL) was added pyrrolidine (4.01 g, 56.40 mmol) at 0° C. The reaction mixture was stirred for 1 h at 0° C. The resulting mixture was diluted with water (100 mL) and extracted with EtOAc (3×200 mL). The combined organic layers was washed with brine (3×100 mL), dried over anhydrous $Na_2SO_4$. After filtration, the filtrate was concentrated under reduced pressure to afford 1-(5-chloro-2-nitrophenyl) pyrrolidine (3.60 g, crude) as an orange solid. MS ESI calculated for $C_{10}H_{11}ClN_2O_2$ [M+H]$^+$, 227.05, found 226.95; $^1$H NMR (400 MHz, CDCl$_3$) δ 7.70 (d, J=8.8 Hz, 1H), 6.91 (d, J=2.1 Hz, 1H), 6.69 (dd, J=8.8, 2.1 Hz, 1H), 3.30-3.19 (m, 4H), 2.09-1.95 (m, 4H).

Step 2: 1-(4-Bromo-5-chloro-2-nitrophenyl) pyrrolidine

To a stirred solution of 1-(5-chloro-2-nitrophenyl) pyrrolidine (1.80 g, 7.94 mmol) in AcOH (20.00 mL) was added NBS (1.48 g, 8.34 mmol) in portions at 0° C. The reaction mixture was stirred for 16 h at room temperature. The resulting mixture was concentrated under reduced pressure. The residue was purified by silica gel column chromatography, eluted with PE/EA (12/1). The fractions contained desired product were combined and concentrated to afford 1-(4-bromo-5-chloro-2-nitrophenyl) pyrrolidine (2.50 g, 97%) as an orange solid. MS ESI calculated for $C_{10}H_{10}BrClN_2O_2$ [M+H]$^+$, 304.97, 306.97, found 305.05, 307.05.

Step 3: 5-Bromo-4-chloro-2-(pyrrolidin-1-yl) aniline

To a stirred solution of 1-(4-bromo-5-chloro-2-nitrophenyl) pyrrolidine (2.50 g, 8.18 mmol) and $NH_4Cl$ (4.38 g, 81.82 mmol) in EtOH (20.00 mL) and $H_2O$ (5.00 mL) was added Fe (4.57 g, 81.82 mmol) in portions at room temperature. The reaction mixture was stirred for 16 h at room temperature. The resulting mixture was filtered, the filter cake was washed with EtOAc (5×50 mL). The filtrate was concentrated under reduced pressure. The residue was purified by silica gel column chromatography, eluted with PE/EA (12/1). The fractions contained desired product were combined and concentrated to afford 5-bromo-4-chloro-2-(pyrrolidin-1-yl) aniline (1.80 g, 79%) as a dark red solid. MS ESI calculated for $C_{10}H_{12}BrClN_2$ [M+H]$^+$, 274.99, 276.99, found 275.10, 277.10.

Step 4: 6-Bromo-7-chloro-2,3-dihydro-1H-benzo[d] pyrrolo[1,2-a]imidazole

To a stirred solution of 5-bromo-4-chloro-2-(pyrrolidin-1-yl)aniline (1.80 g, 6.53 mmol) in EtOAc (20.00 mL) was added $H_2O_2$ (14.81 g, 0.13 mol, 30%) dropwise at room temperature. The reaction mixture was stirred for 16 h at 75° C. The resulting mixture was diluted with water (10 mL) and extracted with EtOAc (5×50 mL). The combined organic layers was washed with brine (2×100 mL), dried over anhydrous $Na_2SO_4$. After filtration, the filtrate was concentrated under reduced pressure. The residue was purified by silica gel column chromatography, eluted with $CH_2Cl_2$/MeOH (12/1) The fractions contained desired product were combined and concentrated to afford 6-bromo-7-chloro-2,3-dihydro-1H-benzo[d]pyrrolo[1,2-a]imidazole (1.20 g, 60%) as a brown solid. MS ESI calculated for $C_{10}H_8BrClN_2$ [M+H]$^+$, 270.96, 272.96, found 270.90, 272.90; $^1$H NMR (400 MHz, CDCl$_3$) δ 7.95 (s, 1H), 7.44 (s, 1H), 4.18-4.07 (m, 2H), 3.09 (dd, J=8.3, 7.1 Hz, 2H), 2.83-2.71 (m, 2H).

Step 5: 1-((3S,5R)-1-Acryloyl-5-(methoxymethyl) pyrrolidin-3-yl)-3-((7-chloro-2,3-dihydro-1H-benzo [d]pyrrolo[1,2-a]imidazol-6-yl)ethynyl)-5-(methylamino)-1H-pyrazole-4-carboxamide To a stirred mixture of 6-bromo-7-chloro-2,3-dihydro-1H-benzo[d]pyrrolo[1,2-a]imidazole (0.16 g, 0.60 mmol), 3-ethynyl-1-[(3S,5R)-5-(methoxymethyl)-1-(prop-2-enoyl) pyrrolidin-3-yl]-5-(methylamino)pyrazole-4-carboxamide (0.20 g, 0.60 mmol), Pd(PPh$_3$)$_2$Cl$_2$ (42.36 mg, 0.06 mmol) and CuI (22.99 mg, 0.12 mmol) in DMF (2.00 mL) was added TEA (0.18 g, 1.81 mmol) dropwise at room temperature. The reaction mixture was degassed with nitrogen for three times and stirred for 1 h at 90° C. The resulting mixture was concentrated under reduced pressure. The residue was purified by silica gel column chromatography, eluted with $CH_2Cl_2$/MeOH (10/1) to afford the crude product which was further purified by reverse flash chromatography with the following conditions: column: C18 silica gel; mobile phase: ACN in water (10 mmol/L $NH_4HCO_3$), 5% to 70% gradient in 40 min; detector: UV 254 nm. The fractions contained desired product were combined and concentrated to afford 1-((3S,5R)-1-acryloyl-5-(methoxymethyl)pyrrolidin-3-yl)-3-((7-chloro-2,3-dihydro-1H-benzo[d]pyrrolo[1,2-a]imidazol-6-yl)ethynyl)-5-(methylamino)-1H-pyrazole-4-carboxamide (26.20 mg, 8%) as an off-white solid. MS ESI calculated for $C_{26}H_{28}ClN_7O_3$ [M+H]$^+$, 522.20, found 522.35; $^1$H NMR (400 MHz, CDCl$_3$) δ 8.03 (s, 1H), 7.48 (s, 1H), 7.19 (s, 1H), 6.83 (s, 1H), 6.56-6.40 (m, 2H), 5.76-5.69 (m, 1H), 5.56-5.47 (m, 1H), 5.37 (s, 1H), 4.61-4.54 (m, 1H), 4.21-4.10 (m, 3H), 4.04 (t, J=9.1 Hz, 1H), 3.92 (d, J=9.6 Hz, 1H), 3.56-3.43 (m, 1H), 3.39 (d, J=4.4 Hz, 3H), 3.15 (s, 2H), 3.05 (d, J=15.3 Hz, 3H), 2.83-2.62 (m, 3H), 2.33 (s, 1H).

Example 287: 1-((3S,5R)-1-Acryloyl-5-(methoxymethyl)pyrrolidin-3-yl)-3-((1-cyclopropyl-5-fluoro-1H-indazol-4-yl)ethynyl)-5-(methylamino)-1H-pyrazole-4-carboxamide

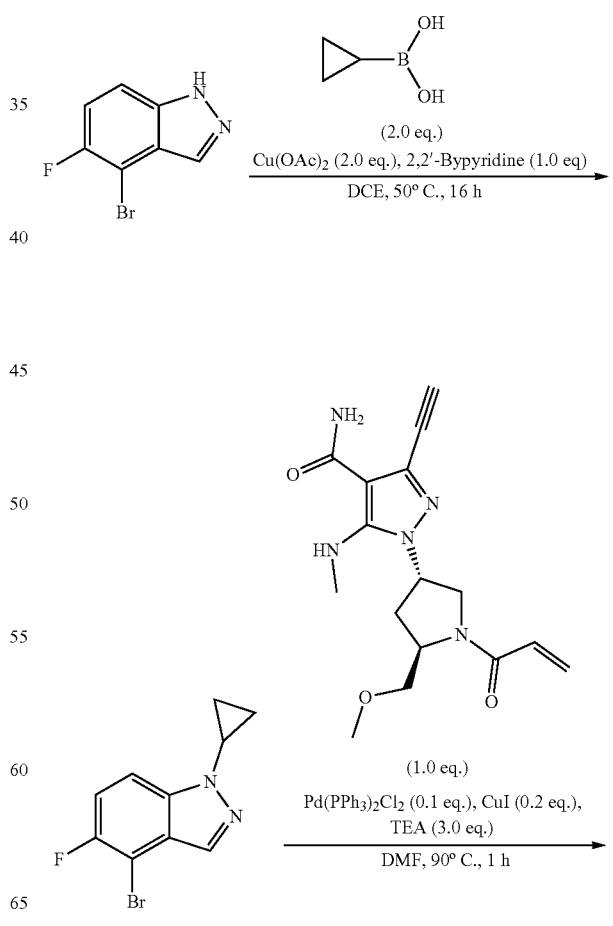

-continued

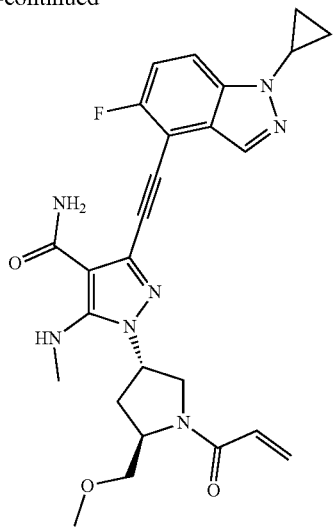

Step 1: 4-Bromo-1-cyclopropyl-5-fluoro-1H-indazole

To a stirred mixture of 4-bromo-5-fluoro-1H-indazole (0.50 g, 2.33 mmol), cyclopropylboronic acid (0.40 g, 4.65 mmol) and 2-(pyridin-2-yl)pyridine (0.36 g, 2.33 mmol) in DCE (10.00 mL) was added Cu(OAc)$_2$ (0.84 g, 4.65 mmol). The reaction mixture was stirred for 16 h at 50° C. under oxygen atmosphere. The resulting mixture was concentrated under reduced pressure. The residue was purified by silica gel column chromatography, eluted with PE/EA (1/1). The fractions contained desired product were combined and concentrated to afford 4-bromo-1-cyclopropyl-5-fluoro-1H-indazole (0.16 g, 27%) as a light orange solid. MS ESI calculated for C$_{10}$H$_8$BrFN$_2$ [M+H]$^+$, 254.99, 256.99, found 254.95, 256.95; $^1$H NMR (400 MHz, Chloroform-d) δ 7.95 (s, 1H), 7.51 (dd, J=9.0, 3.7 Hz, 1H), 7.21 (t, J=8.8 Hz, 1H), 3.66-3.56 (m, 1H), 1.25-1.19 (m, 4H).

Step 2: 1-((3S,5R)-1-Acryloyl-5-(methoxymethyl) pyrrolidin-3-yl)-3-((1-cyclopropyl-5-fluoro-1H-indazol-4-yl)ethynyl)-5-(methylamino)-1H-pyrazole-4-carboxamide To a stirred mixture of 4-bromo-1-cyclopropyl-5-fluoro-1H-indazole (0.16 g, 0.63 mmol), 3-ethynyl-1-[(3S,5R)-5-(methoxymethyl)-1-(prop-2-enoyl)pyrrolidin-3-yl]-5-(methylamino)pyrazole-4-carboxamide (0.21 g, 0.63 mmol), Pd(PPh$_3$)$_2$Cl$_2$ (44.03 mg, 0.06 mmol) and CuI (23.89 mg, 0.13 mmol) in DMF (2.00 mL) was added TEA (0.19 g, 1.88 mmol) at room temperature. The reaction mixture was degassed with nitrogen for three times and stirred for 1 h at 90° C. The resulting mixture was concentrated under reduced pressure. The residue was purified by silica gel column chromatography, eluted with CH$_2$Cl$_2$/MeOH (10/1) to afford the crude product. The crude product was purified by reverse flash chromatography with the following conditions: column: C18 silica gel; mobile phase: ACN in water (10 mmol/L NH$_4$HCO$_3$), 10% to 50% gradient in 30 min; detector: UV 254 nm. The fractions contained desired product were combined and concentrated to afford 1-((3S,5R)-1-acryloyl-5-(methoxymethyl)pyrrolidin-3-yl)-3-((1-cyclopropyl-5-fluoro-1H-indazol-4-yl)ethynyl)-5-(methylamino)-1H-pyrazole-4-carboxamide (47.40 mg, 15%) as a white solid. MS ESI calculated for C$_{26}$H$_{28}$FN$_7$O$_3$ [M+H]$^+$, 506.22, found 506.30; $^1$H NMR (400 MHz, DMSO-d$_6$) δ 8.09 (d, J=3.4 Hz, 1H), 7.87 (dd, J=9.3, 4.0 Hz, 1H), 7.68-7.39 (m, 2H), 6.91 (s, 1H), 6.80-6.43 (m, 2H), 6.17 (dd, J=16.7, 2.4 Hz, 1H), 5.69 (dd, J=10.3, 2.4 Hz, 1H), 5.36-5.14 (m, 1H), 4.47 (d, J=57.4 Hz, 1H), 4.09-3.98 (m, 1H), 3.95-3.69 (m, 2H), 3.68-3.42 (m, 2H), 3.31 (d, J=4.8 Hz, 3H), 2.94 (t, J=5.3 Hz, 3H), 2.72-2.55 (m, 1H), 2.38-2.23 (m, 1H), 1.23-1.04 (m, 4H).

Example 288: 3-(2-{6-Chloro-3-[(1R)-2,2-difluorocyclopropyl]-1,3-benzodiazol-5-yl}ethynyl)-1-[(3S,5R)-5-(methoxymethyl)-1-(prop-2-enoyl)pyrrolidin-3-yl]-5-(methylamino)pyrazole-4-carboxamide

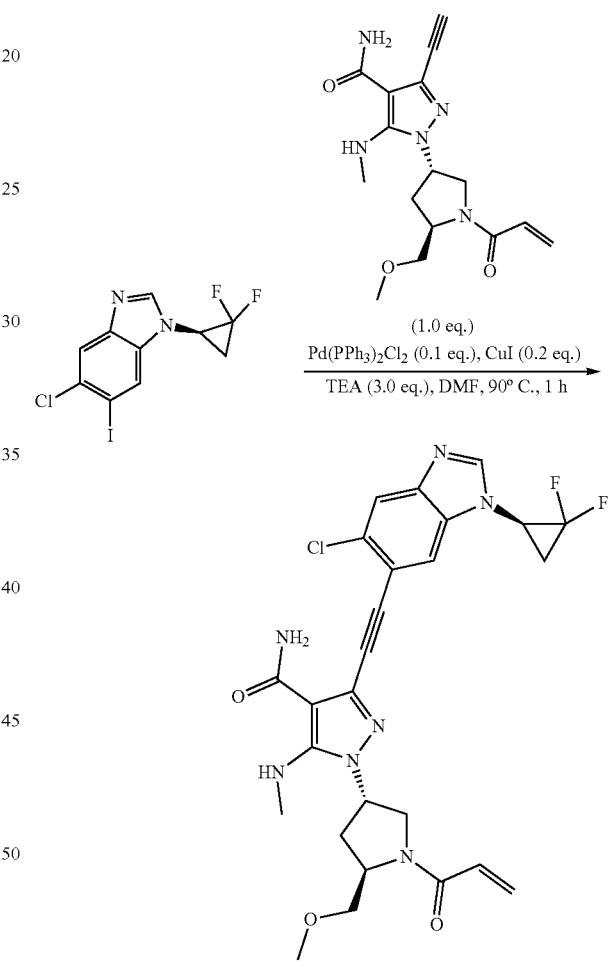

3-(2-{6-chloro-3-[(1R)-2,2-difluorocyclopropyl]-1,3-benzodiazol-5-yl}ethynyl)-1-[(3S,5R)-5-(methoxymethyl)-1-(prop-2-enoyl)pyrrolidin-3-yl]-5-(methylamino)pyrazole-4-carboxamide (stereochemistry arbitrarily assigned). MS ESI calculated for C$_{26}$H$_{26}$ClF$_2$N$_7$O$_3$ [M+H]$^+$, 558.20, found 558.25; $^1$H NMR (400 MHz, CDCl$_3$) δ 8.07 (s, 1H), 7.91 (s, 1H), 7.84 (s, 1H), 7.29 (s, 2H), 6.45 (dd, J=12.4, 7.3 Hz, 2H), 5.73 (dd, J=8.2, 4.4 Hz, 1H), 5.58-5.30 (m, 2H), 4.60 (d, J=9.0 Hz, 1H), 4.08 (dt, J=19.2, 9.2 Hz, 2H), 3.92 (d, J=13.5 Hz, 1H), 3.50 (dd, J=22.8, 6.7 Hz, 2H), 3.40 (d, J=5.0

Hz, 3H), 3.06 (d, J=13.2 Hz, 3H), 2.76-2.71 (m, 1H), 2.35 (dd, J=12.7, 7.2 Hz, 2H), 2.04 (s, 1H).

Example 289: 3-(2-{6-Chloro-3-[(1S)-2,2-difluorocyclopropyl]-1,3-benzodiazol-5-yl}ethynyl)-1-[(3S,5R)-5-(methoxymethyl)-1-(prop-2-enoyl)pyrrolidin-3-yl]-5-(methylamino)pyrazole-4-carboxamide

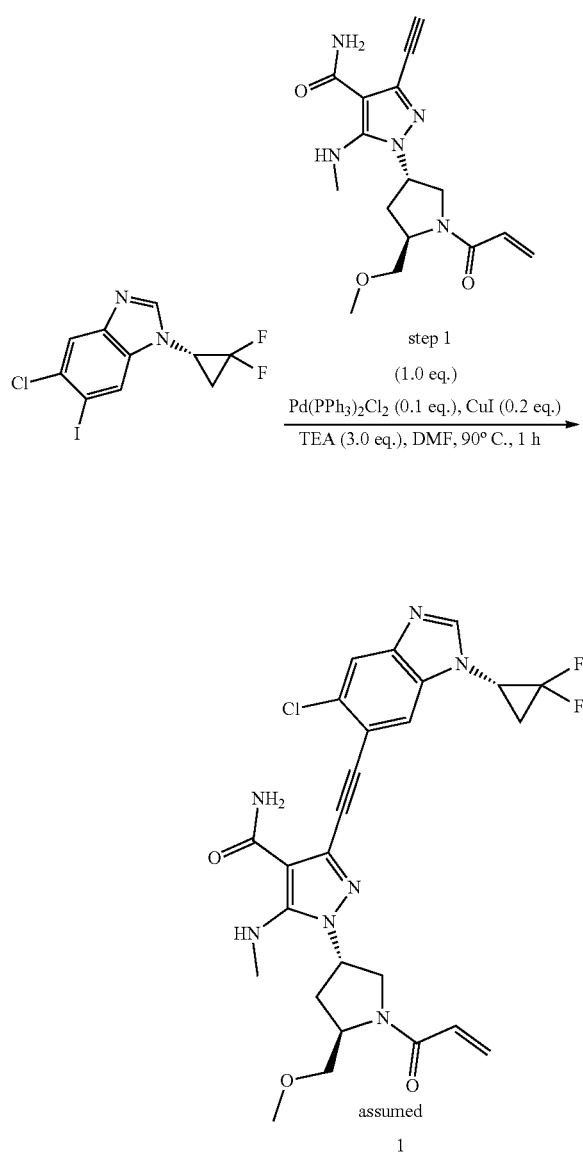 [SMILES: FC1(F)C[C@@H]1n1cnc2cc(Cl)c(I)cc21 ; C#Cc1nn([C@H]2C[C@H](COC)N(C(=O)C=C)C2)c(NC)c1C(N)=O ; C=CC(=O)N1C[C@@H](n2nc(C#Cc3cc4c(cc3Cl)ncn4[C@H]3CC3(F)F)c(C(N)=O)c2NC)C[C@@H]1COC]

3-(2-{6-chloro-3-[(1S)-2,2-difluorocyclopropyl]-1,3-benzodiazol-5-yl}ethynyl)-1-[(3S,5R)-5-(methoxymethyl)-1-(prop-2-enoyl)pyrrolidin-3-yl]-5-(methylamino)pyrazole-4-carboxamide (stereochemistry arbitrarily assigned). MS ESI calculated for $C_{26}H_{26}ClF_2N_7O_3$ [M+H]$^+$, 558.18, found 558.25; $^1$H NMR (400 MHz, CDCl$_3$) δ 8.14 (s, 1H), 7.89 (d, J=25.4 Hz, 2H), 7.21 (s, 1H), 6.57-6.35 (m, 2H), 5.74-5.71 (m, 1H), 5.55-5.51 (m, 1H), 5.44-5.26 (m, 1H), 4.62-4.35 (m, 1H), 4.13-4.05 (m, 2H), 4.01-3.85 (m, 2H), 3.55-3.39 (m, 4H), 3.06 (d, J=13.0 Hz, 3H), 2.76-2.71 (m, 1H), 2.42-2.28 (m, 2H), 2.09-2.02 (m, 1H).

Example 290: 3-(2-{3-Chloro-6-fluoroimidazo[1,2-a]pyridin-7-yl}ethynyl)-1-[(3S,5R)-5-(methoxymethyl)-1-(prop-2-enoyl)pyrrolidin-3-yl]-5-(methylamino)pyrazole-4-carboxamide

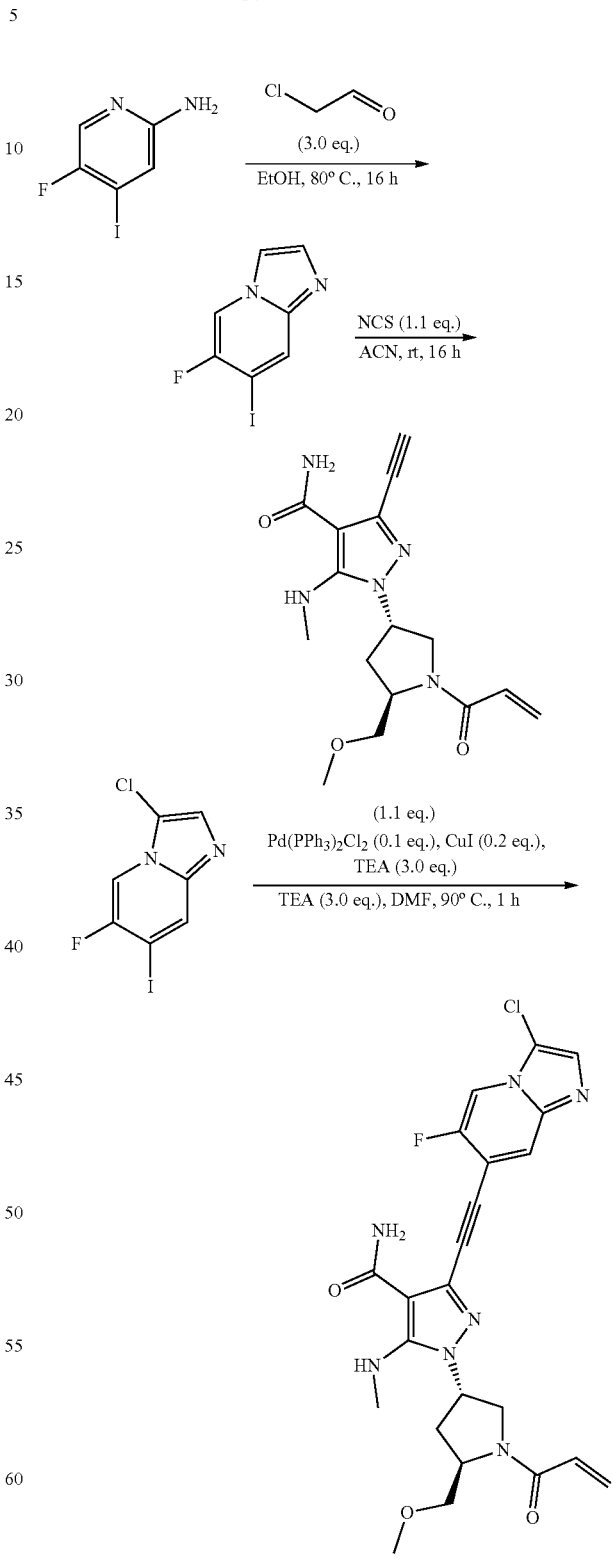

3-(2-{3-chloro-6-fluoroimidazo[1,2-a]pyridin-7-yl}ethynyl)-1-[(3S,5R)-5-(methoxymethyl)-1-(prop-2-enoyl)pyrrolidin-3-yl]-5-(methylamino)pyrazole-4-carboxamide. MS ESI calculated for $C_{23}H_{23}ClFN_7O_3$ [M+H]$^+$, 500.15, found 500.10; $^1$H NMR (400 MHz, CDCl$_3$) δ 8.10 (d, J=4.2 Hz, 1H), 7.90 (d, J=6.3 Hz, 1H), 7.73 (s, 1H), 6.85 (s, 1H), 6.56-6.40 (m, 2H), 5.84-5.73 (m, 1H), 5.60-5.27 (m, 2H), 4.59 (d, J=9.0 Hz, 1H), 4.15-3.99 (m, 2H), 4.10-3.93 (m, 1H), 3.54-3.37 (m, 4H), 3.06 (d, J=14.9 Hz, 3H), 2.71-2.69 (m, 1H), 2.50-2.37 (m, 1H).

II. Biological Evaluation

Example 1: FGFR2 Kinase Assay

Small molecule inhibition of FGFR2 kinase activity was evaluated using a fluorescence-based microfluidic mobility shift assay. FGFR2 catalyzes the production of ADP from ATP during phosphoryl transfer to the substrate peptide, FLPeptide30 (5-FAM-KKKKEEIYFFF-CONH2) (Perkin Elmer, 760430). The mobility shift assay electrophoretically separates the fluorescently labeled peptides (substrate and phosphorylated product) following the kinase reaction. Both substrate and product were measured and the ratio of these values used to generate % conversion of substrate to product by the LabChip EZ reader (Perkin Elmer). Wild type FGFR2 (Carna Bioscience, 08-134) at 0.06 nM was prepared with 1.5 μM substrate, 10 mM MgCl and 100 μM ATP in a buffer containing 50 nM HEPES, 1 mM EGTA, 0.01% Brij-35, 0.05% BSA, and 2 mM DTT prior to addition of compounds in DMSO and incubation for 80 minutes at room temperature. The reaction was terminated by addition of 0.5 M EDTA. IC$_{50}$ values were calculated using the inhibition of conversion ratio using Dotmatics Knowledge Solutions Studies curve fitting (Dotmatics, Bishops Stortford, UK, CM23) and are presented in Table 3.

TABLE 3

| Synthetic Chemistry Example | FGFR2 IC$_{50}$ |
| --- | --- |
| 1 | A |
| 2 | A |
| 3 | A |
| 4 | A |
| 5 | A |
| 6 | A |
| 7 | A |
| 8 | A |
| 9 | B |
| 10 | A |
| 11 | A |
| 12 | A |
| 13 | A |
| 14 | A |
| 15 | A |
| 16 | A |
| 17 | A |
| 18 | A |
| 19 | A |
| 20 | A |
| 21 | A |
| 22 | A |
| 23 | A |
| 24 | B |
| 25 | A |
| 26 | B |
| 27 | A |
| 28 | A |
| 29 | A |
| 30 | A |
| 31 | A |
| 32 | A |
| 33 | A |
| 34 | A |
| 35 | A |
| 36 | B |
| 37 | A |
| 38 | A |
| 39 | B |
| 40 | A |
| 41 | B |
| 42 | A |
| 43 | A |
| 44 | A |
| 45 | A |
| 46 | A |
| 47 | A |
| 48 | B |
| 49 | A |
| 50 | A |
| 51 | A |
| 52 | A |
| 53 | B |
| 54 | A |
| 55 | >500 nM |
| 56 | A |
| 57 | >500 nM |
| 58 | >500 nM |
| 59 | A |
| 60 | A |
| 61 | A |
| 62 | A |
| 63 | >500 nM |
| 64 | A |
| 65 | A |
| 66 | A |
| 67 | A |
| 68 | A |
| 69 | A |
| 70 | A |
| 71 | A |
| 72 | A |
| 73 | A |
| 74 | A |
| 75 | A |
| 76 | A |
| 77 | A |
| 78 | A |
| 79 | A |
| 80 | A |
| 81 | A |
| 82 | A |
| 83 | A |
| 84 | A |
| 85 | A |
| 86 | A |
| 87 | A |
| 88 | A |
| 89 | A |
| 90 | A |
| 91 | A |
| 92 | A |
| 93 | A |
| 94 | A |
| 95 | B |
| 96 | A |
| 97 | A |
| 98 | A |
| 99 | A |
| 100 | A |
| 101 | A |
| 102 | A |
| 103 | A |
| 104 | >500 nM |
| 105 | >500 nM |
| 106 | >500 nM |
| 107 | B |
| 108 | A |
| 109 | A |

TABLE 3-continued

| Synthetic Chemistry Example | FGFR2 IC$_{50}$ |
|---|---|
| 110 | A |
| 111 | A |
| 112 | A |
| 113 | A |
| 114 | A |
| 115 | A |
| 116 | A |
| 117 | A |
| 118 | A |
| 119 | A |
| 120 | A |
| 121 | A |
| 122 | B |
| 123 | A |
| 124 | A |
| 125 | A |
| 126 | A |
| 127 | A |
| 128 | A |
| 129 | B |
| 130 | A |
| 131 | A |
| 132 | A |
| 133 | A |
| 134 | A |
| 135 | A |
| 136 | A |
| 137 | A |
| 138 | A |
| 139 | A |
| 140 | A |
| 141 | A |
| 142 | A |
| 143 | A |
| 144 | A |
| 145 | A |
| 147 | A |
| 148 | A |
| 149 | A |
| 150 | A |
| 151 | A |
| 157 | A |
| 153 | A |
| 154 | A |
| 155 | A |
| 156 | A |
| 157 | A |
| 158 | A |
| 159 | A |
| 161 | A |
| 162 | A |
| 163 | A |
| 164 | A |
| 165 | A |
| 166 | A |
| 167 | A |
| 168 | A |
| 169 | A |
| 170 | A |
| 171 | A |
| 172 | A |
| 173 | A |
| 174 | A |
| 175 | A |
| 176 | A |
| 177 | A |
| 178 | A |
| 179 | A |
| 180 | A |
| 181 | A |
| 182 | A |
| 183 | A |
| 184 | A |
| 185 | A |
| 186 | A |
| 187 | A |

TABLE 3-continued

| Synthetic Chemistry Example | FGFR2 IC$_{50}$ |
|---|---|
| 188 | A |
| 189 | A |
| 190 | A |
| 191 | A |
| 192 | A |
| 193 | A |
| 194 | A |
| 195 | A |
| 196 | A |
| 197 | A |
| 198 | A |
| 199 | A |
| 200 | A |
| 201 | A |
| 202 | A |
| 203 | A |
| 204 | B |
| 205 | A |
| 206 | A |
| 207 | A |
| 208 | A |
| 209 | A |
| 210 | A |
| 211 | A |
| 212 | A |
| 213 | A |
| 214 | A |
| 215 | A |
| 216 | A |
| 217 | >500 nM |
| 218 | A |
| 219 | A |
| 220 | A |
| 221 | A |
| 222 | A |
| 223 | A |
| 224 | A |
| 225 | A |
| 226 | A |
| 227 | A |
| 228 | A |
| 230 | A |
| 231 | A |
| 232 | A |
| 233 | A |
| 234 | A |
| 235 | A |
| 236 | A |
| 237 | A |
| 238 | A |
| 239 | A |
| 240 | A |
| 241 | A |
| 242 | A |
| 243 | A |
| 244 | A |
| 245 | A |
| 246 | A |
| 247 | A |
| 248 | A |
| 249 | A |
| 250 | A |
| 251 | A |
| 252 | A |
| 253 | A |
| 254 | A |
| 256 | A |
| 257 | A |
| 258 | A |
| 259 | A |
| 260 | A |
| 261 | A |
| 262 | A |
| 263 | A |
| 264 | A |
| 265 | A |

TABLE 3-continued

| Synthetic Chemistry Example | FGFR2 IC$_{50}$ |
|---|---|
| 266 | A |
| 267 | A |
| 268 | A |
| 269 | A |
| 270 | A |
| 271 | A |
| 272 | A |
| 273 | A |
| 274 | A |
| 275 | A |
| 276 | A |
| 277 | A |
| 278 | A |
| 279 | A |
| 280 | A |
| 281 | A |
| 282 | A |
| 283 | A |
| 284 | B |
| 285 | A |
| 287 | A |
| 288 | A |
| 289 | >500 nM |
| 290 | A |

Note:
Biochemical assay IC50 data are designated within the following ranges:
A: ≤0.10 µM
B: >0.10 µM to ≤1.0 µM
C: >1.0 µM to ≤10 µM
D: >10 µM to 30 µM III. Preparation of Pharmaceutical Dosage Forms Example 1: Oral Capsule The active ingredient is a compound of Table 1, or a pharmaceutically acceptable salt or solvate thereof. A capsule for oral administration is prepared by mixing 1-1000 mg of active ingredient with starch or other suitable powder blend. The mixture is incorporated into an oral dosage unit such as a hard gelatin capsule, which is suitable for oral administration.

Example 2: Solution for Injection

The active ingredient is a compound of Table 1, or a pharmaceutically acceptable salt thereof, and is formulated as a solution in sesame oil at a concentration of 50 mg-eq/mL.

The examples and embodiments described herein are for illustrative purposes only and various modifications or changes suggested to persons skilled in the art are to be included within the spirit and purview of this application and scope of the appended claims.

The invention claimed is:
1. A compound, or pharmaceutically acceptable salt or solvate thereof, selected from the group consisting of:
1-[(3S,5R)-5-(methoxymethyl)-1-(prop-2-enoyl)pyrrolidin-3-yl]-3-[2-(2-methyl-3H-1,3-benzodiazol-5-yl)ethynyl]-5-(methylamino)pyrazole-4-carboxamide;
(S)-1-(1-acryloylpyrrolidin-3-yl)-3-((2-methyl-1H-benzo[d]imidazol-6-yl)ethynyl)-5-(methylamino)-1H-pyrazole-4-carboxamide;
3-[2-(1-ethyl-2-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;
1-[(3S,5R)-5-(methoxymethyl)-1-(prop-2-enoyl)pyrrolidin-3-yl]-3-[2-(1-methyl-1,3-benzodiazol-5-yl)ethynyl]-5-(methylamino)pyrazole-4-carboxamide;
1-((3S,5R)-1-acryloyl-5-(methoxymethyl)pyrrolidin-3-yl)-3-((1,2-dimethyl-1H-benzo[d]imidazol-5-yl)ethynyl)-5-(methylamino)-1H-pyrazole-4-carboxamide;
1-((3S,5R)-1-acryloyl-5-(methoxymethyl)pyrrolidin-3-yl)-3-((1-ethyl-1H-benzo[d]imidazol-5-yl)ethynyl)-5-(methylamino)-1H-pyrazole-4-carboxamide;
(S)-1-(1-acryloylpyrrolidin-3-yl)-3-((1,2-dimethyl-1H-benzo[d]imidazol-5-yl)ethynyl)-5-(methylamino)-1H-pyrazole-4-carboxamide;
1-((3S,5R)-1-acryloyl-5-(methoxymethyl)pyrrolidin-3-yl)-3-((1-methyl-1H-indazol-5-yl)ethynyl)-5-(methylamino)-1H-pyrazole-4-carboxamide;
1-((3S,5R)-1-acryloyl-5-(methoxymethyl)pyrrolidin-3-yl)-3-((2-methyl-2H-indazol-5-yl)ethynyl)-5-(methylamino)-1H-pyrazole-4-carboxamide;
1-((3S,5R)-1-acryloyl-5-(methoxymethyl)pyrrolidin-3-yl)-3-((1-methyl-2-(trifluoromethyl)-1H-benzo[d]imidazol-5-yl)ethynyl)-5-(methylamino)-1H-pyrazole-4-carboxamide;
1-((3S,5R)-1-acryloyl-5-(methoxymethyl)pyrrolidin-3-yl)-3-((4,6-difluoro-1-methyl-1H-benzo[d]imidazol-5-yl)ethynyl)-5-(methylamino)-1H-pyrazole-4-carboxamide;
1-((3S,5R)-1-acryloyl-5-(methoxymethyl)pyrrolidin-3-yl)-3-((1-cyclopropyl-2-methyl-1H-benzo[d]imidazol-5-yl)ethynyl)-5-(methylamino)-1H-pyrazole-4-carboxamide;
1-((3S,5R)-1-acryloyl-5-(methoxymethyl)pyrrolidin-3-yl)-3-((1-cyclopropyl-1H-benzo[d]imidazol-5-yl)ethynyl)-5-(methylamino)-1H-pyrazole-4-carboxamide;
1-((3S,5R)-1-acryloyl-5-(methoxymethyl)pyrrolidin-3-yl)-3-((1-ethyl-1H-indazol-5-yl)ethynyl)-5-(methylamino)-1H-pyrazole-4-carboxamide;
1-((3S,5R)-1-acryloyl-5-(methoxymethyl)pyrrolidin-3-yl)-3-((2-ethyl-2H-indazol-5-yl)ethynyl)-5-(methylamino)-1H-pyrazole-4-carboxamide;
1-((3S,5R)-1-acryloyl-5-(methoxymethyl)pyrrolidin-3-yl)-3-((1-ethyl-4,6-difluoro-2-methyl-1H-benzo[d]imidazol-5-yl)ethynyl)-5-(methylamino)-1H-pyrazole-4-carboxamide;
1-((3S,5R)-1-acryloyl-5-(methoxymethyl)pyrrolidin-3-yl)-3-((4,6-difluoro-2-methyl-1H-benzo[d]imidazol-5-yl)ethynyl)-5-(methylamino)-1H-pyrazole-4-carboxamide;
1-((3S,5R)-1-acryloyl-5-(methoxymethyl)pyrrolidin-3-yl)-3-((4,6-difluoro-1,2-dimethyl-1H-benzo[d]imidazol-5-yl)ethynyl)-5-(methylamino)-1H-pyrazole-4-carboxamide;
1-((3S,5R)-1-acryloyl-5-(methoxymethyl)pyrrolidin-3-yl)-3-((4,6-difluoro-1-methyl-1H-indazol-5-yl)ethynyl)-5-(methylamino)-1H-pyrazole-4-carboxamide;
1-((3S,5R)-1-acryloyl-5-(methoxymethyl)pyrrolidin-3-yl)-3-((4-fluoro-1,2-dimethyl-1H-benzo[d]imidazol-5-yl)ethynyl)-5-(methylamino)-1H-pyrazole-4-carboxamide;
1-((3S,5R)-1-acryloyl-5-(methoxymethyl)pyrrolidin-3-yl)-3-((1-ethyl-4-fluoro-2-methyl-1H-benzo[d]imidazol-5-yl)ethynyl)-5-(methylamino)-1H-pyrazole-4-carboxamide;
1-((3S,5R)-1-acryloyl-5-(methoxymethyl)pyrrolidin-3-yl)-3-((3-ethyl-2-methyl-3H-imidazo[4,5-b]pyridin-6-yl)ethynyl)-5-(methylamino)-1H-pyrazole-4-carboxamide;

1-((3S,5R)-1-acryloyl-5-(methoxymethyl)pyrrolidin-3-yl)-3-((3-methyl-3H-imidazo[4,5-b]pyridin-6-yl)ethynyl)-5-(methylamino)-1H-pyrazole-4-carboxamide;

1-((3S,5R)-1-acryloyl-5-(methoxymethyl)pyrrolidin-3-yl)-3-((6-cyano-1-ethyl-2-methyl-1H-benzo[d]imidazol-5-yl)ethynyl)-5-(methylamino)-1H-pyrazole-4-carboxamide;

1-((3S,5R)-1-acryloyl-5-(methoxymethyl)pyrrolidin-3-yl)-3-((2-cyclopropyl-1-ethyl-1H-benzo[d]imidazol-5-yl)ethynyl)-5-(methylamino)-1H-pyrazole-4-carboxamide;

1-((3S,5R)-1-acryloyl-5-(methoxymethyl)pyrrolidin-3-yl)-3-(benzo[d]isoxazol-6-ylethynyl)-5-(methylamino)-1H-pyrazole-4-carboxamide;

1-((3S,5R)-1-acryloyl-5-(methoxymethyl)pyrrolidin-3-yl)-3-((1-ethyl-2-(trifluoromethyl)-1H-benzo[d]imidazol-5-yl)ethynyl)-5-(methylamino)-1H-pyrazole-4-carboxamide;

1-((3S,5R)-1-acryloyl-5-(methoxymethyl)pyrrolidin-3-yl)-3-((6-fluoro-1,2-dimethyl-1H-benzo[d]imidazol-5-yl)ethynyl)-5-(methylamino)-1H-pyrazole-4-carboxamide;

1-((3S,5R)-1-acryloyl-5-(methoxymethyl)pyrrolidin-3-yl)-3-((1-ethyl-4,6-difluoro-1H-benzo[d]imidazol-5-yl)ethynyl)-5-(methylamino)-1H-pyrazole-4-carboxamide;

1-((3S,5R)-1-acryloyl-5-(methoxymethyl)pyrrolidin-3-yl)-3-((1-(difluoromethyl)-4,6-difluoro-1H-benzo[d]imidazol-5-yl)ethynyl)-5-(methylamino)-1H-pyrazole-4-carboxamide;

1-((3S,5R)-1-acryloyl-5-(methoxymethyl)pyrrolidin-3-yl)-3-((1-(difluoromethyl)-4,6-difluoro-2-methyl-1H-benzo[d]imidazol-5-yl)ethynyl)-5-(methylamino)-1H-pyrazole-4-carboxamide;

1-((3S,5R)-1-acryloyl-5-(methoxymethyl)pyrrolidin-3-yl)-3-((1-ethyl-6-fluoro-1H-benzo[d]imidazol-5-yl)ethynyl)-5-(methylamino)-1H-pyrazole-4-carboxamide;

1-((3S,5R)-1-acryloyl-5-(methoxymethyl)pyrrolidin-3-yl)-3-((6-chloro-1-ethyl-2-methyl-1H-benzo[d]imidazol-5-yl)ethynyl)-5-(methylamino)-1H-pyrazole-4-carboxamide;

1-((3S,5R)-1-acryloyl-5-(methoxymethyl)pyrrolidin-3-yl)-3-((4,6-difluoro-1-(2,2,2-trifluoroethyl)-1H-benzo[d]imidazol-5-yl)ethynyl)-5-(methylamino)-1H-pyrazole-4-carboxamide;

1-((3S,5R)-1-acryloyl-5-(methoxymethyl)pyrrolidin-3-yl)-3-((4,6-difluoro-2-methyl-1-(2,2,2-trifluoroethyl)-1H-benzo[d]imidazol-5-yl)ethynyl)-5-(methylamino)-1H-pyrazole-4-carboxamide;

3-[2-(3-ethyl-4-fluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

3-[2-(1-ethyl-6-fluoro-2-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

3-[2-(4-chloro-1-ethyl-2-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

3-(2-[1-ethyl-2-methylimidazo[4,5-b]pyridin-5-yl]ethynyl)-1-[(3S,5R)-5-(methoxymethyl)-1-(prop-2-enoyl)pyrrolidin-3-yl]-5-(methylamino)pyrazole-4-carboxamide;

3-[2-(6-fluoro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

3-[2-(4-fluoro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

3-[2-(2-cyclopropyl-1H-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

3-[2-(2-cyclopropyl-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

1-[(3S,5R)-5-(methoxymethyl)-1-(prop-2-enoyl)pyrrolidin-3-yl]-3-[2-(3-methyl-1,2-benzoxazol-6-yl)ethynyl]-5-(methylamino)pyrazole-4-carboxamide;

3-[2-(2-cyclopropyl-1-ethyl-4,6-difluoro-1,3-benzodiazol-5-yl) ethynyl]-1-[(3S,5R)-5-(methoxymethyl)-1-(prop-2-enoyl) pyrrolidin-3-yl]-5-(methylamino) pyrazole-4-carboxamide;

3-[2-[4,6-difluoro-2-(trifluoromethyl)-1H-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide;

3-[2-[1-(difluoromethyl)-4,6-difluoro-2-methyl-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide;

3-(2-[3-Ethyl-2-methylimidazo[4,5-c]pyridin-6-yl]ethynyl)-1-[(3S,5R)-5-(methoxymethyl)-1-(prop-2-enoyl) pyrrolidin-3-yl]-5-(methylamino)pyrazole-4-carboxamide;

3-[2-(2-Amino-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

3-[2-(2-Cyclopropyl-4,6-difluoro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

1-((3S,5R)-1-Acryloyl-5-(methoxymethyl)pyrrolidin-3-yl)-3-((2-cyclopropyl-4-fluoro-1-methyl-1H-benzo[d]imidazol-5-yl)ethynyl)-5-(methylamino)-1H-pyrazole-4-carboxamide;

1-[(3S,5R)-5-(Methoxymethyl)-1-(prop-2-enoyl) pyrrolidin-3-yl]-5-(methylamino)-3-[2-(quinolin-7-yl) ethynyl]pyrazole-4-carboxamide;

1-[(3S,5R)-5-(Methoxymethyl)-1-(prop-2-enoyl)pyrrolidin-3-yl]-5-(methylamino)-3-(2-[pyrazolo[1,5-a]pyrimidin-5-yl]ethynyl)pyrazole-4-carboxamide;

1-((3S,5R)-1-Acryloyl-5-(methoxymethyl)pyrrolidin-3-yl)-3-(imidazo[1,2-a]pyridin-7-ylethynyl)-5-(methylamino)-1H-pyrazole-4-carboxamide;

1-((3S,5R)-1-Acryloyl-5-(methoxymethyl)pyrrolidin-3-yl)-3-(imidazo[1,2-a]pyridin-6-ylethynyl)-5-(methylamino)-1H-pyrazole-4-carboxamide;

1-[(3S,5R)-5-(Methoxymethyl)-1-(prop-2-enoyl)pyrrolidin-3-yl]-5-(methylamino)-3-(2-[pyrazolo[1,5-a]pyridin-5-yl]ethynyl)pyrazole-4-carboxamide;

3-(2-[Imidazo[1,2-a]pyrimidin-6-yl]ethynyl)-1-[(3S,5R)-5-(methoxymethyl)-1-(prop-2-enoyl)pyrrolidin-3-yl]-5-(methylamino)pyrazole-4-carboxamide;

3-(2-[Imidazo[1,2-a]pyrimidin-7-yl]ethynyl)-1-[(3S,5R)-5-(methoxymethyl)-1-(prop-2-enoyl)pyrrolidin-3-yl]-5-(methylamino)pyrazole-4-carboxamide;

3-[2-(1-Tert-butyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

3-[2-[2-(Dimethylamino)-1-methyl-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide;

3-[2-(2-Cyclopropyl-4,6-difluoro-1H-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

3-[2-(2-Cyclopropyl-6-fluoro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

3-(2-[2-Cyclopropyl-3-methylimidazo[4,5-c]pyridin-6-yl]ethynyl)-1-[(3S,5R)-5-(methoxymethyl)-1-(prop-2-enoyl)pyrrolidin-3-yl]-5-(methylamino)pyrazole-4-carboxamide;

1-[(3S,5R)-5-(Methoxymethyl)-1-(prop-2-enoyl) pyrrolidin-3-yl]-5-(methylamino)-3-[2-(quinoxalin-6-yl)ethynyl]pyrazole-4-carboxamide;

1-((3S,5R)-1-Acryloyl-5-(methoxymethyl)pyrrolidin-3-yl)-5-(methylamino)-3-((3-methylquinolin-7-yl)ethynyl)-1H-pyrazole-4-carboxamide;

3-(2-[Imidazo[1,2-b]pyridazin-7-yl]ethynyl)-1-[(3S,5R)-5-(methoxymethyl)-1-(prop-2-enoyl)pyrrolidin-3-yl]-5-(methylamino)pyrazole-4-carboxamide;

1-[(3S,5R)-5-(Methoxymethyl)-1-(prop-2-enoyl)pyrrolidin-3-yl]-5-(methylamino)-3-(2-[pyrazolo[1,5-a]pyridin-6-yl]ethynyl)pyrazole-4-carboxamide;

1-((3S,5R)-1-Acryloyl-5-(methoxymethyl)pyrrolidin-3-yl)-3-((1-ethyl-4-fluoro-1H-benzo[d]imidazol-5-yl)ethynyl)-5-(methylamino)-1H-pyrazole-4-carboxamide;

1-((3S,5R)-1-Acryloyl-5-(methoxymethyl)pyrrolidin-3-yl)-5-(methylamino)-3-((2-methylquinoxalin-6-yl)ethynyl)-1H-pyrazole-4-carboxamide;

3-[2-[1-(Difluoromethyl)-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide;

1-((3S,5R)-1-Acryloyl-5-(methoxymethyl)pyrrolidin-3-yl)-3-((4-fluoro-1-methyl-1H-benzo[d]imidazol-5-yl)ethynyl)-5-(methylamino)-1H-pyrazole-4-carboxamide;

1-((3S,5R)-1-Acryloyl-5-(methoxymethyl)pyrrolidin-3-yl)-5-(methylamino)-3-((3-methylquinoxalin-6-yl)ethynyl)-1H-pyrazole-4-carboxamide;

3-[2-[3-(Difluoromethyl)-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide;

1-[(3S,5R)-5-(Methoxymethyl)-1-(prop-2-enoyl)pyrrolidin-3-yl]-5-(methylamino)-3-[2-(4-methylquinolin-7-yl)ethynyl]pyrazole-4-carboxamide;

1-[(3S,5R)-5-(Methoxymethyl)-1-(prop-2-enoyl)pyrrolidin-3-yl]-5-(methylamino)-3-(2-[3-methylimidazo[1,2-a]pyridin-7-yl]ethynyl)pyrazole-4-carboxamide;

3-[2-[3-(Difluoromethyl)-6-fluoro-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide;

3-[2-[1-(Difluoromethyl)-6-fluoro-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide;

3-[2-(1-Cyclopropyl-4,6-difluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

3-[2-(6-Fluoro-1-methyl-1,3-benzodiazol-5-yl)ethynyl]-5-(methylamino)-1-[(3S,5R)-1-(prop-2-enoyl)-5-[(trifluoromethoxy)methyl]pyrrolidin-3-yl]pyrazole-4-carboxamide;

3-[2-(1-Ethyl-6-fluoro-1,3-benzodiazol-5-yl)ethynyl]-5-(methylamino)-1-[(3S,5R)-1-(prop-2-enoyl)-5-[(trifluoromethoxy)methyl]pyrrolidin-3-yl]pyrazole-4-carboxamide;

3-[2-[1-(Difluoromethyl)-6-fluoro-1,3-benzodiazol-5-yl]ethynyl]-5-(methylamino)-1-[(3S,5R)-1-(prop-2-enoyl)-5-[(trifluoromethoxy)methyl]pyrrolidin-3-yl]pyrazole-4-carboxamide;

3-[2-(6-Chloro-1,2-dimethyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

1-[(3S,5R)-5-(Methoxymethyl)-1-(prop-2-enoyl)pyrrolidin-3-yl]-5-(methylamino)-3-[2-(2-methylquinolin-7-yl)ethynyl]pyrazole-4-carboxamide;

3-[2-(4,6-Difluoro-1-methyl-1,3-benzodiazol-5-yl)ethynyl]-5-(methylamino)-1-[(3S,5R)-1-(prop-2-enoyl)-5-[(trifluoromethoxy)methyl]pyrrolidin-3-yl]pyrazole-4-carboxamide;

3-[2-(1-Ethyl-4,6-difluoro-1,3-benzodiazol-5-yl)ethynyl]-5-(methylamino)-1-[(3S,5R)-1-(prop-2-enoyl)-5-[(trifluoromethoxy)methyl]pyrrolidin-3-yl]pyrazole-4-carboxamide;

3-[2-(6-Fluoro-1H-1,3-benzodiazol-5-yl)ethynyl]-5-(methylamino)-1-[(3S,5R)-1-(prop-2-enoyl)-5-[(trifluoromethoxy)methyl]pyrrolidin-3-yl]pyrazole-4-carboxamide;

3-[2-(6-Chloro-2-methyl-1H-1,3-benzodiazol-5-yl)ethynyl]-5-(methylamino)-1-[(3S,5R)-1-(prop-2-enoyl)-5-[(trifluoromethoxy)methyl]pyrrolidin-3-yl]pyrazole-4-carboxamide;

3-[2-(6-Chloro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

3-[2-(6-Chloro-1-ethyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

3-[2-(6-Fluoro-1H-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

3-[2-(6-Fluoro-2-methyl-1H-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

3-[2-(6-Chloro-1H-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

3-[2-[6-Chloro-3-(difluoromethyl)-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide;

3-[2-[6-Chloro-1-(difluoromethyl)-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide;

3-[2-[6-Chloro-3-(difluoromethyl)-2-methyl-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide;

3-[2-[6-Chloro-1-(difluoromethyl)-2-methyl-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide;

3-[2-(4,6-Difluoro-1-methyl-1,2,3-benzotriazol-5-yl)ethynyl]-1-[(3S,5R)-5-(methoxymethyl)-1-(prop-2-enoyl)pyrrolidin-3-yl]-5-(methylamino)pyrazole-4-carboxamide;

3-[2-(6-Chloro-2-methyl-1H-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

3-[2-(6-Chloro-1-ethyl-4-fluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

3-[2-(6-Chloro-4-fluoro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

3-[2-(6,7-Difluoro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

3-[2-(1,3-Benzothiazol-2-yl)ethynyl]-1-[(3S,5R)-5-(methoxymethyl)-1-(prop-2-enoyl)pyrrolidin-3-yl]-5-(methylamino)pyrazole-4-carboxamide;

3-[2-(1,3-Benzothiazol-5-yl)ethynyl]-1-[(3S,5R)-5-(methoxymethyl)-1-(prop-2-enoyl)pyrrolidin-3-yl]-5-(methylamino)pyrazole-4-carboxamide;

3-(2-[Imidazo[1,2-a]pyridin-2-yl]ethynyl)-1-[(3S,5R)-5-(methoxymethyl)-1-(prop-2-enoyl)pyrrolidin-3-yl]-5-(methylamino)pyrazole-4-carboxamide;

1-((3S,5R)-1-Acryloyl-5-(methoxymethyl)pyrrolidin-3-yl)-3-((3-cyanoimidazo[1,2-a]pyridin-2-yl)ethynyl)-5-(methylamino)-1H-pyrazole-4-carboxamide;

1-[(3S,5R)-5-(Methoxymethyl)-1-(prop-2-enoyl)pyrrolidin-3-yl]-5-(methylamino)-3-(2-[[1,2,4]triazolo[1,5-a]pyridin-6-yl]ethynyl)pyrazole-4-carboxamide;

1-[(3S,5R)-5-(Methoxymethyl)-1-(prop-2-enoyl)pyrrolidin-3-yl]-5-(methylamino)-3-(2-[[1,2,4]triazolo[1,5-a]pyridin-7-yl]ethynyl)pyrazole-4-carboxamide;

3-[2-(1,3-Benzoxazol-5-yl)ethynyl]-1-[(3S,5R)-5-(methoxymethyl)-1-(prop-2-enoyl)pyrrolidin-3-yl]-5-(methylamino)pyrazole-4-carboxamide;

5-[(Cyclopropylmethyl)amino]-3-[2-(1-ethyl-4,6-difluoro-1,3-benzodiazol-5-yl)ethynyl]-1-[(3S,5R)-5-(methoxymethyl)-1-(prop-2-enoyl)pyrrolidin-3-yl]pyrazole-4-carboxamide;

3-[2-[1-(Difluoromethyl)-4,6-difluoro-2-methyl-1,3-benzodiazol-5-yl]ethynyl]-1-[(3S,5R)-5-(methoxymethyl)-1-(prop-2-enoyl)pyrrolidin-3-yl]-5-(methylamino)pyrazole-4-carboxamide;

3-[2-(1-Ethyl-4,6-difluoro-1,3-benzodiazol-5-yl)ethynyl]-1-[(3S,5R)-5-(methoxymethyl)-1-(prop-2-enoyl)pyrrolidin-3-yl]-5-[[3-(morpholin-4-yl)propyl]amino]pyrazole-4-carboxamide;

3-[2-(1-Ethyl-4,6-difluoro-1,3-benzodiazol-5-yl)ethynyl]-5-[[2-(morpholin-4-yl)ethyl]amino]-1-[(3S)-1-(prop-2-enoyl)pyrrolidin-3-yl]pyrazole-4-carboxamide;

3-[2-(6-Chloro-7-fluoro-1-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

3-[2-(1,3-Benzoxazol-2-yl)ethynyl]-1-[(3S,5R)-5-(methoxymethyl)-1-(prop-2-enoyl)pyrrolidin-3-yl]-5-(methylamino)pyrazole-4-carboxamide;

3-[2-(6-Fluoro-1,3-benzoxazol-5-yl)ethynyl]-1-[(3S,5R)-5-(methoxymethyl)-1-(prop-2-enoyl)pyrrolidin-3-yl]-5-(methylamino)pyrazole-4-carboxamide;

3-[2-(1-Ethyl-4,6-difluoro-1,3-benzodiazol-5-yl)ethynyl]-5-[(2-hydroxyethyl)amino]-1-[(3S,5R)-5-(methoxymethyl)-1-(prop-2-enoyl)pyrrolidin-3-yl]pyrazole-4-carboxamide;

3-[2-(1-Ethyl-4,6-difluoro-1,3-benzodiazol-5-yl)ethynyl]-5-[(2-methoxyethyl)amino]-1-[(3S,5R)-5-(methoxymethyl)-1-(prop-2-enoyl)pyrrolidin-3-yl]pyrazole-4-carboxamide;

5-[(Cyclopropylmethyl)amino]-3-[2-(1-ethyl-4,6-difluoro-1,3-benzodiazol-5-yl)ethynyl]-1-[(3S)-1-(prop-2-enoyl)pyrrolidin-3-yl]pyrazole-4-carboxamide;

3-[2-(1-Ethyl-4,6-difluoro-1,3-benzodiazol-5-yl)ethynyl]-5-[(2-methoxyethyl)amino]-1-[(3S)-1-(prop-2-enoyl)pyrrolidin-3-yl]pyrazole-4-carboxamide;

3-[2-(1-Ethyl-4,6-difluoro-1,3-benzodiazol-5-yl)ethynyl]-5-[[3-(morpholin-4-yl)propyl]amino]-1-[(3S)-1-(prop-2-enoyl)pyrrolidin-3-yl]pyrazole-4-carboxamide;

1-((3S,5R)-1-Acryloyl-5-(methoxymethyl)pyrrolidin-3-yl)-3-((7-fluoro-1-methyl-1H-benzo[d]imidazol-5-yl)ethynyl)-5-(methylamino)-1H-pyrazole-4-carboxamide;

3-(2-[7-Fluoro-[1,2,4]triazolo[1,5-a]pyridin-6-yl]ethynyl)-1-[(3S,5R)-5-(methoxymethyl)-1-(prop-2-enoyl)pyrrolidin-3-yl]-5-(methylamino)pyrazole-4-carboxamide 3-[2-(1-Ethyl-4,6-difluoro-1,3-benzodiazol-5-yl)ethynyl]-5-[(2-hydroxy;ethyl)amino]-1-[(3S)-1-(prop-2-enoyl)pyrrolidin-3-yl]pyrazole-4-carboxamide;

3-[2-(6-Chloro-1-cyclopropyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

3-[2-(1-Ethyl-6,7-difluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

3-[2-(6-Chloro-1-ethyl-7-fluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

3-[2-(6,7-Difluoro-1,2-dimethyl-1,3-benzodiazol-5-yl)ethynyl]-1-[(3S,5R)-5-(methoxymethyl)-1-(prop-2-enoyl) pyrrolidin-3-yl]-5-(methylamino) pyrazole-4-carboxamide;

3-[2-(6-Chloro-7-fluoro-1,2-dimethyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

3-[2-(6-Chloro-1-ethyl-1,3-benzodiazol-5-yl)ethynyl]-1-[(3S,5R)-1-(2-fluoroprop-2-enoyl)-5-(methoxymethyl)pyrrolidin-3-yl]-5-(methylamino)pyrazole-4-carboxamide;

3-(2-[6-Fluoro-[1,2,4]triazolo[1,5-a]pyridin-7-yl]ethynyl)-1-[(3S,5R)-5-(methoxymethyl)-1-(prop-2-enoyl)pyrrolidin-3-yl]-5-(methylamino)pyrazole-4-carboxamide;

3-[2-(6-Fluoro-1,3-benzothiazol-5-yl)ethynyl]-1-[(3S,5R)-5-(methoxymethyl)-1-(prop-2-enoyl)pyrrolidin-3-yl]-5-(methylamino)pyrazole-4-carboxamide;

1-((3S,5R)-1-Acryloyl-5-(methoxymethyl)pyrrolidin-3-yl)-3-((6-fluoroimidazo[1,2-a]pyridin-7-yl)ethynyl)-5-(methylamino)-1H-pyrazole-4-carboxamide;

3-[2-(6-Chloro-4-fluoro-1,2-dimethyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

3-[2-(6-Chloro-1,3-benzothiazol-5-yl)ethynyl]-1-[(3S,5R)-5-(methoxymethyl)-1-(prop-2-enoyl)pyrrolidin-3-yl]-5-(methylamino)pyrazole-4-carboxamide;

3-[2-(1-Cyclopropyl-6-fluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

3-[2-(1-Cyclopropyl-6-fluoro-1,3-benzodiazol-5-yl)ethynyl]-5-(methylamino)-1-[(3S)-1-(prop-2-enoyl)pyrrolidin-3-yl]pyrazole-4-carboxamide;

1-((3S,5R)-1-(but-2-ynoyl)-5-(methoxymethyl)pyrrolidin-3-yl)-3-((1-ethyl-4,6-difluoro-1H-benzo[d]imidazol-5-yl)ethynyl)-5-(methylamino)-1H-pyrazole-4-carboxamide;

1-((3S,5R)-1-acryloyl-5-((methoxy-d3)methyl)pyrrolidin-3-yl)-3-((6-chloro-1-ethyl-1H-benzo[d]imidazol-5-yl)ethynyl)-5-(methylamino)-1H-pyrazole-4-carboxamide;

3-[2-(6-fluoro-1-methyl-1,3-benzodiazol-5-yl)ethynyl]-5-(methylamino)-1-[(3S)-1-(prop-2-enoyl)pyrrolidin-3-yl]pyrazole-4-carboxamide;

3-[2-(1-ethyl-6,7-difluoro-1,3-benzodiazol-5-yl)ethynyl]-5-(methylamino)-1-[(3S)-1-(prop-2-enoyl)pyrrolidin-3-yl]pyrazole-4-carboxamide;

3-[2-(6-chloro-1-ethyl-7-fluoro-1,3-benzodiazol-5-yl)ethynyl]-5-(methylamino)-1-[(3S)-1-(prop-2-enoyl)pyrrolidin-3-yl]pyrazole-4-carboxamide;

3-[2-(6-chloro-7-fluoro-1-methyl-1,3-benzodiazol-5-yl)ethynyl]-5-(methylamino)-1-[(3S)-1-(prop-2-enoyl)pyrrolidin-3-yl]pyrazole-4-carboxamide;

3-[2-(1-ethyl-6-fluoro-1,3-benzodiazol-5-yl)ethynyl]-5-(methylamino)-1-[(3S)-1-(prop-2-enoyl)pyrrolidin-3-yl]pyrazole-4-carboxamide;

3-[2-(6-chloro-1-methyl-1,3-benzodiazol-5-yl)ethynyl]-5-(methylamino)-1-[(3S)-1-(prop-2-enoyl)pyrrolidin-3-yl]pyrazole-4-carboxamide;

3-[2-(6,7-difluoro-1-methyl-1,3-benzodiazol-5-yl)ethynyl]-5-(methylamino)-1-[(3S)-1-(prop-2-enoyl)pyrrolidin-3-yl]pyrazole-4-carboxamide;

3-[2-(6-chloro-1-cyclopropyl-7-fluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

3-[2-(6-fluoro-1-methyl-1,3-benzodiazol-5-yl)ethynyl]-1-[(3S,5R)-5-(fluoromethyl)-1-(prop-2-enoyl)pyrrolidin-3-yl]-5-(methylamino)pyrazole-4-carboxamide;

1-[(3S,5R)-5-(methoxymethyl)-1-(prop-2-enoyl)pyrrolidin-3-yl]-5-(methylamino)-3-[2-(4,6,7-trifluoro-1,2-dimethyl-1,3-benzodiazol-5-yl)ethynyl]pyrazole-4-carboxamide;

3-[2-(1-cyclopropyl-6-fluoro-2-methyl-1,3-benzodiazol-5-yl) ethynyl]-1-[(3S,5R)-5-(methoxymethyl)-1-(prop-2-enoyl)pyrrolidin-3-yl]-5-(methylamino)pyrazole-4-carboxamide;

3-[2-(1-cyclopropyl-6,7-difluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

1-[(3S,5R)-5-(methoxymethyl)-1-(prop-2-enoyl)pyrrolidin-3-yl]-5-(methylamino)-3-[2-(4,6,7-trifluoro-1-methyl-1,3-benzodiazol-5-yl)ethynyl]pyrazole-4-carboxamide;

3-[2-(1-cyclopropyl-4,6,7-trifluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

1-[(3S,5R)-5-[(difluoromethoxy)methyl]-1-(prop-2-enoyl)pyrrolidin-3-yl]-3-[2-(1-ethyl-6,7-difluoro-1,3-benzodiazol-5-yl)ethynyl]-5-(methylamino)pyrazole-4-carboxamide;

3-[2-(1-cyclopropyl-1,3-benzodiazol-5-yl)ethynyl]-1-[(3S,5R)-5-[(difluoromethoxy)methyl]-1-(prop-2-enoyl)pyrrolidin-3-yl]-5-(methylamino)pyrazole-4-carboxamide;

1-((3S,5R)-1-acryloyl-5-((difluoromethoxy)methyl)pyrrolidin-3-yl)-3-((1-cyclopropyl-4,6-difluoro-1H-benzo[d]imidazol-5-yl)ethynyl)-5-(methylamino)-1H-pyrazole-4-carboxamide;

3-[2-(1-ethyl-4,6,7-trifluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

3-[2-(1-cyclopropyl-6,7-difluoro-1,3-benzodiazol-5-yl)ethynyl]-1-[(3S,5S)-5-methyl-1-(prop-2-enoyl)pyrrolidin-3-yl]-5-(methylamino)pyrazole-4-carboxamide;

3-[2-(1-cyclopropyl-4,6-difluoro-1,3-benzodiazol-5-yl)ethynyl]-1-[(3S,5S)-5-methyl-1-(prop-2-enoyl)pyrrolidin-3-yl]-5-(methylamino)pyrazole-4-carboxamide;

1-((3S,5R)-1-acryloyl-5-((difluoromethoxy)methyl)pyrrolidin-3-yl)-3-((1-cyclopropyl-6-fluoro-1H-benzo[d]imidazol-5-yl)ethynyl)-5-(methylamino)-1H-pyrazole-4-carboxamide;

3-[2-(6-Chloro-1-cyclopropyl-1,3-benzodiazol-5-yl)ethynyl]-1-[(3S,5R)-5-(difluoromethyl)-1-(prop-2-enoyl)pyrrolidin-3-yl]-5-(methylamino)pyrazole-4-carboxamide;

3-[2-(1-cyclopropyl-4,6-difluoro-1,3-benzodiazol-5-yl)ethynyl]-1-[(3S,5R)-5-(difluoromethyl)-1-(prop-2-enoyl)pyrrolidin-3-yl]-5-(methylamino)pyrazole-4-carboxamide;

1-((3S,5R)-1-acryloyl-5-methylpyrrolidin-3-yl)-3-((1-cyclopropyl-6-fluoro-1H-benzo[d]imidazol-5-yl)ethynyl)-5-(methylamino)-1H-pyrazole-4-carboxamide;

3-[2-(1-cyclopropyl-4,6-difluoro-1,3-benzodiazol-5-yl)ethynyl]-1-[(3S,5R)-5-methyl-1-(prop-2-enoyl)pyrrolidin-3-yl]-5-(methylamino)pyrazole-4-carboxamide;

1-((3S,5R)-1-acryloyl-5-methylpyrrolidin-3-yl)-3-((6-chloro-1-cyclopropyl-1H-benzo[d]imidazol-5-yl)ethynyl)-5-(methylamino)-1H-pyrazole-4-carboxamide;

5-amino-3-[2-(1-cyclopropyl-6-fluoro-1,3-benzodiazol-5-yl)ethynyl]-1-[(3S,5R)-5-(methoxymethyl)-1-(prop-2-enoyl)pyrrolidin-3-yl]pyrazole-4-carboxamide;

5-amino-3-[2-(1-cyclopropyl-6-fluoro-1,3-benzodiazol-5-yl)ethynyl]-1-[(3S)-1-(prop-2-enoyl)pyrrolidin-3-yl]pyrazole-4-carboxamide;

1-((3S,5S)-1-acryloyl-5-methylpyrrolidin-3-yl)-3-((1-cyclopropyl-6-fluoro-1H-benzo[d]imidazol-5-yl)ethynyl)-5-(methylamino)-1H-pyrazole-4-carboxamide;

3-[2-(1-cyclopropyl-6-fluoro-1,3-benzodiazol-5-yl)ethynyl]-1-[(3S,5R)-5-(difluoromethyl)-1-(prop-2-enoyl)pyrrolidin-3-yl]-5-(methylamino)pyrazole-4-carboxamide;

3-[2-(1-cyclopropyl-6,7-difluoro-1,3-benzodiazol-5-yl)ethynyl]-5-(methylamino)-1-[(3S)-1-(prop-2-enoyl)pyrrolidin-3-yl]pyrazole-4-carboxamide;

3-((1-cyclopropyl-6-fluoro-1H-benzo[d]imidazol-5-yl)ethynyl)-1-(1-(2-fluoroacryloyl)azetidin-3-yl)-5-(methylamino)-1H-pyrazole-4-carboxamide;

3-((1-cyclopropyl-4,6-difluoro-1H-benzo[d]imidazol-5-yl)ethynyl)-1-(1-(2-fluoroacryloyl)azetidin-3-yl)-5-(methylamino)-1H-pyrazole-4-carboxamide;

1-((3S,5R)-1-acryloyl-5-(hydroxymethyl)pyrrolidin-3-yl)-3-((1-cyclopropyl-6-fluoro-1H-benzo[d]imidazol-5-yl)ethynyl)-5-(methylamino)-1H-pyrazole-4-carboxamide;

tert-butyl 3-[2-(1-cyclopropyl-6-fluoro-1,3-benzodiazol-5-yl)ethynyl]-5-(methylamino)-1-[1-(prop-2-enoyl)azetidin-3-yl]pyrazole-4-carboxamide;

1-((3S,5R)-1-acryloyl-5-(fluoromethyl)pyrrolidin-3-yl)-3-((1-cyclopropyl-6-fluoro-1H-benzo[d]imidazol-5-yl)ethynyl)-5-(methylamino)-1H-pyrazole-4-carboxamide;

1-((3S,5R)-1-acryloyl-5-(methoxymethyl)pyrrolidin-3-yl)-3-((4,6-difluoro-1H-benzo[d]imidazol-5-yl)ethynyl)-5-(methylamino)-1H-pyrazole-4-carboxamide;

1-((3S,5R)-1-acryloyl-5-(fluoromethyl)pyrrolidin-3-yl)-3-((1-cyclopropyl-1H-benzo[d]imidazol-5-yl)ethynyl)-5-(methylamino)-1H-pyrazole-4-carboxamide;

1-((3S,5R)-1-acryloyl-5-(fluoromethyl)pyrrolidin-3-yl)-3-((1-cyclopropyl-4,6-difluoro-1H-benzo[d]imidazol-5-yl)ethynyl)-5-(methylamino)-1H-pyrazole-4-carboxamide;

3-[2-(1-cyclopropyl-6-fluoro-1,3-benzodiazol-5-yl)ethynyl]-1-[(3S,5S)-5-(fluoromethyl)-1-(prop-2-enoyl)pyrrolidin-3-yl]-5-(methylamino)pyrazole-4-carboxamide;

3-[2-(1-cyclopropyl-4,6-difluoro-1,3-benzodiazol-5-yl)ethynyl]-1-[(3S,5S)-5-(fluoromethyl)-1-(prop-2-enoyl)pyrrolidin-3-yl]-5-(methylamino)pyrazole-4-carboxamide;

3-((1-cyclopropyl-6-fluoro-1H-benzo[d]imidazol-5-yl)ethynyl)-1-((3S,5R)-5-(methoxymethyl)-1-propioloylpyrrolidin-3-yl)-5-(methylamino)-1H-pyrazole-4-carboxamide;

1-((3S,5R)-1-(but-2-ynoyl)-5-(methoxymethyl)pyrrolidin-3-yl)-3-((1-cyclopropyl-6-fluoro-1H-benzo[d]imidazol-5-yl)ethynyl)-5-(methylamino)-1H-pyrazole-4-carboxamide;

3-[2-(1-cyclopropyl-4,6-difluoro-1,3-benzodiazol-5-yl)ethynyl]-1-[(3S,5R)-5-(methoxymethyl)-1-(prop-2-ynoyl)pyrrolidin-3-yl]-5-(methylamino)pyrazole-4-carboxamide;

1-[(3S,5R)-1-(but-2-ynoyl)-5-(methoxymethyl)pyrrolidin-3-yl]-3-[2-(1-cyclopropyl-4,6-difluoro-1,3-benzodiazol-5-yl)ethynyl]-5-(methylamino)pyrazole-4-carboxamide;

3-[2-(1-cyclopropyl-4,6-difluoro-1,3-benzodiazol-5-yl)ethynyl]-5-(methylamino)-1-[(3S)-1-(prop-2-enoyl)pyrrolidin-3-yl]pyrazole-4-carboxamide;

3-[2-(1-cyclopropyl-4,6-difluoro-1,3-benzodiazol-5-yl)ethynyl]-1-[(3S,5R)-5-(hydroxymethyl)-1-(prop-2-enoyl)pyrrolidin-3-yl]-5-(methylamino)pyrazole-4-carboxamide;

3-[2-(1-cyclopropyl-6-fluoro-1,3-benzodiazol-5-yl)ethynyl]-5-(methylamino)-1-[1-(prop-2-ynoyl)pyrrolidin-3-yl]pyrazole-4-carboxamide;

5-amino-3-[2-(1-cyclopropyl-4,6-difluoro-1,3-benzodiazol-5-yl)ethynyl]-1-[(3S,5R)-5-(methoxymethyl)-1-(prop-2-enoyl)pyrrolidin-3-yl]pyrazole-4-carboxamide;

5-amino-3-[2-(1-cyclopropyl-4,6-difluoro-1,3-benzodiazol-5-yl)ethynyl]-1-[(3S)-1-(prop-2-enoyl)pyrrolidin-3-yl]pyrazole-4-carboxamide;

3-[2-(6-chloro-1-ethyl-1,3-benzodiazol-5-yl)ethynyl]-1-[(3S,5R)-5-(hydroxymethyl)-1-(prop-2-enoyl)pyrrolidin-3-yl]-5-(methylamino)pyrazole-4-carboxamide;

3-[2-(6-chloro-1-ethyl-1,3-benzodiazol-5-yl)ethynyl]-5-(methylamino)-1-[1-(prop-2-enoyl)azetidin-3-yl]pyrazole-4-carboxamide;

3-[2-(1-cyclopropyl-4,6-difluoro-1,3-benzodiazol-5-yl)ethynyl]-5-(methylamino)-1-[1-(prop-2-enoyl)azetidin-3-yl]pyrazole-4-carboxamide;

5-amino-3-[2-(6-chloro-1-ethyl-1,3-benzodiazol-5-yl)ethynyl]-1-[(3S,5R)-5-(hydroxymethyl)-1-(prop-2-enoyl)pyrrolidin-3-yl]pyrazole-4-carboxamide;

3-[2-(6-chloro-1-cyclopropyl-1,3-benzodiazol-5-yl)ethynyl]-1-[(3S,5R)-5-(hydroxymethyl)-1-(prop-2-enoyl)pyrrolidin-3-yl]-5-(methylamino)pyrazole-4-carboxamide;

5-amino-3-[2-(6-chloro-1-ethyl-1,3-benzodiazol-5-yl)ethynyl]-1-[(3S,5R)-5-(methoxymethyl)-1-(prop-2-enoyl)pyrrolidin-3-yl]pyrazole-4-carboxamide;

3-[2-(6-chloro-1-cyclopropyl-1,3-benzodiazol-5-yl)ethynyl]-5-(methylamino)-1-[1-(prop-2-enoyl)azetidin-3-yl]pyrazole-4-carboxamide;

3-[2-(1-cyclopropyl-6-fluoro-1,3-benzodiazol-5-yl)ethynyl]-1-[(3S,5R)-5-(hydroxymethyl)-1-(prop-2-ynoyl)pyrrolidin-3-yl]-5-(methylamino)pyrazole-4-carboxamide;

5-amino-3-[2-(6-chloro-1-cyclopropyl-1,3-benzodiazol-5-yl)ethynyl]-1-[(3S,5R)-5-(hydroxymethyl)-1-(prop-2-enoyl)pyrrolidin-3-yl]pyrazole-4-carboxamide;

5-amino-3-[2-(6-chloro-1-cyclopropyl-1,3-benzodiazol-5-yl)ethynyl]-1-[(3S,5R)-5-(methoxymethyl)-1-(prop-2-enoyl)pyrrolidin-3-yl]pyrazole-4-carboxamide;

5-amino-3-[2-(1-cyclopropyl-4,6-difluoro-1,3-benzodiazol-5-yl)ethynyl]-1-[(3S,5R)-5-(hydroxymethyl)-1-(prop-2-enoyl)pyrrolidin-3-yl]pyrazole-4-carboxamide;

5-amino-3-[2-(1-cyclopropyl-6-fluoro-1,3-benzodiazol-5-yl)ethynyl]-1-[1-(prop-2-enoyl)azetidin-3-yl]pyrazole-4-carboxamide;

3-((1-cyclopropyl-6-fluoro-1H-benzo[d]imidazol-5-yl)ethynyl)-1-((3S,5R)-1-(4-hydroxy-4-methylpent-2-ynoyl)-5-(methoxymethyl)pyrrolidin-3-yl)-5-(methylamino)-1H-pyrazole-4-carboxamide;

3-[2-(1-cyclopropyl-6-fluoro-1,3-benzodiazol-5-yl)ethynyl]-1-{1-[(2E)-4-(dimethylamino)but-2-enoyl]azetidin-3-yl}-5-(methylamino)pyrazole-4-carboxamide;

1-((3S,5R)-1-acryloyl-5-(methoxymethyl)pyrrolidin-3-yl)-3-((1-cyclopropyl-6-fluoro-1H-benzo[d]imidazol-5-yl)ethynyl)-5-(ethylamino)-1H-pyrazole-4-carboxamide;

5-amino-3-[2-(1-cyclopropyl-6-fluoro-2-methyl-1,3-benzodiazol-5-yl)ethynyl]-1-[(3S,5R)-5-(methoxymethyl)-1-(prop-2-enoyl)pyrrolidin-3-yl]pyrazole-4-carboxamide;

5-amino-3-[2-(1-cyclopropyl-6-fluoro-1,3-benzodiazol-5-yl)ethynyl]-1-[(3S,5R)-5-(hydroxymethyl)-1-(prop-2-enoyl)pyrrolidin-3-yl]pyrazole-4-carboxamide;

5-amino-3-[2-(6-chloro-1-cyclopropyl-1,3-benzodiazol-5-yl)ethynyl]-1-[1-(prop-2-enoyl)azetidin-3-yl]pyrazole-4-carboxamide;

5-amino-3-[2-(6-chloro-1-ethyl-1,3-benzodiazol-5-yl)ethynyl]-1-[1-(prop-2-enoyl)azetidin-3-yl]pyrazole-4-carboxamide;

5-amino-3-[2-(1-cyclopropyl-4,6-difluoro-1,3-benzodiazol-5-yl)ethynyl]-1-[1-(prop-2-enoyl)azetidin-3-yl]pyrazole-4-carboxamide;

5-amino-3-[2-(1-cyclopropyl-6-fluoro-1,3-benzodiazol-5-yl)ethynyl]-1-[(3S,5R)-5-[(difluoromethoxy)methyl]-1-(prop-2-enoyl)pyrrolidin-3-yl]pyrazole-4-carboxamide;

5-amino-3-[2-(1-cyclopropyl-1,3-benzodiazol-5-yl)ethynyl]-1-[(3S,5R)-5-[(difluoromethoxy)methyl]-1-(prop-2-enoyl)pyrrolidin-3-yl]pyrazole-4-carboxamide;

3-[2-(1-cyclopropyl-6-fluoro-1,3-benzodiazol-5-yl)ethynyl]-5-(methylamino)-1-{[1-(prop-2-enoyl)azetidin-3-yl]methyl}pyrazole-4-carboxamide;

5-amino-3-[2-(6-chloro-1-cyclopropyl-2-methyl-1,3-benzodiazol-5-yl)ethynyl]-1-[(3S,5R)-5-(methoxymethyl)-1-(prop-2-enoyl)pyrrolidin-3-yl]pyrazole-4-carboxamide;

5-amino-3-[2-(1-cyclopropyl-4,6-difluoro-1,3-benzodiazol-5-yl)ethynyl]-1-[(3S,5R)-5-[(difluoromethoxy)methyl]-1-(prop-2-enoyl)pyrrolidin-3-yl]pyrazole-4-carboxamide;

3-[2-(1-cyclopropyl-6-fluoro-1,3-benzodiazol-5-yl)ethynyl]-5-(cyclopropylamino)-1-[(3S,5R)-5-(methoxymethyl)-1-(prop-2-enoyl)pyrrolidin-3-yl]pyrazole-4-carboxamide;

3-[2-(1-cyclopropyl-6-fluoro-1,3-benzodiazol-5-yl)ethynyl]-1-[(3S,5R)-5-(2-hydroxypropan-2-yl)-1-(prop-2-enoyl)pyrrolidin-3-yl]-5-(methylamino)pyrazole-4-carboxamide;

3-[2-(1-cyclopropyl-6-fluoro-1,3-benzodiazol-5-yl)ethynyl]-1-[(3S,5R)-5-[(1R)-1-hydroxyethyl]-1-(prop-2-enoyl)pyrrolidin-3-yl]-5-(methylamino)pyrazole-4-carboxamide;

3-[2-(1-cyclopropyl-6-fluoro-1,3-benzodiazol-5-yl)ethynyl]-1-[(3S,5R)-5-[(1S)-1-hydroxyethyl]-1-(prop-2-enoyl)pyrrolidin-3-yl]-5-(methylamino)pyrazole-4-carboxamide;

1-((3S,5R)-1-acryloyl-5-((R)-1-hydroxyethyl)pyrrolidin-3-yl)-3-((6-chloro-1-cyclopropyl-2-methyl-1H-benzo[d]imidazol-5-yl)ethynyl)-5-(methylamino)-1H-pyrazole-4-carboxamide;

1-((3S,5R)-1-acryloyl-5-((S)-1-hydroxyethyl)pyrrolidin-3-yl)-3-((6-chloro-1-cyclopropyl-2-methyl-1H-benzo[d]imidazol-5-yl)ethynyl)-5-(methylamino)-1H-pyrazole-4-carboxamide;

3-[2-(6-chloro-1-cyclopropyl-1,3-benzodiazol-5-yl)ethynyl]-1-[(3S,5R)-5-[(1R)-1-hydroxyethyl]-1-(prop-2-enoyl)pyrrolidin-3-yl]-5-(methylamino)pyrazole-4-carboxamide;

3-[2-(6-Chloro-1-cyclopropyl-1,3-benzodiazol-5-yl)ethynyl]-1-[(3S,5R)-5-[(1S)-1-hydroxyethyl]-1-(prop-2-enoyl)pyrrolidin-3-yl]-5-(methylamino)pyrazole-4-carboxamide;

3-[2-(1-cyclopropyl-6-fluoro-2-methyl-1,3-benzodiazol-5-yl)ethynyl]-1-[(3S,5R)-5-[(1R)-1-hydroxyethyl]-1-(prop-2-enoyl)pyrrolidin-3-yl]-5-(methylamino)pyrazole-4-carboxamide;

3-[2-(1-cyclopropyl-6-fluoro-2-methyl-1,3-benzodiazol-5-yl)ethynyl]-1-[(3S,5R)-5-[(1S)-1-hydroxyethyl]-1-(prop-2-enoyl)pyrrolidin-3-yl]-5-(methylamino)pyrazole-4-carboxamide;

3-[2-(6-chloro-1-cyclopropyl-1,3-benzodiazol-5-yl)ethynyl]-1-[(3S,5R)-1-(4-hydroxy-4-methylpent-2-ynoyl)-5-(methoxymethyl)pyrrolidin-3-yl]-5-(methylamino)pyrazole-4-carboxamide;

3-[2-(1-cyclopropyl-6-fluoro-2-methyl-1,3-benzodiazol-5-yl)ethynyl]-1-[(3S,5R)-1-(4-hydroxy-4-methylpent-2-ynoyl)-5-(methoxymethyl)pyrrolidin-3-yl]-5-(methylamino)pyrazole-4-carboxamide;

3-[2-(6-chloro-1-cyclopropyl-2-methyl-1,3-benzodiazol-5-yl)ethynyl]-1-[(3S,5R)-1-(4-hydroxy-4-methylpent-2-ynoyl)-5-(methoxymethyl)pyrrolidin-3-yl]-5-(methylamino)pyrazole-4-carboxamide;

1-((3S,5R)-1-acryloyl-5-(methoxymethyl)pyrrolidin-3-yl)-3-((1-cyclobutyl-6-fluoro-1H-benzo[d]imidazol-5-yl)ethynyl)-5-(methylamino)-1H-pyrazole-4-carboxamide;

1-((3S,5R)-1-acryloyl-5-(methoxymethyl)pyrrolidin-3-yl)-3-((1-cyclobutyl-6-fluoro-2-methyl-1H-benzo[d]imidazol-5-yl)ethynyl)-5-(methylamino)-1H-pyrazole-4-carboxamide;

3-[2-(6-chloro-1-cyclobutyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

1-((3S,5R)-1-acryloyl-5-(methoxymethyl)pyrrolidin-3-yl)-3-((6-chloro-1-cyclobutyl-2-methyl-1H-benzo[d]imidazol-5-yl)ethynyl)-5-(methylamino)-1H-pyrazole-4-carboxamide;

3-{2-[6-fluoro-1-(oxetan-3-yl)-1,3-benzodiazol-5-yl]ethynyl}-1-[(3S,5R)-5-(methoxymethyl)-1-(prop-2-enoyl)pyrrolidin-3-yl]-5-(methylamino)pyrazole-4-carboxamide;

3-{2-[6-fluoro-2-methyl-1-(oxetan-3-yl)-1,3-benzodiazol-5-yl]ethynyl}-1-[(3S,5R)-5-(methoxymethyl)-1-(prop-2-enoyl)pyrrolidin-3-yl]-5-(methylamino)pyrazole-4-carboxamide;

3-[2-(6-fluoro-3-methylquinolin-7-yl)ethynyl]-1-[(3S,5R)-5-(methoxymethyl)-1-(prop-2-enoyl)pyrrolidin-3-yl]-5-(methylamino)pyrazole-4-carboxamide;

1-((3S,5R)-1-acryloyl-5-(methoxymethyl)pyrrolidin-3-yl)-3-((6-fluoro-1-isopropyl-1H-benzo[d]imidazol-5-yl)ethynyl)-5-(methylamino)-1H-pyrazole-4-carboxamide;

3-{2-[6-fluoro-1-(1-methylcyclopropyl)-1,3-benzodiazol-5-yl]ethynyl}-1-[(3S,5R)-5-(methoxymethyl)-1-(prop-2-enoyl)pyrrolidin-3-yl]-5-(methylamino)pyrazole-4-carboxamide;

1-((3S,5R)-1-acryloyl-5-(methoxymethyl)pyrrolidin-3-yl)-3-((1-(1-cyanocyclopropyl)-6-fluoro-1H-benzo[d]imidazol-5-yl)ethynyl)-5-(methylamino)-1H-pyrazole-4-carboxamide;

5-amino-3-[2-(1-cyclopropyl-6-fluoro-1,3-benzodiazol-5-yl)ethynyl]-1-[(3S,5R)-5-[(1R)-1-hydroxyethyl]-1-(prop-2-enoyl)pyrrolidin-3-yl]pyrazole-4-carboxamide;

5-amino-3-[2-(1-cyclopropyl-6-fluoro-1,3-benzodiazol-5-yl)ethynyl]-1-[(3S,5R)-5-[(1S)-1-hydroxyethyl]-1-(prop-2-enoyl)pyrrolidin-3-yl]pyrazole-4-carboxamide;

5-amino-3-[2-(6-chloro-1-cyclopropyl-1,3-benzodiazol-5-yl)ethynyl]-1-[(3S,5R)-5-[(1R)-1-hydroxyethyl]-1-(prop-2-enoyl)pyrrolidin-3-yl]pyrazole-4-carboxamide;

5-amino-3-[2-(6-chloro-1-cyclopropyl-1,3-benzodiazol-5-yl)ethynyl]-1-[(3S,5R)-5-[(1S)-1-hydroxyethyl]-1-(prop-2-enoyl)pyrrolidin-3-yl]pyrazole-4-carboxamide;

1-((3S,5R)-1-acryloyl-5-((R)-1-hydroxyethyl)pyrrolidin-3-yl)-5-amino-3-((6-chloro-1-cyclopropyl-2-methyl-1H-benzo[d]imidazol-5-yl)ethynyl)-1H-pyrazole-4-carboxamide;

1-((3S,5R)-1-Acryloyl-5-((S)-1-hydroxyethyl)pyrrolidin-3-yl)-5-amino-3-((6-chloro-1-cyclopropyl-2-methyl-1H-benzo[d]imidazol-5-yl)ethynyl)-1H-pyrazole-4-carboxamide;

5-amino-3-[2-(1-cyclopropyl-6-fluoro-2-methyl-1,3-benzodiazol-5-yl)ethynyl]-1-[(3S,5R)-5-[(1R)-1-hydroxyethyl]-1-(prop-2-enoyl)pyrrolidin-3-yl]pyrazole-4-carboxamide;

5-amino-3-[2-(1-cyclopropyl-6-fluoro-2-methyl-1,3-benzodiazol-5-yl)ethynyl]-1-[(3S,5R)-5-[(1S)-1-hydroxyethyl]-1-(prop-2-enoyl)pyrrolidin-3-yl]pyrazole-4-carboxamide;

3-{2-[6-chloro-1-(oxetan-3-yl)-1,3-benzodiazol-5-yl]ethynyl}-1-[(3S,5R)-5-(methoxymethyl)-1-(prop-2-enoyl)pyrrolidin-3-yl]-5-(methylamino)pyrazole-4-carboxamide;

3-{2-[6-chloro-2-methyl-1-(oxetan-3-yl)-1,3-benzodiazol-5-yl]ethynyl}-1-[(3S,5R)-5-(methoxymethyl)-1-(prop-2-enoyl)pyrrolidin-3-yl]-5-(methylamino)pyrazole-4-carboxamide;

3-[2-(1-cyclopropyl-6-fluoro-1,3-benzodiazol-5-yl)ethynyl]-5-[(2-hydroxyethyl)amino]-1-[(3S,5R)-5-(methoxymethyl)-1-(prop-2-enoyl)pyrrolidin-3-yl]pyrazole-4-carboxamide;

3-[2-(1-cyclopropyl-4,6-difluoro-1,3-benzodiazol-5-yl)ethynyl]-5-[(2-hydroxyethyl)amino]-1-[(3S,5R)-5-(methoxymethyl)-1-(prop-2-enoyl)pyrrolidin-3-yl]pyrazole-4-carboxamide;

3-[2-(1-cyclopropyl-6-fluoro-2-methyl-1,3-benzodiazol-5-yl)ethynyl]-5-[(2-hydroxyethyl)amino]-1-[(3S,5R)-5-(methoxymethyl)-1-(prop-2-enoyl)pyrrolidin-3-yl]pyrazole-4-carboxamide;

1-((3S,5R)-1-acryloyl-5-(methoxymethyl)pyrrolidin-3-yl)-3-((6-chloro-1-cyclopropyl-2-methyl-1H-benzo[d]imidazol-5-yl)ethynyl)-5-((2-hydroxyethyl)amino)-1H-pyrazole-4-carboxamide;

3-[2-(6-fluoro-2H-1,3-benzodioxol-5-yl)ethynyl]-1-[(3S,5R)-5-(methoxymethyl)-1-(prop-2-enoyl)pyrrolidin-3-yl]-5-(methylamino)pyrazole-4-carboxamide;

3-[2-(3-chloro-6-fluoroquinolin-7-yl)ethynyl]-1-[(3S,5R)-5-(methoxymethyl)-1-(prop-2-enoyl)pyrrolidin-3-yl]-5-(methylamino)pyrazole-4-carboxamide;

1-((3S,5R)-1-acryloyl-5-(methoxymethyl)pyrrolidin-3-yl)-3-((6-fluoro-3-methylimidazo[1,2-a]pyridin-7-yl)ethynyl)-5-(methylamino)-1H-pyrazole-4-carboxamide;

1-((3S,5R)-1-acryloyl-5-(methoxymethyl)pyrrolidin-3-yl)-3-((6-chloro-3-methylquinolin-7-yl)ethynyl)-5-(methylamino)-1H-pyrazole-4-carboxamide;

3-[2-(1-cyclopropyl-6-methyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide;

1-((3S,5R)-1-acryloyl-5-(methoxymethyl)pyrrolidin-3-yl)-3-((7-fluoro-2,3-dihydro-1H-benzo[d]pyrrolo[1,2-a]imidazol-6-yl)ethynyl)-5-(methylamino)-1H-pyrazole-4-carboxamide;

3-(2-{6-chloro-3-cyclopropylimidazo[1,2-a]pyridin-7-yl}ethynyl)-1-[(3S,5R)-5-(methoxymethyl)-1-(prop-2-enoyl)pyrrolidin-3-yl]-5-(methylamino)pyrazole-4-carboxamide;

3-(2-{3-cyano-6-fluoroimidazo[1,2-a]pyridin-7-yl}ethynyl)-1-[(3S,5R)-5-(methoxymethyl)-1-(prop-2-enoyl)pyrrolidin-3-yl]-5-(methylamino)pyrazole-4-carboxamide;

3-(2-{3-cyanopyrazolo[1,5-a]pyridin-6-yl}ethynyl)-1-[(3S,5R)-5-(methoxymethyl)-1-(prop-2-enoyl)pyrrolidin-3-yl]-5-(methylamino)pyrazole-4-carboxamide;

3-[2-(3, 6-difluoroquinolin-7-yl)ethynyl]-1-[(3S,5R)-5-(methoxymethyl)-1-(prop-2-enoyl)pyrrolidin-3-yl]-5-(methylamino)pyrazole-4-carboxamide;

3-[2-(3,6-dimethylquinolin-7-yl)ethynyl]-1-[(3S,5R)-5-(methoxymethyl)-1-(prop-2-enoyl)pyrrolidin-3-yl]-5-(methylamino)pyrazole-4-carboxamide;

1-((3S,5R)-1-acryloyl-5-(methoxymethyl)pyrrolidin-3-yl)-3-((6-fluoro-4-methylcinnolin-7-yl)ethynyl)-5-(methylamino)-1H-pyrazole-4-carboxamide;

3-[2-(6-chloro-3-fluoroquinolin-7-yl)ethynyl]-1-[(3S,5R)-5-(methoxymethyl)-1-(prop-2-enoyl)pyrrolidin-3-yl]-5-(methylamino)pyrazole-4-carboxamide;

1-((3S,5R)-1-acryloyl-5-(methoxymethyl)pyrrolidin-3-yl)-3-((6-chloro-4-methylcinnolin-7-yl)ethynyl)-5-(methylamino)-1H-pyrazole-4-carboxamide;

3-(2-{3-cyanoimidazo[1,2-a]pyridin-7-yl}ethynyl)-1-[(3S,5R)-5-(methoxymethyl)-1-(prop-2-enoyl)pyrrolidin-3-yl]-5-(methylamino)pyrazole-4-carboxamide;

1-((3S,5R)-1-acryloyl-5-(methoxymethyl)pyrrolidin-3-yl)-3-((3-cyano-4-methoxypyrazolo[1,5-a]pyridin-6-yl)ethynyl)-5-(methylamino)-1H-pyrazole-4-carboxamide;

3-(2-{1-[(1S)-2,2-Difluorocyclopropyl]-6-fluoro-1,3-benzodiazol-5-yl}ethynyl)-1-[(3S,5R)-5-(methoxymethyl)-1-(prop-2-enoyl)pyrrolidin-3-yl]-5-(methylamino)pyrazole-4-carboxamide;

3-{2-[1-((R)-(2,2-difluorocyclopropyl)-6-fluoro-1,3-benzodiazol-5-yl]ethynyl}-1-[(3S,5R)-5-(methoxymethyl)-1-(prop-2-enoyl)pyrrolidin-3-yl]-5-(methylamino)pyrazole-4-carboxamide;

3-{2-[3-(difluoromethyl)-6-fluoroquinolin-7-yl]ethynyl}-1-[(3S,5R)-5-(methoxymethyl)-1-(prop-2-enoyl)pyrrolidin-3-yl]-5-(methylamino)pyrazole-4-carboxamide;

3-[2-(6-fluoro-4-methylquinolin-7-yl)ethynyl]-1-[(3S,5R)-5-(methoxymethyl)-1-(prop-2-enoyl)pyrrolidin-3-yl]-5-(methylamino)pyrazole-4-carboxamide;

1-((3S,5R)-1-acryloyl-5-(methoxymethyl)pyrrolidin-3-yl)-3-((1-methyl-1H-indazol-4-yl)ethynyl)-5-(methylamino)-1H-pyrazole-4-carboxamide;

3-[2-(1-cyclopropylindazol-4-yl)ethynyl]-1-[(3S,5R)-5-(methoxymethyl)-1-(prop-2-enoyl)pyrrolidin-3-yl]-5-(methylamino)pyrazole-4-carboxamide;

3-(2-{imidazo[1,5-a]pyridin-8-yl}ethynyl)-1-[(3S,5R)-5-(methoxymethyl)-1-(prop-2-enoyl)pyrrolidin-3-yl]-5-(methylamino)pyrazole-4-carboxamide;

3-(2-{imidazo[1,5-a]pyridin-5-yl}ethynyl)-1-[(3S,5R)-5-(methoxymethyl)-1-(prop-2-enoyl)pyrrolidin-3-yl]-5-(methylamino)pyrazole-4-carboxamide;

3-(2-{6-chloro-1-[(1R)-2,2-difluorocyclopropyl]-1,3-benzodiazol-5-yl}ethynyl)-1-[(3S,5R)-5-(methoxymethyl)-1-(prop-2-enoyl)pyrrolidin-3-yl]-5-(methylamino)pyrazole-4-carboxamide;

3-(2-{6-Chloro-1-[(1S)-2,2-difluorocyclopropyl]-1,3-benzodiazol-5-yl}ethynyl)-1-[(3S,5R)-5-(methoxymethyl)-1-(prop-2-enoyl)pyrrolidin-3-yl]-5-(methylamino)pyrazole-4-carboxamide;

3-[2-(6-chloro-4-methylquinolin-7-yl)ethynyl]-1-[(3S,5R)-5-(methoxymethyl)-1-(prop-2-enoyl)pyrrolidin-3-yl]-5-(methylamino)pyrazole-4-carboxamide;

1-((3S,5R)-1-acryloyl-5-(methoxymethyl)pyrrolidin-3-yl)-3-((6-fluoro-3,4-dimethylquinolin-7-yl)ethynyl)-5-(methylamino)-1H-pyrazole-4-carboxamide;

3-(2-{3-cyclopropyl-6-fluoroimidazo[1,2-a]pyridin-7-yl}ethynyl)-1-[(3S,5R)-5-(methoxymethyl)-1-(prop-2-enoyl)pyrrolidin-3-yl]-5-(methylamino)pyrazole-4-carboxamide;

3-(2-{3-cyclopropyl-4-methoxypyrazolo[1,5-a]pyridin-6-yl}ethynyl)-1-[(3S,5R)-5-(methoxymethyl)-1-(prop-2-enoyl)pyrrolidin-3-yl]-5-(methylamino)pyrazole-4-carboxamide;

1-((3S,5R)-1-acryloyl-5-(methoxymethyl)pyrrolidin-3-yl)-3-((7-chloro-2,3-dihydro-1H-benzo[d]pyrrolo[1,2-a]imidazol-6-yl)ethynyl)-5-(methylamino)-1H-pyrazole-4-carboxamide;

1-((3S,5R)-1-acryloyl-5-(methoxymethyl)pyrrolidin-3-yl)-3-((1-cyclopropyl-5-fluoro-1H-indazol-4-yl)ethynyl)-5-(methylamino)-1H-pyrazole-4-carboxamide;

3-(2-{6-chloro-3-[(1R)-2,2-difluorocyclopropyl]-1,3-benzodiazol-5-yl}ethynyl)-1-[(3S,5R)-5-(methoxymethyl)-1-(prop-2-enoyl)pyrrolidin-3-yl]-5-(methylamino)pyrazole-4-carboxamide;

3-(2-{6-chloro-3-[(1S)-2,2-difluorocyclopropyl]-1,3-benzodiazol-5-yl}ethynyl)-1-[(3S,5R)-5-(methoxymethyl)-1-(prop-2-enoyl)pyrrolidin-3-yl]-5-(methylamino)pyrazole-4-carboxamide; and 3-(2-{3-chloro-6-fluoroimidazo[1,2-a]pyridin-7-yl}ethynyl)-1-[(3S,5R)-5-(methoxymethyl)-1-(prop-2-enoyl)pyrrolidin-3-yl]-5-(methylamino)pyrazole-4-carboxamide.

2. A pharmaceutical composition comprising a compound described in claim 1, or pharmaceutically acceptable salt or solvate thereof, and a pharmaceutically acceptable excipient.

3. The compound, or pharmaceutically acceptable salt or solvate thereof, of claim 1 having the structure of: 1-((3S,5R)-1-acryloyl-5-(methoxymethyl)pyrrolidin-3-yl)-3-((1-ethyl-4,6-difluoro-1H-benzo[d]imidazol-5-yl)ethynyl)-5-(methylamino)-1H-pyrazole-4-carboxamide.

4. The pharmaceutical composition of claim 2, comprising the compound having the structure of: 1-((3S,5R)-1-acryloyl-5-(methoxymethyl)pyrrolidin-3-yl)-3-((1-ethyl-4,6-difluoro-1H-benzo[d]imidazol-5-yl)ethynyl)-5-(methylamino)-1H-pyrazole-4-carboxamide, or pharmaceutically acceptable salt or solvate thereof, and a pharmaceutically acceptable excipient.

5. The compound, or pharmaceutically acceptable salt or solvate thereof, of claim 1 having the structure of: 3-[2-(1-Cyclopropyl-4,6-difluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide.

6. The pharmaceutical composition of claim 2, comprising the compound having the structure of: 3-[2-(1-Cyclopropyl-4,6-difluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide, or pharmaceutically acceptable salt or solvate thereof, and a pharmaceutically acceptable excipient.

7. The compound, or pharmaceutically acceptable salt or solvate thereof, of claim 1 having the structure of: 3-[2-(6-Chloro-1-ethyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide.

8. The pharmaceutical composition of claim 2, comprising the compound having the structure of: 3-[2-(6-Chloro-1-ethyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide, or pharmaceutically acceptable salt or solvate thereof, and a pharmaceutically acceptable excipient.

9. The compound, or pharmaceutically acceptable salt or solvate thereof, of claim 1 having the structure of: 3-[2-(6-Chloro-1-cyclopropyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide.

10. The pharmaceutical composition of claim 2, comprising the compound having the structure of: 3-[2-(6-Chloro-1-cyclopropyl-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide, or pharmaceutically acceptable salt or solvate thereof, and a pharmaceutically acceptable excipient.

11. The compound, or pharmaceutically acceptable salt or solvate thereof, of claim 1 having the structure of: 3-[2-(1-Cyclopropyl-6-fluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide.

12. The pharmaceutical composition of claim 2, comprising the compound having the structure of: 3-[2-(1-Cyclopropyl-6-fluoro-1,3-benzodiazol-5-yl)ethynyl]-1-[(3S,5R)-5-(methoxymethyl)-1-(prop-2-enoyl)pyrrolidin-3-yl]-5-(methylamino)pyrazole-4-carboxamide, or pharmaceutically acceptable salt or solvate thereof, and a pharmaceutically acceptable excipient.

13. The compound, or pharmaceutically acceptable salt or solvate thereof, of claim 1 having the structure of: 5-amino-3-[2-(6-chloro-1-cyclopropyl-1,3-benzodiazol-5-yl)ethynyl]-1-[(3S,5R)-5-(methoxymethyl)-1-(prop-2-enoyl)pyrrolidin-3-yl]pyrazole-4-carboxamide.

14. The pharmaceutical composition of claim 2, comprising the compound having the structure of: 5-amino-3-[2-(6-chloro-1-cyclopropyl-1,3-benzodiazol-5-yl)ethynyl]-1-[(3S,5R)-5-(methoxymethyl)-1-(prop-2-enoyl)pyrrolidin-3-yl]pyrazole-4-carboxamide, or pharmaceutically acceptable salt or solvate thereof, and a pharmaceutically acceptable excipient.

* * * * *